United States Patent
Davicioni et al.

(10) Patent No.: US 10,513,737 B2
(45) Date of Patent: Dec. 24, 2019

(54) CANCER DIAGNOSTICS USING NON-CODING TRANSCRIPTS

(71) Applicant: DECIPHER BIOSCIENCES, INC., San Diego, CA (US)

(72) Inventors: Elai Davicioni, La Jolla, CA (US); Nicholas George Erho, Vancouver (CA); Ismael A. Vergara Correa, West Vancouver (CA)

(73) Assignee: DECIPHER BIOSCIENCES, INC., San Diego, CA (US)

( * ) Notice: Subject to any disclaimer, the term of this patent is extended or adjusted under 35 U.S.C. 154(b) by 848 days.

(21) Appl. No.: 14/365,085

(22) PCT Filed: Dec. 13, 2012

(86) PCT No.: PCT/US2012/069571
§ 371 (c)(1),
(2) Date: Jun. 12, 2014

(87) PCT Pub. No.: WO2013/090620
PCT Pub. Date: Jun. 20, 2013

(65) Prior Publication Data
US 2015/0011401 A1    Jan. 8, 2015

Related U.S. Application Data

(60) Provisional application No. 61/730,426, filed on Nov. 27, 2012, provisional application No. 61/652,044, filed on May 25, 2012, provisional application No. 61/570,194, filed on Dec. 13, 2011.

(51) Int. Cl.
| | | |
|---|---|---|
| *C12Q 1/68* | (2018.01) | |
| *C12Q 1/6886* | (2018.01) | |
| *C12N 15/11* | (2006.01) | |
| *G16B 20/00* | (2019.01) | |
| *G16B 25/00* | (2019.01) | |

(52) U.S. Cl.
CPC .......... *C12Q 1/6886* (2013.01); *C12N 15/111* (2013.01); *C12N 2310/141* (2013.01); *C12N 2320/10* (2013.01); *C12Q 2600/106* (2013.01); *C12Q 2600/118* (2013.01); *C12Q 2600/158* (2013.01); *C12Q 2600/178* (2013.01); *G16B 20/00* (2019.02); *G16B 25/00* (2019.02)

(58) Field of Classification Search
CPC .............................. C12N 15/111; C12Q 1/6886
See application file for complete search history.

(56) References Cited

U.S. PATENT DOCUMENTS

| | | |
|---|---|---|
| 3,645,691 A | 2/1972 | Guenter et al. |
| 3,687,808 A | 8/1972 | Thomas, Jr. et al. |
| 5,130,238 A | 7/1992 | Malek et al. |
| 5,143,854 A | 9/1992 | Pinung et al. |
| 5,288,514 A | 2/1994 | Ellman |
| 5,384,261 A | 1/1995 | Winkle et al. |
| 5,399,491 A | 3/1995 | Kacian et al. |
| 5,455,166 A | 10/1995 | Walker |
| 5,494,810 A | 2/1996 | Barany et al. |
| 5,538,848 A | 7/1996 | Livak et al. |
| 5,677,195 A | 10/1997 | Winkler et al. |
| 5,705,365 A | 1/1998 | Ryder et al. |
| 5,710,029 A | 1/1998 | Ryder et al. |
| 5,744,305 A | 4/1998 | Fodor et al. |
| 5,830,711 A | 11/1998 | Barany et al. |
| 5,846,717 A | 12/1998 | Brow et al. |
| 5,854,033 A | 12/1998 | Lizardi |
| 5,888,779 A | 3/1999 | Kacian et al. |
| 5,965,360 A | 10/1999 | Zain et al. |
| 5,985,557 A | 11/1999 | Prudent et al. |
| 5,989,815 A | 11/1999 | Skolnick et al. |
| 5,994,069 A | 11/1999 | Hall et al. |
| 6,001,567 A | 12/1999 | Brow et al. |
| 6,022,692 A | 2/2000 | Coulie et al. |
| 6,027,887 A | 2/2000 | Zavada et al. |
| 6,090,543 A | 7/2000 | Prudent et al. |
| 6,136,182 A | 10/2000 | Dolan et al. |
| 6,218,523 B1 | 4/2001 | French |
| 6,225,051 B1 | 5/2001 | Sugiyama et al. |
| 6,251,639 B1 | 6/2001 | Kurn |
| 6,268,142 B1 | 7/2001 | Duff et al. |
| 6,410,278 B1 | 6/2002 | Notomi et al. |

(Continued)

FOREIGN PATENT DOCUMENTS

| | | |
|---|---|---|
| EP | 2 366 800 A1 | 9/2011 |
| WO | WO 1990/015070 A1 | 12/1990 |

(Continued)

OTHER PUBLICATIONS

US 5,962,233 A, 10/1999, Livak et al. (withdrawn)
Kikuchi et al.; Expression profiles of non-small cell lung cancers on cDNA microarrays: Identification of genes for prediction of lymph-node metastasis and sensitivity to anti-cancer drugs; Oncogene (2003) 22, 2192-2205 (Year: 2003).*

(Continued)

*Primary Examiner* — Antonio Galisteo Gonzalez
(74) *Attorney, Agent, or Firm* — Knobbe, Martens, Olson & Bear LLP

(57) ABSTRACT

Disclosed herein, in certain instances, are methods for the diagnosis, prognosis and determination of cancer progression of a cancer in a subject. Further disclosed herein, in certain instances, are methods for determining the treatment modality of a cancer in a subject. The methods comprise expression-based analysis of non-coding targets and coding targets. Further disclosed herein, in certain instances, are probe sets for use in assessing a cancer status in a subject.

7 Claims, 71 Drawing Sheets
Specification includes a Sequence Listing.

(56) References Cited

U.S. PATENT DOCUMENTS

| | | |
|---|---|---|
| 6,436,642 B1 | 8/2002 | Gould-Rothberg et al. |
| 6,630,358 B1 | 10/2003 | Wagner et al. |
| 6,723,506 B2 | 4/2004 | Fletcher et al. |
| 7,186,514 B2 | 3/2007 | Zavada et al. |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,280,922 B2 | 10/2007 | Mei et al. |
| 7,300,788 B2 | 11/2007 | Matsuzaki et al. |
| 7,319,011 B2 | 1/2008 | Riggins et al. |
| 7,323,305 B2 | 1/2008 | Leamon et al. |
| 7,335,762 B2 | 2/2008 | Rothberg et al. |
| 7,358,061 B2 | 4/2008 | Yamamoto et al. |
| 7,361,488 B2 | 4/2008 | Fan et al. |
| 7,378,233 B2 | 5/2008 | Sidransky et al. |
| 7,407,755 B2 | 8/2008 | Lubinski et al. |
| 7,541,169 B2 | 6/2009 | Freimuth et al. |
| 7,598,052 B2 | 10/2009 | Giordano et al. |
| 7,662,553 B2 | 2/2010 | Lenz et al. |
| 7,767,391 B2 | 8/2010 | Scott et al. |
| 7,901,881 B2 | 3/2011 | Libutti et al. |
| 7,901,888 B2 | 3/2011 | Kebebew |
| 7,914,988 B1 | 3/2011 | Chudin et al. |
| 7,927,826 B2 | 4/2011 | Riggins et al. |
| 8,008,009 B2 | 8/2011 | Choquet-Kastylevsky et al. |
| 8,202,692 B2 | 6/2012 | Giordano et al. |
| 8,273,539 B2 | 9/2012 | Klee et al. |
| 8,293,880 B2 | 10/2012 | Cote et al. |
| 8,299,233 B2 | 10/2012 | Andre et al. |
| 8,338,109 B2 | 12/2012 | Vasmatzis et al. |
| 8,354,228 B2 | 1/2013 | Ron |
| 8,465,914 B2 | 6/2013 | Brown et al. |
| 8,541,170 B2 | 9/2013 | Kennedy et al. |
| 8,568,971 B2 | 10/2013 | Brown et al. |
| 8,669,057 B2 | 3/2014 | Kennedy et al. |
| 8,802,699 B2 | 8/2014 | Aharonov et al. |
| 8,828,656 B2 | 9/2014 | Bullerdiek et al. |
| 8,877,445 B2 | 11/2014 | Shackney |
| 8,945,829 B2 | 2/2015 | Keutgen et al. |
| 9,040,286 B2 | 5/2015 | Zon et al. |
| 9,074,258 B2 | 7/2015 | Davicion et al. |
| 9,096,906 B2 | 8/2015 | Aharonov et al. |
| 9,157,123 B2 | 10/2015 | Xing |
| 9,175,352 B2 | 11/2015 | Keutgen et al. |
| 9,206,482 B2 | 12/2015 | Davicioni et al. |
| 9,234,244 B2 | 1/2016 | Zeiger et al. |
| 9,495,515 B1 | 11/2016 | Giulia et al. |
| 9,587,279 B2 | 3/2017 | Fahey, III et al. |
| 9,617,604 B2 | 4/2017 | Davicion et al. |
| 9,708,667 B2 | 7/2017 | Yanai et al. |
| 9,714,452 B2 | 7/2017 | Davicioni et al. |
| 9,856,537 B2 | 1/2018 | Kennedy et al. |
| 9,994,907 B2 | 6/2018 | Davicioni et al. |
| 10,114,924 B2 | 10/2018 | Kennedy et al. |
| 2001/0051344 A1 | 12/2001 | Shalon et al. |
| 2002/0076735 A1 | 6/2002 | Williams et al. |
| 2002/0119463 A1 | 8/2002 | Fads |
| 2002/0168638 A1 | 11/2002 | Schlegel et al. |
| 2002/0169137 A1 | 11/2002 | Reiner et al. |
| 2002/0182586 A1 | 12/2002 | Morris et al. |
| 2003/0119168 A1 | 6/2003 | Madison et al. |
| 2003/0152980 A1 | 8/2003 | Golub et al. |
| 2003/0186248 A1 | 10/2003 | Erlander et al. |
| 2003/0190602 A1 | 10/2003 | Pressman et al. |
| 2003/0194734 A1 | 10/2003 | Jatkoe |
| 2003/0224399 A1 | 12/2003 | Reed et al. |
| 2003/0235820 A1 | 12/2003 | Mack |
| 2004/0009481 A1 | 1/2004 | Schlegel et al. |
| 2004/0018493 A1 | 1/2004 | Anastasio et al. |
| 2004/0019466 A1 | 1/2004 | Minor et al. |
| 2004/0029114 A1 | 2/2004 | Mack et al. |
| 2004/0058378 A1 | 3/2004 | Kong et al. |
| 2004/0259086 A1 | 12/2004 | Schlegel et al. |
| 2005/0042222 A1 | 2/2005 | Yamamoto et al. |
| 2005/0048533 A1 | 3/2005 | Sidransky et al. |
| 2005/0064455 A1 | 3/2005 | Baker et al. |
| 2005/0118625 A1 | 6/2005 | Mounts |
| 2005/0137805 A1 | 6/2005 | Lewin et al. |
| 2005/0202442 A1 | 9/2005 | Morris et al. |
| 2005/0227917 A1 | 10/2005 | Williams et al. |
| 2005/0240357 A1 | 10/2005 | Minor |
| 2005/0250125 A1 | 11/2005 | Novakoff |
| 2005/0260646 A1 | 11/2005 | Baker et al. |
| 2005/0266443 A1 | 12/2005 | Croce et al. |
| 2006/0019256 A1 | 1/2006 | Clarke et al. |
| 2006/0019615 A1 | 1/2006 | Ditmer |
| 2006/0035244 A1 | 2/2006 | Riggins et al. |
| 2006/0046253 A1 | 3/2006 | Nakao |
| 2006/0083744 A1 | 4/2006 | Chen et al. |
| 2006/0088851 A1 | 4/2006 | Erlander et al. |
| 2006/0094061 A1 | 5/2006 | Brys et al. |
| 2006/0105360 A1 | 5/2006 | Croce et al. |
| 2006/0127907 A1 | 6/2006 | Matsubara et al. |
| 2006/0134663 A1 | 6/2006 | Harkin et al. |
| 2006/0204989 A1 | 9/2006 | Kopreski |
| 2006/0211017 A1 | 9/2006 | Chinnaiyan et al. |
| 2007/0020657 A1 | 1/2007 | Grebe et al. |
| 2007/0031873 A1 | 2/2007 | Wang et al. |
| 2007/0037165 A1 | 2/2007 | Venter et al. |
| 2007/0037186 A1 | 2/2007 | Jiang et al. |
| 2007/0048738 A1 | 3/2007 | Donkena et al. |
| 2007/0065827 A1 | 3/2007 | Pauloski et al. |
| 2007/0065833 A1 | 3/2007 | Gupta |
| 2007/0083334 A1 | 4/2007 | Mintz et al. |
| 2007/0099197 A1 | 5/2007 | Afar et al. |
| 2007/0099209 A1 | 5/2007 | Clarke et al. |
| 2007/0105133 A1 | 5/2007 | Clarke et al. |
| 2007/0148667 A1 | 6/2007 | Williams et al. |
| 2007/0148687 A1 | 6/2007 | Bedingham et al. |
| 2007/0161004 A1 | 7/2007 | Brown et al. |
| 2007/0172841 A1 | 7/2007 | Wang |
| 2007/0172844 A1 | 7/2007 | Lancaster et al. |
| 2007/0212702 A1 | 9/2007 | Tomlins et al. |
| 2007/0220621 A1 | 9/2007 | Clarke et al. |
| 2007/0238119 A1 | 10/2007 | Yu et al. |
| 2007/0259352 A1 | 11/2007 | Bentwich et al. |
| 2007/0275915 A1 | 11/2007 | Hallenbeck et al. |
| 2008/0009001 A1 | 1/2008 | Bettuzzi et al. |
| 2008/0028302 A1 | 1/2008 | Meschkat |
| 2008/0044824 A1 | 2/2008 | Giordano et al. |
| 2008/0076674 A1 | 3/2008 | Litman et al. |
| 2008/0124344 A1 | 5/2008 | Combs et al. |
| 2008/0131892 A1 | 6/2008 | Becker et al. |
| 2008/0145841 A1 | 6/2008 | Libutti et al. |
| 2008/0254470 A1 | 10/2008 | Berlkin |
| 2008/0274457 A1 | 11/2008 | Eng et al. |
| 2008/0281568 A1 | 11/2008 | Kao et al. |
| 2009/0020433 A1 | 1/2009 | Cohen et al. |
| 2009/0036415 A1 | 2/2009 | Rubin et al. |
| 2009/0062144 A1 | 3/2009 | Guo |
| 2009/0075921 A1 | 3/2009 | Ikegawa |
| 2009/0149333 A1 | 6/2009 | Knudsen et al. |
| 2009/0191535 A1 | 7/2009 | Connelly et al. |
| 2009/0204333 A1 | 8/2009 | Friend et al. |
| 2009/0239221 A1 | 9/2009 | Chinnaiyan et al. |
| 2009/0280490 A1 | 11/2009 | Baker et al. |
| 2009/0298082 A1 | 12/2009 | Klee et al. |
| 2010/0055704 A1 | 3/2010 | Giordano et al. |
| 2010/0075384 A1 | 3/2010 | Kong et al. |
| 2010/0099093 A1 | 4/2010 | Weaver et al. |
| 2010/0130377 A1 | 5/2010 | Vasmatzis et al. |
| 2010/0131286 A1 | 5/2010 | Houlgatte et al. |
| 2010/0131432 A1 | 5/2010 | Kennedy et al. |
| 2010/0178653 A1 | 7/2010 | Aharonov et al. |
| 2010/0257617 A1 | 10/2010 | Ami et al. |
| 2010/0279327 A1 | 11/2010 | Ossovskaya |
| 2010/0285979 A1 | 11/2010 | Zeiger et al. |
| 2011/0009286 A1 | 1/2011 | Andre et al. |
| 2011/0045462 A1 | 2/2011 | Fu et al. |
| 2011/0092375 A1 | 4/2011 | Zamore et al. |
| 2011/0136683 A1 | 6/2011 | Davicioni |
| 2011/0152110 A1 | 6/2011 | Vierlinger et al. |
| 2011/0178163 A1 | 7/2011 | Chowdhury |
| 2011/0212855 A1 | 9/2011 | Rafnar et al. |

(56) References Cited

U.S. PATENT DOCUMENTS

| | | |
|---|---|---|
| 2011/0229894 A1 | 9/2011 | Levy et al. |
| 2011/0230372 A1 | 9/2011 | Willman et al. |
| 2011/0236903 A1* | 9/2011 | McClelland ......... C12Q 1/6886 435/6.14 |
| 2011/0287946 A1 | 11/2011 | Gudmundsson et al. |
| 2011/0294123 A1 | 12/2011 | Nakamura et al. |
| 2011/0312520 A1 | 12/2011 | Kennedy et al. |
| 2012/0015839 A1 | 1/2012 | Chinnaiyan |
| 2012/0015843 A1 | 1/2012 | Von et al. |
| 2012/0115743 A1 | 5/2012 | Davicioni et al. |
| 2012/0122698 A1 | 5/2012 | Stacey et al. |
| 2012/0122718 A1 | 5/2012 | Reisman |
| 2012/0157334 A1 | 6/2012 | Beaudenon-Huibregtse et al. |
| 2012/0172243 A1 | 7/2012 | Davicioni et al. |
| 2012/0214165 A1 | 8/2012 | Walfish et al. |
| 2012/0220474 A1 | 8/2012 | Kennedy et al. |
| 2012/0304318 A1 | 11/2012 | Ohnuma et al. |
| 2013/0004974 A1 | 1/2013 | Klee et al. |
| 2013/0023434 A1 | 1/2013 | Van Laar |
| 2013/0142728 A1 | 6/2013 | Beaudenon-Huibregtse et al. |
| 2013/0150257 A1 | 6/2013 | Abdueva et al. |
| 2013/0172203 A1 | 7/2013 | Yeatman et al. |
| 2013/0184999 A1 | 7/2013 | Ding |
| 2013/0225662 A1 | 8/2013 | Kennedy et al. |
| 2013/0231258 A1 | 9/2013 | Wilde et al. |
| 2013/0273543 A1 | 10/2013 | Gudmundsson et al. |
| 2013/0302808 A1 | 11/2013 | Vasmatzis |
| 2013/0302810 A1 | 11/2013 | Latham et al. |
| 2013/0303826 A1 | 11/2013 | Jurisica et al. |
| 2014/0066323 A1 | 3/2014 | Buerki et al. |
| 2014/0080731 A1 | 3/2014 | Davicioni et al. |
| 2014/0087961 A1 | 3/2014 | Sulem et al. |
| 2014/0099261 A1 | 4/2014 | Keutgen et al. |
| 2014/0121126 A1 | 5/2014 | Bivona et al. |
| 2014/0143188 A1 | 5/2014 | Mackey et al. |
| 2014/0228237 A1 | 8/2014 | Kennedy et al. |
| 2014/0243240 A1 | 8/2014 | Soldin et al. |
| 2014/0302042 A1 | 10/2014 | Chin et al. |
| 2014/0315199 A1 | 10/2014 | Rhodes et al. |
| 2014/0315739 A1 | 10/2014 | Aharonov et al. |
| 2014/0349856 A1 | 11/2014 | Schnabel et al. |
| 2014/0349864 A1 | 11/2014 | Kennedy et al. |
| 2014/0371096 A1 | 12/2014 | Umbright et al. |
| 2015/0011401 A1 | 1/2015 | Davicioni et al. |
| 2015/0038376 A1 | 2/2015 | Tian et al. |
| 2015/0099665 A1 | 4/2015 | Rosenfeld et al. |
| 2015/0141470 A1 | 5/2015 | Garraway et al. |
| 2015/0275306 A1 | 10/2015 | Bernards et al. |
| 2015/0299808 A1 | 10/2015 | Gonzalez et al. |
| 2015/0307947 A1 | 10/2015 | Basu et al. |
| 2015/0368724 A1 | 12/2015 | Aharonov et al. |
| 2016/0024586 A1 | 1/2016 | Delfour et al. |
| 2016/0032400 A1 | 2/2016 | Gomis et al. |
| 2016/0068915 A1 | 3/2016 | Kennedy et al. |
| 2016/0076108 A1 | 3/2016 | Davicioni et al. |
| 2016/0115546 A1 | 4/2016 | Rosenfeld et al. |
| 2016/0120832 A1 | 5/2016 | Rabinowitz et al. |
| 2016/0251729 A1 | 9/2016 | Chinnaiyan |
| 2016/0312305 A1 | 10/2016 | Kennedy et al. |
| 2016/0312306 A1 | 10/2016 | Kennedy et al. |
| 2016/0312307 A1 | 10/2016 | Kennedy et al. |
| 2016/0312308 A1 | 10/2016 | Kennedy et al. |
| 2016/0348184 A1 | 12/2016 | Chinnaiyan |
| 2017/0145513 A1 | 5/2017 | Kennedy et al. |
| 2017/0166980 A1 | 6/2017 | Fahey, III et al. |
| 2017/0329894 A1 | 11/2017 | Kennedy et al. |
| 2018/0016642 A1 | 1/2018 | Kennedy et al. |
| 2018/0030540 A1 | 2/2018 | Davicioni et al. |
| 2018/0068058 A1 | 3/2018 | Abdueva et al. |
| 2018/0122508 A1 | 5/2018 | Wilde et al. |
| 2018/0127832 A1 | 5/2018 | Kennedy et al. |

FOREIGN PATENT DOCUMENTS

| | | |
|---|---|---|
| WO | WO 1992/010092 A1 | 6/1992 |
| WO | WO 1993/009668 A1 | 5/1993 |
| WO | WO 1993/022684 A1 | 11/1993 |
| WO | WO 1998/045420 A2 | 10/1998 |
| WO | WO 2001/060860 A2 | 8/2001 |
| WO | WO 2001/066753 A1 | 9/2001 |
| WO | WO 2002/000929 A1 | 1/2002 |
| WO | WO 2002/083921 A2 | 10/2002 |
| WO | WO 2003/012067 A2 | 2/2003 |
| WO | WO 2004/037972 A2 | 5/2004 |
| WO | WO 2005/040396 A2 | 5/2005 |
| WO | WO 2005/085471 A2 | 9/2005 |
| WO | WO 2005/100608 A2 | 10/2005 |
| WO | WO 2006/047484 A2 | 5/2006 |
| WO | WO 2006/091776 A2 | 8/2006 |
| WO | WO 2006/110264 A2 | 10/2006 |
| WO | WO 2006/127537 A2 | 11/2006 |
| WO | WO 2006/135596 A2 | 12/2006 |
| WO | WO 2007/056049 A2 | 5/2007 |
| WO | WO 2007/070621 A2 | 6/2007 |
| WO | WO 2007/081720 A2 | 7/2007 |
| WO | WO 2008/023087 A2 | 2/2008 |
| WO | WO 2008/046911 A2 | 4/2008 |
| WO | WO 2008/086478 A2 | 7/2008 |
| WO | WO 2008/112283 A2 | 9/2008 |
| WO | WO 2009/009432 A2 | 1/2009 |
| WO | WO 2009/020521 A2 | 2/2009 |
| WO | WO 2009/020905 A2 | 2/2009 |
| WO | WO 2009/045115 A1 | 4/2009 |
| WO | WO 2009/143603 A1 | 12/2009 |
| WO | WO 2010/056374 A2 | 5/2010 |
| WO | WO 2010/056374 A3 | 9/2010 |
| WO | WO 2010/099598 A1 | 9/2010 |
| WO | WO 2010/124372 A1 | 11/2010 |
| WO | WO 2011/150453 A1 | 12/2011 |
| WO | WO 2012/031008 A2 | 3/2012 |
| WO | WO 2012/068383 A2 | 5/2012 |
| WO | WO 2012/135008 A1 | 10/2012 |
| WO | WO 2013/088457 A1 | 6/2013 |
| WO | WO 2013/090620 A1 | 6/2013 |
| WO | WO 2014/028884 A2 | 2/2014 |
| WO | WO 2014/043803 A1 | 3/2014 |
| WO | WO 2015/071876 A2 | 5/2015 |
| WO | WO 2017/059549 A1 | 4/2017 |
| WO | WO 2018/165600 A1 | 9/2018 |

OTHER PUBLICATIONS

Perez et al.; Long, abundantly expressed non-coding transcripts are altered in cancer; Human Molecular Genetics, 2008, vol. 17, No. 5; 642-655; published online Nov. 15, 2007 (Year: 2007).*

Bauer et al., "Identification of Markers of Taxane Sensitivity Using Proteomic and Genomic Analyses of Breast Tumor from Patients Receiving Neoadjuvant Paclitaxel and Radiation," *Clin. Cancer Res.* (2010), 16(2):681-690, American Association for Cancer Research.

Dawood, Shaheenah, "Novel Biomarkers of Metastatic Cancer," *Expert Rev. Mol. Diagn.* (2010), 10(5):581-590, Expert Reviews Ltd.

Rotblat et al., "A Possible Role for Long Non-Coding RNA in Modulating Signaling Pathways," *Med. Hypotheses* (2011), 77:962-965, Elsevier.

Edwards, Julianna K. et al.: "*MicroRNAs and Ultraconserved Genes as Diagnostic Markers and Therapeutic Targets in Cancer and Cardiovascular Diseases*", Journal of Cardiovascular Translational Research, vol. 3, No. 3, May 5, 2010, pp. 271-279.

Gibb, Ewan A. et al.: "*The functional role of long non-coding RNA in human carcinomas*", Molecular Cancer, Biomed Central, London, GB, vol. 10, No. 1, Apr. 13, 2011, p. 38.

Martens-Uzunova, E. S. et al.: "*Diagnostic and prognostic signatures from the small non-coding RNA transcriptome in prostate cancer*", Oncogene, vol. 31, No. 8, Jul. 18, 2011, pp. 978-991.

Supplementary European Search Report dated Aug. 31, 2015 regarding EP 12 85 7492.

Abdueva et al., "Quantitative Expression Profiting in Formalin-Fixed Paraffin-Embedded Samples by Affymetrix Microarrays,"

(56) References Cited

OTHER PUBLICATIONS

Journal of Molecular Diagnostics (Jul. 2010) vol. 12, No. 4, pp. 409-417.
Agell et al., "A 12-Gene Expression Signature Is Associated with Aggressive Histological in Prostate Cancer: SEC14L1 and TCEB1 Genes Are Potential Markers of Progression," Am J Pathol (2012) vol. 181 (5), pp. 1585-1594.
Aldred et al., "Papillary and follicular thyroid carcinomas show distinctly different microarray expression profiles and can be distinguished by a minimum of five genes," J Clin Oncol. (2004) 22(17):3531-9.
Amundson et al., "Integrating global gene expression and radiation survival parameters across the 60 cell lines of the National Cancer Institute Anticancer Drug Screen," Cancer Research (2008) 68(2):415-424.
Ausubel, et al. Current Protocols in Molecular Biology. Wiley & Sons, New York (1995) Table of Contents.
Baetke et al., "Molecular Pathways Involved in Prostate Carcinogenesis: Insights from Public Microarray Datasets," PLoS ONE (2012) 7(11):e49831, 1-11.
Ballman et al., "Faster cyclic loess: normalizing RNA arrays via linear models," Bioinformatics, 2004, 20 :2778-2786.
Bannert et al., "Retroelements and the human genome: new perspectives on an old relation." PNAS (Oct. 5, 2004) vol. 101, Suppl. 2, pp. 14572-14579.
Barlow et al., "Analysis of Case-Cohort Designs," J Clin Epidemiol (1999) vol. 52 (12), 1165-1172.
Bergstralh et al., "Software for optimal matching in observation al studies," Epidemiology (1996) 7(3):331-332.
Best et al., "Molecular differentiation of high- and moderate-grade human prostate cancer by cDNA microarray analysis", Diagn Mol Pathol. (2003) 12(2):63-70.
Bibikova et al., "Quantitative gene expression profiling in formalin-fixed, paraffin-embedded tissues using universal bead arrays," Am J Pathol. (2004) 165:1799-1807.
Bibikova et al., "Gene expression profiles in formalin-fixed, paraffin-embedded tissues obtained with a novel assay for microarray analysis," Clin Chem., 2004, 50:2384-2386.
Bibikova et al., "Expression signatures that correlated with Gleason score and relapse in prostate cancer," Genomics (2007) 89(6):666-672.
Birney et al., "Identification and analysis of functional elements in 1% of the human genome by the ENCODE pilot project." Nature Jun. 14, 2007; 447(7146):799-816.
Boorjian et al., "Long-term risk of clinical progression after biochemical recurrence following radical prostatectomy: the mpact of time from surgery to recurrence." Eur Urol. (Jun. 2011) 59(6):893-9.
Boormans et al., "Identification of TDRD1 as a direct target gene of ERG in primary prostate cancer," Int J Cancer (2013) vol. 133 (2), pp. 335-345.
Bostwick et al., "Prognostic factors in prostate cancer: College of American Pathologists consensus statement," Arch Pathol Lab Med (2000) 124(7):995-1000.
Bott et al., "Prostate cancer management: (2) an update on locally advanced and metastatic disease", Postgrad Med J, Dec. 3, 2003, 79(937), 643-645.
Breiman, "Random Forests," Machine Learning (2001) 45:5-32.
Brouha et al., "Hot L1s account for the bulk of retrotransposition in the human population." PNAS USA (Apr. 29, 2003) 100(9):5280-5.
Bull et al., "Identification of potential diagnostic markers of prostate cancer and prostatic intraepithelial neoplasia using cDNA microarrav," British J Cancer (Jun. 1, 2001) 84(11):1512-1519.
Bussmakers et al., "DD3: a new prostate-specific gene, highly overexpressed in prostate cancer." Cancer Res. (Dec. 1, 1999) 59(23):5975-9.
Cerutti et al. "Diagnosis of suspicious thyroid nodules using four protein biomarkers," Clin Cancer Res. (2006) 12(11 Pt 1):3311-8.

Chalitchagorn et al., "Distinctive pattern of LINE-1 methylation level in normal tissues and the association with carcinogenesis." Oncogene (Nov. 18, 2004) 23(54):8841-6.
Che et al.: "Prognostic Value of Abnormal p53 Expression in Locally Advanced Prostate Cancer Treated With Androgen Deprivation and Radiotherapy: A Study Based on RTOG 9202"; International Journal of Radiation: Oncology Biology Physics (Nov. 15, 2007) vol. 69, No. 4, pp. 1117-1123.
Chen et al., "Hepsin and maspin are inversely expressed in laser capture microdissectioned prostate cancer," J Urol. (Apr. 2003) 169(4):1316-1319.
Chen et al.: "Molecular determinants of resistance to antiandrogen therapy"; Nature Medicine, Nature Publishing Group, New York, NY (Jan. 1, 2004) vol. 10, No. 1, pp. 33-39.
Chen et al., "Significance of noninvasive diagnosis of prostate cancer with cytologic examination of prostatic fluid," J Nippon Med Sch. (Jun. 2006) 73(3):129-135.
Chen et al., "Deregulation of a Hox Protein Regulatory Network Spanning Prostate Cancer Initiation and Progression," Clin Cancer Res (Jun. 2012) 18(16):4291-4302.
Cheng et al. "Cell Proliferation in Prostate Cancer Patients with Lymph Node Metastasis", Clin Cancer Res (Oct. 1999) 5(10): 2820-2823.
Cheville et at., "Gene Panel Model Predictive of Outcome in Men at High-Risk of Systemic Progression and Death From Prostate Cancer After Radical Retropubic Prostatectomy," Journal of Clinical Oncology (Aug. 20, 2008) vol. 26 , No. 24.
Chifman et al., "Conservation of immune gene signatures in solid tumors and prognostic implications," BMC Cancer (2016) 16:911, pp. 1-17. DOI 10.1186/S12885-016-2948-Z.
Chow et al., "LINE-1 activity in facultative heterochromatin formation during X chromosome inactivation," Cell (Jun. 11, 2010) 141(6):956-69.
Cibas, et al. "The Bethesda System for Reporting Thyroid Cytopathology," Am J Clin Pathol. (Nov. 2009) 132(5):658-65. doi: 10.1309/AJCPPHLWMI3JV4LA.
Clancy et al., "Profiling networks of distinct immune-cells in tumors," BMC Bioinformatics (2016) 17:263, pp. 1-15. DOI 10.1186/s12859-016-1141-3.
Clark-Langone et al. "Riornarker discovery for colon cancer using a 761 gene RT-PCR assay 2007," BMC Genomics (2007) 8:279 pp. 1-18.
Cooperberg et al., "The CAPRA-S score: A straightforward tool for improved prediction of outcomes after radical prostatectomy," Cancer (2011) vol. 117 (22), pp. 5039-5046.
Cordaux et al., "The impact of retrotransposons on human genome evolution." Nat Rev Genet. (Oct. 2009) 10(10):691-703.
Cuzik et al., "Prognostic value of an RNA expression signature derived from cell cycle proliferation genes in patients with prostate cancer: a restrospective study," thelancet.com/oncology (Mar. 2011) vol. 12, pp. 245-255.
Dalela et al., "Contemporary Role of the Decipher Test in Prostate Cancer Management: Current Practice and Future Perspectives," Rev. Urol. (2016), 18(1):1-9, MedReviews®, LLC.
Dalsgaard Sorensen et al.: "Discovery of prostate cancer biomarkers by microarray gene expression profiling"; Expert Review of Molecular Diagnostics, vol. 10, No. 1, Jan. 1, 2010, pp. 49-64.
D'Amico et al., "Cancer-specific mortality after surgery or radiation for patients with clinically localized prostate cancer managed during the prostate-specific antigen era," J Clin Oncol. (2003) 21:2163-2172.
Day et al., "Estimating enrichment of repetitive elements from high-throughput sequence data." Genome Biol. (2010) 11 (6):R69.
Dechassa et al., "Architecture of the SWI/SNF-nucleosome complex," Mol Cell Biol. (Oct. 2008) vol. 28, No. 19, pp. 6010-6021.
Demichelis et al., "TMPRSS2:ERG gene fusion associated with lethal prostate cancer in a watchful waiting cohort," Oncogene (2007) 26:4596-4599.
Dhanasekaran et al., "Delineation of prognostic biomarkers in prostate cancer," Nature (2001) 412: 822-826.
Dougherty, "The fundamental role of pattern recognition for gene-expression/microarray data in bioinformatics," Pattern recognition (2005) 38:2226-2228.

(56) References Cited

OTHER PUBLICATIONS

Eder et al., "Genes differentially expressed in prostate cancer," BJU Int. (May 2004) 93(8): 1151-1155.
Englisch, et al., "Chemically Modified Oligonucleotides as Probes and Inhibitors," Angew. Chem. Int. Ed. Eng. (1991) 30:613-629.
Erho et al., "Discovery and Validation of a Prostate Cancer Genomic Classifier that Predicts Early Metastasis Following Radical Prostatectomy," PLoS ONE (2013) 8(6):e66855, 1-12.
Ernst et al., "Decrease and gain of gene expression are equally discriminatory markers for prostate carcinoma: a gene expression analysis on total and microdissected prostate tissue," Am J Pathol. (Jun. 2002) 160(6):2169-2180.
Etzioni et al. "The case for early detection", Nature Reviews | Cancer (Apr. 2003) vol. 3, pp. 1-10.
Fan et al., "Concordance among gene-expression-based predictors for breast cancer," N Engl J Med. (2006) 355:560-569.
Finley et al., "Discrimination of benign and malignant thyroid nodules by molecular profiling," Ann Surg. (2004) 240(3):425-36; discussion 436-7.
Finley et al., "Advancing the molecular diagnosis of thyroid nodules: defining benign lesions by molecular profiling," Thyroid (2005) 15(6):562-8.
Fodor et al., "Light-directed, spatially addressable parallel chemical synthesis," Science (Feb. 15, 1991) 251(4995):767-773.
Foley et al., "Molecular pathology of prostate cancer: the key to identifying new biomarkers of disease," Endocrine-Related Cancer (2004) 11:477-488.
Fontaine, et al., "Increasing the number of thyroid lesions classes in microarray analysis improves the relevance of diagnostic markers," PLoS One (Oct. 29, 2009) 4(10):e7632. doi: 10.1371/journal.pone. 0007632.
Fryknas et al., "Molecular markers for discrimination of benign and malignant follicular thyroid tumors," Tumour Biol. (2006) 27(4):211-20.
Fujarewicz et al., "A multi-gene approach to differentiate papillary thyroid carcinoma from benign lesions: gene selection using support vector machines with bootstrapping," Endocr Relat Cancer (Sep. 2007) 14(3):809-26.
Gait. Chapter 16: Oligoribonucleotides. Antisense Research and Applications, Crookeand Lebleu Eds., CRC Press (1993) pp. 289-302.
Galamb et al., "Diagnostic mRNA Expression Patterns of Inflamed, Benign, and Malignant Colorectal Biopsy Specimen and their Correlation with Peripheral Blood Results," Cancer Epidemiology, Biomarkers & Prevention (Oct. 2008) 17(10):2835-2845.
Gao et al., "VISTA is an inhibitory immune checkpoint that is increased after ipilimumab therapy in patients with prostate cancer," Nat Med. (May 2017) 23(5):551-555.
Genevieve de Saint Basile et al., "Severe Combined Immunodeficiency Caused by Deficiency in Either the Ii or the E Subunit of CD3," Journal of Clinical Investigation (2004) vol. 114, No. 10. p. 1512-1517.
Giordano et al., "Organ-Specific Molecular Classification of Primary Lung, Colon, and Ovarian Adenocarcinomas Using Gene Expression Profiles," Am J Pathol (2001) 159(4):1231-1238.
Glinsky et al., "Gene expression profiling predicts clinical outcome of prostate cancer," J Clin Investigation (2004) 113(6):913-923.
Glinsky et al., "Microarray analysis identifies a death-from-cancer signature predicting therapy i failure in patients with multiple types of cancer," J Clin Invest. (2005) 115: 1503-1521.
Greenbaum et al.: "Comparing protein abundance and mRNA expression levels on a genomic scale"; Genome Biology (2003) 4(9):117.1-117.8.
Griffith et al., "Meta-analysis and meta-review of thyroid cancer gene expression profiling studies identifies important diagnostic biomarkers," J Clin Oncol. (2006) 24(31):5043-51.
Griffith, et al. Biomarker panel diagnosis of thyroid cancer: a critical review. Expert Rev Anticancer Ther. (Sep. 2008) 8(9):1399-413. doi: 10.1586/14737140.8.9.1399.

Gupta et al., "Long non-coding RNA HOTAIR reprograms chromatin state to promote cancer metastasis," Nature (Apr. 15, 2010) 464(7291): 1071-6.
Guttman et al., "Chromatin signature reveals over a thousand highly conserved large non-coding RNAs in mammals", Nature (Mar. 12, 2009) 458(7235):223-7.
Guttman et al., "Ab initio reconstruction of transcriptomes of pluripotent and lineage committed cells reveals gene structures of thousands of lincRNAs," Nat Biotechnol. (May 2010) 28(5):503-10.
Hai Man et al.: "Multiple regions within 8q24 independently affect risk for prostate cancer"; Nat Genet. (2007) 39:638-644.
Hamada et al., "Diagnostic usefulness of PCR profiling of the differentially expressed marker genes in thyroid papillary carcinomas," Cancer Lett. (Jun. 28, 2005) 224(2):289-301. Epub Nov. 18, 2004.
He et al., "The antisense transcriptomes of human cells", Science (Dec. 19, 2008) 322(5909): 1855-7.
Heemers, H. V. et al.: "Identification of a Clinically Relevant Androgen-Dependent Gene Signature in Prostate Cancer"; Cancer Research, vol. 71, No. 5 (2011) pp. 1978-1988.
Heidenreich et al., "EAU Guidelines on Prostate Cancer. Part 1: Screening, Diagnosis, and Treatment of Clinically Localised Disease," European Urology (2011) vol. 59, pp. 61-71.
Henshall et al., "Survival Analysis of Genome-Wide Gene Expression Profiles of Prostate ancers Identifies New Prognostic Targets of Disease Relapse," Cancer Research (Jul. 15, 2003) 63, 14196-4203.
Holzbeierlein et al., "Gene expression analysis of human prostate carcinoma during hormonal therapy identifies androgen-responsive genes and mechanisms of therapy resistance," Am. J . Pathol. (Jan. 2004) 164(1):217-227.
Hornberger et al., "A Multigene Prognostic Assay for Selection of Adjuvant Chemotherapy in Patients with T3, Stage II Colon Cancer: Impact on Quality-Adjusted Life Expectancy and Costs," Value in Health 15 (2012) pp. 1014-1021.
Huarte et al., "Large non-coding RNAs: missing links in cancer?" Human Molecular Genetics (Oct. 15, 2010) 19(2): R152-R161.
Hughes et al., "Molecular pathology of prostate cancer," J Clin Pathol. (Jul. 2005) 58(7):673-684.
Hughes et al., "Topoisomerase II—a expression increases with increasing Gleason score and with hormone insensitivity in prostate carcinoma," J Clin Pathol. (Jul. 2006) 59(7): 721-724.
Jenkins et al., "Prognostic significance of ailetic imbalance of chromosome arms 71, 8p, 16q, and 18q in stage T3NOMO prostate cancer," Genes, Chromosomes & Cancer (1998) 21:131-143.
Jhavar et al., "Integration of ERG gene mapping and geneDexpression profiling identifies distinct categories of human prostate cancer," BJUI (2008) vol. 103 (9), pp. 1256-1269.
Kanehisa, "Use of statistical criteria for screening potential homologies in nucleic acid sequences," Nucleic Acids Res. (Jan. 11, 1984) 12(1 Pt 1):203-13.
Karayi et al., "Molecular biology of prostate cancer," Prostate Cancer Prostatic Dis. (2004) 7(1):6-20.
Karnes et al., "The ability of biomarkers to predict systemic progression in men with high-risk prostate cancer treated surgically is dependent on ERG status," Cancer Res. (Nov. 9, 2010) 70(22):8994-9002, Epub.
Kasraeian, et al. , "A comparison of fine-needle aspiration, core biopsy, and surgical biopsy in the diagnosis of extremity soft tissue masses," Clin Orthop Relat Res. (Nov. 2010) 468(11):2992-3002.
Kawamorita et al., "Radical prostatectomy for high-risk prostate cancer: Biochemical outcome," International Journal of Urology (2009) 16:733-738.
Kebebew et al., "Diagnostic and extent of disease multigene assay for malignant thyroid neoplasms," Cancer (2006) 106(12):2592-7.
Khor et al.: "Bcl-2 and Bax Expression Predict Prostate Cancer Outcome in Men Treated with Androgen Deprivation and Radiotherapy on Radiation Therapy Oncology Group Protocol 92-02"; Clinical Cancer Research (Jun. 15, 2007) vol. 13, No. 12, pp. 3585-3590.

(56) References Cited

OTHER PUBLICATIONS

Kiessling, et al., "D-TMPP: A novel androgen-regulated gene preferentially expressed in prostate and prostate cancer that is the first characterized member of an eukaryotic gene family," The Prostate (2005) 64:387-400.
Kishi et al., "Expression of the survivin gene in prostate cancer: correlation with clinicopathological characteristics, proliferative activity and apoptosis," J Urol. (May 2004) 171(5): 1855-1860.
Klee et al., "Candidate Serum Biomarkers for Prostate Adenocarcinoma identified by mRNA Differences in Prostate Tissue and Verified with Protein Measurements in Tissue and Blood," Clinical Chemistry (2012) 58(3):599-609.
Kosari et al., "Identification of biomarkers for prostate cancer," Clin. Cancer Res. (2008) 1734-1743.
Koshkin et al., "LNA (locked nucleic acids): An RNA mimic forming exceedingly stable LNA," LNA duplexes. J Am Chem Soc (1998) 120:13252-13253.
Koshkin et al., "LNA (locked nucleic acids): synthesis of the adenine, cytosine, guanine 5-methylcytosine, thymine and uracil bicyclonucleoside monomers, oligomerisation, and unprecedented nucleic acid recognition," Tetrahedron (1998) 54(14):3607-3630.
Kroschwitz The Concise Encyclopedia of Polymer Science and Engineering (1990) (pp. 858-859).
Kube et al., "Optimization of laser capture microdissection and RNA amplification for gene expression profiling of prostate cancer," BMC Mol. Biol. (2007) 8:25.
Kumar, et al., "The first analogues of LNA (locked nucleic acids): phosphorothioate-LNA and 2'-thio-LNA," Bioorg Med Chem Lett. (Aug. 18, 1998) 8(16):2219-22.
Landers et al.: "Use of multiple biomarkers for a molecular diagnosis of prostate cancer"; Int. J. Cancer (May 10, 2005) 114 pp. 950-956.
Lapointe et al., "Gene expression profiling identifies clinically relevant subtypes of prostate cancer," PNAS USA (2004) 101:811-816.
Latulippe et al., "Comprehensive Gene Expression Analysis of Prostate Cancer Reveals Distinct Transcriptional Programs Associated with Metastatic Disease," Cancer Res. (2002) 62:4499-4506.
Lin et al., "Nuclear receptor-induced chromosomal proximity and DNA breaks underlie specific translocations in cancer," Cell (Dec. 11, 2009) 139(6):1069-83.
Liong et al., "Blood-Based Biomarkers of Aggressive Prostate Cancer," PLoS ONE (Sep. 2012) vol. 7, Issue 7, e45802, pp. 1-7.
Lockstone, "Exon array data analysis using Affymetrix power tools and R statistical software," Briefings in bioinformatics (2011) vol. 12.(6), pp. 634-644.
Luo et al., "Human Prostate Cancer and Benign Prostatic Hyperplasia : Molecular Dissection by Gene Expression Profiling," Cancer Res. (2001) 61:4683-4688.
Magee et al., "Expression Profiling Reveals Hepsin Overexpression in Prostate Cancer," Cancer Res. (2001) 61:5692-5696.
Martin, "A New Access to 2'-O-Alkylated Ribonucleosides and Properties of 2'-O-Alkylated Oligoribonucleotides," Helv. Chim. Acta. (1995) 78:486-504. (in German with English abstract).
Mazzanti, et al., "Using gene expression profiling to differentiate benign versus malignant thyroid tumors," Cancer Res. (Apr. 15, 2004) 64(8):2898-903.
McCall et al., "Frozen robust multiarray analysis (fRMA)", Biostatistics (2010) vol. 11 (2), 242-253.
Mercer, DW, "Use of multiple markers to enhance clinical utility", Immunol Ser. (1990) 53: 39-54.
Mineva et al., "Differential expression of alphaB-crystallin and Hsp27-1 in anaplastic thyroid carcinomas because of tumor-specific alphaB-crystallin gene (CRYAB) silencing," Cell Stress Chaperones (Autumn 2005) 10(3):171-84.
Nakagawa et al., "A Tissue Biomarker Panel Predicting Systemic Progression after PSA Recurrence Post-Definitive Prostate Cancer Therapy," PLos ONE (2008) 3(5):e2318, 14 pages.
Newson, Roger, "Confidence intervals for rank statistics: Somers' D and extensions," The Stata Journal (Sep. 2006) 6(3):309-334.
Nielsen et al., "Sequence-selective recognition of DNA by strand displacement with a thymine-substituted polyamide," Science (1991) 254: 1497-1500.
Noordzij et al. "The prognostic value of CD44 isoforms in prostate cancer patients treated by radical prostatectomy", Clin Cancer Res (May 1997) 3(5): 805-815.
Norman, James, "Thyroid Nodule Ultrasound", Endocrine website (Updated Oct. 13, 2010) http://www.endocrineweb.com/noduleus.html.
Ong et al., "Expression Profiling Identifies a Novel "-Methylacyl-CoA Racemase Exon with Fumarate Hydratase Homology," Cancer Research (Jun. 15, 2003) 63:3296-3301.
Parker et al., "High expression levels of surviving protein independently predict a poor outcome for patients who undergo surgery for clear cell renal cell carcinoma," Cancer (2006) 107:37-45.
Pascal et al., "Correlation of mRNA and protein levels: Cell type-specific gene expression of cluster designation antigens in the prostate," BMC Genomics (2008) 9:246 (13 pages).
Patel et al., "Preoperative PSA velocity is an independent prognostic factor for relapse after radical prostatectomy," J Clin Oncol. (2005) 23:6157-6162.
Penney et al., "mRNA Expression Signature of Gleason Grade Predicts Lethal Prostate Cancer," J Clin Oncol (Jun. 10, 2011) vol. 29, No. 17, pp. 2391-2396.
Penney et al., "Appendix (online only) of Penney et al., J Clin Oncol 29:2391 (Jun. 2011; online May 2, 2011)" pp. 1-9.
Pereira et al, "Coagulation factor V and VIIIN ratio as predictors of outcome in paracetamol induced fulminant hepatic failure: relation to other prognostic indicators," Gut (1992) 33:98-102.
Pienta et al. "The current state of preclinical prostate cancer animal models"; Prostate (2008) 69: 629-639.
Pilepich et al., "Phase III radiation therapy oncology group (RTOG) trial 86-10 of androgen deprivation adjuvant to definitive radiotherapy in locally advanced carcinoma of the prostate," Int. J. Radiation Oncology Biol. Phys. (2001) vol. 50, No. 5, pp. 1243-1252.
Pinover et al., "Validation of a treatment policy for patients with prostate specific antigen failure after three-dimensional conformal prostate radiation therapy," Cancer (Feb. 15, 2003) vol. 97, No. 4, pp. 1127-1133.
Pittoni et al., "The Dark Side of Mast Cell-Targeted Therapy in Prostate Cancer," Cancer Res. (2012) 72(4):831-835.
Porkka et al: Molecular mechanisms of prostate cancer; Eur Urol. (2004) 45(6):683-691.
Pound et al., "Natural history of progression after PSA elevation following radical prostatectomy," JAMA (1999) 281:1591-1597.
Prasad et al., "Identification of genes differentially expressed in benign versus malignant thyroid tumors," Clin Cancer Res. (2008) 14(11):3327-37.
Prensner et al., "Transcriptome Sequencing Identifies PCAT-1, a Novel lincRNA Implicated in Prostate Cancer Progression," (2012) 29 (8): 742-749.
Puskas, et al., "Gene profiling identifies genes specific for well-differentiated epithelial thyroid tumors," Cell Mol Biol (Noisy-le-grand) (Sep. 5, 2005) 51(2):177-86.
Reis et al., "Antisense intronic non-coding RNA levels correlate to the degree of tumor differentiation in prostate cancer," Oncogene (2004) 23(39):6684-6692.
Rhodes et al., "Multiplex biomarker approach for determining risk of prostatespecific antigen-defined recurrence of prostate cancer," J Nat Cancer Inst. (May 7, 2003) vol. 95, No. 9, pp. 661-668.
Rhodes et al., "ONCOMINE: A Cancer Microarray Database and Integrated Data-Mining Platform," Neoplasia (2004) 6:1-6.
Rhodes et al., "Large-scale meta-analysis of cancer microarray data identifies common transcriptional profiles of neoplastic transformation and progression," Proc Nat Acad Sci USA (2004) 101:9309-9314.
Rinn et al., "Functional demarcation of active and silent chromatin domains in human HOX loci by noncoding RNAs," Cell (Jun. 29, 2007) 129(7):1311-23.
Robertson et al., "DNA in radical prostatectomy specimens. Prognostic value of tumor ploidy," Acta Oncologica (1991) 30(2):205-207.

(56) References Cited

OTHER PUBLICATIONS

Robinson, et al., "A comparison of Affymetrix gene expression arrays," BMC Bioinformatics (Nov. 15, 2007) 8:449.
Robinson et al., "A dynamic programming approach for the alignment of signal peaks in multiple gas chromatography-mass spectrometry experiments," BMC Bioinformatics (2007) 8.1:419.
Rotunno et al., "A Gene Expression Signature from Peripheral Whole Blood for Stage I Lung Adenocarcinoma," Cancer Prevention Research (Jul. 8, 2011) 4(10) 1599-1607.
Rubin et al., "Molecular genetics of human prostate cancer," Modern Pathol. (2004) 17(3):380-388.
Sanghvi, "Heterocyclic base modifications in nucleic acids and their applications in antisense oligonucleotides in Antisense Research and Applications," Crooke, S. T. And Lebleu, B., ed., CRC Press. (1993) Ch 15 274-285.
Saramaki et al., "Amplification of EIF3S3 gene is associated with advanced stage in prostate cancer," Am J Pathol. (2001) 159:2089-2094.
Sato et al., "Clinical significance of alterations of chromosome 8 in high-grade, advanced, nonmetastatic prostate carcinoma," J Natl Cancer Inst. (1999) 91:1574-1580.
Savinainen et al., "Expression and copy No. analysis of TRPS 1, EIF3S3 and MYC genes in breast and prostate cancer," Br J Cancer (2004) 90: 1041-1046.
Schumacher et al., "A Common 8q24 Variant in Prostate and Breast Cancer from a Large Nested Case-Control Study," Cancer Res. (2007) 67:2951-2956.
Severi et al., "The Common Variant rs1447295 on Chromosome 8q24 and Prostate Cancer Risk: Results from an Australian Population-based Case-Control Study", Cancer Epidemiology, Biomarkers & Prevention (2007) 16:610-611.
Shariat et al., "Survivin expression is associated with features of biologically aggressive prostate carcinoma," Cancer (2004) 100(4): 751-757.
Shariat et al., "An updated catalog of prostate cancer predictive tools," Cancer (2008) 113(11):3062-6.
Shen et al., "The SWI/SNF ATPase Brm is a gatekeeper of proliferative control in prostate cancer," Cancer Res. (Dec. 15, 2008) 68(24):10154-62.
Shibru et al., "Does the 3-gene diagnostic assay accurately distinguish benign from malignant thyroid neoplasms?" Cancer (Sep. 1, 2008) 113(5):930-5. doi: 10.1002/cncr.23703.
Shipley et al., "Radiation therapy for clinically localized prostate cancer: a multi-institutional pooled analysis," JAMA (1999) 281:1598-1604.
Simmons et al., "Natural history of biochemical recurrence after radical prostatectomy: risk assessment for secondary herapy," Eur Urol. (May 2007) 51(5):1175-84.
Singh et al., "LNA (locked nucleic acids): synthesis and high-affinity nucleic acid recognition," Chem Commun (1998) 4:455-456.
Singh et al., "Synthesis of 2'-amino-LNA: A novel conformationally restricted high-affinity oligonucleotide analogues with a handle," J Bio Chem (1998) 63:10035-10039.
Singh et al., "Gene expression correlates of clinical prostate cancer behavior," Cancer Cell (Mar. 2002) vol. 1, pp. 1203-1209.
Srikantan et al., "PCGEM1, a prostate-specific gene, is overexpressed in prostate cancer," PNAS (Oct. 24, 2000) 97(22): 12216-12221.
Stephenson et al., "Integration of gene expression profiling and clinical variables to predict prostate carcinoma recurrence after radical prostatectomy," Cancer (Jul. 15, 2005) 104(2):290-298.
Subramanian et al., "Gene set enrichment analysis: a knowledge-based approach for interpreting genome-wide expression profiles," PNAS USA (2005) 102:15545-15550.
Taft et al., "Non-coding RNAs: regulators of disease," J Pathol. (Jan. 2010) 220(2):126-39.
Taylor et al., "Integrative genomic profiling of human prostate cancer," Cancer Cell (Jul. 13, 2010) vol. 18 (1), pp. 11-22.
Thompson et al., "Adjuvant and Salvage Radiotherapy After Prostatectomy: AUA/ASTRO Guideline," J Urol. (2013) 190(2):441-449.
Thorsen et al., "Alternative Splicing in Colon, Bladder, and Prostate Cancer Identified by Exon Array Analysis," Molecular & Cellular Proteomics (Mar. 18, 2008) vol. 7, No. 7, pp. 1214-1224.
Tockman et al., "Considerations in bringing a cancer biomarker to clinical application," Cancer Research (1992) 52:2711-2718.
Tomlins et al., "Recurrent Fusion of TMPRSS2 and ETS Transcription Factor Genes in Prostate Cancer," Science (2005) 310(5748):644-648.
Tomlins et al., "TMPRSS2:ETV4 Gene Fusions Define a Third Molecular Subtype of Prostate Cancer," Cancer Res. (2006) 66:3396-3400.
Tomlins et al., "Distinct classes of chromosomal rearrangements create oncogenic ETS gene fusions in prostate cancer," Nature (Aug. 2, 2007) 448(7153):595-9.
Tricoli et al., "Detection of prostate cancer and predicting progression: current and future diagnostic markers," Clinical Cancer Research (Jun. 15, 2004) 10:3943-3953.
True et al., "A molecular correlate to the Gleason grading system for prostate adenocarcinoma," PNAS (Jul. 18, 2006) vol. 103, No. 29, pp. 10991-10996.
Tsuchiya et al., "Mapping and gene expression profile of the minimally overrepresented 8q24 region in prostate cancer," Am J Pathol. (May 2002) 160(5):1799-1806.
Vanaja et al., "Transcriptional Silencing of Zinc Finger Protein 185 Identified Profiling Is Associated with Prostate Cancer Progression," Cancer Research (Jul. 15, 2003) 63:3877-3882.
Vanaja et al., "PDLIM4 Represseion by Hypermethylation as a Potential Biomarker for Prostate Cancer," Clin. Cancer Res. (2006) 12(4):1128-1136.
Varambally et al., "Integrative Genomic and Proteomic Analysis of Prostate Cancer Reveals Signatures of Metastatic Progression," Cancer Cell (Nov. 2005) 8(5):393-406.
Varela et al., "Exome sequencing identifies frequent mutation of the SWI/SNF complex gene PBRM1 in renal carcinoma," Nature (Jan. 27, 2011) 469(7331):539-42.
Varricchi et al., "Are Mast Cells MASTers in Cancer?" Front Immunol. ePub (Apr. 12, 2017) 8:424.
Vickers et al., "Extensions to decision curve analysis, a novel method for evaluating diagnostic tests, prediction models and molecular markers," BMC Medical Informatics and Decision Making, (2008) 8(53):1-17.
Wang et al., "Two common chromosome 8q24 variants are associated with increased risk for prostate cancer," Cancer Res. (2007) 67:2944-2950.
Wang et al., "RNA-Seq: a revolutionary tool for transcriptomics," Nature Reviews/Genetics (Jan. 2009) vol. 10, pp. 57-63.
Watson et al., "Future opportunities for the diagnosis and treatment of prostate cancer," Prostate Cancer Prostatic Dis. (2004) 7:S8-S13.
Weber et al., "The prognostic value of expression of HIF1[alpha], EGFR and VEGF-A, in localized prostate cancer for intermediate- and high-risk patients treated with radiation therapy with or without androgen deprivation therapy," Radiation Oncology (Apr. 30, 2012) vol. 7, No. 66, 8 pages.
Welsh et al., "Analysis of Gene Expression Identifies Candidate Markers and Pharmacological Targets in Prostate Cancer," Cancer Res. (Aug. 15, 2001) 61:5974-5978.
Wiegand et al., "ARID1A mutations in endometriosis-associated ovarian carcinomas," N Engl J Med. (Oct. 14, 2010) 363 (16):1532-43.
Yap et al., "Molecular interplay of the noncoding RNA ANRIL and methylated histone H3 lysine 27 by polycomb CBX7 n transcriptional silencing of INK4a," Mol Cell. (Jun. 11, 2010) 38(5):662-74.
Yates et al., "X:Map: annotation and visualization of genome structure for Affymetrix exon array analysis," Nucleic Acids Res. (2008) vol. 36:D780-D786.
Yegnasubramanian et al., "DNA hypomethylation arises later in prostate cancer progression than CpG island hypermethylation and contributes to metastatic tumor heterogeneity," Cancer Res. (Nov. 1, 2008) 68(21): pp. 8954-8967.

(56) References Cited

OTHER PUBLICATIONS

Yu et al., "Gene expression alterations in prostate cancer predicting tumor aggression and preceding development of malignancy," J Clin Oncol. (Jul. 15, 2004) 22(14):2790-2799.
Yu et al., "An integrated network of androgen receptor, polycomb, and TMPRSS2-ERG gene fusions in prostate cancer progression," Cancer Cell. (May 18, 2010) 17(5):443-54.
Yukinawa et al., "A multi-class predictor based on a probabilistic model: application to gene expression profiling-based diagnosis of thyroid tumors," BMC Genomics (Jul. 27, 2006) 7:190.
Zelefsky et al., "High dose radiation delivered by intensity modulated conformal radiotherapy improves the outcome of localized prostate cancer," The Journal of Urology (Sep. 2001) 166(3):876-881.
Zhao et al., "Development and validation of a 24-gene predictor of response to postoperative radiotherapy in prostate cancer: a matched, retrospective analysis," Lancet Oncol (2016) 17, pp. 1612-1620.
GenBank Accession No. AA462934 dated Jun. 10, 1997, 2 pages.
GenBank Accession No. AA920095 dated Apr. 20, 1998, 2 pages.
GenBank Accession No. AB028840 dated Jan. 12, 2000, 2 pages.
GenBank Accession No. AB030836 dated Oct. 23, 1999, 2 pages.
GenBank Accession No. AB036741 dated Dec. 22, 2000, 3 pages.
GenBank Accession No. AF077349 dated Dec. 14, 2000, 2 pages.
GenBank Accession No. AF077351 dated Dec. 20, 2000, 3 pages.
GenBank Accession No. AF115517 dated Nov. 23, 2005, 4 pages.
GenBank Accession No. AI413910 dated Feb. 9, 1999, 2 pages.
GenBank Accession No. AI414999 dated Feb. 9, 1999, 2 pages.
GenBank Accession No. AI425960 dated Mar. 9, 1999, 2 pages.
GenBank Accession No. AI851940 dated Jul. 15, 1999, 2 pages.
GenBank Accession No. AK018022 dated Sep. 19, 2008, 4 pages.
GenBank Accession No. AK019341 dated Sep. 19, 2008, 3 pages.
GenBank Accession No. AK019342 dated Sep. 19, 2008, 3 pages.
GenBank Accession No. AK034387 dated Sep. 19, 2008, 4 pages.
GenBank Accession No. AK038229 dated Sep. 19, 2008, 4 pages.
GenBank Accession No. AK038434 dated Sep. 19, 2008, 4 pages.
GenBank Accession No. AK041534 dated Sep. 19, 2008, 4 pages.
GenBank Accession No. AK042683 dated Sep. 19, 2008, 4 pages.
GenBank Accession No. AK136096 dated Sep. 19, 2008, 4 pages.
GenBank Accession No. AK136101 dated Sep. 19, 2008, 4 pages.
GenBank Accession No. AK142768 dated Sep. 19, 2008, 3 pages.
GenBank Accession No. AL591433 dated Jan. 15, 2009, 56 pages.
GenBank Accession No. BC004702 dated Jul. 15, 2006, 3 pages.
GenBank Accession No. BC055737 dated Jul. 15, 2006, 2 pages.
GenBank Accession No. BC086799 dated Sep. 21, 2006, 3 pages.
GenBank Accession No. BF449664 dated Dec. 1, 2000, 1 page.
GenBank Accession No. BG063957 dated Jan. 26, 2001, 2 pages.
GenBank Accession No. BG077309 dated Dec. 17, 2003, 2 pages.
GenBank Accession No. BM114282 dated Jan. 30, 2002, 2 pages.
GenBank Accession No. BY023910 dated Dec. 6, 2002, 2 pages.
GenBank Accession No. CN724527 dated May 18, 2004, 2 pages.
GenBank Accession No. NM_000130 dated Oct. 18, 2009, 6 pages.
GenBank Accession No. NM_000493 dated Mar. 15, 2009, 4 pages.
GenBank Accession No. NM_000598, GI No. 62243067, dated Jun. 6, 2010, 5 pages.
GenBank Accession No. NM_000688, GI No. 40316942, dated Apr. 11, 2010, 5 pages.
GenBank Accession No. NM_001013398; GI No. 62243247, dated Jun. 6, 2010, 5 pages.
GenBank Accession No. NM_001034 dated Oct. 5, 2009, 5 pages.
GenBank Accession No. NM_001039573, GI No. 221316683, dated Mar. 4, 2010, 5 pages.
GenBank Accession No. NM_001049 dated Jun. 21, 2009, 4 pages.
GenBank Accession No. NM_001067 dated Oct. 18, 2009, 5 pages.
GenBank Accession No. NM_001098533, GI No. 237858579, dated May 7, 2010, 5 pages.
GenBank Accession No. NM_001130851; GI No. 195927024, dated Mar. 5, 2010, 4 pages.
GenBank Accession No. NM_001136154 dated Jan. 8, 2012, 6 pages.
GenBank Accession No. NM_001136155 dated Jan. 8, 2012, 6 pages.
GenBank Accession No. NM_001143998, GI No. 221316675, dated Mar. 4, 2010, 5 pages.
GenBank Accession No. NM_001143999, GI No. 221316679, dated Mar. 5, 2010, 5 pages.
GenBank Accession No. NM_001144001, GI No. 221316686, dated Mar. 4, 2010, 5 pages.
GenBank Accession No. NM_001160367, GI No. 237858581, dated May 7, 2010, 5 pages.
GenBank Accession No. NM_001786 dated Nov. 1, 2009, 4 pages.
GenBank Accession No. NM_001844 dated Sep. 28, 2009, 7 pages.
GenBank Accession No. NM_003003, GI No. 221316681, dated Mar. 4, 2010, 5 pages.
GenBank Accession No. NM_003014; GI No. 170784837, dated Mar. 13, 2010, 5 pages.
GenBank Accession No. NM_003184; GI No. 115527086, dated Mar. 4, 2010, 7 pages.
GenBank Accession No. NM_003873.3 dated Oct. 18, 2009, 4 pages.
GenBank Accession No. NM_004336; GI No. 211938448, dated Mar. 14, 2010, 6 pages.
GenBank Accession No. NM_004449 dated Jan. 8, 2012, 6 pages.
GenBank Accession No. NM_005025.2 dated Jul. 12, 2009, 4 pages.
GenBank Accession No. NM_005192, GI No. 195927023, dated Mar. 4, 2010, 4 pages.
GenBank Accession No. NM_005651.1 dated Oct. 27, 2009, 3 pages.
GenBank Accession No. NM_006265, GI No. 208879448, dated Apr. 11, 2010, 6 pages.
GenBank Accession No. NM_006558 dated 812109, 3 pages.
GenBank Accession No. NM_006727 dated Oct. 18, 2009, 3 pages.
GenBank Accession No. NM_006819; GI No. 110225356, dated 517/2010, 5 pages.
GenBank Accession No. NM_012152; GI No. 183396778, dated Apr. 5, 2010, 5 pages.
GenBank Accession No. NM_014846; GI No. 120952850, dated Mar. 4, 2010, 6 pages.
GenBank Accession No. NM_016623; GI No. 42734437, dated Mar. 29, 2009, 4 pages.
GenBank Accession No. NM_018930 dated Feb. 10, 2008, _ pages.
GenBank Accession No. NM_031966 GI No. 34304372, dated Jun. 6, 2010, 5 pages.
GenBank Accession No. NM_032334; GI No. 223468686, dated Mar. 5, 2010, 3 pages.
GenBank Accession No. NM_052987, GI No. 237858574, dated 517/2010, 5 pages.
GenBank Accession No. NM_052988, GI No. 237858573, dated 517/2010, 5 pages.
GenBank Accession No. NM_080546; GI No. 112363101, dated 517/2010, 6 pages.
GenBank Accession No. NM_080607 dated Sep. 3, 2009, 2 pages.
GenBank Accession No. NM_133445 dated Sep. 20, 2009, 5 pages.
GenBank Accession No. NM_138455; GI No. 34147546, dated May 7, 2010, 3 pages.
GenBank Accession No. NM_182918 dated Jan. 8, 2012, 6 pages.
GenBank Accession No. NM_199166, GI No. 40316938, dated Apr. 11, 2010, 5 pages.
GenBank Accession No. NP_001058 dated Dec. 25, 2011, 9 pages.
GenBank Accession No. W34764 dated May 13, 1996, 2 pages.
Supplemental Table 1 of U.S. Appl. No. 61/057,698, filed May 30, 2008, 13 pages.
Supplemental Table 2 of U.S. Appl. No. 61/057,698, filed May 30, 2008, 15 pages.
Supplemental Table 3 of U.S. Appl. No. 61/057,698, filed May 30, 2008, 21 pages.
Supplemental Table 4 of U.S. Appl. No. 61/057,698, filed May 30, 12008, 1 page.
Supplemental Table 5 of U.S. Appl. No. 61/057,698, filed May 30, 12008, 2 pages.

(56) References Cited

OTHER PUBLICATIONS

Supplemental Table 6 of U.S. Appl. No. 61/057,698, filed May 30, 2008, 1 page.

* cited by examiner

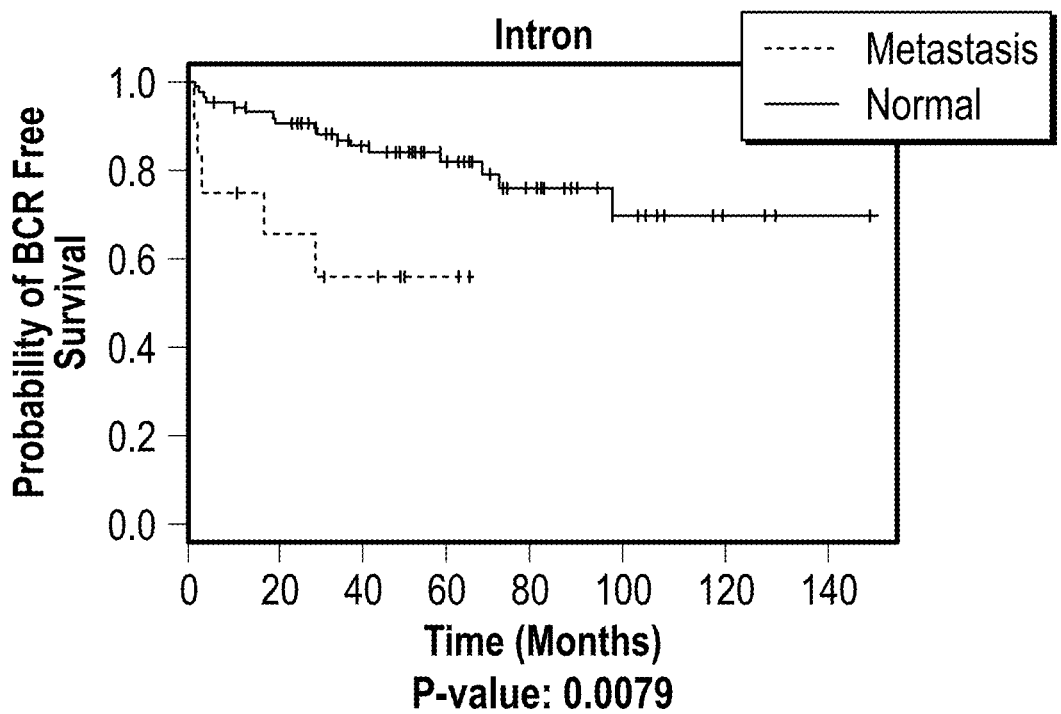
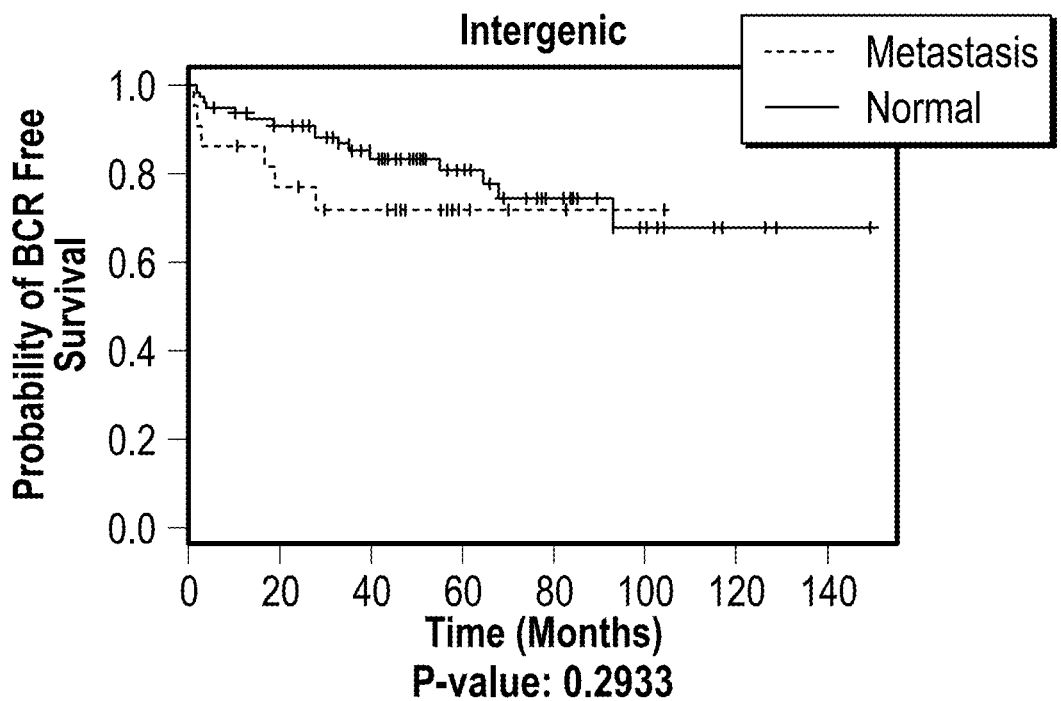
FIG. 9

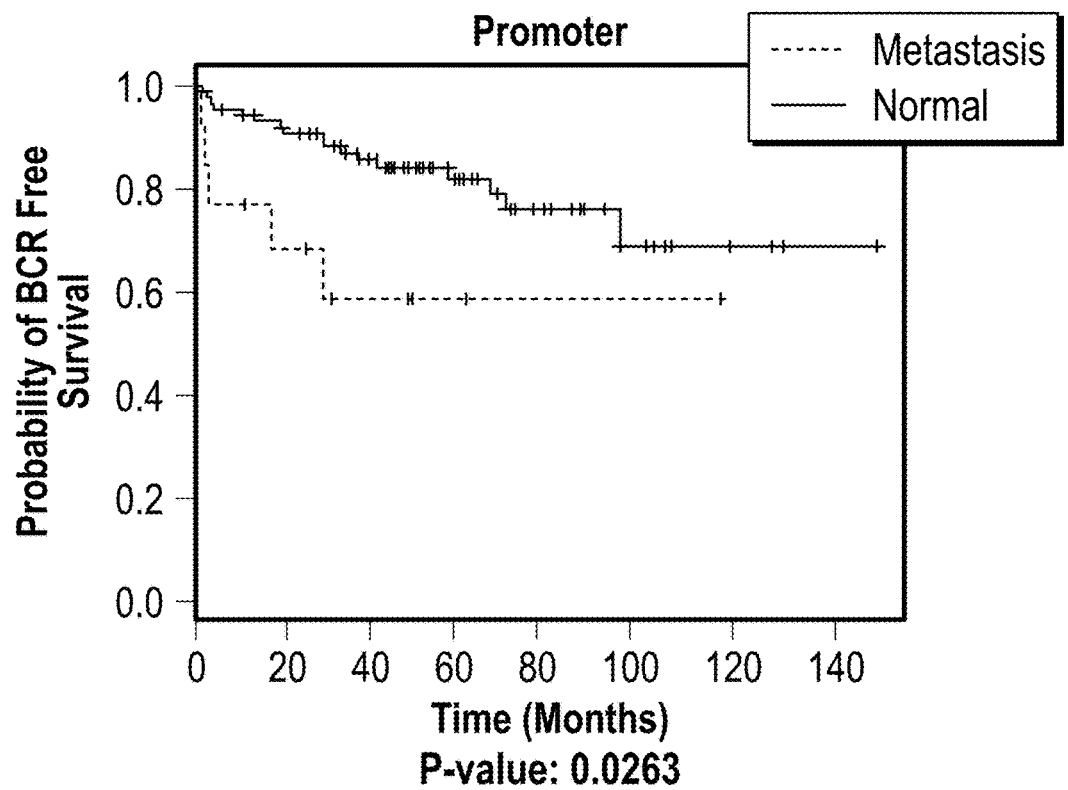
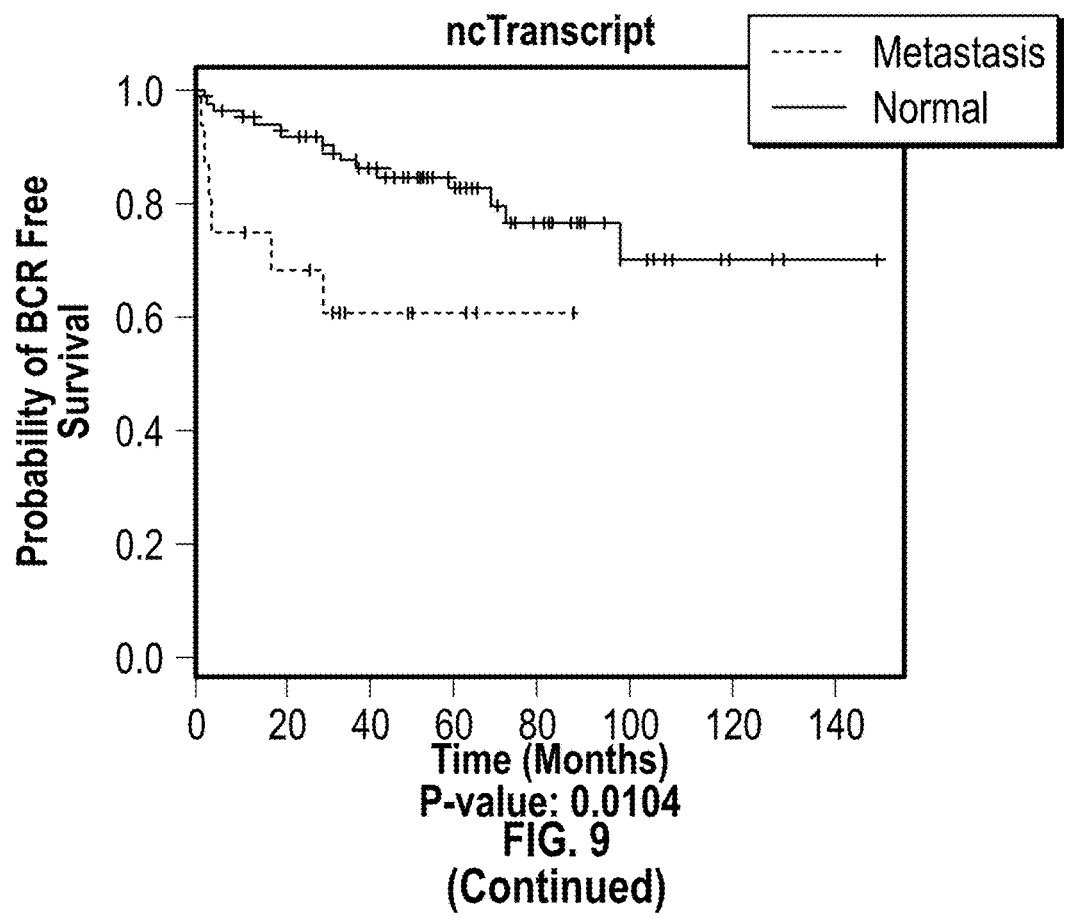
FIG. 9
(Continued)

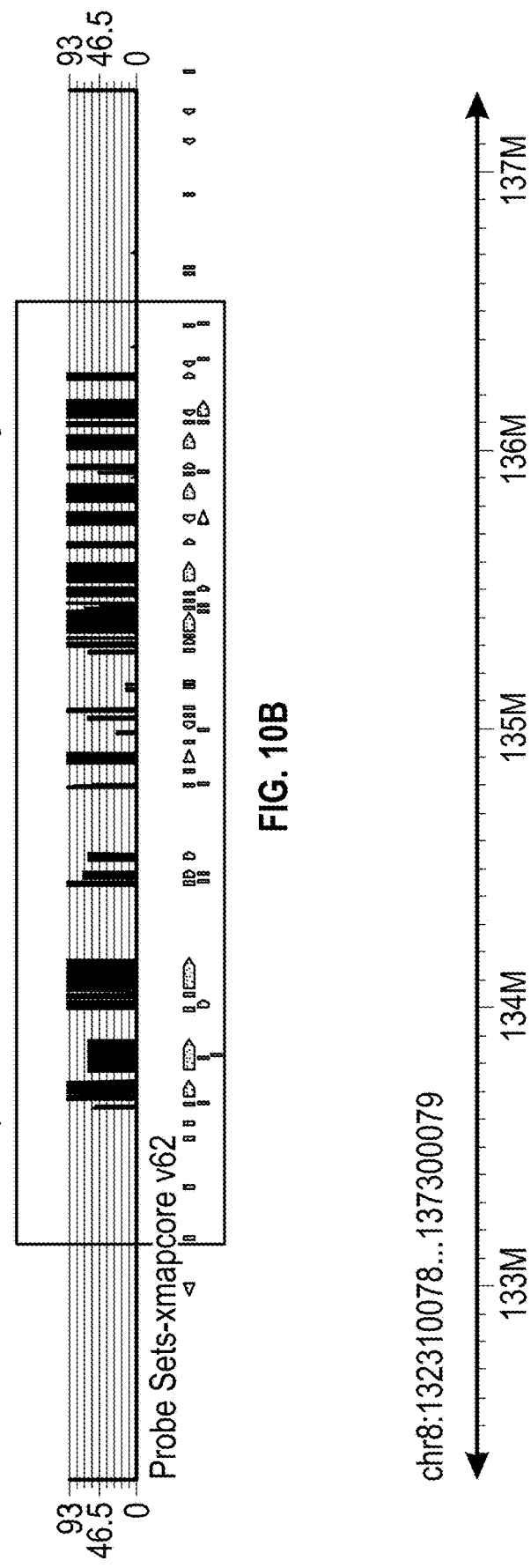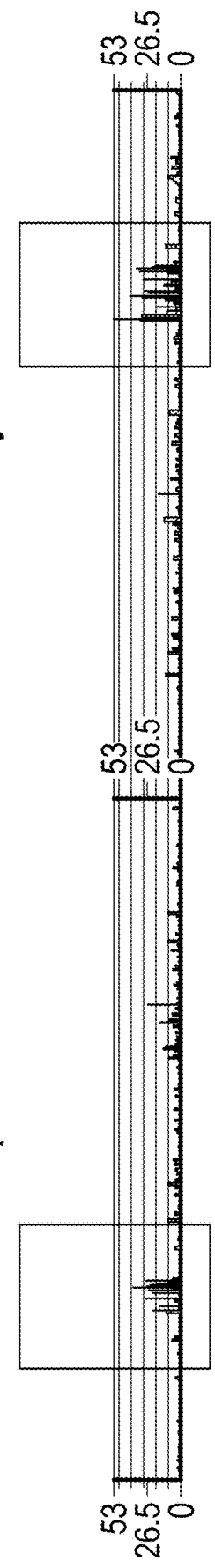
FIG. 10B
FIG. 10C

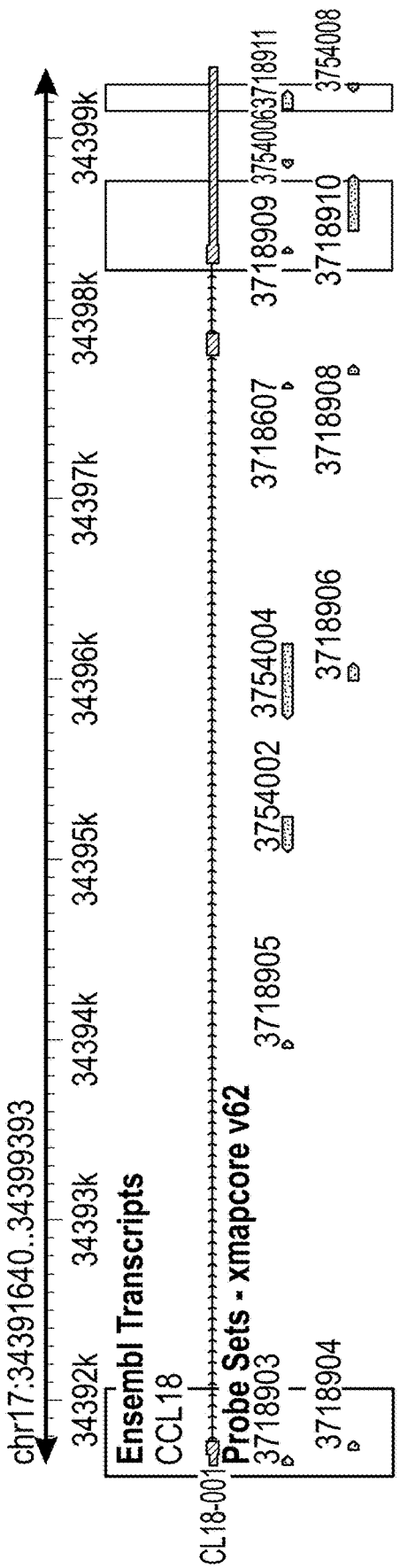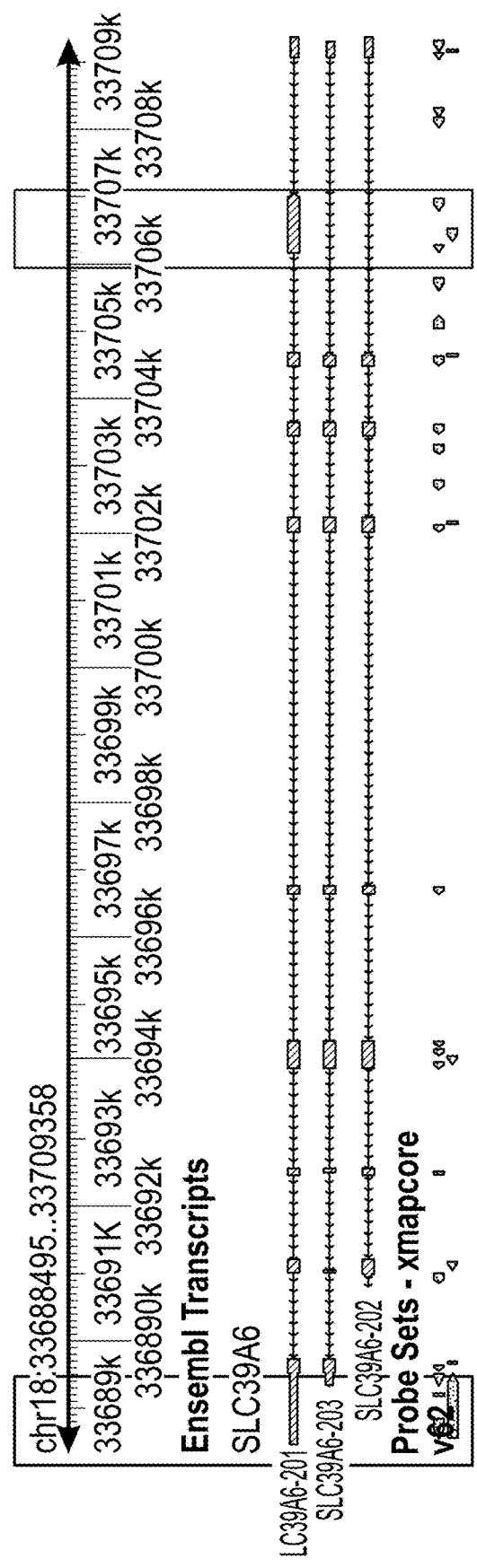
FIG. 15A
FIG. 15B

FIG. 21
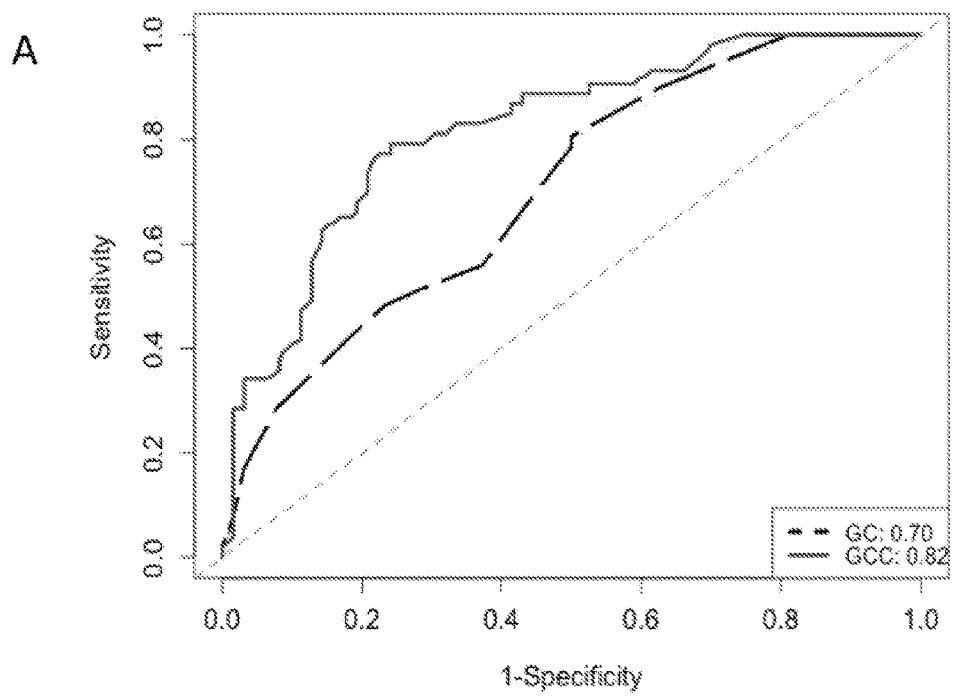
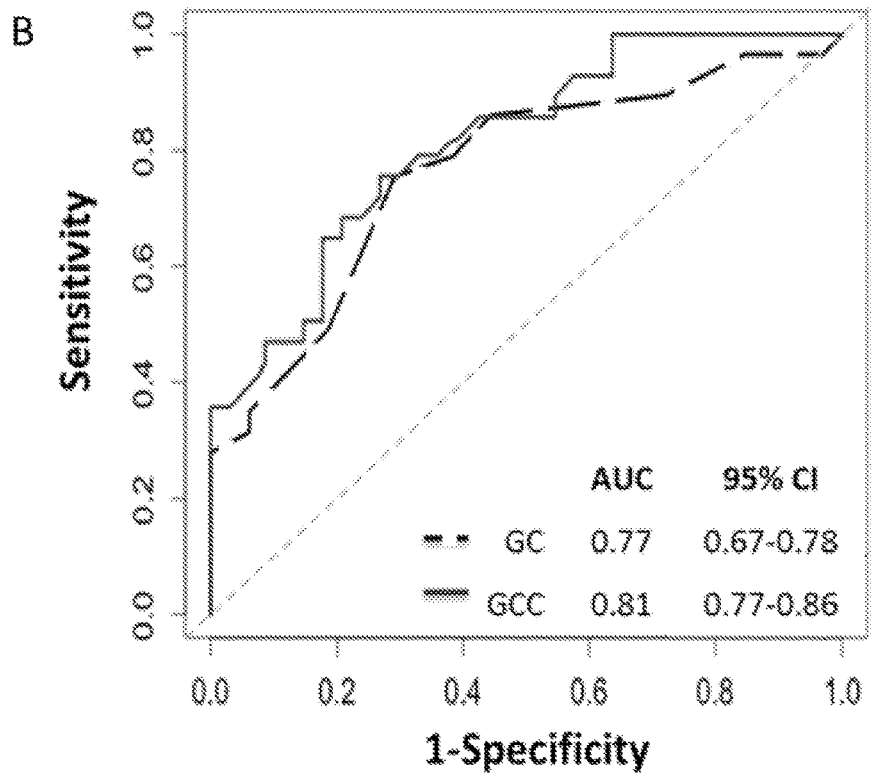

FIG. 24
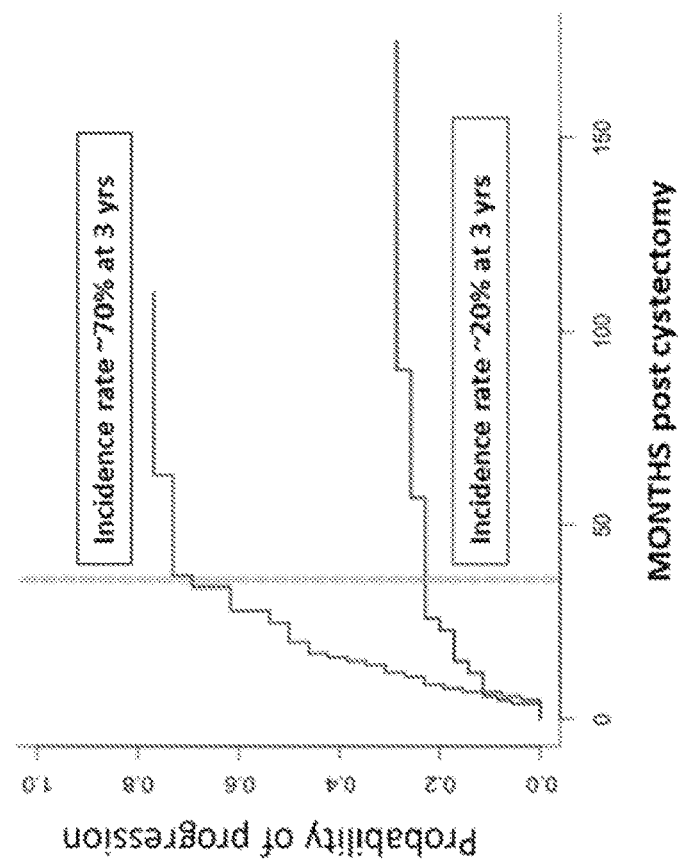
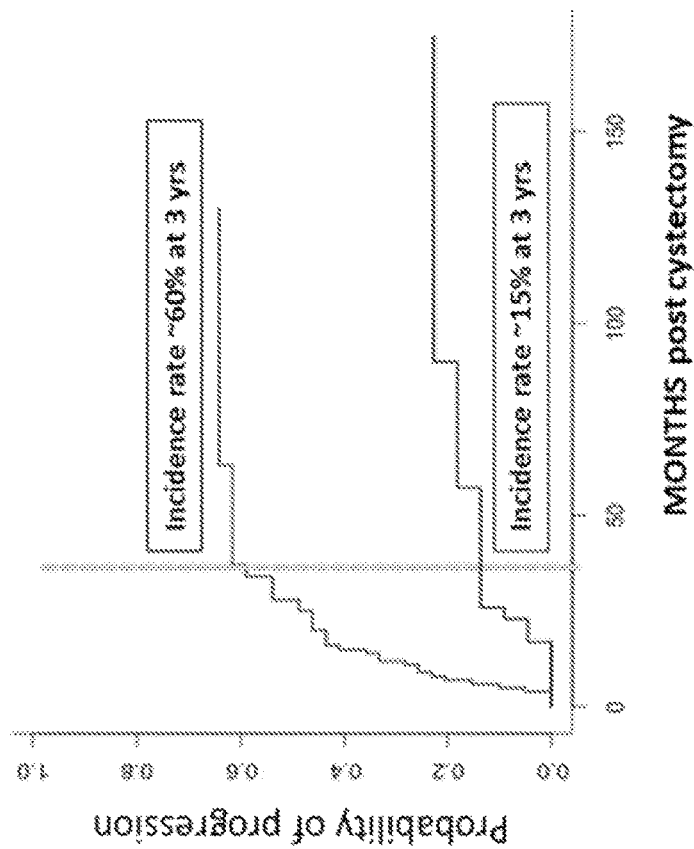

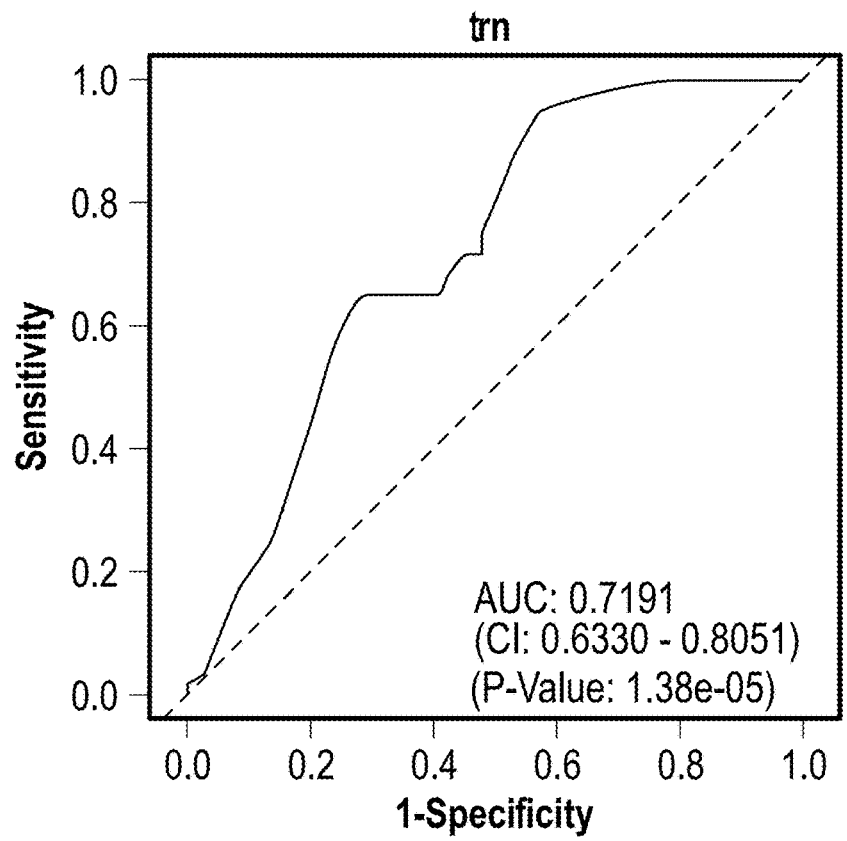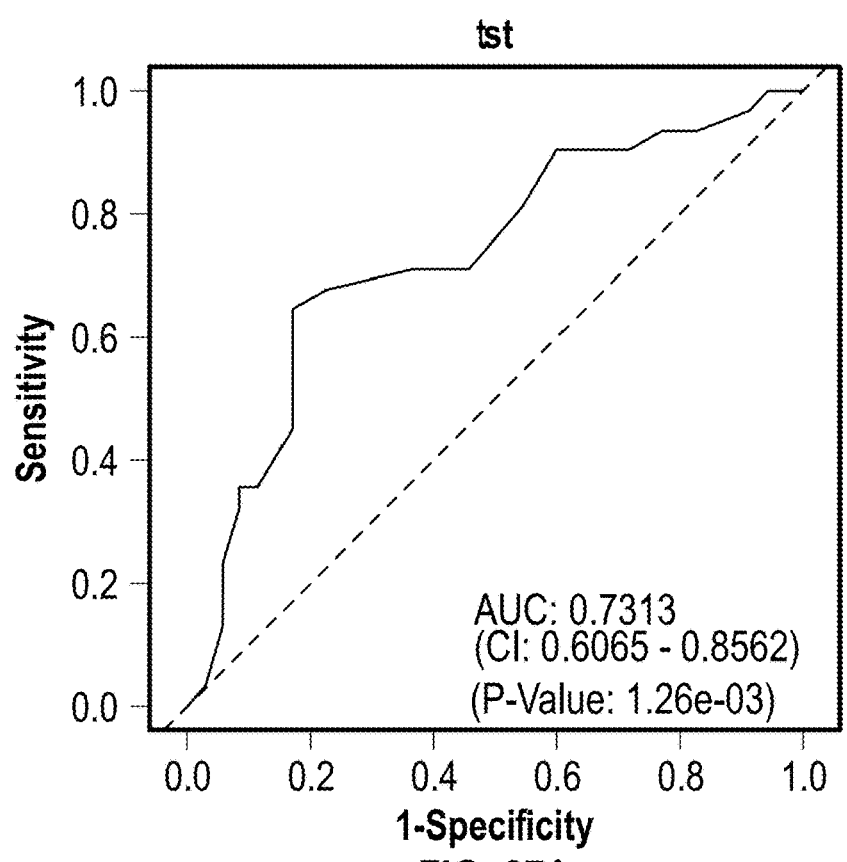
FIG. 27A

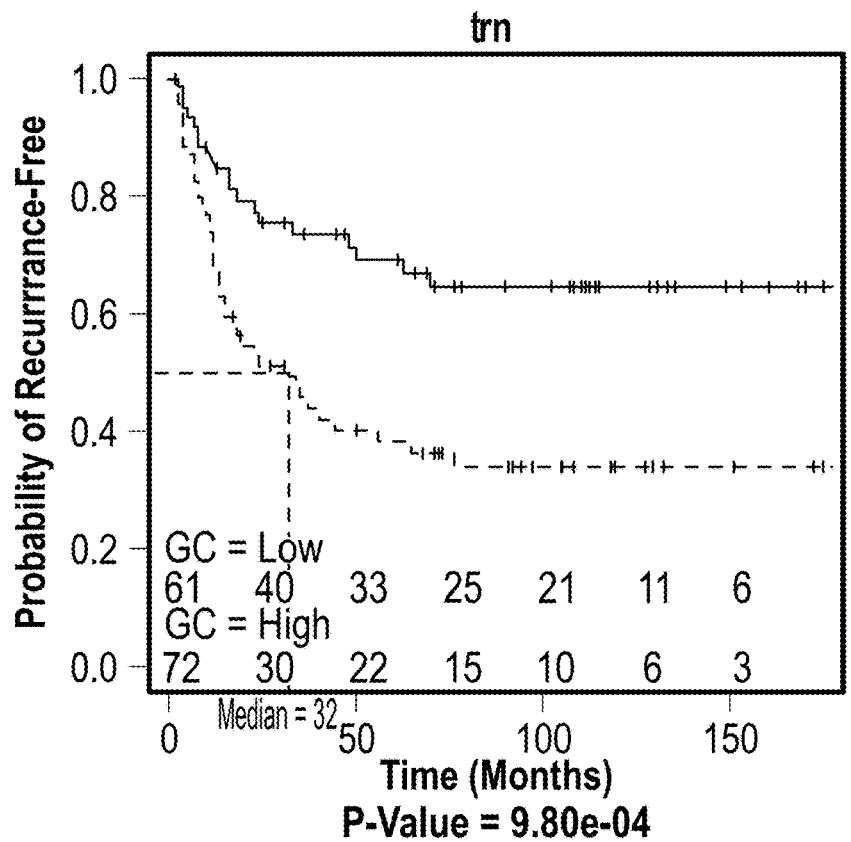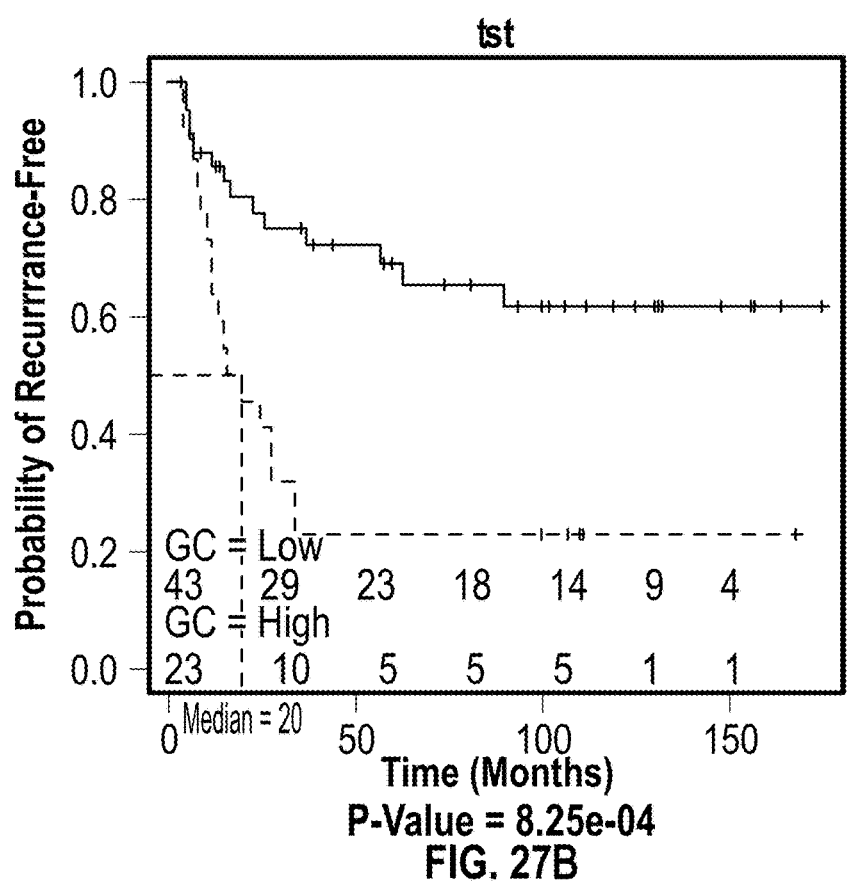
FIG. 27B

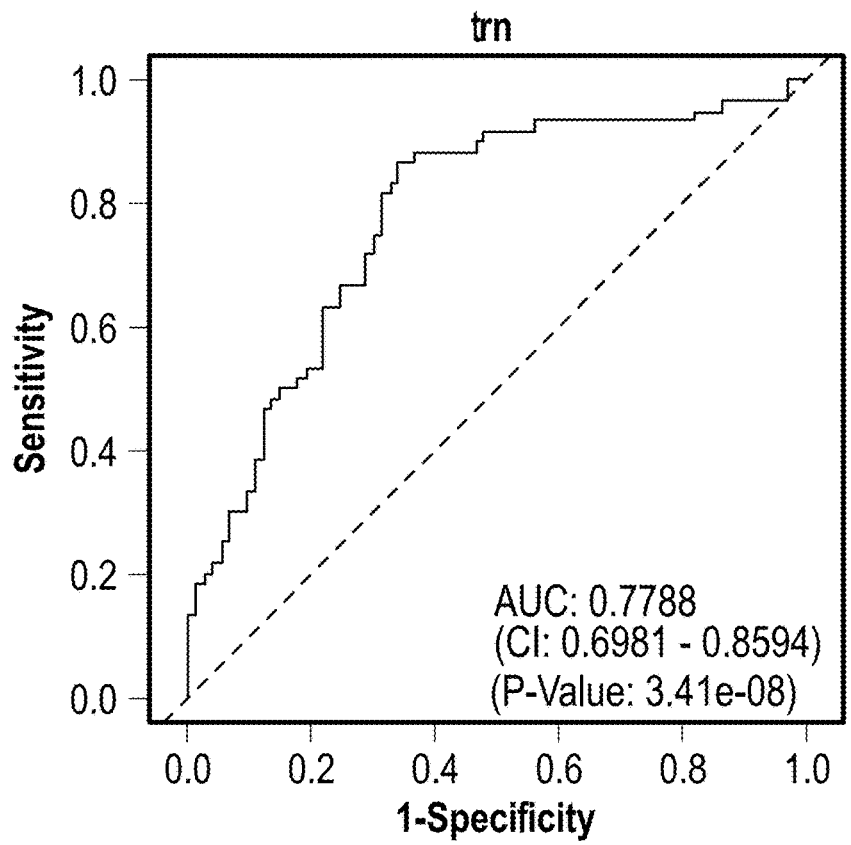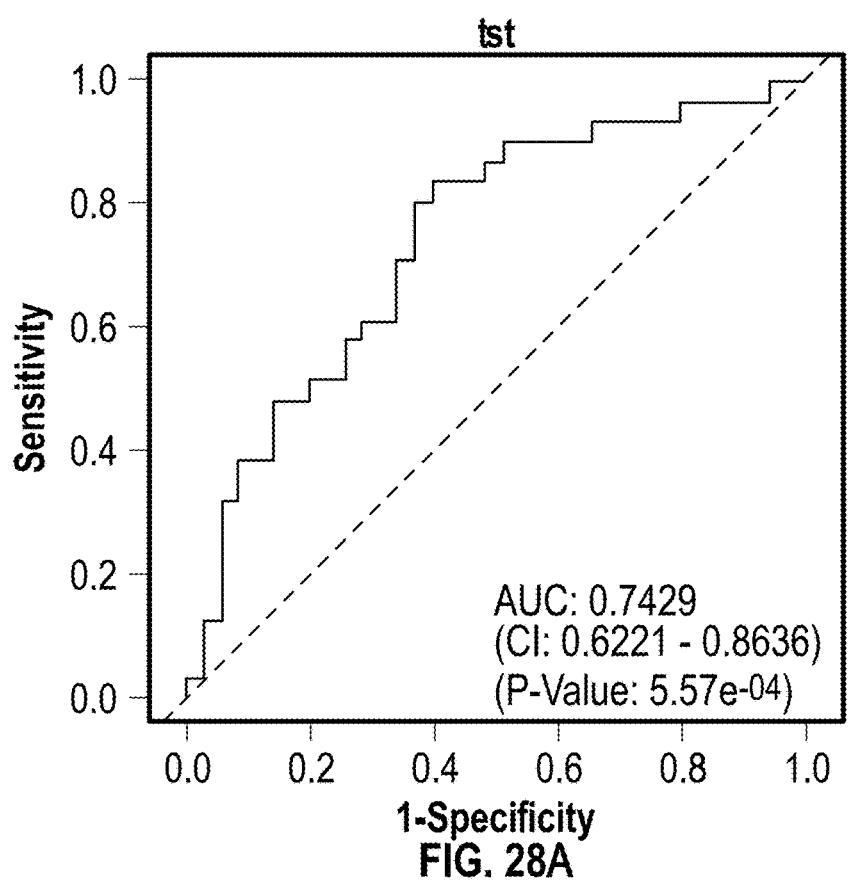
FIG. 28A

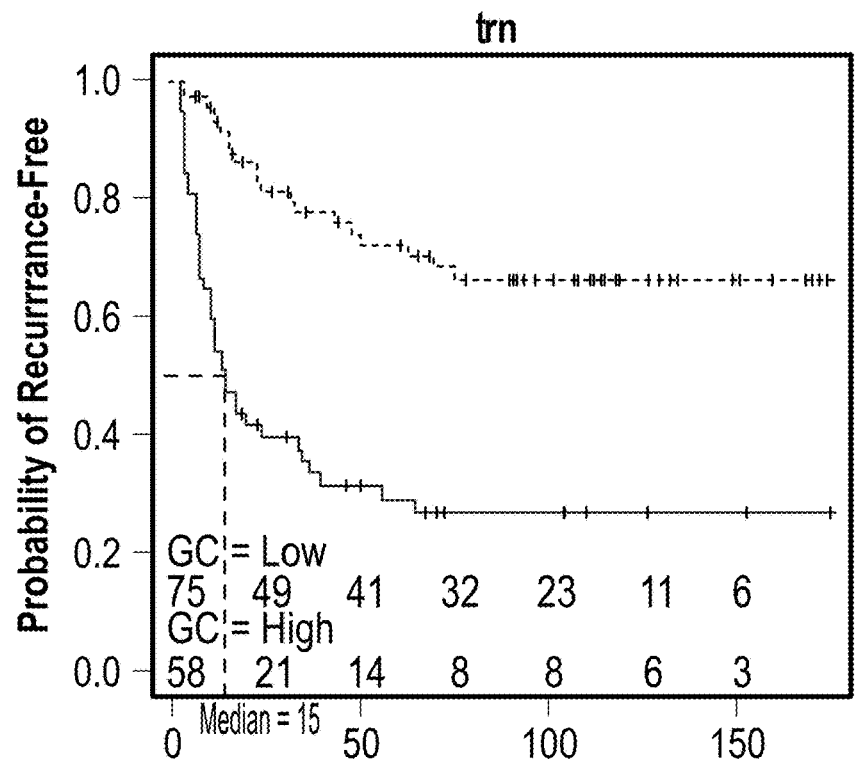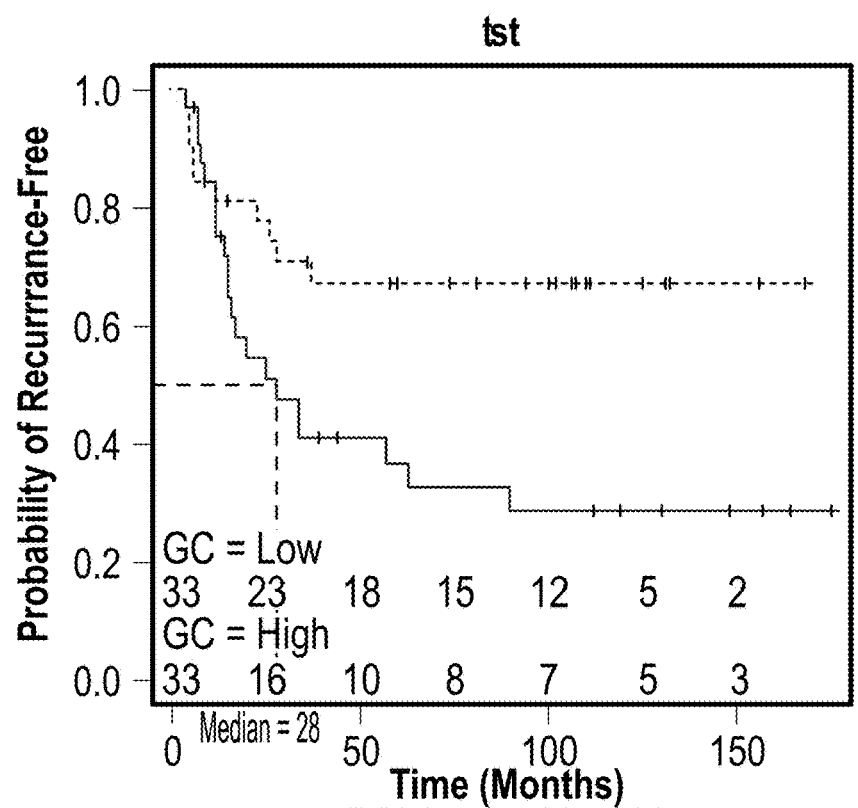
FIG. 28B

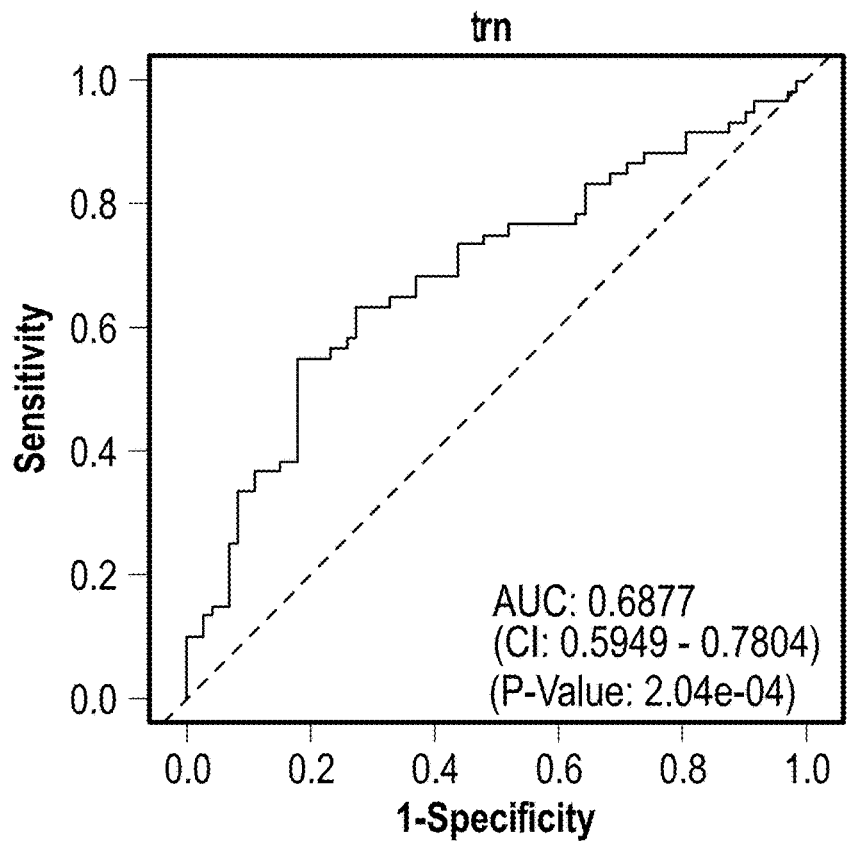
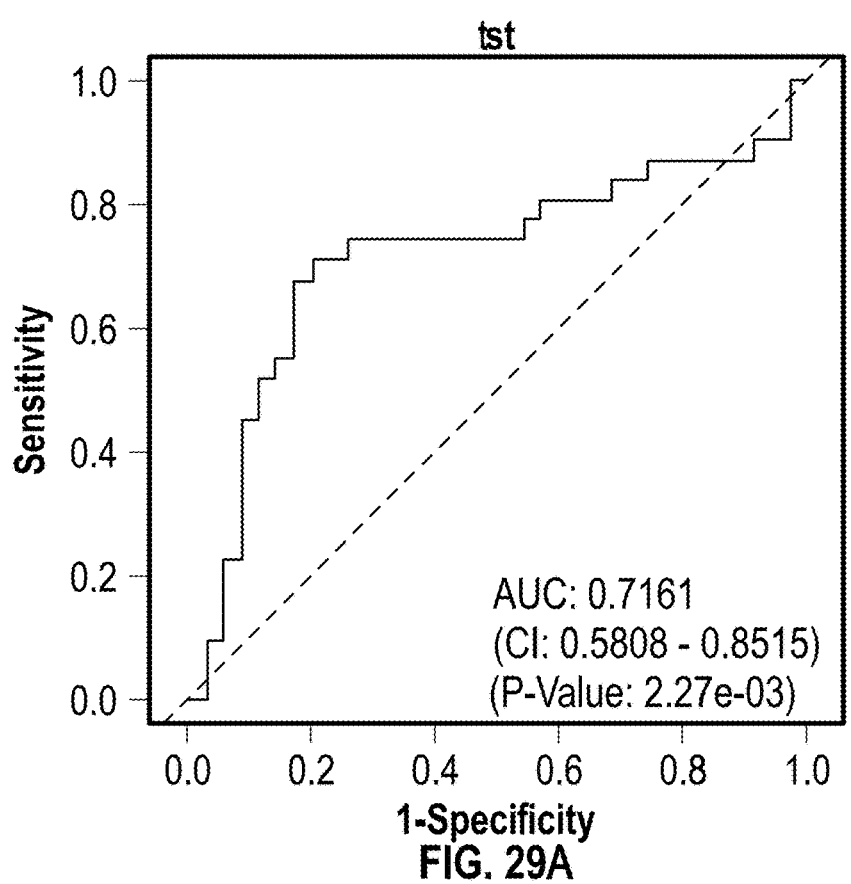
FIG. 29A

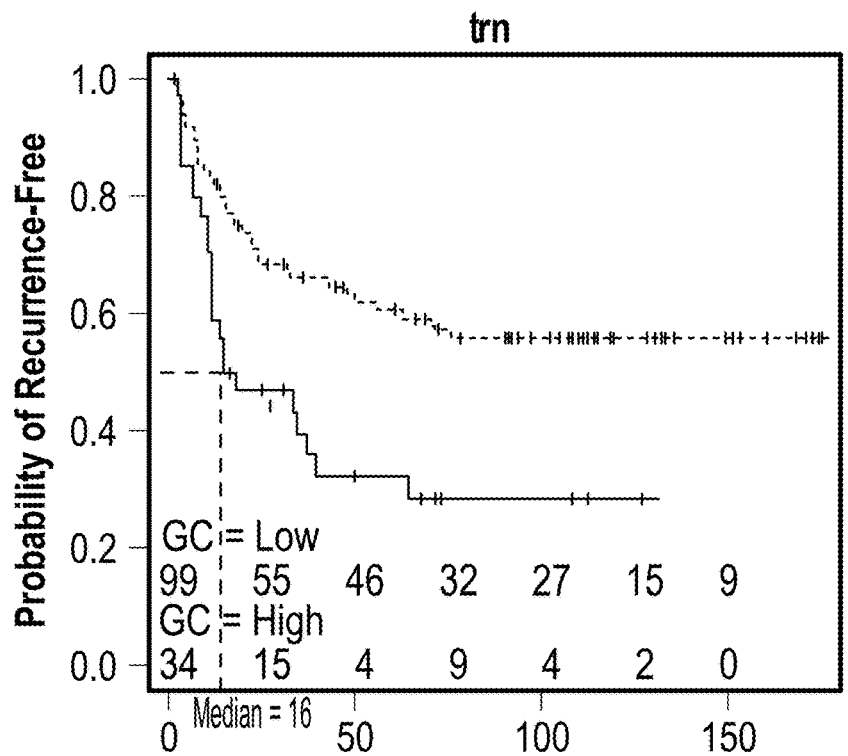
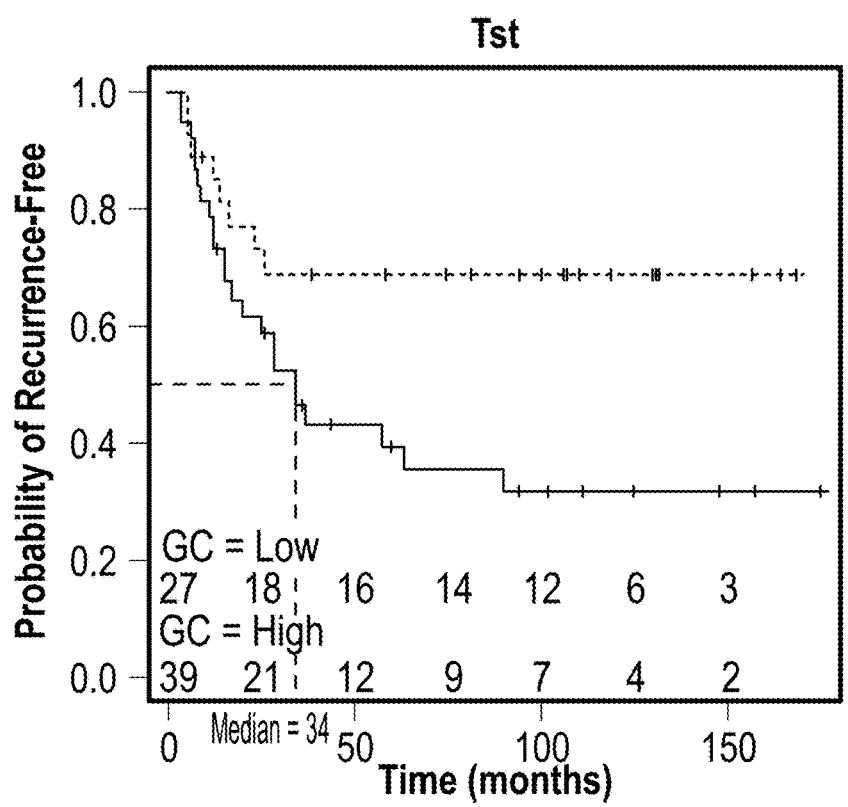
FIG. 29B

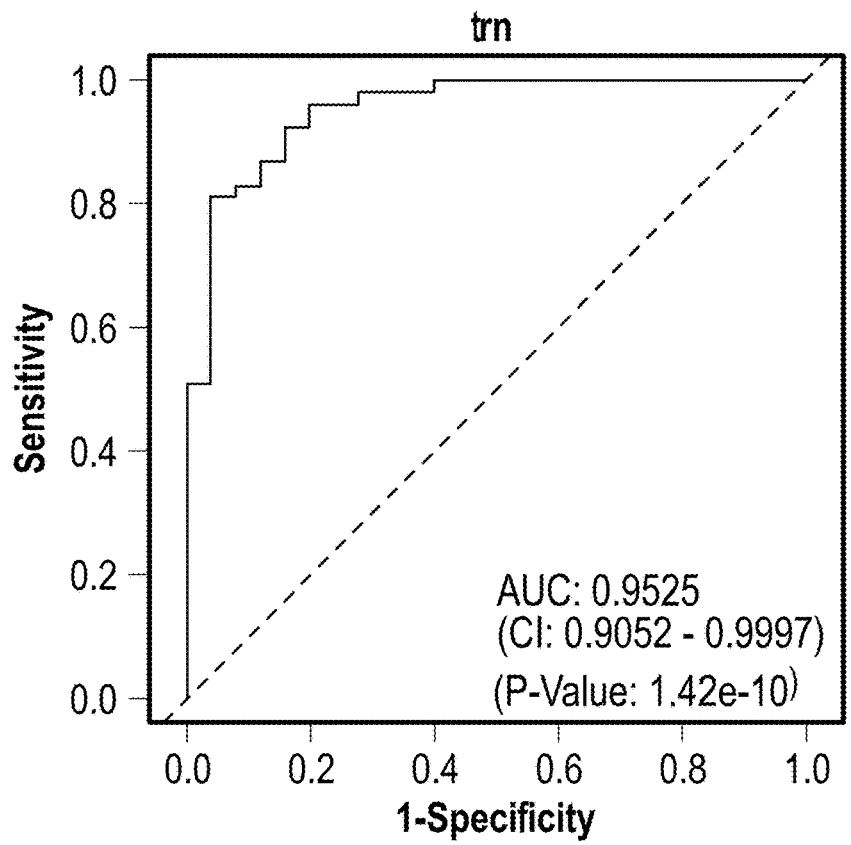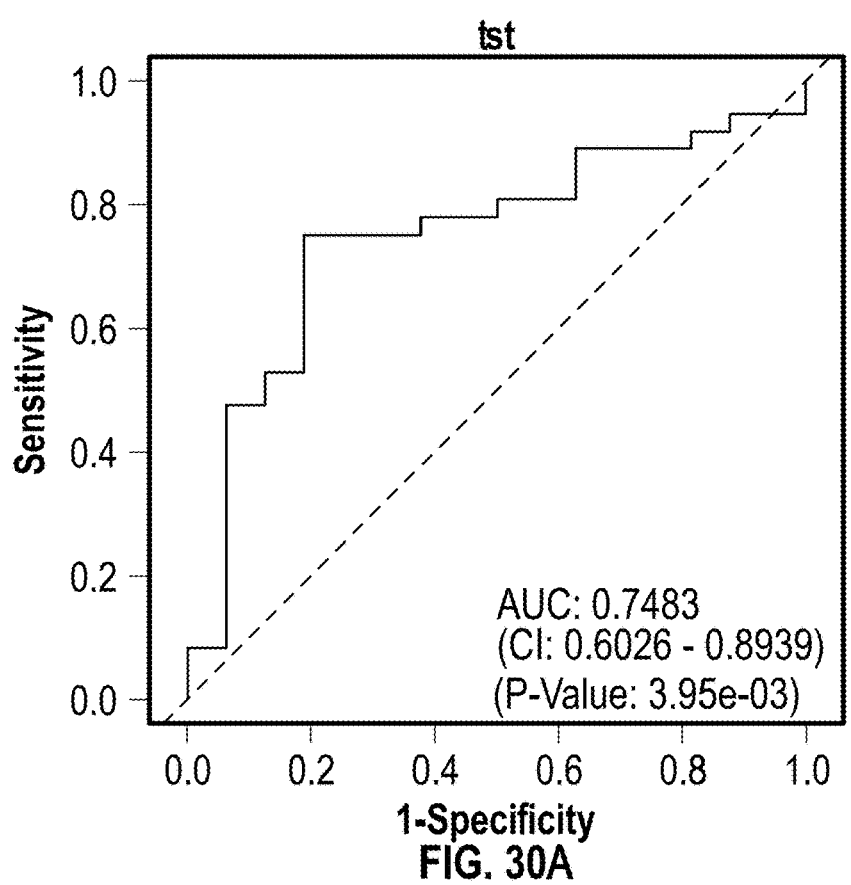
FIG. 30A

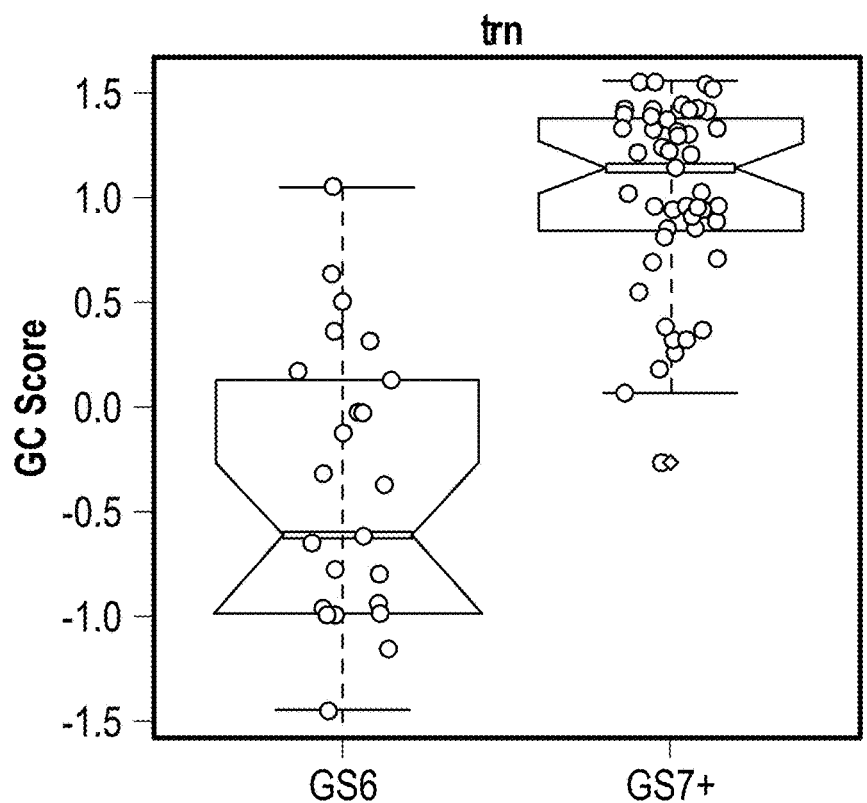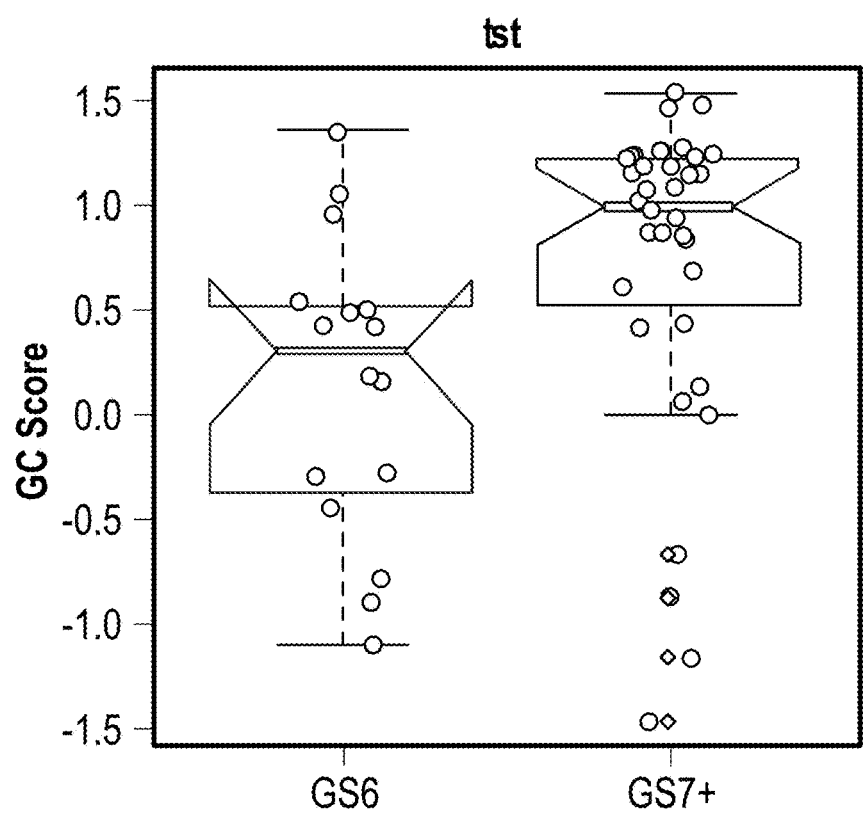
FIG. 30B

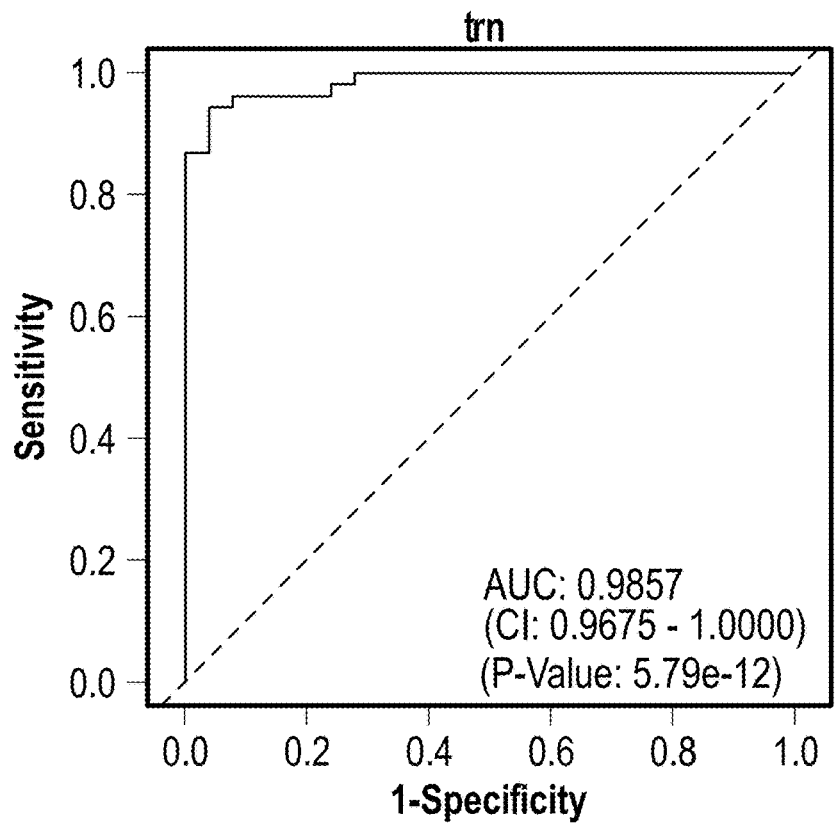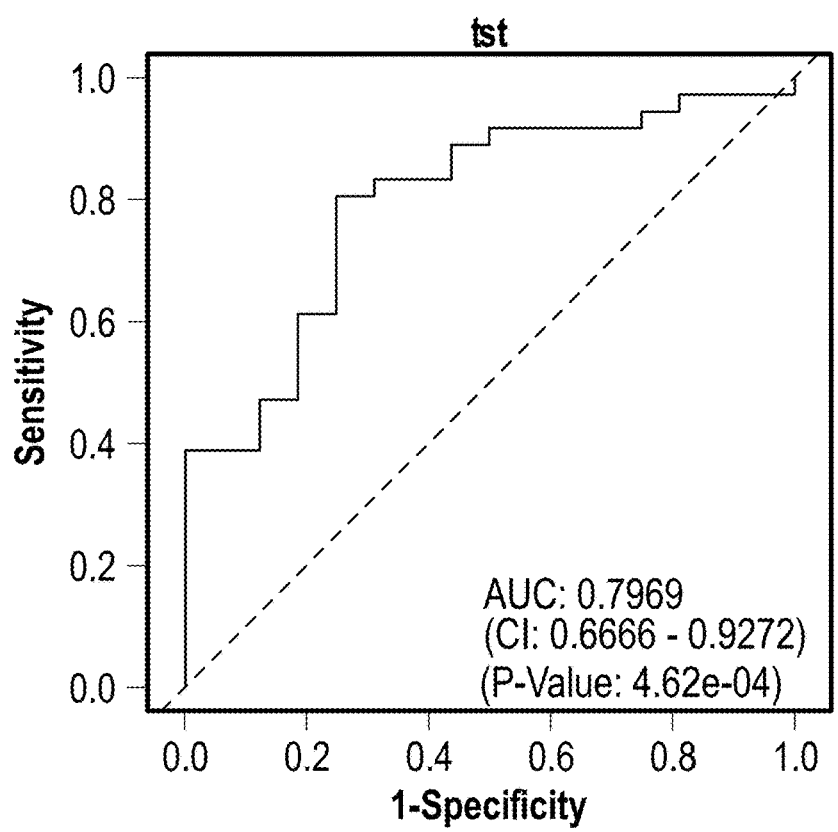
FIG. 31A

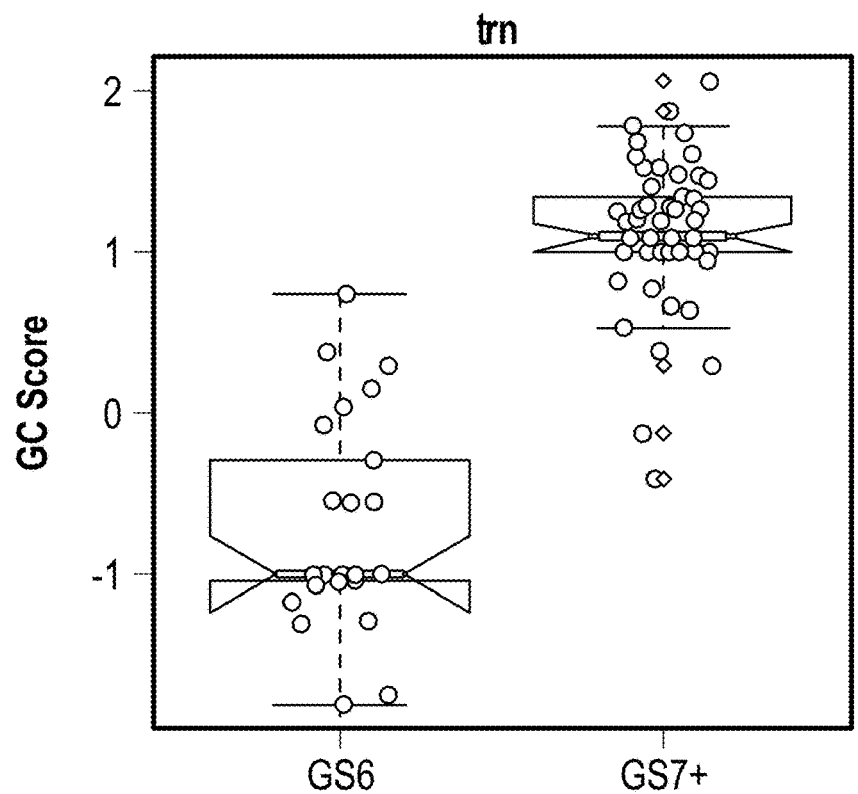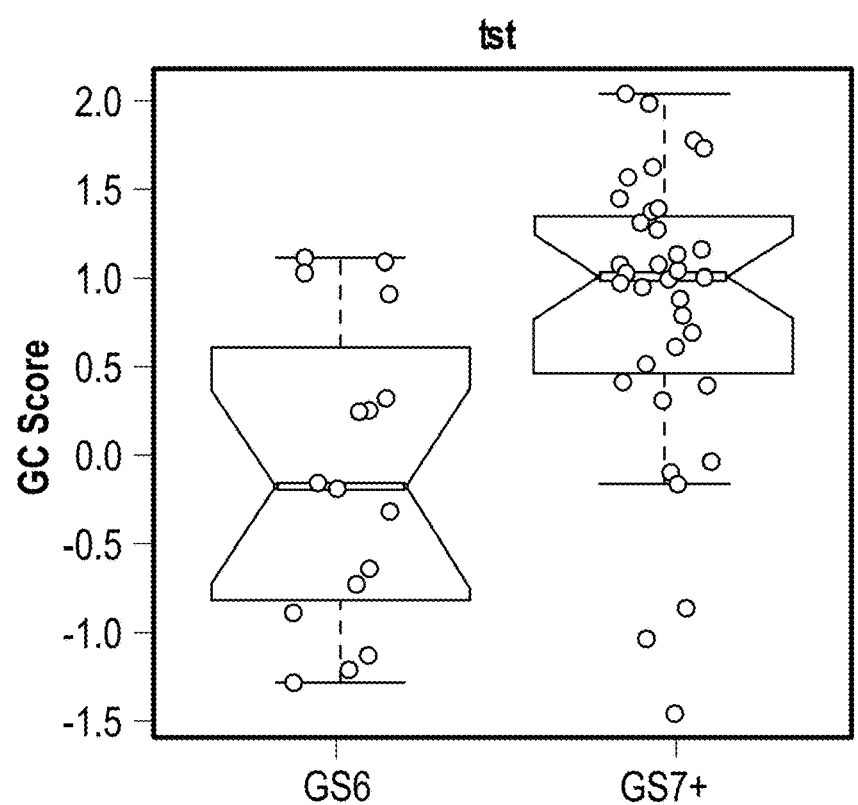
FIG. 31B

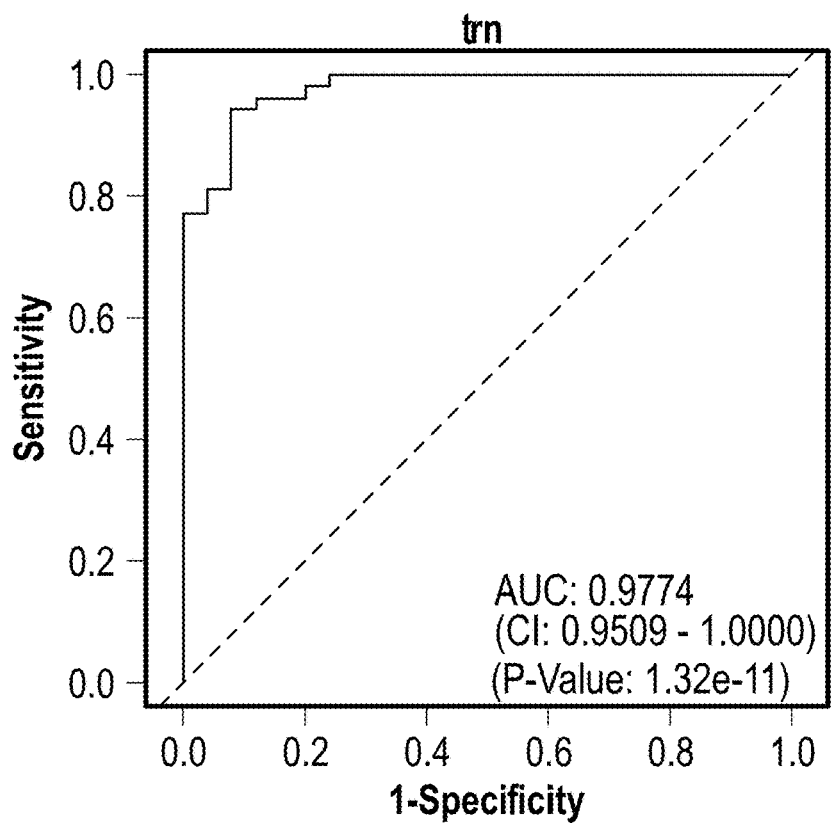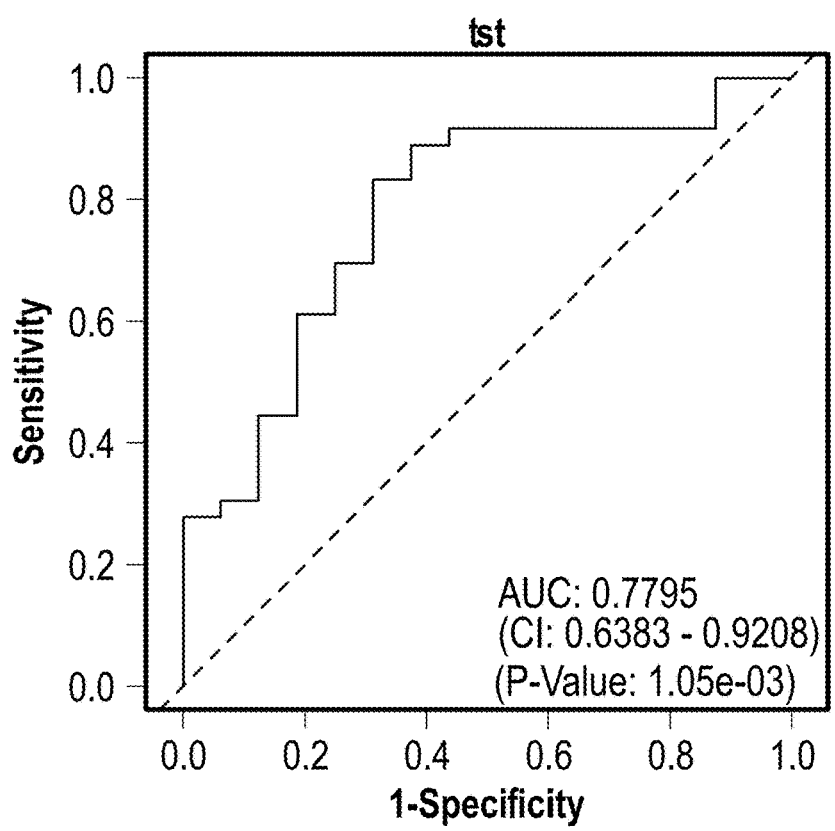
FIG. 32A

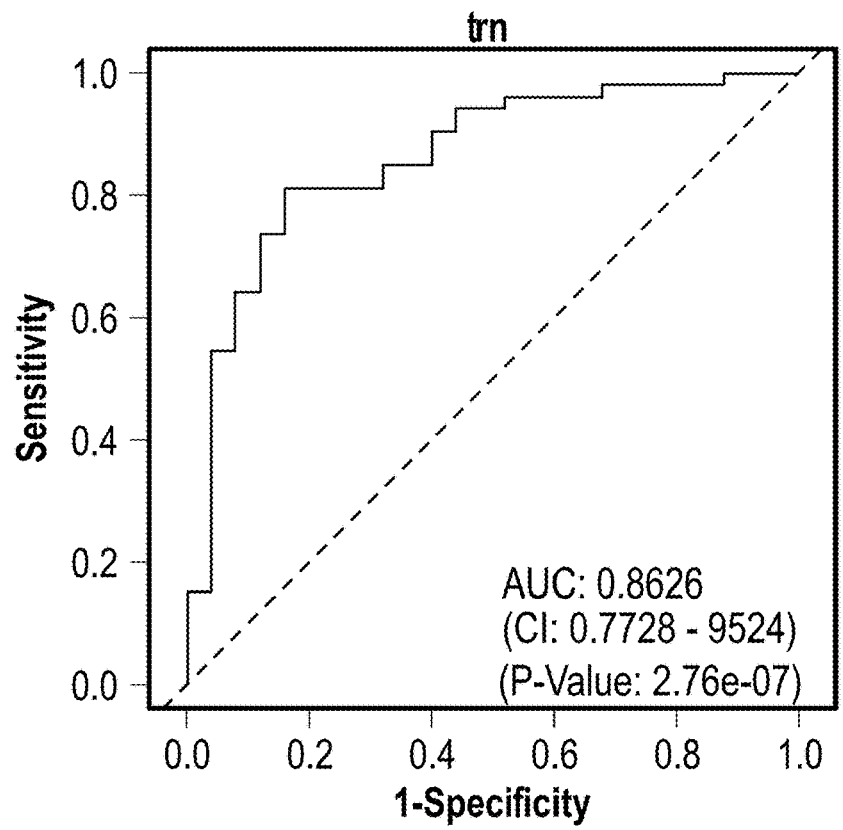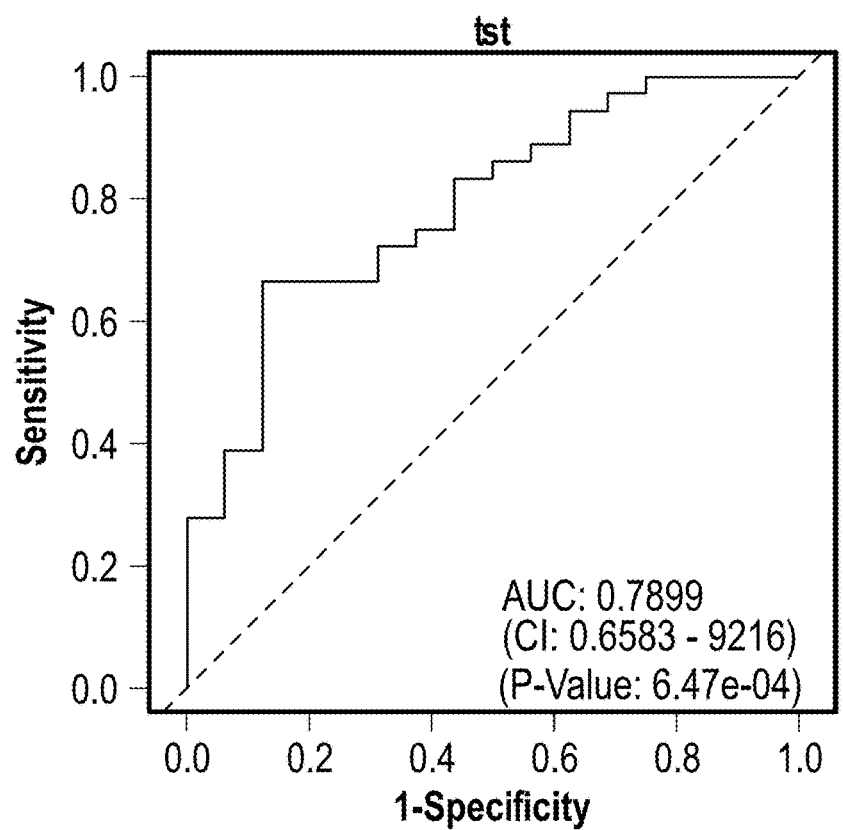
FIG. 33A

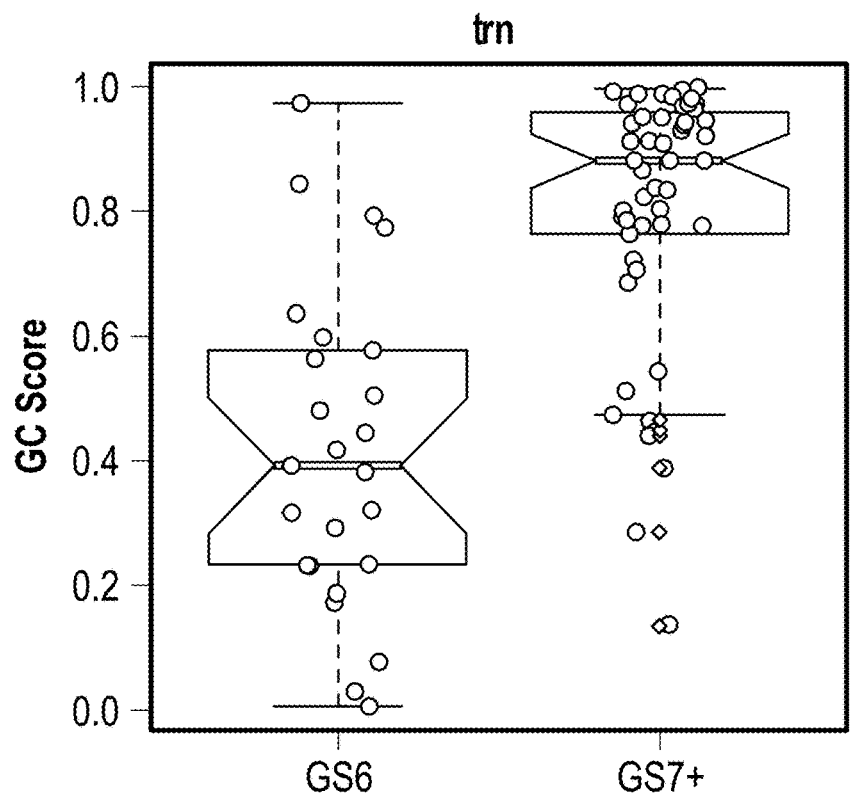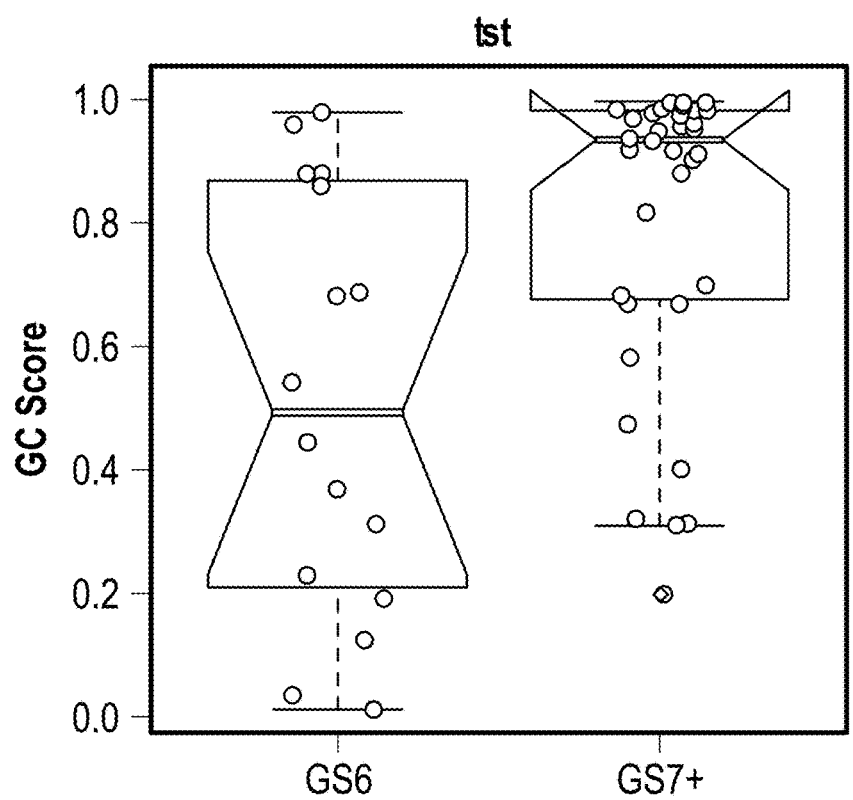
FIG. 33B

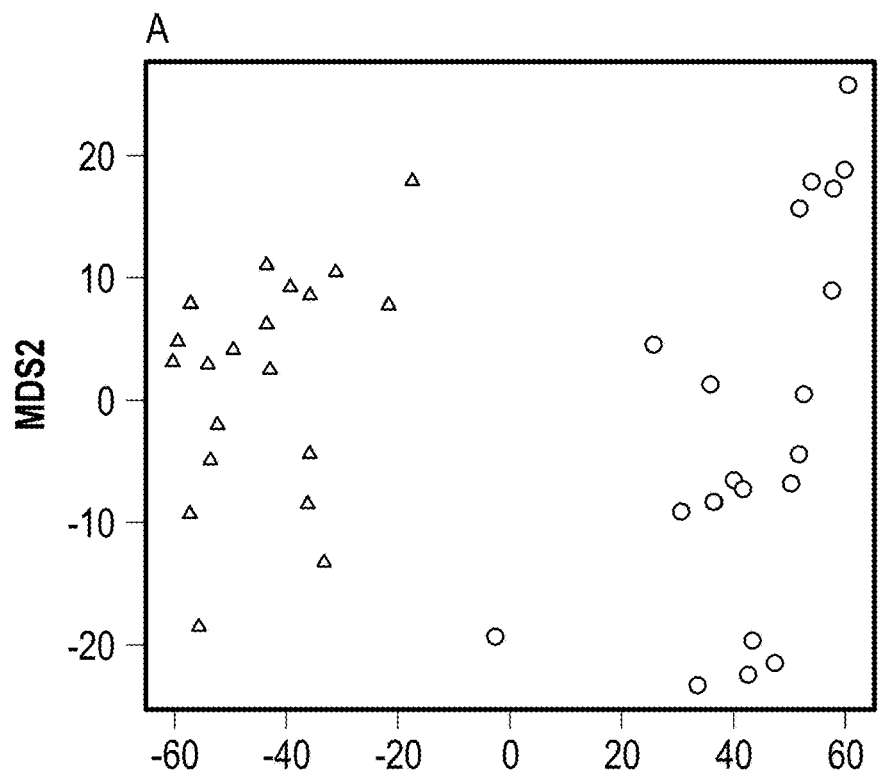
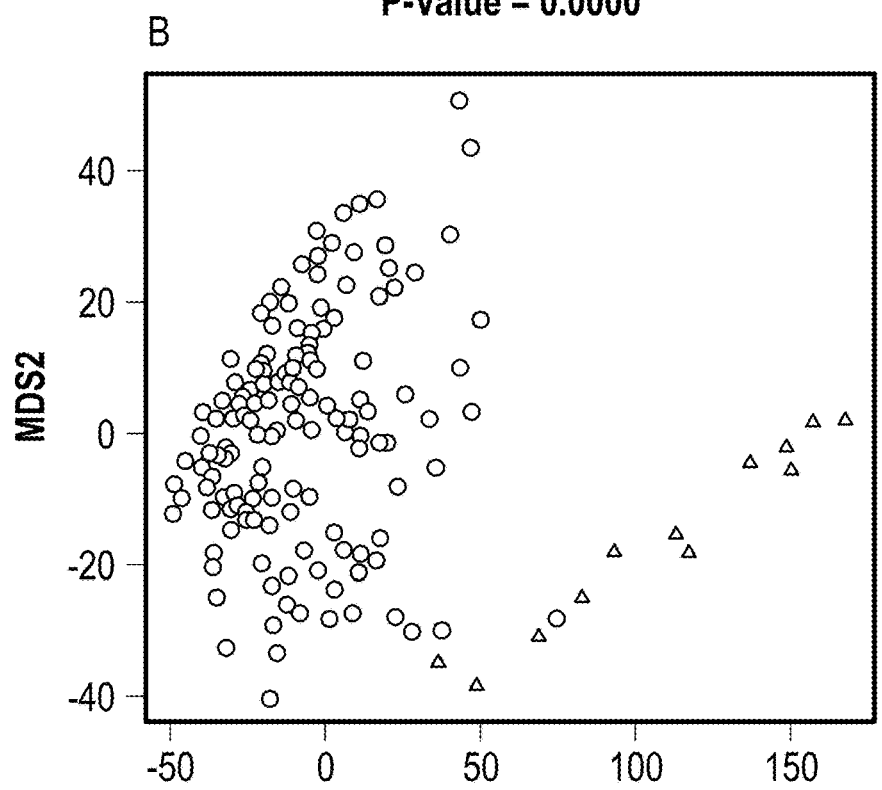
FIG. 49

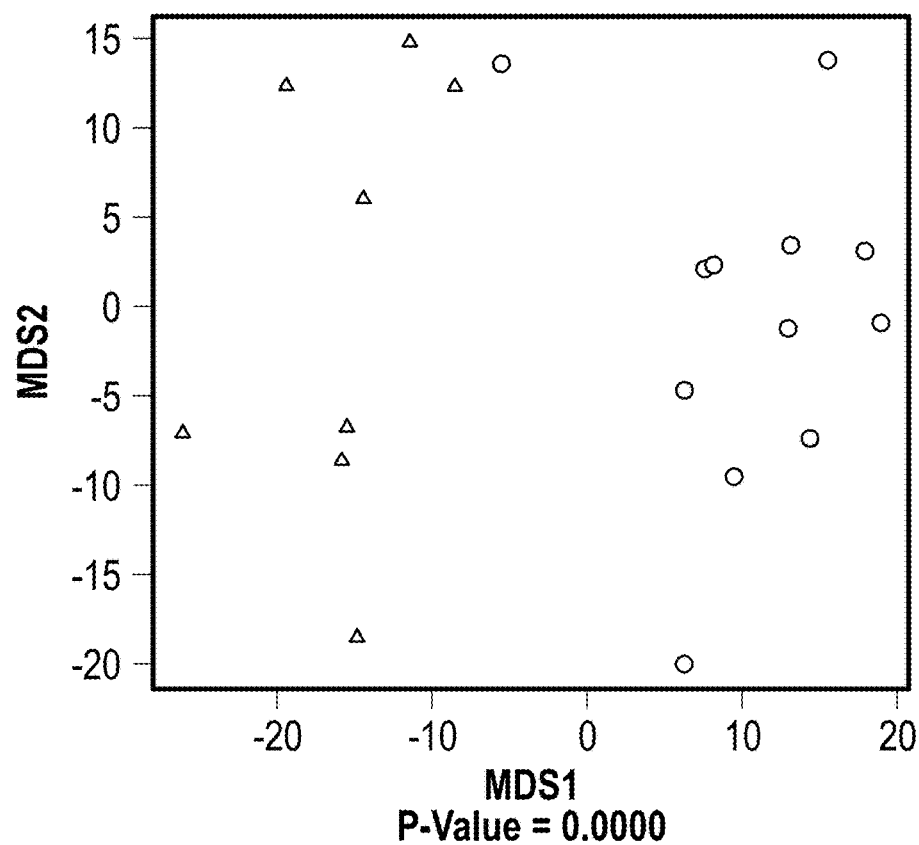
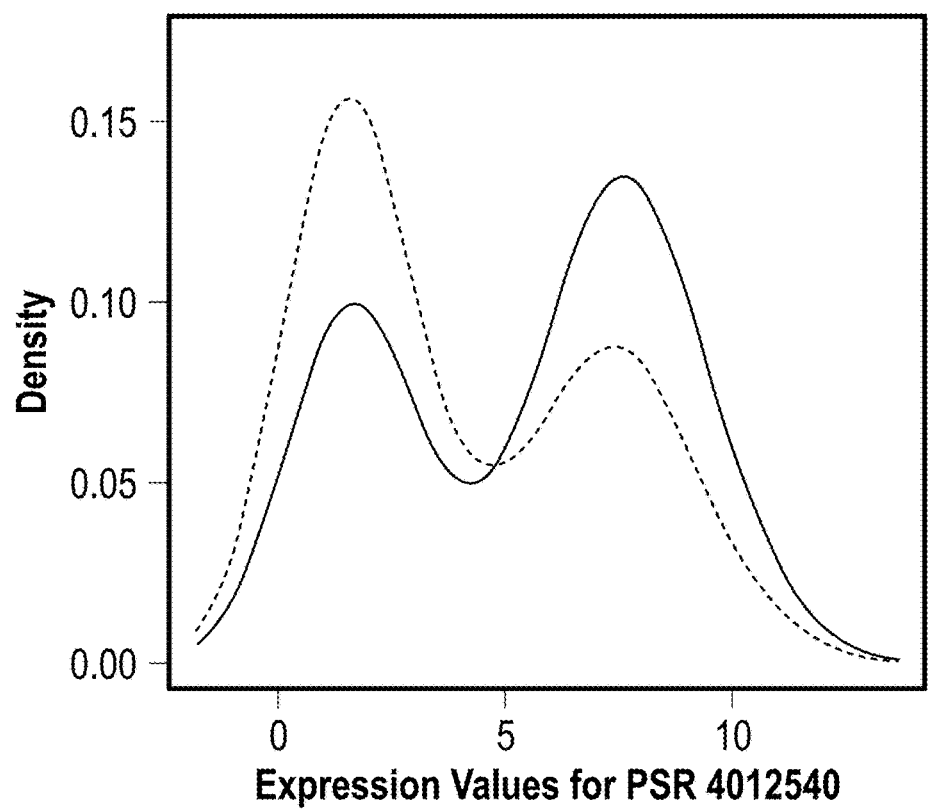
FIG. 50

SEQUENCE LISTING

<160> NUMBER OF SEQ ID NOS: 903

<210> SEQ ID NO 1
<211> LENGTH: 60
<212> TYPE: DNA
<213> ORGANISM: Artificial Sequence
<220> FEATURE:
<223> OTHER INFORMATION: Synthetic

<400> SEQUENCE: 1
cctgccatgt acgtcgccat tcaagctgtg ctctccctct atgcctctgg ccgcacgaca    60

<210> SEQ ID NO 2
<211> LENGTH: 52
<212> TYPE: DNA
<213> ORGANISM: Artificial Sequence
<220> FEATURE:
<223> OTHER INFORMATION: Synthetic

<400> SEQUENCE: 2
ggctcagagc aagcgaggga tcctaactct caaatacccc attgaacacg gc    52

<210> SEQ ID NO 3
<211> LENGTH: 147
<212> TYPE: DNA
<213> ORGANISM: Artificial Sequence
<220> FEATURE:
<223> OTHER INFORMATION: Synthetic

<400> SEQUENCE: 3
ggattcaggt gatggcgtca cccacaatgt ccccatctat gaaggctatg ccctgcccca    60
tgccatcatg cgcctggact tggctggccg tgacctcacg gactacctca tgaagatcct    120
cacagagaga ggctattcct ttgtgac    147

<210> SEQ ID NO 4
<211> LENGTH: 29
<212> TYPE: DNA
<213> ORGANISM: Artificial Sequence
<220> FEATURE:
<223> OTHER INFORMATION: Synthetic

<400> SEQUENCE: 4
tgaaggtggt atcatcggtc ctgcagctt    29

<210> SEQ ID NO 5
<211> LENGTH: 84
<212> TYPE: DNA
<213> ORGANISM: Artificial Sequence

```
<220> FEATURE:
<223> OTHER INFORMATION: Synthetic

<400> SEQUENCE: 5
ctgcgtgtag cacctgaaga gcaccccacc ctgctcacag aggctcccct aaatcccaag    60
gccaacaggg aaaagatgac ccag                                          84

<210> SEQ ID NO 6
<211> LENGTH: 26
<212> TYPE: DNA
<213> ORGANISM: Artificial Sequence
<220> FEATURE:
<223> OTHER INFORMATION: Synthetic

<400> SEQUENCE: 6
catccgcatc aacttcgacg tcacgg                                        26

<210> SEQ ID NO 7
<211> LENGTH: 86
<212> TYPE: DNA
<213> ORGANISM: Artificial Sequence
<220> FEATURE:
<223> OTHER INFORMATION: Synthetic

<400> SEQUENCE: 7
gcatggagtc cgctggaatt catgagacaa cctacaattc catcatgaag tgtgacattg    60
acatccgtaa ggacttatat gccaac                                        86

<210> SEQ ID NO 8
<211> LENGTH: 90
<212> TYPE: DNA
<213> ORGANISM: Artificial Sequence
<220> FEATURE:
<223> OTHER INFORMATION: Synthetic

<400> SEQUENCE: 8
tgctcagaaa gtttgccacc tcatgggaat taatgtgaca gatttcacca gatccatcct    60
cactcctcgt atcaaggttg ggcgagatgt                                    90

<210> SEQ ID NO 9
<211> LENGTH: 121
<212> TYPE: DNA
<213> ORGANISM: Artificial Sequence
<220> FEATURE:
<223> OTHER INFORMATION: Synthetic

<400> SEQUENCE: 9
tttggccaag gcaacatatg agcgcctttt ccgctggata ctcacccgcg tgaacaaagc    60
cctggacaag acccatcggc aaggggcttc cttcctgggg atcctggata tagctggatt   120
t                                                                  121

<210> SEQ ID NO 10
<211> LENGTH: 88
<212> TYPE: DNA
<213> ORGANISM: Artificial Sequence
<220> FEATURE:
<223> OTHER INFORMATION: Synthetic

<400> SEQUENCE: 10
ctataatgcg agtgcctggc tgaccaagaa tatggacccg ctgaatgaca acgtgacttc    60
cctgctcaat gcctcctccg acaagttt                                      88
```

<210> SEQ ID NO 11
<211> LENGTH: 26
<212> TYPE: DNA
<213> ORGANISM: Artificial Sequence
<220> FEATURE:
<223> OTHER INFORMATION: Synthetic

<400> SEQUENCE: 11
agagagaaat tgtgcgagac atcaag                                          26

<210> SEQ ID NO 12
<211> LENGTH: 109
<212> TYPE: DNA
<213> ORGANISM: Artificial Sequence
<220> FEATURE:
<223> OTHER INFORMATION: Synthetic

<400> SEQUENCE: 12
ggaggagtcc cagcgcatca acgccaaccg caggaagctg cagcgggagc tggatgaggc      60
cacggagagc aacgaggcca tgggccgcga ggtgaacgca ctcaagagc                 109

<210> SEQ ID NO 13
<211> LENGTH: 28
<212> TYPE: DNA
<213> ORGANISM: Artificial Sequence
<220> FEATURE:
<223> OTHER INFORMATION: Synthetic

<400> SEQUENCE: 13
atcgggagga ccagtccatt ctatgcac                                        28

<210> SEQ ID NO 14
<211> LENGTH: 75
<212> TYPE: DNA
<213> ORGANISM: Artificial Sequence
<220> FEATURE:
<223> OTHER INFORMATION: Synthetic

<400> SEQUENCE: 14
aagcagcttc tacaagcaaa cccgattctg gaggctttcg gcaacgccaa aacagtgaag      60
aacgacaact cctca                                                      75

<210> SEQ ID NO 15
<211> LENGTH: 123
<212> TYPE: DNA
<213> ORGANISM: Artificial Sequence
<220> FEATURE:
<223> OTHER INFORMATION: Synthetic

<400> SEQUENCE: 15
ggagggcttc aacaactaca ccttcctctc caatggcttt gtgcccatcc cagcagccca      60
ggatgatgag atgttccagg aaaccgtgga ggccatggca atcatgggtt cagcgagga     120 gga                                                                  123

<210> SEQ ID NO 16
<211> LENGTH: 107
<212> TYPE: DNA
<213> ORGANISM: Artificial Sequence
<220> FEATURE:
<223> OTHER INFORMATION: Synthetic

<400> SEQUENCE: 16
accagtcaat cagggagtcc cgccacttcc agatagacta cgatgaggac gggaactgct      60

```
ctttaattat tagtgatgtt tgcggggatg acgatgccaa gtacacc                    107

<210> SEQ ID NO 17
<211> LENGTH: 90
<212> TYPE: DNA
<213> ORGANISM: Artificial Sequence
<220> FEATURE:
<223> OTHER INFORMATION: Synthetic

<400> SEQUENCE: 17
aaggtctgga ggacgtagag ttattgaaaa tgcagatggt tctgaggagg aaacggacac    60
tcgagacgca gacttcaatg gaaccaaggc                                     90

<210> SEQ ID NO 18
<211> LENGTH: 145
<212> TYPE: DNA
<213> ORGANISM: Artificial Sequence
<220> FEATURE:
<223> OTHER INFORMATION: Synthetic

<400> SEQUENCE: 18
cctggaccag atggccaaga tgacggagag ctcgctgccc agcgcctcca agaccaagaa    60
gggcatgttc cgcacagtgg ggcagctgta caaggagcag ctgggcaagc tgatgaccac   120
gctacgcaac accacgccca acttc                                        145

<210> SEQ ID NO 19
<211> LENGTH: 37
<212> TYPE: DNA
<213> ORGANISM: Artificial Sequence
<220> FEATURE:
<223> OTHER INFORMATION: Synthetic

<400> SEQUENCE: 19
ggaagatgcc cgtgcctcca gagatgagat ctttgcc                             37

<210> SEQ ID NO 20
<211> LENGTH: 53
<212> TYPE: DNA
<213> ORGANISM: Artificial Sequence
<220> FEATURE:
<223> OTHER INFORMATION: Synthetic

<400> SEQUENCE: 20
cttcacgagt atgagacgga actggaagac gagcgaaagc aacgtgccct ggc            53

<210> SEQ ID NO 21
<211> LENGTH: 77
<212> TYPE: DNA
<213> ORGANISM: Artificial Sequence
<220> FEATURE:
<223> OTHER INFORMATION: Synthetic

<400> SEQUENCE: 21
caagctggat gcgttcctgg tgctggagca gctgcggtgc aatggggtgc tggaaggcat    60
tcgcatctgc cggcagg                                                   77

<210> SEQ ID NO 22
<211> LENGTH: 39
<212> TYPE: DNA
<213> ORGANISM: Artificial Sequence
<220> FEATURE:
<223> OTHER INFORMATION: Synthetic
```

```
<400> SEQUENCE: 22
ctgctagaaa aatcacgggc aattcgccaa gccagagac                                39

<210> SEQ ID NO 23
<211> LENGTH: 33
<212> TYPE: DNA
<213> ORGANISM: Artificial Sequence
<220> FEATURE:
<223> OTHER INFORMATION: Synthetic

<400> SEQUENCE: 23
caccacgcac acaactacta caattccgcc tag                                      33

<210> SEQ ID NO 24
<211> LENGTH: 49
<212> TYPE: DNA
<213> ORGANISM: Artificial Sequence
<220> FEATURE:
<223> OTHER INFORMATION: Synthetic

<400> SEQUENCE: 24
cctgttcacg gcctatcttg gagtcggcat ggcaaacttt atggctgag                     49

<210> SEQ ID NO 25
<211> LENGTH: 82
<212> TYPE: DNA
<213> ORGANISM: Artificial Sequence
<220> FEATURE:
<223> OTHER INFORMATION: Synthetic

<400> SEQUENCE: 25
gccaaactgc ggctggaagt caacatgcag gcgctcaagg gccagttcga aagggatctc         60
caagcccggg acgagcagaa tg                                                  82

<210> SEQ ID NO 26
<211> LENGTH: 79
<212> TYPE: DNA
<213> ORGANISM: Artificial Sequence
<220> FEATURE:
<223> OTHER INFORMATION: Synthetic

<400> SEQUENCE: 26
gctgaaacgg aagctggagg gtgatgccag cgacttccac gagcagatcg ctgacctcca         60
ggcgcagatc gcagagctc                                                      79

<210> SEQ ID NO 27
<211> LENGTH: 69
<212> TYPE: DNA
<213> ORGANISM: Artificial Sequence
<220> FEATURE:
<223> OTHER INFORMATION: Synthetic

<400> SEQUENCE: 27
ccagctggat ggagattctt ctcaaatctg atgactcag gacgttgcaa tctgtgtggg          60
gaagagagc                                                                 69

<210> SEQ ID NO 28
<211> LENGTH: 77
<212> TYPE: DNA
<213> ORGANISM: Artificial Sequence
<220> FEATURE:
<223> OTHER INFORMATION: Synthetic

<400> SEQUENCE: 28
```

```
gctactctag ctcgcattga cctggagcgc agaattgaat ctctcaacga ggagatcgcg    60
ttccttaaga aagtgca                                                  77

<210> SEQ ID NO 29
<211> LENGTH: 91
<212> TYPE: DNA
<213> ORGANISM: Artificial Sequence
<220> FEATURE:
<223> OTHER INFORMATION: Synthetic

<400> SEQUENCE: 29
aggtgacggt gctgaagaag gccctggatg aagagacgcg gtcccatgag gctcaggtcc    60
aggagatgag gcagaaacac gcacaggcgg t                                  91

<210> SEQ ID NO 30
<211> LENGTH: 128
<212> TYPE: DNA
<213> ORGANISM: Artificial Sequence
<220> FEATURE:
<223> OTHER INFORMATION: Synthetic

<400> SEQUENCE: 30
cccagagcgg aagtactcag tctggatcgg gggctctatc ctggcctctc tctccacctt    60
ccagcagatg tggatcagca agcctgagta tgatgaggca gggccctcca ttgtccacag   120
gaagtgct                                                           128

<210> SEQ ID NO 31
<211> LENGTH: 182
<212> TYPE: DNA
<213> ORGANISM: Artificial Sequence
<220> FEATURE:
<223> OTHER INFORMATION: Synthetic

<400> SEQUENCE: 31
ttgccagcac cgtggaagct ctggaagagg ggaagaagag gttccagaag gagatcgaga    60
acctcaccca gcagtacgag gagaaggcgg ccgcttatga taaactggaa aagaccaaga   120
acaggcttca gcaggagctg gacgacctgg ttgttgattt ggacaaccag cggcaactcg   180
tg                                                                 182

<210> SEQ ID NO 32
<211> LENGTH: 54
<212> TYPE: DNA
<213> ORGANISM: Artificial Sequence
<220> FEATURE:
<223> OTHER INFORMATION: Synthetic

<400> SEQUENCE: 32
gccatcccgc ttagcctgcc tcacccacac ccgtgtggta ccttcagccc tggc           54

<210> SEQ ID NO 33
<211> LENGTH: 31
<212> TYPE: DNA
<213> ORGANISM: Artificial Sequence
<220> FEATURE:
<223> OTHER INFORMATION: Synthetic

<400> SEQUENCE: 33
gaaaaggcca agaatcttac caagctgaaa a                                  31

<210> SEQ ID NO 34
```

```
<211> LENGTH: 48
<212> TYPE: DNA
<213> ORGANISM: Artificial Sequence
<220> FEATURE:
<223> OTHER INFORMATION: Synthetic

<400> SEQUENCE: 34
gcagctgacc gccatgaagg tgattcagag gaactgcgcc gcctacct              48

<210> SEQ ID NO 35
<211> LENGTH: 328
<212> TYPE: DNA
<213> ORGANISM: Artificial Sequence
<220> FEATURE:
<223> OTHER INFORMATION: Synthetic

<400> SEQUENCE: 35
cgcagaaggg ccaactcagt gacgatgaga agttcctctt tgtggacaaa aacttcatca    60
acagcccagt ggcccaggct gactgggccg ccaagagact cgtctgggtc ccctcggaga   120
agcagggctt cgaggcagcc agcattaagg aggagaaggg ggatgaggtg gttgtggagc   180
tggtggagaa tggcaagaag gtcacggttg ggaaagatga catccagaag atgaacccac   240
ccaagttctc caaggtggag gacatggcgg agctgacgtg cctcaacgaa gcctccgtgc   300
tacacaacct gagggagcgg tacttctc                                    328

<210> SEQ ID NO 36
<211> LENGTH: 78
<212> TYPE: DNA
<213> ORGANISM: Artificial Sequence
<220> FEATURE:
<223> OTHER INFORMATION: Synthetic

<400> SEQUENCE: 36
tgagagcgtc acagggatgc ttaacgaggc cgaggggaag gccattaagc tggccaagga    60
cgtggcgtcc ctcagttc                                                 78

<210> SEQ ID NO 37
<211> LENGTH: 41
<212> TYPE: DNA
<213> ORGANISM: Artificial Sequence
<220> FEATURE:
<223> OTHER INFORMATION: Synthetic

<400> SEQUENCE: 37
aaaacgggca atgctgtgag agccattgga agactgtcct c                       41

<210> SEQ ID NO 38
<211> LENGTH: 33
<212> TYPE: DNA
<213> ORGANISM: Artificial Sequence
<220> FEATURE:
<223> OTHER INFORMATION: Synthetic

<400> SEQUENCE: 38
ctacgagatc ctggcggcga atgccatccc caa                                33

<210> SEQ ID NO 39
<211> LENGTH: 39
<212> TYPE: DNA
<213> ORGANISM: Artificial Sequence
<220> FEATURE:
<223> OTHER INFORMATION: Synthetic

<400> SEQUENCE: 39
```
ctgcaacttg agaaggtcac ggctgaggcc aagatcaag 39

<210> SEQ ID NO 40
<211> LENGTH: 158
<212> TYPE: DNA
<213> ORGANISM: Artificial Sequence
<220> FEATURE:
<223> OTHER INFORMATION: Synthetic

<400> SEQUENCE: 40
agaaccccac agacgaatac ctggagggca tgatgagcga ggccccgggg cccatcaact 60
tcaccatgtt cctcaccatg tttggggaga agctgaacgg cacggacccc gaggatgtga 120
ttcgcaacgc ctttgcctgc ttcgacgagg aagcctca 158

<210> SEQ ID NO 41
<211> LENGTH: 87
<212> TYPE: DNA
<213> ORGANISM: Artificial Sequence
<220> FEATURE:
<223> OTHER INFORMATION: Synthetic

<400> SEQUENCE: 41
ccacatctct ttcttattgg ctgcattgga gttagtggca agacgaagtg ggatgtgctc 60
gatggggtgg ttagacggct gttcaaa 87

<210> SEQ ID NO 42
<211> LENGTH: 53
<212> TYPE: DNA
<213> ORGANISM: Artificial Sequence
<220> FEATURE:
<223> OTHER INFORMATION: Synthetic

<400> SEQUENCE: 42
ggtcaaggaa ctcaaggttt cgctgccgtg gagtggatgc aatagaaac tgg 53

<210> SEQ ID NO 43
<211> LENGTH: 28
<212> TYPE: DNA
<213> ORGANISM: Artificial Sequence
<220> FEATURE:
<223> OTHER INFORMATION: Synthetic

<400> SEQUENCE: 43
ttaccggcgg ggagctgttt gaagacat 28

<210> SEQ ID NO 44
<211> LENGTH: 31
<212> TYPE: DNA
<213> ORGANISM: Artificial Sequence
<220> FEATURE:
<223> OTHER INFORMATION: Synthetic

<400> SEQUENCE: 44
gcagatgatg gcggcttgac tgaacagagt g 31

<210> SEQ ID NO 45
<211> LENGTH: 889
<212> TYPE: DNA
<213> ORGANISM: Artificial Sequence
<220> FEATURE:
<223> OTHER INFORMATION: Synthetic

<400> SEQUENCE: 45

```
tagggcctga gctgcctatg aattggtgga ttgttaagga gagggtggaa atgcatgacc    60
gatgtgctgg gaggtctgtg gaaatgtgtg acaagagtgt gagtgtggaa gtcagcgtct   120
gcgaaacagg cagcaacaca gaggagtctg tgaacgacct cacactcctc aagacaaact   180
tgaatctcaa agaagtgcgg tctatcggtt gtggagattg ttctgttgac gtgaccgtct   240
gctctccaaa ggagtgcgcc tcccggggcg tgaacactga ggctgttagc caggtggaag   300
ctgccgtcat ggcagtgcct cgtactgcag accaggacac tagcacagat ttggaacagg   360
tgcaccagtt caccaacacc gagacggcca ccctcataga gtcctgcacc aacacttgtc   420
taagcacttt ggacaagcag accagcaccc agactgtgga gacgcggaca gtagctgtag   480
gagaaggccg tgtcaaggac atcaactcct ccaccaagac gcggtccatt ggtgttggaa   540
cgttgctttc tggccattct gggtttgaca ggccatcagc tgtgaagacc aaagagtcag   600
gtgtggggca gataaatatt aacgacaact atctggttgg tctcaaaatg aggactatag   660
cttgtgggcc accacagttg actgtggggc tgacagccag cagaaggagc gtggggttg    720 gggatgaccc tgtaggggaa tctctggaga accccagcc tcaagctcca cttgaatga    780 tgactggcct ggatcactac attgagcgta ccagaagct gctggcagaa cagcagacac   840
tgctggctga gaactacagt gaactggcag aagctttcgg ggaacctca               889
```

<210> SEQ ID NO 46
<211> LENGTH: 79
<212> TYPE: DNA
<213> ORGANISM: Artificial Sequence
<220> FEATURE:
<223> OTHER INFORMATION: Synthetic

<400> SEQUENCE: 46

```
attggcctgg accagatctg ggacgacctc agagccggca tccagcaggt gtacacacgg    60
cagagcatgg ccaagtcca                                                  79
```

<210> SEQ ID NO 47
<211> LENGTH: 30
<212> TYPE: DNA
<213> ORGANISM: Artificial Sequence
<220> FEATURE:
<223> OTHER INFORMATION: Synthetic

<400> SEQUENCE: 47

```
cagtagagcc aagttgggag gtggtgaaaa                                      30
```

<210> SEQ ID NO 48
<211> LENGTH: 26
<212> TYPE: DNA
<213> ORGANISM: Artificial Sequence
<220> FEATURE:
<223> OTHER INFORMATION: Synthetic

<400> SEQUENCE: 48

```
ctgtgtccag tcaggctgcg caggcg                                          26
```

<210> SEQ ID NO 49
<211> LENGTH: 62
<212> TYPE: DNA
<213> ORGANISM: Artificial Sequence
<220> FEATURE:
<223> OTHER INFORMATION: Synthetic

<400> SEQUENCE: 49

```
gttggtggtt cgtcagcact gccgaggagc aaggctgggt ccctgcaacg tgcctcgaag    60
``` gc                                                                      62

<210> SEQ ID NO 50
<211> LENGTH: 88
<212> TYPE: DNA
<213> ORGANISM: Artificial Sequence
<220> FEATURE:
<223> OTHER INFORMATION: Synthetic

<400> SEQUENCE: 50
ggggcagaca ctaccgaaga tggggatgag aagagcctgg agaaacagaa gcacagtgcc      60
accactgtgt tcggagcaaa cacccca                                          88

<210> SEQ ID NO 51
<211> LENGTH: 36
<212> TYPE: DNA
<213> ORGANISM: Artificial Sequence
<220> FEATURE:
<223> OTHER INFORMATION: Synthetic

<400> SEQUENCE: 51
tatgcgctga tggagaaaga cgccctccag gtggcc                                36

<210> SEQ ID NO 52
<211> LENGTH: 25
<212> TYPE: DNA
<213> ORGANISM: Artificial Sequence
<220> FEATURE:
<223> OTHER INFORMATION: Synthetic

<400> SEQUENCE: 52
ggttagagtg gacagcccca ctatg                                            25

<210> SEQ ID NO 53
<211> LENGTH: 32
<212> TYPE: DNA
<213> ORGANISM: Artificial Sequence
<220> FEATURE:
<223> OTHER INFORMATION: Synthetic

<400> SEQUENCE: 53
tcctggggga ccagacggtc tcagacaatg ag                                    32

<210> SEQ ID NO 54
<211> LENGTH: 55
<212> TYPE: DNA
<213> ORGANISM: Artificial Sequence
<220> FEATURE:
<223> OTHER INFORMATION: Synthetic

<400> SEQUENCE: 54
ggtgcagacc gtactccatc cctccctgtg agcaccacgt caacggctcc cggcc           55

<210> SEQ ID NO 55
<211> LENGTH: 891
<212> TYPE: DNA
<213> ORGANISM: Artificial Sequence
<220> FEATURE:
<223> OTHER INFORMATION: Synthetic

<400> SEQUENCE: 55
cagagtccgc ccagtcatgc acagactcca gtggaagttt tgccaaactg aatggtctct      60
ttgacagccc tgtcaaggaa taccaacaga atattgattc tcctaaactg tatagtaacc     120

```
tgctaaccag tcggaaagag ctaccaccca atggagatac taaatccatg gtaatggacc      180
atcgagggca acctccagag ttggctgctc ttcctactcc tgagtctaca cccgtgcttc      240
accagaagac cctgcaggcc atgaagagcc actcagaaaa ggcccatggc catggagctt      300
caaggaaaga aaccctcag ttttttccgt ctagtccgcc acctcattcc ccattaagtc       360
atgggcatat ccccagtgcc attgttcttc caaatgctac ccatgactac aacacgtctt      420
tctcaaactc caatgctcac aaagctgaaa agaagcttca aaacattgat caccctctca      480
caaagtcatc cagtaagaga gatcaccggc gttctgttga ttccagaaat accctcaatg      540
atctcctgaa gcatctgaat gacccaaata gtaaccccaa agccatcatg ggagacatcc      600
agatggcaca ccagaactta atgctggatc ccatgggatc gatgtctgag gtcccaccta      660
aagtccctaa ccgggaggca tcgctatact cccctccttc aactctcccc agaaatagcc      720
caaccaagcg agtggatgtc cccaccactc ctggagtccc aatgacttct ctggaaagac      780
aaagaggtta tcacaaaaat tcctcccaga ggcactctat atctgctatg cctaaaaact      840
taaactcacc aaatggtgtt ttgttatcca gacagcctag tatgaaccgt g              891
```

<210> SEQ ID NO 56
<211> LENGTH: 97
<212> TYPE: DNA
<213> ORGANISM: Artificial Sequence
<220> FEATURE:
<223> OTHER INFORMATION: Synthetic

<400> SEQUENCE: 56

```
ttagccatcc tggtgatagt gattatggag gtgtacaaat cgtgggccaa gatgagactg      60
atgaccggcc tgaatgtccc tatggaccat cctgtta                              97
```

<210> SEQ ID NO 57
<211> LENGTH: 52
<212> TYPE: DNA
<213> ORGANISM: Artificial Sequence
<220> FEATURE:
<223> OTHER INFORMATION: Synthetic

<400> SEQUENCE: 57

```
cctccttctc agtagcagag tccagtgcct tgcagagcct gaagcctggg ga              52
```

<210> SEQ ID NO 58
<211> LENGTH: 39
<212> TYPE: DNA
<213> ORGANISM: Artificial Sequence
<220> FEATURE:
<223> OTHER INFORMATION: Synthetic

<400> SEQUENCE: 58

```
gttgccagag gtgtactgtg tcatcagccg ccttggctg                             39
```

<210> SEQ ID NO 59
<211> LENGTH: 147
<212> TYPE: DNA
<213> ORGANISM: Artificial Sequence
<220> FEATURE:
<223> OTHER INFORMATION: Synthetic

<400> SEQUENCE: 59

```
gtgcatcaag tacatgcggc agatctcgga gggagtggag tacatccaca agcagggcat      60
cgtgcacctg gacctcaagc cggagaacat catgtgtgtc aacaagacgg gcaccaggat      120
caagctcatc gactttggtc tggccag                                         147
```

<210> SEQ ID NO 60
<211> LENGTH: 109
<212> TYPE: DNA
<213> ORGANISM: Artificial Sequence
<220> FEATURE:
<223> OTHER INFORMATION: Synthetic

<400> SEQUENCE: 60
ttgggtcagt tccaacatgc cctggatgag ctcctggcat ggctgacaca caccgagggc    60
ttgctaagtg agcagaaacc tgttggagga gaccctaaag ccattgaaa             109

<210> SEQ ID NO 61
<211> LENGTH: 44
<212> TYPE: DNA
<213> ORGANISM: Artificial Sequence
<220> FEATURE:
<223> OTHER INFORMATION: Synthetic

<400> SEQUENCE: 61
tttgaagatt ctgcaaccgg ggcacagcca cctttataac aacc                  44

<210> SEQ ID NO 62
<211> LENGTH: 54
<212> TYPE: DNA
<213> ORGANISM: Artificial Sequence
<220> FEATURE:
<223> OTHER INFORMATION: Synthetic

<400> SEQUENCE: 62
tgcttgccat atccaattga acacccctac cacacacaca tctgtcgcgg cgcc        54

<210> SEQ ID NO 63
<211> LENGTH: 138
<212> TYPE: DNA
<213> ORGANISM: Artificial Sequence
<220> FEATURE:
<223> OTHER INFORMATION: Synthetic

<400> SEQUENCE: 63
tctggagtca atacctggcg agatcaactg agaccaacac agctgcttca aaatgtcgcc    60
agattcaaag gcttcccaca acccatcctt tccgaagatg ggagtagaat cagatatgga   120
ggacgagact acagcttg                                                138

<210> SEQ ID NO 64
<211> LENGTH: 61
<212> TYPE: DNA
<213> ORGANISM: Artificial Sequence
<220> FEATURE:
<223> OTHER INFORMATION: Synthetic

<400> SEQUENCE: 64
aaagctggac aagatctggc ctaagcttcg ggtcctggcg cgatcttctc ccactgacaa    60
g                                                                  61

<210> SEQ ID NO 65
<211> LENGTH: 27
<212> TYPE: DNA
<213> ORGANISM: Artificial Sequence
<220> FEATURE:
<223> OTHER INFORMATION: Synthetic

<400> SEQUENCE: 65

```
gtaggagagt tgagtgctgc aatggat                                          27

<210> SEQ ID NO 66
<211> LENGTH: 81
<212> TYPE: DNA
<213> ORGANISM: Artificial Sequence
<220> FEATURE:
<223> OTHER INFORMATION: Synthetic

<400> SEQUENCE: 66
gttcaccaac ccatgcaaga ccatgaagtt catcgtgtgg cgccgcttta agtgggtcat      60
catcggcttg ctgttcctgc t                                                81

<210> SEQ ID NO 67
<211> LENGTH: 126
<212> TYPE: DNA
<213> ORGANISM: Artificial Sequence
<220> FEATURE:
<223> OTHER INFORMATION: Synthetic

<400> SEQUENCE: 67
ttcggatcta ccctctgccg gatgacccca gcgtgccagc ccctcccaga cagtttcggg      60
aattacctga cagcgtccca caggaatgca cggttaggat ttacattgtt cgaggcttag     120
agctcc                                                                126

<210> SEQ ID NO 68
<211> LENGTH: 118
<212> TYPE: DNA
<213> ORGANISM: Artificial Sequence
<220> FEATURE:
<223> OTHER INFORMATION: Synthetic

<400> SEQUENCE: 68
tctggtcttt gagaagtgcg agctggcgac ctgcactccc cgggaacctg gagtggctgg      60
cggagacgtc tgctcctccg actccttcaa cgaggacatc gcggtcttcg ccaagcag       118

<210> SEQ ID NO 69
<211> LENGTH: 41
<212> TYPE: DNA
<213> ORGANISM: Artificial Sequence
<220> FEATURE:
<223> OTHER INFORMATION: Synthetic

<400> SEQUENCE: 69
gtacaggaca gccagcgtca tcattgcttt gactgatgga g                          41

<210> SEQ ID NO 70
<211> LENGTH: 36
<212> TYPE: DNA
<213> ORGANISM: Artificial Sequence
<220> FEATURE:
<223> OTHER INFORMATION: Synthetic

<400> SEQUENCE: 70
ctgaggtcac ccagtcagag attgctcaga agcaaa                                36

<210> SEQ ID NO 71
<211> LENGTH: 156
<212> TYPE: DNA
<213> ORGANISM: Artificial Sequence
<220> FEATURE:
<223> OTHER INFORMATION: Synthetic

<400> SEQUENCE: 71
```

```
tttccaccgc aaagcatcag tgatcatggt agacgagctg ctgtcagcct acccacacca    60
gctttccttc tctgaggctg gccttcgaat catgataacc agccactttc cccccaagac   120
ccggctctcc atggccagtc gcatgttgat caatga                             156
```

<210> SEQ ID NO 72
<211> LENGTH: 42
<212> TYPE: DNA
<213> ORGANISM: Artificial Sequence
<220> FEATURE:
<223> OTHER INFORMATION: Synthetic

<400> SEQUENCE: 72

```
cggcagcggt ggaaggccct tttgtcacct tggacatgga ag                       42
```

<210> SEQ ID NO 73
<211> LENGTH: 96
<212> TYPE: DNA
<213> ORGANISM: Artificial Sequence
<220> FEATURE:
<223> OTHER INFORMATION: Synthetic

<400> SEQUENCE: 73

```
cggcggccca tggactcaag gctggagcac gtggactttg agtgcctttt tacctgcctc    60
agtgtgcgcc agctcatccg aatctttgcc tcactg                              96
```

<210> SEQ ID NO 74
<211> LENGTH: 27
<212> TYPE: DNA
<213> ORGANISM: Artificial Sequence
<220> FEATURE:
<223> OTHER INFORMATION: Synthetic

<400> SEQUENCE: 74

```
tacgatgagc tgccccatta cggcggg                                        27
```

<210> SEQ ID NO 75
<211> LENGTH: 29
<212> TYPE: DNA
<213> ORGANISM: Artificial Sequence
<220> FEATURE:
<223> OTHER INFORMATION: Synthetic

<400> SEQUENCE: 75

```
tgcgggacca caatagcgag ctccgcttc                                      29
```

<210> SEQ ID NO 76
<211> LENGTH: 81
<212> TYPE: DNA
<213> ORGANISM: Artificial Sequence
<220> FEATURE:
<223> OTHER INFORMATION: Synthetic

<400> SEQUENCE: 76

```
ctgctcgttg ctctgtctca gtatttccgc gcaccaattc gactcccaga ccatgtttcc    60
atccaagtgg ttgtggtcca g                                              81
```

<210> SEQ ID NO 77
<211> LENGTH: 31
<212> TYPE: DNA
<213> ORGANISM: Artificial Sequence
<220> FEATURE:
<223> OTHER INFORMATION: Synthetic -continued

<400> SEQUENCE: 77
ggctgtggtg tctcttcatt gggattggag a                              31

<210> SEQ ID NO 78
<211> LENGTH: 136
<212> TYPE: DNA
<213> ORGANISM: Artificial Sequence
<220> FEATURE:
<223> OTHER INFORMATION: Synthetic

<400> SEQUENCE: 78
tgcagggagt tccagcgagg aaactgtgcc cggggagaga ccgactgccg ctttgcacac    60
cccgcagaca gcaccatgat cgacacaagt gacaacaccg taaccgtttg tatggattac   120 ataaagggc gttgca                                                   136

<210> SEQ ID NO 79
<211> LENGTH: 119
<212> TYPE: DNA
<213> ORGANISM: Artificial Sequence
<220> FEATURE:
<223> OTHER INFORMATION: Synthetic

<400> SEQUENCE: 79
gagcccagtg aaggcctcat attccctgg gttctgaata taactagagc cccttagccc    60
caacggcttt cctaaatttt ccacatccaa gcctaacagt ctccccatgt gtttgtgta   119

<210> SEQ ID NO 80
<211> LENGTH: 49
<212> TYPE: DNA
<213> ORGANISM: Artificial Sequence
<220> FEATURE:
<223> OTHER INFORMATION: Synthetic

<400> SEQUENCE: 80
gcctttgaca ccttgttcga ccatgcccca gacaagctga atgtggtga              49

<210> SEQ ID NO 81
<211> LENGTH: 178
<212> TYPE: DNA
<213> ORGANISM: Artificial Sequence
<220> FEATURE:
<223> OTHER INFORMATION: Synthetic

<400> SEQUENCE: 81
ggagaagaac ctgctacagg aacagctgca ggcagagaca gagctgtatg cagaggctga    60
ggagatgcgg gtgcggctgg cggccaagaa gcaggagctg gaggagatac tgcatgagat   120
ggaggcccgc ctggaggagg aggaagacag gggccagcag ctacaggctg aaaggaag    178

<210> SEQ ID NO 82
<211> LENGTH: 46
<212> TYPE: DNA
<213> ORGANISM: Artificial Sequence
<220> FEATURE:
<223> OTHER INFORMATION: Synthetic

<400> SEQUENCE: 82
ctccttgagg agaggattag tgacttaacg acaaatcttg cagaag                  46

<210> SEQ ID NO 83
<211> LENGTH: 63
<212> TYPE: DNA
<213> ORGANISM: Artificial Sequence

```
<220> FEATURE:
<223> OTHER INFORMATION: Synthetic

<400> SEQUENCE: 83
aaggggttct gaggtccata ccaagaagac ggtgatgatc aagaccatcg agacacggga    60
tgg                                                                 63

<210> SEQ ID NO 84
<211> LENGTH: 29
<212> TYPE: DNA
<213> ORGANISM: Artificial Sequence
<220> FEATURE:
<223> OTHER INFORMATION: Synthetic

<400> SEQUENCE: 84
gaagaagatc aatgagtcaa cccaaaatt                                     29

<210> SEQ ID NO 85
<211> LENGTH: 194
<212> TYPE: DNA
<213> ORGANISM: Artificial Sequence
<220> FEATURE:
<223> OTHER INFORMATION: Synthetic

<400> SEQUENCE: 85
gccaaggcga acctagacaa gaataagcag acgctggaga agagaacgc agacctggcc    60 ggggagctgc gggtcctggg ccaggccaag caggaggtgg aacataagaa gaagaagctg   120
gaggcgcagg tgcaggagct gcagtccaag tgcagcgatg gggagcgggc ccgggcggag   180
ctcaatgaca aagt                                                    194

<210> SEQ ID NO 86
<211> LENGTH: 186
<212> TYPE: DNA
<213> ORGANISM: Artificial Sequence
<220> FEATURE:
<223> OTHER INFORMATION: Synthetic

<400> SEQUENCE: 86
tctcttccaa atacgcggat gagagggaca gagctgaggc agaagccagg gagaaggaaa    60
ccaaggccct gtccctggct cgggcccttg aagaggcctt ggaagccaaa gaggaactcg   120
agcggaccaa caaaatgctc aaagccgaaa tggaagacct ggtcagctcc aaggatgacg   180
tgggca                                                             186

<210> SEQ ID NO 87
<211> LENGTH: 146
<212> TYPE: DNA
<213> ORGANISM: Artificial Sequence
<220> FEATURE:
<223> OTHER INFORMATION: Synthetic

<400> SEQUENCE: 87
gcctcttctg cgtggtggtc aaccccctata aacacctgcc catctactcg gagaagatcg   60
tcgacatgta caagggcaag aagaggcacg agatgccgcc tcacatctac gccatcgcag   120
acacggccta ccggagcatg cttcaa                                       146

<210> SEQ ID NO 88
<211> LENGTH: 67
<212> TYPE: DNA
<213> ORGANISM: Artificial Sequence
<220> FEATURE:
```

<223> OTHER INFORMATION: Synthetic

<400> SEQUENCE: 88

| tgaagcccca cgacattttt gaggccaacg acctgtttga gaacaccaac catacacagg | 60 |
|---|---|
| tgcagtc | 67 |

<210> SEQ ID NO 89
<211> LENGTH: 1511
<212> TYPE: DNA
<213> ORGANISM: Artificial Sequence
<220> FEATURE:
<223> OTHER INFORMATION: Synthetic

<400> SEQUENCE: 89

| cttgagtccc tgagaatgcc tagcaaagtc ctcaacttac ttaatttcag atatgtcacc | 60 |
|---|---|
| tcctaatctg ggtccaagga gtataatatt tttaatgagt caaaaatcca actcagattg | 120 |
| acctaaaata tatttatctt ctttgcacac ttaaaaaatc caggagcacc ccaaaataga | 180 |
| catgtaccgt tatattaagt aagcaggaga cttaggattt gtgctgtagc cacaagaaag | 240 |
| acagtgatca gtgatatcaa acatcaggaa tcagccttta tgtaacataa cagctgtcct | 300 |
| cctatggtga aaggttcaaa tgtagtgaag gtataaccta tattgactga gatttccctt | 360 |
| ttaggtagtg ccttatctct attactagtg ttaaaggaat aaggaatcta tgaaggacag | 420 |
| ggagcagctc tggtctgtca atctcagcca cctgtttgat atcacagaga agatactcgg | 480 |
| aggattgttg gaatgtatat agtttagtaa gaagtgggta agaaagaggg tcttaattac | 540 |
| tgagcactta ttatgtatta ggttctttgc cagatgtttt tacatatata aactcatttc | 600 |
| agaaaactta tttaaagtaa atggggccgg gtatggtggt tcatgcctgg aatcctagca | 660 |
| ctttgggagg ctgaggtagg aggactgctt gaggccggga gttggagacc agcctgagca | 720 |
| acatagtgag accctgtctc aataataata ataataatag taataatgaa gtaaatggga | 780 |
| taaggaaaga aggataatta tctttaaagg ttgattccca ccctccctcc ccagttactt | 840 |
| aaggaactaa gtgagtacat ctccagttgc ccatgaaagc ataagtttgt tttcctcagc | 900 |
| tgaggcaagt ggtagagtat acaggataac gaagtaacat gtaaaaggca ggacgcacat | 960 |
| aaaggtgtac atggctattg tttcacctgg agaaaccaca tgattgggac ctgaaggttt | 1020 |
| actgactgac tacaggggct gattgtgaag cacgaggaac cccatgtgtg tggagactgt | 1080 |
| agggtgagag cacacaatta ttagcatcat ttctgagtga tctcacagat ttttttttctt | 1140 |
| gtgtttgctt tgcttttttga caactgcttc tcccacgttc cttgcaattc tattctctca | 1200 |
| ccttcacttt actatttgta ttcgatggac caggataatt caggcaaggt taccttgtaa | 1260 |
| actttaattg gccacacacc atgttgtcac ccagctggct atgaagtgaa taatggtact | 1320 |
| gaaagtaaac ctgaagacct ttctcagatc tattttaagt ctgagtctga ccaaccatgg | 1380 |
| aaaatattcg acatgaatta atgtagagaa ctataaagca tttatgacag ctccaagaaa | 1440 |
| aatcatctac tctatgcagg agatatgttt agagacctct cagaaaaact tgcctggttt | 1500 |
| gagggtacac a | 1511 |

<210> SEQ ID NO 90
<211> LENGTH: 110
<212> TYPE: DNA
<213> ORGANISM: Artificial Sequence
<220> FEATURE:
<223> OTHER INFORMATION: Synthetic

<400> SEQUENCE: 90

```
acggacaagt ctttcgtgga gaagctgtgc acggagcagg gcagccaccc caagttccag      60
aagcccaagc agctcaagga caagactgag ttctccatca tccattatgc                110
```

<210> SEQ ID NO 91
<211> LENGTH: 27
<212> TYPE: DNA
<213> ORGANISM: Artificial Sequence
<220> FEATURE:
<223> OTHER INFORMATION: Synthetic
<400> SEQUENCE: 91

```
gagaatgagc ttaaggagct ggaacag                                          27
```

<210> SEQ ID NO 92
<211> LENGTH: 27
<212> TYPE: DNA
<213> ORGANISM: Artificial Sequence
<220> FEATURE:
<223> OTHER INFORMATION: Synthetic
<400> SEQUENCE: 92

```
ggggcaacca atggaaaaga caagaca                                          27
```

<210> SEQ ID NO 93
<211> LENGTH: 53
<212> TYPE: DNA
<213> ORGANISM: Artificial Sequence
<220> FEATURE:
<223> OTHER INFORMATION: Synthetic
<400> SEQUENCE: 93

```
tgcttcaaga agaaacccgg cagaagctca acgtgtctac gaagctgcgc cag             53
```

<210> SEQ ID NO 94
<211> LENGTH: 112
<212> TYPE: DNA
<213> ORGANISM: Artificial Sequence
<220> FEATURE:
<223> OTHER INFORMATION: Synthetic
<400> SEQUENCE: 94

```
acaaatccta tcactatacc gactcactac tacagaggga aaatgaaagg aatctatttt      60
caaggcagaa agcacctttg gcaagtttca atcacagctc ggcactgtat tc             112
```

<210> SEQ ID NO 95
<211> LENGTH: 106
<212> TYPE: DNA
<213> ORGANISM: Artificial Sequence
<220> FEATURE:
<223> OTHER INFORMATION: Synthetic
<400> SEQUENCE: 95

```
agcaaaatct tcttccgaac tggcgtcctg gcccacctag aggaggagcg agatttgaag      60
atcaccgatg tcatcatggc cttccaggcg atgtgtcgtg gctact                   106
```

<210> SEQ ID NO 96
<211> LENGTH: 30
<212> TYPE: DNA
<213> ORGANISM: Artificial Sequence
<220> FEATURE:
<223> OTHER INFORMATION: Synthetic
<400> SEQUENCE: 96

```
gtgtggaaac catctgttgt ggaagagtaa                                       30
```

<210> SEQ ID NO 97
<211> LENGTH: 807
<212> TYPE: DNA
<213> ORGANISM: Artificial Sequence
<220> FEATURE:
<223> OTHER INFORMATION: Synthetic

<400> SEQUENCE: 97

```
tctacagttt tgcaccacgg caagaaaacc aaaaccaaa acaaacaaac aaaaaaaacc        60
caacaacaac ccagaacaaa gcaaaaccca gcagactgta cttagcattg tctaaatcca      120
ttctcaaatt ccaaatatca cagacacccc tcacacaagg aatataaaaa ccaccaccct      180
ccagcctggg caacgtagta aaacctcatc tatacaagaa tttaaaaata agctgggcgt      240
ggtggtacac acctgtggtc ccagctacta gggaggctga gccaggaaga acgctccagc      300
ccaggacttc gaggctgcaa tgagctataa ttgcatcatt gcactccagc ctgggcaaca      360
gagaccctgt ctcaaccacc accaccacca caccccctac taccccctgta ttcaaggtaa      420
aaattgaagt ttgtatgatg taagagatga gaaaaaccca acaggaaaca cagacacatc      480
ctccagttct atcaatggat tgtgcagaca ctgagttttt agaaaaacat atccacggta      540
accggtccct ggcaattctg tttacatgaa atggggagaa agtcaccgaa atgggtgccg      600
ccggccccca ctcccaattc attccctaac ctgcaaacct ttccaacttc tcacgtcagg      660
cctttgagaa ttctttcccc ctctcctggt ttccacacct cagacacgca cagttcacca      720
agtgccttct gtagtcacat gaattgaaaa ggagacgctg ctcccacgga ggggagcagg      780
aatgctgcac tgtttacacc ctgactg                                          807
```

<210> SEQ ID NO 98
<211> LENGTH: 783
<212> TYPE: DNA
<213> ORGANISM: Artificial Sequence
<220> FEATURE:
<223> OTHER INFORMATION: Synthetic

<400> SEQUENCE: 98

```
cagcagttga tacctagcag cgttattgat gggcattaat ctatgttagt tggcacctta       60
agatactagt gcagctagat ttcatttagg gaaatcacca gtaacttgac tgaccaattg      120
attttagaga gaaagtaacc aaaccaaata tttatctggg caaagtcata aattctccac      180
ttgaatgcgc tcatgaaaaa taaggccaaa acaagagttc tgggccacag ctcagcccag      240
agggttcctg gggatgggag gcctctctct ccccaccccc tgactctaga gaactgggtt      300
ttctcccagt actccagcaa ttcatttctg aaagcagttg agccacttta ttccaaagta      360
cactgcagat gttcaaactc tccatttctc tttcccttc cacctgccag ttttgctgac      420
tctcaacttg tcatgagtgt aagcattaag gacattatgc ttcttcgatt ctgaagacag      480
gtccctgctc atggatgact ctggcttcct taggaaaata ttttcttcc aaaatcagta      540
ggaaatctaa acttatcccc tctttgcaga tgtctagcag cttcagacat ttggttaaga      600
acccatggga aaaaaaaaat ccttgctaat gtggtttcct ttgtaaacca ggattcttat      660
ttgtgctgtt atagaatatc agctctgaac gtgtggtaaa gatttttgtg tttgaatata      720
ggagaaatca gtttgctgaa aagttagtct taattatcta ttggccacga tgaaacagat      780
ttc                                                                    783
```

```
<210> SEQ ID NO 99
<211> LENGTH: 2261
<212> TYPE: DNA
<213> ORGANISM: Artificial Sequence
<220> FEATURE:
<223> OTHER INFORMATION: Synthetic

<400> SEQUENCE: 99
```

| | | | | | |
|---|---|---|---|---|---|
| ggccgaggga | gtctatgaaa | atctcccctt | ttttactttt | ttaaagagta | ctcccggcat | 60 |
| ggtcaatttc | ctttatagtt | aatccgtaaa | ggtttccagt | taattcatgc | cttaaaaggc | 120 |
| actgcaattt | tattttgag | ttgggactt | tacaaaacac | ttttttccct | ggagtcttct | 180 |
| ctccacttct | ggagatgaat | ttctatgttt | tgcacctggt | cacagacatg | gcttgcatct | 240 |
| gtttgaaact | acaattaatt | atagatgtca | aaacattaac | cagattaaag | taatatattt | 300 |
| aagagtaaat | tttgcttgca | tgtgctaata | tgaaataaca | gactaacatt | ttaggggaaa | 360 |
| aataaataca | atttagactc | taaaaagtct | tttcaaaaag | aaatgggaaa | taggcagact | 420 |
| gtttatgtta | aaaaaattct | tgctaaatga | tttcatcttt | aggaaaaaat | tacttgccat | 480 |
| atagagctaa | attcatctta | agacttgaat | gaattgcttt | ctatgtacag | aactttaaac | 540 |
| aatatagtat | ttatggcgag | gacagctgta | gtctgttgtg | atatttcaca | ttctatttgc | 600 |
| acaggttccc | tggcactggt | agggtagatg | attattggga | atcgcttaca | gtaccatttc | 660 |
| attttttggc | actaggtcat | taagtagcac | acagtctgaa | tgccttttc | tggagtggcc | 720 |
| agttcctatc | agactgtgca | gacttgcgct | tctctgcacc | ttatcccta | gcacccaaac | 780 |
| atttaatttc | actggtggga | ggtagacctt | gaagacaatg | aagagaatgc | cgatactcag | 840 |
| actgcagctg | gaccggcaag | ctggctgtgt | acaggaaaat | tggaagcaca | cagtggactg | 900 |
| tgcctcttaa | agatgccttt | cccaaccctc | cattcatggg | atgcaggtct | ttctgagctc | 960 |
| aagggtgaaa | gatgaataca | ataacaacca | tgaacccacc | tcacggaagc | ttttttttgca | 1020 |
| ctttgaacag | aagtcattgc | agttggggtg | ttttgtccag | ggaaacagtt | tattaaatag | 1080 |
| aaggatgttt | tggggaagga | actggatatc | tctcctgcag | cccagcaccg | agatacccag | 1140 |
| gacgggcctg | gggggcgaga | aaggccccca | tgctcatggg | ccgcggagtg | tggacctgta | 1200 |
| gataggcacc | accgagttta | agatactggg | atgagcatgc | ttcattggat | tcattttatt | 1260 |
| ttacacgtca | gtattgtttt | aaagtttctg | tctgtaaagt | gtagcatcat | atataaaaag | 1320 |
| agtttcgcta | gcagcgcatt | tttttagtt | caggctagct | tctttcacat | aatgctgtct | 1380 |
| cagctgtatt | tccagtaaca | cagcatcatc | gcactgactg | tggcgcactg | gggaataaca | 1440 |
| gtctgagcta | gcaccaccct | cagccaggct | acaacgacag | cactggaggg | tcttccctct | 1500 |
| cagattcacc | tggaggccct | cagaccccca | gggtgcacgt | ctccccaggt | cctgggagtg | 1560 |
| gctaccgcag | gtagtttctg | gagagcacgt | tttcttcatt | gataagtgga | ggagaaatgc | 1620 |
| agcacagctt | tcaagatact | attttaaaaa | caccatgaat | cagatagga | aagaaagttg | 1680 |
| attggaatag | caagtttaaa | cctttgttgt | ccatctgcca | aatgaactag | tgattgtcag | 1740 |
| actggtatgg | aggtgactgc | tttgtaaggt | tttgtcgttt | ctaatacaga | cagagatgtg | 1800 |
| ctgattttgt | tttagctgta | acaggtaatg | gttttggat | agatgattga | ctggtgagaa | 1860 |
| tttggtcaag | gtgacagcct | cctgtctgat | gacaggacag | actggtggtg | aggagtctaa | 1920 |
| gtgggctcag | tttgatgtca | gtgtctgggc | tcatgacttg | taaatggaag | ctgatgtgaa | 1980 |
| caggtaatta | atattatgac | ccacttctat | ttactttggg | aaatatcttg | gatcttaatt | 2040 |
| atcatctgca | agtttcaaga | agtattctgc | caaaagtatt | tacaagtatg | gactcatgag | 2100 |

```
ctattgttgg ttgctaaatg tgaatcacgc gggagtgagt gtgcccttca cactgtgaca    2160
ttgtgacatt gtgacaagct ccatgtcctt taaaatcagt cactctgcac acaagagaaa    2220
tcaacttcgt ggttggatgg ggccggaaca caaccagtct t                         2261

<210> SEQ ID NO 100
<211> LENGTH: 230
<212> TYPE: DNA
<213> ORGANISM: Artificial Sequence
<220> FEATURE:
<223> OTHER INFORMATION: Synthetic

<400> SEQUENCE: 100
cagcttgcag cccaaccgag atacaaacag aacatcattg caagaactca ggccccatct      60
gactacccct cccctgaaga ctcaaagagg gaccgtcttt ttggcgagca ggcctgttga     120
gtgtgggtga tttcttggct cagctagaag catccctcca gaaggggggcc cgttttgtga    180 aatgagaata agccctttcc ttccatagcg agatcttcct ccacgtcggg                 230

<210> SEQ ID NO 101
<211> LENGTH: 26
<212> TYPE: DNA
<213> ORGANISM: Artificial Sequence
<220> FEATURE:
<223> OTHER INFORMATION: Synthetic

<400> SEQUENCE: 101
ctgccaccag agaccgtcct cacccc                                           26

<210> SEQ ID NO 102
<211> LENGTH: 144
<212> TYPE: DNA
<213> ORGANISM: Artificial Sequence
<220> FEATURE:
<223> OTHER INFORMATION: Synthetic

<400> SEQUENCE: 102
cctctacagg gttagagttt ggagagagca gactggcggg gggcccattg gggggaaggg      60
gaccctccgc tctgtagtgc tacagggtcc aacatagagc cgggtgtccc caacagcgcc    120
caaaggacgc actgagcaac gcta                                            144

<210> SEQ ID NO 103
<211> LENGTH: 46
<212> TYPE: DNA
<213> ORGANISM: Artificial Sequence
<220> FEATURE:
<223> OTHER INFORMATION: Synthetic

<400> SEQUENCE: 103
caaggatccc ctcgagacta ctctgttacc agtcatgaaa cattaa                     46

<210> SEQ ID NO 104
<211> LENGTH: 122
<212> TYPE: DNA
<213> ORGANISM: Artificial Sequence
<220> FEATURE:
<223> OTHER INFORMATION: Synthetic

<400> SEQUENCE: 104
cccagatgtc attcgtgctg aaagaaccag aacaactctc tgctccctgc caagcatgaa      60
gcggttgtga ccccaggaaa ccacagtgac tttgactctg gttcagctga catgctcgag    120
tc                                                                    122
```

<210> SEQ ID NO 105
<211> LENGTH: 65
<212> TYPE: DNA
<213> ORGANISM: Artificial Sequence
<220> FEATURE:
<223> OTHER INFORMATION: Synthetic

<400> SEQUENCE: 105
cagtggcgtt tgtaatgaga gcactttctt tttttctat tcactggag cacaataaat    60 ggctg    65

<210> SEQ ID NO 106
<211> LENGTH: 78
<212> TYPE: DNA
<213> ORGANISM: Artificial Sequence
<220> FEATURE:
<223> OTHER INFORMATION: Synthetic

<400> SEQUENCE: 106
ggagcaaact gcatgcccag agcccagcg gacacacgcg gtttggtttg cagcgactgg    60
catactatgt ggatgtga    78

<210> SEQ ID NO 107
<211> LENGTH: 60
<212> TYPE: DNA
<213> ORGANISM: Artificial Sequence
<220> FEATURE:
<223> OTHER INFORMATION: Synthetic

<400> SEQUENCE: 107
tggtccccaa cagcgacata gcccatccct gcctggtcac agggcatgcc ccggccacct    60

<210> SEQ ID NO 108
<211> LENGTH: 75
<212> TYPE: DNA
<213> ORGANISM: Artificial Sequence
<220> FEATURE:
<223> OTHER INFORMATION: Synthetic

<400> SEQUENCE: 108
caagcaacag aggaccaatg caacaagaac acaaatgtga aatcatgggc tgactgagac    60
aattctgtcc atgta    75

<210> SEQ ID NO 109
<211> LENGTH: 247
<212> TYPE: DNA
<213> ORGANISM: Artificial Sequence
<220> FEATURE:
<223> OTHER INFORMATION: Synthetic

<400> SEQUENCE: 109
tgcagccatg gtcacgagtc atttctgcct gactgctcca gctaacttcc agggtctcag    60
caaactgctg ttttcacga gtatcaactt tcatactgac gcgtctgtaa tctgttctta   120
tgctcatttt gtattttcct ttcaactcca ggaatatcct tgagcatatg agagtcacat   180
ccaggtgatg tgctctggta tggaatttga accccaatg gggccttggc actaagactg   240
gaatgta    247

<210> SEQ ID NO 110
<211> LENGTH: 37
<212> TYPE: DNA

<213> ORGANISM: Artificial Sequence
<220> FEATURE:
<223> OTHER INFORMATION: Synthetic

<400> SEQUENCE: 110
ggctctgtca ctgagcaatg gtaactgcac ctgggca        37

<210> SEQ ID NO 111
<211> LENGTH: 687
<212> TYPE: DNA
<213> ORGANISM: Artificial Sequence
<220> FEATURE:
<223> OTHER INFORMATION: Synthetic

<400> SEQUENCE: 111
gctgctgtca caaatacccca tcttaggatc ccatcagctt cccatccccc accagacagc    60
cacagtaccc tcactttctc cctattgttc tttcaaatcc tgttctcagg aaagaaactg    120
ccactaattc attcacacta aggtgtaaat gattgataat aggaatgagt tacctcttcc    180
cacagacatt tgtttttaag tatgacagag cagggcctta atcccaaggg aaaaggttat    240
ggaactggag ggggtgagct ttctgggtag aaggagactt cctgaatttc cttaaaaccc    300
agtaagagta agacctgttg ttttggaagg tctgctccac catctaagag cactgttttt    360 tttttttttgt tgttgttgtt gttttacggt ctctgaggga atatagtaaa aatgcatatg    420
cacgtgcaat ttgcacggca gcatttcacc gattgtggac tgtattggct aatgtgtttc    480
ctggtcttta gatgcaaacc attaataaca ctatcttatc tcatagtttt ttcaggggtg    540
cttcttgatt agtagggaat tttgaacacc tctttaaata cagctagaaa ataaaaccaa    600
tttgtaaagc cacatttgca tatgatgcca gcctcacgca tttgtatatc tccagaaatt    660
caggtatgcc tcaccaattt gcccgtc    687

<210> SEQ ID NO 112
<211> LENGTH: 210
<212> TYPE: DNA
<213> ORGANISM: Artificial Sequence
<220> FEATURE:
<223> OTHER INFORMATION: Synthetic

<400> SEQUENCE: 112
tcttctgttg caggactaac ctttgagaaa tccttttgtg aagtcattgc ctgctcaaga    60
atgtacagtg gctccccaat gccttggagg ccataaggcc agccagttct agctctctat    120
tacctgtccc cactcaactg actcatacct gtttccggct gcatcactat gtgccccaca    180
gagaacgatg atcgtcacct ctgtgcctga    210

<210> SEQ ID NO 113
<211> LENGTH: 107
<212> TYPE: DNA
<213> ORGANISM: Artificial Sequence
<220> FEATURE:
<223> OTHER INFORMATION: Synthetic

<400> SEQUENCE: 113
atcattgaat ggatcggcta tgccctggcc acttggtccc tcccagcact tgcatttgca    60
tttttctcac tttgtttcct tgggctgcga gcttttcacc accatag    107

<210> SEQ ID NO 114
<211> LENGTH: 373
<212> TYPE: DNA
<213> ORGANISM: Artificial Sequence
<220> FEATURE:
<223> OTHER INFORMATION: Synthetic

<400> SEQUENCE: 114

```
tccagtgttc gccattccag atgtcacttt gcgtcctcag aggggactct ggggcagcca      60
ccatggccgg cttgtctgga ggcccttgga gatctaggat gggcgctggt cgtggctttg     120
gagaactttc cttctccaaa caaatgcagg aaactcaaga ttcagcatcc tagaattgtc     180
tctggcaagt tggtttccag ccatagtgag tgggaacaat ggccccagag gctgtgtggc     240
agtttaaaca cagtttccac tgccttccct tccctaaag agtaaacaca ggagataata      300
ctttctaaca actcatcgtt atcaagggcc tactatgtgc tgcttgtttt ggctgcatgc     360
gtaaacacat ctc                                                        373
```

<210> SEQ ID NO 115
<211> LENGTH: 58
<212> TYPE: DNA
<213> ORGANISM: Artificial Sequence
<220> FEATURE:
<223> OTHER INFORMATION: Synthetic

<400> SEQUENCE: 115

```
gtcagatccg agctcgccat ccagtttcct ctccactagt ccccccagtt ggagatct       58
```

<210> SEQ ID NO 116
<211> LENGTH: 114
<212> TYPE: DNA
<213> ORGANISM: Artificial Sequence
<220> FEATURE:
<223> OTHER INFORMATION: Synthetic

<400> SEQUENCE: 116

```
tataaccttt gtgtgcgtgt atgttgtgtg tgtgcatgtg tggcgtatat gtgtgttaca      60
ggttaatgcc ttcttggaat tgtgttaatg ttctcttggt ttattatgcc atca           114
```

<210> SEQ ID NO 117
<211> LENGTH: 47
<212> TYPE: DNA
<213> ORGANISM: Artificial Sequence
<220> FEATURE:
<223> OTHER INFORMATION: Synthetic

<400> SEQUENCE: 117

```
tccaaatcat tcctagccaa agctctgact cgttacctat gtgtttt                   47
```

<210> SEQ ID NO 118
<211> LENGTH: 122
<212> TYPE: DNA
<213> ORGANISM: Artificial Sequence
<220> FEATURE:
<223> OTHER INFORMATION: Synthetic

<400> SEQUENCE: 118

```
tgtgattcta agtcaggccc ttgtgactga accaccatga ggctggactg tggggactcg      60
ggtatcccag aggcagagca caccaggtct gggaggggg ccactcagac ggcaacattg      120
tc                                                                    122
```

<210> SEQ ID NO 119
<211> LENGTH: 728
<212> TYPE: DNA
<213> ORGANISM: Artificial Sequence
<220> FEATURE:

<223> OTHER INFORMATION: Synthetic

<400> SEQUENCE: 119

```
gatcacgccg ttatgttgcc tcaaatagtt ttagaagaga aaaaaaaata tatccttgtt      60
ttccacacta tgtgtgttgt tcccaaaaga atgactgttt tggttcatca gtgaattcac     120
catccaggag agactgtggt atatatttta aacctgttgg gccaatgaga aagaaccac      180
actggagatc atgatgaact tttggctgaa cctcatcact cgaactccag cttcaagaat     240
gtgttttcat gcccggcctt tgttcctcca taaatgtgtc ctttagtttc aaacagatct     300
ttatagttcg tgcttcataa gccaattctt attattattt tggggggact cttcttcaaa     360
gagcttgcca atgaagattt aaagacagag caggagcttc ttccaggagt tctgagcctt     420
ggttgtggac aaaacaatct taagttgggc agctttcctc aacacaaaaa aaagttatta     480
atggtcattg aaccataact aggactttat cagaaactca aagcttgggg gataaaaagg     540
agcaagagaa tactgtaaca aacttcgtac agagttcggt ctattaattg tttcatgtta     600
gatattctat gtgtttacct caattgaaaa aaaaaagaat gtttttgcta gtatcagatc     660
tgctgtggaa ttggtattgt atgtccatga attcttcttt tctcagcacg tgttcctcac     720
tagaagaa                                                              728
```

<210> SEQ ID NO 120
<211> LENGTH: 935
<212> TYPE: DNA
<213> ORGANISM: Artificial Sequence
<220> FEATURE:
<223> OTHER INFORMATION: Synthetic

<400> SEQUENCE: 120

```
ttgggttgtc actctagagc atgtcaaact ttgtacttca aaatatattt agtatgattg      60
ttagtggtaa catatatcaa ggctttgaat taactgtttt atttaatttt cacaagaagc     120
acttatttta gccataggaa aaccaatctg agctacaaat agttctttaa ataagcccca     180
ggttatttag ctattctaga aagtgccgac ttctttcaag aagcaggcat tgtaggacag     240
ctgagaatta tcacatagcc taaattctag cctggcagca agagtcacat ctgagatgtc     300
caaaaaaaaa aaaaaaacac ctgatctaca ttgaaagggg gtagactaac gtatgtgaga     360
ccatttccct atttgcagtt acaaggttaa agaactttga aggtcattcg gctgctaaga     420
ggcatgtcga acactctgtg tggctctttc acagtaaacc ctcctaagag cagaagacac     480
atggctgtta gtgtctgcgt ttagatttaa tttctcaaat aaaggcccctt ggctgcgtat     540
catttcatcc agttataaac tagggctcct gcaagcaccc ccattctaag ggtgaattat     600
tgaaatcagt tgctatttga tgagtcacaa ctggcccagc aggcagggca tttgaagtca     660
tggtcatcaa aaagaaatga tgttttttg aaaagctaaa tgcttaaaat gcttctagag     720
ggaagtcgtg gggcgtgtgc tcattctctt taaaatcagg gttgttgagt ttgttttaa      780
acattttat aagttcatga gaaaaatat ataaattcta agaaccaaca ctgtattccc       840
agaaacatga ccctcgctgg tcttgggtcc acatatcatt ggactctggg ggacacaaag     900
atgcctgtga cactttggtg ttgccgagtt agtca                                 935
```

<210> SEQ ID NO 121
<211> LENGTH: 396
<212> TYPE: DNA
<213> ORGANISM: Artificial Sequence
<220> FEATURE:
<223> OTHER INFORMATION: Synthetic

<400> SEQUENCE: 121

```
tctctgggta taacaagtca caagcaattc actctccagt attaacacag aaacttaatc      60
caatattcct gacaacgaaa tcattttgct gcctataatg catccatgat gatttacaaa     120
gataaagttt aaatagtaaa aattgtattt tcagagtatc cactacatgc caagtttttg     180
cacatgatat ggtaaggtat gagatttcat agtcacatta caaaaaaaaa tttccccaga     240
gaataaatac aacattatgg gtatgagaag aggcaagtaa gtcaagtctg cagggagttt     300
tgaaaaagag aaatactgga aagagctgcg ctctcttgtg tgttctcctg gtgttctcct     360
gtgctcacct cttagcttgc taaacgtgac cttccc                              396
```

<210> SEQ ID NO 122
<211> LENGTH: 672
<212> TYPE: DNA
<213> ORGANISM: Artificial Sequence
<220> FEATURE:
<223> OTHER INFORMATION: Synthetic

<400> SEQUENCE: 122

```
cttggcaccc acagtaagcc ttgtaggagc tcaaagtgcc tcaggcaatc tgtgagcaga      60
atagcaattt tattactttg tcattaaacc aatttcacag cagtattgtt tgttaatgag     120
cagcggcaaa cgagcgaaga tgtcacacac tggaatagca gagagatttg tgacccaagc     180
tcacagcact aagatggaaa gaccacggct ataaaaaagg aaatactttg ggatgaaatg     240
caaagtctat acagcagagc ttgtgtttat gagctaccat tttgctaaga gctgtgagag     300
aaataaaggt ctggaaatat gcagttaaaa cagggcctat aaaattaaaa ccaaattaaa     360
gtatagcaga ggattactgc acagactgta ctcgacaaaa tatattttaa gtgacgaggt     420
gaaatctaaa tcagttttgt ttgaatttgg ttggtattta tgaaattcaa taaaaaaaaa     480
tgaaaaaata tccaaacaaa gcagccgcct caccccttgtg tggtctctga gccataaacg     540
tgcatcactt tgaggaaatt caacttgcca atccttaaat aattagcaac ttcttgattc     600
acagggtgcg ccctccatc ttcatgaaag ccttctctgt tactttatct cttcgtaagg     660
acgttgccca tg                                                        672
```

<210> SEQ ID NO 123
<211> LENGTH: 512
<212> TYPE: DNA
<213> ORGANISM: Artificial Sequence
<220> FEATURE:
<223> OTHER INFORMATION: Synthetic

<400> SEQUENCE: 123

```
gaaagccgca ctgctctgat gctgagatag tgttcctact tgttcaagag tgagttcaaa      60
agtgagccta gccacctaat tttcactagc agcacagact ggaaatgccc agcaggatta     120
cagctttgag actcactctg gagtacaaca gactatcccg cccctctcag atcagaccct     180
aaagtctgtt ctaaaattgt ccactgtggg tgctgagaga agggggccca acatagcgt     240
gtgtttcatg tcaaactaat gggctaccct ggagagattt cagagttctc atttgtttac     300
tcacttgggc cctcagtcaa ggtctgatct ttggaagagc aaattttttcc aaattttgaa     360
taatctctttt ctagcaagag gctatgaatt cctttgtcca tcacttttttg gctactcgga     420
gccaccttca acataccact caaagctttt cctcatttaa caataggctg taatatacta     480
gttctgaacc tttgctgggt catggacttc tc                                   512
```

<210> SEQ ID NO 124
<211> LENGTH: 1024
<212> TYPE: DNA
<213> ORGANISM: Artificial Sequence
<220> FEATURE:
<223> OTHER INFORMATION: Synthetic

<400> SEQUENCE: 124

| | | | | | |
|---|---|---|---|---|---|
| tgcccacttg | caaaagaggc | tgttggcagc | aacacttcac | cactagaaac | ctttactcca | 60 |
| attcgaaaca | tgccttaacg | cacagtgtga | attacccact | ctcgtggccc | acagaggttg | 120 |
| actcattcag | gccccctttt | gttcagatga | ggaaactgag | gctgactccg | aagcctgggg | 180 |
| gctttcagat | gtggagtggg | tccctgtgcc | caggtgatga | ggggaccagg | cgggtctgga | 240 |
| gcagggctgg | agtggggctc | agatgtagta | ggctggcagt | taaaggtgcc | agatgtgagc | 300 |
| caggctgctg | ggtttgaatc | ctggagctgc | ctcatagcag | cagtaggact | ttgggtaact | 360 |
| tacataggtg | ctgtatgcct | cagtgacctc | atctgtaata | tagagatgat | aagagtacct | 420 |
| gtctcattgg | tctactgagt | tgtccggatt | aactcattaa | atgagttaaa | actcatgaag | 480 |
| cccttggaac | tgtgactgac | acatagtaag | tactcaataa | aaaataactg | ctaagaccag | 540 |
| ccacagtggc | tcacacctgt | aatctgagca | ttctgggagg | ccaaggcgga | gaatcccttt | 600 |
| gagcccagta | tttcaagacc | agcctaaagg | tcaacatagg | cagactctgt | ctctactata | 660 |
| cattttaga | ttaaattttt | ataataataa | taaccactaa | aatgtgatta | ctaaagacag | 720 |
| cttcttcaca | gtacaaagag | atgctcttct | gagtaccaac | tctttggagg | ataaactgcc | 780 |
| cttataccctt | caaaaataac | acttgccata | tatcaagtcc | tttcaagtac | ctggagattt | 840 |
| acccagcact | ctgagataaa | taccattatc | cctctgggca | cacagaggct | cagagaggtt | 900 |
| tagtcatttg | cccaaagtca | cacagcctgt | acgaggccag | gctgggactc | aaactcagtt | 960 |
| ctgactgatt | ctaaaatcat | gtgtttaact | gctgcactct | aggaccaccc | gcaatggatc | 1020 |
| tgtg | | | | | | 1024 |

<210> SEQ ID NO 125
<211> LENGTH: 53
<212> TYPE: DNA
<213> ORGANISM: Artificial Sequence
<220> FEATURE:
<223> OTHER INFORMATION: Synthetic

<400> SEQUENCE: 125
ccatcccgtg tctcgatggt cttgatcatc accgtcttct ggtatggac ctc     53

<210> SEQ ID NO 126
<211> LENGTH: 665
<212> TYPE: DNA
<213> ORGANISM: Artificial Sequence
<220> FEATURE:
<223> OTHER INFORMATION: Synthetic

<400> SEQUENCE: 126

| | | | | | |
|---|---|---|---|---|---|
| ctagtgcttg | ggatcgtaca | tgttaatttt | ctgaaagata | attctaagtg | aaatttaaaa | 60 |
| taaataaatt | tttaatgacc | tgggtcttaa | ggatttagga | aaaatatgca | tgctttaatt | 120 |
| gcatttccaa | agtagcatct | tgctagacct | agttgagtca | ggataacaga | gagataccac | 180 |
| atggcaagaa | aaacaaagtg | acaattgtag | agtcctcaat | tgtgtttaca | ttaatagtgg | 240 |
| tgttttacc | tatgaaatta | ttctggatct | aataggacat | tttacaaaat | ggcaagtatg | 300 |
| gaaaccatg | gattctgaaa | gttaaaaatt | tagttgttct | ccccaatgtg | tattttaatt | 360 |

```
tggatggcag tctcatgcag attttttaaa agattcttta ataacatgat ttgtttgcct    420
ttctagattt ctttatcttt ctgaccagca acttagggag cagaatttaa attaggaaga    480
caaagggaaa gattcattta aaccatattt ttacaaagtt tgtcatttgc cccaaggtca    540
aattttaaat tcttaatttt cattttattt cccattttag gtaaaagttt gcatttaatc    600
ttagaattat gttattttttg ttagtagtgt ggaaacttag agaacttatt gtatggtgcc    660
ttgca                                                                665
```

<210> SEQ ID NO 127
<211> LENGTH: 1149
<212> TYPE: DNA
<213> ORGANISM: Artificial Sequence
<220> FEATURE:
<223> OTHER INFORMATION: Synthetic

<400> SEQUENCE: 127

```
ctcctatgtc tttcaccggg caatccaagt acatgtggct tcatacccac tccctgtcaa     60
tgcaggacaa ctctgtaatc aagaattttt tgacttgaag gcagtactta tagaccttat    120
taaaggtatg cattttatac atgtaacaga gtagcagaaa tttaaactct gaagccacaa    180
agacccagag caaacccact cccaaatgaa aaccccagtc atggcttcct ttttcttggt    240
taattaggaa agatgagaaa ttattaggta gaccttgaat acaggagccc tctcctcata    300
gtgctgaaaa gatactgatg cattgacctc atttcaaatt tgtgcagtgt cttagttgat    360
gagtgcctct gttttccaga agatttcaca atccccggaa aactggtatg gctattcttg    420
aaggccaggt tttaataacc acaaacaaaa aggcatgaac ctgggtggct tatgagagag    480
tagagaacaa catgaccctg gatggctact aagaggatag agaacagttt tacaatagac    540
attgcaaact ctcatgtttt tggaaactag tggcaatatc caaataatga gtagtgtaaa    600
acaaagagaa ttaatgatga ggttacatgc tgcttgcctc caccagatgt ccacaacaat    660
atgaagtaca gcagaagccc caagcaactt tcctttcctg gagcttcttc cttgtagttc    720
tcaggacctg ttcaagaagg tgtctcctag gggcagcctg aatgcctccc tcaaaggacc    780
tgcaggcaga gactgaaaat tgcagacaga ggggcacgtc tgggcagaaa acctgtttttg    840 tttggctcag acatatagtt tttttttttt ttacaaagtt tcaaaaactt aaaaatcagg    900
agattccttc ataaaactct agcattctag tttcatttaa aaagttggag gatctgaaca    960
tacagagccc acatttccac accagaactg gaactacgta gctagtaagc atttgagttt   1020
gcaaactctt gtgaaggggt caccccagca tgagtgctga gatatggact ctctaaggaa   1080
ggggccgaac gcttgtaatt ggaatacatg gaaatatttg tcttctcagg cctatgtttg   1140
cggaatgca                                                          1149
```

<210> SEQ ID NO 128
<211> LENGTH: 701
<212> TYPE: DNA
<213> ORGANISM: Artificial Sequence
<220> FEATURE:
<223> OTHER INFORMATION: Synthetic

<400> SEQUENCE: 128

```
gcagtgtgtt gctcagtaac ttccaggacc atcctcacta tccaaggaga tgatgggatg     60
aagttttgca aatggcaagg cctggctcta atgcacagag caaagcacat ctttctttgc    120
tgtgtgaagt tgcaaaatga ttacactatt tccttgagga gaacagttat agacacccag    180
```

```
tgttatgcat tagtcagtgt tgtataattg atcttttttt aatcccctcc attagcaaat    240
agaagaagat tgtgcagaga ctgaagatgg catggtgtgg tgattggcag gagacattgt   300
gataggactc gagtcccaac tctgctactc agtagctctg tgagcttgga caagttaacc   360
aaccatagtc tctttatttg taaaatgggg ataataatag accctatatc acatgattgt   420
tatcagtatt aaatggaaga acgcatgtgg aatacttgac atagagtaag cattcaataa   480
ttgttagcta ttaacagtga tacttattaa tagctaacac agtgacatat gtgtattcag   540
attctaagcc ggtgcaccca gtcctccctt cacaagagga aagtgtcagc attgccagaa   600
acattgtatg tcctcagtgc tggtggctcc agctacctgt cctcccctta gcaatttggt   660
attgtccaaa catttaggtt tctgaacatg cctgaggctt a                       701
```

<210> SEQ ID NO 129
<211> LENGTH: 1579
<212> TYPE: DNA
<213> ORGANISM: Artificial Sequence
<220> FEATURE:
<223> OTHER INFORMATION: Synthetic

<400> SEQUENCE: 129

```
gtgtgtgtga cattctctca tgggacaatg ttggggtttt tcagactgac aggactgcaa    60
gagggagaaa ggaattttgt caatcaaaat tattctgtat tgcaactttt ctcagagatt   120 gcaaggatt tttaggtag agattatttt tccttatgaa aaatgatctg ttttaaatga    180
gataaaatag gagaagttcc tggcttaacc tgttcttaca tattaaagaa aagttactta   240
ctgtatttat gaaatactca gcttaggcat ttttacttta accctaaat tgattttgta    300 aatgccacaa atgcatagaa ttgttaccaa cctccaaagg gctctttaaa atcatatttt   360
ttattcattt gaggatgtct tataaagact gaaggcaaag gtcagattgc ttacgggtgt   420 tattttata agttgttgaa ttccttaatt taaaaaagct cattattttt tgcacactca    480
caatattctc tctcagaaat caatggcatt tgaaccacca aaaagaaata aagggctgag   540
tgcggtggct cacgcctgta atcccagcac tttggggagc caggcgggc agattgcttg    600 aacccaggag ttcaagacca gcctgggcag catggtgaaa ccctgtatct acaaaaaata   660
caaaaattag ccaggcatgg tggtgggtgc ctgtagttcc agctacttgg gaggctgagg   720
tgggaaaatg acttgagccc aggaggagga ggctgcagtg agctaagatt gcaccactgc   780
actccaacct gggcgacaag agtgaaactg tgtctctcaa aaaaaaaaa aaacaaacaa    840 aaacaaaaac aaaacaaaac aaacaaaac aaaacaggta aggattcccc tgttttcctc    900
tctttaattt taaagttatc agttccgtaa agtctctgta accaaacata ctgaagacag   960
caacagaagt cacgttcagg gactggctca cacctgtaat cccagcactt tgggagatgg   1020
aggtaaaagg atctcttgag cccaggagtt caagaccagc ttgggcaaca tagcaagact   1080
ccatctctta aaaataaaa atagtaacat tagccaggtg tagcagcaca catctgcagc   1140
agctactcag gaggctgagg tggaaagatc gcttgtgcac agaagttcga ggctgcagtg   1200
agctatatga tcatgtcact gcactccagc ctgtgtgacc gagcaagacc ctatctcaaa   1260
aaaattaatt aattaattaa ttaattaatt taaaaaggaa gtcatgttca tttacttttcc   1320 acttcagtgt gtatcgtgta gtattttgga ggttggaaag tgaaacgtag gaatcctgaa   1380
gattttttcc acttctagtt tgcagtgctc agtgcacaat atacattttg ctgaatgaat   1440
aaacagaaat agggaagtaa acctacaaat attttaggga gaagctcact tcttcctttt   1500
ctcaggaaac caagcaagca aacatatcgt tccaatttta aaacccagtg accaaagcct   1560
```
ttggaactat gaatttgca 1579

<210> SEQ ID NO 130
<211> LENGTH: 567
<212> TYPE: DNA
<213> ORGANISM: Artificial Sequence
<220> FEATURE:
<223> OTHER INFORMATION: Synthetic

<400> SEQUENCE: 130
cctggctgat tcttggtct cttgccctca ttcaccgaat taattctcta cactgctgca       60
aaactgatct ttctaaacac aggtcagctc atgtcactca cctcctcaga aatcttcagt      120
agctcttcat taaccaacag ggggttccta actcccgtc ttggcattgg aggaccttc        180
cctgcctgat ccccgcgatc atcttttcct gcaatattta ctcaggccag tgctcacccc     240
ttctttaaaa tgctggtgct ggctcaagag aggcaaacag ccatctctct cattcttatc    300
ttccctgtca agacttcaca taggtggact gatgctagac tatgatgatg agtctccagt    360
gaaagtttct aagtagaact ctctcagggt ttctagaagc attttgttt aagaaaatat      420
tgtgggggga gcgggatttt taaatggtgg agctcatggt aaacaaaatt atgtgtgcaa     480
aatgttaata gagcctttct aatattcttg tgattaactc tggtgacagt tggctgagtg    540
ttcttgtttc tgcaacgcct gtctttg                                          567

<210> SEQ ID NO 131
<211> LENGTH: 78
<212> TYPE: DNA
<213> ORGANISM: Artificial Sequence
<220> FEATURE:
<223> OTHER INFORMATION: Synthetic

<400> SEQUENCE: 131
ctgattttat caaaggtttg ccagccaata aagtgcatcc caagtataca ggggagaaag      60
ctagactcct acagggtc                                                     78

<210> SEQ ID NO 132
<211> LENGTH: 2966
<212> TYPE: DNA
<213> ORGANISM: Artificial Sequence
<220> FEATURE:
<223> OTHER INFORMATION: Synthetic

<400> SEQUENCE: 132
tctcaggcat tgttggggca taagctcaca ctgtaagctt ttctcatgaa ttcactagac      60
ataacgtgga aggaaaacgt agtcttttgg gagtacaggg aagccagccc ctcaaagctt     120
atggaagaca tacctgcaat ggaagctgtt gcccaatgtc tccattacta tctttcaaaa    180
gagaagccag acccagcttc agatcaaaag ttcttgagac agaggaacaa aaccaatcga    240
tttccaggga agctaatcaa ctctcttttc cctctaccac aaaactgccc tgctggagtg    300
gttctgaacc tgtacccagg actcgatgtg gtcactaata caattaacc tgaactgagt     360
ccacagaact ccactcggaa ctttcttctt ttttaactag tggcccaatc attcccacca    420
tctctgtgct gataagtacg tgtcctagat gagaaccctg aagaatgcag accttcttcc    480
cccgaaggag atgccacaag ctctccaaca cagcccccctt tagttccaaa gactagagat   540
gaccacattg gtagaagtat atctcgaggc acaggaaggg agcccacca gggataattc     600
agacaggact agagaataac atcatttcac atacccctggg ataaacaccc tgggttccta  660

```
tagaaggact attacttatg ggagtccaac ttctccttt gttttgttat tatcagttta      720
tctttctccc actccacttt tccttcaagg taccaatcct ttcctgttcc tcgtttggcc      780
atctttcttt ttctgcctcc acattgggag gggaggactt ctcagttcta acaagctgcc      840
atactcctaa gaaagccatt tttgaaaaat ttaacaatcc aggttcttct ggagaactca      900
ttctccacac gcacagtttg ctgcaaaagg aagttgcaag aatttcttga ggaagaaact      960
ggtgacttgg tccatcagtc acgaagttct ttctattctc gtttagtttt caagaaatta     1020
ttggtttgtg ttgctctggg gaaattggaa atcattacat tgtaaagaca aatatggatg     1080
atatttacaa gagagaattt cagatctggg ttttttgaaag aaaacagaat tgcgcattga     1140
aaacgatgga aggaaaaaga caatggtcta atgtgcattc ctcattacct ctcgtggctt     1200
tggctgggag ttggaaaaag ctaaaatttc agaacagtct ctgtaaggct ctctgtggct     1260
ccagttcacc attttatatt gttgcatgct gtagaaagga gctattgctg ttgttttgtt     1320
tttttattta aatcactaag gcactgtttt tatcttttgt aaaaaaaaaa aaaaagttgt     1380
tcactgtgca cttatagaaa aaataatcaa aaatgttggg attttagaag ctctcttttt     1440
gataaaccaa agatttagaa gtcattccat tgttaacttg taaaaatgtg tgaacacaga     1500
gagttttgg tgattgctac tctgaaagct gccagatctt attctggggg tgggatgtgg     1560
aggaatacac atacacacac aaacatacat gtatgtataa tagatatata catatgtgta     1620
tattatatct gtgtgtgcat gtatctccaa aagcggcgtt acagagttct acaccaaaag     1680
cctttaaccc ttaatctgct gtgaatgata cctggccttt ctcactatga atttctgatt     1740
aaccaaccag actacacgtt gcctctctgt gtatgactaa cggctccaac ccgatgactc     1800
acagctactt gcttatcgtg aacaagctca tcttggcaat gaatatggat gtgaaaagac     1860
agaacagctt caccattagt agctggaaat ggtatcacag tctcttatag aggaaatatga    1920
aaggaacaag aaaatcattt tacattcctt ttatctgtat tgtgctttaa aagatccaca     1980
tggtaaattt tttattttgc ttttatgtca gtcatcagaa ccaaaaaaat ccagaagaaa     2040
aaattgccag tgtttccttt gaagatgaag ctactgggga agaaaacctt attaatacac     2100
tccacacatt tgttcattcc tcagctgttg gtgttttctt ggggtcttga caaagcttgc     2160
tggtcagtgc acttttcagg tgtcacgttt tgctgtttgt atgttttttc ttcccttac     2220
ttcctttgga aaacaaactc acacagtgcc cctactctga gacctgggac tgagtgttaa     2280
ttatttttttc cttgggtatt tctatctgag agactagacc tagttaggag gcctctgtac     2340
ttctccagat tgtaccttttt tatggggatc tttgaggcta tgacccagga ctgatagata     2400
tgccttacgg aagacaaaag ataaaatggt tcctatatcc taatgcaaac caacacagtt     2460
aaaagagcag atctctggat aactgctctc aacctgcttc tacagtctcc acaaccgca     2520
ttcaccctct ctcttcatag ctcagacatg aaatttgagg gagaaaactg gagataattg     2580
ggagaaaatt tgatgaagttg gctgcttcca gtagatcaga taatccatga atttgtctcc     2640
cattgagaat tttatttaa attcttttaa actcttcgtt gtgtcttttg tgatgacaaa     2700
tcaggcatga ctaaaagatg tacagagact tacgaagatg gtcacattca agttccctaa     2760
tgctcttaga acctgaagat gaccatgtgt agttttctta agacctctga accccatgg      2820
tgatgaagac ttgaagacat ttgcagctat ctgctgcagt ctggtagatt catacttatc     2880
taaagaagtc aaaaaattta ttcgtgcaag tgcttgcagg aagccagtgc ttattagtag     2940
tgaccctgct tctatcaacg ttattg                                          2966
```

<210> SEQ ID NO 133
<211> LENGTH: 341
<212> TYPE: DNA
<213> ORGANISM: Artificial Sequence
<220> FEATURE:
<223> OTHER INFORMATION: Synthetic

<400> SEQUENCE: 133

```
gatcgctgtg ctaggtctga ccaaaaccag agggcagtct agtcctgggg gtaaagccct      60
cagatcccag ggtacactct tctccattcc ctccacccac ttgcctgtca ccccagtcac     120
ctaagcaatc actgggccca gaggagagga gacagacaca cactggctcc tggacctaaa     180
gggtatgagc tggagctaag gccagctaga gcttccactg tcagccctca ctgtcagtcc     240
cactgcaccc ccctgtgcct gctgggcact gggcactagc tagatgcttt aggttgcttc     300
agctgatcct tcaactctgt gaggtggata ccaatattct a                         341
```

<210> SEQ ID NO 134
<211> LENGTH: 100
<212> TYPE: DNA
<213> ORGANISM: Artificial Sequence
<220> FEATURE:
<223> OTHER INFORMATION: Synthetic

<400> SEQUENCE: 134

```
ccctggaggg atcctagaaa gcattgtcat attgccatct ccattagctc acttttaaac      60
aactaggggtg ctggaagaac ctttgtctga gggtagttca                          100
```

<210> SEQ ID NO 135
<211> LENGTH: 173
<212> TYPE: DNA
<213> ORGANISM: Artificial Sequence
<220> FEATURE:
<223> OTHER INFORMATION: Synthetic

<400> SEQUENCE: 135

```
gtacaccctg gcaaggcttc tcttcagact gaagcagcaa ttctgccact accagcagca      60
accaggacgt ctgttctttg tgggggccag atcagaagag agaggcccct gtgacgcccg     120
ggctgcttgg tcacaactct gtccaattca aggatgttta tcggcctctc tta            173
```

<210> SEQ ID NO 136
<211> LENGTH: 1783
<212> TYPE: DNA
<213> ORGANISM: Artificial Sequence
<220> FEATURE:
<223> OTHER INFORMATION: Synthetic

<400> SEQUENCE: 136

```
ggctgcatgg ttatccctct cagtgcaata tagctaaagg ggcttgaaat gctgggagta      60
gtcttaaaca gcccattctt gaaaggtttt cattaactca ctctaaacat ctaaattaaa     120
aatgttttttg ttttcactat agtaaacagg agtgtaacat tgcaggtttg gtacatttct     180
gaatgcctct ccacacactg aagcacaaga gccactgaaa aaagctatat gataaatatt     240
ttaaaaatta tttatctgtg ttgcattaca tgaggcctta tctcccagac acttaataaa     300
agagctaatg agaagaagag ctaaattcta agattttgat gtttggtcat taaacattac     360
agacaccagt gatcagagaa aaaacagaa gaaataatga gaaagtgaca taaaaaattt     420
taaatgcagc aagatatatc agaatcacga tatctggcct tttatttatc tatcggctca     480
ctactactac tacgcacaca atttatcact taaaagaaaa atacataatg ttgttagaat     540
```

```
ttatcagcag taatgctcca agctctatct ttctacaaaa atttcatatc agtaggtttg      600
cttgaggatt ctagatttgg taagattgca gtttgcacag agaaaaagat atcaatatca      660
ataggaaaat attcttttag aatttctcca tggagctgac aacatcttag aatgtatcgt      720
cctagacaga gactattgga agaaaaaact ttccttattt ctaaaattta aattcaaagt      780
atcttctggt ggggacgaag agagagagag gagaaaggtt gcttgctgtg actggcagga     840 tttttgagc agtctgctgc tttcactcca ctaaagaaac aaaactttca gaagtttcat       900
ttcccttcta taaaccacaa atccaaaaca aaagaaagtg gaataagata gtctttaaag     960
ctaatcttgg ttttgctaat ttgtaagctt tcaccagcag ttcttgtttt gctctgtttt      1020
gattttgagt gaatctcata ttcctggctc tggtggagaa ttttcgtgct tttaaagatt     1080
aattaattta gtcctttttg caatggtttg ttcttttcgg catctaggaa ttaaagaaag      1140
tgctcaacca taaataaatg tagttatgtc caaagtacct tcacatagac acactataca     1200
caggcgtggg ccttttggaa acacctgaag gccaaatgtc tgactgtgag tggaagatcc     1260
agagtgtgct gatagaggaa gcttttctca tccctcgaga gcaaagaggg tgatggaggc     1320
aagagtcaga gagccctgtt ctcttcttca tgtacactgc aaagggcaac ttctctagaa     1380
gcattaaaag tgtcaattag gttttcaagt aagcgtcatt tattcatata tacattcatt     1440
tgtcttttta tttacaaaat taaatcattt tcccatgaac attaaaatgg gaagagagaa     1500
caaagaaaat agagttgaat aataataaca ttgattctgg accagacact gggctggaca     1560
ataactcgag ggttacctta tttatttaca caaagacccg atgaggtaca cactaattat     1620
tttcatctcc ctattaccaa tcatgagact gaagctgaga agggttaaaa acttgcctaa     1680
gctcacacaa ctaagaagtg tccgagctgg gctttgaacc caaggtttga tcaagggttg     1740
tgcccttaac tgccatacca tcctgcctca cagatctggg tta                       1783

<210> SEQ ID NO 137
<211> LENGTH: 105
<212> TYPE: DNA
<213> ORGANISM: Artificial Sequence
<220> FEATURE:
<223> OTHER INFORMATION: Synthetic

<400> SEQUENCE: 137
ctcacaaata ggagtagcaa ttctaggtgg tagggttgtg tacggaaccc ctggctgtct       60
gcatatatct cagaattacc ccaggaccat tgtcccaaag tctag                      105

<210> SEQ ID NO 138
<211> LENGTH: 2070
<212> TYPE: DNA
<213> ORGANISM: Artificial Sequence
<220> FEATURE:
<223> OTHER INFORMATION: Synthetic

<400> SEQUENCE: 138
ttcccgacaa taagctccaa cgtgggcata gttgaacaag ctatgcctca aaatgccaac       60
gccatatgct tattagcctg tgtgcatcat tccagacggg cctaatcatt ccaggactga      120
aaccagaatc gctgaaagcc cttgaaatac attcaataat tcatatgtta aaacttggat     180
atctgttcag cccaaatgaa atcttccttt taaaaaacgt ctacattatt gaaaattgtt     240
caatgtgctt ttcagagtga cggtgagaat tttatgcatg tatcttgcct gcatatttga     300
tatgttacaa acttccaaaa ttcaaggtgc agcgatccac agaacgttgt acatttaaga    360
agtgattcct tcaagctaat ttaaaatttc attgaacaca tggtgaccag gaaaactttt    420
```

```
tttcaagcac tgttggaaag caccacaaag ccctttagaa ttaatctgga tttgtttctc      480
aagttctgct gaagtttaaa aaaaaacttt attatacaaa taactcaaaa ttttcctgtg      540
taaaactaaa cctgtagttt taaaacataa tcctgtttgc attagagctc actgtctttt      600
tgtgatggaa actgtgttcg tatggaatga ctaaaaatct tttatttggt ttgtttcaaa      660
ttacaattgc tgatggacaa tttgtattgc agcgagaaca acagaatgaa agaaatgtat      720
ctctgtgcgg ctatacatat acatacataa aattgatttt taaatttaaa acatatggaa      780
aacaaaacat tgaacagttt gaattttgcc aagttggaca ttaaagtaaa atgaagtga       840 aatcatgcat tgaaagaaaa cattttgttt ctaaattagt ctaccattga gtgagaataa      900
tcaatatcaa gaagaagac tatctttctc aactaaacaa taatattcca atcagcttgg      960
gaagacctga aacttgaata agcagtggaa atgccaaata taacagaggg tatgtgctac     1020
agagaagtaa aaagggtttg acttttatg atgggatttt ttttttctgg gtatgtaatc     1080 tattttttt ttaaactgga aagcattttt gtcagtgtga atgagggtca atagtgcagc     1140
cagtggtgac attttctttt attttgcaaa atgctttaa aaccaaaggc tgctctagtt     1200
gatggacagt atcagtcttg atctaaattg taggacactt tttcatgtaa cataacattt     1260
ggggattggg tttatttagt gtaatgaaga taatttgata taaaatatt ttgtgtatat     1320 atatatattt ttactttgtt ttctaaattg ctgtttgcag taacagtaag cgcaaagcaa     1380
aatatataag ttatgactgt atgatcagat gaagtatgag ttcttttggt ttgcatcctt     1440
aaatagttag agatctctga taaaaacttt ggaatctttg caaacaata caaaatgcc      1500 aaaatgtgag catgtcaatg aaaactaaag acaaatactt cactctttt catactatta     1560 taagttattc tggtattaaa tatgttaata aaagtgtttt tgttttgaca tatttcagtt     1620
aaatgaatga atgctggttg tatttatttt gaatgagtca tgattcatgt ttgccatctt     1680
tttaaaaaaa tcagcaaatt tcttctatgt tataaattat agatgacaag gcaatatagg     1740
acaactattc acatgatttt ttttaatacc aaaggttgga agattttata attaacatgt     1800
caagaagact ttatagtaag cacatccttg gtaatatctc caattgcaat gacttttta      1860 tttatttttt cttttgctgc tttaacattt tctggatatt aaaatcccc cagtccttta     1920 aaagaatctt gaacaatgct gagccggcag ctgaaaatct aactcataat ttatgttgta     1980
gagaaataga attcctcta ttctttgttt tgccatatgt aatcattta ataaaattaa       2040 taactgccag gagttcttga cagatttaaa                                      2070
```

<210> SEQ ID NO 139
<211> LENGTH: 599
<212> TYPE: DNA
<213> ORGANISM: Artificial Sequence
<220> FEATURE:
<223> OTHER INFORMATION: Synthetic

<400> SEQUENCE: 139

```
gtcgccttcc tatgtatgac gaaacaagaa acagagattt ccaattgctc ttttgtcttc       60
agacatttag taatataaag tacctatttt tatgctgaaa tgtttataca ggtttattaa      120
tagcaagtgc aactaactgg cggcatgcct tgcaacacat tttgatatat tagccatgct      180
tccgggtaaa ggcaagcccc aaactcctta tcttttgcag tctctctggg atcagtaaaa      240
gaaaaaaaaa ataatgtgct taagaagtgg gactgtaaat atgtatattt aactttgtat      300
agcccatgta cctaccttgt atagaaaaat aatttttaaaa atttgaatgg aagggggtaa     360
```

```
aggaagtcat gaagtttttt tgcattttta tttaaatgaa ggaattccaa ataactcacc    420
tacagatttt tagcacaaaa atagccattg taaagtgtta aaatttacga taagtattct    480
attggggagg aaaggtaact ctgatctcag ttacagtttt tttttccttt ttaatttcat    540
tattttgggt ttttggtttt tgcagtccta tttatctgca gtcgtattaa gtcctattg     599
```

<210> SEQ ID NO 140
<211> LENGTH: 698
<212> TYPE: DNA
<213> ORGANISM: Artificial Sequence
<220> FEATURE:
<223> OTHER INFORMATION: Synthetic

<400> SEQUENCE: 140

```
tctcagcata tgttgcagga caccaaaagg aagaaaacaa tcaagcaaat aaaataaaca    60
gtcaaacaaa ccaggagttt aaaacaacaa ccccaacaac agaagccttg gcaaagagga    120
ataagtgatc agcaagtgaa cacactctat gtcaactctc cttttatcca gctgagattt    180
atggtaactt atttaattaa tggtcctgtc tgatgcatcc ttgatggcaa gcttcaaatc    240
tgatttggta tcaccgagga aaccttgccc ccatcactca gcattgcact tagatacaga    300
atgagttaga taaacttggc ttgtctagag acccatgtca tcttaaccta aagggaaatc    360
ttattgcgtt atcataaaat tgatgatatc ttagggtcag aattgccctt ttttttttatt    420 ttgaatggga agttctcact aaaacaatcc tgagatttct taatttcatg gttctttaaa    480
tattataaac acagagtcaa catagaatga aattgtattt gttaaaatac acacattgga    540
ggacaagagc agatgactac ttttcgaagt aatgctgctc cttcctaaaa gtctgttttc    600
aatcctggta atattagggg cactgcggca cctaagaagc cttaaatgag agctaatcca    660
atctagagag cgatggtgtc agcatttcgg tctgcata                            698
```

<210> SEQ ID NO 141
<211> LENGTH: 132
<212> TYPE: DNA
<213> ORGANISM: Artificial Sequence
<220> FEATURE:
<223> OTHER INFORMATION: Synthetic

<400> SEQUENCE: 141

```
cagggcatga gacattcagc gtagaggtta aaacgagggc cctgggttag gaaccccagc    60
tcagttctca gctctgtacc cttggaaaat tcccttccca tggagctttg tggatgcaca    120
aggacttgca ca                                                        132
```

<210> SEQ ID NO 142
<211> LENGTH: 33
<212> TYPE: DNA
<213> ORGANISM: Artificial Sequence
<220> FEATURE:
<223> OTHER INFORMATION: Synthetic

<400> SEQUENCE: 142

```
gtggcttgtt tacgtatgtt tctggagcca att                                 33
```

<210> SEQ ID NO 143
<211> LENGTH: 767
<212> TYPE: DNA
<213> ORGANISM: Artificial Sequence
<220> FEATURE:
<223> OTHER INFORMATION: Synthetic

<400> SEQUENCE: 143

```
cccaagcctg tctaaggtta ctgtgtatta gacagggccg aactagtgtg ctgagcaaaa    60
agaattgaag caaattgtat ttacttagcc gcttctggga gccacttcag cctttcccct   120
cccctccact tcttgggtaa tctgacctga agcatagtcc aggagcagag ttagccagaa   180
atgcctcctg ctgccccagc cttagagagc tcccatctca atcattgagc ctgaaggctt   240
caagcccaag aatgcaacaa gaccccagc ctacatttct cagctcccct ggagccagct    300
gatcctgtaa cgctgctgga ggtcagtctg agctaccaag actgtcccta gacaaaggtg   360
gagtccccca cactgcccaa gaccaaatcc ctcactcaac ctgctgaggt gtggatgggg   420
aaacagaggc aaaactgagg cacctgatgc attcagcctg ctgtgcagca gtgccattga   480
ctgccctgat gttcagagag aaacgcacac aaggtttgcc catgagaatt ggggagcaga   540
tggccaagca gataggttat gtctgttttc tgagtgatga agtcaggaag ccctgtggct   600
ctggaggcca cttgtggttc attcttttcc catatccttg gcttttagaa atggttacct   660
tcaggacagt gcagctgcat ttatcagagc actattgcta agttttcttt tctggcttgt   720
gttttttctgg gacagtttag aattgggagg cctattctca tagaaca           767
```

<210> SEQ ID NO 144
<211> LENGTH: 615
<212> TYPE: DNA
<213> ORGANISM: Artificial Sequence
<220> FEATURE:
<223> OTHER INFORMATION: Synthetic

<400> SEQUENCE: 144

```
ccttcagaag catgggacta cctcccatct agttctcgtt tctaaaccta ggggagatgc    60
tatctttgct gcaataatct tagcctacat cttggaatgg aaatggcctt ggtggaaatg   120
gtcttcaact cctctggtcc aagctcaggc cctgtgaccc tggaacaatc cccttcctgg   180
tcctccatgt aggagcaata acattcccct gccagcagca ccagccattc tgatgattaa   240
atggtatcgg actctgtttt ccaaactcag tcattcagat gcccctatt ttatttcttc     300
catgtctgca aatgattata atattttttaa atgtaggatg agtcctttttt attacacata  360
gaaatagcta ctgtaaatag caaactctaa cactgtgcct aattaggaaa taaaggtaac   420
cataaataca gtaaaaatga aacaatgtta ttatggttta acctgatagt gtggcttgca   480
aggccctggg cctgaagcct gggcaataag tgagagttag aaaggtgtca aagacatgat   540
agcagcaaac tgaggctttg taccccacgg taaataggac tgaaagcaaa ttcacaggga   600
gcaactgatc cattc                                                   615
```

<210> SEQ ID NO 145
<211> LENGTH: 547
<212> TYPE: DNA
<213> ORGANISM: Artificial Sequence
<220> FEATURE:
<223> OTHER INFORMATION: Synthetic

<400> SEQUENCE: 145

```
gagtggccac ttgattagag acctagcaca ggaggaagag atgggcaggg agagtgacgg    60
ggagcagcac agtccctggg agcccgaagt gggtgggcac agggctccct aggagaatgg   120
aaggacatct atgagctgta gcccaagagg aagaggtcac tggggctaga tgcggcagac   180
cctcgcaggc tttgggaagg gcttcagaat tcagcctgag ggcaatgggg agcccttttg   240
ggatattaaa cttgagtaag atatgagcat atttgcatct tgaaaaatca ttatgggaag   300
```

```
atggctggga agagaggagg agtggcagaa gaaagatagg ttggagacaa ttgattgctc    360
gatgatataa aatgttaagt accatgaatg atgctgttag gctggaatgc gccaagcata    420
aaggtggggc atggcatcaa aaggtaggtc aacatattaa ataattccat gtattgaaat    480
atccagaaaa tatatagaca gatctataga gatagaaact ggtctgccca ggactagggg    540
ttgtcta                                                              547
```

<210> SEQ ID NO 146
<211> LENGTH: 754
<212> TYPE: DNA
<213> ORGANISM: Artificial Sequence
<220> FEATURE:
<223> OTHER INFORMATION: Synthetic

<400> SEQUENCE: 146

```
cactggtctg cccttcctaa attaagtatg cacttcaatt tgatgagtgg aaacagtcta     60
tctgggcagt aaccagggag ctttgtgcct agtagattgc ttctgttctg cacttctttg    120
gtttcccacc tcaatgtaaa aaatagctag caatgaagtc cagaagttgt caatggttca    180
tccccagaag aatgcataat gtccaaagtt gtatgtgtat gatgtcttca atggtattaa    240
gttatttcaa attcttagtt cacctacata aatcatttct aacaagcatc ttcttaacca    300
actttatgca cagtgtatgt ttgtaagtgc ttctgcacga atgtttatac atgactgttt    360
ccatagtact tatgttttta aaatattca gtcatttcct actataatcc tcatgtatcc    420
atgtaactga ctcaaaaata cttcagccac agaaagctaa aactgagcaa atctcattct    480
tcttttccat ccccttgca tgtggctggc atttagtaat gattaataat atggccagct    540
gaataacaga ggtttgagac acaattcttt ctcaaaggag tcagctaagc tgggtctact    600 tatgacaaa catctaaatg tgtggaagta tctgatattt gacaatggta aatttccact    660
tagctagcta gcattgtcag acttcaatct cctcatggct ctggccgtcc tgttttaagc    720
atgataattg ttggccacat ctcacatagt tctc                                754
```

<210> SEQ ID NO 147
<211> LENGTH: 568
<212> TYPE: DNA
<213> ORGANISM: Artificial Sequence
<220> FEATURE:
<223> OTHER INFORMATION: Synthetic

<400> SEQUENCE: 147

```
agtttctagt tgacttccat ctgcaataaa tcatgtacag gatgaggtaa tatactacaa     60
cttatgtcta ttgacttagg attttatctt taagaggata gatcctagat gtgaatagct    120
aaggaagttt gagtgttttc tcctcccttg ctttcaaata gctttgaaag atcacttta    180 tagtgcatga taaatagcta catatgaata atctgatggc attctgtaag agtaacagtg    240
cttcaaaatc gtaacctgct gggatgtttt gttacatgcc atcaagtgtg attgtattca    300
tggaatagtg tttactgttg ctcaatattg taaaggaaat aaaagataat tcccatatctg   360 agggaaatt tctcaaatat tttaattaaa aggtccctac agttacccat ataaacctta    420
gtcaaataag ataacaaatt ttcttgatct cctttaaaaa ttcttttatg tataaaaata    480
attatattta ttaaaaactc caacagtaca gaattatttg gaaaaaaga tagaaatcta    540 ccattctcct atccatgcct gagagata                                       568
```

<210> SEQ ID NO 148
<211> LENGTH: 376

```
<212> TYPE: DNA
<213> ORGANISM: Artificial Sequence
<220> FEATURE:
<223> OTHER INFORMATION: Synthetic

<400> SEQUENCE: 148
cggagagccc tcttgcatga gtttcggctt tgccaagatt ccagggactt gaggacagct      60
attgagttat ggttacgtga ctgccacatt ggggcttgga ggcatctggc agatggttgg     120
gaatgggctg gcaccacact aattaggcca cgatgatcca gtttgactca gggaaaccca     180
gaagtcatag tgctctttgc agaatgacac aagatgtcaa catgctttgt tgtgtacttt     240
gaacagggat tggtttcaca agctgaaaag ttgaatctgt cacatgtatg cagcataaaa     300
tcacagccgt gagaacatgt atacagcagg aagacaagcg actgagctag cacggctga     360 ctagctctga gctttc                                                     376

<210> SEQ ID NO 149
<211> LENGTH: 58
<212> TYPE: DNA
<213> ORGANISM: Artificial Sequence
<220> FEATURE:
<223> OTHER INFORMATION: Synthetic

<400> SEQUENCE: 149
aaaagccctc tctgcaatct cgcttctcgt gtccgcccg cttctcttat tcgtgtta       58

<210> SEQ ID NO 150
<211> LENGTH: 129
<212> TYPE: DNA
<213> ORGANISM: Artificial Sequence
<220> FEATURE:
<223> OTHER INFORMATION: Synthetic

<400> SEQUENCE: 150
aggctatcgg gaaactctgg tccagccaca gtggtctggc cacacaggga gccatgtaga     60
gacctccatc tccagccagg atgacaccgg tctgcggttc ccagctcgtc gtcaagatgg    120
gatcatcca                                                            129

<210> SEQ ID NO 151
<211> LENGTH: 33
<212> TYPE: DNA
<213> ORGANISM: Artificial Sequence
<220> FEATURE:
<223> OTHER INFORMATION: Synthetic

<400> SEQUENCE: 151
ctgggatctg ccaacgaaga tgagctcttg cag                                  33

<210> SEQ ID NO 152
<211> LENGTH: 304
<212> TYPE: DNA
<213> ORGANISM: Artificial Sequence
<220> FEATURE:
<223> OTHER INFORMATION: Synthetic

<400> SEQUENCE: 152
ctcgggaaag gatcatcgcc gttgaaatga aagagagac agagagaaaa aaaaaagag       60 aacccacatg aagctctgaa accaaacagc atcctgccat gagcttccca gagacagaag    120
agactggagc aaagtcggaa acacagagaa gcacggcttc ccctcagcac agaccctcca    180
gactgggtct cagagccgtg ccacccaccc tcccacacag ccggccacag ggagaactgg    240
```
tgctaaccag ggtgcttgct ttggtcacgt tcaacgcact acagagctac gacacaggga    300
aacc                                                                304

<210> SEQ ID NO 153
<211> LENGTH: 108
<212> TYPE: DNA
<213> ORGANISM: Artificial Sequence
<220> FEATURE:
<223> OTHER INFORMATION: Synthetic

<400> SEQUENCE: 153
tgtggtaccc aattgccgcc ttgtgtcttg ctcgaatctc aggacaattc tggtttcagg    60
cgtaaatgga tgtgcttgta gttcagggt ttggccaaga atcatcac                108

<210> SEQ ID NO 154
<211> LENGTH: 529
<212> TYPE: DNA
<213> ORGANISM: Artificial Sequence
<220> FEATURE:
<223> OTHER INFORMATION: Synthetic

<400> SEQUENCE: 154
tgatgggcta aacaggcaac ttttcaaaaa cacagctatc atagaaaaga aacttgcctc    60
atgtaaactg gattgagaaa ttctcagtga ttctgcaatg gattttttt taatgcagaa   120 gtaatgtata ctctagtatt ctggtgtttt tatatttatg taataatttc ttaaaaccat   180
tcagacagat aactatttaa ttttttttaa gaaagttgga aaggtctctc ctcccaagga   240
cagtggctgg aagagttggg gcacagccag ttctgaatgt tggtggaggg tgtagtggct   300
ttttggctca gcatccagaa acaccaaacc aggctggcta acaagtggc cgcgtgtaaa    360 aacagacagc tctgagtcaa atctgggccc ttccacaagg gtcctctgaa ccaagcccca   420
ctcccttgct aggggtgaaa gcattacaga gagatggagc catctatcca agaagccttc   480
actcaccttc actgctgctg ttgcaactcg gctgttctgg actctgatg                529

<210> SEQ ID NO 155
<211> LENGTH: 30
<212> TYPE: DNA
<213> ORGANISM: Artificial Sequence
<220> FEATURE:
<223> OTHER INFORMATION: Synthetic

<400> SEQUENCE: 155
tgggcctgtc gtgccagtcc tgggggcgag                                     30

<210> SEQ ID NO 156
<211> LENGTH: 71
<212> TYPE: DNA
<213> ORGANISM: Artificial Sequence
<220> FEATURE:
<223> OTHER INFORMATION: Synthetic

<400> SEQUENCE: 156
cccgccaggc attgcaggct tagtcgtggc tactgttctc ctgtgccgct gcatcgctct    60
ctcccgggaa a                                                        71

<210> SEQ ID NO 157
<211> LENGTH: 1449
<212> TYPE: DNA
<213> ORGANISM: Artificial Sequence
<220> FEATURE:
<223> OTHER INFORMATION: Synthetic

<400> SEQUENCE: 157

```
ggcggctatt ctaaaagtgt ctttctatca ctgttaaggg gggggaaaag tgaggttcga        60
ggatgacgta ggtaactctc ccctcccaag tccatgttcc aagtggctat gtaaagcaag       120
atgatacaga aagctgctct aaaatctcac tgagtgattt caccttcgcc tactatgaaa       180
tgtctcatca gacctgacat gtctgagata accaaggtga ttcaggattt gatcaaaaga       240
agtctagtaa gaattaatta cacagaagcc tcctttcatt tctatgggcc aaacaaaggc       300
catggataac cctacccgct ttatgtcatt acccattggg aaacacaatg gctacttctg       360
ttagggtaca ttgaccttgg tcaagcatct taaagaaggc aaccctaatt gagagctgtc       420
ttggctaata ctctgcacca caattgtgat gtcctagtcc taccactaga gggcatggta       480
cagcctggca aaagttaaaa ggggtgtggc agctcccatc aggtctggag gtggtctata       540
agcacagttg acagttgtgc attgggatgg gtggagaaag acgacaagag agcagagaat       600
ctgctgatgt ggctgcgctt acttttagtg actttatgta cttatattaa cagctggaaa       660
taggttgttg ggttttgagc aggctgttat agtgaggaat gttcattttt aaatgttcct       720
aacagatttt gcttttgaaa aatgcttgtt acatgaataa tttgtggacc agggattgct       780
tttctgaagg cagtataggg aacatgaata ttcaagatga aatacaaaaa ttatgtttaa       840
gggtcatagt gtataagtag cttcctagga aacccttgt gtatctttc agactggggt       900
ggggctgag catgcttgtg cagaaagaag ccatagccag aaaggacaga atctctcccc       960
cactcccttg ccccataacc aaacataagc tagctagtct tgtctaatag atgggattta      1020
ctataggtga agatagccct catattcaag gacagaagct ctggcaggag taaattagca      1080
aagcagaaat agtaccctt cattcttgga ggtgctttga aattttaggt agaatataat      1140
cgaaattatg gaggttcctt agtgctcaat aatataagac ctggtgttat tagaacgagt      1200
ctttcttata aactaacaga gcaggtatat gcctgttaga ccttagctgt ggggttcctt      1260
tactattggg tgaatcatta ggtataaaaa ataatcatca accaggcaaa ttactttgct      1320
tcctagctga tgtcatccca cattggtaca ggtgttattc agtactgggt ggttcagcag      1380
ggaagccggg tgggaccagt gtgtctgtca tgaaaccact aactgcattc ctgactgaag      1440
agccatctg                                                             1449
```

<210> SEQ ID NO 158
<211> LENGTH: 78
<212> TYPE: DNA
<213> ORGANISM: Artificial Sequence
<220> FEATURE:
<223> OTHER INFORMATION: Synthetic

<400> SEQUENCE: 158

```
gtgagggtga cgttagcatt accccaacc tcattttagt tgcctaagca ttgcctggcc        60
ttcctgtcta gtctctcc                                                    78
```

<210> SEQ ID NO 159
<211> LENGTH: 213
<212> TYPE: DNA
<213> ORGANISM: Artificial Sequence
<220> FEATURE:
<223> OTHER INFORMATION: Synthetic

<400> SEQUENCE: 159

```
tgtccatgtg cgcaacccctt aacgagcaat agaatgtatg gtcacctggg tgtggccagt        60
```

```
gcccgctgtg ccctgcatga ttctgtgttg ccgctgctgc atagttccca gccccatcct    120
gtcctgctca ctcatggggg cttccagacc ccggccccac cagggcttgt gtcataggga    180 gcccttttgca ctcctcgtgt gttggcaaac gca                                 213
```

<210> SEQ ID NO 160
<211> LENGTH: 1130
<212> TYPE: DNA
<213> ORGANISM: Artificial Sequence
<220> FEATURE:
<223> OTHER INFORMATION: Synthetic

<400> SEQUENCE: 160

```
ccctggcagg ctccttctaa acatgcctgt tgacctggag ctggcgccac caactccagg     60
gcctttccag ggccagacag gtaacacgca tgaacccgag tgacagctct gacgggctgt    120
ttcggtgtca ggagacaaag ctggcagggg caggggtgaa ctggaggcaa gtcaagtcac    180
ctgtggcctg tggggctgaa tgtgggcccg tgttgccag atcctttgtc ataagaagct     240
agaaatccag attttatgtg tgtgtaattt gtaaatgctg aaagctagcc tgaattttttt    300 tttttttttt ttgagacaga gtctcgctct gtcgcccagg ctggagtgca gtggcgcgat    360
ctcagctcac tgcaagctcc gcctcctggg ttcacgccat cctcctgcct cggcctcctg    420
agcagctggg actacaggcg catgctacga cgcctggcta attttttgta ttttttagtag    480 agacggggtt tcaccgtgtt aaccaggatg gtctcgatct cctgaccttg tgatccaccc    540
accttggcct cccaaagtgc tgggattaca ggcgtgagcc accacgcccg gccactagcc    600
tgaatttcaa tcaaggggttg gctgatactg tgtgtccagg gtggactgga tttgtcctgg    660
ggggttctct ggtttgctgc ctcctgacca catgatgggg ccttcgaggt cgaggacaac    720
tgttcccatt agattgcacc ctctgccctc aggttcttga gggtgtgtgg acacagaggc    780
tttccatggg atgtccctga gccggccctt gattggggcc tcaccattta cagggccgtt    840
ttattctgca aaccgaaact tgggtcatgt gacctgatgg gattatggga ctccctccag    900
gtgcccgaga caaggttgat atttccaaaa tattttggtg atttagtggg acaagcaaat    960
gacagaatac cggagaaggc agggatcgtg ggtgtcagga gccagagggg aggggggacag   1020 atgtgctgtg tacaggacaa ggtgtcaggt gactccttcc cagcagggcc tcgcagatgc   1080
acaagcacgg agctggtggg ttttgcccaa gaaaggtcac gcggcacatg                1130
```

<210> SEQ ID NO 161
<211> LENGTH: 356
<212> TYPE: DNA
<213> ORGANISM: Artificial Sequence
<220> FEATURE:
<223> OTHER INFORMATION: Synthetic

<400> SEQUENCE: 161

```
ctgtcgcgat ggagaagtac taaaatctat gaaagagttc taatgtagat ttaaggtcat     60
gagaagtctc cggcaaagtg gcattttaaa gtaatccctc agtcgtggag ctactccaat    120
gagaagcctg ccactccagg gcgcaccacg gaggaggatc cccagacaag aagacctggc    180
tccccagagg agtgcggaaa gccagcatgg ctagaggaca cagaatgagg gagaagacgg    240
atccgatcgc aggcatcggg agtgctgatt tttctccttt gaaaaacagg ttgccatcta    300 ccttttttaaa tgtcccactg tgtaggaaaa ctctggggaa agctacgtca gcaata        356
```

<210> SEQ ID NO 162
<211> LENGTH: 103

```
<212> TYPE: DNA
<213> ORGANISM: Artificial Sequence
<220> FEATURE:
<223> OTHER INFORMATION: Synthetic

<400> SEQUENCE: 162
caagccgaga tgctgacgtt gctgagcaac gagatggtga gcatcagtgc aaatgcacca      60
ttcagcacat cagtcatatg cccagtgcag ttacaagatg ttg                       103

<210> SEQ ID NO 163
<211> LENGTH: 355
<212> TYPE: DNA
<213> ORGANISM: Artificial Sequence
<220> FEATURE:
<223> OTHER INFORMATION: Synthetic

<400> SEQUENCE: 163
tgtggcccac acgtcatccg atgctgcgtg ctcacacttc acggcatctc cagcacctgc      60
taggccatgc gtgtcccttg gtgacgccgt ggggtagatc cctgatttca gtggccctca     120
tttaaagtac acgtgcaagt cagactggga gagccccgac gggacagtct cggtctgtac     180
ctgcacctgc cgtgctgtgc taggcgggtt tccttcctgt gagagctttt ctcactgttc     240
accagggaca gcagtcacct tcctaggagt tcacaggcag tgcgcatgtg ggagcggatc     300
tggggagacc ttcattggcc gcctctgatg tccgcagtgt gtcaggtcac caaca         355

<210> SEQ ID NO 164
<211> LENGTH: 102
<212> TYPE: DNA
<213> ORGANISM: Artificial Sequence
<220> FEATURE:
<223> OTHER INFORMATION: Synthetic

<400> SEQUENCE: 164
taccaagaat gctgtcaggg tcattgccta caaactgatg atgctgtgca gaattgcgcc      60
tctactgtaa ggctttcccg gtcctacttg gcgagtctta at                       102

<210> SEQ ID NO 165
<211> LENGTH: 29
<212> TYPE: DNA
<213> ORGANISM: Artificial Sequence
<220> FEATURE:
<223> OTHER INFORMATION: Synthetic

<400> SEQUENCE: 165
cccagaaggc agccgtatca ggaggttag                                        29

<210> SEQ ID NO 166
<211> LENGTH: 145
<212> TYPE: DNA
<213> ORGANISM: Artificial Sequence
<220> FEATURE:
<223> OTHER INFORMATION: Synthetic

<400> SEQUENCE: 166
aactgaggac gcgtggattc tactcaagcc tccaagtagt ggcatatcag tcttggagct      60
cctagctggt gatacggaga gggctttgga ggacttggga cagcagggcc aattttttg     120 cccaagtgcc taggctgcta actca                                           145

<210> SEQ ID NO 167
<211> LENGTH: 49
<212> TYPE: DNA
```

```
<213> ORGANISM: Artificial Sequence
<220> FEATURE:
<223> OTHER INFORMATION: Synthetic

<400> SEQUENCE: 167
gatggccacg cagatcagca ctcggggcag ccagtgtacc attgggcag          49

<210> SEQ ID NO 168
<211> LENGTH: 116
<212> TYPE: DNA
<213> ORGANISM: Artificial Sequence
<220> FEATURE:
<223> OTHER INFORMATION: Synthetic

<400> SEQUENCE: 168
cacagcggag tctgtcctgt gacgcgcaag tctgagggtc tgggcggcgg gcggctgggt    60
ctgtgcattt ctggttgcac cgcggcgctt cccagcacca acatgtaacc ggcatg      116

<210> SEQ ID NO 169
<211> LENGTH: 192
<212> TYPE: DNA
<213> ORGANISM: Artificial Sequence
<220> FEATURE:
<223> OTHER INFORMATION: Synthetic

<400> SEQUENCE: 169
tgctagtcat gcacctcaga cagtgcaagg tgcttccttt gatctatcat gtcagcagtg    60
ggagaggtcc ttagcctaac agaggtctga ctaaaagaac agccttcaaa gtgagtgtca   120
ttttcagaaa taaccatgct ctgccagatc tgtatggggt tttttaatcg catgctgctg   180
acagaacgtt tc                                                       192

<210> SEQ ID NO 170
<211> LENGTH: 782
<212> TYPE: DNA
<213> ORGANISM: Artificial Sequence
<220> FEATURE:
<223> OTHER INFORMATION: Synthetic

<400> SEQUENCE: 170
cgtgctcatc gtccatagtc ccatattttc ttataataaa cagtagtact ggcaggcaca    60
gtaggggcac aaggcatctg tcttattcaa gacaagtttg agacactgga aaaaagata   120 cttgttgtgt gtgttggaca gagtggcgag gctgagcact gtcacagggg cctcccatgt   180
taagagggac tgtggggatg atgtcagaac aagacgtggt ggatttgagg ttgatcgagt   240
attaatacta ctgcctctcc ttgtcttagt gggtatttaa aatagtaaat aagagagagg   300
aaggaggtga cgttcaggtg ctgtgggaag caggcttggc ggaggggtat gatgatgaga   360
ccctcattgt tcactggctc catcgcactc ctccctgggg ccgtgtgcct gttccattct   420
tcccaccatt cgaactgagc gaatctggca aggagacac gtctgtggga atgcgtagat    480
tccgcctcgg aagagagcta gcgcaacact aagaaaagca ggcttcttgt ttattctcag   540
gacctttttg taacagggct acattctgca aactgcttac aaaggaagac tatacgtctt   600
aacaaattat ttagccactg agtcctcccg attcggacct gttttagtaa tggcagaaga   660
atccctgagc aggttcaggt gccctagatg actagggtgc tgagctctgg cgccttctgt   720
ccccactctt tgcctccccg ccccttccct gagccacccc agcaagtggg tgtctttttct  780 cc                                                                 782
```

```
<210> SEQ ID NO 171
<211> LENGTH: 27
<212> TYPE: DNA
<213> ORGANISM: Artificial Sequence
<220> FEATURE:
<223> OTHER INFORMATION: Synthetic

<400> SEQUENCE: 171
agagggctgc tcaactgcaa ggacgct                                          27

<210> SEQ ID NO 172
<211> LENGTH: 470
<212> TYPE: DNA
<213> ORGANISM: Artificial Sequence
<220> FEATURE:
<223> OTHER INFORMATION: Synthetic

<400> SEQUENCE: 172
tctggggtca ccgagaaagt ctaaaaacag gaggctgaag gtactgtgat ggctttaaaa      60
atggccacct tattaaatag ggattgtatc aatattgaaa tgaagacaat ctttccaact     120
ttgggtgttt cacttgctgt tttaattgtt tgtttttaac actttgtagg tttgtgtttt     180
cataatcttt aatttgaaac tcatgtgtcc tcatggatcg tggatgcctt catttcttga     240
gctctcaatg cagacattta aatggctgca atcagtagag tgacccgcgg atggcataaa     300
tgcacctcct tttcttggcc ttggatctat gggtctggga ttgtggtcat ctcctcaatc     360
ctcaaaaaga ggctgaatca atgtggccgt gggtgggaac ttacatacag aacccaatga     420
agaacttgac tgtctaaaca aggggcctc gcatggagct gtaaagcatc                 470

<210> SEQ ID NO 173
<211> LENGTH: 396
<212> TYPE: DNA
<213> ORGANISM: Artificial Sequence
<220> FEATURE:
<223> OTHER INFORMATION: Synthetic

<400> SEQUENCE: 173
cctggctgag tctagacgtc tgataaccac gtaggtgggt aaggtaacca ctgggatggc      60
tggaaggtgt tacccaggga aactgaaggc caggatgaaa ataaaagcaa acggtttccc     120
cttgggcaat gactgccatc aggattctgc tgctgataaa atgctgctcc tttgttctgc     180
ttcctgcgtg ttcatccata tgatagctgt tagacatttc attcagcttt cacccacctg     240
gcactgcttc agtgccaacc aacggcaagg tgctccccag ctgccatggg gagccgggta     300
caaatagacc tcagcgaagc cctgcgtgca tgcaaactgc gtttgccttt tgcattctgc     360
ttttctctcg gggccatgct tgggacactt acacgc                               396

<210> SEQ ID NO 174
<211> LENGTH: 120
<212> TYPE: DNA
<213> ORGANISM: Artificial Sequence
<220> FEATURE:
<223> OTHER INFORMATION: Synthetic

<400> SEQUENCE: 174
acaatggtgt cttcagcggc cgaaaggagg ggcaggggaa gccccagcag caggagcagg      60
tgtgtggcag cccttcacaa ggggctttca tgtctcagtt gtatgttgcc agtgtcactt     120

<210> SEQ ID NO 175
<211> LENGTH: 250
<212> TYPE: DNA
```

<213> ORGANISM: Artificial Sequence
<220> FEATURE:
<223> OTHER INFORMATION: Synthetic

<400> SEQUENCE: 175

| | | |
|---|---|---|
| tccctgtgta ggatggcttc ccgttatttt tttttaagc aaagtaaatg aacatcaaat | 60 |
| ttccatagtc agctgctgtc tttctgccca ctgagagctc tttggtgaag gcaaagtcct | 120 |
| ccttcttcat tagcggtctc ccatgtgggg ccacatcttc cctcaccagg aacccagtgg | 180 |
| gcgcgctcca gccccctca gcttgccttt tgcgtggtca ttagagctag ggcacacgtc | 240 |
| atgctgattc | 250 |

<210> SEQ ID NO 176
<211> LENGTH: 28
<212> TYPE: DNA
<213> ORGANISM: Artificial Sequence
<220> FEATURE:
<223> OTHER INFORMATION: Synthetic

<400> SEQUENCE: 176
tggggccaag acatcaagag tagagcag                    28

<210> SEQ ID NO 177
<211> LENGTH: 99
<212> TYPE: DNA
<213> ORGANISM: Artificial Sequence
<220> FEATURE:
<223> OTHER INFORMATION: Synthetic

<400> SEQUENCE: 177

| | | |
|---|---|---|
| tttctcacct tgctgcggcc tgctgtttgg caggacgact tgactggctg cgctgtggtt | 60 |
| tctgcgcctg tgatggctcc ttctgaatgc cctctgagc | 99 |

<210> SEQ ID NO 178
<211> LENGTH: 410
<212> TYPE: DNA
<213> ORGANISM: Artificial Sequence
<220> FEATURE:
<223> OTHER INFORMATION: Synthetic

<400> SEQUENCE: 178

| | | |
|---|---|---|
| taggcccgtt tcacgtggga gcatgggagc cacgaccctt cttaagacat gtatcactgt | 60 |
| agagggaagg aacagaggcc ctgggcccttt cctatcagaa ggacatggtg aaggctggga | 120 |
| acgtgaggag aggcaatggc cacggcccat tttggctgta gcacatggca cgttggctgt | 180 |
| gtggccttgg cccacctgtg agtttaaagc aaggctttaa atgactttgg agagggtcac | 240 |
| aaatcctaaa agaagcattg aagtgaggtg tcatggatta attgaccct gtctatggaa | 300 |
| ttacatgtaa aacattatct tgtcactgta gtttggtttt atttgaaaac ctgacaaaaa | 360 |
| aaaagttcca ggtgtggaat atggggtta tctgtacatc ctgggcatt | 410 |

<210> SEQ ID NO 179
<211> LENGTH: 159
<212> TYPE: DNA
<213> ORGANISM: Artificial Sequence
<220> FEATURE:
<223> OTHER INFORMATION: Synthetic

<400> SEQUENCE: 179

| | | |
|---|---|---|
| aataagaaag gctgctgact ttaccatctg aggccacaca tctgctgaaa tggagataat | 60 |
| taacatcact agaaacagca agatgacaat ataatgtcta agtagtgaca tgttttttgca | 120 |

| catttccagc cccttaaat atccacacac acaggaagc | 159 |

<210> SEQ ID NO 180
<211> LENGTH: 437
<212> TYPE: DNA
<213> ORGANISM: Artificial Sequence
<220> FEATURE:
<223> OTHER INFORMATION: Synthetic

<400> SEQUENCE: 180

| gctgagccct aactgatacg ctgtgtttcc agtgtccctc atccactaga ctcagtggtg | 60 |
| tcaggaatgg tgtggtattt tgttataaat ttaactcctt agatggacac acagagagcc | 120 |
| tcgataaata tttttaatcc atcaatgcaa ggagtgtggt tgtcagaagt cagctaaaag | 180 |
| tccaagttta aatctaagct ccgccgttca cagcttgggt gacctcagct tcttttttgg | 240 |
| aaatgaagtt catatttcc gagcactttt tctgtgccag gtgcttccaa atgtatctcg | 300 |
| tttaatcctc acaacatacc tcagaggaag acatcatttt tacaagtaag gaaatagagg | 360 |
| ctcagagaga tgaagtggtt gacccgggct gtctatcttg taaatggtgg gctgtgattc | 420 |
| ccacacgact ggagttt | 437 |

<210> SEQ ID NO 181
<211> LENGTH: 456
<212> TYPE: DNA
<213> ORGANISM: Artificial Sequence
<220> FEATURE:
<223> OTHER INFORMATION: Synthetic

<400> SEQUENCE: 181

| ttggcttatc agttggcatg acctctgaag atcttttgc tctgaatgtt ttaatcatca | 60 |
| agttctggtg gttatccaag gtgatcctaa tctactttgg ggtggaggga ggaagtggtg | 120 |
| tcaggagaga tcaaaccagg ccaccttgag ctgaaagctc tgaaggagaa ggattccttg | 180 |
| aaatggaggt aatttttgaa ttataataag tgagaagact gcaagggaga caagctgagg | 240 |
| gacaaatgct ctgtgctttt ctcctcactt tcacaaacag gaggagaact tccactgacc | 300 |
| tagcagtagt ttgctcctcc aggctgtcat gtcttctgat catgtctttt atgaggtgaa | 360 |
| tttctcctca tgaaagacta gactttaagg agagattctg tgcaggtccc tacagtgtgg | 420 |
| agatggattg attgggccta cagattgcag ctaatc | 456 |

<210> SEQ ID NO 182
<211> LENGTH: 422
<212> TYPE: DNA
<213> ORGANISM: Artificial Sequence
<220> FEATURE:
<223> OTHER INFORMATION: Synthetic

<400> SEQUENCE: 182

| gcgtgcatgt gcgtttttag caacacatct accaaccctg tgcatgactg atgttgggga | 60 |
| aaagaaaag taaaaaactt cccaactcac tttgtgttat gtggaggaaa tgtgtattac | 120 |
| caatggggtt gttagctttt aaatcaaaat actgattaca gatgtacaat ttagcttaat | 180 |
| cagaaagcct ctccagagaa gtttggtttc tttgctgcaa gaggaatgag gctctgtaac | 240 |
| cttatctaag aacttggaag ccgtcagcca agtcgccaca tttctctgca aaatgtcata | 300 |
| gcttatataa atgtacagta ttcaattgta atgcatgcct tcggttgtaa gtagccagat | 360 |
| ccctctccag tgacattgga acatgctact ttttaattgg ccctgtacag tttgcttatt | 420 | ta                                                                       422

<210> SEQ ID NO 183
<211> LENGTH: 42
<212> TYPE: DNA
<213> ORGANISM: Artificial Sequence
<220> FEATURE:
<223> OTHER INFORMATION: Synthetic

<400> SEQUENCE: 183
cctgccatgc cgctgccacc gcggagcctg caggtgctcc tg                           42

<210> SEQ ID NO 184
<211> LENGTH: 365
<212> TYPE: DNA
<213> ORGANISM: Artificial Sequence
<220> FEATURE:
<223> OTHER INFORMATION: Synthetic

<400> SEQUENCE: 184
gctcactgtc ttaggcctcg tcttggttcc tgcatgctcc acctgcctgt tctggtctct        60
aaactcaatt gaatgacttg atgttacagc tttcaagcag agaagtgtgg ggtgatggtg       120
gcaagacaga ggggcgccat tactctcatc gctcctttg tggtggcagt cgtattctcc        180
tcctggggtt tctcttgtgt tggcgagtgt atcaaagtga agtgtgtttc cattgattca       240
gtaactgttg agtgtgccct cagtgtggat ggcaccagcc cagtgggtg cactcctcag        300 cattcgggat tcttccttt gtccctctgg ggcttgcaca caggcaggca cactcacgtg        360
gaatc                                                                    365

<210> SEQ ID NO 185
<211> LENGTH: 74
<212> TYPE: DNA
<213> ORGANISM: Artificial Sequence
<220> FEATURE:
<223> OTHER INFORMATION: Synthetic

<400> SEQUENCE: 185
tttgtgtgca cccagtgaga aggtttattt tgactttata gatgggatat ctagagctgg        60
agtcctatat tcag                                                          74

<210> SEQ ID NO 186
<211> LENGTH: 1615
<212> TYPE: DNA
<213> ORGANISM: Artificial Sequence
<220> FEATURE:
<223> OTHER INFORMATION: Synthetic

<400> SEQUENCE: 186
agccctgtgc ctgattctta taataagtac atatataaag taactataat ttttatttta        60
atccagttaa atggctagca gaaggctttg accaatggac ctgggcatcc aaagttacca       120
catttgttcc tgggattgta gagatgtaga gaccaggttt tgccaaacaa atcccaaata       180
tggccggtgc agtggcttat gcctttaacc ccaacacttt gggaggctga ggtgggagga       240
atgcctgaag ctcaggagtt tgagaccagc ctgggcaaca cagcaagacc ccatctctat       300 aattttttt taattggctg ggcatggtgg tgcatgcctg tggtcctggc tgcttggcag        360
tatgaggtgg agcccaggag tcaaaggctg catggagcca tgatcacggc actgtactcc       420
aggctgggtg acaaagtgag accctgtctc aagaaaaaa taataataat aataataata       480
tccaggctgg gggcgatgac tcacgcctgt aatcctagca ctttgggagg ccaaggggg       540

```
tggattgctt gaggccagga gttcaagacc agcctgggca acatggtgaa acctcgtctc    600
tactaaaaat acaaaaatta gccaggtgtg tgggcacaca tctatagtcc cagctactgg    660
ggaggctgag gcacaagaat tgcttgagcc cgggaggtag aggttgcagt gagtggagac    720
tgtgccactg cactccagcc taaaaaaaag aaaaaaaaat ggaaataccc ctcagtagga    780
gagaacatgg tctacattct gccttccgaa atccatatta acatttggtg gctgcttgtt    840
gaagctaggt gatagcatta gagagtcctg gtgtcatgaa agccagagca tcctagtgaa    900
ctttcaggga tggggtggaa ggtggagaag aaatgggcta tggagtagtt cagaatgtct    960
ccaatggggc tacttttgag agagaatgct ctctttcacc atttgtcttc caggatatga   1020
acagaatata gagttgctat cttccttaga gtgtgaaagt ctaggctgtc tgcaagacag   1080
catgttatgg ttttattat ttttattga ttgattgatt gtagagacgg catctcgctg   1140
tgttgcccag gctggtctca aactcgtggc ctcaactgat cttcccacct cagcctccca   1200
gagtgctggg attatgggtg tgaaccacag cacttggcca tggtaatggt ttttaaaaaa   1260
gggatcacca gctgtgaact tggaagcctt aggtgtgaac tctgtgatat tattcaacct   1320
ctctgaacct atttcttacc atcaaaatga aagttatctg ccctatttag ctgattgggt   1380
tgctgtgtgg ctcaaatgat gcagtcaatt tgtaaactgt aacgtgctgc acagatgtta   1440
ggtattctgg tcttctgatt gtgtgcttgg ctttctagct gcttgaagcc gctcagagct   1500
tatgtatcac caagggttag agatgtagtg ctacccacct ctttcatcct gcaccccaa   1560 tttctccact tgtccatttc cacaaatgta tccctggaga cactgtgata atttc         1615

<210> SEQ ID NO 187
<211> LENGTH: 73
<212> TYPE: DNA
<213> ORGANISM: Artificial Sequence
<220> FEATURE:
<223> OTHER INFORMATION: Synthetic

<400> SEQUENCE: 187
gaaactcaag gcatttatct ctttgggctg cttgtccttg cctgagctga agcctgatgc     60
ctcccataag ttg                                                       73

<210> SEQ ID NO 188
<211> LENGTH: 72
<212> TYPE: DNA
<213> ORGANISM: Artificial Sequence
<220> FEATURE:
<223> OTHER INFORMATION: Synthetic

<400> SEQUENCE: 188
tccatttctt cgttccacat gaccacagtt tgcaagtgta ttccatggag aagtggagtg     60
attgggaatt ac                                                        72

<210> SEQ ID NO 189
<211> LENGTH: 580
<212> TYPE: DNA
<213> ORGANISM: Artificial Sequence
<220> FEATURE:
<223> OTHER INFORMATION: Synthetic

<400> SEQUENCE: 189
ggtccaggag taaatgccaa tttcacatat aatgtagaca gattatctga tgggcatcta     60
tcagatacaa agtctgcccc ttttcatgt ccttttgtc taaatatagt cattatcatc     120
```

| | |
|---|---|
| atcatcatca tcatcaaatc atttcatcac catcagaaat gcttatacat tatcctgatg | 180 |
| tataccaaag ctactgtttg gaaagaaact aaaataaaag tccaggtcac ttaaccatac | 240 |
| agggctgatg ttagatgaaa gcaagcatcg ataccaaatg caattttaca taatattacc | 300 |
| tgtcaacaaa atatatttgg acagccgcat ggtaatttta cacattatgt gtaaacaaag | 360 |
| tattggtggc atcacatggt aaaaactcag taatttcacc tcagaaattc ttcttcacat | 420 |
| cagaaatgta gtttgtgcat tgaggctatc tgattgatgt ttatgcctct ctgcttggga | 480 |
| tatattcatg agaataaata atagaaacct ctcccaatga atgcagtctg tctgaattca | 540 |
| ttgatcttta tgcagtggag atattctgca caagccgcta | 580 |

<210> SEQ ID NO 190
<211> LENGTH: 203
<212> TYPE: DNA
<213> ORGANISM: Artificial Sequence
<220> FEATURE:
<223> OTHER INFORMATION: Synthetic

<400> SEQUENCE: 190

| | |
|---|---|
| cgtactcttg ctagggcttt tcatggagat gtagaaatgg tagtaagtgc caaggcccca | 60 |
| gaaccctcat gtttgggtcc gactcccaca ttgccagaga ctaggcagct cacacaggtg | 120 |
| tcccaagctg tctttctcac aggccgcatt gaaggcattt atgaaatgag accccctctt | 180 |
| cctcatccgt agtgacaggg ctg | 203 |

<210> SEQ ID NO 191
<211> LENGTH: 419
<212> TYPE: DNA
<213> ORGANISM: Artificial Sequence
<220> FEATURE:
<223> OTHER INFORMATION: Synthetic

<400> SEQUENCE: 191

| | |
|---|---|
| tggataaaac ttcagccggc cttctcttta tgtgcctggc gcctctcttt tctctgggtt | 60 |
| tttggaagtc tgcctgccca gcccctcagc tggggccttc cccacttctg ccccgcccca | 120 |
| ctgggtcctc ccagggtagg aggcaatctc tgactgtctt ccgaggctct gttgcttctc | 180 |
| cttcatcacc aaatgccagg aatttgtcag atgctgtttg taactcaaaa gaaagaaaga | 240 |
| aaagaaaaaa gatacaggaa ggaaggaagg cagaaaaaga gaaagaaaga atgcgtgcag | 300 |
| cagatgttgg gaaagttaat ttcttcatta ttttgcatcc atcccagttc ggatctcagc | 360 |
| atggggtagg gaatcctctg ttgtccccat ctgtcgaggc aacagtgagt cccatcatg | 419 |

<210> SEQ ID NO 192
<211> LENGTH: 912
<212> TYPE: DNA
<213> ORGANISM: Artificial Sequence
<220> FEATURE:
<223> OTHER INFORMATION: Synthetic

<400> SEQUENCE: 192

| | |
|---|---|
| caaccaattg agacactgag gcctaaagaa attattggct ataataatga ggtgattgcc | 60 |
| ttagctatca cgccagattt gctctttttgt tttctcctga tattttaaac tcttccttgc | 120 |
| tggaatatta ataactcaaa gataaaaagg gtacaacttg tttccatgtg ggaggtagga | 180 |
| agaacattgc ttttggagtc agttctaggc ctggtgactc tttgacttgc cagttgtgtg | 240 |
| ccatgatcac tccaagcatc catttttctca tgtgtaaaaa gcatgttaaa aattttaaat | 300 |
| gaggagttta aaaattacac tcccagtagg cttactatga ggactaaaat aaataaaagt | 360 |

-continued

```
gtgaaatgca gtgccaagca cataatagct gctcaataaa tggaagctaa attattttcc    420
acagttatct ttcaaatttc actttgatca gttttcacag actatcttct aagcaaattc    480
tgtaggtgtt tgccttcgga aaagtgcgtt tgttgtcagt gaatggttac agggaaaagg    540
agatacttgt catgcagctg gaaacatgaa aacttggccc tgtgttctta aaaatgaaaa    600
ctccctgcag gatgggtcaa gttgctacca taggctggag cctatgattc tcagagcagc    660
atcactctta atggcactgt tctgcatgcc cttaccttgc tcattttgct gggctcagta    720
ctaattttca tccctaggc aggcaaaacta gtgtcattg tggcagttcc ttccatacta    780
agaggaagca ttgatcacta agagtcagca tggtttacta tgagtaaatt aaaccagacc    840
tatcttgacc tctgacaagg ttgtcgtgat gaccatgtca gtttggttcc ttgctgtatg    900
cccagtgtct ga                                                       912
```

<210> SEQ ID NO 193
<211> LENGTH: 270
<212> TYPE: DNA
<213> ORGANISM: Artificial Sequence
<220> FEATURE:
<223> OTHER INFORMATION: Synthetic

<400> SEQUENCE: 193

```
cgccatgggg tggttcgaag aaccatgatg aaggctggtt cgaattgtga tgaccatttt     60
tgtccacatc tcctaggacc cataagccag agtttctctg gagcttatag ctagaagggg    120
ttctgggtcc tggagtgcag gcctgtcaac tttacaggag agcactagat tgctttctga    180
agtggctgaa ccaggttatg cttccatcag ctgtgtatga gcatccccat cttcttgacc    240
acacttgaag ccatcagttt ccttgaagca                                    270
```

<210> SEQ ID NO 194
<211> LENGTH: 632
<212> TYPE: DNA
<213> ORGANISM: Artificial Sequence
<220> FEATURE:
<223> OTHER INFORMATION: Synthetic

<400> SEQUENCE: 194

```
tatgtgcagc acaaaatgtc gtttcttatg tttgttccta taatgcgttc tggcacttat     60
gtgatgcttc acttaaaaat acttagctct ttctttttcc ccccaaatca ataacttaa    120 tgcctgctcc aaataagcta aaatagtttt gataatttc tagcaaatgg caaactttta    180
ccttttagca gttaaaaact ttctgaaata tttaaaaatc actttgacag tatattaaag    240
tgagtgaaag tctttatcta aagatcccac tcaacttttc gtgtacttaa aatattatag    300
gaaaattgag gaggtgactt attatagaaa taagaagact taaatgaata aattttctga    360
aaggaaagtg actcttgtga aagatctcaa atggcagact tcattttgtg ttttatcttt    420
gctggctttt actcacctac actcatttac aaatccatga aaatggttca aggtcattg    480 gtgaaacttg agaacaaatg caaaacttcc aactatggga aataggtaga aatacatttt    540
aaaaacattg ggtttattaa attgggttga ttttattact aatttataaa tcagtcaaaa    600
atgtaacgcc aagttcattg tcctagagcg aa                                 632
```

<210> SEQ ID NO 195
<211> LENGTH: 576
<212> TYPE: DNA
<213> ORGANISM: Artificial Sequence
<220> FEATURE:

<223> OTHER INFORMATION: Synthetic

<400> SEQUENCE: 195

```
gcactgccgt actcttggga aatttgtcca aggccacccg gctgagcagc ggttgaacca      60
ggacaccatc aggcatgcgt ttcttgtctc caccacaccc tcaacccact tcccaacgcg     120
ccttgcgaca ggggctgcgg tattgcatcc acatgactga taaactagta aacacacatg     180
aattcatttt aaaagtgtat tcaatcagtt aggtaaacta aaaaccttaa gtcttcgttc     240
gatttggaat gcagccagag aacaaatgga aaattttca aggtagagaa gatgaaaact     300
cagaacgccc tcttgtggca tctctaccca ccctaggaac actatggctc ttcccctaca     360
catggtgatt gctaaccttg ctacaagacg ttggacacac acacacacac acacacacac     420
acacacacac tgaggttcct tttgcccccct cacttttgag ccagtgacta ctgaaaccct    480
ctccattgtt gcaccaccag caatgccccc atcacttcct ctcatttact tccacaggct     540
ggttcatcct caaagccctc cttacgtaga tctgtg                               576
```

<210> SEQ ID NO 196
<211> LENGTH: 129
<212> TYPE: DNA
<213> ORGANISM: Artificial Sequence
<220> FEATURE:
<223> OTHER INFORMATION: Synthetic

<400> SEQUENCE: 196

```
tctggcagct cttagtcatg tcttggaggg aggacgggca tccagggctg accggtcaac      60
gtccagcacc tcccagggac tatgggaaga ctgagtggtg ggtctcgtcc tctcgggata    120
cttgcgctt                                                             129
```

<210> SEQ ID NO 197
<211> LENGTH: 610
<212> TYPE: DNA
<213> ORGANISM: Artificial Sequence
<220> FEATURE:
<223> OTHER INFORMATION: Synthetic

<400> SEQUENCE: 197

```
ccatccagct gatcggctct agttctatgg tcctgttggc ttctaggatt ccttgttgtt      60
gtagtcaatt gggggaagaa ggtgcagagg gagtgcacag agttaacatc ctatcagccc    120
aagcttcacc tcggcacccg agtctcaggc agtctccctg gcttctacat aggcagtgct    180
tcttcctcat tgtgtggggc tttgattttg taattccaag agcctggggc tcctggcaag    240
gaaaatggtt ttcaaataat ggtttcgaga aacaaagctg gggaagaggc aatgtaagct    300
caggctctgg caggcaggca gagatcctgg gaaggctggg tgctgactgc acatggagca    360
atgggaaggg atgctggtga gaggagacgg gggcacttaa gctccggccc cagctctgct    420
ctcagtgccc ggctctgtgg tcttgggctg gccccctccc ttctctggc catagttttc     480
ccatctgtat agcaaggcca ttggacaaaa tggtccctct gcagatgtgg cttctgagtt    540
gtttgtgcct gagggacagc cagtgttggg aagttccccc aggaggtccc tgagccgagt    600
ctgaactttg                                                            610
```

<210> SEQ ID NO 198
<211> LENGTH: 208
<212> TYPE: DNA
<213> ORGANISM: Artificial Sequence
<220> FEATURE:
<223> OTHER INFORMATION: Synthetic

<400> SEQUENCE: 198

```
tgttctgagt caggcatgga ggtatcttct cataatcaaa agataagcaa gaaacagtta    60
actgcccgca aggattccac aattttgaat cctaacttca gatgctatct ccttacctca   120
tttggcacgt gcattgtgc tggtatacat acctttttca gcacataaac tcatttggca    180
catgtgccaa ggattgccaa ctatctta                                       208
```

<210> SEQ ID NO 199
<211> LENGTH: 44
<212> TYPE: DNA
<213> ORGANISM: Artificial Sequence
<220> FEATURE:
<223> OTHER INFORMATION: Synthetic

<400> SEQUENCE: 199

```
gtcaccatgg aacgtgtgca tagatgatgt tcccgtgtct ttca                     44
```

<210> SEQ ID NO 200
<211> LENGTH: 86
<212> TYPE: DNA
<213> ORGANISM: Artificial Sequence
<220> FEATURE:
<223> OTHER INFORMATION: Synthetic

<400> SEQUENCE: 200

```
cagttctcag acatttacgg gaaagctctg gtggcgtgtt agatgcagtt catctctctc    60
tgtttgcagc gctctcaata gagacc                                         86
```

<210> SEQ ID NO 201
<211> LENGTH: 363
<212> TYPE: DNA
<213> ORGANISM: Artificial Sequence
<220> FEATURE:
<223> OTHER INFORMATION: Synthetic

<400> SEQUENCE: 201

```
cttgactgtc acgatagaaa gaggaagcag aagaatgaag acaaagccat ttaaaatttt    60
cttgttcttt acctttttgca taaaaggtat tcagttcaca aatgatgtaa aatttaatta  120
aggcaagtga ctgtcctgag aaagtcatta aaaccctcat gtcatttctc taatcaaaag   180
gctgccacgc ttctattatt tctttattac aacccttat ttttatttct tcaagttaaa    240
ctggagcctg agccatcata agcctcttgc tagtgatttt ttaaatcagt gatttacact   300
ttgaaaaacc aattttttttt attttccaa tttatattgg ttagatccat agggtcactt    360
tga                                                                 363
```

<210> SEQ ID NO 202
<211> LENGTH: 301
<212> TYPE: DNA
<213> ORGANISM: Artificial Sequence
<220> FEATURE:
<223> OTHER INFORMATION: Synthetic

<400> SEQUENCE: 202

```
ggctgatgac ttctcacagt gtatctcaaa gcattattgc atgtcccact tggttgatag    60
ggcatctcta gcctgacaga tttatctgtt gagaacagga ttatgcattt gaaaccagtt  120
taattcttag caagacaatg cacatgtctt atgtagattt tgttgttggt ttttttctcc   180
ttcgtaagtt actcggggaa agtcatgtca atataaatca gtggtaatga aatcaacatt   240
```

```
atagcatctt tgataatgca tttgctaaag cctttctgga cgtttaccca gctctcaatg    300
a                                                                    301

<210> SEQ ID NO 203
<211> LENGTH: 116
<212> TYPE: DNA
<213> ORGANISM: Artificial Sequence
<220> FEATURE:
<223> OTHER INFORMATION: Synthetic

<400> SEQUENCE: 203
caatttccac cgcggccatt tgttaaacgc atagctgcca tcttcagtga ttatttccaa    60
gtaacatcta tgtttctgaa taaaaatcca tttgaatctc aagtcagatt tgccag       116

<210> SEQ ID NO 204
<211> LENGTH: 335
<212> TYPE: DNA
<213> ORGANISM: Artificial Sequence
<220> FEATURE:
<223> OTHER INFORMATION: Synthetic

<400> SEQUENCE: 204
actcggtgag cttaaccgta cactgagctg gtgcagccgg ggatccatct cagcccctgc    60
ttcccactca gccagaccca gaccctgcat tccagctttg gttgtgtgga ttctctagag   120
aaggacccct tggctgtttgt ccccatgcat ttcttgatgt caggcagcag catctgccag   180
ttgtgactgt cctgcctgga ctacaggttt ggttgggtgt gccctacaaa ccttgctcct   240
ctcaaacgtg ctctgccgtg gtgtagcttc tggcgcttca ctcttctgtc cgctgggatc   300
cctagggggg ctggatgctc gtaccagact gtgga                              335

<210> SEQ ID NO 205
<211> LENGTH: 131
<212> TYPE: DNA
<213> ORGANISM: Artificial Sequence
<220> FEATURE:
<223> OTHER INFORMATION: Synthetic

<400> SEQUENCE: 205
gtttggcgta atacggaagc cctcagagca gtacgcttca agcagtttat gaagtcctta    60
gcgtctttct tatggccgaa aatagtttgg aatgggttga acaatgggc caacctaacc    120 agatgaaact g                                                        131

<210> SEQ ID NO 206
<211> LENGTH: 98
<212> TYPE: DNA
<213> ORGANISM: Artificial Sequence
<220> FEATURE:
<223> OTHER INFORMATION: Synthetic

<400> SEQUENCE: 206
ataaataagt gaagagctag tccgctgtga gtctcctcag tgacacaggg ctggatcacc    60
atcgacggca ctttctgagt actcagtgca gcaaagaa                           98

<210> SEQ ID NO 207
<211> LENGTH: 49
<212> TYPE: DNA
<213> ORGANISM: Artificial Sequence
<220> FEATURE:
<223> OTHER INFORMATION: Synthetic

<400> SEQUENCE: 207
```

```
tctatgcggc acccagatt tcttgggatc tgatgctaga ccttggagg            49

<210> SEQ ID NO 208
<211> LENGTH: 129
<212> TYPE: DNA
<213> ORGANISM: Artificial Sequence
<220> FEATURE:
<223> OTHER INFORMATION: Synthetic

<400> SEQUENCE: 208
ccatatgaag taaggactga ttatccttt tttataaatg aggaaattga gtcacagggg    60
ggttggtagc tagtctagga tcacacagtt tgttggaggg ggtagtgtat gcacgtgccc   120
acttttca                                                           129

<210> SEQ ID NO 209
<211> LENGTH: 2092
<212> TYPE: DNA
<213> ORGANISM: Artificial Sequence
<220> FEATURE:
<223> OTHER INFORMATION: Synthetic

<400> SEQUENCE: 209
ggccctgctg cctaaactgt gcgttcataa ccaaatcatt tcatatttct aaccctcaaa    60
acaaagctgt tgtaatatct gatctctacg gttccttctg ggcccaacat tctccatata   120
tccagccaca ctcattttta atatttagtt cccagatctg tactgtgacc tttctacact   180
gtagaataac attactcatt tgttcaaag acccttcgtg ttgctgccta atatgtagct    240
gactgttttt cctaaggagt gttctggccc aggggatctg tgaacaggct gggaagcatc   300
tcaagatctt tccagggtta tacttactag cacacagcat gatcattacg gagtgaatta   360
tctaatcaac atcatcctca gtgtctttgc ccatactgaa attcatttcc cacttttgtg   420
cccattctca agacctcaaa atgtcattcc attaatatca caggattaac ttttttttt    480 aacctggaag aattcaatgt tacatgcagc tatgggaatt taattacata ttttgttttc   540
cagtgcaaag atgactaagt cctttatccc tccccttgt ttgatttttt ttccagtata    600
aagttaaaat gcttagcctt gtactgaggc tgtatacagc cacagcctct ccccatccct   660
ccagccttat ctgtcatcac catcaacccc tcccatgcac ctaaacaaaa tctaacttgt   720
aattccttga acatgtcagg catacattat tccttctgcc tgagaagctc ttccttgtct   780
cttaaatcta gaatgatgta agttttgaa taagttgact atcttacttc atgcaaagaa    840
gggacacata tgagattcat catcacatga gacagcaaat actaaaagtg taatttgatt   900
ataagagttt agataaatat atgaaatgca agagccacag agggaatgtt tatggggcac   960
gtttgtaagc ctgggatgtg aagcaaaggc agggaacctc atagtatctt atataatata  1020
cttcatttct ctatctctat cacaatatcc aacaagcttt tcacagaatt catgcagtgc  1080
aaatccccaa aggtaacctt tatccatttc atggtgagtg cgctttagaa ttttggcaaa  1140
tcatactggt cacttatctc aactttgaga tgtgtttgtc cttgtagtta attgaaagaa  1200
atagggcact cttgtgagcc actttagggt tcactcctgg caataaagaa tttacaaaga  1260
gctactcagg accagttgtt aagagctctg tgtgtgtgtg tgtgtgtgtg agtgtacatg  1320
ccaaagtgtg cctctctctc tttgacccat tatttcagac ttaaaaacaa gcatgttttc  1380
aaatggcact atgagctgcc aatgatgtat caccaccata tctcattatt ctccagtaaa  1440
tgtgataata atgtcatctg ttaacataaa aaaagtttga cttcacaaaa gcagctggaa  1500
```

-continued

| | |
|---|---|
| atggacaacc acaatatgca taaatctaac tcctaccatc agctacacac tgcttgacat | 1560 |
| atattgttag aagcacctcg catttgtggg ttctcttaag caaaatactt gcattaggtc | 1620 |
| tcagctgggg ctgtgcatca ggcggtttga gaaatattca attctcagca gaagccagaa | 1680 |
| tttgaattcc ctcatctttt aggaatcatt taccaggttt ggagaggatt cagacagctc | 1740 |
| aggtgctttc actaatgtct ctgaacttct gtccctcttt gtgttcatgg atagtccaat | 1800 |
| aaataatgtt atctttgaac tgatgctcat aggagagaat ataagaactc tgagtgatat | 1860 |
| caacattagg gattcaaaga aatattagat ttaagctcac actggtcaaa aggaaccaag | 1920 |
| atacaaagaa ctctgagctg tcatcgtccc catctctgtg agccacaacc aacagcagga | 1980 |
| cccaacgcat gtctgagatc cttaaatcaa ggaaaccagt gtcatgagtt gaattctcct | 2040 |
| attatggatg ctagcttctg gccatctctg gctctcctct tgacacatat ta | 2092 |

<210> SEQ ID NO 210
<211> LENGTH: 90
<212> TYPE: DNA
<213> ORGANISM: Artificial Sequence
<220> FEATURE:
<223> OTHER INFORMATION: Synthetic

<400> SEQUENCE: 210

| | |
|---|---|
| gtgtccctgt tgtggtactt ctgcaagtcc tccttctgga tggccacctt ccctgcaaca | 60 |
| caagcagaga agacttcacc acgggcacag | 90 |

<210> SEQ ID NO 211
<211> LENGTH: 34
<212> TYPE: DNA
<213> ORGANISM: Artificial Sequence
<220> FEATURE:
<223> OTHER INFORMATION: Synthetic

<400> SEQUENCE: 211

| | |
|---|---|
| gaccctcgta gtgtgccggt caatgcttgc cttt | 34 |

<210> SEQ ID NO 212
<211> LENGTH: 69
<212> TYPE: DNA
<213> ORGANISM: Artificial Sequence
<220> FEATURE:
<223> OTHER INFORMATION: Synthetic

<400> SEQUENCE: 212

| | |
|---|---|
| tgcagggcgg tttgccgctg ccaccctcgg caccatctct gaactgcccg cttttccgga | 60 |
| ggagcggaa | 69 |

<210> SEQ ID NO 213
<211> LENGTH: 101
<212> TYPE: DNA
<213> ORGANISM: Artificial Sequence
<220> FEATURE:
<223> OTHER INFORMATION: Synthetic

<400> SEQUENCE: 213

| | |
|---|---|
| gggtgacgtt gctgatagct caatacttaa cgtacagcag gaaggagcac tgaggcagtg | 60 |
| gcttgagctc agtctgtggg aggagacctg ttttgatcca g | 101 |

<210> SEQ ID NO 214
<211> LENGTH: 1077
<212> TYPE: DNA
<213> ORGANISM: Artificial Sequence
<220> FEATURE:
<223> OTHER INFORMATION: Synthetic

<400> SEQUENCE: 214

```
cagggtctga tgattttggc gtttccctgc ttcccaattg acctggctgt gctgttggct      60
gttcttgcac actcaaggtg gttttgccat tggcttcctc cctcagcctg cctctgggat     120
tatgccactg ctattctttt ttatctacca tcagcacaat gaaatcatca ttttgtctt      180
caaggtacca aattctggtg atattggtgc tttcttgcag ctacttatca tgagaagtga     240
atggtctcat agtgaacaca gtcatggtta tagtgttcat acgttccaga gacatgtttc     300
ctataattat gccctgcaca ttttttctatc atacaatcct tagattacag ctctttggtt    360
ttcaacagct ttgtccaatt ccatctttcc cagtttctct accttgatga atatccttc      420
ttgcctggtt ttacatattt aaataacaaa ttccaaaagt aaagagtatc tgaggcagtc     480
acatgacata aggacaaatt caagccatct ggacttgca gagggtgggg agaccgtgtc      540
aacacacaca atttaaaaa ttttcttccct ttcaatcttt taaaaacaaa acttttata     600
aaataaaaat gtaatttaaa aaggctacct gtcttggcaa gtagctgatc agcctgcatt    660
ggtgagcagg ccattccata acctggtttc ttgctcctta attgacagca tggagctaac    720
gtacttaatt tcagctcttt ctacgtgatt tgactcattc tgttaacatt aactgttttt     780
cagtcttctc aactagactg aactccttaa gtgcaagaaa tacacgctta gtaaatgttt    840
gttggaccag acactgcacc ttatgaaatt aaagaccaga acattctcat ggtagcatta    900
cagacactga tggcaaaggt actgtgggat ttgggtttgg ctaataagct ctgtggtggt    960
gtttcagaag gaaaatggtg ctctcttagt tctatggaac atagtggtcc agatcttcta   1020
ctgtaaccag gcccaaagct ggctaatctg gagggctctg ccttagggat acttata      1077
```

<210> SEQ ID NO 215
<211> LENGTH: 174
<212> TYPE: DNA
<213> ORGANISM: Artificial Sequence
<220> FEATURE:
<223> OTHER INFORMATION: Synthetic

<400> SEQUENCE: 215

```
attctgagtt accaacacgt tgtgcgtgca ttgatgaccc ggcttcctgg cctgcccttg      60
gtgcctgagc cccagtaatg attgccctct atgttgggag aagaagggag aaagtagtac     120
aagtagtgaa gaaaaaaatg taggtggtgt tggtggttga gagtacatgg caca           174
```

<210> SEQ ID NO 216
<211> LENGTH: 41
<212> TYPE: DNA
<213> ORGANISM: Artificial Sequence
<220> FEATURE:
<223> OTHER INFORMATION: Synthetic

<400> SEQUENCE: 216

```
gtaagtgagt gggcctgagt tgagaagatc ctggccttgg a                          41
```

<210> SEQ ID NO 217
<211> LENGTH: 28
<212> TYPE: DNA
<213> ORGANISM: Artificial Sequence
<220> FEATURE:
<223> OTHER INFORMATION: Synthetic

<400> SEQUENCE: 217

```
acctgccacc ggctggcaca caccaccc                                          28
```

<210> SEQ ID NO 218
<211> LENGTH: 26
<212> TYPE: DNA
<213> ORGANISM: Artificial Sequence
<220> FEATURE:
<223> OTHER INFORMATION: Synthetic

<400> SEQUENCE: 218

```
ctgcagccga gggagaccag gaagat                                            26
```

<210> SEQ ID NO 219
<211> LENGTH: 316
<212> TYPE: DNA
<213> ORGANISM: Artificial Sequence
<220> FEATURE:
<223> OTHER INFORMATION: Synthetic

<400> SEQUENCE: 219

```
catcccgaag tgtggctaag ccgcccggag gaacacaaag ggcatacgcg cacgcacact       60
taaagtttta aaacacgatt tatttatttt tgtctgctgc aacgctggga gaaatgtggt      120
ctttggaagg aagctctcca gtgtgtaacc ttcctattat tttggccccc acactgtggc      180
tttagtagaa caggagcaaa caagtttata aggcaaggag gtggagagat taaaagagca      240
ttctcttgca tttatgaagt gtcactccgg tgtgtatgta ggtgaagcct ttggcctcgt      300
ctgaaatgcc cattaa                                                     316
```

<210> SEQ ID NO 220
<211> LENGTH: 3546
<212> TYPE: DNA
<213> ORGANISM: Artificial Sequence
<220> FEATURE:
<223> OTHER INFORMATION: Synthetic

<400> SEQUENCE: 220

```
tctgaagagc aagcgcccac tgatgctgag gtcaacaaaa tcagagaagc tgacatttcc       60 atttttttgcc aatacttcag gtgacctcat aatgaaaccc ttgctgctct acagaaaatt     120
gtgcccaaac cctctcaggg gaaataaatg agccaagttt ccagtgtact agcaagcaaa     180
cagaaaagcc cagatgaatc ttcctctcct taagggatgg tttgaacagt actttcttgt     240
ggatgttcaa gactacttaa aagaaaaaaa aataccttga attcaaagtc ctgctgattc     300
ttcagtctat ttggtgcttc aggtacattt gccaatatgc atcctcatgg taaggttgtc     360
tttataacta gccacatgtc tgagattctt gagcctttca gtcagtgttt gatctggcca     420
ttcaggaagg cttattataa actaatgtat aactttgttc acaatctcgc aaagtttcca     480
ctgtctgaaa atcctagtgc atgagactcc tacatcgtta ttaatggcat atccttaata     540
aaagtttggc ttttgatttt taatgggttt tcaggagata acttcccaaa gaggcattag     600
atagtttaac agagcctgtc attaatgtga cctgtgagaa gacttggcta gaggtggtga     660
aatatctttc ctctatccct cccaaagaca agaaaaacct atggatgagg atgaaaattt     720
ggcacaagag caatcattgg cggaagttga atctgaaact gttgacacca attcaagtta     780
atgctgctag aggctgatcc tcaggaagct ttcttgtctc cagaggttat tatcataagt     840
gatgatgaag acaattagga ggctgtggga ctggaaacaa atacagcaat aagaaacagg     900
agcaaaattt ttgaacaag attaaaacct ccctaagaag gtaattaaaa ttggcatctt       960
tacatgtgtc agatattacc tgttcaaaat ttgagtgact tagagttcta taaagaggtg    1020
```

```
ctatgatgcc atcaaacata atcatattgg acagaaacaa tcttcaatag aacttaaatc    1080
atgtgccatt taatactgtt gctggacagc tgataaaact accttctgac aaagtttgat    1140
ttaattagac tctaataaaa ggtcctatga gactttctaa agactatat tgggaagaaa     1200 gaaacctcag aaaagtctaa attatcaagt agtaccattt aaatactctt actggacagc    1260
taataagcta ccttcagaca aagattgaat gattaaattg aactccatac agaactgcta    1320
aggtgtcttc aaaaaggact tgagaagatg aaagcatctt tagaagggcc acttaaattc    1380
acttgcttga tagaaataaa gcctcaagca agttgttata acttcaggat tcgacttcac    1440
tgactctaag agtatagaca tccataattt gaactaatga atagtccact tctgttcatt    1500
gcttctctgt caccccccatt tgccactacc ataatgagtg atagatacat cttcatcacc   1560
tctgaaaatc atctcaggat ctaaatggaa actgtataaa gcctatcatt tttactgatt    1620
taaactatgt aaactcatta ttcttttat gtaatgtgct gttgttattg tttacctgca     1680 taaaatatt tatgagggtt ttcaacagtt tacttgagac ctcattttg cccattttt       1740 tccttcccga tatcatgatc tcctcagctg aactttctta ccttgggggt tgttcaggaa    1800
ctgactctca tggggaaaga gggattacta tttctgtgtt cctatctctt ggtaactgct    1860
taaccacagt cagtcttgaa ctaatggaag gagcactgga cttgggttct tgagacctgg    1920
gttcatgttc agttctgcca ctgattattg tgacattggg ccagtcactt gatttctctg    1980
agcctcagtt tcatcacctg ttaagtgagg atagtaatac ctggcacaaa tatcacaata    2040
ttagtgataa ttgaatataa ttataagtac ccaatggcta ttaaaagtaa aactaggaag    2100
tgctgaataa ccataatatc attatatttg tagcattttg gaccttatca atgaacaact    2160
gagaaaacta ggttttgaa ttcttttact ttttaaagta acttcctccc atttttatgt     2220
caattataga aaattttaaa aagaaaatta aatgtgccta taattttata agccggaggt    2280
aactaagttg gtattttcct tcttagtacc tctttgtctc atcataaatt gttcatcaat    2340
gtcaaaaact tggaaaataa agataagcat atagaaaaaa ataaaaacca cccataatca    2400
caaatcccag aagcaatgtt aatattttgg tggatttatt tccagtcttt ttctatggct    2460
atatgtgcac atatataatt tttacataga aaaagtcata atgcatacag ctttgttgct    2520
tttagcattt ttatcatgaa tattttccta catttatgca agtatttgt aaatatcatt     2580 ttcaatggtg tataatattt catcatagga tgacatcatg gtttagttaa ccatttctt     2640 ttgttggata tttgagggtc tttccaaatt tggccattgt aatttcacaa tgtctttttc    2700
attacctaac tgaaaatatt tgctttggtg aaagcagagg attttttgtt gtttgtttgt    2760 ttgttttga agaagtcctt ttaatagcta catttcattg actaagtgga acttcaagag     2820
acaggtagaa gaaaaaaaa aagaaacagt agatgtaatt tcaagattga ggatttattt     2880
tgttagtgac tgttccagaa gctgaatttt ggtgttagag caattcagga gggacagttt    2940
gccaccattt tatgatactt tactgtagaa aagttttcag gatttagacc aggaaagaga    3000
catcctaacc atatgggttg atttttatttt atggaccctg tgaagtctgg gactgatcag   3060
gtttctcttt tgttggctac tagaaagctt ggagtcaaat gtgtggtcaa tgcatagcac    3120
ttgtaatggg actctacggt atgtatgcac tttgtattag ctttctgcca ggctccattt    3180
cgtgttccta tctttattgt ttttgttttt tccttttact ttcttatcta ctttgaattt    3240
atgctatcat gttgtatttt gtgtattctt gtaagccacc tgacatccat cttggaacat    3300
ggtggggaat aaacacacta ataaataaat acattaataa atacatgaat aaataaacca    3360
```

```
ataaggaaaa aacaatgagg caaatgaatg cagccaggac tctgaaaatt gcatagtgcc    3420
tccaagaata atcaatgtta aggacttgaa gcttggaaga acatattgga aagaagcagg    3480
tgaggctgcg aggctgcatt tagaggtgac gtgttctgtg tgacgtctgt gtctactgaa    3540
gcatgc                                                                3546

<210> SEQ ID NO 221
<211> LENGTH: 223
<212> TYPE: DNA
<213> ORGANISM: Artificial Sequence
<220> FEATURE:
<223> OTHER INFORMATION: Synthetic

<400> SEQUENCE: 221
gagctggaag tagacaccat gtatcttttc attagagaag caaaccccca aaggagaagc     60
attgtcaggc ttctctcttt gccatggcct ttgcctatac ccttgagcag tgatctgagt    120
cggctgagat gcagatgtta agcctgggca gaaaagcgct gctctctgca tggtccggga    180
gagacccctc tccagccggt ggcatgctcg ttacgcaaca ctg                       223

<210> SEQ ID NO 222
<211> LENGTH: 619
<212> TYPE: DNA
<213> ORGANISM: Artificial Sequence
<220> FEATURE:
<223> OTHER INFORMATION: Synthetic

<400> SEQUENCE: 222
gcaccatatg tgagtattcc agatatccaa ggtcctctgg acaccccagt ctcttccaca     60
aagctgcctc ctcagagcct gctgtcccgt cttctaggaa tgtacccatt tgaaaaccca    120
cactcacact accacaacac atacactgtt tcttgctggt cgttccttta atctcagtgg    180
aagatatctc atagagaact gttggtgatt gcttaacttg gttgggagga aaatagatca    240
agcaggtgac aacctgcata ttggggattt tcctatgctg aaaattgtta ttctgttgca    300
gcactccacc ctcccttcac agccccaaaa aagagaagta cgagtgctgc tgatgttcag    360
ggtttgaata tgttttggtt taagatgttc agtggaatta gagagaattt catcctgggc    420
agtgcagtca ggctggagga gtattttggt ttcatattac taaaccttgt tttcccatcc    480
cagctgcttg tgtgctatct tggggccact gagaacctgg ctgggctctg cggggtggga    540
gtgttgtccc ggggctgagt ccagccaggg gtgaggtcgt cttggtgcac atcttgcacg    600
ttgcatgaag ctcagagcc                                                 619

<210> SEQ ID NO 223
<211> LENGTH: 41
<212> TYPE: DNA
<213> ORGANISM: Artificial Sequence
<220> FEATURE:
<223> OTHER INFORMATION: Synthetic

<400> SEQUENCE: 223
cccagaccca tgtgcggctg tgcaaattct ttctgggttg a                         41

<210> SEQ ID NO 224
<211> LENGTH: 81
<212> TYPE: DNA
<213> ORGANISM: Artificial Sequence
<220> FEATURE:
<223> OTHER INFORMATION: Synthetic

<400> SEQUENCE: 224
```
gcagcgctgg atgccggagc aggtgcttct gcaagaagct gttctgcatc ctctccttgc    60
tgcatcttgg tccactgcct c                                              81

<210> SEQ ID NO 225
<211> LENGTH: 350
<212> TYPE: DNA
<213> ORGANISM: Artificial Sequence
<220> FEATURE:
<223> OTHER INFORMATION: Synthetic

<400> SEQUENCE: 225
tccaggccag ccaggtattg attgaagaaa tctagaaagg caaatggacc actgttatac    60
tgacagtgtt tgtctaacca gctgagtgtg gcattttga ggaatggggc cagagagcca    120
agcccagggc tactgcaagt tgggaagtct aatagattct acttctacca gaattctggg   180
attccaaaga atgataccttt cagtgtaagg gtaaattaga aataagcctc catagtactc   240
ataatgggcc acaagaaaaa ctgaccattt caaattttgg caagagtgga gaagagagaa   300
attgccactg agaatttgga accatgaggc agcctcacac aagtttgtgg              350

<210> SEQ ID NO 226
<211> LENGTH: 175
<212> TYPE: DNA
<213> ORGANISM: Artificial Sequence
<220> FEATURE:
<223> OTHER INFORMATION: Synthetic

<400> SEQUENCE: 226
caacctagcc ctccatgagg actgagcgca tgagagatcc tgagccacag ccgcccagcc    60
ctgctcctct cgaatttctg acctacagga actgcaagaa gtaatgaaag actgctgttt   120
aaagccactg cattttggca tgatttgtta tgcagtcgta gataaccaga aaaca        175

<210> SEQ ID NO 227
<211> LENGTH: 209
<212> TYPE: DNA
<213> ORGANISM: Artificial Sequence
<220> FEATURE:
<223> OTHER INFORMATION: Synthetic

<400> SEQUENCE: 227
ggtttcagca cccaagactt agacccacaa gaacttaaaa tgaggaaaaa gaaaagttc     60 aggtttaaag gcctgtcagc actcagaaag atacctgttt cagctaaaca ttttctaact   120
tattaagaga atctactaat gtctactcta cctgactaac ctacaaacac ttctcacaac   180
ttcttttagg attgtgacac caactgccc                                     209

<210> SEQ ID NO 228
<211> LENGTH: 26
<212> TYPE: DNA
<213> ORGANISM: Artificial Sequence
<220> FEATURE:
<223> OTHER INFORMATION: Synthetic

<400> SEQUENCE: 228
ctttctggat gcaccattta cccttt                                         26

<210> SEQ ID NO 229
<211> LENGTH: 442
<212> TYPE: DNA
<213> ORGANISM: Artificial Sequence
<220> FEATURE:

<223> OTHER INFORMATION: Synthetic

<400> SEQUENCE: 229

```
aacatgggtt tgtcgtgct ctccttttg cctcctgca atattcctgt tctttttgct      60
ggcactgaga tcctctcatc tcgggaagct attcgctcag acgaatcgta aaaggctggc    120
tgggaccacg gggcaggctg gggccatgga gggggctgtg ctgggccagc aatcggactt   180
gaaaccctc tggagaaggc gtcaggggga ggagtgactg cagagtaagg tggaggtgca    240
ggaaagtcag caatgggact cgtcatgttt cgggttggcg agaagggggt agctggctga   300
ttcacagacc ctgggaaggg tttggccgtt ctattcatgg ggaccatcct ctggatgttt   360
gctgtctcag atgtcccact gaagccattc tgttggggaa catggccaag accatgactc   420
acctcgatgt agcttttgct ca                                            442
```

<210> SEQ ID NO 230
<211> LENGTH: 68
<212> TYPE: DNA
<213> ORGANISM: Artificial Sequence
<220> FEATURE:
<223> OTHER INFORMATION: Synthetic

<400> SEQUENCE: 230

```
ccaccatcac ctggacgctg aatggaaaga ccctcaagac caccaagttc atcgtcctct    60
cccaggaa                                                            68
```

<210> SEQ ID NO 231
<211> LENGTH: 63
<212> TYPE: DNA
<213> ORGANISM: Artificial Sequence
<220> FEATURE:
<223> OTHER INFORMATION: Synthetic

<400> SEQUENCE: 231

```
tcaagaagtc ggaatttta ggacagttac agtctgcatt taaggatcct gatggacagg     60
ctg                                                                 63
```

<210> SEQ ID NO 232
<211> LENGTH: 126
<212> TYPE: DNA
<213> ORGANISM: Artificial Sequence
<220> FEATURE:
<223> OTHER INFORMATION: Synthetic

<400> SEQUENCE: 232

```
gagagcgcag tctttctgtc tcatgatact gattaccaca caaaagcatt ggtgaagaaa    60
caactgactg agttgagtta gggagttttt tcagagtaat tttgactagt tgcaattttc   120
gatttg                                                              126
```

<210> SEQ ID NO 233
<211> LENGTH: 271
<212> TYPE: DNA
<213> ORGANISM: Artificial Sequence
<220> FEATURE:
<223> OTHER INFORMATION: Synthetic

<400> SEQUENCE: 233

```
ccgggacttg gcagtacttg aaacaggagg aatacaccag cctaaatgta cagactttgt    60
agccgagccc actcgatcgg tctgtgcctt cacgtgacca ccatctgtgc ctccctcgct   120
ccatccaaat ttgtgtaggc tgctccttgg agctatgcct aaaatatagc tacaccagag   180
```

```
-continued ccctggaaac tgtagtcaag taacaggcct cactgttttt tttctttgga ttaaaagtgt    240
atatctctct actgagagggt ttccagcttt a                                   271

<210> SEQ ID NO 234
<211> LENGTH: 28
<212> TYPE: DNA
<213> ORGANISM: Artificial Sequence
<220> FEATURE:
<223> OTHER INFORMATION: Synthetic

<400> SEQUENCE: 234
accctaatgt ttgccacaat gtttgtat                                        28

<210> SEQ ID NO 235
<211> LENGTH: 93
<212> TYPE: DNA
<213> ORGANISM: Artificial Sequence
<220> FEATURE:
<223> OTHER INFORMATION: Synthetic

<400> SEQUENCE: 235
ttccttctac tcaatctgac cgaggtcctc caggtcaagg acagcgaggc tctcagtccc    60 acttccccctt ggcacataga agaggcagtg cgc                                 93

<210> SEQ ID NO 236
<211> LENGTH: 494
<212> TYPE: DNA
<213> ORGANISM: Artificial Sequence
<220> FEATURE:
<223> OTHER INFORMATION: Synthetic

<400> SEQUENCE: 236
ttggagcccg taggaatatt gaagaagtta gtgaagaaat gctatacagt catttgttga    60
ttaatgaagg gggataaggt ctgagacatg tgtcgttagg tgatttattc attgtgcaaa   120
caccatagag tgtatggtac ttacacaaac ctagagggta tagcctacta aacacctagg   180
ctacaaactt gtacagtgtg ttactgtact gaatactgtc aacaattgta acacaaatca   240
ccaggcgata ggaattttttt agttctattg taatcttatg aggctactct catatatgca   300 gccccctcatt gaccaaaaca tcattatgca gtgcatgacc atattgagag tattcgtttt   360
ttatttacta aaaaatagtc aaaacttgag gaggaagaga cagatgtcac tagaaaaagg   420
gagaagtccg gtaagggaga agtcagcttc ctgaggtgga atcgtattac ctttgggatt   480
aggacatttc attg                                                      494

<210> SEQ ID NO 237
<211> LENGTH: 343
<212> TYPE: DNA
<213> ORGANISM: Artificial Sequence
<220> FEATURE:
<223> OTHER INFORMATION: Synthetic

<400> SEQUENCE: 237
cccacaggca gctttggtgt tctcatgtta tagttcttaa tctaaattgt aggtgctaaa    60
caaaactacc tgccttaatg gtaggcagag gtatttgaaa aattaatgat ctacttgttt   120
gctgaatgtc cacaatacaa gctttgattt aaaaaaatca tgttaggata gcatgtttat   180
tacatactat ttattatcat acttaatatt tcttgcctat caaaagtaaa aacctgatgc   240
tttatgttaa atgtttcttg cccattggag cctgttcatg gcaattcttt gtccaagaag   300
```
agtaatggta ttgtctctttt ctatgtgtct cggtaattca ggc        343

<210> SEQ ID NO 238
<211> LENGTH: 489
<212> TYPE: DNA
<213> ORGANISM: Artificial Sequence
<220> FEATURE:
<223> OTHER INFORMATION: Synthetic

<400> SEQUENCE: 238
tctaaccttg gctccggggt attgccgaaa ccagtccagg cacgtcacaa atgtctgact        60
tctcccagag gcttcagaag cacaatgagc agcagaggag agccatggag ccaagcacag        120
tctcatttaa cctccccaaa agcttgggaa gtgggtggtg ttatagcccc attttacaga        180
tgagaaaaac tgaggcttat ttaagcagct cacctaaagt cacatattga ttgtgctgag        240
ctgagattgt accctaatct gccttcaaat ccatgttttt acccattgca tgtgattatg        300
gaacctggga ccgaggagca ggaggagaac attctaaatt ctgctcccat cttgtcttta        360
catctcaggt cacttttagc aaagacagac ccggacactt gccattaata ctacaggctt        420
ccttcctcct accccttcc cccaatctta ttcatctcac ctctccagta ggtcgtggac        480
tcatgcatt        489

<210> SEQ ID NO 239
<211> LENGTH: 49
<212> TYPE: DNA
<213> ORGANISM: Artificial Sequence
<220> FEATURE:
<223> OTHER INFORMATION: Synthetic

<400> SEQUENCE: 239
ggcaggggtt gggacaagtg ctaagtatgc aagactcaag ggaagagct        49

<210> SEQ ID NO 240
<211> LENGTH: 1163
<212> TYPE: DNA
<213> ORGANISM: Artificial Sequence
<220> FEATURE:
<223> OTHER INFORMATION: Synthetic

<400> SEQUENCE: 240
cctgggatga ccacaattcc ttccaatttc tgcggctcca tcctaagcca ataaaattat        60
actttaacaa actattcaac tgatttacaa cacacatgat gactgaggca ttcgggaacc        120
ccttcatcca aaagaataaa cttttaaatg gatataaatg attttttaact cgttccaata        180
tgccttataa accacttaac ctgattctgt gacagttgca tgatttaacc caatgggaca        240
agttacagtg ttcaattcaa tactataggc tgtagagtga aagtcaaatc accatataca        300
ggtgctttaa atttaataac aagttgtgaa atataataga gattgaaatg ttggttgtat        360
gtggtaaatg taagagtaat acagtctctt gtactttcct cactgttttg ggtactgcat        420
attattgaat ggcccctatc attcatgaca tcttgagttt tcttgaaaag acaatagagt        480
gtaacaaata ttttgtcaga aatcccatta tcaaatcatg agttgaaaga ttttgactat        540
tgaaaaccaa attctagaac ttactatcag tattcttatt tcaaaggaa ataattttct        600
aaatatttga ttttcagaat cagttttta atagtaaagt taacatacca tatagatttt        660
ttttactttt tatattctac tctgaagtta tttttatgctt ttcttatcaa tttcaaatct        720
caaaaatcac agctcttatc tagagtatca taatattgct atatttgttc atatgtggag        780
tgacaaattt tgaaaagtag agtgcttcct ttttattga gatgtgacag tctttacatg        840

```
gttaggaata agtgacagtt aagtgaatat cacaattact agtatgttgg tttttctgct    900
tcattcctaa gtattacgtt tctttattgc agatgtcaga tcaaaaagtc acctgtaggt    960
tgaaaaagct accgtattcc attttgtaaa aataacaata ataataataa taataattag   1020
ttttaagctc atttcccact tcaatgcaat actgaaaact ggctaaaaat accaaatcaa   1080
tatactgcta atggtacttt gaagagtatg caaaactgga aggccaggag gaggcaaata   1140
atatgtcttt ccgatggtgt ctc                                           1163

<210> SEQ ID NO 241
<211> LENGTH: 94
<212> TYPE: DNA
<213> ORGANISM: Artificial Sequence
<220> FEATURE:
<223> OTHER INFORMATION: Synthetic

<400> SEQUENCE: 241
ggcggccacc aagtcgctga agcagaaaga caagaagctg aaggaaatct tgctgcaggt     60
ggaggacgag cgcaagatgg ccgagcagta caag                                94

<210> SEQ ID NO 242
<211> LENGTH: 83
<212> TYPE: DNA
<213> ORGANISM: Artificial Sequence
<220> FEATURE:
<223> OTHER INFORMATION: Synthetic

<400> SEQUENCE: 242
tccattattg ctgcccggaa gcagagtgtg gaggaaattg tccgagatca ctgggccaaa     60
tttggccgcc actactattg cag                                            83

<210> SEQ ID NO 243
<211> LENGTH: 56
<212> TYPE: DNA
<213> ORGANISM: Artificial Sequence
<220> FEATURE:
<223> OTHER INFORMATION: Synthetic

<400> SEQUENCE: 243
tggtgaacag cctgtaccct gatggctcca agccggtgaa ggtgcccgag aaccca         56

<210> SEQ ID NO 244
<211> LENGTH: 112
<212> TYPE: DNA
<213> ORGANISM: Artificial Sequence
<220> FEATURE:
<223> OTHER INFORMATION: Synthetic

<400> SEQUENCE: 244
aggagaccac cgcgctcgtg tgtgacaatg gctctggcct gtgcaaggca ggcttcgcag     60
gagatgatgc ccccgggct gtcttcccct ccattgtggg ccgccctcgc ca             112

<210> SEQ ID NO 245
<211> LENGTH: 110
<212> TYPE: DNA
<213> ORGANISM: Artificial Sequence
<220> FEATURE:
<223> OTHER INFORMATION: Synthetic

<400> SEQUENCE: 245
gcgaagacga aaggaaacaa ggtgaacgtg ggagtgaagt acgcagagaa gcaggagcgg     60
```
aaattcgagc cggggaagct aagagaaggg cggaacatca ttgggctgca    110

<210> SEQ ID NO 246
<211> LENGTH: 74
<212> TYPE: DNA
<213> ORGANISM: Artificial Sequence
<220> FEATURE:
<223> OTHER INFORMATION: Synthetic

<400> SEQUENCE: 246
gaccctgatg gctttgggca gcttggcagt gaccaagaat gatgggcact accgtggaga    60
tcccaactgg ttta    74

<210> SEQ ID NO 247
<211> LENGTH: 99
<212> TYPE: DNA
<213> ORGANISM: Artificial Sequence
<220> FEATURE:
<223> OTHER INFORMATION: Synthetic

<400> SEQUENCE: 247
acccttcttc ttggcgagac cacgatgatg caacctcaac ccactcagca ggcacccccag    60 ggccctccag tgggggccat gcttcccaga gcggagaca    99

<210> SEQ ID NO 248
<211> LENGTH: 95
<212> TYPE: DNA
<213> ORGANISM: Artificial Sequence
<220> FEATURE:
<223> OTHER INFORMATION: Synthetic

<400> SEQUENCE: 248
cacgaactgt gcgataactt ctgccaccga tacattagct gtttgaaggg gaaaatgccc    60
atcgacctcg tcattgatga aagagacggc agctc    95

<210> SEQ ID NO 249
<211> LENGTH: 209
<212> TYPE: DNA
<213> ORGANISM: Artificial Sequence
<220> FEATURE:
<223> OTHER INFORMATION: Synthetic

<400> SEQUENCE: 249
tcagacgggc acatctattg gaggtgatgc cagaagaggc ttcttgggct cgggatattc    60
ttcctcggcc actacccagc aggaaaaactc atacggaaaa gccgtcagca gtcaaaccaa    120
cgtcagaact ttctctccaa cctatggcct tttaagaaat actgaggctc aagtgaaaac    180
attccctgac agaccaaaag ccggagata    209

<210> SEQ ID NO 250
<211> LENGTH: 68
<212> TYPE: DNA
<213> ORGANISM: Artificial Sequence
<220> FEATURE:
<223> OTHER INFORMATION: Synthetic

<400> SEQUENCE: 250
ctctttctac aatgagcttc gtgttgcccc tgaagagcat cccaccctgc tcacggaggc    60
acccctga    68

<210> SEQ ID NO 251
<211> LENGTH: 78

```
<212> TYPE: DNA
<213> ORGANISM: Artificial Sequence
<220> FEATURE:
<223> OTHER INFORMATION: Synthetic

<400> SEQUENCE: 251
tgggaatgtg ctttgcagcc gagtcagatg tccaaatgtt cattgccttt ctcctgtgca    60
tattcctcat ctgtgctg                                                  78

<210> SEQ ID NO 252
<211> LENGTH: 141
<212> TYPE: DNA
<213> ORGANISM: Artificial Sequence
<220> FEATURE:
<223> OTHER INFORMATION: Synthetic

<400> SEQUENCE: 252
agcgcaggag cataagaggg aattcacaga gagccagctg caggagggaa agcatgtcat    60
tggccttcag atgggcagca acagaggggc ctcccaggcc ggcatgacag gctacggacg   120
acctcggcag atcatcagtt a                                             141

<210> SEQ ID NO 253
<211> LENGTH: 109
<212> TYPE: DNA
<213> ORGANISM: Artificial Sequence
<220> FEATURE:
<223> OTHER INFORMATION: Synthetic

<400> SEQUENCE: 253
ggcctaagga tcattttctc ggatgcatca cggctcatct tccggctcag ttcctccagt    60
ggtgtgcggg ccaccctcag actgtacgca gagagctacg agagggatc               109

<210> SEQ ID NO 254
<211> LENGTH: 28
<212> TYPE: DNA
<213> ORGANISM: Artificial Sequence
<220> FEATURE:
<223> OTHER INFORMATION: Synthetic

<400> SEQUENCE: 254
ggggtgatgg tgggaatggg acaaaaag                                       28

<210> SEQ ID NO 255
<211> LENGTH: 174
<212> TYPE: DNA
<213> ORGANISM: Artificial Sequence
<220> FEATURE:
<223> OTHER INFORMATION: Synthetic

<400> SEQUENCE: 255
gttggattgc cagcttgtac ctggcccttc tgtttggcca cgctattgtt cctcatcatg    60
accacaaaaa attccaacat ctacaagatg cccctcagta agttactta tcctgaagaa   120 aaccgcatct tctacctgca agccaagaaa agaatggtgg aaagccctt gtga         174

<210> SEQ ID NO 256
<211> LENGTH: 43
<212> TYPE: DNA
<213> ORGANISM: Artificial Sequence
<220> FEATURE:
<223> OTHER INFORMATION: Synthetic

<400> SEQUENCE: 256
```
ggcaatgagc gcttccgctg ccctgagacc ctcttccagc ctt    43

<210> SEQ ID NO 257
<211> LENGTH: 84
<212> TYPE: DNA
<213> ORGANISM: Artificial Sequence
<220> FEATURE:
<223> OTHER INFORMATION: Synthetic

<400> SEQUENCE: 257
tcatcctccc ttgagaagag ttacgagttg cctgatgggc aagtgatcac catcggaaat    60
gaacgtttcc gctgcccaga gacc    84

<210> SEQ ID NO 258
<211> LENGTH: 146
<212> TYPE: DNA
<213> ORGANISM: Artificial Sequence
<220> FEATURE:
<223> OTHER INFORMATION: Synthetic

<400> SEQUENCE: 258
ggttggatcc caagacgaca tattatatca tgagggacct ggaggccctg gtcacagaca    60
aatccttcat tggccagcag tttgctgtgg ggagccatgt ctacagcgtg gcgaagacgg    120
atagttttga atacgtggac cctgtg    146

<210> SEQ ID NO 259
<211> LENGTH: 55
<212> TYPE: DNA
<213> ORGANISM: Artificial Sequence
<220> FEATURE:
<223> OTHER INFORMATION: Synthetic

<400> SEQUENCE: 259
aaagcagaag cgagacctcg gcgaggagct ggaggcccta agacagagc tggaa    55

<210> SEQ ID NO 260
<211> LENGTH: 74
<212> TYPE: DNA
<213> ORGANISM: Artificial Sequence
<220> FEATURE:
<223> OTHER INFORMATION: Synthetic

<400> SEQUENCE: 260
aggcctcctc accagtcagt gcatccccag tgcctgtggg cattcccacc tcgccaaagc    60
aagaatcagc ctca    74

<210> SEQ ID NO 261
<211> LENGTH: 92
<212> TYPE: DNA
<213> ORGANISM: Artificial Sequence
<220> FEATURE:
<223> OTHER INFORMATION: Synthetic

<400> SEQUENCE: 261
ttgaggacat ctactttgga ctctgggggtt tcaacagctc tctggcctgc attgcaatgg    60
gaggaatgtt catggcgctc acctggcaaa cc    92

<210> SEQ ID NO 262
<211> LENGTH: 300
<212> TYPE: DNA
<213> ORGANISM: Artificial Sequence
<220> FEATURE:
<223> OTHER INFORMATION: Synthetic

<400> SEQUENCE: 262

```
gtgacttggt ccaaaagacc tgggcacttg gtctaacttt tcaaacatta tctaacctct    60
gaatctggaa taaccaaact gtaagttgac ttaattcaca gaagtgcagt gatggtaaaa   120
tgaaatagca tgagtagagt gataagtgtg atgcaaatga agtcatatc ttcattacta    180 ggctttatttt attaaatata gctaaagtac tctaaacgta tatgtctaca cttttttgaa   240
catggatagt ttttacataa ctgtactgaa agaaagggca ctaattacta tgcgctctaa   300
```

<210> SEQ ID NO 263
<211> LENGTH: 33
<212> TYPE: DNA
<213> ORGANISM: Artificial Sequence
<220> FEATURE:
<223> OTHER INFORMATION: Synthetic

<400> SEQUENCE: 263

```
agctctcagg ttcgtgggaa agctaacata caa                                 33
```

<210> SEQ ID NO 264
<211> LENGTH: 36
<212> TYPE: DNA
<213> ORGANISM: Artificial Sequence
<220> FEATURE:
<223> OTHER INFORMATION: Synthetic

<400> SEQUENCE: 264

```
atgaatatgt caatgctgaa tgcaaatcag ggaaag                              36
```

<210> SEQ ID NO 265
<211> LENGTH: 113
<212> TYPE: DNA
<213> ORGANISM: Artificial Sequence
<220> FEATURE:
<223> OTHER INFORMATION: Synthetic

<400> SEQUENCE: 265

```
tgagtgtagt attggtagga tccttcagca ccctgcttct gttatggaag ctcaatggga    60
aaattcctct ctccccagcc cttggcagac agagctcatg atggtagagt ttt          113
```

<210> SEQ ID NO 266
<211> LENGTH: 123
<212> TYPE: DNA
<213> ORGANISM: Artificial Sequence
<220> FEATURE:
<223> OTHER INFORMATION: Synthetic

<400> SEQUENCE: 266

```
agaattttca tggtgttatg catgctgaaa aatgcattgc attttgaaaa ttttagcaaa    60
ggatacgtca atgactgcag catgattcag gcaccttccc tggcagtcca caactctgtt   120
atc                                                                 123
```

<210> SEQ ID NO 267
<211> LENGTH: 67
<212> TYPE: DNA
<213> ORGANISM: Artificial Sequence
<220> FEATURE:
<223> OTHER INFORMATION: Synthetic

<400> SEQUENCE: 267

```
atgttcttgt cattcgttaa gttgcaaaat tcagcaactt acaatgagta ttactactat    60
``` tgtactg 67

<210> SEQ ID NO 268
<211> LENGTH: 30
<212> TYPE: DNA
<213> ORGANISM: Artificial Sequence
<220> FEATURE:
<223> OTHER INFORMATION: Synthetic

<400> SEQUENCE: 268
acttgaaatt gtgtccagaa ctggtgggtt 30

<210> SEQ ID NO 269
<211> LENGTH: 640
<212> TYPE: DNA
<213> ORGANISM: Artificial Sequence
<220> FEATURE:
<223> OTHER INFORMATION: Synthetic

<400> SEQUENCE: 269
aatggttgtt caagccaggc ctgcctcatt gaaagggtga atcttccctt cactggaagg 60
aagtgagaga attagtcaag cagctatctg aggaaagaac attccaagta aagaatatac 120
agcccataca ttgttggatg tgtgtacatt gaaattttg tgcagtaaaa tgaatatttc 180
atttacctat ataatttac ataaataaa atatattttg aatgtgagtt gttccaaac 240 aaatcatttt cttgccttca aaccactga gcttaaagaa ctctttcaag tgtcattaga 300
gatagattcc aactacaatc aacattgtgg aatccagagg aggcaaaatg aaggaagcag 360
cactcattac aaaatgctgc tttgtaaaga attaattctg tcctggtatg tttcacatta 420
ggtaatatga aggaaatgaa tatgtcatga accctccttg aggatgtggg ggaattaaaa 480
gtaatttcgc ttaatatcca actctcactt ttggctttgt agtcagaggg aaacaatgct 540
ttcccaggtt ctaaggtaaa cgttaaaagg ttacaaggag acttggaaga gtcaaggaac 600
gcttccacca actattcctg ccattccagt tgggagggtt 640

<210> SEQ ID NO 270
<211> LENGTH: 261
<212> TYPE: DNA
<213> ORGANISM: Artificial Sequence
<220> FEATURE:
<223> OTHER INFORMATION: Synthetic

<400> SEQUENCE: 270
aatttactgc ctgctcgttt ggagatctat aacctttata cttagacagt ttttaaaaa 60 gtataacagc aattatttct cccaatttat ttaatgccgt ttttttcattg catccattaa 120 aatattttac ttttataagc aatgatacca ggaagttatc gtttgaatag tctgctggag 180
gagtagggca aagtagttaa gatcaattgt tctttcagaa ggctgctgct ttctagctgc 240
atgactttgg gtacgttatt t 261

<210> SEQ ID NO 271
<211> LENGTH: 36
<212> TYPE: DNA
<213> ORGANISM: Artificial Sequence
<220> FEATURE:
<223> OTHER INFORMATION: Synthetic

<400> SEQUENCE: 271
caaactttga gtttgaccctc tataaagaca ctaaaa 36

```
<210> SEQ ID NO 272
<211> LENGTH: 61
<212> TYPE: DNA
<213> ORGANISM: Artificial Sequence
<220> FEATURE:
<223> OTHER INFORMATION: Synthetic

<400> SEQUENCE: 272
gaacaatatg aaaatactct actgaaaatt gatgaaattg aagagaaagg ccattatgaa      60
a                                                                     61

<210> SEQ ID NO 273
<211> LENGTH: 154
<212> TYPE: DNA
<213> ORGANISM: Artificial Sequence
<220> FEATURE:
<223> OTHER INFORMATION: Synthetic

<400> SEQUENCE: 273
acagcattga taaacctgta gctagactaa ccaagagaga agacccaaat aaagaaaaac      60
agaaataaaa aaggagacat tacagctgat aaccacagaa atacaaaaga ttatcaggca     120
ttattataaa ctacaataca ctaaccaact ggaa                                 154

<210> SEQ ID NO 274
<211> LENGTH: 223
<212> TYPE: DNA
<213> ORGANISM: Artificial Sequence
<220> FEATURE:
<223> OTHER INFORMATION: Synthetic

<400> SEQUENCE: 274
taattcagta tgctgtccag gggcctggaa atcactcagc acagtctacc accattggca      60
catgaacact tctcccaggg tctaaggaca ggctgacata acatgctaat accaccagag     120
ctggcactca cccagatgta ccacatcagg ccaggaagca gaaactacca acatcccagc     180
aaaccatgtg gaggccccca aatcagactg cttgggccta aca                      223

<210> SEQ ID NO 275
<211> LENGTH: 251
<212> TYPE: DNA
<213> ORGANISM: Artificial Sequence
<220> FEATURE:
<223> OTHER INFORMATION: Synthetic

<400> SEQUENCE: 275
aggatatcac tgcaggtcat aaagacatta gaaagatagt aagggactac tataaataat      60
tttatgccaa taaatttgga aatttagatg aaattgacaa gttcttgaaa aaatagcact     120
aaaacagata taagaacaag tagcaaatat gaatagtttg aaatctacta agaaattgt      180 atctggggct caagatgcct gactagatgc aactagaatg tgcctcctcc atggatagga     240
accaaaatag c                                                          251

<210> SEQ ID NO 276
<211> LENGTH: 488
<212> TYPE: DNA
<213> ORGANISM: Artificial Sequence
<220> FEATURE:
<223> OTHER INFORMATION: Synthetic

<400> SEQUENCE: 276
tggcatgaca tagctaaagc actgaaggaa aaagtatttt atcctagaat agtatatcca      60
```

```
gtgaaaatat cctttaaaaa tgtgggagaa ataaagactt ctccagacaa actaaaataa    120
gggatttcat caataccaga tctgtcctat aagaaatgct gaaagaagtt cttcagtctg    180
aaataaaagg atgttaatga attagaaatc atttgaaggt gaaaaactca ctaataatag    240
gaagtacaca gaaagagaac aaaaaaacac tgcaattttg gtgtgttaac tactcatatc    300
ttgagtagaa agataaaaaa gatgaaccaa tcagaaataa ccacaacttc ttaagacata    360
gacagtacaa taaatttaa atgcaaacaa caaaaagttt aaaagctggg ggatgaagtc      420
aaagtgtaca gttttatta gttttctttc tgagtgtttg tttatgcagt tagtgataag      480
ttatcatc                                                              488
```

```
<210> SEQ ID NO 277
<211> LENGTH: 44
<212> TYPE: DNA
<213> ORGANISM: Artificial Sequence
<220> FEATURE:
<223> OTHER INFORMATION: Synthetic

<400> SEQUENCE: 277
gtaaacttag gaggcgtagt gctccaggtt gatctggcgg ttga                     44
```

```
<210> SEQ ID NO 278
<211> LENGTH: 36
<212> TYPE: DNA
<213> ORGANISM: Artificial Sequence
<220> FEATURE:
<223> OTHER INFORMATION: Synthetic

<400> SEQUENCE: 278
gtcaaagaga tattctccca cgccagattc gggcgc                              36
```

```
<210> SEQ ID NO 279
<211> LENGTH: 32
<212> TYPE: DNA
<213> ORGANISM: Artificial Sequence
<220> FEATURE:
<223> OTHER INFORMATION: Synthetic

<400> SEQUENCE: 279
tggagcgctc gagaagcctg ggctccacta tg                                  32
```

```
<210> SEQ ID NO 280
<211> LENGTH: 135
<212> TYPE: DNA
<213> ORGANISM: Artificial Sequence
<220> FEATURE:
<223> OTHER INFORMATION: Synthetic

<400> SEQUENCE: 280
ggaatttcgt aattaaatga tatgtaaaat ttgaatatta tttgttcagt cttattcttc    60
cagaacctca gttactttct tttattaatt cagacagtta ccacagtact agtcagctat    120
tactcagttc tgatc                                                     135
```

```
<210> SEQ ID NO 281
<211> LENGTH: 211
<212> TYPE: DNA
<213> ORGANISM: Artificial Sequence
<220> FEATURE:
<223> OTHER INFORMATION: Synthetic

<400> SEQUENCE: 281
tggtgtacta acagcactga ttctgttagc aacaagtagt ggtagacaac tagaaatatg    60
```

```
tcagttttaaa acttgtgaag ttggttgtta caaatctcca ttctgtgtat ctccattctg    120
aatactagat acacatctcc atgtgtatct ccattctgaa tactaggtac aacgattttg    180
tctcttggaa aatttccttg tccactgagt a                                    211
```

<210> SEQ ID NO 282
<211> LENGTH: 71
<212> TYPE: DNA
<213> ORGANISM: Artificial Sequence
<220> FEATURE:
<223> OTHER INFORMATION: Synthetic

<400> SEQUENCE: 282

```
tctcacctgt ggaactcatt acctgcatta agttttctct gctttcaata ttcagtttag     60
ccgggcgcga t                                                          71
```

<210> SEQ ID NO 283
<211> LENGTH: 145
<212> TYPE: DNA
<213> ORGANISM: Artificial Sequence
<220> FEATURE:
<223> OTHER INFORMATION: Synthetic

<400> SEQUENCE: 283

```
aatatggcca tgacaccaga atcacaaac atgatgagaa tggaatgact ggggaagaag       60
tgccagatgc ttcacttgta aatgaagacc cagcctctgg ggatgcagat accacctccc    120
tgaagaagct gaatatctgc agata                                          145
```

<210> SEQ ID NO 284
<211> LENGTH: 185
<212> TYPE: DNA
<213> ORGANISM: Artificial Sequence
<220> FEATURE:
<223> OTHER INFORMATION: Synthetic

<400> SEQUENCE: 284

```
catagctagg cagtgttgga gatcagcagg aactagacac aatgaatgga tatggcatca     60
atactcatga acatgccatt cttccagcag tgcttggcaa ctcaggttga ggaacagaga    120
aggtggatgg cttaggtaat ggaattggat gcttttttaaa tgtcagtggc tgtcaaaact    180
gtata                                                                185
```

<210> SEQ ID NO 285
<211> LENGTH: 82
<212> TYPE: DNA
<213> ORGANISM: Artificial Sequence
<220> FEATURE:
<223> OTHER INFORMATION: Synthetic

<400> SEQUENCE: 285

```
atgtctcaga cctctccata cttcatctgt acttcttgat cgcttttatt cttgaaatta     60
atacaagaag gtctctcatt ta                                              82
```

<210> SEQ ID NO 286
<211> LENGTH: 152
<212> TYPE: DNA
<213> ORGANISM: Artificial Sequence
<220> FEATURE:
<223> OTHER INFORMATION: Synthetic

<400> SEQUENCE: 286

```
cttagtgggg tttggaactg cctgagaata ttcctataga aactgggtca tcttgccttc    60
tgtgccacta gaacctcctg tctctccaat agctgcttct ctctaattct tcaccatagt   120
tttctttctg tggtcttttg aggttctctc ct                                 152
```

<210> SEQ ID NO 287
<211> LENGTH: 497
<212> TYPE: DNA
<213> ORGANISM: Artificial Sequence
<220> FEATURE:
<223> OTHER INFORMATION: Synthetic

<400> SEQUENCE: 287

```
ctttcactgt tatgccggtg atttgaatgt aaagcagttt tatttaaatc aatataattt    60
aataaaaaca tatttaaatt tgggttaga ttaaaaattt tctctattgc caatacttgg   120
tttgaactca attaggctct ctttacataa gagactacat taaacacaga catatatgag   180 gtattttttga gacatttgaa tgtaatatat tgtaatttta ccatttattt tgtctcctaa   240
attgacattt aaataatcag aatctctagc tcaatattca aattaacatt tcttcccctt   300
aaaatggtgg gttacctcct tcctggaagg agcggaatgt gagtaacatt tcttcctttc   360
catgtttttc tcaatcaaat ggcacaaagg attttcttga ctgcttgaaa actaaaaaca   420
gtttcccaga gtttattaag ttcatattaa ttttttaatgc aaatacctgt tattaaaact   480
ctaagtaggg caggcgc                                                  497
```

<210> SEQ ID NO 288
<211> LENGTH: 71
<212> TYPE: DNA
<213> ORGANISM: Artificial Sequence
<220> FEATURE:
<223> OTHER INFORMATION: Synthetic

<400> SEQUENCE: 288

```
cattgggctc cagagtatcg acggcgctct cctgtgatgt aggccgtgaa tttcacgtga    60
tgtgcacctt g                                                        71
```

<210> SEQ ID NO 289
<211> LENGTH: 200
<212> TYPE: DNA
<213> ORGANISM: Artificial Sequence
<220> FEATURE:
<223> OTHER INFORMATION: Synthetic

<400> SEQUENCE: 289

```
tgcacctgtt tagtttgtga caatctgagc ccagtacatg gttctctgat tcctaagcca    60
ggagtctctc tgtaaccaaa ctgctattat gtgagcatag aacagctctc aaagtaaatg   120
tcccacttct atttctggca ggttatgttt agctaccttt ccaaaagagt cccaatccta   180
gtatgccttt caacagtgtc                                              200
```

<210> SEQ ID NO 290
<211> LENGTH: 95
<212> TYPE: DNA
<213> ORGANISM: Artificial Sequence
<220> FEATURE:
<223> OTHER INFORMATION: Synthetic

<400> SEQUENCE: 290

```
tgaataaact cattcgtccc tcaaaccaga aattatttga ggttatcaat aacttctcca    60
tggaagagtt tgttagagtt ttggtcagga aaaca                              95
```

<210> SEQ ID NO 291
<211> LENGTH: 208
<212> TYPE: DNA
<213> ORGANISM: Artificial Sequence
<220> FEATURE:
<223> OTHER INFORMATION: Synthetic

<400> SEQUENCE: 291

```
aagttcctga agtgtgtcat ccctctgcta gacatctaag ggatgacttt tttcacaaat    60
catattaact caccagtaca atagtagtaa tactcattgt aagttgctga attttgcaac   120
ttaacgaatg acaagaacat ggcataggtc agtgatgcat gttatgctta attttgagtg   180
agtgacttgc atgttatatc tctgcctg                                      208
```

<210> SEQ ID NO 292
<211> LENGTH: 184
<212> TYPE: DNA
<213> ORGANISM: Artificial Sequence
<220> FEATURE:
<223> OTHER INFORMATION: Synthetic

<400> SEQUENCE: 292

```
ggtcgccagt catcccgcac aaaaaacctg tccctggtgt cctcgtcctc cagaggcaac    60
acgtctaccc tccgtagggg cccagggtcc aggaggaagg tgcctgggca gttttccatc   120
acaacagcct tgaacactct caaccggatg gtccattctc cttcagggcg ccatatggta   180
gaga                                                                184
```

<210> SEQ ID NO 293
<211> LENGTH: 87
<212> TYPE: DNA
<213> ORGANISM: Artificial Sequence
<220> FEATURE:
<223> OTHER INFORMATION: Synthetic

<400> SEQUENCE: 293

```
cagagaggtg gtaactcccg agtaagcaat gccaatcctt caggcaaaga taaggaagaa    60
ccgcacagct gctccaacat aaagtgg                                        87
```

<210> SEQ ID NO 294
<211> LENGTH: 77
<212> TYPE: DNA
<213> ORGANISM: Artificial Sequence
<220> FEATURE:
<223> OTHER INFORMATION: Synthetic

<400> SEQUENCE: 294

```
gtatcctggc atccatctgt ggtggccttg tgatgctttt gcctgaaacc aagggtattg    60
ccttgccaga gacagtg                                                   77
```

<210> SEQ ID NO 295
<211> LENGTH: 48
<212> TYPE: DNA
<213> ORGANISM: Artificial Sequence
<220> FEATURE:
<223> OTHER INFORMATION: Synthetic

<400> SEQUENCE: 295

```
actaacctct gcagtttaac cttgagcgat accttttccc atgaatag                 48
```

<210> SEQ ID NO 296

```
<211> LENGTH: 89
<212> TYPE: DNA
<213> ORGANISM: Artificial Sequence
<220> FEATURE:
<223> OTHER INFORMATION: Synthetic

<400> SEQUENCE: 296
tggaggctgc ctgatcgagc tggcacagga gctcctggtc atcatggtgg gcaagcaggt    60
catcaacaac atgcaggagg tcctcatcc                                      89

<210> SEQ ID NO 297
<211> LENGTH: 69
<212> TYPE: DNA
<213> ORGANISM: Artificial Sequence
<220> FEATURE:
<223> OTHER INFORMATION: Synthetic

<400> SEQUENCE: 297
gatcgccatt cttgattatc ataatcaagt tcggggcaaa gtgttccac cggcagcaaa    60 tatggaata                                                            69

<210> SEQ ID NO 298
<211> LENGTH: 75
<212> TYPE: DNA
<213> ORGANISM: Artificial Sequence
<220> FEATURE:
<223> OTHER INFORMATION: Synthetic

<400> SEQUENCE: 298
aacgatttcg agatttacta ctgcctccat ctagtcaaga ctccgaaatt ctgcccttca    60
ttcaatctag aaatt                                                     75

<210> SEQ ID NO 299
<211> LENGTH: 167
<212> TYPE: DNA
<213> ORGANISM: Artificial Sequence
<220> FEATURE:
<223> OTHER INFORMATION: Synthetic

<400> SEQUENCE: 299
tactgataat ctcaaggagg cagagaccca tgctgagttg gctgagagat cagtagccaa    60
gctggaaaag acaattgatg acttggaaga taaactgaaa tgcaccaaag aggaacacct   120
ctgtacacaa aggatgctgg accagacttt gcttgacctg aatgaga                 167

<210> SEQ ID NO 300
<211> LENGTH: 109
<212> TYPE: DNA
<213> ORGANISM: Artificial Sequence
<220> FEATURE:
<223> OTHER INFORMATION: Synthetic

<400> SEQUENCE: 300
aaaatcttgc aaaatcggca gaggcttggg cggctacttg catttgggac catggacctt    60
cttacttact gagattttg ggccaaaatc tatctgtacg cactggaag                109

<210> SEQ ID NO 301
<211> LENGTH: 118
<212> TYPE: DNA
<213> ORGANISM: Artificial Sequence
<220> FEATURE:
<223> OTHER INFORMATION: Synthetic

<400> SEQUENCE: 301
```

```
caggagctga tcctccttgc aaagctgtgc cttgcagaga tgcacgtgtg catttcagct    60
acatcatgcc gcgctgttgt aatactgtat aaagacctca atctatccag agtatttt    118

<210> SEQ ID NO 302
<211> LENGTH: 118
<212> TYPE: DNA
<213> ORGANISM: Artificial Sequence
<220> FEATURE:
<223> OTHER INFORMATION: Synthetic

<400> SEQUENCE: 302
caggagctga tcctccttgc aaagctgtgc cttgcagaga tgcacgtgtg catttcagct    60
acatcatgcc gcgctgttgt aatactgtat aaagacctca atctatccag agtatttt    118

<210> SEQ ID NO 303
<211> LENGTH: 44
<212> TYPE: DNA
<213> ORGANISM: Artificial Sequence
<220> FEATURE:
<223> OTHER INFORMATION: Synthetic

<400> SEQUENCE: 303
ttgcacactg ttccaacttg ccgtgaacac attttttgct cttt                     44

<210> SEQ ID NO 304
<211> LENGTH: 49
<212> TYPE: DNA
<213> ORGANISM: Artificial Sequence
<220> FEATURE:
<223> OTHER INFORMATION: Synthetic

<400> SEQUENCE: 304
caaagaagct aagcacattg cagatgaggc agatgggaag tatgaagag                49

<210> SEQ ID NO 305
<211> LENGTH: 96
<212> TYPE: DNA
<213> ORGANISM: Artificial Sequence
<220> FEATURE:
<223> OTHER INFORMATION: Synthetic

<400> SEQUENCE: 305
tgtctgtgtc aatgcgtgga tgctggacct cacccaagcc atcctgaacc tcggcttcct    60
gactggagca ttcaccttag gctatgcagc agacag                              96

<210> SEQ ID NO 306
<211> LENGTH: 225
<212> TYPE: DNA
<213> ORGANISM: Artificial Sequence
<220> FEATURE:
<223> OTHER INFORMATION: Synthetic

<400> SEQUENCE: 306
tggagtcgta tgatgcccct tgccttgttt atattggctg tcagcgctta actgggactg    60
aagtatctgg gtaacaaaaa ttgatataat gacttaatgc gccttattct ctttgagcta   120
catcagttta gagcacttct gagagaaaaa tgtctggaaa atatcaggga gtcatttatc   180
aacctgtttt cattagcata ctgcctagct ctggcaagga tttga                   225

<210> SEQ ID NO 307
<211> LENGTH: 136
<212> TYPE: DNA
```

<213> ORGANISM: Artificial Sequence
<220> FEATURE:
<223> OTHER INFORMATION: Synthetic

<400> SEQUENCE: 307

```
cggagaaggt tagaatggat ttgaaagaat gtggttggat tcaaagaagc cctaggagac    60
ccaacaagtc agcatttttc tcttgtgaaa agaaccacct gccaacccca gcctgttcca   120
ttgctgacat cagagg                                                   136
```

<210> SEQ ID NO 308
<211> LENGTH: 98
<212> TYPE: DNA
<213> ORGANISM: Artificial Sequence
<220> FEATURE:
<223> OTHER INFORMATION: Synthetic

<400> SEQUENCE: 308

```
ctgaagctag acaggcagca ggacagtgcc gcccgggaca gaacagacat gcacaggacc    60
tggcgggaga cttttctgga taatcttcgt gcggctgg                            98
```

<210> SEQ ID NO 309
<211> LENGTH: 192
<212> TYPE: DNA
<213> ORGANISM: Artificial Sequence
<220> FEATURE:
<223> OTHER INFORMATION: Synthetic

<400> SEQUENCE: 309

```
atgatagcaa tctctgccgt cagcagtgca ctcctgttct cccttctctg tgaagcaagt    60
accgtcgtcc tactcaattc cactgactca tccccgccaa ccataatttt cactgatatt   120
gaagcagctc tgaaagcaca attagattca gcggatatcc caaagccag gcggaagcgc   180
tacatttcgc ag                                                       192
```

<210> SEQ ID NO 310
<211> LENGTH: 428
<212> TYPE: DNA
<213> ORGANISM: Artificial Sequence
<220> FEATURE:
<223> OTHER INFORMATION: Synthetic

<400> SEQUENCE: 310

```
agcagtcatg cctgagggtt ttataaaggc aggccaaagg cccagtcttt ctgggacccc    60
tcttgttagt gccaaccagg gggtaacagg aatgcctgtg tctgcttta ctgttattct   120
ctccaaagct tacccagcaa taggaactcc cataccattt gataaaattt tgtataacag   180
gcaacagcat tatgacccaa ggactggaat ctttacttgt cagataccag gaatatacta   240
tttttcatac cacgtgcatg tgaaagggac tcatgtttgg gtaggcctgt ataagaatgg   300
cacccctgta atgtacacct atgatgaata caccaaaggc tacctggatc aggcttcagg   360
gagtgccatc atcgatctca cagaaaatga ccaggtgtgg ctccagcttc ccaatgccga   420
gtcaaatg                                                            428
```

<210> SEQ ID NO 311
<211> LENGTH: 132
<212> TYPE: DNA
<213> ORGANISM: Artificial Sequence
<220> FEATURE:
<223> OTHER INFORMATION: Synthetic

<400> SEQUENCE: 311

```
atatcgctct attctccagt tggtcaagcc atggtatgat gaagtgaaag attatgcttt        60
tccatatccc caggattgca accccagatg tcctatgaga tgttttggtc ccatgtgcac       120
acattatacg ca                                                          132
```

<210> SEQ ID NO 312
<211> LENGTH: 44
<212> TYPE: DNA
<213> ORGANISM: Artificial Sequence
<220> FEATURE:
<223> OTHER INFORMATION: Synthetic

<400> SEQUENCE: 312

```
atctgtgtgg cgacgtgcag tttacttggt atgcaactat gccc                        44
```

<210> SEQ ID NO 313
<211> LENGTH: 48
<212> TYPE: DNA
<213> ORGANISM: Artificial Sequence
<220> FEATURE:
<223> OTHER INFORMATION: Synthetic

<400> SEQUENCE: 313

```
gctgtatatt gatggtcctt ttggaagtcc atttgaggaa tcactgaa                    48
```

<210> SEQ ID NO 314
<211> LENGTH: 191
<212> TYPE: DNA
<213> ORGANISM: Artificial Sequence
<220> FEATURE:
<223> OTHER INFORMATION: Synthetic

<400> SEQUENCE: 314

```
gtcttcgttt gattactgcc agttatttcc agcatgctaa atccctaccc acgttccagc        60
ctctaggtga gtcagtgcgt cactctgtct cccgtccaat taattatttc tcatcactcc       120
ctcaatccaa gtaacaaacc ttgaaacacg aacatagaca ccaggcttat tggggcgtgc       180
acagccaaga c                                                           191
```

<210> SEQ ID NO 315
<211> LENGTH: 97
<212> TYPE: DNA
<213> ORGANISM: Artificial Sequence
<220> FEATURE:
<223> OTHER INFORMATION: Synthetic

<400> SEQUENCE: 315

```
cccgttggct gattactcgg aagaaggag ataaagcatt acagatcctg agacgcattg         60
ctaagtgcaa tgggaaatac ctctcatcaa attactc                                97
```

<210> SEQ ID NO 316
<211> LENGTH: 235
<212> TYPE: DNA
<213> ORGANISM: Artificial Sequence
<220> FEATURE:
<223> OTHER INFORMATION: Synthetic

<400> SEQUENCE: 316

```
catttggggc aaatggttca cattcatttt agggttagtg gtcatgctgt ttattttct         60 ctgctataca aagttcctct tagggtctg cctcatgaca ctaaaaaatg aatagagatt       120
ctactgtagg ttatctccta ggcttgagtt caacatttgt ttggattttt gaagaaagtc      180
```

```
aaatcaagca atgctcccaa atgatgtctt tgtaaattca taccctctgg cccta      235
```

```
<210> SEQ ID NO 317
<211> LENGTH: 213
<212> TYPE: DNA
<213> ORGANISM: Artificial Sequence
<220> FEATURE:
<223> OTHER INFORMATION: Synthetic

<400> SEQUENCE: 317
agatgacagc gcaagagtca gattaatgaa agatcaatag acattattca gtcttgaaaa    60
aattgtgaac agggatgcag ggatcagtgg gacaatatca gaagctctaa tacatgttgt   120
cataggatgg ggtggggtg aatgaaaaaa taatggctga aaatatccca aatttgatga    180
atgatataaa tgtagagtca agaagctcaa tca                                 213
```

```
<210> SEQ ID NO 318
<211> LENGTH: 28
<212> TYPE: DNA
<213> ORGANISM: Artificial Sequence
<220> FEATURE:
<223> OTHER INFORMATION: Synthetic

<400> SEQUENCE: 318
acggaacaaa ggatgagcag cccgaggg                                       28
```

```
<210> SEQ ID NO 319
<211> LENGTH: 315
<212> TYPE: DNA
<213> ORGANISM: Artificial Sequence
<220> FEATURE:
<223> OTHER INFORMATION: Synthetic

<400> SEQUENCE: 319
ttggcaccaa tcctagactc acgtgtgccc cagaataaca ttcagactct cagctggtct    60
tgtgttacac atccatggac cggttcactc catcatatac agctctctgc tccgtgtccc   120
ctgggctcaa gtcaagcagt cggtgacaga tttcattccc aataacagaa tcggtttgca   180
tgactcccca tacatgttgc agctttgaaa acattcatct cagagttagg tataaagaca   240
taaaaatgtg tgtcaagccc tcgttagctg atgaggtaaa tgcatggaca acttcctagg   300
acttctcggc tctgc                                                    315
```

```
<210> SEQ ID NO 320
<211> LENGTH: 38
<212> TYPE: DNA
<213> ORGANISM: Artificial Sequence
<220> FEATURE:
<223> OTHER INFORMATION: Synthetic

<400> SEQUENCE: 320
atcattgaag gagacatggg atgcacagag gaacgagc                            38
```

```
<210> SEQ ID NO 321
<211> LENGTH: 87
<212> TYPE: DNA
<213> ORGANISM: Artificial Sequence
<220> FEATURE:
<223> OTHER INFORMATION: Synthetic

<400> SEQUENCE: 321
aggacgggaa caccacagtg cactacgccc tcctcagcgc ctcctgggct gtgctctgct    60
actacgccga agacctgcgc ctgaagc                                        87
```

<210> SEQ ID NO 322
<211> LENGTH: 2473
<212> TYPE: DNA
<213> ORGANISM: Artificial Sequence
<220> FEATURE:
<223> OTHER INFORMATION: Synthetic

<400> SEQUENCE: 322

```
tgcgagagtc tctttgcaaa tcgaagaagg gagacatgtt gggagcaagc cccccagagt      60
ctggccataa actggcccca aaactggcca taagcaaaac ctctgcagca ctaaaacatg     120
tccataatgg ccctaacgcc caatctggaa ggttgtgggt ttatgggaat gagagcaagg     180
aacacctggc ctgcccaggg cggaaaaccg cttaaaggca ttcttaagcc acaaacaaaa     240
gcatgagcga tctgtgtctt acgggtgtgt tcctgctgca attaattcag cccatcccctt     300
tgtttcccat aagggatact tttagttaat ttaatatcta tagaaacaat gctaatgact     360
ggtttgctgt taaatgaagg ggtgggttgc ccctccacac ctgtgggtgt ttctcgttag     420
gtggaacgag agacttggaa aagagacaca gagacaaagt atagagaaag aaaagtgggc     480
ccaggggacc agcattcagc atacagagga tccacactgg caccggcctc tgagttccct     540
tagtatttat tgatcattat cgagcatggc aggataatag gataatagtg gagagaaggt     600
cagaaggtaa acacatgaac aaaggtctct gcatcataaa caaggtaaag aattaagtgc     660
tgtgctttag atatgtatac acataaacat ctcaatgcct taaagagcag tattgctgcc     720
cgcatgtcat acctcagcc ctaaggcggt ttccctat ctcagtagat ggaagtatat     780
tccatgtaaa gtaaatcggc tttacaccca gacattccat tgcccagaga cgagcaggag     840
acagaagcct tcctcttatc tcaactgcaa agaggtgttc cttcctcttt tactaatcct     900
cctcagcaca gacccttat gggtgtcggg ctggggatg gtcaggtctt tccctccca     960
cgaggccata tttcagacta tcacatgggg agaaaccttg acaatacct ggctttccta    1020
ggcagaggtc cctgcggcct ttgcagtatt ttgcgtctct gggtacttga gattagggag    1080
tggtttgaga ttagggagtg gtgatgactc ttaaggagca tgctgccttc aagcatttgt    1140
ttaacaaagc acatcttgca cagcccttaa tccatttaac cctgagttga cacagcacat    1200
gtttcaggga gcacagggtt gggggtaagg ttacagatta acggcatctc aaggcagaag    1260
aattttttctt aatacagaac aaatggagt ctcctatgtc tacttctttc tacacagaca    1320
cagtaacaat ctgatctctc tttcccac agttaataa tatgtgggta aatctctgtt    1380
gggggctctc agctctgaag gctgtgagac ccctgatttt ctacttcaca cctctatatt    1440
tttgtgtgtg tgtctttaat tcctctagcg ctgctgagtt agtgaccgag ctggtctcgg    1500
cagaggtggg cgggtctttt gagttcagga gttcaagagc agcctggcca acatggtgaa    1560
accccttctc tactaaaaat atgaaaatta tccgggcatg gtggtgtgcc tctgtacttt    1620
cagctactca ggaagctgag gcacaagaat tgctggaaca tgggaggtgg aggctgcagt    1680
gagctgagat catgccactg cactccagcc caggcaatag agtaagactc tgtctcaaaa    1740
caaaaagagt tttaggccag gtgtggtggc tcacgcctgt aatcccagca ctttgggagg    1800
ctgaggtggg cagatcacct gaggtcagga gttcgagacc agtctggcca acatggcgaa    1860
accccatctc tctctactaa aaatacaaaa tttagccagg tgtggtggtg ggtgcctgta    1920
atcacagctg cttgggaggc tgaggcagga gaattggttg aacccaggag gcagaggtta    1980
cagtgagcag agatcgtgcc actgcattcc agccgggta agagagcgag actctgcctc    2040
```

```
aaaaaaagaa ggcttagtgt gcaactcatc agagttgcac agggcagaga agaatggga      2100 aaaaaacaat ttctagaaaa cttttcgaat tttctgatca acaccaaata ttccaaatag      2160
gaaaaataca aaaaaatcca tacctatatg tggcataata tgattgtaga gcaccaaagt      2220
aaaagatctt attttttatt aaaattaaaa aaaaattaaa atagagggtc tcactatgct      2280
gcccaggctg gtcttgaact cctggcttca agctatcctc ccaccatggc atcctaaagt      2340
gctgggattg caggcatgag ctgctgcatc tggcccaaag taaaagatct tagaagcggc      2400
cagaaaaaat agatttgggc tgggcatgaa tagattgatc accaaaaagg tggcagacta      2460
acttctcgac aga                                                         2473

<210> SEQ ID NO 323
<211> LENGTH: 30
<212> TYPE: DNA
<213> ORGANISM: Artificial Sequence
<220> FEATURE:
<223> OTHER INFORMATION: Synthetic

<400> SEQUENCE: 323
tttttggcat ctaacatggt gaagaaagga                                        30

<210> SEQ ID NO 324
<211> LENGTH: 34
<212> TYPE: DNA
<213> ORGANISM: Artificial Sequence
<220> FEATURE:
<223> OTHER INFORMATION: Synthetic

<400> SEQUENCE: 324
gctgtggagc cttagttgag atttcagcat ttcc                                   34

<210> SEQ ID NO 325
<211> LENGTH: 165
<212> TYPE: DNA
<213> ORGANISM: Artificial Sequence
<220> FEATURE:
<223> OTHER INFORMATION: Synthetic

<400> SEQUENCE: 325
gtatatggac gacttcttac tcatgttagc ccattcattt catcagagca tcttcacaca       60
tcagtgttca ctctctatag atttatttgc atattgtcta aatatgtttt tttctgttat      120
tattttacac ttttttatttt gcttcattct ctgttgagtt cctca                     165

<210> SEQ ID NO 326
<211> LENGTH: 176
<212> TYPE: DNA
<213> ORGANISM: Artificial Sequence
<220> FEATURE:
<223> OTHER INFORMATION: Synthetic

<400> SEQUENCE: 326
cttgagtcct ggaatcgacc ttttctccaa ggagccttgt tccttttagt ggggaaaggt       60
atttagaagc taagatcttg gtgttggctg tgttcactac aattggtgta tctacttctc      120
catcctccag cgtcctctgg tgatcgagaa tctgaagttc caggttttca taggcc          176

<210> SEQ ID NO 327
<211> LENGTH: 40
<212> TYPE: DNA
<213> ORGANISM: Artificial Sequence
<220> FEATURE:
<223> OTHER INFORMATION: Synthetic
```

<400> SEQUENCE: 327
gggtttgctg tttggatcaa ggaatcaatg gattgccaga                           40

<210> SEQ ID NO 328
<211> LENGTH: 87
<212> TYPE: DNA
<213> ORGANISM: Artificial Sequence
<220> FEATURE:
<223> OTHER INFORMATION: Synthetic

<400> SEQUENCE: 328
gatggagagc ataagccatt cactattgtg ttagaaagag aaaatgacac tttgggattc     60
aatattatag gaggtcgacc aaatcag                                         87

<210> SEQ ID NO 329
<211> LENGTH: 26
<212> TYPE: DNA
<213> ORGANISM: Artificial Sequence
<220> FEATURE:
<223> OTHER INFORMATION: Synthetic

<400> SEQUENCE: 329
caggcattct gatttattga ttgtgg                                          26

<210> SEQ ID NO 330
<211> LENGTH: 43
<212> TYPE: DNA
<213> ORGANISM: Artificial Sequence
<220> FEATURE:
<223> OTHER INFORMATION: Synthetic

<400> SEQUENCE: 330
tcttcatctt gtcttacgct ttccgagcaa gttcaaacca gaa                       43

<210> SEQ ID NO 331
<211> LENGTH: 84
<212> TYPE: DNA
<213> ORGANISM: Artificial Sequence
<220> FEATURE:
<223> OTHER INFORMATION: Synthetic

<400> SEQUENCE: 331
gcaccaacaa atgtggttgc tccataatgg agagaatgtc aagaatgttg actatcttta     60
gacctgcttc attaatagat aaga                                            84

<210> SEQ ID NO 332
<211> LENGTH: 113
<212> TYPE: DNA
<213> ORGANISM: Artificial Sequence
<220> FEATURE:
<223> OTHER INFORMATION: Synthetic

<400> SEQUENCE: 332
aaccgcatgc acgaatccct gaagcttttt gacagcatct gcaacaacaa atggttcaca     60
gacacgtcca tcatcctgtt tcttaacaag aaggacatat ttgaagagaa gat           113

<210> SEQ ID NO 333
<211> LENGTH: 201
<212> TYPE: DNA
<213> ORGANISM: Artificial Sequence
<220> FEATURE:
<223> OTHER INFORMATION: Synthetic

<400> SEQUENCE: 333

```
caggcccaag tgcatactcg ggttctttcc aactcagaat catctctgat tccacaaaag      60
tgagtttagt ttcctatctg aattaacaac tttaaaggag actataatag ttaaaagtgg     120
aagaatagaa ataaataaat ttaaaatgaa attaattaaa gtagaagaga agggttctgt     180
tccatgtacg attaatgtgc c                                               201
```

<210> SEQ ID NO 334
<211> LENGTH: 55
<212> TYPE: DNA
<213> ORGANISM: Artificial Sequence
<220> FEATURE:
<223> OTHER INFORMATION: Synthetic

<400> SEQUENCE: 334

```
cctggcatct atttcctctg tgcaaaggga accatgtata tgagcttata aatac           55
```

<210> SEQ ID NO 335
<211> LENGTH: 28
<212> TYPE: DNA
<213> ORGANISM: Artificial Sequence
<220> FEATURE:
<223> OTHER INFORMATION: Synthetic

<400> SEQUENCE: 335

```
ctctttggcg ttgctaagag actgccat                                        28
```

<210> SEQ ID NO 336
<211> LENGTH: 513
<212> TYPE: DNA
<213> ORGANISM: Artificial Sequence
<220> FEATURE:
<223> OTHER INFORMATION: Synthetic

<400> SEQUENCE: 336

```
ttcctaccgc atgcattttc taatgtttgg ggtggatggt gtgtcggtta tggaaggcat      60
agacgtcatt acaggtgcta cgatctcaca cacacacaag gaaatgttag tctccttatt    120
ttatgattgg aaaatcaatg acctagaggc aaaatggcat gtttaaggac ctgggatgac    180
aagtcattct gcagtcagcc acagagccaa atttggactc ctcaaccaga actccatgaa    240
aagcctgact tgccaaaaca ctgtgctgga aaagctaagc ccctttcatt tgtgaagtaa    300
atttttaaatt caagatattt agtttagaga attgagtctt gagatgtaaa ctacatgaga    360
tttctttggt ttcaattgaa taatattcac taacaaatga tttactaaaa tacgtatttc    420
ttggtcctta tcatgtaatg acagattcac aacagcaata aggatggaga tttccccaat    480
aattaataac accgagagta gcaatatttt tta                                  513
```

<210> SEQ ID NO 337
<211> LENGTH: 79
<212> TYPE: DNA
<213> ORGANISM: Artificial Sequence
<220> FEATURE:
<223> OTHER INFORMATION: Synthetic

<400> SEQUENCE: 337

```
gtagagccta cgtccttcat gagaaaaatg acacaaatct cagtattctt tgtttggagt      60
ctcttgacat ccatgtgag                                                   79
```

<210> SEQ ID NO 338
<211> LENGTH: 34

```
<212> TYPE: DNA
<213> ORGANISM: Artificial Sequence
<220> FEATURE:
<223> OTHER INFORMATION: Synthetic

<400> SEQUENCE: 338
ttaggacacg gacatttcta tttggcagcc aaca                          34

<210> SEQ ID NO 339
<211> LENGTH: 178
<212> TYPE: DNA
<213> ORGANISM: Artificial Sequence
<220> FEATURE:
<223> OTHER INFORMATION: Synthetic

<400> SEQUENCE: 339
cggaagactt gccacttttc atgtcatttg acatttttg tttgctgaag tgaaaaaaaa    60
agataaaggt tgtacggtgg tctttgaatt atatgtctaa ttctatgtgt tttgtctttt  120
tcttaaatat tatgtgaaat caaagcgcca tatgtagaat tatatcttca ggactatt    178

<210> SEQ ID NO 340
<211> LENGTH: 29
<212> TYPE: DNA
<213> ORGANISM: Artificial Sequence
<220> FEATURE:
<223> OTHER INFORMATION: Synthetic

<400> SEQUENCE: 340
gcttctgtcc caagaggcac tagctgggg                                29

<210> SEQ ID NO 341
<211> LENGTH: 118
<212> TYPE: DNA
<213> ORGANISM: Artificial Sequence
<220> FEATURE:
<223> OTHER INFORMATION: Synthetic

<400> SEQUENCE: 341
aacattggag aagtatctct ttgtaatgct aaaagaagt gaaatcaac agacttatct    60 aatgaatgca gatgtggcag aaagaatgag tagcactacc gttgactctg aagagaga   118

<210> SEQ ID NO 342
<211> LENGTH: 269
<212> TYPE: DNA
<213> ORGANISM: Artificial Sequence
<220> FEATURE:
<223> OTHER INFORMATION: Synthetic

<400> SEQUENCE: 342
actactagac ttgctaaact tggactgttg tgaattagaa cctaaaattg aagagattaa    60
tattaggcgc ctatattttg cttctaaatc aagaataaa attattagca gtatggtttc   120
ttttactgat gaacatgttt gtattgaaca aggaacacat actaatatct attgagtgcc  180
tactatgtgc taatctccaa caaattgatt tggggatgct aagaagaatt atgtgccagt  240
gttaccctca aggagcaata ctgtatata                                   269

<210> SEQ ID NO 343
<211> LENGTH: 29
<212> TYPE: DNA
<213> ORGANISM: Artificial Sequence
<220> FEATURE:
<223> OTHER INFORMATION: Synthetic
```

```
<400> SEQUENCE: 343
aatctcatct ctatgacatc cctatcctg                                              29

<210> SEQ ID NO 344
<211> LENGTH: 316
<212> TYPE: DNA
<213> ORGANISM: Artificial Sequence
<220> FEATURE:
<223> OTHER INFORMATION: Synthetic

<400> SEQUENCE: 344
ctcagtctat gaaagccagg ttagcttgct tcttcctcc ctaaatcctc catcctcatg            60
accaacaaag aaatagttga atcattttcc aggcacatct ggggaggat gtggggccat           120 tggaggctgt ccttcctaga taagtcttta ggagtgagaa caaggagtct tacccctcctc         180 tgtccaccca cccccatgaa tgggcctggc tccagccagg agttgtggtt tttcctgagc          240
tcctcaccta tctcttctgg atttcacatt ggcaacggg gttgcaaagt gctcttcgtg           300
ctctttggac agtgcc                                                          316

<210> SEQ ID NO 345
<211> LENGTH: 332
<212> TYPE: DNA
<213> ORGANISM: Artificial Sequence
<220> FEATURE:
<223> OTHER INFORMATION: Synthetic

<400> SEQUENCE: 345
tggttgcatt gcacgtagaa agtggaataa tgtaatgagc tttgaaacca taataatgaa           60
tgtctgaata atgacattat ttcttgcgtt tgtaatactg ttaattaaat ctatgtcgat          120
cctgttggaa ttcataaaat catctaaaaa tttttctaaa tatacagtgt tgttttcccc          180
attgtatctt gatctcaagc aacaaatggt aaaagtatag ctattaatgt cattaaatgt          240
gaattgtttc aacattatga agggttcctc ttggtaagtg cagaaggag ccaggcttag           300 gtttgaagtg agactgactt tattcccttc tt                                        332

<210> SEQ ID NO 346
<211> LENGTH: 482
<212> TYPE: DNA
<213> ORGANISM: Artificial Sequence
<220> FEATURE:
<223> OTHER INFORMATION: Synthetic

<400> SEQUENCE: 346
ctcctgaatg ctggccagac aaatggaaat ctgccagggt tgggtacccc catgacagca           60
gccagcctgc cctcttagtc cctgacagct gcagtgacag catctgtgat tgcaaagcgt          120
gacaatttat atctctcatt tcatcacacc atctatcagc agacagtcag gctttaaaaa          180
tcaatcccac actgactcag tccccagcag agatggcctc tgacaacagt atccacactg          240
caggctggac aagggcccta ttaattttga gactcagcca aatttccttc tgaccctaag          300
ctggtgaatc cctgctcctt tgctttggtt ggggttggtg tgagctaagg ctgtgatccc          360
atttgctcct atggcctcca ggtggcctgg gcctccatga atgggccaca tggtcatact          420
gaatgcttga ttacactcag acctagcagt cgtctgggcg cagctggttt atggatcact          480
tt                                                                         482

<210> SEQ ID NO 347
<211> LENGTH: 26
```

```
<212> TYPE: DNA
<213> ORGANISM: Artificial Sequence
<220> FEATURE:
<223> OTHER INFORMATION: Synthetic

<400> SEQUENCE: 347
atggcctttg aatcatactt aagttt                                              26

<210> SEQ ID NO 348
<211> LENGTH: 137
<212> TYPE: DNA
<213> ORGANISM: Artificial Sequence
<220> FEATURE:
<223> OTHER INFORMATION: Synthetic

<400> SEQUENCE: 348
accgaggagg agattctctt taattatcaa agacacatct tttcaggggg ccaacaaagc         60
atttatttca cccgccaaac taaggagag ttattccagt ttaggaggaa gatgcaagcg         120
gtttgggacc ttgaaca                                                        137

<210> SEQ ID NO 349
<211> LENGTH: 402
<212> TYPE: DNA
<213> ORGANISM: Artificial Sequence
<220> FEATURE:
<223> OTHER INFORMATION: Synthetic

<400> SEQUENCE: 349
tggaggctaa tcttgtttgt tatactttag tcattaattc aaagtaaagg agttgttaat         60
gaactggaaa ctccttttga attatggtag caatcagaat attttatat tagccagttt         120 taccttgaag acctattttt aaaaactacc tgtgtctctg gacttagttg caaatgcata        180
ttaaaacaaa atcccccaa tttctgtgct ttcttatttg aaaggccatt tctaggggga         240
aaacagttcc caaacacatt atacatgttg gaaaagttta tctctaacct tttgaattaa        300
acaatttcag aattgaaaac agtaaggtga attttaggcc ataactctt ttctataatc         360 ttgactcttt taagattagg cagttcagat agtcttatac ta                           402

<210> SEQ ID NO 350
<211> LENGTH: 166
<212> TYPE: DNA
<213> ORGANISM: Artificial Sequence
<220> FEATURE:
<223> OTHER INFORMATION: Synthetic

<400> SEQUENCE: 350
acctagttgg ctttcatcta attcattgcc attttaagtg tgtattattt tagagcaaac         60
ttagaaaaac agcacatttc tagtaactta cgacattcga tgaatgataa atgttcaagt        120
tagactaaag gaactttatt ccaacttcta gtaactactt tcttca                       166

<210> SEQ ID NO 351
<211> LENGTH: 64
<212> TYPE: DNA
<213> ORGANISM: Artificial Sequence
<220> FEATURE:
<223> OTHER INFORMATION: Synthetic

<400> SEQUENCE: 351
agcattatct aaactgcagt cactgtgagg tagacgaatg tcacatggac cctgaaagcc         60
acaa                                                                      64
```

<210> SEQ ID NO 352
<211> LENGTH: 134
<212> TYPE: DNA
<213> ORGANISM: Artificial Sequence
<220> FEATURE:
<223> OTHER INFORMATION: Synthetic

<400> SEQUENCE: 352

```
ttcacaggac ttcgccacgc tgctttggaa tctttcacac cccctaccc ccagatacct      60 ttgaaaaatt tgaggttcct gttccttgtt tctcagtgta ttcatttctt ccctgactat    120
gacatgttaa aaaa                                                      134
```

<210> SEQ ID NO 353
<211> LENGTH: 25
<212> TYPE: DNA
<213> ORGANISM: Artificial Sequence
<220> FEATURE:
<223> OTHER INFORMATION: Synthetic

<400> SEQUENCE: 353

```
cttcaacgat gagaagtttg cagat                                           25
```

<210> SEQ ID NO 354
<211> LENGTH: 48
<212> TYPE: DNA
<213> ORGANISM: Artificial Sequence
<220> FEATURE:
<223> OTHER INFORMATION: Synthetic

<400> SEQUENCE: 354

```
ggaaagacga gaactattta tatgacacca actatggtag cacagtag                  48
```

<210> SEQ ID NO 355
<211> LENGTH: 25
<212> TYPE: DNA
<213> ORGANISM: Artificial Sequence
<220> FEATURE:
<223> OTHER INFORMATION: Synthetic

<400> SEQUENCE: 355

```
tgcccctaga tctgacagtg aagag                                           25
```

<210> SEQ ID NO 356
<211> LENGTH: 161
<212> TYPE: DNA
<213> ORGANISM: Artificial Sequence
<220> FEATURE:
<223> OTHER INFORMATION: Synthetic

<400> SEQUENCE: 356

```
gcagcagtcc caaatagtca aaatgctact atctctgtac ctccattgac ttctgtttct     60
gtaaagcctc agcttggctg tactgaggat tatttgcttt ccaaattacc atctgatggc    120
aaagaagtac catttgtggt gcccaagttt aagttatctt a                        161
```

<210> SEQ ID NO 357
<211> LENGTH: 30
<212> TYPE: DNA
<213> ORGANISM: Artificial Sequence
<220> FEATURE:
<223> OTHER INFORMATION: Synthetic

<400> SEQUENCE: 357

```
gtggtgtatg cggatatccg aaagaattaa                                      30
```

<210> SEQ ID NO 358
<211> LENGTH: 31
<212> TYPE: DNA
<213> ORGANISM: Artificial Sequence
<220> FEATURE:
<223> OTHER INFORMATION: Synthetic

<400> SEQUENCE: 358
gaagttcaga agctacagac tcttgtttct g         31

<210> SEQ ID NO 359
<211> LENGTH: 73
<212> TYPE: DNA
<213> ORGANISM: Artificial Sequence
<220> FEATURE:
<223> OTHER INFORMATION: Synthetic

<400> SEQUENCE: 359
gaagcttctg cagttcaagc gttggttctg gtcaatagta gagaagatga gcatgacaga         60
acgacaagat ctt         73

<210> SEQ ID NO 360
<211> LENGTH: 27
<212> TYPE: DNA
<213> ORGANISM: Artificial Sequence
<220> FEATURE:
<223> OTHER INFORMATION: Synthetic

<400> SEQUENCE: 360
ctgttgctga aacttactat cagacag         27

<210> SEQ ID NO 361
<211> LENGTH: 74
<212> TYPE: DNA
<213> ORGANISM: Artificial Sequence
<220> FEATURE:
<223> OTHER INFORMATION: Synthetic

<400> SEQUENCE: 361
gctcagaaaa agaagttcga gcagcagcac ttgtattaca gacaatctgg ggatataagg         60
aactgcggaa gcca         74

<210> SEQ ID NO 362
<211> LENGTH: 141
<212> TYPE: DNA
<213> ORGANISM: Artificial Sequence
<220> FEATURE:
<223> OTHER INFORMATION: Synthetic

<400> SEQUENCE: 362
cttaccagcg ttataggcca gtatcaactt caagttcaac cactccatcc tcttcacttt         60
ctactatgag cagttcactg tatgcttcaa gtcaactaaa caggccaaat agtcttgtag         120
gcataacttc tgcttactcc a         141

<210> SEQ ID NO 363
<211> LENGTH: 31
<212> TYPE: DNA
<213> ORGANISM: Artificial Sequence
<220> FEATURE:
<223> OTHER INFORMATION: Synthetic

<400> SEQUENCE: 363
tgtgcaagta gtactcgatg gactaagtaa t                                      31

<210> SEQ ID NO 364
<211> LENGTH: 49
<212> TYPE: DNA
<213> ORGANISM: Artificial Sequence
<220> FEATURE:
<223> OTHER INFORMATION: Synthetic

<400> SEQUENCE: 364
ttgcaaattc catatctaca atggtacacg tccatgtgaa tcagtttcc                   49

<210> SEQ ID NO 365
<211> LENGTH: 42
<212> TYPE: DNA
<213> ORGANISM: Artificial Sequence
<220> FEATURE:
<223> OTHER INFORMATION: Synthetic

<400> SEQUENCE: 365
ctggccagtg attcacgaaa acgcaaattg ccatgtgata ct                          42

<210> SEQ ID NO 366
<211> LENGTH: 25
<212> TYPE: DNA
<213> ORGANISM: Artificial Sequence
<220> FEATURE:
<223> OTHER INFORMATION: Synthetic

<400> SEQUENCE: 366
ttggatgact gcaatgcctt ggaat                                             25

<210> SEQ ID NO 367
<211> LENGTH: 51
<212> TYPE: DNA
<213> ORGANISM: Artificial Sequence
<220> FEATURE:
<223> OTHER INFORMATION: Synthetic

<400> SEQUENCE: 367
cttcttcctg aatcacgatg gaaaaacctt cttaaccttg atgttattaa g                51

<210> SEQ ID NO 368
<211> LENGTH: 25
<212> TYPE: DNA
<213> ORGANISM: Artificial Sequence
<220> FEATURE:
<223> OTHER INFORMATION: Synthetic

<400> SEQUENCE: 368
tcctcgtttt atcctgatgg tggag                                             25

<210> SEQ ID NO 369
<211> LENGTH: 34
<212> TYPE: DNA
<213> ORGANISM: Artificial Sequence
<220> FEATURE:
<223> OTHER INFORMATION: Synthetic

<400> SEQUENCE: 369
tttttgacaa caggtcctat gattcattac acag                                   34

<210> SEQ ID NO 370
<211> LENGTH: 124
<212> TYPE: DNA
<213> ORGANISM: Artificial Sequence

```
<220> FEATURE:
<223> OTHER INFORMATION: Synthetic

<400> SEQUENCE: 370
ggaccactgc atggaatgtt aatcaatact ccatatgtga ccaaagacct gctgcaatca    60
aagaggttcc aggcacaatc cttagggaca acatacatat atgatatccc agagatgttt  120
cggc                                                                124

<210> SEQ ID NO 371
<211> LENGTH: 25
<212> TYPE: DNA
<213> ORGANISM: Artificial Sequence
<220> FEATURE:
<223> OTHER INFORMATION: Synthetic

<400> SEQUENCE: 371
aacctgtaag tgtaatggct ggaaa                                          25

<210> SEQ ID NO 372
<211> LENGTH: 136
<212> TYPE: DNA
<213> ORGANISM: Artificial Sequence
<220> FEATURE:
<223> OTHER INFORMATION: Synthetic

<400> SEQUENCE: 372
cgccctatta ggagaattac acatatctca ggtactttag aagatgaaga tgaagatgaa    60
gataatgatg acattgtcat gctagagaaa aaaatacgaa catctagtat gccagagcag  120
gcccataaag tctgtg                                                   136

<210> SEQ ID NO 373
<211> LENGTH: 26
<212> TYPE: DNA
<213> ORGANISM: Artificial Sequence
<220> FEATURE:
<223> OTHER INFORMATION: Synthetic

<400> SEQUENCE: 373
aaacctaaga cttgtgagac tgatgc                                         26

<210> SEQ ID NO 374
<211> LENGTH: 25
<212> TYPE: DNA
<213> ORGANISM: Artificial Sequence
<220> FEATURE:
<223> OTHER INFORMATION: Synthetic

<400> SEQUENCE: 374
catgaacggg gacctgaagt actga                                          25

<210> SEQ ID NO 375
<211> LENGTH: 28
<212> TYPE: DNA
<213> ORGANISM: Artificial Sequence
<220> FEATURE:
<223> OTHER INFORMATION: Synthetic

<400> SEQUENCE: 375
agtttttaca gattacgagc atgacaaa                                       28

<210> SEQ ID NO 376
<211> LENGTH: 35
<212> TYPE: DNA
```

```
<213> ORGANISM: Artificial Sequence
<220> FEATURE:
<223> OTHER INFORMATION: Synthetic

<400> SEQUENCE: 376
tccctcttat tctggaagtg atatgccaag aaatg                                    35

<210> SEQ ID NO 377
<211> LENGTH: 39
<212> TYPE: DNA
<213> ORGANISM: Artificial Sequence
<220> FEATURE:
<223> OTHER INFORMATION: Synthetic

<400> SEQUENCE: 377
agacctggat tttttccgga agatgtggat tgactggaa                                39

<210> SEQ ID NO 378
<211> LENGTH: 39
<212> TYPE: DNA
<213> ORGANISM: Artificial Sequence
<220> FEATURE:
<223> OTHER INFORMATION: Synthetic

<400> SEQUENCE: 378
taaagatgat aatcaggaaa tagccagcat ggaaagaca                                39

<210> SEQ ID NO 379
<211> LENGTH: 108
<212> TYPE: DNA
<213> ORGANISM: Artificial Sequence
<220> FEATURE:
<223> OTHER INFORMATION: Synthetic

<400> SEQUENCE: 379
agcagtgata atagcgatac acatcaaagt ggaggtagtg acattgaaat ggatgagcaa         60
cttattaata gaaccaaaca tgtgcaacaa cgactttcag acacagag                      108

<210> SEQ ID NO 380
<211> LENGTH: 42
<212> TYPE: DNA
<213> ORGANISM: Artificial Sequence
<220> FEATURE:
<223> OTHER INFORMATION: Synthetic

<400> SEQUENCE: 380
ttcagaacaa gagctagagc gattaagaag cgaaaataag ga                            42

<210> SEQ ID NO 381
<211> LENGTH: 25
<212> TYPE: DNA
<213> ORGANISM: Artificial Sequence
<220> FEATURE:
<223> OTHER INFORMATION: Synthetic

<400> SEQUENCE: 381
aagaaccaga tgactgcttc acaga                                               25

<210> SEQ ID NO 382
<211> LENGTH: 27
<212> TYPE: DNA
<213> ORGANISM: Artificial Sequence
<220> FEATURE:
<223> OTHER INFORMATION: Synthetic

<400> SEQUENCE: 382
```

```
gtcggcaggt tctaaaagat ctagtta                                          27
```

<210> SEQ ID NO 383
<211> LENGTH: 63
<212> TYPE: DNA
<213> ORGANISM: Artificial Sequence
<220> FEATURE:
<223> OTHER INFORMATION: Synthetic

<400> SEQUENCE: 383

```
accttgcaac ggatgtcctt gttgatcagc acgttcttgc ccttgtagtt gaagatgaca     60
tga                                                                    63
```

<210> SEQ ID NO 384
<211> LENGTH: 81
<212> TYPE: DNA
<213> ORGANISM: Artificial Sequence
<220> FEATURE:
<223> OTHER INFORMATION: Synthetic

<400> SEQUENCE: 384

```
atgatgatgc tgttaactac attcaacaaa aatcctttaa aacagctgtt ttcaaccaac     60
tttcgctgtg aatgtacttt t                                                81
```

<210> SEQ ID NO 385
<211> LENGTH: 25
<212> TYPE: DNA
<213> ORGANISM: Artificial Sequence
<220> FEATURE:
<223> OTHER INFORMATION: Synthetic

<400> SEQUENCE: 385

```
ctgccagctg aatcaacagg gtaaa                                            25
```

<210> SEQ ID NO 386
<211> LENGTH: 72
<212> TYPE: DNA
<213> ORGANISM: Artificial Sequence
<220> FEATURE:
<223> OTHER INFORMATION: Synthetic

<400> SEQUENCE: 386

```
ccatcttcaa gtttggactc atagacttgg gttaaagatt ttacttttg ctccatttca      60 ctattttgtt tt                                                          72
```

<210> SEQ ID NO 387
<211> LENGTH: 25
<212> TYPE: DNA
<213> ORGANISM: Artificial Sequence
<220> FEATURE:
<223> OTHER INFORMATION: Synthetic

<400> SEQUENCE: 387

```
tgggtcttct cttcaagcaa cagac                                            25
```

<210> SEQ ID NO 388
<211> LENGTH: 146
<212> TYPE: DNA
<213> ORGANISM: Artificial Sequence
<220> FEATURE:
<223> OTHER INFORMATION: Synthetic

<400> SEQUENCE: 388

```
gcattttgag gacttcgttt ggatcccaat tcaaacaaaa taactgtgaa gagatttttt      60
cgaacaacag aggagattca attacacact gggttacatg atctgaagga actggcattt     120
ttttaaatgt gtgataacgg cactga                                          146
```

<210> SEQ ID NO 389
<211> LENGTH: 273
<212> TYPE: DNA
<213> ORGANISM: Artificial Sequence
<220> FEATURE:
<223> OTHER INFORMATION: Synthetic

<400> SEQUENCE: 389

```
agggtgatta ggaattaact ggacaaagaa gagggaaagt ctttgcaagt agaggaaaga      60
atctgcttgg agctcagata actattattt gaaaacataa tgacatctag ttcaaacttg     120
tgactgagtt ccacagtaga attcacagaa aaaaaattat taaatataat atttccatca     180
gtctgtgtct aaaagattaa aaaagagcaa ataacaatct taataaactg atgatagatt     240
atagcctcat ctcttccaac atccgattct gtg                                  273
```

<210> SEQ ID NO 390
<211> LENGTH: 25
<212> TYPE: DNA
<213> ORGANISM: Artificial Sequence
<220> FEATURE:
<223> OTHER INFORMATION: Synthetic

<400> SEQUENCE: 390

```
gaaatgttca agatggtcag gaaag                                            25
```

<210> SEQ ID NO 391
<211> LENGTH: 25
<212> TYPE: DNA
<213> ORGANISM: Artificial Sequence
<220> FEATURE:
<223> OTHER INFORMATION: Synthetic

<400> SEQUENCE: 391

```
cctgtttcct ctcgatatgc tacag                                            25
```

<210> SEQ ID NO 392
<211> LENGTH: 25
<212> TYPE: DNA
<213> ORGANISM: Artificial Sequence
<220> FEATURE:
<223> OTHER INFORMATION: Synthetic

<400> SEQUENCE: 392

```
ctgttcatcc tgctgtagat ctgtt                                            25
```

<210> SEQ ID NO 393
<211> LENGTH: 34
<212> TYPE: DNA
<213> ORGANISM: Artificial Sequence
<220> FEATURE:
<223> OTHER INFORMATION: Synthetic

<400> SEQUENCE: 393

```
aaatgttgac aattgggacg atgtaaatgt aaag                                  34
```

<210> SEQ ID NO 394
<211> LENGTH: 25
<212> TYPE: DNA
<213> ORGANISM: Artificial Sequence

```
<220> FEATURE:
<223> OTHER INFORMATION: Synthetic

<400> SEQUENCE: 394
gcaaaggtgt ccaaattatg cagac                                          25

<210> SEQ ID NO 395
<211> LENGTH: 25
<212> TYPE: DNA
<213> ORGANISM: Artificial Sequence
<220> FEATURE:
<223> OTHER INFORMATION: Synthetic

<400> SEQUENCE: 395
gcaaaggtgt ccaaattatg cagac                                          25

<210> SEQ ID NO 396
<211> LENGTH: 25
<212> TYPE: DNA
<213> ORGANISM: Artificial Sequence
<220> FEATURE:
<223> OTHER INFORMATION: Synthetic

<400> SEQUENCE: 396
caaaacgact cactgggttt ttcat                                          25

<210> SEQ ID NO 397
<211> LENGTH: 25
<212> TYPE: DNA
<213> ORGANISM: Artificial Sequence
<220> FEATURE:
<223> OTHER INFORMATION: Synthetic

<400> SEQUENCE: 397
agagaaagtg aagattcgat ttgag                                          25

<210> SEQ ID NO 398
<211> LENGTH: 25
<212> TYPE: DNA
<213> ORGANISM: Artificial Sequence
<220> FEATURE:
<223> OTHER INFORMATION: Synthetic

<400> SEQUENCE: 398
tcagaattaa acctgtggcc caggt                                          25

<210> SEQ ID NO 399
<211> LENGTH: 25
<212> TYPE: DNA
<213> ORGANISM: Artificial Sequence
<220> FEATURE:
<223> OTHER INFORMATION: Synthetic

<400> SEQUENCE: 399
tgccaaagat taagggagc ctttg                                           25

<210> SEQ ID NO 400
<211> LENGTH: 25
<212> TYPE: DNA
<213> ORGANISM: Artificial Sequence
<220> FEATURE:
<223> OTHER INFORMATION: Synthetic

<400> SEQUENCE: 400
cgtccgatta gtgccatggc tggca                                          25
```

```
<210> SEQ ID NO 401
<211> LENGTH: 25
<212> TYPE: DNA
<213> ORGANISM: Artificial Sequence
<220> FEATURE:
<223> OTHER INFORMATION: Synthetic

<400> SEQUENCE: 401
ctcatgggaa gggaactccg tgtca                                    25

<210> SEQ ID NO 402
<211> LENGTH: 57
<212> TYPE: DNA
<213> ORGANISM: Artificial Sequence
<220> FEATURE:
<223> OTHER INFORMATION: Synthetic

<400> SEQUENCE: 402
agagttatga aggaacaggt tgtccttgtc tggagtcaag ctaaacacat gatttgt    57

<210> SEQ ID NO 403
<211> LENGTH: 25
<212> TYPE: DNA
<213> ORGANISM: Artificial Sequence
<220> FEATURE:
<223> OTHER INFORMATION: Synthetic

<400> SEQUENCE: 403
ggataggaat aaagcaagac agtta                                    25

<210> SEQ ID NO 404
<211> LENGTH: 47
<212> TYPE: DNA
<213> ORGANISM: Artificial Sequence
<220> FEATURE:
<223> OTHER INFORMATION: Synthetic

<400> SEQUENCE: 404
taagatctgt aacactgagg aagtaccaat aaagagctgc taacact            47

<210> SEQ ID NO 405
<211> LENGTH: 25
<212> TYPE: DNA
<213> ORGANISM: Artificial Sequence
<220> FEATURE:
<223> OTHER INFORMATION: Synthetic

<400> SEQUENCE: 405
aggacaagag ccctagagtg gcctg                                    25

<210> SEQ ID NO 406
<211> LENGTH: 25
<212> TYPE: DNA
<213> ORGANISM: Artificial Sequence
<220> FEATURE:
<223> OTHER INFORMATION: Synthetic

<400> SEQUENCE: 406
gcagatacac gtggacaaaa gactt                                    25

<210> SEQ ID NO 407
<211> LENGTH: 25
<212> TYPE: DNA
<213> ORGANISM: Artificial Sequence
<220> FEATURE:
<223> OTHER INFORMATION: Synthetic
```

<400> SEQUENCE: 407
gtaacacagc aggagctcat gtttt                                        25

<210> SEQ ID NO 408
<211> LENGTH: 25
<212> TYPE: DNA
<213> ORGANISM: Artificial Sequence
<220> FEATURE:
<223> OTHER INFORMATION: Synthetic

<400> SEQUENCE: 408
atgcctacaa ttcctgctac ttgag                                        25

<210> SEQ ID NO 409
<211> LENGTH: 27
<212> TYPE: DNA
<213> ORGANISM: Artificial Sequence
<220> FEATURE:
<223> OTHER INFORMATION: Synthetic

<400> SEQUENCE: 409
attggctttt agtttatcag tgaataa                                      27

<210> SEQ ID NO 410
<211> LENGTH: 118
<212> TYPE: DNA
<213> ORGANISM: Artificial Sequence
<220> FEATURE:
<223> OTHER INFORMATION: Synthetic

<400> SEQUENCE: 410
tctctggggg aatttcattt gcatctatgt ttttagctat ctgtgataac ttgttaaata   60
ttaaaaagat attttgcttc tattggaaca tttgtatact cgcaactata tttctgta   118

<210> SEQ ID NO 411
<211> LENGTH: 96
<212> TYPE: DNA
<213> ORGANISM: Artificial Sequence
<220> FEATURE:
<223> OTHER INFORMATION: Synthetic

<400> SEQUENCE: 411
tcagaagtcg ctgtccttac tactttgcg gaagtatgga agtcacaact acacagagat    60
ttctcagcct acaaattgtg tctatacatt tctaag                             96

<210> SEQ ID NO 412
<211> LENGTH: 66
<212> TYPE: DNA
<213> ORGANISM: Artificial Sequence
<220> FEATURE:
<223> OTHER INFORMATION: Synthetic

<400> SEQUENCE: 412
cttacatacc gtgagaagtt acgtaacatt tactcctttg taaatgtttc cctatcatca   60
gacaaa                                                             66

<210> SEQ ID NO 413
<211> LENGTH: 28
<212> TYPE: DNA
<213> ORGANISM: Artificial Sequence
<220> FEATURE:
<223> OTHER INFORMATION: Synthetic

<400> SEQUENCE: 413
cacttcatat ggagttaaac ttggtcag    28

<210> SEQ ID NO 414
<211> LENGTH: 59
<212> TYPE: DNA
<213> ORGANISM: Artificial Sequence
<220> FEATURE:
<223> OTHER INFORMATION: Synthetic

<400> SEQUENCE: 414 tgtactttc agaatattat cgtgacactt tcaacatgta gggatatcag cgtttctct    59

<210> SEQ ID NO 415
<211> LENGTH: 59
<212> TYPE: DNA
<213> ORGANISM: Artificial Sequence
<220> FEATURE:
<223> OTHER INFORMATION: Synthetic

<400> SEQUENCE: 415
cactgttgta gtaaagagac atatttcatg aatggcattg atgctaataa atcctttgc    59

<210> SEQ ID NO 416
<211> LENGTH: 129
<212> TYPE: DNA
<213> ORGANISM: Artificial Sequence
<220> FEATURE:
<223> OTHER INFORMATION: Synthetic

<400> SEQUENCE: 416
ggagcactac catctgtttt caacatgaaa tgccacacac atagaactcc aacatcaatt    60
tcattgcaca gactgactgt agttaatttt gtcacagaat ctatggactg aatctaatgc    120
ttccaaaaa    129

<210> SEQ ID NO 417
<211> LENGTH: 25
<212> TYPE: DNA
<213> ORGANISM: Artificial Sequence
<220> FEATURE:
<223> OTHER INFORMATION: Synthetic

<400> SEQUENCE: 417
ctgaaatgag actttattct gaaat    25

<210> SEQ ID NO 418
<211> LENGTH: 63
<212> TYPE: DNA
<213> ORGANISM: Artificial Sequence
<220> FEATURE:
<223> OTHER INFORMATION: Synthetic

<400> SEQUENCE: 418
ttttgtacaa cagtggaatt ttctgtcatg gataatgtgc ttgagtccct ataatctata    60
gac    63

<210> SEQ ID NO 419
<211> LENGTH: 30
<212> TYPE: DNA
<213> ORGANISM: Artificial Sequence
<220> FEATURE:
<223> OTHER INFORMATION: Synthetic

<400> SEQUENCE: 419
tgtttttccg caattgaagg ttgtatgtaa                                      30

<210> SEQ ID NO 420
<211> LENGTH: 61
<212> TYPE: DNA
<213> ORGANISM: Artificial Sequence
<220> FEATURE:
<223> OTHER INFORMATION: Synthetic

<400> SEQUENCE: 420
ccttgcatat tacttgagct taaactgaca acctggatgt aaataggagc ctttctactg      60
g                                                                     61

<210> SEQ ID NO 421
<211> LENGTH: 27
<212> TYPE: DNA
<213> ORGANISM: Artificial Sequence
<220> FEATURE:
<223> OTHER INFORMATION: Synthetic

<400> SEQUENCE: 421
ttctcttctt taggcaatga ttaagtt                                         27

<210> SEQ ID NO 422
<211> LENGTH: 293
<212> TYPE: DNA
<213> ORGANISM: Artificial Sequence
<220> FEATURE:
<223> OTHER INFORMATION: Synthetic

<400> SEQUENCE: 422
ccactggcct gtaattgttt gatatatttg tttaaactct ttgtataatg tcagagactc      60
atgtttaata cataggtgat tgtacctca gagtattttt taaaggattc tttccaagcg     120
agatttaatt ataaggtagt acctaatttg ttcaatgtat aacattctca ggatttgtaa    180
cacttaaatg atcagacaga ataatatttt ctagttatta tgtgcaagat gagttgctat    240
ttttctgatg ctcattctga tacaactatt tttcgtgtca aatatctact gtg           293

<210> SEQ ID NO 423
<211> LENGTH: 139
<212> TYPE: DNA
<213> ORGANISM: Artificial Sequence
<220> FEATURE:
<223> OTHER INFORMATION: Synthetic

<400> SEQUENCE: 423
tacaagctta ttcacatttt gcttcctaat cttttttgttg tacagggatt caggtttctt    60
attcttacaa catgattgtt tatatgtgaa gcacatcttg ctgttgcctt attttttgatg   120 ctttttattca tgacaagaa                                                139

<210> SEQ ID NO 424
<211> LENGTH: 28
<212> TYPE: DNA
<213> ORGANISM: Artificial Sequence
<220> FEATURE:
<223> OTHER INFORMATION: Synthetic

<400> SEQUENCE: 424
acagaatcag gcatgctgtt aataaata                                       28

<210> SEQ ID NO 425

```
<211> LENGTH: 31
<212> TYPE: DNA
<213> ORGANISM: Artificial Sequence
<220> FEATURE:
<223> OTHER INFORMATION: Synthetic

<400> SEQUENCE: 425
tctgatttca ttgttcgctt ctgtaattct g                              31

<210> SEQ ID NO 426
<211> LENGTH: 46
<212> TYPE: DNA
<213> ORGANISM: Artificial Sequence
<220> FEATURE:
<223> OTHER INFORMATION: Synthetic

<400> SEQUENCE: 426
caagctgatg attgttgcat tttggagttg caacaacatt aaaaca             46

<210> SEQ ID NO 427
<211> LENGTH: 149
<212> TYPE: DNA
<213> ORGANISM: Artificial Sequence
<220> FEATURE:
<223> OTHER INFORMATION: Synthetic

<400> SEQUENCE: 427
ggccatgtgc tttaacgtta cggtaatact ttactttagg catccctcct gttgctagca   60 gcctttgac ctatctgcaa tgcagtgttc tcagtaggaa atgttcatct gttacatgga   120
aaaaatgttg atggtgcatt gtaaaatta                                    149

<210> SEQ ID NO 428
<211> LENGTH: 32
<212> TYPE: DNA
<213> ORGANISM: Artificial Sequence
<220> FEATURE:
<223> OTHER INFORMATION: Synthetic

<400> SEQUENCE: 428
tgctggttta agatgattca gattatcctt gt                             32

<210> SEQ ID NO 429
<211> LENGTH: 25
<212> TYPE: DNA
<213> ORGANISM: Artificial Sequence
<220> FEATURE:
<223> OTHER INFORMATION: Synthetic

<400> SEQUENCE: 429
tgaatgcgtg acaataagat attcc                                     25

<210> SEQ ID NO 430
<211> LENGTH: 26
<212> TYPE: DNA
<213> ORGANISM: Artificial Sequence
<220> FEATURE:
<223> OTHER INFORMATION: Synthetic

<400> SEQUENCE: 430
tggcccagaa agtgattcat ttgtaa                                    26

<210> SEQ ID NO 431
<211> LENGTH: 305
<212> TYPE: DNA
<213> ORGANISM: Artificial Sequence
```

```
<220> FEATURE:
<223> OTHER INFORMATION: Synthetic

<400> SEQUENCE: 431
gacaacccgg gatcgtttgc aagtaactga atccattgcg acattgtgaa ggcttaaatg     60
agtttagatg ggaaatagcg ttgttatcgc ctttgggttta aattatttga tgagttccac    120
ttgtatcatg gcctacccga ggagaagagg agtttgttaa ctgggcctat gtagtagcct    180
catttaccat cgtttgtatt actgaccaca tatgcttgtc actgggaaag aagcctgttt    240
cagctgcctg aacgcagttt ggatgtcttt gaggacagac attgcccgga aactcagtct    300
attta                                                                305

<210> SEQ ID NO 432
<211> LENGTH: 34
<212> TYPE: DNA
<213> ORGANISM: Artificial Sequence
<220> FEATURE:
<223> OTHER INFORMATION: Synthetic

<400> SEQUENCE: 432
gttaatattg tcatcgatac aaataaagtg aaat                                 34

<210> SEQ ID NO 433
<211> LENGTH: 35
<212> TYPE: DNA
<213> ORGANISM: Artificial Sequence
<220> FEATURE:
<223> OTHER INFORMATION: Synthetic

<400> SEQUENCE: 433
caataactgt ggtctataca gagtcaatat atttt                                35

<210> SEQ ID NO 434
<211> LENGTH: 25
<212> TYPE: DNA
<213> ORGANISM: Artificial Sequence
<220> FEATURE:
<223> OTHER INFORMATION: Synthetic

<400> SEQUENCE: 434
gtcgcctgcg aggccgctgg ccagg                                           25

<210> SEQ ID NO 435
<211> LENGTH: 25
<212> TYPE: DNA
<213> ORGANISM: Artificial Sequence
<220> FEATURE:
<223> OTHER INFORMATION: Synthetic

<400> SEQUENCE: 435
caggccttct gcaaatcagt gctgg                                           25

<210> SEQ ID NO 436
<211> LENGTH: 25
<212> TYPE: DNA
<213> ORGANISM: Artificial Sequence
<220> FEATURE:
<223> OTHER INFORMATION: Synthetic

<400> SEQUENCE: 436
taaggatgga attcaacttt accta                                           25

<210> SEQ ID NO 437
```

```
<211> LENGTH: 133
<212> TYPE: DNA
<213> ORGANISM: Artificial Sequence
<220> FEATURE:
<223> OTHER INFORMATION: Synthetic

<400> SEQUENCE: 437
tacacgtaaa ccacaaaaga gtagcattcc attttcttga agtgcacatg atattatgaa    60
caatacaaat gcattatttt tatcattaat agtttaatca ttaattatct cataagtcaa   120
tgcagagagt gaa                                                      133

<210> SEQ ID NO 438
<211> LENGTH: 77
<212> TYPE: DNA
<213> ORGANISM: Artificial Sequence
<220> FEATURE:
<223> OTHER INFORMATION: Synthetic

<400> SEQUENCE: 438
ctcacttatt taactggcaa ctatccattt aggttaggca aaggcacggt aacatgttgc    60
gcaggatgtt ttactga                                                   77

<210> SEQ ID NO 439
<211> LENGTH: 93
<212> TYPE: DNA
<213> ORGANISM: Artificial Sequence
<220> FEATURE:
<223> OTHER INFORMATION: Synthetic

<400> SEQUENCE: 439
caggggtatg gaacatgctg tcatatttca ttcataacac acatgtacta tagctctagg    60
caacagatgg acaatcgctt gtttgaacta caa                                 93

<210> SEQ ID NO 440
<211> LENGTH: 25
<212> TYPE: DNA
<213> ORGANISM: Artificial Sequence
<220> FEATURE:
<223> OTHER INFORMATION: Synthetic

<400> SEQUENCE: 440
ccacatggtc atcattagcc agctg                                          25

<210> SEQ ID NO 441
<211> LENGTH: 65
<212> TYPE: DNA
<213> ORGANISM: Artificial Sequence
<220> FEATURE:
<223> OTHER INFORMATION: Synthetic

<400> SEQUENCE: 441
cttttggatg tgataagctt tgtaattgtc ttttaatgag ctctcatctt ggagagatac    60
attct                                                                65

<210> SEQ ID NO 442
<211> LENGTH: 25
<212> TYPE: DNA
<213> ORGANISM: Artificial Sequence
<220> FEATURE:
<223> OTHER INFORMATION: Synthetic

<400> SEQUENCE: 442
gtgatcgcct actacgagac aaaaa                                          25
```

<210> SEQ ID NO 443
<211> LENGTH: 27
<212> TYPE: DNA
<213> ORGANISM: Artificial Sequence
<220> FEATURE:
<223> OTHER INFORMATION: Synthetic

<400> SEQUENCE: 443
atttatcttc cactgaattg gcagaaa                                        27

<210> SEQ ID NO 444
<211> LENGTH: 33
<212> TYPE: DNA
<213> ORGANISM: Artificial Sequence
<220> FEATURE:
<223> OTHER INFORMATION: Synthetic

<400> SEQUENCE: 444
gtcaggtaaa catgtatgtt cagtccttca cta                                 33

<210> SEQ ID NO 445
<211> LENGTH: 25
<212> TYPE: DNA
<213> ORGANISM: Artificial Sequence
<220> FEATURE:
<223> OTHER INFORMATION: Synthetic

<400> SEQUENCE: 445
ggaactatga acttgcctat ctaac                                          25

<210> SEQ ID NO 446
<211> LENGTH: 47
<212> TYPE: DNA
<213> ORGANISM: Artificial Sequence
<220> FEATURE:
<223> OTHER INFORMATION: Synthetic

<400> SEQUENCE: 446
acatggaatg acttagttac agaccagaca tattgttact gggaatg                  47

<210> SEQ ID NO 447
<211> LENGTH: 167
<212> TYPE: DNA
<213> ORGANISM: Artificial Sequence
<220> FEATURE:
<223> OTHER INFORMATION: Synthetic

<400> SEQUENCE: 447
agaggaatgt ttgctacctt tagcggtgaa aaaagaaaga gagtcaagaa ttttgttgga    60
ttgtgtttgt gtgtgcatat atttgatatc atcattatat ttgtaatctt tggacttgta   120
atcatagcct gtttattcta ctgtgccatt aaatatactt taccttta                167

<210> SEQ ID NO 448
<211> LENGTH: 26
<212> TYPE: DNA
<213> ORGANISM: Artificial Sequence
<220> FEATURE:
<223> OTHER INFORMATION: Synthetic

<400> SEQUENCE: 448
aagtaatgag cactttctac tcaagc                                         26

<210> SEQ ID NO 449

```
<211> LENGTH: 26
<212> TYPE: DNA
<213> ORGANISM: Artificial Sequence
<220> FEATURE:
<223> OTHER INFORMATION: Synthetic

<400> SEQUENCE: 449
catccctagc acagatatct acaaaa                                              26

<210> SEQ ID NO 450
<211> LENGTH: 33
<212> TYPE: DNA
<213> ORGANISM: Artificial Sequence
<220> FEATURE:
<223> OTHER INFORMATION: Synthetic

<400> SEQUENCE: 450
gtccatcagg attcaaactg taatggcatt tgg                                      33

<210> SEQ ID NO 451
<211> LENGTH: 44
<212> TYPE: DNA
<213> ORGANISM: Artificial Sequence
<220> FEATURE:
<223> OTHER INFORMATION: Synthetic

<400> SEQUENCE: 451
agtttcttgt cttctacaac aatgatcgga gtaaggcctt taaa                          44

<210> SEQ ID NO 452
<211> LENGTH: 32
<212> TYPE: DNA
<213> ORGANISM: Artificial Sequence
<220> FEATURE:
<223> OTHER INFORMATION: Synthetic

<400> SEQUENCE: 452
acacaaacgt atatcgtatg ttctccaaag ag                                       32

<210> SEQ ID NO 453
<211> LENGTH: 25
<212> TYPE: DNA
<213> ORGANISM: Artificial Sequence
<220> FEATURE:
<223> OTHER INFORMATION: Synthetic

<400> SEQUENCE: 453
ttgacctcaa atgcagtgag ttctg                                               25

<210> SEQ ID NO 454
<211> LENGTH: 25
<212> TYPE: DNA
<213> ORGANISM: Artificial Sequence
<220> FEATURE:
<223> OTHER INFORMATION: Synthetic

<400> SEQUENCE: 454
gggcgtgata gtgcacgcct acaaa                                               25

<210> SEQ ID NO 455
<211> LENGTH: 100
<212> TYPE: DNA
<213> ORGANISM: Artificial Sequence
<220> FEATURE:
<223> OTHER INFORMATION: Synthetic

<400> SEQUENCE: 455
```

```
gtgagggaat atgtccaatt aattagtgtg tatgaaaaga aactgttaaa cctaactgtc    60
cgaattgaca tcatggagaa ggataccatt tcttacactg                          100
```

<210> SEQ ID NO 456
<211> LENGTH: 173
<212> TYPE: DNA
<213> ORGANISM: Artificial Sequence
<220> FEATURE:
<223> OTHER INFORMATION: Synthetic

<400> SEQUENCE: 456

```
tctaggacga gctatagaaa agctattgag agtatctagt taatcagtgc agtagttgga    60
aaccttgctg gtgtatgtga tgtgcttctg tgcttttgaa tgactttatc atctagtctt   120
tgtctatttt tcctttgatg ttcaagtcct agtctatagg attggcagtt taa          173
```

<210> SEQ ID NO 457
<211> LENGTH: 44
<212> TYPE: DNA
<213> ORGANISM: Artificial Sequence
<220> FEATURE:
<223> OTHER INFORMATION: Synthetic

<400> SEQUENCE: 457

```
ttgctttgat cgtttaaaag catcatatga tacactgtgt gttt                     44
```

<210> SEQ ID NO 458
<211> LENGTH: 46
<212> TYPE: DNA
<213> ORGANISM: Artificial Sequence
<220> FEATURE:
<223> OTHER INFORMATION: Synthetic

<400> SEQUENCE: 458

```
tattcaatct ctggcacaat gcagcctctg tagaaaagat attagg                   46
```

<210> SEQ ID NO 459
<211> LENGTH: 35
<212> TYPE: DNA
<213> ORGANISM: Artificial Sequence
<220> FEATURE:
<223> OTHER INFORMATION: Synthetic

<400> SEQUENCE: 459

```
atgcagcaat gcgtgctcga ccattcaagg ttgat                               35
```

<210> SEQ ID NO 460
<211> LENGTH: 259
<212> TYPE: DNA
<213> ORGANISM: Artificial Sequence
<220> FEATURE:
<223> OTHER INFORMATION: Synthetic

<400> SEQUENCE: 460

```
ttcaactgca gctcgggcga cttcatcttc tgctgcggga cttgtggctt ccggttctgc    60
tgcacgttta agaagcggcg actgaaccaa agcacctgca ccaactacga cacgccgctc   120
tggctcaaca ccggcaagcc ccccgcccgc aaggacgacc ccttgcacga ccccaccaag   180
gacaagacca acctgatcgt ctacatcatc tgcggggtgg tggccgtcat ggtgctcgtg   240
ggcatcttca ccaagctgg                                                259
```

<210> SEQ ID NO 461

```
<211> LENGTH: 80
<212> TYPE: DNA
<213> ORGANISM: Artificial Sequence
<220> FEATURE:
<223> OTHER INFORMATION: Synthetic

<400> SEQUENCE: 461
ggcctactgt gaagctcacg tgcgggaaga tcctctcatc attccagtgc ctgcatcaga    60
aaaccccttt cgcgagaaga                                                80

<210> SEQ ID NO 462
<211> LENGTH: 538
<212> TYPE: DNA
<213> ORGANISM: Artificial Sequence
<220> FEATURE:
<223> OTHER INFORMATION: Synthetic

<400> SEQUENCE: 462
tcactgaatt ttaaccggac ctggcaagac tacaagagag gtttcggcag cctgaatgac    60 gaggggaag gagaattctg gctaggcaat gactacctcc acttactaac ccaaaggggc    120
tctgttctta gggttgaatt agaggactgg gctgggaatg aagcttatgc agaatatcac    180
ttccgggtag gctctgaggc tgaaggctat gccctccaag tctcctccta tgaaggcact    240
gcgggtgatg ctctgattga gggttccgta gaggaagggg cagagtacac ctctcacaac    300
aacatgcagt tcagcacctt tgacagggat gcagaccagt gggaagagaa ctgtgcagaa    360
gtctatgggg gaggctggtg gtataataac tgccaagcag ccaatctcaa tggaatctac    420
taccctgggg gctcctatga cccaaggaat aacagtcctt atgagattga aatggagtg    480 gtctgggttt cctttagagg ggcagattat cccctcaggg ctgttcgcat gaaaatta     538

<210> SEQ ID NO 463
<211> LENGTH: 144
<212> TYPE: DNA
<213> ORGANISM: Artificial Sequence
<220> FEATURE:
<223> OTHER INFORMATION: Synthetic

<400> SEQUENCE: 463
ccagttccag gcctggggag aatgtgacct gaacacagcc ctgaagacca gaactggaag    60
tctgaagcga gccctgcaca atgccgaatg ccagaagact gtcaccatct ccaagccctg    120
tggcaaactg accaagccca aacc                                           144

<210> SEQ ID NO 464
<211> LENGTH: 148
<212> TYPE: DNA
<213> ORGANISM: Artificial Sequence
<220> FEATURE:
<223> OTHER INFORMATION: Synthetic

<400> SEQUENCE: 464
atgagtgcca atctgctat cagcaaggaa attttgcac ctcttgatga aggatgctg      60 ggagctgtcc aagtcaagag gaggacaaag aaaaagattc ctttcttggc aactggaggt    120
caaggcgaat atttaactta tatctgcc                                       148

<210> SEQ ID NO 465
<211> LENGTH: 251
<212> TYPE: DNA
<213> ORGANISM: Artificial Sequence
<220> FEATURE:
<223> OTHER INFORMATION: Synthetic
```

<400> SEQUENCE: 465
ggttctgctc ctcgacggcc tgaactgcag gcagtgtggc gtgcagcatg tgaaaaggtg    60
gttcctgctg ctggcgctgc tcaactccgt cgtgaacccc atcatctact cctacaagga   120
cgaggacatg tatggcacca tgaagaagat gatctgctgc ttctctcagg agaacccaga   180
gaggcgtccc tctcgcatcc cctccacagt cctcagcagg agtgacacag gcagccagta   240
catagaggat a                                                        251

<210> SEQ ID NO 466
<211> LENGTH: 40
<212> TYPE: DNA
<213> ORGANISM: Artificial Sequence
<220> FEATURE:
<223> OTHER INFORMATION: Synthetic

<400> SEQUENCE: 466
tggtcatccg cgtgttcatc gcctcttcct cgggcttcgt                          40

<210> SEQ ID NO 467
<211> LENGTH: 28
<212> TYPE: DNA
<213> ORGANISM: Artificial Sequence
<220> FEATURE:
<223> OTHER INFORMATION: Synthetic

<400> SEQUENCE: 467
aggaagaaca gagagcccgc aaagacct                                       28

<210> SEQ ID NO 468
<211> LENGTH: 145
<212> TYPE: DNA
<213> ORGANISM: Artificial Sequence
<220> FEATURE:
<223> OTHER INFORMATION: Synthetic

<400> SEQUENCE: 468
tgccacccag atgaacaacg cagtgccac ctctcctctg ctccagcaga tgggccatcc     60
acattcgtac ccgaacctgg gccagatctc caaccccctat gaacagcagc caccaggaaa  120
agagctcaac aagtacgcct cctta                                         145

<210> SEQ ID NO 469
<211> LENGTH: 111
<212> TYPE: DNA
<213> ORGANISM: Artificial Sequence
<220> FEATURE:
<223> OTHER INFORMATION: Synthetic

<400> SEQUENCE: 469
actggggtga ccttaacctg gtgctgccct gtctggagta ccacaacaac acatggacat    60
ggctagactt tgccatggct gtcaaaaggg acagccgcaa agccctggtt g            111

<210> SEQ ID NO 470
<211> LENGTH: 51
<212> TYPE: DNA
<213> ORGANISM: Artificial Sequence
<220> FEATURE:
<223> OTHER INFORMATION: Synthetic

<400> SEQUENCE: 470
tggcacagtc agatgtcgag aaactttgct atgcctccga agtcaatgcc c             51

<210> SEQ ID NO 471
<211> LENGTH: 91
<212> TYPE: DNA
<213> ORGANISM: Artificial Sequence
<220> FEATURE:
<223> OTHER INFORMATION: Synthetic

<400> SEQUENCE: 471
cctcacaata tggaaagacg ggacaaccta tggaactatc tgtgacttcc atgtaccaag    60
acaaggacgc tatagctagg gtagtgagac c                                  91

<210> SEQ ID NO 472
<211> LENGTH: 215
<212> TYPE: DNA
<213> ORGANISM: Artificial Sequence
<220> FEATURE:
<223> OTHER INFORMATION: Synthetic

<400> SEQUENCE: 472
cagtggatga atgtcggaac cttatgaaat gtgactcatc tgacctttca gagattggaa    60
ctgccccaca gtgctgttct gctaactctt cttctctgcc ctctaaagtc cctgcttccc   120
tttctttcct ttttagtacc ggggtgtaca taatcgatcc atcataatca tcagttcatg   180
acatgttctc atcattgatc catagcacgg ccttg                              215

<210> SEQ ID NO 473
<211> LENGTH: 38
<212> TYPE: DNA
<213> ORGANISM: Artificial Sequence
<220> FEATURE:
<223> OTHER INFORMATION: Synthetic

<400> SEQUENCE: 473
cctgcaaagt aaggtgtatg gggaagcaag tagatagt                            38

<210> SEQ ID NO 474
<211> LENGTH: 29
<212> TYPE: DNA
<213> ORGANISM: Artificial Sequence
<220> FEATURE:
<223> OTHER INFORMATION: Synthetic

<400> SEQUENCE: 474
gctgatctca ctgtgatctt cctggtgtt                                      29

<210> SEQ ID NO 475
<211> LENGTH: 83
<212> TYPE: DNA
<213> ORGANISM: Artificial Sequence
<220> FEATURE:
<223> OTHER INFORMATION: Synthetic

<400> SEQUENCE: 475
gactcgagaa aaaacagagc tcagacttga gacacgggct tccctctata ggggtcaaaa    60
accagggcgg agagagataa cca                                            83

<210> SEQ ID NO 476
<211> LENGTH: 39
<212> TYPE: DNA
<213> ORGANISM: Artificial Sequence
<220> FEATURE:
<223> OTHER INFORMATION: Synthetic

<400> SEQUENCE: 476
ttgtacctgc agttttcgca gagtagatca aggactgca 39

<210> SEQ ID NO 477
<211> LENGTH: 351
<212> TYPE: DNA
<213> ORGANISM: Artificial Sequence
<220> FEATURE:
<223> OTHER INFORMATION: Synthetic

<400> SEQUENCE: 477
ttgtctctca gtcggctaag tgctctccca ccaggtcacc taaaacgacc agcagagaca      60
cccaagaggc tgagctgtga ggatcacctg aacctgagcc tgggaagtgg aggttgcagt     120
gagctgtgat cacaccactg tgctccagcc tgggcaacgg agtgaaaccc tgtctcaaga     180
aaaaaaaaaa aaaaaaagga ccagcagtga catttgttaa atatcgaggg tggttgaaca     240
tccactattt ataaggaaat gttatttccc acaaatctca ttcctcagaa atcagtgaaa     300
gacagaccct gtctcggatt ctataaagca gtgtgactga tgtggccaaa c              351

<210> SEQ ID NO 478
<211> LENGTH: 653
<212> TYPE: DNA
<213> ORGANISM: Artificial Sequence
<220> FEATURE:
<223> OTHER INFORMATION: Synthetic

<400> SEQUENCE: 478
cagcgtcctg ggaatgtcat ttctgctcca ctccttggac tcgctgagct gtctccgcct      60
ccacctatct tcctacagac ctcccttcta gttttctgtc aattctttga gccagcaaac     120
tccatccagt acattctttc ttctttcatg aaagagcttg agttggatgt aaatatatat     180
gacctaacaa ttccacccct aggtgtatac cctacagaaa tgtgtacatg tgttcatcca     240
gagacatgct ctaaatcttc acaaaaacac tctccataat aaccccgaac aggaaagcac     300
cccaatgccc atgttggctg gataagcaca ttagggtata ttcacacgat ggaatcccag     360
actgcaatgg gaatgagctg caactccacc cccaacttgg agtgtattca ccaaccctag     420
tgttgaacga gataaggcaa aaatgcacca taggattcca tttatataaa gtttaaaacc     480
cagcaaaatt catccatgcg gttgcaagta gagatcagtc ctaagaagac agtaaccaga     540
agcgggcatg aggtggtgct tctggggtgt tctgtttctt gatctggttg ccggttacct     600
gggtgctttc cgtttgtgaa cattcttgga gctgtacact tttgatctgg gca            653

<210> SEQ ID NO 479
<211> LENGTH: 37
<212> TYPE: DNA
<213> ORGANISM: Artificial Sequence
<220> FEATURE:
<223> OTHER INFORMATION: Synthetic

<400> SEQUENCE: 479
tctgaattca cctctcatct gacgactgac agctgct                               37

<210> SEQ ID NO 480
<211> LENGTH: 237
<212> TYPE: DNA
<213> ORGANISM: Artificial Sequence
<220> FEATURE:
<223> OTHER INFORMATION: Synthetic

<400> SEQUENCE: 480

```
gcaagccgca gaacggagcg atttcctccg agaaagttga ggatggagcc ttttttttccg    60 caccgtcccc gcgatggcat gggccccgag aatgctgccc cgaggctccc agtgtggggg    120
agctcggggt cgctgcgcct ctagcttgag cgcagaaatc cgcgaatcac tccgatcttc    180
gcgaactctg gcatcttcta ggaaaatcat tactgccaaa actgaggcga gcttttc      237
```

<210> SEQ ID NO 481
<211> LENGTH: 31
<212> TYPE: DNA
<213> ORGANISM: Artificial Sequence
<220> FEATURE:
<223> OTHER INFORMATION: Synthetic

<400> SEQUENCE: 481

```
acctgcactg gctcctgcaa atgcaaagag t                                   31
```

<210> SEQ ID NO 482
<211> LENGTH: 73
<212> TYPE: DNA
<213> ORGANISM: Artificial Sequence
<220> FEATURE:
<223> OTHER INFORMATION: Synthetic

<400> SEQUENCE: 482

```
ctgctgcccc atgagctgtg ccaagtgtgc ccagggctgc atctgcaaag ggcatcaga     60 gaagtgcagc tgc                                                       73
```

<210> SEQ ID NO 483
<211> LENGTH: 28
<212> TYPE: DNA
<213> ORGANISM: Artificial Sequence
<220> FEATURE:
<223> OTHER INFORMATION: Synthetic

<400> SEQUENCE: 483

```
tgtgtctgca aagggacgtt ggagaact                                       28
```

<210> SEQ ID NO 484
<211> LENGTH: 63
<212> TYPE: DNA
<213> ORGANISM: Artificial Sequence
<220> FEATURE:
<223> OTHER INFORMATION: Synthetic

<400> SEQUENCE: 484

```
catgggctga gccaagtgtg cccacggctg catctgcaaa gggacgtcgg agaagtgcag    60
ctg                                                                  63
```

<210> SEQ ID NO 485
<211> LENGTH: 39
<212> TYPE: DNA
<213> ORGANISM: Artificial Sequence
<220> FEATURE:
<223> OTHER INFORMATION: Synthetic

<400> SEQUENCE: 485

```
gaaaagcgtg caagtatcag tgatgctgcc ctgttagac                           39
```

<210> SEQ ID NO 486
<211> LENGTH: 57
<212> TYPE: DNA
<213> ORGANISM: Artificial Sequence
<220> FEATURE:
<223> OTHER INFORMATION: Synthetic

<400> SEQUENCE: 486
tgcaatttca tcagcaccag aaagtttggg aagtttttca gatgagtaaa ggaccag    57

<210> SEQ ID NO 487
<211> LENGTH: 90
<212> TYPE: DNA
<213> ORGANISM: Artificial Sequence
<220> FEATURE:
<223> OTHER INFORMATION: Synthetic

<400> SEQUENCE: 487
ccagtacaaa cctacctacg tggtgtacta ctcccagact ccgtacgcct tcacgtcctc    60
ctccatgctg aggcgcaata caccgcttct    90

<210> SEQ ID NO 488
<211> LENGTH: 36
<212> TYPE: DNA
<213> ORGANISM: Artificial Sequence
<220> FEATURE:
<223> OTHER INFORMATION: Synthetic

<400> SEQUENCE: 488
tgctagcaaa caccatcaga ttgtgaaaat ggacct    36

<210> SEQ ID NO 489
<211> LENGTH: 32
<212> TYPE: DNA
<213> ORGANISM: Artificial Sequence
<220> FEATURE:
<223> OTHER INFORMATION: Synthetic

<400> SEQUENCE: 489
gtatctggac tctcttaagg ctattgtttt ta    32

<210> SEQ ID NO 490
<211> LENGTH: 30
<212> TYPE: DNA
<213> ORGANISM: Artificial Sequence
<220> FEATURE:
<223> OTHER INFORMATION: Synthetic

<400> SEQUENCE: 490
acctttgaaa ctcacaactc tacgacacct    30

<210> SEQ ID NO 491
<211> LENGTH: 69
<212> TYPE: DNA
<213> ORGANISM: Artificial Sequence
<220> FEATURE:
<223> OTHER INFORMATION: Synthetic

<400> SEQUENCE: 491
ccctccgatg cctaataaag ttctctagcc cacatcttct ggaagcattg aaatccttag    60
caccagcgg    69

<210> SEQ ID NO 492
<211> LENGTH: 33
<212> TYPE: DNA
<213> ORGANISM: Artificial Sequence
<220> FEATURE:
<223> OTHER INFORMATION: Synthetic

<400> SEQUENCE: 492

```
actgctcact tgcataccca acaagagaat gaa                                    33
```

<210> SEQ ID NO 493
<211> LENGTH: 177
<212> TYPE: DNA
<213> ORGANISM: Artificial Sequence
<220> FEATURE:
<223> OTHER INFORMATION: Synthetic

<400> SEQUENCE: 493

```
ggaaggacac cactggtacc agctgcgcca ggctctgaac cagcggttgc tgaagccagc       60
ggaagcagcg ctctatacgg atgctttcaa tgaggtgatt gatgacttta tgactcgact      120
ggaccagctg cgggcagaga gtgcttcggg gaaccaggtg tcggacatgg ctcaact        177
```

<210> SEQ ID NO 494
<211> LENGTH: 168
<212> TYPE: DNA
<213> ORGANISM: Artificial Sequence
<220> FEATURE:
<223> OTHER INFORMATION: Synthetic

<400> SEQUENCE: 494

```
ttgctacatc ctgttcgaga aacgcattgg ctgcctgcag cgatccatcc ccgaggacac       60
cgtgaccttc gtcagatcca tcgggttaat gttccagaac tcactctatg ccaccttcct     120
ccccaagtgg actcgccccg tgctgccttt ctggaagcga tacctgga                  168
```

<210> SEQ ID NO 495
<211> LENGTH: 80
<212> TYPE: DNA
<213> ORGANISM: Artificial Sequence
<220> FEATURE:
<223> OTHER INFORMATION: Synthetic

<400> SEQUENCE: 495

```
agctgattga tgagaagctc gaagatatgg aggcccaact gcaggcagca gggccagatg       60
gcatccaggt gtctggctac                                                  80
```

<210> SEQ ID NO 496
<211> LENGTH: 160
<212> TYPE: DNA
<213> ORGANISM: Artificial Sequence
<220> FEATURE:
<223> OTHER INFORMATION: Synthetic

<400> SEQUENCE: 496

```
acacgctgac atgggccctg taccacctct caaaggaccc tgagatccag gaggccttgc       60
acgaggaagt ggtgggtgtg gtgccagccg ggcaagtgcc ccagcacaag gactttgccc     120
acatgccgtt gctcaaagct gtgcttaagg agactctgcg                           160
```

<210> SEQ ID NO 497
<211> LENGTH: 52
<212> TYPE: DNA
<213> ORGANISM: Artificial Sequence
<220> FEATURE:
<223> OTHER INFORMATION: Synthetic

<400> SEQUENCE: 497

```
acaaactccc ggatcataga aaaggaaatt gaagttgatg gcttcctctt cc               52
```

<210> SEQ ID NO 498
<211> LENGTH: 37

<212> TYPE: DNA
<213> ORGANISM: Artificial Sequence
<220> FEATURE:
<223> OTHER INFORMATION: Synthetic

<400> SEQUENCE: 498
gagtgtggcc cgcattgtcc tggttcccaa taagaaa                              37

<210> SEQ ID NO 499
<211> LENGTH: 1704
<212> TYPE: DNA
<213> ORGANISM: Artificial Sequence
<220> FEATURE:
<223> OTHER INFORMATION: Synthetic

<400> SEQUENCE: 499

```
ggtgctgggc ctactaatga cttcattaac cgagtcttcc atacagaata gtgagtgtcc      60
acaactttgc gtatgtgaaa ttcgtccctg gtttacccca cagtcaactt acagagaagc     120
caccactgtt gattgcaatg acctccgctt aacaaggatt cccagtaacc tctctagtga     180
cacacaagtg cttctcttac agagcaataa catcgcaaag actgtggatg agctgcagca     240
gcttttcaac ttgactgaac tagatttctc ccaaaacaac tttactaaca ttaaggaggt     300
cgggctggca aacctaaccc agctcacaac gctgcatttg gaggaaaatc agattaccga     360
gatgactgat tactgtctac aagacctcag caaccttcaa gaactctaca tcaaccacaa     420
ccaaattagc actatttctg ctcatgcttt tgcaggctta aaaaatctat taaggctcca     480
cctgaactcc aacaaattga agttattga tagtcgctgg tttgattcta cacccaacct     540
ggaaattctc atgatcggag aaaaccctgt gattggaatt ctggatatga acttcaaacc     600
cctcgcaaat ttgagaagct agttttggc aggaatgtat ctcactgata ttcctggaaa     660
tgctttggtg ggtctggata gccttgagag cctgtctttt tatgataaca aactggttaa     720
agtccctcaa cttgccctgc aaaaagttcc aaatttgaaa ttcttagacc tcaacaaaaa     780
ccccattcac aaaatccaag aaggggactt caaaaatatg cttcggttaa agaactggg     840
aatcaacaat atgggcgagc tcgtttctgt cgaccgctat gccctggata acttgcctga     900
actcacaaag ctggaagcca ccaataaccc taaactctct tacatccacc gcttggcttt     960
ccgaagtgtc cctgctctgg aaagcttgat gctgaacaac aatgccttga atgccattta    1020
ccaaaagaca gtcgaatccc tccccaatct gcgtgagatc agtatccata gcaatccccc    1080
caggtgtgac tgtgtgatcc actggattaa ctccaacaaa accaacatcc gcttcatgga    1140
gcccctgtcc atgttctgtg ccatgccgcc cgaatataaa gggcaccagg tgaaggaagt    1200
tttaatccag gattcgagtg aacagtgcct cccaatgata tctcacgaca gcttcccaaa    1260
tcgtttaaac gtggatatcg gcacgacggt tttcctagac tgtcgagcca tggctgagcc    1320
agaacctgaa atttactggg tcactcccat tggaaataag ataactgtgg aaacccttc    1380
agataaatac aagctaagta gcgaaggtac cttggaaata tctaacatac aaattgaaga    1440
ctcaggaaga tacacatgtg ttgcccagaa tgtccaaggg gcagacactc gggtggcaac    1500
aattaaggtt aatgggaccc ttctggatgg tacccaggtg ctaaaaatat acgtcaagca    1560
gacagaatcc cattccatct tagtgtcctg gaaagttaat tccaatgtca tgacgtcaaa    1620
cttaaaatgg tcgtctgcca ccatgaagat tgataaccct cacataacat atactgccag    1680
ggtcccagtc gatgtccatg aata                                            1704
```

<210> SEQ ID NO 500

```
<211> LENGTH: 88
<212> TYPE: DNA
<213> ORGANISM: Artificial Sequence
<220> FEATURE:
<223> OTHER INFORMATION: Synthetic

<400> SEQUENCE: 500
aggaccaact tctcagccga atagctccaa gcaaactgtc ctgtcttggc aagctgcaat      60
cgatgctgct agacaggcca aggctgcc                                         88

<210> SEQ ID NO 501
<211> LENGTH: 38
<212> TYPE: DNA
<213> ORGANISM: Artificial Sequence
<220> FEATURE:
<223> OTHER INFORMATION: Synthetic

<400> SEQUENCE: 501
tctcccaaag aaaacgtcag caatacgcca agagcaaa                              38

<210> SEQ ID NO 502
<211> LENGTH: 78
<212> TYPE: DNA
<213> ORGANISM: Artificial Sequence
<220> FEATURE:
<223> OTHER INFORMATION: Synthetic

<400> SEQUENCE: 502
aacagccgac ctgcccgcgc cctttttctgt ttatcactca ataacccat ccgaagagcc      60 tgcattagta tagtggaa                                                    78

<210> SEQ ID NO 503
<211> LENGTH: 25
<212> TYPE: DNA
<213> ORGANISM: Artificial Sequence
<220> FEATURE:
<223> OTHER INFORMATION: Synthetic

<400> SEQUENCE: 503
ggccttagct atttacatcc cattc                                            25

<210> SEQ ID NO 504
<211> LENGTH: 96
<212> TYPE: DNA
<213> ORGANISM: Artificial Sequence
<220> FEATURE:
<223> OTHER INFORMATION: Synthetic

<400> SEQUENCE: 504
gcgggaacca ctcaagcggc aaatctggag gctttgatgt caaagccctc cgtgcctttc      60
gagtgttgcg accacttcga ctagtgtcag gagtgc                                96

<210> SEQ ID NO 505
<211> LENGTH: 129
<212> TYPE: DNA
<213> ORGANISM: Artificial Sequence
<220> FEATURE:
<223> OTHER INFORMATION: Synthetic

<400> SEQUENCE: 505
tcagggaatg gacgccagtg tactgccaat ggcacggaat gtaggagtgg ctgggttggc      60
ccgaacggag gcatcaccaa ctttgataac tttgcctttg ccatgcttac tgtgtttcag     120
tgcatcacc                                                             129
```

<210> SEQ ID NO 506
<211> LENGTH: 99
<212> TYPE: DNA
<213> ORGANISM: Artificial Sequence
<220> FEATURE:
<223> OTHER INFORMATION: Synthetic

<400> SEQUENCE: 506
tgatgctatg ggatttgaat tgccctgggt gtattttgtc agtctcgtca tctttgggtc    60 attttttcgta ctaaatcttg tacttggtgt attgagcgg                           99

<210> SEQ ID NO 507
<211> LENGTH: 51
<212> TYPE: DNA
<213> ORGANISM: Artificial Sequence
<220> FEATURE:
<223> OTHER INFORMATION: Synthetic

<400> SEQUENCE: 507
gtgtattttg ttagtctgat catccttggc tcatttttcg tccttaacct g              51

<210> SEQ ID NO 508
<211> LENGTH: 77
<212> TYPE: DNA
<213> ORGANISM: Artificial Sequence
<220> FEATURE:
<223> OTHER INFORMATION: Synthetic

<400> SEQUENCE: 508
acagtggccg acttgcttaa agaggataag aagaaaaaga agttttgctg ctttcggcaa    60
cgcagggcta aagatca                                                   77

<210> SEQ ID NO 509
<211> LENGTH: 94
<212> TYPE: DNA
<213> ORGANISM: Artificial Sequence
<220> FEATURE:
<223> OTHER INFORMATION: Synthetic

<400> SEQUENCE: 509
tggcgtcgct ggaaccgatt caatcgcaga agatgtaggg ccgccgtgaa gtctgtcacg    60
ttttactggc tggttatcgt cctggtgttt ctga                                94

<210> SEQ ID NO 510
<211> LENGTH: 193
<212> TYPE: DNA
<213> ORGANISM: Artificial Sequence
<220> FEATURE:
<223> OTHER INFORMATION: Synthetic

<400> SEQUENCE: 510
ttggctctgt tcacctgcga gatgctggta aaaatgtaca gcttgggcct ccaagcatat    60
ttcgtctctc tttttcaaccg gtttgattgc ttcgtggtgt gtggtggaat cactgagacg   120
atcttggtgg aactggaaat catgtctccc ctggggatct ctgtgtttcg gtgtgtgcgc    180
ctcttaagaa tct                                                       193

<210> SEQ ID NO 511
<211> LENGTH: 147
<212> TYPE: DNA
<213> ORGANISM: Artificial Sequence
<220> FEATURE:

<223> OTHER INFORMATION: Synthetic

<400> SEQUENCE: 511

```
gtggcatcct tattaaactc catgaagtcc atcgcttcgc tgttgcttct gcttttctc        60
ttcattatca tcttttcctt gcttgggatg cagctgtttg cggcaagtt taattttgat      120
gaaacgcaaa ccaagcggag caccttt                                          147
```

<210> SEQ ID NO 512
<211> LENGTH: 71
<212> TYPE: DNA
<213> ORGANISM: Artificial Sequence
<220> FEATURE:
<223> OTHER INFORMATION: Synthetic

<400> SEQUENCE: 512

```
gcgaagactg gaatgctgtg atgtacgatg gcatcatggc ttacgggggc ccatcctctt       60
caggaatgat c                                                            71
```

<210> SEQ ID NO 513
<211> LENGTH: 35
<212> TYPE: DNA
<213> ORGANISM: Artificial Sequence
<220> FEATURE:
<223> OTHER INFORMATION: Synthetic

<400> SEQUENCE: 513

```
atattctact gaatgtcttc ttggccatcg ctgta                                  35
```

<210> SEQ ID NO 514
<211> LENGTH: 25
<212> TYPE: DNA
<213> ORGANISM: Artificial Sequence
<220> FEATURE:
<223> OTHER INFORMATION: Synthetic

<400> SEQUENCE: 514

```
ggctgatgct gaaagtctga acact                                             25
```

<210> SEQ ID NO 515
<211> LENGTH: 29
<212> TYPE: DNA
<213> ORGANISM: Artificial Sequence
<220> FEATURE:
<223> OTHER INFORMATION: Synthetic

<400> SEQUENCE: 515

```
cagaagtcaa ccagatagcc aacagtgac                                         29
```

<210> SEQ ID NO 516
<211> LENGTH: 85
<212> TYPE: DNA
<213> ORGANISM: Artificial Sequence
<220> FEATURE:
<223> OTHER INFORMATION: Synthetic

<400> SEQUENCE: 516

```
cccgtcctcg aaggatctcg gagttgaaca tgaaggaaaa aattgccccc atccctgaag       60
ggagcgcttt cttcattctt agcaa                                             85
```

<210> SEQ ID NO 517
<211> LENGTH: 129
<212> TYPE: DNA
<213> ORGANISM: Artificial Sequence

```
<220> FEATURE:
<223> OTHER INFORMATION: Synthetic

<400> SEQUENCE: 517
atccgcgtag gctgccacaa gctcatcaac caccacatct tcaccaacct catccttgtc    60
ttcatcatgc tgagcagcgc tgccctggcc gcagaggacc ccatccgcag ccactccttc   120
cggaacacg                                                            129

<210> SEQ ID NO 518
<211> LENGTH: 55
<212> TYPE: DNA
<213> ORGANISM: Artificial Sequence
<220> FEATURE:
<223> OTHER INFORMATION: Synthetic

<400> SEQUENCE: 518
gggttacttt gactatgcct tcacagccat ctttactgtt gagatcctgt tgaag          55

<210> SEQ ID NO 519
<211> LENGTH: 33
<212> TYPE: DNA
<213> ORGANISM: Artificial Sequence
<220> FEATURE:
<223> OTHER INFORMATION: Synthetic

<400> SEQUENCE: 519
ttggagcttt cctccacaaa ggggccttct gca                                  33

<210> SEQ ID NO 520
<211> LENGTH: 45
<212> TYPE: DNA
<213> ORGANISM: Artificial Sequence
<220> FEATURE:
<223> OTHER INFORMATION: Synthetic

<400> SEQUENCE: 520
agattctgag ggtcttaagg gtcctgcgtc ccctcagggc catca                     45

<210> SEQ ID NO 521
<211> LENGTH: 69
<212> TYPE: DNA
<213> ORGANISM: Artificial Sequence
<220> FEATURE:
<223> OTHER INFORMATION: Synthetic

<400> SEQUENCE: 521
cacgtggtcc agtgcgtctt cgtggccatc cggaccatcg gcaacatcat gatcgtcacc    60
accctcctg                                                             69

<210> SEQ ID NO 522
<211> LENGTH: 34
<212> TYPE: DNA
<213> ORGANISM: Artificial Sequence
<220> FEATURE:
<223> OTHER INFORMATION: Synthetic

<400> SEQUENCE: 522
gggaagttct atcgctgtac ggatgaagcc aaaa                                 34

<210> SEQ ID NO 523
<211> LENGTH: 94
<212> TYPE: DNA
<213> ORGANISM: Artificial Sequence
<220> FEATURE:
```

<223> OTHER INFORMATION: Synthetic

<400> SEQUENCE: 523
ttgacagtcc tgtggtccgt gaacggatct ggcaaaacag tgatttcaac ttcgacaacg    60
tcctctctgc tatgatggcg ctcttcacag tctc    94

<210> SEQ ID NO 524
<211> LENGTH: 125
<212> TYPE: DNA
<213> ORGANISM: Artificial Sequence
<220> FEATURE:
<223> OTHER INFORMATION: Synthetic

<400> SEQUENCE: 524
tggagagaac atcggcccaa tctacaacca ccgcgtggag atctccatct tcttcatcat    60
ctacatcatc attgtagctt tcttcatgat gaacatcttt gtgggctttg tcatcgttac    120
atttc    125

<210> SEQ ID NO 525
<211> LENGTH: 98
<212> TYPE: DNA
<213> ORGANISM: Artificial Sequence
<220> FEATURE:
<223> OTHER INFORMATION: Synthetic

<400> SEQUENCE: 525
cagtgtgttg aatacgcctt gaaagcacgt cccttgcgga gatacatccc caaaaacccc    60
taccagtaca agttctggta cgtggtgaac tcttcgcc    98

<210> SEQ ID NO 526
<211> LENGTH: 93
<212> TYPE: DNA
<213> ORGANISM: Artificial Sequence
<220> FEATURE:
<223> OTHER INFORMATION: Synthetic

<400> SEQUENCE: 526
cactacgagc agtccaagat gttcaatgat gccatggaca ttctgaacat ggtcttcacc    60
ggggtgttca ccgtcgagat ggttttgaaa gtc    93

<210> SEQ ID NO 527
<211> LENGTH: 55
<212> TYPE: DNA
<213> ORGANISM: Artificial Sequence
<220> FEATURE:
<223> OTHER INFORMATION: Synthetic

<400> SEQUENCE: 527
ggaacacgtt tgactccctc atcgtaatcg gcagcattat agacgtggcc ctcag    55

<210> SEQ ID NO 528
<211> LENGTH: 76
<212> TYPE: DNA
<213> ORGANISM: Artificial Sequence
<220> FEATURE:
<223> OTHER INFORMATION: Synthetic

<400> SEQUENCE: 528
ctatttcact gatgcatgga acactttga tgccttaatt gttgttggta gcgtcgttga    60
tattgctata actgaa    76

```
<210> SEQ ID NO 529
<211> LENGTH: 27
<212> TYPE: DNA
<213> ORGANISM: Artificial Sequence
<220> FEATURE:
<223> OTHER INFORMATION: Synthetic

<400> SEQUENCE: 529
gtccctgtcc caactgctac acctggg                                           27

<210> SEQ ID NO 530
<211> LENGTH: 102
<212> TYPE: DNA
<213> ORGANISM: Artificial Sequence
<220> FEATURE:
<223> OTHER INFORMATION: Synthetic

<400> SEQUENCE: 530
aagagagcaa tagaatctcc atcacctttt tccgtctttt ccgagtgatg cgattggtga       60
agcttctcag caggggggaa ggcatccgga cattgctgtg ga                         102

<210> SEQ ID NO 531
<211> LENGTH: 40
<212> TYPE: DNA
<213> ORGANISM: Artificial Sequence
<220> FEATURE:
<223> OTHER INFORMATION: Synthetic

<400> SEQUENCE: 531
gcgctcccgt atgtggccct cctcatagcc atgctgttct                             40

<210> SEQ ID NO 532
<211> LENGTH: 71
<212> TYPE: DNA
<213> ORGANISM: Artificial Sequence
<220> FEATURE:
<223> OTHER INFORMATION: Synthetic

<400> SEQUENCE: 532
gttgccatga gagataacaa ccagatcaat aggaacaata acttccagac gtttccccag       60
gcggtgctgc t                                                            71

<210> SEQ ID NO 533
<211> LENGTH: 90
<212> TYPE: DNA
<213> ORGANISM: Artificial Sequence
<220> FEATURE:
<223> OTHER INFORMATION: Synthetic

<400> SEQUENCE: 533
tgagtcagat tacaaccccg gggaggagta tacatgtggg agcaactttg ccattgtcta       60
tttcatcagt ttttacatgc tctgtgcatt                                        90

<210> SEQ ID NO 534
<211> LENGTH: 94
<212> TYPE: DNA
<213> ORGANISM: Artificial Sequence
<220> FEATURE:
<223> OTHER INFORMATION: Synthetic

<400> SEQUENCE: 534
atcatcaatc tgtttgtggc tgtcatcatg gataatttcg actatctgac ccgggactgg       60
tctattttgg ggcctcacca tttagatgaa ttca                                   94
```

<210> SEQ ID NO 535
<211> LENGTH: 84
<212> TYPE: DNA
<213> ORGANISM: Artificial Sequence
<220> FEATURE:
<223> OTHER INFORMATION: Synthetic

<400> SEQUENCE: 535
aacaccttga tgtggtcact ctgcttcgac gcatccagcc tcccctgggg tttgggaagt     60
tatgtccaca cagggtagcg tgca     84

<210> SEQ ID NO 536
<211> LENGTH: 59
<212> TYPE: DNA
<213> ORGANISM: Artificial Sequence
<220> FEATURE:
<223> OTHER INFORMATION: Synthetic

<400> SEQUENCE: 536
catgtttaat gcaaccctgt ttgctttggt tcgaacggct cttaagatca agaccgaag     59

<210> SEQ ID NO 537
<211> LENGTH: 28
<212> TYPE: DNA
<213> ORGANISM: Artificial Sequence
<220> FEATURE:
<223> OTHER INFORMATION: Synthetic

<400> SEQUENCE: 537
attacttgac caagttgtcc ctccagct     28

<210> SEQ ID NO 538
<211> LENGTH: 115
<212> TYPE: DNA
<213> ORGANISM: Artificial Sequence
<220> FEATURE:
<223> OTHER INFORMATION: Synthetic

<400> SEQUENCE: 538
cgtggggaag ttctatgcca ctttcctgat acaggactac tttaggaaat tcaagaaacg     60
gaaagaacaa ggactggtgg gaaagtaccc tgcgaagaac accacaattg cccta     115

<210> SEQ ID NO 539
<211> LENGTH: 87
<212> TYPE: DNA
<213> ORGANISM: Artificial Sequence
<220> FEATURE:
<223> OTHER INFORMATION: Synthetic

<400> SEQUENCE: 539
tgcttgaacg gatgctttag aatttttctgc ctgagctacg gcaccaagct ggttagtcgg     60
aaggcgtttg tggctaaggc cttgaaa     87

<210> SEQ ID NO 540
<211> LENGTH: 66
<212> TYPE: DNA
<213> ORGANISM: Artificial Sequence
<220> FEATURE:
<223> OTHER INFORMATION: Synthetic

<400> SEQUENCE: 540
gcgggattaa ggacactgca tgacattggg ccagaaatcc ggcgtgctat atcgtgtgat     60
ttgcaa     66

<210> SEQ ID NO 541
<211> LENGTH: 260
<212> TYPE: DNA
<213> ORGANISM: Artificial Sequence
<220> FEATURE:
<223> OTHER INFORMATION: Synthetic

<400> SEQUENCE: 541

```
tggtgccctg cttggaaacc atgtcaatca tgttaatagt gataggagag attcccttca      60
gcagaccaat accacccacc gtcccctgca tgtccaaagg ccttcaattc cacctgcaag     120
tgatactgag aaaccgctgt ttcctccagc aggaaattcg gtgtgtcata accatcataa     180
ccataattcc ataggaaagc aagttcccac ctcaacaaat gccaatctca ataatgccaa     240
tatgtccaaa gctgcccatg                                                 260
```

<210> SEQ ID NO 542
<211> LENGTH: 118
<212> TYPE: DNA
<213> ORGANISM: Artificial Sequence
<220> FEATURE:
<223> OTHER INFORMATION: Synthetic

<400> SEQUENCE: 542

```
gctcccaact atttgccggg aagacccaga gatacatggc tatttcaggg accccccactg     60 cttgggggag caggagtatt tcagtagtga ggaatgctac gaggatgaca gctcgccc       118
```

<210> SEQ ID NO 543
<211> LENGTH: 121
<212> TYPE: DNA
<213> ORGANISM: Artificial Sequence
<220> FEATURE:
<223> OTHER INFORMATION: Synthetic

<400> SEQUENCE: 543

```
ggctactaca gcagataccc aggcagaaac atcgactctg agaggccccg aggctaccat      60
catccccaag gattcttgga ggacgatgac tcgcccgttt gctatgattc acggagatct     120
c                                                                     121
```

<210> SEQ ID NO 544
<211> LENGTH: 192
<212> TYPE: DNA
<213> ORGANISM: Artificial Sequence
<220> FEATURE:
<223> OTHER INFORMATION: Synthetic

<400> SEQUENCE: 544

```
atccgaaggc ttgggacgct atgcaaggga cccaaaattt gtgtcagcaa caaaacacga      60
aatcgctgat gcctgtgacc tcaccatcga cgagatggag agtgcagcca gcaccctgct     120
taatgggaac gtgcgtcccc gagccaacgg ggatgtgggc cccctctcac accggcagga    180
ctatgagcta ca                                                         192
```

<210> SEQ ID NO 545
<211> LENGTH: 48
<212> TYPE: DNA
<213> ORGANISM: Artificial Sequence
<220> FEATURE:
<223> OTHER INFORMATION: Synthetic

<400> SEQUENCE: 545

```
gatgtggtcc atgtgatgct caatggatcc cgcagtaaaa tctttgac            48
```

<210> SEQ ID NO 546
<211> LENGTH: 75
<212> TYPE: DNA
<213> ORGANISM: Artificial Sequence
<220> FEATURE:
<223> OTHER INFORMATION: Synthetic

<400> SEQUENCE: 546

```
tgggagtgtg aagtccata atttgcaacc agagaaggtt cagacactag aggcctgggt   60
gatacatggt ggaag                                                   75
```

<210> SEQ ID NO 547
<211> LENGTH: 30
<212> TYPE: DNA
<213> ORGANISM: Artificial Sequence
<220> FEATURE:
<223> OTHER INFORMATION: Synthetic

<400> SEQUENCE: 547

```
cctgaggatt catcttgcac atctgagatc                                   30
```

<210> SEQ ID NO 548
<211> LENGTH: 28
<212> TYPE: DNA
<213> ORGANISM: Artificial Sequence
<220> FEATURE:
<223> OTHER INFORMATION: Synthetic

<400> SEQUENCE: 548

```
ggtgctggac aagtgtcaag aggtcatc                                     28
```

<210> SEQ ID NO 549
<211> LENGTH: 32
<212> TYPE: DNA
<213> ORGANISM: Artificial Sequence
<220> FEATURE:
<223> OTHER INFORMATION: Synthetic

<400> SEQUENCE: 549

```
agaaggttct ggacaagtgt caagaggtca tc                                32
```

<210> SEQ ID NO 550
<211> LENGTH: 36
<212> TYPE: DNA
<213> ORGANISM: Artificial Sequence
<220> FEATURE:
<223> OTHER INFORMATION: Synthetic

<400> SEQUENCE: 550

```
ttagttgaaa aatggagaga tcagcttagt aaaaga                            36
```

<210> SEQ ID NO 551
<211> LENGTH: 150
<212> TYPE: DNA
<213> ORGANISM: Artificial Sequence
<220> FEATURE:
<223> OTHER INFORMATION: Synthetic

<400> SEQUENCE: 551

```
gtcacaacgg tggtggatgt aaaagagatc ttcaagtcct catcacccat ccctcgaact   60
caagtcccgc tcattacaaa ttcttcttgc cagtgtccac acatcctgcc ccatcaagat  120
gttctcatca tgtgttacga gtggcgctca                                  150
```

<210> SEQ ID NO 552
<211> LENGTH: 54
<212> TYPE: DNA
<213> ORGANISM: Artificial Sequence
<220> FEATURE:
<223> OTHER INFORMATION: Synthetic

<400> SEQUENCE: 552
cggtgcaagt gtaaaaaggt gaagccaact ttggcaacgt atctcagcaa aaac        54

<210> SEQ ID NO 553
<211> LENGTH: 41
<212> TYPE: DNA
<213> ORGANISM: Artificial Sequence
<220> FEATURE:
<223> OTHER INFORMATION: Synthetic

<400> SEQUENCE: 553
caggaaaggc ctcttgatgt tgactgtaaa cgcctaagcc c                      41

<210> SEQ ID NO 554
<211> LENGTH: 27
<212> TYPE: DNA
<213> ORGANISM: Artificial Sequence
<220> FEATURE:
<223> OTHER INFORMATION: Synthetic

<400> SEQUENCE: 554
atgttaagtg gatagacatc acaccag                                      27

<210> SEQ ID NO 555
<211> LENGTH: 205
<212> TYPE: DNA
<213> ORGANISM: Artificial Sequence
<220> FEATURE:
<223> OTHER INFORMATION: Synthetic

<400> SEQUENCE: 555
gcgcatccct atgtgccggc acatgccctg gaacatcacg cggatgccca accacctgca    60
ccacagcacg caggagaacg ccatcctggc catcgagcag tacgaggagc tggtggacgt   120
gaactgcagc gccgtgctgc gcttcttcct ctgtgccatg tacgcgccca tttgcaccct   180
ggagttcctg cacgaccta tcaag                                         205

<210> SEQ ID NO 556
<211> LENGTH: 28
<212> TYPE: DNA
<213> ORGANISM: Artificial Sequence
<220> FEATURE:
<223> OTHER INFORMATION: Synthetic

<400> SEQUENCE: 556
atggtttggg ccacttccaa tcggatag                                     28

<210> SEQ ID NO 557
<211> LENGTH: 105
<212> TYPE: DNA
<213> ORGANISM: Artificial Sequence
<220> FEATURE:
<223> OTHER INFORMATION: Synthetic

<400> SEQUENCE: 557
ggattggaga agcaccatat aaagtagggg taccatgttc atcttgtcct ccaagttatg    60

```
gggatcttg tactgacaat ctgtgttttc caggagttac gtcaa        105
```

<210> SEQ ID NO 558
<211> LENGTH: 252
<212> TYPE: DNA
<213> ORGANISM: Artificial Sequence
<220> FEATURE:
<223> OTHER INFORMATION: Synthetic

<400> SEQUENCE: 558

```
acttggaggt ggaccatttc atgcactgca acatctccag tcacagtgcg gatctccccg    60
tgaacgatga ctggtcccac ccggggatcc tctatgtcat ccctgcagtt tatggggtta   120
tcattctgat aggcctcatt ggcaacatca ctttgatcaa gatcttctgt acagtcaagt   180
ccatgcgaaa cgttccaaac ctgttcattt ccagtctggc tttgggagac ctgctcctcc   240
taataacgtg tg                                                      252
```

<210> SEQ ID NO 559
<211> LENGTH: 357
<212> TYPE: DNA
<213> ORGANISM: Artificial Sequence
<220> FEATURE:
<223> OTHER INFORMATION: Synthetic

<400> SEQUENCE: 559

```
atcccggaag cgacttgcca agacagtgct ggtgtttgtg ggcctgttcg ccttctgctg    60
gctccccaat catgtcatct acctgtaccg ctcctaccac tactctgagg tggacacctc   120
catgctccac tttgtcacca gcatctgtgc ccgcctcctg gccttcacca actcctgcgt   180
gaaccccttt gccctctacc tgctgagcaa gagtttcagg aaacagttca cactcagct   240
gctctgttgc cagcctggcc tgatcatccg gtctcacagc actggaagga gtacaacctg   300
catgacctcc ctcaagagta ccaacccctc cgtggccacc tttagcctca tcaatgg     357
```

<210> SEQ ID NO 560
<211> LENGTH: 113
<212> TYPE: DNA
<213> ORGANISM: Artificial Sequence
<220> FEATURE:
<223> OTHER INFORMATION: Synthetic

<400> SEQUENCE: 560

```
tagtcttggc tcgacatgag gatgggggtt tgggaccagt tctgagtgag aatcagactt    60
gccccaagtt gccattagct cccctgcag aatgtcttca gaatcggggc ccg         113
```

<210> SEQ ID NO 561
<211> LENGTH: 239
<212> TYPE: DNA
<213> ORGANISM: Artificial Sequence
<220> FEATURE:
<223> OTHER INFORMATION: Synthetic

<400> SEQUENCE: 561

```
gagcttacct tgaacctttg aattgggcca aattgcgatg accactgcat cctggaaaat    60
tttatttcac cagcactaca actcctcaac agcaccaacc aataaactat ggattttgt   120
actaagccag ttgcctcttt caaaacaact tgtcaacttg tctaatcacc ctcagctttt   180
tttaaaaacc cctcctctac cctctctctt cagaacacaa gtggcttcta gctgaatct   239
```

<210> SEQ ID NO 562
<211> LENGTH: 205

```
<212> TYPE: DNA
<213> ORGANISM: Artificial Sequence
<220> FEATURE:
<223> OTHER INFORMATION: Synthetic

<400> SEQUENCE: 562
gatgcttgac atccctaact agacagatga gggttgaagt tagtttttgg tggggttgga      60
ggtgaacatc aactaccttc ctagttccag gtaatataga acatggagtg aagtgtagat     120
aaatgggtct ggtgggtccc gaggtcatct tatcacataa tgactaattt acattatgga     180
acccagtaca aagtgttcca gttag                                           205

<210> SEQ ID NO 563
<211> LENGTH: 166
<212> TYPE: DNA
<213> ORGANISM: Artificial Sequence
<220> FEATURE:
<223> OTHER INFORMATION: Synthetic

<400> SEQUENCE: 563
taaagccaca agtcaccctt tgctgaagtc agtattagta gttggaagca gtgtgttatt      60 cttgaccccca tgaagtggca cttattaagt agcttgcttt tccataatta tggcctagct    120
ttttaaaacc tactatgaac accacaagca tagagttttc caaaag                    166

<210> SEQ ID NO 564
<211> LENGTH: 376
<212> TYPE: DNA
<213> ORGANISM: Artificial Sequence
<220> FEATURE:
<223> OTHER INFORMATION: Synthetic

<400> SEQUENCE: 564
tggagaacaa cattggggcc cttgacttta gatttcagtg gggacctaca aaaggaaaa       60 atggaaaggg aattctgaag tcttaaggtg ggctatctga agttggatc cctgggtgaa      120 aaagatttta taatattaga tgagttgaga gaaccaatgt gaattaaagc tgactggctt    180
aaaaaaaata aacccatcaa aattagtaag ggaataatgt tattcattgc ctttttttcg    240
ttgagttatg aaagctcttc gaagatgaag gttttatgaa actcaagatc tctccagagg    300
ccgggcacag tggctcacgc ctgtaattcc agcactttgg gaggctgagg tgagcagatt    360
gcgagtccag aagtga                                                    376

<210> SEQ ID NO 565
<211> LENGTH: 134
<212> TYPE: DNA
<213> ORGANISM: Artificial Sequence
<220> FEATURE:
<223> OTHER INFORMATION: Synthetic

<400> SEQUENCE: 565
tgtgcagccg aagaatgagt gtaacatgat ccttgcaaca gaagaaaagg acacggagag      60
gtcatttggt aggaggctcc actgtgagat gaccaccgat gattacttct gccgaaaacc     120
tagcagtcac agca                                                      134

<210> SEQ ID NO 566
<211> LENGTH: 99
<212> TYPE: DNA
<213> ORGANISM: Artificial Sequence
<220> FEATURE:
<223> OTHER INFORMATION: Synthetic
```

-continued

```
<400> SEQUENCE: 566
tttgggattg gtttagaggc agctgaacga aacttatttt tcatctgtag taaataccTt    60
tcatttaatg tgaatggtaa aatcaaaggg cagacgctg                           99

<210> SEQ ID NO 567
<211> LENGTH: 177
<212> TYPE: DNA
<213> ORGANISM: Artificial Sequence
<220> FEATURE:
<223> OTHER INFORMATION: Synthetic

<400> SEQUENCE: 567
cttgcctgtg gcaccagatg ccttacagtg gccaggaatg ctgcgggaca gtctactttg    60
attgctttct ttcctccatg gctgagatct gagtgtagtg ttaactgggc ttaaaaatca   120
agtccgttgt atctgcatgg tcacgtagtt cggcatctca tggcttttgc acctaga     177

<210> SEQ ID NO 568
<211> LENGTH: 155
<212> TYPE: DNA
<213> ORGANISM: Artificial Sequence
<220> FEATURE:
<223> OTHER INFORMATION: Synthetic

<400> SEQUENCE: 568
tgaatgacca tacaaggact ccatggtata ttcttgtaga tcattagtta attatcaaca    60
attggctaat gattaatgtt tgcctgagag gctgactttt tgtccattag taatgacatc   120
ccaggaaaca cctggcagag ttcgtcttta atttc                              155

<210> SEQ ID NO 569
<211> LENGTH: 180
<212> TYPE: DNA
<213> ORGANISM: Artificial Sequence
<220> FEATURE:
<223> OTHER INFORMATION: Synthetic

<400> SEQUENCE: 569
agagagcctc aaaatgacca gagtagatgg actcgtgtag taaaactta cccaaagttg     60 gtttcctaat gatataatgt gaaacagtct atgtgctata caaataatta tatctctttt   120
gttaagcctt acgtcatttt gacaaaggct ttacttgatt gagtattgac ggcttttcca   180

<210> SEQ ID NO 570
<211> LENGTH: 25
<212> TYPE: DNA
<213> ORGANISM: Artificial Sequence
<220> FEATURE:
<223> OTHER INFORMATION: Synthetic

<400> SEQUENCE: 570
ttggggaaga agaatatcca atccg                                          25

<210> SEQ ID NO 571
<211> LENGTH: 93
<212> TYPE: DNA
<213> ORGANISM: Artificial Sequence
<220> FEATURE:
<223> OTHER INFORMATION: Synthetic

<400> SEQUENCE: 571
agtgcaatgt gtcatgggct ctgaaggtct tacgttgagg aatggcaata ttatcagaat    60
tacgtgtcca gcttcccaag cttactactt tga                                 93
```

<210> SEQ ID NO 572
<211> LENGTH: 444
<212> TYPE: DNA
<213> ORGANISM: Artificial Sequence
<220> FEATURE:
<223> OTHER INFORMATION: Synthetic

<400> SEQUENCE: 572

```
cccattttga gggactgcca agctgcttgc caaagcagct gcgccatttt acattaccac    60
cagcaacatg tggaggttcc aatttctgta cgtctttgct aacacttgtt attgtctatc   120
tttttaatta tagccatcat agtgcatatg aagtggtatc tcattgtagt tttgatttgc   180
atttctctga tgactaataa tagtgagcat cttttcatgt gcttattagc cgtttgtatc   240
aaatcctttg ctcattttta aattgaattt ttaaaattat tggtttgtgg cagggcatgg   300
tggctcatgc ctgtaatccc agcactttgg gaggccaagg cgggtcggtc acctgaggcc   360
aggagttcga gaccagcctg gccagcatgg tgaaaccctg tctctactaa aaatacaaaa   420
aatagtcaga catggtcaca ggca                                          444
```

<210> SEQ ID NO 573
<211> LENGTH: 195
<212> TYPE: DNA
<213> ORGANISM: Artificial Sequence
<220> FEATURE:
<223> OTHER INFORMATION: Synthetic

<400> SEQUENCE: 573

```
tctggactttt caccttggga cattctcagt ttccacccca ctgtttctga gggtcgaaag    60
gtttgggtgt atatgtaggg aaagataatt ggtaggctct gaagcacaca gttcatttgt   120
ttttcaataa ggaagagtca tgttagaaat tttgtccttt cttccagaag gtacactata   180
tagcctggag ccaca                                                    195
```

<210> SEQ ID NO 574
<211> LENGTH: 61
<212> TYPE: DNA
<213> ORGANISM: Artificial Sequence
<220> FEATURE:
<223> OTHER INFORMATION: Synthetic

<400> SEQUENCE: 574

```
tccaaagaca agcttaatga ctgctgtgcc aacacacaaa actacaagat acatttaagc    60
a                                                                    61
```

<210> SEQ ID NO 575
<211> LENGTH: 160
<212> TYPE: DNA
<213> ORGANISM: Artificial Sequence
<220> FEATURE:
<223> OTHER INFORMATION: Synthetic

<400> SEQUENCE: 575

```
gtacctctcc agattagaca agatgatatt aaatatttcc atcttacaga tgagcaaatt    60
cagacttaga gacgataagg tactagcccc ctggaaaaca actgcactga acctaggtcc   120
tttatttctg aacaagacag gcatcgtgtt gaacttcatg                         160
```

<210> SEQ ID NO 576
<211> LENGTH: 281
<212> TYPE: DNA

```
<213> ORGANISM: Artificial Sequence
<220> FEATURE:
<223> OTHER INFORMATION: Synthetic

<400> SEQUENCE: 576
tagccattct gcactcttca ggagagaaga acaacctggg gccatgtgtt caataaagag      60
atggggctgg cacattgttg aggaggagaa ggaggatttc aaatggaggg cttttttgaag    120 aaggcattga acacctcccc acccacccct gccctgcact tctccctgta gctcagaaac     180
cttttaatag ccatgggacc aacatctagc agctggcttg gttttgctgg tccttgcttt    240
aaaatgggga tacatatccc tgctttacag acctgctgtg g                         281

<210> SEQ ID NO 577
<211> LENGTH: 86
<212> TYPE: DNA
<213> ORGANISM: Artificial Sequence
<220> FEATURE:
<223> OTHER INFORMATION: Synthetic

<400> SEQUENCE: 577
agttacgatt aatgtgagca gcttctctca ttccagaaat gtgacctctg gttacagcaa      60
atgtgacaac atgaattacc ttcaat                                           86

<210> SEQ ID NO 578
<211> LENGTH: 135
<212> TYPE: DNA
<213> ORGANISM: Artificial Sequence
<220> FEATURE:
<223> OTHER INFORMATION: Synthetic

<400> SEQUENCE: 578
gaagcaaccc atatatccct caacgggcga atggataaac tcattgtgat gtatttgtgt      60
aatgggatat tacagaacaa caaaagaaa tgaactgctg ataaaacaac gtggatgagt     120
gtcagaaaca ttatg                                                      135

<210> SEQ ID NO 579
<211> LENGTH: 29
<212> TYPE: DNA
<213> ORGANISM: Artificial Sequence
<220> FEATURE:
<223> OTHER INFORMATION: Synthetic

<400> SEQUENCE: 579
gtgggtttca gaatcactgg tgctttgag                                        29

<210> SEQ ID NO 580
<211> LENGTH: 46
<212> TYPE: DNA
<213> ORGANISM: Artificial Sequence
<220> FEATURE:
<223> OTHER INFORMATION: Synthetic

<400> SEQUENCE: 580
aagtaccctg gggagagagt ttatggagtg ttctttgctt ggataa                    46

<210> SEQ ID NO 581
<211> LENGTH: 112
<212> TYPE: DNA
<213> ORGANISM: Artificial Sequence
<220> FEATURE:
<223> OTHER INFORMATION: Synthetic

<400> SEQUENCE: 581
```

```
ggtgggtcca atatgtagaa aggcacactt agaacaggac tatttggatg tgtgggaagt    60
gggatcatta agttctggtg gaaagaaacc tatggtagag ttctttgata aa           112

<210> SEQ ID NO 582
<211> LENGTH: 276
<212> TYPE: DNA
<213> ORGANISM: Artificial Sequence
<220> FEATURE:
<223> OTHER INFORMATION: Synthetic

<400> SEQUENCE: 582
gcaggagttt tgtcctctac caagaccttt cctgaaaatc acttatcaag acagtttcct    60
gtaagaaaaa gccatatccc agctgatttt ccttcctggg gccaaaatct gctattattc   120
ggcctgaaag ccttgatgac tctgtgtgtg tgtgtgtgtg tgtgtgtgtg tgtgtgtgtg   180
tgtgtgtgtg tgtgtgtgtg tgtatggatg cttgtgtgtg tgtatgggga atatgtgatt   240
aatgtgtgtt ggctgctgtt gtctctgatt tggcta                             276

<210> SEQ ID NO 583
<211> LENGTH: 398
<212> TYPE: DNA
<213> ORGANISM: Artificial Sequence
<220> FEATURE:
<223> OTHER INFORMATION: Synthetic

<400> SEQUENCE: 583
tcctgaggac agttgccaag accacacaag ctttgctgga tgagggccgc caagaggggt    60
tgccagacat tttatgtgtc ctctgagatg cttttctttc tgctgaggct tcccaaatca   120
agctgtttcc tggaacctca ccaggcttca tgaaggagaa ctatagaacg attattgacc   180
agaaattaat cagcattgtt gcttgagatt taaacaattt ccatagcatg ccctttttt    240 gtctgttcta aagtgagata catttataat tgctttattt gtctggatcc aaatataatg   300
cagattaatt gttataaaac gatagcaaaa tgagctggat tgggtgggct tttggtagtc   360
cccatttgta gatttcagcc gctgagcttg tccttatt                           398

<210> SEQ ID NO 584
<211> LENGTH: 185
<212> TYPE: DNA
<213> ORGANISM: Artificial Sequence
<220> FEATURE:
<223> OTHER INFORMATION: Synthetic

<400> SEQUENCE: 584
ctcctagtaa acctcagtgg ccttaggcta gggttggaca tgtgagggtg gtgtctattc    60
ctggagaaat aacatcgcat ttgatttgc cacaggagct ttctatacaa ggttaacagc   120
aatcctgttg tgaattcctt ggcgcctcat gtctcctaaa cccagctaaa ctgacggagg   180
ccatg                                                               185

<210> SEQ ID NO 585
<211> LENGTH: 410
<212> TYPE: DNA
<213> ORGANISM: Artificial Sequence
<220> FEATURE:
<223> OTHER INFORMATION: Synthetic

<400> SEQUENCE: 585
ctgagatcct gtagagtgcc cggctctggt ccagaggcga ggggtgccag gatgtctcag    60
```

```
acacagacag cggccttgtg cttaggcgtt cattatctca tggggtagcc cattttgaag    120
cagtgcagaa gggcacatat tcagtagagg tgcagaccca gaggctctgt gagctgcact    180
agagagatga ggaggcatct ccccggcga  ctgacgatgg gctggcatgc ctccacctcc    240
gcccctccgc cccctcgccc tcccaaccac caccttccct ctctgcctgc tactcccctc    300
ttactttccc attgatattt tgttgttgt  ttaagcaaat tattattatt tttttaaatt    360
ttagcctcaa gagtcttcat aatttttta  gggaacacta gaggtactgc              410

<210> SEQ ID NO 586
<211> LENGTH: 157
<212> TYPE: DNA
<213> ORGANISM: Artificial Sequence
<220> FEATURE:
<223> OTHER INFORMATION: Synthetic

<400> SEQUENCE: 586
ggtgcagggt actctttgga aattctgag  tgtagcattt tctggatttc ccagcaggtg     60
gccacacttt acacacacat caacgttgta ctcaatgtca cccaagaggt ggctctggag    120
aatgtggaag cactgtgtca gctgcaaagt attacgc                             157

<210> SEQ ID NO 587
<211> LENGTH: 116
<212> TYPE: DNA
<213> ORGANISM: Artificial Sequence
<220> FEATURE:
<223> OTHER INFORMATION: Synthetic

<400> SEQUENCE: 587
tgtgctgagt tgacttctct gtccgcagtt cccctccac  ctgtgctctg ggttgttgat     60
gtgcaggtta gaagagggag gttgttgagg gtattagtgt tgcaggggag gctgtt        116

<210> SEQ ID NO 588
<211> LENGTH: 425
<212> TYPE: DNA
<213> ORGANISM: Artificial Sequence
<220> FEATURE:
<223> OTHER INFORMATION: Synthetic

<400> SEQUENCE: 588
gcaccgtgta ggcactgcag tgacagtgtg gaatgaaatg gtttctttct tcgtgaagct     60
tatatctaat gatggaggcc aaaatgacaa ttacaaactc gtataaatgc tttgaaagaa    120
aggttcatgt gctgtgagag ggtttaacag gcacaactgc tgtcagttta ttgggtagga    180
gcatcctgga agtgaagaat gagtagtcca catatccagg caaggtggga caagaagcta    240
gggcaagggt attctagtca agggaaaacc cacagaaagg aggtacagta ggaaggagca    300
gaggatgctg gaggaactga atgaagctag ggtgacagga actgggagag ctggagatga    360
agtcagatga aaggaaagag actggccggc agaatccagg tcacgtagga cctttagact    420
atgtc                                                                425

<210> SEQ ID NO 589
<211> LENGTH: 56
<212> TYPE: DNA
<213> ORGANISM: Artificial Sequence
<220> FEATURE:
<223> OTHER INFORMATION: Synthetic

<400> SEQUENCE: 589
gaaaaggtag caggtgttaa ttatggaatc taggtgaggt aggcatatgg gtgttc         56
```

<210> SEQ ID NO 590
<211> LENGTH: 197
<212> TYPE: DNA
<213> ORGANISM: Artificial Sequence
<220> FEATURE:
<223> OTHER INFORMATION: Synthetic

<400> SEQUENCE: 590
tggtagactg agaacttaag gatgcatatg ataatctcca gagtaatgac ttaaaagggg    60
tactaaaaag ctaaagaag agataaaatg gaatattaaa tagtactaaa ttatccaaaa   120
taagtcagaa aaggaagaaa aaggaacaaa gaacatatag taccaacaac gagatggtag   180
acaaacccag taatatc                                                 197

<210> SEQ ID NO 591
<211> LENGTH: 277
<212> TYPE: DNA
<213> ORGANISM: Artificial Sequence
<220> FEATURE:
<223> OTHER INFORMATION: Synthetic

<400> SEQUENCE: 591
cgtggaacat tcaccgacat agaccatatc ttggccatga aagtctcatt acctctcgat    60 tgaaattta caagtatct tgttctaat ggcagtagat ttaaaacaga agccaataac     120
aggctgttta taaaccttcc caaatgtttg gaaattaaat aacctataac tcaaaaata    180 ataaaaatta gaaatactt tgaaactgat aaaatccaac tgggaaattg tatgatccgt    240
tgaatgcagt gcttggaggg acatttatag ctatatc                           277

<210> SEQ ID NO 592
<211> LENGTH: 103
<212> TYPE: DNA
<213> ORGANISM: Artificial Sequence
<220> FEATURE:
<223> OTHER INFORMATION: Synthetic

<400> SEQUENCE: 592
atggcagaga ctcaggctgt tttgccaaaa cccaggtcgc tttccccagc tgtgcaggct    60
cgtattctgc tgaagctgct gttggttatt cctgggaccc tgg                    103

<210> SEQ ID NO 593
<211> LENGTH: 80
<212> TYPE: DNA
<213> ORGANISM: Artificial Sequence
<220> FEATURE:
<223> OTHER INFORMATION: Synthetic

<400> SEQUENCE: 593
cagatggggt gtcacggggc cctgacaagg aaggtccaca tgaggggaga tgattacact    60
ggtgtgctag acccaggga                                               80

<210> SEQ ID NO 594
<211> LENGTH: 101
<212> TYPE: DNA
<213> ORGANISM: Artificial Sequence
<220> FEATURE:
<223> OTHER INFORMATION: Synthetic

<400> SEQUENCE: 594
ttcctgcatg cctatatgaa gtggcgccaa ggggaaatag agacatggga agaaatacat    60

```
gagaaatgga cagacaacat tgtccgttcc tgcctgcaag g                 101
```

<210> SEQ ID NO 595
<211> LENGTH: 112
<212> TYPE: DNA
<213> ORGANISM: Artificial Sequence
<220> FEATURE:
<223> OTHER INFORMATION: Synthetic

<400> SEQUENCE: 595

```
cacgtcccat atggtggata taggaactgc atatgtgtgc aagtgtagtt ttgcatctgc    60
acgtgaatct atgaatatct agattttcta acccacttaa gggctgcata tg          112
```

<210> SEQ ID NO 596
<211> LENGTH: 330
<212> TYPE: DNA
<213> ORGANISM: Artificial Sequence
<220> FEATURE:
<223> OTHER INFORMATION: Synthetic

<400> SEQUENCE: 596

```
ggccatgttt ggaaagctac ctagtgaaga gtccttcccc agtctggtgt cctctagggg    60
tgtccagcat agcgtagccc acttgcgttc cagctccacc agttcccttc atgttgaaac   120
ctcctccatc ccttgtaggg gagatgggga tggagtctaa tcgctctctc ttcatccgtg   180
tactgttccc tcgtcaaccc agaaagaacc cactgttcag ccacagcagc tgagtgggc    240 ttttctagtg accccactct gtatggccgc tcgagatcta aagggcatta gctggtatag   300
gccacctgtt aactactcgg gccagcttta                                    330
```

<210> SEQ ID NO 597
<211> LENGTH: 51
<212> TYPE: DNA
<213> ORGANISM: Artificial Sequence
<220> FEATURE:
<223> OTHER INFORMATION: Synthetic

<400> SEQUENCE: 597

```
gtgctgtgtg gacgcagttt tccgagctct gtgttgttag catgtaactc t             51
```

<210> SEQ ID NO 598
<211> LENGTH: 45
<212> TYPE: DNA
<213> ORGANISM: Artificial Sequence
<220> FEATURE:
<223> OTHER INFORMATION: Synthetic

<400> SEQUENCE: 598

```
tgcatgttct actttccatt gggtttgacc tctccatgat aaccc                    45
```

<210> SEQ ID NO 599
<211> LENGTH: 33
<212> TYPE: DNA
<213> ORGANISM: Artificial Sequence
<220> FEATURE:
<223> OTHER INFORMATION: Synthetic

<400> SEQUENCE: 599

```
taagagccat gccaaggact tctctctttg tct                                 33
```

<210> SEQ ID NO 600
<211> LENGTH: 27
<212> TYPE: DNA
<213> ORGANISM: Artificial Sequence

```
<220> FEATURE:
<223> OTHER INFORMATION: Synthetic

<400> SEQUENCE: 600
gtagacgtgt tggtcacatg tgatgag                                          27

<210> SEQ ID NO 601
<211> LENGTH: 70
<212> TYPE: DNA
<213> ORGANISM: Artificial Sequence
<220> FEATURE:
<223> OTHER INFORMATION: Synthetic

<400> SEQUENCE: 601
ggcagactgc gtgctaatgg aaagtggagc atggccgtcg cagtgtgagc gcagaagtgc      60
ggacctaggc                                                             70

<210> SEQ ID NO 602
<211> LENGTH: 820
<212> TYPE: DNA
<213> ORGANISM: Artificial Sequence
<220> FEATURE:
<223> OTHER INFORMATION: Synthetic

<400> SEQUENCE: 602
gagttccttt tgtatgccag tccgccatga cctcctgagc gtccggccct gctctctgca      60
gagacccagt ccagaataca gtgagaagtg gacaggccag gaagctcaga tacacccatt     120
gaaactaaca catacacccg catgccaaaa ccaatccagg caacacctca ggttccatct     180
taacgtgtcc acaggaaaca ccaccacacc caaacctcat ctaacattgt ccgtctttaa     240
ttcgtgctca gagccagtct ggggatgcct ctttggaagc agtgtggtct agtttcaagg     300
acactgggag tcagggaacc tgggttctag tcccagtttc agcattcact tgctgcgtga     360
ccttgggcaa gacacttaac ctctctgtgc ctcagtttcc cccatctgta aatgggtt       420 aataatgtcg acctacctca cagggctgtt gtgaggaata gctaagtgat tgtaaagcac     480
tttgaacgta taattgctta ttaagactac aacaataata atatcatatg cctgtttact     540
accagaactt taagaaattc ttgttttcct ttgatctctt ttctgttctg taccatactt     600
acccattgag aagaaaaatt ccccccttt aaagaaatct aggcaatgca caaagatgtc      660
aacagaggta accctgcagg ttgcattttc acatcttaag aatagcagat ttttgcccaa     720
gatgttggtc gataagggtg tctgatcttg aattctcagc tgattccaag tggtggttgg     780
agtctgtaca tctgatgctg agcccaagac acccaaagtg                           820

<210> SEQ ID NO 603
<211> LENGTH: 54
<212> TYPE: DNA
<213> ORGANISM: Artificial Sequence
<220> FEATURE:
<223> OTHER INFORMATION: Synthetic

<400> SEQUENCE: 603
tcataggccc ttgagaccgt gtggatatag tgaacccaac tcttggtaga cttg            54

<210> SEQ ID NO 604
<211> LENGTH: 153
<212> TYPE: DNA
<213> ORGANISM: Artificial Sequence
<220> FEATURE:
<223> OTHER INFORMATION: Synthetic
```

```
<400> SEQUENCE: 604
ttctggactt aacactcctc agctgtaaaa tgaggtagga aatctgatgt gatttctagt      60
tggggacatt ctagaagatt ccatattgta tctcaaatga ctgttcagag acacagtctt     120
taggtgctca ctctagagag gactgtgata agc                                  153

<210> SEQ ID NO 605
<211> LENGTH: 206
<212> TYPE: DNA
<213> ORGANISM: Artificial Sequence
<220> FEATURE:
<223> OTHER INFORMATION: Synthetic

<400> SEQUENCE: 605
acagaagtgg tgtgcagatc gtttcagatc aatttatcat aaaatctaag ttgataggtg      60
ttctcttaat gatgttctta tactgcctgt tcaccttgac cctttagctt tgagtagatt     120
agagagtgta ggggaaagat cttttcccct tcaaatactc aaaggatcat gtgttctctt     180
gagcagttct gcaaatccat atagga                                          206

<210> SEQ ID NO 606
<211> LENGTH: 653
<212> TYPE: DNA
<213> ORGANISM: Artificial Sequence
<220> FEATURE:
<223> OTHER INFORMATION: Synthetic

<400> SEQUENCE: 606
ttcatgaact gtcggccttc ctgtgtaagt gggtcaggca ccatgtgacc tgctcactgc      60
cagtttcttc tttgaataga tgtttatttc atggatcatt ttgaagattc tccgtgggtg     120
tgcaacatgg ttttagaatg ttgggtaatt tctcatgtgt tctttgagat ggatggcttc     180
tcagtcgtct ttgcagtcag ccactgtaga cttgagtttc tctcttgctg tcttcatttt     240
attgctccat atctgaggaa aaccatgtga aaaatcccta gacacatagg agccctgaga     300
agtggtggca gggaatgctt gggggacaaa acagattta gagttacggg tatttaatt      360 aaaaaaagag agacccagaa ttgttttca cttaaatgag caattatatc tttaacttgg     420
ggatggaaat atgttgtgaa atttgtttag tcagctccct ctgaaataaa taaaattaca     480
gtgatgatat cattcttgtt taaaatgttt gaaaaggtat caagacaaag tgattaaggc     540
ctaactgttt gccaaatttt ctttaaagct ccattttgg ggtatttcta tgccaaaaaa     600
catcttaaac tgatgaacat atagttctcc gcacttgtat tggctggttt tta            653

<210> SEQ ID NO 607
<211> LENGTH: 303
<212> TYPE: DNA
<213> ORGANISM: Artificial Sequence
<220> FEATURE:
<223> OTHER INFORMATION: Synthetic

<400> SEQUENCE: 607
tccactggat atagcctcga ctgtactcac caggttctcc acaccctaag ccacatgcca      60
gatttgttta gcagattcag tggagcaggt tcattcatgg gggcaccaaa ccaaaagtcc     120
ttttaaaaac agttacctat gatttaaaag tgtgaagtga ttgtagtatg atggggaaac     180
agtgggccaa ctatcatgag aattaggaga tctggacagc tacatgatct ctttgatcat     240
atagttttct tacttgctca gtgcagcagt agtgccaacc tgtcctcaga cggggatgta     300
ata                                                                   303
```

<210> SEQ ID NO 608
<211> LENGTH: 360
<212> TYPE: DNA
<213> ORGANISM: Artificial Sequence
<220> FEATURE:
<223> OTHER INFORMATION: Synthetic

<400> SEQUENCE: 608

```
ggttgtggac cactgagcta atgcagtgca tctcagtgat tactgtccat cagaagcttg    60
ttaaaaaata ttcttgagca ccaccccaa  aggttctggt tcagtaggtc aagggtgggg   120
cccaagaatt tgatttctat aatgctttta agtgaagcca atacagacca cacttagagt   180
aacatgttct aattttttta tgaaccagga attaataaac tgggcagata gtaaagcatt   240
gcccacagag gttgaaagag actttcagat tcatcgagtc taatctcatc agatggttga   300
gcttcttcca caaatccccc accaagtggg tctctttgaa tgctctacca acaaggatcc   360
```

<210> SEQ ID NO 609
<211> LENGTH: 461
<212> TYPE: DNA
<213> ORGANISM: Artificial Sequence
<220> FEATURE:
<223> OTHER INFORMATION: Synthetic

<400> SEQUENCE: 609

```
tccaggcctt ttaatgaaca gtcttctgct ttttctctta acaatataat ttctcctatg    60
gaacaatttg aaagccatgc atgcaaattt agactaaaag caatggacac aaaagaaacc   120
tgtatacatt cttcggtatt acgcacatgt gatgagtggt gcttttgggc acttgcctga   180
cagtagcttg gacagaaaag acactggagc ctcagagaat aactattgaa gcaattctgg   240
aattaagaaa taaggcctga atgagatgg  taaagatgt  tagaggaaga gaagcaaggt   300
aagacaaggt gacacacaga atcagaaatg atgaacagga agcaactttt aaaataaatg   360
ttttctgagt agctactaat atgccaagcc ctgtgctggg cattgacatt gcagcagtga   420
acaaaacaga cacgatcctg gctctcgtca agtttatatt t                      461
```

<210> SEQ ID NO 610
<211> LENGTH: 262
<212> TYPE: DNA
<213> ORGANISM: Artificial Sequence
<220> FEATURE:
<223> OTHER INFORMATION: Synthetic

<400> SEQUENCE: 610

```
gatggaaagt aagggcaaca aaataaactt gagagccaca aacctgtggg ttacagttaa    60
aattataaaa cactgtcaaa atttaattaa ttttaggaag ttcactttgt cctcacaaca   120 ggttttttgaa gtatattttt ctaagtattt aatacgtact cttaacagtc tgcaaatttg   180
caaaacctga agtaatgag  tggttaattg acttaagatt ttttccagaa tcaaattcct   240
ttctccatac atacatgcgt tg                                           262
```

<210> SEQ ID NO 611
<211> LENGTH: 126
<212> TYPE: DNA
<213> ORGANISM: Artificial Sequence
<220> FEATURE:
<223> OTHER INFORMATION: Synthetic

<400> SEQUENCE: 611

```
tgagggccaa gacacaagat gaagctttgg cttcttaaaa agatgggacg aatgcatctg    60
tcagtggctg gttacagcaa tgggttagaa tatttaatga gggaggtcat cactcctgct   120
tccctt                                                              126
```

<210> SEQ ID NO 612
<211> LENGTH: 65
<212> TYPE: DNA
<213> ORGANISM: Artificial Sequence
<220> FEATURE:
<223> OTHER INFORMATION: Synthetic

<400> SEQUENCE: 612

```
gggtcacaag ccaatagaca agccagtcct tttgaatcct ttactcatgg ccttgagagg    60
aacca                                                                65
```

<210> SEQ ID NO 613
<211> LENGTH: 651
<212> TYPE: DNA
<213> ORGANISM: Artificial Sequence
<220> FEATURE:
<223> OTHER INFORMATION: Synthetic

<400> SEQUENCE: 613

```
gggctgggat tattgtcttc atatacaaag gatagtcttt tttttttgtt tctattttgc    60
aaagtaccca ttttcagcac aatacaaaag gtagatataa tgctgtgtac tttttaaaat   120
aatcttttga atattataca ttcatactgt ccaaaaatta gaaatataa aaaggaatac    180 agtggaagcc tccatgaccc cacaggtaac cactagcatt attttctagt agtcttttat   240 gtgtttatt tatgcagtct tttatgtatt ttatgtagta ttttatgcag tcttccaatt    300
tccttatgca tatacaaaca taaaaatata ttctgatagt ttcttctttt gttacacgaa   360
aatggtatac tattcatagg gttgggcacc ttggttttgt tttgtttttt ttttccatt    420 taagaaaata tattggaaat atttctatat ctgtatgtaa agagtttcct ccttttcttt   480
cttttccttt ttttaacaa atgtgtaata tttatattta tgccataatt tatttaacca    540
gcccctattg ataggaatat gggtcatttt tcaatctttc atttttacaa acagcatgta   600
tgataacctt gtgcatctaa atagtttcac aagaatacct gtgggataat a            651
```

<210> SEQ ID NO 614
<211> LENGTH: 561
<212> TYPE: DNA
<213> ORGANISM: Artificial Sequence
<220> FEATURE:
<223> OTHER INFORMATION: Synthetic

<400> SEQUENCE: 614

```
tctaatcccg gccttggctt tctggtgacc aacccccatc ctgaagctgg ccagggactg    60
ccagccatca atcaatcatt agcatgcaaa aagacatact ttggagactc caaggatttt   120
aggaattcta tggcagaaaa tggagatgaa caccaaatag aaggccgggc acagtggctc   180
acgcttgtaa tcccaacact ttgggagacc aaggtgggtg atcacctgag gtcaggagtt   240
tgagaccagc ctggccaact tagtgaaacc ctgtctctac tagaaacaca aaaaattagc   300
caggcgtggt ggcaggcgcc tgtaatccca gctactcagg aggctgaggc aagagaatca   360
cttgaaccca ggaggcggag gttgcagtga ccgagatgg cgccactgca ttccagcctg    420
ggcaacaaga acgaaattcc gtctcaaaaa aaaaaaaaa agaccaaata tatatttcac    480
aatatcatag ataatgaatg gcatttttaa aaaaaagttt gtctattaac tgcttaccgt    540
```

```
gttcttgcca tgtaggttct g                                              561

<210> SEQ ID NO 615
<211> LENGTH: 162
<212> TYPE: DNA
<213> ORGANISM: Artificial Sequence
<220> FEATURE:
<223> OTHER INFORMATION: Synthetic

<400> SEQUENCE: 615 acagggggcgc atttgcctca caaggaacat ttggcaatgt cgggagatat tctgggttat     60
acaagtggga gattaggaat gctactggca tctagtgggc agaggccagg atactgtgaa    120
acatcctata atgcacagga gagctcccta caacaaacaa tt                       162

<210> SEQ ID NO 616
<211> LENGTH: 75
<212> TYPE: DNA
<213> ORGANISM: Artificial Sequence
<220> FEATURE:
<223> OTHER INFORMATION: Synthetic

<400> SEQUENCE: 616
tgctttgcga tgcatttgaa ataccgtttg tggccagata aattacgatt gcttttcaag     60
gttacatggt gtttc                                                      75

<210> SEQ ID NO 617
<211> LENGTH: 286
<212> TYPE: DNA
<213> ORGANISM: Artificial Sequence
<220> FEATURE:
<223> OTHER INFORMATION: Synthetic

<400> SEQUENCE: 617
ggtccacaga gaatagtcca tgatctgtac aaacatccag agagctgctt tctcccatgg     60
cctcccacag gtctgactgc cagagagtag aagcaagagg ggtgaaaata gaggagtacc    120
tgctgtgctg tcatttcagg tctgctctgg agaagaacat gggctaagaa ttatcttta    180 tgatctgaaa aagctgtctg aagttccttc caagcttatc agcctcctaa cctgagcttt    240
aacaaaaccc ggtatggtag agtcctagtg tgccaatcca gctttc                   286

<210> SEQ ID NO 618
<211> LENGTH: 98
<212> TYPE: DNA
<213> ORGANISM: Artificial Sequence
<220> FEATURE:
<223> OTHER INFORMATION: Synthetic

<400> SEQUENCE: 618
tggagctgcg ttgaatgcaa acttgaggtg tttcccttga ggaattcttg tcttcaaacg     60
tctgcagagt aatggaccat gttacaactt tcctgttc                             98

<210> SEQ ID NO 619
<211> LENGTH: 121
<212> TYPE: DNA
<213> ORGANISM: Artificial Sequence
<220> FEATURE:
<223> OTHER INFORMATION: Synthetic

<400> SEQUENCE: 619
gatggcactg atgcattaga ccctcagcag cctgcaattg caaatctgcg aggtttcatt     60
```

```
cggcccataa agcaaacatt tgaacttaca cagaatgagc acttaaatac gggtgcaata      120
a                                                                     121

<210> SEQ ID NO 620
<211> LENGTH: 98
<212> TYPE: DNA
<213> ORGANISM: Artificial Sequence
<220> FEATURE:
<223> OTHER INFORMATION: Synthetic

<400> SEQUENCE: 620
tgtagcccat tggtcacag tagcctcact tctgctacgc ttgcaacaac aactctttgg       60
aaatcaaccg ctattctata tttgtgttca cgttagtg                             98

<210> SEQ ID NO 621
<211> LENGTH: 221
<212> TYPE: DNA
<213> ORGANISM: Artificial Sequence
<220> FEATURE:
<223> OTHER INFORMATION: Synthetic

<400> SEQUENCE: 621
gggcctaggc tttgtgcaca ctgttcgatg aaaccaaggc ttaccaagct ctactttatt      60
ccgtatctgg atggtcattt catttctcct agcccacacc cagacacaca cttctcaaat     120
acacacgaca atttcactat ctcacaatct cttactgtaa ctttggcctt cagaaacacc     180
ctttgttata ttgcaggcgg ccaagcatta agtccagctg a                         221

<210> SEQ ID NO 622
<211> LENGTH: 48
<212> TYPE: DNA
<213> ORGANISM: Artificial Sequence
<220> FEATURE:
<223> OTHER INFORMATION: Synthetic

<400> SEQUENCE: 622
acctgtgcca gctcctgcaa atgcaaagag tacaaatgca cctcctgc                   48

<210> SEQ ID NO 623
<211> LENGTH: 72
<212> TYPE: DNA
<213> ORGANISM: Artificial Sequence
<220> FEATURE:
<223> OTHER INFORMATION: Synthetic

<400> SEQUENCE: 623
ccattgtata cccttccttg gtgaatgttc tgatatttgc ttcccatccc aagttgtttc      60
agcccctatt ag                                                         72

<210> SEQ ID NO 624
<211> LENGTH: 182
<212> TYPE: DNA
<213> ORGANISM: Artificial Sequence
<220> FEATURE:
<223> OTHER INFORMATION: Synthetic

<400> SEQUENCE: 624
cggatccgtg ttgcaccttc tcctgctgcc acgtgtgagg caactctgcg tgtctcctag      60
ctgctccctg acagcttctc tgcatgtgtt tggactctga tgtcctctca gtgtgttgct    120
tttggattga actgtgattc tttctgcctg tatctgtctg tgagattccg tgtttccaat    180
gc                                                                   182
```

<210> SEQ ID NO 625
<211> LENGTH: 148
<212> TYPE: DNA
<213> ORGANISM: Artificial Sequence
<220> FEATURE:
<223> OTHER INFORMATION: Synthetic

<400> SEQUENCE: 625

```
ggagatttca gatggaccta gaatgaggaa ggcaggctac tcaacagttg tggatttggg      60
agtctggaca ctccttgagc tgtgcagttt taattctttc ttaaataaag atacaaagga     120
caatttagga catggaaaac cctagcta                                        148
```

<210> SEQ ID NO 626
<211> LENGTH: 239
<212> TYPE: DNA
<213> ORGANISM: Artificial Sequence
<220> FEATURE:
<223> OTHER INFORMATION: Synthetic

<400> SEQUENCE: 626

```
tgacctctgg ggtaggttac tatcctcttt gtcctgccag taccccctaga aatttgactt     60 aattgctgca tctagggact tagggatttt tcccaaatgc tgtgtagaaa gtcactggag    120
ttaaatctac tccaaccatt tttctgctgt ttcttgaaaa dacaggatga ttcatttaca    180
tctcttttcc ttcacagaat catgagggaa gtattgtgat taccagtgtt aagcatttg    239
```

<210> SEQ ID NO 627
<211> LENGTH: 294
<212> TYPE: DNA
<213> ORGANISM: Artificial Sequence
<220> FEATURE:
<223> OTHER INFORMATION: Synthetic

<400> SEQUENCE: 627

```
acagctcctc cttcttgata ttgcacatgc acttcagttc atggctagct gtatagcttc     60
cgtctgtaaa cttgtatttt caagaatcct tggtattgaa tttttagaaa tgctcacata    120
attgttggga ctgattcatt cctccacgat atgcctcctc tctctgatat cctgctaact    180
gtagccgttg tggcatttga gatgacagga catatatata tatggcccca cacttgacct    240
tgagtgcctg aatgctctga aatcaagcat atggcacagc gctcaagact tttg          294
```

<210> SEQ ID NO 628
<211> LENGTH: 120
<212> TYPE: DNA
<213> ORGANISM: Artificial Sequence
<220> FEATURE:
<223> OTHER INFORMATION: Synthetic

<400> SEQUENCE: 628

```
ccagactcga gaggtgggag gaactccttg cacacaccct gagcttttgc cacttctatc     60
atttttgagc aactccctct cagctaaaag gccacccctt tatcgcattg ctgtccttgg    120
```

<210> SEQ ID NO 629
<211> LENGTH: 191
<212> TYPE: DNA
<213> ORGANISM: Artificial Sequence
<220> FEATURE:
<223> OTHER INFORMATION: Synthetic

<400> SEQUENCE: 629

```
tgaaataatt catgccacgg acctgtgcac atgcctggaa ttgagagaca cagttaaaag      60
actccaagtt gctttctgcc ttttgaaaac tcctgaaaac catcccttttg gactctggaa    120 ttctacacag ctcaaccaag actttgcttg aatgtttaca ttttctgctc gctgtcctac    180
atatcacaat a                                                          191

<210> SEQ ID NO 630
<211> LENGTH: 168
<212> TYPE: DNA
<213> ORGANISM: Artificial Sequence
<220> FEATURE:
<223> OTHER INFORMATION: Synthetic

<400> SEQUENCE: 630
ctgtgctttt accagtagca tgacccctttc tgaagccatc cgtagaaagt actttgtcct    60
ccaaaaagct aacatacggt tttgaagcag cattgaaact tttgtagcaa tctggtctat    120
agacttttaa ctcaagaagc taaggctaga cttgttacct tcgttgaa                  168

<210> SEQ ID NO 631
<211> LENGTH: 332
<212> TYPE: DNA
<213> ORGANISM: Artificial Sequence
<220> FEATURE:
<223> OTHER INFORMATION: Synthetic

<400> SEQUENCE: 631
agaggagggg acaagccagt tctcctttgc agcaaaaaat tacatgtata tattattaag     60
ataatatata cattggattt tattttttta aaaagtttat tttgctccat ttttgaaaaa    120
gagagagctt gggtggcgag cggttttttt tttaaatcaa ttatccttat tttctgttat    180
ttgtccccgt ccctccccac cccctgctg aagcgagaat aagggcaggg accgcggctc     240
ctacctcttg gtgatcccct tccccattcc gccccgcct caacgcccag cacagtgccc    300
tgcacacagt agtcgctcaa taaatgttcg tg                                  332

<210> SEQ ID NO 632
<211> LENGTH: 1879
<212> TYPE: DNA
<213> ORGANISM: Artificial Sequence
<220> FEATURE:
<223> OTHER INFORMATION: Synthetic

<400> SEQUENCE: 632
agccatcggt ctagcatatc agtcactggg cccaacatat ccattttttaa accctttccc    60 ccaaatacac tgcgtcctgg ttcctgttta gctgttctga aatacggtgt gtaagtaagt    120
cagaacccag ctaccagtga ttattgcgag ggcaatggga cctcataaat aaggttttct    180
gtgatgtgac gccagtttac ataagagaat atcactccga tggtcggttt ctgactgtca    240
cgctaagggc aactgtaaac tggaataata atgcactcgc aaccaggtaa acttagatac    300
actagtttgt ttaaaattat agattactg tacatgactt gtaatatact ataatttgta    360
tttgtaaaga gatggtctat attttgtaat tactgtattg tatttgaact gcagcaatat    420
ccatgggtcc taataattgt agttccccac taaaatctag aaattattag tatttttact    480
cgggctatcc agaagtagaa gaaatagagc caattctcat ttattcagcg aaaatcctct    540
ggggttaaaa tttaagttt gaaagaactt gacactacag aaattttct aaaatatttt    600 gagtcactat aaacctatca tctttccaca agatatacca gatgactatt tgcagtcttt    660 tcttttgggca agagttccat gattttgata ctgtaccttt ggatccacca tgggttgcaa    720
```

```
ctgtctttgg ttttgtttgt ttgacttgaa ccaccctctg gtaagtaagt aagtgaatta      780
cagagcaggt ccagctggct gctctgcccc ttgggtatcc atagttacgg ttttctctgt      840
ggcccaccca gggtgttttt tgcatcgctg gtgcagaaat gcataggtgg atgagatata      900
gctgctcttg tcctctgggg actggtggtg ctgcttaaga ataaggggt gctgggaca       960 gaggagcaac gtggtgatct ataggattgg agtgtcgggg tctgtacaaa tcgtattgtt     1020
gccttttaca aaactgctgt actgtatgtt ctctttgagg gcttttatat gcaattgaat     1080
gagggctgaa gttttcatta gaatgcactc acactctgac tgtacgtcct gatgaaaacc     1140
cacttttgga taattagaac cgtcaaggct tcattttctg tcaacagaat taggccgact     1200
gtcaggttac cttggcaggg attccctgca atcaaaaaga tagatgatag gtagcaattt     1260
tggtccaaaa ttttaatag tatacagaca acctgttaat ttttttttt tttttttttt      1320 ttgtaaataa caaacaccac tttgttatga agaccttaca aacctcttct taagacattc     1380
ttactctgat ccaggcaaaa acacttcaag gtttgtaaat gactctttcc tgacataaat     1440 cctttttat taaaatgcaa aatgttcttc agaataaaac tgtgtaataa ttttatact      1500 tgggagtgct ccttgcacag agctgtcatt tgccagtgag agcctccgac agggcaggta     1560
ctgtgccagg gcagctctga aattatggat attcttatcc tcctggttcc ttcggtgcca     1620
atggtaacct aataccagcc gcagggagcg ccatttctcc taaagggcta caccactgtc     1680
aacattatcc tggactctgt gtctctctct gttgggtctt gtggcatcac atcaggccaa     1740
aattgccaga ccaggaccct aagtgtctga tagaggcgat gatctttcc aaagtcagta     1800 cttacaaact ggcattctta caggctgcac catttcctag tatgtctgct ttaagcctgg     1860
ttcaacctct catcgaata                                                  1879

<210> SEQ ID NO 633
<211> LENGTH: 914
<212> TYPE: DNA
<213> ORGANISM: Artificial Sequence
<220> FEATURE:
<223> OTHER INFORMATION: Synthetic

<400> SEQUENCE: 633
ccagtcgctg tggttgtttt agctccttga ctccttgtgg tttatgtcat catacatgac       60
tcagcatacc tgctggtgca gagctgaaga ttttggaggg tcctccacaa taaggtcaat      120
gccagagacg gaagcctttt tccccaaagt cttaaaataa cttatatcat cagcatacct      180
ttattgtgat ctatcaatag tcaagaaaaa ttattgtata agattagaat gaaaattgta      240
tgttaagtta cttcactta attctcatgt gatccttta tgttatttat atattggtaa       300
catcctttct attgaaaaat caccacacca aactctctt attagaacag gcaagtgaag      360
aaaagtgaat gctcaagttt ttcagaaagc attacatttc caaatgaatg accttgttgc      420
atgatgtatt tttgtaccct tcctacagat agtcaaacca taaacttcat ggtcatgggt      480
catgttggtg aaaattattc tgtaggatat aagctaccca cgtacttggt gctttacccc      540
aacccttcca acagtgctgt gaggttggta ttatttcatt ttttagatga gaaaatggga      600
gctcagagag gttatatatt taagttggtg caaaagtaat tgcaagtttt gccaccgaaa      660
ggaatggcaa aaccacaatt attttttgaac caacctaata atttaccgta agtcctacat      720
ttagtatcaa gctagagact gaatttgaac tcaactctgt ccaactccaa aattcatgtg      780
ctttttcctt ctaggccttt cataccaaac taatagtagt ttatattctc ttccaacaaa      840
```

```
tgcatattgg attaaattga ctagaatgga atctggaata tagttcttct ggatggctcc      900
aaaacacatg tttt                                                        914

<210> SEQ ID NO 634
<211> LENGTH: 28
<212> TYPE: DNA
<213> ORGANISM: Artificial Sequence
<220> FEATURE:
<223> OTHER INFORMATION: Synthetic

<400> SEQUENCE: 634
tgttgttgca atgttagtga tgttttaa                                          28

<210> SEQ ID NO 635
<211> LENGTH: 46
<212> TYPE: DNA
<213> ORGANISM: Artificial Sequence
<220> FEATURE:
<223> OTHER INFORMATION: Synthetic

<400> SEQUENCE: 635
aaataatgct tgttacaatt cgacctaata tgtgcattgt aaaata                      46

<210> SEQ ID NO 636
<211> LENGTH: 88
<212> TYPE: DNA
<213> ORGANISM: Artificial Sequence
<220> FEATURE:
<223> OTHER INFORMATION: Synthetic

<400> SEQUENCE: 636
gtttgccctt tggtacagaa ggtgagttaa agctggtgga aaaggcttat tgcattgcat       60
tcagagtaac ctgtgtgcat actctaga                                          88

<210> SEQ ID NO 637
<211> LENGTH: 25
<212> TYPE: DNA
<213> ORGANISM: Artificial Sequence
<220> FEATURE:
<223> OTHER INFORMATION: Synthetic

<400> SEQUENCE: 637
caaagtaaac tcggtggcct cttct                                             25

<210> SEQ ID NO 638
<211> LENGTH: 309
<212> TYPE: DNA
<213> ORGANISM: Artificial Sequence
<220> FEATURE:
<223> OTHER INFORMATION: Synthetic

<400> SEQUENCE: 638
cgaggtgatg ggacttctta acacacattt ctataatacc catgaaatga taatttgtaa       60
aataacactt agtgatatct ggaaataata attcaattaa gcaaccacga atttcaccct      120
ggagatattt tttcttattt gagtccacca aaggataatg ccaacttata taagttctca     180
aatcatgcct tccgcttagt ctcattttat tcattcagtc gtcatgagtt gagtgcttac     240
tacatgcaag gcactctgct agttatattc taataatgca gagataatta gacatggttc     300
ccgccctca                                                              309

<210> SEQ ID NO 639
<211> LENGTH: 526
```

<212> TYPE: DNA
<213> ORGANISM: Artificial Sequence
<220> FEATURE:
<223> OTHER INFORMATION: Synthetic

<400> SEQUENCE: 639

```
ttccatacac gtttgcagtt tcttgtacac atttggatac tttgaaagat gacagattgt    60
taaatccatt caatggtaaa gaaactcacc atctggagat tgagtctact tgttaatgaa   120
tgactagccc aattatcctt ataaattgaa tatggtgacc aaatgctttg atatcatact   180
actctgcctt tgtgggcaca tatgtagaca ctactaaaaa taaatatttt tggagattaa   240
aatggagaat agaagtaatt acattattta ggtcttaatc caactttttt ctaatatatc   300
taaacaattg aaagggaagc ttattcatgg aatattggct tgatttatct agaaagtttt   360
tccttcttca attttactat attcattcta caggaacagc aataagtact attaaacaga   420
agatggctac actaagttcc aattttgttg ctgaattgct tctgtgagtt cacttttcag   480
ttctaaggaa gaataatatt tgctacatat ttcacagggg ttctta              526
```

<210> SEQ ID NO 640
<211> LENGTH: 122
<212> TYPE: DNA
<213> ORGANISM: Artificial Sequence
<220> FEATURE:
<223> OTHER INFORMATION: Synthetic

<400> SEQUENCE: 640

```
cccacctttc catgcttaag acaaaaatgt cttaaatata aagctgtgat tatatcaaaa    60
atccagataa atcatcaaat atatcagatt aagaccaggg tttacacact taggcaatag   120
tc                                                                  122
```

<210> SEQ ID NO 641
<211> LENGTH: 160
<212> TYPE: DNA
<213> ORGANISM: Artificial Sequence
<220> FEATURE:
<223> OTHER INFORMATION: Synthetic

<400> SEQUENCE: 641

```
gtttaattc aacagtccaa cattatttag gtgttacaga gtgtaaatat atttctttgg    60
gagttatttt cttttaaaa tcttttata gcttggcaat gtccaaagtc aaatatcacc   120
taaactggtt agattacttc tacagctaat aatattgcag                         160
```

<210> SEQ ID NO 642
<211> LENGTH: 1340
<212> TYPE: DNA
<213> ORGANISM: Artificial Sequence
<220> FEATURE:
<223> OTHER INFORMATION: Synthetic

<400> SEQUENCE: 642

```
tggctacttg acctacagca aaagccattt ctgtaccata aaatttgtt gtgcaatatt     60
agaattatca tatgtttcct acatctgaca gcacctaaaa tgtttgataa tattaacatg   120
tatctaagag gaaaaagag ttaatatatt ctggcaccca ctttcctagt aatgttttcc   180
atgattttcc agttctgagg cacttattaa agtgcttttt ttttctgaa ttaattaggt   240
attggtaaaa tatatttta aatttagtta gctttataaa cacaattaga attacaatta   300
attaacagag gtataattgt ctcacttca gaagtgatca tttatttta tttagcacag   360
```

```
gtcataagaa aaatatatag aaaaataatc aatttcatat ataaaaggat tatttctcca    420 ccttttaatta ttggcctatc atttgttagt gttatttggt catattattg aactaatgta   480
ttattccatt caaagtcttt ctagatttaa aaatgtatgc aaaagcttag gattatatca    540
tgtgtaacta ttatagataa catcctaaac cttcagtttta gatatataat tgactgggtg   600
taatctcttt tgtaatctgt tttgacagat ttcttaaatt atgttagcat aatcaaggaa    660
gatttacctt gaagcacttt ccaaattgat actttcaaac ttattttaaa gcagtagaac    720
cttttctatg aactaaatca catgcaaaac tccaacctgt agtatacata aaatggactt    780
acttattcct ctcaccttct ccagtgccta ggaatattct tctctgagcc ctaggattga    840
ttctatcaca cagagcaaca ttaatctaaa tggtttagct ccctcttttt tctctaaaaa    900
caatcagcta ataaaaaaaa aatttgaggg cctaaattat ttcaatggtt gtttgaaata    960
ttcagttcag tttgtacctg ttagcagtct ttcagtttgg gggagaatta aatactgtgc   1020
taagctggtg cttggataca tattacagca tcttgtgttt tatttgacaa acagaattttt  1080 ggtgccataa tattttgaga attagagaag attgtgatgc atatatataa acactatttt   1140
taaaaaatat ctaaatatgt ctcacatatt tatataatcc tcaaatatac tgtaccattt   1200
tagatatttt ttaaacagat taatttggag aagtttttatt cattacctaa ttctgtggca  1260
aaaatggtgc ctctgatgtt gtgatatagt attgtcagtg tgtacatata taaaacctgt   1320
gtaaacctct gtccttatga                                                1340

<210> SEQ ID NO 643
<211> LENGTH: 25
<212> TYPE: DNA
<213> ORGANISM: Artificial Sequence
<220> FEATURE:
<223> OTHER INFORMATION: Synthetic

<400> SEQUENCE: 643
ttcatcaact cagtcatcaa attcc                                            25

<210> SEQ ID NO 644
<211> LENGTH: 27
<212> TYPE: DNA
<213> ORGANISM: Artificial Sequence
<220> FEATURE:
<223> OTHER INFORMATION: Synthetic

<400> SEQUENCE: 644
tcttcccatg cactattctg gaggttt                                          27

<210> SEQ ID NO 645
<211> LENGTH: 300
<212> TYPE: DNA
<213> ORGANISM: Artificial Sequence
<220> FEATURE:
<223> OTHER INFORMATION: Synthetic

<400> SEQUENCE: 645
gcacactctg atcaactctt ctctgccgac agtcattttg ctgaatttca gccaaaaata     60
ttatgcattt tgatgcttta ttcaaggcta tacctcaaac ttttttcttct cagaatccag   120 gatttcacag gatacttgta tatatggaaa acaagcaagt ttatattttt ggacagggaa    180
atgtgtgtaa gaaagtatat taacaaatca atgcctccgt caagcaaaca atcatatgta    240
tacttttttt ctacgttatc tcatctcctt gttttcagtg tgcttcaata atgcaggtta   300
```

```
<210> SEQ ID NO 646
<211> LENGTH: 80
<212> TYPE: DNA
<213> ORGANISM: Artificial Sequence
<220> FEATURE:
<223> OTHER INFORMATION: Synthetic

<400> SEQUENCE: 646
tttccaaaac ttgcacgtgt ccctgaattc catctgactc taattttatg agaattgcag      60
aactctgatg gcaataaata                                                  80

<210> SEQ ID NO 647
<211> LENGTH: 175
<212> TYPE: DNA
<213> ORGANISM: Artificial Sequence
<220> FEATURE:
<223> OTHER INFORMATION: Synthetic

<400> SEQUENCE: 647
gcttcaggtg accacaatag caacacctcc ctattctgtt atttcttagt gtaggtagac      60
aattctttca ggagcagagc agcgtcctat aatcctagac cttttcatga cgtgtaaaaa     120
atgatgtttc atcctctgat tgccccaata aaaatctttg ttgtccatcc ctata          175

<210> SEQ ID NO 648
<211> LENGTH: 34
<212> TYPE: DNA
<213> ORGANISM: Artificial Sequence
<220> FEATURE:
<223> OTHER INFORMATION: Synthetic

<400> SEQUENCE: 648
gtttcgacag ctgattacac agttgctgtc ataa                                  34

<210> SEQ ID NO 649
<211> LENGTH: 66
<212> TYPE: DNA
<213> ORGANISM: Artificial Sequence
<220> FEATURE:
<223> OTHER INFORMATION: Synthetic

<400> SEQUENCE: 649
ctggcaatat agcaactatg aagagaaaag ctactaataa aattaaccca acgcatagaa      60
gacttt                                                                 66

<210> SEQ ID NO 650
<211> LENGTH: 129
<212> TYPE: DNA
<213> ORGANISM: Artificial Sequence
<220> FEATURE:
<223> OTHER INFORMATION: Synthetic

<400> SEQUENCE: 650
tctctagcta taagtcttaa ttatacaaca aaatactatt tttatattta tgtttggtaa      60
attcaataac tttcctcatc atttggaaag tcaaattgtt tattgcttcc ctacagtttt     120
ttctgaatc                                                             129

<210> SEQ ID NO 651
<211> LENGTH: 25
<212> TYPE: DNA
<213> ORGANISM: Artificial Sequence
<220> FEATURE:
<223> OTHER INFORMATION: Synthetic
```

```
<400> SEQUENCE: 651
ctgggattct taccctacaa accag                                          25

<210> SEQ ID NO 652
<211> LENGTH: 83
<212> TYPE: DNA
<213> ORGANISM: Artificial Sequence
<220> FEATURE:
<223> OTHER INFORMATION: Synthetic

<400> SEQUENCE: 652
ttcaaagaaa tacatccttg gtttacactc aaaagtcaaa ttaaattctt tcccaatgcc    60
ccaactaatt ttgagattca gtc                                            83

<210> SEQ ID NO 653
<211> LENGTH: 25
<212> TYPE: DNA
<213> ORGANISM: Artificial Sequence
<220> FEATURE:
<223> OTHER INFORMATION: Synthetic

<400> SEQUENCE: 653
agggaaaagt taagacgaat cactg                                          25

<210> SEQ ID NO 654
<211> LENGTH: 27
<212> TYPE: DNA
<213> ORGANISM: Artificial Sequence
<220> FEATURE:
<223> OTHER INFORMATION: Synthetic

<400> SEQUENCE: 654
atcttccaac aacgtttgtc ctcaaat                                        27

<210> SEQ ID NO 655
<211> LENGTH: 33
<212> TYPE: DNA
<213> ORGANISM: Artificial Sequence
<220> FEATURE:
<223> OTHER INFORMATION: Synthetic

<400> SEQUENCE: 655
cctattacag ctaatctcgt tttaaatctg ctc                                 33

<210> SEQ ID NO 656
<211> LENGTH: 63
<212> TYPE: DNA
<213> ORGANISM: Artificial Sequence
<220> FEATURE:
<223> OTHER INFORMATION: Synthetic

<400> SEQUENCE: 656
tatgtaacaa tcttgcacag tgctgctaat gtaaatttca gttttcgcc tctaggacaa     60 aca                                                                  63

<210> SEQ ID NO 657
<211> LENGTH: 235
<212> TYPE: DNA
<213> ORGANISM: Artificial Sequence
<220> FEATURE:
<223> OTHER INFORMATION: Synthetic

<400> SEQUENCE: 657
tttgaagtca actgtatcac gtcgcataac ctaatcacaa agtaatatc cacaaaatta     60
```

```
atagtcctac agatgatgta gggtgtgtac agcaggaagc aggaaatctt gggggttgtc    120
atagaattct gctaaatatg cctagagaca cacatcctta actggacttt aggtttatca    180
tttgtgttct ctggcctcag tgttttcaat tgtggatca tgtaccaata gcatc          235
```

```
<210> SEQ ID NO 658
<211> LENGTH: 215
<212> TYPE: DNA
<213> ORGANISM: Artificial Sequence
<220> FEATURE:
<223> OTHER INFORMATION: Synthetic

<400> SEQUENCE: 658
```

```
ggcctcatta atatagtggc tgatggtacc tactaacctt caatgggtcg cctcctacct    60
attctcattt cattagcttt ttgaaggaca gggtagacta gatcaagaaa agagataaaa    120
agaaatagta catattcaca cttatgtaat tacatcccct tccatggaaa cttgggaata    180
aagaggtatt tcaaggtcat gtagaaaaag taaac                               215
```

```
<210> SEQ ID NO 659
<211> LENGTH: 25
<212> TYPE: DNA
<213> ORGANISM: Artificial Sequence
<220> FEATURE:
<223> OTHER INFORMATION: Synthetic

<400> SEQUENCE: 659
```

```
gttgtgggga ttaagacatt aattc                                          25
```

```
<210> SEQ ID NO 660
<211> LENGTH: 200
<212> TYPE: DNA
<213> ORGANISM: Artificial Sequence
<220> FEATURE:
<223> OTHER INFORMATION: Synthetic

<400> SEQUENCE: 660
```

```
tctcactttg catttagtca aaagaaaaaa tgctttatag caaaatgaaa gagaacatga    60
aatgcttctt tctcagttta ttggttgaat gtgtatctat ttgagtctgg aaataactaa    120
tgtgtttgat aattagttta gtttgtggct tcatggaaac tccctgtaaa ctaaaagctt    180
cagggttatg tctatgttca                                                200
```

```
<210> SEQ ID NO 661
<211> LENGTH: 327
<212> TYPE: DNA
<213> ORGANISM: Artificial Sequence
<220> FEATURE:
<223> OTHER INFORMATION: Synthetic

<400> SEQUENCE: 661
```

```
agccctcact ctaaagtcac ttgtcacaca ttctatcaaa taagggagaa aaaacaaac     60 actatatcca attatagttt tccacctgaa actaccaaaa tagaaaaaaa aaattttcct    120
attaaaatgg aaaaagtcta agtgctcagg tagaatcatt gaattatcat ttttgctaga    180
gttgacctta tgcatttcaa ggctggcacc atcatgtaca ggaacaatat gctcattgct    240
cctcccaccc atccccacca tgatgaagaa aagagctgat tagtgaacaa ctaataaata    300
tgtgccatct gggtactagt aacttta                                        327
```

```
<210> SEQ ID NO 662
```

```
<211> LENGTH: 224
<212> TYPE: DNA
<213> ORGANISM: Artificial Sequence
<220> FEATURE:
<223> OTHER INFORMATION: Synthetic

<400> SEQUENCE: 662
caggtataag gttagatgct acatctagga gcattcaaga tatacattaa tttaaacttt      60
tattagtcta actttctgtt aagtctctta gctttgaaac ataaaagaga aatcaagccc     120 aaattttag aggaaggcta aggtatacta ttggcagttg tagttttaat tgtaattgac     180
tgattaacca agtaatttat aaaatgttac ctatactgtc agtg                     224

<210> SEQ ID NO 663
<211> LENGTH: 224
<212> TYPE: DNA
<213> ORGANISM: Artificial Sequence
<220> FEATURE:
<223> OTHER INFORMATION: Synthetic

<400> SEQUENCE: 663
ccgactaaca tggtaataga cctgaatgca taatgagttc ttactttgct atcatcaaaa     60
gacttttcat cacagttaca tactttctaa tttatggaaa aacagcattt ggaaaacaaa    120
tgttttgttt ttattttttt aaagatttaa aaaataaatc aactagggac taggaatcaa    180
caactgtgag tgagttaaac tgtgttgaaa tactaaaggg ttgt                     224

<210> SEQ ID NO 664
<211> LENGTH: 231
<212> TYPE: DNA
<213> ORGANISM: Artificial Sequence
<220> FEATURE:
<223> OTHER INFORMATION: Synthetic

<400> SEQUENCE: 664
ttcttgccta aacattggac tgtactttgc atttttttct ttaaaaattt ctattctaac     60
acaacttggt tgatttttcc tggtctactt tatggttatt agacatactc atgggtatta    120
ttagatttca taatggtcaa tgataatagg aattacatgg agcccaacag agaatatttg    180
ctcaatacat ttttgttaat atatttagga acttaatgga gtctctcagt g             231

<210> SEQ ID NO 665
<211> LENGTH: 118
<212> TYPE: DNA
<213> ORGANISM: Artificial Sequence
<220> FEATURE:
<223> OTHER INFORMATION: Synthetic

<400> SEQUENCE: 665
ctagagttct catttattca ggatacctat tcttactgta ttaaaatttg gatatgtgtt     60
tcattctgtc tcaaaaatca cattttattc tgagaaggtt ggttaaaaga tggcagaa     118

<210> SEQ ID NO 666
<211> LENGTH: 37
<212> TYPE: DNA
<213> ORGANISM: Artificial Sequence
<220> FEATURE:
<223> OTHER INFORMATION: Synthetic

<400> SEQUENCE: 666
gtgctagttg atatcatgat tgatttggtc ttcttgg                              37
```

<210> SEQ ID NO 667
<211> LENGTH: 108
<212> TYPE: DNA
<213> ORGANISM: Artificial Sequence
<220> FEATURE:
<223> OTHER INFORMATION: Synthetic

<400> SEQUENCE: 667

```
ttacgttagt actgcagagg aaataacttg gaagttacag ggaataacaa taggtactag      60
aaattgagtg ctatgggtac gtattagatc gttagctcat ttagtatc                  108
```

<210> SEQ ID NO 668
<211> LENGTH: 127
<212> TYPE: DNA
<213> ORGANISM: Artificial Sequence
<220> FEATURE:
<223> OTHER INFORMATION: Synthetic

<400> SEQUENCE: 668

```
ctatagaagg ttattgtagt tatctttagt actatgttat tttaggaggc ctgtgtttaa      60
attttacaat tcattaacag gactgatggc attttgtagg aactacttag gaacaagttt     120
gcatttc                                                               127
```

<210> SEQ ID NO 669
<211> LENGTH: 28
<212> TYPE: DNA
<213> ORGANISM: Artificial Sequence
<220> FEATURE:
<223> OTHER INFORMATION: Synthetic

<400> SEQUENCE: 669

```
gacacttagg tgataacaat tctggtat                                         28
```

<210> SEQ ID NO 670
<211> LENGTH: 423
<212> TYPE: DNA
<213> ORGANISM: Artificial Sequence
<220> FEATURE:
<223> OTHER INFORMATION: Synthetic

<400> SEQUENCE: 670

```
gggctctcta gaaaggtaat tattatctga tataatagtt tagtctgtga tgcttctttt      60
aacatatttg taagttttaa ccaaatggtt aaagaaattt gcttttaac ccttaaacct      120 cacatatcca caagtctcta aattccatag gatgctatgg atttctagtt gcctagttca     180
tgtcttttac ttagaaaacg tcagaaaacc caaacttctc gtgacttcaa aaagtgtaat     240
tgtacctgaa acttcttttc cttcagattt cttatttatg ttttctgata ggttttaag     300 attaatctttt tcagaaggat gctctaaaaa tctggccaat tgattatcc tcttccaact    360 tggaaaaaat atgtatttaa aatgagacta gaatttgaat gaccttcttt catgaactc     420 tga                                                                   423
```

<210> SEQ ID NO 671
<211> LENGTH: 26
<212> TYPE: DNA
<213> ORGANISM: Artificial Sequence
<220> FEATURE:
<223> OTHER INFORMATION: Synthetic

<400> SEQUENCE: 671

```
gttgttgcct ctaacatgta taaagg                                           26
```

<210> SEQ ID NO 672
<211> LENGTH: 63
<212> TYPE: DNA
<213> ORGANISM: Artificial Sequence
<220> FEATURE:
<223> OTHER INFORMATION: Synthetic

<400> SEQUENCE: 672

```
aagtcattat cttgctttgg aatcattatc tggcattatc aacttgcatt tggttccaca      60
aca                                                                   63
```

<210> SEQ ID NO 673
<211> LENGTH: 25
<212> TYPE: DNA
<213> ORGANISM: Artificial Sequence
<220> FEATURE:
<223> OTHER INFORMATION: Synthetic

<400> SEQUENCE: 673

```
gtgagaaaaa acaagtcata taaaa                                           25
```

<210> SEQ ID NO 674
<211> LENGTH: 206
<212> TYPE: DNA
<213> ORGANISM: Artificial Sequence
<220> FEATURE:
<223> OTHER INFORMATION: Synthetic

<400> SEQUENCE: 674

```
aggaataatt gatcaagatg acataaaatt tacaaattta tttgtgccta ataatagtct      60
caaattacat aaggcaaaaa ctgatagaat gaaaggaaga aataggcaat tataattgga     120
aattttaatg tctctcagaa gttgatagag taaccaacaa aaaatcagca gacagaaaac     180
ctgaacaaca ttatcagtca ctttga                                         206
```

<210> SEQ ID NO 675
<211> LENGTH: 31
<212> TYPE: DNA
<213> ORGANISM: Artificial Sequence
<220> FEATURE:
<223> OTHER INFORMATION: Synthetic

<400> SEQUENCE: 675

```
ctgggcccctt tacagttgat acccaaagca g                                   31
```

<210> SEQ ID NO 676
<211> LENGTH: 432
<212> TYPE: DNA
<213> ORGANISM: Artificial Sequence
<220> FEATURE:
<223> OTHER INFORMATION: Synthetic

<400> SEQUENCE: 676

```
tctgggtact aggagtagac catccattct tgatttgaac tgtttctgca ggtactcatt      60
tgttcaaaca ctgcctattt cgttttgcaa cagatctatt ttagaaaatc tttatattga     120
gcaaacagca gtctcactat agcctctact tgttggtcat aatctgccag aggaagctta     180
cctgatgatg atggtgctgc tgctgctgat aatgatggtg atggtaatga cgaacatgac     240
acaagatcac aggcactgtg ctaagcatta aacacataca atcttattta atcctcataa     300
tgttatggca taaatattac ccctctttta aagatgaaca aacagatgat taaggggta      360 aagttgcttt gatctttaat attaatttgt gtctttctca cttcaaattc agcgatgaac     420
```
cctattccta tg                                                                432

<210> SEQ ID NO 677
<211> LENGTH: 25
<212> TYPE: DNA
<213> ORGANISM: Artificial Sequence
<220> FEATURE:
<223> OTHER INFORMATION: Synthetic

<400> SEQUENCE: 677
cctttgatct taagattgtt ggcat                                                  25

<210> SEQ ID NO 678
<211> LENGTH: 134
<212> TYPE: DNA
<213> ORGANISM: Artificial Sequence
<220> FEATURE:
<223> OTHER INFORMATION: Synthetic

<400> SEQUENCE: 678
actgtggctt caatagcctc atagaagtgt ccttcctttt taacaaaggg aatccaagat            60
ggcggaaagg tcctaacatt gagcatataa tccatctctt tgctaaacta gatgtttcct           120
tccagatttc tatg                                                             134

<210> SEQ ID NO 679
<211> LENGTH: 58
<212> TYPE: DNA
<213> ORGANISM: Artificial Sequence
<220> FEATURE:
<223> OTHER INFORMATION: Synthetic

<400> SEQUENCE: 679
atggaagcaa aagggacaga cttgaagctg tacttccaga ctctcatgga agctccag             58

<210> SEQ ID NO 680
<211> LENGTH: 279
<212> TYPE: DNA
<213> ORGANISM: Artificial Sequence
<220> FEATURE:
<223> OTHER INFORMATION: Synthetic

<400> SEQUENCE: 680
gagcaatgct taacccatcg gaatgtatac cctaagcaaa actgtcaacc aggcaaaggg            60
tgttctttct cttctggcgc tctgctcttc gtccctgtcc ccagcagccc atctgctact          120
ggaacttgtt cacagagtcc ttctgccaac ttatcatatt cttgttccag gaacttttct          180
gctttaagta aaggatcttc tcccaacgag tatgctcctg catttgcaga tacagcacag          240
ctccatgcat ttgtagccct gccatattag tgtcctagc                                 279

<210> SEQ ID NO 681
<211> LENGTH: 761
<212> TYPE: DNA
<213> ORGANISM: Artificial Sequence
<220> FEATURE:
<223> OTHER INFORMATION: Synthetic

<400> SEQUENCE: 681
ccctaggtag gagataacaa gtatgtacca ttactgaata ttaaatcctt ctttaccata            60
gctacagtta agtaggtgta tctcagaaac ctaaggtagt tttaaatgta gtgaaattgt          120
ccacagcaag ctggcccaag tgctcacatt ttatacccgc tctgtcttag tgcgttgcaa          180

```
gagaggagta tatacagtag ttccccctta tccacagggg tacattctaa gacccccggt    240
gggtgactga aaccacagat agtaccgaat cttatacata ctatgttttt tttctaaaca    300
taaataccta caataaagtt taatttttaa attaggcacc ataattaata ataaaacaga    360
acagttataa caatatacta taataaaatt atgtgtatgt gatctctctt tctctctccc    420
tctcaaaata tttttaatat ctctccagaa ttcagtgcaa ataattccat catactcact    480
tcagaaaagt gaagatagtc ttgtacatga gtagattcaa attttattgt cgtggtttcc    540
aaagttttat ttttctcacc aatggaactt ttgattcaaa taaaatatcc aagggatttc    600
agcttataaa acacacaaaa ttgataatga gttttccaag gtactgtgtg tgtgaatgtg    660
tatgtctgtg tatgtgtgtg tcgtctgtat gttttcccca cctcttgtag aagctacgaa    720
gcacctttcc atattattga ggtttcctgt acgtagactg a                       761
```

<210> SEQ ID NO 682
<211> LENGTH: 142
<212> TYPE: DNA
<213> ORGANISM: Artificial Sequence
<220> FEATURE:
<223> OTHER INFORMATION: Synthetic

<400> SEQUENCE: 682

```
acctggactg aagttcgcat tgaactctac aacattctgt gggatatatt gttcaaaaag     60
atattgttgt tttccatgat ttagcaagca actaattttc tcccaagctg attttattca    120
atatggttac gttggttaaa ta                                            142
```

<210> SEQ ID NO 683
<211> LENGTH: 93
<212> TYPE: DNA
<213> ORGANISM: Artificial Sequence
<220> FEATURE:
<223> OTHER INFORMATION: Synthetic

<400> SEQUENCE: 683

```
cagtatatga tatggcagag ttgcacagaa gaatcagaac attgttttag agaaacgttg     60
ggcaattaat taagccagct gattaagttt taa                                  93
```

<210> SEQ ID NO 684
<211> LENGTH: 203
<212> TYPE: DNA
<213> ORGANISM: Artificial Sequence
<220> FEATURE:
<223> OTHER INFORMATION: Synthetic

<400> SEQUENCE: 684

```
ttcaccactg tagatcccat gcatggatct atgtagtatg ctctgactct aataggactg     60
tatatactgt tttaagaatg ggctgaaatc agaatgcctg tttgtggttt catatgcaat    120
aatatatttt tttaaaaatg tggacttcat aggaaggcgt gagtacaatt agtataatgc    180
ataactcatt gttgtcctag ata                                           203
```

<210> SEQ ID NO 685
<211> LENGTH: 100
<212> TYPE: DNA
<213> ORGANISM: Artificial Sequence
<220> FEATURE:
<223> OTHER INFORMATION: Synthetic

<400> SEQUENCE: 685

```
gccaaaacca atatgcttat aagaaataat gaaaagttca tccatttctg ataaagttct     60
```

```
ctatggcaaa gtctttcaaa tacgagataa ctgcaaaata                    100
```

<210> SEQ ID NO 686
<211> LENGTH: 450
<212> TYPE: DNA
<213> ORGANISM: Artificial Sequence
<220> FEATURE:
<223> OTHER INFORMATION: Synthetic

<400> SEQUENCE: 686

```
ttccaaatac tcatggtgca caagaaggtt atgtatgcac agtatttcta atttattcaa     60
attcaatttg aatttggtct gaagctatct tgtatgaaat gttagctttc ctgatattta    120
ataatattta ttatgtttgc atataagctc aaaaaattaa tgcaaaagta tactttactc    180
atggttatct tcaggtaaat attagtggtt atgtttaaaa gcctgatttt atatagatga    240
agttgagaaa aaaaagagt atggaaaggt aaattaggtc ttagtcttga ttctgttacc    300
agctgtttga ccttgagtaa ctcttcaccc ttcaatgggc cccagtttgc tcctctatga    360
attttaaggg gttggactag ttgacagacc aggccccttc caagtctaac atttcaaaat    420
cctaacattc caggttctat catcttgata                                    450
```

<210> SEQ ID NO 687
<211> LENGTH: 27
<212> TYPE: DNA
<213> ORGANISM: Artificial Sequence
<220> FEATURE:
<223> OTHER INFORMATION: Synthetic

<400> SEQUENCE: 687

```
ttgtattttg catactcaag gtgagaa                                        27
```

<210> SEQ ID NO 688
<211> LENGTH: 25
<212> TYPE: DNA
<213> ORGANISM: Artificial Sequence
<220> FEATURE:
<223> OTHER INFORMATION: Synthetic

<400> SEQUENCE: 688

```
gatctaccat acccattgac taact                                          25
```

<210> SEQ ID NO 689
<211> LENGTH: 26
<212> TYPE: DNA
<213> ORGANISM: Artificial Sequence
<220> FEATURE:
<223> OTHER INFORMATION: Synthetic

<400> SEQUENCE: 689

```
gagatacatc atcatatcac ggaaag                                         26
```

<210> SEQ ID NO 690
<211> LENGTH: 28
<212> TYPE: DNA
<213> ORGANISM: Artificial Sequence
<220> FEATURE:
<223> OTHER INFORMATION: Synthetic

<400> SEQUENCE: 690

```
atcagctttg agtgaacttt gacagaag                                       28
```

<210> SEQ ID NO 691

<211> LENGTH: 363
<212> TYPE: DNA
<213> ORGANISM: Artificial Sequence
<220> FEATURE:
<223> OTHER INFORMATION: Synthetic

<400> SEQUENCE: 691

```
cctgtaccct tatgcagagc aagcattcca tcctaagtta taaactacag tgatgtttaa      60
ttttgaagcc aggtctacat tatttaatta atggcttcaa aaggtggaga tgcactttat    120
ttaatgtctt tccctagcta attcttactc tcaccttaaa tatgctttct tgttgcatat    180
atgcacagat acacacacac acacacacga aaataaataa atgttcatat tcttctgttc    240
aacagacatt tattttctcc tctcccttga ataagaaaat aagttttcca ttcctatgaa    300
ctgtctaata tctttctatt acagaagggg aaactgaggc tgggaaaggc taaatgactt    360
atc                                                                  363
```

<210> SEQ ID NO 692
<211> LENGTH: 229
<212> TYPE: DNA
<213> ORGANISM: Artificial Sequence
<220> FEATURE:
<223> OTHER INFORMATION: Synthetic

<400> SEQUENCE: 692

```
gtcctcagtg taccactact tagagatatg tatcataaaa ataaaatctg taaaccatag      60
gtaatgatta tataaaatac ataatatttt tcaattttga aaactctaat tgtccattct    120
tgcttgactc tactattaag tttgaaaata gttaccttca aaggccaaga gaattctatt    180
tgaagcatgc tctgtaagtt gcttcctaac atccttggac tgagaaatt                229
```

<210> SEQ ID NO 693
<211> LENGTH: 141
<212> TYPE: DNA
<213> ORGANISM: Artificial Sequence
<220> FEATURE:
<223> OTHER INFORMATION: Synthetic

<400> SEQUENCE: 693

```
ctggttaatt agcaatttaa gaccagagcc aaattatccc aagagcatac attcttttgg      60
ttttcctaac tttgtgaaaa aaattgatgc agctgttttt aacccacgtt tttataggac    120
ctacttcttt gtagataacc a                                              141
```

<210> SEQ ID NO 694
<211> LENGTH: 34
<212> TYPE: DNA
<213> ORGANISM: Artificial Sequence
<220> FEATURE:
<223> OTHER INFORMATION: Synthetic

<400> SEQUENCE: 694

```
tgatgctgtc actaccgtgg gaaataagat cttt                                 34
```

<210> SEQ ID NO 695
<211> LENGTH: 105
<212> TYPE: DNA
<213> ORGANISM: Artificial Sequence
<220> FEATURE:
<223> OTHER INFORMATION: Synthetic

<400> SEQUENCE: 695

```
cacctgacat gaaccgtgag gatgttgact acgcaatccg gaaagctttc caagtatgga      60
```
gtaatgttac cccttgaaa ttcagcaaga ttaacacagg catgg    105

<210> SEQ ID NO 696
<211> LENGTH: 25
<212> TYPE: DNA
<213> ORGANISM: Artificial Sequence
<220> FEATURE:
<223> OTHER INFORMATION: Synthetic

<400> SEQUENCE: 696
agataaacaa acttccagtg acaaa    25

<210> SEQ ID NO 697
<211> LENGTH: 340
<212> TYPE: DNA
<213> ORGANISM: Artificial Sequence
<220> FEATURE:
<223> OTHER INFORMATION: Synthetic

<400> SEQUENCE: 697
tgcttcaagc caatgcaaaa agttcataca ttatattccc tatttcattg tgtttagaat    60
atattatatt gtttaaatgc cactaccaca gtgtaatttt ttttttttta atactgaatc    120
tctggaataa tggtaaggtc aaaatatatt gtattgagag tttaaaaatt aagagcaatt    180
tttaaaaatg taacaaacat ctaaatatct gacaataaaa tctgaaatgc tgtaacttca    240
acattaactg caccatccaa attcttgtga cttacgcatt tttgcccaat ttaacctttc    300
tgatgttccc ctgcccccag acaccataaa tgcattgtaa    340

<210> SEQ ID NO 698
<211> LENGTH: 31
<212> TYPE: DNA
<213> ORGANISM: Artificial Sequence
<220> FEATURE:
<223> OTHER INFORMATION: Synthetic

<400> SEQUENCE: 698
ttccaggact gtcataatga tctgtacttc c    31

<210> SEQ ID NO 699
<211> LENGTH: 231
<212> TYPE: DNA
<213> ORGANISM: Artificial Sequence
<220> FEATURE:
<223> OTHER INFORMATION: Synthetic

<400> SEQUENCE: 699
ctgctgtggt ttgtaagaac tcattgacta actcaaggtc acaaaaattt tctcctttat    60
tttttctag acattttata gcttcaggtt ttatactgag gtctatgatt tatttgggat    120
taattcgaca aatgtaaatt tgtcgaaaag actattttc tttactaaat tgcttttgca    180
cctttatcac caatcagttg tctgtatatt catgggatta tttctaaact c    231

<210> SEQ ID NO 700
<211> LENGTH: 25
<212> TYPE: DNA
<213> ORGANISM: Artificial Sequence
<220> FEATURE:
<223> OTHER INFORMATION: Synthetic

<400> SEQUENCE: 700
atttacagct tgtagcaatt atgta    25

<210> SEQ ID NO 701
<211> LENGTH: 81
<212> TYPE: DNA
<213> ORGANISM: Artificial Sequence
<220> FEATURE:
<223> OTHER INFORMATION: Synthetic

<400> SEQUENCE: 701
ctaccataaa gtccgtaagt gaatacaacg aatgtaattg acataataat tgaaaatcat    60
tgactatacc taaaatagtt c    81

<210> SEQ ID NO 702
<211> LENGTH: 128
<212> TYPE: DNA
<213> ORGANISM: Artificial Sequence
<220> FEATURE:
<223> OTHER INFORMATION: Synthetic

<400> SEQUENCE: 702
gctctggcta tatcaaataa aagtgtcaag agtgagcatc cttgccttgt gctgaatcac    60
aaaggaatac ctttcagttt ttctccattg attatgatag cagtgggctt ttcacagtgg   120
gctttact    128

<210> SEQ ID NO 703
<211> LENGTH: 40
<212> TYPE: DNA
<213> ORGANISM: Artificial Sequence
<220> FEATURE:
<223> OTHER INFORMATION: Synthetic

<400> SEQUENCE: 703
tcttagcatc caatcttatg gaccattttc atacaaagcc    40

<210> SEQ ID NO 704
<211> LENGTH: 26
<212> TYPE: DNA
<213> ORGANISM: Artificial Sequence
<220> FEATURE:
<223> OTHER INFORMATION: Synthetic

<400> SEQUENCE: 704
ctccaacaat aaagcacaga gtggat    26

<210> SEQ ID NO 705
<211> LENGTH: 25
<212> TYPE: DNA
<213> ORGANISM: Artificial Sequence
<220> FEATURE:
<223> OTHER INFORMATION: Synthetic

<400> SEQUENCE: 705
ttagatgtca ttgaatcctt ttcaa    25

<210> SEQ ID NO 706
<211> LENGTH: 25
<212> TYPE: DNA
<213> ORGANISM: Artificial Sequence
<220> FEATURE:
<223> OTHER INFORMATION: Synthetic

<400> SEQUENCE: 706
ttcttaaagt ttggcaataa atcca    25

```
<210> SEQ ID NO 707
<211> LENGTH: 39
<212> TYPE: DNA
<213> ORGANISM: Artificial Sequence
<220> FEATURE:
<223> OTHER INFORMATION: Synthetic

<400> SEQUENCE: 707
gtggccacat catgcaaata tagtctcacc attcctagg                               39

<210> SEQ ID NO 708
<211> LENGTH: 149
<212> TYPE: DNA
<213> ORGANISM: Artificial Sequence
<220> FEATURE:
<223> OTHER INFORMATION: Synthetic

<400> SEQUENCE: 708
tcttggcaga actgctctat tgctcaagga agacttagtt tctggaaata ttccccgggt        60
gagttaaggg ttgtgtaaaa atgcaagaat ggaatacgaa atgattttca ttttgatggt       120
tacttatgaa gtttttgtgt tccgtagaa                                        149

<210> SEQ ID NO 709
<211> LENGTH: 30
<212> TYPE: DNA
<213> ORGANISM: Artificial Sequence
<220> FEATURE:
<223> OTHER INFORMATION: Synthetic

<400> SEQUENCE: 709
cattcatctt tgaataacgt ctccttgttt                                        30

<210> SEQ ID NO 710
<211> LENGTH: 283
<212> TYPE: DNA
<213> ORGANISM: Artificial Sequence
<220> FEATURE:
<223> OTHER INFORMATION: Synthetic

<400> SEQUENCE: 710
cagagccaga tctttagacg tgatggattc ccaagtttcg ttcttaaaat agacaaactg        60
aggccaagag tgcaccagcc tgccaagcac agacatgaca cctaaggact ttcctcccct       120
aagtgtgtgg ttctggggag ccagccttcc tttgtccttc ataaccccag tcactgcctt       180
tccagccttc tgccaggtct ggggctcaga tggagataag cttttcacag aagaccctca       240
ctcgaaagat ccaccactta tctcccatct ccgacagtgc atg                         283

<210> SEQ ID NO 711
<211> LENGTH: 28
<212> TYPE: DNA
<213> ORGANISM: Artificial Sequence
<220> FEATURE:
<223> OTHER INFORMATION: Synthetic

<400> SEQUENCE: 711
atgtattttg tagcaacttc gatggagc                                          28

<210> SEQ ID NO 712
<211> LENGTH: 26
<212> TYPE: DNA
<213> ORGANISM: Artificial Sequence
<220> FEATURE:
<223> OTHER INFORMATION: Synthetic
```

<400> SEQUENCE: 712
ctgacacgac acttttctgt ggtttc 26

<210> SEQ ID NO 713
<211> LENGTH: 69
<212> TYPE: DNA
<213> ORGANISM: Artificial Sequence
<220> FEATURE:
<223> OTHER INFORMATION: Synthetic

<400> SEQUENCE: 713
gtacaatcac tacaacatgc tctgccaccc actccttttc cagtgacact acttgagcca 60
cacactttc 69

<210> SEQ ID NO 714
<211> LENGTH: 32
<212> TYPE: DNA
<213> ORGANISM: Artificial Sequence
<220> FEATURE:
<223> OTHER INFORMATION: Synthetic

<400> SEQUENCE: 714
cgtctttggt caggaacttt ataatgtgct at 32

<210> SEQ ID NO 715
<211> LENGTH: 31
<212> TYPE: DNA
<213> ORGANISM: Artificial Sequence
<220> FEATURE:
<223> OTHER INFORMATION: Synthetic

<400> SEQUENCE: 715
agcagccttg acaaaacgtt cctggaactc a 31

<210> SEQ ID NO 716
<211> LENGTH: 150
<212> TYPE: DNA
<213> ORGANISM: Artificial Sequence
<220> FEATURE:
<223> OTHER INFORMATION: Synthetic

<400> SEQUENCE: 716
gctatccaca gcttacagca atttgataaa atatactttt gtgaacaaaa attgagacat 60
ttacattttc tccctatgtg gtcgctccag acttgggaaa ctattcatga atatttatat 120
tgtatggtaa tatagttatt gcacaagttc 150

<210> SEQ ID NO 717
<211> LENGTH: 59
<212> TYPE: DNA
<213> ORGANISM: Artificial Sequence
<220> FEATURE:
<223> OTHER INFORMATION: Synthetic

<400> SEQUENCE: 717
tttgactaga atgtcgtatt tgaggatata aacccatagg taataaaccc acaggtact 59

<210> SEQ ID NO 718
<211> LENGTH: 27
<212> TYPE: DNA
<213> ORGANISM: Artificial Sequence
<220> FEATURE:
<223> OTHER INFORMATION: Synthetic

<400> SEQUENCE: 718
tgcaaaataa cgacttatct gcttttc                                    27

<210> SEQ ID NO 719
<211> LENGTH: 26
<212> TYPE: DNA
<213> ORGANISM: Artificial Sequence
<220> FEATURE:
<223> OTHER INFORMATION: Synthetic

<400> SEQUENCE: 719
gcaatagaag acacgtctag cttgaa                                     26

<210> SEQ ID NO 720
<211> LENGTH: 105
<212> TYPE: DNA
<213> ORGANISM: Artificial Sequence
<220> FEATURE:
<223> OTHER INFORMATION: Synthetic

<400> SEQUENCE: 720
gaaccattgg agatactcat tactctttga aggcttacag tggaatgaat tcaaatacga    60
cttatttgag gaattgaagt tgactttatg gagctgataa gaatc                  105

<210> SEQ ID NO 721
<211> LENGTH: 329
<212> TYPE: DNA
<213> ORGANISM: Artificial Sequence
<220> FEATURE:
<223> OTHER INFORMATION: Synthetic

<400> SEQUENCE: 721
agcgaccaca tagggagaaa atgtaaatgt ctcaattttt gttcacaaaa gtatatttta    60
tcaaattgct gtaagctgtg gatagcttaa aagaaaaaaa gtttcctgaa atctgggaaa   120
caagacattt aaagaatcag caaaatttca aataaaaaat tatgaaaata ttatcctcat   180
tagttcattt agtcccatga aattaattat tttctctgct tgatcttggt ggacagtttc   240
atgaagctgt cagttagttc attaaagttt tggaaattct cagacagtgc agtggtatca   300
gaaacttgta ttcaagagta caggtcaga                                    329

<210> SEQ ID NO 722
<211> LENGTH: 223
<212> TYPE: DNA
<213> ORGANISM: Artificial Sequence
<220> FEATURE:
<223> OTHER INFORMATION: Synthetic

<400> SEQUENCE: 722
atgcctcata ttgtatctag attggtctta aacatgctct gcacttctct gccttcatgg    60 aagactttg ctgatatttc cttcacttga tacactttg gcttttccac cctctccctg    120
cccccaattt ctgcttgcca gaataatatc tgttcttctt tcattcattt atttaacaac   180
tattgagaca ctgttgtagg tgcttggata cacctagtga aca                    223

<210> SEQ ID NO 723
<211> LENGTH: 25
<212> TYPE: DNA
<213> ORGANISM: Artificial Sequence
<220> FEATURE:
<223> OTHER INFORMATION: Synthetic

<400> SEQUENCE: 723
aaagaagtga agcaaacgga tggga                                         25

<210> SEQ ID NO 724
<211> LENGTH: 26
<212> TYPE: DNA
<213> ORGANISM: Artificial Sequence
<220> FEATURE:
<223> OTHER INFORMATION: Synthetic

<400> SEQUENCE: 724
ttctgatgct gtatttaacc actata                                        26

<210> SEQ ID NO 725
<211> LENGTH: 234
<212> TYPE: DNA
<213> ORGANISM: Artificial Sequence
<220> FEATURE:
<223> OTHER INFORMATION: Synthetic

<400> SEQUENCE: 725
ctgcctcagg gtaatctgaa ttttctatct caagttagag attactcttc acccttccc    60 aagcagatat taaagtctct tattctgttt ttttcccttta aaaagtatca gatctgtcaa  120
gagttgtttc ttcagaatct tctattgcca aaaactgttc ttataatcta ttttatcatt   180
cactcacttt gtcactgatt aacatattag caccaaagtt caaccaatgc ttac          234

<210> SEQ ID NO 726
<211> LENGTH: 25
<212> TYPE: DNA
<213> ORGANISM: Artificial Sequence
<220> FEATURE:
<223> OTHER INFORMATION: Synthetic

<400> SEQUENCE: 726
tttgcaaaag cacggatgtg gatga                                         25

<210> SEQ ID NO 727
<211> LENGTH: 26
<212> TYPE: DNA
<213> ORGANISM: Artificial Sequence
<220> FEATURE:
<223> OTHER INFORMATION: Synthetic

<400> SEQUENCE: 727
atgtccatgt ccatcttaat gtcttt                                        26

<210> SEQ ID NO 728
<211> LENGTH: 27
<212> TYPE: DNA
<213> ORGANISM: Artificial Sequence
<220> FEATURE:
<223> OTHER INFORMATION: Synthetic

<400> SEQUENCE: 728
aggtactgaa tgactaggaa acaggaa                                       27

<210> SEQ ID NO 729
<211> LENGTH: 26
<212> TYPE: DNA
<213> ORGANISM: Artificial Sequence
<220> FEATURE:
<223> OTHER INFORMATION: Synthetic

<400> SEQUENCE: 729
gagcacctga tcttcggaga tgcctg                                        26

<210> SEQ ID NO 730
<211> LENGTH: 362
<212> TYPE: DNA
<213> ORGANISM: Artificial Sequence
<220> FEATURE:
<223> OTHER INFORMATION: Synthetic

<400> SEQUENCE: 730

```
tctgtgacag ttggtattgt cagtctttca ctagagattt caatgagtta aacataagcg      60
acactcagtt cattattctt agtaatgagg gatgaagaca ggacataagc aaagtgaata     120
acaaaaatag aaattttatc cacaaaaaat caatacctcc tttgctcagc taatgtgcaa     180
tagtgatagt ctagacaaat taaagaaatt ccattttatt ttaaacactc tagttacttt     240
tgtgtagtct aacatattgt acatattagg tactcactaa atctcctttg attggtttcc     300
ttagccttac tctgagatgt tttattcagt taacaaatgc ttacataatg cttgcagtga     360
gc                                                                    362
```

<210> SEQ ID NO 731
<211> LENGTH: 25
<212> TYPE: DNA
<213> ORGANISM: Artificial Sequence
<220> FEATURE:
<223> OTHER INFORMATION: Synthetic

<400> SEQUENCE: 731

```
gacagatctt cttgtgttta gtgaa                                            25
```

<210> SEQ ID NO 732
<211> LENGTH: 34
<212> TYPE: DNA
<213> ORGANISM: Artificial Sequence
<220> FEATURE:
<223> OTHER INFORMATION: Synthetic

<400> SEQUENCE: 732

```
taggataatt ggttctagaa ttgaattcaa aagt                                  34
```

<210> SEQ ID NO 733
<211> LENGTH: 25
<212> TYPE: DNA
<213> ORGANISM: Artificial Sequence
<220> FEATURE:
<223> OTHER INFORMATION: Synthetic

<400> SEQUENCE: 733

```
ttttggtaag tgctcaggca acctg                                            25
```

<210> SEQ ID NO 734
<211> LENGTH: 166
<212> TYPE: DNA
<213> ORGANISM: Artificial Sequence
<220> FEATURE:
<223> OTHER INFORMATION: Synthetic

<400> SEQUENCE: 734

```
attgcatgaa cacatatttg ctgccagaaa taattattac attgccttct tcatattgaa      60
aactaacagt tcttaaaagg gaagcagagg tgttaaagag cttggttaca atttattgct     120
aagagtttgg actttacatt aggaagatag cctctgaaat acaacg                    166
```

<210> SEQ ID NO 735

<211> LENGTH: 27
<212> TYPE: DNA
<213> ORGANISM: Artificial Sequence
<220> FEATURE:
<223> OTHER INFORMATION: Synthetic

<400> SEQUENCE: 735
aataataata tttaggcatg agctctt                                         27

<210> SEQ ID NO 736
<211> LENGTH: 25
<212> TYPE: DNA
<213> ORGANISM: Artificial Sequence
<220> FEATURE:
<223> OTHER INFORMATION: Synthetic

<400> SEQUENCE: 736
tggtaatacg ggactttatt tgtga                                           25

<210> SEQ ID NO 737
<211> LENGTH: 25
<212> TYPE: DNA
<213> ORGANISM: Artificial Sequence
<220> FEATURE:
<223> OTHER INFORMATION: Synthetic

<400> SEQUENCE: 737
taagtaggga gtggactccc ttctc                                           25

<210> SEQ ID NO 738
<211> LENGTH: 397
<212> TYPE: DNA
<213> ORGANISM: Artificial Sequence
<220> FEATURE:
<223> OTHER INFORMATION: Synthetic

<400> SEQUENCE: 738
tgccctctat aaacttcgga ctgtgcactc acattaacag tgtgtaaaag gacttgtttc     60
ttgtacacat ttggctaaca ttaactatac taaatctttt caagcacctg atgtagtttc    120
tttaattata ggtagatttg dacattttt ggatacattt cgtggctgtt taacttcttt    180
cctttaaatt gactgaatgg ctttgtccat ttttctattg agtcatttca ttttttttct    240
gatttgtttg gatttctttt tgtataattt atattttccc tggatagttg caagaaattg    300
ttaataaatt gttctccctg gctccttttcc tgtggtatat ccctggttcc catgtcgtta    360
tctctcctta ctgtcctcat ttcgaaggca cactttc                            397

<210> SEQ ID NO 739
<211> LENGTH: 25
<212> TYPE: DNA
<213> ORGANISM: Artificial Sequence
<220> FEATURE:
<223> OTHER INFORMATION: Synthetic

<400> SEQUENCE: 739
gcaacacctc ttcctcttat tgaaa                                           25

<210> SEQ ID NO 740
<211> LENGTH: 25
<212> TYPE: DNA
<213> ORGANISM: Artificial Sequence
<220> FEATURE:
<223> OTHER INFORMATION: Synthetic

<400> SEQUENCE: 740
gtaattcgta tgcaagaagc tacac 25

```
<210> SEQ ID NO 741
<211> LENGTH: 110
<212> TYPE: DNA
<213> ORGANISM: Artificial Sequence
<220> FEATURE:
<223> OTHER INFORMATION: Synthetic

<400> SEQUENCE: 741
```
atttagggat tagttacagt tatgctgttt cgtaaaattg gcatttgatt ctatatttta 60
tgcatagatt ttttttaaaa gcactcttct gtagaattgc acttagacca 110

```
<210> SEQ ID NO 742
<211> LENGTH: 25
<212> TYPE: DNA
<213> ORGANISM: Artificial Sequence
<220> FEATURE:
<223> OTHER INFORMATION: Synthetic

<400> SEQUENCE: 742
```
gccttcttga tctggaagtc agagg 25

```
<210> SEQ ID NO 743
<211> LENGTH: 25
<212> TYPE: DNA
<213> ORGANISM: Artificial Sequence
<220> FEATURE:
<223> OTHER INFORMATION: Synthetic

<400> SEQUENCE: 743
```
tttagcatga actggtgttg aaatt 25

```
<210> SEQ ID NO 744
<211> LENGTH: 157
<212> TYPE: DNA
<213> ORGANISM: Artificial Sequence
<220> FEATURE:
<223> OTHER INFORMATION: Synthetic

<400> SEQUENCE: 744
```
agatgagctg ctcagactct acagcatgac gactacaatt tcttttcata aaacttcttc 60
tcttcttgga attattaatt cctatctgct tcctagctga taaagcttag aaaaggcagt 120
tattccttct ttccaaccag ctttgctcga gttagaa 157

```
<210> SEQ ID NO 745
<211> LENGTH: 25
<212> TYPE: DNA
<213> ORGANISM: Artificial Sequence
<220> FEATURE:
<223> OTHER INFORMATION: Synthetic

<400> SEQUENCE: 745
```
actttacagt cagaatcaga ccact 25

```
<210> SEQ ID NO 746
<211> LENGTH: 27
<212> TYPE: DNA
<213> ORGANISM: Artificial Sequence
<220> FEATURE:
<223> OTHER INFORMATION: Synthetic

<400> SEQUENCE: 746
```

```
tgaggacctt ggtaatgttt cttcctg                                          27

<210> SEQ ID NO 747
<211> LENGTH: 25
<212> TYPE: DNA
<213> ORGANISM: Artificial Sequence
<220> FEATURE:
<223> OTHER INFORMATION: Synthetic

<400> SEQUENCE: 747
ttgctttggt ggaatatgta tgcta                                            25

<210> SEQ ID NO 748
<211> LENGTH: 25
<212> TYPE: DNA
<213> ORGANISM: Artificial Sequence
<220> FEATURE:
<223> OTHER INFORMATION: Synthetic

<400> SEQUENCE: 748
tcacaactct ataaacccaa ccgaa                                            25

<210> SEQ ID NO 749
<211> LENGTH: 25
<212> TYPE: DNA
<213> ORGANISM: Artificial Sequence
<220> FEATURE:
<223> OTHER INFORMATION: Synthetic

<400> SEQUENCE: 749
agatgaaaca actgagggcc aaaaa                                            25

<210> SEQ ID NO 750
<211> LENGTH: 25
<212> TYPE: DNA
<213> ORGANISM: Artificial Sequence
<220> FEATURE:
<223> OTHER INFORMATION: Synthetic

<400> SEQUENCE: 750
gagaatgaac tccaccactt acgaa                                            25

<210> SEQ ID NO 751
<211> LENGTH: 25
<212> TYPE: DNA
<213> ORGANISM: Artificial Sequence
<220> FEATURE:
<223> OTHER INFORMATION: Synthetic

<400> SEQUENCE: 751
atgtcagctc cttgtttacc aataa                                            25

<210> SEQ ID NO 752
<211> LENGTH: 31
<212> TYPE: DNA
<213> ORGANISM: Artificial Sequence
<220> FEATURE:
<223> OTHER INFORMATION: Synthetic

<400> SEQUENCE: 752
acaactatct taactgcaaa acttgtgttc t                                     31

<210> SEQ ID NO 753
<211> LENGTH: 26
<212> TYPE: DNA
<213> ORGANISM: Artificial Sequence
```

```
<220> FEATURE:
<223> OTHER INFORMATION: Synthetic

<400> SEQUENCE: 753
atgggagtag gaaagctaat caaaaa                                         26

<210> SEQ ID NO 754
<211> LENGTH: 25
<212> TYPE: DNA
<213> ORGANISM: Artificial Sequence
<220> FEATURE:
<223> OTHER INFORMATION: Synthetic

<400> SEQUENCE: 754
taaatctata atatggctgg aggca                                          25

<210> SEQ ID NO 755
<211> LENGTH: 25
<212> TYPE: DNA
<213> ORGANISM: Artificial Sequence
<220> FEATURE:
<223> OTHER INFORMATION: Synthetic

<400> SEQUENCE: 755
gcttctctcc agacttgggc ttaag                                          25

<210> SEQ ID NO 756
<211> LENGTH: 25
<212> TYPE: DNA
<213> ORGANISM: Artificial Sequence
<220> FEATURE:
<223> OTHER INFORMATION: Synthetic

<400> SEQUENCE: 756
aaaagaagag tagtccaagg tgtgg                                          25

<210> SEQ ID NO 757
<211> LENGTH: 32
<212> TYPE: DNA
<213> ORGANISM: Artificial Sequence
<220> FEATURE:
<223> OTHER INFORMATION: Synthetic

<400> SEQUENCE: 757
ttacttagtc ttctatgtat agctatcaag ga                                  32

<210> SEQ ID NO 758
<211> LENGTH: 25
<212> TYPE: DNA
<213> ORGANISM: Artificial Sequence
<220> FEATURE:
<223> OTHER INFORMATION: Synthetic

<400> SEQUENCE: 758
atgctgcaaa atgtaccagt acctg                                          25

<210> SEQ ID NO 759
<211> LENGTH: 25
<212> TYPE: DNA
<213> ORGANISM: Artificial Sequence
<220> FEATURE:
<223> OTHER INFORMATION: Synthetic

<400> SEQUENCE: 759
atgactctga ctagccagca ggaag                                          25
```

```
<210> SEQ ID NO 760
<211> LENGTH: 25
<212> TYPE: DNA
<213> ORGANISM: Artificial Sequence
<220> FEATURE:
<223> OTHER INFORMATION: Synthetic

<400> SEQUENCE: 760
gctgtccttt gtgtcagcat catga                                          25

<210> SEQ ID NO 761
<211> LENGTH: 482
<212> TYPE: DNA
<213> ORGANISM: Artificial Sequence
<220> FEATURE:
<223> OTHER INFORMATION: Synthetic

<400> SEQUENCE: 761
aagtgaagtt tgaagtctgc tctctgcaaa gagggtggga gtgggtggag aagaggcttg     60
ttttaaaagc caaaaacaga aagtaaaaag aaatgggaaa gtaaaaccaa agcagcaagt   120
gactctcttc tgatgtgcac ttttcatttt tctcccccac atttcagtgt tagaaagaaa   180
acgagaggag ctagggaaag aaggagttgg ggacagaaga ctaagatttc aacgtgaaat   240
tccatttaca aaggctttac tgcaaacaat agctaattta gtcctgtaaa catgcattta   300
tcatacattt taattttaat attaaaaata ctgcatgtaa atgttctgaa ctaaaggtag   360
atagcaatat gtagtttgcc ataaaatgaa tgcatgtctt attcttttcc atagttcttc   420
attaatgaga cttgtagtca agaatagatt gaagatacca ttctccttgt gtagttcaaa   480
aa                                                                 482

<210> SEQ ID NO 762
<211> LENGTH: 25
<212> TYPE: DNA
<213> ORGANISM: Artificial Sequence
<220> FEATURE:
<223> OTHER INFORMATION: Synthetic

<400> SEQUENCE: 762
gcacagcaca gcttgggtta tctgg                                          25

<210> SEQ ID NO 763
<211> LENGTH: 25
<212> TYPE: DNA
<213> ORGANISM: Artificial Sequence
<220> FEATURE:
<223> OTHER INFORMATION: Synthetic

<400> SEQUENCE: 763
accctgccca ttggatgtta gctga                                          25

<210> SEQ ID NO 764
<211> LENGTH: 25
<212> TYPE: DNA
<213> ORGANISM: Artificial Sequence
<220> FEATURE:
<223> OTHER INFORMATION: Synthetic

<400> SEQUENCE: 764
aaaattttat catctggtca tggtg                                          25

<210> SEQ ID NO 765
<211> LENGTH: 25
```

```
<212> TYPE: DNA
<213> ORGANISM: Artificial Sequence
<220> FEATURE:
<223> OTHER INFORMATION: Synthetic

<400> SEQUENCE: 765
atttgggaca gctttacaat gttat                                              25

<210> SEQ ID NO 766
<211> LENGTH: 25
<212> TYPE: DNA
<213> ORGANISM: Artificial Sequence
<220> FEATURE:
<223> OTHER INFORMATION: Synthetic

<400> SEQUENCE: 766
tcaggaacct ttcaaaaata catgc                                              25

<210> SEQ ID NO 767
<211> LENGTH: 27
<212> TYPE: DNA
<213> ORGANISM: Artificial Sequence
<220> FEATURE:
<223> OTHER INFORMATION: Synthetic

<400> SEQUENCE: 767
cccctaccct tgttctcag cagcaag                                             27

<210> SEQ ID NO 768
<211> LENGTH: 25
<212> TYPE: DNA
<213> ORGANISM: Artificial Sequence
<220> FEATURE:
<223> OTHER INFORMATION: Synthetic

<400> SEQUENCE: 768
gacactgtga gcttgatact gctgg                                              25

<210> SEQ ID NO 769
<211> LENGTH: 42
<212> TYPE: DNA
<213> ORGANISM: Artificial Sequence
<220> FEATURE:
<223> OTHER INFORMATION: Synthetic

<400> SEQUENCE: 769
gaaaccaaat ggtgtgccac aaattaggga acacaagcaa ac                           42

<210> SEQ ID NO 770
<211> LENGTH: 261
<212> TYPE: DNA
<213> ORGANISM: Artificial Sequence
<220> FEATURE:
<223> OTHER INFORMATION: Synthetic

<400> SEQUENCE: 770
gaatgatcca tcttccttaa ggctgctaca ccataactag gagctttaaa aaaaaggggg        60
gggcatttac tctctgaggc actcaaaaaa gcacatgctt ttaattgagg gatgggggtg       120
acaatggatc attctgttga ttttaactat ctcatatttg ttaacagcat catttccatg       180
gatagctttc tgaaagactg cctatccact tagaggtgag gagaagtaat agggaggaa        240 accctgccga gctgcaaaaa g                                                 261

<210> SEQ ID NO 771
```

<211> LENGTH: 25
<212> TYPE: DNA
<213> ORGANISM: Artificial Sequence
<220> FEATURE:
<223> OTHER INFORMATION: Synthetic

<400> SEQUENCE: 771
gcctaggtga cccaaagtaa tggga                                          25

<210> SEQ ID NO 772
<211> LENGTH: 25
<212> TYPE: DNA
<213> ORGANISM: Artificial Sequence
<220> FEATURE:
<223> OTHER INFORMATION: Synthetic

<400> SEQUENCE: 772
cctccgcgca attcagctgc agctg                                          25

<210> SEQ ID NO 773
<211> LENGTH: 25
<212> TYPE: DNA
<213> ORGANISM: Artificial Sequence
<220> FEATURE:
<223> OTHER INFORMATION: Synthetic

<400> SEQUENCE: 773
ccagctccac tgaaacaggg gaaat                                          25

<210> SEQ ID NO 774
<211> LENGTH: 174
<212> TYPE: DNA
<213> ORGANISM: Artificial Sequence
<220> FEATURE:
<223> OTHER INFORMATION: Synthetic

<400> SEQUENCE: 774
ggtgccctaa ccacttcctg aaatctggcc tgattttaa tagcttttac ctaagttcct     60
cagattctct gattcatagt tttcaaaata tcttgtctcc tatttttgta tattgttctc   120
ggcttcttct gcattttaac tcaagtatag gcaattctca ctatatttac tgga         174

<210> SEQ ID NO 775
<211> LENGTH: 27
<212> TYPE: DNA
<213> ORGANISM: Artificial Sequence
<220> FEATURE:
<223> OTHER INFORMATION: Synthetic

<400> SEQUENCE: 775
tgaatgccat agtagtgaat gaatact                                        27

<210> SEQ ID NO 776
<211> LENGTH: 25
<212> TYPE: DNA
<213> ORGANISM: Artificial Sequence
<220> FEATURE:
<223> OTHER INFORMATION: Synthetic

<400> SEQUENCE: 776
cctatatggc atcgcagtct gcaaa                                          25

<210> SEQ ID NO 777
<211> LENGTH: 25
<212> TYPE: DNA
<213> ORGANISM: Artificial Sequence

```
<220> FEATURE:
<223> OTHER INFORMATION: Synthetic

<400> SEQUENCE: 777
gtggctctca gactttacta atcat                                         25

<210> SEQ ID NO 778
<211> LENGTH: 25
<212> TYPE: DNA
<213> ORGANISM: Artificial Sequence
<220> FEATURE:
<223> OTHER INFORMATION: Synthetic

<400> SEQUENCE: 778
acttgctata cataagatga ttcac                                         25

<210> SEQ ID NO 779
<211> LENGTH: 28
<212> TYPE: DNA
<213> ORGANISM: Artificial Sequence
<220> FEATURE:
<223> OTHER INFORMATION: Synthetic

<400> SEQUENCE: 779
gtatgcttat ctgtttatct tagccaaa                                      28

<210> SEQ ID NO 780
<211> LENGTH: 25
<212> TYPE: DNA
<213> ORGANISM: Artificial Sequence
<220> FEATURE:
<223> OTHER INFORMATION: Synthetic

<400> SEQUENCE: 780
atgctgaaat acttctgcct tttag                                         25

<210> SEQ ID NO 781
<211> LENGTH: 25
<212> TYPE: DNA
<213> ORGANISM: Artificial Sequence
<220> FEATURE:
<223> OTHER INFORMATION: Synthetic

<400> SEQUENCE: 781
atgctgaaat acttctgcct tttag                                         25

<210> SEQ ID NO 782
<211> LENGTH: 26
<212> TYPE: DNA
<213> ORGANISM: Artificial Sequence
<220> FEATURE:
<223> OTHER INFORMATION: Synthetic

<400> SEQUENCE: 782
gcagaaacga tgcagtggag catcag                                        26

<210> SEQ ID NO 783
<211> LENGTH: 25
<212> TYPE: DNA
<213> ORGANISM: Artificial Sequence
<220> FEATURE:
<223> OTHER INFORMATION: Synthetic

<400> SEQUENCE: 783
atgaattcgg ttccgtaagt ttgag                                         25
```

<210> SEQ ID NO 784
<211> LENGTH: 25
<212> TYPE: DNA
<213> ORGANISM: Artificial Sequence
<220> FEATURE:
<223> OTHER INFORMATION: Synthetic

<400> SEQUENCE: 784
ctgtaagagt cagagctttc tggga                                  25

<210> SEQ ID NO 785
<211> LENGTH: 29
<212> TYPE: DNA
<213> ORGANISM: Artificial Sequence
<220> FEATURE:
<223> OTHER INFORMATION: Synthetic

<400> SEQUENCE: 785
cttgatgtga cagagtagtg tgttttcat                              29

<210> SEQ ID NO 786
<211> LENGTH: 25
<212> TYPE: DNA
<213> ORGANISM: Artificial Sequence
<220> FEATURE:
<223> OTHER INFORMATION: Synthetic

<400> SEQUENCE: 786
cataaagaat gcacatgaac agcag                                  25

<210> SEQ ID NO 787
<211> LENGTH: 40
<212> TYPE: DNA
<213> ORGANISM: Artificial Sequence
<220> FEATURE:
<223> OTHER INFORMATION: Synthetic

<400> SEQUENCE: 787
atgctgtacc cctcggagac aaattccacc ctcgagtgcg                  40

<210> SEQ ID NO 788
<211> LENGTH: 391
<212> TYPE: DNA
<213> ORGANISM: Artificial Sequence
<220> FEATURE:
<223> OTHER INFORMATION: Synthetic

<400> SEQUENCE: 788
gcatgttcag aatcttggat ccctaagttc aatatattgg acatatttag gaactctgga    60
aattatgttg ttttcacata tctagtaact tactagatga atcagtagat ttcattaaag   120
tatatctaat aacagataat tatgatgtac ttctgggttg acatgcatgt ctctcattat   180
cagctatcag tattagtgtc atgctttgga gacagttatc ttttgaaggt tttgggttc    240 ttatgaacct catttttccc aggaagtttc tgtaattcct cctatgccta ttcttgtctt   300
ttctgtctgc ttgcagtgta agttatttag atcagaggca attattttc aggaagaaag    360 aaatcatcaa gtgacactcc taaaggcagt a                                  391

<210> SEQ ID NO 789
<211> LENGTH: 25
<212> TYPE: DNA
<213> ORGANISM: Artificial Sequence
<220> FEATURE:
<223> OTHER INFORMATION: Synthetic

<400> SEQUENCE: 789
tttgaaacag gtgactctag ccatg          25

<210> SEQ ID NO 790
<211> LENGTH: 25
<212> TYPE: DNA
<213> ORGANISM: Artificial Sequence
<220> FEATURE:
<223> OTHER INFORMATION: Synthetic

<400> SEQUENCE: 790
ggatgttcgg agaccatttt tccaa          25

<210> SEQ ID NO 791
<211> LENGTH: 25
<212> TYPE: DNA
<213> ORGANISM: Artificial Sequence
<220> FEATURE:
<223> OTHER INFORMATION: Synthetic

<400> SEQUENCE: 791
ttctgcttct gctataggag agtga          25

<210> SEQ ID NO 792
<211> LENGTH: 25
<212> TYPE: DNA
<213> ORGANISM: Artificial Sequence
<220> FEATURE:
<223> OTHER INFORMATION: Synthetic

<400> SEQUENCE: 792
tgcatgtgct tgttgatact ccgca          25

<210> SEQ ID NO 793
<211> LENGTH: 25
<212> TYPE: DNA
<213> ORGANISM: Artificial Sequence
<220> FEATURE:
<223> OTHER INFORMATION: Synthetic

<400> SEQUENCE: 793
ataaaactgt caggcccaaa taaat          25

<210> SEQ ID NO 794
<211> LENGTH: 25
<212> TYPE: DNA
<213> ORGANISM: Artificial Sequence
<220> FEATURE:
<223> OTHER INFORMATION: Synthetic

<400> SEQUENCE: 794
gactttgaga caagcttagg catca          25

<210> SEQ ID NO 795
<211> LENGTH: 55
<212> TYPE: DNA
<213> ORGANISM: Artificial Sequence
<220> FEATURE:
<223> OTHER INFORMATION: Synthetic

<400> SEQUENCE: 795
ctcctctggc tctaatagt caatgattgt gtagccatgc ctatcagtaa aaaga          55

<210> SEQ ID NO 796

```
<211> LENGTH: 25
<212> TYPE: DNA
<213> ORGANISM: Artificial Sequence
<220> FEATURE:
<223> OTHER INFORMATION: Synthetic

<400> SEQUENCE: 796
gaatcaaaac agacgagcaa aaaga                                          25

<210> SEQ ID NO 797
<211> LENGTH: 25
<212> TYPE: DNA
<213> ORGANISM: Artificial Sequence
<220> FEATURE:
<223> OTHER INFORMATION: Synthetic

<400> SEQUENCE: 797
ttgaagccag cctgaacaat ggcag                                          25

<210> SEQ ID NO 798
<211> LENGTH: 25
<212> TYPE: DNA
<213> ORGANISM: Artificial Sequence
<220> FEATURE:
<223> OTHER INFORMATION: Synthetic

<400> SEQUENCE: 798
atctctgggg tgttacagag acaaa                                          25

<210> SEQ ID NO 799
<211> LENGTH: 31
<212> TYPE: DNA
<213> ORGANISM: Artificial Sequence
<220> FEATURE:
<223> OTHER INFORMATION: Synthetic

<400> SEQUENCE: 799
gatattcaga attcaattgc caagtgccaa a                                   31

<210> SEQ ID NO 800
<211> LENGTH: 30
<212> TYPE: DNA
<213> ORGANISM: Artificial Sequence
<220> FEATURE:
<223> OTHER INFORMATION: Synthetic

<400> SEQUENCE: 800
atttgcatct ttaagttcta cattcacttc                                     30

<210> SEQ ID NO 801
<211> LENGTH: 25
<212> TYPE: DNA
<213> ORGANISM: Artificial Sequence
<220> FEATURE:
<223> OTHER INFORMATION: Synthetic

<400> SEQUENCE: 801
agaacttcag ccaaagcatc tgaga                                          25

<210> SEQ ID NO 802
<211> LENGTH: 190
<212> TYPE: DNA
<213> ORGANISM: Artificial Sequence
<220> FEATURE:
<223> OTHER INFORMATION: Synthetic

<400> SEQUENCE: 802
```

```
ctcaggatcc caacctttat gtatcagttt gccctcttgt tgaatatatt tactgtccag        60
tgctactccc tctatctgtg tgaaaaaatt atttcaaatt tccacatcag gaaacatcc        120 atgaatgctt gccaagacaa ccgggaaaaa aacagtaagg tcatattcat gactgtaaaa      180
cccttgtttc                                                              190
```

<210> SEQ ID NO 803
<211> LENGTH: 353
<212> TYPE: DNA
<213> ORGANISM: Artificial Sequence
<220> FEATURE:
<223> OTHER INFORMATION: Synthetic

<400> SEQUENCE: 803

```
ttcaagtaga cctagaagag agttttaaaa aacaaaacaa tgtaagtaaa ggatatttct      60
gaatcttaaa attcatccca tgtgtgatca taaactcata aaaataattt taagatgtcg      120
gaaaaggata ctttgattaa ataaaaacac tcatggatat gtaaaaactg tcaagattaa      180
aatttaatag tttcatttat ttgttatttt atttgtaaga aatagtgatg aacaaagatc      240 cttttcata ctgatacctg gttgtatatt atttgatgca acagttttct gaaatgatat       300
ttcaaattgc atcaagaaat taaaatcatc tatctgagta gtcaaaatac aag            353
```

<210> SEQ ID NO 804
<211> LENGTH: 25
<212> TYPE: DNA
<213> ORGANISM: Artificial Sequence
<220> FEATURE:
<223> OTHER INFORMATION: Synthetic

<400> SEQUENCE: 804

```
ttatgtcaaa acatttccag agact                                             25
```

<210> SEQ ID NO 805
<211> LENGTH: 121
<212> TYPE: DNA
<213> ORGANISM: Artificial Sequence
<220> FEATURE:
<223> OTHER INFORMATION: Synthetic

<400> SEQUENCE: 805

```
gcaaagcagt ttagcaatga ccagatgtaa ttcattttgg agttctaagt ttgaacttaa      60
tcaatatgaa cttacagcca tggaagaagt gattatcatt tgttatttgc tggcacaaga     120
a                                                                      121
```

<210> SEQ ID NO 806
<211> LENGTH: 62
<212> TYPE: DNA
<213> ORGANISM: Artificial Sequence
<220> FEATURE:
<223> OTHER INFORMATION: Synthetic

<400> SEQUENCE: 806

```
gggatagtga ggcatcgcaa tgtaagactc gggattagta cacacttgtt gattaatgga      60
aa                                                                      62
```

<210> SEQ ID NO 807
<211> LENGTH: 204
<212> TYPE: DNA
<213> ORGANISM: Artificial Sequence
<220> FEATURE:

<223> OTHER INFORMATION: Synthetic

<400> SEQUENCE: 807

```
tgtcacctct tagtacaaag ccatgccaga cactgcacct actctgcact ctaatgagaa      60
caatccggaa aggatgattt tcaagggaga gtgacctctt cctggagatc tgaggttatg     120
ttacagtatt gtggagtttt gttgcttaaa attctcctcc tgtcctcaca ggcaattttg     180
ctagagttgc aatcctcaca tttg                                            204
```

<210> SEQ ID NO 808
<211> LENGTH: 52
<212> TYPE: DNA
<213> ORGANISM: Artificial Sequence
<220> FEATURE:
<223> OTHER INFORMATION: Synthetic

<400> SEQUENCE: 808

```
gatccagcaa ttacaacgga gtcaaaaatt aaaccggacc atctctccaa ct              52
```

<210> SEQ ID NO 809
<211> LENGTH: 45
<212> TYPE: DNA
<213> ORGANISM: Artificial Sequence
<220> FEATURE:
<223> OTHER INFORMATION: Synthetic

<400> SEQUENCE: 809

```
tgccaaggag gcgtattctt caatatttgg aatagacgtg ttctc                      45
```

<210> SEQ ID NO 810
<211> LENGTH: 202
<212> TYPE: DNA
<213> ORGANISM: Artificial Sequence
<220> FEATURE:
<223> OTHER INFORMATION: Synthetic

<400> SEQUENCE: 810

```
gtgcatacat tatgatacag ccctgatctt taaaaggagc aaaaatcaga gaatcgtatg      60
tcttaaagaa ctatttcctt acttttttat gctaggtaat gcccatgtga caaacatgta    120
aatattcatc aaagaccaca tgtatatatt ttaaaggcat ttttttcttct ccccaactgt    180
atgtatagct agaatctgct tg                                             202
```

<210> SEQ ID NO 811
<211> LENGTH: 28
<212> TYPE: DNA
<213> ORGANISM: Artificial Sequence
<220> FEATURE:
<223> OTHER INFORMATION: Synthetic

<400> SEQUENCE: 811

```
attctttact gaactgtgat ttgacatt                                         28
```

<210> SEQ ID NO 812
<211> LENGTH: 34
<212> TYPE: DNA
<213> ORGANISM: Artificial Sequence
<220> FEATURE:
<223> OTHER INFORMATION: Synthetic

<400> SEQUENCE: 812

```
gttagtgata ttaacagcga aaagagattt ttgt                                  34
```

```
<210> SEQ ID NO 813
<211> LENGTH: 45
<212> TYPE: DNA
<213> ORGANISM: Artificial Sequence
<220> FEATURE:
<223> OTHER INFORMATION: Synthetic

<400> SEQUENCE: 813
ttaagtgagg catctcaatt gcaagatttt ctctgcatcg gtcag              45

<210> SEQ ID NO 814
<211> LENGTH: 105
<212> TYPE: DNA
<213> ORGANISM: Artificial Sequence
<220> FEATURE:
<223> OTHER INFORMATION: Synthetic

<400> SEQUENCE: 814
cttcatgctt aatacaaaca cttctaatgg ctcattgatt ataatgtatt atcacatttt    60
attttatcct cagacatgat tgactttcta aaggcttgaa tcaaa                  105

<210> SEQ ID NO 815
<211> LENGTH: 234
<212> TYPE: DNA
<213> ORGANISM: Artificial Sequence
<220> FEATURE:
<223> OTHER INFORMATION: Synthetic

<400> SEQUENCE: 815
atggcaggat tcaacatcta tttgctttat aagatattga taaaaatgta tctcattcat    60
aatggtgtag caactacttt ttaatggggt tttactatgc tcttttgttt ccattggctt   120
tataaattag gatttgactt tgctttaatt acatgttttt aattacccag ttatctagtt   180
atcaaatgaa aatgttatta ctaatataat tggaactcat aaaatgctta gctg         234

<210> SEQ ID NO 816
<211> LENGTH: 27
<212> TYPE: DNA
<213> ORGANISM: Artificial Sequence
<220> FEATURE:
<223> OTHER INFORMATION: Synthetic

<400> SEQUENCE: 816
tttccttatt tcatgattgt ggccatt                                       27

<210> SEQ ID NO 817
<211> LENGTH: 270
<212> TYPE: DNA
<213> ORGANISM: Artificial Sequence
<220> FEATURE:
<223> OTHER INFORMATION: Synthetic

<400> SEQUENCE: 817
ttatgcagat aaaacctcca ggtagcaggc ttcagagaga atagattata aatgtttctt    60
agcagactta aaaaggtgcc agaagatcag ggaaaagacc tggaaaggga aagggaatct   120
ctatagaatg tcaattatcc tcacaagaga tagctttgta gggccatttc aaaatatatc   180
aaaggaatat attttagggt aaaatacttc agtttctttc agggccttct atgtgccata   240
tgatgctgta ctaaagtaag gctggaattt                                   270

<210> SEQ ID NO 818
<211> LENGTH: 147
<212> TYPE: DNA
```

<213> ORGANISM: Artificial Sequence
<220> FEATURE:
<223> OTHER INFORMATION: Synthetic

<400> SEQUENCE: 818

```
cttctgttat ctcttattcc agagaaaaat ctgctgtcac tagattaaat gcactttttg    60
agttgtccta atgacatcag tttggttttc attttgaaag aattagggca tctgacattt   120
cagccttatc atagtccatt ttcaatt                                       147
```

<210> SEQ ID NO 819
<211> LENGTH: 395
<212> TYPE: DNA
<213> ORGANISM: Artificial Sequence
<220> FEATURE:
<223> OTHER INFORMATION: Synthetic

<400> SEQUENCE: 819

```
tgaggtggct ttgccatttt atacccataa ttaaataaaa gggcaaaatc ccccctgata    60
aataccatgt ttatcatggc acataaaact ttatggcaga aagccaaggc caattgacat   120
atatatttaa aggtaccatg gaaagtaaat gctaactctg aatttaaaac agtgggaaga   180
tgattagtaa gagttggttt cttgaaaagg aattgttctg gtaatagtca tctttaatga   240
cttccacgga ttattcagtg tttctttagg gatatgcata ggacactggt gcttcagtag   300
aaacccccagt tttggtgtat taaagataca tccattcttg actgatcttt aatctagagt   360
gtggttttag ccaagtcttt gaatctcatt tagtc                              395
```

<210> SEQ ID NO 820
<211> LENGTH: 200
<212> TYPE: DNA
<213> ORGANISM: Artificial Sequence
<220> FEATURE:
<223> OTHER INFORMATION: Synthetic

<400> SEQUENCE: 820

```
tttaaggtga aatctctaat atttataaaa gtagcaaaat aaatgcataa ttaaaatata    60
tttggacata acagacttgg aagcagatga tacagacttc ttttttttcat aatcaggtta   120
gtgtaagaaa ttgccatttg aaacaatcca ttttgtaact gaaccttatg aaatatatgt   180
atttcatggt acgtattctc                                               200
```

<210> SEQ ID NO 821
<211> LENGTH: 58
<212> TYPE: DNA
<213> ORGANISM: Artificial Sequence
<220> FEATURE:
<223> OTHER INFORMATION: Synthetic

<400> SEQUENCE: 821

```
tcactgtgta gagaacatat atgcataaac ataggtcaat tatatgtctc cattagaa      58
```

<210> SEQ ID NO 822
<211> LENGTH: 31
<212> TYPE: DNA
<213> ORGANISM: Artificial Sequence
<220> FEATURE:
<223> OTHER INFORMATION: Synthetic

<400> SEQUENCE: 822

```
gcaacttttc cgtcaatcaa aaatgattct g                                   31
```

<210> SEQ ID NO 823
<211> LENGTH: 75
<212> TYPE: DNA
<213> ORGANISM: Artificial Sequence
<220> FEATURE:
<223> OTHER INFORMATION: Synthetic

<400> SEQUENCE: 823

```
ggtaaaggat agactcacat ttacaagtag tgaaggtcca agagttctaa atacaggaaa    60
tttcttagga actca                                                    75
```

<210> SEQ ID NO 824
<211> LENGTH: 238
<212> TYPE: DNA
<213> ORGANISM: Artificial Sequence
<220> FEATURE:
<223> OTHER INFORMATION: Synthetic

<400> SEQUENCE: 824

```
cctacctcag agcttcacat atatatatga aaaaaaaagt gcttcaaata actaataagt    60
ttaggaagta ggcctatcct aaagcacaaa aatatttat ttatgagtaa aaaatatttt    120
tataagtaca taattatttc aacaatatgt tacttttgtc attttcccta catattcttt    180
tatatatttt gaactgtaga catgtagcat attctagcac attgcagtaa tgacaact     238
```

<210> SEQ ID NO 825
<211> LENGTH: 83
<212> TYPE: DNA
<213> ORGANISM: Artificial Sequence
<220> FEATURE:
<223> OTHER INFORMATION: Synthetic

<400> SEQUENCE: 825

```
aaggaagata ttactctcat aattccatac tggtggaaac ctatctgaga atgtctattt    60
cattaatcct cttgagtatg ttc                                           83
```

<210> SEQ ID NO 826
<211> LENGTH: 366
<212> TYPE: DNA
<213> ORGANISM: Artificial Sequence
<220> FEATURE:
<223> OTHER INFORMATION: Synthetic

<400> SEQUENCE: 826

```
tattcttagg gcttttgtgt atgtctgact tgtttttaaa taacttcctc agcaatgcag    60
accttaattt ttatattttt ttaaagtagc taacatagca gtaggcactt aagcatttag    120
tcaatgatat tggtagaaat agtaaaatac atcctttaaa tatatatcta agcatatatt    180
ttaaaaggag caaaaataaa accaaagtgt tagtaaattt tgatttatta gatattttag    240
aaaaataata gaattctgaa gttttaaaaa tgtcagtaat taatttatttt tcattttcag    300 aaatatatgc atgcagttat gttttatttg attgttgact taggctatgt ctgtatacag    360
taacca                                                              366
```

<210> SEQ ID NO 827
<211> LENGTH: 50
<212> TYPE: DNA
<213> ORGANISM: Artificial Sequence
<220> FEATURE:
<223> OTHER INFORMATION: Synthetic

<400> SEQUENCE: 827

```
gaatatcact acctcaggtt acggtacaca ggctataatt gatgatgatg        50
```

<210> SEQ ID NO 828
<211> LENGTH: 36
<212> TYPE: DNA
<213> ORGANISM: Artificial Sequence
<220> FEATURE:
<223> OTHER INFORMATION: Synthetic

<400> SEQUENCE: 828

```
tcctgtccct tgaccttaac tctgatggtt cttcac                        36
```

<210> SEQ ID NO 829
<211> LENGTH: 190
<212> TYPE: DNA
<213> ORGANISM: Artificial Sequence
<220> FEATURE:
<223> OTHER INFORMATION: Synthetic

<400> SEQUENCE: 829

```
tggcgccact atactgctaa acctatgcat gaaggtagtg actaggatgg aaatctgtca    60
gtgctacaaa aatatgtatg aacaaaataa ttttcaccct ttgataaagc tacaagatat   120
aaaatttaga atacttatat aatttcatac tagatatgtg aaaaatatgc catgctagaa   180
ccatcttgtt                                                          190
```

<210> SEQ ID NO 830
<211> LENGTH: 38
<212> TYPE: DNA
<213> ORGANISM: Artificial Sequence
<220> FEATURE:
<223> OTHER INFORMATION: Synthetic

<400> SEQUENCE: 830

```
cattgagaga tacaaagcgt tttctagaga gtgtttct                      38
```

<210> SEQ ID NO 831
<211> LENGTH: 27
<212> TYPE: DNA
<213> ORGANISM: Artificial Sequence
<220> FEATURE:
<223> OTHER INFORMATION: Synthetic

<400> SEQUENCE: 831

```
gtgactatag aggctaacaa gaatgga                                  27
```

<210> SEQ ID NO 832
<211> LENGTH: 276
<212> TYPE: DNA
<213> ORGANISM: Artificial Sequence
<220> FEATURE:
<223> OTHER INFORMATION: Synthetic

<400> SEQUENCE: 832

```
gaggcagccc tttcttatgc agaaaataca atacgcactg catgagaagc ttgagagtgg    60
attctaatcc aggtctgtcg accttggata tcatgcatgt gggaaggtgg gtgtggtgag   120 aaaagttttta aggcaagagt agatggccat gttcaacttt acaaaatttc ttggaaaact   180
ggcagtattt tgaactgcat cttctttggt accggaacct gcagaaacag tgtgagaaat   240
taagtcctgg ttcactgcgc agtagcaaag atggtc                            276
```

<210> SEQ ID NO 833
<211> LENGTH: 200

```
<212> TYPE: DNA
<213> ORGANISM: Artificial Sequence
<220> FEATURE:
<223> OTHER INFORMATION: Synthetic

<400> SEQUENCE: 833
gctcccattt tttgcactgg aattacttgc caaatggcct tttcaccatc tgaaatagtt    60
aatgtattca cttcttaaat gagcaaaagt cttcaaacta ttaagaaaga gccatagact   120
gagtgcaggc accagtgtgc tcttattact gtgtcaatta aatgaatgta tttgaatgtt   180
tggatactta cctctgaatg                                                200

<210> SEQ ID NO 834
<211> LENGTH: 584
<212> TYPE: DNA
<213> ORGANISM: Artificial Sequence
<220> FEATURE:
<223> OTHER INFORMATION: Synthetic

<400> SEQUENCE: 834
cctcttacac atgacaagtt ttggcttgtt ggttttttcag aagcgaagaa atatggcatt    60
gaaaatgatg ctgagtgtga agaaatgtag aggactcatt tttgatcccc cagggagacc   120
tatttttact ataaatttac tccaataatg agatgtgtag gaggatttac cattacatag   180
ttttaataca tttcagcgtc attggagact aaacattttc tttcagagta actgatagtt   240
tctagctacc taaataagga tcttttctaa atctgacaag aaattttgaa agtttttttca   300 caatggcatt ctagagtcat ctctagaatg atgatattag atattaatca ttatttttata   360 aagagaagac ttaatgaata catctgatga atgcattggt tataaggcta atagtttttac   420 atataagcta gaaacaaaat gagtctgttt gtgaaattat ctcctctact ctagtggaag   480
aatctgtagt gagattacta ataaaggact aatgttttat catttgattt gttcagatgg   540
gtaatgcaaa aaaaacttta gccttctgtg aagtaacctt agga                    584

<210> SEQ ID NO 835
<211> LENGTH: 42
<212> TYPE: DNA
<213> ORGANISM: Artificial Sequence
<220> FEATURE:
<223> OTHER INFORMATION: Synthetic

<400> SEQUENCE: 835
gtaaacagat gtaattagag acattggctc tttgtttagg cc                       42

<210> SEQ ID NO 836
<211> LENGTH: 26
<212> TYPE: DNA
<213> ORGANISM: Artificial Sequence
<220> FEATURE:
<223> OTHER INFORMATION: Synthetic

<400> SEQUENCE: 836
tgagggtatc agaaccaata ctggac                                          26

<210> SEQ ID NO 837
<211> LENGTH: 574
<212> TYPE: DNA
<213> ORGANISM: Artificial Sequence
<220> FEATURE:
<223> OTHER INFORMATION: Synthetic

<400> SEQUENCE: 837
```

```
ccctgtaaaa ccccttggctt ctatgaaggc cattgaataa ctgcgatatg cctgtgaaaa    60
atcacaaaag gtgcaaagtc ccctcgcaat aaagatcagt cacgatgaga tttgcaccaa    120
ttgaactttt aagattgtaa atatttttgt cttgcagagc tgatgcatat ccattaaaaa    180
gtatatctta gtgagcctta tcttcaagtt agcagcgaga agagtaacaa aaacgtgcca    240
atttaaaata ctgaaattct gggaaaatgt tttacttatg agtatttctt agtattgggc    300
tagtgtgata agatggcag catgttttga tatctactca gaaattcatt tcacaaacga     360
agatgtttta gagttggtga acatacctgg cccattactg acaaaaccaa ttaccgtatt    420
tattggtaat agagctgttt acaggatgct cactgtaaaa aaaaaaaaaa aagaaagag    480 aaagaagaaa aaaaatcctg ctttttttt tttatctctc tctcttttga aacaagagaa     540
caatcccatt cacacatagt agctgccttc tttg                                574
```

<210> SEQ ID NO 838  
<211> LENGTH: 170  
<212> TYPE: DNA  
<213> ORGANISM: Artificial Sequence  
<220> FEATURE:  
<223> OTHER INFORMATION: Synthetic

<400> SEQUENCE: 838

```
gatcctgcta tgattcttca ctgggggaa agaagataca tttagaaaat tggttatctc    60
agattcttag tatggtttta gttagttagt tttaccactt ggtagagtta atgatttgac    120
aaatgacatt tgcttcttat tatcagccag ttggttgcta gctttaaaga                170
```

<210> SEQ ID NO 839  
<211> LENGTH: 73  
<212> TYPE: DNA  
<213> ORGANISM: Artificial Sequence  
<220> FEATURE:  
<223> OTHER INFORMATION: Synthetic

<400> SEQUENCE: 839

```
acatattttc aagttgaatg tcttctgtta atttctcttt attttgtttg ccagtgaata    60
tagaacctct ttt                                                        73
```

<210> SEQ ID NO 840  
<211> LENGTH: 101  
<212> TYPE: DNA  
<213> ORGANISM: Artificial Sequence  
<220> FEATURE:  
<223> OTHER INFORMATION: Synthetic

<400> SEQUENCE: 840

```
cttttgaatt acagagatat aaatgaagta ttatctgtaa aaattgttat aattagagtt    60
gtgatacaga gtatatttcc attcagacaa tatatcataa c                        101
```

<210> SEQ ID NO 841  
<211> LENGTH: 31  
<212> TYPE: DNA  
<213> ORGANISM: Artificial Sequence  
<220> FEATURE:  
<223> OTHER INFORMATION: Synthetic

<400> SEQUENCE: 841

```
tttagatgtt taacttgaac tgttctgaat t                                    31
```

<210> SEQ ID NO 842  
<211> LENGTH: 145

```
<212> TYPE: DNA
<213> ORGANISM: Artificial Sequence
<220> FEATURE:
<223> OTHER INFORMATION: Synthetic

<400> SEQUENCE: 842
ttcaatatta gcaagacagc atgccttcaa atcaatctgt aaaactaaga aacttaaatt     60
ttagttctta ctgcttaatt caaataataa ttagtaagct agcaaatagt aatctgtaag    120
cataagctta tgcttaaatt caagt                                          145

<210> SEQ ID NO 843
<211> LENGTH: 36
<212> TYPE: DNA
<213> ORGANISM: Artificial Sequence
<220> FEATURE:
<223> OTHER INFORMATION: Synthetic

<400> SEQUENCE: 843
cattgctgta atctagtgag gcatcttgga cttctg                               36

<210> SEQ ID NO 844
<211> LENGTH: 47
<212> TYPE: DNA
<213> ORGANISM: Artificial Sequence
<220> FEATURE:
<223> OTHER INFORMATION: Synthetic

<400> SEQUENCE: 844
tatatgcatc ctttgacttt gaatggctgc cataattgtt tactgag                   47

<210> SEQ ID NO 845
<211> LENGTH: 83
<212> TYPE: DNA
<213> ORGANISM: Artificial Sequence
<220> FEATURE:
<223> OTHER INFORMATION: Synthetic

<400> SEQUENCE: 845
tgtcaaacaa tgtgtaactc cagttataca acattactg tatctcattg gggatacgaa     60
gctctacaca cttgaagatg gtg                                             83

<210> SEQ ID NO 846
<211> LENGTH: 107
<212> TYPE: DNA
<213> ORGANISM: Artificial Sequence
<220> FEATURE:
<223> OTHER INFORMATION: Synthetic

<400> SEQUENCE: 846
gtccagactt ggagtacaag taataagaag aataaaactt aatcccttaa gtagattcac     60
cataagttag ctcagagcaa ttccagtgca agtatggtct gtgatcc                  107

<210> SEQ ID NO 847
<211> LENGTH: 892
<212> TYPE: DNA
<213> ORGANISM: Artificial Sequence
<220> FEATURE:
<223> OTHER INFORMATION: Synthetic

<400> SEQUENCE: 847
gcattggatt tactagacga aaaccatacc tctcttcaat caaaatgaaa acaaagcaaa     60
tgaatactgg acagtcttaa caattttata agttataaaa tgactttaga gcaccctcct   120
```

```
tcattactttt tgcaaaaaca tactgactca gggctctttt tttctttttg catatgacaa      180
ctgttactag aaatacaggc tactggtttt gcatagatca ttcatcttaa ttttggtacc      240
agttaaaaat acaaatgtac tatattgtag tcattttaaa gtacacaaag ggcacaatca      300
aaatgagatg cactcattta aatctgcatt cagtgaatgt attgggagaa aaataggtct      360
tgcaggtttc cttttgaatt ttaagtatca taaatatttt taaagtaaat aatacggggt      420
gtcagtaata tctgcagaat gaatgcagtc tttcatgcta atgagttagt ctggaaaaat      480
aaagtcttat tttctatgtt ttattcatag aaatggagta ttaattttta atattttcac      540
catatgtgat aacaaaggat ctttcatgaa tgtccaaggg taagtcagta ttaattaatg      600
ctgtattaca aggcaatgct accttcttta ttcccccttt gaactaccttt tgaagtcact      660 atgagcacat ggatagaaat ttaacttttt tttgtaaagc aagcttaaaa tgttatgta       720 tacatacccca gcaacttta taaatgtgtt aaacaatttt actgatttt ataataaata       780 ttttggtaag attttgaata atatgaattc aggcagatat actaaactgc ttttatttac      840
ttgtttagaa aattgtatat atatgtttgt gtatcctaac agctgctatg aa              892

<210> SEQ ID NO 848
<211> LENGTH: 29
<212> TYPE: DNA
<213> ORGANISM: Artificial Sequence
<220> FEATURE:
<223> OTHER INFORMATION: Synthetic

<400> SEQUENCE: 848
gctttgtaaa tcaaactgtg gactaaata                                         29

<210> SEQ ID NO 849
<211> LENGTH: 28
<212> TYPE: DNA
<213> ORGANISM: Artificial Sequence
<220> FEATURE:
<223> OTHER INFORMATION: Synthetic

<400> SEQUENCE: 849
gctgctcttc atttgatttc gaggcaag                                          28

<210> SEQ ID NO 850
<211> LENGTH: 50
<212> TYPE: DNA
<213> ORGANISM: Artificial Sequence
<220> FEATURE:
<223> OTHER INFORMATION: Synthetic

<400> SEQUENCE: 850
tctagaagga tttattggct tcatcagaca taggctagga ttctcacggg                  50

<210> SEQ ID NO 851
<211> LENGTH: 26
<212> TYPE: DNA
<213> ORGANISM: Artificial Sequence
<220> FEATURE:
<223> OTHER INFORMATION: Synthetic

<400> SEQUENCE: 851
aagtggcagt acaactgagt atggtg                                            26

<210> SEQ ID NO 852
<211> LENGTH: 199
<212> TYPE: DNA
<213> ORGANISM: Artificial Sequence
```

```
<220> FEATURE:
<223> OTHER INFORMATION: Synthetic

<400> SEQUENCE: 852
ccatggatta gaagcattag ttctcagtac ttgaagacaa acttctaaaa agaaaatata      60
tgctctgaac atctgaaatg ggctagactt tcaagtaaaa ttgcttcatt tctcattaac    120
tgaagagcta ttgatccaag tcatacttgc catttaatgt aaattatttt taaactttgc    180
tgtacaaaac cattaagtg                                                  199

<210> SEQ ID NO 853
<211> LENGTH: 200
<212> TYPE: DNA
<213> ORGANISM: Artificial Sequence
<220> FEATURE:
<223> OTHER INFORMATION: Synthetic

<400> SEQUENCE: 853
gaaaaagggg tatcagtcta atctcatgga gaaaaactac ttgcaaaaac ttcttaagaa     60
gatgtctttt attgtctaca atgatttcta gtctttaaaa actgtgtttg agatttgttt   120
ttaggttggt cgctaatgat ggctgtatct cccttcactg tctcttccta cattaccact   180
actacatgct ggcaaaggtg                                                 200

<210> SEQ ID NO 854
<211> LENGTH: 30
<212> TYPE: DNA
<213> ORGANISM: Artificial Sequence
<220> FEATURE:
<223> OTHER INFORMATION: Synthetic

<400> SEQUENCE: 854
gattgaaagc cagctatttg gtaatgtttg                                       30

<210> SEQ ID NO 855
<211> LENGTH: 29
<212> TYPE: DNA
<213> ORGANISM: Artificial Sequence
<220> FEATURE:
<223> OTHER INFORMATION: Synthetic

<400> SEQUENCE: 855
ttttatgacc taacagcaca gattgtgtt                                        29

<210> SEQ ID NO 856
<211> LENGTH: 25
<212> TYPE: DNA
<213> ORGANISM: Artificial Sequence
<220> FEATURE:
<223> OTHER INFORMATION: Synthetic

<400> SEQUENCE: 856
tcatctttgc ctaaacagag attct                                            25

<210> SEQ ID NO 857
<211> LENGTH: 380
<212> TYPE: DNA
<213> ORGANISM: Artificial Sequence
<220> FEATURE:
<223> OTHER INFORMATION: Synthetic

<400> SEQUENCE: 857
tctgtaacag tgattctctt gggtcatata aaggactgag ttatggagtt acctaccctc     60
```

-continued

```
ttcgactcat cttttaattt gtcatagaaa aacaactgtt gtacattgtg ttaaaagtta    120
aattctatgg ccagagtgtg atttggaaaa gaaaactgaa gtaagttgga agcagagtga    180
agaaaataac tctgccattt tcttccaact caccctacag catctctgtt ttccagcctc    240
actgggttaa gtcttcaaat gtagcccttt gcttctaaga caatcccatg ttacaaagca    300
tcaataatcc tcctctgaac attttcctca aaagttctaa ctacaaagca gttagccctg    360
atgttctgat aaaagtctaa                                                380
```

<210> SEQ ID NO 858
<211> LENGTH: 25
<212> TYPE: DNA
<213> ORGANISM: Artificial Sequence
<220> FEATURE:
<223> OTHER INFORMATION: Synthetic

<400> SEQUENCE: 858

```
ccttaagctg ctcgatttct taaag                                           25
```

<210> SEQ ID NO 859
<211> LENGTH: 34
<212> TYPE: DNA
<213> ORGANISM: Artificial Sequence
<220> FEATURE:
<223> OTHER INFORMATION: Synthetic

<400> SEQUENCE: 859

```
tggttaccaa aggcaacagt tgttatccag tggg                                 34
```

<210> SEQ ID NO 860
<211> LENGTH: 31
<212> TYPE: DNA
<213> ORGANISM: Artificial Sequence
<220> FEATURE:
<223> OTHER INFORMATION: Synthetic

<400> SEQUENCE: 860

```
tgggtatcag tggatacaca cgatgcaaca a                                    31
```

<210> SEQ ID NO 861
<211> LENGTH: 94
<212> TYPE: DNA
<213> ORGANISM: Artificial Sequence
<220> FEATURE:
<223> OTHER INFORMATION: Synthetic

<400> SEQUENCE: 861

```
agagaggcaa cacttattat ccacagggta acagtggtta ccagcgatgc aatacttatt    60
atccaccggg taacggtggt taccaatgag acat                                 94
```

<210> SEQ ID NO 862
<211> LENGTH: 25
<212> TYPE: DNA
<213> ORGANISM: Artificial Sequence
<220> FEATURE:
<223> OTHER INFORMATION: Synthetic

<400> SEQUENCE: 862

```
ggcaacaact attatccacc gtgta                                           25
```

<210> SEQ ID NO 863
<211> LENGTH: 209
<212> TYPE: DNA
<213> ORGANISM: Artificial Sequence
<220> FEATURE:
<223> OTHER INFORMATION: Synthetic

<400> SEQUENCE: 863

| | |
|---|---|
| gtaccattga ttacccatga gacaatgctt attttccccc ggggaacagt ggttacccta | 60 |
| gaggcaatac ttattatcca cagggtaaca gtgataaccc tagaggcaat acttattatc | 120 |
| cactgggtaa cagtggttac cgacaaggca acacttatta tccaaagggc aacagtggtt | 180 |
| acccaggagg aaacaggtat tatccaccg | 209 |

<210> SEQ ID NO 864
<211> LENGTH: 347
<212> TYPE: DNA
<213> ORGANISM: Artificial Sequence
<220> FEATURE:
<223> OTHER INFORMATION: Synthetic

<400> SEQUENCE: 864

| | |
|---|---|
| acagtcgtta tctatgaggc agtacttatt atccacctgg ttacagtggt tacctgggag | 60 |
| gcaatgctta ttatccaccg ggtaacagtg gttaccctca aggcaacaag tattatccac | 120 |
| caggtaacag tggttaccct agaggcaaca ctaattatcc attgggtaac agtggttact | 180 |
| cgcaaggcaa caattattat ccagcaggta acagtggata catgcgatgc aacaattatt | 240 |
| atccaccggg taacagtgct tacccgtgag gcaacactta ttatccacgg ggtaacattg | 300 |
| attacccaca aggcaatact tactatcctc tgggtaacag tgctttc | 347 |

<210> SEQ ID NO 865
<211> LENGTH: 47
<212> TYPE: DNA
<213> ORGANISM: Artificial Sequence
<220> FEATURE:
<223> OTHER INFORMATION: Synthetic

<400> SEQUENCE: 865

| | |
|---|---|
| taaaccaggt atcagtggtt atgcatgagg cgacacttat tattcac | 47 |

<210> SEQ ID NO 866
<211> LENGTH: 25
<212> TYPE: DNA
<213> ORGANISM: Artificial Sequence
<220> FEATURE:
<223> OTHER INFORMATION: Synthetic

<400> SEQUENCE: 866

| | |
|---|---|
| taacatttag tatccactgg gtaac | 25 |

<210> SEQ ID NO 867
<211> LENGTH: 27
<212> TYPE: DNA
<213> ORGANISM: Artificial Sequence
<220> FEATURE:
<223> OTHER INFORMATION: Synthetic

<400> SEQUENCE: 867

| | |
|---|---|
| ttacccatga ggcagcaaat attattc | 27 |

<210> SEQ ID NO 868
<211> LENGTH: 94
<212> TYPE: DNA
<213> ORGANISM: Artificial Sequence
<220> FEATURE:
<223> OTHER INFORMATION: Synthetic

<400> SEQUENCE: 868

```
tatccactgg gtcacagtgc ttttccacga gagaatactt attatccaat gggtaacagt    60
ggttacccat aagtcgatac atattatcca ccag                                94
```

<210> SEQ ID NO 869
<211> LENGTH: 143
<212> TYPE: DNA
<213> ORGANISM: Artificial Sequence
<220> FEATURE:
<223> OTHER INFORMATION: Synthetic

<400> SEQUENCE: 869

```
tgcgtaacag tggttaccaa caagacaaca cttattatcc actgggtaac aatggttacc    60
cacaaaacgt cacttattat ccacagggta acagtggtta cccacgaggc aacacttatt   120
atccatgcat taacagttgt tac                                           143
```

<210> SEQ ID NO 870
<211> LENGTH: 1401
<212> TYPE: DNA
<213> ORGANISM: Artificial Sequence
<220> FEATURE:
<223> OTHER INFORMATION: Synthetic

<400> SEQUENCE: 870

```
aggatccact gggtaccaat ggttgcccac gaggcaatac ttactatcca ctgggtaaca    60
ctggtttccc acgaggcaac acttttatc caccagataa cagtggctac gcacgagata   120
acacttattt tccacagggt aagaattgtt acccacgaca cagcacttat tatcaagtgg   180
gtaatactgg ttacgcaaga ggcaacactt attataaacc ggggaacagt ggttactcac   240
aaggcaatac ttattatcca cagggtaaca gttgttaccc acgaggcaat acttattatc   300
cactgggtaa cagtgatcac cctagaggca atacttatta tccactggga acagtggtt   360
acctacgagg caacacttat tatccacagg ataacagtgg ttacccatga ggcaatactt   420
actatccacc aggtaacagt ggttacccat gaggcaatac ttattatcca ctgggtaaca   480
gtgactaccc atgaggcaac acttattatt gaccaggtaa cagtggttac cctagaagca   540
ataccctatta tccaacagat aacagtggtt acccatgcgg taatacttat tatccagtgg   600
gtagcagtgg ttacccataa gacaatcctt attatcctcc gggtaacagt ggtgaccaat   660
gaggcaatac ttagtatcca ccgggtacca atggttaccc acgaggcaat acttactatc   720
caccaggtaa cactggtttc ccacgaggcg cacttaata tccaccgggt cacagtggtt   780
acccatgagg caacacttat tatccacagg gtaagagttg ttacccacga ggcaacactt   840
attatccagc gggtaacact ggttacccac gaggcaacac ttattacaaa ctggataaca   900
gtggtttccc acgaggcaat acttattatg cagcagatta cagtggttac ccatgaggca   960
atacttatta tccgccaggt aagagtggtt acccatgagg caatacttat tatcaactgg  1020
gtaacactgg tttcccatga ggcaacactt attatccatc gggtaaccgt gcttacccac  1080
aaggcaacac ttattatcca catggtaaca gtggttacca aggaggcaat acttattacg  1140
cattgggtaa cagtggttac ccacgaggca gtacttttta ccaccgggt aacagtggtt  1200
accctagagg caacacttat tccattgg gtaacagtgg ttaccctaaa ggcaacactt  1260
attatgcacc gggtaacacc ggttacccgt gaggcaacta ttattttcca ctgggtaaca  1320
gtggttagcc acgaggcaac acgtattatc caccggttaa cagtggttac ccacgaggca  1380
acatttgata tccagcagat a                                           1401
```

<210> SEQ ID NO 871
<211> LENGTH: 26
<212> TYPE: DNA
<213> ORGANISM: Artificial Sequence
<220> FEATURE:
<223> OTHER INFORMATION: Synthetic

<400> SEQUENCE: 871
atcaggcaaa agttagtatc cagcgg                                   26

<210> SEQ ID NO 872
<211> LENGTH: 139
<212> TYPE: DNA
<213> ORGANISM: Artificial Sequence
<220> FEATURE:
<223> OTHER INFORMATION: Synthetic

<400> SEQUENCE: 872
tttcctacga ggcaatacat attacccaat gggtaacagt ggtaacccac gaggcaatac    60
gtattatcca cagggtaaca gtggttacct atgaggcaat acttattatc aactggttaa   120
cagtggtatc ccatgaagc                                              139

<210> SEQ ID NO 873
<211> LENGTH: 28
<212> TYPE: DNA
<213> ORGANISM: Artificial Sequence
<220> FEATURE:
<223> OTHER INFORMATION: Synthetic

<400> SEQUENCE: 873
ccacgaggca attcttgtta tccatagg                                    28

<210> SEQ ID NO 874
<211> LENGTH: 375
<212> TYPE: DNA
<213> ORGANISM: Artificial Sequence
<220> FEATURE:
<223> OTHER INFORMATION: Synthetic

<400> SEQUENCE: 874
ggccatacat attatccacc gggtgacagt ggttacccaa gaggcaatac ttattatcca    60
tgtggtagaa gtggttgccc atgaggcaat acttattatc cactgggtaa cagtggttac   120
ccaagaggca atacttatta tacacccagt aacagtggtt acccacagtg caacacttat   180
tatccactgg gtaactgtgg ttacgcatga ggcaactcgt attacccact gggaaacagt   240
ggtaacccac gaggcaatac gtattatcca acaggtaaca gtggttaccc acaaggccac   300
acgtattatc cactgggtaa cagtggttac ccacaaggca atacttatta tccagtcatt   360
agaagtggtt accca                                                  375

<210> SEQ ID NO 875
<211> LENGTH: 25
<212> TYPE: DNA
<213> ORGANISM: Artificial Sequence
<220> FEATURE:
<223> OTHER INFORMATION: Synthetic

<400> SEQUENCE: 875
atcaagttca ctaaagcagg aatga                                       25

<210> SEQ ID NO 876

```
<211> LENGTH: 28
<212> TYPE: DNA
<213> ORGANISM: Artificial Sequence
<220> FEATURE:
<223> OTHER INFORMATION: Synthetic

<400> SEQUENCE: 876
ttctggagga aacttgtaat attggaga                                          28

<210> SEQ ID NO 877
<211> LENGTH: 44
<212> TYPE: DNA
<213> ORGANISM: Artificial Sequence
<220> FEATURE:
<223> OTHER INFORMATION: Synthetic

<400> SEQUENCE: 877
tttaagcaac agtttgactg catacaaaat tcctgggtca catc                        44

<210> SEQ ID NO 878
<211> LENGTH: 49
<212> TYPE: DNA
<213> ORGANISM: Artificial Sequence
<220> FEATURE:
<223> OTHER INFORMATION: Synthetic

<400> SEQUENCE: 878
ttctctactg caatgctgag gtctcagtaa atcgattttt gtctgtgca                   49

<210> SEQ ID NO 879
<211> LENGTH: 29
<212> TYPE: DNA
<213> ORGANISM: Artificial Sequence
<220> FEATURE:
<223> OTHER INFORMATION: Synthetic

<400> SEQUENCE: 879
gagtgctcac tccataagac ccttacatt                                         29

<210> SEQ ID NO 880
<211> LENGTH: 194
<212> TYPE: DNA
<213> ORGANISM: Artificial Sequence
<220> FEATURE:
<223> OTHER INFORMATION: Synthetic

<400> SEQUENCE: 880
tgtgtaactg cacacggcct atctcatctg aataaggcct tactctcaga ccccttttgc       60
agtacagcag gggtgctgat aaccaaggcc cattttcctg gcctgttatg tgtgtgatta      120
tatttgtcca ggtttctgtg tactagacaa ggaagcctcc tctgccccat cccatctacg      180
cataatcttt cttt                                                        194

<210> SEQ ID NO 881
<211> LENGTH: 27
<212> TYPE: DNA
<213> ORGANISM: Artificial Sequence
<220> FEATURE:
<223> OTHER INFORMATION: Synthetic

<400> SEQUENCE: 881
gtgccagctc cataagaacc ttacatt                                           27

<210> SEQ ID NO 882
<211> LENGTH: 177
```

```
<212> TYPE: DNA
<213> ORGANISM: Artificial Sequence
<220> FEATURE:
<223> OTHER INFORMATION: Synthetic

<400> SEQUENCE: 882
caaccatgca ccttggacat aaatgtgtgt aactgcacat ggcccatccc atctgaataa    60
ggtcctactc tcagacccct tttgcagtac agtaggtgtg ctgataacca aggcccctct   120
tcctggcctg ttaacgtatg tgattatatt tgtctgggtt ccagtgtata agacatg      177

<210> SEQ ID NO 883
<211> LENGTH: 183
<212> TYPE: DNA
<213> ORGANISM: Artificial Sequence
<220> FEATURE:
<223> OTHER INFORMATION: Synthetic

<400> SEQUENCE: 883
tgagcatagg cactcacctt ggacatgaat gtgcataact gcacatggcc catcccatct    60
gaataaggtc ctactctcag acccttttg cagtacagca ggggtgctga tcaccaaggc   120 ccctttcct ggcctgttat gtgtgtgatt atatttgttc cagttcctgt gtaatagaca   180
tgg                                                                 183

<210> SEQ ID NO 884
<211> LENGTH: 31
<212> TYPE: DNA
<213> ORGANISM: Artificial Sequence
<220> FEATURE:
<223> OTHER INFORMATION: Synthetic

<400> SEQUENCE: 884
tccactccat ataccettac atttggacaa t                                    31

<210> SEQ ID NO 885
<211> LENGTH: 28
<212> TYPE: DNA
<213> ORGANISM: Artificial Sequence
<220> FEATURE:
<223> OTHER INFORMATION: Synthetic

<400> SEQUENCE: 885
ccctctccat aagacgctta cgtttgga                                        28

<210> SEQ ID NO 886
<211> LENGTH: 169
<212> TYPE: DNA
<213> ORGANISM: Artificial Sequence
<220> FEATURE:
<223> OTHER INFORMATION: Synthetic

<400> SEQUENCE: 886
gcaccttaga catggatttg cataactaca cacagctcaa cctatctgaa taaaatccta    60
ctctcagacc cctttttgcag tacagcaggg gtgctgatca ccaaggccct ttttcctggc   120
ctggtatgcg tgtgattatg tttgtcccgg ttcctgtgta ttagacatg                169

<210> SEQ ID NO 887
<211> LENGTH: 32
<212> TYPE: DNA
<213> ORGANISM: Artificial Sequence
<220> FEATURE:
<223> OTHER INFORMATION: Synthetic
```

<400> SEQUENCE: 887

| ggagtgccca ctccataaga ctctcacatt tg | 32 |

<210> SEQ ID NO 888
<211> LENGTH: 26
<212> TYPE: DNA
<213> ORGANISM: Artificial Sequence
<220> FEATURE:
<223> OTHER INFORMATION: Synthetic

<400> SEQUENCE: 888

| ttatttggag agtctaggtg cacaat | 26 |

<210> SEQ ID NO 889
<211> LENGTH: 2126
<212> TYPE: DNA
<213> ORGANISM: Artificial Sequence
<220> FEATURE:
<223> OTHER INFORMATION: Synthetic

<400> SEQUENCE: 889

| tttcgttgta tcctgcctgc ctagcatcca gttcctcccc agccctgctc ccagcaaacc | 60 |
| cctagtctag cccagccct actcccaccc cgccccagcc ctgccccagc ccagtcccc | 120 |
| taacccccca gccctagccc cagtcccagt cctagttcct cagtcccgcc cagcttctct | 180 |
| cgaaagtcac tctaattttc attgattcag tgctcaaaat aagttgtcca ttgcttatcc | 240 |
| tattatactg ggatattccg tttacccttg gcattgctga tcttcagtac tgactccttg | 300 |
| accattttca gttaatgcat acaatcccat tgtctgtga tctcaggaca agaatttcc | 360 |
| ttactcggta cgttgaagtt agggaatgtc aattgagagc tttctatcag agcattattg | 420 |
| cccacaattt gagttactta tcattttctc gatcccctgc ccttaaagga gaaaccattt | 480 |
| ctctgtcatt gcttctgtag tcacagtccc aattttgagt agtgatcttt tcttgtgtac | 540 |
| tgtgttggcc acctaaaact ctttgcattg agtaaaattc taattgccaa taatcctacc | 600 |
| cattggatta gacagcactc tgaaccccat ttgcattcag caggggtcg cagacaaccc | 660 |
| gtcttttgtt ggacagttaa aatgctcagt cccaattgtc atagctttgc ctattaaaca | 720 |
| aaggcaccct actgcgcttt tgctgtgct tctggagaat cctgctgttc ttggacaatt | 780 |
| aaagaacaaa gtagtaattg ctaattgtct cacccattaa tcatgaagac taccagtcgc | 840 |
| ccttgcattt gccttgaggc agcgctgact acctgagatt taagagtttc ttaaattatt | 900 |
| gagtaaaatc ccaattatcc atagttctgt tagttacact atggcctttg caaacatctt | 960 |
| tgcataacag cagtgggact gactcattct tagagcccct tcccttggaa tattaatgga | 1020 |
| tacaatagta attattcatg gttctgcgta acagagaaga cccacttatg tgtatgcctt | 1080 |
| tatcattgct cctagatagt gtgaactacc taccaccttg cattaatatg taaaacacta | 1140 |
| attgcccata gtcccactca ttagtctagg atgtcctctt tgccattgct gctgagttct | 1200 |
| gactacccaa gtttccttct cttaaacagt tgatatgcat aattgcatat attcatggtt | 1260 |
| ctgtgcaata aaaatggatt ctcaccccat cccaccttct gtgggatgtt gctaacgagt | 1320 |
| gcagattatt caataacagc tcttgaacag ttaatttgca cagttgcaat tgtccagagt | 1380 |
| cctgtccatt agaaagggac tctgtatcct atttgcacgc tacaatgtgg gctgatcacc | 1440 |
| caaggactct tcttgtgcat tgatgttcat aattgtattt gtccacgatc ttgtgcacta | 1500 |
| acccttccac tcccttttgta ttccagcagg ggacccttac tactcaagac ctctgtacta | 1560 |
| ggacagttta tgtgcacaat cctaattgat tagaactgag tctttttatat caaggtccct | 1620 |

| | |
|---|---:|
| gcatcatctt tgctttacat caagagggtg ctggttacct aatgcccctc ctccagaaat | 1680 |
| tattgatgtg caaaatgcaa tttccctatc tgctgttagt ctggggtctc atcccctcat | 1740 |
| attcctttg tcttacagca gggggtactt gggactgtta atgcgcataa ttgcaattat | 1800 |
| ggtcttttcc attaaattaa gatcccaact gctcacaccc tcttagcatt acagtagagg | 1860 |
| gtgctaatca caaggacatt tcttttgtac tgttaatgtg ctacttgcat ttgtccctct | 1920 |
| tcctgtgcac taaagacccc actcacttcc ctagtgttca gcagtggatg acctctagtc | 1980 |
| aagacctttg cactaggata gttaatgtga accatggcaa ctgatcacaa caatgtcttt | 2040 |
| cagatcagat ccattttatc ctccttgttt tacagcaagg gatattaatt acctatgtta | 2100 |
| cctttccctg ggactatgaa tgtgca | 2126 |

<210> SEQ ID NO 890
<211> LENGTH: 548
<212> TYPE: DNA
<213> ORGANISM: Artificial Sequence
<220> FEATURE:
<223> OTHER INFORMATION: Synthetic

<400> SEQUENCE: 890

| | |
|---|---:|
| gccgtggata cctgcctttt aattctttt tattcgccca tcggggccgc ggatacctgc | 60 |
| ttttatttt ttttcctta gcccatcggg gtatcggata cctgctgatt cccttcccct | 120 |
| ctgaaccccc aacactctgg cccatcgggg tgacggatat ctgcttttta aaattttct | 180 |
| ttttttggcc catcggggct tcggatacct gctttttttt ttttattttt tccttgccca | 240 |
| tcggggcctc ggatacctgc tttaattttt gttttctgg cccatcgggg ccgcggatac | 300 |
| ctgctttgat tttttttttt catcgcccat cggtgctttt tatggatgaa aaatgttgg | 360 |
| ttttgtgggt tgttgcactc tctggaatat ctacactttt ttttgctgct gatcatttgg | 420 |
| tggtgtgtga gtgtacctac cgctttggca gagaatgact ctgcagttaa gctaagggcg | 480 |
| tgttcagatt gtggaggaaa agtggccgcc attttagact tgccgcataa ctcggcttag | 540 |
| ggctagtc | 548 |

<210> SEQ ID NO 891
<211> LENGTH: 1647
<212> TYPE: DNA
<213> ORGANISM: Artificial Sequence
<220> FEATURE:
<223> OTHER INFORMATION: Synthetic

<400> SEQUENCE: 891

| | |
|---|---:|
| atggtgatta ctttctgtgg ggctcggaac tacatgccct aggatataaa aatgatgtta | 60 |
| tcattataga gtgctcacag aaggaaatga agtaatatag gtgtgagatc cagaccaaaa | 120 |
| gtcatttaac aagtttattc agtgatgaaa acatgggaca aatggactaa tataaggcag | 180 |
| tgtactaagc tgagtagaga gataaagtcc tgtccagaag atacatgctt cctggcctga | 240 |
| ttgaggagat ggaaaatttt tgcaaaaaac aaggtgttgt ggtcttccat ccagtttctt | 300 |
| aagtgctgat gataaaagtg aattagaccc accttgacct ggcctacaga agtaaaggag | 360 |
| taaaaataaa tgcctcaggc gtgctttttg attcatttga taaacaaagc atcttttatg | 420 |
| tggaatatac cattctgggt cctgaggata agagagatga gggcattaga tcactgacag | 480 |
| ctgaagatag aagaacatct ttggtttgat tgtttaaata atatttcaat gcctattctc | 540 |
| tgcaaggtac tatgtttcgt aaattaaata ggtctggccc agaagaccca ctcaattgcc | 600 |

```
tttgagatta aaaaaaaaaa aaaaagaaa gaaaaatgca agtttctttc aaaataaaga    660
gacatttttc ctagtttcag gaatccccca aatcacttcc tcattggctt agtttaaagc   720
caggagactg ataaaagggc tcagggtttg ttctttaatt cattaactaa acattctgct   780
tttattacag ttaaatggtt caagatgtaa caactagttt taaaggtatt tgctcattgg   840
tctggcttag agacaggaag acatatgagc aataaaaaaa agattctttt gcatttacca   900
atttagtaaa aatttattaa aactgaataa agtgctgttc ttaagtgctt gaaagacgta   960
aaccaaagtg cactttatct catttatctt atggtggaaa cacaggaaca aattctctaa   1020
gagactgtgt ttctttagtt gagaagaaac ttcattgagt agctgtgata tgttcgatac   1080
taaggaaaaa ctaaacagat caccttttgac atgcgttgta gagtgggaat aagagagggc   1140
tttttatttt ttcgttcata cgagtattga tgaagatgat actaaatgct aaatgaaata   1200
tatctgctcc aaaaggcatt tattctgact tggagatgca acaaaaacac aaaaatggaa   1260
tgaagtgata ctcttcatca aacagaagtg actgttatct caaccatttt gttaaatcct   1320
aaacagaaaa caaaaaaaat catgacgaaa agacacttgc ttattaattg gcttggaaag   1380
tagaatatag gagaaaggtt actgtttatt ttttttcatg tattcattca ttctacaaat   1440
atattcgggt gccaataggt acttggtata aggttttttgg ccccagagac atgggaaaaa   1500
aatgcatgcc ttcccagaga atgcctaata ctttcctttt ggcttgtttt cttgttaggg   1560
gcatggctta gtccctaaat aacattgtgt ggtttaattc ctactccgta tctcttctac   1620
cactctggcc actacgataa gcaggta                                       1647

<210> SEQ ID NO 892
<211> LENGTH: 105
<212> TYPE: DNA
<213> ORGANISM: Artificial Sequence
<220> FEATURE:
<223> OTHER INFORMATION: Synthetic

<400> SEQUENCE: 892
tgtgaactca ctgttaaagg cactgaaaat ttatcatatt tcatttagcc acagccaaaa    60
ataaggcaat acctatgtta gcattttgtg aactctaagg cacca                    105

<210> SEQ ID NO 893
<211> LENGTH: 472
<212> TYPE: DNA
<213> ORGANISM: Artificial Sequence
<220> FEATURE:
<223> OTHER INFORMATION: Synthetic

<400> SEQUENCE: 893
ggactaagct tgttgtggtc acctataatg tgccagatac catgctgggt gctagagcta    60
ccaaaggggg aaaagtattc tcatagaaca aaaaatttca gaaggtgca tattaaagtg     120 ctttgtaaac taaagcatga tacaaatgtc aatgggctac atatttatga atgaatgaat   180
ggatgaatga atattaagtg cctcttacat accagctatt ttgggtactg taaaatacaa   240
gattaattct cctatgtaat aagaggaaag tttatcctct atactattca gatgtaagga   300
atgatatatt gcttaatttt aaacaatcaa gactttactg gtgaggttaa gttaaattat   360
tactgataca ttttttccagg taaccaggaa agagctagta tgaggaaatg aagtaataga   420
tgtgagatcc agaccgaaag tcacttaatt cagcttgcga atgtgctttc ta            472

<210> SEQ ID NO 894
<211> LENGTH: 460
```

```
<212> TYPE: DNA
<213> ORGANISM: Artificial Sequence
<220> FEATURE:
<223> OTHER INFORMATION: Synthetic

<400> SEQUENCE: 894
ggggacagcc tgaactccct gctcatagta gtggccaaat aatttggtgg actgtgccaa      60
cgctactcct gggtttaata cccatctcta ggcttaaaga tgagagaacc tgggactgtt     120
gagcatgttt aatactttcc ttgattttt tcttcctgtt tatgtgggaa gttgatttaa      180
atgactgata atgtgtatga aagcactgta aaacataaga gaaaaaccaa ttagtgtatt     240
ggcaatcatg cagttaacat ttgaaagtgc agtgtaaatt gtgaagcatt atgtaaatca     300
ggggtccaca gttttctgt aaggggtcaa atcataaata ctttagactg tgggccatat      360
ggtttctgtt acatatttgt tttttaaaca acgtttttat aaggtcaaaa tcattcttag     420
tttttgagcc aattggattt ggcctgctgt tcatagctta                           460

<210> SEQ ID NO 895
<211> LENGTH: 404
<212> TYPE: DNA
<213> ORGANISM: Artificial Sequence
<220> FEATURE:
<223> OTHER INFORMATION: Synthetic

<400> SEQUENCE: 895
tctcaagact aacggccgga atctggaggc ccatgaccca gaacccagga aggatagaag      60
cttgaagacc tggggaaatc ccaagatgag aaccctaaac cctacctctt ttctattgtt     120
tacacttctt actcttagat atttccagtt ctcctgttta tctttaagcc tgattctttt     180
gagatgtact ttttgatgtt gccggttacc tttagattga cagtattatg cctgggccag     240
tcttgagcca gctttaaatc acagctttta cctatttgtt aggctatagt gttttgtaaa     300
cttctgtttc tattcacatc ttctccactt gagagagaca ccaaaatcca gtcagtatct     360
aatctggctt ttgttaactt ccctcaggag cagacattca tata                      404

<210> SEQ ID NO 896
<211> LENGTH: 713
<212> TYPE: DNA
<213> ORGANISM: Artificial Sequence
<220> FEATURE:
<223> OTHER INFORMATION: Synthetic

<400> SEQUENCE: 896
tgtctccttt ttgggtcaca tgctgtgtgc tttttgtcct tttcttgttc tgtctacctc      60
tcctttctct gcctacctct cttttctctt tgtgaactgt gattatttgt taccccttcc     120
ccttctcgtt cgttttaaat ttcacctttt ttctgagtct ggcctccttt ctgctgtttc     180
tactttttat ctcacatttc tcatttctgc atttcctttc tgcctctctt gggctattct     240
ctctctcctc ccctgcgtgc ctcagcatct cttgctgttt gtgattttct atttcagtat     300
taatctctgt tggcttgtat ttgttctctg cttcttccct ttctactcac ctttgagtat     360
ttcagcctct tcatgaatct atctccctct ctttgatttc atgtaatctc tccttaaata     420
tttctttgca tatgtgggca agtgtacgtg tgtgtgtgtc atgtgtggca gaggggcttc     480
ctaacccctg cctgataggt gcagaacgtc ggctatcaga gcaagcattg tggagcggtt     540
ccttatgcca ggctgccatg tgagatgatc caagaccaaa acaaggccct agactgcagt     600
aaaacccaga actcaagtag ggcagaaggt ggaaggctca tatggataga aggcccaaag     660
```

-continued tataagacag atggtttgag acttgagacc cgaggactaa gatggaaagc cca        713

<210> SEQ ID NO 897
<211> LENGTH: 150
<212> TYPE: DNA
<213> ORGANISM: Artificial Sequence
<220> FEATURE:
<223> OTHER INFORMATION: Synthetic

<400> SEQUENCE: 897
tcattgttcc tatctgccaa atcattatac ttcctacaag cagtgcagag agctgagtct    60
tcagcaggtc caagaaattt gaacacactg aaggaagtca gccttcccac ctgaagatca   120
acatgcctgg cactctagca cttgaggata                                    150

<210> SEQ ID NO 898
<211> LENGTH: 168
<212> TYPE: DNA
<213> ORGANISM: Artificial Sequence
<220> FEATURE:
<223> OTHER INFORMATION: Synthetic

<400> SEQUENCE: 898
cctcagaaga ataggcttgt tgttttacag tgttagtgat ccattccctt tgacgatccc    60
taggtggaga tggggcatga ggatcctcca ggggaaaagc tcactaccac tgggcaacaa   120
ccctaggtca ggaggttctg tcaagatact ttcctggtcc cagatagg              168

<210> SEQ ID NO 899
<211> LENGTH: 50
<212> TYPE: DNA
<213> ORGANISM: Artificial Sequence
<220> FEATURE:
<223> OTHER INFORMATION: Synthetic

<400> SEQUENCE: 899
cccattgaag ataccacgct gcatgtgtcc ttagtagtca tgtctcctta              50

<210> SEQ ID NO 900
<211> LENGTH: 115
<212> TYPE: DNA
<213> ORGANISM: Artificial Sequence
<220> FEATURE:
<223> OTHER INFORMATION: Synthetic

<400> SEQUENCE: 900
aagaatattg tttctcggag aaggatgtca aaagatcggc ccagctcagg gagcagtttg    60
ccctactagc tcctcggaca gctgtaaaga agagtctctg gctctttaga atact       115

<210> SEQ ID NO 901
<211> LENGTH: 1676
<212> TYPE: DNA
<213> ORGANISM: Artificial Sequence
<220> FEATURE:
<223> OTHER INFORMATION: Synthetic

<400> SEQUENCE: 901
gggtgcccac tccttatgat ctttacattt gaacagttaa tgtgaataat tgcagttgtc    60 cacaaccta tcacttctag gaccattata cctcttttgc attactgtgg ggtatactgt   120
ttccctccaa ggccccttct ggtggactat caacatataa ttgaaatttt cttttgtctt   180
tgtcagtaga ttaaggtcat accccatcac ctttcctttg tagtacaaca gggtgtcctg   240
atcaaccaaa gtcctgttgt tttggactgt taatatgtgc aattacattt gctcctgatc   300

```
tgtgcactag ataaggatcc tacctacttt cttagtgttt ttagcaggta gtgcccacta      360
ctcaagactg tcacttggaa tgttcatgtg cacaaactca attctctaag catgttcctg      420
taccaccttt gctttagagc aggggatga tattcactaa gtgccccttc ttttggactt       480
aatatgcatt aatgcaattg tccacctctt cttttagact aagagttgat ctccacatat      540
tccccttgca tcagggcat gttaattatg aatgaaccct tttcttttaa tattaatgtc       600
ataattgtat ttgtggacct gtgtaggaga aaaagaccct atgttcctcc cattacccctt     660 tggattgctg ctgagaagtg ttaactactc ataatctcag ctcttggaca attaatagca      720
ttaataacaa ttatcaaggg cactgatcat tagataagac tcctgcttcc tcgttgctta     780
catcgggggt actgacccac taaggcccct tgtactgtta atgtgaatat ttgcaattat      840
atatgtctcc ttctggtaga gtgggatatt atgccctagt atcccctttg cattactgca     900
ggggctgctg actactcaaa acttctcctg ggactgttaa taggcacaat ggcagttatc      960
aatggttttc tccctcccctg accttgttaa gcaagcgccc cacccacc ttagtttccc      1020 atggcataat aaagtataag cattggagta ttccatgcac ttgtctatca aacagtggtc     1080
catactccca accctttgc attgcgccag tgtgtaaaat cacaggtagc catggtgtca     1140
tgctttatat acgaagtctt ccctctctct gccccttgtg tgcccttggc ccttttttac     1200
agactattgc tcacaatctc aggtgtccat atttgcagct attaggtaag attgtgctgt     1260
ctccctcttc ccttccctct gccctgcccc ttttgcctct tgctgggta atgttgacca      1320 gacaaggccc tttctcttgg acttaaacaa ttctcagttg cactttcctt ggtcccaccc     1380
attatacatg aaccctcta cttcctttcg cattgcttct gagtatgctg actacccaaa     1440
gccccttctg tgttattaat aaacacagta ctgattgtcc catttttcag cccatcagtc     1500
caagatctcc ctaccacttt ggtgtgttgg tgcagtgttg actatgaaaa gcaggcctga     1560
actaggtgga taagccttca ctcattttct ttcatttatt aatgatccta gtttcaatta     1620
ttgtcagatt ctggggacaa gaaccattct tgcccacctg tgttactgct ttactg         1676
```

<210> SEQ ID NO 902
<211> LENGTH: 218
<212> TYPE: DNA
<213> ORGANISM: Artificial Sequence
<220> FEATURE:
<223> OTHER INFORMATION: Synthetic

<400> SEQUENCE: 902

```
tttgcagcaa agtcacccctt acaaagaagc taatatggaa accacatgta acttagccag      60
actatattgt gtagcttcaa gaacttgcag tacattacca gctgtgattc tcctgataat      120
tcaagggagc tcaaagtcac aagaagaaaa atgaaaggaa aaacagcag ccctattcag      180 aaattggttt gaagatgtaa ttgctctagt ttggatta                             218
```

<210> SEQ ID NO 903
<211> LENGTH: 34
<212> TYPE: DNA
<213> ORGANISM: Artificial Sequence
<220> FEATURE:
<223> OTHER INFORMATION: Synthetic

<400> SEQUENCE: 903

```
atggtggctg taaaactagg atccctgacg attg                                  34
```

CANCER DIAGNOSTICS USING NON-CODING TRANSCRIPTS

CROSS-REFERENCE TO RELATED APPLICATIONS

This application is a 35 USC § 371 National Stage application of International Application No. PCT/US2012/069571 filed Dec. 13, 2012; which claims the benefit under 35 USC § 119(e) to U.S. Application Ser. No. 61/703,426 filed Nov. 27, 2012, U.S. Application Ser. No. 61/652,044 filed May 25, 2012, U.S. Application Ser. No. 61/570,194 filed Dec. 13, 2011. The disclosure of each of the prior applications is considered part of and is incorporated by reference in the disclosure of this application.

This application claims benefit of priority under 35 U.S.C. § 119(e) from U.S. Provisional Patent Application No. 61/570,194, filed Dec. 13, 2011, U.S. Provisional Patent Application No. 61/652,044, filed May 25, 2012, and U.S. Provisional Patent Application No. 61/730,426, filed Nov. 27, 2012, which are incorporated herein by reference in their entirety.

BACKGROUND OF THE INVENTION

Cancer is the uncontrolled growth of abnormal cells anywhere in a body. The abnormal cells are termed cancer cells, malignant cells, or tumor cells. Many cancers and the abnormal cells that compose the cancer tissue are further identified by the name of the tissue that the abnormal cells originated from (for example, breast cancer, lung cancer, colon cancer, prostate cancer, pancreatic cancer, thyroid cancer). Cancer is not confined to humans; animals and other living organisms can get cancer. Cancer cells can proliferate uncontrollably and form a mass of cancer cells. Cancer cells can break away from this original mass of cells, travel through the blood and lymph systems, and lodge in other organs where they can again repeat the uncontrolled growth cycle. This process of cancer cells leaving an area and growing in another body area is often termed metastatic spread or metastatic disease. For example, if breast cancer cells spread to a bone (or anywhere else), it can mean that the individual has metastatic breast cancer.

Standard clinical parameters such as tumor size, grade, lymph node involvement and tumor-node-metastasis (TNM) staging (American Joint Committee on Cancer at the world wide web at cancerstaging.org) may correlate with outcome and serve to stratify patients with respect to (neo)adjuvant chemotherapy, immunotherapy, antibody therapy and/or radiotherapy regimens. Incorporation of molecular markers in clinical practice may define tumor subtypes that are more likely to respond to targeted therapy. However, stage-matched tumors grouped by histological or molecular subtypes may respond differently to the same treatment regimen. Additional key genetic and epigenetic alterations may exist with important etiological contributions. A more detailed understanding of the molecular mechanisms and regulatory pathways at work in cancer cells and the tumor microenvironment (TME) could dramatically improve the design of novel anti-tumor drugs and inform the selection of optimal therapeutic strategies. The development and implementation of diagnostic, prognostic and therapeutic biomarkers to characterize the biology of each tumor may assist clinicians in making important decisions with regard to individual patient care and treatment. Thus, disclosed herein are methods, compositions and systems for the analysis of coding and/or non-coding targets for the diagnosis, prognosis, and monitoring of a cancer.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

To aid in the understanding of the present invention, a list of commonly used abbreviations is provided in Table 1. Disclosed herein are compositions, systems, and methods for diagnosing, predicting, and/or monitoring the status or outcome of a cancer in a subject. In some instances, the method comprises (a) assaying an expression level in a sample from the subject for a plurality of targets, wherein the plurality of targets comprises a coding target and a non-coding target, wherein the non-coding target is a non-coding RNA transcript selected from the group consisting of piRNA, tiRNA, PASR, TASR, aTASR, TSSa-RNA, snRNA, RE-RNA, uaRNA, x-ncRNA, hY RNA, usRNA, snaR, vtRNA, T-UCRs, pseudogenes, GRC-RNAs, aRNAs, PALRs, PROMPTs, and LSINCTs; and (b) diagnosing, predicting, and/or monitoring the status or outcome of a cancer based on the expression levels of the plurality of targets.

In some instances, the method comprises (a) assaying an expression level in a sample from the subject for a plurality of targets, wherein the plurality of targets comprises a coding target and a non-coding target, wherein the non-coding target is not selected from the group consisting of a miRNA and an intronic sequence; and (b) diagnosing, predicting, and/or monitoring the status or outcome of a cancer based on the expression levels of the plurality of targets.

Alternatively, the method comprises (a) assaying an expression level in a sample from the subject for a plurality of targets, wherein the plurality of targets comprises a coding target and a non-coding target, wherein the non-coding target is not selected from the group consisting of a miRNA, an intronic sequence, and a UTR sequence; and (b) diagnosing, predicting, and/or monitoring the status or outcome of a cancer based on the expression levels of the plurality of targets.

In other instances, the method comprises (a) assaying an expression level in a sample from the subject for a plurality of targets, wherein (i) the plurality of targets consist essentially of a non-coding target or a non-exonic transcript; (ii) the non-coding target is selected from the group consisting of a UTR sequence, an intronic sequence, or a non-coding RNA transcript, and (iii) the non-coding RNA transcript is selected from the group consisting of piRNA, tiRNA, PASR, TASR, aTASR, TSSa-RNA, snRNA, RE-RNA, uaRNA, x-ncRNA, hY RNA, usRNA, snaR, vtRNA, T-UCRs, pseudogenes, GRC-RNAs, aRNAs, PALRs, PROMPTs, and LSINCTs; and (b) diagnosing, predicting, and/or monitoring the status or outcome of a cancer based on the expression levels of the plurality of targets. In some embodiments, the method further comprises assaying an expression level of a coding target.

In some instances, the method comprises (a) assaying an expression level in a sample from the subject for a plurality of targets, wherein the plurality of targets comprises a non-coding target, wherein the non-coding target is a non-coding RNA transcript and the non-coding RNA transcript is non-polyadenylated; and (b) diagnosing, predicting, and/or monitoring the status or outcome of a cancer based on the expression levels of the plurality of targets. In some embodiments, the method further comprises assaying an expression level of a coding target.

Alternatively, the method comprises (a) providing a sample from a subject; (b) conducting a reaction to determine an expression level in a sample from the subject for a plurality of targets, wherein the plurality of targets are identified based on a classifier; and (c) diagnosing, predicting, and/or monitoring the status or outcome of a cancer based on the expression levels of the plurality of targets.

The method may comprise (a) providing a sample from a subject; (b) conducting a reaction to determine an expression level in a sample from the subject for a plurality of targets, wherein the plurality of targets are identified based on at least one probe selection region (PSR); and (c) diagnosing, predicting, and/or monitoring the status or outcome of a cancer based on the expression levels of the plurality of targets.

In other instances, the method comprises (a) providing a sample from a subject; (b) conducting a reaction to determine an expression level in a sample from the subject for a plurality of targets, wherein at least about 10% of the plurality of targets are non-coding targets; and (c) diagnosing, predicting, and/or monitoring the status or outcome of a cancer based on the expression levels of the plurality of targets.

Further disclosed herein in some embodiments is a method of analyzing a cancer in an individual in need thereof, comprising: (a) obtaining an expression profile from a sample obtained from the individual, wherein the expression profile comprises one or more targets selected from Table 6; and (b) comparing the expression profile from the sample to an expression profile of a control or standard. In some embodiments, the method further comprises providing diagnostic or prognostic information to the individual about the cardiovascular disorder based on the comparison.

Further disclosed herein in some embodiments is a method of diagnosing cancer in an individual in need thereof, comprising (a) obtaining an expression profile from a sample obtained from the individual, wherein the expression profile comprises one or more targets selected from Table 6; (b) comparing the expression profile from the sample to an expression profile of a control or standard; and (c) diagnosing a cancer in the individual if the expression profile of the sample (i) deviates from the control or standard from a healthy individual or population of healthy individuals, or (ii) matches the control or standard from an individual or population of individuals who have or have had the cancer.

Further disclosed herein in some embodiments is a method of predicting whether an individual is susceptible to developing a cancer, comprising (a) obtaining an expression profile from a sample obtained from the individual, wherein the expression profile comprises one or more targets selected from Table 6; (b) comparing the expression profile from the sample to an expression profile of a control or standard; and (c) predicting the susceptibility of the individual for developing a cancer based on (i) the deviation of the expression profile of the sample from a control or standard derived from a healthy individual or population of healthy individuals, or (ii) the similarity of the expression profiles of the sample and a control or standard derived from an individual or population of individuals who have or have had the cancer.

Further disclosed herein in some embodiments is a method of predicting an individual's response to a treatment regimen for a cancer, comprising (a) obtaining an expression profile from a sample obtained from the individual, wherein the expression profile comprises one or more targets selected from Table 6; (b) comparing the expression profile from the sample to an expression profile of a control or standard; and (c) predicting the individual's response to a treatment regimen based on (a) the deviation of the expression profile of the sample from a control or standard derived from a healthy individual or population of healthy individuals, or (b) the similarity of the expression profiles of the sample and a control or standard derived from an individual or population of individuals who have or have had the cancer.

Disclosed herein in some embodiments is a method of prescribing a treatment regimen for a cancer to an individual in need thereof, comprising (a) obtaining an expression profile from a sample obtained from the individual, wherein the expression profile comprises one or more targets selected from Table 6; (b) comparing the expression profile from the sample to an expression profile of a control or standard; and (c) prescribing a treatment regimen based on (i) the deviation of the expression profile of the sample from a control or standard derived from a healthy individual or population of healthy individuals, or (ii) the similarity of the expression profiles of the sample and a control or standard derived from an individual or population of individuals who have or have had the cancer.

In some embodiments, the methods disclosed herein further comprise diagnosing the individual with a cancer if the expression profile of the sample (a) deviates from the control or standard from a healthy individual or population of healthy individuals, or (b) matches the control or standard from an individual or population of individuals who have or have had the cancer.

The methods disclosed herein can further comprise predicting the susceptibility of the individual for developing a cancer based on (a) the deviation of the expression profile of the sample from a control or standard derived from a healthy individual or population of healthy individuals, or (b) the similarity of the expression profiles of the sample and a control or standard derived from an individual or population of individuals who have or have had the cancer. In some instances, the methods disclosed herein further comprise prescribing a treatment regimen based on (a) the deviation of the expression profile of the sample from a control or standard derived from a healthy individual or population of healthy individuals, or (b) the similarity of the expression profiles of the sample and a control or standard derived from an individual or population of individuals who have or have had the cancer. Alternatively, or additionally, the methods disclosed herein further comprise altering a treatment regimen prescribed or administered to the individual based on (a) the deviation of the expression profile of the sample from a control or standard derived from a healthy individual or population of healthy individuals, or (b) the similarity of the expression profiles of the sample and a control or standard derived from an individual or population of individuals who have or have had the cancer.

In some instances, the methods disclosed herein further comprise predicting the individual's response to a treatment regimen based on (a) the deviation of the expression profile of the sample from a control or standard derived from a healthy individual or population of healthy individuals, or (b) the similarity of the expression profiles of the sample and a control or standard derived from an individual or population of individuals who have or have had the cancer. In some instances, the deviation is the expression level of one or more targets from the sample is greater than the expression level of one or more targets from a control or standard derived from a healthy individual or population of healthy individuals. Alternatively, or additionally, the deviation is the expression level of one or more targets from the sample is at least about 30% greater than the expression level of one or more targets from a control or standard derived from a healthy individual or population of healthy individuals. In some embodiments, the deviation is the expression level of one or more targets from the sample is less than the expression level of one or more targets from a control or standard derived from a healthy individual or population of healthy individuals. In some instances, the deviation is the expression level of one or more targets from the sample is at least about 30% less than the expression level of one or more targets from a control or standard derived from a healthy individual or population of healthy individuals.

The methods disclosed herein can further comprise using a machine to isolate the target or the probe from the sample. Alternatively, or additionally, the methods disclosed herein further comprise contacting the sample with a label that specifically binds to the target, the probe, or a combination thereof. In some embodiments, the methods disclosed herein further comprise contacting the sample with a label that specifically binds to a target selected from Table 6. In some embodiments, the methods disclosed herein further comprise amplifying the target, the probe, or any combination thereof. The methods disclosed herein can further comprise sequencing the target, the probe, or any combination thereof. In some instances, the method further comprises quantifying the expression level of the plurality of targets. In some embodiments, the method further comprises labeling the plurality of targets.

In some instances, the methods disclosed herein further comprise converting the expression levels of the target sequences into a likelihood score that indicates the probability that a biological sample is from a patient who will a clinical outcome. In some instances, the clinical outcome is an exhibition of: (a) no evidence of disease; (b) no disease progression; (c) disease progression; (d) metastasis; (e) no metastasis; (f) systemic cancer; or (g) biochemical recurrence.

In some embodiments, the methods disclosed herein further comprise quantifying the expression level of the plurality of targets. In some instances, the method further comprises labeling the plurality of targets. In some instances, the target sequences are differentially expressed in the cancer. In some embodiments, the differential expression is dependent on aggressiveness. The expression profile can be determined by a method selected from the group consisting of RT-PCR, Northern blotting, ligase chain reaction, array hybridization, and a combination thereof. Alternatively, the expression profile is determined by RNA-Seq.

In some instances, the methods disclosed herein can diagnose, prognose, and/or monitor the status or outcome of a cancer in a subject with an accuracy of at least about 50%. In other instances, the methods disclosed herein can diagnose, prognose, and/or monitor the status or outcome of a cancer in a subject with an accuracy of at least about 60%. The methods disclosed herein can diagnose, prognose, and/or monitor the status or outcome of a cancer in a subject with an accuracy of at least about 65%. Alternatively, the methods disclosed herein can diagnose, prognose, and/or monitor the status or outcome of a cancer in a subject with an accuracy of at least about 70%. In some instances, the methods disclosed herein can diagnose, prognose, and/or monitor the status or outcome of a cancer in a subject with an accuracy of at least about 75%. In other instances, the methods disclosed herein can diagnose, prognose, and/or monitor the status or outcome of a cancer in a subject with an accuracy of at least about 80%. The methods disclosed herein can diagnose, prognose, and/or monitor the status or outcome of a cancer in a subject with an accuracy of at least about 85%. Alternatively, the methods disclosed herein can diagnose, prognose, and/or monitor the status or outcome of a cancer in a subject with an accuracy of at least about 90%. The methods disclosed herein can diagnose, prognose, and/or monitor the status or outcome of a cancer in a subject with an accuracy of at least about 95%.

In some instances, assaying the expression level of a plurality of targets comprises the use of a probe set. Assaying the expression level of a plurality of targets can comprise the use of a probe selection region (PSR). Alternatively, or additionally, assaying the expression level of a plurality of targets can comprise the use of an ICE block. In some embodiments, obtaining the expression level comprises the use of a classifier. The classifier may comprise a probe selection region (PSR). In some instances, the classifier comprises the use of an algorithm. The algorithm can comprise a machine learning algorithm. In some instances, obtaining the expression level also comprise sequencing the plurality of targets. In some embodiments, obtaining the expression level may also comprise amplifying the plurality of targets. In some embodiments, obtaining the expression level may also comprise quantifying the plurality of targets.

In some embodiments, the diagnosing, predicting, and/or monitoring the status or outcome of a cancer comprises determining the malignancy or malignant potential of the cancer or tumor. Alternatively, the diagnosing, predicting, and/or monitoring the status or outcome of a cancer comprises determining the stage of the cancer. The diagnosing, predicting, and/or monitoring the status or outcome of a cancer can comprise determining the tumor grade. Alternatively, the diagnosing, predicting, and/or monitoring the status or outcome of a cancer comprises assessing the risk of developing a cancer. In some embodiments, the diagnosing, predicting, and/or monitoring the status or outcome of a cancer includes assessing the risk of cancer recurrence. In some embodiments, diagnosing, predicting, and/or monitoring the status or outcome of a cancer may comprise determining the efficacy of treatment.

In some embodiments, diagnosing, predicting, and/or monitoring the status or outcome of a cancer may comprise determining a therapeutic regimen. Determining a therapeutic regimen may comprise administering an anti-cancer therapeutic. Alternatively, determining the treatment for the cancer may comprise modifying a therapeutic regimen. Modifying a therapeutic regimen may comprise increasing, decreasing, or terminating a therapeutic regimen.

Further disclosed herein is a kit for analyzing a cancer, comprising (a) a probe set comprising a plurality of target sequences, wherein the plurality of target sequences comprises at least one target sequence listed in Table 6; and (b) a computer model or algorithm for analyzing an expression level and/or expression profile of the target sequences in a sample. In some embodiments, the kit further comprises a computer model or algorithm for correlating the expression level or expression profile with disease state or outcome. In some embodiments, the kit further comprises a computer model or algorithm for designating a treatment modality for the individual. In some embodiments, the kit further comprises a computer model or algorithm for normalizing expression level or expression profile of the target sequences. In some embodiments, the kit further comprises a computer model or algorithm comprising a robust multi-chip average (RMA), probe logarithmic intensity error estimation (PLIER), non-linear fit (NLFIT) quantile-based, nonlinear normalization, or a combination thereof.

Further disclosed herein is a kit for analyzing a cancer, comprising (a) a probe set comprising a plurality of target sequences, wherein the plurality of target sequences hybridizes to one or more targets selected from Table 6; and (b) a computer model or algorithm for analyzing an expression level and/or expression profile of the target sequences in a sample. In some embodiments, the kit further comprises a computer model or algorithm for correlating the expression level or expression profile with disease state or outcome. In some embodiments, the kit further comprises a computer model or algorithm for designating a treatment modality for the individual. In some embodiments, the kit further comprises a computer model or algorithm for normalizing expression level or expression profile of the target sequences. In some embodiments, the kit further comprises a computer model or algorithm comprising a robust multichip average (RMA), probe logarithmic intensity error estimation (PLIER), non-linear fit (NLFIT) quantile-based, nonlinear normalization, or a combination thereof.

Disclosed herein, in some embodiments, is a classifier for diagnosing, predicting, and/or monitoring the outcome or status of a cancer in a subject. The classifier may comprise a classifier as disclosed in Table 17. The classifier can comprise a classifier as disclosed in Table 19. The classifier can comprise the GLM2, KNN12, KNN16, NB20, SVM5, SVM11, SVM20 classifiers or any combination thereof. The classifier can comprise a GLM2 classifier. Alternatively, the classifier comprises a KNN12 classifier. The classifier can comprise a KNN16 classifier. In other instances, the classifier comprises a NB20 classifier. The classifier may comprise a SVM5 classifier. In some instances, the classifier comprises a SVM11 classifier. Alternatively, the classifier comprises a SVM20 classifier. Alternatively, the classifier comprises one or more Inter-Correlated Expression (ICE) blocks disclosed herein. The classifier can comprise one or more probe sets disclosed herein. In some instances, the classifiers disclosed herein have an AUC value of at least about 0.50. In other instances, the classifiers disclosed herein have an AUC value of at least about 0.60. The classifiers disclosed herein can have an AUC value of at least about 0.70.

Further disclosed herein, is an Inter-Correlated Expression (ICE) block for diagnosing, predicting, and/or monitoring the outcome or status of a cancer in a subject. The ICE block may comprise one or more ICE Block IDs as disclosed in Tables 22-24. The ICE block can comprise Block ID_2879, Block ID_2922, Block ID_4271, Block ID_4627, Block ID_5080, or any combination thereof. Alternatively, the ICE block comprises Block ID_6592, Block ID_4226, Block ID_6930, Block ID_7113, Block ID_5470, or any combination thereof. In other instances, the ICE block comprises Block ID_7716, Block ID_4271, Block ID_5000, Block ID_5986, Block ID_1146, Block ID_7640, Block ID_4308, Block ID_1532, Block ID_2922, or any combination thereof. The ICE block can comprise Block ID_2922. Alternatively, the ICE block comprises Block ID_5080. In other instances, the ICE block comprises Block ID_6592. The ICE block can comprise Block ID_4627. Alternatively, the ICE block comprises Block ID_7113. In some instances, the ICE block comprises Block ID_5470. In other instances, the ICE block comprises Block ID_5155. The ICE block can comprise Block ID_6371. Alternatively, the ICE block comprises Block ID_2879.

Further disclosed herein, is a probe set for diagnosing, predicting, and/or monitoring the outcome or status of a cancer in a subject. The probe set may comprise a plurality of probes, wherein (i) the probes in the set are capable of detecting an expression level of at least one non-coding target; and (ii) the expression level determines the cancer status of the subject with at least about 40% specificity. In some embodiments, the probe set further comprises a probe capable of detecting an expression level of at least one coding target.

Further disclosed herein, is a probe set for diagnosing, predicting, and/or monitoring the outcome or status of a cancer in a subject. The probe set may comprise a plurality of probes, wherein (i) the probes in the set are capable of detecting an expression level of at least one non-coding target; and (ii) the expression level determines the cancer status of the subject with at least about 40% accuracy. In some embodiments, the probe set further comprises a probe capable of detecting an expression level of at least one coding target.

Further disclosed herein, is a probe selection region (PSR) for diagnosing, predicting, and/or monitoring the outcome or status of a cancer in a subject. The PSR can comprise any of the probe sets disclosed herein. Alternatively, the PSR comprises any of the probe sets as disclosed in Tables 4, 15, 17, 19, 22-24, and 27-30 (see 'Probe set ID' column). In some instances, the probe set comprises probe set ID 2518027. Alternatively, the probe set comprises probe set ID 3046448; 3046449; 3046450; 3046457; 3046459; 3046460; 3046461; 3046462; 3046465; 3956596; 3956601; 3956603; 3103704; 3103705; 3103706; 3103707; 3103708; 3103710; 3103712; 3103713; 3103714; 3103715; 3103717; 3103718; 3103720; 3103721; 3103725; 3103726; 2719689; 2719692; 2719694; 2719695; 2719696; 2642733; 2642735; 2642738; 2642739; 2642740; 2642741; 2642744; 2642745; 2642746; 2642747; 2642748; 2642750; 2642753; 3970026; 3970034; 3970036; 3970039; 2608321; 2608324; 2608326; 2608331; 2608332; 2536222; 2536226; 2536228; 2536229; 2536231; 2536232; 2536233; 2536234; 2536235; 2536236; 2536237; 2536238; 2536240; 2536241; 2536243; 2536245; 2536248; 2536249; 2536252; 2536253; 2536256; 2536260; 2536261; 2536262; 3670638; 3670639; 3670641; 3670644; 3670645; 3670650; 3670659; 3670660; 3670661; 3670666, a complement thereof, a reverse complement thereof, or any combination thereof.

Further disclosed herein in some embodiments is a system for analyzing a cancer, comprising: (a) a probe set comprising a plurality of target sequences, wherein (i) the plurality of target sequences hybridizes to one or more targets selected from Table 6; or (ii) the plurality of target sequences comprises one or more target sequences selected SEQ ID NOs: 1-903; and (b) a computer model or algorithm for analyzing an expression level and/or expression profile of the target hybridized to the probe in a sample from a subject suffering from a cancer.

In some instances, the plurality of targets disclosed herein comprises at least 5 targets selected from Table 6. In some embodiments, the plurality of targets comprises at least 10 targets selected from Table 6. In some embodiments, the plurality of targets comprises at least 15 targets selected from Table 6. In some embodiments, the plurality of targets comprises at least 20 targets selected from Table 6. In some embodiments, the plurality of targets comprises at least 30 targets selected from Table 6. In some embodiments, the plurality of targets comprises at least 35 targets selected from Table 6. In some embodiments, the plurality of targets comprises at least 40 targets selected from Table 6.

In some instances, the systems disclosed herein further comprise an electronic memory for capturing and storing an expression profile. The systems disclosed herein can further comprise a computer-processing device, optionally connected to a computer network. Alternatively, or additionally, the systems disclosed herein further comprise a software module executed by the computer-processing device to analyze an expression profile. In some instances, the systems disclosed herein further comprise a software module executed by the computer-processing device to compare the expression profile to a standard or control. The systems disclosed herein can further comprise a software module executed by the computer-processing device to determine the expression level of the target. The systems disclosed herein can further comprise a machine to isolate the target or the probe from the sample. In some instances systems disclosed herein further comprises a machine to sequence the target or the probe. Alternatively, or additionally, the systems disclosed herein further comprise a machine to amplify the target or the probe. The systems disclosed herein can further comprise a label that specifically binds to the target, the probe, or a combination thereof. In some embodiments, the systems disclosed herein further comprise a software module executed by the computer-processing device to transmit an analysis of the expression profile to the individual or a medical professional treating the individual. In some embodiments, the systems disclosed herein further comprise a software module executed by the computer-processing device to transmit a diagnosis or prognosis to the individual or a medical professional treating the individual. In some instances, the systems disclosed herein further comprise a sequencer for sequencing the plurality of targets. In other instances, the systems disclosed herein further comprise an instrument for amplifying the plurality of targets. In some embodiments, the systems disclosed herein further comprise a label for labeling the plurality of targets.

In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the cancer is a prostate cancer. In some embodiments, the cancer is a pancreatic cancer. In some embodiments, the cancer is a thyroid cancer. In some embodiments, the cancer is a lung cancer. In some instances, the cancer is a bladder cancer.

In some embodiments, the non-coding target and the coding target are nucleic acid sequences. In some embodiments, the nucleic acid sequence is a DNA sequence. In some embodiments, the nucleic acid sequence is an RNA sequence.

The non-coding target can be selected from Tables 4, 6-8, 14, 15, 17, 19, 22, 23, 26-30, or any combination thereof. In some embodiments, the non-coding target is selected from an intronic sequence, a sequence within the UTR, or a non-coding RNA transcript. In some embodiments, the non-coding target is an intronic sequence or partially overlaps with an intronic sequence. In some embodiments, the non-coding target is a UTR sequence or partially overlaps with a UTR sequence.

In some embodiments, the non-coding target is a non-coding RNA transcript. In some embodiments, the non-coding RNA transcript is selected from the group consisting of PASR, TASR, aTASR, TSSa-RNA, RE-RNA, uaRNA, x-ncRNA, hY RNA, usRNA, snaR, vtRNA, T-UCRs, pseudogenes, GRC-RNAs, aRNAs, PALRs, PROMPTs, and LSINCTs. In some embodiments, the non-coding RNA transcript is non-polyadenylated.

In some instances, the coding target is selected from Tables 4, 6-8, 14, 15, 17, 19, 22, 23, 26-30, or any combination thereof. In some embodiments, the coding target is an exon-coding transcript. In some embodiments, the exon-coding transcript is an exonic sequence.

In some instances, the plurality of targets comprises at least about 2 targets selected from Tables 4, 6-8, 14, 15, 17, 19, 22, 23, 26-30, or any combination thereof. Alternatively, or additionally, the plurality of targets comprises at least about 3 targets selected from Tables 4, 6-8, 14, 15, 17, 19, 22, 23, 26-30, or any combination thereof. The plurality of targets can comprise at least about 5 targets selected from Tables 4, 6-8, 14, 15, 17, 19, 22, 23, 26-30, or any combination thereof. The plurality of targets can comprise at least about 10 targets selected from Tables 4, 6-8, 14, 15, 17, 19, 22, 23, 26-30, or any combination thereof. The plurality of targets can comprise at least about 15 targets selected from Tables 4, 6-8, 14, 15, 17, 19, 22, 23, 26-30, or any combination thereof. The plurality of targets can comprise at least about 20 targets selected from Tables 4, 6-8, 14, 15, 17, 19, 22, 23, 26-30, or any combination thereof. The plurality of targets can comprise at least about 25 targets selected from Tables 4, 6-8, 14, 15, 17, 19, 22, 23, 26-30, or any combination thereof. In some instances, the plurality of targets comprises at least about 30, 40, 50, 60, 70, 80, 90, 100, 125, 150, 175, 200, 225, 250, 275, 300, 325, 350, 375, 400, or 425 targets selected from Tables 4, 6-8, 14, 15, 17, 19, 22, 23, 26-30, or any combination thereof. In other instances, the plurality of targets comprises at least about 450, 475, 500, 525, 550, 575, 600, 625, 650, 675, 700, 725, 750, 775, 800, 825, 850, 875, or 900 targets selected from Tables 4, 6-8, 14, 15, 17, 19, 22, 23, 26-30, or any combination thereof.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

'metastatic-like') using the biochemical recurrence (BCR) end point for coding (a), non-coding (b) and non-exonic (c).

Figure 5:
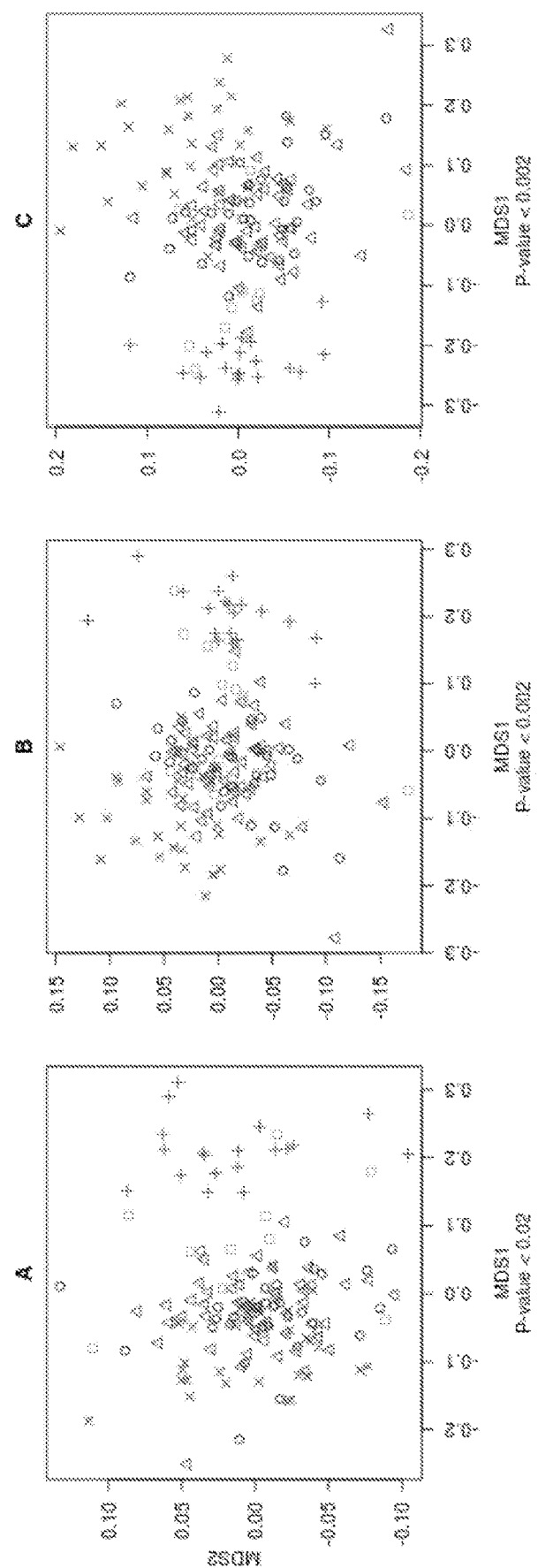

FIG. 5. MDS plots of the distribution of primary tumour samples with Gleason score of 6 (circle), 7 (triangle), 8 and 9 (square) compared to metastatic (+) and normal (x) tissues for coding (a), non-coding (b) and non-exonic (c) PSRs.

Figure 6:
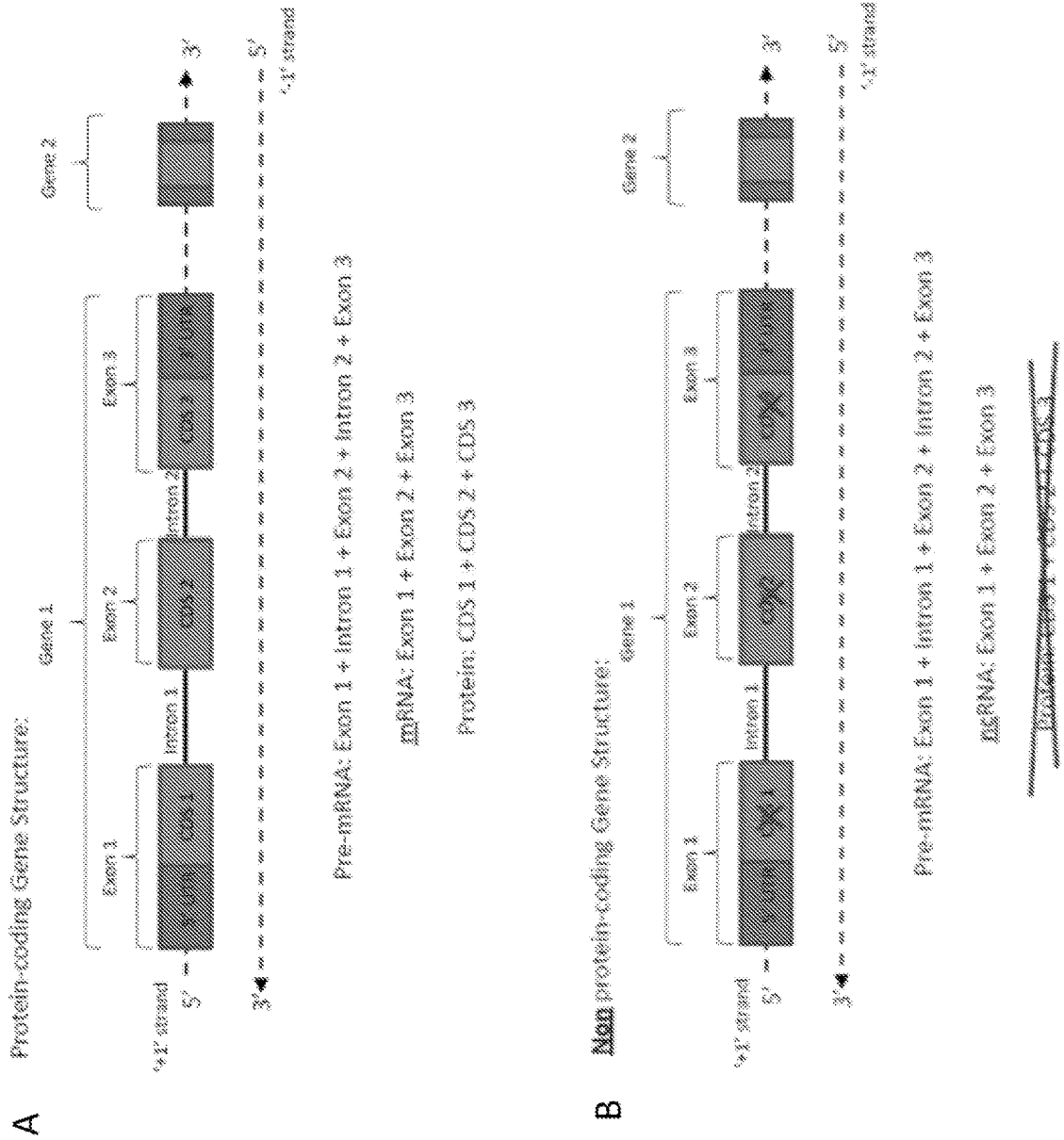

FIG. 6. Illustration of (a) protein-coding and (b) non protein-coding gene structures.

Figure 7:
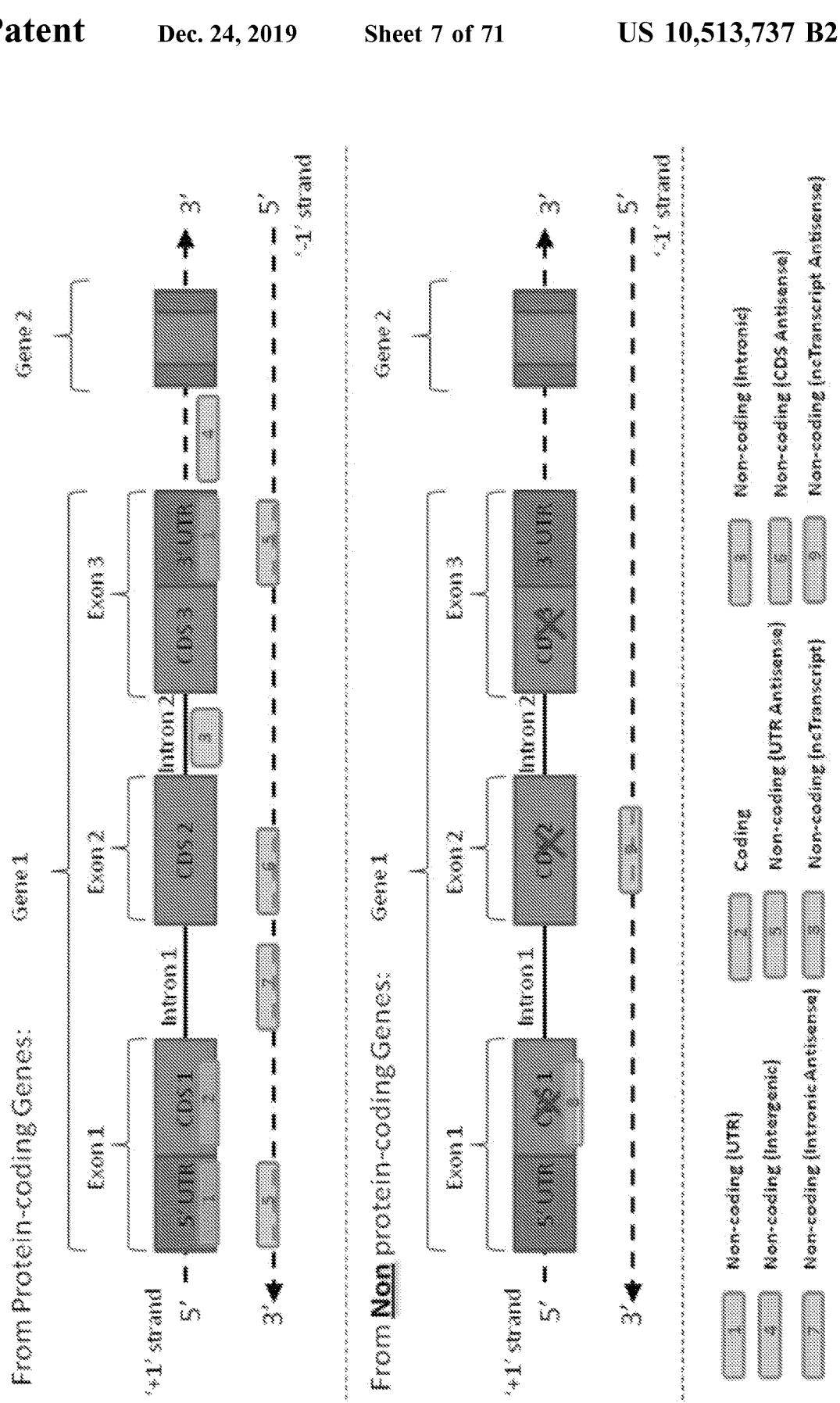

FIG. 7. Illustration of the categorization of probe selection regions.

Figure 8:
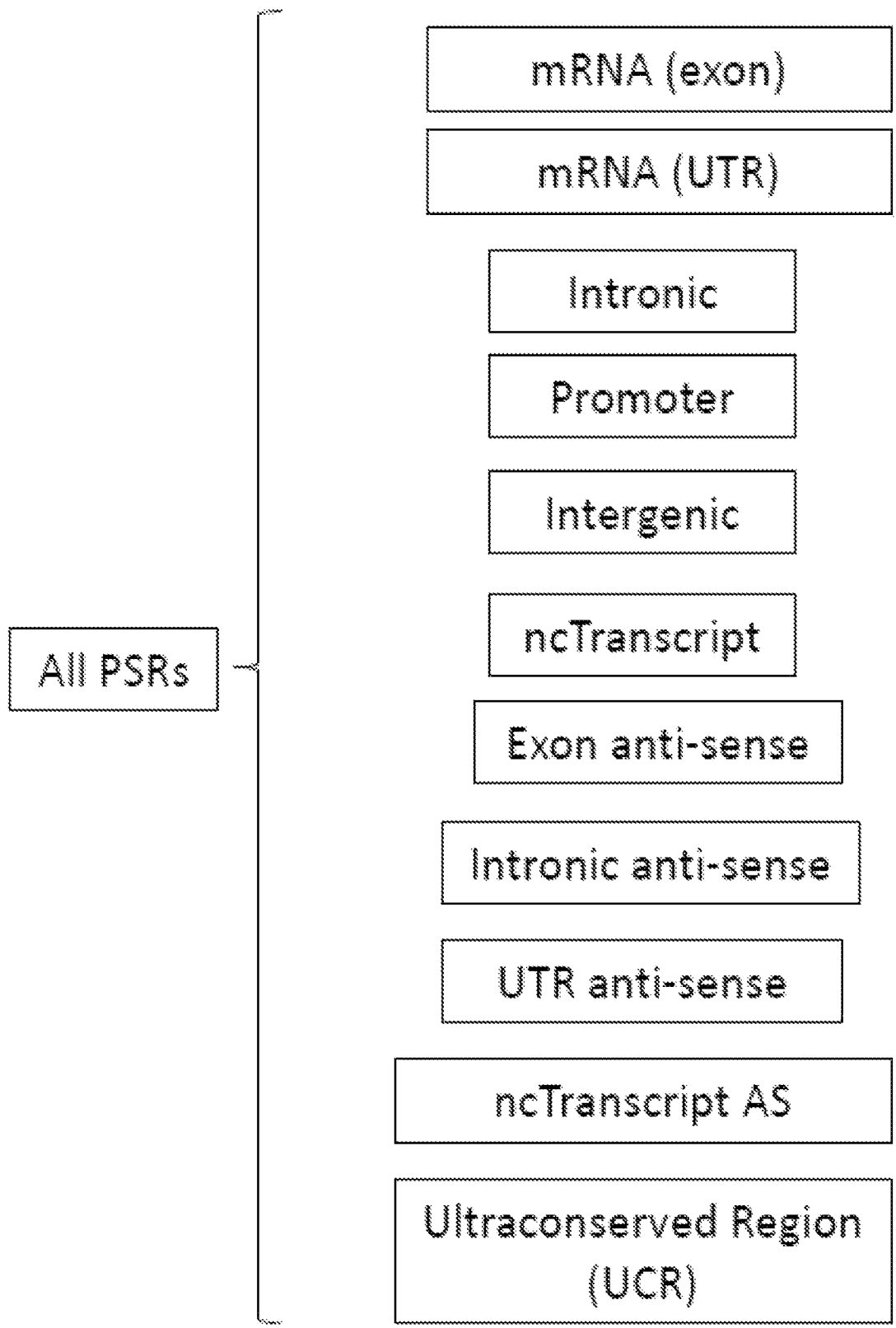

FIG. 8. List of potential probe selection regions.

Figure 9:
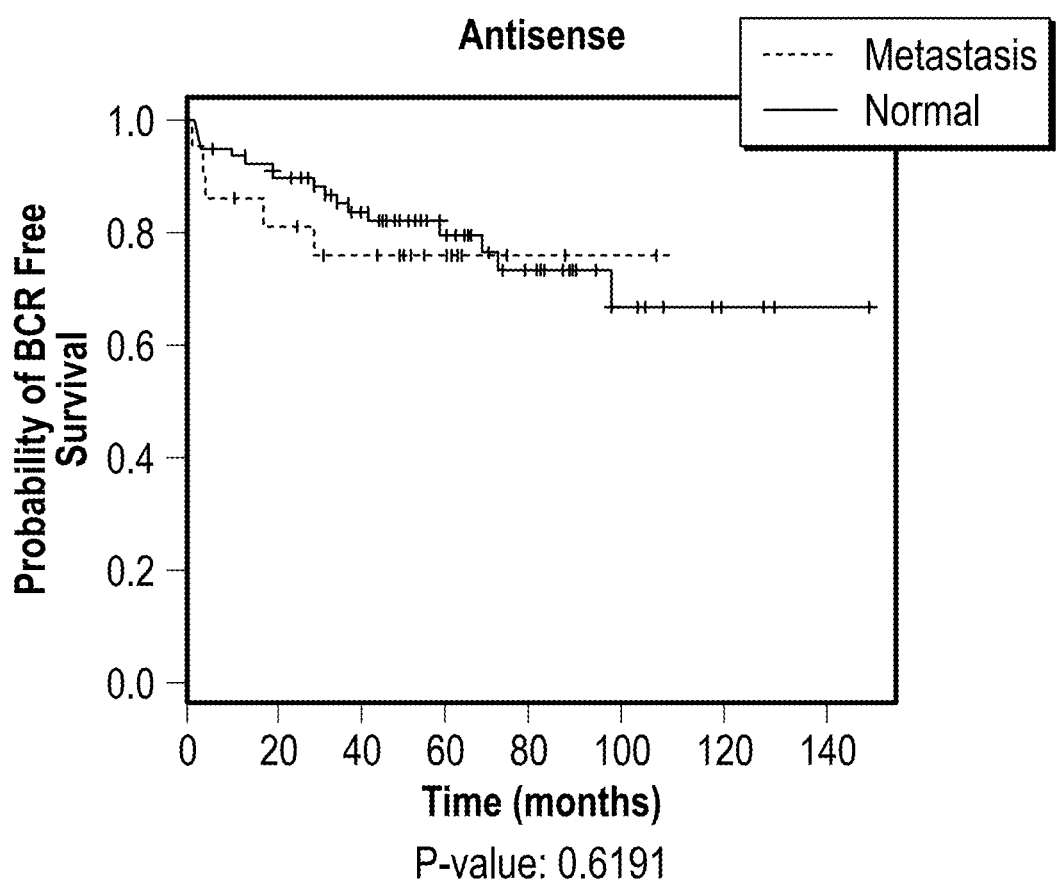

FIG. 9. BCR KMM plot in MSKCC for different KNN models based on PSR genomic subsets FIG. 10. Illustration of syntenic blocks.

Figure 11:
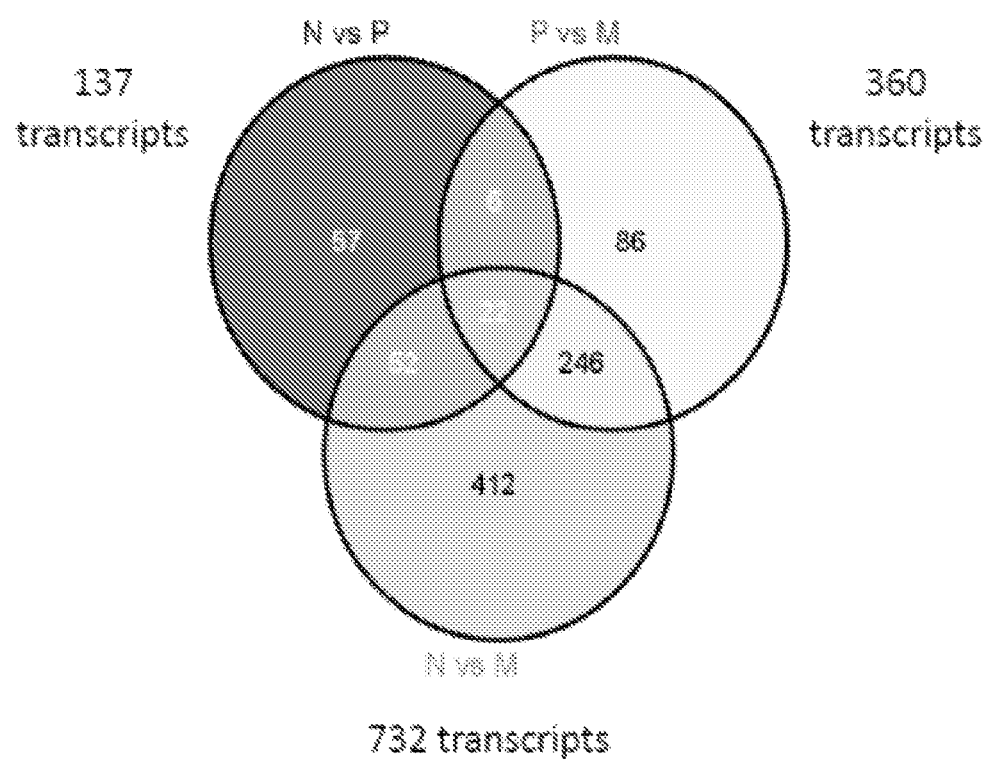

FIG. 11. Venn Diagram distribution of differentially expressed transcripts across pairwise comparison. N vs P: Normal Adjacent versus Primary tumor comparison. P vs M: Primary Tumor versus Metastatic sample comparison. N vs M: Normal adjacent versus Metastatic Sample comparison.

Figure 12:
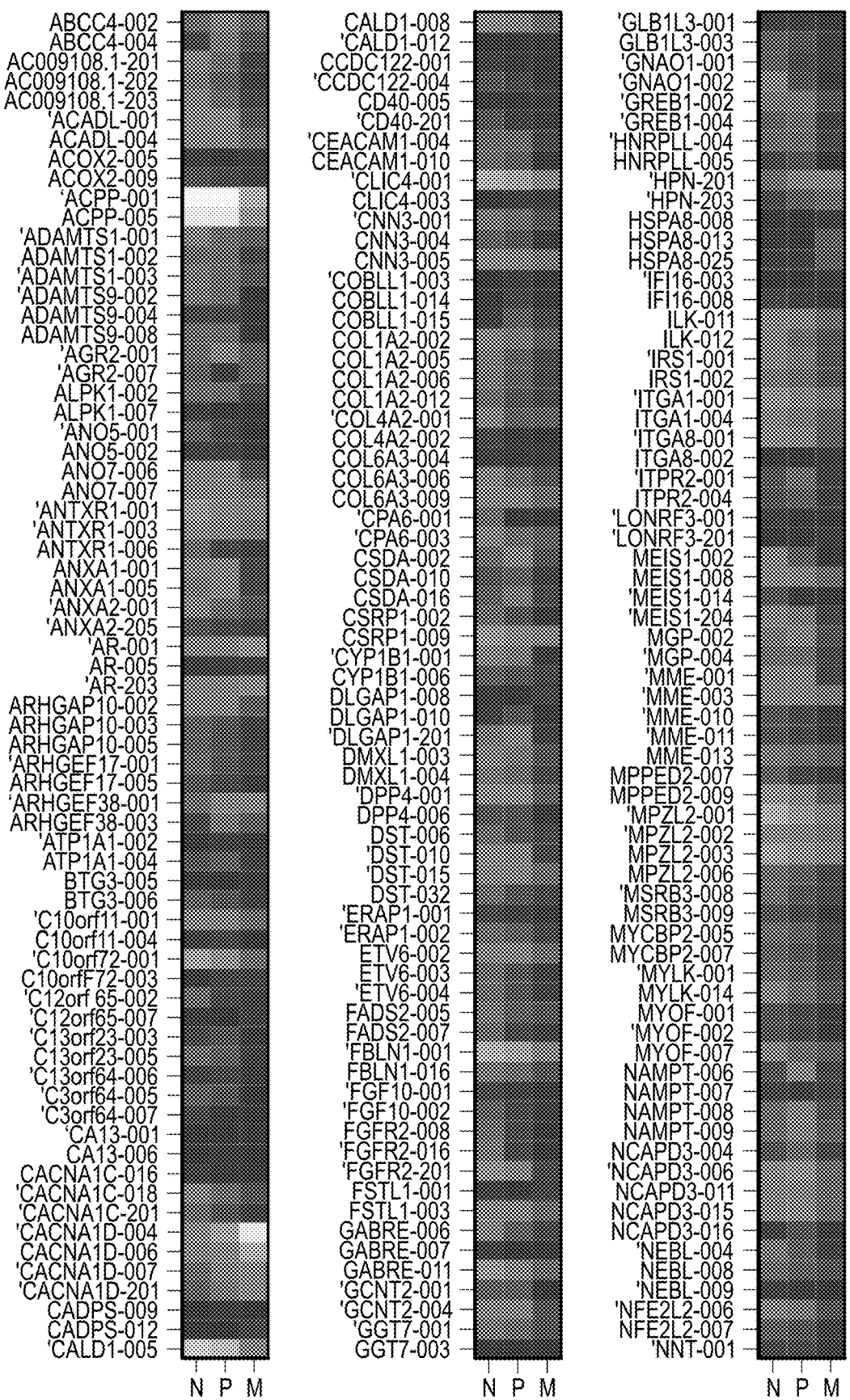
Figure 12:
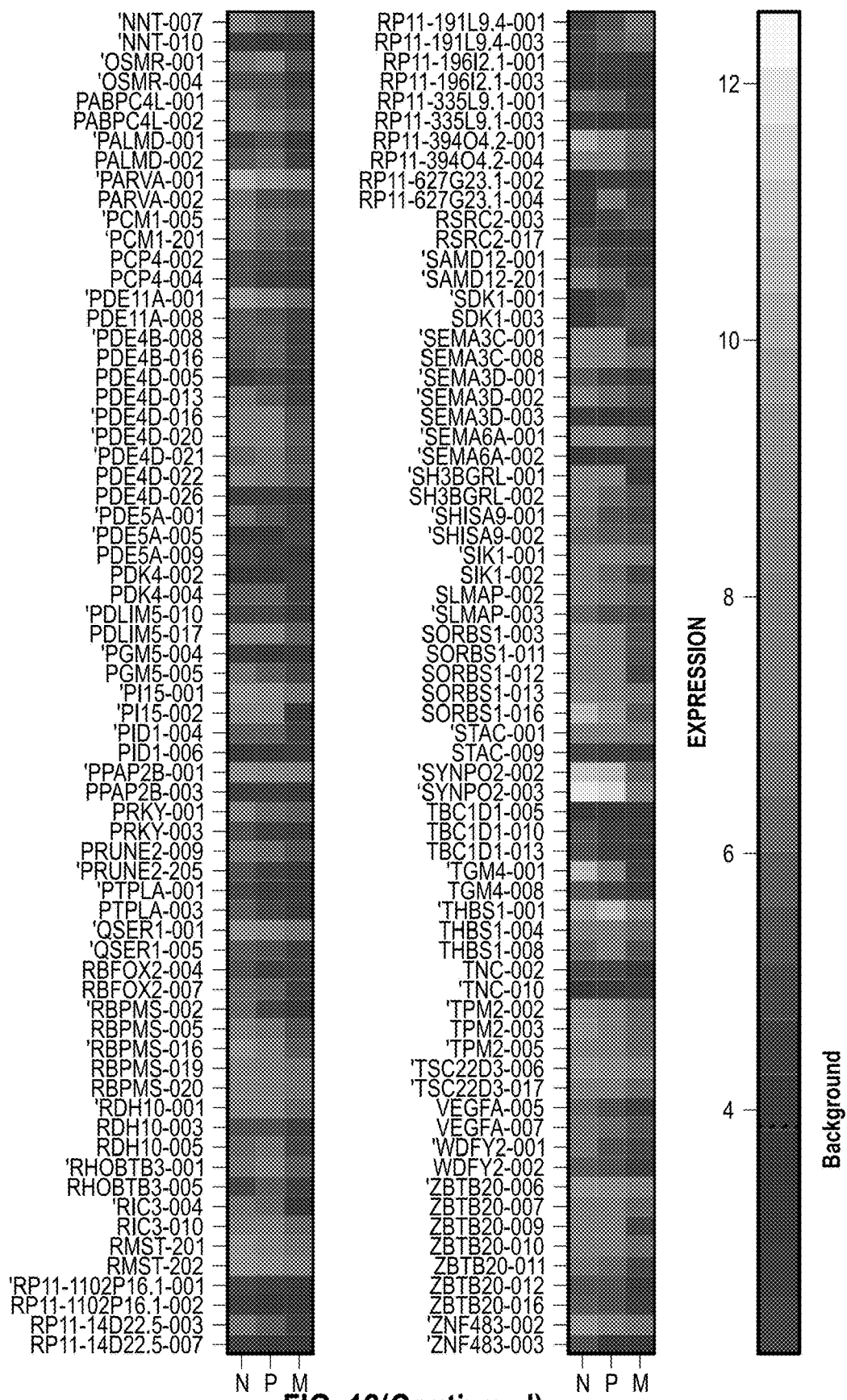

FIG. 12. Heat map of genes with two or more transcripts differentially expressed across any pairwise comparison. Transcript names are provided as annotated in Ensembl. Heatmap is colored according to median expression values for Normal (N), Primary (P) and metastatic (M) samples. '*' indicates that the transcript is protein-coding. Background indicates the expression value considered as background level based on control probe sets on the HuEx array.

Figure 13:
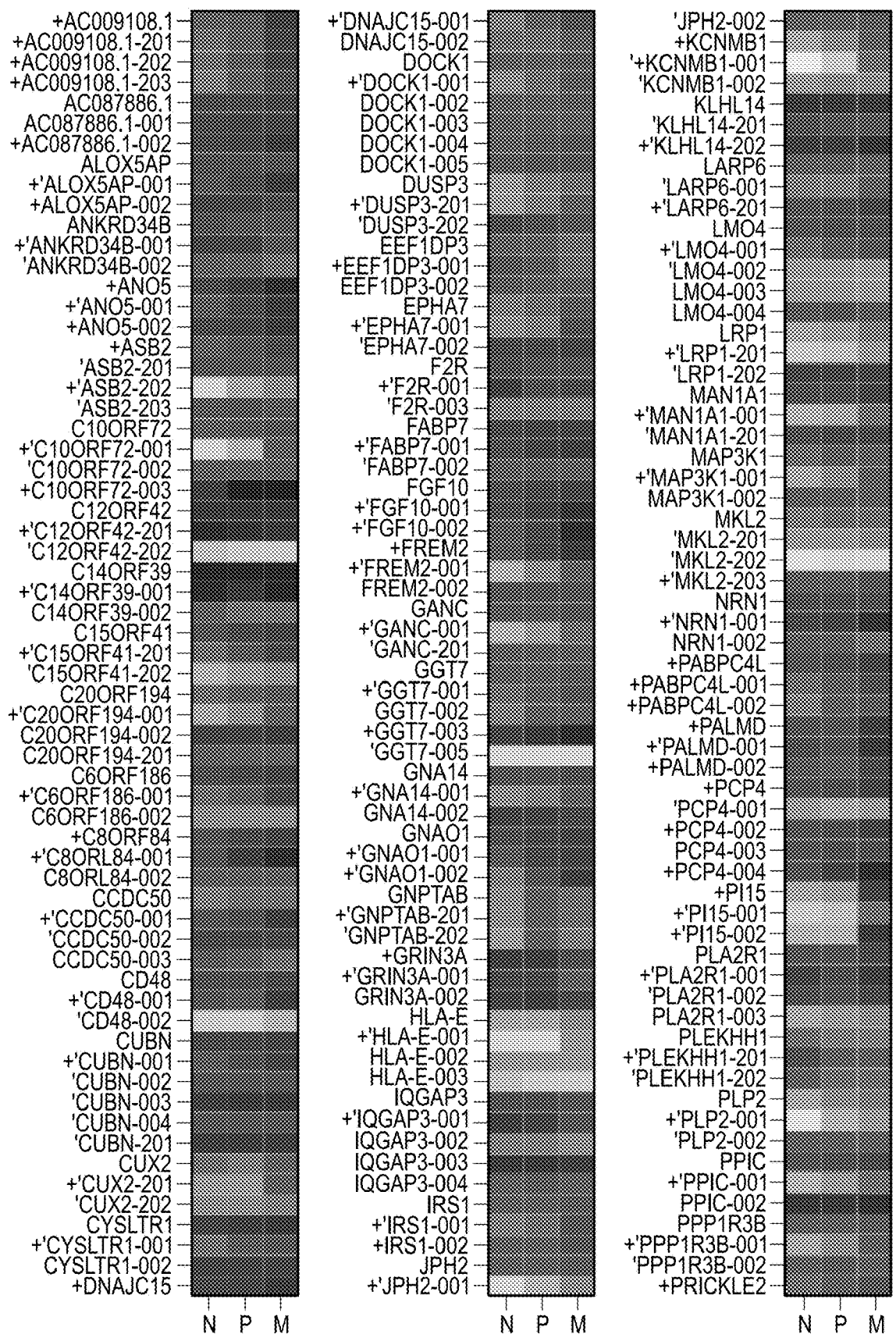
Figure 13:
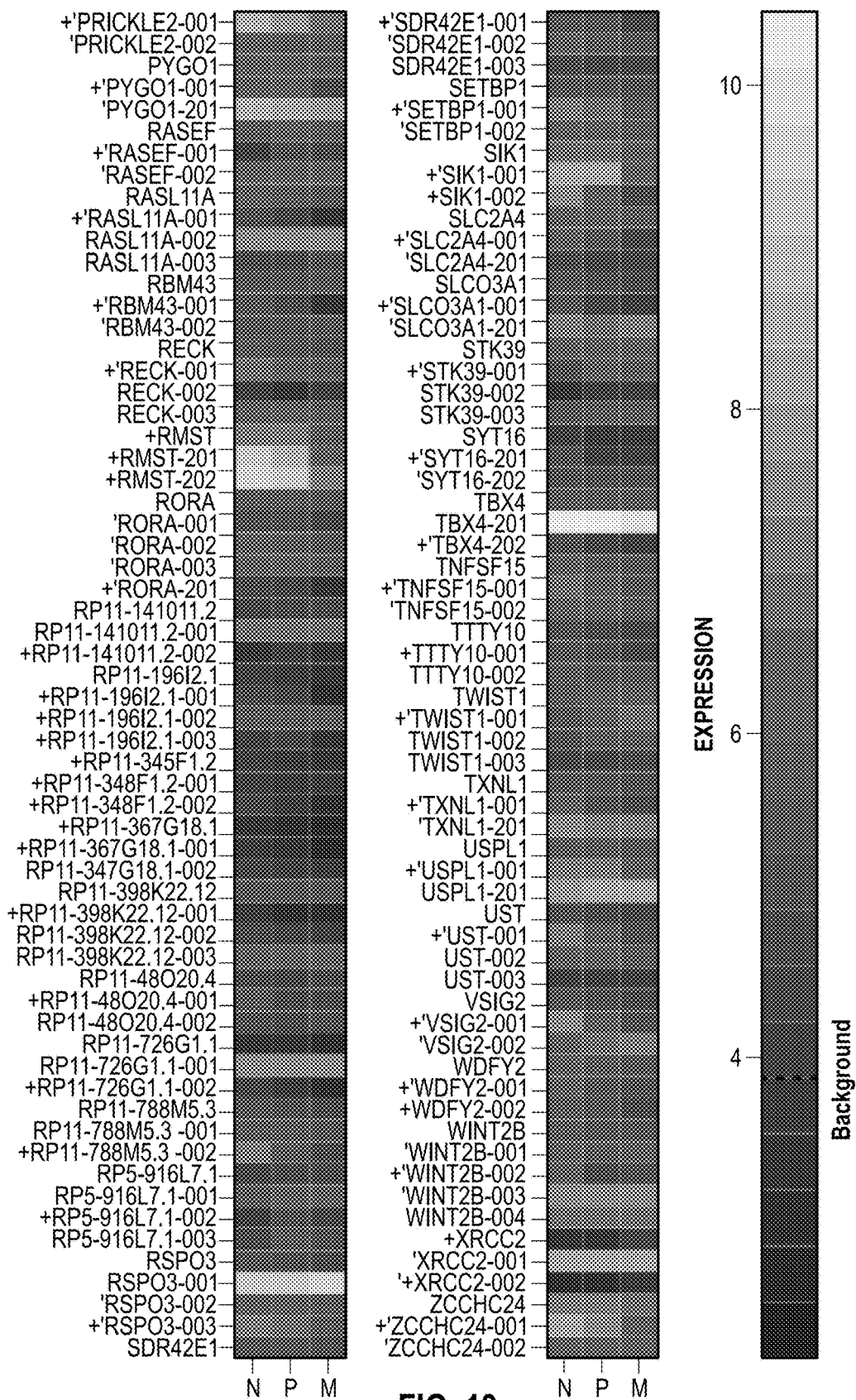

FIG. 13. Heat map of genes with one or more transcripts differentially expressed across any pairwise comparison for which all transcripts were assessed. Transcript names are provided as annotated in Ensembl. Gene names are annotated based on their gene symbol. Heatmap is colored according to median expression values for Normal (N), Primary (P) and metastatic (M) samples. '*' indicates that the transcript is protein-coding. '+' indicates significant differential expression of a given transcript or gene. Background indicates the expression value considered as background level based on control probe sets on the HuEx array.

Figure 14:
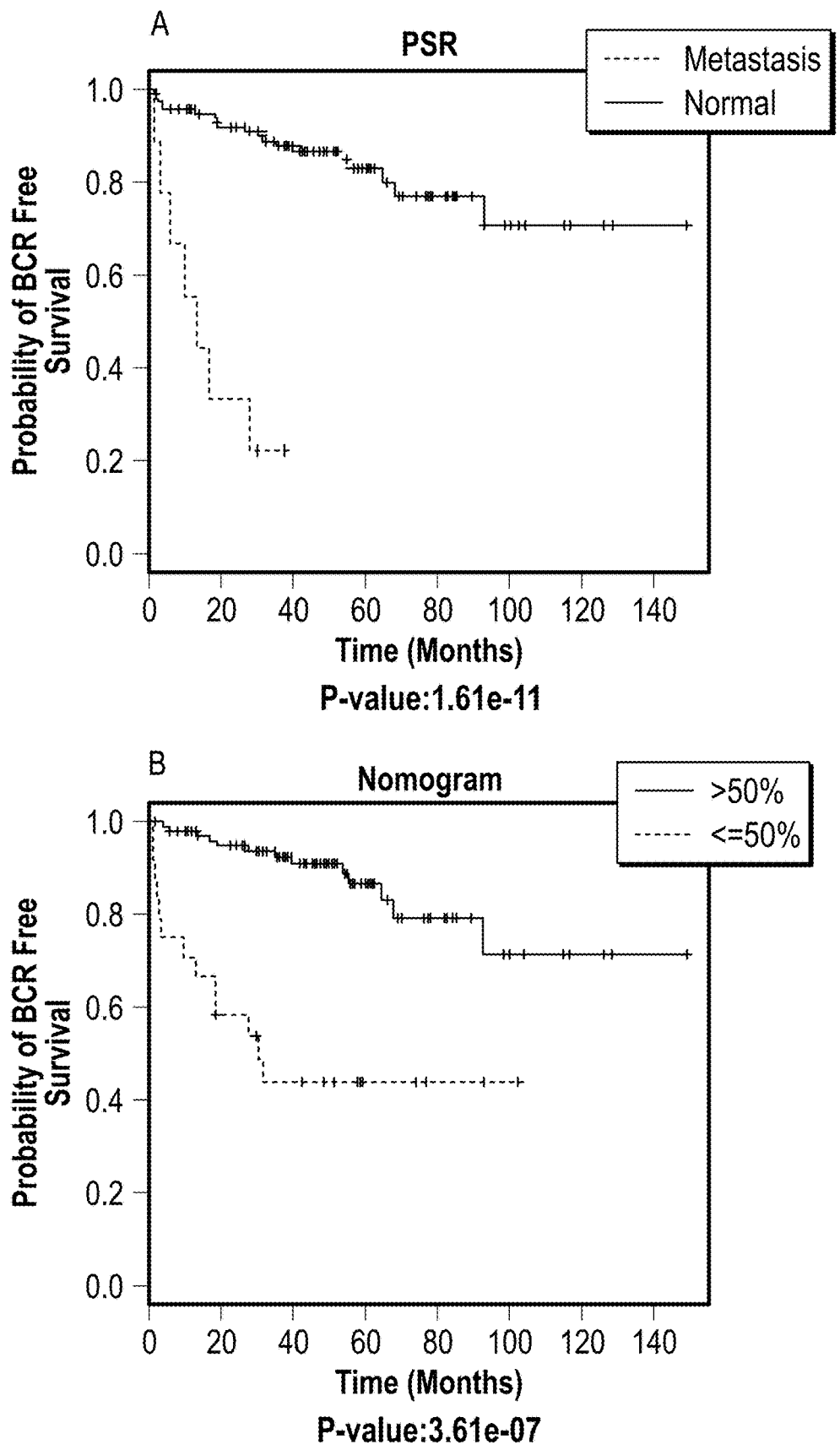
Figure 14:
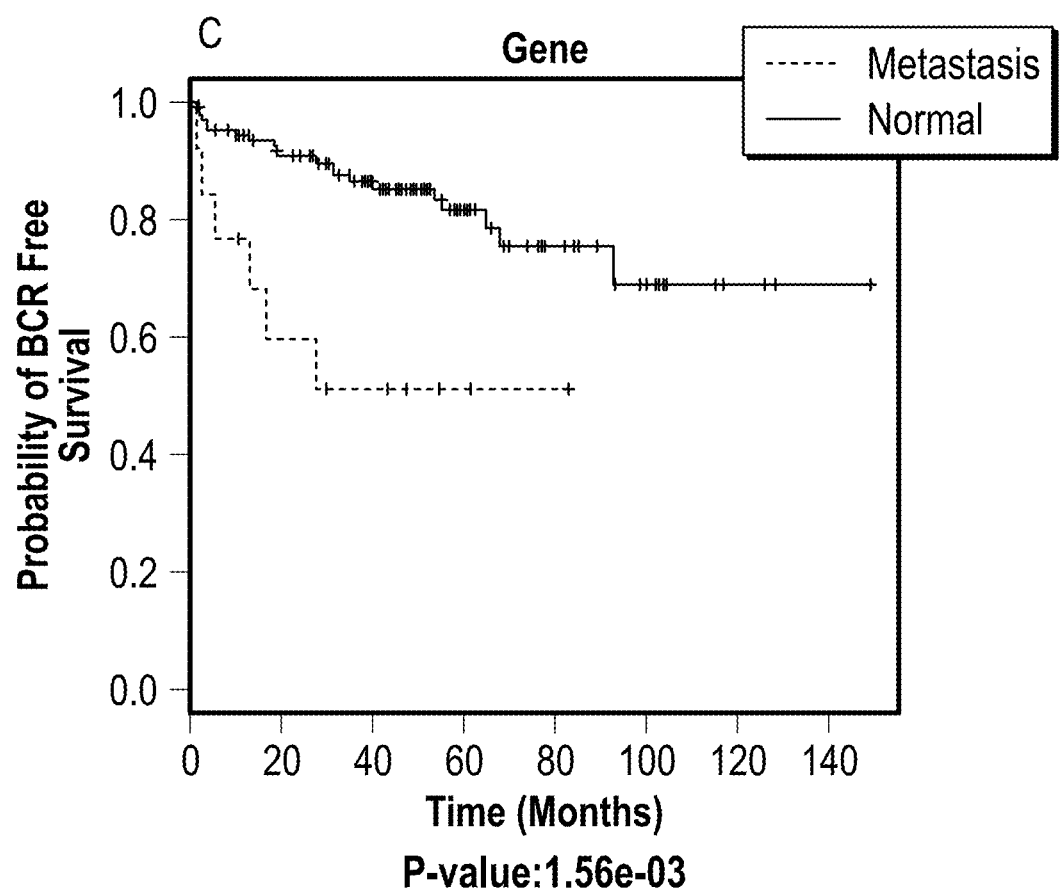

FIG. 14. Kaplan Meier plots of the two groups of primary tumor samples classified by KNN ("normal-like" vs "metastatic-like") using the BCR endpoint for (a) Transcripts (represented by transcript-specific PSRs), (b) Kaftan nomogram and (c) Genes.

FIG. 15. Illustration of filtered and kept TS-PSRs. A) TS-PSR of a gene having only one transcript annotated. B) TS-PSRs for only one transcript of a gene with two or more transcripts. c) A gene for which at least two of its transcripts has a TS-PSR.

Figure 16:
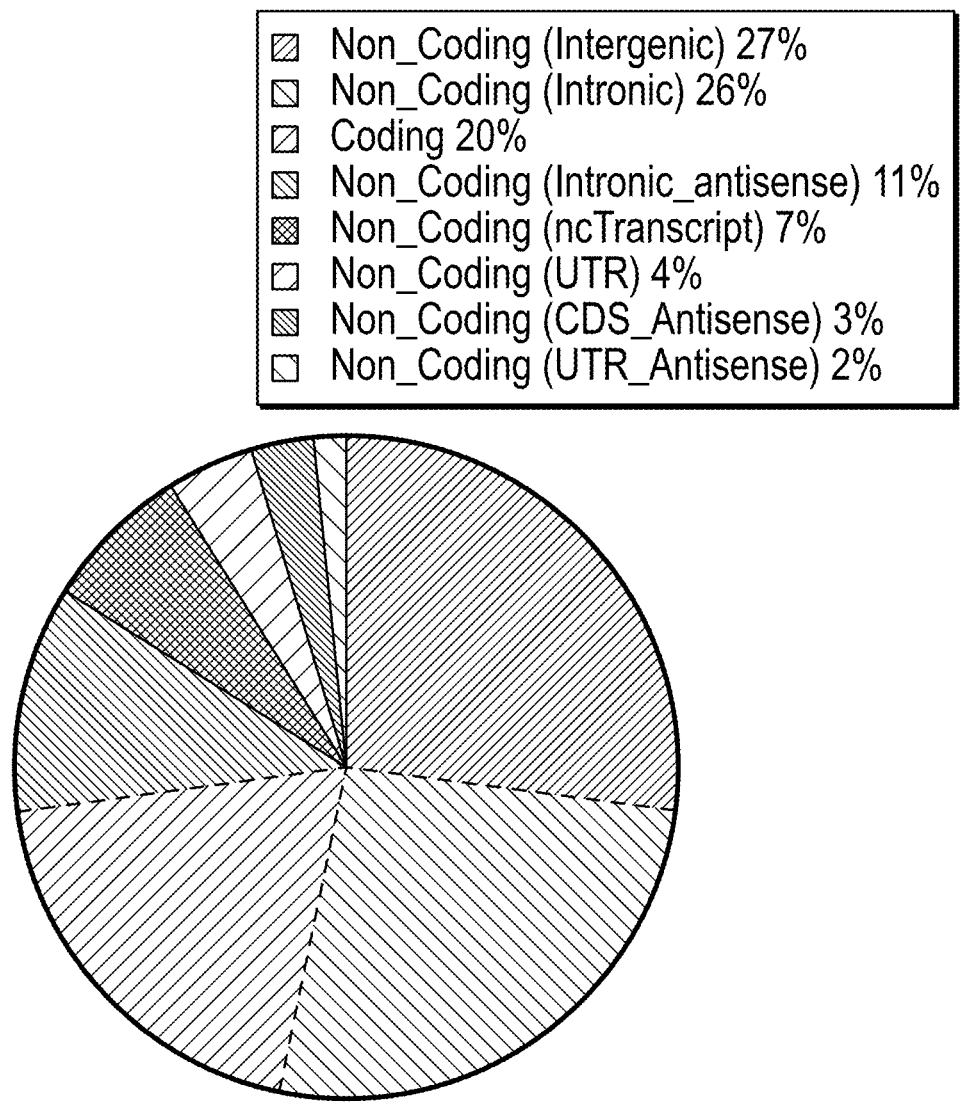

FIG. 16. Genomic Annotation and Distribution of the PSRs found differentially expressed within chr2q31.3 region.

Figure 17:
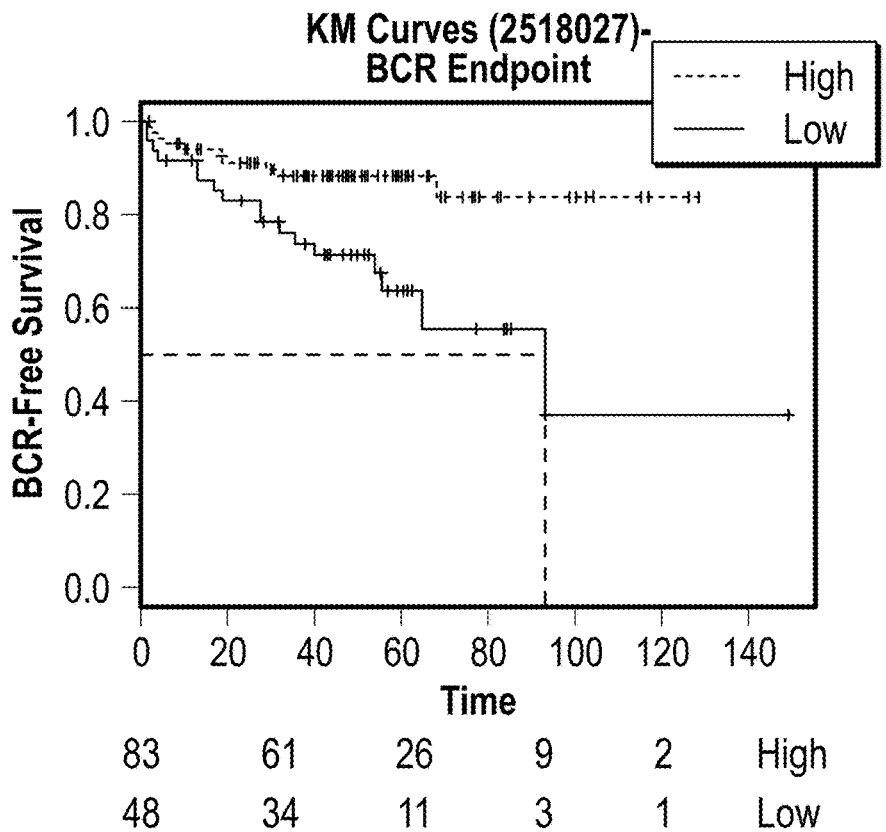

FIG. 17. KM curve for a PSR (Probe set ID 2518027) for the BCR endpoint. P-value=0.00.

Figure 18:
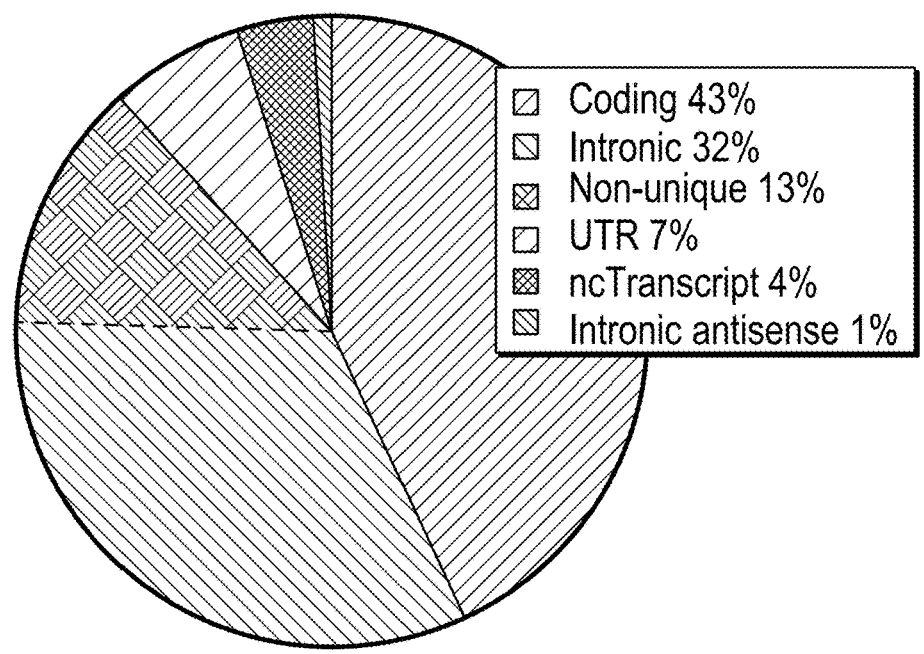

FIG. 18. Distribution of PSRs differentially expressed between low risk (GS<7) and high risk (GS>7) samples.

FIG. 19. (a) Box plots showing DIGS-RF12 segregating the Gleason 3+4 samples from the Gleason 4+3 samples. (b) KM plot of BCR-Free survival based on the groups predicted by DIGS-RF12.

FIG. 20. Genes with transcript-specific PSRs differentially expressed based on MSKCC data. (a) Gene CHRAC1. (b) Gene IMPDH1

FIG. 21. Depicts the ROC curves at 4 years (a) Survival ROC curves at 4 years for the training set for GC and GCC for patients with progression. (b) Survival ROC curves at 4 years for the testing set for GC and GCC for patients with progression.

Figure 22:
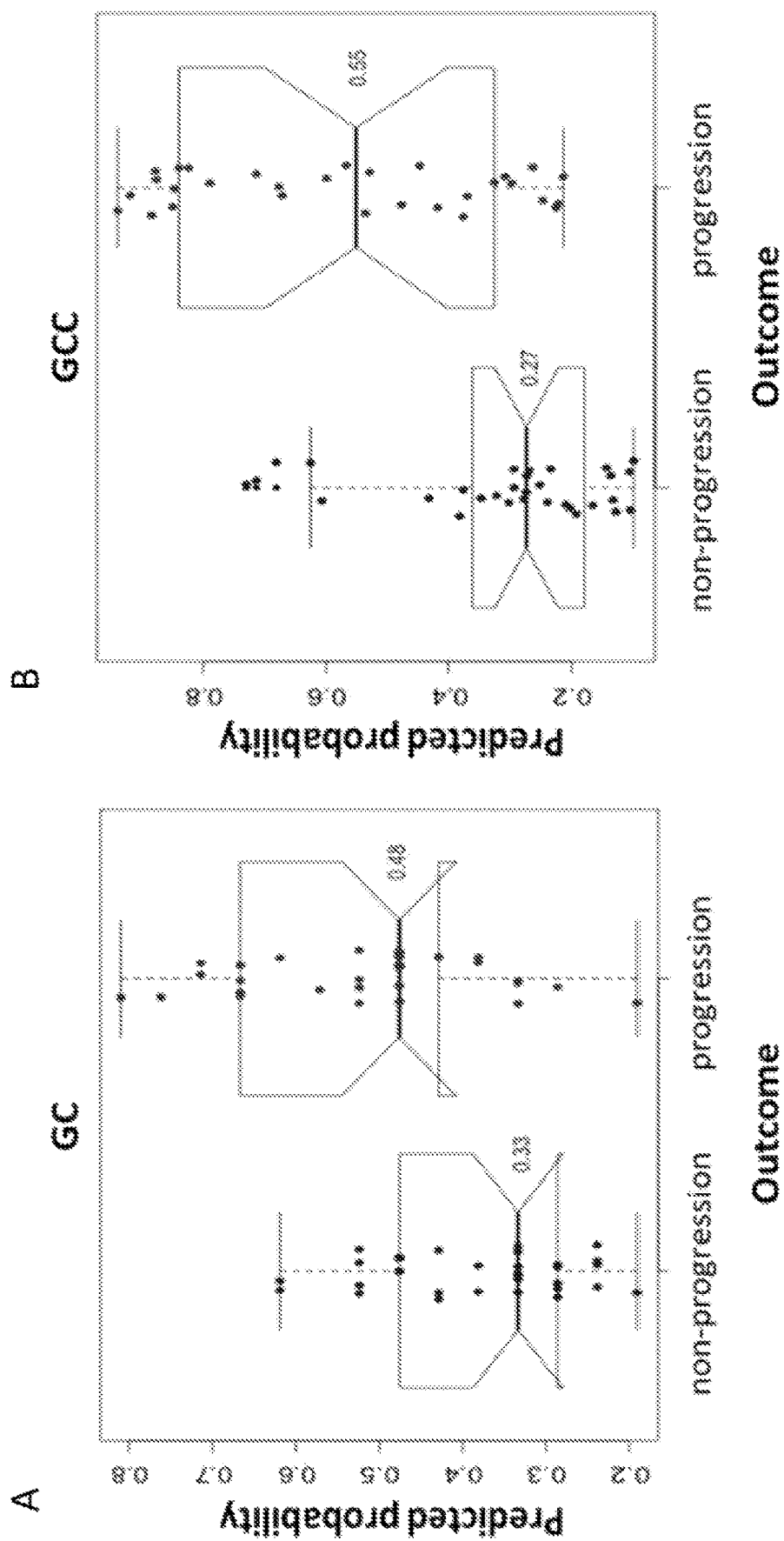

FIG. 22. Discrimination Box plots for GC and GCC. Box plots depict the distribution of classifier scores between patients with and without progression. Boxes extend between the 25th and 75th percentiles (lower and upper quartiles, respectively), and the notch represents the 50th percentile (median). Whiskers extend indicating 95% confidence intervals.

Figure 23:
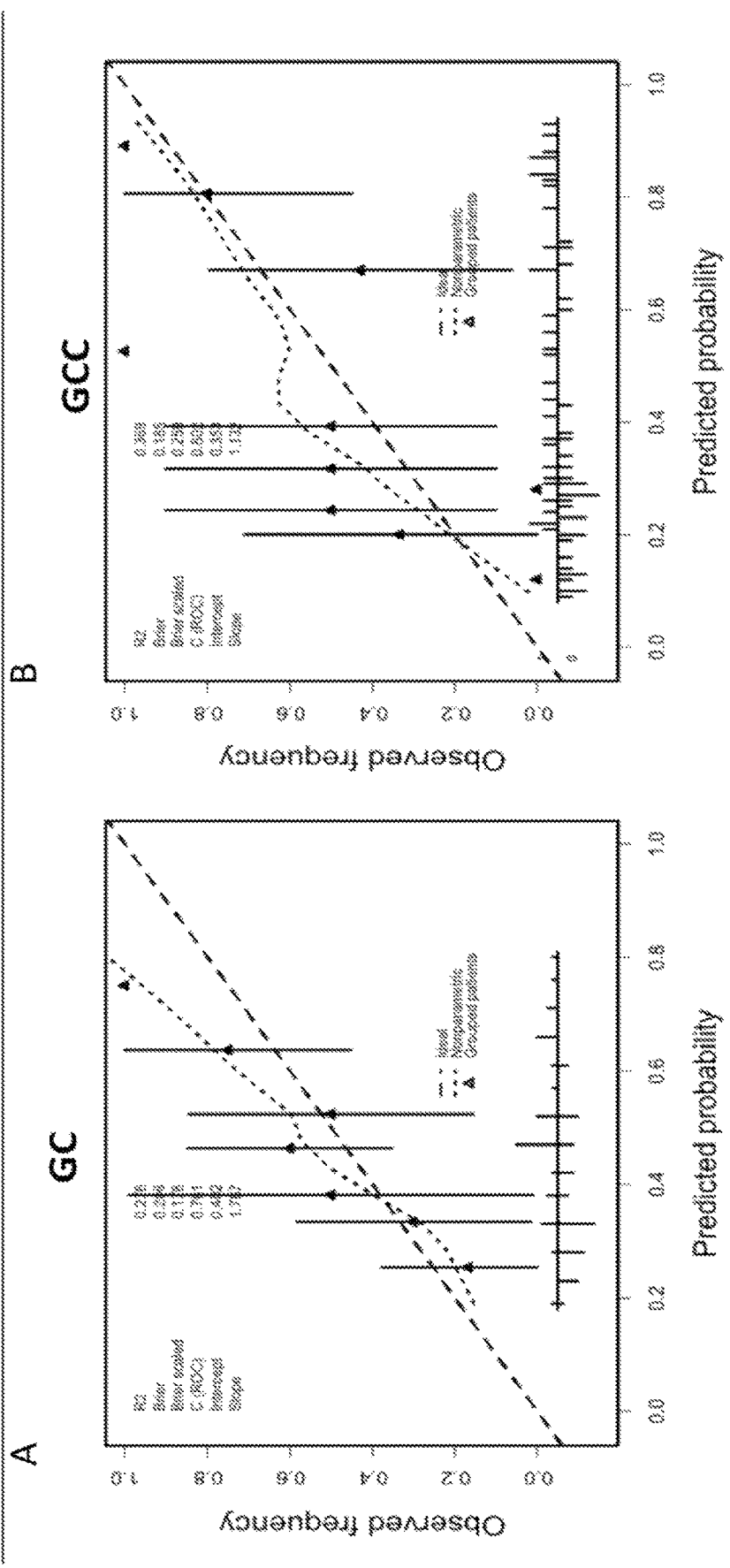

FIG. 23. Calibration plots for GC and GCC. Calibration plots segregate the classifier scores into quintiles. For each quintile, mean score is plotted against the total proportion of patients who experienced progression. Perfect calibration, represented by the dashed 45-degree line, implies that the mean score is roughly equivalent to the proportion of patients who experienced progression (e.g. if the mean score is 0.20, then approximately 20% of patients in that quintile group experienced progression). Triangles represent the grouped patients, plotted by mean classifier score of that group against the observed frequency of progression. Compared to a poor model, a classifier that is a good discriminator will have a greater distance between the groups. The 95% confidence intervals are plotted for each group. Intercept indicates whether the predictions are systemically too high or too low, and an optimal slope approximately equals 1; slopes <1 indicate overfitting of the classifier.

FIG. 24. Cumulative incidence of disease progression for GC and GCC. Cumulative incidence curves were constructed using competing risks analysis to accommodate censoring due to death and other events that bias Kaplan-Meier estimates of incidence.

Figure 25:
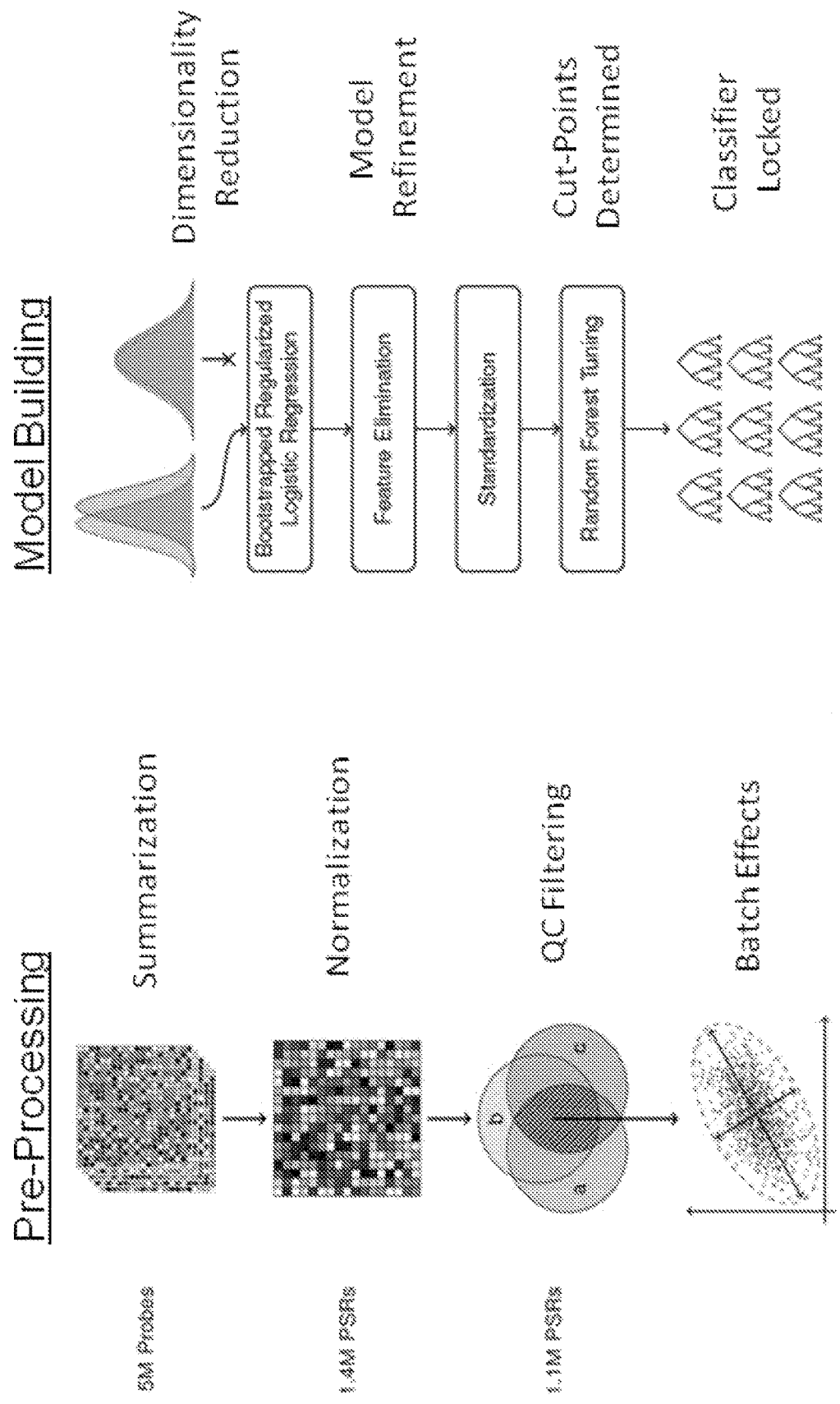

FIG. 25. Illustration of probe selection methods

FIG. 26. ROC curves (A) and KM plots (B) for NB20. (A) ROC curves are shown separately for training (trn) and testing (tst) sets. 95% confidence intervals for AUC as well as P-values for the significance of the P-values based on the non-parametric Wilcoxon test. (B) Kaplan Meier curves on the training (trn) and testing (tst) sets for two groups of patients (GC=Low and GC=High) based on PAM clustering.

FIG. 27. ROC curves (A) and KM plots (B) for KNN12. (A) ROC curves are shown separately for training (trn) and testing (tst) sets. 95% confidence intervals for AUC as well as P-values for the significance of the P-values based on the non-parametric Wilcoxon test. (B) Kaplan Meier curves on the training (trn) and testing (tst) sets for two groups of patients (GC=Low and GC=High) based on PAM clustering.

FIG. 28. ROC curves (A) and KM plots (B) for GLM2. (A) ROC curves are shown separately for training (trn) and testing (tst) sets. 95% confidence intervals for AUC as well as P-values for the significance of the P-values based on the non-parametric Wilcoxon test. (B) Kaplan Meier curves on the training (trn) and testing (tst) sets for two groups of patients (GC=Low and GC=High) based on PAM clustering.

FIG. 29. ROC curves (A) and KM plots (B) for a PSR intronic to gene MECOM (probe set ID 2704702). (A) ROC curves are shown separately for training (trn) and testing (tst) sets. 95% confidence intervals for AUC as well as P-values for the significance of the P-values based on the non-parametric Wilcoxon test. (B) Kaplan Meier curves on the training (trn) and testing (tst) sets for two groups of patients (GC=Low and GC=High) based on PAM clustering.

FIG. 30. ROC curves (A) and box plots (B) for SVM20. (A) ROC curves are shown separately for training (left) and testing (right) sets. 95% confidence intervals for AUC as well as P-values for the significance of the P-values based on the non-parametric Wilcoxon test. (B) Box plots on the training (left) and testing (right) sets. Notches represent 95% confidence intervals for the scores associated to a given group (GS6 or GS7+).

FIG. 31. ROC curves (A) and box plots (B) for SVM11. (A) ROC curves are shown separately for training (left) and testing (right) sets. 95% confidence intervals for AUC as well as P-values for the significance of the P-values based on the non-parametric Wilcoxon test. (B) Box plots on the training (left) and testing (right) sets. Notches represent 95% confidence intervals for the scores associated to a given group (GS6 or GS7+).

FIG. 32. ROC curves (A) and box plots (B) for SVM5. (A) ROC curves are shown separately for training (left) and testing (right) sets. 95% confidence intervals for AUC as well as P-values for the significance of the P-values based on the non-parametric Wilcoxon test. (B) Box plots on the training (left) and testing (right) sets. Notches represent 95% confidence intervals for the scores associated to a given group (GS6 or GS7+).

FIG. 33. ROC curves (A) and box plots (B) for GLM2. (A) ROC curves are shown separately for training (left) and testing (right) sets. 95% confidence intervals for AUC as well as P-values for the significance of the P-values based on the non-parametric Wilcoxon test. (B) Box plots on the training (left) and testing (right) sets. Notches represent 95% confidence intervals for the scores associated to a given group (GS6 or GS7+).

Figure 34:
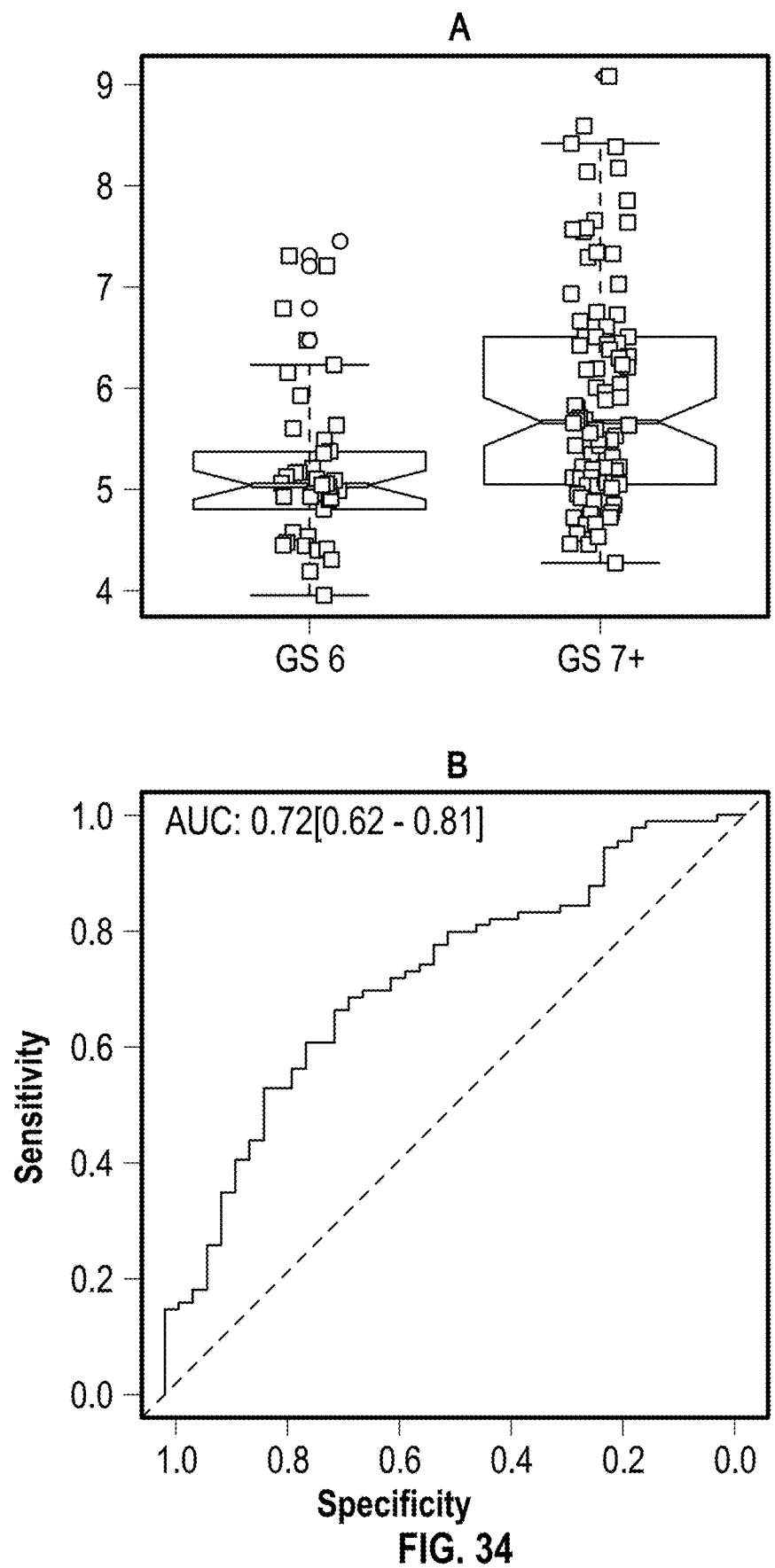

FIG. 34. Box plot (A) and ROC curve (B) for ICE Block 7716 for GS endpoint. (A) Box plot. Notches represent 95% confidence intervals for the scores associated to a given group (GS6 or GS7+). (B) ROC curve. 95% confidence interval for the AUC is provided as a metric of the statistical significance.

Figure 35:
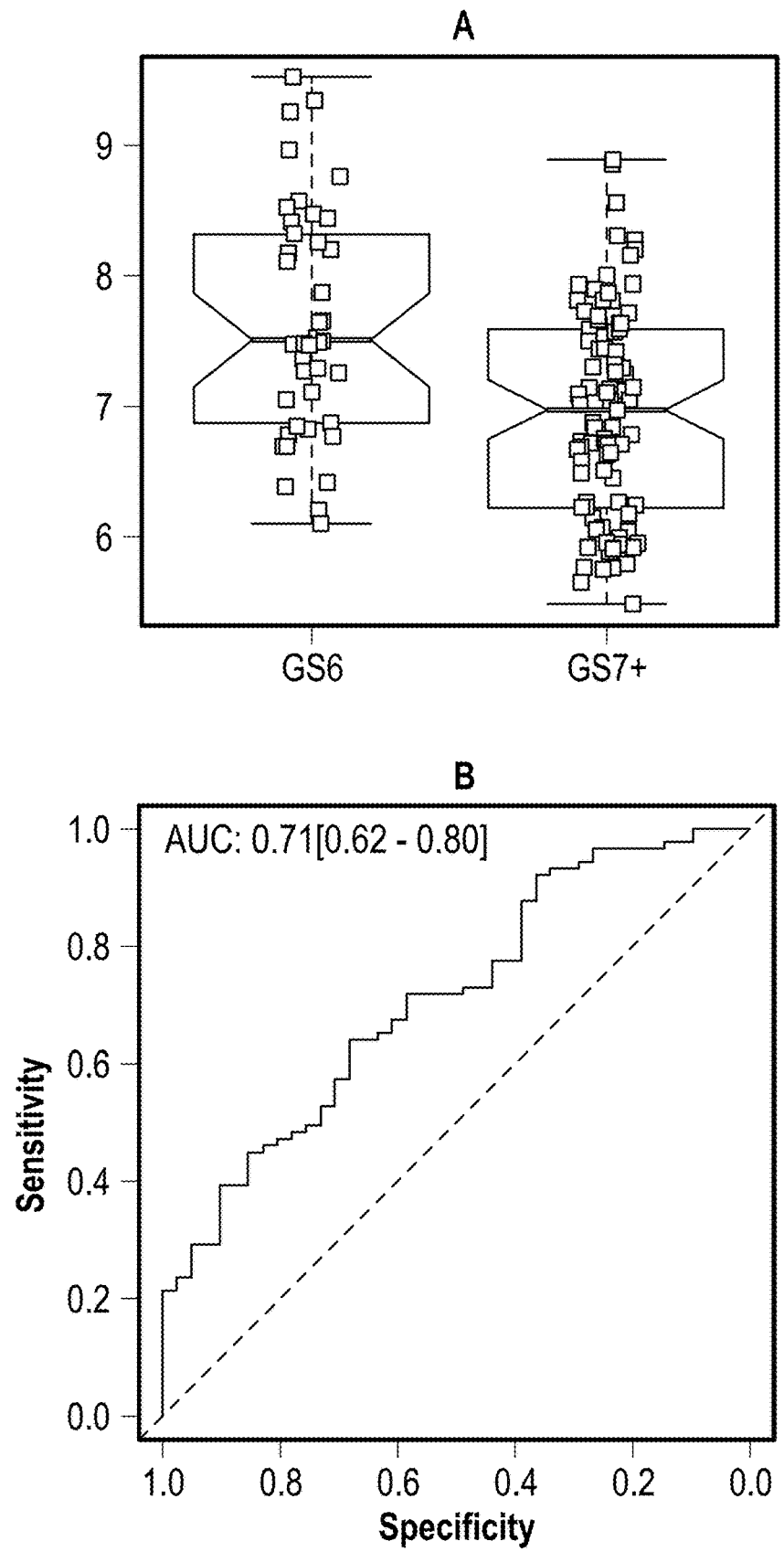

FIG. 35. Box plot (A) and ROC curve (B) for ICE Block 4271 for GS endpoint. (A) Box plot. Notches represent 95% confidence intervals for the scores associated to a given group (GS6 or GS7+). (B) ROC curve. 95% confidence interval for the AUC is provided as a metric of the statistical significance.

Figure 36:
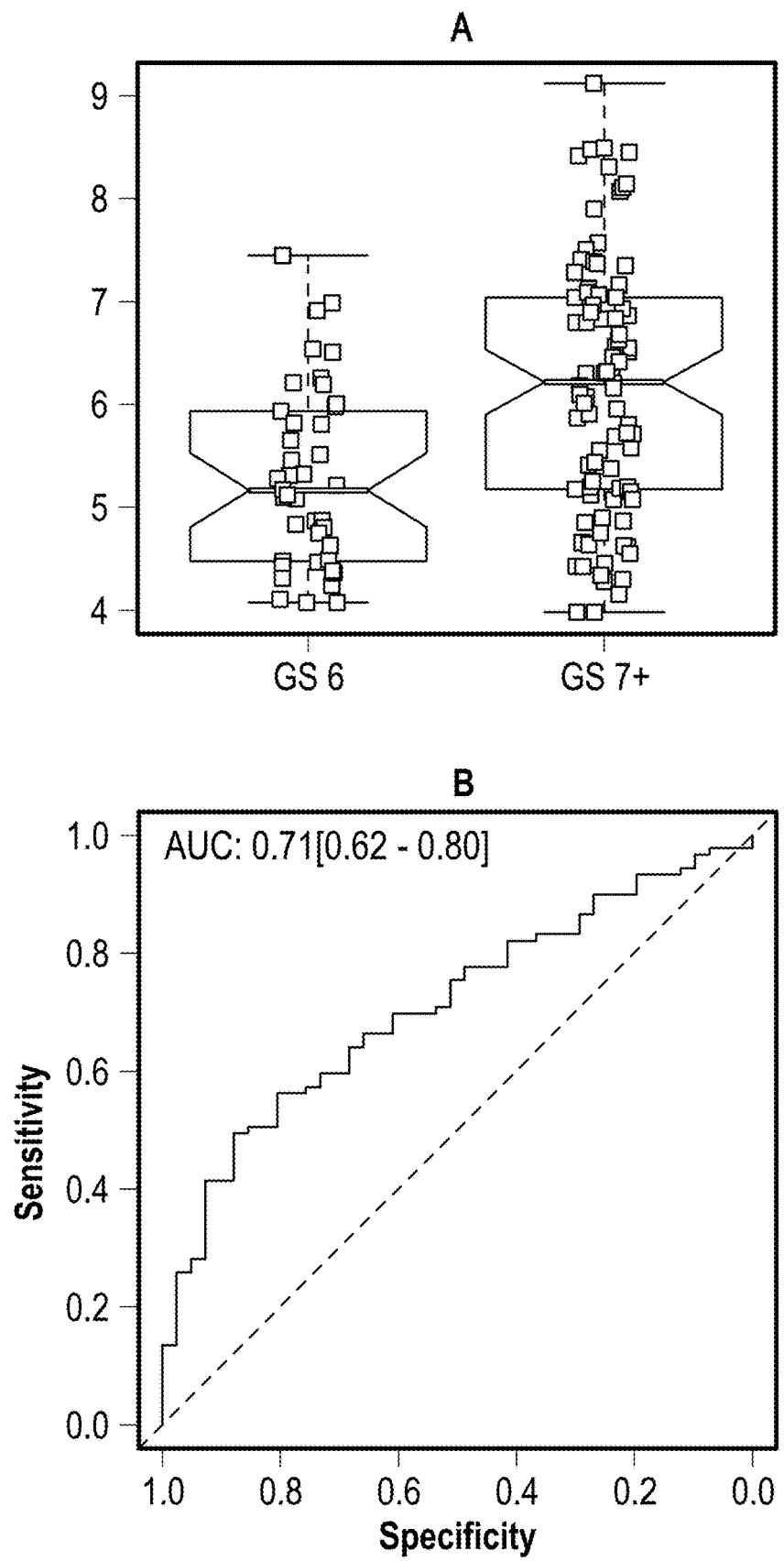

FIG. 36. Box plot (A) and ROC curve (B) for ICE Block 5000 for GS endpoint. (A) Box plot. Notches represent 95% confidence intervals for the scores associated to a given group (GS6 or GS7+). (B) ROC curve. 95% confidence interval for the AUC is provided as a metric of the statistical significance.

Figure 37:
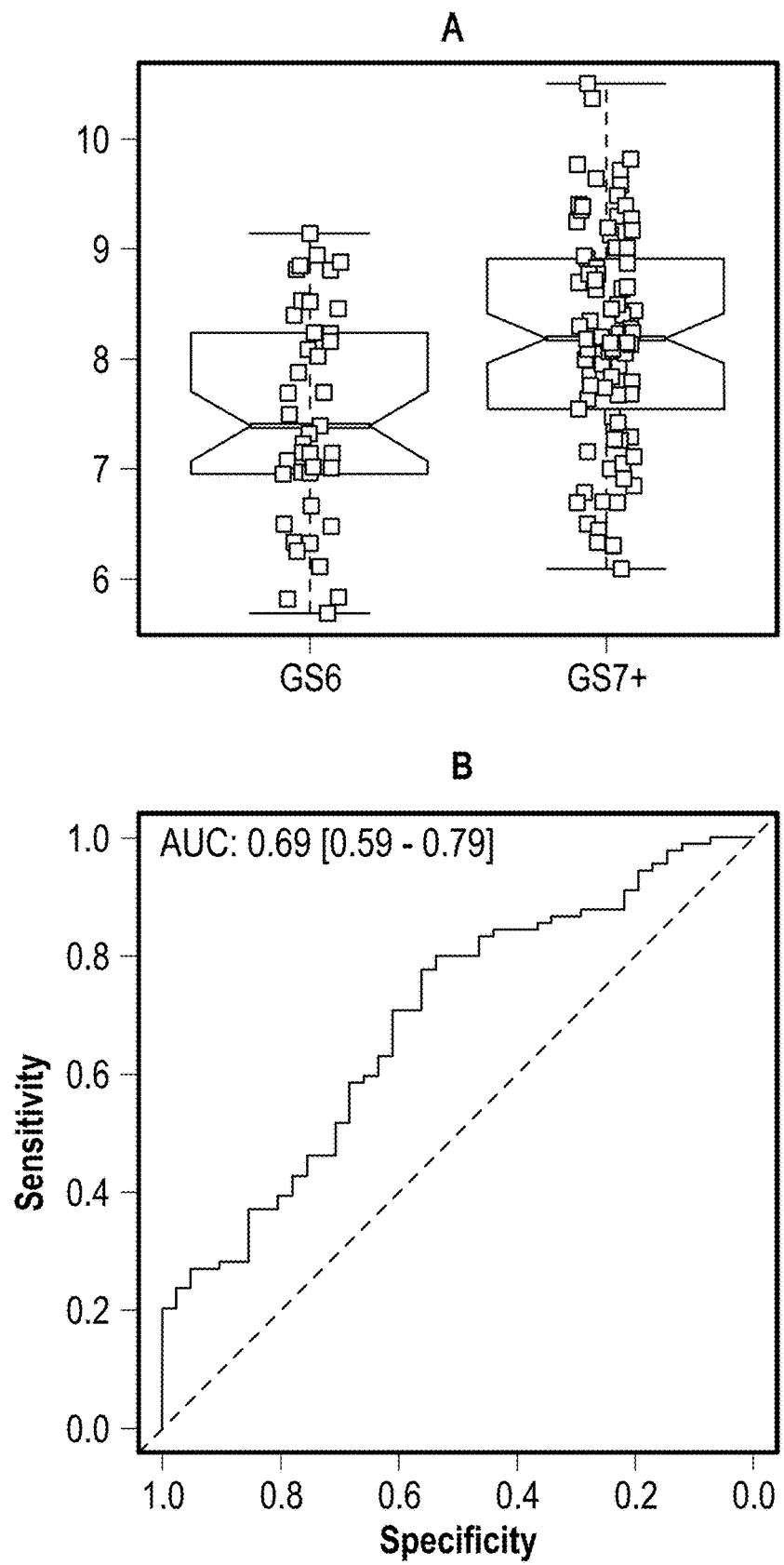

FIG. 37. Box plot (A) and ROC curve (B) for ICE Block 2922 for GS endpoint. (A) Box plot. Notches represent 95% confidence intervals for the scores associated to a given group (GS6 or GS7+). (B) ROC curve. 95% confidence interval for the AUC is provided as a metric of the statistical significance.

Figure 38:
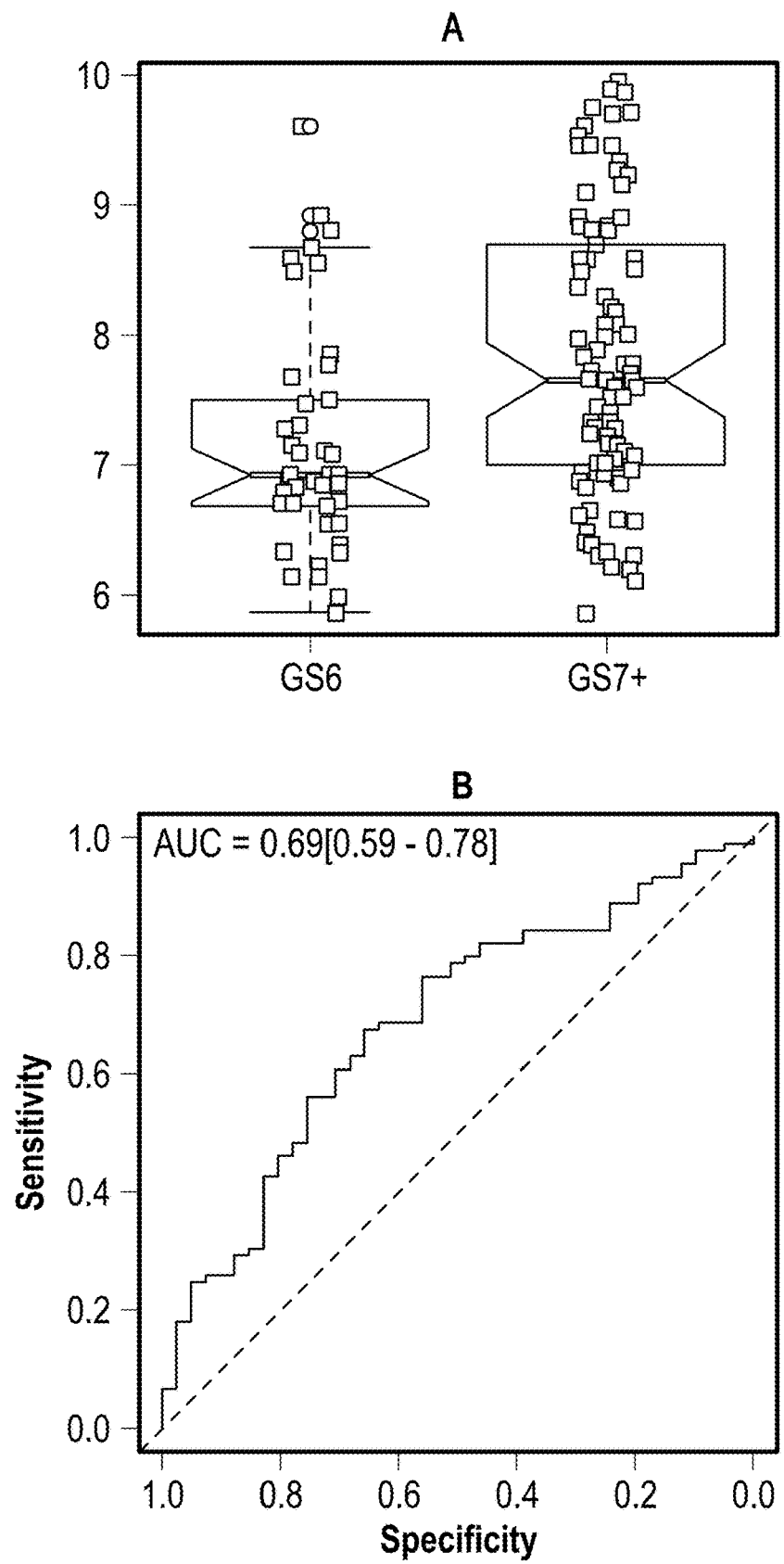

FIG. 38. Box plot (A) and ROC curve (B) for ICE Block 5080 for GS endpoint. (A) Box plot. Notches represent 95% confidence intervals for the scores associated to a given group (GS6 or GS7+). (B) ROC curve. 95% confidence interval for the AUC is provided as a metric of the statistical significance.

Figure 39:
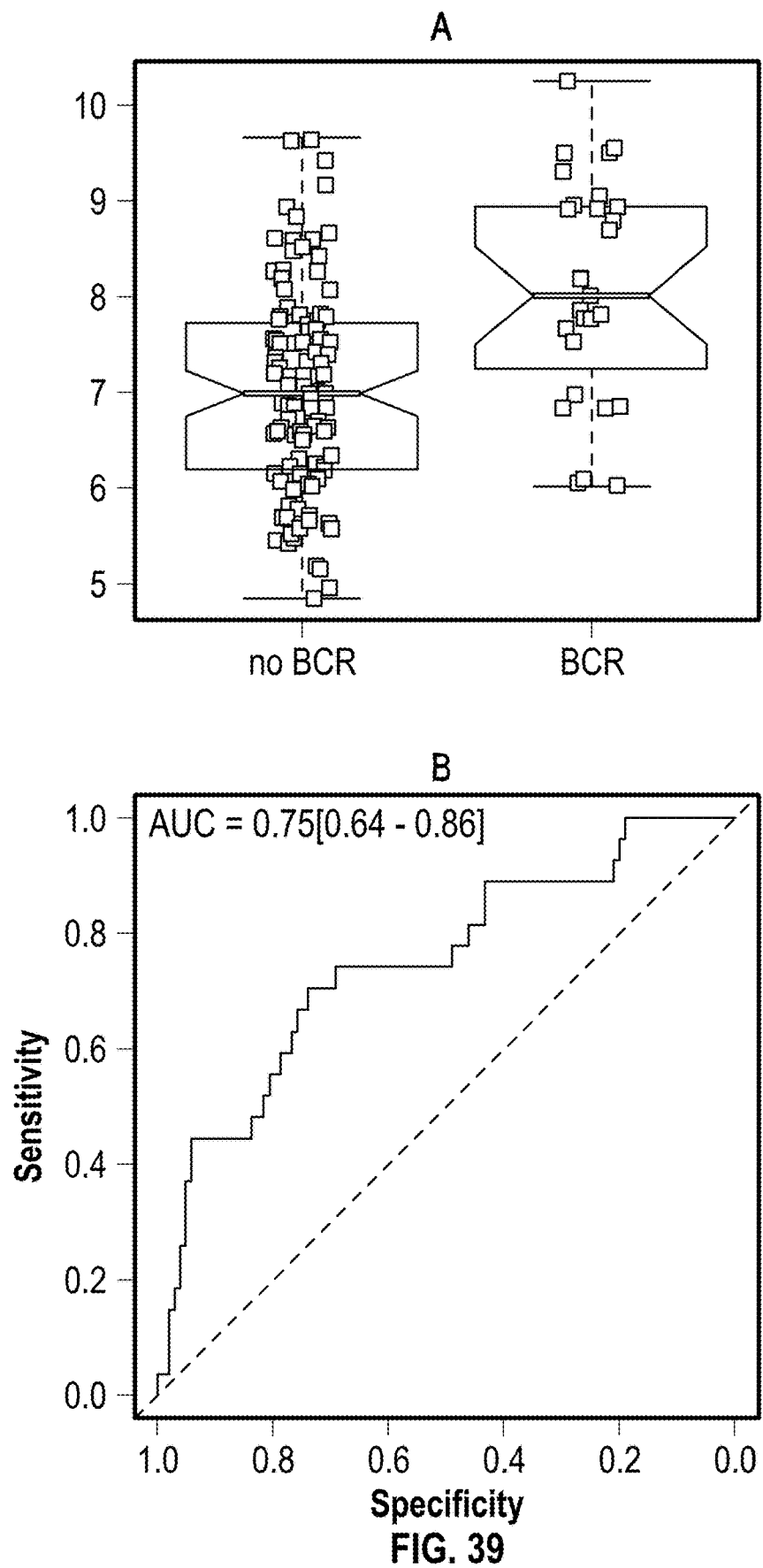
Figure 39:
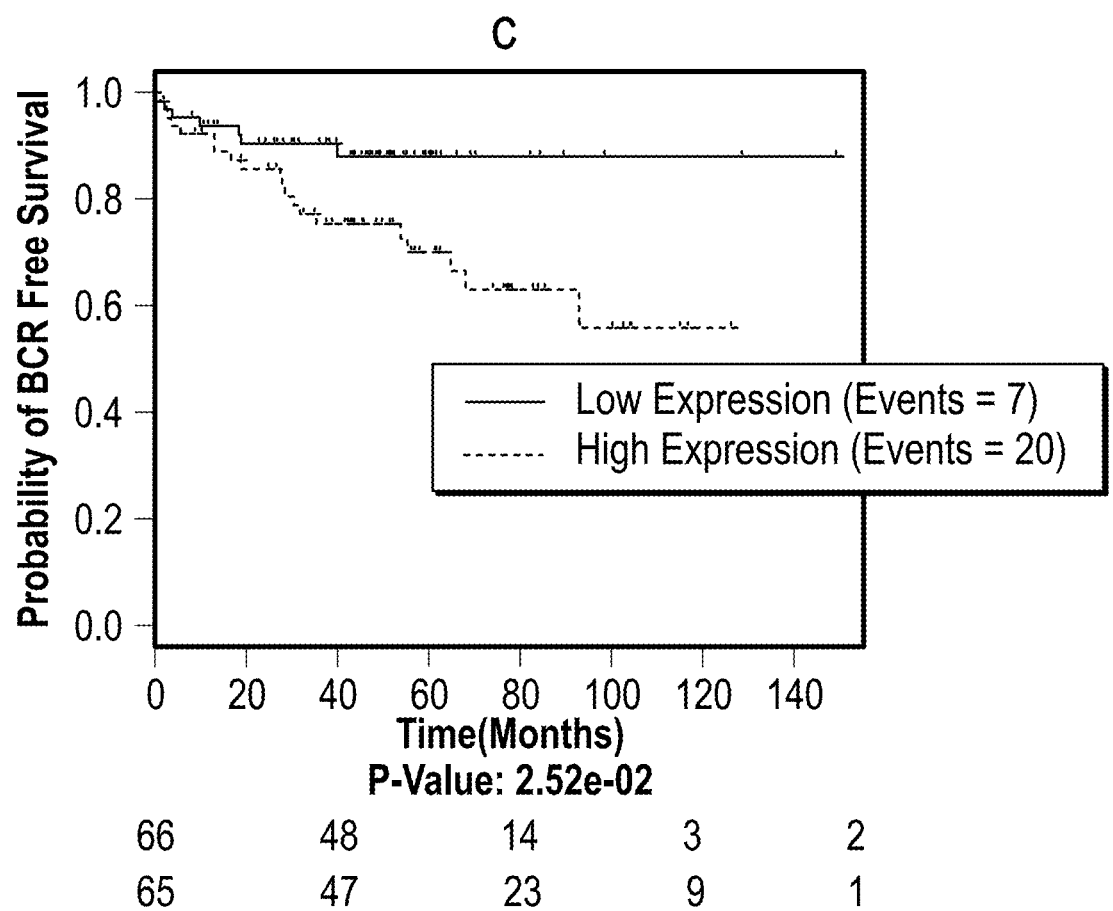

FIG. 39. Box plot (A), ROC curve (B) and KM plots (C) for ICE Block 6592 for BCR endpoint. (A) Box plot. Notches represent 95% confidence intervals for the scores associated to a given group (BCR or non-BCR). (B) ROC curve. 95% confidence interval for the AUC is provided as a metric of the statistical significance. (C) Kaplan Meier curve for two groups of patients based on median split into high and low expression groups. Chi-square P-value indicates the statistical significance of the difference between the curves for both groups.

Figure 40:
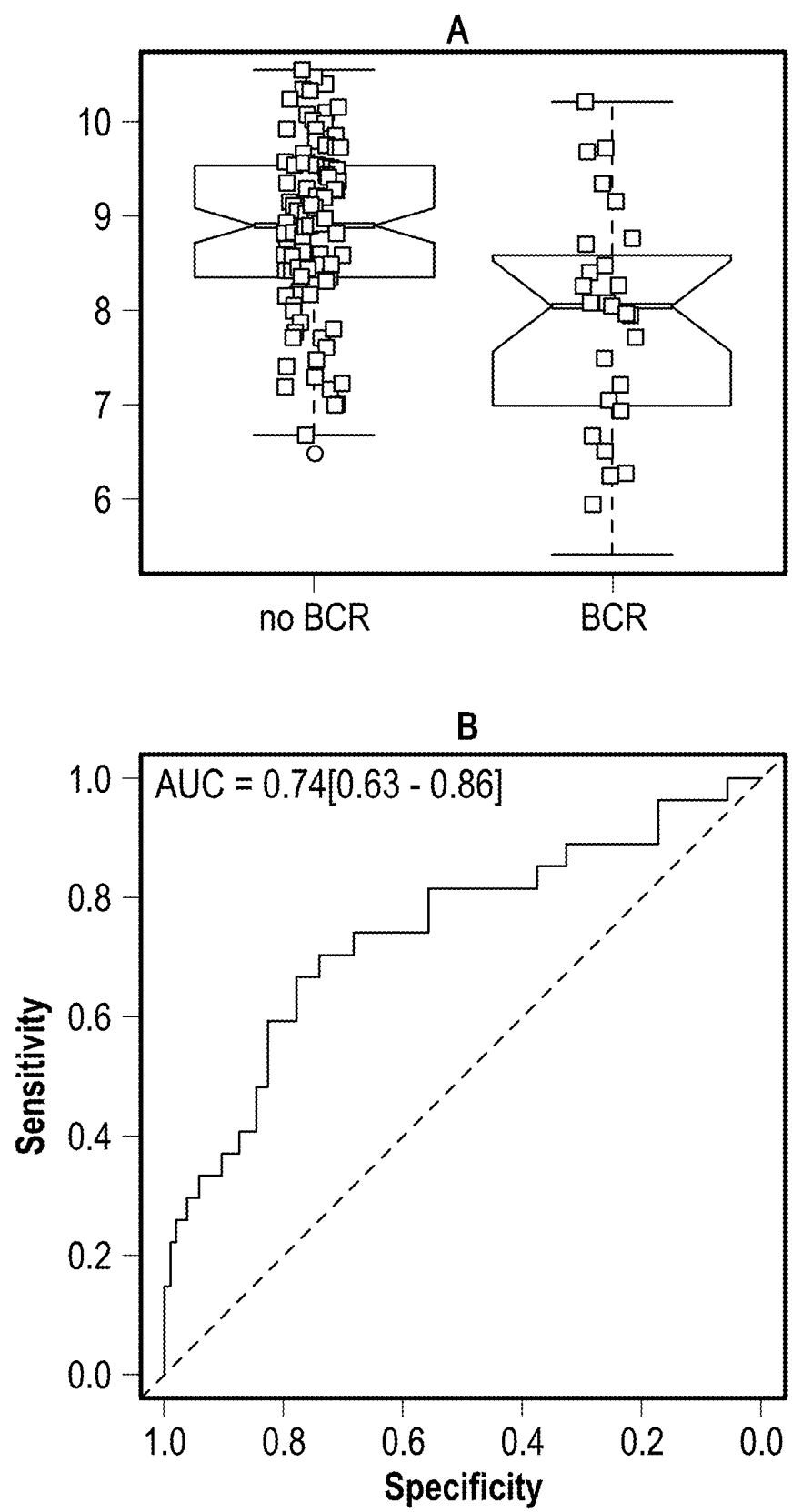
Figure 40:
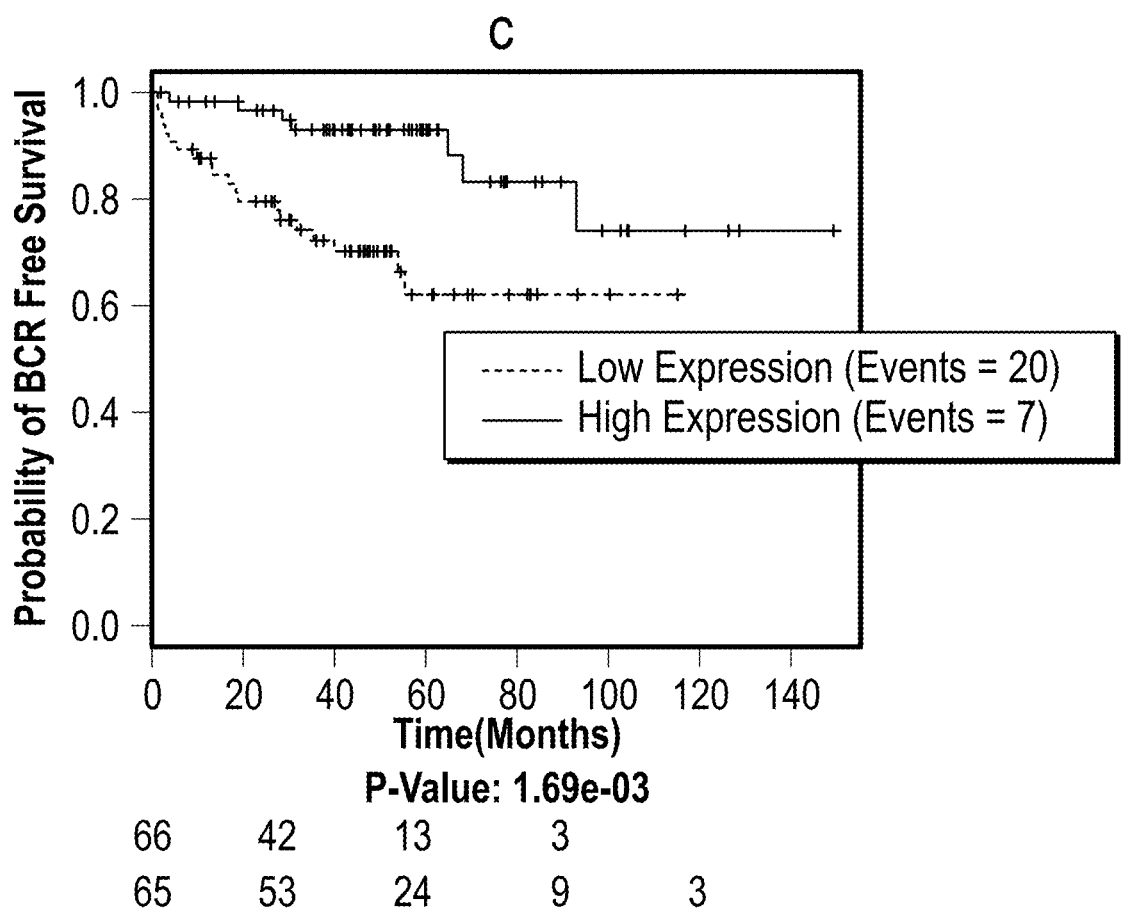

FIG. 40. Box plot (A), ROC curve (B) and KM plots (C) for ICE Block 4627 for BCR endpoint. (A) Box plot. Notches represent 95% confidence intervals for the scores associated to a given group (BCR or non-BCR). (B) ROC curve. 95% confidence interval for the AUC is provided as a metric of the statistical significance. (C) Kaplan Meier curve for two groups of patients based on median split into high and low expression groups. Chi-square P-value indicates the statistical significance of the difference between the curves for both groups.

Figure 41:
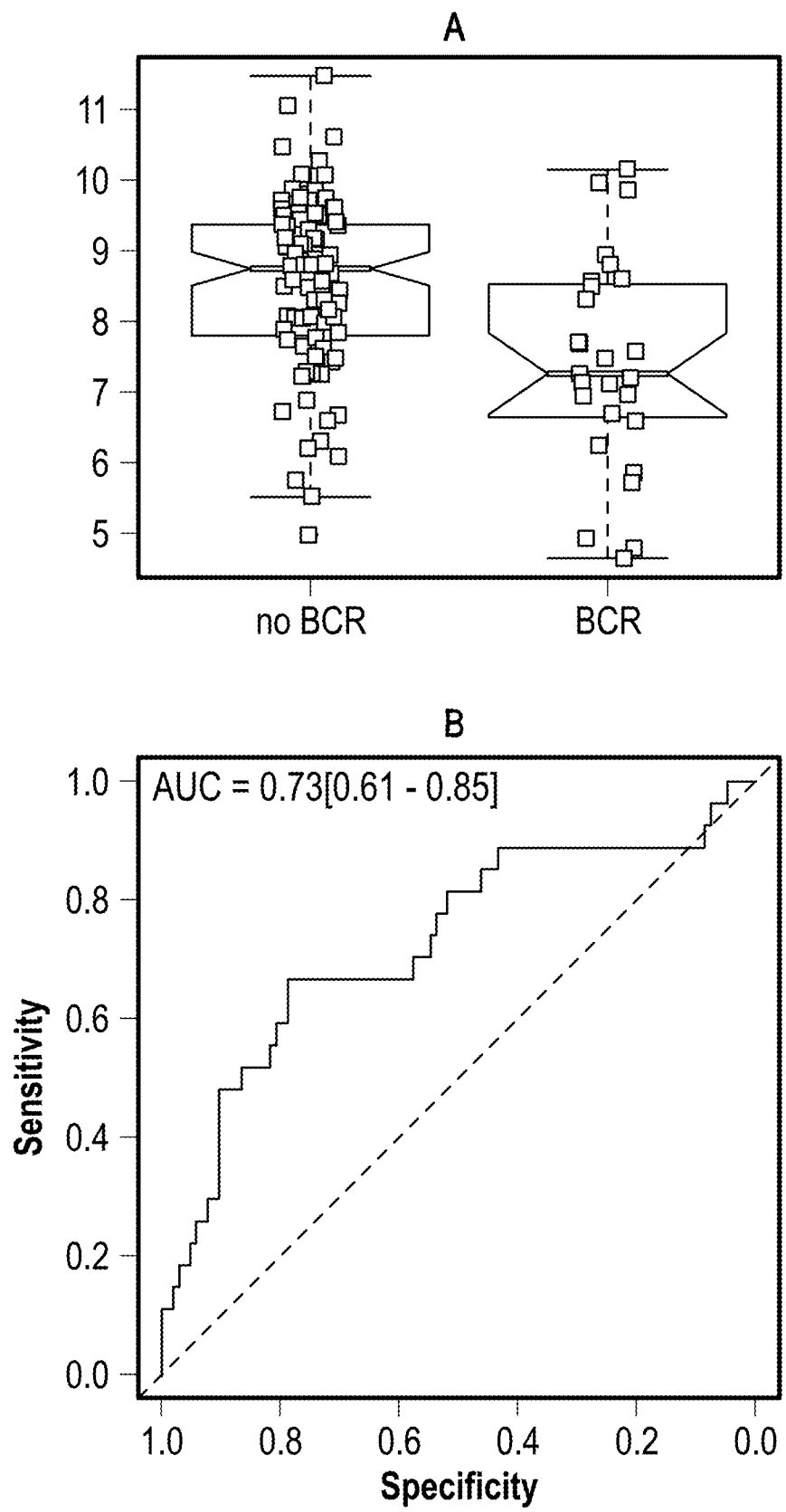
Figure 41:
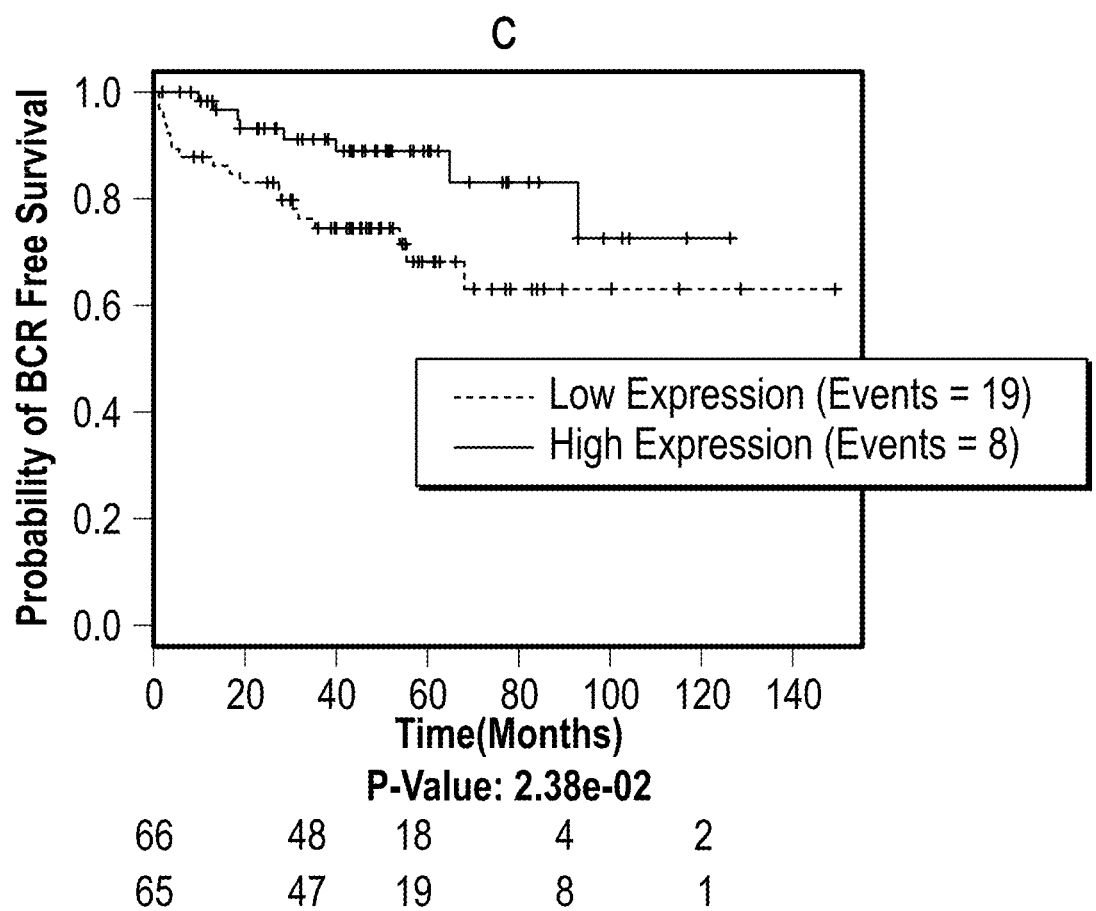

FIG. 41. Box plot (A), ROC curve (B) and KM plots (C) for ICE Block 7113 for BCR endpoint. (A) Box plot. Notches represent 95% confidence intervals for the scores associated to a given group (BCR or non-BCR). (B) ROC curve. 95% confidence interval for the AUC is provided as a metric of the statistical significance. (C) Kaplan Meier curve for two groups of patients based on median split into high and low expression groups. Chi-square P-value indicates the statistical significance of the difference between the curves for both groups.

Figure 42:
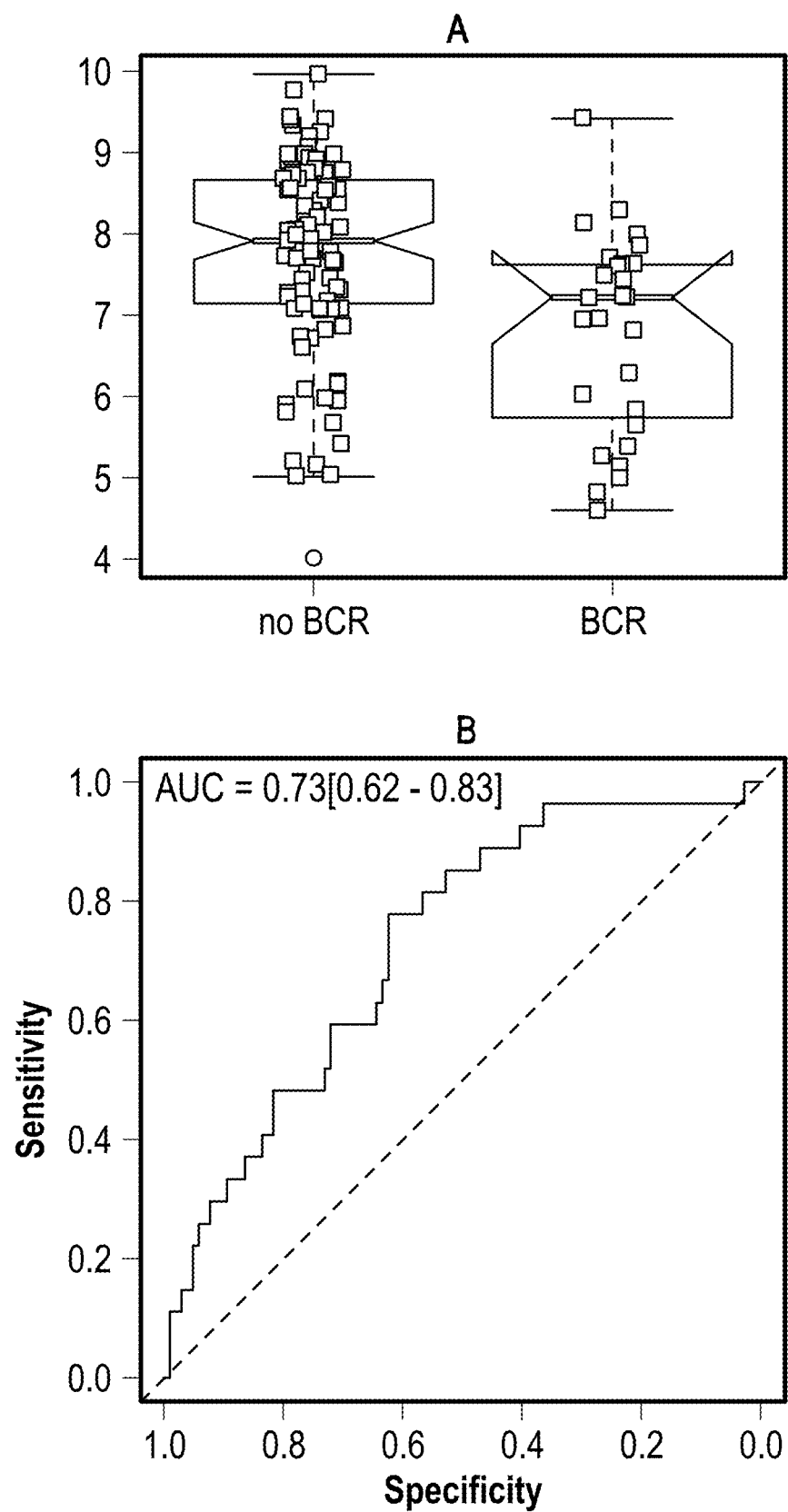
Figure 42:
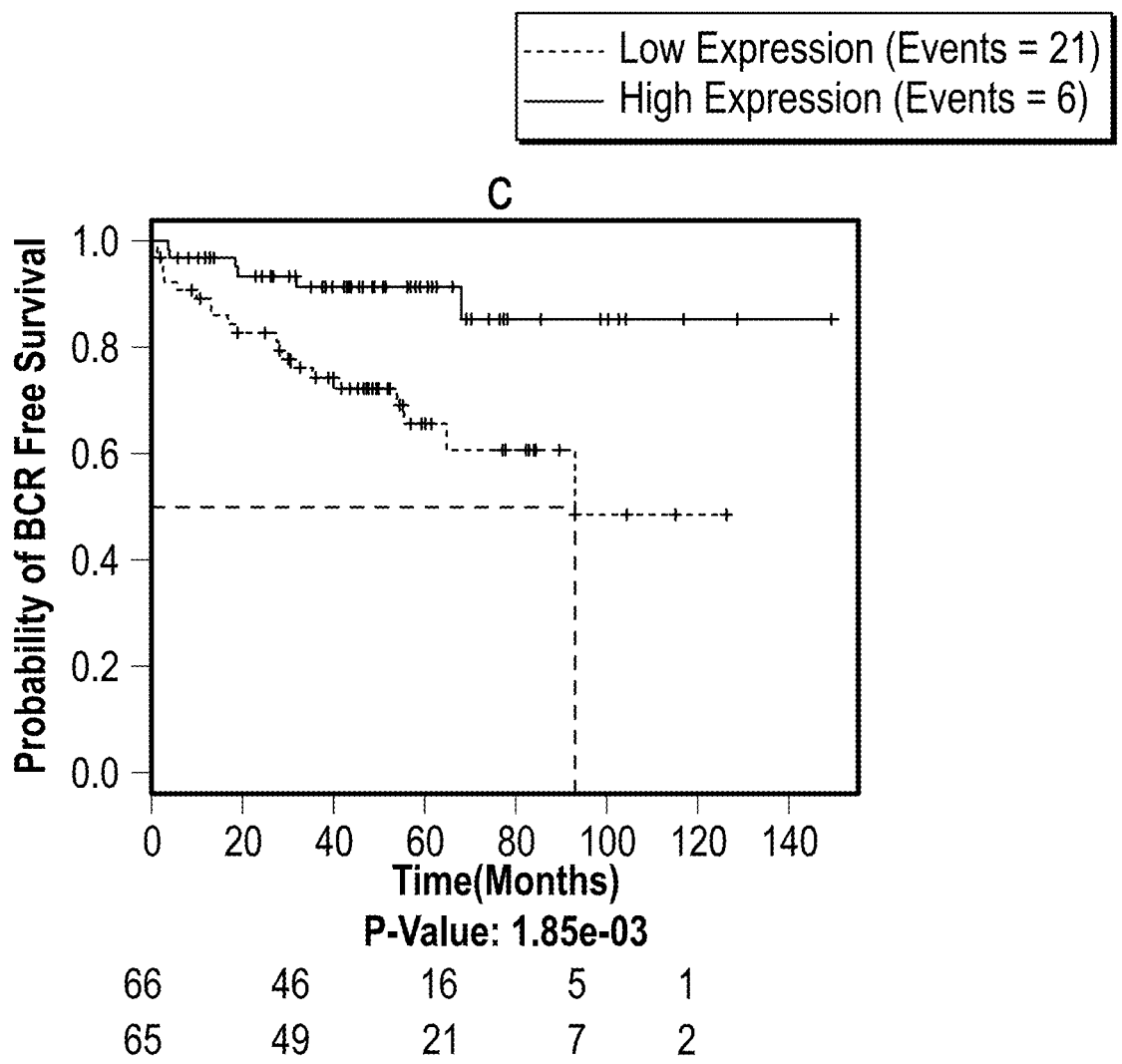

FIG. 42. Box plot (A), ROC curve (B) and KM plots (C) for ICE Block 5470 for BCR endpoint. (A) Box plot. Notches represent 95% confidence intervals for the scores associated to a given group (BCR or non-BCR). (B) ROC curve. 95% confidence interval for the AUC is provided as a metric of the statistical significance. (C) Kaplan Meier curve for two groups of patients based on median split into high and low expression groups. Chi-square P-value indicates the statistical significance of the difference between the curves for both groups.

Figure 43:
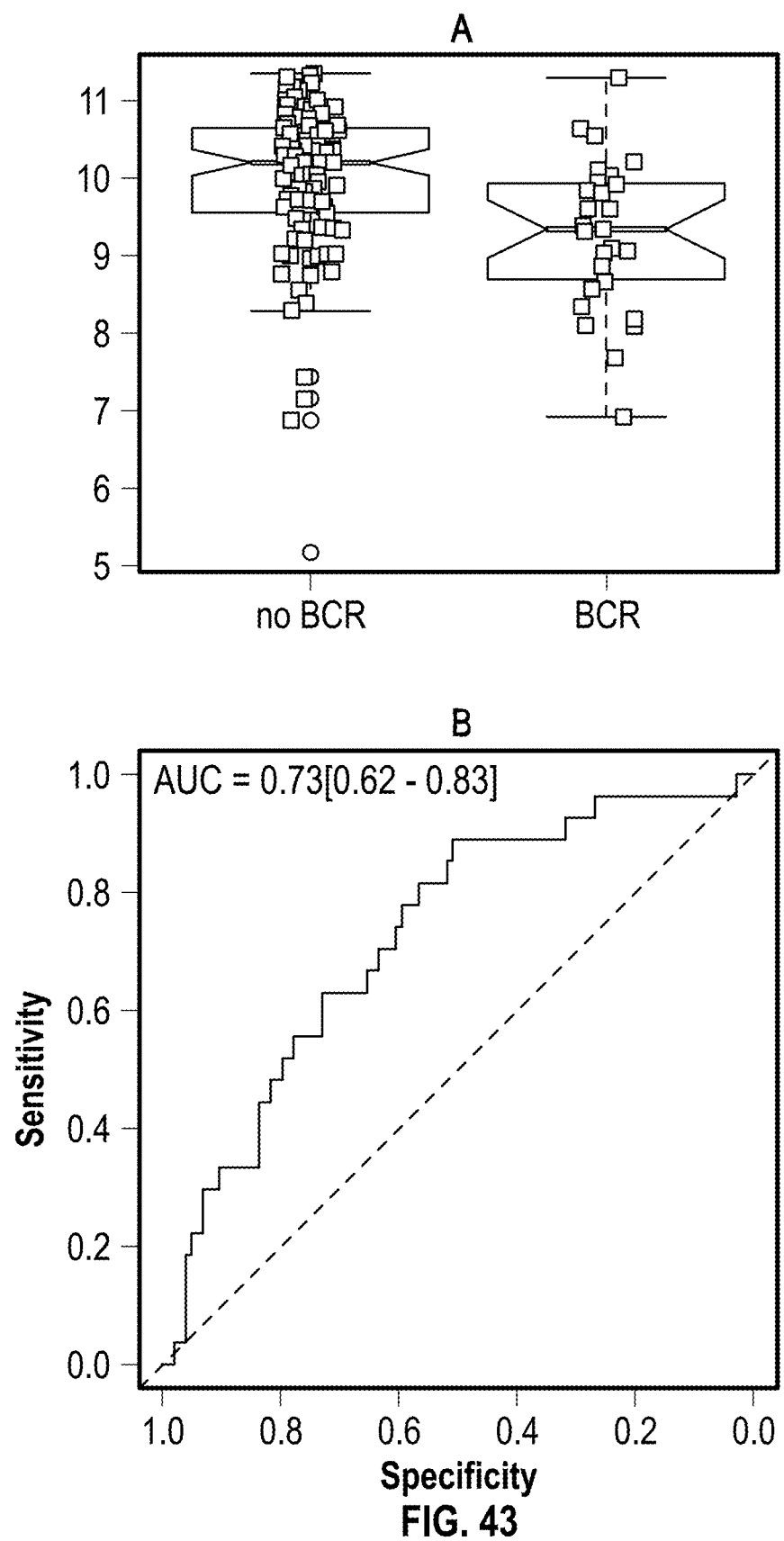
Figure 43:
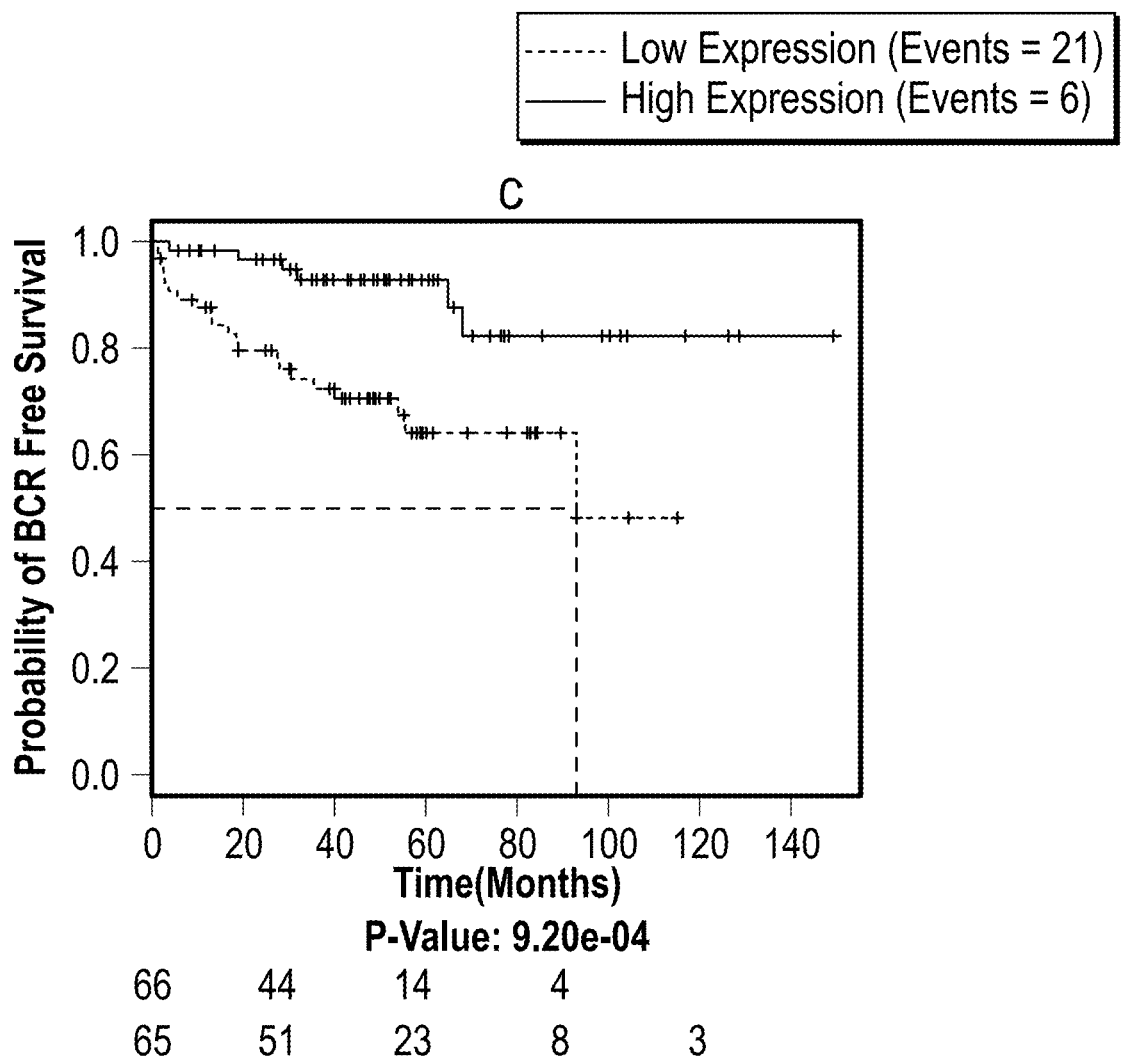

FIG. 43. Box plot (A), ROC curve (B) and KM plots (C) for ICE Block 5155 for BCR endpoint. (A) Box plot. Notches represent 95% confidence intervals for the scores associated to a given group (BCR or non-BCR). (B) ROC curve. 95% confidence interval for the AUC is provided as a metric of the statistical significance. (C) Kaplan Meier curve for two groups of patients based on median split into high and low expression groups. Chi-square P-value indicates the statistical significance of the difference between the curves for both groups.

Figure 44:
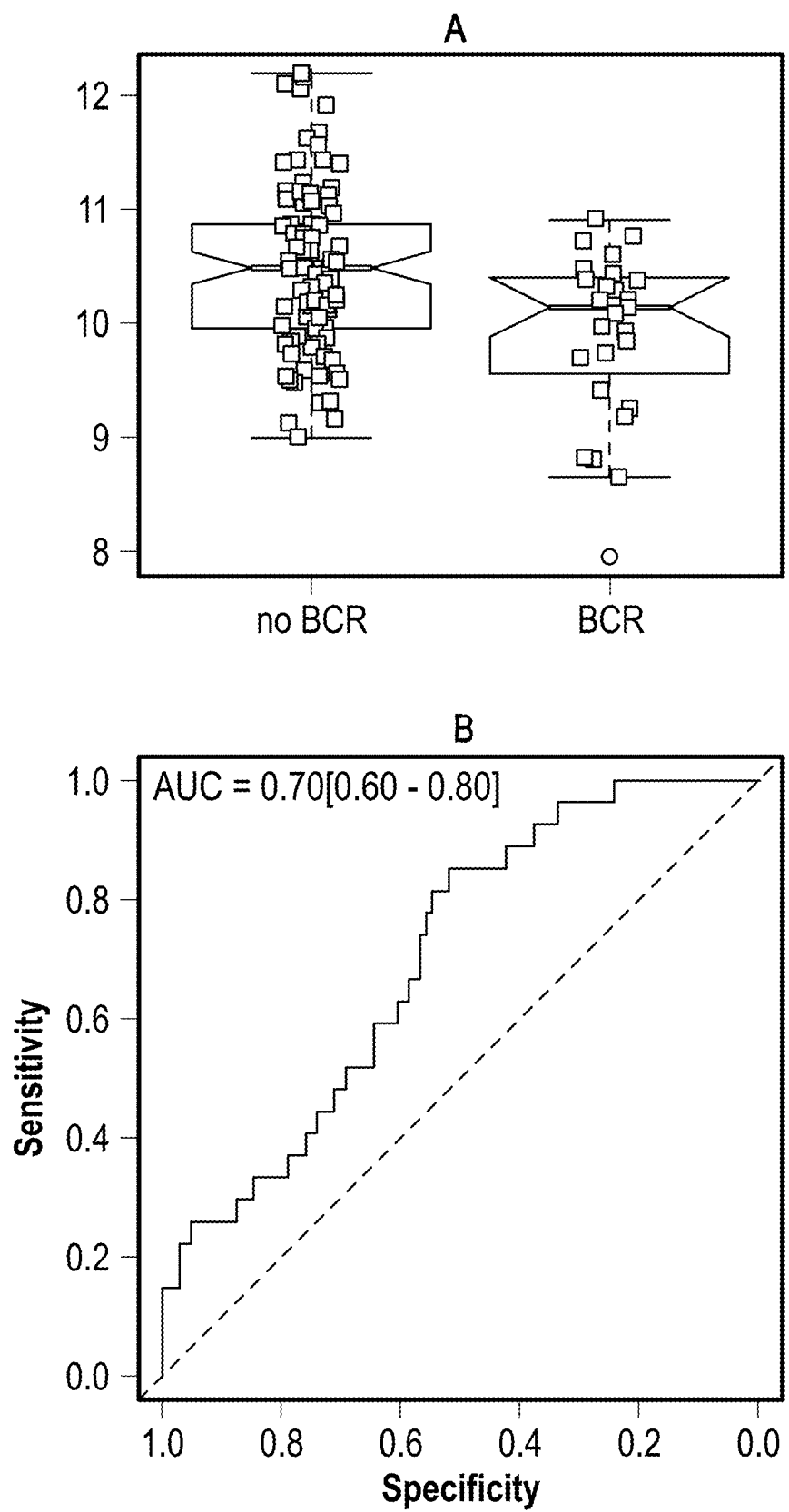
Figure 44:
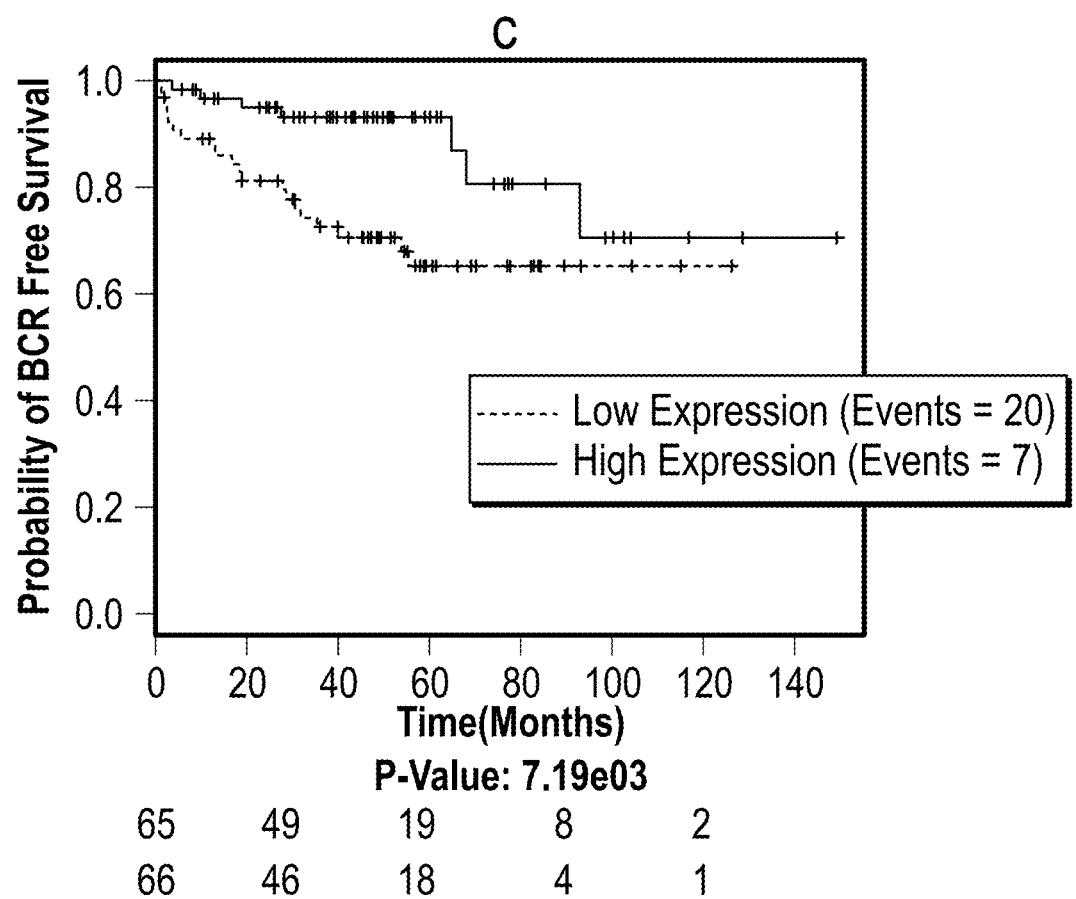

FIG. 44. Box plot (A), ROC curve (B) and KM plots (C) for ICE Block 6371 for BCR endpoint. (A) Box plot. Notches represent 95% confidence intervals for the scores associated to a given group (BCR or non-BCR). (B) ROC curve. 95% confidence interval for the AUC is provided as a metric of the statistical significance. (C) Kaplan Meier curve for two groups of patients based on median split into high and low expression groups. Chi-square P-value indicates the statistical significance of the difference between the curves for both groups.

Figure 45:
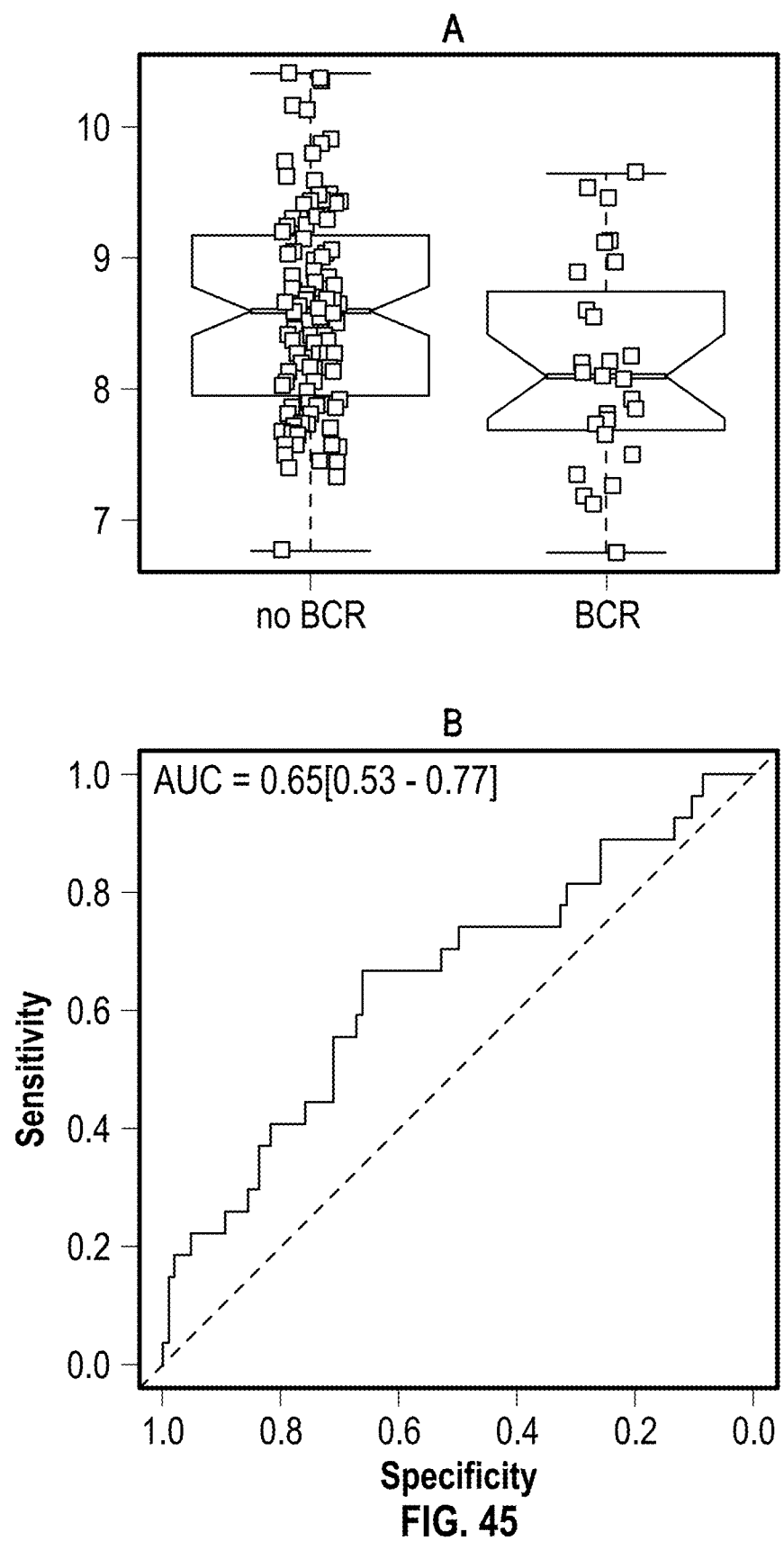
Figure 45:
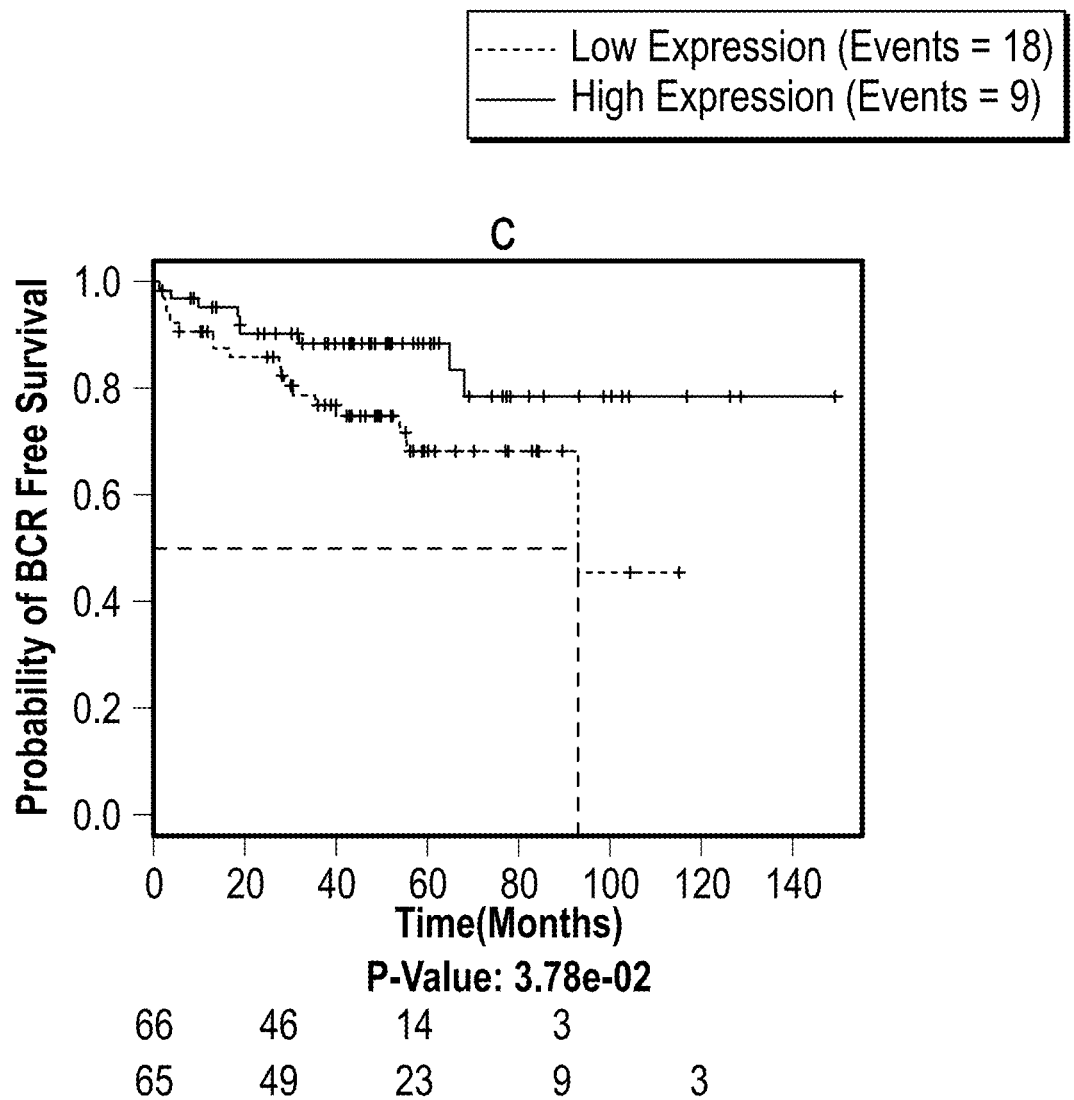

FIG. 45. Box plot (A), ROC curve (B) and KM plots (C) for ICE Block 2879 for BCR endpoint. (A) Box plot. Notches represent 95% confidence intervals for the scores associated to a given group (BCR or non-BCR). (B) ROC curve. 95% confidence interval for the AUC is provided as a metric of the statistical significance. (C) Kaplan Meier curve for two groups of patients based on median split into high and low expression groups. Chi-square P-value indicates the statistical significance of the difference between the curves for both groups.

Figure 46:
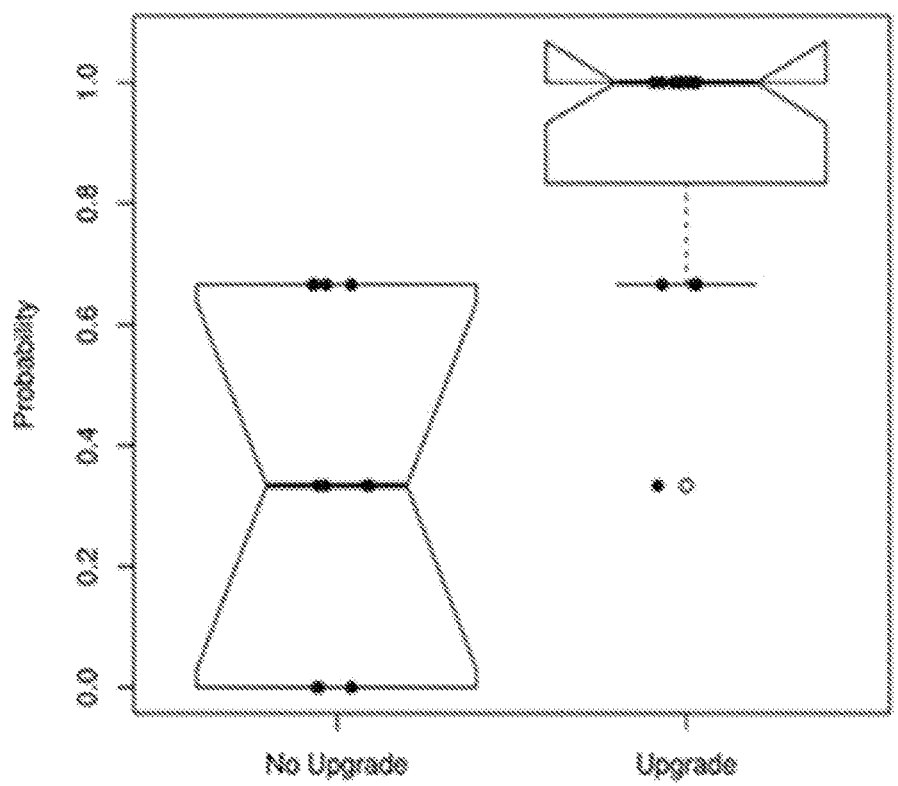

FIG. 46. Discrimination of KNN16 in MSKCC upgrading testing set.

Figure 47:
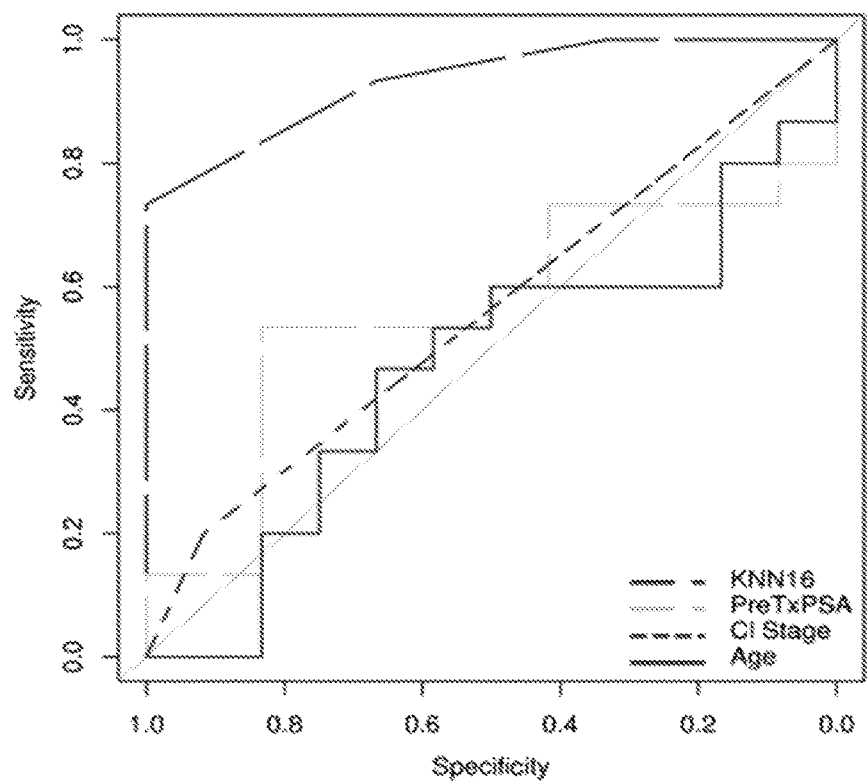

FIG. 47. ROC plot of clinical and pathological factors in comparison to KNN16.

Figure 48:
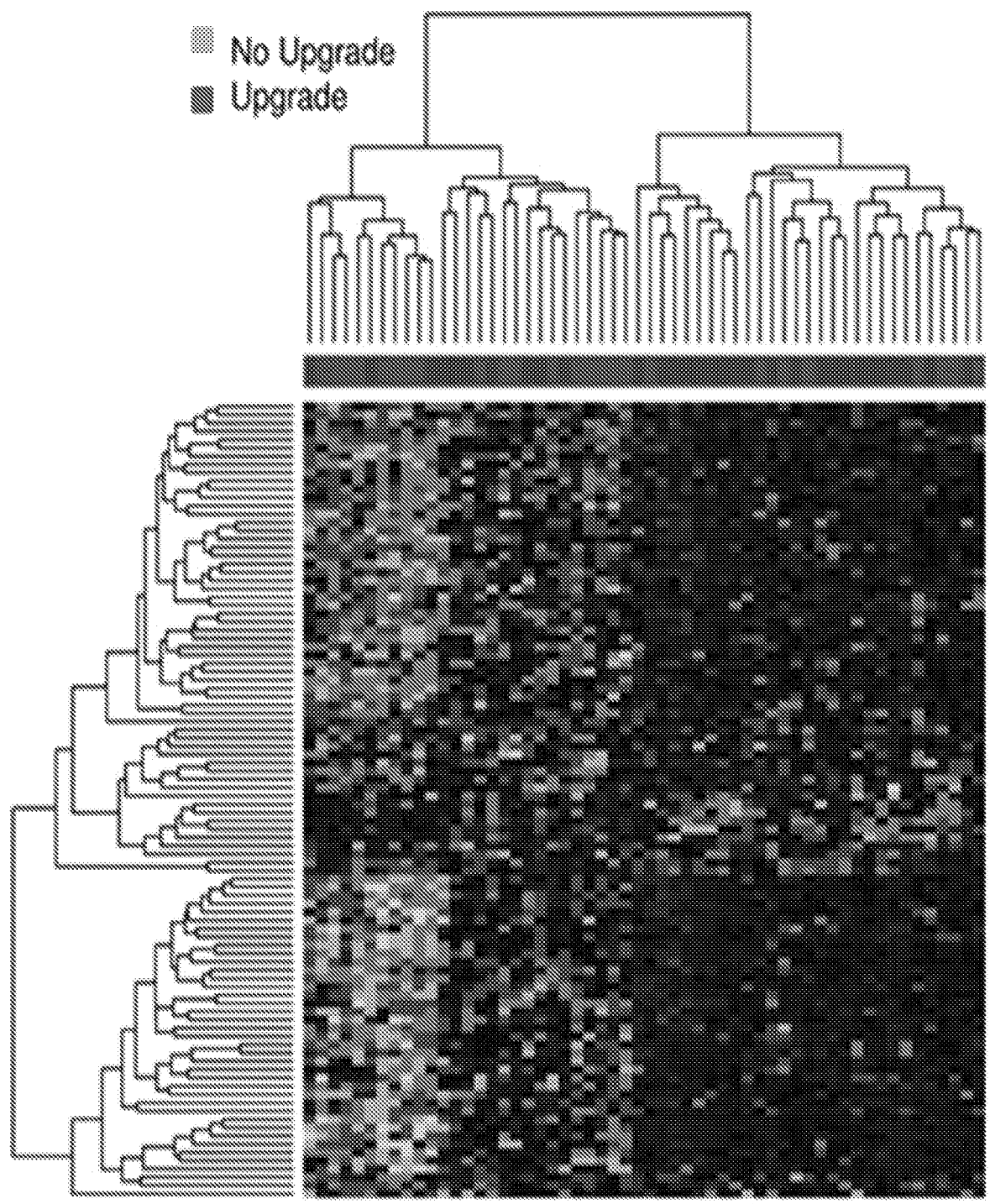

FIG. 48. Heatmap of the 98 selected features in the pooled training and testing set.

FIG. 49. Multidimensional scaling of normal and tumor samples for lung and colorectal cancer. (A) MDS plots of normal (triangle) and cancer (circle) matched lung samples using differentially expressed non-coding RNA features. (B)

MDS plots of normal (triangle) and cancer (circle) colorectal samples using differentially expressed non-coding RNA features.

FIG. 50. Multidimensional scaling and expression density curve of tumor samples at different progression stages for lung and colorectal cancer. (A) MDS plots of tumor stage I (triangle) and stages II and III (circle) lung samples using differentially expressed non-coding RNA features. (B) Expression density of the XIST-associated PSR 4012540 for stage II (dotted line) and stage III (solid line) colorectal carcinomas.

Table 1. List of Abbreviations.

Table 2. Summary of the clinical characteristics of the dataset used in Example 1.

Table 3. Definitions of Ensembl 'Transcript Biotype' annotations for non-coding transcripts found differentially expressed.

Table 4. Long non-coding RNAs differentially expressed in prostate cancer.

Table 5. Logistic regression analysis for prediction of the probability of clinical recurrence (CR). SVI: Seminal Vesicle Invasion; ECE: Extracapsular Extension; SMS: Surgical Margin Status; LNI: Lymph node Involvement; PreTxPSA: Pre-operative PSA; PGS: Pathological Gleason Score.

Table 6. List of Coding probe selection regions (coding PSRs) and Non-coding probe selection regions (non-coding PSRs).

Table 7. Protein-coding genes with non-coding transcripts differentially expressed. NvsP: Normal Adjacent versus Primary tumor comparison. PvsM: Primary Tumor versus Metastatic sample comparison. NvsM: Normal adjacent versus Metastatic Sample comparison.

Table 8. Transcripts found differentially expressed across all pairwise comparison (top) and across Normal vs Primary Tumor and Primary Tumor vs Metastatic samples comparisons (bottom). (*) indicates upregulation. No (*) indicates downregulation. N.A.: Not Applicable.

Table 9. Multivariable Logistic Regression Analysis of transcripts (represented by Transcript-Specific PSRs) and genes adjusted by Kattan Nomogram. KNN-positive: metastatic-like. *: Greater than 50% probability of BCR used as cut-off OR: Odds Ratio. CI: Confidence Interval.

Table 10. Characteristics of the study population.

Table 11. Multivariable Cox proportional hazards modeling of clinicopathologic features.

Table 12. Classifier performance of clinicopathologic features. In addition, two multivariate clinical classifiers were built using a logistic model (CC1) as well as a Cox model (CC2).

Table 13. Multivariable Cox proportional hazards modeling of GC and clinicopathologic features.

Table 14. Raw clinical data, QC results, training and testing sets and classifier scores for each of the 251 samples.

Table 15. List of probe sets and associated genes that overlap with KNN89 PSRs.

Table 16. Machine Learning algorithms, ranking, standardization methods and number of features included in each classifier. Additionally, the performance based on AUC is included for the training and testing sets.

Table 17. Sequences composing the classifiers. For each sequence, the chromosomal coordinates, associated gene (if not intergenic), type of feature (coding or non-coding), and classifier(s) are listed.

Table 18. Machine Learning algorithms, ranking, standardization methods and number of features included in each classifier. Additionally, the performance based on AUC is included for the training and testing sets.

Table 19. Sequences composing the classifiers. For each sequence, the chromosomal coordinates, associated gene (if not intergenic), type of feature (coding or non-coding), and classifier(s) are listed.

Table 20. Number of ICE blocks found across different comparisons and different correlation thresholds. Numbers in parenthesis indicate the number of ICE blocks found differentially expressed when using a P-value threshold of 0.05.

Table 21. Number of ICE blocks differentially expressed across different compositions of coding and non-coding PSRs, different correlation thresholds and different comparisons. The number of ICE blocks found differentially expressed is obtained by using a P-value threshold of 0.05.

Table 22. ICE blocks found differentially expressed for the Gleason Score comparison when using a strict correlation threshold of 0.9. For each ICE block, the following information is provided: Block ID, Wilcoxon P-value, chromosomal location, number of overlapping genes across the genomic span of the ICE block, overlapping genes, Composition of the ICE block as a percentage of coding and non-coding PSRs, number of PSRs composing the ICE block and Probe set IDs that correspond to the PSRs composing the ICE block.

Table 23. ICE blocks found differentially expressed for the Biochemical Recurrence comparison when using a strict correlation threshold of 0.9. For each ICE block, the following information is provided: Block ID, Wilcoxon P-value, chromosomal location, number of overlapping genes across the genomic span of the ICE block, overlapping genes, Composition of the ICE block as a percentage of coding and non-coding PSRs, number of PSRs composing the ICE block and Probe set IDs that correspond to the PSRs composing the ICE block.

Table 24. Sequences and Probe set IDs associated to the PSRs composing the ICE blocks assessed in FIGS. 33-44.

Table 25. The number of cases and controls in the training and testing set.

Table 26. Features used for modeling a KNN classifier.

Table 27. Differentially expressed non-coding RNA features between normal and tumor lung cancer. For each feature, sequence number ID, probe set IDs and associated gene are listed.

Table 28. Differentially expressed non-coding RNA features between normal and tumor colorectal cancer. For each feature, sequence number ID, probe set IDs and associated gene are listed.

Table 29. Differentially expressed non-coding RNA features between stage I and stage II+III lung cancer. For each feature, sequence number ID, probe set IDs and associated gene are listed.

Table 30. Differentially expressed non-coding RNA features between stage II and stage III colorectal cancer. For each feature, sequence number ID, probe set IDs and associated gene are listed.

DETAILED DESCRIPTION OF THE INVENTION

The present invention discloses systems and methods for diagnosing, predicting, and/or monitoring the status or outcome of a cancer in a subject using expression-based analysis of coding targets, non-coding targets, and/or non-exonic transcripts. Generally, the method comprises (a) optionally providing a sample from a subject suffering from a cancer;

(b) assaying the expression level for a plurality of targets in the sample; and (c) diagnosing, predicting and/or monitoring the status or outcome of the cancer based on the expression level of the plurality of targets.

Assaying the expression level for a plurality of targets in the sample may comprise applying the sample to a microarray. In some instances, assaying the expression level may comprise the use of an algorithm. The algorithm may be used to produce a classifier. Alternatively, the classifier may comprise a probe selection region. Assaying the expression level for a plurality of targets may comprise detecting and/or quantifying the plurality of targets.

In some instances, the plurality of targets may comprise a coding target and a non-coding target and the non-coding target is selected from the group consisting of piRNA, tiRNA, PASR, TASR, aTASR, TSSa-RNA, snRNA, RE-RNA, uaRNA, x-ncRNA, hY RNA, usRNA, snaR, vtRNA, T-UCRs, pseudogenes, GRC-RNAs, aRNAs, PALRs, PROMPTs, and LSINCTs. Alternatively, the plurality of targets may comprise a coding target and a non-coding target, wherein the non-coding target does not comprise a miRNA, an intronic sequence, and a UTR sequence. In other instances, the plurality of targets may consist essentially of a non-coding target selected from the group consisting of a UTR sequence, an intronic sequence, or a non-coding RNA transcript, wherein the non-coding RNA transcript comprises a piRNA, tiRNA, PASR, TASR, aTASR, TSSa-RNA, snRNA, RE-RNA, uaRNA, x-ncRNA, hY RNA, usRNA, snaR, vtRNA, T-UCRs, pseudogenes, GRC-RNAs, aRNAs, PALRs, PROMPTs, or LSINCTs. The plurality of targets may also comprise a non-coding target, wherein the non-coding target is a non-coding RNA transcript and the non-coding RNA transcript is non-polyadenylated.

In some instances, the plurality of targets comprises a coding target and/or a non-coding target comprises a sequence selected from SEQ ID NOs.: 1-903. In other instances, the plurality of targets comprises a coding target and/or a non-coding target comprises a sequence selected from SEQ ID NOs.: 1-352. Alternatively, the plurality of targets comprises a coding target and/or a non-coding target comprises a sequence selected from SEQ ID NOs.: 353-441. In other instances, the plurality of targets comprises a coding target and/or a non-coding target comprises a sequence selected from SEQ ID NOs.: 322-352. Alternatively, the plurality of targets comprises a coding target and/or a non-coding target comprises a sequence selected from SEQ ID NOs.: 292-321. Optionally, the plurality of targets comprises a coding target and/or a non-coding target comprises a sequence selected from SEQ ID NOs.: 231-261. In some instances, the plurality of targets comprises a coding target and/or a non-coding target located on chr2q31.3. In some instances, the coding target and/or non-coding target comprises a sequence selected from SEQ ID NOs.: 262-291.

Further disclosed herein, is a probe set for diagnosing, predicting, and/or monitoring a cancer in a subject. In some instances, the probe set comprises a plurality of probes capable of detecting an expression level of at least one non-coding RNA transcript, wherein the expression level determines the cancer status or outcome of the subject with at least about 45% specificity. In some instances, the probe set comprises a plurality of probes capable of detecting an expression level of at least one non-coding RNA transcript, wherein the expression level determines the cancer status or outcome of the subject with at least about 45% accuracy.

Further disclosed herein are methods for characterizing a patient population. Generally, the method comprises: (a) providing a sample from a subject; (b) assaying the expression level for a plurality of targets in the sample; and (c) characterizing the subject based on the expression level of the plurality of targets. In some instances, the plurality of targets comprises one or more coding targets and one or more non-coding targets. In some instances, the coding target comprises an exonic region or a fragment thereof. The non-coding targets can comprise a non-exonic region or a fragment thereof. Alternatively, the non-coding target may comprise the UTR of an exonic region or a fragment thereof.

In some instances, characterizing the subject comprises determining whether the subject would respond to an anti-cancer therapy. Alternatively, characterizing the subject comprises identifying the subject as a non-responder to an anti-cancer therapy. Optionally, characterizing the subject comprises identifying the subject as a responder to an anti-cancer therapy.

Before the present invention is described in further detail, it is to be understood that this invention is not limited to the particular methodology, compositions, articles or machines described, as such methods, compositions, articles or machines can, of course, vary. It is also to be understood that the terminology used herein is for the purpose of describing particular embodiments only, and is not intended to limit the scope of the present invention.

Definitions

Unless defined otherwise or the context clearly dictates otherwise, all technical and scientific terms used herein have the same meaning as commonly understood by one of ordinary skill in the art to which this invention belongs. In describing the present invention, the following terms may be employed, and are intended to be defined as indicated below.

The term "polynucleotide" as used herein refers to a polymer of greater than one nucleotide in length of ribonucleic acid (RNA), deoxyribonucleic acid (DNA), hybrid RNA/DNA, modified RNA or DNA, or RNA or DNA mimetics, including peptide nucleic acids (PNAs). The polynucleotides may be single- or double-stranded. The term includes polynucleotides composed of naturally-occurring nucleobases, sugars and covalent internucleoside (backbone) linkages as well as polynucleotides having non-naturally-occurring portions which function similarly. Such modified or substituted polynucleotides are well known in the art and for the purposes of the present invention, are referred to as "analogues."

"Complementary" or "substantially complementary" refers to the ability to hybridize or base pair between nucleotides or nucleic acids, such as, for instance, between a sensor peptide nucleic acid or polynucleotide and a target polynucleotide. Complementary nucleotides are, generally, A and T (or A and U), or C and G. Two single-stranded polynucleotides or PNAs are said to be substantially complementary when the bases of one strand, optimally aligned and compared and with appropriate insertions or deletions, pair with at least about 80% of the bases of the other strand, usually at least about 90% to 95%, and more preferably from about 98 to 100%.

Alternatively, substantial complementarity exists when a polynucleotide may hybridize under selective hybridization conditions to its complement. Typically, selective hybridization may occur when there is at least about 65% complementarity over a stretch of at least 14 to 25 bases, for example at least about 75%, or at least about 90% complementarity. See, M. Kanehisa, *Nucleic Acids Res.* 12:203 (1984).

"Preferential binding" or "preferential hybridization" refers to the increased propensity of one polynucleotide to bind to its complement in a sample as compared to a noncomplementary polymer in the sample.

Hybridization conditions may typically include salt concentrations of less than about 1M, more usually less than about 500 mM, for example less than about 200 mM. In the case of hybridization between a peptide nucleic acid and a polynucleotide, the hybridization can be done in solutions containing little or no salt. Hybridization temperatures can be as low as 5° C., but are typically greater than 22° C., and more typically greater than about 30° C., for example in excess of about 37° C. Longer fragments may require higher hybridization temperatures for specific hybridization as is known in the art. Other factors may affect the stringency of hybridization, including base composition and length of the complementary strands, presence of organic solvents and extent of base mismatching, and the combination of parameters used is more important than the absolute measure of any one alone. Other hybridization conditions which may be controlled include buffer type and concentration, solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art.

"Multiplexing" herein refers to an assay or other analytical method in which multiple analytes can be assayed simultaneously.

A "target sequence" as used herein (also occasionally referred to as a "PSR" or "probe selection region") refers to a region of the genome against which one or more probes can be designed. Exemplary probe selection regions are depicted in FIGS. 7-8. A "target sequence" may be a coding target or a non-coding target. A "target sequence" may comprise exonic and/or non-exonic sequences. Alternatively, a "target sequence" may comprise an ultraconserved region. An ultraconserved region is generally a sequence that is at least 200 base pairs and is conserved across multiple species. An ultraconserved region may be exonic or non-exonic. Exonic sequences may comprise regions on a protein-coding gene, such as an exon, UTR, or a portion thereof. Non-exonic sequences may comprise regions on a protein-coding, non protein-coding gene, or a portion thereof. For example, non-exonic sequences may comprise intronic regions, promoter regions, intergenic regions, a non-coding transcript, an exon anti-sense region, an intronic anti-sense region, UTR anti-sense region, non-coding transcript anti-sense region, or a portion thereof.

As used herein, a probe is any polynucleotide capable of selectively hybridizing to a target sequence, a complement thereof, a reverse complement thereof, or to an RNA version of the target sequence, the complement thereof, or the reverse complement thereof. A probe may comprise ribonucleotides, deoxyribonucleotides, peptide nucleic acids, and combinations thereof. A probe may optionally comprise one or more labels. In some embodiments, a probe may be used to amplify one or both strands of a target sequence or an RNA form thereof, acting as a sole primer in an amplification reaction or as a member of a set of primers.

As used herein, the term "probe set" refers to a set of synthetic oligonucleotide probes. The oligonucleotide probes can be on Exon arrays that interrogate gene expression from one exon. Often, the probe set comprises four probes. Probes of the probe set can anneal to the sense strand of a coding transcript and/or a non-coding transcript. In some instances, the probes of the probe set are located on an array. The probes of the probe set can be located on the array in an antisense orientation. In some instances, a probe set can refer to a probe set as described by Affymetrix (at the world wide web at microarrays.ca/services/exonarray_design_technote.pdf).

As used herein, the term "probe selection region" ("PSR") is often the smallest unit on an array for expression profiling. In some instances, a PSR is represented by an individual probe set. The PSR can be an exon or overlap with an exon. The PSR can comprise or overlap with at least a portion of a coding transcript. Alternatively, a PSR can comprise or overlap with at least a portion of a non-coding transcript. In some instances, an exon cluster (e.g., a group of overlapping exons) can be divided into multiple PSRs. In some instances, a probe set can refer to a PSR as described by Affymetrix (at the world wide web at microarrays.ca/services/exonarray_design_technote.pdf). In some instances, the terms "PSR", "probe selection region", and "probe set" can be used interchangeably to refer to a region on a coding transcript and/or non-coding transcript. In some instances, the region represented by the probe set comprises a sequence that is antisense to the PSR.

In some instances, the probe sets and PSRs can be used to interrogate expression from coding transcripts and/or non-coding transcripts. Probe set IDs as disclosed in Tables 17, 19, 22-24, and 27-30 refer to probe sets as described by Affymetrix (at the world wide web at affymetrix.com/analysis/index.affx).

As used herein, a non-coding target may comprise a nucleotide sequence. The nucleotide sequence is a DNA or RNA sequence. A non-coding target may include a UTR sequence, an intronic sequence, or a non-coding RNA transcript. A non-coding target also includes sequences which partially overlap with a UTR sequence or an intronic sequence. A non-coding target also includes non-exonic transcripts.

As used herein, a non-coding RNA (ncRNA) transcript is an RNA transcript that does not encode a protein. ncRNAs include short ncRNAs and long ncRNAs (lncRNAs). Short ncRNAs are ncRNAs that are generally 18-200 nucleotides (nt) in length. Examples of short ncRNAs include, but are not limited to, microRNAs (miRNAs), piwi-associated RNAs (piRNAs), short interfering RNAs (siRNAs), promoter-associated short RNAs (PASRs), transcription initiation RNAs (tiRNAs), termini-associated short RNAs (TASRs), antisense termini associated short RNAs (aTASRs), small nucleolar RNAs (snoRNAs), transcription start site antisense RNAs (TSSa-RNAs), small nuclear RNAs (snRNAs), retroposon-derived RNAs (RE-RNAs), 3'UTR-derived RNAs (uaRNAs), x-ncRNA, human Y RNA (hY RNA), unusually small RNAs (usRNAs), small NF90-associated RNAs (snaRs), vault RNAs (vtRNAs), small Cajal body-specific RNAs (scaRNAs), and telomere specific small RNAs (tel-sRNAs). LncRNAs are cellular RNAs, exclusive of rRNAs, greater than 200 nucleotides in length and having no obvious protein-coding capacity (Lipovich L, et al., MacroRNA underdogs in a microRNA world: evolutionary, regulatory, and biomedical significance of mammalian long non-protein-coding RNA, *Biochim Biophys Acta*, 2010, 1799(9): 597-615). LncRNAs include, but are not limited to, large or long intergenic ncRNAs (lincRNAs), transcribed ultraconserved regions (T-UCRs), pseudogenes, GAA-repeat containing RNAs (GRC-RNAs), long intronic ncRNAs, antisense RNAs (aRNAs), promoter-associated long RNAs (PALRs), promoter upstream transcripts (PROMPTs), and long stress-induced non-coding transcripts (LSINCTs).

As used herein, a coding target includes nucleotide sequences that encode for a protein and peptide sequences. The nucleotide sequence is a DNA or RNA sequence. The coding target includes protein-coding sequence. Protein-coding sequences include exon-coding sequences (e.g., exonic sequences).

As used herein, diagnosis of cancer may include the identification of cancer in a subject, determining the malignancy of the cancer, or determining the stage of the cancer.

As used herein, prognosis of cancer may include predicting the clinical outcome of the patient, assessing the risk of cancer recurrence, determining treatment modality, or determining treatment efficacy.

"Having" is an open-ended phrase like "comprising" and "including," and includes circumstances where additional elements are included and circumstances where they are not.

"Optional" or "optionally" means that the subsequently described event or circumstance may or may not occur, and that the description includes instances where the event or circumstance occurs and instances in which it does not.

As used herein, the term "metastasis" ("Mets") describes the spread of a cancer from one part of the body to another. A tumor formed by cells that have spread can be called a "metastatic tumor" or a "metastasis." The metastatic tumor often contains cells that are like those in the original (primary) tumor.

As used herein, the term "progression" describes the course of a disease, such as a cancer, as it becomes worse or spreads in the body.

As used herein, the term "about" refers to approximately +/−10% variation from a given value. It is to be understood that such a variation is always included in any given value provided herein, whether or not it is specifically referred to.

Use of the singular forms "a," "an," and "the" include plural references unless the context clearly dictates otherwise. Thus, for example, reference to "a polynucleotide" includes a plurality of polynucleotides, reference to "a target" includes a plurality of such targets, reference to "a normalization method" includes a plurality of such methods, and the like. Additionally, use of specific plural references, such as "two," "three," etc., read on larger numbers of the same subject, unless the context clearly dictates otherwise.

Terms such as "connected," "attached," "linked" and "conjugated" are used interchangeably herein and encompass direct as well as indirect connection, attachment, linkage or conjugation unless the context clearly dictates otherwise.

Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values, which are about the same quantity or amount as the recited value, are also within the scope of the invention, as are ranges based thereon. Where a combination is disclosed, each sub-combination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Coding and Non-Coding Targets

The methods disclosed herein often comprise assaying the expression level of a plurality of targets. The plurality of targets may comprise coding targets and/or non-coding targets of a protein-coding gene or a non protein-coding gene. As depicted in FIG. 6A, a protein-coding gene structure may comprise an exon and an intron. The exon may further comprise a coding sequence (CDS) and an untranslated region (UTR). The protein-coding gene may be transcribed to produce a pre-mRNA and the pre-mRNA may be processed to produce a mature mRNA. The mature mRNA may be translated to produce a protein.

As depicted in FIG. 6B, a non protein-coding gene structure may comprise an exon and intron. Usually, the exon region of a non protein-coding gene primarily contains a UTR. The non protein-coding gene may be transcribed to produce a pre-mRNA and the pre-mRNA may be processed to produce a non-coding RNA (ncRNA).

FIG. 7 illustrates potential targets (e.g., probe selection regions) within a protein-coding gene and a non protein-coding gene. A coding target may comprise a coding sequence of an exon. A non-coding target may comprise a UTR sequence of an exon, intron sequence, intergenic sequence, promoter sequence, non-coding transcript, CDS antisense, intronic antisense, UTR antisense, or non-coding transcript antisense. A non-coding transcript may comprise a non-coding RNA (ncRNA).

Figure 20A:
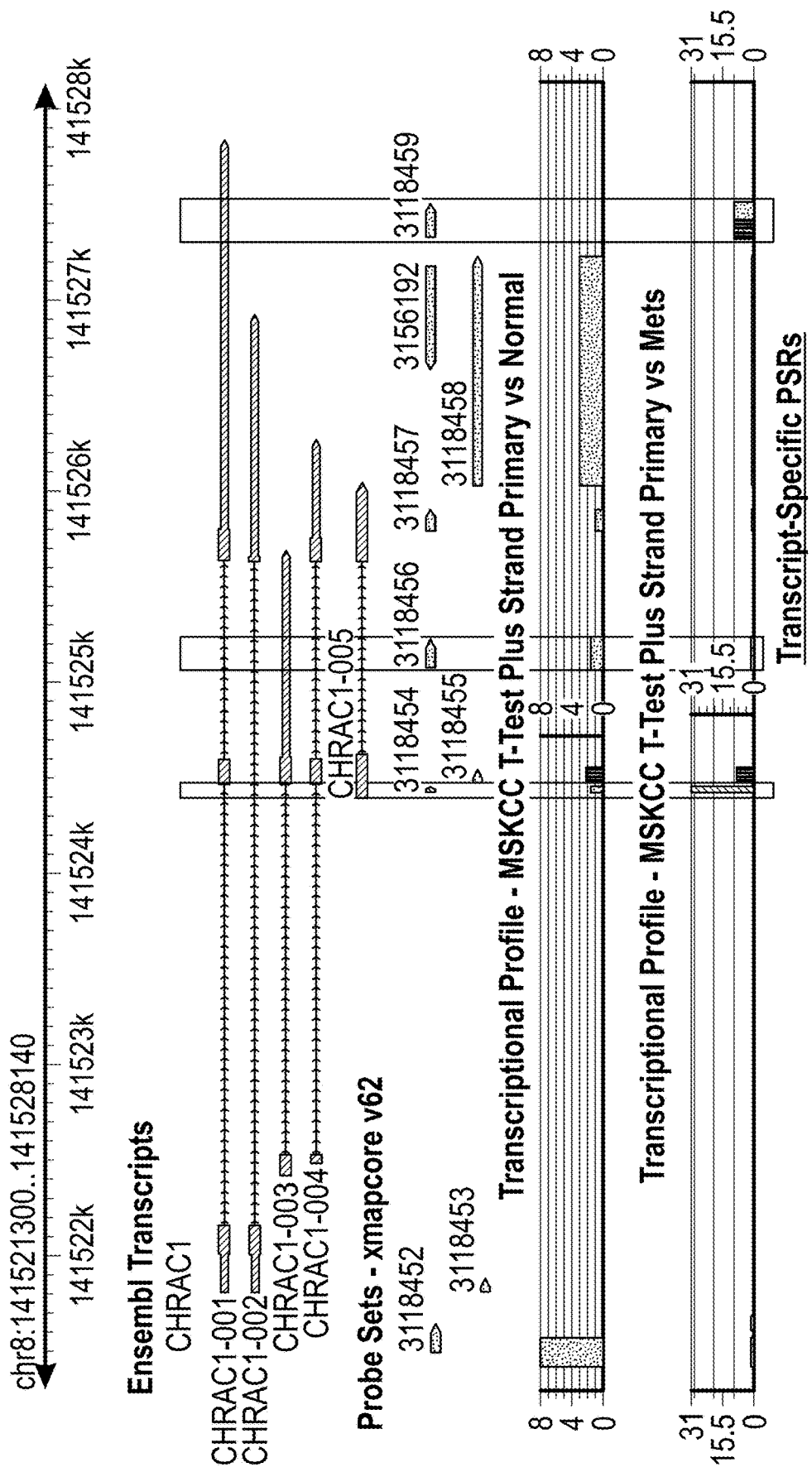
Figure 20B:
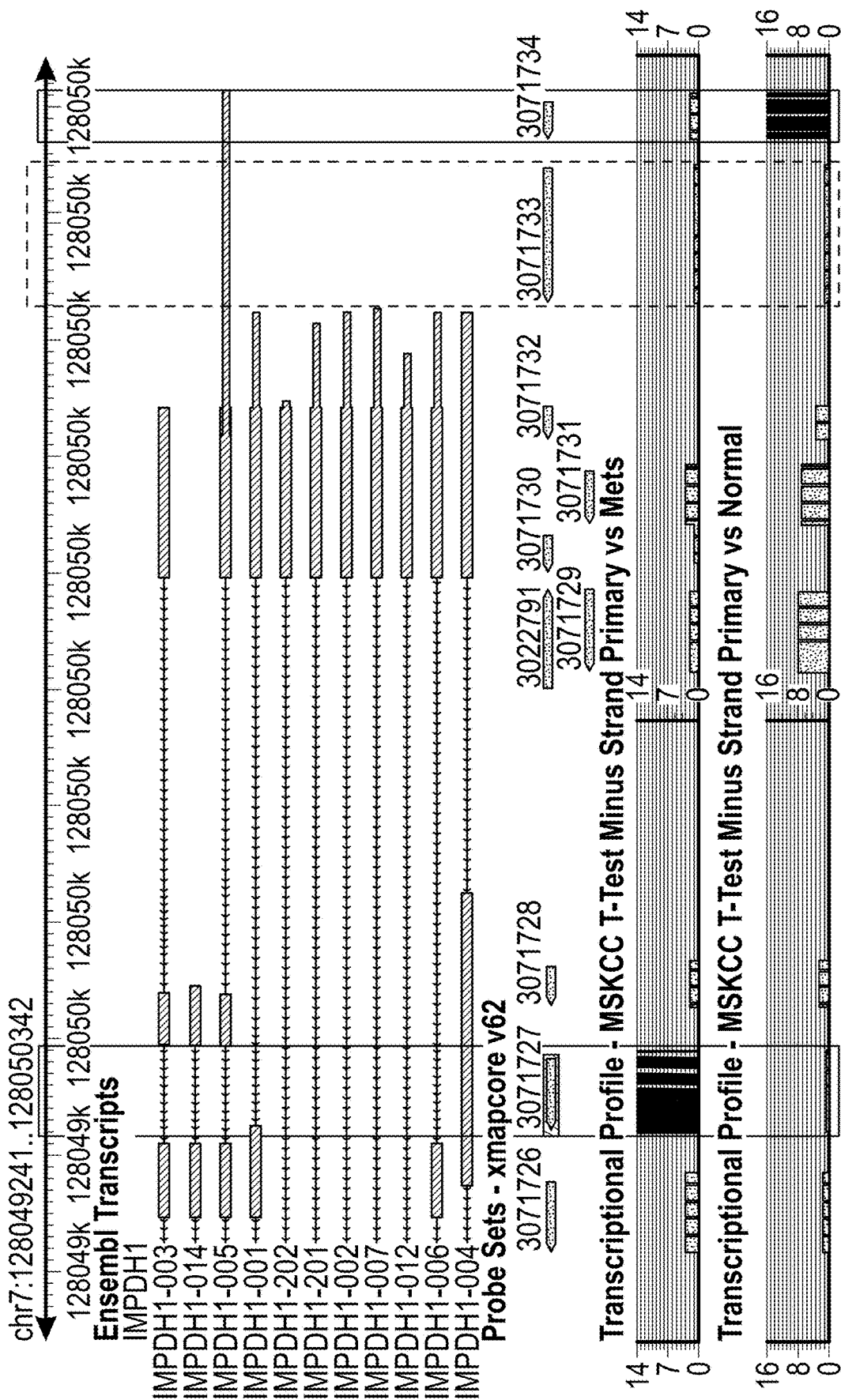

In some instances, the plurality of targets may be differentially expressed. For example, as shown in FIG. 20A, the CHRAC1-001 transcript specific probe selection region (probe set ID 3118459), the CHRAC1-003 transcript specific probe selection region (probe set ID 3118456) and the CHRAC1-005 transcript specific p probe selection region (probe set ID 3118454) demonstrate that the CHRAC1-001, -003, and -005 transcripts are differentially expressed in the Primary vs Normal and the Primary vs Mets. FIG. 20B provides another example of the differential expression of gene with transcript-specific PSRs.

Figure 10A:
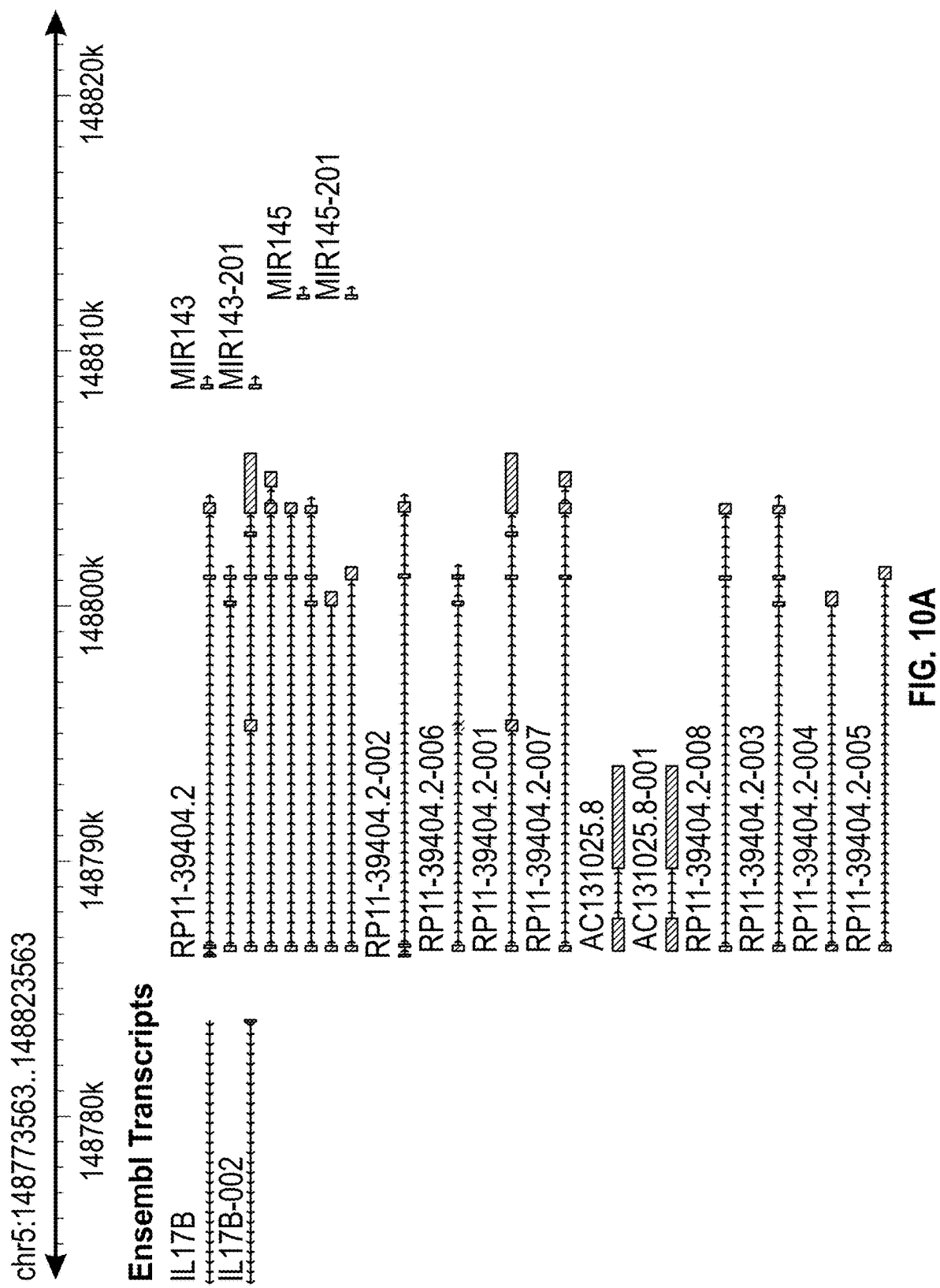

In some instances, adjacent and differentially expressed PSRs can form a block of differentially expressed PSRs (e.g., syntenic block). For example, as shown in FIG. 10B, a plurality of differentially expressed and adjacent PSRs (based on the bars of the transcriptional profile) may form one syntenic block (as depicted by the rectangle). A syntenic block may comprise one or more genes. The syntenic block as depicted in FIG. 10B corresponds to the three genes, RP11-39404.2, MIR143, MIR145 depicted in FIG. 10A. In some instances, the syntenic block may comprise PSRs specific to a coding target, non-coding targets, or a combination thereof. In some instances, as shown in FIG. 10A-B, the syntenic block comprises PSRs specific to a non-coding target. In some instances, the syntenic blocks may be categorized according to their components. For example, the syntenic block depicted in FIG. 10B would be a non-coding syntenic block differentially expressed which is composed of non-coding targets such as miRNAs, intergenic regions, etc.

In some instances, a plurality of PSRs is differentially expressed. The differentially expressed PSRs may form one or more syntenic blocks. As shown in FIG. 10C, differentially expressed PSRs may form two or more syntenic blocks (as outlined by the boxes). In some instances, the two or more syntenic blocks may correspond to one or more molecules. For example, two or more syntenic blocks could correspond to a non-coding target. Alternatively, two or more syntenic blocks may correspond to a coding target.

In some instances, the non-coding target comprises a sequence that at least partially overlaps with a sequence selected from SEQ ID NOs.: 1-903. In some instances, the non-coding target comprises a sequence that at least partially overlaps with a sequence selected from SEQ ID NOs.: 1-352. Alternatively, the non-coding target comprises a sequence that at least partially overlaps with a sequence selected from SEQ ID NOs.: 353-441. The non-coding target can comprise a sequence that at least partially overlaps with a sequence selected from SEQ ID NOs.: 353-361, 366, 369, 383-385, 387, 390, 391, 397-399, 410, 411, 421, 422, 434, 436, 458, and 459. In other instances, the non-coding target comprises a sequence that at least partially overlaps with a sequence selected from SEQ ID NOs.: 322-352. Alternatively, the non-coding target comprises a sequence that at least partially overlaps with a sequence selected from SEQ ID NOs.: 292-321. The non-coding target can comprise a sequence that at least partially overlaps with a sequence selected from SEQ ID NOs.: 460-480. The non-coding target can comprise a sequence that at least partially overlaps with a sequence selected from SEQ ID NOs.: 293, 297, 300, 303, 309, 311, 312, 316, and 481-642. Optionally, the non-coding target comprises a sequence that at least partially overlaps with a sequence selected from SEQ ID NOs.: 231-261. The non-coding target can comprise a sequence that at least partially overlaps with a sequence selected from SEQ ID NOs.: 442-457. In some instances, the non-coding target comprises a sequence that at least partially overlaps with a sequence selected from SEQ ID NOs.: 436, 643-721. The non-coding target can comprise a sequence that at least partially overlaps with a sequence selected from SEQ ID NOs.: 722-801. The non-coding target can comprise a sequence that at least partially overlaps with a sequence selected from SEQ ID NOs.: 653, 663, 685 and 802-878. In some instances, the non-coding target comprises a sequence that at least partially overlaps with a sequence selected from SEQ ID NOs.: 879-903. In some instances, the non-coding target is located on chr2q31.3. In some instances, the non-coding target comprises a sequence that at least partially overlaps with a sequence selected from SEQ ID NOs.: 262-291. In some instances, the non-coding target is a lncRNA. The lncRNA can be a vlncRNA or vlincRNA.

In some instances, the non-coding target comprises a sequence that is complementary to at least a portion of a sequence selected from SEQ ID NOs.: 1-903. In some instances, the non-coding target comprises a sequence that is complementary to at least a portion of a sequence selected from SEQ ID NOs.: 1-352. Alternatively, the non-coding target comprises a sequence that is complementary to at least a portion of a sequence selected from SEQ ID NOs.: 353-441. The non-coding target can comprise a sequence that is complementary to at least a portion of a sequence selected from SEQ ID NOs.: 353-361, 366, 369, 383-385, 387, 390, 391, 397-399, 410, 411, 421, 422, 434, 436, 458, and 459. In other instances, the non-coding target comprises a sequence that is complementary to at least a portion of a sequence selected from SEQ ID NOs.: 322-352. Alternatively, the non-coding target comprises a sequence that is complementary to at least a portion of a sequence selected from SEQ ID NOs.: 292-321. The non-coding target can comprise a sequence that is complementary to at least a portion of a sequence selected from SEQ ID NOs.: 460-480. The non-coding target can comprise a sequence that is complementary to at least a portion of a sequence selected from SEQ ID NOs.: 293, 297, 300, 303, 309, 311, 312, 316, and 481-642. Optionally, the non-coding target comprises a sequence that is complementary to at least a portion of a sequence selected from SEQ ID NOs.: 231-261. The non-coding target can comprise a sequence that is complementary to at least a portion of a sequence selected from SEQ ID NOs.: 442-457. In some instances, the non-coding target comprises a sequence that is complementary to at least a portion of a sequence selected from SEQ ID NOs.: 436, 643-721. The non-coding target can comprise a sequence that is complementary to at least a portion of a sequence selected from SEQ ID NOs.: 722-801. The non-coding target can comprise a sequence that is complementary to at least a portion of a sequence selected from SEQ ID NOs.: 653, 663, 685 and 802-878. In some instances, the non-coding target comprises a sequence that is complementary to at least a portion of a sequence selected from SEQ ID NOs.: 879-903. In some instances, the non-coding target comprises a sequence that is complementary to a sequence located on chr2q31.3. In some instances, the non-coding target comprises a sequence that is complementary to at least a portion of a sequence selected from SEQ ID NOs.: 262-291.

In some instances, the coding target comprises a sequence that at least partially overlaps with a sequence selected from SEQ ID NOs.: 1-903. In some instances, the coding target comprises a sequence that at least partially overlaps with a sequence selected from SEQ ID NOs.: 1-352. Alternatively, the coding target comprises a sequence that at least partially overlaps with a sequence selected from SEQ ID NOs.: 353-441. The coding target can comprise a sequence that at least partially overlaps with a sequence selected from SEQ ID NOs.: 353-361, 366, 369, 383-385, 387, 390, 391, 397-399, 410, 411, 421, 422, 434, 436, 458, and 459. In other instances, the coding target comprises a sequence that at least partially overlaps with a sequence selected from SEQ ID NOs.: 322-352. Alternatively, the coding target comprises a sequence that at least partially overlaps with a sequence selected from SEQ ID NOs.: 292-321. The coding target can comprise a sequence that at least partially overlaps with a sequence selected from SEQ ID NOs.: 460-480. The coding target can comprise a sequence that at least partially overlaps with a sequence selected from SEQ ID NOs.: 293, 297, 300, 303, 309, 311, 312, 316, and 481-642. Optionally, the coding target comprises a sequence that at least partially overlaps with a sequence selected from SEQ ID NOs.: 231-261. The coding target can comprise a sequence that at least partially overlaps with a sequence selected from SEQ ID NOs.: 442-457. In some instances, the coding target comprises a sequence that at least partially overlaps with a sequence selected from SEQ ID NOs.: 436, 643-721. The coding target can comprise a sequence that at least partially overlaps with a sequence selected from SEQ ID NOs.: 722-801. The coding target can comprise a sequence that at least partially overlaps with a sequence selected from SEQ ID NOs.: 653, 663, 685 and 802-878. In some instances, the coding target comprises a sequence that at least partially overlaps with a sequence selected from SEQ ID NOs.: 879-903. In some instances, the coding target is located on chr2q31.3. In some instances, the coding target comprises a sequence that at least partially overlaps with a sequence selected from SEQ ID NOs.: 262-291.

In some instances, the coding target comprises a sequence that is complementary to at least a portion of a sequence selected from SEQ ID NOs.: 1-903. In some instances, the coding target comprises a sequence that is complementary to at least a portion of a sequence selected from SEQ ID NOs.: 1-352. Alternatively, the coding target comprises a sequence that is complementary to at least a portion of a sequence selected from SEQ ID NOs.: 353-441. The coding target can comprise a sequence that is complementary to at least a portion of a sequence selected from SEQ ID NOs.: 353-361, 366, 369, 383-385, 387, 390, 391, 397-399, 410, 411, 421, 422, 434, 436, 458, and 459. In other instances, the coding target comprises a sequence that is complementary to at least a portion of a sequence selected from SEQ ID NOs.: 322-352. Alternatively, the coding target comprises a sequence that is complementary to at least a portion of a sequence selected from SEQ ID NOs.: 292-321. The coding target can comprise a sequence that is complementary to at least a portion of a sequence selected from SEQ ID NOs.: 460-480. The coding target can comprise a sequence that is complementary to at least a portion of a sequence selected from SEQ ID NOs.: 293, 297, 300, 303, 309, 311, 312, 316, and 481-642. Optionally, the coding target comprises a sequence that is complementary to at least a portion of a sequence selected from SEQ ID NOs.: 231-261. The coding target can comprise a sequence that is complementary to at least a portion of a sequence selected from SEQ ID NOs.: 442-457. In some instances, the coding target comprises a sequence that is complementary to at least a portion of a sequence selected from SEQ ID NOs.: 436, 643-721. The coding target can comprise a sequence that is complementary to at least a portion of a sequence selected from SEQ ID NOs.: 722-801. The coding target can comprise a sequence that is complementary to at least a portion of a sequence selected from SEQ ID NOs.: 653, 663, 685 and 802-878. In some instances, the coding target comprises a sequence that is complementary to at least a portion of a sequence selected from SEQ ID NOs.: 879-903. In some instances, the coding target comprises a sequence that is complementary to a sequence located on chr2q31.3. In some instances, the coding target comprises a sequence that is complementary to at least a portion of a sequence selected from SEQ ID NOs.: 262-291.

In some instances, the plurality of targets comprises a coding target and/or a non-coding target. The plurality of targets can comprise any of the coding targets and/or non-coding targets disclosed herein. In some instances, the plurality of targets comprises a coding target and/or a non-coding target, wherein the coding target and/or the non-coding target comprises a sequence that at least partially overlaps with a sequence selected from SEQ ID NOs.: 1-903. In some instances, the plurality of targets comprises a coding target and/or a non-coding target, wherein the coding target and/or the non-coding target comprises a sequence that at least partially overlaps with a sequence selected from SEQ ID NOs.: 1-352. Alternatively, the plurality of targets comprises a coding target and/or a non-coding target, wherein the coding target and/or the non-coding target comprises a sequence that at least partially overlaps with a sequence selected from SEQ ID NOs.: 353-441. The plurality of targets comprises a coding target and/or a non-coding target, wherein the coding target and/or the non-coding target can comprise a sequence that at least partially overlaps with a sequence selected from SEQ ID NOs.: 353-361, 366, 369, 383-385, 387, 390, 391, 397-399, 410, 411, 421, 422, 434, 436, 458, and 459. In other instances, the plurality of targets comprises a coding target and/or a non-coding target, wherein the coding target and/or the non-coding target comprises a sequence that at least partially overlaps with a sequence selected from SEQ ID NOs.: 322-352. Alternatively, the plurality of targets comprises a coding target and/or a non-coding target, wherein the coding target and/or the non-coding target comprises a sequence that at least partially overlaps with a sequence selected from SEQ ID NOs.: 292-321. The plurality of targets comprises a coding target and/or a non-coding target, wherein the coding target and/or the non-coding target can comprise a sequence that at least partially overlaps with a sequence selected from SEQ ID NOs.: 460-480. The plurality of targets comprises a coding target and/or a non-coding target, wherein the coding target and/or the non-coding target can comprise a sequence that at least partially overlaps with a sequence selected from SEQ ID NOs.: 293, 297, 300, 303, 309, 311, 312, 316, and 481-642. Optionally, the plurality of targets comprises a coding target and/or a non-coding target, wherein the coding target and/or the non-coding target comprises a sequence that at least partially overlaps with a sequence selected from SEQ ID NOs.: 231-261. The plurality of targets comprises a coding target and/or a non-coding target, wherein the coding target and/or the non-coding target can comprise a sequence that at least partially overlaps with a sequence selected from SEQ ID NOs.: 442-457. In some instances, the plurality of targets comprises a coding target and/or a non-coding target, wherein the coding target and/or the non-coding target comprises a sequence that at least partially overlaps with a sequence selected from SEQ ID NOs.: 436, 643-721. The plurality of targets comprises a coding target and/or a non-coding target, wherein the coding target and/or the non-coding target can comprise a sequence that at least partially overlaps with a sequence selected from SEQ ID NOs.: 722-801. The plurality of targets comprises a coding target and/or a non-coding target, wherein the coding target and/or the non-coding target can comprise a sequence that at least partially overlaps with a sequence selected from SEQ ID NOs.: 653, 663, 685 and 802-878. In some instances, the plurality of targets comprises a coding target and/or a non-coding target, wherein the coding target and/or the non-coding target comprises a sequence that at least partially overlaps with a sequence selected from SEQ ID NOs.: 879-903. In some instances, the plurality of targets comprises a coding target and/or a non-coding target, wherein the coding target and/or the non-coding target is located on chr2q31.3. In some instances, the plurality of targets comprises a coding target and/or a non-coding target, wherein the coding target and/or the non-coding target comprises a sequence that at least partially overlaps with a sequence selected from SEQ ID NOs.: 262-291.

In some instances, the plurality of targets comprises a coding target and/or a non-coding target, wherein the coding target and/or the non-coding target comprises a sequence that is complementary to at least a portion of a sequence selected from SEQ ID NOs.: 1-903. In some instances, the plurality of targets comprises a coding target and/or a non-coding target, wherein the coding target and/or the non-coding target comprises a sequence that is complementary to at least a portion of a sequence selected from SEQ ID NOs.: 1-352. Alternatively, the plurality of targets comprises a coding target and/or a non-coding target, wherein the coding target and/or the non-coding target comprises a sequence that is complementary to at least a portion of a sequence selected from SEQ ID NOs.: 353-441. The plurality of targets comprises a coding target and/or a non-coding target, wherein the coding target and/or the non-coding target can comprise a sequence that is complementary to at least a portion of a sequence selected from SEQ ID NOs.: 353-361, 366, 369, 383-385, 387, 390, 391, 397-399, 410, 411, 421, 422, 434, 436, 458, and 459. In other instances, the plurality of targets comprises a coding target and/or a non-coding target, wherein the coding target and/or the non-coding target comprises a sequence that is complementary to at least a portion of a sequence selected from SEQ ID NOs.: 322-352. Alternatively, the plurality of targets comprises a coding target and/or a non-coding target, wherein the coding target and/or the non-coding target comprises a sequence that is complementary to at least a portion of a sequence selected from SEQ ID NOs.: 292-321. The plurality of targets comprises a coding target and/or a non-coding target, wherein the coding target and/or the non-coding target can comprise a sequence that is complementary to at least a portion of a sequence selected from SEQ ID NOs.: 460-480. The plurality of targets comprises a coding target and/or a non-coding target, wherein the coding target and/or the non-coding target can comprise a sequence that is complementary to at least a portion of a sequence selected from SEQ ID NOs.: 293, 297, 300, 303, 309, 311, 312, 316, and 481-642. Optionally, the plurality of targets comprises a coding target and/or a non-coding target, wherein the coding target and/or the non-coding target comprises a sequence that is complementary to at least a portion of a sequence selected from SEQ ID NOs.: 231-261. The plurality of targets comprises a coding target and/or a non-coding target, wherein the coding target and/or the non-coding target can comprise a sequence that is complementary to at least a portion of a sequence selected from SEQ ID NOs.: 442-457. In some instances, the plurality of targets comprises a coding target and/or a non-coding target, wherein the coding target and/or the non-coding target comprises a sequence that is complementary to at least a portion of a sequence selected from SEQ ID NOs.: 436, 643-721. The plurality of targets comprises a coding target and/or a non-coding target, wherein the coding target and/or the non-coding target can comprise a sequence that is complementary to at least a portion of a sequence selected from SEQ ID NOs.: 722-801. The plurality of targets comprises a coding target and/or a non-coding target, wherein the coding target and/or the non-coding target can comprise a sequence that is complementary to at least a portion of a sequence selected from SEQ ID NOs.: 653, 663, 685 and 802-878. In some instances, the plurality of targets comprises a coding target and/or a non-coding target, wherein the coding target and/or the non-coding target comprises a sequence that is complementary to at least a portion of a sequence selected from SEQ ID NOs.: 879-903. In some instances, the plurality of targets comprises a coding target and/or a non-coding target, wherein the coding target and/or the non-coding target comprises a sequence that is complementary to a sequence located on chr2q31.3. In some instances, the plurality of targets comprises a coding target and/or a non-coding target, wherein the coding target and/or the non-coding target comprises a sequence that is complementary to at least a portion of a sequence selected from SEQ ID NOs.: 262-291.

Alternatively, a non-coding target comprises a UTR sequence, an intronic sequence, or a non-coding RNA transcript. In some instances, a non-coding target comprises sequences which partially overlap with a UTR sequence or an intronic sequence. A non-coding target also includes non-exonic transcripts. Exonic sequences may comprise regions on a protein-coding gene, such as an exon, UTR, or a portion thereof. Non-exonic sequences may comprise regions on a protein-coding, non protein-coding gene, or a portion thereof. For example, non-exonic sequences may comprise intronic regions, promoter regions, intergenic regions, a non-coding transcript, an exon anti-sense region, an intronic anti-sense region, UTR anti-sense region, non-coding transcript anti-sense region, or a portion thereof.

In some instances, the coding target and/or non-coding target is at least about 70% identical to a sequence selected from SEQ ID NOs.: 1-903. Alternatively, the coding target and/or non-coding target is at least about 80% identical to a sequence selected from SEQ ID NOs.: 1-903. In some instances, the coding target and/or non-coding target is at least about 85% identical to a sequence selected from SEQ ID NOs.: 1-903. In some instances, the coding target and/or non-coding target is at least about 90% identical to a sequence selected from SEQ ID NOs.: 1-903. Alternatively, the coding target and/or non-coding target are at least about 95% identical to a sequence selected from SEQ ID NOs.: 1-903.

In some instances, the plurality of targets comprises two or more sequences selected from (a) SEQ ID NOs.: 1-903; (b) SEQ ID NOs.: 1-352; (c) SEQ ID NOs.: 322-352; (d) SEQ ID NOs.: 292-321; (e) SEQ ID NOs.: 231-261; (f) coding target and/or a non-coding target located on chr2q31.3; (g) SEQ ID NOs.: 262-291; (h) SEQ ID NOs.: 353-441; (i) SEQ ID NOs.: 353-361, 366, 369, 383-385, 387, 390, 391, 397-399, 410, 411, 421, 422, 434, 436, 458, 459; (j) SEQ ID NOs.: 460-480; (k) SEQ ID NOs.: 293, 297, 300, 303, 309, 311, 312, 316, 481-642; (l) SEQ ID NOs.: 442-457; (m) SEQ ID NOs.: 436, 643-721; (n) SEQ ID NOs.: 722-801; (o) SEQ ID NOs.: 653, 663, 685, 802-878; (p) SEQ ID NOs.: 879-903; (q) a sequence with at least 80% identity to sequences listed in a-p; or (r) a complement thereof. In some instances, the plurality of targets comprises three or more sequences selected (a) SEQ ID NOs.: 1-903; (b) SEQ ID NOs.: 1-352; (c) SEQ ID NOs.: 322-352; (d) SEQ ID NOs.: 292-321; (e) SEQ ID NOs.: 231-261; (f) coding target and/or a non-coding target located on chr2q31.3; (g) SEQ ID NOs.: 262-291; (h) SEQ ID NOs.: 353-441; (i) SEQ ID NOs.: 353-361, 366, 369, 383-385, 387, 390, 391, 397-399, 410, 411, 421, 422, 434, 436, 458, 459; (j) SEQ ID NOs.: 460-480; (k) SEQ ID NOs.: 293, 297, 300, 303, 309, 311, 312, 316, 481-642; (l) SEQ ID NOs.: 442-457; (m) SEQ ID NOs.: 436, 643-721; (n) SEQ ID NOs.: 722-801; (o) SEQ ID NOs.: 653, 663, 685, 802-878; (p) SEQ ID NOs.: 879-903; (q) a sequence with at least 80% identity to sequences listed in a-p; or (r) a complement thereof. In some instances, the plurality of targets comprises five or more sequences selected from (a) SEQ ID NOs.: 1-903; (b) SEQ ID NOs.: 1-352; (c) SEQ ID NOs.: 322-352; (d) SEQ ID NOs.: 292-321; (e) SEQ ID NOs.: 231-261; (f) coding target and/or a non-coding target located on chr2q31.3; (g) SEQ ID NOs.: 262-291; (h) SEQ ID NOs.: 353-441; (i) SEQ ID NOs.: 353-361, 366, 369, 383-385, 387, 390, 391, 397-399, 410, 411, 421, 422, 434, 436, 458, 459; (j) SEQ ID NOs.: 460-480; (k) SEQ ID NOs.: 293, 297, 300, 303, 309, 311, 312, 316, 481-642; (l) SEQ ID NOs.: 442-457; (m) SEQ ID NOs.: 436, 643-721; (n) SEQ ID NOs.: 722-801; (o) SEQ ID NOs.: 653, 663, 685, 802-878; (p) SEQ ID NOs.: 879-903; (q) a sequence with at least 80% identity to sequences listed in a-p; or (r) a complement thereof. In some instances, the plurality of targets comprises six or more sequences selected from (a) SEQ ID NOs.: 1-903; (b) SEQ ID NOs.: 1-352; (c) SEQ ID NOs.: 322-352;

(d) SEQ ID NOs.: 292-321; (e) SEQ ID NOs.: 231-261; (f) coding target and/or a non-coding target located on chr2q31.3; (g) SEQ ID NOs.: 262-291; (h) SEQ ID NOs.: 353-441; (i) SEQ ID NOs.: 353-361, 366, 369, 383-385, 387, 390, 391, 397-399, 410, 411, 421, 422, 434, 436, 458, 459; (j) SEQ ID NOs.: 460-480; (k) SEQ ID NOs.: 293, 297, 300, 303, 309, 311, 312, 316, 481-642; (l) SEQ ID NOs.: 442-457; (m) SEQ ID NOs.: 436, 643-721; (n) SEQ ID NOs.: 722-801; (o) SEQ ID NOs.: 653, 663, 685, 802-878; (p) SEQ ID NOs.: 879-903; (q) a sequence with at least 80% identity to sequences listed in a-p; or (r) a complement thereof. In some instances, the plurality of targets comprises ten or more sequences selected from (a) SEQ ID NOs.: 1-903; (b) SEQ ID NOs.: 1-352; (c) SEQ ID NOs.: 322-352; (d) SEQ ID NOs.: 292-321; (e) SEQ ID NOs.: 231-261; (f) coding target and/or a non-coding target located on chr2q31.3; (g) SEQ ID NOs.: 262-291; (h) SEQ ID NOs.: 353-441; (i) SEQ ID NOs.: 353-361, 366, 369, 383-385, 387, 390, 391, 397-399, 410, 411, 421, 422, 434, 436, 458, 459; (j) SEQ ID NOs.: 460-480; (k) SEQ ID NOs.: 293, 297, 300, 303, 309, 311, 312, 316, 481-642; (l) SEQ ID NOs.: 442-457; (m) SEQ ID NOs.: 436, 643-721; (n) SEQ ID NOs.: 722-801; (o) SEQ ID NOs.: 653, 663, 685, 802-878; (p) SEQ ID NOs.: 879-903; (q) a sequence with at least 80% identity to sequences listed in a-p; or (r) a complement thereof. In some instances, the plurality of targets comprises fifteen or more sequences selected from (a) SEQ ID NOs.: 1-903; (b) SEQ ID NOs.: 1-352; (c) SEQ ID NOs.: 322-352; (d) SEQ ID NOs.: 292-321; (e) SEQ ID NOs.: 231-261; (f) coding target and/or a non-coding target located on chr2q31.3; (g) SEQ ID NOs.: 262-291; (h) SEQ ID NOs.: 353-441; (i) SEQ ID NOs.: 353-361, 366, 369, 383-385, 387, 390, 391, 397-399, 410, 411, 421, 422, 434, 436, 458, 459; (j) SEQ ID NOs.: 460-480; (k) SEQ ID NOs.: 293, 297, 300, 303, 309, 311, 312, 316, 481-642; (l) SEQ ID NOs.: 442-457; (m) SEQ ID NOs.: 436, 643-721; (n) SEQ ID NOs.: 722-801; (o) SEQ ID NOs.: 653, 663, 685, 802-878; (p) SEQ ID NOs.: 879-903; (q) a sequence with at least 80% identity to sequences listed in a-p; or (r) a complement thereof. In some instances, the plurality of targets comprises twenty or more sequences selected from (a) SEQ ID NOs.: 1-903; (b) SEQ ID NOs.: 1-352; (c) SEQ ID NOs.: 322-352; (d) SEQ ID NOs.: 292-321; (e) SEQ ID NOs.: 231-261; (f) coding target and/or a non-coding target located on chr2q31.3; (g) SEQ ID NOs.: 262-291; (h) SEQ ID NOs.: 353-441; (i) SEQ ID NOs.: 353-361, 366, 369, 383-385, 387, 390, 391, 397-399, 410, 411, 421, 422, 434, 436, 458, 459; (j) SEQ ID NOs.: 460-480; (k) SEQ ID NOs.: 293, 297, 300, 303, 309, 311, 312, 316, 481-642; (l) SEQ ID NOs.: 442-457; (m) SEQ ID NOs.: 436, 643-721; (n) SEQ ID NOs.: 722-801; (o) SEQ ID NOs.: 653, 663, 685, 802-878; (p) SEQ ID NOs.: 879-903; (q) a sequence with at least 80% identity to sequences listed in a-p; or (r) a complement thereof. In some instances, the plurality of targets comprises twenty five or more sequences selected from (a) SEQ ID NOs.: 1-903; (b) SEQ ID NOs.: 1-352; (c) SEQ ID NOs.: 322-352; (d) SEQ ID NOs.: 292-321; (e) SEQ ID NOs.: 231-261; (f) coding target and/or a non-coding target located on chr2q31.3; (g) SEQ ID NOs.: 262-291; (h) SEQ ID NOs.: 353-441; (i) SEQ ID NOs.: 353-361, 366, 369, 383-385, 387, 390, 391, 397-399, 410, 411, 421, 422, 434, 436, 458, 459; (j) SEQ ID NOs.: 460-480; (k) SEQ ID NOs.: 293, 297, 300, 303, 309, 311, 312, 316, 481-642; (l) SEQ ID NOs.: 442-457; (m) SEQ ID NOs.: 436, 643-721; (n) SEQ ID NOs.: 722-801; (o) SEQ ID NOs.: 653, 663, 685, 802-878; (p) SEQ ID NOs.: 879-903; (q) a sequence with at least 80% identity to sequences listed in a-p; or (r) a complement thereof. In some instances, the plurality of targets comprises thirty or more sequences selected from (a) SEQ ID NOs.: 1-903; (b) SEQ ID NOs.: 1-352; (c) SEQ ID NOs.: 322-352; (d) SEQ ID NOs.: 292-321; (e) SEQ ID NOs.: 231-261; (f) coding target and/or a non-coding target located on chr2q31.3; (g) SEQ ID NOs.: 262-291; (h) SEQ ID NOs.: 353-441; (i) SEQ ID NOs.: 353-361, 366, 369, 383-385, 387, 390, 391, 397-399, 410, 411, 421, 422, 434, 436, 458, 459; (j) SEQ ID NOs.: 460-480; (k) SEQ ID NOs.: 293, 297, 300, 303, 309, 311, 312, 316, 481-642; (l) SEQ ID NOs.: 442-457; (m) SEQ ID NOs.: 436, 643-721; (n) SEQ ID NOs.: 722-801; (o) SEQ ID NOs.: 653, 663, 685, 802-878; (p) SEQ ID NOs.: 879-903; (q) a sequence with at least 80% identity to sequences listed in a-p; or (r) a complement thereof.

In some instances, the plurality of targets disclosed herein comprises a target that is at least about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 650, 700, 750, 800, 850, 900, 950, or 1000 bases or base pairs in length. In other instances, the plurality of targets disclosed herein comprises a target that is at least about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 650, 700, 750, 800, 850, 900, 950, or 1000 kilo bases or kilo base pairs in length. Alternatively, the plurality of targets disclosed herein comprises a target that is at least about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 650, 700, 750, 800, 850, 900, 950, or 1000 mega bases or mega base pairs in length. The plurality of targets disclosed herein can comprise a target that is at least about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 650, 700, 750, 800, 850, 900, 950, or 1000 giga bases or giga base pairs in length.

In some instances, the non-coding target is at least about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 650, 700, 750, 800, 850, 900, 950, or 1000 bases or base pairs in length. In other instances, the non-coding target is at least about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 650, 700, 750, 800, 850, 900, 950, or 1000 kilo bases or kilo base pairs in length. Alternatively, the non-coding target is at least about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 650, 700, 750, 800, 850, 900, 950, or 1000 mega bases or mega base pairs in length. The non-coding target can be at least about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 650, 700, 750, 800, 850, 900, 950, or 1000 giga bases or giga base pairs in length.

In some instances, the coding target is at least about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 650, 700, 750, 800, 850, 900, 950, or 1000 bases or base pairs in length. In other instances, the coding target is at least about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 650, 700, 750, 800, 850, 900, 950, or 1000 kilo bases or kilo base pairs in length. Alternatively, the coding target is at least about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 650, 700, 750, 800, 850, 900, 950, or 1000 mega bases or mega base pairs in length. The coding target can be at least about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 650, 700, 750, 800, 850, 900, 950, or 1000 giga bases or giga base pairs in length.

Non-Coding RNAs

In some instances, the plurality of targets comprises a non-coding RNA. Generally, non-coding RNAs (ncRNAs) are functional transcripts that do not code for proteins. ncRNAs are loosely grouped into two major classes based on transcript size: small ncRNAs and large ncRNAs (lncRNAs).

Small ncRNAs

Small ncRNAs are typically 18 to 200 nucleotides (nt) in size and may be processed from longer precursors. Examples of small ncRNAs include, but are not limited to, microRNAs (miRNAs), piwi-associated RNAs (piRNAs), short interfering RNAs (siRNAs), promoter-associated short RNAs (PASRs), transcription initiation RNAs (tiRNAs), termini-associated short RNAs (TASRs), antisense termini associated short RNAs (aTASRs), small nucleolar RNAs (snoRNAs), transcription start site antisense RNAs (TSSa-RNAs), small nuclear RNAs (snRNAs), retroposon-derived RNAs (RE-RNAs), 3'UTR-derived RNAs (uaRNAs), x-ncRNA, human Y RNA (hY RNA), unusually small RNAs (usRNAs), small NF90-associated RNAs (snaRs), vault RNAs (vtRNAs), small Cajal body-specific RNAs (scaRNAs), and telomere specific small RNAs (tel-sRNAs).

miRNAs miRNAs can be divided into two subclasses: canonical and non-canonical miRNAs. Canonical miRNAs may initially be transcribed as long RNAs that contain hairpins. The 60-75 nt hairpins can be recognized by the RNA-binding protein Dgcr8 (DiGeorge syndrome critical region 8), which may direct the RNase III enzyme Drosha to cleave the base of the hairpin. Following cleavage by the Drosha-Dgcr8 complex, also called the microprocessor, the released hairpin may be transported to the cytoplasm, where Dicer, another RNase III enzyme, then cleaves it into a single short 18-25 nt dsRNA. Non-canonical miRNAs may bypass processing by the microprocessor by using other endonucleases or by direct transcription of a short hairpin. The resulting pre-miRNAs can then be exported from the nucleus and cleaved once by Dicer.

piRNAs

The piRNAs may differ from the miRNAs and endo-siRNAs in that they often do not require Dicer for their processing. piRNAs may be 25-32 nt in length, and can be expressed in the germline in mammals. They may be defined by their interaction with the Piwi proteins, a distinct family of Argonaute proteins (including Miwi, Miwi2 and Mili in mouse; also known as Piwil1, Piwil4 and Piwil2, respectively). piRNAs can be generated from long single-stranded RNA precursors that are often encoded by complex and repetitive intergenic sequences.

siRNAs siRNAs can be derived from long dsRNAs in the form of either sense or antisense RNA pairs or as long hairpins, which may then directly be processed by Dicer consecutively along the dsRNA to produce multiple siRNAs. Therefore, canonical miRNAs, non-canonical miRNAs and endo-siRNAs may involve Dicer processing and can be ~21 nt in length. Furthermore, in all three cases, one strand of the Dicer product may associate with an Argonaute protein (Ago 1-4 in mammals; also known as Eif2c1-4) to form the active RISC (RNA-induced silencing complex). Often, these ribonucleoprotein complexes may be able to bind to and control the levels and translation of their target mRNAs, if the match between the small RNA and its target is perfect, the target is cleaved; if not, the mRNA is destabilized through as yet unresolved mechanisms.

PASRs, tiRNAs, and TSSa-RNAs

PASRs can be broadly defined as short transcripts, generally 20-200 nt long, capped, with 5' ends that coincide with the transcription start sites (TSSs) of protein and non-coding genes. TiRNAs are predominantly 18 nt in length and generally found downstream of TSSs. TSSa-RNAs can be 20-90 nt long and may be localized within −250 to +50 base pairs of transcription start sites (TSSs). PASRs, tiRNAs, and TSSa-RNAs may strongly associate with highly expressed genes and regions of RNA Polymerase II (RNAPII) binding, may be weakly expressed, and may show bidirectional distributions that mirror RNAPII (Taft J, et al., Evolution, biogenesis and function of promoter-associated RNAs, *Cell Cycle*, 2009, 8(15):2332-2338).

TASRs and aTASRs

TASRs may be 22-200 nt in length and are found to cluster at 5' and 3' termini of annotated genes. aTASRs can be found within 50 bp and antisense to 3' UTRs of annotated transcripts.

snoRNAs

SnoRNAs represent one of the largest groups of functionally diverse trans-acting ncRNAs currently known in mammalian cells. snoRNAs can range between 60-150 nucleotides in length. From a structural basis, snoRNAs may fall into two categories termed box C/D snoRNAs (SNORDs) and box H/ACA snoRNAs (SNORAs). SNORDs can serve as guides for the 2'-O-ribose methylation of rRNAs or snRNAs, whereas SNORAs may serve as guides for the isomerization of uridine residues into pseudouridine.

snRNAs snRNAs, historically referred to as U-RNAs, may be less than 200 nt long and may play key roles in pre-mRNA splicing. snRNAs are further divided into two main categories based on shared sequences and associated proteins. Sm-class RNAs can have a 5' trimethylguanosine cap and bind several Sm proteins. Lsm-RNAs may possess a monomethylphosphate 5' cap and a uridine rich 3' end acting as a binding site for Lsm proteins. Sm class of snRNAs (U1, U2, U4 and U5) are synthesized by RNA Pol II. For Sm class, pre-snRNAs are transcribed and 5' monomethylguanosine capped in the nucleus, exported via multiple factors to the cytoplasm for further processing. After cytoplamic hypermethylation of 5' cap (trimethylguanosine) and 3' trimming, the snRNA is translocated back into the nucleus. snRNPs for Sm class snRNAs are also assembled in the cytosol. Lsm snRNA (U6 and other snoRNAs) are transcribed by Pol III and keep the monomethylguanosine 5' cap and in the nucleus. Lsm snRNAs never leave the nucleus.

lncRNAs

LncRNAs are cellular RNAs, exclusive of rRNAs, greater than 200 nucleotides in length and having no obvious protein-coding capacity (Lipovich L, et al., MacroRNA underdogs in a microRNA world: evolutionary, regulatory, and biomedical significance of mammalian long non-protein-coding RNA, *Biochim Biophys Acta,* 2010, 1799(9): 597-615). LncRNAs include, but are not limited to, large or long intergenic ncRNAs (lincRNAs), transcribed ultraconserved regions (T-UCRs), pseudogenes, GAA-repeat containing RNAs (GRC-RNAs), long intronic ncRNAs, antisense RNAs (aRNAs), promoter-associated long RNAs (PALRs), promoter upstream transcripts (PROMPTs), long stress-induced non-coding transcripts (LSINCTs), very long non-coding RNAs (vlncRNAs), and very long intergenic non-coding RNA (vlincRNAs). vlncRNAs (very long non-coding RNAs) are a type of lncRNAs that are often greater than 5 kb long and for which detailed information is available. vlincRNAs (very long intergenic non-coding RNAs) are generally expressed intergenic regions. In some instances, the vlincRNAs are at least about 30 kb, 40 kb, 50 kb, 60 kb, 70 kb, 80 kb, 90 kb, or 100 kb in length (Kapranov P et al., 2010, *BMC Biol,* 8:149).

T-UCRs

T-UCRs are transcribed genomic elements longer than 200 base pairs (bp) (range: 200-779 bp) that are absolutely conserved (100% identity with no insertion or deletions) among mouse, rat, and human genomes. T-UCRs may be intergenic (located between genes), intronic, exonic, partially exonic, exon containing, or "multiple" (location varies because of gene splice variants).

Pseudogenes

Pseudogenes are commonly defined as sequences that resemble known genes but cannot produce functional proteins. Pseudogenes can be broadly classified into two categories: processed and nonprocessed. Nonprocessed pseudogenes usually contain introns, and they are often located next to their paralogous parent gene. Processed pseudogenes are thought to originate through retrotransposition; accordingly, they lack introns and a promoter region, but they often contain a polyadenylation signal and are flanked by direct repeats.

Probes/Primers

The present invention provides for a probe set for diagnosing, monitoring and/or predicting a status or outcome of a cancer in a subject comprising a plurality of probes, wherein (i) the probes in the set are capable of detecting an expression level of at least one non-coding target; and (ii) the expression level determines the cancer status of the subject with at least about 40% specificity.

The probe set may comprise one or more polynucleotide probes. Individual polynucleotide probes comprise a nucleotide sequence derived from the nucleotide sequence of the target sequences, complementary sequences thereof, or reverse complement sequences thereof. The nucleotide sequence of the polynucleotide probe is designed such that it corresponds to, is complementary to, or is reverse complementary to the target sequences. The polynucleotide probe can specifically hybridize under either stringent or lowered stringency hybridization conditions to a region of the target sequences, to the complement thereof, or to a nucleic acid sequence (such as a cDNA, RNA) derived therefrom.

The selection of the polynucleotide probe sequences and determination of their uniqueness may be carried out in silico using techniques known in the art, for example, based on a BLASTN search of the polynucleotide sequence in question against gene sequence databases, such as the Human Genome Sequence, UniGene, dbEST or the non-redundant database at NCBI. In one embodiment of the invention, the polynucleotide probe is complementary to a region of a target mRNA derived from a target sequence in the probe set. Computer programs can also be employed to select probe sequences that may not cross hybridize or may not hybridize non-specifically.

FIG. 25 illustrates in an exemplary approach to selecting probes, also referred to herein as biomarkers, useful in diagnosing, predicting, and/or monitoring the status or outcome of a cancer, in accordance with an embodiment of this invention. In some instances, microarray hybridization of RNA, extracted from prostate cancer tissue samples and amplified, may yield a dataset that is then summarized and normalized by the fRMA technique (See McCall et al., "Frozen robust multiarray analysis (fRMA)," *Biostatistics Oxford England* 11.2 (2010): 242-253). The raw expression values captured by the probes can be summarized and normalized into PSR values. Cross-hybridizing probe sets, highly variable PSRs (e.g., PSRs with variance above the 90th percentile), and probe sets containing less than 4 probes can be removed or filtered. Following fRMA and filtration, the data can be decomposed into its principal components and an analysis of variance model can be used to determine the extent to which a batch effect remains present in the first 10 principal components (see Leek et al. "Tackling the widespread and critical impact of batch effects in high-throughput data," *Nat. Rev. Genetics* 11.10 (2010): 733-739).

These remaining probe sets can be further refined by filtration by a T-test between CR (clinical recurrence) and non-CR samples. In some instances, the probe sets with a P-value of >0.01 can be removed or filtered. The remaining probe sets can undergo further selection. Feature selection can be performed by regularized logistic regression using the elastic-net penalty (see Zou & Hastie, "Regularization and variable selection via the elastic net," *Journal of the Royal Stat. Soc.—Series B: Statistical Methodology* 67.2 (2005): 301-320). The regularized regression can be bootstrapped over 1000 times using all training data. With each iteration of bootstrapping, probe sets that have non-zero co-efficient following 3-fold cross validation can be tabulated. In some instances, probe sets that were selected in at least 25% of the total runs can be used for model building.

One skilled in the art understands that the nucleotide sequence of the polynucleotide probe need not be identical to its target sequence in order to specifically hybridize thereto. The polynucleotide probes of the present invention, therefore, comprise a nucleotide sequence that is at least about 65% identical to a region of the coding target or non-coding target. In another embodiment, the nucleotide sequence of the polynucleotide probe is at least about 70% identical a region of the coding target or non-coding target. In another embodiment, the nucleotide sequence of the polynucleotide probe is at least about 75% identical a region of the coding target or non-coding target. In another embodiment, the nucleotide sequence of the polynucleotide probe is at least about 80% identical a region of the coding target or non-coding target. In another embodiment, the nucleotide sequence of the polynucleotide probe is at least about 85% identical a region of the coding target or non-coding target. In another embodiment, the nucleotide sequence of the polynucleotide probe is at least about 90% identical a region of the coding target or non-coding target. In a further embodiment, the nucleotide sequence of the polynucleotide probe is at least about 95% identical to a region of the coding target or non-coding target.

Methods of determining sequence identity are known in the art and can be determined, for example, by using the BLASTN program of the University of Wisconsin Computer Group (GCG) software or provided on the NCBI website. The nucleotide sequence of the polynucleotide probes of the present invention may exhibit variability by differing (e.g. by nucleotide substitution, including transition or transversion) at one, two, three, four or more nucleotides from the sequence of the coding target or non-coding target.

Other criteria known in the art may be employed in the design of the polynucleotide probes of the present invention. For example, the probes can be designed to have <50% G content and/or between about 25% and about 70% G+C content. Strategies to optimize probe hybridization to the target nucleic acid sequence can also be included in the process of probe selection.

Hybridization under particular pH, salt, and temperature conditions can be optimized by taking into account melting temperatures and by using empirical rules that correlate with desired hybridization behaviors. Computer models may be used for predicting the intensity and concentration-dependence of probe hybridization.

The polynucleotide probes of the present invention may range in length from about 15 nucleotides to the full length of the coding target or non-coding target. In one embodiment of the invention, the polynucleotide probes are at least about 15 nucleotides in length. In another embodiment, the polynucleotide probes are at least about 20 nucleotides in length. In a further embodiment, the polynucleotide probes are at least about 25 nucleotides in length. In another embodiment, the polynucleotide probes are between about 15 nucleotides and about 500 nucleotides in length. In other embodiments, the polynucleotide probes are between about 15 nucleotides and about 450 nucleotides, about 15 nucleotides and about 400 nucleotides, about 15 nucleotides and about 350 nucleotides, about 15 nucleotides and about 300 nucleotides, about 15 nucleotides and about 250 nucleotides, about 15 nucleotides and about 200 nucleotides in length. In some embodiments, the probes are at least 15 nucleotides in length. In some embodiments, the probes are at least 15 nucleotides in length. In some embodiments, the probes are at least 20 nucleotides, at least 25 nucleotides, at least 50 nucleotides, at least 75 nucleotides, at least 100 nucleotides, at least 125 nucleotides, at least 150 nucleotides, at least 200 nucleotides, at least 225 nucleotides, at least 250 nucleotides, at least 275 nucleotides, at least 300 nucleotides, at least 325 nucleotides, at least 350 nucleotides, at least 375 nucleotides in length.

The polynucleotide probes of a probe set can comprise RNA, DNA, RNA or DNA mimetics, or combinations thereof, and can be single-stranded or double-stranded. Thus the polynucleotide probes can be composed of naturally-occurring nucleobases, sugars and covalent internucleoside (backbone) linkages as well as polynucleotide probes having non-naturally-occurring portions which function similarly. Such modified or substituted polynucleotide probes may provide desirable properties such as, for example, enhanced affinity for a target gene and increased stability. The probe set may comprise a probe that hybridizes to or corresponds to a coding target and/or a non-coding target. Preferably, the probe set comprises a plurality of probes that hybridizes to or corresponds to a combination of a coding target and non-coding target.

The probe set may comprise a plurality of probes that hybridizes to or corresponds to at least about 5 coding targets and/or non-coding targets. Alternatively, the probe set comprises a plurality of probes that hybridizes to or corresponds to at least about 10 coding targets and/or non-coding targets. The probe set may comprise a plurality of probes that hybridizes to or corresponds to at least about 15 coding targets and/or non-coding targets. In some instances, the probe set comprises a plurality of probes that hybridizes to or corresponds to at least about 20 coding targets and/or non-coding targets. Alternatively, the probe set comprises a plurality of probes that hybridizes to or corresponds to at least about 30 coding targets and/or non-coding targets. The probe set can comprise a plurality of probes that hybridizes to or corresponds to at least about 35, 40, 45, 50, 55, 60, 65, 70, 75, 80, 85, 90, 95, or 100 coding targets and/or non-coding targets.

The probe set may comprise a plurality of probes that hybridizes to or corresponds to at least about 5 non-coding targets. Alternatively, the probe set comprises a plurality of probes that hybridizes to or corresponds to at least about 10 non-coding targets. The probe set may comprise a plurality of probes that hybridizes to or corresponds to at least about 15 non-coding targets. In some instances, the probe set comprises a plurality of probes that hybridizes to or corresponds to at least about 20 non-coding targets. Alternatively, the probe set comprises a plurality of probes that hybridizes to or corresponds to at least about 30 non-coding targets. The probe set can comprise a plurality of probes that hybridizes to or corresponds to at least about 35, 40, 45, 50, 55, 60, 65, 70, 75, 80, 85, 90, 95, or 100 non-coding targets.

The probe set may comprise a plurality of probes, wherein at least about 5% of the plurality of probes hybridize to or correspond to non-coding targets. The probe set may comprise a plurality of probes, wherein at least about 8% of the plurality of probes hybridize to or correspond to non-coding targets. The probe set may comprise a plurality of probes, wherein at least about 10% of the plurality of probes hybridize to or correspond to non-coding targets. The probe set may comprise a plurality of probes, wherein at least about 12% of the plurality of probes hybridize to or correspond to non-coding targets. The probe set may comprise a plurality of probes, wherein at least about 15% of the plurality of probes hybridize to or correspond to non-coding targets. The probe set may comprise a plurality of probes, wherein at least about 18% of the plurality of probes hybridize to or correspond to non-coding targets. The probe set may comprise a plurality of probes, wherein at least about 20% of the plurality of probes hybridize to or correspond to non-coding targets. In some instances, the probe set comprises a plurality of probes, wherein at least about 25% of the plurality of probes hybridize to or correspond to non-coding targets. The probe set may comprise a plurality of probes, wherein at least about 30% of the plurality of probes hybridize to or correspond to non-coding targets. Alternatively, the probe set comprises a plurality of probes, wherein at least about 35% of the plurality of probes hybridize to or correspond to non-coding targets. In some instances, the probe set comprises a plurality of probes, wherein at least about 40% of the plurality of probes hybridize to or correspond to non-coding targets. In other instances, the probe set comprises a plurality of probes, wherein at least about 45% of the plurality of probes hybridize to or correspond to non-coding targets. The probe set may comprise a plurality of probes, wherein at least about 50% of the plurality of probes hybridize to or correspond to non-coding targets. The probe set may comprise a plurality of probes, wherein at least about 55% of the plurality of probes hybridize to or correspond to non-coding targets. Alternatively, the probe set comprises a plurality of probes, wherein at least about 60% of the plurality of probes hybridize to or correspond to non-coding targets. The probe set may comprise a plurality of probes, wherein at least about 65% of the plurality of probes hybridize to or correspond to non-coding targets. The probe set may comprise a plurality of probes, wherein at least about 70% of the plurality of probes hybridize to or correspond to non-coding targets. The probe set may comprise a plurality of probes, wherein at least about 75% of the plurality of probes hybridize to or correspond to non-coding targets. The probe set may comprise a plurality of probes, wherein at least about 80% of the plurality of probes hybridize to or correspond to non-coding targets. The probe set may comprise a plurality of probes, wherein at least about 85% of the plurality of probes hybridize to or correspond to non-coding targets. The probe set may comprise a plurality of probes, wherein at least about 90% of the plurality of probes hybridize to or correspond to non-coding targets. The probe set may comprise a plurality of probes, wherein at least about 95% of the plurality of probes hybridize to or correspond to non-coding targets. The probe set may comprise a plurality of probes, wherein at least about 97% of the plurality of probes hybridize to or correspond to non-coding targets.

The probe set can comprise a plurality of probes, wherein less than about 95% of the plurality of probes hybridize to or correspond to coding targets. The probe set can comprise a plurality of probes, wherein less than about 90% of the plurality of probes hybridize to or correspond to coding targets. Alternatively, the probe set comprises a plurality of probes, wherein less than about 85% of the plurality of probes hybridize to or correspond to coding targets. In some instances, the probe set comprises a plurality of probes, wherein less than about 80% of the plurality of probes hybridize to or correspond to coding targets. In other instances, the probe set comprises a plurality of probes, wherein less than about 75% of the plurality of probes hybridize to or correspond to coding targets. The probe set can comprise a plurality of probes, wherein less than about 70% of the plurality of probes hybridize to or correspond to coding targets. The probe set can comprise a plurality of probes, wherein less than about 65% of the plurality of probes hybridize to or correspond to coding targets. The probe set can comprise a plurality of probes, wherein less than about 60% of the plurality of probes hybridize to or correspond to coding targets. In some instances, the probe set comprises a plurality of probes, wherein less than about 55% of the plurality of probes hybridize to or correspond to coding targets. In other instances, the probe set comprises a plurality of probes, wherein less than about 50% of the plurality of probes hybridize to or correspond to coding targets. Alternatively, the probe set comprises a plurality of probes, wherein less than about 945% of the plurality of probes hybridize to or correspond to coding targets. The probe set can comprise a plurality of probes, wherein less than about 40% of the plurality of probes hybridize to or correspond to coding targets. The probe set can comprise a plurality of probes, wherein less than about 35% of the plurality of probes hybridize to or correspond to coding targets. The probe set can comprise a plurality of probes, wherein less than about 30% of the plurality of probes hybridize to or correspond to coding targets. The probe set can comprise a plurality of probes, wherein less than about 25% of the plurality of probes hybridize to or correspond to coding targets. In some instances, the probe set comprises a plurality of probes, wherein less than about 20% of the plurality of probes hybridize to or correspond to coding targets. In other instances, the probe set comprises a plurality of probes, wherein less than about 15% of the plurality of probes hybridize to or correspond to coding targets. Alternatively, the probe set comprises a plurality of probes, wherein less than about 12% of the plurality of probes hybridize to or correspond to coding targets. The probe set can comprise a plurality of probes, wherein less than about 10% of the plurality of probes hybridize to or correspond to coding targets. The probe set can comprise a plurality of probes, wherein less than about 8% of the plurality of probes hybridize to or correspond to coding targets. The probe set can comprise a plurality of probes, wherein less than about 5% of the plurality of probes hybridize to or correspond to coding targets. The probe set can comprise a plurality of probes, wherein less than about 3% of the plurality of probes hybridize to or correspond to coding targets.

The probe set may comprise a plurality of probes, wherein (i) the probes in the set are capable of detecting an expression level of at least one non-coding target; and (ii) the expression level determines the cancer status of the subject with at least about 40% specificity. In some embodiments, the probe set further comprises a probe capable of detecting an expression level of at least one coding target. The probe set can comprise any of the probe sets as disclosed in Tables 17, 19, 22-24, and 27-30 (see 'Probe set ID' column). In some instances, the probe set comprises probe set ID 2518027. Alternatively, the probe set comprises probe set ID 3046448; 3046449; 3046450; 3046457; 3046459; 3046460; 3046461; 3046462; 3046465; 3956596; 3956601; 3956603; 3103704; 3103705; 3103706; 3103707; 3103708; 3103710; 3103712; 3103713; 3103714; 3103715; 3103717; 3103718; 3103720; 3103721; 3103725; 3103726; 2719689; 2719692; 2719694; 2719695; 2719696; 2642733; 2642735; 2642738; 2642739; 2642740; 2642741; 2642744; 2642745; 2642746; 2642747; 2642748; 2642750; 2642753; 3970026; 3970034; 3970036; 3970039; 2608321; 2608324; 2608326; 2608331; 2608332; 2536222; 2536226; 2536228; 2536229; 2536231; 2536232; 2536233; 2536234; 2536235; 2536236; 2536237; 2536238; 2536240; 2536241; 2536243; 2536245; 2536248; 2536249; 2536252; 2536253; 2536256; 2536260; 2536261; 2536262; 3670638; 3670639; 3670641; 3670644; 3670645; 3670650; 3670659; 3670660; 3670661; 3670666, a complement thereof, a reverse complement thereof, or any combination thereof.

Further disclosed herein, is a classifier for use in diagnosing, predicting, and/or monitoring the outcome or status of a cancer in a subject. The classifier may comprise a classifier as disclosed in Table 17. The classifier can comprise a classifier as disclosed in Table 19. The classifier can comprise the GLM2, KNN12, KNN16, NB20, SVM5, SVM11, SVM20 classifiers or any combination thereof. The classifier can comprise a GLM2 classifier. Alternatively, the classifier comprises a KNN12 classifier. The classifier can comprise a KNN16 classifier. In other instances, the classifier comprises a NB20 classifier. The classifier may comprise a SVM5 classifier. In some instances, the classifier comprises a SVM11 classifier. Alternatively, the classifier comprises a SVM20 classifier. Alternatively, the classifier comprises one or more Inter-Correlated Expression (ICE) blocks disclosed herein. The classifier can comprise one or more probe sets disclosed herein.

The classifier may comprise at least about 5 coding targets and/or non-coding targets. Alternatively, the classifier comprises at least about 10 coding targets and/or non-coding targets. The classifier may comprise at least about 15 coding targets and/or non-coding targets. In some instances, the classifier comprises at least about 20 coding targets and/or non-coding targets. Alternatively, the classifier comprises at least about 30 coding targets and/or non-coding targets. The classifier can comprise at least about 35, 40, 45, 50, 55, 60, 65, 70, 75, 80, 85, 90, 95, or 100 coding targets and/or non-coding targets.

The classifier may comprise at least about 5 non-coding targets. Alternatively, the classifier comprises at least about 10 non-coding targets. The classifier may comprise at least about 15 non-coding targets. In some instances, the classifier comprises at least about 20 non-coding targets. Alternatively, the classifier comprises at least about 30 non-coding targets. The classifier can comprise at least about 35, 40, 45, 50, 55, 60, 65, 70, 75, 80, 85, 90, 95, or 100 non-coding targets.

The classifier may comprise at least about 5% non-coding targets. The classifier may comprise at least about 8% non-coding targets. The classifier may comprise at least about 10% non-coding targets. The classifier may comprise at least about 12% non-coding targets. The classifier may comprise at least about 15% non-coding targets. The classifier may comprise at least about 18% non-coding targets. The classifier may comprise at least about 20% non-coding targets. In some instances, the classifier comprises at least about 25% non-coding targets. The classifier may comprise at least about 30% non-coding targets. Alternatively, the classifier comprises at least about 35% non-coding targets. In some instances, the classifier comprises at least about 40% non-coding targets. In other instances, the classifier comprises at least about 45% non-coding targets. The classifier may comprise at least about 50% non-coding targets. The classifier may comprise at least about 55% non-coding targets. Alternatively, the classifier comprises at least about 60% non-coding targets. The classifier may comprise at least about 65% non-coding targets. The classifier may comprise at least about 70% non-coding targets. The classifier may comprise at least about 75% non-coding targets. The classifier may comprise at least about 80% non-coding targets. The classifier may comprise at least about 85% non-coding targets. The classifier may comprise at least about 90% non-coding targets. The classifier may comprise at least about 95% non-coding targets. The classifier may comprise at least about 97% non-coding targets.

The classifier can comprise less than about 95% coding targets. The classifier can comprise less than about 90% coding targets. Alternatively, the classifier comprises less than about 85% coding targets. In some instances, the classifier comprises less than about 80% coding targets. In other instances, the classifier comprises less than about 75% coding targets. The classifier can comprise less than about 70% coding targets. The classifier can comprise less than about 65% coding targets. The classifier can comprise less than about 60% coding targets. In some instances, the classifier comprises less than about 55% coding targets. In other instances, the classifier comprises less than about 50% coding targets. Alternatively, the classifier comprises less than about 45% coding targets. The classifier can comprise less than about 40% coding targets. The classifier can comprise less than about 35% coding targets. The classifier can comprise less than about 30% coding targets. The classifier can comprise less than about 25% coding targets. In some instances, the classifier comprises less than about 20% coding targets. In other instances, the classifier comprises less than about 15% coding targets. Alternatively, the classifier comprises less than about 12% coding targets. The classifier can comprise less than about 10% coding targets. The classifier can comprise less than about 8% coding targets. The classifier can comprise less than about 5% coding targets. The classifier can comprise less than about 3% coding targets.

Further disclosed herein, is an Inter-Correlated Expression (ICE) block for diagnosing, predicting, and/or monitoring the outcome or status of a cancer in a subject. The ICE block may comprise one or more ICE Block IDs as disclosed in Tables 22-24. The ICE block can comprise Block ID_2879, Block ID_2922, Block ID_4271, Block ID_4627, Block ID_5080, or any combination thereof. Alternatively, the ICE block comprises Block ID_6592, Block ID_4226, Block ID_6930, Block ID_7113, Block ID_5470, or any combination thereof. In other instances, the ICE block comprises Block ID_7716, Block ID_4271, Block ID_5000, Block ID_5986, Block ID_1146, Block ID_7640, Block ID_4308, Block ID_1532, Block ID_2922, or any combination thereof. The ICE block can comprise Block ID_2922. Alternatively, the ICE block comprises Block ID_5080. In other instances, the ICE block comprises Block ID_6592. The ICE block can comprise Block ID_4627. Alternatively, the ICE block comprises Block ID_7113. In some instances, the ICE block comprises Block ID_5470. In other instances, the ICE block comprises Block ID_5155. The ICE block can comprise Block ID_6371. Alternatively, the ICE block comprises Block ID_2879.

The ICE block may comprise at least about 5 coding targets and/or non-coding targets. Alternatively, the ICE block comprises at least about 10 coding targets and/or non-coding targets. The ICE block may comprise at least about 15 coding targets and/or non-coding targets. In some instances, the ICE block comprises at least about 20 coding targets and/or non-coding targets. Alternatively, the ICE block comprises at least about 30 coding targets and/or non-coding targets. The ICE block can comprise at least about 35, 40, 45, 50, 55, 60, 65, 70, 75, 80, 85, 90, 95, or 100 coding targets and/or non-coding targets.

The ICE block may comprise at least about 5 non-coding targets. Alternatively, the ICE block comprises at least about 10 non-coding targets. The ICE block may comprise at least about 15 non-coding targets. In some instances, the ICE block comprises at least about 20 non-coding targets. Alternatively, the ICE block comprises at least about 30 non-coding targets. The ICE block can comprise at least about 35, 40, 45, 50, 55, 60, 65, 70, 75, 80, 85, 90, 95, or 100 non-coding targets.

The ICE block may comprise at least about 5% non-coding targets. The ICE block may comprise at least about 8% non-coding targets. The ICE block may comprise at least about 10% non-coding targets. The ICE block may comprise at least about 12% non-coding targets. The ICE block may comprise at least about 15% non-coding targets. The ICE block may comprise at least about 18% non-coding targets. The ICE block may comprise at least about 20% non-coding targets. In some instances, the ICE block comprises at least about 25% non-coding targets. The ICE block may comprise at least about 30% non-coding targets. Alternatively, the ICE block comprises at least about 35% non-coding targets. In some instances, the ICE block comprises at least about 40% non-coding targets. In other instances, the ICE block comprises at least about 45% non-coding targets. The ICE block may comprise at least about 50% non-coding targets. The ICE block may comprise at least about 55% non-coding targets. Alternatively, the ICE block comprises at least about 60% non-coding targets. The ICE block may comprise at least about 65% non-coding targets. The ICE block may comprise at least about 70% non-coding targets. The ICE block may comprise at least about 75% non-coding targets.

The ICE block may comprise at least about 80% non-coding targets. The ICE block may comprise at least about 85% non-coding targets. The ICE block may comprise at least about 90% non-coding targets. The ICE block may comprise at least about 95% non-coding targets. The ICE block may comprise at least about 97% non-coding targets.

The ICE block can comprise less than about 95% coding targets. The ICE block can comprise less than about 90% coding targets. Alternatively, the ICE block comprises less than about 85% coding targets. In some instances, the ICE block comprises less than about 80% coding targets. In other instances, the ICE block comprises less than about 75% coding targets. The ICE block can comprise less than about 70% coding targets. The ICE block can comprise less than about 65% coding targets. The ICE block can comprise less than about 60% coding targets. In some instances, the ICE block comprises less than about 55% coding targets. In other instances, the ICE block comprises less than about 50% coding targets. Alternatively, the ICE block comprises less than about 45% coding targets. The ICE block can comprise less than about 40% coding targets. The ICE block can comprise less than about 35% coding targets. The ICE block can comprise less than about 30% coding targets. The ICE block can comprise less than about 25% coding targets. In some instances, the ICE block comprises less than about 20% coding targets. In other instances, the ICE block comprises less than about 15% coding targets. Alternatively, the ICE block comprises less than about 12% coding targets. The ICE block can comprise less than about 10% coding targets. The ICE block can comprise less than about 8% coding targets. The ICE block can comprise less than about 5% coding targets. The ICE block can comprise less than about 3% coding targets.

Further disclosed herein, is a digital Gleason score predictor for prognosing the risk of biochemical recurrence. The digital Gleason score predictor can comprise a classifier. The classifier can comprise at least one non-coding target. In some instances, the classifier further comprises at least one coding-target. In some instances, the digital Gleason score predictor comprises a plurality of targets, wherein the plurality of targets comprise at least one coding target and at least one non-coding target. The non-coding target, coding target and plurality of targets can be any of the targets disclosed herein. The targets can be selected from any of Tables 4, 6-9, 15, 16, 17, 19, 22-24, and 26-30. The targets can comprise a sequence comprising at least a portion of any of SEQ ID NOs.: 1-903. In some instances, the accuracy of the digital Gleason score predictor to predict the risk of biochemical occurrence is at least about 45%, 50%, 55%, 60%, 65%, 70%, 75%, 80%, 85%, 90%, 92%, 95%, 97%, 98%, 99% or 100%. The accuracy of the digital Gleason score predictor to predict the risk of biochemical occurrence can be at least about 50%. Alternatively, the accuracy of the digital Gleason score predictor to predict the risk of biochemical occurrence is at least about 55%. In some instances, the accuracy of the digital Gleason score predictor to predict the risk of biochemical occurrence is at least about 60%. In other instances, the accuracy of the digital Gleason score predictor to predict the risk of biochemical occurrence is at least about 65%. The accuracy of the digital Gleason score predictor to predict the risk of biochemical occurrence can be at least about 70%. Alternatively, the accuracy of the digital Gleason score predictor to predict the risk of biochemical occurrence is at least about 75%. In some instances, the accuracy of the digital Gleason score predictor to predict the risk of biochemical occurrence is at least about 80%. In other instances, the accuracy of the digital Gleason score predictor to predict the risk of biochemical occurrence is at least about 85%.

In some instances, the probe sets, PSRs, ICE blocks, and classifiers disclosed herein are clinically significant. In some instances, the clinical significance of the probe sets, PSRs, ICE blocks, and classifiers is determined by the AUC value. In order to be clinically significant, the AUC value is at least about 0.5, 0.55, 0.6, 0.65, 0.7, 0.75, 0.8, 0.85, 0.9, or 0.95. The clinical significant of the probe sets, PSRs, ICE blocks, and classifiers can be determined by the percent accuracy. For example, a probe set, PSR, ICE block, and/or classifier is determined to be clinically significant if the accuracy of the probe set, PSR, ICE block and/or classifier is at least about 50%, 55%, 60%, 65%, 70%, 72%, 75%, 77%, 80%, 82%, 84%, 86%, 88%, 90%, 92%, 94%, 96%, or 98%. In other instances, the clinical significance of the probe sets, PSRs, ICE blocks, and classifiers is determined by the median fold difference (MDF) value. In order to be clinically significant, the MDF value is at least about 0.8, 0.9, 1.0, 1.1, 1.2, 1.3, 1.4, 1.5, 1.6, 1.7, 1.9, or 2.0. In some instances, the MDF value is greater than or equal to 1.1. In other instances, the MDF value is greater than or equal to 1.2. Alternatively, or additionally, the clinical significance of the probe sets, PSRs, ICE blocks, and classifiers is determined by the t-test P-value. In some instances, in order to be clinically significant, the t-test P-value is less than about 0.070, 0.065, 0.060, 0.055, 0.050, 0.045, 0.040, 0.035, 0.030, 0.025, 0.020, 0.015, 0.010, 0.005, 0.004, or 0.003. The t-test P-value can be less than about 0.050. Alternatively, the t-test P-value is less than about 0.010. In some instances, the clinical significance of the probe sets, PSRs, ICE blocks, and classifiers is determined by the clinical outcome. For example, different clinical outcomes can have different minimum or maximum thresholds for AUC values, MDF values, t-test P-values, and accuracy values that would determine whether the probe set, PSR, ICE block, and/or classifier is clinically significant. In another example, a probe set, PSR, ICE block, or classifier can be considered clinically significant if the P-value of the t-test was lower than about 0.08, 0.07, 0.06, 0.05, 0.04, 0.03, 0.02, or 0.01 in any of the following comparisons: BCR vs non-BCR, CP vs non-CP, PCSM vs non-PCSM. Additionally, a probe set, PSR, ICE block, or classifier is determined to be clinically significant if the P-values of the differences between the KM curves for BCR vs non-BCR, CP vs non-CP, PCSM vs non-PCSM is lower than about 0.08, 0.07, 0.06, 0.05, 0.04, 0.03, 0.02, or 0.01.

The system of the present invention further provides for primers and primer pairs capable of amplifying target sequences defined by the probe set, or fragments or subsequences or complements thereof. The nucleotide sequences of the probe set may be provided in computer-readable media for in silico applications and as a basis for the design of appropriate primers for amplification of one or more target sequences of the probe set.

Primers based on the nucleotide sequences of target sequences can be designed for use in amplification of the target sequences. For use in amplification reactions such as PCR, a pair of primers can be used. The exact composition of the primer sequences is not critical to the invention, but for most applications the primers may hybridize to specific sequences of the probe set under stringent conditions, particularly under conditions of high stringency, as known in the art. The pairs of primers are usually chosen so as to generate an amplification product of at least about 50 nucleotides, more usually at least about 100 nucleotides. Algorithms for the selection of primer sequences are generally known, and are available in commercial software packages. These primers may be used in standard quantitative or qualitative PCR-based assays to assess transcript expression levels of RNAs defined by the probe set. Alternatively, these primers may be used in combination with probes, such as molecular beacons in amplifications using real-time PCR.

In one embodiment, the primers or primer pairs, when used in an amplification reaction, specifically amplify at least a portion of a nucleic acid depicted in one of Table 6 (or subgroups thereof as set forth herein), an RNA form thereof, or a complement to either thereof.

As is known in the art, a nucleoside is a base-sugar combination and a nucleotide is a nucleoside that further includes a phosphate group covalently linked to the sugar portion of the nucleoside. In forming oligonucleotides, the phosphate groups covalently link adjacent nucleosides to one another to form a linear polymeric compound, with the normal linkage or backbone of RNA and DNA being a 3' to 5' phosphodiester linkage. Specific examples of polynucleotide probes or primers useful in this invention include oligonucleotides containing modified backbones or non-natural internucleoside linkages. As defined in this specification, oligonucleotides having modified backbones include both those that retain a phosphorus atom in the backbone and those that lack a phosphorus atom in the backbone. For the purposes of the present invention, and as sometimes referenced in the art, modified oligonucleotides that do not have a phosphorus atom in their internucleoside backbone can also be considered to be oligonucleotides.

Exemplary polynucleotide probes or primers having modified oligonucleotide backbones include, for example, those with one or more modified internucleotide linkages that are phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Exemplary modified oligonucleotide backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include morpholino linkages (formed in part from the sugar portion of a nucleoside); siloxane backbones; sulfide, sulfoxide and sulphone backbones; formacetyl and thioformacetyl backbones; methylene formacetyl and thioformacetyl backbones; alkene containing backbones; sulphamate backbones; methyleneimino and methylenehydrazino backbones; sulphonate and sulfonamide backbones; amide backbones; and others having mixed N, 0, S and $CH_2$ component parts.

The present invention also contemplates oligonucleotide mimetics in which both the sugar and the internucleoside linkage of the nucleotide units are replaced with novel groups. The base units are maintained for hybridization with an appropriate nucleic acid target compound. An example of such an oligonucleotide mimetic, which has been shown to have excellent hybridization properties, is a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza-nitrogen atoms of the amide portion of the backbone.

The present invention also contemplates polynucleotide probes or primers comprising "locked nucleic acids" (LNAs), which may be novel conformationally restricted oligonucleotide analogues containing a methylene bridge that connects the 2'-O of ribose with the 4'-C. LNA and LNA analogues may display very high duplex thermal stabilities with complementary DNA and RNA, stability towards 3'-exonuclease degradation, and good solubility properties. Synthesis of the LNA analogues of adenine, cytosine, guanine, 5-methylcytosine, thymine and uracil, their oligomerization, and nucleic acid recognition properties have been described. Studies of mismatched sequences show that LNA obey the Watson-Crick base pairing rules with generally improved selectivity compared to the corresponding unmodified reference strands.

LNAs may form duplexes with complementary DNA or RNA or with complementary LNA, with high thermal affinities. The universality of LNA-mediated hybridization has been emphasized by the formation of exceedingly stable LNA:LNA duplexes. LNA:LNA hybridization was shown to be the most thermally stable nucleic acid type duplex system, and the RNA-mimicking character of LNA was established at the duplex level. Introduction of three LNA monomers (T or A) resulted in significantly increased melting points toward DNA complements.

Synthesis of 2'-amino-LNA and 2'-methylamino-LNA has been described and thermal stability of their duplexes with complementary RNA and DNA strands reported. Preparation of phosphorothioate-LNA and 2'-thio-LNA have also been described.

Modified polynucleotide probes or primers may also contain one or more substituted sugar moieties. For example, oligonucleotides may comprise sugars with one of the following substituents at the 2' position: OH; F; O-, S-, or N-alkyl; O-, S-, or N-alkenyl; 0-, S- or N-alkynyl; or O-alkyl-O-alkyl, wherein the alkyl, alkenyl and alkynyl may be substituted or unsubstituted $C_1$ to $C_{10}$ alkyl or C2 to $C_{10}$ alkenyl and alkynyl. Examples of such groups are: $O[(CH_2)_nO]_mCH_3$, $O(CH_2)_nOCH_3$, $O(CH_2)_nNH_2$, $O(CH_2)_nCH_3ONH_2$, and $O(CH_2)_nON[((CH_2)_nCH_3)]_2$, where n and m are from 1 to about 10. Alternatively, the oligonucleotides may comprise one of the following substituents at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Specific examples include 2'-methoxyethoxy (2'-O—$CH_2CH_2OCH_3$, also known as 2'-O-(2-methoxyethyl) or 2'-MOE), 2'-dimethylaminooxyethoxy ($O(CH2)2ON(CH_3)_2$ group, also known as 2'-DMA0E), 2'-methoxy (2'-O—$CH_3$), 2'-aminopropoxy (2'-$OCH_2CH_2CH_2NH_2$) and 2'-fluoro (2'-F).

Similar modifications may also be made at other positions on the polynucleotide probes or primers, particularly the 3' position of the sugar on the 3' terminal nucleotide or in 2'-5' linked oligonucleotides and the 5' position of 5' terminal nucleotide. Polynucleotide probes or primers may also have sugar mimetics such as cyclobutyl moieties in place of the pentofuranosyl sugar.

Polynucleotide probes or primers may also include modifications or substitutions to the nucleobase. As used herein, "unmodified" or "natural" nucleobases include the purine bases adenine (A) and guanine (G), and the pyrimidine bases thymine (T), cytosine (C) and uracil (U).

Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808; The Concise Encyclopedia Of Polymer Science And Engineering, (1990) pp 858-859, Kroschwitz, J. I., ed. John Wiley & Sons; Englisch et al., *Angewandte Chemie, Int. Ed.*, 30:613 (1991); and Sanghvi, Y. S., (1993) *Antisense Research and Applications*, pp 289-302, Crooke, S. T. and Lebleu, B., ed., CRC Press. Certain of these nucleobases are particularly useful for increasing the binding affinity of the polynucleotide probes of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C.

One skilled in the art recognizes that it is not necessary for all positions in a given polynucleotide probe or primer to be uniformly modified. The present invention, therefore, contemplates the incorporation of more than one of the aforementioned modifications into a single polynucleotide probe or even at a single nucleoside within the probe or primer.

One skilled in the art also appreciates that the nucleotide sequence of the entire length of the polynucleotide probe or primer does not need to be derived from the target sequence. Thus, for example, the polynucleotide probe may comprise nucleotide sequences at the 5' and/or 3' termini that are not derived from the target sequences. Nucleotide sequences which are not derived from the nucleotide sequence of the target sequence may provide additional functionality to the polynucleotide probe. For example, they may provide a restriction enzyme recognition sequence or a "tag" that facilitates detection, isolation, purification or immobilization onto a solid support. Alternatively, the additional nucleotides may provide a self-complementary sequence that allows the primer/probe to adopt a hairpin configuration. Such configurations are necessary for certain probes, for example, molecular beacon and Scorpion probes, which can be used in solution hybridization techniques.

The polynucleotide probes or primers can incorporate moieties useful in detection, isolation, purification, or immobilization, if desired. Such moieties are well-known in the art (see, for example, Ausubel et al., (1997 & updates) *Current Protocols in Molecular Biology*, Wiley & Sons, New York) and are chosen such that the ability of the probe to hybridize with its target sequence is not affected.

Examples of suitable moieties are detectable labels, such as radioisotopes, fluorophores, chemiluminophores, enzymes, colloidal particles, and fluorescent microparticles, as well as antigens, antibodies, haptens, avidin/streptavidin, biotin, haptens, enzyme cofactors/substrates, enzymes, and the like.

A label can optionally be attached to or incorporated into a probe or primer polynucleotide to allow detection and/or quantitation of a target polynucleotide representing the target sequence of interest. The target polynucleotide may be the expressed target sequence RNA itself, a cDNA copy thereof, or an amplification product derived therefrom, and may be the positive or negative strand, so long as it can be specifically detected in the assay being used. Similarly, an antibody may be labeled.

In certain multiplex formats, labels used for detecting different targets may be distinguishable. The label can be attached directly (e.g., via covalent linkage) or indirectly, e.g., via a bridging molecule or series of molecules (e.g., a molecule or complex that can bind to an assay component, or via members of a binding pair that can be incorporated into assay components, e.g. biotin-avidin or streptavidin). Many labels are commercially available in activated forms which can readily be used for such conjugation (for example through amine acylation), or labels may be attached through known or determinable conjugation schemes, many of which are known in the art.

Labels useful in the invention described herein include any substance which can be detected when bound to or incorporated into the biomolecule of interest. Any effective detection method can be used, including optical, spectroscopic, electrical, piezoelectrical, magnetic, Raman scattering, surface plasmon resonance, colorimetric, calorimetric, etc. A label is typically selected from a chromophore, a lumiphore, a fluorophore, one member of a quenching system, a chromogen, a hapten, an antigen, a magnetic particle, a material exhibiting nonlinear optics, a semiconductor nanocrystal, a metal nanoparticle, an enzyme, an antibody or binding portion or equivalent thereof, an aptamer, and one member of a binding pair, and combinations thereof. Quenching schemes may be used, wherein a quencher and a fluorophore as members of a quenching pair may be used on a probe, such that a change in optical parameters occurs upon binding to the target introduce or quench the signal from the fluorophore. One example of such a system is a molecular beacon. Suitable quencher/fluorophore systems are known in the art. The label may be bound through a variety of intermediate linkages. For example, a polynucleotide may comprise a biotin-binding species, and an optically detectable label may be conjugated to biotin and then bound to the labeled polynucleotide. Similarly, a polynucleotide sensor may comprise an immunological species such as an antibody or fragment, and a secondary antibody containing an optically detectable label may be added.

Chromophores useful in the methods described herein include any substance which can absorb energy and emit light. For multiplexed assays, a plurality of different signaling chromophores can be used with detectably different emission spectra. The chromophore can be a lumophore or a fluorophore. Typical fluorophores include fluorescent dyes, semiconductor nanocrystals, lanthanide chelates, polynucleotide-specific dyes and green fluorescent protein.

Coding schemes may optionally be used, comprising encoded particles and/or encoded tags associated with different polynucleotides of the invention. A variety of different coding schemes are known in the art, including fluorophores, including SCNCs, deposited metals, and RF tags.

Polynucleotides from the described target sequences may be employed as probes for detecting target sequences expression, for ligation amplification schemes, or may be used as primers for amplification schemes of all or a portion of a target sequences. When amplified, either strand produced by amplification may be provided in purified and/or isolated form.

In one embodiment, polynucleotides of the invention include (a) a nucleic acid depicted in Table 6; (b) an RNA form of any one of the nucleic acids depicted in Table 6; (c) a peptide nucleic acid form of any of the nucleic acids depicted in Table 6; (d) a nucleic acid comprising at least 20 consecutive bases of any of (a-c); (e) a nucleic acid comprising at least 25 bases having at least 90% sequenced identity to any of (a-c); and (f) a complement to any of (a-e).

Complements may take any polymeric form capable of base pairing to the species recited in (a)-(e), including nucleic acid such as RNA or DNA, or may be a neutral polymer such as a peptide nucleic acid. Polynucleotides of the invention can be selected from the subsets of the recited nucleic acids described herein, as well as their complements.

In some embodiments, polynucleotides of the invention comprise at least 20 consecutive bases of the nucleic acids as depicted in Table 6 or a complement thereto. The polynucleotides may comprise at least 21, 22, 23, 24, 25, 27, 30, 32, 35 or more consecutive bases of the nucleic acid sequences as depicted in Table 6, as applicable.

The polynucleotides may be provided in a variety of formats, including as solids, in solution, or in an array. The polynucleotides may optionally comprise one or more labels, which may be chemically and/or enzymatically incorporated into the polynucleotide.

In one embodiment, solutions comprising polynucleotide and a solvent are also provided. In some embodiments, the solvent may be water or may be predominantly aqueous. In some embodiments, the solution may comprise at least two, three, four, five, six, seven, eight, nine, ten, twelve, fifteen, seventeen, twenty or more different polynucleotides, including primers and primer pairs, of the invention. Additional substances may be included in the solution, alone or in combination, including one or more labels, additional solvents, buffers, biomolecules, polynucleotides, and one or more enzymes useful for performing methods described herein, including polymerases and ligases. The solution may further comprise a primer or primer pair capable of amplifying a polynucleotide of the invention present in the solution.

In some embodiments, one or more polynucleotides provided herein can be provided on a substrate. The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonates, or combinations thereof. Conducting polymers and photoconductive materials can be used.

Substrates can be planar crystalline substrates such as silica based substrates (e.g. glass, quartz, or the like), or crystalline substrates used in, e.g., the semiconductor and microprocessor industries, such as silicon, gallium arsenide, indium doped GaN and the like, and include semiconductor nanocrystals.

The substrate can take the form of an array, a photodiode, an optoelectronic sensor such as an optoelectronic semiconductor chip or optoelectronic thin-film semiconductor, or a biochip. The location(s) of probe(s) on the substrate can be addressable; this can be done in highly dense formats, and the location(s) can be microaddressable or nanoaddressable.

Silica aerogels can also be used as substrates, and can be prepared by methods known in the art. Aerogel substrates may be used as free standing substrates or as a surface coating for another substrate material.

The substrate can take any form and typically is a plate, slide, bead, pellet, disk, particle, microparticle, nanoparticle, strand, precipitate, optionally porous gel, sheets, tube, sphere, container, capillary, pad, slice, film, chip, multiwell plate or dish, optical fiber, etc. The substrate can be any form that is rigid or semi-rigid. The substrate may contain raised or depressed regions on which an assay component is located. The surface of the substrate can be etched using known techniques to provide for desired surface features, for example trenches, v-grooves, mesa structures, or the like.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials. The surface can be optically transparent and can have surface Si—OH functionalities, such as those found on silica surfaces.

The substrate and/or its optional surface can be chosen to provide appropriate characteristics for the synthetic and/or detection methods used. The substrate and/or surface can be transparent to allow the exposure of the substrate by light applied from multiple directions. The substrate and/or surface may be provided with reflective "mirror" structures to increase the recovery of light.

The substrate and/or its surface is generally resistant to, or is treated to resist, the conditions to which it is to be exposed in use, and can be optionally treated to remove any resistant material after exposure to such conditions.

The substrate or a region thereof may be encoded so that the identity of the sensor located in the substrate or region being queried may be determined. Any suitable coding scheme can be used, for example optical codes, RFID tags, magnetic codes, physical codes, fluorescent codes, and combinations of codes.

Preparation of Probes and Primers

The polynucleotide probes or primers of the present invention can be prepared by conventional techniques well-known to those skilled in the art. For example, the polynucleotide probes can be prepared using solid-phase synthesis using commercially available equipment. As is well-known in the art, modified oligonucleotides can also be readily prepared by similar methods. The polynucleotide probes can also be synthesized directly on a solid support according to methods standard in the art. This method of synthesizing polynucleotides is particularly useful when the polynucleotide probes are part of a nucleic acid array.

Polynucleotide probes or primers can be fabricated on or attached to the substrate by any suitable method, for example the methods described in U.S. Pat. No. 5,143,854, PCT Publ. No. WO 92/10092, U.S. patent application Ser. No. 07/624,120, filed Dec. 6, 1990 (now abandoned), Fodor et al., Science, 251: 767-777 (1991), and PCT Publ. No. WO 90/15070). Techniques for the synthesis of these arrays using mechanical synthesis strategies are described in, e.g., PCT Publication No. WO 93/09668 and U.S. Pat. No. 5,384,261. Still further techniques include bead based techniques such as those described in PCT Appl. No. PCT/US93/04145 and pin based methods such as those described in U.S. Pat. No. 5,288,514. Additional flow channel or spotting methods applicable to attachment of sensor polynucleotides to a substrate are described in U.S. patent application Ser. No. 07/980,523, filed Nov. 20, 1992, and U.S. Pat. No. 5,384,261.

Alternatively, the polynucleotide probes of the present invention can be prepared by enzymatic digestion of the naturally occurring target gene, or mRNA or cDNA derived therefrom, by methods known in the art.

Diagnostic Samples

Diagnostic samples for use with the systems and in the methods of the present invention comprise nucleic acids suitable for providing RNA expression information. In principle, the biological sample from which the expressed RNA is obtained and analyzed for target sequence expression can be any material suspected of comprising cancer tissue or cells. The diagnostic sample can be a biological sample used directly in a method of the invention. Alternatively, the diagnostic sample can be a sample prepared from a biological sample.

In one embodiment, the sample or portion of the sample comprising or suspected of comprising cancer tissue or cells can be any source of biological material, including cells, tissue, secretions, or fluid, including bodily fluids. Non-limiting examples of the source of the sample include an aspirate, a needle biopsy, a cytology pellet, a bulk tissue preparation or a section thereof obtained for example by surgery or autopsy, lymph fluid, blood, plasma, serum, tumors, and organs. Alternatively, or additionally, the source of the sample can be urine, bile, excrement, sweat, tears, vaginal fluids, spinal fluid, and stool. In some instances, the sources of the sample are secretions. In some instances, the secretions are exosomes.

The samples may be archival samples, having a known and documented medical outcome, or may be samples from current patients whose ultimate medical outcome is not yet known.

In some embodiments, the sample may be dissected prior to molecular analysis. The sample may be prepared via macrodissection of a bulk tumor specimen or portion thereof, or may be treated via microdissection, for example via Laser Capture Microdissection (LCM).

The sample may initially be provided in a variety of states, as fresh tissue, fresh frozen tissue, fine needle aspirates, and may be fixed or unfixed. Frequently, medical laboratories routinely prepare medical samples in a fixed state, which facilitates tissue storage. A variety of fixatives can be used to fix tissue to stabilize the morphology of cells, and may be used alone or in combination with other agents. Exemplary fixatives include crosslinking agents, alcohols, acetone, Bouin's solution, Zenker solution, Hely solution, osmic acid solution and Carnoy solution.

Crosslinking fixatives can comprise any agent suitable for forming two or more covalent bonds, for example, an aldehyde. Sources of aldehydes typically used for fixation include formaldehyde, paraformaldehyde, glutaraldehyde or formalin. Preferably, the crosslinking agent comprises formaldehyde, which may be included in its native form or in the form of paraformaldehyde or formalin. One of skill in the art would appreciate that for samples in which crosslinking fixatives have been used special preparatory steps may be necessary including for example heating steps and proteinase-k digestion; see methods.

One or more alcohols may be used to fix tissue, alone or in combination with other fixatives. Exemplary alcohols used for fixation include methanol, ethanol and isopropanol.

Formalin fixation is frequently used in medical laboratories. Formalin comprises both an alcohol, typically methanol, and formaldehyde, both of which can act to fix a biological sample.

Whether fixed or unfixed, the biological sample may optionally be embedded in an embedding medium. Exemplary embedding media used in histology including paraffin, Tissue-Tek® V.I.P.™, Paramat, Paramat Extra, Paraplast, Paraplast X-tra, Paraplast Plus, Peel Away Paraffin Embedding Wax, Polyester Wax, Carbowax Polyethylene Glycol, Polyfin™, Tissue Freezing Medium TFMFM, Cryo-Gef™, and OCT Compound (Electron Microscopy Sciences, Hatfield, Pa.). Prior to molecular analysis, the embedding material may be removed via any suitable techniques, as known in the art. For example, where the sample is embedded in wax, the embedding material may be removed by extraction with organic solvent(s), for example xylenes. Kits are commercially available for removing embedding media from tissues. Samples or sections thereof may be subjected to further processing steps as needed, for example serial hydration or dehydration steps.

In some embodiments, the sample is a fixed, wax-embedded biological sample. Frequently, samples from medical laboratories are provided as fixed, wax-embedded samples, most commonly as formalin-fixed, paraffin embedded (FFPE) tissues.

Whatever the source of the biological sample, the target polynucleotide that is ultimately assayed can be prepared synthetically (in the case of control sequences), but typically is purified from the biological source and subjected to one or more preparative steps. The RNA may be purified to remove or diminish one or more undesired components from the biological sample or to concentrate it. Conversely, where the RNA is too concentrated for the particular assay, it may be diluted.

RNA Extraction

RNA can be extracted and purified from biological samples using any suitable technique. A number of techniques are known in the art, and several are commercially available (e.g., FormaPure nucleic acid extraction kit, Agencourt Biosciences, Beverly Mass., High Pure FFPE RNA Micro Kit, Roche Applied Science, Indianapolis, Ind.). RNA can be extracted from frozen tissue sections using TRIzol (Invitrogen, Carlsbad, Calif.) and purified using RNeasy Protect kit (Qiagen, Valencia, Calif.). RNA can be further purified using DNAse I treatment (Ambion, Austin, Tex.) to eliminate any contaminating DNA. RNA concentrations can be made using a Nanodrop ND-1000 spectrophotometer (Nanodrop Technologies, Rockland, Del.). RNA can be further purified to eliminate contaminants that interfere with cDNA synthesis by cold sodium acetate precipitation. RNA integrity can be evaluated by running electropherograms, and RNA integrity number (RIN, a correlative measure that indicates intactness of mRNA) can be determined using the RNA 6000 PicoAssay for the Bioanalyzer 2100 (Agilent Technologies, Santa Clara, Calif.).

Kits

Kits for performing the desired method(s) are also provided, and comprise a container or housing for holding the components of the kit, one or more vessels containing one or more nucleic acid(s), and optionally one or more vessels containing one or more reagents. The reagents include those described in the composition of matter section above, and those reagents useful for performing the methods described, including amplification reagents, and may include one or more probes, primers or primer pairs, enzymes (including polymerases and ligases), intercalating dyes, labeled probes, and labels that can be incorporated into amplification products.

In some embodiments, the kit comprises primers or primer pairs specific for those subsets and combinations of target sequences described herein. At least two, three, four or five primers or pairs of primers suitable for selectively amplifying the same number of target sequence-specific polynucleotides can be provided in kit form. In some embodiments, the kit comprises from five to fifty primers or pairs of primers suitable for amplifying the same number of target sequence-representative polynucleotides of interest.

In some embodiments, the primers or primer pairs of the kit, when used in an amplification reaction, specifically amplify a non-coding target, coding target, or non-exonic target described herein, at least a portion of a nucleic acid depicted in one of SEQ ID NOs.: 1-903, an RNA form thereof, or a complement to either thereof. The kit may include a plurality of such primers or primer pairs which can specifically amplify a corresponding plurality of different amplify a non-coding target, coding target, or non-exonic transcript described herein, nucleic acids depicted in one of SEQ ID NOs.: 1-903, RNA forms thereof, or complements thereto. At least two, three, four or five primers or pairs of primers suitable for selectively amplifying the same number of target sequence-specific polynucleotides can be provided in kit form. In some embodiments, the kit comprises from five to fifty primers or pairs of primers suitable for amplifying the same number of target sequence-representative polynucleotides of interest.

The reagents may independently be in liquid or solid form. The reagents may be provided in mixtures. Control samples and/or nucleic acids may optionally be provided in the kit. Control samples may include tissue and/or nucleic acids obtained from or representative of tumor samples from patients showing no evidence of disease, as well as tissue and/or nucleic acids obtained from or representative of tumor samples from patients that develop systemic cancer.

The nucleic acids may be provided in an array format, and thus an array or microarray may be included in the kit. The kit optionally may be certified by a government agency for use in prognosing the disease outcome of cancer patients and/or for designating a treatment modality.

Instructions for using the kit to perform one or more methods of the invention can be provided with the container, and can be provided in any fixed medium. The instructions may be located inside or outside the container or housing, and/or may be printed on the interior or exterior of any surface thereof. A kit may be in multiplex form for concurrently detecting and/or quantitating one or more different target polynucleotides representing the expressed target sequences.

Devices

Devices useful for performing methods of the invention are also provided. The devices can comprise means for characterizing the expression level of a target sequence of the invention, for example components for performing one or more methods of nucleic acid extraction, amplification, and/or detection. Such components may include one or more of an amplification chamber (for example a thermal cycler), a plate reader, a spectrophotometer, capillary electrophoresis apparatus, a chip reader, and or robotic sample handling components. These components ultimately can obtain data that reflects the expression level of the target sequences used in the assay being employed.

The devices may include an excitation and/or a detection means. Any instrument that provides a wavelength that can excite a species of interest and is shorter than the emission wavelength(s) to be detected can be used for excitation. Commercially available devices can provide suitable excitation wavelengths as well as suitable detection component.

Exemplary excitation sources include a broadband UV light source such as a deuterium lamp with an appropriate filter, the output of a white light source such as a xenon lamp or a deuterium lamp after passing through a monochromator to extract out the desired wavelength(s), a continuous wave (cw) gas laser, a solid state diode laser, or any of the pulsed lasers. Emitted light can be detected through any suitable device or technique; many suitable approaches are known in the art. For example, a fluorimeter or spectrophotometer may be used to detect whether the test sample emits light of a wavelength characteristic of a label used in an assay.

The devices typically comprise a means for identifying a given sample, and of linking the results obtained to that sample. Such means can include manual labels, barcodes, and other indicators which can be linked to a sample vessel, and/or may optionally be included in the sample itself, for example where an encoded particle is added to the sample. The results may be linked to the sample, for example in a computer memory that contains a sample designation and a record of expression levels obtained from the sample. Linkage of the results to the sample can also include a linkage to a particular sample receptacle in the device, which is also linked to the sample identity.

The devices also comprise a means for correlating the expression levels of the target sequences being studied with a prognosis of disease outcome. Such means may comprise one or more of a variety of correlative techniques, including lookup tables, algorithms, multivariate models, and linear or nonlinear combinations of expression models or algorithms. The expression levels may be converted to one or more likelihood scores, reflecting a likelihood that the patient providing the sample may exhibit a particular disease outcome. The models and/or algorithms can be provided in machine readable format and can optionally further designate a treatment modality for a patient or class of patients.

The device also comprises output means for outputting the disease status, prognosis and/or a treatment modality. Such output means can take any form which transmits the results to a patient and/or a healthcare provider, and may include a monitor, a printed format, or both. The device may use a computer system for performing one or more of the steps provided.

The methods disclosed herein may also comprise the transmission of data/information. For example, data/information derived from the detection and/or quantification of the target may be transmitted to another device and/or instrument. In some instances, the information obtained from an algorithm may also be transmitted to another device and/or instrument. Transmission of the data/information may comprise the transfer of data/information from a first source to a second source. The first and second sources may be in the same approximate location (e.g., within the same room, building, block, campus). Alternatively, first and second sources may be in multiple locations (e.g., multiple cities, states, countries, continents, etc).

Transmission of the data/information may comprise digital transmission or analog transmission. Digital transmission may comprise the physical transfer of data (a digital bit stream) over a point-to-point or point-to-multipoint communication channel. Examples of such channels are copper wires, optical fibres, wireless communication channels, and storage media. The data may be represented as an electromagnetic signal, such as an electrical voltage, radiowave, microwave, or infrared signal.

Analog transmission may comprise the transfer of a continuously varying analog signal. The messages can either be represented by a sequence of pulses by means of a line code (baseband transmission), or by a limited set of continuously varying wave forms (passband transmission), using a digital modulation method. The passband modulation and corresponding demodulation (also known as detection) can be carried out by modem equipment. According to the most common definition of digital signal, both baseband and passband signals representing bit-streams are considered as digital transmission, while an alternative definition only considers the baseband signal as digital, and passband transmission of digital data as a form of digital-to-analog conversion.

Amplification and Hybridization

Following sample collection and nucleic acid extraction, the nucleic acid portion of the sample comprising RNA that is or can be used to prepare the target polynucleotide(s) of interest can be subjected to one or more preparative reactions. These preparative reactions can include in vitro transcription (IVT), labeling, fragmentation, amplification and other reactions. mRNA can first be treated with reverse transcriptase and a primer to create cDNA prior to detection, quantitation and/or amplification; this can be done in vitro with purified mRNA or in situ, e.g., in cells or tissues affixed to a slide.

By "amplification" is meant any process of producing at least one copy of a nucleic acid, in this case an expressed RNA, and in many cases produces multiple copies. An amplification product can be RNA or DNA, and may include a complementary strand to the expressed target sequence. DNA amplification products can be produced initially through reverse translation and then optionally from further amplification reactions. The amplification product may include all or a portion of a target sequence, and may optionally be labeled. A variety of amplification methods are suitable for use, including polymerase-based methods and ligation-based methods. Exemplary amplification techniques include the polymerase chain reaction method (PCR), the lipase chain reaction (LCR), ribozyme-based methods, self sustained sequence replication (3SR), nucleic acid sequence-based amplification (NASBA), the use of Q Beta replicase, reverse transcription, nick translation, and the like.

Asymmetric amplification reactions may be used to preferentially amplify one strand representing the target sequence that is used for detection as the target polynucleotide. In some cases, the presence and/or amount of the amplification product itself may be used to determine the expression level of a given target sequence. In other instances, the amplification product may be used to hybridize to an array or other substrate comprising sensor polynucleotides which are used to detect and/or quantitate target sequence expression.

The first cycle of amplification in polymerase-based methods typically forms a primer extension product complementary to the template strand. If the template is single-stranded RNA, a polymerase with reverse transcriptase activity is used in the first amplification to reverse transcribe the RNA to DNA, and additional amplification cycles can be performed to copy the primer extension products. The primers for a PCR must, of course, be designed to hybridize to regions in their corresponding template that can produce an amplifiable segment; thus, each primer must hybridize so that its 3' nucleotide is paired to a nucleotide in its complementary template strand that is located 3' from the 3' nucleotide of the primer used to replicate that complementary template strand in the PCR.

The target polynucleotide can be amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity that can copy the target polynucleotide can be used, including DNA polymerases, RNA polymerases, reverse transcriptases, enzymes having more than one type of polymerase or enzyme activity. The enzyme can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase® T7, Sequenase® Version 2.0 T7, Tub, Taq, Tth, Pfic, Pfu, Tsp, Tfl, Tli and *Pyrococcus* sp GB-D DNA polymerases; RNA polymerases such as *E. coli*, SP6, T3 and T7 RNA polymerases; and reverse transcriptases such as AMV, M-MuLV, MMLV, RNAse H MMLV (SuperScript®), SuperScript® II, ThermoScript®, HIV-1, and RAV2 reverse transcriptases. All of these enzymes are commercially available. Exemplary polymerases with multiple specificities include RAV2 and Tli (exo-) polymerases. Exemplary thermostable polymerases include Tub, Taq, Tth, Pfic, Pfu, Tsp, Tfl, Tli and *Pyrococcus* sp. GB-D DNA polymerases.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions (e.g., manganese), optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used, for example centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different target polynucleotides or different regions of a particular target polynucleotide within the sample.

An amplification reaction can be performed under conditions which allow an optionally labeled sensor polynucleotide to hybridize to the amplification product during at least part of an amplification cycle. When the assay is performed in this manner, real-time detection of this hybridization event can take place by monitoring for light emission or fluorescence during amplification, as known in the art.

Where the amplification product is to be used for hybridization to an array or microarray, a number of suitable commercially available amplification products are available. These include amplification kits available from NuGEN, Inc. (San Carlos, Calif.), including the WTA-Ovation™ System, WT-Ovation™ System v2, WT-Ovation™ Pico System, WT-Ovation™ FFPE Exon Module, WT-Ovation™ FFPE Exon Module RiboAmp and RiboAmp$^{Plus}$ RNA Amplification Kits (MDS Analytical Technologies (formerly Arcturus) (Mountain View, Calif.), Genisphere, Inc. (Hatfield, Pa.), including the RampUp Plus™ and SenseAmp™ RNA Amplification kits, alone or in combination. Amplified nucleic acids may be subjected to one or more purification reactions after amplification and labeling, for example using magnetic beads (e.g., RNAClean magnetic beads, Agencourt Biosciences).

Multiple RNA biomarkers (e.g., RNA targets) can be analyzed using real-time quantitative multiplex RT-PCR platforms and other multiplexing technologies such as GenomeLab GeXP Genetic Analysis System (Beckman Coulter, Foster City, Calif.), SmartCycler® 9600 or GeneXpert® Systems (Cepheid, Sunnyvale, Calif.), ABI 7900 HT Fast Real Time PCR system (Applied Biosystems, Foster City, Calif.), LightCycler® 480 System (Roche Molecular Systems, Pleasanton, Calif.), xMAP 100 System (Luminex, Austin, Tex.) Solexa Genome Analysis System (Illumina, Hayward, Calif.), OpenArray Real Time qPCR (BioTrove, Woburn, Mass.) and BeadXpress System (Illumina, Hayward, Calif.). Alternatively, or additional, coding targets and/or non-coding targets can be analyzed using RNA-Seq. In some instances, coding and/or non-coding targets are analyzed by sequencing.

Detection and/or Quantification of Target Sequences

Any method of detecting and/or quantitating the expression of the encoded target sequences can in principle be used in the invention. The expressed target sequences can be directly detected and/or quantitated, or may be copied and/or amplified to allow detection of amplified copies of the expressed target sequences or its complement.

Methods for detecting and/or quantifying a target can include Northern blotting, sequencing, array or microarray hybridization, by enzymatic cleavage of specific structures (e.g., an Invader® assay, Third Wave Technologies, e.g. as described in U.S. Pat. Nos. 5,846,717, 6,090,543; 6,001,567; 5,985,557; and 5,994,069) and amplification methods (e.g. RT-PCR, including in a TaqMan® assay (PE Biosystems, Foster City, Calif., e.g. as described in U.S. Pat. Nos. 5,962,233 and 5,538,848)), and may be quantitative or semi-quantitative, and may vary depending on the origin, amount and condition of the available biological sample. Combinations of these methods may also be used. For example, nucleic acids may be amplified, labeled and subjected to microarray analysis.

In some instances, assaying the expression level of a plurality of targets comprises amplifying the plurality of targets. Amplifying the plurality of targets can comprise PCR, RT-PCR, qPCR, digital PCR, and nested PCR.

In some instances, the target sequences are detected by sequencing. Sequencing methods may comprise whole genome sequencing or exome sequencing. Sequencing methods such as Maxim-Gilbert, chain-termination, or high-throughput systems may also be used. Additional, suitable sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, shotgun sequencing and SOLiD sequencing.

Additional methods for detecting and/or quantifying a target sequence can comprise single-molecule sequencing (e.g., Illumina, Helicos, PacBio, ABI SOLID), in situ hybridization, bead-array technologies (e.g., Luminex xMAP, Illumina BeadChips), branched DNA technology (e.g., Panomics, Genisphere), and Ion Torrent™.

In some instances, methods for detecting and/or quantifying a target sequence comprise transcriptome sequencing techniques. Transcription sequencing (e.g., RNA-seq, "Whole Transcriptome Shotgun Sequencing" ("WTSS")) may comprise the use of high-throughput sequencing technologies to sequence cDNA in order to get information about a sample's RNA content. Transcriptome sequencing can provide information on differential expression of genes, including gene alleles and differently spliced transcripts, non-coding RNAs, post-transcriptional mutations or editing, and gene fusions. Transcriptomes can also be sequenced by methods comprising Sanger sequencing, Serial analysis of gene expression (SAGE), cap analysis gene expression (CAGE), and massively parallel signature sequencing (MPSS). In some instances, transcriptome sequencing can comprise a variety of platforms. A non-limiting list of exemplary platforms include an Illumina Genome Analyzer platform, ABI Solid Sequencing, and Life Science's 454 Sequencing.

Reverse Transcription for ORT-PCR Analysis

Reverse transcription can be performed by any method known in the art. For example, reverse transcription may be performed using the Omniscript kit (Qiagen, Valencia, Calif.), Superscript III kit (Invitrogen, Carlsbad, Calif.), for RT-PCR. Target-specific priming can be performed in order to increase the sensitivity of detection of target sequences and generate target-specific cDNA.

TaqMan® Gene Expression Analysis

TaqMan®RT-PCR can be performed using Applied Biosystems Prism (ABI) 7900 HT instruments in a 5 1.11 volume with target sequence-specific cDNA equivalent to 1 ng total RNA.

Primers and probes concentrations for TaqMan analysis are added to amplify fluorescent amplicons using PCR cycling conditions such as 95° C. for 10 minutes for one cycle, 95° C. for 20 seconds, and 60° C. for 45 seconds for 40 cycles. A reference sample can be assayed to ensure reagent and process stability. Negative controls (e.g., no template) should be assayed to monitor any exogenous nucleic acid contamination.

Classification Arrays

The present invention contemplates that a classifier, ICE block, PSR, probe set or probes derived therefrom may be provided in an array format. In the context of the present invention, an "array" is a spatially or logically organized collection of polynucleotide probes. An array comprising probes specific for a coding target, non-coding target, or a combination thereof may be used. Alternatively, an array comprising probes specific for two or more of transcripts listed in Table 6 or a product derived thereof can be used. Desirably, an array may be specific for at least about 5, 10, 15, 20, 25, 30, 50, 75, 100, 150, 200 or more of transcripts listed in Table 6. The array can be specific for at least about 250, 300, 350, 400 or more transcripts listed in Table 6. Expression of these sequences may be detected alone or in combination with other transcripts. In some embodiments, an array is used which comprises a wide range of sensor probes for prostate-specific expression products, along with appropriate control sequences. In some instances, the array may comprise the Human Exon 1.0 ST Array (HuEx 1.0 ST, Affymetrix, Inc., Santa Clara, Calif.).

Typically the polynucleotide probes are attached to a solid substrate and are ordered so that the location (on the substrate) and the identity of each are known. The polynucleotide probes can be attached to one of a variety of solid substrates capable of withstanding the reagents and conditions necessary for use of the array. Examples include, but are not limited to, polymers, such as (poly)tetrafluoroethylene, (poly)vinylidenedifluoride, polystyrene, polycarbonate, polypropylene and polystyrene; ceramic; silicon; silicon dioxide; modified silicon; (fused) silica, quartz or glass; functionalized glass; paper, such as filter paper; diazotized cellulose; nitrocellulose filter; nylon membrane; and polyacrylamide gel pad. Substrates that are transparent to light are useful for arrays that may be used in an assay that involves optical detection.

Examples of array formats include membrane or filter arrays (for example, nitrocellulose, nylon arrays), plate arrays (for example, multiwell, such as a 24-, 96-, 256-, 384-, 864- or 1536-well, microtitre plate arrays), pin arrays, and bead arrays (for example, in a liquid "slurry"). Arrays on substrates such as glass or ceramic slides are often referred to as chip arrays or "chips." Such arrays are well known in the art. In one embodiment of the present invention, the Cancer Prognosticarray is a chip.

Annotation of Probe Selection Regions

In some instances, the methods disclosed herein comprise the annotation of one or more probe selection regions (PSRs). In some instances, the PSRs disclosed are annotated into categories (e.g., coding, non-coding). Annotation of the PSRs can utilize a variety of software packages. In some instances, annotation of the PSRs comprises the use of the xmapcore package (Yates et al 2010), which is the human genome version hg19, and Ensembl gene annotation v62, which can be integrated with the xmapcore packages. In some instances, the method for annotating a PSR comprises (a) annotating a PSR as Non_Coding (intronic), wherein the PSR is returned by the intronic( ) function; and/or (b) further analyzing a PSR, wherein the PSR is returned by the exonic( ) function. Further analysis of the PSR can comprise (a) annotating the PSR as Coding, wherein the PSR is returned by the coding.probesets( ) function; (b) annotating the PSR as Non_Coding (UTR), wherein the PSR is returned by the utr.probestes( ) function; and/or (c) annotating the PSR as Non_Coding (ncTRANSCRIPT), wherein the PSR is not annotated as Coding or NON_Coding (UTR). PSRs that are not annotated as Non_Coding (intronic), Non_Coding (UTR), Non_Coding (ncTRANSCRIPT), or Coding can be referred to as the remaining PSRs.

The methods disclosed herein can further comprise detailed annotation of the remaining PSRs. Detailed annotation of the remaining PSRs can comprise determining the chromosome, start position, end position, and strand for each remaining PSR. Detailed annotation of the remaining PSRs can comprise utilization of the probeset.to.hit( ) function. In some instances, the remaining PSRs can be further annotated. Further annotation of the remaining PSRs can comprise inspection of a genomic span of each remaining PSR for the presence of genes, exons and protein-coding sequences. Often, the opposite strand of the PSR is used in the inspection of the genomic span. In some instances, inspection of the genomic span can comprise the use of one or more computer functions. In some instances, the computer functions are a genes.in.range( ) function, exons.in.range( ) function, and/or proteins.in.range( ) function (respectively). The remaining PSRs can be annotated as (a) Non_Coding (CDS_Antisense), wherein a protein is returned for the proteins.in.range( ) function; (b) Non_Coding (UTR_Antisense), wherein (i) a protein is not returned for the proteins.in.range( ) function, and (ii) the overlapping feature of the gene in the opposite strand is a UTR; (c) Non_Coding (ncTRANSCRIPT_Antisense), wherein (i) a protein is not returned for the proteins.in.range( ) function, and (ii) the overlapping feature of the gene in the opposite strand is not a UTR; (d) Non_Coding (Intronic_Antisense), wherein (i) a gene is returned for the genes.in.range( ) function, (ii) an exon is not returned for the exons.in.range( ), and (iii) a protein is not returned for the proteins.in.range( ) function; and (e) Non_Coding (Intergenic), wherein the remaining PSR does not overlap with any coding or non-coding gene feature in the sense or antisense strand.

In some instances, the methods disclosed herein further comprise additional annotation of a PSR with respect to transcripts and genes. Additional annotation of the PSR can comprise the use of the probeset.to.transcript( ) and/or probeset.to.gene( ) functions. In some instances, PSRs are annotated as Non_Coding (Non_Unique), wherein the PSR is obtained using the unreliable( ) function from xmapcore. In some instances, a PSR is annotated as Non_Coding (Intergenic) when the PSR maps to more than one region.

Data Analysis

In some embodiments, one or more pattern recognition methods can be used in analyzing the expression level of target sequences. The pattern recognition method can comprise a linear combination of expression levels, or a nonlinear combination of expression levels. In some embodiments, expression measurements for RNA transcripts or combinations of RNA transcript levels are formulated into linear or non-linear models or algorithms (e.g., an 'expression signature') and converted into a likelihood score. This likelihood score can indicate the probability that a biological sample is from a patient who may exhibit no evidence of disease, who may exhibit local disease, who may exhibit systemic cancer, or who may exhibit biochemical recurrence. The likelihood score can be used to distinguish these disease states. The models and/or algorithms can be provided in machine readable format, and may be used to correlate expression levels or an expression profile with a disease state, and/or to designate a treatment modality for a patient or class of patients.

Assaying the expression level for a plurality of targets may comprise the use of an algorithm or classifier. Array data can be managed, classified, and analyzed using techniques known in the art. Assaying the expression level for a plurality of targets may comprise probe set modeling and data pre-processing. Probe set modeling and data pre-processing can be derived using the Robust Multi-Array (RMA) algorithm or variants GC-RMA, fRMA, Probe Logarithmic Intensity Error (PLIER) algorithm or variant iterPLIER. Variance or intensity filters can be applied to pre-process data using the RMA algorithm, for example by removing target sequences with a standard deviation of <10 or a mean intensity of <100 intensity units of a normalized data range, respectively.

Alternatively, assaying the expression level for a plurality of targets may comprise the use of a machine learning algorithm. The machine learning algorithm may comprise a supervised learning algorithm. Examples of supervised learning algorithms may include Average One-Dependence Estimators (AODE), Artificial neural network (e.g., Back-propagation), Bayesian statistics (e.g., Naive Bayes classifier, Bayesian network, Bayesian knowledge base), Case-based reasoning, Decision trees, Inductive logic programming, Gaussian process regression, Group method of data handling (GMDH), Learning Automata, Learning Vector Quantization, Minimum message length (decision trees, decision graphs, etc.), Lazy learning, Instance-based learning Nearest Neighbor Algorithm, Analogical modeling, Probably approximately correct learning (PAC) learning, Ripple down rules, a knowledge acquisition methodology, Symbolic machine learning algorithms, Subsymbolic machine learning algorithms, Support vector machines, Random Forests, Ensembles of classifiers, Bootstrap aggregating (bagging), and Boosting. Supervised learning may comprise ordinal classification such as regression analysis and Information fuzzy networks (IFN). Alternatively, supervised learning methods may comprise statistical classification, such as AODE, Linear classifiers (e.g., Fisher's linear discriminant, Logistic regression, Naive Bayes classifier, Perceptron, and Support vector machine), quadratic classifiers, k-nearest neighbor, Boosting, Decision trees (e.g., C4.5, Random forests), Bayesian networks, and Hidden Markov models.

The machine learning algorithms may also comprise an unsupervised learning algorithm. Examples of unsupervised learning algorithms may include Artificial neural network, Data clustering, Expectation-maximization algorithm, Self-organizing map, Radial basis function network, Vector Quantization, Generative topographic map, Information bottleneck method, and IBSEAD. Unsupervised learning may also comprise association rule learning algorithms such as Apriori algorithm, Eclat algorithm and FP-growth algorithm. Hierarchical clustering, such as Single-linkage clustering and Conceptual clustering, may also be used. Alternatively, unsupervised learning may comprise partitional clustering such as K-means algorithm and Fuzzy clustering.

In some instances, the machine learning algorithms comprise a reinforcement learning algorithm. Examples of reinforcement learning algorithms include, but are not limited to, Temporal difference learning, Q-learning and Learning Automata. Alternatively, the machine learning algorithm may comprise Data Pre-processing.

Preferably, the machine learning algorithms may include, but are not limited to, Average One-Dependence Estimators (AODE), Fisher's linear discriminant, Logistic regression, Perceptron, Multilayer Perceptron, Artificial Neural Networks, Support vector machines, Quadratic classifiers, Boosting, Decision trees, C4.5, Bayesian networks, Hidden Markov models, High-Dimensional Discriminant Analysis, and Gaussian Mixture Models. The machine learning algorithm may comprise support vector machines, Naïve Bayes classifier, k-nearest neighbor, high-dimensional discriminant analysis, or Gaussian mixture models. In some instances, the machine learning algorithm comprises Random Forests.

The methods, systems, devices, and kits disclosed herein can further comprise a computer, an electronic device, computer software, a memory device, or any combination thereof. In some instances, the methods, systems, devices, and kits disclosed herein further comprise one or more computer software programs for (a) analysis of the target (e.g., expression profile, detection, quantification); (b) diagnosis, prognosis and/or monitoring the outcome or status of a cancer in a subject; (c) determination of a treatment regimen; (d) analysis of a classifier, probe set, probe selection region, ICE block, or digital Gleason score predictor as disclosed herein. Analysis of a classifier, probe set, probe selection region, ICE block or digital Gleason score predictor can comprise determining the AUC value, MDF value, percent accuracy, P-value, clinical significance, or any combination thereof. The software program can comprise (a) bigmemory, which can be used to load large expression matrices; (b) matrixStats, which can be used in statistics on matrices like row medians, column medians, row ranges; (c) genefilter, which can be used as a fast calculation of t-tests, ROC, and AUC; (d) pROC, which can be used to plot ROC curves and calculate AUC's and their 95% confidence intervals; (e) ROCR, which can be used to plot ROC curves and to calculate AUCs; (f) pROCR, which can be used to plot ROC curves and to calculate AUCs; (g) snow or doSMP, which can be used for parallel processing; (h) caret, which can be used for K-Nearest-Neighbour (KNN), Null Model, and classifier analysis; (i) e1071, which can be used for Support Vector Machines (SVM), K-Nearest-Neighbour (KNN), Naive Bayes, classifier tuning, and sample partitioning; (j) randomForest, which can be used for Random forest model; (k) HDClassif, which can be used for HDDA model; (l) rpart, which can be used for recursive partitioning model; (m) rms, which can be used for logistic regression model; (n) survival, which can be used for coxph model, km plots, and other survival analysis; (o) iterator, intertools, foreach, which can be used for iteration of large matrices; (p) frma, which can be used to package for frozen robust microarray analysis; (q) epitools, which can be used for odds ratios; (r) Proxy, which can be used for distance calculations; (s) boot, which can be used for Bootstrapping; (t) glmnet, which can be used to regularize general linear model; (u) gplots, which can be used to generate plots and figures; (v) scatterplot3d, which can be used to generate 3d scatter plots, (w) heatmap.plus, which can be used to generate heatmaps; (x) vegan, which can be used to determine MDS p-values; (y) xlsx, which can be used to work with excel spread sheets; (z) xtable, which can be used to work with R tables to latex; (aa) ffpe, which can be used for Cat plots; and (ab) xmapcore, which can be used for annotation of PSRs with respect to Ensembl annotation. In some instances, the software program is xmapcore. In other instances, the software program is caret. In other instances, the software program is e1071. The software program can be Proxy. Alternatively, the software program is gplots. In some instances, the software program is scatterplot3 d.

Additional Techniques and Tests

Factors known in the art for diagnosing and/or suggesting, selecting, designating, recommending or otherwise determining a course of treatment for a patient or class of patients suspected of having cancer can be employed in combination with measurements of the target sequence expression. The methods disclosed herein may include additional techniques such as cytology, histology, ultrasound analysis, MRI results, CT scan results, and measurements of PSA levels.

Certified tests for classifying disease status and/or designating treatment modalities may also be used in diagnosing, predicting, and/or monitoring the status or outcome of a cancer in a subject. A certified test may comprise a means for characterizing the expression levels of one or more of the target sequences of interest, and a certification from a government regulatory agency endorsing use of the test for classifying the disease status of a biological sample.

In some embodiments, the certified test may comprise reagents for amplification reactions used to detect and/or quantitate expression of the target sequences to be characterized in the test. An array of probe nucleic acids can be used, with or without prior target amplification, for use in measuring target sequence expression.

The test is submitted to an agency having authority to certify the test for use in distinguishing disease status and/or outcome. Results of detection of expression levels of the target sequences used in the test and correlation with disease status and/or outcome are submitted to the agency. A certification authorizing the diagnostic and/or prognostic use of the test is obtained.

Also provided are portfolios of expression levels comprising a plurality of normalized expression levels of the target sequences described Table 6. Such portfolios may be provided by performing the methods described herein to obtain expression levels from an individual patient or from a group of patients. The expression levels can be normalized by any method known in the art; exemplary normalization methods that can be used in various embodiments include Robust Multichip Average (RMA), probe logarithmic intensity error estimation (PLIER), non-linear fit (NLFIT) quantile-based and nonlinear normalization, and combinations thereof. Background correction can also be performed on the expression data; exemplary techniques useful for background correction include mode of intensities, normalized using median polish probe modeling and sketch-normalization.

In some embodiments, portfolios are established such that the combination of genes in the portfolio exhibit improved sensitivity and specificity relative to known methods. In considering a group of genes for inclusion in a portfolio, a small standard deviation in expression measurements correlates with greater specificity. Other measurements of variation such as correlation coefficients can also be used in this capacity. The invention also encompasses the above methods where the expression level determines the status or outcome of a cancer in the subject with at least about 45% specificity. In some embodiments, the expression level determines the status or outcome of a cancer in the subject with at least about 50% specificity. In some embodiments, the expression level determines the status or outcome of a cancer in the subject with at least about 55% specificity. In some embodiments, the expression level determines the status or outcome of a cancer in the subject with at least about 60% specificity. In some embodiments, the expression level determines the status or outcome of a cancer in the subject with at least about 65% specificity. In some embodiments, the expression level determines the status or outcome of a cancer in the subject with at least about 70% specificity. In some embodiments, the expression level determines the status or outcome of a cancer in the subject with at least about 75% specificity. In some embodiments, the expression level determines the status or outcome of a cancer in the subject with at least about 80% specificity. In some embodiments, the expression level determines the status or outcome of a cancer in the subject with at least about 85% specificity. In some embodiments, the expression level determines the status or outcome of a cancer in the subject with at least about 90% specificity. In some embodiments, the expression level determines the status or outcome of a cancer in the subject with at least about 95% specificity.

The invention also encompasses any of the methods disclosed herein where the accuracy of diagnosing, monitoring, and/or predicting a status or outcome of a cancer is at least about 45%. In some embodiments, the accuracy of diagnosing, monitoring, and/or predicting a status or outcome of a cancer is at least about 50%. In some embodiments, the accuracy of diagnosing, monitoring, and/or predicting a status or outcome of a cancer is at least about 55%. In some embodiments, the accuracy of diagnosing, monitoring, and/or predicting a status or outcome of a cancer is at least about 60%. In some embodiments, the accuracy of diagnosing, monitoring, and/or predicting a status or outcome of a cancer is at least about 65%. In some embodiments, the accuracy of diagnosing, monitoring, and/or predicting a status or outcome of a cancer is at least about 70%. In some embodiments, the accuracy of diagnosing, monitoring, and/or predicting a status or outcome of a cancer is at least about 75%. In some embodiments, the accuracy of diagnosing, monitoring, and/or predicting a status or outcome of a cancer is at least about 80%. In some embodiments, the accuracy of diagnosing, monitoring, and/or predicting a status or outcome of a cancer is at least about 85%. In some embodiments, the accuracy of diagnosing, monitoring, and/or predicting a status or outcome of a cancer is at least about 90%. In some embodiments, the accuracy of diagnosing, monitoring, and/or predicting a status or outcome of a cancer is at least about 95%.

The invention also encompasses the any of the methods disclosed herein where the sensitivity is at least about 45%. In some embodiments, the sensitivity is at least about 50%. In some embodiments, the sensitivity is at least about 55%. In some embodiments, the sensitivity is at least about 60%. In some embodiments, the sensitivity is at least about 65%. In some embodiments, the sensitivity is at least about 70%. In some embodiments, the sensitivity is at least about 75%. In some embodiments, the sensitivity is at least about 80%. In some embodiments, the sensitivity is at least about 85%. In some embodiments, the sensitivity is at least about 90%. In some embodiments, the sensitivity is at least about 95%.

In some instances, the methods disclosed herein may comprise the use of a genomic-clinical classifier (GCC) model. A general method for developing a GCC model may comprise (a) providing a sample from a subject suffering from a cancer; (b) assaying the expression level for a plurality of targets; (c) generating a model by using a machine learning algorithm. In some instances, the machine learning algorithm comprises Random Forests.

Cancer

The systems, compositions and methods disclosed herein may be used to diagnosis, monitor and/or predict the status or outcome of a cancer. Generally, a cancer is characterized by the uncontrolled growth of abnormal cells anywhere in a body. The abnormal cells may be termed cancer cells, malignant cells, or tumor cells. Many cancers and the abnormal cells that compose the cancer tissue are further identified by the name of the tissue that the abnormal cells originated from (for example, breast cancer, lung cancer, colon cancer, prostate cancer, pancreatic cancer, thyroid cancer). Cancer is not confined to humans; animals and other living organisms can get cancer.

In some instances, the cancer may be malignant. Alternatively, the cancer may be benign. The cancer may be a recurrent and/or refractory cancer. Most cancers can be classified as a carcinoma, sarcoma, leukemia, lymphoma, myeloma, or a central nervous system cancer.

The cancer may be a sarcoma. Sarcomas are cancers of the bone, cartilage, fat, muscle, blood vessels, or other connective or supportive tissue. Sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g. alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

Alternatively, the cancer may be a carcinoma. Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penic cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some instances, the cancer is a skin cancer, such as a basal cell carcinoma, squamous, melanoma, nonmelanoma, or actinic (solar) keratosis. Preferably, the cancer is a prostate cancer. Alternatively, the cancer may be a thyroid cancer. The cancer can be a pancreatic cancer. In some instances, the cancer is a bladder cancer.

In some instances, the cancer is a lung cancer. Lung cancer can start in the airways that branch off the trachea to supply the lungs (bronchi) or the small air sacs of the lung (the alveoli). Lung cancers include non-small cell lung carcinoma (NSCLC), small cell lung carcinoma, and mesotheliomia. Examples of NSCLC include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

Alternatively, the cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. In some instances, the cancer is a meningioma.

The cancer may be leukemia. The leukemia may be an acute lymphocytic leukemia, acute myelocytic leukemia, chronic lymphocytic leukemia, or chronic myelocytic leukemia. Additional types of leukemias include hairy cell leukemia, chronic myelomonocytic leukemia, and juvenile myelomonocytic-leukemia.

In some instances, the cancer is a lymphoma. Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenström macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

Cancer Staging

Diagnosing, predicting, or monitoring a status or outcome of a cancer may comprise determining the stage of the cancer. Generally, the stage of a cancer is a description (usually numbers I to IV with IV having more progression) of the extent the cancer has spread. The stage often takes into account the size of a tumor, how deeply it has penetrated, whether it has invaded adjacent organs, how many lymph nodes it has metastasized to (if any), and whether it has spread to distant organs. Staging of cancer can be used as a predictor of survival, and cancer treatment may be determined by staging. Determining the stage of the cancer may occur before, during, or after treatment. The stage of the cancer may also be determined at the time of diagnosis.

Cancer staging can be divided into a clinical stage and a pathologic stage. Cancer staging may comprise the TNM classification. Generally, the TNM Classification of Malignant Tumours (TNM) is a cancer staging system that describes the extent of cancer in a patient's body. T may describe the size of the tumor and whether it has invaded nearby tissue, N may describe regional lymph nodes that are involved, and M may describe distant metastasis (spread of cancer from one body part to another). In the TNM (Tumor, Node, Metastasis) system, clinical stage and pathologic stage are denoted by a small "c" or "p" before the stage (e.g., cT3N1M0 or pT2N0).

Often, clinical stage and pathologic stage may differ. Clinical stage may be based on all of the available information obtained before a surgery to remove the tumor. Thus, it may include information about the tumor obtained by physical examination, radiologic examination, and endoscopy. Pathologic stage can add additional information gained by examination of the tumor microscopically by a pathologist. Pathologic staging can allow direct examination of the tumor and its spread, contrasted with clinical staging which may be limited by the fact that the information is obtained by making indirect observations at a tumor which is still in the body. The TNM staging system can be used for most forms of cancer.

Alternatively, staging may comprise Ann Arbor staging. Generally, Ann Arbor staging is the staging system for lymphomas, both in Hodgkin's lymphoma (previously called Hodgkin's disease) and Non-Hodgkin lymphoma (abbreviated NHL). The stage may depend on both the place where the malignant tissue is located (as located with biopsy, CT scanning and increasingly positron emission tomography) and on systemic symptoms due to the lymphoma ("B symptoms": night sweats, weight loss of >10% or fevers). The principal stage may be determined by location of the tumor. Stage I may indicate that the cancer is located in a single region, usually one lymph node and the surrounding area. Stage I often may not have outward symptoms. Stage II can indicate that the cancer is located in two separate regions, an affected lymph node or organ and a second affected area, and that both affected areas are confined to one side of the diaphragm—that is, both are above the diaphragm, or both are below the diaphragm. Stage III often indicates that the cancer has spread to both sides of the diaphragm, including one organ or area near the lymph nodes or the spleen. Stage IV may indicate diffuse or disseminated involvement of one or more extralymphatic organs, including any involvement of the liver, bone marrow, or nodular involvement of the lungs.

Modifiers may also be appended to some stages. For example, the letters A, B, E, X, or S can be appended to some stages. Generally, A or B may indicate the absence of constitutional (B-type) symptoms is denoted by adding an "A" to the stage; the presence is denoted by adding a "B" to the stage. E can be used if the disease is "extranodal" (not in the lymph nodes) or has spread from lymph nodes to adjacent tissue. X is often used if the largest deposit is >10 cm large ("bulky disease"), or whether the mediastinum is wider than ⅓ of the chest on a chest X-ray. S may be used if the disease has spread to the spleen.

The nature of the staging may be expressed with CS or PS. CS may denote that the clinical stage as obtained by doctor's examinations and tests. PS may denote that the pathological stage as obtained by exploratory laparotomy (surgery performed through an abdominal incision) with splenectomy (surgical removal of the spleen).

Therapeutic Regimens

Diagnosing, predicting, or monitoring a status or outcome of a cancer may comprise treating a cancer or preventing a cancer progression. In addition, diagnosing, predicting, or monitoring a status or outcome of a cancer may comprise identifying or predicting responders to an anti-cancer therapy. In some instances, diagnosing, predicting, or monitoring may comprise determining a therapeutic regimen. Determining a therapeutic regimen may comprise administering an anti-cancer therapy. Alternatively, determining a therapeutic regimen may comprise modifying, recommending, continuing or discontinuing an anti-cancer regimen. In some instances, if the sample expression patterns are consistent with the expression pattern for a known disease or disease outcome, the expression patterns can be used to designate one or more treatment modalities (e.g., therapeutic regimens, anti-cancer regimen). An anti-cancer regimen may comprise one or more anti-cancer therapies. Examples of anti-cancer therapies include surgery, chemotherapy, radiation therapy, immunotherapy/biological therapy, photodynamic therapy.

Surgical oncology uses surgical methods to diagnose, stage, and treat cancer, and to relieve certain cancer-related symptoms. Surgery may be used to remove the tumor (e.g., excisions, resections, debulking surgery), reconstruct a part of the body (e.g., restorative surgery), and/or to relieve symptoms such as pain (e.g., palliative surgery). Surgery may also include cryosurgery. Cryosurgery (also called cryotherapy) may use extreme cold produced by liquid nitrogen (or argon gas) to destroy abnormal tissue. Cryosurgery can be used to treat external tumors, such as those on the skin. For external tumors, liquid nitrogen can be applied directly to the cancer cells with a cotton swab or spraying device. Cryosurgery may also be used to treat tumors inside the body (internal tumors and tumors in the bone). For internal tumors, liquid nitrogen or argon gas may be circulated through a hollow instrument called a cryoprobe, which is placed in contact with the tumor. An ultrasound or MRI may be used to guide the cryoprobe and monitor the freezing of the cells, thus limiting damage to nearby healthy tissue. A ball of ice crystals may form around the probe, freezing nearby cells. Sometimes more than one probe is used to deliver the liquid nitrogen to various parts of the tumor. The probes may be put into the tumor during surgery or through the skin (percutaneously). After cryosurgery, the frozen tissue thaws and may be naturally absorbed by the body (for internal tumors), or may dissolve and form a scab (for external tumors).

Chemotherapeutic agents may also be used for the treatment of cancer. Examples of chemotherapeutic agents include alkylating agents, anti-metabolites, plant alkaloids and terpenoids, vinca alkaloids, podophyllotoxin, taxanes, topoisomerase inhibitors, and cytotoxic antibiotics. Cisplatin, carboplatin, and oxaliplatin are examples of alkylating agents. Other alkylating agents include mechlorethamine, cyclophosphamide, chlorambucil, ifosfamide. Alkylating agents may impair cell function by forming covalent bonds with the amino, carboxyl, sulfhydryl, and phosphate groups in biologically important molecules. Alternatively, alkylating agents may chemically modify a cell's DNA.

Anti-metabolites are another example of chemotherapeutic agents. Anti-metabolites may masquerade as purines or pyrimidines and may prevent purines and pyrimidines from becoming incorporated in to DNA during the "S" phase (of the cell cycle), thereby stopping normal development and division. Antimetabolites may also affect RNA synthesis. Examples of metabolites include azathioprine and mercaptopurine.

Alkaloids may be derived from plants and block cell division may also be used for the treatment of cancer. Alkyloids may prevent microtubule function. Examples of alkaloids are vinca alkaloids and taxanes. Vinca alkaloids may bind to specific sites on tubulin and inhibit the assembly of tubulin into microtubules (M phase of the cell cycle). The vinca alkaloids may be derived from the Madagascar periwinkle, *Catharanthus roseus* (formerly known as *Vinca rosea*). Examples of vinca alkaloids include, but are not limited to, vincristine, vinblastine, vinorelbine, or vindesine. Taxanes are diterpenes produced by the plants of the genus *Taxus* (yews). Taxanes may be derived from natural sources or synthesized artificially. Taxanes include paclitaxel (Taxol) and docetaxel (Taxotere). Taxanes may disrupt microtubule function. Microtubules are essential to cell division, and taxanes may stabilize GDP-bound tubulin in the microtubule, thereby inhibiting the process of cell division. Thus, in essence, taxanes may be mitotic inhibitors. Taxanes may also be radiosensitizing and often contain numerous chiral centers.

Alternative chemotherapeutic agents include podophyllotoxin. Podophyllotoxin is a plant-derived compound that may help with digestion and may be used to produce cytostatic drugs such as etoposide and teniposide. They may prevent the cell from entering the G1 phase (the start of DNA replication) and the replication of DNA (the S phase).

Topoisomerases are essential enzymes that maintain the topology of DNA Inhibition of type I or type II topoisomerases may interfere with both transcription and replication of DNA by upsetting proper DNA supercoiling. Some chemotherapeutic agents may inhibit topoisomerases. For example, some type I topoisomerase inhibitors include camptothecins: irinotecan and topotecan. Examples of type II inhibitors include amsacrine, etoposide, etoposide phosphate, and teniposide.

Another example of chemotherapeutic agents is cytotoxic antibiotics. Cytotoxic antibiotics are a group of antibiotics that are used for the treatment of cancer because they may interfere with DNA replication and/or protein synthesis.

Cytotoxic antibiotics include, but are not limited to, actinomycin, anthracyclines, doxorubicin, daunorubicin, valrubicin, idarubicin, epirubicin, bleomycin, plicamycin, and mitomycin.

In some instances, the anti-cancer treatment may comprise radiation therapy. Radiation can come from a machine outside the body (external-beam radiation therapy) or from radioactive material placed in the body near cancer cells (internal radiation therapy, more commonly called brachytherapy). Systemic radiation therapy uses a radioactive substance, given by mouth or into a vein that travels in the blood to tissues throughout the body.

External-beam radiation therapy may be delivered in the form of photon beams (either x-rays or gamma rays). A photon is the basic unit of light and other forms of electromagnetic radiation. An example of external-beam radiation therapy is called 3-dimensional conformal radiation therapy (3D-CRT). 3D-CRT may use computer software and advanced treatment machines to deliver radiation to very precisely shaped target areas. Many other methods of external-beam radiation therapy are currently being tested and used in cancer treatment. These methods include, but are not limited to, intensity-modulated radiation therapy (IMRT), image-guided radiation therapy (IGRT), Stereotactic radiosurgery (SRS), Stereotactic body radiation therapy (SBRT), and proton therapy.

Intensity-modulated radiation therapy (IMRT) is an example of external-beam radiation and may use hundreds of tiny radiation beam-shaping devices, called collimators, to deliver a single dose of radiation. The collimators can be stationary or can move during treatment, allowing the intensity of the radiation beams to change during treatment sessions. This kind of dose modulation allows different areas of a tumor or nearby tissues to receive different doses of radiation. IMRT is planned in reverse (called inverse treatment planning). In inverse treatment planning, the radiation doses to different areas of the tumor and surrounding tissue are planned in advance, and then a high-powered computer program calculates the required number of beams and angles of the radiation treatment. In contrast, during traditional (forward) treatment planning, the number and angles of the radiation beams are chosen in advance and computers calculate how much dose may be delivered from each of the planned beams. The goal of IMRT is to increase the radiation dose to the areas that need it and reduce radiation exposure to specific sensitive areas of surrounding normal tissue.

Another example of external-beam radiation is image-guided radiation therapy (IGRT). In IGRT, repeated imaging scans (CT, MRI, or PET) may be performed during treatment. These imaging scans may be processed by computers to identify changes in a tumor's size and location due to treatment and to allow the position of the patient or the planned radiation dose to be adjusted during treatment as needed. Repeated imaging can increase the accuracy of radiation treatment and may allow reductions in the planned volume of tissue to be treated, thereby decreasing the total radiation dose to normal tissue.

Tomotherapy is a type of image-guided IMRT. A tomotherapy machine is a hybrid between a CT imaging scanner and an external-beam radiation therapy machine. The part of the tomotherapy machine that delivers radiation for both imaging and treatment can rotate completely around the patient in the same manner as a normal CT scanner. Tomotherapy machines can capture CT images of the patient's tumor immediately before treatment sessions, to allow for very precise tumor targeting and sparing of normal tissue.

Stereotactic radiosurgery (SRS) can deliver one or more high doses of radiation to a small tumor. SRS uses extremely accurate image-guided tumor targeting and patient positioning. Therefore, a high dose of radiation can be given without excess damage to normal tissue. SRS can be used to treat small tumors with well-defined edges. It is most commonly used in the treatment of brain or spinal tumors and brain metastases from other cancer types. For the treatment of some brain metastases, patients may receive radiation therapy to the entire brain (called whole-brain radiation therapy) in addition to SRS. SRS requires the use of a head frame or other device to immobilize the patient during treatment to ensure that the high dose of radiation is delivered accurately.

Stereotactic body radiation therapy (SBRT) delivers radiation therapy in fewer sessions, using smaller radiation fields and higher doses than 3D-CRT in most cases. SBRT may treat tumors that lie outside the brain and spinal cord. Because these tumors are more likely to move with the normal motion of the body, and therefore cannot be targeted as accurately as tumors within the brain or spine, SBRT is usually given in more than one dose. SBRT can be used to treat small, isolated tumors, including cancers in the lung and liver. SBRT systems may be known by their brand names, such as the CyberKnife®.

In proton therapy, external-beam radiation therapy may be delivered by proton. Protons are a type of charged particle. Proton beams differ from photon beams mainly in the way they deposit energy in living tissue. Whereas photons deposit energy in small packets all along their path through tissue, protons deposit much of their energy at the end of their path (called the Bragg peak) and deposit less energy along the way. Use of protons may reduce the exposure of normal tissue to radiation, possibly allowing the delivery of higher doses of radiation to a tumor.

Other charged particle beams such as electron beams may be used to irradiate superficial tumors, such as skin cancer or tumors near the surface of the body, but they cannot travel very far through tissue.

Internal radiation therapy (brachytherapy) is radiation delivered from radiation sources (radioactive materials) placed inside or on the body. Several brachytherapy techniques are used in cancer treatment. Interstitial brachytherapy may use a radiation source placed within tumor tissue, such as within a prostate tumor. Intracavitary brachytherapy may use a source placed within a surgical cavity or a body cavity, such as the chest cavity, near a tumor. Episcleral brachytherapy, which may be used to treat melanoma inside the eye, may use a source that is attached to the eye. In brachytherapy, radioactive isotopes can be sealed in tiny pellets or "seeds." These seeds may be placed in patients using delivery devices, such as needles, catheters, or some other type of carrier. As the isotopes decay naturally, they give off radiation that may damage nearby cancer cells. Brachytherapy may be able to deliver higher doses of radiation to some cancers than external-beam radiation therapy while causing less damage to normal tissue.

Brachytherapy can be given as a low-dose-rate or a high-dose-rate treatment. In low-dose-rate treatment, cancer cells receive continuous low-dose radiation from the source over a period of several days. In high-dose-rate treatment, a robotic machine attached to delivery tubes placed inside the body may guide one or more radioactive sources into or near a tumor, and then removes the sources at the end of each treatment session. High-dose-rate treatment can be given in one or more treatment sessions. An example of a high-dose-rate treatment is the MammoSite® system. Bracytherapy may be used to treat patients with breast cancer who have undergone breast-conserving surgery.

The placement of brachytherapy sources can be temporary or permanent. For permanent brachytherapy, the sources may be surgically sealed within the body and left there, even after all of the radiation has been given off. In some instances, the remaining material (in which the radioactive isotopes were sealed) does not cause any discomfort or harm to the patient. Permanent brachytherapy is a type of low-dose-rate brachytherapy. For temporary brachytherapy, tubes (catheters) or other carriers are used to deliver the radiation sources, and both the carriers and the radiation sources are removed after treatment. Temporary brachytherapy can be either low-dose-rate or high-dose-rate treatment. Brachytherapy may be used alone or in addition to external-beam radiation therapy to provide a "boost" of radiation to a tumor while sparing surrounding normal tissue.

In systemic radiation therapy, a patient may swallow or receive an injection of a radioactive substance, such as radioactive iodine or a radioactive substance bound to a monoclonal antibody. Radioactive iodine (131I) is a type of systemic radiation therapy commonly used to help treat cancer, such as thyroid cancer. Thyroid cells naturally take up radioactive iodine. For systemic radiation therapy for some other types of cancer, a monoclonal antibody may help target the radioactive substance to the right place. The antibody joined to the radioactive substance travels through the blood, locating and killing tumor cells. For example, the drug ibritumomab tiuxetan (Zevalin®) may be used for the treatment of certain types of B-cell non-Hodgkin lymphoma (NHL). The antibody part of this drug recognizes and binds to a protein found on the surface of B lymphocytes. The combination drug regimen of tositumomab and iodine I 131 tositumomab (Bexxar®) may be used for the treatment of certain types of cancer, such as NHL. In this regimen, nonradioactive tositumomab antibodies may be given to patients first, followed by treatment with tositumomab antibodies that have 131I attached. Tositumomab may recognize and bind to the same protein on B lymphocytes as ibritumomab. The nonradioactive form of the antibody may help protect normal B lymphocytes from being damaged by radiation from 131I.

Some systemic radiation therapy drugs relieve pain from cancer that has spread to the bone (bone metastases). This is a type of palliative radiation therapy. The radioactive drugs samarium-153-lexidronam (Quadramet®) and strontium-89 chloride (Metastron®) are examples of radiopharmaceuticals may be used to treat pain from bone metastases.

Biological therapy (sometimes called immunotherapy, biotherapy, or biological response modifier (BRM) therapy) uses the body's immune system, either directly or indirectly, to fight cancer or to lessen the side effects that may be caused by some cancer treatments. Biological therapies include interferons, interleukins, colony-stimulating factors, monoclonal antibodies, vaccines, gene therapy, and nonspecific immunomodulating agents.

Interferons (IFNs) are types of cytokines that occur naturally in the body. Interferon alpha, interferon beta, and interferon gamma are examples of interferons that may be used in cancer treatment.

Like interferons, interleukins (ILs) are cytokines that occur naturally in the body and can be made in the laboratory. Many interleukins have been identified for the treatment of cancer. For example, interleukin-2 (IL-2 or aldesleukin), interleukin 7, and interleukin 12 have may be used as an anti-cancer treatment. IL-2 may stimulate the growth and activity of many immune cells, such as lymphocytes, that can destroy cancer cells. Interleukins may be used to treat a number of cancers, including leukemia, lymphoma, and brain, colorectal, ovarian, breast, kidney and prostate cancers.

Colony-stimulating factors (CSFs) (sometimes called hematopoietic growth factors) may also be used for the treatment of cancer. Some examples of CSFs include, but are not limited to, G-CSF (filgrastim) and GM-CSF (sargramostim). CSFs may promote the division of bone marrow stem cells and their development into white blood cells, platelets, and red blood cells. Bone marrow is critical to the body's immune system because it is the source of all blood cells. Because anticancer drugs can damage the body's ability to make white blood cells, red blood cells, and platelets, stimulation of the immune system by CSFs may benefit patients undergoing other anti-cancer treatment, thus CSFs may be combined with other anti-cancer therapies, such as chemotherapy. CSFs may be used to treat a large variety of cancers, including lymphoma, leukemia, multiple myeloma, melanoma, and cancers of the brain, lung, esophagus, breast, uterus, ovary, prostate, kidney, colon, and rectum.

Another type of biological therapy includes monoclonal antibodies (MOABs or MoABs). These antibodies may be produced by a single type of cell and may be specific for a particular antigen. To create MOABs, human cancer cells may be injected into mice. In response, the mouse immune system can make antibodies against these cancer cells. The mouse plasma cells that produce antibodies may be isolated and fused with laboratory-grown cells to create "hybrid" cells called hybridomas. Hybridomas can indefinitely produce large quantities of these pure antibodies, or MOABs. MOABs may be used in cancer treatment in a number of ways. For instance, MOABs that react with specific types of cancer may enhance a patient's immune response to the cancer. MOABs can be programmed to act against cell growth factors, thus interfering with the growth of cancer cells.

MOABs may be linked to other anti-cancer therapies such as chemotherapeutics, radioisotopes (radioactive substances), other biological therapies, or other toxins. When the antibodies latch onto cancer cells, they deliver these anti-cancer therapies directly to the tumor, helping to destroy it. MOABs carrying radioisotopes may also prove useful in diagnosing certain cancers, such as colorectal, ovarian, and prostate.

Rituxan® (rituximab) and Herceptin® (trastuzumab) are examples of MOABs that may be used as a biological therapy. Rituxan may be used for the treatment of non-Hodgkin lymphoma. Herceptin can be used to treat metastatic breast cancer in patients with tumors that produce excess amounts of a protein called HER2. Alternatively, MOABs may be used to treat lymphoma, leukemia, melanoma, and cancers of the brain, breast, lung, kidney, colon, rectum, ovary, prostate, and other areas.

Cancer vaccines are another form of biological therapy. Cancer vaccines may be designed to encourage the patient's immune system to recognize cancer cells. Cancer vaccines may be designed to treat existing cancers (therapeutic vaccines) or to prevent the development of cancer (prophylactic vaccines). Therapeutic vaccines may be injected in a person after cancer is diagnosed. These vaccines may stop the growth of existing tumors, prevent cancer from recurring, or eliminate cancer cells not killed by prior treatments. Cancer vaccines given when the tumor is small may be able to eradicate the cancer. On the other hand, prophylactic vaccines are given to healthy individuals before cancer develops. These vaccines are designed to stimulate the immune system to attack viruses that can cause cancer. By targeting these cancer-causing viruses, development of certain cancers may be prevented. For example, cervarix and gardasil are vaccines to treat human papilloma virus and may prevent cervical cancer. Therapeutic vaccines may be used to treat melanoma, lymphoma, leukemia, and cancers of the brain, breast, lung, kidney, ovary, prostate, pancreas, colon, and rectum. Cancer vaccines can be used in combination with other anti-cancer therapies.

Gene therapy is another example of a biological therapy. Gene therapy may involve introducing genetic material into a person's cells to fight disease. Gene therapy methods may improve a patient's immune response to cancer. For example, a gene may be inserted into an immune cell to enhance its ability to recognize and attack cancer cells. In another approach, cancer cells may be injected with genes that cause the cancer cells to produce cytokines and stimulate the immune system.

In some instances, biological therapy includes nonspecific immunomodulating agents. Nonspecific immunomodulating agents are substances that stimulate or indirectly augment the immune system. Often, these agents target key immune system cells and may cause secondary responses such as increased production of cytokines and immunoglobulins. Two nonspecific immunomodulating agents used in cancer treatment are *bacillus* Calmette-Guerin (BCG) and levamisole. BCG may be used in the treatment of superficial bladder cancer following surgery. BCG may work by stimulating an inflammatory, and possibly an immune, response. A solution of BCG may be instilled in the bladder. Levamisole is sometimes used along with fluorouracil (5-FU) chemotherapy in the treatment of stage III (Dukes' C) colon cancer following surgery. Levamisole may act to restore depressed immune function.

Photodynamic therapy (PDT) is an anti-cancer treatment that may use a drug, called a photosensitizer or photosensitizing agent, and a particular type of light. When photosensitizers are exposed to a specific wavelength of light, they may produce a form of oxygen that kills nearby cells. A photosensitizer may be activated by light of a specific wavelength. This wavelength determines how far the light can travel into the body. Thus, photosensitizers and wavelengths of light may be used to treat different areas of the body with PDT.

In the first step of PDT for cancer treatment, a photosensitizing agent may be injected into the bloodstream. The agent may be absorbed by cells all over the body but may stay in cancer cells longer than it does in normal cells. Approximately 24 to 72 hours after injection, when most of the agent has left normal cells but remains in cancer cells, the tumor can be exposed to light. The photosensitizer in the tumor can absorb the light and produces an active form of oxygen that destroys nearby cancer cells. In addition to directly killing cancer cells, PDT may shrink or destroy tumors in two other ways. The photosensitizer can damage blood vessels in the tumor, thereby preventing the cancer from receiving necessary nutrients. PDT may also activate the immune system to attack the tumor cells.

The light used for PDT can come from a laser or other sources. Laser light can be directed through fiber optic cables (thin fibers that transmit light) to deliver light to areas inside the body. For example, a fiber optic cable can be inserted through an endoscope (a thin, lighted tube used to look at tissues inside the body) into the lungs or esophagus to treat cancer in these organs. Other light sources include light-emitting diodes (LEDs), which may be used for surface tumors, such as skin cancer. PDT is usually performed as an outpatient procedure. PDT may also be repeated and may be used with other therapies, such as surgery, radiation, or chemotherapy.

Extracorporeal photopheresis (ECP) is a type of PDT in which a machine may be used to collect the patient's blood cells. The patient's blood cells may be treated outside the body with a photosensitizing agent, exposed to light, and then returned to the patient. ECP may be used to help lessen the severity of skin symptoms of cutaneous T-cell lymphoma that has not responded to other therapies. ECP may be used to treat other blood cancers, and may also help reduce rejection after transplants.

Additionally, photosensitizing agent, such as porfimer sodium or Photofrin®, may be used in PDT to treat or relieve the symptoms of esophageal cancer and non-small cell lung cancer. Porfimer sodium may relieve symptoms of esophageal cancer when the cancer obstructs the esophagus or when the cancer cannot be satisfactorily treated with laser therapy alone. Porfimer sodium may be used to treat non-small cell lung cancer in patients for whom the usual treatments are not appropriate, and to relieve symptoms in patients with non-small cell lung cancer that obstructs the airways. Porfimer sodium may also be used for the treatment of precancerous lesions in patients with Barrett esophagus, a condition that can lead to esophageal cancer.

Laser therapy may use high-intensity light to treat cancer and other illnesses. Lasers can be used to shrink or destroy tumors or precancerous growths. Lasers are most commonly used to treat superficial cancers (cancers on the surface of the body or the lining of internal organs) such as basal cell skin cancer and the very early stages of some cancers, such as cervical, penile, vaginal, vulvar, and non-small cell lung cancer.

Lasers may also be used to relieve certain symptoms of cancer, such as bleeding or obstruction. For example, lasers can be used to shrink or destroy a tumor that is blocking a patient's trachea (windpipe) or esophagus. Lasers also can be used to remove colon polyps or tumors that are blocking the colon or stomach.

Laser therapy is often given through a flexible endoscope (a thin, lighted tube used to look at tissues inside the body). The endoscope is fitted with optical fibers (thin fibers that transmit light). It is inserted through an opening in the body, such as the mouth, nose, anus, or vagina. Laser light is then precisely aimed to cut or destroy a tumor.

Laser-induced interstitial thermotherapy (LITT), or interstitial laser photocoagulation, also uses lasers to treat some cancers. LITT is similar to a cancer treatment called hyperthermia, which uses heat to shrink tumors by damaging or killing cancer cells. During LITT, an optical fiber is inserted into a tumor. Laser light at the tip of the fiber raises the temperature of the tumor cells and damages or destroys them. LITT is sometimes used to shrink tumors in the liver.

Laser therapy can be used alone, but most often it is combined with other treatments, such as surgery, chemotherapy, or radiation therapy. In addition, lasers can seal nerve endings to reduce pain after surgery and seal lymph vessels to reduce swelling and limit the spread of tumor cells.

Lasers used to treat cancer may include carbon dioxide ($CO_2$) lasers, argon lasers, and neodymium:yttrium-aluminum-garnet (Nd:YAG) lasers. Each of these can shrink or destroy tumors and can be used with endoscopes. $CO_2$ and argon lasers can cut the skin's surface without going into deeper layers. Thus, they can be used to remove superficial cancers, such as skin cancer. In contrast, the Nd:YAG laser is more commonly applied through an endoscope to treat internal organs, such as the uterus, esophagus, and colon. Nd:YAG laser light can also travel through optical fibers into specific areas of the body during LITT. Argon lasers are often used to activate the drugs used in PDT.

For patients with high test scores consistent with systemic disease outcome after prostatectomy, additional treatment modalities such as adjuvant chemotherapy (e.g., docetaxel, mitoxantrone and prednisone), systemic radiation therapy (e.g., samarium or strontium) and/or anti-androgen therapy (e.g., surgical castration, finasteride, dutasteride) can be designated. Such patients would likely be treated immediately with anti-androgen therapy alone or in combination with radiation therapy in order to eliminate presumed micro-metastatic disease, which cannot be detected clinically but can be revealed by the target sequence expression signature.

Such patients can also be more closely monitored for signs of disease progression. For patients with intermediate test scores consistent with biochemical recurrence only (BCR-only or elevated PSA that does not rapidly become manifested as systemic disease only localized adjuvant therapy (e.g., radiation therapy of the prostate bed) or short course of anti-androgen therapy would likely be administered. Patients with scores consistent with metastasis or disease progression would likely be administered increased dosage of an anti-cancer therapy and/or administered an adjuvant therapy. For patients with low scores or scores consistent with no evidence of disease (NED) or no disease progression, adjuvant therapy would not likely be recommended by their physicians in order to avoid treatment-related side effects such as metabolic syndrome (e.g., hypertension, diabetes and/or weight gain), osteoporosis, proctitis, incontinence or impotence. Patients with samples consistent with NED or no disease progression could be designated for watchful waiting, or for no treatment. Patients with test scores that do not correlate with systemic disease but who have successive PSA increases could be designated for watchful waiting, increased monitoring, or lower dose or shorter duration anti-androgen therapy.

Target sequences can be grouped so that information obtained about the set of target sequences in the group can be used to make or assist in making a clinically relevant judgment such as a diagnosis, prognosis, or treatment choice.

A patient report is also provided comprising a representation of measured expression levels of a plurality of target sequences in a biological sample from the patient, wherein the representation comprises expression levels of target sequences corresponding to any one, two, three, four, five, six, eight, ten, twenty, thirty, fifty or more of the target sequences depicted in Table 6, or of the subsets described herein, or of a combination thereof. In some instances, the target sequences correspond to any one, two, three, four, five, six, eight, ten, twenty, thirty, fifty or more of the target sequences selected from SEQ ID NOs.: 1-903. In other instances, the target sequences correspond to any one, two, three, four, five, six, eight, ten, twenty, thirty, fifty or more of the target sequences selected from SEQ ID NOs.: 1-352. Alternatively, the target sequences correspond to any one, two, three, four, five, six, eight, ten, twenty, thirty, fifty or more of the target sequences selected from SEQ ID NOs.: 353-441. In some embodiments, the representation of the measured expression level(s) may take the form of a linear or nonlinear combination of expression levels of the target sequences of interest. The patient report may be provided in a machine (e.g., a computer) readable format and/or in a hard (paper) copy. The report can also include standard measurements of expression levels of said plurality of target sequences from one or more sets of patients with known disease status and/or outcome. The report can be used to inform the patient and/or treating physician of the expression levels of the expressed target sequences, the likely medical diagnosis and/or implications, and optionally may recommend a treatment modality for the patient.

Also provided are representations of the gene expression profiles useful for treating, diagnosing, prognosticating, and otherwise assessing disease. In some embodiments, these profile representations are reduced to a medium that can be automatically read by a machine such as computer readable media (magnetic, optical, and the like). The articles can also include instructions for assessing the gene expression profiles in such media. For example, the articles may comprise a readable storage form having computer instructions for comparing gene expression profiles of the portfolios of genes described above. The articles may also have gene expression profiles digitally recorded therein so that they may be compared with gene expression data from patient samples. Alternatively, the profiles can be recorded in different representational format. A graphical recordation is one such format. Clustering algorithms can assist in the visualization of such data.

Exemplary Embodiments

Disclosed herein, in some embodiments, is a method for diagnosing, predicting, and/or monitoring a status or outcome of a cancer in a subject, comprising: (a) assaying an expression level in a sample from the subject for a plurality of targets, wherein the plurality of targets comprises a coding target and a non-coding target, wherein the non-coding target is a non-coding RNA transcript selected from the group consisting of piRNA, tiRNA, PASR, TASR, aTASR, TSSa-RNA, snRNA, RE-RNA, uaRNA, x-ncRNA, hY RNA, usRNA, snaR, vtRNA, T-UCRs, pseudogenes, GRC-RNAs, aRNAs, PALRs, PROMPTs, and LSINCTs; and (b) for diagnosing, predicting, and/or monitoring a status or outcome of a cancer based on the expression levels of the plurality of targets. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the cancer is a prostate cancer. In some embodiments, the cancer is a pancreatic cancer. In some embodiments, the cancer is a thyroid cancer. In some embodiments, the cancer is a bladder cancer. In some embodiments, the cancer is a lung cancer. In some embodiments, the coding target is selected from a sequence listed in Table 6. In some embodiments, the coding target is an exon-coding transcript. In some embodiments, the exon-coding transcript is an exonic sequence. In some embodiments, the non-coding target is selected from a sequence listed in Table 6. The plurality of targets can comprise a coding target and/or a non-coding target selected from SEQ ID NOs.: 1-903. The plurality of targets can comprise a coding target and/or a non-coding target selected from SEQ ID NOs.: 1-352. The plurality of targets can comprise a coding target and/or a non-coding target selected from SEQ ID NOs.: 353-441. In other instances, the plurality of targets comprises a coding target and/or a non-coding target selected from SEQ ID NOs.: 322-352. Alternatively, the plurality of targets comprises a coding target and/or a non-coding target selected from SEQ ID NOs.: 292-321. Optionally, the plurality of targets comprises a coding target and/or a non-coding target selected from SEQ ID NOs.: 231-261. In some instances, the plurality of targets comprises a coding target and/or a non-coding target located on chr2q31.3. In some instances, the coding target and/or non-coding target located on chr2q31.3 is selected from SEQ ID NOs.: 262-291. In some embodiments, the non-coding RNA transcript is snRNA. In some embodiments, the non-coding target and the coding target are nucleic acid sequences. In some embodiments, the nucleic acid sequence is a DNA sequence. In some embodiments, the nucleic acid sequence is an RNA sequence. In some embodiments, the method further comprises assaying an expression level of a lincRNA. In some embodiments, the method further comprises further comprising assaying an expression level of a siRNA. In some embodiments, the method further comprises assaying an expression level of a snoRNA. In some embodiments, the method further comprises assaying an expression level of a non-exonic sequence listed in Table 6. In some instances, the plurality of targets comprises at least about 25% non-coding targets. In some instances, the plurality of targets comprises at least about 5 coding targets and/or non-coding targets. The plurality of targets can comprise at least about 10 coding targets and/or non-coding targets. The plurality of targets can comprise at least about 15 coding targets and/or non-coding targets. The plurality of targets can comprise at least about 20 coding targets and/or non-coding targets. The plurality of targets can comprise at least about 30 coding targets and/or non-coding targets. The plurality of targets can comprise at least about 40 coding targets and/or non-coding targets. In some instances, the plurality of targets comprise at least about 50, 60, 70, 80, 90, 100, 125, 150, 175, 200, 225, 250, 275, 300, 325, 350, 375, 400, 425 coding targets and/or non-coding targets. In some embodiments, the diagnosing, predicting, and/or monitoring the status or outcome of a cancer comprises determining the malignancy of the cancer. In some embodiments, the diagnosing, predicting, and/or monitoring the status or outcome of a cancer includes determining the stage of the cancer. In some embodiments, the diagnosing, predicting, and/or monitoring the status or outcome of a cancer includes assessing the risk of cancer recurrence. In some embodiments, diagnosing, predicting, and/or monitoring the status or outcome of a cancer may comprise determining the efficacy of treatment. In some embodiments, diagnosing, predicting, and/or monitoring the status or outcome of a cancer may comprise determining a therapeutic regimen. Determining a therapeutic regimen may comprise administering an anti-cancer therapeutic. Alternatively, determining the treatment for the cancer may comprise modifying a therapeutic regimen. Modifying a therapeutic regimen may comprise increasing, decreasing, or terminating a therapeutic regimen.

Further disclosed herein, is some embodiments, is a method for diagnosing, predicting, and/or monitoring the status or outcome of a cancer in a subject, comprising: (a) assaying an expression level in a sample from the subject for a plurality of targets, wherein (i) the plurality of targets comprises a coding target and a non-coding target; and (ii) the non-coding target is not selected from the group consisting of a miRNA, an intronic sequence, and a UTR sequence; and (b) diagnosing, predicting, and/or monitoring the status or outcome of a cancer based on the expression levels of the plurality of targets. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the cancer is a prostate cancer. In some embodiments, the cancer is a pancreatic cancer. In some embodiments, the cancer is a thyroid cancer. In some embodiments, the cancer is a lung cancer. In some embodiments, the coding target is selected from a sequence listed in Table 6. The plurality of targets can comprise a coding target and/or a non-coding target selected from SEQ ID NOs.: 1-903. Alternatively, the plurality of targets comprises a coding and/or non-coding target selected from SEQ ID NOs.: 1-352. The plurality of targets can comprise a coding target and/or a non-coding target selected from SEQ ID NOs.: 353-441. In other instances, the plurality of targets comprises a coding target and/or a non-coding target selected from SEQ ID NOs.: 322-352. Alternatively, the plurality of targets comprises a coding target and/or a non-coding target selected from SEQ ID NOs.: 292-321. Optionally, the plurality of targets comprises a coding target and/or a non-coding target selected from SEQ ID NOs.: 231-261. In some instances, the plurality of targets comprises a coding target and/or a non-coding target located on chr2q31.3. In some instances, the coding target and/or non-coding target located on chr2q31.3 is selected from SEQ ID NOs.: 262-291. In some embodiments, the coding target is an exon-coding transcript. In some embodiments, the exon-coding transcript is an exonic sequence. In some embodiments, the coding target is selected from a sequence listed in Table 6. In some embodiments, the non-coding target is a non-coding RNA transcript. In some embodiments, the non-coding RNA transcript is selected from the group consisting of piRNA, tiRNA, PASR, TASR, aTASR, TSSa-RNA, snRNA, RE-RNA, uaRNA, x-ncRNA, hY RNA, usRNA, snaR, vtRNA, T-UCRs, pseudogenes, GRC-RNAs, aRNAs, PALRs, PROMPTs, and LSINCTs. In some embodiments, the non-coding RNA transcript is snRNA. In some embodiments, the method further comprises assaying an expression level of a lincRNA. In some embodiments, the non-coding RNA is not a siRNA. In some embodiments, the non-coding RNA is not a snoRNA. In some embodiments, the method further comprises assaying an expression level of a non-exonic sequence listed in Table 6. In some embodiments, the non-coding target and the coding target are nucleic acid sequences. In some embodiments, the nucleic acid sequence is a DNA sequence. In some embodiments, the nucleic acid sequence is an RNA sequence. In some embodiments, the diagnosing, predicting, and/or monitoring the status or outcome of a cancer comprises determining the malignancy of the cancer. In some embodiments, the diagnosing, predicting, and/or monitoring the status or outcome of a cancer includes determining the stage of the cancer. In some embodiments, the diagnosing, predicting, and/or monitoring the status or outcome of a cancer includes assessing the risk of cancer recurrence. In some embodiments, diagnosing, predicting, and/or monitoring the status or outcome of a cancer may comprise determining the efficacy of treatment. In some embodiments, diagnosing, predicting, and/or monitoring the status or outcome of a cancer may comprise determining a therapeutic regimen. Determining a therapeutic regimen may comprise administering an anti-cancer therapeutic. Alternatively, determining the treatment for the cancer may comprise modifying a therapeutic regimen. Modifying a therapeutic regimen may comprise increasing, decreasing, or terminating a therapeutic regimen.

Further disclosed herein, in some embodiments, is a method for diagnosing, predicting, and/or monitoring the status or outcome of a cancer in a subject, comprising: (a) assaying an expression level in a sample from the subject for a plurality of targets, wherein the plurality of targets consist essentially of a non-coding target or a non-exonic transcript; wherein the non-coding target is selected from the group consisting of a UTR sequence, an intronic sequence, or a non-coding RNA transcript, and wherein the non-coding RNA transcript is selected from the group consisting of piRNA, tiRNA, PASR, TASR, aTASR, TSSa-RNA, snRNA, RE-RNA, uaRNA, x-ncRNA, hY RNA, usRNA, snaR, vtRNA, T-UCRs, pseudogenes, GRC-RNAs, aRNAs, PALRs, PROMPTs, and LSINCTs; and (b) diagnosing, predicting, and/or monitoring the status or outcome of a cancer based on the expression levels of the plurality of targets. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the cancer is a prostate cancer. In some embodiments, the cancer is a pancreatic cancer. In some embodiments, the cancer is a bladder cancer. In some embodiments, the cancer is a thyroid cancer. In some embodiments, the cancer is a lung cancer. In some embodiments, the non-coding target is selected from a sequence listed in Table 6. In some embodiments, the non-coding target is an intronic sequence or partially overlaps with an intronic sequence. In some embodiments, the non-coding target is a UTR sequence or partially overlaps with a UTR sequence. In some embodiments, the non-coding target is a non-coding RNA transcript. In some embodiments, the non-coding RNA transcript is snRNA. In some embodiments, the non-coding target is a nucleic acid sequence. In some embodiments, the nucleic acid sequence is a DNA sequence. In some embodiments, the nucleic acid sequence is an RNA sequence. In some embodiments, the method further comprises assaying an expression level of a lincRNA. In some embodiments, the method further comprises assaying an expression level of a miRNA. In some embodiments, the method further comprises further comprising assaying an expression level of a siRNA. In some embodiments, the method further comprises assaying an expression level of a snoRNA. In some embodiments, the method further comprises assaying an expression level of a non-exonic sequence listed in Table 6. The plurality of targets can comprise a coding target and/or a non-coding target selected from SEQ ID NOs.: 1-903. In some instances, the plurality of targets comprises a coding target and/or a non-coding target selected SEQ ID NOs.: 1-352. Alternatively, the plurality of targets comprises a coding target and/or a non-coding target selected from SEQ ID NOs.: 353-441. In other instances, the plurality of targets comprises a coding target and/or a non-coding target selected from SEQ ID NOs.: 322-352. Alternatively, the plurality of targets comprises a coding target and/or a non-coding target selected from SEQ ID NOs.: 292-321. Optionally, the plurality of targets comprises a coding target and/or a non-coding target selected from SEQ ID NOs.: 231-261. In some instances, the plurality of targets comprises a coding target and/or a non-coding target located on chr2q31.3. In some instances, the coding target and/or non-coding target located on chr2q31.3 is selected from SEQ ID NOs.: 262-291. In some embodiments, the diagnosing, predicting, and/or monitoring the status or outcome of a cancer comprises determining the malignancy of the cancer. In some embodiments, the diagnosing, predicting, and/or monitoring the status or outcome of a cancer includes determining the stage of the cancer. In some embodiments, the diagnosing, predicting, and/or monitoring the status or outcome of a cancer includes assessing the risk of cancer recurrence. In some embodiments, diagnosing, predicting, and/or monitoring the status or outcome of a cancer may comprise determining the efficacy of treatment.

Further disclosed herein, in some embodiments, is a method for diagnosing, predicting, and/or monitoring the status or outcome of a cancer in a subject, comprising: (a) assaying an expression level in a sample from the subject for a plurality of targets, wherein the plurality of targets comprises a non-coding target, wherein the non-coding target is a non-coding RNA transcript and the non-coding RNA transcript is non-polyadenylated; and (b) diagnosing, predicting, and/or monitoring the status or outcome of a cancer based on the expression levels of the plurality of targets. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the cancer is a prostate cancer. In some embodiments, the cancer is a pancreatic cancer. In some embodiments, the cancer is a bladder cancer. In some embodiments, the cancer is a thyroid cancer. In some embodiments, the cancer is a lung cancer. In some embodiments, the non-coding target is selected from a sequence listed in Table 6. In some embodiments, the non-coding RNA transcript is selected from the group consisting of PASR, TASR, aTASR, TSSa-RNA, RE-RNA, uaRNA, x-ncRNA, hY RNA, usRNA, snaR, vtRNA, T-UCRs, pseudogenes, GRC-RNAs, aRNAs, PALRs, PROMPTs, and LSINCTs. In some embodiments, the method further comprises assaying an expression level of a coding target. In some embodiments, the coding target is selected from a sequence listed in Table 6. In some embodiments, the coding target is an exon-coding transcript. In some embodiments, the exon-coding transcript is an exonic sequence. In some embodiments, the method further comprises assaying an expression level of a non-exonic sequence listed in Table 6. The plurality of targets can comprise a coding target and/or a non-coding target selected from SEQ ID NOs.: 1-903. In some instances, the plurality of targets comprises a coding target and/or a non-coding target selected SEQ ID NOs.: 1-352. Alternatively, the plurality of targets comprises a coding target and/or a non-coding target selected from SEQ ID NOs.: 353-441. In other instances, the plurality of targets comprises a coding target and/or a non-coding target selected from SEQ ID NOs.: 322-352. Alternatively, the plurality of targets comprises a coding target and/or a non-coding target selected from SEQ ID NOs.: 292-321. Optionally, the plurality of targets comprises a coding target and/or a non-coding target selected from SEQ ID NOs.: 231-261. In some instances, the plurality of targets comprises a coding target and/or a non-coding target located on chr2q31.3. In some instances, the coding target and/or non-coding target located on chr2q31.3 is selected from SEQ ID NOs.: 262-291. In some embodiments, the non-coding target and the coding target are nucleic acid sequences. In some embodiments, the nucleic acid sequence is a DNA sequence. In some embodiments, the nucleic acid sequence is an RNA sequence. In some embodiments, the method further comprises assaying an expression level of a lincRNA. In some embodiments, the diagnosing, predicting, and/or monitoring the status or outcome of a cancer comprises determining the malignancy of the cancer. In some embodiments, the diagnosing, predicting, and/or monitoring the status or outcome of a cancer includes determining the stage of the cancer. In some embodiments, the diagnosing, predicting, and/or monitoring the status or outcome of a cancer includes assessing the risk of cancer recurrence. In some embodiments, diagnosing, predicting, and/or monitoring the status or outcome of a cancer may comprise determining the efficacy of treatment. In some embodiments, diagnosing, predicting, and/or monitoring the status or outcome of a cancer may comprise determining a therapeutic regimen. Determining a therapeutic regimen may comprise administering an anti-cancer therapeutic. Alternatively, determining the treatment for the cancer may comprise modifying a therapeutic regimen. Modifying a therapeutic regimen may comprise increasing, decreasing, or terminating a therapeutic regimen.

Further disclosed, in some embodiments, is a method for determining a treatment for a cancer in a subject, comprising: (a) assaying an expression level in a sample from the subject for a plurality of targets, wherein (i) the plurality of targets comprises a coding target and a non-coding target; and (ii) the non-coding target is a non-coding RNA transcript selected from the group consisting of piRNA, tiRNA, PASR, TASR, aTASR, TSSa-RNA, snRNA, RE-RNA, uaRNA, x-ncRNA, hY RNA, usRNA, snaR, vtRNA, T-UCRs, pseudogenes, GRC-RNAs, aRNAs, PALRs, PROMPTs, and LSINCTs; and (b) determining the treatment for a cancer based on the expression levels of the plurality of targets. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the cancer is a prostate cancer. In some embodiments, the cancer is a pancreatic cancer. In some embodiments, the cancer is a bladder cancer. In some embodiments, the cancer is a thyroid cancer. In some embodiments, the cancer is a lung cancer. In some embodiments, the coding target is selected from a sequence listed in Table 6. In some embodiments, the coding target is an exon-coding transcript. In some embodiments, the exon-coding transcript is an exonic sequence. In some embodiments, the non-coding target is selected from a sequence listed in Table 6. The plurality of targets can comprise a coding target and/or a non-coding target selected from SEQ ID NOs.: 1-903. In some instances, the plurality of targets comprises a coding target and/or a non-coding target selected SEQ ID NOs.: 1-352. Alternatively, the plurality of targets comprises a coding target and/or a non-coding target selected from SEQ ID NOs.: 353-441. In other instances, the plurality of targets comprises a coding target and/or a non-coding target selected from SEQ ID NOs.: 322-352. Alternatively, the plurality of targets comprises a coding target and/or a non-coding target selected from SEQ ID NOs.: 292-321. Optionally, the plurality of targets comprises a coding target and/or a non-coding target selected from SEQ ID NOs.: 231-261. In some instances, the plurality of targets comprises a coding target and/or a non-coding target located on chr2q31.3. In some instances, the coding target and/or non-coding target located on chr2q31.3 is selected from SEQ ID NOs.: 262-291. In some embodiments, the non-coding RNA transcript is snRNA. In some embodiments, the non-coding target and the coding target are nucleic acid sequences. In some embodiments, the nucleic acid sequence is a DNA sequence. In some embodiments, the nucleic acid sequence is an RNA sequence. In some embodiments, the method further comprises assaying an expression level of a lincRNA. In some embodiments, the method further comprises further comprising assaying an expression level of a siRNA. In some embodiments, the method further comprises assaying an expression level of a snoRNA. In some embodiments, the method further comprises assaying an expression level of a non-exonic sequence listed in Table 6. In some embodiments, determining the treatment for the cancer includes determining the efficacy of treatment. Determining the treatment for the cancer may comprise administering an anti-cancer therapeutic. Alternatively, determining the treatment for the cancer may comprise modifying a therapeutic regimen. Modifying a therapeutic regimen may comprise increasing, decreasing, or terminating a therapeutic regimen.

Further disclosed herein, in some embodiments, is a method of determining a treatment for a cancer in a subject, comprising: (a) assaying an expression level in a sample from the subject for a plurality of targets, wherein (i) the plurality of targets comprises a coding target and a non-coding target; (ii) the non-coding target is not selected from the group consisting of a miRNA, an intronic sequence, and a UTR sequence; and (b) determining the treatment for a cancer based on the expression levels of the plurality of targets. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the cancer is a prostate cancer. In some embodiments, the cancer is a pancreatic cancer. In some embodiments, the cancer is a bladder cancer. In some embodiments, the cancer is a thyroid cancer. In some embodiments, the cancer is a lung cancer. In some embodiments, the coding target is selected from a sequence listed in Table 6. The plurality of targets can comprise a coding target and/or a non-coding target selected from SEQ ID NOs.: 1-903. In some instances, the plurality of targets comprises a coding target and/or a non-coding target selected SEQ ID NOs.: 1-352. Alternatively, the plurality of targets comprises a coding target and/or a non-coding target selected from SEQ ID NOs.: 353-441. In other instances, the plurality of targets comprises a coding target and/or a non-coding target selected from SEQ ID NOs.: 322-352. Alternatively, the plurality of targets comprises a coding target and/or a non-coding target selected from SEQ ID NOs.: 292-321. Optionally, the plurality of targets comprises a coding target and/or a non-coding target selected from SEQ ID NOs.:

231-261. In some instances, the plurality of targets comprises a coding target and/or a non-coding target located on chr2q31.3. In some instances, the coding target and/or non-coding target located on chr2q31.3 is selected from SEQ ID NOs.: 262-291. In some embodiments, the coding target is an exon-coding transcript. In some embodiments, the exon-coding transcript is an exonic sequence. In some embodiments, the non-coding target is selected from a sequence listed in Table 6. In some embodiments, the non-coding target is a non-coding RNA transcript. In some embodiments, the non-coding RNA transcript is selected from the group consisting of piRNA, tiRNA, PASR, TASR, aTASR, TSSa-RNA, snRNA, RE-RNA, uaRNA, x-ncRNA, hY RNA, usRNA, snaR, vtRNA, T-UCRs, pseudogenes, GRC-RNAs, aRNAs, PALRs, PROMPTs, and LSINCTs. In some embodiments, the non-coding RNA transcript is snRNA. In some embodiments, the method further comprises assaying an expression level of a lincRNA. In some embodiments, the method further comprises assaying an expression level of a non-exonic sequence listed in Table 6. In some embodiments, the non-coding RNA is not a siRNA. In some embodiments, the non-coding RNA is not a snoRNA. In some embodiments, the non-coding target and the coding target are nucleic acid sequences. In some embodiments, the nucleic acid sequence is a DNA sequence. In some embodiments, the nucleic acid sequence is an RNA sequence. In some embodiments, determining the treatment for the cancer includes determining the efficacy of treatment. Determining the treatment for the cancer may comprise administering an anti-cancer therapeutic. Alternatively, determining the treatment for the cancer may comprise modifying a therapeutic regimen. Modifying a therapeutic regimen may comprise increasing, decreasing, or terminating a therapeutic regimen Further disclosed herein, in some embodiments, is a method of determining a treatment for a cancer in a subject, comprising: (a) assaying an expression level in a sample from the subject for a plurality of targets, wherein the plurality of targets consist essentially of a non-coding target; wherein the non-coding target is selected from the group consisting of a UTR sequence, an intronic sequence, or a non-coding RNA transcript, and wherein the non-coding RNA transcript is selected from the group consisting of piRNA, tiRNA, PASR, TASR, aTASR, TSSa-RNA, snRNA, RE-RNA, uaRNA, x-ncRNA, hY RNA, usRNA, snaR, vtRNA, T-UCRs, pseudogenes, GRC-RNAs, aRNAs, PALRs, PROMPTs, and LSINCTs; and (b) determining the treatment for a cancer based on the expression levels of the plurality of targets. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the cancer is a prostate cancer. In some embodiments, the cancer is a pancreatic cancer. In some embodiments, the cancer is a bladder cancer. In some embodiments, the cancer is a thyroid cancer. In some embodiments, the cancer is a lung cancer. In some embodiments, the non-coding target is selected from a sequence listed in Table 6. The plurality of targets can comprise a coding target and/or a non-coding target selected from SEQ ID NOs.: 1-903. In some instances, the plurality of targets comprises a coding target and/or a non-coding target selected SEQ ID NOs.: 1-352. Alternatively, the plurality of targets comprises a coding target and/or a non-coding target selected from SEQ ID NOs.: 353-441. In other instances, the plurality of targets comprises a coding target and/or a non-coding target selected from SEQ ID NOs.: 322-352. Alternatively, the plurality of targets comprises a coding target and/or a non-coding target selected from SEQ ID NOs.: 292-321. Optionally, the plurality of targets comprises a coding target and/or a non-coding target selected from SEQ ID NOs.: 231-261. In some instances, the plurality of targets comprises a coding target and/or a non-coding target located on chr2q31.3. In some instances, the coding target and/or non-coding target located on chr2q31.3 is selected from SEQ ID NOs.: 262-291. In some embodiments, the non-coding target is an intronic sequence or partially overlaps with an intronic sequence. In some embodiments, the non-coding target is a UTR sequence or partially overlaps with a UTR sequence. In some embodiments, the non-coding target is a non-coding RNA transcript. In some embodiments, the non-coding RNA transcript is snRNA. In some embodiments, the non-coding target is a nucleic acid sequence. In some embodiments, the nucleic acid sequence is a DNA sequence. In some embodiments, the nucleic acid sequence is an RNA sequence. In some embodiments, the method further comprises assaying an expression level of a miRNA. In some embodiments, the method further comprises further comprising assaying an expression level of a siRNA. In some embodiments, the method further comprises assaying an expression level of a snoRNA. In some embodiments, the method further comprises assaying an expression level of a lincRNA. In some embodiments, the method further comprises assaying an expression level of a non-exonic sequence listed in Table 6. In some embodiments, determining the treatment for the cancer includes determining the efficacy of treatment. Determining the treatment for the cancer may comprise administering an anti-cancer therapeutic. Alternatively, determining the treatment for the cancer may comprise modifying a therapeutic regimen. Modifying a therapeutic regimen may comprise increasing, decreasing, or terminating a therapeutic regimen Further disclosed herein, in some embodiments, is a method of determining a treatment for a cancer in a subject, comprising: (a) assaying an expression level in a sample from the subject for a plurality of targets, wherein the plurality of targets comprises a non-coding target, wherein the non-coding target is a non-coding RNA transcript and the non-coding RNA transcript is non-polyadenylated; and (b) determining a treatment for a cancer based on the expression levels of the plurality of targets. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the cancer is a prostate cancer. In some embodiments, the cancer is a pancreatic cancer. In some embodiments, the cancer is a bladder cancer. In some embodiments, the cancer is a thyroid cancer. In some embodiments, the cancer is a lung cancer. In some embodiments, the non-coding target is selected from a sequence listed in Table 6. In some embodiments, the non-coding RNA transcript is selected from the group consisting of PASR, TASR, aTASR, TSSa-RNA, RE-RNA, uaRNA, x-ncRNA, hY RNA, usRNA, snaR, vtRNA, T-UCRs, pseudogenes, GRC-RNAs, aRNAs, PALRs, PROMPTs, and LSINCTs. In some embodiments, the method further comprises assaying an expression level of a coding target. In some embodiments, the coding target is selected from a sequence listed in Table 6. In some embodiments, the coding target is an exon-coding transcript. In some embodiments, the exon-coding transcript is an exonic sequence. In some embodiments, the non-coding target and the coding target are nucleic acid sequences. In some embodiments, the nucleic acid sequence is a DNA sequence. In some embodiments, the nucleic acid sequence is an RNA sequence. In some embodiments, the method further comprises assaying an expression level of a lincRNA. In some embodiments, the method further comprises assaying an expression level of a non-exonic sequence listed in Table 6. The plurality of targets can comprise a coding target and/or a non-coding target selected from SEQ ID NOs.: 1-903. In some instances, the plurality of targets comprises a coding target and/or a non-coding target selected SEQ ID NOs.: 1-352. Alternatively, the plurality of targets comprises a coding target and/or a non-coding target selected from SEQ ID NOs.: 353-441. In other instances, the plurality of targets comprises a coding target and/or a non-coding target selected from SEQ ID NOs.: 322-352. Alternatively, the plurality of targets comprises a coding target and/or a non-coding target selected from SEQ ID NOs.: 292-321. Optionally, the plurality of targets comprises a coding target and/or a non-coding target selected from SEQ ID NOs.: 231-261. In some instances, the plurality of targets comprises a coding target and/or a non-coding target located on chr2q31.3. In some instances, the coding target and/or non-coding target located on chr2q31.3 is selected from SEQ ID NOs.: 262-291. In some embodiments, determining the treatment for the cancer includes determining the efficacy of treatment. Determining the treatment for the cancer may comprise administering an anti-cancer therapeutic. Alternatively, determining the treatment for the cancer may comprise modifying a therapeutic regimen. Modifying a therapeutic regimen may comprise increasing, decreasing, or terminating a therapeutic regimen The methods disclosed herein can use any of the probe sets, probes, ICE blocks, classifiers, PSRs, and primers described herein to provide expression signatures or profiles from a test sample derived from a subject having or suspected of having cancer. In some embodiments, such methods involve contacting a test sample with the probe sets, probes, ICE blocks, classifiers, PSRs, and primers (either in solution or immobilized) under conditions that permit hybridization of the probe(s) or primer(s) to any target nucleic acid(s) present in the test sample and then detecting any probe:target duplexes or primer:target duplexes formed as an indication of the presence of the target nucleic acid in the sample. Expression patterns thus determined can then be compared to one or more reference profiles or signatures. Optionally, the expression pattern can be normalized.

The methods disclosed herein can use any of the probe sets, probes, ICE blocks, classifiers, PSRs, and primers described herein to provide expression signatures or profiles from a test sample derived from a subject to determine the status or outcome of a cancer. The methods disclosed herein can use any of the probe sets, probes, ICE blocks, classifiers, PSRs, and primers described herein to provide expression signatures or profiles from a test sample derived from a subject to classify the cancer as recurrent or non-recurrent. The methods disclosed herein can use any of the probe sets, probes, ICE blocks, classifiers, PSRs, and primers described herein to provide expression signatures or profiles from a test sample derived from a subject to classify the cancer as metastatic or non-metastatic. In some embodiments, such methods involve the specific amplification of target sequences nucleic acid(s) present in the test sample using methods known in the art to generate an expression profile or signature which is then compared to a reference profile or signature.

In some embodiments, the invention further provides for prognosing patient outcome, predicting likelihood of recurrence after prostatectomy and/or for designating treatment modalities.

In one embodiment, the methods generate expression profiles or signatures detailing the expression of the target sequences having altered relative expression with different cancer outcomes. In some embodiments, the methods detect combinations of expression levels of sequences exhibiting positive and negative correlation with a disease status. In one embodiment, the methods detect a minimal expression signature.

The gene expression profiles of each of the target sequences comprising the portfolio can be fixed in a medium such as a computer readable medium. This can take a number of forms. For example, a table can be established into which the range of signals (e.g., intensity measurements) indicative of disease or outcome is input. Actual patient data can then be compared to the values in the table to determine the patient samples diagnosis or prognosis. In a more sophisticated embodiment, patterns of the expression signals (e.g., fluorescent intensity) are recorded digitally or graphically.

The expression profiles of the samples can be compared to a control portfolio. The expression profiles can be used to diagnose, predict, or monitor a status or outcome of a cancer. For example, diagnosing, predicting, or monitoring a status or outcome of a cancer may comprise diagnosing or detecting a cancer, cancer metastasis, or stage of a cancer. In other instances, diagnosing, predicting, or monitoring a status or outcome of a cancer may comprise predicting the risk of cancer recurrence. Alternatively, diagnosing, predicting, or monitoring a status or outcome of a cancer may comprise predicting mortality or morbidity.

Further disclosed herein are methods for characterizing a patient population. Generally, the method comprises: (a) providing a sample from a subject; (b) assaying the expression level for a plurality of targets in the sample; and (c) characterizing the subject based on the expression level of the plurality of targets. In some instances, the plurality of targets comprises one or more coding targets and one or more non-coding targets. In some instances, the coding target comprises an exonic region or a fragment thereof. The non-coding targets can comprise a non-exonic region or a fragment thereof. Alternatively, the non-coding target may comprise the UTR of an exonic region or a fragment thereof. In some embodiments, the non-coding target is selected from a sequence listed in Table 6. The plurality of targets can comprise a coding target and/or a non-coding target selected from SEQ ID NOs.: 1-903. In some instances, the plurality of targets comprises a coding target and/or a non-coding target selected SEQ ID NOs.: 1-352. Alternatively, the plurality of targets comprises a coding target and/or a non-coding target selected from SEQ ID NOs.: 353-441. In other instances, the plurality of targets comprises a coding target and/or a non-coding target selected from SEQ ID NOs.: 322-352. Alternatively, the plurality of targets comprises a coding target and/or a non-coding target selected from SEQ ID NOs.: 292-321. Optionally, the plurality of targets comprises a coding target and/or a non-coding target selected from SEQ ID NOs.: 231-261. In some instances, the plurality of targets comprises a coding target and/or a non-coding target located on chr2q31.3. In some instances, the coding target and/or non-coding target located on chr2q31.3 is selected from SEQ ID NOs.: 262-291. In some embodiments, the non-coding RNA transcript is selected from the group consisting of PASR, TASR, aTASR, TSSa-RNA, RE-RNA, uaRNA, x-ncRNA, hY RNA, usRNA, snaR, vtRNA, T-UCRs, pseudogenes, GRC-RNAs, aRNAs, PALRs, PROMPTs, and LSINCTs. In some embodiments, the method further comprises assaying an expression level of a coding target. In some embodiments, the coding target is selected from a sequence listed in Table 6. In some embodiments, the coding target is an exon-coding transcript. In some embodiments, the exon-coding transcript is an exonic sequence. In some embodiments, the non-coding target and the coding target are nucleic acid sequences. In some embodiments, the nucleic acid sequence is a DNA sequence. In some embodiments, the nucleic acid sequence is an RNA sequence. In some embodiments, the method further comprises assaying an expression level of a lincRNA. In some embodiments, the method further comprises assaying an expression level of a non-exonic sequence listed in Table 6. In some instances, the method may further comprise diagnosing a cancer in the subject. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the cancer is a prostate cancer. In some embodiments, the cancer is a pancreatic cancer. In some embodiments, the cancer is a bladder cancer. In some embodiments, the cancer is a thyroid cancer. In some embodiments, the cancer is a lung cancer. In some instances, characterizing the subject comprises determining whether the subject would respond to an anti-cancer therapy. Alternatively, characterizing the subject comprises identifying the subject as a non-responder to an anti-cancer therapy. Optionally, characterizing the subject comprises identifying the subject as a responder to an anti-cancer therapy.

Further disclosed herein are methods for selecting a subject suffering from a cancer for enrollment into a clinical trial. Generally, the method comprises: (a) providing a sample from a subject; (b) assaying the expression level for a plurality of targets in the sample; and (c) characterizing the subject based on the expression level of the plurality of targets. In some instances, the plurality of targets comprises one or more coding targets and one or more non-coding targets. In some instances, the coding target comprises an exonic region or a fragment thereof. The non-coding targets can comprise a non-exonic region or a fragment thereof. Alternatively, the non-coding target may comprise the UTR of an exonic region or a fragment thereof. In some embodiments, the non-coding target is selected from a sequence listed in Table 6. The plurality of targets can comprise a coding target and/or a non-coding target selected from SEQ ID NOs.: 1-903. In some instances, the plurality of targets comprises a coding target and/or a non-coding target selected SEQ ID NOs.: 1-352. Alternatively, the plurality of targets comprises a coding target and/or a non-coding target selected from SEQ ID NOs.: 353-441. In other instances, the plurality of targets comprises a coding target and/or a non-coding target selected from SEQ ID NOs.: 322-352. Alternatively, the plurality of targets comprises a coding target and/or a non-coding target selected from SEQ ID NOs.: 292-321. Optionally, the plurality of targets comprises a coding target and/or a non-coding target selected from SEQ ID NOs.: 231-261. In some instances, the plurality of targets comprises a coding target and/or a non-coding target located on chr2q31.3. In some instances, the coding target and/or non-coding target located on chr2q31.3 is selected from SEQ ID NOs.: 262-291. In some embodiments, the non-coding RNA transcript is selected from the group consisting of PASR, TASR, aTASR, TSSa-RNA, RE-RNA, uaRNA, x-ncRNA, hY RNA, usRNA, snaR, vtRNA, T-UCRs, pseudogenes, GRC-RNAs, aRNAs, PALRs, PROMPTs, and LSINCTs. In some embodiments, the method further comprises assaying an expression level of a coding target. In some embodiments, the coding target is selected from a sequence listed in Table 6. In some embodiments, the coding target is an exon-coding transcript. In some embodiments, the exon-coding transcript is an exonic sequence. In some embodiments, the non-coding target and the coding target are nucleic acid sequences. In some embodiments, the nucleic acid sequence is a DNA sequence. In some embodiments, the nucleic acid sequence is an RNA sequence. In some embodiments, the method further comprises assaying an expression level of a lincRNA. In some embodiments, the method further comprises assaying an expression level of a non-exonic sequence listed in Table 6. In some instances, the method may further comprise diagnosing a cancer in the subject. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the cancer is a prostate cancer. In some embodiments, the cancer is a pancreatic cancer. In some embodiments, the cancer is a bladder cancer. In some embodiments, the cancer is a thyroid cancer. In some embodiments, the cancer is a lung cancer. In some instances, characterizing the subject comprises determining whether the subject would respond to an anti-cancer therapy. Alternatively, characterizing the subject comprises identifying the subject as a non-responder to an anti-cancer therapy. Optionally, characterizing the subject comprises identifying the subject as a responder to an anti-cancer therapy.

Further disclosed herein are probe sets comprising one or more probes, wherein the one or more probes hybridize to one or more targets selected from Tables 4, 6-8, 14, 15, 17, 19, 22, 23, 26-30, or any combination thereof. In some instances, the probe sets comprise one or more probes, wherein the one or more probes hybridize to at least about 2 targets selected from Tables 4, 6-8, 14, 15, 17, 19, 22, 23, 26-30, or any combination thereof. Alternatively, or additionally, the probe sets comprise one or more probes, wherein the one or more probes hybridize to at least about 3 targets selected from Tables 4, 6-8, 14, 15, 17, 19, 22, 23, 26-30, or any combination thereof. The probe sets can comprise one or more probes, wherein the one or more probes hybridize to at least about 5 targets selected from Tables 4, 6-8, 14, 15, 17, 19, 22, 23, 26-30, or any combination thereof. The probe sets can comprise one or more probes, wherein the one or more probes hybridize to at least about 10 targets selected from Tables 4, 6-8, 14, 15, 17, 19, 22, 23, 26-30, or any combination thereof. The probe sets can comprise one or more probes, wherein the one or more probes hybridize to at least about 15 targets selected from Tables 4, 6-8, 14, 15, 17, 19, 22, 23, 26-30, or any combination thereof. The probe sets can comprise one or more probes, wherein the one or more probes hybridize to at least about 20 targets selected from Tables 4, 6-8, 14, 15, 17, 19, 22, 23, 26-30, or any combination thereof. The probe sets can comprise one or more probes, wherein the one or more probes hybridize to at least about 25 targets selected from Tables 4, 6-8, 14, 15, 17, 19, 22, 23, 26-30, or any combination thereof. In some instances, the probe sets comprise one or more probes, wherein the one or more probes hybridize to at least about 30, 40, 50, 60, 70, 80, 90, 100, 125, 150, 175, 200, 225, 250, 275, 300, 325, 350, 375, 400, or 425 targets selected from Tables 4, 6-8, 14, 15, 17, 19, 22, 23, 26-30, or any combination thereof. In other instances, the probe sets comprise one or more probes, wherein the one or more probes hybridize to at least about 450, 475, 500, 525, 550, 575, 600, 625, 650, 675, 700, 725, 750, 775, 800, 825, 850, 875, or 900 targets selected from Tables 4, 6-8, 14, 15, 17, 19, 22, 23, 26-30, or any combination thereof.

In some instances, the probe sets disclosed herein comprise one or more probes, wherein the sequence of the one or more probes is identical to at least a portion of a sequence selected from SEQ ID NOs.: 1-903. In some instances, the probe sets comprise one or more probes, wherein the sequence of the one or more probes is identical to at least a portion of a sequence selected from SEQ ID NOs.: 1-352. Alternatively, the probe sets comprise one or more probes, wherein the sequence of the one or more probes is identical to at least a portion of a sequence selected from SEQ ID NOs.: 353-441. The probe sets can comprise one or more probes, wherein the sequence of the one or more probes is identical to at least a portion of a sequence selected from SEQ ID NOs.: 353-361, 366, 369, 383-385, 387, 390, 391, 397-399, 410, 411, 421, 422, 434, 436, 458, and 459. In other instances, the probe sets comprise one or more probes, wherein the sequence of the one or more probes is identical to at least a portion of a sequence selected from SEQ ID NOs.: 322-352. Alternatively, the probe sets comprise one or more probes, wherein the sequence of the one or more probes is identical to at least a portion of a sequence selected from SEQ ID NOs.: 292-321. The probe sets can comprise one or more probes, wherein the sequence of the one or more probes is identical to at least a portion of a sequence selected from SEQ ID NOs.: 460-480. The probe sets can comprise one or more probes, wherein the sequence of the one or more probes is identical to at least a portion of a sequence selected from SEQ ID NOs.: 293, 297, 300, 303, 309, 311, 312, 316, and 481-642. Optionally, the probe sets comprise one or more probes, wherein the sequence of the one or more probes is identical to at least a portion of a sequence selected from SEQ ID NOs.: 231-261. The probe sets can comprise one or more probes, wherein the sequence of the one or more probes is identical to at least a portion of a sequence selected from SEQ ID NOs.: 442-457. In some instances, the probe sets comprise one or more probes, wherein the sequence of the one or more probes is identical to at least a portion of a sequence selected from SEQ ID NOs.: 436, 643-721. The probe sets can comprise one or more probes, wherein the sequence of the one or more probes is identical to at least a portion of a sequence selected from SEQ ID NOs.: 722-801. The probe sets can comprise one or more probes, wherein the sequence of the one or more probes is identical to at least a portion of a sequence selected from SEQ ID NOs.: 653, 663, 685 and 802-878. In some instances, the probe sets comprise one or more probes, wherein the sequence of the one or more probes is identical to at least a portion of a sequence selected from SEQ ID NOs.: 879-903. In some instances, the probe sets comprise one or more probes, wherein the one or more probes hybridize to one or more targets located on chr2q31.3. In some instances, the one or more targets located on chr2q31.3 selected from SEQ ID NOs.: 262-291.

In some instances, the probe sets comprise one or more probes, wherein the sequence of the one or more probes is complementary to at least a portion of a sequence selected from SEQ ID NOs.: 1-903. In some instances, the probe sets comprise one or more probes, wherein the sequence of the one or more probes is complementary to at least a portion of a sequence selected from SEQ ID NOs.: 1-352. Alternatively, the probe sets comprise one or more probes, wherein the sequence of the one or more probes is complementary to at least a portion of a sequence selected from SEQ ID NOs.: 353-441. The probe sets can comprise one or more probes, wherein the sequence of the one or more probes is complementary to at least a portion of a sequence selected from SEQ ID NOs.: 353-361, 366, 369, 383-385, 387, 390, 391, 397-399, 410, 411, 421, 422, 434, 436, 458, and 459. In other instances, the probe sets comprise one or more probes, wherein the sequence of the one or more probes is complementary to at least a portion of a sequence selected from SEQ ID NOs.: 322-352. Alternatively, the probe sets comprise one or more probes, wherein the sequence of the one or more probes is complementary to at least a portion of a sequence selected from SEQ ID NOs.: 292-321. The probe sets can comprise one or more probes, wherein the sequence of the one or more probes is complementary to at least a portion of a sequence selected from SEQ ID NOs.: 460-480. The probe sets can comprise one or more probes, wherein the sequence of the one or more probes is complementary to at least a portion of a sequence selected from SEQ ID NOs.: 293, 297, 300, 303, 309, 311, 312, 316, and 481-642. Optionally, the probe sets comprise one or more probes, wherein the sequence of the one or more probes is complementary to at least a portion of a sequence selected from SEQ ID NOs.: 231-261. The probe sets can comprise one or more probes, wherein the sequence of the one or more probes is complementary to at least a portion of a sequence selected from SEQ ID NOs.: 442-457. In some instances, the probe sets comprise one or more probes, wherein the sequence of the one or more probes is complementary to at least a portion of a sequence selected from SEQ ID NOs.: 436, 643-721. The probe sets can comprise one or more probes, wherein the sequence of the one or more probes is complementary to at least a portion of a sequence selected from SEQ ID NOs.: 722-801. The probe sets can comprise one or more probes, wherein the sequence of the one or more probes is complementary to at least a portion of a sequence selected from SEQ ID NOs.: 653, 663, 685 and 802-878. In some instances, the probe sets comprise one or more probes, wherein the sequence of the one or more probes is complementary to at least a portion of a sequence selected from SEQ ID NOs.: 879-903.

Further disclosed herein are classifiers comprising one or more targets selected from Tables 4, 6-8, 14, 15, 17, 19, 22, 23, 26-30, or any combination thereof. In some instances, the classifiers comprise at least about 2 targets selected from Tables 4, 6-8, 14, 15, 17, 19, 22, 23, 26-30, or any combination thereof. Alternatively, or additionally, the classifiers comprise at least about 3 targets selected from Tables 4, 6-8, 14, 15, 17, 19, 22, 23, 26-30, or any combination thereof. The classifiers can comprise at least about 5 targets selected from Tables 4, 6-8, 14, 15, 17, 19, 22, 23, 26-30, or any combination thereof. The classifiers can comprise at least about 10 targets selected from Tables 4, 6-8, 14, 15, 17, 19, 22, 23, 26-30, or any combination thereof. The classifiers can comprise at least about 15 targets selected from Tables 4, 6-8, 14, 15, 17, 19, 22, 23, 26-30, or any combination thereof. The classifiers can comprise at least about 20 targets selected from Tables 4, 6-8, 14, 15, 17, 19, 22, 23, 26-30, or any combination thereof. The classifiers can comprise at least about 25 targets selected from Tables 4, 6-8, 14, 15, 17, 19, 22, 23, 26-30, or any combination thereof. In some instances, the classifiers comprise at least about 30, 40, 50, 60, 70, 80, 90, 100, 125, 150, 175, 200, 225, 250, 275, 300, 325, 350, 375, 400, or 425 targets selected from Tables 4, 6-8, 14, 15, 17, 19, 22, 23, 26-30, or any combination thereof. In other instances, the classifiers comprise at least about 450, 475, 500, 525, 550, 575, 600, 625, 650, 675, 700, 725, 750, 775, 800, 825, 850, 875, or 900 targets selected from Tables 4, 6-8, 14, 15, 17, 19, 22, 23, 26-30, or any combination thereof. In some instances, the classifiers comprise a classifier selected from Table 17. Alternatively, or additionally, the classifiers comprise a classifier selected from Table 19.

In some instances, the classifiers comprise one or more targets comprising a sequence that at least partially overlaps with a sequence selected from SEQ ID NOs.: 1-903. In some instances, the classifiers comprise one or more targets comprising a sequence that at least partially overlaps with a sequence selected from SEQ ID NOs.: 1-352. Alternatively, the classifiers comprise one or more targets comprising a sequence that at least partially overlaps with a sequence selected from SEQ ID NOs.: 353-441. The classifiers can comprise one or more targets comprising a sequence that at least partially overlaps with a sequence selected from SEQ ID NOs.: 353-361, 366, 369, 383-385, 387, 390, 391, 397-399, 410, 411, 421, 422, 434, 436, 458, and 459. In other instances, the classifiers comprise one or more targets comprising a sequence that at least partially overlaps with a sequence selected from SEQ ID NOs.: 322-352. Alternatively, the classifiers comprise one or more targets comprising a sequence that at least partially overlaps with a sequence selected from SEQ ID NOs.: 292-321. The classifiers can comprise one or more targets comprising a sequence that at least partially overlaps with a sequence selected from SEQ ID NOs.: 460-480. The classifiers can comprise one or more targets comprising a sequence that at least partially overlaps with a sequence selected from SEQ ID NOs.: 293, 297, 300, 303, 309, 311, 312, 316, and 481-642. Optionally, the classifiers comprise one or more targets comprising a sequence that at least partially overlaps with a sequence selected from SEQ ID NOs.: 231-261. The classifiers can comprise one or more targets comprising a sequence that at least partially overlaps with a sequence selected from SEQ ID NOs.: 442-457. In some instances, the classifiers comprise one or more targets comprising a sequence that at least partially overlaps with a sequence selected from SEQ ID NOs.: 436, 643-721. The classifiers can comprise one or more targets comprising a sequence that at least partially overlaps with a sequence selected from SEQ ID NOs.: 722-801. The classifiers can comprise one or more targets comprising a sequence that at least partially overlaps with a sequence selected from SEQ ID NOs.: 653, 663, 685 and 802-878. In some instances, the classifiers comprise one or more targets comprising a sequence that at least partially overlaps with a sequence selected from SEQ ID NOs.: 879-903. In some instances, the classifiers comprise one or more targets located on chr2q31.3. In some instances, the one or more targets located on chr2q31.3 selected from SEQ ID NOs.: 262-291.

In some instances, the classifiers comprise one or more targets comprising a sequence that is complementary to at least a portion of a sequence selected from SEQ ID NOs.: 1-903. In some instances, the classifiers comprise one or more targets comprising a sequence that is complementary to at least a portion of a sequence selected from SEQ ID NOs.: 1-352. Alternatively, the classifiers comprise one or more targets comprising a sequence that is complementary to at least a portion of a sequence selected from SEQ ID NOs.: 353-441. The classifiers can comprise one or more targets comprising a sequence that is complementary to at least a portion of a sequence selected from SEQ ID NOs.: 353-361, 366, 369, 383-385, 387, 390, 391, 397-399, 410, 411, 421, 422, 434, 436, 458, and 459. In other instances, the classifiers comprise one or more targets comprising a sequence that is complementary to at least a portion of a sequence selected from SEQ ID NOs.: 322-352. Alternatively, the classifiers comprise one or more targets comprising a sequence that is complementary to at least a portion of a sequence selected from SEQ ID NOs.: 292-321. The classifiers can comprise one or more targets comprising a sequence that is complementary to at least a portion of a sequence selected from SEQ ID NOs.: 460-480. The classifiers can comprise one or more targets comprising a sequence that is complementary to at least a portion of a sequence selected from SEQ ID NOs.: 293, 297, 300, 303, 309, 311, 312, 316, and 481-642. Optionally, the classifiers comprise one or more targets comprising a sequence that is complementary to at least a portion of a sequence selected from SEQ ID NOs.: 231-261. The classifiers can comprise one or more targets comprising a sequence that is complementary to at least a portion of a sequence selected from SEQ ID NOs.: 442-457. In some instances, the classifiers comprise one or more targets comprising a sequence that is complementary to at least a portion of a sequence selected from SEQ ID NOs.: 436, 643-721. The classifiers can comprise one or more targets comprising a sequence that is complementary to at least a portion of a sequence selected from SEQ ID NOs.: 722-801. The classifiers can comprise one or more targets comprising a sequence that is complementary to at least a portion of a sequence selected from SEQ ID NOs.: 653, 663, 685 and 802-878. In some instances, the classifiers comprise one or more targets comprising a sequence that is complementary to at least a portion of a sequence selected from SEQ ID NOs.: 879-903.

In some instances, the classifiers disclosed herein have an AUC value of at least about 0.50. In other instances, the classifiers disclosed herein have an AUC value of at least about 0.55. The classifiers disclosed herein can have an AUC value of at least about 0.60. Alternatively, the classifiers disclosed herein have an AUC value of at least about 0.65. In some instances, the classifiers disclosed herein have an AUC value of at least about 0.70. In other instances, the classifiers disclosed herein have an AUC value of at least about 0.75. The classifiers disclosed herein can have an AUC value of at least about 0.80. Alternatively, the classifiers disclosed herein have an AUC value of at least about 0.85. The classifiers disclosed herein can have an AUC value of at least about 0.90. In some instances, the classifiers disclosed herein have an AUC value of at least about 0.95.

The probe sets, probes, PSRs, primers, ICE blocks, and classifiers disclosed herein can diagnose, predict, and/or monitor the status or outcome of a cancer in a subject with an accuracy of at least about 50%. In some instances, the probe sets, probes, PSRs, primers, ICE blocks, and classifiers disclosed herein diagnose, predict, and/or monitor the status or outcome of a cancer in a subject with an accuracy of at least about 55%. In other instances, the probe sets, probes, PSRs, primers, ICE blocks, and classifiers disclosed herein diagnose, predict, and/or monitor the status or outcome of a cancer in a subject with an accuracy of at least about 60%. Alternatively, the probe sets, probes, PSRs, primers, ICE blocks, and classifiers disclosed herein diagnose, predict, and/or monitor the status or outcome of a cancer in a subject with an accuracy of at least about 65%. The probe sets, probes, PSRs, primers, ICE blocks, and classifiers disclosed herein can diagnose, predict, and/or monitor the status or outcome of a cancer in a subject with an accuracy of at least about 68%. In some instances, the probe sets, probes, PSRs, primers, ICE blocks, and classifiers disclosed herein diagnose, predict, and/or monitor the status or outcome of a cancer in a subject with an accuracy of at least about 69%. In other instances, the probe sets, probes, PSRs, primers, ICE blocks, and classifiers disclosed herein diagnose, predict, and/or monitor the status or outcome of a cancer in a subject with an accuracy of at least about 70%. Alternatively, the probe sets, probes, PSRs, primers, ICE blocks, and classifiers disclosed herein diagnose, predict, and/or monitor the status or outcome of a cancer in a subject with an accuracy of at least about 71%. The probe sets, probes, PSRs, primers, ICE blocks, and classifiers disclosed herein can diagnose, predict, and/or monitor the status or outcome of a cancer in a subject with an accuracy of at least about 72%. In some instances, the probe sets, probes, PSRs, primers, ICE blocks, and classifiers disclosed herein diagnose, predict, and/or monitor the status or outcome of a cancer in a subject with an accuracy of at least about 73%. In other instances, the probe sets, probes, PSRs, primers, ICE blocks, and classifiers disclosed herein diagnose, predict, and/or monitor the status or outcome of a cancer in a subject with an accuracy of at least about 74%. Alternatively, the probe sets, probes, PSRs, primers, ICE blocks, and classifiers disclosed herein diagnose, predict, and/or monitor the status or outcome of a cancer in a subject with an accuracy of at least about 75%. The probe sets, probes, PSRs, primers, ICE blocks, and classifiers disclosed herein can diagnose, predict, and/or monitor the status or outcome of a cancer in a subject with an accuracy of at least about 76%. In some instances, the probe sets, probes, PSRs, primers, ICE blocks, and classifiers disclosed herein diagnose, predict, and/or monitor the status or outcome of a cancer in a subject with an accuracy of at least about 77%. In other instances, the probe sets, probes, PSRs, primers, ICE blocks, and classifiers disclosed herein diagnose, predict, and/or monitor the status or outcome of a cancer in a subject with an accuracy of at least about 78%. Alternatively, the probe sets, probes, PSRs, primers, ICE blocks, and classifiers disclosed herein diagnose, predict, and/or monitor the status or outcome of a cancer in a subject with an accuracy of at least about 79%. The probe sets, probes, PSRs, primers, ICE blocks, and classifiers disclosed herein can diagnose, predict, and/or monitor the status or outcome of a cancer in a subject with an accuracy of at least about 80%. In some instances, the probe sets, probes, PSRs, primers, ICE blocks, and classifiers disclosed herein diagnose, predict, and/or monitor the status or outcome of a cancer in a subject with an accuracy of at least about 81%. In other instances, the probe sets, probes, PSRs, primers, ICE blocks, and classifiers disclosed herein diagnose, predict, and/or monitor the status or outcome of a cancer in a subject with an accuracy of at least about 82%. Alternatively, the probe sets, probes, PSRs, primers, ICE blocks, and classifiers disclosed herein diagnose, predict, and/or monitor the status or outcome of a cancer in a subject with an accuracy of at least about 83%. The probe sets, probes, PSRs, primers, ICE blocks, and classifiers disclosed herein can diagnose, predict, and/or monitor the status or outcome of a cancer in a subject with an accuracy of at least about 84%. In some instances, the probe sets, probes, PSRs, primers, ICE blocks, and classifiers disclosed herein diagnose, predict, and/or monitor the status or outcome of a cancer in a subject with an accuracy of at least about 85%. In other instances, the probe sets, probes, PSRs, primers, ICE blocks, and classifiers disclosed herein diagnose, predict, and/or monitor the status or outcome of a cancer in a subject with an accuracy of at least about 86%. Alternatively, the probe sets, probes, PSRs, primers, ICE blocks, and classifiers disclosed herein diagnose, predict, and/or monitor the status or outcome of a cancer in a subject with an accuracy of at least about 87%. The probe sets, probes, PSRs, primers, ICE blocks, and classifiers disclosed herein can diagnose, predict, and/or monitor the status or outcome of a cancer in a subject with an accuracy of at least about 88%. In some instances, the probe sets, probes, PSRs, primers, ICE blocks, and classifiers disclosed herein diagnose, predict, and/or monitor the status or outcome of a cancer in a subject with an accuracy of at least about 90%. In other instances, the probe sets, probes, PSRs, primers, ICE blocks, and classifiers disclosed herein diagnose, predict, and/or monitor the status or outcome of a cancer in a subject with an accuracy of at least about 93%. Alternatively, the probe sets, probes, PSRs, primers, ICE blocks, and classifiers disclosed herein diagnose, predict, and/or monitor the status or outcome of a cancer in a subject with an accuracy of at least about 95%. The probe sets, probes, PSRs, primers, ICE blocks, and classifiers disclosed herein can diagnose, predict, and/or monitor the status or outcome of a cancer in a subject with an accuracy of at least about 97%.

Disclosed herein, in some embodiments, are methods for diagnosing, predicting, and/or monitoring a status or outcome of a cancer in a subject, comprising: (a) assaying an expression level in a sample from the subject for one or more targets, wherein the one or more targets are based on a genomic classifier; and (b) for diagnosing, predicting, and/or monitoring a status or outcome of a cancer based on the expression levels of the one or more targets. The genomic classifier can be any of the genomic classifiers disclosed herein. In some instances, the methods further comprise analysis of one or more clinical variables. The clinical variables can be age, lymphovascular invasion, lymph node involvement and intravesical therapy, or any combination thereof. In some instances, the clinical variable is age. Alternatively, the clinical variable is lymphovascular invasion. The clinical variable can be lymph node involvement. In other instances, the clinical variable is intravesical therapy. In some instances, the methods disclosed herein can predict tumor stage.

Further disclosed herein, in some embodiments, are methods of determining a treatment for a cancer in a subject, comprising: (a) assaying an expression level in a sample from the subject for a one or more targets, wherein the one or more targets are based on a genomic classifier; and (b) determining the treatment for a cancer based on the expression levels of the one or more targets. The genomic classifier can be any of the genomic classifiers disclosed herein. In some instances, the methods further comprise analysis of one or more clinical variables. The clinical variables can be age, lymphovascular invasion, lymph node involvement and intravesical therapy, or any combination thereof. In some instances, the clinical variable is age. Alternatively, the clinical variable is lymphovascular invasion. The clinical variable can be lymph node involvement. In other instances, the clinical variable is intravesical therapy. In some instances, the methods disclosed herein can predict tumor stage.

Further disclosed herein are methods for characterizing a patient population. Generally, the method comprises: (a) providing a sample from a subject; (b) assaying an expression level in a sample from the subject for a one or more targets, wherein the one or more targets are based on a genomic classifier; and (c) characterizing the subject based on the expression level of the one or more targets. The genomic classifier can be any of the genomic classifiers disclosed herein. In some instances, the methods further comprise analysis of one or more clinical variables. The clinical variables can be age, lymphovascular invasion, lymph node involvement and intravesical therapy, or any combination thereof. In some instances, the clinical variable is age. Alternatively, the clinical variable is lymphovascular invasion. The clinical variable can be lymph node involvement. In other instances, the clinical variable is intravesical therapy. In some instances, the methods disclosed herein can predict tumor stage.

Further disclosed herein are methods for selecting a subject suffering from a cancer for enrollment into a clinical trial. Generally, the method comprises: (a) providing a sample from a subject; (b) assaying an expression level in a sample from the subject for a one or more targets, wherein the one or more targets are based on a genomic classifier; and (c) characterizing the subject based on the expression level of the one or more targets. The genomic classifier can be any of the genomic classifiers disclosed herein. In some instances, the methods further comprise analysis of one or more clinical variables. The clinical variables can be age, lymphovascular invasion, lymph node involvement and intravesical therapy, or any combination thereof. In some instances, the clinical variable is age. Alternatively, the clinical variable is lymphovascular invasion. The clinical variable can be lymph node involvement. In other instances, the clinical variable is intravesical therapy. In some instances, the methods disclosed herein can predict tumor stage.

Disclosed herein, in some embodiments, is a system for analyzing a cancer, comprising (a) a probe set comprising a plurality of probes, wherein the plurality of probes comprises (i) a sequence that hybridizes to at least a portion of a non-coding target; or (ii) a sequence that is identical to at least a portion of a non-coding target; and (b) a computer model or algorithm for analyzing an expression level and/or expression profile of the target hybridized to the probe in a sample from a subject suffering from a cancer. In some instances, the plurality of probes further comprises a sequence that hybridizes to at least a portion of a coding target. In some instances, the plurality of probes further comprises a sequence that is identical to at least a portion of a coding target. The coding target and/or non-coding target can be selected from Tables 4, 6-8, 14, 15, 17, 19, 22, 23, and 26-30. The coding target and/or non-coding target can comprise a sequence selected from SEQ ID NOs.: 1-903. The coding target and/or non-coding target can comprise any of the coding targets and/or non-coding targets disclosed herein.

In some instances, the system further comprises an electronic memory for capturing and storing an expression profile. The system can further comprise a computer-processing device, optionally connected to a computer network. The system can further comprise a software module executed by the computer-processing device to analyze an expression profile. The system can further comprise a software module executed by the computer-processing device to compare the expression profile to a standard or control. The system can further comprise a software module executed by the computer-processing device to determine the expression level of the target. In some instances, the system further comprises a machine to isolate the target or the probe from the sample. The system can further comprise a machine to sequence the target or the probe. The system can further comprise a machine to amplify the target or the probe. Alternatively, or additionally, the system comprises a label that specifically binds to the target, the probe, or a combination thereof. The system can further comprise a software module executed by the computer-processing device to transmit an analysis of the expression profile to the individual or a medical professional treating the individual. In some instances, the system further comprises a software module executed by the computer-processing device to transmit a diagnosis or prognosis to the individual or a medical professional treating the individual.

The plurality of probes can hybridize to at least a portion of a plurality or targets. Alternatively, or additionally, the plurality of probes can comprise a sequence that is identical to at least a portion of a sequence of a plurality of targets. The plurality of targets can be selected from Tables 4, 6-8, 14, 15, 17, 19, 22, 23, and 26-30. In some instances, the plurality of targets comprise at least about 5 targets selected from Tables 4, 6-8, 14, 15, 17, 19, 22, 23, and 26-30. In other instances, the plurality of targets comprise at least about 10 targets selected from Tables 4, 6-8, 14, 15, 17, 19, 22, 23, and 26-30. The plurality of targets can comprise at least about 15 targets selected from Tables 4, 6-8, 14, 15, 17, 19, 22, 23, and 26-30. Alternatively, the plurality of targets comprise at least about 20 targets selected from Tables 4, 6-8, 14, 15, 17, 19, 22, 23, and 26-30. The sequences of the plurality of targets can comprise at least about 5 sequences selected from SEQ ID NOs: 1-903. The sequences of the plurality of targets can comprise at least about 10 sequences selected from SEQ ID NOs: 1-903. The sequences of the plurality of targets can comprise at least about 15 sequences selected from SEQ ID NOs: 1-903. The sequences of the plurality of targets can comprise at least about 20 sequences selected from SEQ ID NOs: 1-903.

The cancer can be selected from the group consisting of a carcinoma, sarcoma, leukemia, lymphoma, myeloma, and a CNS tumor. In some instances, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some instances, the cancer is a prostate cancer. In other instances, the cancer is a bladder cancer. Alternatively, the cancer is a thyroid cancer. The cancer can be a colorectal cancer. In some instances, the cancer is a lung cancer.

In some instances, disclosed herein, is a probe set for assessing a cancer status or outcome of a subject comprising a plurality of probes, wherein the probes in the set are capable of detecting an expression level of one or more targets. In some instances, the one or more targets are selected from Tables 4, 6-8, 14, 15, 17, 19, 22, 23, and 26-30. In some instances, the one or more targets comprise a non-coding target. The non-coding target can be an intronic sequence or partially overlaps with an intronic sequence. The non-coding target can comprise a UTR sequence or partially overlaps with a UTR sequence. The non-coding target can be a non-coding RNA transcript and the non-coding RNA transcript is non-polyadenylated. Alternatively, or additionally, the one or more targets comprise a coding target. In some instances, the coding target is an exonic sequence. The non-coding target and/or coding target can be any of the non-coding targets and/or coding targets disclosed herein. The one or more targets can comprise a nucleic acid sequence. The nucleic acid sequence can be a DNA sequence. In other instances, the nucleic acid sequence is an RNA sequence.

Further disclosed herein is a kit for analyzing a cancer, comprising (a) a probe set comprising a plurality of plurality of probes, wherein the plurality of probes can detect one or more targets; and (b) a computer model or algorithm for analyzing an expression level and/or expression profile of the target sequences in a sample. In some instances, the kit further comprises a computer model or algorithm for correlating the expression level or expression profile with disease state or outcome. The kit can further comprise a computer model or algorithm for designating a treatment modality for the individual. Alternatively, the kit further comprises a computer model or algorithm for normalizing expression level or expression profile of the target sequences. The kit can further comprise a computer model or algorithm comprising a robust multichip average (RMA), probe logarithmic intensity error estimation (PLIER), non-linear fit (NLFIT) quantile-based, nonlinear normalization, or a combination thereof.

Assessing the cancer status can comprise assessing cancer recurrence risk. Alternatively, or additionally, assessing the cancer status comprises determining a treatment modality. In some instances, assessing the cancer status comprises determining the efficacy of treatment.

The probes can be between about 15 nucleotides and about 500 nucleotides in length. Alternatively, the probes are between about 15 nucleotides and about 450 nucleotides in length. In some instances, the probes are between about 15 nucleotides and about 400 nucleotides in length. In other instances, the probes are between about 15 nucleotides and about 350 nucleotides in length. The probes can be between about 15 nucleotides and about 300 nucleotides in length. Alternatively, the probes are between about 15 nucleotides and about 250 nucleotides in length. In some instances, the probes are between about 15 nucleotides and about 200 nucleotides in length. In other instances, the probes are at least 15 nucleotides in length. Alternatively, the probes are at least 25 nucleotides in length.

In some instances, the expression level determines the cancer status or outcome of the subject with at least 40% accuracy. The expression level can determine the cancer status or outcome of the subject with at least 50% accuracy. The expression level can determine the cancer status or outcome of the subject with at least 60% accuracy. In some instances, the expression level determines the cancer status or outcome of the subject with at least 65% accuracy. In other instances, the expression level determines the cancer status or outcome of the subject with at least 70% accuracy. Alternatively, the expression level determines the cancer status or outcome of the subject with at least 75% accuracy. The expression level can determine the cancer status or outcome of the subject with at least 80% accuracy. In some instances, the expression level determines the cancer status or outcome of the subject with at least 64% accuracy.

Further disclosed herein is a method of analyzing a cancer in an individual in need thereof, comprising (a) obtaining an expression profile from a sample obtained from the individual, wherein the expression profile comprises one or more targets; and (b) comparing the expression profile from the sample to an expression profile of a control or standard.

Disclosed herein, in some embodiments, is a method of diagnosing cancer in an individual in need thereof, comprising (a) obtaining an expression profile from a sample obtained from the individual, wherein the expression profile comprises one or more targets; (b) comparing the expression profile from the sample to an expression profile of a control or standard; and (c) diagnosing a cancer in the individual if the expression profile of the sample (i) deviates from the control or standard from a healthy individual or population of healthy individuals, or (ii) matches the control or standard from an individual or population of individuals who have or have had the cancer.

Further disclosed herein is a method of predicting whether an individual is susceptible to developing a cancer, comprising (a) obtaining an expression profile from a sample obtained from the individual, wherein the expression profile comprises one or more targets; (b) comparing the expression profile from the sample to an expression profile of a control or standard; and (c) predicting the susceptibility of the individual for developing a cancer based on (i) the deviation of the expression profile of the sample from a control or standard derived from a healthy individual or population of healthy individuals, or (ii) the similarity of the expression profiles of the sample and a control or standard derived from an individual or population of individuals who have or have had the cancer.

Also disclosed herein is a method of predicting an individual's response to a treatment regimen for a cancer, comprising (a) obtaining an expression profile from a sample obtained from the individual, wherein the expression profile comprises one or more targets; (b) comparing the expression profile from the sample to an expression profile of a control or standard; and (c) predicting the individual's response to a treatment regimen based on (i) the deviation of the expression profile of the sample from a control or standard derived from a healthy individual or population of healthy individuals, or (ii) the similarity of the expression profiles of the sample and a control or standard derived from an individual or population of individuals who have or have had the cancer.

Disclosed herein is a method of prescribing a treatment regimen for a cancer to an individual in need thereof, comprising (a) obtaining an expression profile from a sample obtained from the individual, wherein the expression profile comprises one or more targets; (b) comparing the expression profile from the sample to an expression profile of a control or standard; and (c) prescribing a treatment regimen based on (i) the deviation of the expression profile of the sample from a control or standard derived from a healthy individual or population of healthy individuals, or (ii) the similarity of the expression profiles of the sample and a control or standard derived from an individual or population of individuals who have or have had the cancer.

In some instances, the one or more targets are selected from Tables 4, 6-8, 14, 15, 17, 19, 22, 23, and 26-30. In some instances, the one or more targets comprise a non-coding target. The non-coding target can be an intronic sequence or partially overlaps with an intronic sequence. The non-coding target can comprise a UTR sequence or partially overlaps with a UTR sequence. The non-coding target can be a non-coding RNA transcript and the non-coding RNA transcript is non-polyadenylated. Alternatively, or additionally, the one or more targets comprise a coding target. In some instances, the coding target is an exonic sequence. The non-coding target and/or coding target can be any of the non-coding targets and/or coding targets disclosed herein. The one or more targets can comprise a nucleic acid sequence. The nucleic acid sequence can be a DNA sequence. In other instances, the nucleic acid sequence is an RNA sequence. The targets can be differentially expressed in the cancer.

The methods disclosed herein can further comprise a software module executed by a computer-processing device to compare the expression profiles. In some instances, the methods further comprise providing diagnostic or prognostic information to the individual about the cardiovascular disorder based on the comparison. In other instances, the method further comprises diagnosing the individual with a cancer if the expression profile of the sample (i) deviates from the control or standard from a healthy individual or population of healthy individuals, or (ii) matches the control or standard from an individual or population of individuals who have or have had the cancer. Alternatively, or additionally, the methods further comprise predicting the susceptibility of the individual for developing a cancer based on (i) the deviation of the expression profile of the sample from a control or standard derived from a healthy individual or population of healthy individuals, or (ii) the similarity of the expression profiles of the sample and a control or standard derived from an individual or population of individuals who have or have had the cancer. The methods disclosed herein can further comprise prescribing a treatment regimen based on (i) the deviation of the expression profile of the sample from a control or standard derived from a healthy individual or population of healthy individuals, or (ii) the similarity of the expression profiles of the sample and a control or standard derived from an individual or population of individuals who have or have had the cancer.

In some instances, the methods disclosed herein further comprise altering a treatment regimen prescribed or administered to the individual based on (i) the deviation of the expression profile of the sample from a control or standard derived from a healthy individual or population of healthy individuals, or (ii) the similarity of the expression profiles of the sample and a control or standard derived from an individual or population of individuals who have or have had the cancer. In other instances, the methods disclosed herein further comprise predicting the individual's response to a treatment regimen based on (a) the deviation of the expression profile of the sample from a control or standard derived from a healthy individual or population of healthy individuals, or (b) the similarity of the expression profiles of the sample and a control or standard derived from an individual or population of individuals who have or have had the cancer. The deviation can be the expression level of one or more targets from the sample is greater than the expression level of one or more targets from a control or standard derived from a healthy individual or population of healthy individuals. Alternatively, the deviation is the expression level of one or more targets from the sample is at least about 30% greater than the expression level of one or more targets from a control or standard derived from a healthy individual or population of healthy individuals. In other instances, the deviation is the expression level of one or more targets from the sample is less than the expression level of one or more targets from a control or standard derived from a healthy individual or population of healthy individuals. The deviation can be the expression level of one or more targets from the sample is at least about 30% less than the expression level of one or more targets from a control or standard derived from a healthy individual or population of healthy individuals.

The methods disclosed herein can further comprise using a machine to isolate the target or the probe from the sample. In some instances, the method further comprises contacting the sample with a label that specifically binds to the target, the probe, or a combination thereof. The method can further comprise contacting the sample with a label that specifically binds to a target selected from Table 6.

In some instances, the method further comprises amplifying the target, the probe, or any combination thereof. Alternatively, or additionally, the method further comprises sequencing the target, the probe, or any combination thereof. Sequencing can comprise any of the sequencing techniques disclosed herein. In some instances, sequencing comprises RNA-Seq.

The methods disclosed herein can further comprise converting the expression levels of the target sequences into a likelihood score that indicates the probability that a biological sample is from a patient who will exhibit no evidence of disease, who will exhibit systemic cancer, or who will exhibit biochemical recurrence.

EXAMPLES

Example 1: Non-Coding RNAs Discriminate Clinical Outcomes in Prostate Cancer

In this study, we performed whole-transcriptome analysis of a publicly available dataset from different types of normal and cancerous prostate tissue and found numerous previously unreported ncRNAs that can discriminate between clinical disease states. We found, by analysis of the entire transcriptome, differentially expressed ncRNAs that accurately discriminated clinical outcomes such as BCR and metastatic disease.

Materials and Methods

Microarray and Clinical Data

The publically available genomic and clinical data was generated by the Memorial Sloan-Kettering Cancer Center (MSKCC) Prostate Oncogenome Project, previously reported by (Taylor et al., 2010). The Human Exon arrays for 131 primary prostate cancer, 29 normal adjacent and 19 metastatic tissue specimens were downloaded from GEO Omnibus at at the world wide web at ncbi.nlm.nih.gov/geo/series GSE21034. The patient and specimen details for the primary and metastases tissues used in this study were summarized in Table 2. For the analysis of the clinical data, the following ECE statuses were summarized to be concordant with the pathological stage: inv-capsule: ECE, focal: ECE+, established: ECE+.

Microarray Pre-Processing

Normalization and Summarization

After removal of the cell line samples, the frozen Robust Multiarray Average (fRMA) algorithm using custom frozen vectors (McCall M N, et al., 2010, *Biostatistics*, 11:254-53) was used to normalize and summarize the 179 microarray samples. These custom vectors were created using the vector creation methods described in McCall M N, et al. (2011, *Bioinformatics*, 12:369).

Sample Subsets

The normalized and summarized data were partitioned into three groups. The first group contained the matched samples from primary localized prostate cancer tumor and normal adjacent samples (n=58) (used for the normal versus primary comparison). The second group contained all of the samples from metastatic tumors (n=19) and all of the localized prostate cancer specimens which were not matched with normal adjacent samples (n=102) (used for the primary versus metastasis comparison). The third group contained all of the samples from metastatic tumors (n=19) and all of the normal adjacent samples (n=29) (used for the normal versus metastasis comparison).

Feature Selection

Probe sets comprising one or more probes that did not align uniquely to the genome were annotated as 'unreliable' and were excluded from further analysis. After cross hybridization, the PSRs corresponding to the remaining probe sets were subjected to univariate analysis and used in the discovery of differentially expressed PSRs between the labeled groups (primary vs. metastatic, normal adjacent vs. primary and normal versus metastatic). For this analysis, the PSRs were selected as differentially expressed if their Holm adjusted t-test P-value was significant (<0.05).

Feature Evaluation and Model Building

Multidimensional-scaling (Pearson's distance) was used to evaluate the ability of the selected features to segregate samples into clinically relevant clusters based on metastatic events and Gleason scores on the primary samples.

A k-nearest-neighbour (KNN) model (k=1, Pearson's correlation distance metric) was trained on the normal and metastatic samples (n=48) using only the features which were found to be differentially expressed between these two groups.

Re-Annotation of the Human Exon Microarray Probe Sets

In order to properly assess the nature of the PSRs found to be differentially expressed in this study, we re-annotated the PSRs using the xmapcore R package (Yates, 2010) as follows: (i) a PSR was re-annotated as coding, if the PSR overlaps with the coding portion of a protein-coding exon, (ii) a PSR was re-annotated as non-coding, if the PSR overlaps with an untranslated region (UTR), an intron, an intergenic region or a non protein-coding transcript, and (iii) a PSR was re-annotated as non-exonic, if the PSR overlaps with an intron, an intergenic region or a non protein-coding transcript. Further annotation of non-coding transcripts was pursued using Ensembl Biomart.

Statistical Analysis

Survival analysis for biochemical recurrence (BCR) and logistic regression for clinical recurrence were performed using the 'survival' and 'lrm' packages in with default values.

Results

Re-Annotation and Categorization of Coding and Non-Coding Differentially Expressed Features Previous transcriptome-wide assessments of differential expression on prostate tissues in the post-prostatectomy setting have been focused on protein-coding features (see Nakagawa et al., 2008 for a comparison of protein-coding gene-based panels). Human Exon Arrays provided a unique opportunity to explore the differential expression of non-coding parts of the genome, with 75% of their probe sets falling in regions other than protein coding sequences. In this study, we used the publicly available Human Exon Array data set from normal, localized primary and metastatic tissues generated by the MSKCC Prostate Oncogenome Project to explore the potential of non-coding regions in prostate cancer prognosis. Previous attempts on this dataset focused only on mRNA and gene-level analysis and concluded that expression analysis was inadequate for discrimination of outcome groups in primary tumors (Taylor et al., 2010). In order to assess the contribution of ncRNA probe sets in differential expression analysis between sample types, we re-assessed the annotation of all PSRs found to be differentially expressed according to their genomic location and categorized them into coding, non-coding and non-exonic. Briefly, a PSR was classified as coding if it fell in a region that encoded for a protein-coding transcript. Otherwise, the PSR was annotated as non-coding. The 'non-exonic' group referred to a subset of the non-coding that excluded all PSRs that fell in UTRs.

Figure 1:
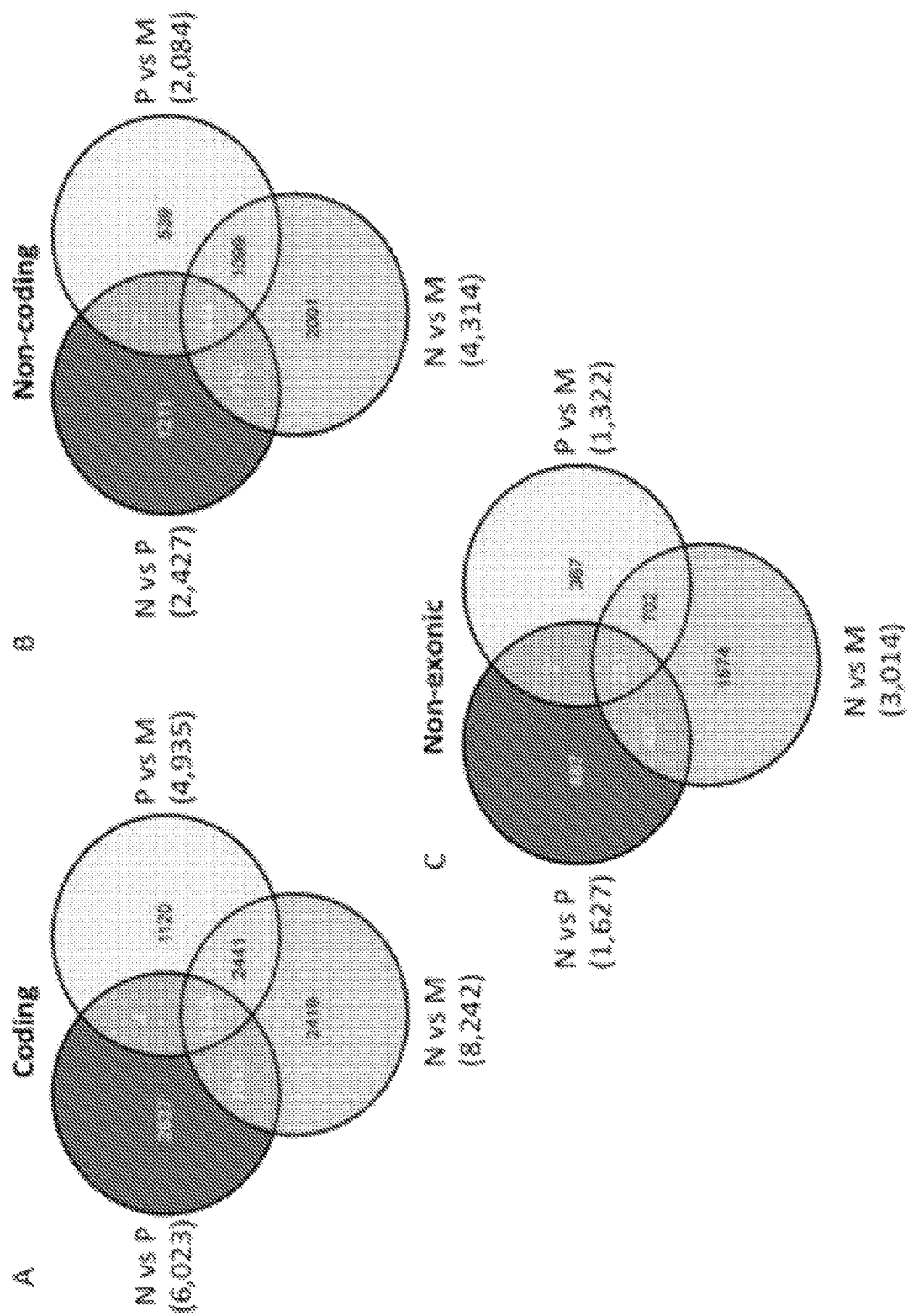
FIG. 1. Venn Diagram of the distribution of coding (a), non-coding (b) and non-exonic (c) PSRs found differentially expressed in normal versus primary tumor tissue (N vs P), primary versus metastatic Tissue (P vs M), and normal versus metastatic tissue (N vs M), respectively.

Based on the above categorization, we assessed each set for the presence of differentially expressed features for each possible pairwise comparison (e.g. primary versus normal, normal versus metastatic and primary versus metastatic). The majority of the differentially expressed PSRs were labeled as 'coding' for a given pairwise comparison (60%, 59% and 53% for normal-primary, primary-metastatic and normal-metastatic comparisons, respectively). For each category, the number of differentially expressed features was highest in normal versus metastatic tissues, which was expected since the metastatic samples have likely undergone major genomic alterations through disease progression as well as possible different expression patterns from interactions with tissues they have metastasized to (FIG. 1). Additionally, for each category there were a significant number of features that were specific to each pairwise comparison. For example, 22% of the coding features were specific to the differentiation between normal and primary and 9% were specific to the primary versus metastatic comparison. The same proportions were observed for the non-coding and non-exonic categories, suggesting that different genomic regions may play a role in the progression from normal to primary and from primary to metastatic.

Figure 2A:
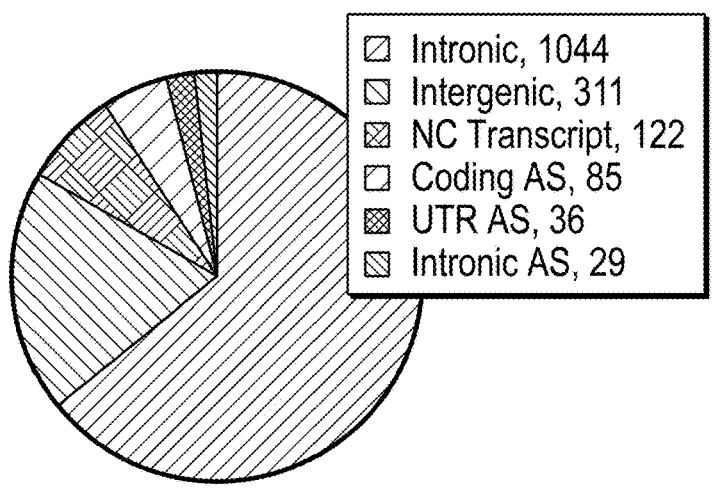
FIG. 2. Annotation of non-exonic PSRs and distribution of non-coding transcripts found to be differentially expressed between normal and primary tumour (a, d), primary tumour and metastatic tissue (b,e) and normal versus metastatic tissue (c,f). Those PSRs in the NC TRANSCRIPT slice of each pie chart are assessed for their overlap with non-coding transcripts to generate the categorization shown at the right for each pairwise comparison. AS: Antisense.
Figure 2B:
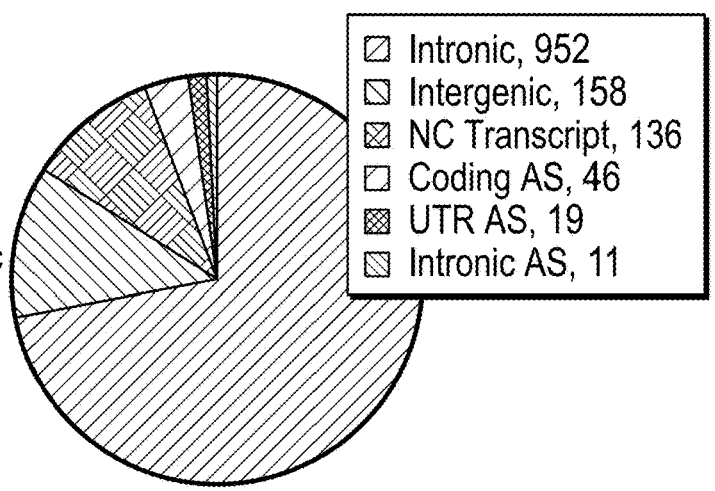
Figure 2C:
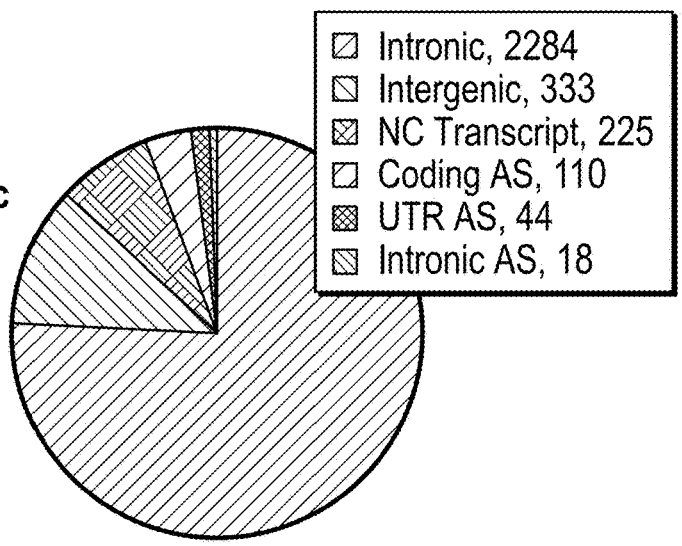
Figure 2D:
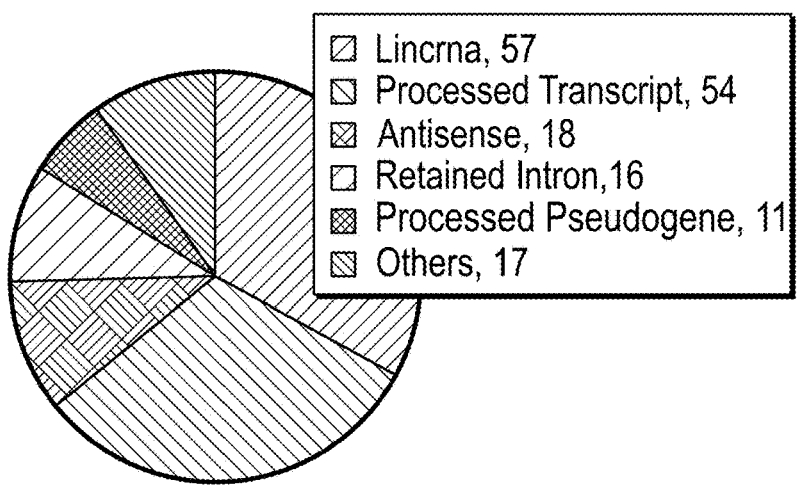
Figure 2E:
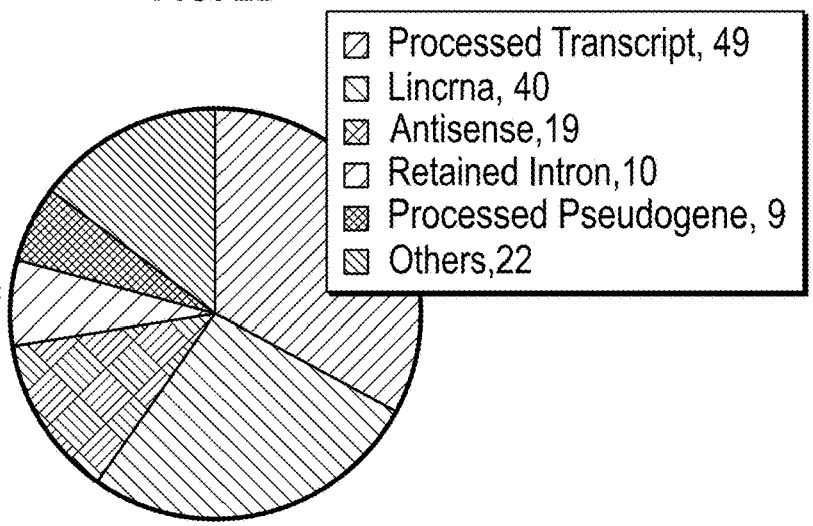
Figure 2F:
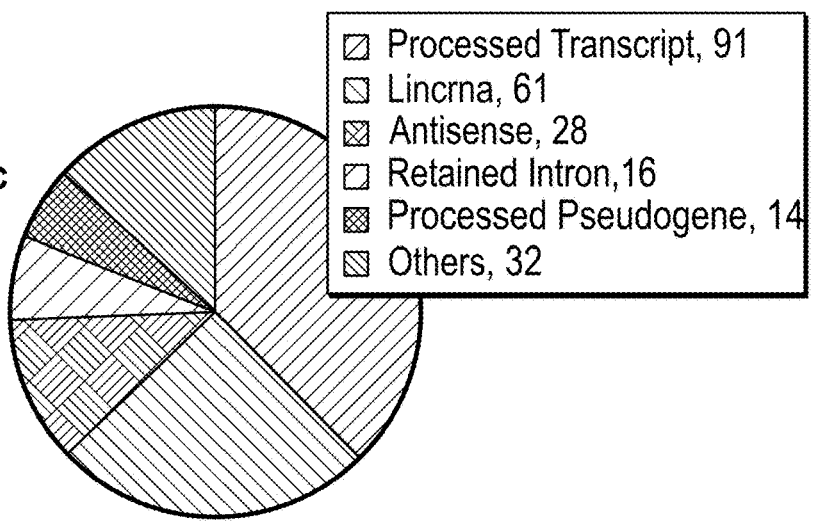

Within the non-coding and non-exonic categories, the majority of the PSRs were 'intronic' for all pairwise comparisons (see FIGS. 2a, 2b and 2c for non-exonic). Also, a large proportion of the PSRs fell in intergenic regions. Still, hundreds of PSRs were found to lie within non-coding transcripts, as reflected by the 'NC Transcript' segment in FIG. 2. The non-coding transcripts found to be differentially expressed in each pairwise comparison were categorized using the 'Transcript Biotype' annotation of Ensembl. For all pairwise comparisons the 'processed transcript', 'lincRNA', 'retained intron', and 'antisense' were the most prevalent (FIG. 2d, FIG. 2e and FIG. 2f; see Table 3 for a definition of each transcript type). Even though 'processed transcript' and 'retained intron' categories were among the most frequent ones, they have a very broad definition.

Previous studies have reported several long non-coding RNAs to be differentially expressed in prostate cancer (Srikantan et al., 2000; Berteaux et al., 2004; Petrovics et al., 2004; Lin et al., 2007; Poliseno et al., 2010; Yap et al., 2010; Chung et al., 2011; Day et al., 2011). Close inspection of our data reveals that four of them (PCGEM1, PCA3, MALAT1 and H19) were differentially expressed (1.5 Median Fold Difference (MFD) threshold) in at least one pairwise comparison (Table 4). After adjusting the P-value for multiple testing however, only seven PSRs from these ncRNA transcripts remain significant (Table 4). In addition, we found two microRNA-encoding transcripts to be differentially expressed in primary tumour versus metastatic (MIR143, MIR145 and MIR221), two in normal versus primary tumour comparison (MIR205 and MIR7) and three in normal versus metastatic (MIR145, MIR205 and MIR221). All these miRNA have been previously reported as differentially expressed in prostate cancer (Clape et al., 2009; Barker et al., 2010; Qin et al., 2010; Szczyrba et al., 2010; Zaman et al., 2010).

Therefore, in addition to the handful of known ncRNAs, our analysis detected many other ncRNAs in regions (e.g., non-coding, non-exonic) that have yet to be explored in prostate cancer and may play a role in the progression of the disease from normal glandular epithelium through distant metastases of prostate cancer.

Assessment of Clinically Significant Prostate Cancer Risk Groups

Figure 3:
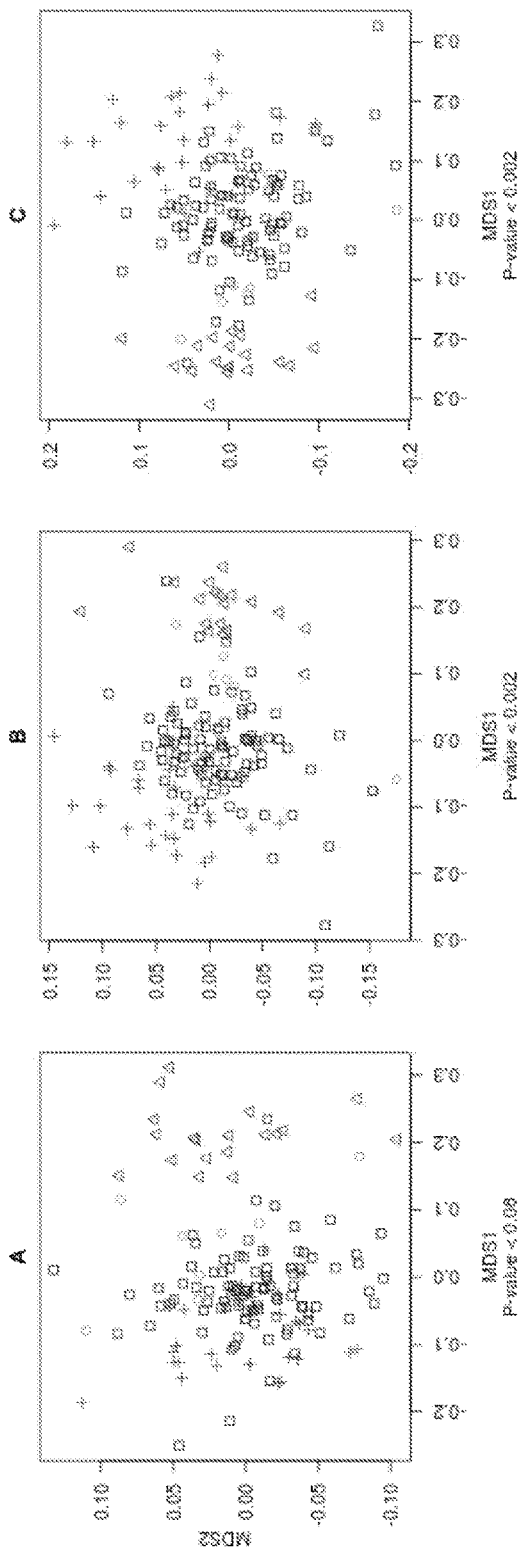
FIG. 3. MDS plots of the distribution of primary tumour samples with (circle) and without (square) metastatic events compared to metastatic (triangle) and normal (+) tissues for coding (a), non-coding (b) and non-exonic (c) probe sets.
Figure 4:
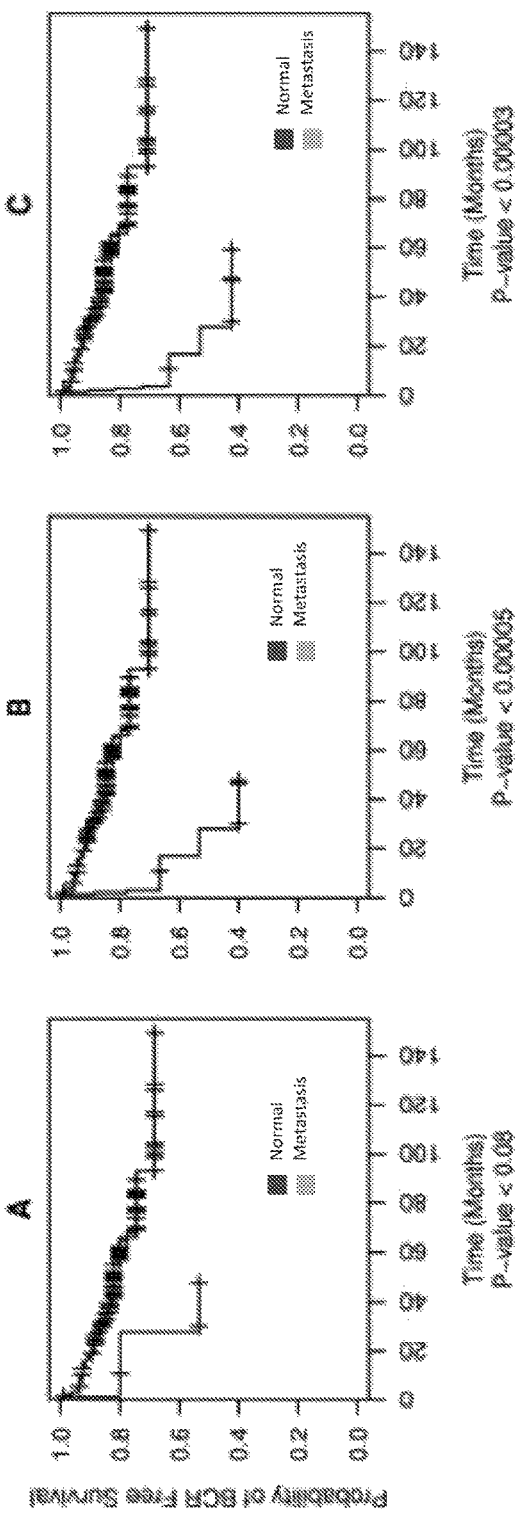
FIG. 4. Kaplan-Meier plots of the two groups of primary tumor samples classified by KNN (more 'normal-like' vs.

Using multidimensional scaling (MDS) we observed that the non-exonic and non-coding subsets of features better segregated primary tumors from patients that progressed to metastatic disease than the coding subset (FIG. 3). Similarly, we found the non-exonic and non-coding subset better discriminated high and low Gleason score samples than the coding subset (FIG. 5). In order to assess the prognostic significance of differentially expressed coding, non-coding and non-exonic features, we developed a k-nearest neighbour (KNN) classifier for each group, trained using features from the comparison of normal and metastatic tissue types (see methods). Next, we used unmatched primary tumors (e.g. removing those tumors that had a matched normal in the training subset) as an independent validation set for the KNN classifier. The higher the KNN score (ranging from 0 to 1), the more likely the patient will be associated to worse outcome. Each primary tumor in the validation set was classified by KNN as either more similar to normal or metastatic tissue. Kaplan-Meier analysis of the two groups of primary tumor samples classified by KNN using the biochemical recurrence (BCR) end point (FIG. 4, 'normal-like'=dark grey line, 'metastatic-like'=light gray line) was done for KNN classifiers derived for each subset of features (e.g., coding, non-coding and non-exonic). As expected, primary tumors classified by KNN as belonging to the metastasis group had a higher rate of BCR. However, we found that for the KNN classifier derived using only the coding subset of features, no statistically significant differences in BCR-free survival were found using log-rank tests for significance (p<0.08) whereas they were highly significant for the non-coding (p<0.00005) and non-exonic (p<0.00003) KNN classifiers. Furthermore, multivariable logistic regression analysis to predict for patients that experienced metastatic disease (e.g., castrate or non-castrate resistant clinical metastatic patients) for each of the three KNN classifiers (e.g., coding, non-coding and non-exonic) was evaluated (Table 5). Adjusting the KNN classifiers for known prognostic clinical variables (e.g. SVI, SMS, Lymph Node Involvement (LNI), pre-treatment PSA values, ECE and Gleason score) revealed that the KNN based on coding feature set had an odds ratio of 2.5 for predicting metastatic disease, but this was not significant ($\chi^2$, p<0.6). The KNN obtained based on the non-coding feature set had a much higher odds ratio of 16 though again being not statistically significant ($\chi^2$, p<0.14). In multivariable analysis, only the KNN based solely on the non-exonic feature set had a statistically significant odds ratio of 30 ($\chi^2$, p<0.05). These results suggest that significantly more predictive information can be obtained from analysis of non-exonic RNAs and that these may have the potential to be used as biomarkers for the prediction of a clinically relevant outcome in primary tumours after prostatectomy.

Discussion

One of the key challenges in prostate cancer was clinical and molecular heterogeneity (Rubin et al., 2011); therefore this common disease provides an appealing opportunity for genomic-based personalized medicine to identify diagnostic, prognostic or predictive biomarkers to assist in clinical decision making. There have been extensive efforts to identify biomarkers based on high-throughput molecular profiling such as protein-coding mRNA expression microarrays (reviewed in Sorenson and Orntoft, 2012), but while many different biomarkers signatures have been identified, none of them were actively being used in clinical practice. The major reason that no new biomarker signatures have widespread use in the clinic was because they fail to show meaningful improvement for prognostication over PSA testing or established pathological variables (e.g., Gleason).

In this study, we assessed the utility of ncRNAs, and particularly non-exonic ncRNAs as potential biomarkers to be used for patients who have undergone prostatectomy but were at risk for recurrent disease and hence further treatment would be considered. We identified many thousands of coding, non-coding and non-exonic RNAs differentially expressed between the different tissue specimens in the MSKCC Oncogenome Project. In a more focused analysis of these feature subset groups (derived from comparison of normal adjacent to primary tumor and metastatic prostate cancer), we found that the coding feature subsets contained substantially less prognostic information than their non-coding counterparts as measured by their ability to discriminate two clinically relevant end-points. First, we observed clustering of those primary tumors from patients that progressed to metastatic disease with true metastatic disease tissue when using the non-exonic features; this was not observed with the coding features. Next, Kaplan-Meier analysis between KNN classifier groups (e.g., more 'normal-like' vs. more 'metastatic-like') among primary tumors showed that only the non-coding and non-exonic feature sets had statistically significant BCR-free survival. Finally, multivariable analysis showed only the non-exonic feature subset KNN classifier was significant after adjusting for established prognostic factors including pre-operative PSA and Gleason scores with an odds ratio of 30 for predicting metastatic disease.

Based on these three main results, we concluded that non-exonic RNAs contain previously unrecognized prognostic information that may be relevant in the clinic for the prediction of cancer progression post-prostatectomy. Perhaps, the reason that previous efforts to develop new biomarker based predictors of outcome in prostate cancer have not translated into the clinic have been because the focus was on mRNA and proteins, largely ignoring the non-coding transcriptome.

These results add to the growing body of literature showing that the 'dark matter' of the genome has potential to shed light on tumor biology, characterize aggressive cancer and improve in the prognosis and prediction of disease progression.

Example 2: Method of Diagnosing a Leukemia in a Subject

A subject arrives at a doctor's office and complains of symptoms including bone and joint pain, easy bruising, and fatigue. The doctor examines the subject and also notices that the subject's lymph nodes were also swollen. Bone marrow and blood samples were obtained from the subject. Microarray analysis of the samples obtained from the subject reveal aberrant expression of a classifier disclosed herein comprising non-coding targets and coding targets and the subject was diagnosed with acute lymphoblastic leukemia.

Example 3: Method of Determining a Treatment for Breast Cancer in a Subject

A subject was diagnosed with breast cancer. A tissue sample was obtained from the subject. Nucleic acids were isolated from the tissue sample and the nucleic acids were applied to a probe set comprising at least ten probes capable of detecting the expression of at least one non-coding target and at least one coding target. Analysis of the expression level of the non-coding targets and coding targets reveals the subject has a tamoxifen-resistant breast cancer and gefitinib was recommended as an alternative therapy.

Example 4: Method of Determining the Prognosis for Pancreatic Cancer in a Subject A subject was diagnosed with pancreatic cancer. A tissue sample was obtained from the subject. The tissue sample was assayed for the expression level of biomarkers comprising at least one non-coding target and at least one coding target. Based on the expression level of the non-coding target, it was determined that the pancreatic cancer has a high risk of recurrence.

Example 5: Method of Diagnosing a Prostate Cancer in a Subject

A subject arrives at a doctor's office and complains of symptoms including inability to urinate standing up, blood in urine, and dull, incessant pain in the pelvis and lower back. The doctor conducts a digital prostate exam and recommends that blood samples were obtained from the subject. The PSA was abnormal, a biopsy was ordered and microarray analysis of the blood and tissue samples obtained from the subject reveal aberrant expression of non-coding targets and the subject was diagnosed with prostate cancer.

Example 6: Method of Determining a Treatment for Lung Cancer in a Subject

A subject was diagnosed with non-small cell lung cancer (NSCLC). A tissue sample was obtained from the subject. Nucleic acids were isolated from the tissue sample and the nucleic acids were applied to a probe set comprising at least five probes capable of detecting the expression of at least one non-coding target. Analysis of the expression level of the non-coding targets reveals the subject has a cisplatin-resistant NSCLC and gemcitabine was recommended as an alternative therapy.

Example 7: Genome-Wide Detection of Differentially Expressed Coding and Non-Coding Transcripts and Clinical Significance in Prostate Cancer Using Transcript-Specific Probe Selection Regions In this study, we performed whole-transcriptome analysis of a publicly available dataset from different types of normal and cancerous prostate tissue and found numerous differentially expressed coding and non-coding transcripts that discriminate between clinical disease states.
Materials and Methods
Microarray and Clinical Data
The publically available genomic and clinical data was generated by the Memorial Sloan-Kettering Cancer Center (MSKCC) Prostate Oncogenome Project, previously reported by Taylor et al., 2010. The Human Exon arrays for 131 primary prostate cancers, 29 normal adjacent and 19 metastatic tissue specimens were downloaded from GEO Omnibus at the world wide web at ncbi.nlm.nih.gov/geo/ series GSE21034. The patient and specimen details for the primary and metastases tissues used in this study were reported in Vergara I A, et al., 2012, Frontiers in Genetics, 3:23. For the analysis of the clinical data, the following ECE statuses were summarized to be concordant with the pathological stage: inv-capsule: ECE−, focal: ECE+, established: ECE+.
Microarray Pre-Processing
Normalization and Summarization
The normalization and summarization of the 179 microarray samples (cell lines samples were removed) was conducted with the frozen Robust Multiarray Average (fRMA) algorithm using custom frozen vectors as described in McCall M N, et al. (2010, *Biostatistics*, 11:254-53). These custom vectors were created using the vector creation methods described in McCall M N, et al. (2011, *Bioinformatics*, 12:369) including all MSKCC samples. Normalization was done by the quantile normalization method and summarization by the robust weighted average method, as implemented in fRMA. Gene-level expression values were obtained by summarizing the probe selection regions (or PSRs) using fRMA and the corresponding Affymetrix Cluster Annotation (www.affymetrix.com/).
Sample Subsets
The normalized and summarized data was partitioned into three groups. The first group contains the samples from primary localized prostate cancer tumor and normal adjacent samples (used for the normal versus primary comparison). The second group contained all of the samples from metastatic tumors and all of the localized prostate cancer specimens (used for the primary versus metastasis comparison). The third group contained all of the samples from metastatic tumors and all of the normal adjacent samples (used for the normal versus metastasis comparison).
Detection of Transcript-Specific PSRs in Human Exon Microarray Probe Sets
Using the xmapcore R package (Yates, 2010), all exonic PSRs that were specific to only one transcript were retrieved, generating a total of 123,521 PSRs. This set of PSRs was further filtered in order to remove all those that correspond to a gene but such that (i) the gene has only one transcript, or (ii) the gene has multiple transcripts, but only one can be tested in a transcript-specific manner. Applying these filters reduced the total number of transcript-specific PSRs to 39,003 which were the main focus of our analysis.
Feature Selection
Based on the set of transcript specific PSRs, those annotated as 'unreliable' by the xmapcore package (Yates, 2010) (one or more probes do not align uniquely to the genome) as well as those not defined as class 1 cross-hybridizing by Affymetrix were excluded from further analysis (at the world wide web at affymetrix.com/analysis/index.affx). Additionally, those PSRs that present median expression values below background level for all of the three tissue types (normal adjacent, primary tumor and metastasis) were excluded from the analysis. The remaining PSRs were subjected to univariate analysis to discover those differentially expressed between the labeled groups (primary vs. metastatic, normal adjacent vs. primary and normal vs. metastatic). For this analysis, PSRs were selected as differentially expressed if their FDR adjusted t-test P-value was significant ($<0.05$) and the Median Fold Difference (MFD) was greater or equal than 1.2. The t-test was applied as implemented in the row t-tests function of the genefilter package (at the world wide web at bioconductor.org/packages/2.3/bioc/html/genefilter.html). The multiple testing corrections were applied using the p-adjust function of the stats package in R.

For a given transcript with two or more transcript-specific PSRs significantly differentially expressed, the one with the best P-value was chosen as representative of the differential expression of the transcript. In order to avoid complex regions, cases for which a transcript specific PSR would overlap with more than one gene (for example within the intron of another gene) were filtered out from the analysis.

Feature Evaluation and Model Building

A k-nearest-neighbour (KNN) model (k=1, Euclidean distance) was trained on the normal and metastatic samples (n=48) using only the top 100 features found to be differentially expressed between these two groups.

Statistical Analysis

Biochemical recurrence and metastatic disease progression end points were used as defined by the "BCR Event" and "Mets Event" columns of the supplementary material provided by (Taylor et al., 2010), respectively. Survival analysis for BCR was performed using the survfit function of the survival package.

Results

Detection of Transcript-Specific PSRs in Human Exon Arrays

Figure 15C:
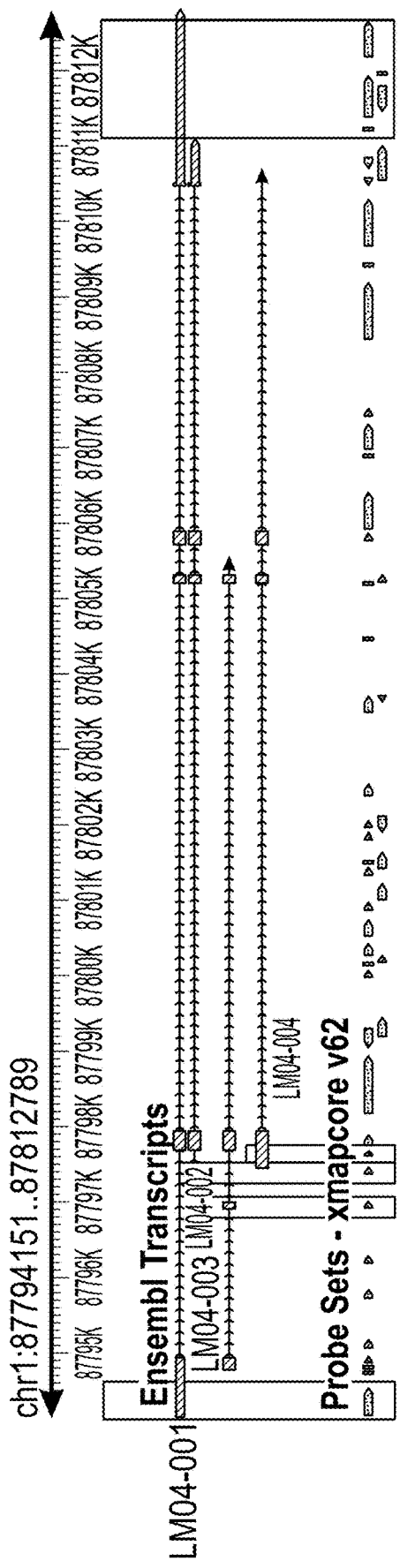

Detection of transcript-specific differential expression was of high interest as different spliced forms of the same gene might play distinct roles during progression of a given disease. For example, in the case of prostate cancer, it has been recently reported that not only does the main transcript associated with the Androgen Receptor (AR) gene play a role in prostate cancer, but other variants, such as v567, function in a distinct manner to that of the main spliced form (Chan et al, J. Biol. Chem, 2012; Li et al, Oncogene, 2012; Hu et al, Prostate, 2011). Affymetrix HuEx arrays provided a unique platform to test the differential expression of the vast majority of exonic regions in the genome. Based on Ensembl v62 and xmapcore (Yates et al 2010), there were 411,681 PSRs that fell within exons of protein-coding and non-coding transcripts. Within this set, a subset of 123,521 PSRs (~10% of the PSRs in the array) allowed for the unequivocal testing of the differential expression of transcripts, as they overlap with the exon of only one transcript. These PSRs, which we called transcript-specific PSRs (TS-PSRs), cover 49,302 transcripts corresponding to 34,599 genes. In this study, we used the publicly available Human Exon Array data set generated by the MSKCC Prostate Oncogenome Project to explore the transcript-specific differential expression through progression of prostate cancer from normal, primary tumor and metastatic tissues. In particular, we focus on the assessment of two or more different transcripts within a gene in a comparative manner. Hence, the set of 123,521 TS-PSRs was further filtered in order to remove all those that correspond to a gene, such that (i) the gene has only one transcript (69,591 TS-PSRs; FIG. 15A), or (ii) the gene has multiple transcripts, but only one can be tested in a transcript-specific manner (14,927 TS-PSRs; FIG. 15B). This generated a final set of 39,003 TS-PSRs corresponding to 22,517 transcripts and 7,867 genes that were used as the basis of this analysis (FIG. 15C).

Differential Expression of Coding and Non-Coding Transcripts Through Prostate Cancer Progression Assessment of the defined set of TS-PSRs yielded 881 transcripts that were differentially expressed between any pairwise comparison on the normal adjacent, primary tumor and metastatic samples (see methods; FIG. 11). These 881 transcripts corresponded to 680 genes, due to genes with two or more transcripts differentially expressed at the same or different stages of cancer progression. Interestingly, 371 (42%) of the differentially expressed transcripts were non-coding. Inspection of their annotation reveals that they fell into several non-coding categories, the most frequent being "retained intron" (n=151) and "processed transcript" (n=186). Additionally, most of the genes associated with these non-coding transcripts were coding, (i.e. they encode at least one functional protein). Examples of non-coding genes with differentially expressed transcripts found in this dataset include the lincRNAs PART1 (Prostate Androgen-Regulated Transcript 1, Lin et al 2000, Cancer Res), MEG3 (Ribarska et al 2012), the PVT1 oncogene, located in the 8q24 susceptibility region (Meyer et al 2011, PLoS Genetics), and the testis-specific lincRNA TTTY10. Other ncRNAs include the small nucleolar RNA host gene 1 (SNHG1) which has been suggested as a useful biomarker for disease progression (Berretta and Moscato, 2011, PLoS ONE), as well as GAS5, located in the 1q25 risk loci (Nam et al 2008; Prstate Cancer Prostatic Dis). Additionally, three pseudogenes were found differentially expressed in this dataset: EEF1DP3, located in a region previously found to be a focal deletion in metastatic tumors (Robbins et al 2011, Genome Research), the Y-linked pseudogene PRKY, which has been found expressed in prostate cancer cell lines (Dasari et al, 2000, Journal of Urology) and PABPC4L.

In addition to the non-coding genes, many coding genes presented one or more non-coding transcripts that were differentially expressed. Table 7 provides a list of genes that have been shown to participate in prostate cancer and that contain one or more non-coding transcripts differentially expressed according to our analysis, including the Androgen Receptor (Chan et al, J. Biol. Chem, 2012; Li et al, Oncogene, 2012; Hu et al, Prostate, 2011), ETV6 (Kibel et al, 2000, The Journal of Urology) and the fibroblast growth receptors FGFR1 and FGFR2 (Naimi et al 2002, The Prostate). Focusing on the individual transcripts of genes known to play a role in prostate cancer progression and their coding ability might shed light on the mechanisms in which each transcript was involved. Overall, the set of non-coding transcripts in both coding and non-coding genes reported here add to the current stream of evidence showing that non-coding RNA molecules may play a significant role in cancer progression (Vergara et al 2012, Kapranov et al 2010).

Genes with Multiple Transcripts Differentially Expressed Through Prostate Cancer Progression The majority of the 881 differentially expressed transcripts came from the comparison between normal adjacent and metastatic samples, in agreement with previous analyses of differential expression of tissue on the MSKCC dataset (Vergara et al., 2012). As shown in FIG. 11, 28 of the differentially expressed transcripts were found throughout the progression from normal adjacent through primary tumor to metastasis, with 22 of them across all three pairwise comparisons (Table 8, top). These 22 transcripts reflected instances of a significant increase or decrease of expression through all stages in the same direction (i.e. always upregulated or downregulated). The remaining 6 transcripts found to be differentially expressed in the normal adjacent vs primary tumor as well as in the primary tumor versus metastatic sample comparison (but not in the normal adjacent versus metastatic samples comparison) were a reflection of differential expression that occurs in different directions in the progression from normal to primary tumor compared to that from primary tumor to metastasis, suggesting that these transcripts play a major role during the primary tumor stage of the disease (Table 8, bottom). In particular, within this set of 28 transcripts there were two AR-sensitive genes, FGFR2 and NAMPT, that presented two transcripts that were differentially expressed throughout progression. In the case of the FGFR2 gene (a fibroblast growth receptor), our observation of significant decrease in expression from normal to metastasis was in agreement with a previous study that shows downregulation of isoforms 'b' and 'c' to be associated with malignant expression in prostate (Naimi et al, 2002, The Prostate). In the case of NAMPT (a nicotinamide phosphoribosyltransferase), the two transcripts showed a peak of expression in the primary tumor tissues compared to normal and metastasis; the rise in primary tumors compared to normal was in full agreement with previously reported elevation of expression during early prostate neoplasia for this gene (Wang et al, 2011, Oncogene). For both genes, the transcripts were differentially expressed in the same direction as the tumor progresses, suggesting that both transcripts were functioning in a cooperative manner. In order to determine if this was a general pattern of the transcripts analyzed here, all of the genes for which at least two transcripts presented differential expression were inspected (FIG. 12). Among the 140 genes for which we find such cases, there was a clear trend for groups of transcripts of the same gene to express in the same direction as the tumor progresses. Two exceptions that were found were genes CALD1 and AGR2. For both of them, the differential expression of one of their transcripts in the progression from primary tumor to metastasis went in the opposite direction compared to the other transcripts. In the case of AGR2, transcript AGR2-001 was downregulated in metastasis compared to primary tumor, whereas AGR2-007 was upregulated. This observation was in agreement with previous reports on a short and long isoform of the same gene (Bu et al, 2011, *The Prostate*). Even though the correspondence of the short and long isoforms to those annotated in Ensembl was not straightforward, alignment of the primers used in Bu et al. (2011) showed overlapping of the short isoform with AGR2-001, and of the long isoform with AGR2-007, which agreed with their divergent expression patterns. In the case of CALD1, while transcript CALD1-012 was upregulated, CALD1-005 and CALD1-008 were downregulated in the progression from primary tumor to metastasis. A previous study on 15 prostate cancer samples showed that CALD1-005 was downregulated in metastatic samples compared to primary tumor, in agreement with our results.

Transcripts Level Resolution of Differential Expression on Fully Tested Genes

Of the 7,867 genes for which one or more transcripts were assessed in this analysis, 1,041 genes were such that all of their transcripts have at least one TS-PSR. Of these, 92 genes were such that at least one of their transcripts was found to be differentially expressed in any pairwise comparison among normal adjacent, primary tumor and metastatic samples. As depicted in FIG. 13, the majority of the genes only have one differentially expressed transcript. This included cases like KCNMB1 and ASB2, two genes that have been previously reported to be differentially expressed in prostate cancer, but for which no observation at the transcript level has been made (Zhang et al 2005, Cancer Genomics and Proteomics; Yu et al 2004, JCO). In the case of KCNMB1, only transcript KCNMB1-001 of the two transcripts was found to be differentially expressed, whereas for ASB2, only transcript ASB2-202 was found to be differentially expressed of the three transcripts annotated for this gene. Also, other genes presented differential expression of their non-coding transcripts only. One example of this was PCP4 (also known as PEP-19), a gene known to be expressed in prostate tissue (Kanamori et al 2003, Mol. Hum. Reprod).

In addition to the expression profile of each transcript for these 92 genes, FIG. 13 shows the corresponding summarized gene-level expression profile for each gene. Of these, only 18 genes present differential expression at the gene level, clearly illustrating that summarization of expression can result in significant loss of information.

TS-PSRs Constitute a Clinically Significant Prostate Cancer Risk Group

In order to assess the prognostic significance of the differentially expressed transcripts, the corresponding TS-PSRs were used to train a KNN classifier on normal and metastatic samples and validated on the primary tumors, such that each primary tumor sample was classified as normal or metastatic based on its distance to the normal and metastatic groups. The higher the KNN score (ranging from 0 to 1), the more likely the patient will be associated to worse outcome. As shown in FIG. 14, the difference in the Kaplan-Meier (KM) curves for the two groups was statistically significant using biochemical recurrence as an endpoint and was comparable to that of the Kattan nomogram (Kattan et al 1999). Further assessment of coding and non-coding differentially expressed transcripts showed both sets to yield statistically significant differences in their KM curves. The corresponding set of differentially expressed genes still presented a statistically significant difference of the KM curves, despite the observed loss of information from the summarization when comparing different tissue types. A multivariable logistic regression analysis of the groups of transcripts and genes differentially expressed showed that the transcripts remain highly statistically significant after adjusting for the Kattan nomogram (p<0.005), whereas the genes resulted in borderline significance after adjustment (p=0.05) (Table 9). These results suggest that differential expression of specific transcripts have unique biomarker potential that adds value to that of classifiers based on clinicopathological variables such as nomograms.

Example 8: Differentially Expressed Non-Coding RNAs in Chr2q31.3 has Prognostic Potential and Clinical Significance Based on Fresh Frozen Samples Methods The publicly available expression profiles of normal and prostate tumor samples, Memorial Sloan Kettering Cancer Center (MSKCC) (Taylor et al., 2010) were downloaded from at the world wide web at ncbi.nlm.nih.gov/geo/query/acc.cgi?acc=GSE21034. The Human Exon arrays for 131 primary prostate cancer, 29 normal adjacent and 19 metastatic tissue specimens were downloaded from GEO Omnibus at the world wide web at ncbi.nlm.nih.gov/geo/series GSE21034. Information on Tissue samples, RNA extraction, RNA amplification and hybridization were disclosed in Taylor et al., 2010. The normalization and summarization of the 179 microarray samples (cell lines samples were removed) was conducted with the frozen Robust Multiarray Average (fRMA) algorithm using custom frozen vectors as described in McCall M N, et al. (2010, *Biostatistics*, 11:254-53). These custom vectors were created using the vector creation methods described in McCall M N, et al. (2011, *Bioinformatics*, 12:369). Quantile normalization and robust weighted average methods were used for normalization and summarization, respectively, as implemented in fRMA.

Feature selection was conducted using a t-test for differential expression on the 857 Probe Selection Regions (or PSRs) within chr2q31.3 region. A PSR was regarded as significantly differentially expressed if the P-value of the t-test was lower than 0.05 in any of the following comparisons: BCR vs non-BCR, CP vs non-CP, PCSM vs non-PCSM. Additionally, a PSR was found significant if the P-values of the differences between the KM curves for BCR vs non-BCR, CP vs non-CP, PCSM vs non-PCSM was lower than 0.05. Table 6, SEQ ID NOs.: 262-291 provides the detail of which comparison(s) yielded the PSR as significant.

Non-Coding Analysis

Using annotation data from the human genome version hg19/GRCh37 (Ensembl annotation release 62) and xmapcore (Yates, 2007), we categorized the PSRs depending on the chromosomal location and orientation with respect to coding and non-coding gene annotation as Coding, Non-coding (UTR), Non-coding (ncTranscript), Non-coding (Intronic), Non-coding (CDS_Antisense), Non-coding (UTR_Antisense), Non-coding (ncTranscript_Antisense), Non-coding (Intronic_Antisense), Non-coding (Intergenic). We additionally used xmapcore to annotate the gene symbol, gene synonym, Ensembl gene ID and biological description for any PSRs that overlapped with a transcript; this excludes alignments to non-coding (non-unique) and non-coding (intergenic) sequences.

Ontology Enrichment Analysis

DAVID Bioinformatics tool was used to assess enrichment of ontology terms (Huang da W, et al., 2009, *Nat Protoc*, 4:44-57; Huang da W, et al., 2009, *Nucleic Acids Res*, 37:1-13).

Results

Based on the criteria defined above, 429 PSRs were found to be differentially expressed within chr2q31.3 (Table 6, SEQ ID NOs.: 262-291). Of these 429 PSRs, the vast majority were non-coding, with only 20% mapping to a protein-coding region of a gene (FIG. 16). The most represented groups in the non-coding category were Intronic PSRs (26%) and Intergenic PSRs (27%). The fact that one of the largest groups was the intergenic one demonstrates that chr2q31.3 had significant unexplored prognostic potential. In fact, DAVID assessment of the functional annotation of these PSRs yielded no significant Gene Ontology terms for Biological Processes, in agreement with the idea that DAVID was a tool built mostly upon protein-coding gene information.

Additionally, approximately 8% of the PSRs overlapped with transcripts that did not encode for a functional protein. The distribution of the non-coding transcripts according to Ensembl annotation (at the world wide web at ensembl.org) were as follows: 6 "processed transcript", 3 "retained intron", 7 "large intergenic non-coding RNA", 4 "processed_pseudogene", 1 "non-sense mediated decay" and 1 snoRNA.

In order to further assess the clinical significance of the selected PSRs, KM curves were built using Biochemical Recurrence (BCR), as endpoint. As depicted in FIG. 17, the PSR corresponding to the probe set ID 2518027 showed a statistically significant difference of the KM curves for BCR endpoint, further demonstrating the prognostic potential of this region.

Example 9: Digital Gleason Score Predictor Based on Differentially Expressed Coding and Non-Coding Features In this study we evaluated the use of differentially expressed coding and non-coding features.

Methods

The publicly available expression profiles of normal and prostate tumor samples, Memorial Sloan Kettering Cancer Center (MSKCC) (Taylor et al., 2010) were downloaded at at the world wide web at ncbi.nlm.nih.gov/geo/query/acc.cgi?acc=GSE21034 and the German Cancer Research Center (DKFZ) (Brase et al., 2011) at the world wide web at ncbi.nlm.nih.gov/geo/query/acc.cgi?acc=GSE29079 were pooled and used to define a training set and a testing set. The training set consisted of all of the samples with a Gleason Score lower than 7 (hereafter called GS<7) and higher than 7 (hereafter called GS>7), whereas the testing set comprised all of the samples with a Gleason Score of 7 (hereafter called GS7). The group of GS7 patients was further split into 3+4 and 4+3 based on the Primary and Secondary Gleason Grades.

Information on tissue samples, RNA extraction, RNA amplification and hybridization can be found elsewhere (Taylor et al., 2010; Brase et al., 2011). The normalization and summarization of the 179 microarray samples (cell lines samples were removed) was conducted with the frozen Robust Multiarray Average (fRMA) algorithm using custom frozen vectors as described in McCall M N, et al. (2010, *Biostatistics*, 11:254-53). These custom vectors were created using the vector creation methods described in McCall M N, et al. (2011, *Bioinformatics*, 12:369). Quantile normalization and robust weighted average methods were used for normalization and summarization, respectively, as implemented in fRMA.

Feature selection was done using a t-test for differential expression between those GS<7 and GS>7 samples. 102 Probe Selection Regions (PSRs) were kept after a Holm P-value adjustment threshold of 0.05. The top 12 PSRs were used to build a random forest classifier with the following parameters: mtry=1, nodesize=26, ntree=4000. The mtry and nodesize parameters were selected via the random forest tune function. The classifier generated with this methodology is hereafter called RF12.

Results

Of the 102 PSRs found differentially expressed, 43% of them were in coding regions (FIG. 18). The rest of the PSRs were distributed within introns, untranslated regions (or UTRs), non-coding transcripts or were non-unique. Non-unique PSRs composed 13% of the differentially expressed PSRs. Some of these PSRs required thorough manual assessment in order to understand their nature; while some of them could be annotated as non-unique due to the presence of allelic variants in the genome assembly, others likely provided differential expression information through the existence of copy-number variations. A partial list of the 102 PSRs identified can be found in Table 6, SEQ ID NOs.: 292-321.

Figure 19A:
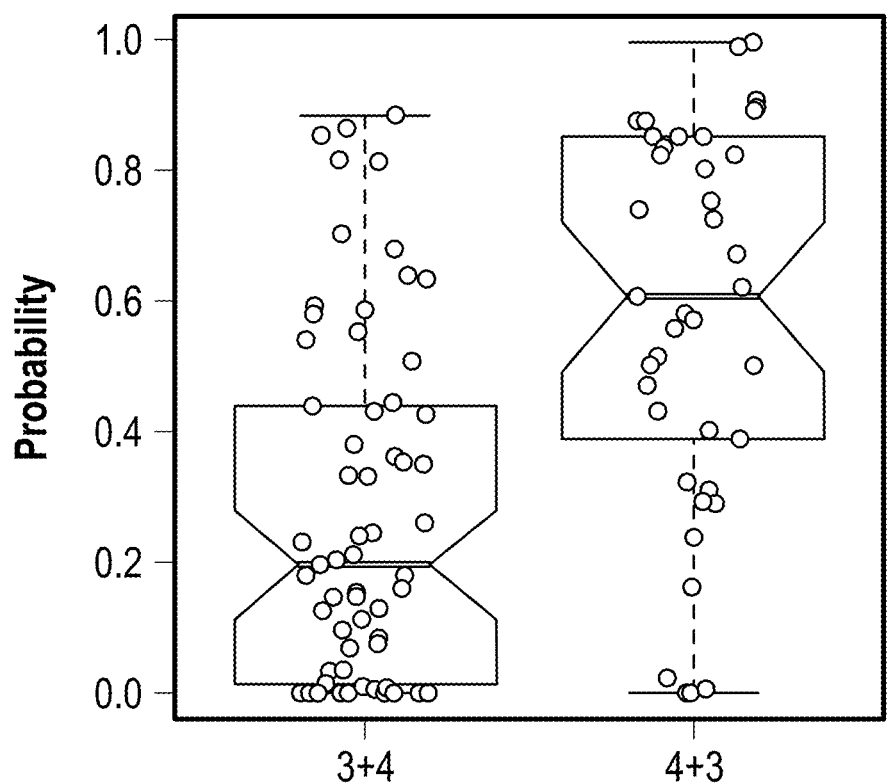

Using the trained RF12 classifier on the GS<7 and GS>7 samples, each GS7 (3+4 and 4+3) sample was assigned a probability of risk. The RF12 score, which ranges from 0 to 1, is the percentage of decision trees in the random forest which label a given patient as having the Gleason grade of the profiled tissue as greater than 3. A higher RF12 score means a worse prognosis for a patient as correlated with Gleason score. The higher the probability, the higher the risk associated to the sample. As shown in FIG. 19A, the probability distributions of the 3+4 samples versus 4+3 samples were significantly different. Those samples with a primary Gleason grade of 3 tended to have a lower probability than those with a primary Gleason grade of 4, which was in agreement with a higher Gleason grade corresponding to a higher risk of prostate cancer progression. Assessment of RF12 performance yielded an accuracy of 74%, which was significantly different to the 61% accuracy that was achieved with a null model. The high performance of the RF12 classifier was confirmed with the AUC metric, yielding an AUC of 77%.

Figure 19B:
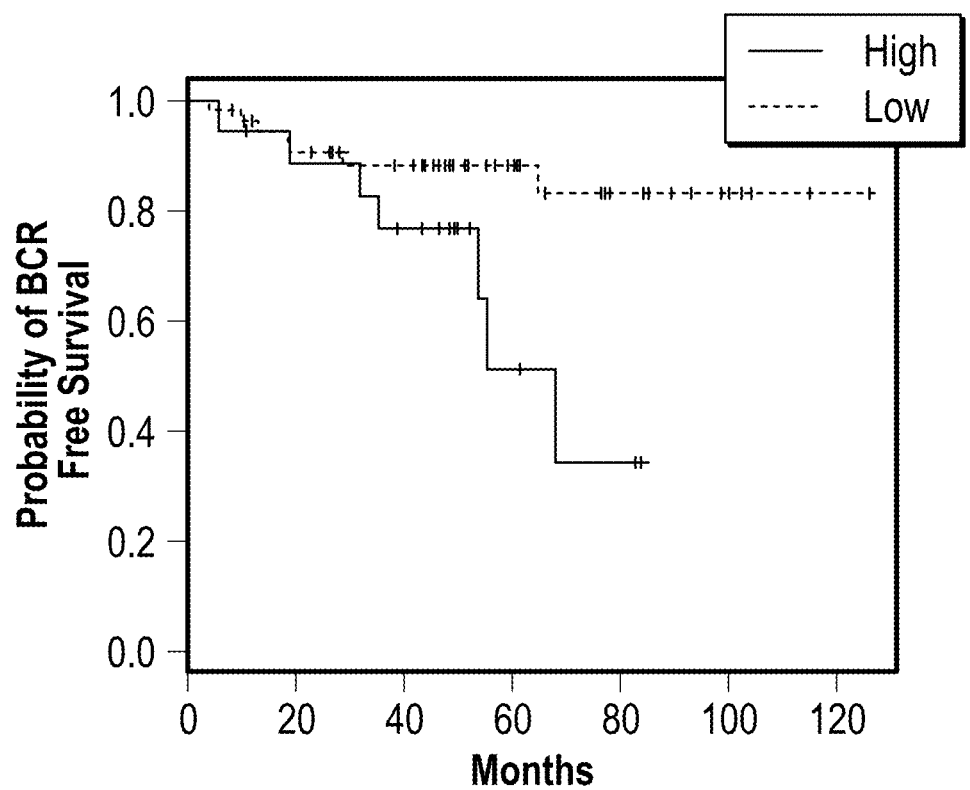

In order to further illustrate the prognostic potential and to assess the clinical significance of this classifier, KM curves on the groups predicted by RF12 were generated using the probability of BCR-free survival as endpoint. As shown in FIG. 19B, the difference between the low and high risk groups was statistically significant (p<0.01), demonstrating the ability of RF12 to discriminate between those samples from patients that were at high risk of progressing to biochemical recurrence versus those that were at low risk.

Example 10: KNN Models Based on PSR Genomic Subsets

In this study, Probe Selection Regions (PSRs) were annotated using xmapcore into the following categories: Intronic, Intergenic, Antisense, ncTranscript and Promoter Region. Antisense refers to a PSR being located in the opposite strand of a gene. Promoter Region was defined as the 2 kbp upstream region of a transcript, excluding the 5'UTR. Following the feature selection methodology in Example 1 based on MSKCC data, all significant PSRs were grouped into categories (e.g., Intronic, Intergenic, Antisense, ncTranscript and Promoter Region). In order to assess the prognostic significance of the PSRs differentially expressed within the categories, we developed a k-nearest neighbour (KNN) classifier for each group based on the top 156 PSRs (k=1, correlation distance), trained using features from the comparison of normal and metastatic tissue types (see Example 1 methods). Next, we used unmatched primary tumors (e.g. removing those tumors that had a matched normal in the training subset) as an independent validation set for each KNN classifier. Each primary tumor in the validation set was classified by each KNN as either more similar to normal or metastatic tissue (FIG. 9). Kaplan-Meier analysis of the two groups of primary tumor samples classified by KNN using the biochemical recurrence (BCR) end point was done for KNN classifiers derived for each subset of features. As expected, primary tumors classified by KNN as belonging to the metastasis group had a higher rate of BCR.

Example 11: Genomic Signature of Coding and Non-Coding Features to Predict Outcome after Radical Cystectomy for Bladder Cancer Methods 251 muscle invasive bladder cancer specimens from University of Southern California/Norris Cancer Center were obtained from patients undergoing radical cystectomies with extended pelvic lymph node dissection between years 1998 and 2004. Archived FFPE specimens sampled corresponded to 0.6 mm punch cores and had a median block age of 13 years. For patients, median follow up was 5 years, median age was 68 years old and the event rate corresponds to 109 patients with progression (43%).

Total RNA was extracted and purified using a modified protocol for the commercially available Agencourt Formapure kit (Beckman Coulter, Indianapolis Ind.). RNA concentrations were determined using a Nanodrop ND-1000 spectrophotometer (Nanodrop Technologies, Rockland, Del.). Purified total RNA was subjected to whole-transcriptome amplification using the WT-Ovation FFPE system according to the manufacturer's recommendation with minor modifications (NuGen, San Carlos, Calif.) and hybridized to Human Exon 1.0 ST GeneChips (Affymetrix, Santa Clara, Calif.) that profiled coding and non-coding regions of the transcriptome using approximately 1.4 million probe selection regions (or PSRs, also referred to as features).

Samples showing a variation of higher than two standard deviation for their average intensities, average background, Relative Log Expression and Median Absolute Deviation were discarded. In addition, filtering was also performed using GNUSE (Global Normalized Unscaled Standard Error), positive versus negative AUC and Percentage of Detected Calls using [0.6,1.4], >0.6 and 20% as thresholds, respectively.

A multivariate outlier detection algorithm was run using the QC metrics provided by Affymetix Power tools available at the world wide web at affymetrix.com/partners_programs/programs/developer/tools/powertools.affx. Samples identified as outliers were also discarded.

The normalization and summarization of the microarray samples were performed with the frozen Robust Multiarray Average (fRMA) algorithm using custom frozen vectors as described in McCall M N, et al. (2010, *Biostatistics*, 11:254-53). These custom vectors were created using the vector creation methods described in McCall M N, et al. (2011, *Bioinformatics*, 12:369). Quantile normalization and robust weighted average methods were used for normalization and summarization, respectively, as implemented in fRMA.

Results

Table 14 shows the raw clinical data, QC results and classifier scores for each of the 251 samples. The characteristics of the study population is summarized in Table 10. Assessment of the prognostic potential of the clinical factors was assessed by multivariable Cox proportional hazards modeling. As shown in Table 11, Tumor Stage (p=0.04) and Lymph Nodes (p<0.001) were found to have statistically significant prognostic potential based on hazard ratios. In order to assess the discriminatory potential of the clinical and pathological factors, samples were divided into a training set (trn) and a testing set (tst) (see Table 14, 'Set' column) and the performance of each variable was assessed by AUC (Table 12) for the progression-free survival endpoint. Progression was defined as any measurable local, regional or systemic disease on post-cystectomy imaging studies.

In agreement with the multivariable analysis, Tumor Stage and Lymph Nodes status had significant performance with a respective AUC of 0.62 and 0.66 for the training set and AUCs of 0.66 and 0.65 for the testing set. Combination of clinical-pathological variables into a multivariate model by either Cox modeling or Logistic Regression resulted in an improved performance (AUCs of 0.72 and 0.71 in the testing set, respectively) compared to these variables as sole classifiers (Table 12).

A genomic classifier (GC) was built based on the Human Exon arrays as follows. First, a ranking of the features by Median Fold Difference (MFD) was generated. Then, a k-nearest neighbour algorithm was applied to an increasingly larger set of features from 10 to 155 based on the MFD ranking. The classifiers (herein referred to as KNN89) were constructed by setting k=21 and number of features=89, achieving an AUC of 0.70 for the training set (FIG. 21A) and an AUC of 0.77 for the testing set (FIG. 21B) based on survival ROC curves at 4 years. The probability, which ranges from 0 to 1, an individual would be classified as having a progression event was based on the expression values of the closest 21 patients in the training cohort of muscle-invasive bladder cancer samples. Low probabilities represent a lower chance a patient would have progression while higher probabilities represent a higher chance a patient would have progression event. The 89 individual features (a.k.a. PSRs) of the KNN89 classifier correspond to coding and non-coding regions of the genome (Table 6, SEQ ID NOs.: 353-441, Table 15) including introns, untranslated regions (or UTRs), features antisense to a given gene as well as intergenic regions. Assessment of the pathways associated to the overlapping genes using KEGG pathway annotation shows that the most represented correspond to Regulation of actin cytoskeleton, focal adhesion and RNA transport (www.genome.jp/kegg/pathway.html).

When combining the GC with the clinical variables Age, Lymphovascular Invasion, Lymph Node Involvement and Intravesical therapy, a new classifier (hereafter referred to as GCC, for Genomic-Clinical Classifier) with enhanced performance was generated, based on the AUC of 0.82 and 0.81 in the training set and testing set respectively (FIG. 21A, FIG. 21B) based on survival ROC curves at 4 years. Discrimination plots for both GC and GCC demonstrated that the separation between the two groups of progression and non-progression samples was statistically significant for both classifiers (FIG. 22). Whereas both calibration plots for GC and GCC showed a good estimation with respect to the true values (FIG. 23), the enhanced performance of the GCC classifier became evident when inspecting the calibration plots, as GCC corrected overestimation of probabilities above 0.5. Still, multivariable analysis of the GC showed that this classifier has unique prognostic potential for the prediction of disease progression after radical cystectomy when adjusted for clinical pathological variables (Table 13).

Cumulative incidence plots depicting the frequency of progression over time were generated for GC-low and GC-high risk groups, as well as for GCC-low and GCC-high risk groups (FIG. 24). The cumulative incidence probabilities of progression were significantly different between the two risk groups for both classifiers. In the case of GC, a 15% incidence for the GC-low risk group was obtained, compared to a 60% incidence for the GC-high risk group at 3 years after radical cystectomy. For the GCC, a 20% incidence of progression for the GCC-low risk group was obtained, compared to a 70% incidence for the GCC-high risk group at 3 years. The 3-fold to 4-fold difference in incidence observed between the low and high risk groups for GC and GCC illustrates the clinical significance of these classifiers.

Example 12: Genomic Signatures of Varying Number of Coding and Non-Coding Features to Predict Outcome after Radical Cystectomy for Bladder Cancer Methods 251 muscle invasive bladder cancer specimens from University of Southern California/Norris Cancer Center were obtained from patients undergoing radical cystectomies with extended pelvic lymph node dissection between years 1998 and 2004. Archived FFPE specimens sampled correspond to 0.6 mm punch cores and have a median block age of 13 years. For patients, median follow up was 5 years, median age was 68 years and the event rate corresponds to 109 patients with progression (43%).

Total RNA was extracted and purified using a modified protocol for the commercially available Agencourt Formapure kit (Beckman Coulter, Indianapolis Ind.). RNA concentrations were determined using a Nanodrop ND-1000 spectrophotometer (Nanodrop Technologies, Rockland, Del.). Purified total RNA was subjected to whole-transcriptome amplification using the WT-Ovation FFPE system according to the manufacturer's recommendation with minor modifications (NuGen, San Carlos, Calif.) and hybridized to Human Exon 1.0 ST GeneChips (Affymetrix, Santa Clara, Calif.) that profiles coding and non-coding regions of the transcriptome using approximately 1.4 million probe selection regions (or PSRs, also referred to as features).

Samples showing a variation higher than two standard deviation for their average intensities, average background, Relative Log Expression and Median Absolute Deviation were discarded. In addition, filtering was also performed using GNUSE (Global Normalized Unscaled Standard Error), positive versus negative AUC and Percentage of Detected Calls using [0.6,1.4], >0.6 and 20% as thresholds, respectively.

Finally, a multivariate outlier detection algorithm was run using the QC metrics provided by Affymetix Power tools available at the world wide web at affymetrix.com/partners_programs/programs/developer/tools/powertools.affx.

Samples identified as outliers were also discarded.

The normalization and summarization of the microarray samples was conducted with the frozen Robust Multiarray Average (fRMA) algorithm using custom frozen vectors as described in McCall M N, et al. (2010, *Biostatistics*, 11:254-53). These custom vectors were created using the vector creation methods described in McCall M N, et al. (2011, *Bioinformatics*, 12:369). Quantile normalization and robust weighted average methods were used for normalization and summarization, respectively, as implemented in fRMA.

The dataset was separated into a training (trn) and a testing set (tst) as specified in column 'Set' of Table 14. Based on this separation, several machine learning algorithms were trained with different number of features (See Table 16 for methods used for feature selection) and their performance assessed on both training and testing sets independently. Performance of the generated classifiers on the training and the testing set based on AUC was also in Table 16.

Results

Figure 26A:
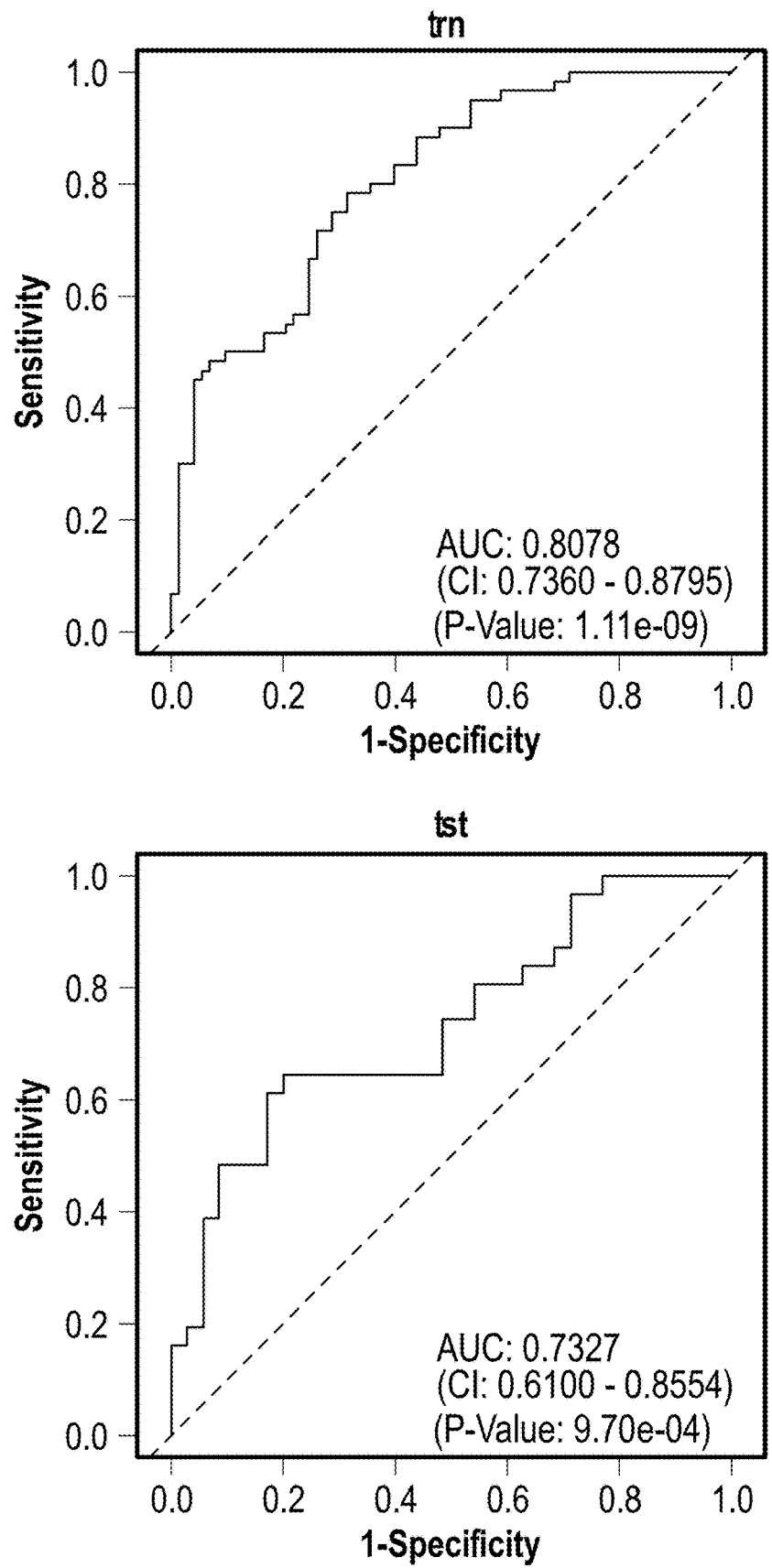
Figure 26B:
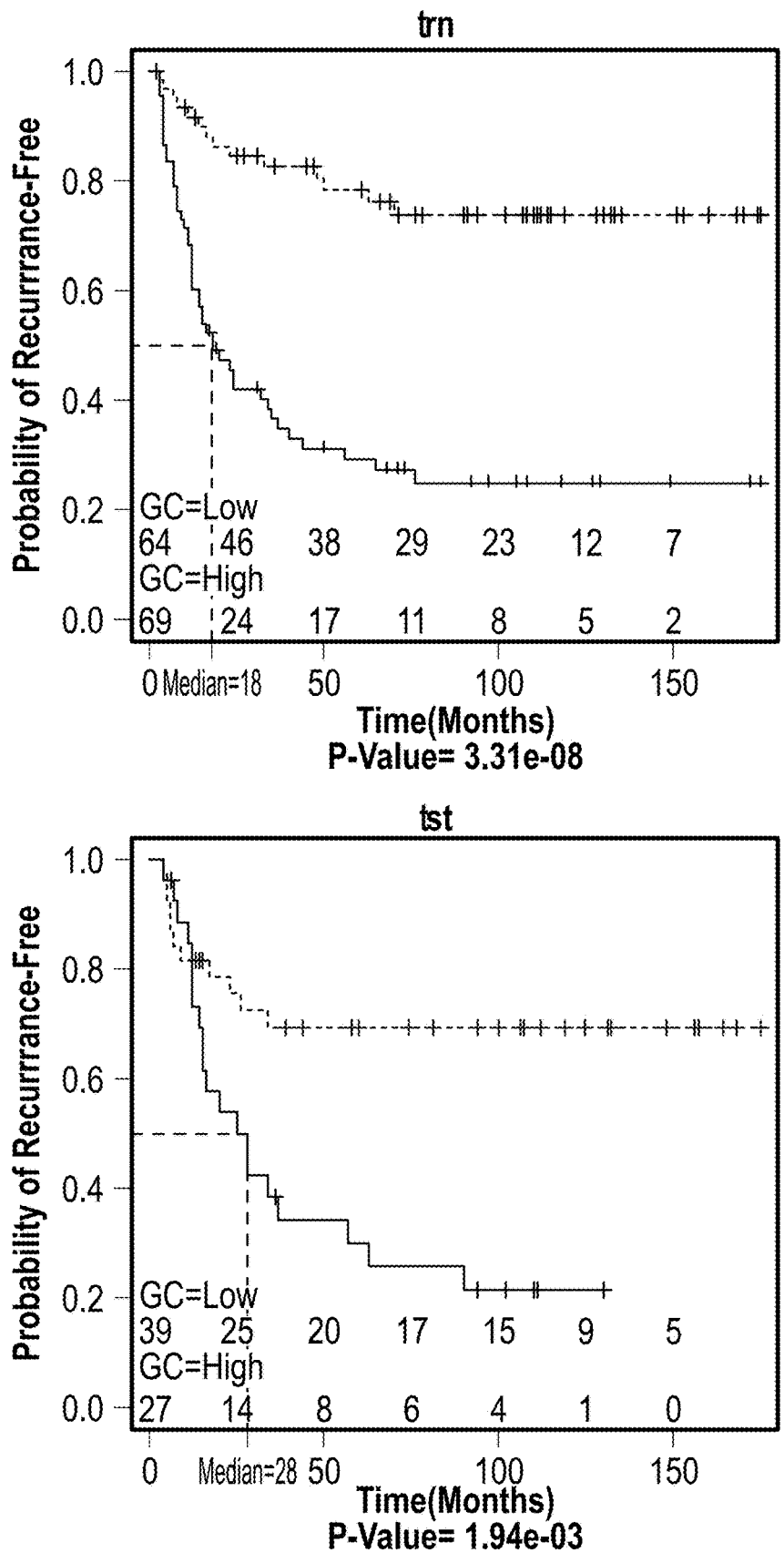

FIG. 26 shows the performance of a classifier, NB20, based on 20 features that were a combination of coding, intronic, intergenic, UTR and antisense regions (Table 17). The probability, which ranges from 0 to 1, an individual would be classified as having a progression event was based on the combined proportion of the progression samples in the training cohort which have similar expression values. Low probabilities represent a lower chance a patient would have progression while higher probabilities represent a higher chance a patient would have progression. This classifier had an AUC of 0.81 on the training set (trn) and an AUC of 0.73 on the testing set (tst), with both AUCs being statistically significant based on Wilcoxon test (FIG. 26A). In order to assess the clinical significance of the classification, after splitting the NB20 classifier scores into two groups by Partitioning Around Medoids (PAM) clustering, Kaplan-Meier curves showed that the two groups represented significantly different groups of high-risk of recurrence vs low-risk of recurrence (FIG. 26B).

FIG. 27 shows the performance of a classifier, KNN12, based on 12 features that were a combination of coding, intronic, intergenic, UTR and antisense regions (Table 17). The probability, which ranges from 0 to 1, an individual would be classified as having a progression event was based on the expression values of the closest 51 patients in the training cohort of muscle-invasive bladder cancer samples.

Low probabilities represent a lower chance a patient would have progression while higher probabilities represent a higher chance a patient would have progression. This classifier had an AUC of 0.72 on the training set and an AUC of 0.73 on the testing set, with both AUCs being statistically significant based on Wilcoxon test (FIG. 27A). In order to assess the clinical significance of the classification, after splitting the KNN12 classifier scores into two groups by PAM clustering, Kaplan-Meier curves showed that the two groups represented significantly different groups of high-risk of recurrence vs low-risk of recurrence (FIG. 27B).

FIG. 28 shows the performance of a classifier, GLM2, based on 2 features that corresponded to a pseudogene (HNRNPA3P1) and the intronic region of a protein-coding gene (MECOM) (Table 17). The probability an individual would be classified as having a progression event was based on the best fit expression profile of the training samples. The probabilities range from 0 to 1, where low probabilities represent a lower chance a patient would have progression while high probabilities represent a higher chance a patient would have progression. This classifier had an AUC of 0.77 on the training set and an AUC of 0.74 on the testing set, with both AUCs being statistically significant based on Wilcoxon test (FIG. 28A). In order to assess the clinical significance of the classification, after splitting the GLM2 classifier scores into two groups by PAM clustering, Kaplan-Meier curves showed that the two groups represented significantly different groups of high-risk of recurrence vs low-risk of recurrence (FIG. 28B).

FIG. 29 shows the performance of a single probe selection region corresponding to probe set ID 2704702 that corresponded to the intronic region of a protein-coding gene (MECOM) (Table 17). This classifier had an AUC of 0.69 on the training set and an AUC of 0.71 on the testing set, with both AUCs being statistically significant based on Wilcoxon test (FIG. 29A). In order to assess the clinical significance of the classification, after splitting this classifier scores into two groups by PAM clustering, Kaplan-Meier curves showed that the two groups represented significantly different groups of high-risk of recurrence vs low-risk of recurrence (FIG. 29B).

Example 13: Genomic Signatures of Varying Number of Coding and Non-Coding Features to Predict Gleason Score of 6 Versus Gleason Score Greater than or Equal to 7

Methods

The publicly available expression profiles of normal and prostate tumor samples from the Memorial Sloan Kettering Cancer Center (MSKCC) (Taylor B S, et al., 2010, *Cancer Cell*, 18:11-22) was downloaded from at the world wide web at ncbi.nlm.nih.gov/geo/query/acc.cgi?acc=GSE21034. Information on Tissue samples, RNA extraction, RNA amplification and hybridization can be found in Taylor B S et al. (2010, *Cancer Cell*, 18:11-22). The normalization and summarization of the 179 microarray samples (cell lines samples were removed) was performed with the frozen Robust Multiarray Average (fRMA) algorithm using custom frozen vectors as described in McCall M N, et al. (2010, *Biostatistics*, 11:242-53). These custom vectors were created using the vector creation methods described in McCall M N, et al. (2011, *Bioinformatics*, 12:369). Quantile normalization and robust weighted average methods were used for normalization and summarization, respectively, as implemented in fRMA.

With the goal of generating classifiers that segregated between samples of Gleason Score of 6 (GS6) versus those with GS greater than or equal to 7 (GS7+), the complete dataset was split into a training set (60%, 78 samples) and a testing set (40%, 52 samples). In the training set, 25 samples were GS6 versus 53 samples that were GS7+. In the testing set, 16 samples were GS6 versus 36 samples that were GS7+.

Based on this separation, several machine learning algorithms were trained with different number of features (see Table 18 for methods used for feature selection) and their performance assessed on both training (trn) and testing (tst) sets independently. Performance of the generated classifiers on the training and the testing set based on AUC was also in Table 18.

Results

FIG. 30 shows the performance of a classifier, SVM20, based on 20 features that were a combination of coding, non-coding transcript, intronic, intergenic and UTR (Table 19). The certainty in which an individual would be classified as having a pathological Gleason grade 4 or higher in their profiled tumor sample was based on the expression values of the top 20 features as ranked by AUC. The GC scores range from negative infinity to positive infinity. Larger values indicate the likelihood that the sample has a pathological Gleason grade of 4 or higher in their profiled tumor sample while smaller values indicate the likelihood that the sample has a pathological Gleason grade of 3 in their profiled tumor sample. This classifier had an AUC of 0.96 on the training set (trn) and an AUC of 0.8 on the testing set (tst), with both AUCs being statistically significant based on Wilcoxon test (FIG. 30A). The fact that notches within box-plots representing 95% confidence intervals of the SVM20 scores associated to those GS6 samples and GS7+ samples don't overlap (FIG. 30B) shows that the segregation generated by this classifier was statistically significant.

FIG. 31 shows the performance of a classifier, SVM11, based on 11 features that were a combination of coding, non-coding transcript, intronic, intergenic and UTR (Table 19). The certainty in which an individual would be classified as having a pathological Gleason grade 4 or higher in their profiled tumor sample was based on the expression values of the top 11 features ranked by AUC. The GC scores range from negative infinity to positive infinity. Larger values indicate the likelihood that the sample has a pathological Gleason grade of 4 or higher in their profiled tumor sample while smaller values indicate the likelihood that the sample has a pathological Gleason grade of 3 in their profiled tumor sample. This classifier had an AUC of 0.96 on the training set (trn) and an AUC of 0.8 on the testing set (tst), with both AUCs being statistically significant based on Wilcoxon test (FIG. 31A). The fact that notches within box-plots representing 95% confidence intervals of the SVM11 scores associated to those GS6 samples and GS7+ samples don't overlap (FIG. 31B) shows that the segregation generated by this classifier was statistically significant.

Figure 32B:
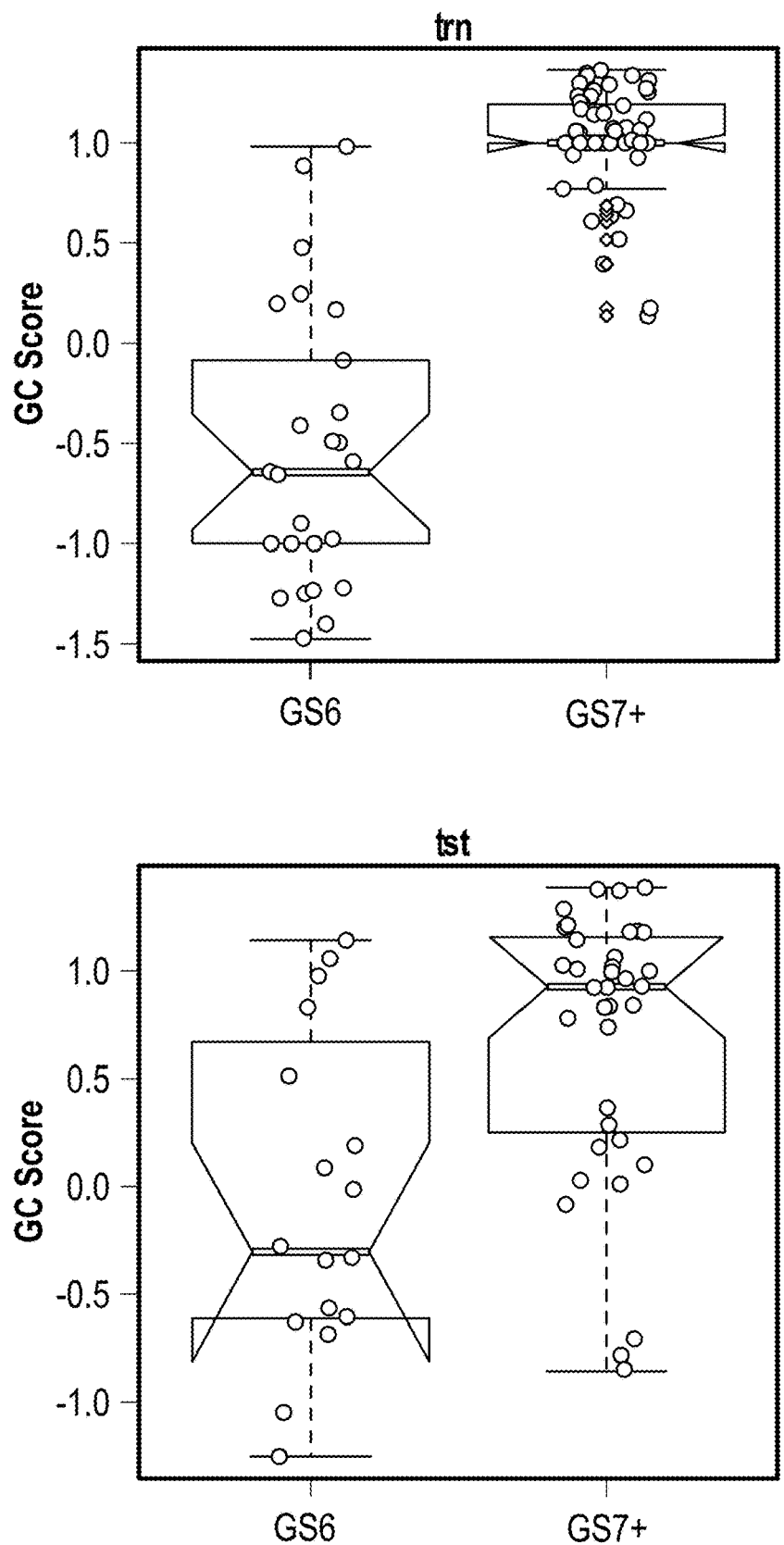

FIG. 32 shows the performance of a classifier, SVM5, based on 5 features that were a combination of coding and intronic (Table 19). The certainty in which an individual would be classified as having a pathological gleason grade 4 or higher in their profiled tumor sample was based on the expression values of the top 5 features ranked by AUC. The GC scores range from negative infinity to positive infinity. Larger values indicate the likelihood the sample has a pathological gleason grade of 4 or higher in their profiled tumor sample while smaller values indicate the likelihood the sample has a pathological gleason grade of 3 in their profiled tumor sample. This classifier had an AUC of 0.98 on the training set (trn) and an AUC of 0.78 on the testing set (tst), with both AUCs being statistically significant based on Wilcoxon test (FIG. 32A). The fact that notches within box-plots representing 95% confidence intervals of the SVM5 scores associated to those GS6 samples and GS7+ samples don't overlap (FIG. 32B) shows that the segregation generated by this classifier was statistically significant.

FIG. 33 shows the performance of a classifier, GLM2, based on 2 features, one of them being intronic to gene STXBP6 and the other corresponding to an intergenic region (Table 19). The probability an individual would be classified as having a pathological gleason grade 4 or higher in their profiled tumor sample was based on the best fit expression profile of the training samples. The probabilities range from 0 to 1 where low probabilities represent a lower chance the pathological gleason grade of the profiled tumor is 4 or higher while high probabilities represent a higher chance the pathological gleason grade of the profiled tumor is 4 or higher. This classifier had an AUC of 0.86 on the training set (trn) and an AUC of 0.79 on the testing set (tst), with both AUCs being statistically significant based on Wilcoxon test (FIG. 33A). The fact that notches within box-plots representing 95% confidence intervals of the GLM2 scores associated to those GS6 samples and GS7+ samples don't overlap (FIG. 33B) shows that the segregation generated by this classifier was statistically significant.

Example 14: Prognostic Potential of Inter-Correlated Expression (ICE) Blocks with Varying Composition of Coding and Non-Coding RNA Methods The publicly available expression profiles of normal and prostate tumor samples, Memorial Sloan Kettering Cancer Center (MSKCC) (Taylor B S, et al., 2010, *Cancer Cell*, 18:11-22) were downloaded from at the world wide web at ncbi.nlm.nih.gov/geo/query/acc.cgi?acc=GSE21034.

The Human Exon arrays for 131 primary prostate cancer, 29 normal adjacent and 19 metastatic tissue specimens were downloaded from GEO Omnibus at the world wide web at ncbi.nlm.nih.gov/geo/series GSE21034. Information on Tissue samples, clinical characteristics, RNA extraction, RNA amplification and hybridization can be found as described in Taylor B S, et al., (2010, *Cancer Cell*, 18:11-22). The normalization and summarization of the 179 microarray samples (cell lines samples were removed) was performed with the frozen Robust Multiarray Average (fRMA) algorithm using custom frozen vectors as described in McCall M N, et al. (2010, *Biostatistics*, 11:242-53). These custom vectors were created using the vector creation methods described in McCall M N, et al. (2011, *Bioinformatics*, 12:369). Quantile normalization and robust weighted average methods were used for normalization and summarization, respectively, as implemented in fRMA.

Annotation of PSRs

Using annotation data from the human genome version hg19/GRCh37 (Ensembl annotation release 62) and xmap-core (Yates, 2007), we categorized the PSRs depending on the chromosomal location and orientation with respect to coding and non-coding gene annotation as Coding, Non-coding (UTR), Non-coding (ncTranscript), Non-coding (Intronic), Non-coding (CDS_Antisense), Non-coding (UTR_Antisense), Non-coding (ncTranscript_Antisense), Non-coding (Intronic_Antisense), Non-coding (Intergenic).

Definition of Inter-Correlated Expression (ICE) Blocks

Affymetrix Human Exon ST 1.0 Arrays provide ~5.6 million probes which were grouped into ~1.4 million probe sets (average of 4 probes per probe set). The expression value captured for each probe was summarized for each probe set. The PSRs corresponding to each probe set fell within coding and non-coding (introns, UTRs) regions of protein-coding and non-protein-coding genes, as well as antisense to genes and intergenic regions.

An additional level of summarization provided by Affymetrix corresponds to probe sets that were grouped into so called transcript clusters. The genomic location of transcript clusters was defined based on the annotation of gene structures from multiple sources. The probe sets that compose these transcript clusters usually correspond to coding segments of protein-coding genes. This summarization was done with the goal of representing into one value the expression of the gene.

The predefined Affymetrix transcript clusters have a number of drawbacks including (i) they were static definitions of the transcribed sequence for a given gene, (ii) they do not account for the expression levels of the samples being assessed, and hence might correspond to sub-optimal representations of the expressed unit. Additionally, novel types of transcribed sequences that challenge the standard exon/intron structure of a gene such as chimeric RNAs (Kannan et al 2011) and very long intergenic non-coding regions (or vlincs, Kapranov et al 2010) have been found to be differentially expressed in cancer, and hence approaches that detect such transcripts were needed.

We proposed a new method that found blocks of neighboring correlated PSRs based on their expression values and show that they have prognostic potential. The correlated expression of these blocks of PSRs should represent one or more molecules that were being transcribed as either a single unit (e.g. chimeric RNAs) or as separate units (e.g. two separate genes) through cancer progression. We call these blocks syntenic blocks or Inter-Correlated Expression (ICE) Blocks.

Given a pooled set of samples from two groups A and B (e.g. primary tumor tissue versus metastatic tumor tissue) a window size W measured in number of PSRs, a correlation threshold T between 0 and 1, a counter C set to 0 and the chromosome, chromosomal location and strand for each PSR, ICE blocks were computed as follows:
1) Define the first block L as the single first PSR in the first chromosome.
2) Measure its correlation to the immediate adjacent PSR P downstream on the same strand using Pearson's correlation metric.
3) If the correlation was greater or equal than T, then merge P to block L. If not, then skip P and add one to counter C.
4) Repeat steps 1)-3) using the right-most PSR of block L. If a new PSR was added to the block, reset C=0.
5) Return block L when C>W or when reached the last PSR within the chromosome. Set C=0.
6) Repeat 1)-4) for each strand of each chromosome.

Once the ICE blocks were defined, the expression values for each of them were summarized based on the median value of the expression associated to the PSRs that compose the ICE Block for each patient. The significance of the differential expression between groups A and B for block L was assessed by computation of a Wilcoxon test P-value.

Results

Given the publicly available MSKCC samples described in Methods, the following comparisons were pursued: (i) Normal Adjacent Tissue versus Primary Tumor, (ii) Primary Tumor versus Metastatic Tissue, (iii) Gleason Score >=7 versus Gleason Score <7 and (iv) Biochemical Recurrence (BCR) vs non-BCR.

The algorithm for ICE block detection was applied to each of the pairwise comparisons. The number of ICE blocks found for each comparison and for a number of different Pearson correlation thresholds is shown in Table 20. As expected, as the correlation threshold gets lower more ICE blocks were found, consistent with the idea that more adjacent PSRs can be merged with lower correlation thresholds. Also shown in Table 20 is the number of ICE blocks found to be significantly differentially expressed (P-value<0.05) between the two conditions for each pairwise comparison. For those comparisons involving different progression states of cancer, the number of ICE blocks found differentially expressed can range from several hundreds (e.g. BCR endpoint with correlation threshold of 0.9) to tens of thousands (e.g. Primary vs Metastasis comparison, correlation threshold of 0.6).

Since ICE Blocks were composed of two or more PSRs, the proportion of coding and non-coding regions that the ICE block consists of can vary depending on where the associated PSRs fell into. Table 21 shows, for different comparisons and correlation thresholds, the frequency of ICE blocks found differentially expressed that correspond to a number of compositions including those that were composed only of coding regions, only intronic regions, only intergenic regions, only antisense regions as well as all other combinations. Additionally, ICE blocks can overlap with two or more adjacent genes (Multigene column in Table 21), suggesting that the two units were being differentially co-expressed either as separate units or as chimeric RNAs. For example, for the BCR endpoint and correlation threshold of 0.8, a previously reported chimeric RNA consisting of genes JAM3 and NCAPD3 was found as an ICE block composed of 65 coding and non-coding PSRs across the genomic span chr11:134018438 . . . 134095174;—with statistically significant differential expression (P-value<0.04).

Table 22 provides a list of all those ICE blocks found differentially expressed for the Gleason Score comparison when using a strict correlation threshold of 0.9. Table 23 provides a list of all those ICE blocks found differentially expressed for the Biochemical Recurrence endpoint when using a strict correlation threshold of 0.9. For each block, the associated P-value that demonstrated the differential expression (p<0.05), the PSRs included within the block, the percentage composition of coding and non-coding as well as the overlapping gene(s) within the same chromosomal location were shown. As seen in Tables 22 and 23, the proportion of coding and non-coding PSRs that an ICE block can be composed of can vary from fully coding to fully non-coding, with multiple proportions in between.

In order to further illustrate the discriminatory ability of these ICE blocks, FIGS. 34-39 show the box-plots (A) and ROC curves (B) for five different ICE blocks (FIG. 34: Block_7716, FIG. 35: Block_4271, FIG. 36: Block_5000, FIG. 37: Block_2922 and FIG. 38: Block_5080) of varying composition of coding and non-coding found to be differentially expressed in GS6 vs GS7+ comparison (Table 22, see Table 24 for sequences associated to each PSR composing these ICE Blocks). For each of these ICE Blocks, box-plots depicting the distribution of the ICE Block expression were displayed for both groups. The fact that notches within box-plots representing 95% confidence intervals of the expression associated to those GS6 samples and GS7+ samples didn't overlap (FIGS. 34A, 35A, 36A, 37A, and 38A) shows that the segregation generated by this classifier was statistically significant. The statistical significance of this segregation was further confirmed by the AUC associated to each of the ROC curves for these ICE Blocks, as the 95% confidence intervals associated to each of the AUCs do not cross the 0.5 lower bound FIGS. 34B, 35B, 36B, 37B and 38B).

FIGS. 39-45 show the box-plots (A), ROC curves (B) and Kaplan-Meier curves (C) for seven different ICE blocks (FIG. 39: Block_6592, FIG. 40: Block_4627, FIG. 41: Block_7113, FIG. 42: Block_5470, FIG. 43: Block_5155, FIG. 44: Block_6371 and FIG. 45: Block_2879) of varying composition of coding and non-coding found to be differentially expressed in BCR versus non-BCR comparison (Table 23, see Table 24 for sequences associated to each PSR composing these ICE Blocks). For each of these ICE Blocks, box-plots depicting the distribution of the ICE block expression were displayed for both groups. The fact that notches within box-plots representing 95% confidence intervals of the expression associated to those GS6 samples and GS7+ samples don't overlap (FIGS. 39A, 40A, 41A, 42A, 43A, 44A, and 45A) shows that the segregation generated by this classifier was statistically significant. The statistical significance of this segregation was further confirmed by the AUC associated to each of the ROC curves for these ICE blocks, as the 95% confidence intervals associated to each of the AUCs do not cross the 0.5 lower bound (FIGS. 39B, 40B, 41B, 42B, 43B, 44B, and 45B). In order to assess the clinical significance of the classification, after splitting the ICE blocks scores into two groups by median split method, Kaplan-Meier curves show that the two groups represent significantly different groups of high-risk of BCR vs low-risk of BCR (FIGS. 39C, 40C, 41C, 42C, 43C, 44C, and 45C).

Example 15: KNN Models for Tumor Upgrading

Methods

Although pure GG3 (i.e. Gleason 3+3) was rarely lethal, some GG3 cancers were associated with clinically metastatic disease. In this example, a signature was developed based on post-RP prostate tumor samples to identify which have transitioned from low risk, as defined by biopsy GS 6, clinical stage either T1 or T2A, and pretreatment PSA≤10 ng/ml, to high risk tumors, as defined by a pathological GS≥7 or a pathological tumor stage >T3A.

The publically available Memorial Sloan Kettering (MSKCC) Prostate Oncogenome project dataset (at the world wide web at ncbi.nlm.nih.gov/geo/query/acc.cgi?acc=GSE21034) was used for this analysis, which consisted of 131 primary tumor microarray samples (Affymetrix Human Exon 1.0 ST array). Information on Tissue samples, RNA extraction, RNA amplification and hybridization can be found as found in, for example, Taylor B S, et al. (2010, *Cancer Cell*, 18:11-22). These samples were preprocessed using frozen Robust Multiarray Average (fRMA), with quantile normalization and robust weighted average summarization (see McCall M N, et al., 2010, *Biostatistics*, 11:242-53 McCall M N, et al., 2011, *Bioinformatics*, 12:369). Of these patients, 56 net the low risk specification defined above. These patient samples were randomly partitioned into a training (n=29) and testing set (n=27) in a manner which ensures the number of cases and controls remained proportional (Table 25).

The 1,411,399 expression features on the array were filtered to remove unreliable probe sets using a cross hybridization and background filter. The cross hybridization filter removes any probe sets which were defined by Affymetrix to have cross hybridization potential (class 1), which ensures that the probe set was measuring only the expression level of only a specific genomic location, Background. filtering removes features with expression levels lower than the median expression level of the background probe sets. These filters reduced the number of features to 891,185. The training set was further processed using median fold difference (MFD>1.4) filter to 157 genomic features then ranked by T-Test P-value. The top 16 features (Table 26) of the training set were used for modeling a KNN classifier (k=3, Euclidean distance).

Results

The KNN model (hereafter called KNN16) was applied to the testing set and analyzed for its ability to distinguish tumors which underwent upgrading from those that remained low risk (FIG. 46). The KNN16 score, which ranges from 0 to 1, is the percentage of the 3 closest training set patients which upgraded as defined by biopsy (Gleason <6, PSA≤10 ng/ml, clinical stage T1 or T2A) transitioning to a higher risk tumor following RP (pathological GS≥7 or a pathological tumor stage >T3A). The higher the KNN16 score, the more likely the patient will experience an upgrading event. As depicted by the non-overlap of the notches for the discrimination plots for both groups (FIG. 46), the low-risk and upgraded groups were significantly different. Additionally, KNN16 (AUC=0.93) had a better ability to discriminate upgraded patients compared to the clinical factors: pretreatment PSA (preTxPSA, AUC=0.52), clinical tumor stage (c1 Stage, AUC=0.63), and patient age (AUC=0.56) (FIG. 47). In terms of accuracy, the model performed with an accuracy of 81% (P-value <0.005) over an accuracy of 56%, achieved by labeling all samples with the majority class (null model).

In order to assess how the expression profiles group, clustering analysis was also performed for the pooled samples from training and testing sets (n=56) (FIG. 48). The 157 genomic features were subjected to a T-Test filter (P-value <0.05) resulting in 98 features. The two distinct clusters observed, one mostly corresponding to samples which had upgrading and the other corresponding mostly to low risk samples, confirm the ability of the selected features to discriminate between low-risk and upgraded samples.

The results based on this signature show that the selected markers have the potential to provide more accurate risk stratification than predictive models based only on clinical parameters, and identify patients who should consider definitive local therapy rather than AS.

Example 16: Non-Coding RNAs Differentially Expressed Through Lung and Colorectal Cancer Data Sets and Methodology Lung Samples The cohort contains 40 samples corresponding to 20 tumor samples and their paired normal tissue. Methodology on the generation and processing of samples was disclosed in Xi L et al (2008, *Nucleic Acids Res*, 36:6535-47). Files with raw expression values for each sample were publicly available at the world wide web at ncbi.nlm.nih.gov/projects/geo/query/acc.cgi?acc=GSE12236.

Colorectal Samples

The cohort contains 173 samples, 160 of which correspond to tumor and the remaining 13 correspond to normal colonic mucosa biopsy. Methodology on the generation and processing of samples was disclosed in Sveen A, et al. (2011, *Genome Med*, 3:32). Files with raw expression values for each sample were publicly available at the world wide web at ncbi.nlm.nih.gov/projects/geo/query/acc.cgi?acc=GSE24551.

Normalization and Summarization

Dataset normalization and summarization was performed with fRMA (McCall M N, et al., 2010, *Biostatistics*, 11:242-53). The fRMA algorithm relates to the RMA (Irizarry R A, et al., 2003, *Biostatistics*, 4:249-64) with the exception that it specifically attempts to consider batch effect during data summarization and was capable of storing the model parameters in so called frozen vectors. fRMA then uses these frozen vectors to normalize and summarize raw expression probes into so-called probes selection regions (PSRs) in log 2 scale. The frozen vectors negate the need to reprocess the entire data set when new data was received in the future. For both colorectal and lung samples, batches were defined based on the date used to measure the expression on the samples as provided in the raw data. In the case of lung samples, a custom set of frozen vectors was generated by randomly selecting 6 arrays from each of 4 batches in the data set; one batch was discarded from the vector creation due to the small number of samples in that batch (McCall M N, et al., 2011, *Bioinformatics*, 12:369). For the colorectal samples, a custom set of frozen vectors was generated by randomly selecting 4 arrays from each of 24 batches in the data set. Seventeen batches were discarded from the vector creation due to the small number of samples (McCall M N, et al., 2011, *Bioinformatics*, 12:369).

Filtering

Cross hybridization and background filtration methods were applied to all PSRs on the array in order to remove poorly behaving PSRs. Two sources of cross-hybridization were used for filtering: (i) probe sets defined as cross-hybridizing by affymetrix (at the world wide web at affymetrix.com) and (ii) probe sets defined as "unreliable" by the xmapcore R package (at the world wide web at xmap.picr.man.ac.uk). The cross hybridization filters reduce the number of PSRs in the analysis from 1,432,150 to 1,109,740.

PSRs with associated expression levels at or below the chip's background expression level did not contain reliable expression information. The background expression of the chip was calculated by taking the median of the linear scale expression values of the 45 anti-genomic background PSRs (Affymetrix Technical Note, 2011). For any type of comparison (e.g. normal tissue versus tumor), if the median expression of both groups was less than the background expression level, then the PSR was removed from further analysis. It should be made clear that, if the expression level for a PSR tended to be above the background threshold in one group but not the other, the PSR remained in the analysis as this could be a sign of a genuine biological difference between the two groups.

Unsupervised Analysis

A PSR was defined as differentially expressed between two groups if the median fold difference was greater or equal than 1.5. For those PSRs complying to that threshold, assessment of the ability to segregate between two groups was done using multidimensional scaling (MDS). MDS plots were shown to visualize the differences between the marker expression levels of two groups in three dimensions. The Pearson distance metric was used in these MDS plots, and the permanova test was used to assess the significance of the segregation (at the world wide web at cran.r-project.org/web/packages/vegan/index.html).

Annotation of Probe Sets (PSRs)

Using annotation data from the human genome version hg19/GRCh37 (Ensembl annotation release 62) and xmapcore (Yates, 2007), we categorized the PSRs depending on the chromosomal location and orientation with respect to coding and non-coding gene annotation as Coding, Non-coding (UTR), Non-coding (ncTranscript), Non-coding (Intronic), Non-coding (CDS_Antisense), Non-coding (UTR_Antisense), Non-coding (ncTranscript_Antisense), Non-coding (Intronic_Antisense), Non-coding (Intergenic).

Ontology Enrichment Analysis

DAVID Bioinformatics tool was used to assess enrichment of ontology terms (Huang da W, et al., 2009, Nat Protoc, 4:44-57; Huang da W, et al., 2009, Nucleic Acids Res, 37:1-13)

Results

Non-Coding RNAs Differentially Expressed Between Normal Tissue and Lung Cancer

Based on the methodology described above, and after filtering 480,135 PSRs because of low expression values compared to background (17.18 threshold), the differential expression of all remaining PSRs was tested. 3,449 PSRs were found to have a Median Fold Difference (MFD) greater or equal than 1.5 (Table 27 provides the top 80 non-coding PSRs). Of these, 1,718 PSRs (~50%) were of non-coding nature (i.e. falling in regions of the genome other than protein-coding regions). Furthermore, ~35% of the PSRs (1,209/3,449) fall within non-coding parts of a protein-coding gene such as UTRs and introns.

Additionally, ~4% of the PSRs were found to overlap with 202 transcripts that did not encode for a functional protein. The distribution of these non-coding transcripts, according to Ensembl annotation (at the world wide web at ensembl.org), were as follows: 79 "processed transcript", 43 "retained intron", 32 "large intergenic non-coding RNA", 23 "antisense", 11 "pseudogene", 10 "non-sense mediated decay", 2 "non_coding", 1 "sense intronic" and 1 "miRNA".

Most of the PSRs were found within the boundaries of a gene, with only ~6% of PSRs (207/3449) being intergenic. In total, 1,205 genes were found to overlap with the PSRs. Ontology enrichment analysis of the genes corrected for multiple testing shows multiple cellular processes expected to be found significantly enriched in the differentiation between normal adjacent and tumor tissues, including cell division, cell adhesion and regulation for muscle development.

The utility of the differentially expressed non-coding features can be seen from their ability to separate normal versus tumor cancer samples using unsupervised techniques (FIG. 49A). The multidimensional scaling (MDS) plot shows that these non-coding features generate a clear segregation between the normal samples and the matched tumor samples; the segregation was found to be statistically significant ($p<0.001$).

Non-Coding RNAs Differentially Expressed Between Normal Tissue and Colorectal Cancer Based on the methodology described above, and after filtering 672,236 PSRs because of low expression values compared to background (33.3 threshold), the differential expression of all remaining PSRs was tested. 4,204 PSRs were found to have a Median Fold Difference (MFD) greater or equal than 1.5 (Table 28 provides the top 80 non-coding PSRs). Of these, 2,949 PSRs (~70%) were of non-coding nature (i.e. falling in regions of the genome other than protein-coding regions). Furthermore, ~55% of the PSRs (2,354/4,204) fall within non-coding parts of a protein-coding gene such as UTRs and introns.

Additionally, ~8% of the PSRs were found to overlap with 368 transcripts that did not encode for a functional protein. The distribution of these non-coding transcripts distribute, according to Ensembl annotation (at the world wide web at ensembl.org), were as follows: 143 "processed transcript", 141 "retained intron", 26 "large intergenic non-coding RNA", 25 "non-sense mediated decay", 18 "pseudogene", 9 "antisense", 2 "sense intronic", 2 "miscRNA", 1 "snRNA" and 1 "non_coding".

Most of the PSRs were found within the boundaries of a gene, with only ~5% of the PSRs (209/4204) being intergenic. In total, 1,650 genes were found to overlap with the PSRs. Ontology enrichment analysis of the genes corrected for multiple testing shows cell adhesion, collagen metabolism and catabolism to be significantly enriched in the differentiation between normal adjacent and tumor tissues; the differential expression of features associated to collagen processes was in agreement with previous studies in colorectal carcinogenesis (Skovbjerg H, et al., 2009, BMC Cancer, 9:136).

The utility of the differentially expressed non-coding features can be seen from their ability to separate normal versus tumor cancer samples using unsupervised techniques (FIG. 49B). The multidimensional scaling (MDS) plot shows that these non-coding features generate a clear segregation between the normal and tumor samples; the segregation was found to be statistically significant ($p<0.001$).

Non-Coding RNAs Differentially Expressed Between Different Stages of Lung Cancer Based on the methodology described above, the ability of non-coding RNAs to discriminate between two groups of lung tumor tissues was explored. In particular, the non-coding RNAs were inspected for their discriminatory ability between early stage lung cancer (12 stage I samples) versus more advanced stages of cancer (3 stage II patients and 5 stage III patients, collectively called the II+III group). After filtering 477,912 PSRs because of low expression values compared to background (17.18 threshold), the differential expression of all remaining PSRs was tested. 618 PSRs were found to have a Median Fold Difference (MFD) greater or equal than 1.5 (Table 29 provides the top 80 non-coding PSRs). Of these, 439 PSRs (71%) were of non-coding nature (i.e. falling in regions of the genome other than protein-coding regions). Furthermore, ~38% of the PSRs (235/618) fell within non-coding parts of a protein-coding gene such as UTRs and introns.

Additionally, ~11% of the PSRs were found to overlap with 67 transcripts that did not encode for a functional protein. The distribution of these non-coding transcripts distribute, according to Ensembl annotation (at the world wide web at ensembl.org), were as follows: 19 "processed transcript", 11 "retained intron", 9 "large intergenic non-coding RNA", 15 "pseudogene", 6 "non-sense mediated decay", 3 "antisense", 1 "misc RNA", 1 "retrotransposed" and 1 "miRNA".

Most of the PSRs were found within the boundaries of a gene; however, approximately 17% of the PSRs (104/618) fell in intergenic regions. In total, 472 genes were found to overlap with the PSRs. Ontology and pathway enrichment analysis of the genes corrected for multiple testing shows no processes or pathways found to be significantly enriched in the differentiation between tumor stages. Given that most of the differentially expressed features were of non-coding nature, and as enrichment analyses greatly rely on the annotation of protein-coding genes, these results suggest that further functional studies on non-coding RNAs were critical for understanding the biology that was involved in the progression of lung cancer.

The utility of the differentially expressed non-coding features can be seen from their ability to separate tumor stage I versus II+III cancer samples using unsupervised techniques (FIG. 50A). The multidimensional scaling (MDS) plot shows that these non-coding features generate a better segregation between different stages than coding features; the segregation was found to be statistically significant (p<0.001).

XIST Non-Coding RNA was Differentially Expressed Between Stages II and III of Colorectal Cancer.

The ability of non-coding RNAs to discriminate between two groups of colorectal tumor tissues was explored. In particular, the non-coding RNAs were inspected for their discriminatory ability between stage II (90 samples) and stage III (70 samples) colorectal cancer samples. Based on the methodology described above, and after filtering 703, 072 PSRs because of low expression values compared to background (33.3 threshold), the differential expression of all remaining PSRs was tested. 35 PSRs were found to have a Median Fold Difference (MFD) greater or equal than 1.5 (Table 30 list the non-coding PSRs found with this threshold). Of these, 25 PSRs (71%) were of non-coding nature (i.e. falling in regions of the genome other than protein-coding regions). In addition to two of these non-coding PSRs falling within the UTRs of protein-coding genes DDX3Y (DEAD (Asp-Glu-Ala-Asp) box polypeptide 3) and KDM5D (lysine (K)-specific demethylase 5D), both Y-linked, the remaining 23 differentially expressed non-coding PSRs correspond to the X-inactive-specific transcript (XIST), a long non-coding RNA gene residing in the X chromosome that plays an essential role in X-chromosome inactivation (Brown C J, 1991, *Nature,* 349:38-44). FIG. 50B illustrates the density of a PSR representative of XIST. As seen there, stage II samples tend to have low expression values whereas stage III samples tend to have high expression values of XIST, suggesting that this gene gets overexpressed through colorectal cancer progression. Highly variable expression of this lncRNA has been detected within BRCA1 primary tumors in breast cancer (Vincent-Salomon A, et al., 2007, *Cancer Res,* 67:5134-40); a recent study shows that XIST presents DNA copy-number variations in microsatellite-unstable sporadic colorectal carcinomas, a particular type of tumor generally regarded as diploid (Lassman S, et al., 2007, *J Mol Med (Berl),* 85:293-304). Interestingly, 38 of the 160 colorectal tumor samples used for this example correspond to microsatellite-unstable colorectal carcinomas. These suggest that the DNA copy-number variation that involves XIST might have an impact on the dosage of the gene at the transcript level that was detected in this analysis due to the inclusion of microsatellite-unstable tumor samples.

Example 17: Comparison of Genomic Signatures with Coding and Non-Coding Features and Genomic Signatures with Coding Features The performance of several previously published classifiers can be compared to new classifiers based on the publicly available genomic and clinical data generated by the Memorial Sloan-Kettering Cancer Center (MSKCC) Prostate Oncogenome Project (Taylor et al., 2010) available from GEO Omnibus at the world wide web at ncbi.nlm.nih.gov/geo/series GSE21034. The previously published classifiers are designed for predicting Biochemical recurrence (BCR) or other endpoint that indicates disease progression based solely on coding features. The newly developed classifiers are designed for predicting BCR and are composed of coding and non-coding features. CEL files for the arrays from the dataset are pre-processed using the fRMA algorithm. The normalized and summarized expression values can be used as input for ranking methods such as Wilcoxon P-test or Median Fold Difference, and a ranking of the features can be generated. This ranking of coding and non-coding features can be used as input to train multiple machine learning algorithms (e.g., Support Vector Machines, K-Nearest Neighbors, Random Forest) that generate classifiers. Classifiers can be selected based on the performance of one or more metrics from Area under the ROC curve (AUC), Accuracy, Sensitivity, Specificity, Negative Predictive Value (NPV) and Positive Predictive Value (PPV). The performance of previously published classifiers and the new classifier can be compared by one or more of the metrics disclosed herein. The newly developed classifiers, containing both coding and non-coding features, that outperform the previously published coding classifiers by a statistically significant difference of the metrics disclosed herein, either measured by a P-value threshold of ≤0.05 or non-overlapping confidence intervals for the metric of performance applied can be used in any of the methods, systems, or kits disclosed herein.

Example 18 Generation of Prognostic Genomic Signatures with Coding and Non-Coding Features for Gastric Cancer Based on the publicly available genomic and clinical data from GEO Omnibus, which can be downloaded at the world wide web at ncbi.nlm.nih.gov/geo/query/acc.cgi?acc=GSE27342 and at the world wide web at ncbi.nlm.nih.gov/geo/query/acc.cgi?acc=GSE13195, a newly developed classifier can be created for discriminating different stages of gastric cancer and can be composed of coding and non-coding features. CEL files for the arrays from the dataset can be pre-processed using the fRMA algorithm. The normalized and summarized expression values can be used as input for ranking methods such as Wilcoxon test or Median Fold Difference (MFD), and a ranking of the features can be generated. This ranking of coding and non-coding features can be used as input to train multiple machine learning algorithms (e.g., Support Vector Machines, K-Nearest Neighbors, and Random Forest) that generate classifiers. Selection of the classifiers for gastric cancer can be based on the performance of one or more metrics from Area under the ROC curve (AUC), Accuracy, Sensitivity, Specificity, Negative Predictive Value (NPV) and Positive Predictive Value (PPV). The newly developed classifier, containing both coding and non-coding features, can show prognostic ability as supported by the statistical significance of the metrics applied.

Example 19 Generation of Prognostic Genomic Signatures with Coding and Non-Coding Features for Neuroblastoma Based on the publicly available genomic and clinical data from GEO Omnibus which can be downloaded at the world wide web at ncbi.nlm.nih.gov/geo/query/acc.cgi?acc=GSE27608, a newly developed classifier can be created for discriminating different stages of neuroblastoma and can be composed of coding and non-coding features. CEL files for the arrays from the dataset can be pre-processed using the fRMA algorithm. The normalized and summarized expression values can be used as input for ranking methods such as Wilcoxon test or Median Fold Difference, and a ranking of the features can be generated. This ranking of coding and non-coding features can be used as input to train multiple machine learning algorithms (e.g., Support Vector Machines, K-Nearest Neighbors, and Random Forest) that generate classifiers. Selection of the classifier for neuroblastoma can be based on the performance of one or more metrics from Area under the ROC curve (AUC), Accuracy, Sensitivity, Specificity, Negative Predictive Value (NPV) and Positive Predictive Value (PPV). The newly developed classifier for neuroblastoma, containing both coding and non-coding features, can show prognostic ability as supported by the statistical significance of the metrics applied.

Example 20 Generation of Prognostic Genomic Signatures with Coding and Non-Coding Features for Glioma Based on the publicly available genomic and clinical data from GEO Omnibus, which can be downloaded at the world wide web at ncbi.nlm.nih.gov/geo/query/acc.cgi?acc=GSE30472, a newly developed classifier is created for discriminating different grades of glioma and can be composed of coding and non-coding features. CEL files for the arrays from the dataset can be pre-processed using the fRMA algorithm. The normalized and summarized expression values can be used as input for ranking methods such as Wilcoxon test or Median Fold Difference, and a ranking of the features can be generated. This ranking of coding and non-coding features can be used as input to train multiple machine learning algorithms (e.g., Support Vector Machines, K-Nearest Neighbors, and Random Forest) that generate classifiers. Selection of the classifiers for glioma can be based on the performance of one or more metrics from Area under the ROC curve (AUC), Accuracy, Sensitivity, Specificity, Negative Predictive Value (NPV) and Positive Predictive Value (PPV). The newly developed classifier, containing both coding and non-coding features, can show prognostic ability as supported by the statistical significance of the metrics applied.

TABLE 1

| Abbreviation | Description |
|---|---|
| AUC | Area Under Curve |
| BCR | Biochemical Recurrence |
| CM | Clinical Model |
| CR | Clinical Recurrence |
| ECE | Extra Capsular Extensions |
| FFPE | Formalin Fixed Paraffin Embedded |
| fRMA | Frozen Robust Multiarray Average |
| GC | Genomic Classifier |
| GCC | Genomic Clinical Classifier |
| IQR | Interquartile Range |
| LNI | Lymph Node Invasion |
| MDA | Mean Decrease in Accuracy |
| MDG | Mean Decrease in Gini |
| MSE | Mean Squared Error |
| NED | No Evidence of Disease |
| OOB | Out of Bag (sampling) |
| PCSM | Prostate Cancer Specific Mortality |
| PSA | Prostate Specific Antigen |
| PSR | Probe Selection Region |

TABLE 1-continued

| Abbreviation | Description |
|---|---|
| RP | Radical Prostatectomy |
| SVI | Seminal Vesicle Invasion |
| SMS | Surgical Margin Status |
| UTR | Untranslated Region |

TABLE 2

| | | Primary tumour | Metastasis |
|---|---|---|---|
| N | | 131 | 19 |
| Median age at Dx (years) | | 58 | 58 |
| Pre-op PSA (ng/ml) | <10 | 108 | 7 |
| | ≥10 <20 | 16 | 1 |
| | ≥20 | 6 | 9 |
| | NA | 1 | 2 |
| Pathological Gleason Score | ≤6 | 41 | 0 |
| | 7 | 74 | 2 |
| | ≥8 | 15 | 7 |
| | NA | 1 | 10 |
| Pathological Stage | T2 | 85 | 1 |
| | T3 | 40 | 7 |
| | T4 | 6 | 2 |
| | NA | 0 | 9 |

TABLE 3

| Name | Definition |
|---|---|
| Processed Transcript | Non-coding transcript that does not contain an ORF. |
| Retained Intron | Non-coding transcript containing intronic sequence. |
| Non-sense Mediated Decay (NMD) | The transcript is thought to go non-sense mediated decay, a process which detects non-sense mutations and prevents the expression of truncated ande erroneous proteins. |
| LincRNA | Large Intergenic Non-Coding RNA, or Long non-coding RNA, usually associated with open chromatin signatures such as histone modification sites. |
| Antisense | Non-coding transcript believed to be an antisense product used in the regulation of the gene to which it belongs. |
| Processed Pseudogene | Non-coding Pseudogene produced by integration of a reverse transcribed mRNA into the genome. |
| Unprocessed Pseudogene | A non-coding pseudogene arising from gene duplication. |
| Pseudogene | A non-coding sequence similar to an active protein |
| MiRNA | MicroRNA is single stranded RNA, typically 21-23 by long, that is thought to be involved in gene regulation (specially inhibition of protein expression) |
| Non Coding | Transcript does not result in a protein product |
| Sense Intronic | Has a long non-coding transcript in introns of a coding gene that does not overlap any exons (from VEGA definition) |

TABLE 4

MFD: Median Fold Difference in this dataset in various comparisons.

| Gene | Probe set ID | Type | Comparison | MFD | P-value | Adjusted P-value |
|---|---|---|---|---|---|---|
| H19 | 3359088 | Intron | Metastatic Vs Primary | 1.86 | <0.3 | 1 |
| MALAT1 | 3335167 | Exon | Normal Vs Primary | 1.56 | <0.1 | 1 |
| MALAT1 | 3335168 | Exon | Normal Vs Primary | 1.73 | <0.2 | 1 |
| MALAT1 | 3335176 | Exon | Normal Vs Primary | 1.78 | <0.05 | 1 |
| MALAT1 | 3335179 | Exon | Normal Vs Primary | 1.59 | <0.7 | 1 |
| MALAT1 | 3335194 | Exon | Metastatic Vs Primary | 0.53 | 0.000 | 0.029 |
| MALAT1 | 3335196 | Exon | Metastatic Vs Primary | 0.63 | 0.000 | 0.001 |
| PCA3 | 3175539 | Exon | Metastatic Vs Primary | 1.50 | <0.02 | 1 |
| PCA3 | 3175540 | Exon | Normal Vs Primary | 1.90 | 0.000 | 1.36E−11 |
| PCA3 | 3175545 | Intron | Normal Vs Primary | 1.53 | 0.000 | 2.33E−09 |
| PCGEM1 | 2520743 | Exon | Metastatic Vs Primary | 0.63 | <0.002 | 0.05 |
| PCGEM1 | 2520744 | Exon | Metastatic Vs Normal | 1.53 | <0.3 | 1 |
| PCGEM1 | 2520744 | Exon | Normal Vs Primary | 0.64 | <0.002 | 0.07 |
| PCGEM1 | 2520745 | Intron | Normal Vs Primary | 1.52 | 0.000 | 0.04 |
| PCGEM1 | 2520746 | Exon | Metastatic Vs Normal | 1.61 | <0.5 | 1 |
| PCGEM1 | 2520749 | Exon | Metastatic Vs Normal | 1.55 | <0.2 | 1 |
| PCGEM1 | 2520749 | Exon | Metastatic Vs Primary | 0.62 | 0.000 | 0.01 |

TABLE 5

SVI: Seminal Vesicle Invasion ECE: Extracapsular Extension, SMS: Surgical Margin Status, LNI: Lymph node Involvement, PreTxPSA: Pre-operative PSA, PGS: Pathological Gleason Score.

| | Classifier | | | | | |
|---|---|---|---|---|---|---|
| | Coding | | Non-Coding | | Non-Exonic | |
| Predictor | Odd Ratio | P-value | Odd Ratio | P-value | Odd Ratio | P-value |
| KNN Positive* | 2.49 | 0.63 | 15.89 | 0.14 | *29.74* | *0.05* |
| SVI | 0.26 | 0.42 | 0.29 | 0.44 | 0.52 | 0.69 |
| SMS | 0.64 | 0.73 | 1.06 | 0.97 | 0.89 | 0.94 |
| LNI | *32.37* | *0.05* | 22.7 | 0.1 | 55.74 | 0.09 |
| log2(Pre-Op PSA) | *0.15* | *0.01* | *0.09* | *0.02* | *0.06* | *0.02* |
| ECE | *41.46* | *0.04* | 225.84 | 0.06 | 356.81 | 0.06 |
| Path Gleason Score | *8.65* | *0.03* | 6.48 | 0.06 | 6.65 | 0.07 |

*KNN Positive: Metastatic-like

TABLE 6

| SEQ ID NO. | Type | Sequence |
|---|---|---|
| 1 | CODING | CCTGCCATGTACGTCGCCATTCAAGCTGTGCTCTCCCTCTATGCCTCTGGCCGCACGACA |
| 2 | CODING | GGCTCAGAGCAAGCGAGGGATCCTAACTCTCAAATACCCCATTGAACACGGC |
| 3 | CODING | GGATTCAGGTGATGGCGTCACCCACAATGTCCCCATCTATGAAGGCTATGCCCTGCCCCATGCCATCATGCGCCTGGACTTGGCTGGCCGTGACCTCACGGACTACCTCATGAAGATCCTCACAGAGAGAGGCTATTCCTTTGTGAC |
| 4 | CODING | TGAAGGTGGTATCATCGGTCCTGCAGCTT |
| 5 | CODING | CTGCGTGTAGCACCTGAAGAGCACCCCACCCTGCTCACAGAGGCTCCCCTAAATCCCAAGGCCAACAGGGAAAAGATGACCCAG |
| 6 | CODING | CATCCGCATCAACTTCGACGTCACGG |
| 7 | CODING | GCATGGAGTCCGCTGGAATTCATGAGACAACCTACAATTCCATCATGAAGTGTGACATTGACATCCGTAAGGACTTATATGCCAAC |
| 8 | CODING | TGCTCAGAAAGTTTGCCACCTCATGGGAATTAATGTGACAGATTTCACCAGATCCATCCTCACTCCTCGTATCAAGGTTGGGCGAGATGT |
| 9 | CODING | TTTGGCCAAGGCAACATATGAGCGCCTTTTCCGCTGGATACTCACCCGCGTGAACAAAGCCCTGGACAAGACCCATCGGCAAGGGCTTCCTTCCTGGGGATCCTGGATATAGCTGGATTT |

TABLE 6-continued

| SEQ ID NO. | Type | Sequence |
|---|---|---|
| 10 | CODING | CTATAATGCGAGTGCCTGGCTGACCAAGAATATGGACCCGCTGAAT GACAACGTGACTTCCCTGCTCAATGCCTCCTCCGACAAGTTT |
| 11 | CODING | AGAGAGAAATTGTGCGAGACATCAAG |
| 12 | CODING | GGAGGAGTCCCAGCGCATCAACGCCAACCGCAGGAAGCTGCAGCG GGAGCTGGATGAGGCCACGGAGAGCAACGAGGCCATGGGCCGCGA GGTGAACGCACTCAAGAGC |
| 13 | CODING | ATCGGGAGGACCAGTCCATTCTATGCAC |
| 14 | CODING | AAGCAGCTTCTACAAGCAAACCCGATTCTGGAGGCTTTCGGCAACG CCAAAACAGTGAAGAACGACAACTCCTCA |
| 15 | CODING | GGAGGGCTTCAACAACTACACCTTCCTCTCCAATGGCTTTGTGCCC ATCCCAGCAGCCCAGGATGATGAGATGTTCCAGGAAACCGTGGAG GCCATGGCAATCATGGGTTTCAGCGAGGAGGA |
| 16 | CODING | ACCAGTCAATCAGGGAGTCCCGCCACTTCCAGATAGACTACGATGA GGACGGGAACTGCTCTTTAATTATTAGTGATGTTTGCGGGGATGAC GATGCCAAGTACACC |
| 17 | CODING | AAGGTCTGGAGGACGTAGAGTTATTGAAAATGCAGATGGTTCTGA GGAGGAAACGGACACTCGAGACGCAGACTTCAATGGAACCAAGGC |
| 18 | CODING | CCTGGACCAGATGGCCAAGATGACGGAGAGCTCGCTGCCCAGCGC CTCCAAGACCAAGAAGGGCATGTTCCGCACAGTGGGGCAGCTGTA CAAGGAGCAGCTGGGCAAGCTGATGACCACGCTACGCAACACCAC GCCCAACTTC |
| 19 | CODING | GGAAGATGCCCGTGCCTCCAGAGATGAGATCTTTGCC |
| 20 | CODING | CTTCACGAGTATGAGACGGAACTGGAAGACGAGCGAAAGCAACGT GCCCTGGC |
| 21 | CODING | CAAGCTGGATGCGTTCCTGGTGCTGGAGCAGCTGCGGTGCAATGGG GTGCTGGAAGGCATTCGCATCTGCCGGCAGG |
| 22 | CODING | CTGCTAGAAAAATCACGGGCAATTCGCCAAGCCAGAGAC |
| 23 | CODING | CACCACGCACACAACTACTACAATTCCGCCTAG |
| 24 | CODING | CCTGTTCACGGCCTATCTTGGAGTCGGCATGGCAAACTTTATGGCT GAG |
| 25 | CODING | GCCAAACTGCGGCTGGAAGTCAACATGCAGGCGCTCAAGGGCCAG TTCGAAAGGGATCTCCAAGCCCGGGACGAGCAGAATG |
| 26 | CODING | GCTGAAACGGAAGCTGGAGGGTGATGCCAGCGACTTCCACGAGCA GATCGCTGACCTCCAGGCGCAGATCGCAGAGCTC |
| 27 | CODING | CCAGCTGGATGGAGATTCTTCTCAAATCTGATGGACTCAGGACGTT GCAATCTGTGTGGGAAGAGAGC |
| 28 | CODING | GCTACTCTAGCTCGCATTGACCTGGAGCGCAGAATTGAATCTCTCA ACGAGGAGATCGCGTTCCTTAAGAAAGTGCA |
| 29 | CODING | AGGTGACGGTGCTGAAGAAGGCCCTGGATGAAGAGACGCGGTCCC ATGAGGCTCAGGTCCAGGAGATGAGGCAGAAACACGCACAGGCGG T |
| 30 | CODING | CCCAGAGCGGAAGTACTCAGTCTGGATCGGGGGCTCTATCCTGGCC TCTCTCTCCACCTTCCAGCAGATGTGGATCAGCAAGCCTGAGTATG ATGAGGCAGGGCCCTCCATTGTCCACAGGAAGTGCT |
| 31 | CODING | TTGCCAGCACCGTGGAAGCTCTGGAAGAGGGGAAGAAGAGGTTCC AGAAGGAGATCGAGAACCTCACCCAGCAGTACGAGGAGAAGGCGG CCGCTTATGATAAACTGGAAAAGACCAAGAACAGGCTTCAGCAGG AGCTGGACGACCTGGTTGTTGATTTGGACAACCAGCGGCAACTCGT G |
| 32 | CODING | GCCATCCCGCTTAGCCTGCCTCACCCACACCCGTGTGGTACCTTCA GCCCTGGC |
| 33 | CODING | GAAAAGGCCAAGAATCTTACCAAGCTGAAAA |

TABLE 6-continued

| SEQ ID NO. | Type | Sequence |
|---|---|---|
| 34 | CODING | GCAGCTGACCGCCATGAAGGTGATTCAGAGGAACTGCGCCGCCTACCT |
| 35 | CODING | CGCAGAAGGGCCAACTCAGTGACGATGAGAAGTTCCTCTTTGTGGACAAAAACTTCATCAACAGCCCAGTGGCCCAGGCTGACTGGGCCGCCAAGAGACTCGTCTGGGTCCCCTCGGAGAAGCAGGGCTTCGAGGCAGCCAGCATTAAGGAGGAGAAGGGGGATGAGGTGGTTGTGGAGCTGGTGGAGAATGGCAAGAAGGTCACGGTTGGGAAAGATGACATCCAGAAGATGAACCCACCCAAGTTCTCCAAGGTGGAGGACATGGCGGAGCTGACGTGCCTCAACGAAGCCTCCGTGCTACACAACCTGAGGGAGCGGTACTTCTC |
| 36 | CODING | TGAGAGCGTCACAGGGATGCTTAACGAGGCCGAGGGGAAGGCCATTAAGCTGGCCAAGGACGTGGCGTCCCTCAGTTC |
| 37 | CODING | AAAACGGGCAATGCTGTGAGAGCCATTGGAAGACTGTCCTC |
| 38 | CODING | CTACGAGATCCTGGCGGCGAATGCCATCCCCAA |
| 39 | CODING | CTGCAACTTGAGAAGGTCACGGCTGAGGCCAAGATCAAG |
| 40 | CODING | AGAACCCCACAGACGAATACCTGGAGGGCATGATGAGCGAGGCCCCGGGGCCCATCAACTTCACCATGTTCCTCACCATGTTTGGGGAGAAGCTGAACGGCACGGACCCCGAGGATGTGATTCGCAACGCCTTTGCCTGCTTCGACGAGGAAGCCTCA |
| 41 | CODING | CCACATCTCTTTCTTATTGGCTGCATTGGAGTTAGTGGCAAGACGAAGTGGGATGTGCTCGATGGGGTGGTTAGACGGCTGTTCAAA |
| 42 | CODING | GGTCAAGGAACTCAAGGTTTCGCTGCCGTGGAGTGGATGCCAATAGAAACTGG |
| 43 | CODING | TTACCGGCGGGGAGCTGTTTGAAGACAT |
| 44 | CODING | GCAGATGATGGCGGCTTGACTGAACAGAGTG |
| 45 | CODING | TAGGGCCTGAGCTGCCTATGAATTGGTGGATTGTTAAGGAGAGGGTGGAAATGCATGACCGATGTGCTGGGAGGTCTGTGGAAATGTGTGACAAGAGTGTGAGTGTGGAAGTCAGCGTCTGCGAAACAGGCAGCAACACAGAGGAGTCTGTGAACGACCTCACACTCCTCAAGACAAACTTGAATCTCAAAGAAGTGCGGTCTATCGGTTGTGGAGATTGTTCTGTTGACGTGACCGTCTGCTCTCCAAAGGAGTGCGCCTCCCGGGGCGTGAACACTGAGGCTGTTAGCCAGGTGGAAGCTGCCGTCATGGCAGTGCCTCGTACTGCAGACCAGGACACTAGCACAGATTTGGAACAGGTGCACCAGTTCACCAACACCGAGACGGCCACCCTCATAGAGTCCTGCACCAACACTTGTCTAAGCACTTTGGACAAGCAGACCAGCACCCAGACTGTGGGAGACGCGGACAGTAGCTGTAGGAGAAGGCCGTGTCAAGGACATCAACTCCTCCACCAAGACGCGGTCCATTGGTGTTGGAACGTTGCTTTCTGGCCATTCTGGGTTTGACAGGCCATCAGCTGTGAAGACCAAAGAGTCAGGTGTGGGCAGATAAATATTAACGACAACTATCTGGTTGGTCTCAAAATGAGGACTATAGCTTGTGGGCCACCACAGTTGACTGTGGGGCTGACAGCCAGCAGAAGGAGCGTGGGGGTTGGGGATGACCCTGTAGGGGAATCTCTGGAGAACCCCCAGCCTCAAGCTCCACTTGGAATGATGACTGGCCTGGATCACTACATTGAGCGTATCCCAGAAGCTGCTGGCAGAACAGCAGACACTGCTGGCTGAGAACTACAGTGAACTGGCAGAAGCTTTCGGGGAACCTCA |
| 46 | CODING | ATTGGCCTGGACCAGATCTGGGACGACCTCAGAGCCGGCATCCAGCAGGTGTACACACGGCAGAGCATGGCCAAGTCCA |
| 47 | CODING | CAGTAGAGCCAAGTTGGGAGGTGGTGAAAA |
| 48 | CODING | CTGTGTCCAGTCAGGCTGCGCAGGCG |
| 49 | CODING | GTTGGTGGTTCGTCAGCACTGCCGAGGAGCAAGGCTGGGTCCCTGCAACGTGCCTCGAAGGC |
| 50 | CODING | GGGGCAGACACTACCGAAGATGGGGATGAGAAGAGCCTGGAGAAACAGAAGCACAGTGCCACCACTGTGTTCGGAGCAAACACCCCCA |
| 51 | CODING | TATGCGCTGATGGAGAAAGACGCCCTCCAGGTGGCC |
| 52 | CODING | GGTTAGAGTGGACAGCCCCACTATG |
| 53 | CODING | TCCTGGGGGACCAGACGGTCTCAGACAATGAG |

TABLE 6-continued

| SEQ ID NO. | Type | Sequence |
|---|---|---|
| 54 | CODING | GGTGCAGACCGTACTCCATCCCTCCCTGTGAGCACCACGTCAACGG CTCCCGGCC |
| 55 | CODING | CAGAGTCCGCCCAGTCATGCACAGACTCCAGTGGAAGTTTTGCCAA ACTGAATGGTCTCTTTGACAGCCCTGTCAAGGAATACCAACAGAAT ATTGATTCTCCTAAACTGTATAGTAACCTGCTAACCAGTCGGAAAG AGCTACCACCCAATGGAGATACTAAATCCATGGTAATGGACCATCG AGGGCAACCTCCAGAGTTGGCTGCTCTTCCTACTCCTGAGTCTACA CCCGTGCTTCACCAGAAGACCCTGCAGGCCATGAAGAGCCACTCAG AAAAGGCCCATGGCCATGGAGCTTCAAGGAAAGAAACCCCTCAGT TTTTTCCGTCTAGTCCGCCACCTCATTCCCCATTAAGTCATGGGCAT ATCCCCAGTGCCATTGTTCTTCCAAATGCTACCCATGACTACAACA CGTCTTTCTCAAACTCCAATGCTCACAAAGCTGAAAAGAAGCTTCA AAACATTGATCACCCTCTCACAAAGTCATCCAGTAAGAGAGATCAC CGGCGTTCTGTTGATTCCAGAAATACCCTCAATGATCTCCTGAAGC ATCTGAATGACCCAAATAGTAACCCCAAAGCCATCATGGGAGACA TCCAGATGGCACACCAGAACTTAATGCTGGATCCCATGGGATCGAT GTCTGAGGTCCACCTAAAGTCCCTAACCGGGAGGCATCGCTATAC TCCCCTCCTTCAACTCTCCCCAGAAATAGCCCAACCAAGCGAGTGG ATGTCCCCACCACTCCTGGAGTCCCAATGACTTCTCTGGAAAGACA AAGAGGTTATCACAAAAATTCCTCCCAGAGGCACTCTATATCTGCT ATGCCTAAAAACTTAAACTCACCAAATGGTGTTTTGTTATCCAGAC AGCCTAGTATGAACCGTG |
| 56 | CODING | TTAGCCATCCTGGTGATAGTGATTATGGAGGTGTACAAATCGTGGG CCAAGATGAGACTGATGACCGGCCTGAATGTCCCTATGGACCATCC TGTTA |
| 57 | CODING | CCTCCTTCTCAGTAGCAGAGTCCAGTGCCTTGCAGAGCCTGAAGCC TGGGGA |
| 58 | CODING | GTTGCCAGAGGTGTACTGTGTCATCAGCCGCCTTGGCTG |
| 59 | CODING | GTGCATCAAGTACATGCGGCAGATCTCGGAGGGAGTGGAGTACAT CCACAAGCAGGGCATCGTGCACCTGGACCTCAAGCCGGAGAACAT CATGTGTGTCAACAAGACGGGCACCAGGATCAAGCTCATCGACTTT GGTCTGGCCAG |
| 60 | CODING | TTGGGTCAGTTCCAACATGCCCTGGATGAGCTCCTGGCATGGCTGA CACACACCGAGGGCTTGCTAAGTGAGCAGAAACCTGTTGGAGGAG ACCCTAAAGCCATTGAAA |
| 61 | CODING | TTTGAAGATTCTGCAACCGGGGCACAGCCACCTTTATAACAACC |
| 62 | CODING | TGCTTGCCATATCCAATTGAACACCCCTACCACACACATCTGTC GCGGCGCC |
| 63 | CODING | TCTGGAGTCAATACCTGGCGAGATCAACTGAGACCAACACAGCTGC TTCAAAATGTCGCCAGATTCAAAGGCTTCCCACAACCCATCCTTTC CGAAGATGGGAGTAGAATCAGATATGGAGGACGAGACTACAGCTT G |
| 64 | CODING | AAAGCTGGACAAGATCTGGCCTAAGCTTCGGGTCCTGGCGCGATCT TCTCCCACTGACAAG |
| 65 | CODING | GTAGGAGAGTTGAGTGCTGCAATGGAT |
| 66 | CODING | GTTCACCAACCCATGCAAGACCATGAAGTTCATCGTGTGGCGCCGC TTTAAGTGGGTCATCATCGGCTTGCTGTTCCTGCT |
| 67 | CODING | TTCGGATCTACCCTCTGCCGGATGACCCCAGCGTGCCAGCCCCTCC CAGACAGTTTCGGGAATTACCTGACAGCGTCCCACAGGAATGCACG GTTAGGATTTACATTGTTCGAGGCTTAGAGCTCC |
| 68 | CODING | TCTGGTCTTTGAGAAGTGCGAGCTGGCGACCTGCACTCCCCGGGAA CCTGGAGTGGCTGGCGGAGACGTCTGCTCCTCCGACTCCTTCAACG AGGACATCGCGGTCTTCGCCAAGCAG |
| 69 | CODING | GTACAGGACAGCCAGCGTCATCATTGCTTTGACTGATGGAG |
| 70 | CODING | CTGAGGTCACCCAGTCAGAGATTGCTCAGAAGCAAA |
| 71 | CODING | TTTCCACCGCAAAGCATCAGTGATCATGGTAGACGAGCTGCTGTCA GCCTACCCACACCAGCTTTCCTTCTCTGAGGCTGGCCTTCGAATCAT GATAACCAGCCACTTTCCCCCCAAGACCCGGCTCTCCATGGCCAGT CGCATGTTGATCAATGA |

TABLE 6-continued

| SEQ ID NO. | Type | Sequence |
|---|---|---|
| 72 | CODING | CGGCAGCGGTGGAAGGCCCTTTTGTCACCTTGGACATGGAAG |
| 73 | CODING | CGGCGGCCCATGGACTCAAGGCTGGAGCACGTGGACTTTGAGTGCC TTTTTACCTGCCTCAGTGTGCGCCAGCTCATCCGAATCTTTGCCTCA CTG |
| 74 | CODING | TACGATGAGCTGCCCCATTACGGCGGG |
| 75 | CODING | TGCGGGACCACAATAGCGAGCTCCGCTTC |
| 76 | CODING | CTGCTCGTTGCTCTGTCTCAGTATTTCCGCGCACCAATTCGACTCCC AGACCATGTTTCCATCCAAGTGGTTGTGGTCCAG |
| 77 | CODING | GGCTGTGGTGTCTCTTCATTGGGATTGGAGA |
| 78 | CODING | TGCAGGGAGTTCCAGCGAGGAAACTGTGCCCGGGGAGAGACCGAC TGCCGCTTTGCACACCCCGCAGACAGCACCATGATCGACACAAGTG ACAACACCGTAACCGTTTGTATGGATTACATAAAGGGGCGTTGCA |
| 79 | CODING | GAGCCCAGTGAAGGCCTCATATTCCCCTGGGTTCTGAATATAACTA GAGCCCCTTAGCCCCAACGGCTTTCCTAAATTTTCCACATCCAAGC CTAACAGTCTCCCCATGTGTTTGTGTA |
| 80 | CODING | GCCTTTGACACCTTGTTCGACCATGCCCCAGACAAGCTGAATGTGG TGA |
| 81 | CODING | GGAGAAGAACCTGCTACAGGAACAGCTGCAGGCAGAGACAGAGCT GTATGCAGAGGCTGAGGAGATGCGGGTGCGGCTGGCGGCCAAGAA GCAGGAGCTGGAGGAGATACTGCATGAGATGGAGGCCCGCCTGGA GGAGGAGGAAGACAGGGGCCAGCAGCTACAGGCTGAAAGGAAG |
| 82 | CODING | CTCCTTGAGGAGAGGATTAGTGACTTAACGACAAATCTTGCAGAAG |
| 83 | CODING | AAGGGGTTCTGAGGTCCATACCAAGAAGACGGTGATGATCAAGAC CATCGAGACACGGGATGG |
| 84 | CODING | GAAGAAGATCAATGAGTCAACCCAAAATT |
| 85 | CODING | GCCAAGGCGAACCTAGACAAGAATAAGCAGACGCTGGAGAAAGA GAACGCAGACCTGGCCGGGGAGCTGCGGGTCCTGGGCCAGGCCAA GCAGGAGGTGGAACATAAGAAGAAGAAGCTGGAGGCGCAGGTGC AGGAGCTGCAGTCCAAGTGCAGCGATGGGGAGCGGGCCCGGGCGG AGCTCAATGACAAAGT |
| 86 | CODING | TCTCTTCCAAATACGCGGATGAGAGGGACAGAGCTGAGGCAGAAG CCAGGGAGAAGGAAACCAAGGCCCTGTCCCTGGCTCGGGCCCTTG AAGAGGCCTTGGAAGCCAAAGAGGAACTCGAGCGGACCAACAAAA TGCTCAAAGCCGAAATGGAAGACCTGGTCAGCTCCAAGGATGACG TGGGCA |
| 87 | CODING | GCCTCTTCTGCGTGGTGGTCAACCCCTATAAACACCTGCCCATCTAC TCGGAGAAGATCGTCGACATGTACAAGGGCAAGAAGAGGCACGAG ATGCCGCCTCACATCTACGCCATCGCAGACACGGCCTACCGGAGCA TGCTTCAA |
| 88 | CODING | TGAAGCCCCACGACATTTTTGAGGCCAACGACCTGTTTGAGAACAC CAACCATACACAGGTGCAGTC |
| 89 | CODING | CTTGAGTCCCTGAGAATGCCTAGCAAAGTCCTCAACTTACTTAATTT CAGATATGTCACCTCCTAATCTGGGTCCAAGGAGTATAATATTTTT AATGAGTCAAAAATCCAACTCAGATTGACCTAAAATATATTTATCT TCTTTGCACACTTAAAAAATCCAGGAGCACCCCAAAATAGACATGT ACCGTTATATTAAGTAAGCAGGAGACTTAGGATTTGTGCTGTAGCC ACAAGAAAGACAGTGATCAGTGATATCAAACATCAGGAATCAGCC TTTATGTAACATAACAGCTGTCCTCCTATGGTGAAAGGTTCAAATG TAGTGAAGGTATAACCTATATTGACTGAGATTTCCCTTTTAGGTAGT GCCTTATCTCTATTACTAGTGTTAAAGGAATAAGGAATCTATGAAG GACAGGGAGCAGCTCTGGTCTGTCAATCTCAGCCACCTGTTTGATA TCACAGAGAAGATACTCGGAGGATTGTTGGAATGTATATAGTTTAG TAAGAAGTGGGTAAGAAAGAGGGTCTTAATTACTGAGCACTTATTA TGTATTAGGTTCTTTGCCAGATGTTTTACATATATAAACTCATTTC AGAAAACTTATTTAAAGTAAATGGGGCCGGGTATGGTGGTTCATGC CTGGAATCCTAGCACTTTGGGAGGCTGAGGTAGGAGGACTGCTTGA GGCCGGGAGTTGGAGACCAGCCTGAGCAACATAGTGAGACCCTGT CTCAATAATAATAATAATAATAGTAATAATGAAGTAAATGGGATA AGGAAAGAAGGATAATTATCTTTAAAGGTTGATTCCCACCCTCCCT |

TABLE 6-continued

| SEQ ID NO. | Type | Sequence |
|---|---|---|
|  |  | CCCCAGTTACTTAAGGAACTAAGTGAGTACATCTCCAGTTGCCCAT
GAAAGCATAAGTTTGTTTTCCTCAGCTGAGGCAAGTGGTAGAGTAT
ACAGGATAACGAAGTAACATGTAAAAGGCAGGACGCACATAAAGG
TGTACATGGCTATTGTTTCACCTGGAGAAACCACATGATTGGGACC
TGAAGGTTTACTGACTGACTACAGGGGCTGATTGTGAAGCACGAGG
AACCCCATGTGTGTGGAGACTGTAGGGTGAGAGCACACAATTATTA
GCATCATTTCTGAGTGATCTCACAGATTTTTTTCTTGTGTTTGCTTT
GCTTTTTGACAACTGCTTCTCCCACGTTCCTTGCAATTCTATTCTCTC
ACCTTCACTTTACTATTTGTATTCGATGGACCAGGATAATTCAGGCA
AGGTTACCTTGTAAACTTTAATTGGCCACACACCATGTTGTCACCC
AGCTGGCTATGAAGTGAATAATGGTACTGAAAGTAAACCTGAAGA
CCTTTCTCAGATCTATTTTAAGTCTGAGTCTGACCAACCATGGAAA
ATATTCGACATGAATTAATGTAGAGAACTATAAAGCATTTATGACA
GCTCCAAGAAAAATCATCTACTCTATGCAGGAGATATGTTTAGAGA
CCTCTCAGAAAAACTTGCCTGGTTTGAGGGTACACA |
| 90 | CODING | ACGGACAAGTCTTTCGTGGAGAAGCTGTGCACGGAGCAGGGCAGC
CACCCCAAGTTCCAGAAGCCCAAGCAGCTCAAGGACAAGACTGAG
TTCTCCATCATCCATTATGC |
| 91 | CODING | GAGAATGAGCTTAAGGAGCTGGAACAG |
| 92 | CODING | GGGGCAACCAATGGAAAAGACAAGACA |
| 93 | CODING | TGCTTCAAGAAGAAACCCGGCAGAAGCTCAACGTGTCTACGAAGC
TGCGCCAG |
| 94 | CODING | ACAAATCCTATCACTATACCGACTCACTACTACAGAGGGAAAATGA
AAGGAATCTATTTTCAAGGCAGAAAGCACCTTTGGCAAGTTTCAAT
CACAGCTCGGCACTGTATTC |
| 95 | CODING | AGCAAAATCTTCTTCCGAACTGGCGTCCTGGCCCACCTAGAGGAGG
AGCGAGATTTGAAGATCACCGATGTCATCATGGCCTTCCAGGCGAT
GTGTCGTGGCTACT |
| 96 | CODING | GTGTGGAAACCATCTGTTGTGGAAGAGTAA |
| 97 | CODING | TCTACAGTTTTGCACCACGGCAAGAAAACCAAAAACCAAAACAAA
CAAACAAAAAAAACCCAACAACAACCCAGAACAAAGCAAAACCC
AGCAGACTGTACTTAGCATTGTCTAAATCCATTCTCAAATTCCAAA
TATCACAGACACCCCTCACACAAGGAATATAAAAACCACCACCCTC
CAGCCTGGGCAACGTAGTAAAACCTCATCTATACAAGAATTTAAAA
ATAAGCTGGGCGTGGTGGTACACACCTGTGGTCCCAGCTACTAGGG
AGGCTGAGCCAGGAAGAACGCTCCAGCCCAGGACTTCGAGGCTGC
AATGAGCTATAATTGCATCATTGCACTCCAGCCTGGGCAACAGAGA
CCCTGTCTCAACCACCACCACCACCACCACCCCTACTACCCCTGTAT
TCAAGGTAAAAATTGAAGTTTGTATGATGTAAGAGATGAGAAAAA
CCCAACAGGAAACACAGACACATCCTCCAGTTCTATCAATGGATTG
TGCAGACACTGAGTTTTTAGAAAAACATATCCACGGTAACCGGTCC
CTGGCAATTCTGTTTACATGAAATGGGGAGAAAGTCACCGAAATGG
GTGCCGCCGGCCCCCACTCCCAATTCATTCCCTAACCTGCAAACCTT
TCCAACTTCTCACGTCAGGCCTTTGAGAATTCTTTCCCCCTCTCCTG
GTTTCCACACCTCAGACACGCACAGTTCACCAAGTGCCTTCTGTAG
TCACATGAATTGAAAAGGAGACGCTGCTCCCACGGAGGGGAGCAG
GAATGCTGCACTGTTTACACCCTGACTG |
| 98 | NON_CODING (UTR) | CAGCAGTTGATACCTAGCAGCGTTATTGATGGGCATTAATCTATGT
TAGTTGGCACCTTAAGATACTAGTGCAGCTAGATTTCATTTAGGGA
AATCACCAGTAACTTGACTGACCAATTGATTTTAGAGAGAAAGTAA
CCAAACCAAATATTTATCTGGGCAAAGTCATAAATTCTCCACTTGA
ATGCGCTCATGAAAAATAAGGCCAAAACAAGAGTTCTGGGCCACA
GCTCAGCCCAGAGGGTTCCTGGGGATGGGAGGCCTCTCTCTCCCCA
CCCCCTGACTCTAGAGAACTGGGTTTTCTCCCAGTACTCCAGCAATT
CATTTCTGAAAGCAGTTGAGCCACTTTATTCCAAAGTACACTGCAG
ATGTTCAAACTCTCCATTTCTCTTTCCCCTTCCACCTGCCAGTTTTGC
TGACTCTCAACTTGTCATGAGTGTAAGCATTAAGGACATTATGCTT
CTTCGATTCTGAAGACAGGTCCCTGCTCATGGATGACTCTGGCTTCC
TTAGGAAAATATTTTTCTTCCAAAATCAGTAGGAAATCTAAACTTA
TCCCCTCTTTGCAGATGTCTAGCAGCTTCAGACATTTGGTTAAGAAC
CCATGGGAAAAAAAAAATCCTTGCTAATGTGGTTTCCTTTGTAAAC
CAGGATTCTTATTTGTGCTGTTATAGAATATCAGCTCTGAACGTGTG
GTAAAGATTTTTGTGTTTGAATATAGGAGAAATCAGTTTGCTGAAA
AGTTAGTCTTAATTATCTATTGGCCACGATGAAACAGATTTC |
| 99 | NON_CODING (UTR) | GGCCGAGGGAGTCTATGAAAATCTCCCCTTTTTTACTTTTTTAAAGA
GTACTCCCGGCATGGTCAATTTCCTTTATAGTTAATCCGTAAAGGTT
TCCAGTTAATTCATGCCTTAAAAGGCACTGCAATTTTATTTTTGAGT |

TABLE 6-continued

| SEQ ID NO. | Type | Sequence |
|---|---|---|
| | | TGGGACTTTTACAAAACACTTTTTTCCCTGGAGTCTTCTCTCCACTT |
| | | CTGGAGATGAATTTCTATGTTTTGCACCTGGTCACAGACATGGCTT |
| | | GCATCTGTTTGAAACTACAATTAATTATAGATGTCAAAACATTAAC |
| | | CAGATTAAAGTAATATATTTAAGAGTAAATTTTGCTTGCATGTGCT |
| | | AATATGAAATAACAGACTAACATTTTAGGGGAAAAATAAATACAA |
| | | TTTAGACTCTAAAAAGTCTTTTCAAAAAGAAATGGGAAATAGGCAG |
| | | ACTGTTTATGTTAAAAAAATTCTTGCTAAATGATTTCATCTTTAGGA |
| | | AAAAATTACTTGCCATATAGAGCTAAATTCATCTTAAGACTTGAAT |
| | | GAATTGCTTTCTATGTACAGAACTTTAAACAATATAGTATTTATGGC |
| | | GAGGACAGCTGTAGTCTGTTGTGATATTTCACATTCTATTTGCACAG |
| | | GTTCCCTGGCACTGGTAGGGTAGATGATTATTGGGAATCGCTTACA |
| | | GTACCATTTCATTTTTTGGCACTAGGTCATTAAGTAGCACACAGTCT |
| | | GAATGCCCTTTTCTGGAGTGGCCAGTTCCTATCAGACTGTGCAGAC |
| | | TTGCGCTTCTCTGCACCTTATCCCTTAGCACCCAAACATTTAATTTC |
| | | ACTGGTGGGAGGTAGACCTTGAAGACAATGAAGAGAATGCCGATA |
| | | CTCAGACTGCAGCTGGACCGGCAAGCTGGCTGTGTACAGGAAAATT |
| | | GGAAGCACACAGTGGACTGTGCCTCTTAAAGATGCCTTTCCCAACC |
| | | CTCCATTCATGGGATGCAGGTCTTTCTGAGCTCAAGGGTGAAAGAT |
| | | GAATACAATAACAACCATGAACCCACCTCACGGAAGCTTTTTTTGC |
| | | ACTTTGAACAGAAGTCATTGCAGTTGGGGTGTTTTGTCCAGGGAAA |
| | | CAGTTTATTAAATAGAAGGATGTTTTGGGGAAGGAACTGGATATCT |
| | | CTCCTGCAGCCCAGCACCGAGATACCCAGGACGGGCCTGGGGGGC |
| | | GAGAAAGGCCCCCATGCTCATGGGCCGCGGAGTGTGGACCTGTAG |
| | | ATAGGCACCACCGAGTTTAAGATACTGGGATGAGCATGCTTCATTG |
| | | GATTCATTTTATTTTACACGTCAGTATTGTTTTAAAGTTTCTGTCTGT |
| | | AAAGTGTAGCATCATATATAAAAAGAGTTTCGCTAGCAGCGCATTT |
| | | TTTTTAGTTCAGGCTAGCTTCTTTCACATAATGCTGTCTCAGCTGTA |
| | | TTTCCAGTAACACAGCATCATCGCACTGACTGTGGCGCACTGGGGA |
| | | ATAACAGTCTGAGCTAGCACCACCCTCAGCCAGGCTACAACGACA |
| | | GCACTGGAGGGTCTTCCCTCTCAGATTCACCTGGAGGCCCTCAGAC |
| | | CCCCAGGGTGCACGTCTCCCCAGGTCCTGGGAGTGGCTACCGCAGG |
| | | TAGTTTCTGGAGAGCACGTTTTCTTCATTGATAAGTGGAGGAGAAA |
| | | TGCAGCACAGCTTTCAAGATACTATTTTAAAAACACCATGAATCAG |
| | | ATAGGGAAAGAAAGTTGATTGGAATAGCAAGTTTAAACCTTTGTTG |
| | | TCCATCTGCCAAATGAACTAGTGATTGTCAGACTGGTATGGAGGTG |
| | | ACTGCTTTGTAAGGTTTTGTCGTTTCTAATACAGACAGAGATGTGCT |
| | | GATTTTGTTTTAGCTGTAACAGGTAATGGTTTTTGGATAGATGATTG |
| | | ACTGGTGAGAATTTGGTCAAGGTGACAGCCTCCTGTCTGATGACAG |
| | | GACAGACTGGTGGTGAGGAGTCTAAGTGGGCTCAGTTTGATGTCAG |
| | | TGTCTGGGCTCATGACTTGTAAATGGAAGCTGATGTGAACAGGTAA |
| | | TTAATATTATGACCCACTTCTATTTACTTTGGGAAATATCTTGGATC |
| | | TTAATTATCATCTGCAAGTTTCAAGAAGTATTCTGCCAAAAGTATTT |
| | | ACAAGTATGGACTCATGAGCTATTGTTGGTTGCTAAATGTGAATCA |
| | | CGCGGGAGTGAGTGTGCCCTTCACACTGTGACATTGTGACATTGT |
| | | ACAAGCTCCATGTCCTTTAAAATCAGTCACTCTGCACACAAGAGAA |
| | | ATCAACTTCGTGGTTGGATGGGGCCGGAACACAACCAGTCTT |
| 100 | NON_CODING (INTRONIC) | CAGCTTGCAGCCCAACCGAGATACAAACAGAACATCATTGCAAGA ACTCAGGCCCCATCTGACTACCCTCCCCTGAAGACTCAAAGAGGG ACCGTCTTTTTGGCGAGCAGGCCTGTTGAGTGTGGGTGATTTCTTGG CTCAGCTAGAAGCATCCCTCCAGAAGGGGGCCCGTTTTGTGAAATG AGAATAAGCCCTTTCCTTCCATAGCGAGATCTTCCTCCACGTCGGG |
| 101 | NON_CODING (UTR) | CTGCCACCAGAGACCGTCCTCACCCC |
| 102 | NON_CODING (UTR) | CCTCTACAGGGTTAGAGTTTGGAGAGAGCAGACTGGCGGGGGGCC CATTGGGGGAAGGGGACCCTCCGCTCTGTAGTGCTACAGGGTCCA ACATAGAGCCGGGTGTCCCAACAGCGCCCAAAGGACGCACTGAG CAACGCTA |
| 103 | NON_CODING (UTR) | CAAGGATCCCCTCGAGACTACTCTGTTACCAGTCATGAAACATTAA |
| 104 | NON_CODING (UTR) | CCCAGATGTCATTCGTGCTGAAAGAACCAGAACAACTCTCTGCTCC CTGCCAAGCATGAAGCGGTTGTGACCCCAGGAAACCACAGTGACTT TGACTCTGGTTCAGCTGACATGCTCGAGTC |
| 105 | NON_CODING (UTR) | CAGTGGCGTTTGTAATGAGAGCACTTTCTTTTTTTTCTATTTCACTG GAGCACAATAAATGGCTG |
| 106 | NON_CODING (UTR) | GGAGCAAACTGCATGCCCAGAGACCCAGCGGACACACGCGGTTTG GTTTGCAGCGACTGGCATACTATGTGGATGTGA |
| 107 | NON_CODING (UTR) | TGGTCCCCAACAGCGACATAGCCCATCCCTGCCTGGTCACAGGGCA TGCCCCGGCCACCT |

TABLE 6-continued

| SEQ ID NO. | Type | Sequence |
|---|---|---|
| 108 | NON_CODING (UTR) | CAAGCAACAGAGGACCAATGCAACAAGAACACAAATGTGAAATCA<br>TGGGCTGACTGAGACAATTCTGTCCATGTA |
| 109 | NON_CODING (UTR) | TGCAGCCATGGTCACGAGTCATTTCTGCCTGACTGCTCCAGCTAAC<br>TTCCAGGGTCTCAGCAAACTGCTGTTTTTCACGAGTATCAACTTTCA<br>TACTGACGCGTCTGTAATCTGTTCTTATGCTCATTTTGTATTTTCCTT<br>TCAACTCCAGGAATATCCTTGAGCATATGAGAGTCACATCCAGGTG<br>ATGTGCTCTGGTATGGAATTTGAAACCCCAATGGGGCCTTGGCACT<br>AAGACTGGAATGTA |
| 110 | NON_CODING (UTR) | GGCTCTGTCACTGAGCAATGGTAACTGCACCTGGGCA |
| 111 | NON_CODING (UTR) | GCTGCTGTCACAAATACCCATCTTAGGATCCCATCAGCTTCCCATCC<br>CCCACCAGACAGCCACAGTACCCTCACTTTCTCCCTATTGTTCTTTC<br>AAATCCTGTTCTCAGGAAAGAAACTGCCACTAATTCATTCACACTA<br>AGGTGTAAATGATTGATAATAGGAATGAGTTACCTCTTCCCACAGA<br>CATTTGTTTTTAAGTATGACAGAGCAGGGCCTTAATCCCAAGGGAA<br>AAGGTTATGGAACTGGAGGGGGTGAGCTTTCTGGGTAGAAGGAGA<br>CTTCCTGAATTTCCTTAAAACCCAGTAAGAGTAAGACCTGTTGTTTT<br>GGAAGGTCTGCTCCACCATCTAAGAGCACTGTTTTTTTTTTTTGTT<br>GTTGTTGTTGTTTTACGGTCTCTGAGGGAATATAGTAAAAATGCAT<br>ATGCACGTGCAATTTGCACGGCAGCATTTCACCGATTGTGGACTGT<br>ATTGGCTAATGTGTTCCTGGTCTTTAGATGCAAACCATTAATAACA<br>CTATCTTATCTCATAGTTTTTTCAGGGGTGCTTCTTGATTAGTAGGG<br>AATTTTGAACACCTCTTTAAATACAGCTAGAAAATAAAACCAATTT<br>GTAAAGCCACATTTGCATATGATGCCAGCCTCACGCATTTGTATAT<br>CTCCAGAAATTCAGGTATGCCTCACCAATTTGCCCGTC |
| 112 | NON_CODING (UTR) | TCTTCTGTTGCAGGACTAACCTTTGAGAAATCCTTTTGTGAAGTCAT<br>TGCCTGCTCAAGAATGTACAGTGGCTCCCCAATGCCTTGGAGGCCA<br>TAAGGCCAGCCAGTTCTAGCTCTCTATTACCTGTCCCCACTCAACTG<br>ACTCATACCTGTTTCCGGCTGCATCACTATGTGCCCCACAGAGAAC<br>GATGATCGTCACCTCTGTGCCTGA |
| 113 | NON_CODING (ncTRANSCRIPT) | ATCATTGAATGGATCGGCTATGCCCTGGCCACTTGGTCCCTCCCAG<br>CACTTGCATTTGCATTTTTCTCACTTTGTTTCCTTGGGCTGCGAGCTT<br>TTCACCACCATAG |
| 114 | NON_CODING (INTRONIC) | TCCAGTGTTCGCCATTCCAGATGTCACTTTGCGTCCTCAGAGGGGA<br>CTCTGGGGCAGCCACCATGGCCGGCTTGTCTGGAGGCCCTTGGAGA<br>TCTAGGATGGGCGCTGGTCGTGGCTTTGGAGAACTTTCCTTCTCCA<br>AACAAATGCAGGAAACTCAAGATTCAGCATCCTAGAATTGTCTCTG<br>GCAAGTTGGTTTCCAGCCATAGTGAGTGGGAACAATGGCCCCAGA<br>GGCTGTGTGGCAGTTTAAACACAGTTTCCACTGCCTTTCCCTTTCCCT<br>AAAGAGTAAACACAGGAGATAATACTTTCTAACAACTCATCGTTAT<br>CAAGGGCCTACTATGTGCTGCTTGTTTTGGCTGCATGCGTAAACAC<br>ATCTC |
| 115 | NON_CODING (UTR) | GTCAGATCCGAGCTCGCCATCCAGTTTCCTCTCCACTAGTCCCCCCA<br>GTTGGAGATCT |
| 116 | NON_CODING (UTR) | TATAACCTTTGTGTGCGTGTATGTTGTGTGTGCATGTGTGGCGTA<br>TATGTGTGTTACAGGTTAATGCCTTCTTGGAATTGTGTTAATGTTCT<br>CTTGGTTTATTATGCCATCA |
| 117 | NON_CODING (UTR) | TCCAAATCATTCCTAGCCAAAGCTCTGACTCGTTACCTATGTGTTTT |
| 118 | NON_CODING (INTRONIC) | TGTGATTCTAAGTCAGGCCCTTGTGACTGAACCACCATGAGGCTGG<br>ACTGTGGGGACTCGGGTATCCCAGAGGCAGAGCACACCAGGTCTG<br>GGAGGGGGGCCACTCAGACGGCAACATTGTC |
| 119 | NON_CODING (UTR) | GATCACGCCGTTATGTTGCCTCAAATAGTTTTAGAAGAGAAAAAAA<br>AATATATCCTTGTTTTCCACACTATGTGTGTTGTTCCCAAAAGAATG<br>ACTGTTTTGGTTCATCAGTGAATTCACCATCCAGGAGAGACTGTGG<br>TATATATTTTAAACCTGTTGGGCCAATGAGAAAAGAACCACACTGG<br>AGATCATGATGAACTTTTGGCTGAACCTCATCACTCGAACTCCAGC<br>TTCAAGAATGTGTTTTCATGCCCGGCCTTTGTTCCTCCATAAATGTG<br>TCCTTTAGTTTCAAACAGATCTTTATAGTTCGTGCTTCATAAGCCAA<br>TTCTTATTATTATTTTTGGGGGACTCTTCTTCAAAGAGCTTGCCAAT<br>GAAGATTTAAAGACAGAGCAGGAGCTTCTTCCAGGAGTTCTGAGCC<br>TTGGTTGTGGACAAAACAATCTTAAGTTGGGCAGCTTTCCTCAACA<br>CAAAAAAAGTTATTAATGGTCATTGAACCATAACTAGGACTTTAT<br>CAGAAACTCAAAGCTTGGGGGATAAAAAGGAGCAAGAGAATACTG<br>TAACAAACTTCGTACAGAGTTCGGTCTATTAATTGTTTCATGTTAGA<br>TATTCTATGTGTTTACCTCAATTGAAAAAAAAAAGAATGTTTTTGCT |

TABLE 6-continued

| SEQ ID NO. | Type | Sequence |
|---|---|---|
| | | AGTATCAGATCTGCTGTGGAATTGGTATTGTATGTCCATGAATTCTT CTTTTCTCAGCACGTGTTCCTCACTAGAAGAA |
| 120 | NON_CODING (INTRONIC) | TTGGGTTGTCACTCTAGAGCATGTCAAACTTTGTACTTCAAAATATA TTTAGTATGATTGTTAGTGGTAACATATATCAAGGCTTTGAATTAAC TGTTTTATTTAATTTTCACAAGAAGCACTTATTTTAGCCATAGGAAA ACCAATCTGAGCTACAAATAGTTCTTTAAAATAAGCCCAGGTTATT TAGCTATTCTAGAAAGTGCCGACTTCTTTCAAGAAGCAGGCATTGT AGGACAGCTGAGAATTATCACATAGCCTAAATTCTAGCCTGGCAGC AAGAGTCACATCTGAGATGTCCAAAAAAAAAAAAAAAACACCTGA TCTACATTGAAAGGGGGTAGACTAACGTATGTGAGACCATTTTCCT ATTTGCAGTTACAAGGTTAAAGAACTTTGAAGGTCATTCGGCTGCT AAGAGGCATGTCGAACACTCTGTGTGGCTCTTTCACAGTAAACCCT CCTAAGAGCAGAAGACACATGGCTGTTAGTGTCTGCGTTTAGATTT AATTTCTCAAATAAAGGCCCTTGGCTGCGTATCATTTCATCCAGTTA TAAACTAGGGCTCCTGCAAGCACCCCCATTCTAAGGGTGAATTATT GAAATCAGTTGCTATTTGATGAGTCACAACTGGCCCAGCAGGCAGG GCATTTGAAGTCATGGTCATCAAAAAGAAATGATTGTTTTTTGAAA AGCTAAATGCTTAAAATGCTTCTAGAGGGAAGTCGTGGGGCGTGTG CTCATTCTCTTTAAAATCAGGGTTGTTGAGTTTGTTTTTAAACATTT TTATAAGTTCATGAGAAAAAATATATAAATTCTAAGAACCAACACT GTATTCCCAGAAACATGACCCTCGCTGGTCTTGGGTCCACATATCA TTGGACTCTGGGGGACACAAAGATGCCTGTGACACTTTGGTGTTGC CGAGTTAGTCA |
| 121 | NON_CODING (INTRONIC) | TCTCTGGGTATAACAAGTCACAAGCAATTCACTCTCCAGTATTAAC ACAGAAACTTAATCCAATATTCCTGACAACGAAATCATTTTGCTGC CTATAATGCATCCATGATGATTTACAAAGATAAAGTTTAAATAGTA AAAATTGTATTTTCAGAGTATCCACTACATGCCAAGTTTTTGCACAT GATATGGTAAGGTATGAGATTTCATAGTCACATTACAAAAAAAAAT TTTCCCAGAGAATAAATACAACATTATGGGTATGAGAAGAGGCAA GTAAGTCAAGTCTGCAGGGAGTTTTGAAAAAGAGAAATACTGGAA AGAGCTGCGCTCTCTTGTGTGTTCTCCTGGTGTTCTCCTGTGCTCAC CTCTTAGCTTGCTAAACGTGACCTTCCC |
| 122 | NON_CODING (INTRONIC) | CTTGGCACCCACAGTAAGCCTTGTAGGAGCTCAAAGTGCCTCAGGC AATCTGTGAGCAGAATAGCAATTTTATTACTTTGTCATTAAACCAA TTTCACAGCAGTATTGTTTGTTAATGAGCAGCGGCAAACGAGCGAA GATGTCACACACTGGAATAGCAGAGAGATTTGTGACCCAAGCTCAC AGCACTAAGATGGAAAGACCACGGCTATAAAAAGGAAATACTTT GGGATGAAATGCAAAGTCTATACAGCAGAGCTTGTGTTTATGAGCT ACCATTTTGCTAAGAGCTGTGAGAGAAATAAAGGTCTGGAAATATG CAGTTAAAACAGGGCCTATAAAATTAAAACCAAATTAAGTATAG CAGAGGATTACTGCACAGACTGTACTCGACAAAATATATTTTAAGT GACGAGGTGAAATCTAAATCAGTTTTGTTTGAATTTGGTTGGTATTT ATGAAATTCAATAAAAAAAAATGAAAAAATATCCAAACAAAGCAG CCGCCTCACCCTTGTGTGGTCTCTGAGCCATAAACGTGCATCACTTT GAGGAAATTCAACTTGCCAATCCTTAAATAATTAGCAACTTCTTGA TTCACAGGGTGCGCCCCTCCATCTTCATGAAAGCCTTCTCTGTTACT TTATCTCTTCGTAAGGACGTTGCCCATG |
| 123 | NON_CODING (INTRONIC) | GAAAGCCGCACTGCTCTGATGCTGAGATAGTGTTCCTACTTGTTCA AGAGTGAGTTCAAAAGTGAGCCTAGCCACCTAATTTTCACTAGCAG CACAGACTGGAAATGCCCAGCAGGATTACAGCTTTGAGACTCACTC TGGAGTACAACAGACTATCCCGCCCCTCTCAGATCAGACCCTAAAG TCTGTTCTAAAATTGTCCACTGTGGGTGCTGAGAGAAGGGGGCCCA AACATAGCGTGTGTTTCATGTCAAACTAATGGGCTACCCTGGAGAG ATTTCAGAGTTCTCATTTGTTTACTCACTTGGGCCCTCAGTCAAGGT CTGATCTTTGGAAGAGCAAATTTTTCCAAATTTTGAATAATCTCTTT CTAGCAAGAGGCTATGAATTCCTTTGTCCATCACTTTTTGGCTACTC GGAGCCACCTTCAACATACCACTCAAAGCTTTTCCTCATTTAACAA TAGGCTGTAATATACTAGTTCTGAACCTTTGCTGGGTCATGGACTTC TC |
| 124 | NON_CODING (ncTRANSCRIPT) | TGCCCACTTGCAAAAGAGGCTGTTGGCAGCAACACTTCACCACTAG AAACCTTTACTCCAATTCGAAACATGCCTTAACGCACAGTGTGAAT TACCCACTCTCGTGGCCCACAGAGGTTGACTCATTCAGGCCCCCTTT TGTTCAGATGAGGAAACTGAGGCTGACTCCGAAGCCTGGGGGCTTT CAGATGTGGAGTGGGTCCCTGTGCCCAGGTGATGAGGGGACCAGG CGGGTCTGGAGCAGGGCTGGAGTGGGGCTCAGATGTAGTAGGCTG GCAGTTAAAGGTGCCAGATGTGAGCCAGGCTGCTGGGTTTGAATCC TGGAGCTGCCTCATAGCAGCAGTAGGACTTTGGGTAACTTACATAG GTGCTGTATGCCTCAGTGACCTCATCTGTAATATAGAGATGATAAG AGTACCTGTCTCATTGGTCTACTGAGTTGTCCGGATTAACTCATTAA ATGAGTTAAAACTCATGAAGCCCTTGGAACTGTGACTGACACATAG TAAGTACTCAATAAAAAATAACTGCTAAGACCAGCCACAGTGGCTC ACACCTGTAATCTGAGCATTCTGGGAGGCCAAGGCGGAAGAATCC |

TABLE 6-continued

| SEQ ID NO. | Type | Sequence |
|---|---|---|
| | | CTTGAGCCCAGTATTTCAAGACCAGCCTAAAGGTCAACATAGGCAG ACTCTGTCTCTACTATACATTTTTAGATTAAATTTTTATAATAATAA TAACCACTAAAATGTGATTACTAAAGACAGCTTCTTCACAGTACAA AGAGATGCTCTTCTGAGTACCAACTCTTTGGAGGATAAACTGCCCT TATACCTTCAAAAATAACACTTGCCATATATCAAGTCCTTTCAAGT ACCTGGAGATTTACCCAGCACTCTGAGATAAATACCATTATCCCTC TGGGCACACAGAGGCTCAGAGAGGTTTAGTCATTTGCCCAAAGTCA CACAGCCTGTACGAGGCCAGGCTGGGACTCAAACTCAGTTCTGACT GATTCTAAAATCATGTGTTTAACTGCTGCACTCTAGGACCACCCGC AATGGATCTGTG |
| 125 | NON_CODING (INTRONIC) | CCATCCCGTGTCTCGATGGTCTTGATCATCACCGTCTTCTTGGTATG GACCTC |
| 126 | NON_CODING (UTR) | CTAGTGCTTGGGATCGTACATGTTAATTTTCTGAAAGATAATTCTAA GTGAAATTTAAAATAAATAAATTTTTAATGACCTGGGTCTTAAGGA TTTAGGAAAAATATGCATGCTTTAATTGCATTTCCAAAGTAGCATC TTGCTAGACCTAGTTGAGTCAGGATAACAGAGAGATACCACATGGC AAGAAAAACAAAGTGACAATTGTAGAGTCCTCAATTGTGTTTACAT TAATAGTGGTGTTTTTACCTATGAAATTATTCTGGATCTAATAGGAC ATTTTACAAAATGGCAAGTATGGAAAACCATGGATTCTGAAAGTTA AAAATTTAGTTGTTCTCCCCAATGTGTATTTTAATTTGGATGGCAGT CTCATGCAGATTTTTTAAAAGATTCTTTAATAACATGATTTGTTTGC CTTTCTAGATTTCTTTATCTTTCTGACCAGCAACTTAGGGAGCAGAA TTTAAATTAGGAAGACAAAGGGAAAGATTCATTTAAACCATATTTT TACAAAGTTTGTCATTTGCCCCAAGGTCAAATTTTAAATTCTTAATT TTCATTTTATTTCCCATTTTAGGTAAAAGTTTGCATTTAATCTTAGA ATTATGTTATTTTTGTTAGTAGTGTGGAAACTTAGAGAACTTATTGT ATGGTGCCTTGCA |
| 127 | NON_CODING (ncTRANSCRIPT) | CTCCTATGTCTTTCACCGGGCAATCCAAGTACATGTGGCTTCATACC CACTCCCTGTCAATGCAGGACAACTCTGTAATCAAGAATTTTTTGA CTTGAAGGCAGTACTTATAGACCTTATTAAAGGTATGCATTTTATA CATGTAACAGAGTAGCAGAAATTTAAACTCTGAAGCCACAAAGAC CCAGAGCAAACCCACTCCCAAATGAAAACCCCAGTCATGGCTTCCT TTTTCTTGGTTAATTAGGAAAGATGAGAAATTATTAGGTAGACCTT GAATACAGGAGCCCTCTCCTCATAGTGCTGAAAAGATACTGATGCA TTGACCTCATTTCAAATTTGTGCAGTGTCTTAGTTGATGAGTGCCTC TGTTTTCCAGAAGATTTCACAATCCCCGGAAAACTGGTATGCTAT TCTTGAAGGCCAGGTTTTAATAACCACAAACAAAAAGGCATGAAC CTGGGTGGCTTATGAGAGAGTAGAGAACAACATGACCCTGGATGG CTACTAAGAGGATAGAGAACAGTTTTACAATAGACATTGCAAACTC TCATGTTTTTGGAAACTAGTGGCAATATCCAAATAATGAGTAGTGT AAAACAAAGAGAATTAATGATGAGGTTACATGCTGCTTGCCTCCAC CAGATGTCCACAACAATATGAAGTACAGCAGAAGCCCCAAGCAAC TTTCCTTTCCTGGAGCTTCTTCCTTGTAGTTCTCAGGACCTGTTCAA GAAGGTGTCTCCTAGGGGCAGCCTGAATGCCTCCCTCAAAGGACCT GCAGGCAGAGACTGAAAATTGCAGACAGAGGGGCACGTCTGGGCA GAAAACCTGTTTTGTTTGGCTCAGACATATAGTTTTTTTTTTTTTTAC AAAGTTTCAAAAACTTAAAAATCAGGAGATTCCTTCATAAAACTCT AGCATTCTAGTTTCATTTAAAAAGTTGGAGGATCTGAACATACAGA GCCCACATTTCCACACCAGAACTGGAACTACGTAGCTAGTAAGCAT TTGAGTTTGCAAACTCTTGTGAAGGGGTCACCCCAGCATGAGTGCT GAGATATGGACTCTCTAAGGAAGGGGCCGAACGCTTGTAATTGGA ATACATGGAAATATTTGTCTTCTCAGGCCTATGTTTGCGGAATGCA |
| 128 | NON_CODING (INTRONIC) | GCAGTGTGTTGCTCAGTAACTTCCAGGACCATCCTCACTATCCAAG GAGATGATGGGATGAAGTTTTGCAAATGGCAAGGCCTGGCTCTAAT GCACAGAGCAAAGCACATCTTTCTTTGCTGTGTGAAGTTGCAAAAT GATTACACTATTTCCTTGAGGAGAACAGTTATAGACACCCAGTGTT ATGCATTAGTCAGTGTTGTATAATTGATCTTTTTTTAATCCCCTCCA TTAGCAAATAGAAGAAGATTGTGCAGAGACTGAAGATGGCATGGT GTGGTGATTGGCAGGAGACATTGTGATAGGACTCGAGTCCCAACTC TGCTACTCAGTAGCTCTGTGAGCTTGGACAAGTTAACCAACCATAG TCTCTTTATTTGTAAAATGGGGATAATAATAGACCCTATATCACAT GATTGTTATCAGTATTAAATGGAAGAACGCATGTGGAATACTTGAC ATAGAGTAAGCATTCAATAATTGTTAGCTATTAACAGTGATACTTA TTAATAGCTAACACAGTGACATATGTGTATTCAGATTCTAAGCCGG TGCACCCAGTCCTCCCCTTCACAAGAGGAAAGTGTCAGCATTGCCAG AAACATTGTATGTCCTCAGTGCTGGTGGCTCCAGCTACCTGTCCTCC CCTTAGCAATTTGGTATTGTCCAAACATTTAGGTTTCTGAACATGCC TGAGGCTTA |
| 129 | NON_CODING (UTR) | GTGTGTGTGACATTCTCTCATGGGACAATGTTGGGGTTTTTCAGACT GACAGGACTGCAAGAGGGAGAAAGGAATTTTGTCAATCAAAATTA TTCTGTATTGCAACTTTTCTCAGAGATTGCAAAGGATTTTTTAGGTA GAGATTATTTTTCCTTATGAAAAATGATCTGTTTTAAATGAGATAA |

TABLE 6-continued

| SEQ ID NO. | Type | Sequence |
|---|---|---|
| | | AATAGGAGAAGTTCCTGGCTTAACCTGTTCTTACATATTAAAGAAA
AGTTACTTACTGTATTTATGAAATACTCAGCTTAGGCATTTTTACTT
TAACCCCTAAATTGATTTTGTAAATGCCACAAATGCATAGAATTGT
TACCAACCTCCAAAGGGCTCTTTAAAATCATATTTTTATTCATTTG
AGGATGTCTTATAAAGACTGAAGGCAAAGGTCAGATTGCTTACGG
GTGTTATTTTTATAAGTTGTTGAATTCCTTAATTTAAAAAAGCTCAT
TATTTTTTGCACACTCACAATATTCTCTCTCAGAAATCAATGGCATT
TGAACCACCAAAAAGAAATAAAGGGCTGAGTGCGGTGGCTCACGC
CTGTAATCCCAGCACTTTGGGGAGCCCAGGCGGGCAGATTGCTTGA
ACCCAGGAGTTCAAGACCAGCCTGGGCAGCATGGTGAAACCCTGT
ATCTACAAAAAATACAAAAATTAGCCAGGCATGGTGGTGGGTGCC
TGTAGTTCCAGCTACTTGGGAGGCTGAGGTGGGAAAATGACTTGAG
CCCAGGAGGAGGAGGCTGCAGTGAGCTAAGATTGCACCACTGCAC
TCCAACCTGGGCGACAAGAGTGAAACTGTGTCTCAAAAAAAAA
AAAAAACAAACAAAAACAAAAACAAAACAAAACAAAACAAAACA
AAACAGGTAAGGATTCCCCTGTTTTCCTCTCTTTAATTTTAAAGTTA
TCAGTTCCGTAAAGTCTCTGTAACCAAACATACTGAAGACAGCAAC
AGAAGTCACGTTCAGGGACTGGCTCACACCTGTAATCCCAGCACTT
TGGGAGATGGAGGTAAAAGGATCTCTTGAGCCCAGGAGTTCAAGA
CCAGCTTGGGCAACATAGCAAGACTCCATCTCTTAAAAAATAAAA
TAGTAACATTAGCCAGGTGTAGCAGCACACATCTGCAGCAGCTACT
CAGGAGGCTGAGGTGGAAAGATCGCTTGTGCACAGAAGTTCGAGG
CTGCAGTGAGCTATATGATCATGTCACTGCACTCCAGCCTGTGTGA
CCGAGCAAGACCCTATCTCAAAAAAATTAATTAATTAATTAATTAA
TTAATTTAAAAAGGAAGTCATGTTCATTTACTTTCCACTTCAGTGTG
TATCGTGTAGTATTTTGGAGGTTGGAAAGTGAAACGTAGGAATCCT
GAAGATTTTTTCCACTTCTAGTTTGCAGTGCTCAGTGCACAATATAC
ATTTTGCTGAATGAATAAACAGAAATAGGGAAGTAAACCTACAAA
TATTTTAGGGAGAAGCTCACTTCTTCCTTTTCTCAGGAAACCAAGC
AAGCAAACATATCGTTCCAATTTTAAAACCCAGTGACCAAAGCCTT
TGGAACTATGAATTTGCA |
| 130 | NON_CODING (INTRONIC) | CCTGGCTGATTTCTTGGTCTCTTGCCCTCATTCACCGAATTAATTCT
CTACACTGCTGCAAAACTGATCTTTCTAAACACAGGTCAGCTCATG
TCACTCACCTCCTCAGAAATCTTCAGTAGCTCTTCATTAACCAACAG
GGGGTTCCTAACTCCCCGTCTTGGCATTGGAGGACCTTTCCCTGCCT
GATCCCCGCGATCATCTTTTCCTGCAATATTTACTCAGGCCAGTGCT
CACCCCTTCTTTAAAATGCTGGTGCTGGCTCAAGAGAGGCAAACAG
CCATCTCTCTCATTCTTATCTTCCCTGTCAAGACTTCACATAGGTGG
ACTGATGCTAGACTATGATGATGAGTCTCCAGTGAAAGTTTCTAAG
TAGAACTCTCTCAGGGTTTCTAGAAGCATTTTTGTTTAAGAAAATAT
TGTGGGGGAGCGGGATTTTTAAATGGTGGAGCTCATGGTAAACA
AAATTATGTGTGCAAAATGTTAATAGAGCCTTTCTAATATTCTTGTG
ATTAACTCTGGTGACAGTTGGCTGAGTGTTCTTGTTTCTGCAACGCC
TGTCTTTG |
| 131 | NON_CODING (INTRONIC) | CTGATTTTATCAAAGGTTTGCCAGCCAATAAAGTGCATCCCAAGTA
TACAGGGGAGAAAGCTAGACTCCTACAGGGTC |
| 132 | NON_CODING (UTR) | TCTCAGGCATTGTTGGGGCATAAGCTCACACTGTAAGCTTTTCTCAT
GAATTCACTAGACATAACGTGGAAGGAAAACGTAGTCTTTTGGGA
GTACAGGGAAGCCAGCCCCTCAAAGCTTATGGAAGACATACCTGC
AATGGAAGCTGTTGCCCAATGTCTCCATTACTATCTTTCAAAAGAG
AAGCCAGACCCAGCTTCAGATCAAAAGTTCTTGAGACAGAGGAAC
AAAACCAATCGATTTCCAGGGAAGCTAATCAACTCTCTTTTCCCTCT
ACCACAAAACTGCCCTGCTGGAGTGGTTCTGAACCTGTACCCAGGA
CTCGATGTGGTCACTAATAACAATTAACCTGAACTGAGTCCACAGA
ACTCCACTCGGAACTTTCTTCTTTTTTAACTAGTGGCCCAATCATTC
CCACCATCTCTGTGCTGATAAGTACGTGTCCTAGATGAGAACCCTG
AAGAATGCAGACCTTCTTCCCCCGAAGGAGATGCCACAAGCTCTCC
AACACAGCCCCCTTTAGTTCCAAAGACTAGAGATGACCACATTGGT
AGAAGTATATCTCGAGGCACAGGAAGGGAGCCCCACCAGGGATAA
TTCAGACAGGACTAGAGAATAACATCATTTCACATACCCTGGGATA
AACACCCTGGGTTCCTATAGAAGGACTATTACTTATGGGAGTCCAA
CTTCTCCTTTTGTTTTGTTATTATCAGTTTATCTTTCTCCCACTCCAC
TTTTCCTTCAAGGTACCAATCCTTTCCTGTTCCTCGTTTGGCCATCTT
TCTTTTTCTGCCTCCACATTGGAGGGGAGGACTTCTCAGTTCTAAC
AAGCTGCCATACTCCTAAGAAAGCCATTTTTGAAAAATTTAACAAT
CCAGGTTCTTCTGGAGAACTCATTCTCCACACGCACAGTTTGCTGC
AAAAGGAAGTTGCAAGAATTCTTGAGGAAGAAACTGGTGACTTG
GTCCATCAGTCACGAAGTTCTTTCTATTCTCGTTTAGTTTTCAAGAA
ATTATTGGTTTGTGTTGCTCTGGGGAAATTGGAAATCATTACATTGT
AAAGACAAATATGGATGATATTTACAAGAGAGAATTTCAGATCTG
GGTTTTTGAAAGAAAACAGAATTGCGCATTGAAAACGATGGAAGG
AAAAAGACAATGGTCTAATGTGCATTCCTCATTACCTCTCGTGGCT
TTGGCTGGGAGTTGGAAAAAGCTAAAATTTCAGAACAGTCTCTGTA
AGGCTCTCTGTGGCTCCAGTTCACCATTTTATATTGTTGCATGCTGT |

TABLE 6-continued

| SEQ ID NO. | Type | Sequence |
|---|---|---|
| | | AGAAAGGAGCTATTGCTGTTGTTTTGTTTTTTTATTTAAATCACTAA
GGCACTGTTTTTATCTTTTGTAAAAAAAAAAAAAAAGTTGTTCACT
GTGCACTTATAGAAAAATAATCAAAAATGTTGGGATTTTAGAAGC
TCTCTTTTTGATAAACCAAAGATTTAGAAGTCATTCCATTGTTAACT
TGTAAAAATGTGTGAACACAGAGAGTTTTTGGTGATTGCTACTCTG
AAAGCTGCCAGATCTTATTCTGGGGGTGGGATGTGGAGGAATACAC
ATACACACACAAACATACATGTATGTATAATAGATATATACATATG
TGTATATTATATCTGTGTGTGCATGTATCTCCAAAAGCGGCGTTACA
GAGTTCTACACCAAAAGCCTTTAACCCTTAATCTGCTGTGAATGAT
ACCTGGCCTTTCTCACTATGAATTTCTGATTAACCAACCAGACTACA
CGTTGCCTCTCTGTGTATGACTAACGGCTCCAACCCGATGACTCAC
AGCTACTTGCTTATCGTGAACAAGCTCATCTTGGCAATGAATATGG
ATGTGAAAGACAGAACAGCTTCACCATTAGTAGCTGGAAATGGT
ATCACAGTCTCTTATAGAGGAATATGAAAGGAACAAGAAAATCAT
TTTACATTCCTTTTATCTGTATTGTGCTTTAAAAGATCCACATGGTA
AATTTTTTATTTTGCTTTTATGTCAGTCATCAGAACCAAAAAAATCC
AGAAGAAAAAATTGCCAGTGTTTCCTTTGAAGATGAAGCTACTGGG
GAAGAAAACCTTATTAATACACTCCACACATTTGTTCATTCCTCAG
CTGTTGGTGTTTTCTTGGGGTCTTGACAAAGCTTGCTGGTCAGTGCA
CTTTTCAGGTGTCACGTTTTGCTGTTTGTATGTTTTTTCTTCCCCTTA
CTTCCTTTGGAAAACAAACTCACACAGTGCCCCTACTCTGAGACCT
GGGACTGAGTGTTAATTATTTTTTCCTTGGGTATTTCTATCTGAGAG
ACTAGACCTAGTTAGGAGGCCTCTGTACTTCTCCAGATTGTACCTTT
TTATGGGGATCTTTGAGGCTATGACCCAGGACTGATAGATATGCCT
TACGGAAGACAAAAGATAAAATGGTTCCTATATCCTAATGCAAACC
AACACAGTTAAAAGAGCAGATCTCTGGATAACTGCTCTCAACCTGC
TTCTACAGTCTCCACAAACCGCATTCACCCTCTCTCTTCATAGCTCA
GACATGAAATTTGAGGGAGAAAACTGGAGATAATTGGGAGAAAAT
TGATGAAGTTGGCTGCTTCCAGTAGATCAGATAATCCATGAATTTG
TCTCCCATTGAGAATTTTTATTTTAAATTCTTTTAAACTCTTCGTTGTG
TCTTTTGTGATGACAAATCAGGCATGACTAAAAGATGTACAGAGAC
TTACGAAGATGGTCACATTCAAGTTCCCTAATGCTCTTAGAACCTG
AAGATGACCATGTGTAGTTTTCTTAAGACCTCTGAACCCCCATGGT
GATGAAGACTTGAAGACATTTGCAGCTATCTGCTGCAGTCTGGTAG
ATTCATACTTATCTAAAGAAGTCAAAAAATTTATTCGTGCAAGTGC
TTGCAGGAAGCCAGTGCTTATTAGTAGTGACCCTGCTTCTATCAAC
GTTATTG |
| 133 | NON_CODING (UTR) | GATCGCTGTGCTAGGTCTGACCAAAACCAGAGGGCAGTCTAGTCCT
GGGGGTAAAGCCCTCAGATCCCAGGGTACACTCTTCTCCATTCCCT
CCACCCACTTGCCTGTCACCCCAGTCACCTAAGCAATCACTGGGCC
CAGAGGAGAGGAGACAGACACACACTGGCTCCTGGACCTAAAGGG
TATGAGCTGGAGCTAAGGCCAGCTAGAGCTTCCACTGTCAGCCCTC
ACTGTCAGTCCCACTGCACCCCCCTGTGCCTGCTGGGCACTGGGCA
CTAGCTAGATGCTTTAGGTTGCTTCAGCTGATCCTTCAACTCTGTGA
GGTGGATACCAATATTCTA |
| 134 | NON_CODING (UTR) | CCCTGGAGGGATCCTAGAAAGCATTGTCATATTGCCATCTCCATTA
GCTCACTTTTAAACAACTAGGGTGCTGGAAGAACCTTTGTCTGAGG
GTAGTTCA |
| 135 | NON_CODING (UTR) | GTACACCCTGGCAAGGCTTCTCTTCAGACTGAAGCAGCAATTCTGC
CACTACCAGCAGCAACCAGGACGTCTGTTCTTTGTGGGGGCCAGAT
CAGAAGAGAGAGGCCCCTGTGACGCCCGGGCTGCTTGGTCACAAC
TCTGTCCAATTCAAGGATGTTTATCGGCCTCTCTTA |
| 136 | NON_CODING (INTRONIC) | GGCTGCATGGTTATCCCTCTCAGTGCAATATAGCTAAAGGGGCTTG
AAATGCTGGGAGTAGTCTTAAACAGCCCATTCTTGAAAGGTTTTCA
TTAACTCACTCTAAACATCTAAATTAAAAATGTTTTTGTTTTCACTA
TAGTAAACAGGAGTGTAACATTGCAGGTTTGGTACATTTCTGAATG
CCTCTCCACACACTGAAGCACAAGAGCCACTGAAAAAAGCTATAT
GATAAATATTTTAAAAATTATTTATCTGTGTTGCATTACATGAGGCC
TTATCTCCCAGACACTTAATAAAAGAGCTAATGAGAAGAAGAGCT
AAATTCTAAGATTTTGATGTTTGGTCATTAAACATTACAGACACCA
GTGATCAGAGAAAAAACAGAAGAAATAATGAGAAAGTGACATA
AAAAATTTTAAATGCAGCAAGATATATCAGAATCACGATATCTGGC
CTTTTATTTATCTATCGGCTCACTACTACTACTACGCACACAATTTA
TCACTTAAAAGAAAAATACATAATGTTGTTAGAATTTATCAGCAGT
AATGCTCCAAGCTCTATCTTTCTACAAAAATTTCATATCAGTAGGTT
TGCTTGAGGATTCTAGATTTGGTAAGATTGCAGTTTGCACAGAGAA
AAAGATATCAATATCAATAGGAAAATATTCTTTTAGAATTTCTCCA
TGGAGCTGACAACATCTTAGAATGTATCGTCCTAGACAGAGACTAT
TGGAAGAAAAACTTTCCTTATTTCTAAAATTTAAATTCAAAGTAT
CTTCTGGTGGGACGAAGAGAGAGAGGAGAAAGGTTGCTTGCT
GTGACTGGCAGGATTTTTTGAGCAGTCTGCTGCTTTCACTCCACTAA
AGAAACAAAACTTTCAGAAGTTTCATTTCCCTTCTATAAACCACAA
ATCCAAAACAAAGAAAGTGGAATAAGATAGTCTTTAAAGCTAAT
CTTGGTTTTGCTAATTTGTAAGCTTTCACCAGCAGTTCTTGTTTTGCT
CTGTTTTGATTTTGAGTGAATCTCATATTCCTGGCTCTGGTGGAGAA
TTTTCGTGCTTTTAAAGATTAATTAATTTAGTCCTTTTTGCAATGGTT |

TABLE 6-continued

| SEQ ID NO. | Type | Sequence |
|---|---|---|
| | | TGTTCTTTTCGGCATCTAGGAATTAAAGAAAGTGCTCAACCATAAA<br>TAAATGTAGTTATGTCCAAAGTACCTTCACATAGACACACTATACA<br>CAGGCGTGGGCCTTTTGGAAACACCTGAAGGCCAAATGTCTGACTG<br>TGAGTGGAAGATCCAGAGTGTGCTGATAGAGGAAGCTTTTCTCATC<br>CCTCGAGAGCAAAGAGGGTGATGGAGGCAAGAGTCAGAGAGCCCT<br>GTTCTCTTCTTCATGTACACTGCAAAGGGCAACTTCTCTAGAAGCAT<br>TAAAAGTGTCAATTAGGTTTTCAAGTAAGCGTCATTTATTCATATAT<br>ACATTCATTTGTCTTTTTATTTACAAAATTAAATCATTTTCCCATGA<br>ACATTAAAATGGGAAGAGAGAACAAAGAAAATAGAGTTGAATAAT<br>AATAACATTGATTCTGGACCAGACACTGGGCTGGACAATAACTCGA<br>GGGTTACCTTATTTATTTACACAAAGACCCGATGAGGTACACACTA<br>ATTATTTTCATCTCCCTATTACCAATCATGAGACTGAAGCTGAGAA<br>GGGTTAAAAACTTGCCTAAGCTCACACAACTAAGAAGTGTCCGAGC<br>TGGGCTTTGAACCCAAGGTTTGATCAAGGGTTGTGCCCTTAACTGC<br>CATACCATCCTGCCTCACAGATCTGGGTTA |
| 137 | NON_CODING (UTR) | CTCACAAATAGGAGTAGCAATTCTAGGTGGTAGGGTTGTGTACGGA<br>ACCCCTGGCTGTCTGCATATATCTCAGAATTACCCCAGGACCATTG<br>TCCCAAAGTCTAG |
| 138 | NON_CODING (UTR) | TTCCCGACAATAAGCTCCAACGTGGGCATAGTTGAACAAGCTATGC<br>CTCAAAATGCCAACGCCATATGCTTATTAGCCTGTGTGCATCATTCC<br>AGACGGGCCTAATCATTCCAGGACTGAAACCAGAATCGCTGAAAG<br>CCCTTGAAATACATTCAATAATTCATATGTTAAAACTTGGATATCTG<br>TTCAGCCCAAATGAAATCTTCCTTTTAAAAAACGTCTACATTATTGA<br>AAATTGTTCAATGTGCTTTTCAGAGTGACGGTGAGAATTTTATGCA<br>TGTATCTTGCCTGCATATTTGATATGTTACAAACTTCCAAAATTCAA<br>GGTGCAGCGATCCACAGAACGTTGTACATTTAAGAAGTGATTCCTT<br>CAAGCTAATTTAAAATTTCATTGAACACATGGTGACCAGGAAAACT<br>TTTTTTCAAGCACTGTTGGAAAGCACCCACAAAGCCCTTTAGAATTA<br>ATCTGGATTTGTTTCTCAAGTTCTGCTGAAGTTTAAAAAAAAACTTT<br>ATTATACAAATAACTCAAAATTTTCCTGTGTAAAACTAAACCTGTA<br>GTTTTAAAACATAATCCTGTTTGCATTAGAGCTCACTGTCTTTTTGT<br>GATGGAAACTGTGTTCGTATGGAATGACTAAAAATCTTTTATTTGG<br>TTTGTTTCAAATTACAATTGCTGATGGACAATTTGTATTGCAGCGAG<br>AACAACAGAATGAAAGAAATGTATCTCTGTGCGGCTATACATATAC<br>ATACATAAAATTGATTTTTAAATTTAAAACATATGGAAAACAAAAC<br>ATTGAACAGTTTGAATTTTGCCAAGTTGGACATTAAAGTAAAAATG<br>AAGTGAAATCATGCATTGAAAGAAAACATTTTGTTTCTAAATTAGT<br>CTACCATTGAGTGAGAATAATCAATATCAAGAAAGAAGACTATCTT<br>TCTCAACTAAACAATAATATTCCAATCAGCTTGGGAAGACCTGAAA<br>CTTGAATAAGCAGTGGAAATGCCAAATATAACAGAGGGTATGTGC<br>TACAGAGAAGTAAAAAGGGTTTGACTTTTTATGATGGGATTTTTTTT<br>TTCTGGGTATGTAATCTATTTTTTTTTTAAACTGGAAAGCATTTTTG<br>TCAGTGTGAATGAGGGTCAATAGTGCAGCCAGTGGTGACATTTTTC<br>TTTATTTTGCAAAATGCTTTTAAAACCAAAGGCTGCTCTAGTTGATG<br>GACAGTATCAGTCTTGATCTAAATTGTAGGACACTTTTTCATGTAAC<br>ATAACATTTGGGGATTGGGTTTATTTAGTGTAATGAAGATAATTTG<br>ATATAAAAATATTTTGTGTATATATATATATTTTTACTTTGTTTTCTA<br>AATTGCTGTTTGCAGTAACAGTAAGCGCAAAGCAAATATATAAGT<br>TATGACTGTATGATCAGATGAAGTATGAGTTCTTTTGGTTTGCATCC<br>TTAAATAGTTAGAGATCTCTGATAAAAACTTTGGAATCTTTGCAAA<br>ACAATACAAAAATGCCAAAATGTGAGCATGTCAATGAAAACTAAA<br>GACAAATACTTCACTCTTTTTCATACTATTATAAGTTATTCTGGTAT<br>TAAATATGTTAATAAAAGTGTTTTTGTTTTGACATATTTCAGTTAAA<br>TGAATGAATGCTGGTTGTATTTTATTTGAATGAGTCATGATTCATGT<br>TTGCCATCTTTTTAAAAAAATCAGCAAATTTCTTCTATGTTATAAAT<br>TATAGATGACAAGGCAATATAGGACAACTATTCACATGATTTTTTT<br>TAATACCAAAGGTTGGAAGATTTTATAATTAACATGTCAAGAAGAC<br>TTTATAGTAAGCACATCCTTGGTAATATCTCCAATTGCAATGACTTT<br>TTAATTTATTTTTTCTTTTGCTGCTTTAACATTTTCTGGATATTAAAA<br>TCCCCCCAGTCCTTTAAAAGAATCTTGAACAATGCTGAGCCGGCAG<br>CTGAAAATCTAACTCATAATTTATGTTGTAGAGAAATAGAATTACC<br>TCTATTCTTTGTTTTGCCATATGTAATCATTTTAATAAAATTAATAA<br>CTGCCAGGAGTTCTTGACAGATTTAAA |
| 139 | NON_CODING (UTR) | GTCGCCTTCCTATGTATGACGAAACAAGAAACAGAGATTTCCAATT<br>GCTCTTTTGTCTTCAGACATTTAGTAATATAAAGTACCTATTTTTAT<br>GCTGAAATGTTTATACAGGTTTATTAATAGCAAGTGCAACTAACTG<br>GCGGCATGCCTTGCAACACATTTTGATATATTAGCCATGCTTCCGG<br>GTAAAGGCAAGCCCCAAACTCCTTATCTTTTGCAGTCTCTCTGGGA<br>TCAGTAAAAGAAAAAAAAAATAATGTGCTTAAGAAGTGGGACTGT<br>AAATATGTATATTTAACTTTGTATAGCCCATGTACCTACCTTGTATA<br>GAAAAATAATTTTAAAAATTTGAATGGAAGGGGGTAAAGGAAGTC<br>ATGAAGTTTTTTGCATTTTTATTTAAATGAAGGAATTCCAAATAAC<br>TCACCTACAGATTTTTAGCACAAAAATAGCCATTGTAAAGTGTTAA<br>AATTTACGATAAGTATTCTATTGGGGAGGAAAGGTAACTCTGATCT |

TABLE 6-continued

| SEQ ID NO. | Type | Sequence |
|---|---|---|
| | | CAGTTACAGTTTTTTTTTCCTTTTTAATTTCATTATTTTGGGTTTTTG<br>GTTTTTGCAGTCCTATTTATCTGCAGTCGTATTAAGTCCTATTG |
| 140 | NON_CODING (UTR) | TCTCAGCATATGTTGCAGGACACCAAAAGGAAGAAAACAATCAAG<br>CAAATAAAATAAACAGTCAAACAAACCAGGAGTTTAAAACAACAA<br>CCCCAACAACAGAAGCCTTGGCAAAGAGGAATAAGTGATCAGCAA<br>GTGAACACACTCTATGTCAACTCTCCTTTTATCCAGCTGAGATTTAT<br>GGTAACTTATTTAATTAATGGTCCTGTCTGATGCATCCTTGATGGCA<br>AGCTTCAAATCTGATTTGGTATCACCGAGGAAACCTTGCCCCCATC<br>ACTCAGCATTGCACTTAGATACAGAATGAGTTAGATAAACTTGGCT<br>TGTCTAGAGACCCATGTCATCTTAACCTAAAGGGAAATCTTATTGC<br>GTTATCATAAAATTGATGATATCTTAGGGTCAGAATTGCCCTTTTTT<br>TTTATTTTGAATGGGAAGTTCTCACTAAAACAATCCTGAGATTTCTT<br>AATTTCATGGTTCTTTAAATATTATAAACACAGAGTCAACATAGAA<br>TGAAATTGTATTTGTTAAAATACACACATTGGAGGACAAGAGCAGA<br>TGACTACTTTTCGAAGTAATGCTGCTCCTTCCTAAAAGTCTGTTTTC<br>AATCCTGGTAATATTAGGGGCACTGCGGCACCTAAGAAGCCTTAAA<br>TGAGAGCTAATCCAATCTAGAGAGCGATGGTGTCAGCATTTCGGTC<br>TGCATA |
| 141 | NON_CODING (ncTRANSCRIPT) | CAGGGCATGAGACATTCAGCGTAGAGGTTAAAACGAGGGCCCTGG<br>GTTAGGAACCCCAGCTCAGTTCTCAGCTCTGTACCCTTGGAAAATT<br>CCCTTCCCATGGAGCTTTGTGGATGCACAAGGACTTGCACA |
| 142 | NON_CODING (ncTRANSCRIPT) | GTGGCTTGTTTACGTATGTTTCTGGAGCCAATT |
| 143 | NON_CODING (UTR) | CCCAAGCCTGTCTAAGGTTACTGTGTATTAGACAGGGCCGAACTAG<br>TGTGCTGAGCAAAAAGAATTGAAGCAAATTGTATTTACTTAGCCGC<br>TTCTGGGAGCCACTTCAGCCTTTCCCCTCCCCTCCCACTTCTTGGGTA<br>ATCTGACCTGAAGCATAGTCCAGGAGCAGAGTTAGCCAGAAATGC<br>CTCCTGCTGCCCCAGCCTTAGAGAGCTCCCATCTCAATCATTGAGC<br>CTGAAGGCTTCAAGCCCAAGAATGCAACAAGACCCCCAGCCTACA<br>TTTCTCAGCTCCCCTGGAGCCAGCTGATCCTGTAACGCTGCTGGAG<br>GTCAGTCTGAGCTACCAAGACTGTCCCTAGACAAAGGTGGAGTCCC<br>CCACACTGCCCAAGACCAAATCCCTCACTCAACCTGCTGAGGTGTG<br>GATGGGGAAACAGAGGCAAAACTGAGGCACCTGATGCATTCAGCC<br>TGCTGTGCAGCAGTGCCATTGACTGCCCTGATGTTCAGAGAGAAAC<br>GCACACAAGGTTTGCCCATGAGAATTGGGGAGCAGATGGCCAAGC<br>AGATAGGTTATGTCTGTTTTCTGAGTGATGAAGTCAGGAAGCCCTG<br>TGGCTCTGGAGGCCACTTGTGGTTCATTCTTTTCCCATATCCTTGGC<br>TTTTAGAAATGGTTACCTTCAGGACAGTGCAGCTGCATTTATCAGA<br>GCACTATTGCTAAGTTTTCTTTTCTGGCTTGTGTTTTCTGGGACAG<br>TTTAGAATTGGGAGGCCTATTCTCATAGAACA |
| 144 | NON_CODING (ncTRANSCRIPT) | CCTTCAGAAGCATGGGACTACCTCCCATCTAGTTCTCGTTTCTAAAC<br>CTAGGGGAGATGCTATCTTTGCTGCAATAATCTTAGCCTACATCTTG<br>GAATGGAAATGGCCTTGGTGGAAATGGTCTTCAACTCCTCTGGTCC<br>AAGCTCAGGCCCTGTGACCCTGGAACAATCCCCTTCCTGGTCCTCC<br>ATGTAGGAGCAATAACATTCCCTTGCCAGCAGCACCAGCCATTCTG<br>ATGATTAAATGGTATCGGACTCTGTTTTCCAAACTCAGTCATTCAG<br>ATGCCCCCTATTTTATTTCTTCCATGTCTGCAAATGATTATAATATT<br>TTTAAATGTAGGATGAGTCCTTTTTATTACACATAGAAATAGCTACT<br>GTAAATAGCAAACTCTAACACTGTGCCTAATTAGGAAATAAAGGTA<br>ACCATAAATACAGTAAAAATGAAACAATGTTATTATGGTTTAACCT<br>GATAGTGTGGCTTGCAAGGCCCTGGGCCTGAAGCCTGGGCAATAA<br>GTGAGAGTTAGAAAGGTGTCAAAGACATGATAGCAGCAAACTGAG<br>GCTTTGTACCCCACGGTAAATAGGACTGAAAGCAAATTCACAGGG<br>AGCAACTGATCCATTC |
| 145 | NON_CODING (INTERGENIC) | GAGTGGCCACTTGATTAGAGACCTAGCACAGGAGGAAGAGATGGG<br>CAGGGAGAGTGACGGGGAGCAGCACAGTCCCTGGGAGCCCGAAGT<br>GGGTGGGCACAGGGCTCCCTAGGAGAATGGAAGGACATCTATGAG<br>CTGTAGCCCAAGAGGAAGAGGTCACTGGGGCTAGATGCGGCAGAC<br>CCTCGCAGGCTTTGGGAAGGGCTTCAGAATTCAGCCTGAGGGCAAT<br>GGGGAGCCCTTTTGGGATATTAAACTTGAGTAAGATATGAGCATAT<br>TTGCATCTTGAAAAATCATTATGGGAAGATGGCTGGGAAGAGAGG<br>AGGAGTGGCAGAAGAAAGATAGGTTGGAGACAATTGATTGCTCGA<br>TGATATAAAATGTTAAGTACCATGAATGATGCTGTTAGGCTGGAAT<br>GCGCCAAGCATAAAGGTGGGGCATGGCATCAAAAGGTAGGTCAAC<br>ATATTAAATAATTCCATGTATTGAAATATCCAGAAAATATATAGAC<br>AGATCTATAGAGATAGAAACTGGTCTGCCCAGGACTAGGGGTTGTC<br>TA |
| 146 | NON_CODING (ncTRANSCRIPT) | CACTGGTCTGCCCTTCCTAAATTAAGTATGCACTTCAATTTGATGAG<br>TGGAAACAGTCTATCTGGGCAGTAACCAGGGAGCTTTGTGCCTAGT<br>AGATTGCTTCTGTTCTGCACTTCTTTGGTTTCCCACCTCAATGTAAA |

TABLE 6-continued

| SEQ ID NO. | Type | Sequence |
|---|---|---|
| | | AAATAGCTAGCAATGAAGTCCAGAAGTTGTCAATGGTTCATCCCCA<br>GAAGAATGCATAATGTCCAAAGTTGTATGTGTATGATGTCTTCAAT<br>GGTATTAAGTTATTTCAAATTCTTAGTTCACCTACATAAATCATTTC<br>TAACAAGCATCTTCTTAACCAACTTTATGCACAGTGTATGTTTGTAA<br>GTGCTTCTGCACGAATGTTTATACATGACTGTTTCCATAGTACTTAT<br>GTTTTTAAAAATATTCAGTCATTTCCTACTATAATCCTCATGTATCC<br>ATGTAACTGACTCAAAAATACTTCAGCCACAGAAAGCTAAAACTG<br>AGCAAATCTCATTCTTCTTTTCCATCCCCTTTGCATGTGGCTGGCAT<br>TTAGTAATGATTAATAATATGGCCAGCTGAATAACAGAGGTTTGAG<br>ACACAATTCTTTCTCAAAGGAGTCAGCTAAGCTGGGTCTACTTATG<br>GACAAACATCTAAATGTGTGGAAGTATCTGATATTTGACAATGGTA<br>AATTTCCACTTAGCTAGCTAGCATTGTCAGACTTCAATCTCCTCATG<br>GCTCTGGCCGTCCTGTTTTAAGCATGATAATTGTTGGCCACATCTCA<br>CATAGTTCTC |
| 147 | NON_CODING (INTRONIC) | AGTTTCTAGTTGACTTCCATCTGCAATAAATCATGTACAGGATGAG<br>GTAATATACTACAACTTATGTCTATTGACTTAGGATTTTATCTTTAA<br>GAGGATAGATCCTAGATGTGAATAGCTAAGGAAGTTTGAGTGTTTT<br>CTCCTCCCTTGCTTTCAAATAGCTTTGAAAGATCACTTTTATAGTGC<br>ATGATAAATAGCTACATATGAATAATCTGATGGCATTCTGTAAGAG<br>TAACAGTGCTTCAAAATCGTAACCTGCTGGGATGTTTTGTTACATG<br>CCATCAAGTGTGATTGTATTCATGGAATAGTGTTTACTGTTGCTCAA<br>TATTGTAAAGGAAATAAAAGATAATTCCCTATCTGAGGGGAAATTT<br>CTCAAATATTTTAATTAAAAGGTCCCTACAGTTACCCATATAAACC<br>TTAGTCAAATAAGATAACAAATTTTCTTGATCTCCTTTAAAAATTCT<br>TTTATGTATAAAAATAATTATATTTATTAAAAACTCCAACAGTACA<br>GAATTATTTGGAAAAAAAGATAGAAATCTACCATTCTCCTATCCAT<br>GCCTGAGAGATA |
| 148 | NON_CODING (INTRONIC) | CGGAGAGCCCTCTTGCATGAGTTTCGGCTTTGCCAAGATTCCAGGG<br>ACTTGAGGACAGCTATTGAGTTATGGTTACGTGACTGCCACATTGG<br>GGCTTGGAGGCATCTGGCAGATGGTTGGGAATGGGCTGGCACCAC<br>ACTAATTAGGCCACGATGATCCAGTTTGACTCAGGGAAACCCAGAA<br>GTCATAGTGCTCTTTGCAGAATGACACAAGATGTCAACATGCTTTG<br>TTGTGTACTTTGAACAGGGATTGGTTTCACAAGCTGAAAAGTTGAA<br>TCTGTCACATGTATGCAGCATAAAATCACAGCCGTGAGAACATGTA<br>TACAGCAGGAAGACAAGCGACTGAGCTAGGCACGGCTGACTAGCT<br>CTGAGCTTTC |
| 149 | NON_CODING (UTR) | AAAAGCCCTCTCTGCAATCTCGCTTCTCGTGTCCGCCCCGCTTCTCT<br>TATTCGTGTTA |
| 150 | NON_CODING (INTERGENIC) | AGGCTATCGGGAAACTCTGGTCCAGCCACAGTGGTCTGGCCACACA<br>GGGAGCCATGTAGAGACCTCCATCTCCAGCCAGGATGACACCGGTC<br>TGCGGTTCCCAGCTCGTCGTCAAGATGGGATCATCCA |
| 151 | NON_CODING (INTRONIC) | CTGGGATCTGCCAACGAAGATGAGCTCTTGCAG |
| 152 | NON_CODING (UTR) | CTCGGGAAAGGATCATCGCCGTTGAAATGAAAAGAGAGACAGAGA<br>GAAAAAAAAAAAGAGAACCCACATGAAGCTCTGAAACCAAACAGC<br>ATCCTGCCATGAGCTTCCCAGAGACAGAAGAGACTGGAGCAAAGT<br>CGGAAACACAGAGAAGCACGGCTTCCCCTCAGCACAGACCCTCCA<br>GACTGGGTCTCAGAGCCGTGCCACCCACCCTCCCACACAGCCGGCC<br>ACAGGGAGAACTGGTGCTAACCAGGGTGCTTGCTTTGGTCACGTTC<br>AACGCACTACAGAGCTACGACACAGGGAAACC |
| 153 | NON_CODING (UTR) | TGTGGTACCCAATTGCCGCCTTGTGTCTTGCTCGAATCTCAGGACA<br>ATTCTGGTTTCAGGCGTAAATGGATGTGCTTGTAGTTCAGGGGTTT<br>GGCCAAGAATCATCAC |
| 154 | NON_CODING (UTR) | TGATGGGCTAAACAGGCAACTTTTCAAAAACACAGCTATCATAGAA<br>AAGAAACTTGCCTCATGTAAACTGGATTGAGAAATTCTCAGTGATT<br>CTGCAATGGATTTTTTTTTAATGCAGAAGTAATGTATACTCTAGTAT<br>TCTGGTGTTTTTATATTTATGTAATAATTTCTTAAAACCATTCAGAC<br>AGATAACTATTTAATTTTTTTAAGAAAGTTGGAAAGGTCTCTCCTC<br>CCAAGGACAGTGGCTGGAAGAGTTGGGGCACAGCCAGTTCTGAAT<br>GTTGGTGGAGGGTGTAGTGGCTTTTTGGCTCAGCATCCAGAAACAC<br>CAAACCAGGCTGGCTAAACAAGTGGCCGCGTGTAAAAACAGACAG<br>CTCTGAGTCAAATCTGGGCCCTTCCACAAGGGTCCTCTGAACCAAG<br>CCCCACTCCCTTGCTAGGGGTGAAAGCATTACAGAGAGATGGAGCC<br>ATCTATCCAAGAAGCCTTCACTCACCTTCACTGCTGCTGTTGCAACT<br>CGGCTGTTCTGGACTCTGATG |
| 155 | NON_CODING (UTR) | TGGGCCTGTCGTGCCAGTCCTGGGGGCGAG |

TABLE 6-continued

| SEQ ID NO. | Type | Sequence |
|---|---|---|
| 156 | NON_CODING (UTR) | CCCGCCAGGCATTGCAGGCTTAGTCGTGGCTACTGTTCTCCTGTGCC GCTGCATCGCTCTCTCCCGGGAAA |
| 157 | NON_CODING (UTR) | GGCGGCTATTCTAAAAGTGTCTTTCTATCACTGTTAAGGGGGGGG AAAGTGAGGTTCGAGGATGACGTAGGTAACTCTCCCCTCCCAAGTC CATGTTCCAAGTGGCTATGTAAAGCAAGATGATACAGAAAGCTGCT CTAAAATCTCACTGAGTGATTTCACCTTCGCCTACTATGAAATGTCT CATCAGACCTGACATGTCTGAGATAACCAAGGTGATTCAGGATTTG ATCAAAAGAAGTCTAGTAAGAATTAATTACACAGAAGCCTCCTTTC ATTTCTATGGGCCAAACAAAGGCCATGGATAACCCTACCCGCTTTA TGTCATTACCCATTGGGAAACACAATGGCTACTTCTGTTAGGGTAC ATTGACCTTGGTCAAGCATCTTAAAGAAGGCAACCCTAATTGAGAG CTGTCTTGGCTAATACTCTGCACCACAATTGTGATGTCCTAGTCCTA CCACTAGAGGGCATGGTACAGCCTGGCAAAAGTTAAAAGGGGTGT GGCAGCTCCCATCAGGTCTGGAGGTGGTCTATAAGCACAGTTGACA GTTGTGCATTGGGATGGGTGGAGAAAGACGACAAGAGAGCAGAGA ATCTGCTGATGTGGCTGCGCTTACTTTTAGTGACTTTATGTACTTAT ATTAACAGCTGGAAATAGGTTGTTGGGTTTTGAGCAGGCTGTTATA GTGAGGAATGTTCATTTTTAAATGTTCCTAACAGATTTTGCTTTTGA AAAATGCTTGTTACATGAATAATTTGTGGACCAGGGATTGCTTTTCT GAAGGCAGTATAGGGAACATGAATATTCAAGATGAAATACAAAAA TTATGTTTAAGGGTCATAGTGTATAAGTAGCTTCCTAGGAAACCCT TTGTGTATCTTTTCAGACTGGGGTGGGGGCTGAGCATGCTTGTGCA GAAAGAAGCCATAGCCAGAAAGGACAGAATCTCTCCCCCACTCCC TTGCCCCATAACCAAACATAAGCTAGCTAGTCTTGTCTAATAGATG GGATTTACTATAGGTGAAGATAGCCCTCATATTCAAGGACAGAAGC TCTGGCAGGAGTAAATTAGCAAAGCAGAAATAGTACCCTTTCATTC TTGGAGGTGCTTTGAAATTTTAGGTAGAATATAATCGAAATTATGG AGGTTCCTTAGTGCTCAATAATATAAGACCTGGTGTTATTAGAACG AGTCTTTCTTATAAACTAACAGAGCAGGTATATGCCTGTTAGACCT TAGCTGTGGGGTTCCTTTACTATTGGGTGAATCATTAGGTATAAAA AATAATCATCAACCAGGCAAATTACTTTGCTTCCTAGCTGATGTCA TCCCACATTGGTACAGGTGTTATTCAGTACTGGGTGGTTCAGCAGG GAAGCCGGGTGGGACCAGTGTGTCTGTCATGAAACCACTAACTGCA TTCCTGACTGAAGAGCCATCTG |
| 158 | NON_CODING (UTR) | GTGAGGGTGACGTTAGCATTACCCCCAACCTCATTTTAGTTGCCTA AGCATTGCCTGGCCTTCCTGTCTAGTCTCTCC |
| 159 | NON_CODING (UTR) | TGTCCATGTGCGCAACCCTTAACGAGCAATAGAATGTATGGTCACC TGGGTGTGGCCAGTGCCCGCTGTGCCCTGCATGATTCTGTGTTGCC GCTGCTGCATAGTTCCCAGCCCCATCCTGTCCTGCTCACTCATGGGG GCTTCCAGACCCCGGCCCCACCAGGGCTTGTGTCATAGGGAGCCCT TTGCACTCCTCGTGTGTTGGCAAACGCA |
| 160 | NON_CODING (INTERGENIC) | CCCTGGCAGGCTCCTTCTAAACATGCCTGTTGACCTGGAGCTGGCG CCACCAACTCCAGGGCCTTTCCAGGGCCAGACAGGTAACACGCATG AACCCGAGTGACAGCTCTGACGGGCTGTTTCGGTGTCAGGAGACAA AGCTGGCAGGGGCAGGGTGAACTGGAGGCAAGTCAAGTCACCTG TGGCCTGTGGGGCTGAATGTGGGCCCGGTGTTGCCAGATCCTTTGT CATAAGAAGCTAGAAATCCAGATTTTATGTGTGTGTAATTTGTAAA TGCTGAAAGCTAGCCTGAATTTTTTTTTTTTTTTGAGACAGAGT CTCGCTCTGTCGCCCAGGCTGGAGTCAGTGGCGCGATCTCAGCTC ACTGCAAGCTCCGCCTCCTGGGTTCACGCCATCCTCCTGCCTCGGCC TCCTGAGCAGCTGGGACTACAGGCGCATGCTACGACGCCTGGCTAA TTTTTTGTATTTTTAGTAGAGACGGGGTTTCACCGTGTTAACCAGGA TGGTCTCGATCTCCTGACCTTGTGATCCACCCACCTTGGCCTCCCAA AGTGCTGGGATTACAGGCGTGAGCCACCACGCCCGGCCACTAGCCT GAATTTCAATCAAGGGTTGGCTGATACTGTGTGTCCAGGGTGGACT GGATTTGTCCTGGGGGGTTCTCTGGTTTGCTGCCTCCTGACCACATG ATGGGGCCTTCGAGGTCGAGGACAACTGTTCCCATTAGATTGCACC CTCTGCCCTCAGGTTCTTGAGGGTGTGTGGACACAGAGGCTTTCCA TGGGATGTCCCTGAGCCGGCCCTTGATTGGGGCCTCACCATTTACA GGGCCGTTTTATTCTGCAAACCGAAACTTGGGTCATGTGACCTGAT GGGATTATGGGACTCCCTCCAGGTGCCCGAGACAAGGTTGATATTT CCAAAATATTTTGGTGATTTAGTGGGACAAGCAAATGACAGAATAC CGGAGAAGGCAGGGATCGTGGGTGTCAGGAGCCAGAGGGGAGGG GGACAGATGTGCTGTGTACAGGACAAGGTGTCAGGTGACTCCTTCC CAGCAGGGCCTCGCAGATGCACAAGCACGGAGCTGGTGGGTTTTG CCCAAGAAAGGTCACGCGGCACATG |
| 161 | NON_CODING (INTERGENIC) | CTGTCGCGATGGAGAAGTACTAAAATCTATGAAAGAGTTCTAATGT AGATTTAAGGTCATGAGAAGTCTCCGGCAAAGTGGCATTTTAAAGT AATCCCTCAGTCGTGGAGCTACTCAATGAGAAGCCTGCCACTCCA GGGCGCACCACGGAGGAGGATCCCCAGACAAGAAGACCTGGCTCC CCAGAGGAGTGCGGAAAGCCAGCATGGCTAGAGGACACAGAATGA GGGAGAAGACGGATCCGATCGCAGGCATCGGGAGTGCTGATTTTTC |

TABLE 6-continued

| SEQ ID NO. | Type | Sequence |
|---|---|---|
| | | TCCTTTGAAAAACAGGTTGCCATCTACCTTTTTAAATGTCCCACTGT GTAGGAAAACTCTGGGGAAAGCTACGTCAGCAATA |
| 162 | NON_CODING (UTR) | CAAGCCGAGATGCTGACGTTGCTGAGCAACGAGATGGTGAGCATC AGTGCAAATGCACCATTCAGCACATCAGTCATATGCCCAGTGCAGT TACAAGATGTTG |
| 163 | NON_CODING (INTRONIC) | TGTGGCCCACACGTCATCCGATGCTGCGTGCTCACACTTCACGGCA TCTCCAGCACCTGCTAGGCCATGCGTGTCCCTTGGTGACGCCGTGG GGTAGATCCCTGATTTCAGTGGCCCTCATTTAAAGTACACGTGCAA GTCAGACTGGGAGAGCCCCGACGGGACAGTCTCGGTCTGTACCTGC ACCTGCCGTGCTGTGCTAGGCGGGTTTCCTTCCTGTGAGAGCTTTTC TCACTGTTCACCAGGGACAGCAGTCACCTTCCTAGGAGTTCACAGG CAGTGCGCATGTGGGAGCGGATCTGGGGAGACCTTCATTGGCCGCC TCTGATGTCCGCAGTGTGTCAGGTCACCAACA |
| 164 | NON_CODING (INTRONIC) | TACCAAGAATGCTGTCAGGGTCATTGCCTACAAACTGATGATGCTG TGCAGAATTGCGCCTCTACTGTAAGGCTTTCCCGGTCCTACTTGGCG AGTCTTAAT |
| 165 | NON_CODING (INTRONIC) | CCCAGAAGGCAGCCGTATCAGGAGGTTAG |
| 166 | NON_CODING (UTR) | AACTGAGGACGCGTGGATTCTACTCAAGCCTCCAAGTAGTGGCATA TCAGTCTTGGAGCTCCTAGCTGGTGATACGGAGAGGGCTTTGGAGG ACTTGGGACAGCAGGGCCAATTTTTTTGCCCAAGTGCCTAGGCTGC TAACTCA |
| 167 | NON_CODING (INTRONIC) | GATGGCCACGCAGATCAGCACTCGGGGCAGCCAGTGTACCATTGG GCAG |
| 168 | NON_CODING (UTR) | CACAGCGGAGTCTGTCCTGTGACGCGCAAGTCTGAGGGTCTGGGCG GCGGGCGGCTGGGTCTGTGCATTTCTGGTTGCACCGCGGCGCTTCC CAGCACCAACATGTAACCGGCATG |
| 169 | NON_CODING (INTRONIC) | TGCTAGTCATGCACCTCAGACAGTGCAAGGTGCTTCCTTTGATCTAT CATGTCAGCAGTGGGAGAGGTCCTTAGCCTAACAGAGGTCTGACTA AAAGAACAGCCTTCAAAGTGAGTGTCATTTTCAGAAATAACCATGC TCTGCCAGATCTGTATGGGGTTTTTTAATCGCATGCTGCTGACAGA ACGTTTC |
| 170 | NON_CODING (UTR) | CGTGCTCATCGTCCATAGTCCCATATTTTCTTATAATAAACAGTAGT ACTGGCAGGCACAGTAGGGGCACAAGGCATCTGTCTTATTCAAGAC AAGTTTGAGACACTGGAAAAAAGATACTTGTTGTGTGTGTTGGAC AGAGTGGCGAGGCTGAGCACTGTCACAGGGGCCTCCCATGTTAAG AGGGACTGTGGGGATGATGTCAGAACAAGACGTGGTGGATTTGAG GTTGATCGAGTATTAATACTACTGCCTCTCCTTGTCTTAGTGGGTAT TTAAAATAGTAAATAAGAGAGAGGAAGGAGGTGACGTTCAGGTGC TGTGGGAAGCAGGCTTGGCGGAGGGGTATGATGATGAGACCCTCA TTGTTCACTGGCTCCATCGCACTCCTCCCTGGGGCCGTGTGCCTGTT CCATTCTTCCCACCATTCGAACTGAGCGAATCTGGCAAAGGAGACA CGTCTGTGGGAATGCGTAGATTCCGCCTCGGAAGAGAGCTAGCGCA ACACTAAGAAAAGCAGGCTTCTTGTTTATTCTCAGGACCTTTTTGTA ACAGGGCTACATTCTGCAAACTGCTTACAAAGGAAGACTATACGTC TTAACAAATTATTTAGCCACTGAGTCCTCCCGATTCGGACCTGTTTT AGTAATGGCAGAAGAATCCCTGAGCAGGTTCAGGTGCCCTAGATG ACTAGGGTGCTGAGCTCTGGCGCCTTCTGTCCCCACTCTTTGCCTCC CCGCCCCTTCCCTGAGCCACCCCAGCAAGTGGGTGTCTTTTCTCC |
| 171 | NON_CODING (UTR) | AGAGGGCTGCTCAACTGCAAGGACGCT |
| 172 | NON_CODING (UTR) | TCTGGGGTCACCGAGAAAGTCTAAAAACAGGAGGCTGAAGGTACT GTGATGGCTTTAAAAATGGCCACCTTATTAAATAGGGATTGTATCA ATATTGAAATGAAGACAATCTTTCCAACTTTGGGTGTTTCACTTGCT GTTTTAATTGTTTGTTTTAACACTTTGTAGGTTTGTGTTTTCATAAT CTTTAATTTGAAACTCATGTGTCCTCATGGATCGTGGATGCCTTCAT TTCTTGAGCTCTCAATGCAGACATTTAAATGGCTGCAATCAGTAGA GTGACCCGCGGATGGCATAAATGCACCTCCTTTTCTTGGCCTTGGA TCTATGGGTCTGGGATTGTGGTCATCCTCAATCCTCAAAAAGAG GCTGAATCAATGTGGCCGTGGGTGGGAACTTACATACAGAACCCA ATGAAGAACTTGACTGTCTAAACAAGGGGGCCTCGCATGGAGCTGT AAAGCATC |
| 173 | NON_CODING (INTRONIC) | CCTGGCTGAGTCTAGACGTCTGATAACCACGTAGGTGGGTAAGGTA ACCACTGGGATGGCTGGAAGGTGTTACCCAGGGAAACTGAAGGCC AGGATGAAAATAAAAGCAAACGGTTTCCCCTTGGGCAATGACTGC |

TABLE 6-continued

| SEQ ID NO. | Type | Sequence |
|---|---|---|
|  |  | CATCAGGATTCTGCTGCTGATAAAATGCTGCTCCTTTGTTCTGCTTC CTGCGTGTTCATCCATATGATAGCTGTTAGACATTTCATTCAGCTTT CACCCACCTGGCACTGCTTCAGTGCCAACCAACGGCAAGGTGCTCC CCAGCTGCCATGGGGAGCCGGGTACAAATAGACCTCAGCGAAGCC CTGCGTGCATGCAAACTGCGTTTGCCTTTTGCATTCTGCTTTTCTCT CGGGGCCATGCTTGGGACACTTACACGC |
| 174 | NON_CODING (INTRONIC) | ACAATGGTGTCTTCAGCGGCCGAAAGGAGGGGCAGGGGAAGCCCC AGCAGCAGGAGCAGGTGTGTGGCAGCCCTTCACAAGGGGCTTTCAT GTCTCAGTTGTATGTTGCCAGTGTCACTT |
| 175 | NON_CODING (UTR) | TCCCTGTGTAGGATGGCTTCCCGTTATTTTTTTTTAAGCAAAGTAA ATGAACATCAAATTTCCATAGTCAGCTGCTGTCTTTCTGCCCACTGA GAGCTCTTTGGTGAAGGCAAAGTCCTCCTTCTTCATTAGCGGTCTCC CATGTGGGGCCACATCTTCCCTCACCAGGAACCCAGTGGGCGCGCT CCAGCCCCCCTCAGCTTGCCTTTTGCGTGGTCATTAGAGCTAGGGC ACACGTCATGCTGATTC |
| 176 | NON_CODING (ncTRANSCRIPT) | TGGGGCCAAGACATCAAGAGTAGAGCAG |
| 177 | NON_CODING (INTRONIC) | TTTCTCACCTTGCTGCGGCCTGCTGTTTGGCAGGACGACTTGACTGG CTGCGCTGTGGTTTCTGCGCCTGTGATGGCTCCTTCTGAATGCCCTC TGAGC |
| 178 | NON_CODING (UTR) | TAGGCCCGTTTTCACGTGGAGCATGGGAGCCACGACCCTTCTTAAG ACATGTATCACTGTAGAGGGAAGGAACAGAGGCCCTGGGCCCTTC CTATCAGAAGGACATGGTGAAGGCTGGGAACGTGAGGAGAGGCAA TGGCCACGGCCCATTTTGGCTGTAGCACATGGCACGTTGGCTGTGT GGCCTTGGCCCACCTGTGAGTTTAAAGCAAGGCTTTAAATGACTTT GGAGAGGGTCACAAATCCTAAAAGAAGCATTGAAGTGAGGTGTCA TGGATTAATTGACCCCTGTCTATGGAATTACATGTAAAACATTATCT TGTCACTGTAGTTTGGTTTTATTTGAAAACCTGACAAAAAAAAAGT TCCAGGTGTGGAATATGGGGGTTATCTGTACATCCTGGGGCATT |
| 179 | NON_CODING (ncTRANSCRIP)T | AATAAGAAAGGCTGCTGACTTTACCATCTGAGGCCACACATCTGCT GAAATGGAGATAATTAACATCACTAGAAACAGCAAGATGACAATA TAATGTCTAAGTAGTGACATGTTTTTGCACATTTCCAGCCCCTTAA ATATCCACACACACAGGAAGC |
| 180 | NON_CODING (INTERGENIC) | GCTGAGCCCTAACTGATACGCTGTGTTTCCAGTGTCCCTCATCCACT AGACTCAGTGGTGTCAGGAATGGTGTGGTATTTTGTTATAAATTTA ACTCCTTAGATGGACACACAGAGAGCCTCGATAAATATTTTTAATC CATCAATGCAAGGAGTGTGGTTGTCAGAAGTCAGCTAAAAGTCCA AGTTTAAATCTAAGCTCCGCCGTTCACAGCTTGGGTGACCTCAGCT TCTTTTTTTGGAAATGAAGTTCATATTTTCCGAGCACTTTTTCTGTGC CAGGTGCTTCCAAATGTATCTCGTTTAATCCTCACAACATACCTCAG AGGAAGACATCATTTTTACAAGTAAGGAAATAGAGGCTCAGAGAG ATGAAGTGGTTGACCCGGGCTGTCTATCTTGTAAATGGTGGGCTGT GATTCCCACACGACTGGAGTTT |
| 181 | NON_CODING (INTRONIC) | TTGGCTTATCAGTTGGCATGACCTCTGAAGATCTTTTTGCTCTGAAT GTTTTAATCATCAAGTTCTGGTGGTTATCCAAGGTGATCCTAATCTA CTTTGGGGTGGAGGGAGGAAGTGGTGTCAGGAGAGATCAAACCAG GCCACCTTGAGCTGAAAGCTCTGAAGGAGAAGGATTCCTTGAAATG GAGGTAATTTTTGAATTATAATAAGTGAGAAGACTGCAAGGGAGA CAAGCTGAGGGACAAATGCTCTGTGCTTTTCTCCTCACTTTCACAA ACAGGAGGAGAACTTCCACTGACCTAGCAGTAGTTTGCTCCTCCAG GCTGTCATGTCTTCTGATCATGTCTTTTATGAGGTGAATTTCTCCTC ATGAAAGACTAGACTTTAAGGAGAGATTCTGTGCAGGTCCCTACAG TGTGGAGATGGATTGATTGGGCCTACAGATTGCAGCTAATC |
| 182 | NON_CODING (UTR) | GCGTGCATGTGCGTTTTTAGCAACACATCTACCAACCCTGTGCATG ACTGATGTTGGGGAAAAAGAAAAGTAAAAAACTTCCCAACTCACT TTGTGTTATGTGGAGGAAATGTGTATTACCAATGGGTTGTTAGCT TTTAAATCAAAATACTGATTACAGATGTACAATTTAGCTTAATCAG AAAGCCTCTCCAGAGAAGTTTGGTTTCTTTGCTGCAAGAGGAATGA GGCTCTGTAACCTTATCTAAGAACTTGGAAGCCGTCAGCCAAGTCG CCACATTTCTCTGCAAAATGTCATAGCTTATATAAATGTACAGTATT CAATTGTAATGCATGCCTTCGGTTGTAAGTAGCCAGATCCCTCTCC AGTGACATTGGAACATGCTACTTTTAATTGGCCCTGTACAGTTTGC TTATTTA |
| 183 | NON_CODING (INTERGENIC) | CCTGCCATGCCGCTGCCACCGCGGAGCCTGCAGGTGCTCCTG |

TABLE 6-continued

| SEQ ID NO. | Type | Sequence |
|---|---|---|
| 184 | NON_CODING (INTRONIC) | GCTCACTGTCTTAGGCCTCGTCTTGGTTCCTGCATGCTCCACCTGCC<br>TGTTCTGGTCTCTAAACTCAATTGAATGACTTGATGTTACAGCTTTC<br>AAGCAGAGAAGTGTGGGGTGATGGTGGCAAGACAGAGGGGCGCCA<br>TTACTCTCATCGCTCCTTTTGTGGTGGCAGTCGTATTCTCCTCCTGG<br>GGTTTCTCTTGTGTTGGCGAGTGTATCAAAGTGAAGTGTGTTTCCAT<br>TGATTCAGTAACTGTTGAGTGTGCCCTCAGTGTGGATGGCACCAGC<br>CCAGTGGGGTGCACTCCTCAGCATTCGGGATTCTTCCTTTTGTCCCT<br>CTGGGGCTTGCACACAGGCAGGCACACTCACGTGGAATC |
| 185 | NON_CODING (INTRONIC) | TTTGTGTGCACCCAGTGAGAAGGTTTATTTTGACTTTATAGATGGG<br>ATATCTAGAGCTGGAGTCCTATATTCAG |
| 186 | NON_CODING (INTRONIC) | AGCCCTGTGCCTGATTCTTATAATAAGTACATATATAAAGTAACTA<br>TAATTTTTATTTTAATCCAGTTAAATGGCTAGCAGAAGGCTTTGACC<br>AATGGACCTGGGCATCCAAAGTTACCACATTTGTTCCTGGGATTGT<br>AGAGATGTAGAGACCAGGTTTTGCCAAACAAATCCCAAATATGGC<br>CGGTGCAGTGGCTTATGCCTTTAACCCCAACACTTTGGGAGGCTGA<br>GGTGGGAGGAATGCCTGAAGCTCAGGAGTTTGAGACCAGCCTGGG<br>CAACACAGCAAGACCCCATCTCTATAATTTTTTTTTAATTGGCTGGG<br>CATGGTGGTGCATGCCTGTGGTCCTGGCTGCTTGGCAGTATGAGGT<br>GGAGCCCAGGAGTCAAAGGCTGCATGGAGCCATGATCACGGCACT<br>GTACTCCAGGCTGGGTGACAAAGTGAGACCCTGTCTCAAAGAAAA<br>AATAATAATAATAATAATAATATCCAGGCTGGGGGCGATGACTCAC<br>GCCTGTAATCCTAGCACTTTGGGAGGCCAAGGGGGGTGGATTGCTT<br>GAGGCCAGGAGTTCAAGACCAGCCTGGGCAACATGGTGAAACCTC<br>GTCTCTACTAAAAATACAAAAATTAGCCAGGTGTGTGGGCACACAT<br>CTATAGTCCCAGCTACTGGGGAGGCTGAGGCACAAGAATTGCTTGA<br>GCCCGGGAGGTAGAGGTTGCAGTGAGTGGAGACTGTGCCACTGCA<br>CTCCAGCCTAAAAAAAAGAAAAAAAAAATGGAAATACCCCTCAGTA<br>GGAGAGAACATGGTCTACATTCTGCCTTCCGAAATCCATATTAACA<br>TTTGGTGGCTGCTTGTTGAAGCTAGGTGATAGCATTAGAGAGTCCT<br>GGTGTCATGAAAGCCAGAGCATCCTAGTGAACTTTCAGGGATGGG<br>GTGGAAGGTGGAGAAGAAATGGGCTATGGAGTAGTTCAGAATGTC<br>TCCAATGGGGCTACTTTTGAGAGAGAATGCTCTCTTTCACCATTTGT<br>CTTCCAGGATATGAACAGAATATAGAGTTGCTATCTTCCTTAGAGT<br>GTGAAAGTCTAGGCTGTCTGCAAGACAGCATGTTATGGTTTTTATT<br>ATTTTTTATTGATTGATTGATTGTAGAGACGGCATCTCGCTGTGTTG<br>CCCAGGCTGGTCTCAAACTCGTGGCCTCAACTGATCTTCCCACCTC<br>AGCCTCCCAGAGTGCTGGGATTATGGGTGTGAACCACAGCACTTGG<br>CCATGGTAATGGTTTTTAAAAAAGGGATCACCAGCTGTGAACTTGG<br>AAGCCTTAGGTGTGAACTCTGTGATATTATTCAACCTCTCTGAACCT<br>ATTTCTTACCATCAAAATGAAAGTTATCTGCCCTATTTAGCTGATTG<br>GGTTGCTGTGTGGCTCAAATGATGCAGTCAATTTGTAAACTGTAAC<br>GTGCTGCACAGATGTTAGGTATTCTGGTCTTCTGATTGTGTGCTTGG<br>CTTTCTAGCTGCTTGAAGCCGCTCAGAGCTTATGTATCACCAAGGG<br>TTAGAGATGTAGTGCTACCCACCTCTTTCATCCTGCACCCCCAATTT<br>CTCCACTTGTCCATTTCCACAAATGTATCCCTGGAGACACTGTGATA<br>ATTTC |
| 187 | NON_CODING (INTRONIC) | GAAACTCAAGGCATTTATCTCTTTGGGCTGCTTGTCCTTGCCTGAGC<br>TGAAGCCTGATGCCTCCCATAAGTTG |
| 188 | NON_CODING (INTRONIC) | TCCATTTCTTCGTTCCACATGACCACAGTTTGCAAGTGTATTCCATG<br>GAGAAGTGGAGTGATTGGGAATTAC |
| 189 | NON_CODING (INTRONIC) | GGTCCAGGAGTAAATGCCAATTTCACATATAATGTAGACAGATTAT<br>CTGATGGGCATCTATCAGATACAAAGTCTGCCCCTTTTTCATGTCCT<br>TTTTGTCTAAATATAGTCATTATCATCATCATCATCATCAAATC<br>ATTTCATCACCATCAGAAATGCTTATACATTATCCTGATGTATACCA<br>AAGCTACTGTTTGGAAAGAAACTAAAATAAAAGTCCAGGTCACTTA<br>ACCATACAGGGCTGATGTTAGATGAAAGCAAGCATCGATACCAAA<br>TGCAATTTTACATAATATTACCTGTCAACAAAATATATTTGGACAG<br>CCGCATGGTAATTTTACACATTATGTGTAAACAAAGTATTGGTGGC<br>ATCACATGGTAAAAACTCAGTAATTTCACCTCAGAAATTCTTCTTC<br>ACATCAGAAATGTAGTTTGTGCATTGAGGCTATCTGATTGATGTTT<br>ATGCCTCTCTGCTTGGGATATATTCATGAGAATAAATAATAGAAAC<br>CTCTCCCAATGAATGCAGTCTGTCTGAATTCATTGATCTTTATGCAG<br>TGGAGATATTCTGCACAAGCCGCTA |
| 190 | NON_CODING (INTERGENIC) | CGTACTCTTGCTAGGGCTTTTCATGGAGATGTAGAAATGGTAGTAA<br>GTGCCAAGGCCCCAGAACCCTCATGTTTGGGTCCGACTCCCACATT<br>GCCAGAGACTAGGCAGCTCACACAGGTGTCCCAAGCTGTCTTTCTC<br>ACAGGCCGCATTGAAGGCATTTATGAAATGAGACCCCCTCTTCCTC<br>ATCCGTAGTGACAGGGCTG |

TABLE 6-continued

| SEQ ID NO. | Type | Sequence |
|---|---|---|
| 191 | NON_CODING (INTRONIC) | TGGATAAAACTTCAGCCGGCCTTCTCTTTATGTGCCTGGCGCCTCTC<br>TTTTCTCTGGGTTTTTGGAAGTCTGCCTGCCCAGCCCCTCAGCTGGG<br>GCCTTCCCCACTTCTGCCCCGCCCCACTGGGTCCTCCCAGGGTAGG<br>AGGCAATCTCTGACTGTCTTCCGAGGCTCTGTTGCTTCTCCTTCATC<br>ACCAAATGCCAGGAATTTGTCAGATGCTGTTTGTAACTCAAAAGAA<br>AGAAAGAAAAGAAAAAGATACAGGAAGGAAGGAAGGCAGAAAA<br>AGAGAAAGAAAGAATGCGTGCAGCAGATGTTGGGAAAGTTAATTT<br>CTTCATTATTTTGCATCCATCCCAGTTCGGATCTCAGCATGGGGTAG<br>GGAATCCTCTGTTGTCCCCATCTGTCGAGGCAACAGTGAGTCCCAT<br>CATG |
| 192 | NON_CODING (INTRONIC) | CAACCAATTGAGACACTGAGGCCTAAAGAAATTATTGGCTATAATA<br>ATGAGGTGATTGCCTTAGCTATCACGCCAGATTTGCTCTTTTGTTTT<br>CTCCTGATATTTTAAACTCTTCCTTGCTGGAATATTAATAACTCAAA<br>GATAAAAAGGGTACAACTTGTTTCCATGTGGGAGGTAGGAAGAAC<br>ATTGCTTTTGGAGTCAGTTCTAGGCCTGGTGACTCTTTGACTTGCCA<br>GTTGTGTGCCATGATCACTCCAAGCATCCATTTTCTCATGTGTAAAA<br>AGCATGTTAAAAATTTTAAATGAGGAGTTTAAAAATTACACTCCCA<br>GTAGGCTTACTATGAGGACTAAAATAAATAAAAGTGTGAAATGCA<br>GTGCCAAGCACATAATAGCTGCTCAATAAATGGAAGCTAAATTATT<br>TTCCACAGTTATCTTTCAAATTTCACTTTGATCAGTTTTCACAGACT<br>ATCTTCTAAGCAAATTCTGTAGGTGTTTGCCTTCGGAAAAGTGCGTT<br>TGTTGTCAGTGAATGGTTACAGGGAAAAGGAGATACTTGTCATGCA<br>GCTGGAAACATGAAAACTTGGCCCTGTGTTCTTAAAAATGAAAACT<br>CCCTGCAGGATGGGTCAAGTTGCTACCATAGGCTGGAGCCTATGAT<br>TCTCAGAGCAGCATCACTCTTAATGGCACTGTTCTGCATGCCCTTAC<br>CTTGCTCATTTTGCTGGGCTCAGTACTAATTTTCATCCCCTAGGCAG<br>GCAAACTAAGTGTCATTGTGGCAGTTCCTTCCATACTAAGAGGAAG<br>CATTGATCACTAAGAGTCAGCATGGTTTACTATGAGTAAATTAAAC<br>CAGACCTATCTTGACCTCTGACAAGGTTGTCGTGATGACCATGTCA<br>GTTTGGTTCCTTGCTGTATGCCCAGTGTCTGA |
| 193 | NON_CODING (ncTRANSCRIPT) | CGCCATGGGGTGGTTCGAAGAACCATGATGAAGGCTGGTTCGAATT<br>GTGATGACCATTTTTGTCCACATCTCCTAGGACCCATAAGCCAGAG<br>TTTCTCTGGAGCTTATAGCTAGAAGGGGTTCTGGGTCCTGGAGTGC<br>AGGCCTGTCAACTTTACAGGAGAGCACTAGATTGCTTTCTGAAGTG<br>GCTGAACCAGGTTATGCTTCCATCAGCTGTGTATGAGCATCCCCAT<br>CTTCTTGACCACACTTGAAGCCATCAGTTTCCTTGAAGCA |
| 194 | NON_CODING (INTRONIC) | TATGTGCAGCACAAAATGTCGTTTCTTATGTTTGTTCCTATAATGCG<br>TTCTGGCACTTATGTGATGCTTCACTTAAAAATACTTAGCTCTTTCT<br>TTTTCCCCCCAAATCAATAACTTTAATGCCTGCTCCAAATAAGCTAA<br>AATAGTTTTGATAATTTTCTAGCAAATGGCAAACTTTTACCTTTTAG<br>CAGTTAAAAACTTTCTGAAATATTTAAAAATCACTTTGACAGTATA<br>TTAAAGTGAGTGAAAGTCTTTATCTAAAGATCCCACTCAACTTTTC<br>GTGTACTTAAAATATTATAGGAAAATTGAGGAGGTGACTTATTATA<br>GAAATAAGAAGACTTAAATGAATAAATTTTCTGAAAGGAAAGTGA<br>CTCTTGTGAAAGATCTCAAATGGCAGACTTCATTTTGTGTTTTATCT<br>TTGCTGGCTTTTACTCACCTACACTCATTTACAAATCCATGAAAATG<br>GTTCAAAGGTCATTGGTGAAACTTGAGAACAAATGCAAAACTTCCA<br>ACTATGGGAAATAGGTAGAAATACATTTTAAAAACATTGGGTTTAT<br>TAAATTGGGTTGATTTTATTACTAATTTTATAAATCAGTCAAAAATGT<br>AACGCCAAGTTCATTGTCCTAGAGCGAA |
| 195 | NON_CODING (INTERGENIC) | GCACTGCCGTACTCTTGGGAAATTTGTCCAAGGCCACCCGGCTGAG<br>CAGCGGTTGAACCAGGACACCATCAGGCATGCGTTTCTTGTCTCCA<br>CCACACCCTCAACCCACTTCCCAACGCGCCTTGCGACAGGGGCTGC<br>GGTATTGCATCCACATGACTGATAAACTAGTAAACACACATGAATT<br>CATTTTAAAAGTGTATTCAATCAGTTAGGTAAACTAAAAACCTTAA<br>GTCTTCGTTCGATTTGGAATGCAGCCAGAGAACAAATGGAAAATTT<br>TTCAAGGTAGAGAAGATGAAAACTCAGAACGCCCTCTTGTGGCATC<br>TCTACCCACCCTAGGAACACTATGGCTCTTCCCTACACATGGTGA<br>TTGCTAACCTTGCTACAAGACGTTGGACACACACACACACACAC<br>ACACACACACACACACTGAGGTTCCTTTTGCCCCCTCACTTTTGAGC<br>CAGTGACTACTGAAACCCTCTCCATTGTTGCACCACCAGCAATGCC<br>CCCATCACTTCCTCTCATTTACTTCCACAGGCTGGTTCATCCTCAAA<br>GCCCTCCTTACGTAGATCTGTG |
| 196 | NON_CODING (INTRONIC) | TCTGGCAGCTCTTAGTCATGTCTTGGAGGGAGGACGGGCATCCAGG<br>GCTGACCGGTCAACGTCCAGCACCTCCCAGGGACTATGGGAAGACT<br>GAGTGGTGGGTCTCGTCCTCTCGGGATACTTGCGCTT |
| 197 | NON_CODING (ncTRANSCRIPT) | CCATCCAGCTGATCGGCTCTAGTTCTATGGTCCTGTTGGCTTCTAGG<br>ATTCCTTGTTGTTGTAGTCAATTGGGGGAAGAAGGTGCAGAGGGAG<br>TGCACAGAGTTAACATCCTATCAGCCCAAGCTTCACCTCGGCACCC<br>GAGTCTCAGGCAGTCTCCCTGGCTTCTACATAGGCAGTGCTTCTTCC |

TABLE 6-continued

| SEQ ID NO. | Type | Sequence |
|---|---|---|
| | | TCATTGTGTGGGGCTTTGATTTTGTAATTCCAAGAGCCTGGGGCTCC TGGCAAGGAAAATGGTTTTCAAATAATGGTTTCGAGAAACAAAGCT GGGGAAGAGGCAATGTAAGCTCAGGCTCTGGCAGGCAGGCAGAGA TCCTGGGAAGGCTGGGTGCTGACTGCACATGGAGCAATGGGAAGG GATGCTGGTGAGAGGAGACGGGGGCACTTAAGCTCCGGCCCCAGC TCTGCTCTCAGTGCCCGGCTCTGTGGTCTTGGGCTGGCCCCCTCCCT TCTCTGGGCCATAGTTTTCCCATCTGTATAGCAAGGCCATTGGACA AAATGGTCCCTCTGCAGATGTGGCTTCTGAGTTGTTTGTGCCTGAG GGACAGCCAGTGTTGGGAAGTTCCCCCAGGAGGTCCCTGAGCCGA GTCTGAACTTTG |
| 198 | NON_CODING (INTRONIC) | TGTTCTGAGTCAGGCATGGAGGTATCTTCTCATAATCAAAAGATAA GCAAGAAACAGTTAACTGCCCGCAAGGATTCCACAATTTTGAATCC TAACTTCAGATGCTATCTCCTTACCTCATTTGGCACGTGCATTTGTG CTGGTATACATACCTTTTTCAGCACATAAACTCATTTGGCACATGTG CCAAGGATTGCCAACTATCTTA |
| 199 | NON_CODING (INTRONIC) | GTCACCATGGAACGTGTGCATAGATGATGTTCCCGTGTCTTTCA |
| 200 | NON_CODING (INTRONIC) | CAGTTCTCAGACATTTACGGGAAAGCTCTGGTGGCGTGTTAGATGC AGTTCATCTCTCTGTTTGCAGCGCTCTCAATAGAGACC |
| 201 | NON_CODING (INTRONIC) | CTTGACTGTCACGATAGAAAGAGGAAGCAGAAGAATGAAGACAAA GCCATTTAAAATTTTCTTGTTCTTTACCTTTTGCATAAAAGGTATTC AGTTCACAAATGATGTAAAATTTAATTAAGGCAAGTGACTGTCCTG AGAAAGTCATTAAAACCCTCATGTCATTTCTCTAATCAAAAGGCTG CCACGCTTCTATTATTTCTTTATTACAACCCTTTATTTTTATTTCTTC AAGTTAAACTGGAGCCTGAGCCATCATAAGCCTCTTGCTAGTGATT TTTTAAATCAGTGATTTACACTTTGAAAAACCAATTTTTTTATTTTT CCAATTTATATTGGTTAGATCCATAGGGTCACTTTGA |
| 202 | NON_CODING (INTRONIC) | GGCTGATGACTTCTCACAGTGTATCTCAAAGCATTATTGCATGTCCC ACTTGGTTGATAGGGCATCTCTAGCCTGACAGATTTATCTGTTGAG AACAGGATTATGCATTTGAAACCAGTTTAATTCTTAGCAAGACAAT GCACATGTCTTATGTAGATTTTGTTGTTGGTTTTTTTCTCCTTCGTAA GTTACTCGGGGAAAGTCATGTCAATATAAATCAGTGGTAATGAAAT CAACATTATAGCATCTTTGATAATGCATTTGCTAAAGCCTTTCTGGA CGTTTACCCAGCTCTCAATGA |
| 203 | NON_CODING (INTRONIC) | CAATTTCCACCGCGGCCATTTGTTAAACGCATAGCTGCCATCTTCA GTGATTATTTCCAAGTAACATCTATGTTTCTGAATAAAAATCCATTT GAATCTCAAGTCAGATTTGCCAG |
| 204 | NON_CODING (INTRONIC) | ACTCGGTGAGCTTAACCGTACACTGAGCTGGTGCAGCCGGGGATCC ATCTCAGCCCCTGCTTCCCACTCAGCCAGACCCAGACCCTGCACTC CAGCTTTGGTTGTGTGGATTCTCTAGAGAAGGACCCTTGGCTGTTTG TCCCCATGCATTTCTTGATGTCAGGCAGCAGCATCTGCCAGTTGTG ACTGTCCTGCCTGGACTACAGGTTTGGTTGGGTGCCCTACAAAC CTTGCTCCTCTCAAACGTGCTCTGCCGTGGTAGCTTCTGGCGCTT CACTCTTCTGTCCGCTGGGATCCCTAGGGGGGCTGGATGCTCGTAC CAGACTGTGGA |
| 205 | NON_CODING (INTRONIC) | GTTTGGCGTAATACGGAAGCCCTCAGAGCAGTACGCTTCAAGCAGT TTATGAAGTCCTTAGCGTCTTTCTTATGGCCGAAAATAGTTTGGAAT GGGTTGAAACAATGGGCCAACCTAACCAGATGAAACTG |
| 206 | NON_CODING (ncTRANSCRIPT) | ATAAATAAGTGAAGAGCTAGTCCGCTGTGAGTCTCCTCAGTGACAC AGGGCTGGATCACCATCGACGGCACTTTCTGAGTACTCAGTGCAGC AAAGAA |
| 207 | NON_CODING (INTRONIC) | TCTATGCGGCCACCCAGATTTCTTGGGATCTGATGCTAGACCTTGG AGG |
| 208 | NON_CODING (INTRONIC) | CCATATGAAGTAAGGACTGATTATCCTTTTTTTATAAATGAGGAAA TTGAGTCACAGGGGGGTTGGTAGCTAGTCTAGGATCACACAGTTTG TTGGAGGGGGTAGTGTATGCACGTGCCCACTTTTTCA |
| 209 | NON_CODING (ncTRANSCRIPT) | GGCCCTGCTGCCTAAACTGTGCGTTCATAACCAAATCATTTCATATT TCTAACCCTCAAAACAAAGCTGTTGTAATATCTGATCTCTACGGTTC CTTCTGGGCCCAACATTCTCCATATATCCAGCACACTCATTTTTAA TATTTAGTTCCCAGATCTGTACTGTGACCTTTCTACACTGTAGAATA ACATTACTCATTTTGTTCAAAGACCCTTCGTGTTGCTGCCTAATATG TAGCTGACTGTTTTTCCTAAGGAGTGTTCTGGCCCAGGGGATCTGT GAACAGGCTGGAAGCATCTCAAGATCTTTCCAGGGTTATACTTAC TAGCACACAGCATGATCATTACGGAGTGAATTATCTAATCAACATC |

TABLE 6-continued

| SEQ ID NO. | Type | Sequence |
|---|---|---|
| | | ATCCTCAGTGTCTTTGCCCATACTGAAATTCATTTCCCACTTTTGTG
CCCATTCTCAAGACCTCAAAATGTCATTCCATTAATATCACAGGAT
TAACTTTTTTTTTAACCTGGAAGAATTCAATGTTACATGCAGCTAT
GGGAATTTAATTACATATTTTGTTTTCCAGTGCAAAGATGACTAAG
TCCTTTATCCCTCCCCTTTGTTTGATTTTTTTTCCAGTATAAAGTTAA
AATGCTTAGCCTTGTACTGAGGCTGTATACAGCCACAGCCTCTCCC
CATCCCTCCAGCCTTATCTGTCATCACCATCAACCCCTCCCATGCAC
CTAAACAAAATCTAACTTGTAATTCCTTGAACATGTCAGGCATACA
TTATTCCTTCTGCCTGAGAAGCTCTTCCTTGTCTCTTAAATCTAGAA
TGATGTAAAGTTTTGAATAAGTTGACTATCTTACTTCATGCAAAGA
AGGGACACATATGAGATTCATCATCACATGAGACAGCAAATACTA
AAAGTGTAATTTGATTATAAGAGTTTAGATAAATATATGAAATGCA
AGAGCCACAGAGGGAATGTTTATGGGGCACGTTTGTAAGCCTGGG
ATGTGAAGCAAAGGCAGGGAACCTCATAGTATCTTATATAATATAC
TTCATTTCTCTATCTCTATCACAATATCCAACAAGCTTTTCACAGAA
TTCATGCAGTGCAAATCCCCAAAGGTAACCTTTATCCATTTCATGGT
GAGTGCGCTTTAGAATTTTGGCAAATCATACTGGTCACTTATCTCA
ACTTTGAGATGTGTTTGTCCTTGTAGTTAATTGAAAGAAATAGGGC
ACTCTTGTGAGCCACTTTAGGGTTCACTCCTGGCAATAAAGAATTT
ACAAAGAGCTACTCAGGACCAGTTGTTAAGAGCTCTGTGTGTGTGT
GTGTGTGTGAGTGTACATGCCAAAGTGTGCCTCTCTCTTTGAC
CCATTATTTCAGACTTAAAAACAAGCATGTTTTCAAATGGCACTAT
GAGCTGCCAATGATGTATCACCACCATATCTCATTATTCTCCAGTA
AATGTGATAATAATGTCATCTGTTAACATAAAAAAAGTTTGACTTC
ACAAAAGCAGCTGGAAATGGACAACCACAATATGCATAAATCTAA
CTCCTACCATCAGCTACACACTGCTTGACATATATTGTTAGAAGCA
CCTCGCATTTGTGGGTTCTCTTAAGCAAAATACTTGCATTAGGTCTC
AGCTGGGGCTGTGCATCAGGCGGTTTGAGAAATATTCAATTCTCAG
CAGAAGCCAGAATTTGAATTCCCTCATCTTTTAGGAATCATTTACC
AGGTTTGGAGAGGATTCAGACAGCTCAGGTGCTTTCACTAATGTCT
CTGAACTTCTGTCCCTCTTTGTGTTCATGGATAGTCCAATAAATAAT
GTTATCTTTGAACTGATGCTCATAGGAGAGAATATAAGAACTCTGA
GTGATATCAACATTAGGGATTCAAAGAAATATTAGATTTAAGCTCA
CACTGGTCAAAAGGAACCAAGATACAAAGAACTCTGAGCTGTCAT
CGTCCCCATCTCTGTGAGCCACAACCAACAGCAGGACCCAACGCAT
GTCTGAGATCCTTAAATCAAGGAAACCAGTGTCATGAGTTGAATTC
TCCTATTATGGATGCTAGCTTCTGGCCATCTCTGGCTCTCCTCTTGA
CACATATTA |
| 210 | NON_CODING (CDS_ANTISENSE) | GTGTCCCTGTTGTGGTACTTCTGCAAGTCCTCCTTCTGGATGGCCAC
CTTCCCTGCAACACAAGCAGAGAAGACTTCACCACGGGCACAG |
| 211 | NON_CODING (INTRONIC) | GACCCTCGTAGTGTGCCGGTCAATGCTTGCCTTT |
| 212 | NON_CODING (INTRONIC) | TGCAGGGCGGTTTGCCGCTGCCACCCTCGGCACCATCTCTGAACTG
CCCGCTTTTCCGGAGGAGCGGAA |
| 213 | NON_CODING (INTRONIC) | GGGTGACGTTGCTGATAGCTCAATACTTAACGTACAGCAGGAAGG
AGCACTGAGGCAGTGGCTTGAGCTCAGTCTGTGGGAGGAGACCTGT
TTTGATCCAG |
| 214 | NON_CODING (INTRONIC) | CAGGGTCTGATGATTTTGGCGTTTCCCTGCTTCCCAATTGACCTGGC
TGTGCTGTTGGCTGTTCTTGCACACTCAAGGTGGTTTTGCCATTGGC
TTCCTCCCTCAGCCTGCCTCTGGGATTATGCCACTGCTATTCTTTTTT
ATCTACCATCAGCACAATGAAATCATCATTTTTGTCTTCAAGGTACC
AAATTCTGGTGATATTGGTGCTTTCTTGCAGCTACTTATCATGAGAA
GTGAATGGTCTCATAGTGAACACAGTCATGGTTATAGTGTTCATAC
GTTCCAGAGACATGTTTCCTATAATTATGCCCTGCACATTTTTCTAT
CATACAATCCTTAGATTACAGCTCTTTGGTTTTCAACAGCTTTGTCC
AATTCCATCTTTCCCAGTTTCTCTACCTTGATGAAATATCCTTCTTG
CCTGGTTTTACATATTTAAATAACAAATTCCAAAAGTAAAGAGTAT
CTGAGGCAGTCACATGACATAAGGACAAATTCAAGCCATCTTGGAC
TTGCAGAGGGTGGGGAGACCGTGTCAACACACACAATTTTAAAAA
TTTCTTCCCTTTCAATCTTTTAAAAACAAAACTTTTTATAAAATAAA
AATGTAATTTAAAAAGGCTACCTGTCTTGGCAAGTAGCTGATCAGC
CTGCATTGGTGAGCAGGCCATTCCATAACCTGGTTTCTTGCTCCTTA
ATTGACAGCATGGAGCTAACGTACTTAATTTCAGCTCTTTCTACGTG
ATTTGACTCATTCTGTTAACATTAACTGTTTTTCAGTCTTCTCAACT
AGACTGAACTCCTTAAGTGCAAGAAATACACGCTTAGTAAATGTTT
GTTGGACCAGACACTGCACCTTATGAAATTAAAGACCAGAACATTC
TCATGGTAGCATTACAGACACTGATGGCAAAGGTACTGGGGATTT
GGGTTTGGCTAATAAGCTCTGTGGTGGTGTTTCAGAAGGAAAATGG
TGCTCTCTTAGTTCTATGGAACATAGTGGTCCAGATCTTCTACTGTA
ACCAGGCCCAAAGCTGGCTAATCTGGAGGGCTCTGCCTTAGGGATA
CTTATA |

TABLE 6-continued

| SEQ ID NO. | Type | Sequence |
|---|---|---|
| 215 | NON_CODING (INTRONIC) | ATTCTGAGTTACCAACACGTTGTGCGTGCATTGATGACCCGGCTTC CTGGCCTGCCCTTGGTGCCTGAGCCCCAGTAATGATTGCCCTCTATG TTGGGAGAAGAAGGGAGAAAGTAGTACAAGTAGTGAAGAAAAAA ATGTAGGTGGTGTTGGTGGTTGAGAGTACATGGCACA |
| 216 | NON_CODING (ncTRANSCRIPT) | GTAAGTGAGTGGGCCTGAGTTGAGAAGATCCTGGCCTTGGA |
| 217 | NON_CODING (INTRONIC) | ACCTGCCACCGGCTGGCACACACCACCC |
| 218 | NON_CODING (ncTRANSCRIPT) | CTGCAGCCGAGGGAGACCAGGAAGAT |
| 219 | NON_CODING (INTRONIC) | CATCCCGAAGTGTGGCTAAGCCGCCCGGAGGAACACAAAGGGCAT ACGCGCACGCACACTTAAAGTTTTAAAACACGATTTATTTATTTTG TCTGCTGCAACGCTGGGAGAAATGTGGTCTTTGGAAGGAAGCTCTC CAGTGTGTAACCTTCCTATTATTTTGGCCCCACACTGTGGCTTTAG TAGAACAGGAGCAAACAAGTTTATAAGGCAAGGAGGTGGAGAGAT TAAAAGAGCATTCTCTTGCATTTATGAAGTGTCACTCCGGTGTGTAT GTAGGTGAAGCCTTTGGCCTCGTCTGAAATGCCCATTAA |
| 220 | NON_CODING (INTRONIC) | TCTGAAGAGCAAGCGCCCACTGATGCTGAGGTCAACAAAATCAGA GAAGCTGACATTTCCATTTTTTGCCAATACTTCAGGTGACCTCATAA TGAAACCCTTGCTGCTCTACAGAAAATTGTGCCCAAACCCTCTCAG GGGAAATAAATGAGCCAAGTTTCCAGTGTACTAGCAAGCAAACAG AAAAGCCCAGATGAATCTTCCTCTCCTTAAGGGATGGTTTGAACAG TACTTTCTTGTGGATGTTCAAGACTACTTAAAAGAAAAAAAAATAC CTTGAATTCAAAGTCCTGCTGATTCTTCAGTCTATTTGGTGCTTCAG GTACATTTGCCAATATGCATCCTCATGGTAAGGTTGTCTTTATAACT AGCCACATGTCTGAGATTCTTGAGCCTTTCAGTCAGTGTTTGATCTG GCCATTCAGGAAGGCTTATTATAAACTAATGTATAACTTTGTTCAC AATCTCGCAAAGTTTCCACTGTCTGAAATCCTAGTGCATGAGACT CCTACATCGTTATTAATGGCATATCCTTAATAAAAGTTTGGCTTTTG ATTTTTAATGGGTTTTCAGGAGATAACTTCCCAAAGAGGCATTAGA TAGTTTAACAGAGCCTGTCATTAATGTGACCTGTGAGAAGACTTGG CTAGAGGTGGTGAAATATCTTTCCTCTATCCCTCCCAAAGACAAGA AAAACCTATGGATGAGGATGAAAATTTGGCACAAGAGCAATCATT GGCGGAAGTTGAATCTGAAACTGTTGACACCAATTCAAGTTAATGC TGCTAGAGGCTGATCCTCAGGAAGCTTTCTTGTCTCCAGAGGTTATT ATCATAAGTGATGATGAAGACAATTAGGAGGCTGTGGGACTGGAA ACAAATACAGCAATAAGAAACAGGAGCAAAATTTTTAGAACAAGA TTAAAAACCTCCCTAAGAAGGTAATTAAAATTGGCATCTTTACATGT GTCAGATATTACCTGTTCAAAATTTGAGTGACTTAGAGTTCTATAA AGAGGTGCTATGATGCCATCAAACATAATCATATTGGACAGAAAC AATCTTCAATAGAACTTAAATCATGTGCCATTTAATACTGTTGCTGG ACAGCTGATAAAACTACCTTCTGACAAAGTTTGATTTAATTAGACT CTAATAAAAGGTCCTATGAGACTTTCTAAAAGACTATATTGGGAAG AAAGAAACCTCAGAAAAGTCTAAATTATCAAGTAGTACCATTTAAA TACTCTTACTGGACAGCTAATAAGCTACCTTCAGACAAAGATTGAA TGATTAAATTGAACTCCATACAGAACTGCTAAGGTGTCTTCAAAAA GGACTTGAGAAGATGAAAGCATCTTTAGAAGGGCCACTTAAATTCA CTTGCTTGATAGAAATAAAGCCTCAAGCAAGTTGTTATAACTTCAG GATTCGACTTCACTGACTCTAAGAGTATAGACATCCATAATTTGAA CTAATGAATAGTCCACTTCTGTTCATTGCTTCTCTGTCACCCCCATT TGCCACTACCATAATGAGTGATAGATACATCTTCATCACCTCTGGA AATCATCTCAGGATCTAAATGGAAACTGTATAAAGCCTATCATTTT TACTGATTTAAACTATGTAAACTCATTATTCTTTTTATGTAATGTGC TGTTGTTATTGTTTACCTGCATAAAAATATTTATGAGGGTTTTCAAC AGTTTACTTGAGACCTCATTTTTGCCCATTTTTTTCCTTCCCGATATC ATGATCTCCTCAGCTGAACTTTCTTACCTTGGGGGTTGTTCAGGAAC TGACTCTCATGGGGAAGAGGGATTACTATTTCTGTGTTCCTATCTC TTGGTAACTGCTTAACCACAGTCAGTCTTGAACTAATGGAAGGAGC ACTGGACTTGGGTTCTTGAGACCTGGGTTCATGTTCAGTTCTGCCAC TGATTATTGTGACATTGGGCCAGTCACTTGATTTCTCTGAGCCTCAG TTTCATCACCTGTTAAGTGAGGATAGTAATACCTGGCACAAATATC ACAATATTAGTGATAATTGAATATAATTATAAGTACCCAATGGCTA TTAAAAGTAAAACTAGGAAGTGCTGAATAACCATAATATCATTATA TTTGTAGCATTTTGGACCTTATCAATGAACAACTGAGAAAACTAGG TTTTTGAATTCTTTTACTTTTTAAAGTAACTTCCTCCCATTTTATGT CAATTATAGAAAATTTTAAAAAGAAAATTAAATGTGCCTATAATTT TATAAGCCGGAGGTAACTAAGTTGGTATTTTTCTTCTTAGTACCTCT TTGTCTCATCATAAATTGTTCATCAATGTCAAAAACTTGGAAAATA AAGATAAGCATATAGAAAAAAATAAAAACCACCCATAATCACAAA TCCCAGAAGCAATGTTAATATTTTGGTGGATTTATTTCCAGTCTTTT TCTATGCTATATGTGCACATATATAATTTTTACATAGAAAAGTC ATAATGCATACAGCTTTGTTGCTTTTAGCATTTTTATCATGAATATT |

TABLE 6-continued

| SEQ ID NO. | Type | Sequence |
|---|---|---|
| | | TTCCTACATTTATGCAAAGTATTTGTAAATATCATTTTCAATGGTGT<br>ATAATATTTCATCATAGGATGACATCATGGTTTAGTTAACCATTTTC<br>TTTTGTTGGATATTTGAGGGTCTTTCCAAATTTGGCCATTGTAATTT<br>CACAATGTCTTTTTCATTACCTAACTGAAAATATTTGCTTTGGTGAA<br>AGCAGAGGATTTTTTGTTGTTTGTTTGTTTGTTTTTGAAGAAGTCCT<br>TTTAATAGCTACATTTCATTGACTAAGTGGAACTTCAAGAGACAGG<br>TAGAAGAAAAAAAAAAGAAACAGTAGATGTAATTTCAAGATTGA<br>GGATTTATTTTGTTAGTGACTGTTCCAGAAGCTGAATTTGGTGTTA<br>GAGCAATTCAGGAGGGACAGTTTGCCACCATTTTATGATACTTTAC<br>TGTAGAAAAGTTTTCAGGATTTAGACCAGGAAAGAGACATCCTAAC<br>CATATGGGTTGATTTTATTTTATGGACCCTGTGAAGTCTGGGACTGA<br>TCAGGTTTCTCTTTTGTTGGCTACTAGAAAGCTTGGAGTCAAATGTG<br>TGGTCAATGCATAGCACTTGTAATGGGACTCTACGGTATGTATGCA<br>CTTTGTATTAGCTTTCTGCCAGGCTCCATTTCGTGTTCCTATCTTTAT<br>TGTTTTTGTTTTTTCCTTTTACTTTCTTATCTACTTTGAATTTATGCTA<br>TCATGTTGTATTTTGTGTATTCTTGTAAGCCACCTGACATCCATCTT<br>GGAACATGGTGGGAATAAACACACTAATAAATAAATACATTAAT<br>AAATACATGAATAAATAAACCAATAAGGAAAAAACAATGAGGCAA<br>ATGAATGCAGCCAGGACTCTGAAAATTGCATAGTGCCTCCAAGAAT<br>AATCAATGTTAAGGACTTGAAGCTTGGAAGAACATATTGGAAAGA<br>AGCAGGTGAGGCTGCGAGGCTGCATTTAGAGGTGACGTGTTCTGTG<br>TGACGTCTGTGTCTACTGAAGCATGC |
| 221 | NON_CODING (INTRONIC) | GAGCTGGAAGTAGACACCATGTATCTTTTCATTAGAGAAGCAAACC<br>CCCAAAGGAGAAGCATTGTCAGGCTTCTCTCTTTGCCATGGCCTTT<br>GCCTATACCCTTGAGCAGTGATCTGAGTCGGCTGAGATGCAGATGT<br>TAAGCCTGGGCAGAAAAGCGCTGCTCTCTGCATGGTCCGGGAGAG<br>ACCCCTCTCCAGCCGGTGGCATGCTCGTTACGCAACACTG |
| 222 | NON_CODING (INTRONIC) | GCACCATATGTGAGTATTCCAGATATCCAAGGTCCTCTGGACACCC<br>CAGTCTCTTCCACAAAGCTGCCTCCTCAGAGCCTGCTGTCCCGTCTT<br>CTAGGAATGTACCCATTTGAAAACCCACACTCACACTACCACAACA<br>CATACACTGTTTCTTGCTGGTCGTTCCTTTAATCTCAGTGGAAGATA<br>TCTCATAGAGAACTGTTGGTGATTGCTTAACTTGGTTGGGAGGAAA<br>ATAGATCAAGCAGGTGACAACCTGCATATTGGGGATTTTCCTATGC<br>TGAAAATTGTTATTCTGTTGCAGCACTCCACCCTCCCTTCACAGCCC<br>CAAAAAAGAGAAGTACGAGTGCTGCTGATGTTCAGGGTTTGAATAT<br>GTTTTGGTTTAAGATGTTCAGTGGAATTAGAGAGAATTTCATCCTG<br>GGCAGTGCAGTCAGGCTGGAGGAGTATTTTGGTTTCATATTACTAA<br>ACCTTGTTTTCCCATCCCAGCTGCTTGTGTGCTATCTTGGGGCCACT<br>GAGAACCTGGCTGGGCTCTGCGGGTGGGAGTGTTGTCCCGGGGCT<br>GAGTCCAGCCAGGGGTGAGGTCGTCTTGGTGCACATCTTGCACGTT<br>GCATGAAGCTCAGAGCC |
| 223 | NON_CODING (INTRONIC_ANTISENSE) | CCCAGACCCATGTGCGGCTGTGCAAATTCTTTCTGGGTTGA |
| 224 | NON_CODING (UTR_ANTISENSE) | GCAGCGCTGGATGCCGGAGCAGGTGCTTCTGCAAGAAGCTGTTCTG<br>CATCCTCTCCTTGCTGCATCTTGGTCCACTGCCTC |
| 225 | NON_CODING (INTRONIC_ANTISENSE) | TCCAGGCCAGCCAGGTATTGATTGAAGAAATCTAGAAAGGCAAAT<br>GGACCACTGTTATACTGACAGTGTTTGTCTAACCAGCTGAGTGTGG<br>GCATTTTGAGGAATGGGGCCAGAGAGCCAAGCCCAGGGCTACTGC<br>AAGTTGGGAAGTCTAATAGATTCTACTTCTACCAGAATTCTGGGAT<br>TCCAAAGAATGATACCTTCAGTGTAAGGGTAAATTAGAAATAAGCC<br>TCCATAGTACTCATAATGGGCCACAAGAAAAACTGACCATTTCAAA<br>TTTTGGCAAGAGTGGAGAAGAGAGAAATTGCCACTGAGAATTTGG<br>AACCATGAGGCAGCCTCACACAAGTTTGTGG |
| 226 | NON_CODING (ncTRANSCRIPT) | CAACCTAGCCCTCCATGAGGACTGAGCGCATGAGAGATCCTGAGCC<br>ACAGCCGCCCAGCCCTGCTCCTCTCGAATTTCTGACCTACAGGAAC<br>TGCAAGAAGTAATGAAAGACTGCTGTTTAAAGCCACTGCATTTTGG<br>CATGATTTGTTATGCAGTCGTAGATAACCAGAAAACA |
| 227 | NON_CODING (CDS_ANTISENSE) | GGTTTCAGCACCCAAGACTTAGACCCACAAGAACTTAAAATGAGG<br>AAAAAGAAAAAGTTCAGGTTTAAAGGCCTGTCAGCACTCAGAAAG<br>ATACCTGTTTCAGCTAAACATTTTCTAACTTATTAAGAGAATCTACT<br>AATGTCTACTCTACCTGACTAACCTACAAACACTTCTCACAACTTCT<br>TTTAGGATTGTGACACCAACTGCCC |
| 228 | NON_CODING (INTRONIC) | CTTTCTGGATGCACCATTTACCCTTT |
| 229 | NON_CODING (CDS_ANTISENSE) | AACATGGGTTTTGTCGTGCTTCTCCTTTTGGCCTCCTGCAATATTCC<br>TGTTCTTTTTGCTGGCACTGAGATCCTCTCATCTCGGGAAGCTATTC<br>GCTCAGACGAATCGTAAAAGGCTGGCTGGGACCACGGGGCAGGCT |

TABLE 6-continued

| SEQ ID NO. | Type | Sequence |
|---|---|---|
| | | GGGGCCATGGAGGGGGCTGTGCTGGGCCAGCAATCGGACTTGAAA<br>CCCCTCTGGAGAAGGCGTCAGGGGGAGGAGTGACTGCAGAGTAAG<br>GTGGAGGTGCAGGAAAGTCAGCAATGGGACTCGTCATGTTTCGGGT<br>TGGCGAGAAGGGGGTAGCTGGCTGATTCACAGACCCTGGGAAGGG<br>TTTGGCCGTTCTATTCATGGGGACCATCCTCTGGATGTTTGCTGTCT<br>CAGATGTCCCACTGAAGCCATTCTGTTGGGGAACATGGCCAAGACC<br>ATGACTCACCTCGATGTAGCTTTTGCTCA |
| 230 | NON_CODING (ncTRANSCRIPT) | CCACCATCACCTGGACGCTGAATGGAAAGACCCTCAAGACCACCA<br>AGTTCATCGTCCTCTCCCAGGAA |
| 231 | NON_CODING (INTRONIC) | TCAAGAAGTCGGAATTTTTAGGACAGTTACAGTCTGCATTTAAGGA<br>TCCTGATGGACAGGCTG |
| 232 | NON_CODING (INTRONIC) | GAGAGCGCAGTCTTTCTGTCTCATGATACTGATTACCACACAAAAG<br>CATTGGTGAAGAAACAACTGACTGAGTTGAGTTAGGGAGTTTTTTC<br>AGAGTAATTTTGACTAGTTGCAATTTTCGATTTG |
| 233 | NON_CODING (INTRONIC) | CCGGGACTTGGCAGTACTTGAAACAGGAGGAATACACCAGCCTAA<br>ATGTACAGACTTTGTAGCCGAGCCCACTCGATCGGTCTGTGCCTTC<br>ACGTGACCACCATCTGTGCCTCCCTCGCTCCATCCAAATTTGTGTAG<br>GCTGCTCCTTGGAGCTATGCCTAAAATATAGCTACACCAGAGCCCT<br>GGAAACTGTAGTCAAGTAACAGGCCTCACTGTTTTTTTCTTTGGAT<br>TAAAAGTGTATATCTCTCTACTGAGGGGTTTCCAGCTTTA |
| 234 | NON_CODING (INTRONIC) | ACCCTAATGTTTGCCACAATGTTTGTAT |
| 235 | NON_CODING (ncTRANSCRIPT) | TTCCTTCTACTCAATCTGACCGAGGTCCTCCAGGTCAAGGACAGCG<br>AGGCTCTCAGTCCCACTTCCCCTTGGCACATAGAAGAGGCAGTGCG<br>C |
| 236 | NON_CODING (INTRONIC) | TTGGAGCCCGTAGGAATATTGAAGAAGTTAGTGAAGAAATGCTAT<br>ACAGTCATTTGTTGATTAATGAAGGGGATAAGGTCTGAGACATGT<br>GTCGTTAGGTGATTTATTCATTGTGCAAACACCATAGAGTGTATGG<br>TACTTACACAAACCTAGAGGGTATAGCCTACTAAACACCTAGGCTA<br>CAAACTTGTACAGTGTGTTACTGTACTGAATACTGTCAACAATTGT<br>AACACAAATCACCAGGCGATAGGAATTTTTTAGTTCTATTGTAATC<br>TTATGAGGCTACTCTCATATATGCAGCCCCTCATTGACCAAAACAT<br>CATTATGCAGTGCATGACCATATTGAGAGTATTCGTTTTTTATTTAC<br>TAAAAAATAGTCAAAACTTGAGGAGGAAGAGACAGATGTCACTAG<br>AAAAAGGGAGAAGTCCGGTAAGGGAGAAGTCAGCTTCCTGAGGTG<br>GAATCGTATTACCTTTGGGATTAGGACATTTCATTG |
| 237 | NON_CODING (INTRONIC) | CCCACAGGCAGCTTTGGTGTTCTCATGTTATAGTTCTTAATCTAAAT<br>TGTAGGTGCTAAACAAAACTACCTGCCTTAATGGTAGGCAGAGGTA<br>TTTGAAAAATTAATGATCTACTTGTTTGCTGAATGTCCACAATACA<br>AGCTTTGATTTAAAAAAATCATGTTAGGATAGCATGTTTATTACAT<br>ACTATTTATTATCATACTTAATATTTCTTGCCTATCAAAAGTAAAAA<br>CCTGATGCTTTATGTTAAATGTTTCTTGCCCATTGGAGCCTGTTCAT<br>GGCAATTCTTTGTCCAAGAAGAGTAATGGTATTGTCTCTTTCTATGT<br>GTCTCGGTAATTCAGGC |
| 238 | NON_CODING (INTERGENIC) | TCTAACCTTGGCTCCGGGGTATTGCCGAAACCAGTCCAGGCACGTC<br>ACAAATGTCTGACTTCTCCCAGAGGCTTCAGAAGCACAATGAGCAG<br>CAGAGGAGAGCCATGGAGCCAAGCACAGTCTCATTTAACCTCCCCA<br>AAAGCTTGGGAAGTGGGTGGTGTTATAGCCCCATTTTACAGATGAG<br>AAAAACTGAGGCTTATTTAAGCAGCTCACCTAAAGTCACATATTGA<br>TTGTGCTGAGCTGAGATTGTACCCTAATCTGCCTTCAAATCCATGTT<br>TTTACCCATTGCATGTGATTATGGAACCTGGGACCGAGGAGCAGGA<br>GGAGAACATTCTAAATTCTGCTCCCATCTTGTCTTTACATCTCAGGT<br>CACTTTTAGCAAAGACAGACCCGGACATTGCCATTAATACTACAG<br>GCTTCCTTCCTCCTACCCCCTTCCCCCAATCTTATTCATCTCACCTCT<br>CCAGTAGGTCGTGGACTCATGCATT |
| 239 | NON_CODING (ncTRANSCRIPT) | GGCAGGGGTTGGGACAAGTGCTAAGTATGCAAGACTCAAGGGAAG<br>AGCT |
| 240 | NON_CODING (INTERGENIC) | CCTGGGATGACCACAATTCCTTCCAATTTCTGCGGCTCCATCCTAAG<br>CCAAATAAATTATACTTTAACAAACTATTCAACTGATTTACAACAC<br>ACATGATGACTGAGGCATTCGGGAACCCCTTCATCCAAAAGAATAA<br>ACTTTTAAATGGATATAAATGATTTTTAACTCGTTCCAATATGCCTT<br>ATAAACCACTTAACCTGATTCTGTGACAGTTGCATGATTTAACCCA<br>ATGGGACAAGTTACAGTGTTCAATTCAATACTATAGGCTGTAGAGT<br>GAAAGTCAAATCACCCATATACAGGTGCTTTAAATTTAATAACAAGT<br>TGTGAAATATAATAGAGATTGAAATGTTGGTTGTATGTGGTAAATG<br>TAAGAGTAATACAGTCTCTTGTACTTTCCTCACTGTTTTGGGTACTG |

TABLE 6-continued

| SEQ ID NO. | Type | Sequence |
|---|---|---|
| | | CATATTATTGAATGGCCCCTATCATTCATGACATCTTGAGTTTTCTT<br>GAAAAGACAATAGAGTGTAACAAATATTTTGTCAGAAATCCCATTA<br>TCAAATCATGAGTTGAAAGATTTTGACTATTGAAAACCAAATTCTA<br>GAACTTACTATCAGTATTCTTATTTTCAAAGGAAATAATTTTCTAAA<br>TATTTGATTTTCAGAATCAGTTTTTTAATAGTAAAGTTAACATACCA<br>TATAGATTTTTTTTACTTTTATATTCTACTCTGAAGTTATTTTATGC<br>TTTTCTTATCAATTTCAAATCTCAAAAATCACAGCTCTTATCTAGAG<br>TATCATAATATTGCTATATTTGTTCATATGTGGAGTGACAAATTTTG<br>AAAAGTAGAGTGCTTCCTTTTTTATTGAGATGTGACAGTCTTTACAT<br>GGTTAGGAATAAGTGACAGTTAAGTGAATATCACAATTACTAGTAT<br>GTTGGTTTTTCTGCTTCATTCCTAAGTATTACGTTTCTTTATTGCAGA<br>TGTCAGATCAAAAGTCACCTGTAGGTTGAAAAAGCTACCGTATTC<br>CATTTTGTAAAAATAACAATAATAATAATAATAATAATTAGTTTTA<br>AGCTCATTTCCCACTTCAATGCAATACTGAAAACTGGCTAAAAATA<br>CCAAATCAATATACTGCTAATGGTACTTTGAAGAGTATGCAAAACT<br>GGAAGGCCAGGAGGAGGCAAATAATATGTCTTTCCGATGGTGTCTC |
| 241 | CODING | GGCGGCCACCAAGTCGCTGAAGCAGAAAGACAAGAAGCTGAAGGA<br>AATCTTGCTGCAGGTGGAGGACGAGCGCAAGATGGCCGAGCAGTA<br>CAAG |
| 242 | CODING | TCCATTATTGCTGCCCGGAAGCAGAGTGTGGAGGAAATTGTCCGAG<br>ATCACTGGGCCAAATTTGGCCGCCACTACTATTGCAG |
| 243 | CODING | TGGTGAACAGCCTGTACCCTGATGGCTCCAAGCCGGTGAAGGTGCC<br>CGAGAACCCA |
| 244 | CODING | AGGAGACCACCGCGCTCGTGTGTGACAATGGCTCTGGCCTGTGCAA<br>GGCAGGCTTCGCAGGAGATGATGCCCCCCGGGCTGTCTTCCCCTCC<br>ATTGTGGGCCGCCCTCGCCA |
| 245 | CODING | GCGAAGACGAAAGGAAACAAGGTGAACGTGGGAGTGAAGTACGC<br>AGAGAAGCAGGAGCGGAAATTCGAGCCGGGGAAGCTAAGAGAAG<br>GGCGGAACATCATTGGGCTGCA |
| 246 | CODING | GACCCTGATGGCTTTGGGCAGCTTGGCAGTGACCAAGAATGATGGG<br>CACTACCGTGGAGATCCCAACTGGTTTA |
| 247 | CODING | ACCCTTCTTCTTGGCGAGACCACGATGATGCAACCTCAACCCACTC<br>AGCAGGCACCCCAGGGCCCTCCAGTGGGGGCCATGCTTCCCAGAG<br>CGGAGACA |
| 248 | CODING | CACGAACTGTGCGATAACTTCTGCCACCGATACATTAGCTGTTTGA<br>AGGGGAAAATGCCCATCGACCTCGTCATTGATGAAAGAGACGGCA<br>GCTC |
| 249 | CODING | TCAGACGGGCACATCTATTGGAGGTGATGCCAGAAGAGGCTTCTTG<br>GGCTCGGGATATTCTTCCTCGGCCACTACCCAGCAGGAAAACTCAT<br>ACGGAAAAGCCGTCAGCAGTCAAACCAACGTCAGAACTTTCTCTCC<br>AACCTATGGCCTTTTAAGAAATACTGAGGCTCAAGTGAAAACATTC<br>CCTGACAGACCAAAAGCCGGAGATA |
| 250 | CODING | CTCTTTCTACAATGAGCTTCGTGTTGCCCCTGAAGAGCATCCCACCC<br>TGCTCACGGAGGCACCCCTGA |
| 251 | CODING | TGGGAATGTGCTTTGCAGCCGAGTCAGATGTCCAAATGTTCATTGC<br>CTTTCTCCTGTGCATATTCCTCATCTGTGCTG |
| 252 | CODING | AGCGCAGGAGCATAAGAGGGAATTCACAGAGAGCCAGCTGCAGGA<br>GGGAAAGCATGTCATTGGCCTTCAGATGGGCAGCAACAGAGGGGC<br>CTCCCAGGCCGGCATGACAGGCTACGGACGACCTCGGCAGATCATC<br>AGTTA |
| 253 | CODING | GGCCTAAGGATCATTTTCTCGGATGCATCACGGCTCATCTTCCGGCT<br>CAGTTCCTCCAGTGGTGTGCGGGCCACCCTCAGACTGTACGCAGAG<br>AGCTACGAGAGGGATC |
| 254 | CODING | GGGGTGATGGTGGGAATGGGACAAAAAG |
| 255 | CODING | GTTGGATTGCCAGCTTGTACCTGGCCCTTCTGTTTGGCCACGCTATT<br>GTTCCTCATCATGACCACAAAAAATTCCAACATCTACAAGATGCCC<br>CTCAGTAAAGTTACTTATCCTGAAGAAACCGCATCTTCTACCTGC<br>AAGCCAAGAAAAGAATGGTGGAAAGCCCTTTGTGA |
| 256 | CODING | GGCAATGAGCGCTTCCGCTGCCCTGAGACCCTCTTCCAGCCTT |

TABLE 6-continued

| SEQ ID NO. | Type | Sequence |
|---|---|---|
| 257 | CODING | TCATCCTCCCTTGAGAAGAGTTACGAGTTGCCTGATGGGCAAGTGA<br>TCACCATCGGAAATGAACGTTTCCGCTGCCCAGAGACC |
| 258 | CODING | GGTTGGATCCCAAGACGACATATTATATCATGAGGGACCTGGAGGC<br>CCTGGTCACAGACAAATCCTTCATTGGCCAGCAGTTTGCTGTGGGG<br>AGCCATGTCTACAGCGTGGCGAAGACGGATAGTTTTGAATACGTGG<br>ACCCTGTG |
| 259 | CODING | AAAGCAGAAGCGAGACCTCGGCGAGGAGCTGGAGGCCCTAAAGAC<br>AGAGCTGGAA |
| 260 | CODING | AGGCCTCCTCACCAGTCAGTGCATCCCCAGTGCCTGTGGGCATTCC<br>CACCTCGCCAAAGCAAGAATCAGCCTCA |
| 261 | CODING | TTGAGGACATCTACTTTGGACTCTGGGGTTTCAACAGCTCTCTGGCC<br>TGCATTGCAATGGGAGGAATGTTCATGGCGCTCACCTGGCAAACC |
| 262 | NON_CODING (INTERGENIC) | GTGACTTGGTCCAAAAGACCTGGGCACTTGGTCTAACTTTTCAAAC<br>ATTATCTAACCTCTGAATCTGGAATAACCAAACTGTAAGTTGACTT<br>AATTCACAGAAGTGCAGTGATGGTAAAATGAAATAGCATGAGTAG<br>AGTGATAAGTGTGATGCAAATGAAAGTCATATCTTCATTACTAGGC<br>TTTATTTATTAAATATAGCTAAAGTACTCTAAACGTATATGTCTACA<br>CTTTTTTGAACATGGATAGTTTTTACATAACTGTACTGAAAGAAAG<br>GGCACTAATTACTATGCGCTCTAA |
| 263 | NON_CODING (INTERGENIC) | AGCTCTCAGGTTCGTGGGAAAGCTAACATACAA |
| 264 | NON_CODING (INTERGENIC) | ATGAATATGTCAATGCTGAATGCAAATCAGGGAAAG |
| 265 | NON_CODING (INTERGENIC) | TGAGTGTAGTATTGGTAGGATCCTTCAGCACCCTGCTTCTGTTATGG<br>AAGCTCAATGGGAAAATTCCTCTCTCCCCAGCCCTTGGCAGACAGA<br>GCTCATGATGGTAGAGTTTT |
| 266 | NON_CODING (INTERGENIC) | AGAATTTTCATGGTGTTATGCATGCTGAAAAATGCATTGCATTTTG<br>AAAATTTTAGCAAAGGATACGTCAATGACTGCAGCATGATTCAGGC<br>ACCTTCCCTGGCAGTCCACAACTCTGTTATC |
| 267 | NON_CODING (INTERGENIC) | ATGTTCTTGTCATTCGTTAAGTTGCAAAATTCAGCAACTTACAATGA<br>GTATTACTACTATTGTACTG |
| 268 | NON_CODING (ncTRANSCRIPT) | ACTTGAAATTGTGTCCAGAACTGGTGGGTT |
| 269 | NON_CODING (INTERGENIC) | AATGGTTGTTCAAGCCAGGCCTGCCTCATTGAAAGGGTGAAATCTT<br>CCTTCACTGGAAGGAAGTGAGAGAATTAGTCAAGCAGCTATCTGA<br>GGAAAGAACATTCCAAGTAAAGAATATACAGCCCATACATTGTTG<br>GATGTGTGTACATTGAATTTTTGTGCAGTAAAATGAATATTTCATT<br>TACCTATATAATTTTACATAAAATAAAATATATTTTGAATGTGAGTT<br>TGTTCCAAACAAATCATTTTCTTGCCTTCAAAACCACTGAGCTTAAA<br>GAACTCTTTCAAGTGTCATTAGAGATAGATTCCAACTACAATCAAC<br>ATTGTGGAATCCAGAGGAGGCAAAATGAAGGAAGCAGCACTCATT<br>ACAAAATGCTGCTTTGTAAAGAATTAATTCTGTCCTGGTATGTTTCA<br>CATTAGGTAATATGAAGGAAATGAATATGTCATGAACCCTCCTTGA<br>GGATGTGGGGAATTAAAAGTAATTTCGCTTAATATCCAACTCTCA<br>CTTTTGGCTTTGTAGTCAGAGGGAAACAATGCTTTCCCAGGTTCTA<br>AGGTAAACGTTAAAAGGTTACAAGGAGACTTGGAAGAGTCAAGGA<br>ACGCTTCCACCAACTATTCCTGCCATTCCAGTTGGGAGGGTT |
| 270 | NON_CODING (INTERGENIC) | AATTTACTGCCTGCTCGTTTGGAGATCTATAACCTTTATACTTAGAC<br>AGTTTTTTAAAAAGTATAACAGCAATTATTTCTCCCAATTTATTTAA<br>TGCCGTTTTTTCATTGCATCCATTAAAATATTTTACTTTTATAAGCA<br>ATGATACCAGGAAGTTATCGTTTGAATAGTCTGCTGGAGGAGTAGG<br>GCAAAGTAGTTAAGATCAATTGTTCTTTCAGAAGGCTGCTGCTTTCT<br>AGCTGCATGACTTTGGGTACGTTATTT |
| 271 | NON_CODING (INTERGENIC) | CAAACTTTGAGTTTGACCTCTATAAAGACACTAAAA |
| 272 | NON_CODING (INTERGENIC) | GAACAATATGAAAATACTCTACTGAAAATTGATGAAATTGAAGAG<br>AAAGGCCATTATGAAA |

TABLE 6-continued

| SEQ ID NO. | Type | Sequence |
|---|---|---|
| 273 | NON_CODING (INTERGENIC) | ACAGCATTGATAAACCTGTAGCTAGACTAACCAAGAGAGAAGACC CAAATAAAGAAAAACAGAAATAAAAAAGGAGACATTACAGCTGAT AACCACAGAAATACAAAAGATTATCAGGCATTATTATAAACTACA ATACACTAACCAACTGGAA |
| 274 | NON_CODING (INTERGENIC) | TAATTCAGTATGCTGTCCAGGGGCCTGGAAATCACTCAGCACAGTC TACCACCATTGGCACATGAACACTTCTCCCAGGGTCTAAGGACAGG CTGACATAACATGCTAATACCACCAGAGCTGGCACTCACCCAGATG TACCACATCAGGCCAGGAAGCAGAAACTACCAACATCCCAGCAAA CCATGTGGAGGCCCCCAAATCAGACTGCTTGGGCCTAACA |
| 275 | NON_CODING (INTERGENIC) | AGGATATCACTGCAGGTCATAAAGACATTAGAAAGATAGTAAGGG ACTACTATAAATAATTTTATGCCAATAAATTTGGAAATTTAGATGA AATTGACAAGTTCTTGAAAAAATAGCACTAAAACAGATATAAGAA CAAGTAGCAAATATGAATAGTTTGAAATCTACTAAAGAAATTGTAT CTGGGGCTCAAGATGCCTGACTAGATGCAACTAGAATGTGCCTCCT CCATGGATAGGAACCAAAATAGC |
| 276 | NON_CODING (INTERGENIC) | TGGCATGACATAGCTAAAGCACTGAAGGAAAAAGTATTTTATCCTA GAATAGTATATCCAGTGAAAATATCCTTTAAAAATGTGGGAGAAAT AAAGACTTCTCCAGACAAACTAAAATAAGGGATTTCATCAATACCA GATCTGTCCTATAAGAAATGCTGAAAGAAGTTCTTCAGTCTGAAAT AAAAGGATGTTAATGAATTAGAAATCATTTGAAGGTGAAAAACTC ACTAATAATAGGAAGTACACAGAAAGAGAACAAAAAAACACTGCA ATTTTGGTGTGTTAACTACTCATATCTTGAGTAGAAAGATAAAAAA GATGAACCAATCAGAAATAACCACAACTTCTTAAGACATAGACAG TACAATAAAATTTAAATGCAAACAACAAAAAGTTTAAAAGCTGGG GGATGAAGTCAAAGTGTACAGTTTTTATTAGTTTTCTTTCTGAGTGT TTGTTTATGCAGTTAGTGATAAGTTATCATC |
| 277 | NON_CODING (UTR_ANTISENSE) | GTAAACTTAGGAGGCGTAGTGCTCCAGGTTGATCTGGCGGTTGA |
| 278 | NON_CODING (UTR_ANTISENSE) | GTCAAAGAGATATTCTCCCACGCCAGATTCGGGCGC |
| 279 | NON_CODING (INTERGENIC) | TGGAGCGCTCGAGAAGCCTGGGCTCCACTATG |
| 280 | NON_CODING (INTERGENIC) | GGAATTTCGTAATTAAATGATATGTAAAATTTGAATATTATTTGTTC AGTCTTATTCTTCCAGAACCTCAGTTACTTTCTTTTATTAATTCAGA CAGTTACCACAGTACTAGTCAGCTATTACTCAGTTCTGATC |
| 281 | NON_CODING (INTERGENIC) | TGGTGTACTAACAGCACTGATTCTGTTAGCAACAAGTAGTGGTAGA CAACTAGAAATATGTCAGTTTAAAACTTGTGAAGTTGGTTGTTACA AATCTCCATTCTGTGTATCTCCATTCTGAATACTAGATACACATCTC CATGTGTATCTCCATTCTGAATACTAGGTACAACGATTTTGTCTCTT GGAAAATTTCCTTGTCCACTGAGTA |
| 282 | NON_CODING (INTERGENIC) | TCTCACCTGTGGAACTCATTACCTGCATTAAGTTTTCTCTGCTTTCA ATATTCAGTTTAGCCGGGCGCGAT |
| 283 | NON_CODING (INTERGENIC) | AATATGGCCATGACACCAGAAATCACAAACATGATGAGAATGGAA TGACTGGGGAAGAAGTGCCAGATGCTTCACTTGTAAATGAAGACCC AGCCTCTGGGGATGCAGATACCACCTCCCTGAAGAAGCTGAATATC TGCAGATA |
| 284 | NON_CODING (INTERGENIC) | CATAGCTAGGCAGTGTTGGAGATCAGCAGGAACTAGACACAATGA ATGGATATGGCATCAATACTCATGAACATGCCATTCTTCCAGCAGT GCTTGGCAACTCAGGTTGAGGAACAGAGAAGGTGGATGGCTTAGG TAATGGAATTGGATGCTTTTTAAATGTCAGTGGCTGTCAAAACTGT ATA |
| 285 | NON_CODING (INTERGENIC) | ATGTCTCAGACCTCTCCATACTTCATCTGTACTTCTTGATCGCTTTT ATTCTTGAAATTAATACAAGAAGGTCTCTCATTTA |
| 286 | NON_CODING (INTERGENIC) | CTTAGTGGGGTTTGGAACTGCCTGAGAATATTCCTATAGAAACTGG GTCATCTTGCCTTCTGTGCCACTAGAACCTCCTGTCTCTCCAATAGC TGCTTCTCTCTAATTCTTCACCATAGTTTTCTTTCTGTGGTCTTTTGA GGTTCTCTCCT |
| 287 | NON_CODING (INTERGENIC) | CTTTCACTGTTATGCCGGTGATTTGAATGTAAAGCAGTTTTATTTAA ATCAATATAATTTAATAAAAACATATTTAAATTTTGGGTTAGATTA AAAATTTTCTCTATTGCCAATACTTGGTTTGAACTCAATTAGGCTCT CTTTTACATAAGAGACTACATTAAACACAGACATATATGAGGTATTT TTGAGACATTTGAATGTAATATATTGTAATTTTACCATTTATTTTGT |

TABLE 6-continued

| SEQ ID NO. | Type | Sequence |
|---|---|---|
| | | CTCCTAAATTGACATTTAAATAATCAGAATCTCTAGCTCAATATTCA AATTAACATTTTCTTCCCTTAAAATGGTGGGTTACCTCCTTCCTGGA AGGAGCGGAATGTGAGTAACATTTCTTCCTTTCCATGTTTTTCTCAA TCAAATGGCACAAAGGATTTTCTTGACTGCTTGAAAACTAAAAACA GTTTCCCAGAGTTTATTAAGTTCATATTAATTTTTAATGCAAATACC TGTTATTAAAACTCTAAGTAGGGCAGGCGC |
| 288 | NON_CODING (INTERGENIC) | CATTGGGCTCCAGAGTATCGACGGCGCTCTCCTGTGATGTAGGCCG TGAATTTCACGTGATGTGCACCTTG |
| 289 | NON_CODING (INTERGENIC) | TGCACCTGTTTAGTTTGTGACAATCTGAGCCCAGTACATGGTTCTCT GATTCCTAAGCCAGGAGTCTCTCTGTAACCAAACTGCTATTATGTG AGCATAGAACAGCTCTCAAAGTAAATGTCCCACTTCTATTTCTGGC AGGTTATGTTTAGCTACCTTTCCAAAAGAGTCCCAATCCTAGTATG CCTTTCAACAGTGTC |
| 290 | NON_CODING (INTERGENIC) | TGAATAAACTCATTCGTCCCTCAAACCAGAAATTATTTGAGGTTAT CAATAACTTCTCCATGGAAGAGTTTGTTAGAGTTTTGGTCAGGAAA ACA |
| 291 | NON_CODING (INTERGENIC) | AAGTTCCTGAAGTGTGTCATCCCTCTGCTAGACATCTAAGGGATGA CTTTTTTCACAAATCATATTAACTCACCAGTACAATAGTAGTAATAC TCATTGTAAGTTGCTGAATTTTGCAACTTAACGAATGACAAGAACA TGGCATAGGTCAGTGATGCATGTTATGCTTAATTTTGAGTGAGTGA CTTGCATGTTATATCTCTGCCTG |
| 292 | CODING | GGTCGCCAGTCATCCCGCACAAAAAACCTGTCCCTGGTGTCCTCGT CCTCCAGAGGCAACACGTCTACCCTCCGTAGGGGCCCAGGGTCCAG GAGGAAGGTGCCTGGGCAGTTTTCCATCACAACAGCCTTGAACACT CTCAACCGGATGGTCCATTCTCCTTCAGGGCGCCATATGGTAGAGA |
| 293 | NON_CODING (INTRONIC) | CAGAGAGGTGGTAACTCCCGAGTAAGCAATGCCAATCCTTCAGGC AAAGATAAGGAAGAACCGCACAGCTGCTCCAACATAAAGTGG |
| 294 | CODING | GTATCCTGGCATCCATCTGTGGTGGCCTTGTGATGCTTTTGCCTGAA ACCAAGGGTATTGCCTTGCCAGAGACAGTG |
| 295 | NON_CODING (INTRONIC) | ACTAACCTCTGCAGTTTAACCTTGAGCGATACCTTTTCCCATGAATA G |
| 296 | CODING | TGGAGGCTGCCTGATCGAGCTGGCACAGGAGCTCCTGGTCATCATG GTGGGCAAGCAGGTCATCAACAACATGCAGGAGGTCCTCATCC |
| 297 | CODING | GATCGCCATTCTTGATTATCATAATCAAGTTCGGGGCAAAGTGTTC CCACCGGCAGCAAATATGGAATA |
| 298 | NON_CODING (NON_UNIQUE) | AACGATTTCGAGATTTACTACTGCCTCCATCTAGTCAAGACTCCGA AATTCTGCCCTTCATTCAATCTAGAAATT |
| 299 | NON_CODING (NON_UNIQUE) | TACTGATAATCTCAAGGAGGCAGAGACCCATGCTGAGTTGGCTGAG AGATCAGTAGCCAAGCTGGAAAAGACAATTGATGACTTGGAAGAT AAAACTGAAATGCACCAAAGAGGAACACCTCTGTACACAAAGGATG CTGGACCAGACTTTGCTTGACCTGAATGAGA |
| 300 | CODING | AAAATCTTGCAAAATCGGCAGAGGCTTGGGCGGCTACTTGCATTTG GGACCATGGACCTTCTTACTTACTGAGATTTTTGGGCCAAAATCTAT CTGTACGCACTGGAAG |
| 301 | CODING | GTGGTGAATGTACCTGTCACGATGTTGATCCGACTGGGGACTGGGG AGATATTCATGGGACACCTGTGAATGTGATGAGAGGGACTGTAG AGCTGTCTATGACCGATATTCTGATGACTTC |
| 302 | NON_CODING (NON_UNIQUE) | CAGGAGCTGATCCTCCTTGCAAAGCTGTGCCTTGCAGAGATGCACG TGTGCATTTCAGCTACATCATGCCGCGCTGTTGTAATACTGTATAAA GACCTCAATCTATCCAGAGTATTTT |
| 303 | NON_CODING (INTRONIC) | TTGCACACTGTTCCAACTTGCCGTGAACACATTTTTTGCTCTTT |
| 304 | NON_CODING (NON_UNIQUE) | CAAAGAAGCTAAGCACATTGCAGATGAGGCAGATGGGAAGTATGA AGAG |
| 305 | CODING | TGTCTGTGTCAATGCGTGGATGCTGGACCTCACCCAAGCCATCCTG AACCTCGGCTTCCTGACTGGAGCATTCACCTTAGGCTATGCAGCAG ACAG |

TABLE 6-continued

| SEQ ID NO. | Type | Sequence |
|---|---|---|
| 306 | NON_CODING (INTRONIC) | TGGAGTCGTATGATGCCCTTGCCTTGTTTTATATTGGCTGTCAGCGC<br>TTAACTGGGACTGAAGTATCTGGGTAACAAAAATTGATATAATGAC<br>TTAATGCGCCTTATTCTCTTTGAGCTACATCAGTTTAGAGCACTTCT<br>GAGAGAAAAATGTCTGGAAAATATCAGGGAGTCATTTATCAACCT<br>GTTTTCATTAGCATACTGCCTAGCTCTGGCAAGGATTTGA |
| 307 | NON_CODING (INTRONIC) | CGGAGAAGGTTAGAATGGATTTGAAAGAATGTGGTTGGATTCAAA<br>GAAGCCCTAGGAGACCCAACAAGTCAGCATTTTTCTCTTGTGAAAA<br>GAACCACCTGCCAACCCCAGCCTGTTCCATTGCTGACATCAGAGG |
| 308 | CODING | CTGAAGCTAGACAGGCAGCAGGACAGTGCCGCCCGGGACAGAACA<br>GACATGCACAGGACCTGGCGGGAGACTTTTCTGGATAATCTTCGTG<br>CGGCTGG |
| 309 | CODING | ATGATAGCAATCTCTGCCGTCAGCAGTGCACTCCTGTTCTCCCTTCT<br>CTGTGAAGCAAGTACCGTCGTCCTACTCAATTCCACTGACTCATCC<br>CCGCCAACCAATAATTTCACTGATATTGAAGCAGCTCTGAAAGCAC<br>AATTAGATTCAGCGGATATCCCCAAAGCCAGGCGGAAGCGCTACA<br>TTTCGCAG |
| 310 | CODING | AGCAGTCATGCCTGAGGGTTTTATAAAGGCAGGCCAAAGGCCCAG<br>TCTTTCTGGGACCCCTCTTGTTAGTGCCAACCAGGGGGTAACAGGA<br>ATGCCTGTGTCTGCTTTTACTGTTATTCTCTCCAAAGCTTACCCAGC<br>AATAGGAACTCCCATACCATTTGATAAAATTTTGTATAACAGGCAA<br>CAGCATTATGACCCAAGGACTGGAATCTTTACTTGTCAGATACCAG<br>GAATATACTATTTTTCATACCACGTGCATGTGAAAGGGACTCATGT<br>TTGGGTAGGCCTGTATAAGAATGGCACCCCTGTAATGTACACCTAT<br>GATGAATACACCAAAGGCTACCTGGATCAGGCTTCAGGGAGTGCC<br>ATCATCGATCTCACAGAAAATGACCAGGTGTGGCTCCAGCTTCCCA<br>ATGCCGAGTCAAATG |
| 311 | CODING | ATATCGCTCTATTCTCCAGTTGGTCAAGCCATGGTATGATGAAGTG<br>AAAGATTATGCTTTTCCATATCCCCAGGATTGCAACCCCAGATGTC<br>CTATGAGATGTTTTGGTCCCATGTGCACACATTATACGCA |
| 312 | CODING | ATCTGTGTGGCGACGTGCAGTTTACTTGGTATGCAACTATGCCC |
| 313 | NON_CODING (NON_UNIQUE) | GCTGTATATTGATGGTCCTTTTGGAAGTCCATTTGAGGAATCACTG<br>AA |
| 314 | NON_CODING (NON_UNIQUE) | GTCTTCGTTTGATTACTGCCAGTTATTTCCAGCATGCTAAATCCCTA<br>CCCACGTTCCAGCCTCTAGGTGAGTCAGTGCGTCACTCTGTCTCCCG<br>TCCAATTAATTATTTCTCATCACTCCCTCAATCCAAGTAACAAACCT<br>TGAAACACGAACATAGACACCAGGCTTATTGGGCGTGCACAGCC<br>AAGAC |
| 315 | CODING | CCCGTTGGCTGATTACTCGGAAGAAAGGAGATAAAGCATTACAGA<br>TCCTGAGACGCATTGCTAAGTGCAATGGGAAATACCTCTCATCAAA<br>TTACTC |
| 316 | NON_CODING (UTR) | CATTTGGGGCAAATGGTTCACATTCATTTTAGGGTTAGTGGTCATG<br>CTGTTTATTTTTCTCTGCTATACAAAGTTCCTCTTAGGGGTCTGCCT<br>CATGACACTAAAAAATGAATAGAGATTCTACTGTAGGTTATCTCCT<br>AGGCTTGAGTTCAACATTTGTTTGGATTTTTGAAGAAAGTCAAATC<br>AAGCAATGCTCCCAAATGATGTCTTTGTAAATTCATACCCTCTGGC<br>CCTA |
| 317 | NON_CODING (INTRONIC) | AGATGACAGCGCAAGAGTCAGATTAATGAAAGATCAATAGACATT<br>ATTCAGTCTTGAAAAAATTGTGAACAGGGATGCAGGGATCAGTGG<br>GACAATATCAGAAGCTCTAATACATGTTGTCATAGGATGGGGTGGG<br>GGTGAATGAAAAAATAATGGCTGAAAATATCCCAAATTTGATGAA<br>TGATATAAATGTAGAGTCAAGAAGCTCAATCA |
| 318 | CODING | ACGGAACAAAGGATGAGCAGCCCGAGGG |
| 319 | NON_CODING (NON_UNIQUE) | TTGGCACCAATCCTAGACTCACGTGTGCCCCAGAATAACATTCAGA<br>CTCTCAGCTGGTCTTGTGTTACACATCCATGACCGGTTCACTCCAT<br>CATATACAGCTCTCTGCTCCGTGTCCCCTGGGCTCAAGTCAAGCAG<br>TCGGTGACAGATTTCATTCCCAATAACAGAATCGGTTTGCATGACT<br>CCCCATACATGTTGCAGCTTTGAAAACATTCATCTCAGAGTTAGGT<br>ATAAAGACATAAAAATGTGTCAAGCCCTCGTTAGCTGATGAGGT<br>AAATGCATGGACAACTTCCTAGGACTTCTCGGCTCTGC |
| 320 | NON_CODING (ncTRANSCRIPT) | ATCATTGAAGGAGACATGGGATGCACAGAGGAACGAGC |

TABLE 6-continued

| SEQ ID NO. | Type | Sequence |
|---|---|---|
| 321 | CODING | AGGACGGGAACACCACAGTGCACTACGCCCTCCTCAGCGCCTCCTG GGCTGTGCTCTGCTACTACGCCGAAGACCTGCGCCTGAAGC |
| 322 | CODING | TGCGAGAGTCTCTTTGCAAATCGAAGAAGGGAGACATGTTGGGAG CAAGCCCCCCAGAGTCTGGCCATAAACTGGCCCCAAAACTGGCCAT AAGCAAAACCTCTGCAGCACTAAAACATGTCCATAATGGCCCTAAC GCCCAATCTGGAAGGTTGTGGGTTTATGGGAATGAGAGCAAGGAA CACCTGGCCTGCCCAGGGCGGAAAACCGCTTAAAGGCATTCTTAAG CCACAAACAAAAGCATGAGCGATCTGTGTCTTACGGGTGTGTTCCT GCTGCAATTAATTCAGCCCATCCCTTTGTTTCCCATAAGGGATACTT TTAGTTAATTTAATATCTATAGAAACAATGCTAATGACTGGTTTGCT GTTAAATGAAGGGGTGGGTTGCCCCTCCACACCTGTGGGTGTTTCT CGTTAGGTGGAACGAGAGACTTGGAAAAGAGACACAGAGACAAAG TATAGAGAAAGAAAAGTGGGCCCAGGGGACCAGCATTCAGCATAC AGAGGATCCACACTGGCACCGGCCTCTGAGTTCCCTTAGTATTTAT TGATCATTATCGAGCATGGCAGGATAATAGGATAATAGTGGAGAG AAGGTCAGAAGGTAAACACATGAACAAAGGTCTCTGCATCATAAA CAAGGTAAAGAATTAAGTGCTGTGCTTTAGATATGTATACACATAA ACATCTCAATGCCTTAAAGAGCAGTATTGCTGCCCGCATGTCATAC CTACAGCCCTAAGGCGGTTTTCCCCTATCTCAGTAGATGGAAGTAT ATTCCATGTAAAGTAAATCGGCTTTACACCCAGACATTCCATTGCC CAGAGACGAGCAGGAGACAGAAGCCTTCCTCTTATCTCAACTGCAA AGAGGTGTTCCTTCCTCTTTTACTAATCCTCCTCAGCACAGACCCTT TATGGGTGTCGGGCTGGGGGATGGTCAGGTCTTTCCCTTCCCACGA GGCCATATTTCAGACTATCACATGGGGAGAAACCTTGGACAATACC TGGCTTTCCTAGGCAGAGGTCCCTGCGGCCTTTGCAGTATTTTGCGT CTCTGGGTACTTGAGATTAGGGAGTGGTTTGAGATTAGGGAGTGGT GATGACTCTTAAGGAGCATGCTGCCTTCAAGCATTTGTTTAACAAA GCACATCTTGCACAGCCCTTAATCCATTTAACCCTGAGTTGACACA GCACATGTTTCAGGGAGCACAGGGTTGGGGGTAAGGTTACAGATT AACGGCATCTCAAGGCAGAAGAATTTTTCTTAATACAGAACAAAT GGAGTCTCCTATGTCTACTTCTTTCTACACAGACACAGTAACAATCT GATCTCTCTTTTCCCCACAGTTAATAAATATGTGGGTAAATCTCTGT TGGGGGCTCTCAGCTCTGAAGGCTGTGAGACCCCTGATTTTCTACTT CACACCTCTATATTTTTGTGTGTGTGTCTTTAATTCCTCTAGCGCTG CTGAGTTAGTGACCGAGCTGGTCTCGGCAGAGGTGGGCGGGTCTTT TGAGTTCAGGAGTTCAAGAGCAGCCTGGCCAACATGGTGAAACCC CTTCTCTACTAAAAATATGAAAATTATCCGGGCATGGTGGTGTGCC TCTGTACTTTCAGCTACTCAGGAAGCTGAGGCACAAGAATTGCTGG AACATGGGAGGTGGAGGCTGCAGTGAGCTGAGATCATGCCACTGC ACTCCAGCCCAGGCAATAGAGTAAGACTCTGTCTCAAAACAAAAA GAGTTTTAGGCCAGGTGTGGTGGCTCACGCCTGTAATCCCAGCACT TTGGGAGGCTGAGGTGGGCAGATCACCTGAGGTCAGGAGTTCGAG ACCAGTCTGGCCAACATGGCGAAACCCCATCTCTCTACTAAAAA TACAAAATTTAGCCAGGTGTGGTGGTGGGTGCCTGTAATCACAGCT GCTTGGGAGGCTGAGGCAGGAGAATTGGTTGAACCCAGGAGGCAG AGGTTACAGTGAGCAGAGATCGTGCCACTGCATTCCAGCCGGGGTA AGAGAGCGAGACTCTGCCTCAAAAAAAGAAGGCTTAGTGTGCAAC TCATCAGAGTTGCACAGGGCAGAGAAAGAATGGGAAAAAAACAAT TTCTAGAAAACTTTTCGAATTTTCTGATCAACACCAAATATTCCAAA TAGGAAAAATACAAAAAAATCCATACCTATATGTGGCATAAATATG ATTGTAGAGCACCAAAGTAAAAGATCTTATTTTTTATTAAAATTAA AAAAAAATTAAAATAGAGGGTCTCACTATGCTGCCCAGGCTGGTCT TGAACTCCTGGCTTCAAGCTATCCTCCCACCATGGCATCCTAAAGT GCTGGGATTGCAGGCATGAGCTGCTGCATCTGGCCCAAAGTAAAA GATCTTAGAAGCGGCCAGAAAAAATAGATTTGGGCTGGGCATGAA TAGATTGATCACCAAAAAGGTGGCAGACTAACTTCTCGACAGA |
| 323 | CODING | TTTTTGGCATCTAACATGGTGAAGAAAGGA |
| 324 | CODING | GCTGTGGAGCCTTAGTTGAGATTTCAGCATTTCC |
| 325 | CODING | GTATATGGACGACTTCTTACTCATGTTAGCCCATTCATTTCATCAGA GCATCTTCACACATCAGTGTTCACTCTCTATAGATTTATTTGCATAT TGTCTAAATATGTTTTTTTCTGTTATTATTTTACACTTTTTATTTTGCT TCATTCTCTGTTGAGTTCCTCA |
| 326 | NON_CODING (ncTRANSCRIPT) | CTTGAGTCCTGGAATCGACCTTTTCTCCAAGGAGCCTTGTTCCTTTT AGTGGGAAAGGTATTTAGAAGCTAAGATCTTGGTGTTGGCTGTGT TCACTACAATTGGTGTATCTACTTCTCCATCCTCCAGCGTCCTCTGG TGATCGAGAATCTGAAGTTCCAGGTTTTCATAGGCC |
| 327 | CODING | GGGTTTGCTGTTTGGATCAAGGAATCAATGGATTGCCAGA |
| 328 | CODING | GATGGAGAGCATAAGCCATTCACTATTGTGTTAGAAAGAGAAAAT GACACTTTGGGATTCAATATTATAGGAGGTCGACCAAATCAG |

TABLE 6-continued

| SEQ ID NO. | Type | Sequence |
|---|---|---|
| 329 | NON_CODING (ncTRANSCRIPT) | CAGGCATTCTGATTTATTGATTGTGG |
| 330 | CODING | TCTTCATCTTGTCTTACGCTTTCCGAGCAAGTTCAAACCAGAA |
| 331 | CODING | GCACCAACAAATGTGGTTGCTCCATAATGGAGAGAATGTCAAGAA TGTTGACTATCTTTAGACCTGCTTCATTAATAGATAAGA |
| 332 | CODING | AACCGCATGCACGAATCCCTGAAGCTTTTTGACAGCATCTGCAACA ACAAATGGTTCACAGACACGTCCATCATCCTGTTTCTTAACAAGAA GGACATATTTGAAGAGAAGAT |
| 333 | CODING | CAGGCCCAAGTGCATACTCGGGTTCTTTCCAACTCAGAATCATCTC TGATTCCACAAAAGTGAGTTTAGTTTCCTATCTGAATTAACAACTTT AAAGGAGACTATAATAGTTAAAAGTGGAAGAATAGAAATAAATAA ATTTAAAATGAAATTAATTAAAGTAGAAGAGAAGGGTTCTGTTCCA TGTACGATTAATGTGCC |
| 334 | CODING | CCTGGCATCTATTTCCTCTGTGCAAAGGGAACCATGTATATGAGCT TATAAATAC |
| 335 | NON_CODING (ncTRANSCRIPT) | CTCTTTGGCGTTGCTAAGAGACTGCCAT |
| 336 | CODING | TTCCTACCGCATGCATTTTCTAATGTTTGGGGTGGATGGTGTGTCGG TTATGGAAGGCATAGACGTCATTACAGGTGCTACGATCTCACACAC ACACAAGGAAATGTTAGTCTCCTTATTTTATGATTGGAAAATCAAT GACCTAGAGGCAAAATGGCATGTTTAAGGACCTGGGATGACAAGT CATTCTGCAGTCAGCCACAGAGCCAAATTTGGACTCCTCAACCAGA ACTCCATGAAAAGCCTGACTTTGCCAAACACTGTGCTGGAAAAGCT AAGCCCCTTTCATTTGTGAAGTAAATTTTAAATTCAAGATATTTAGT TTAGAGAATTGAGTCTTGAGATGTAAACTACATGAGATTTCTTTGG TTTCAATTGAATAATATTCACTAACAAATGATTTACTAAAATACGT ATTTCTTGGTCCTTATCATGTAATGACAGATTCACAACAGCAATAA GGATGGAGATTTCCCCAATAATTAATAACACCGAGAGTAGCAATAT TTTTTA |
| 337 | NON_CODING (ncTRANSCRIPT) | GTAGAGCCTACGTCCTTCATGAGAAAAATGACACAAATCTCAGTAT TCTTTGTTTGGAGTCTCTTGACATCCATGTGAG |
| 338 | NON_CODING (ncTRANSCRIPT) | TTAGGACACGGACATTTCTATTTGGCAGCCAACA |
| 339 | CODING | CGGAAGACTTGCCACTTTTCATGTCATTTGACATTTTTGTTTGCTG AAGTGAAAAAAAAGATAAAGGTTGTACGGTGGTCTTTGAATTAT ATGTCTAATTCTATGTGTTTTGTCTTTTTCTTAAATATTATGTGAAAT CAAAGCGCCATATGTAGAATTATATCTTCAGGACTATT |
| 340 | NON_CODING (ncTRANSCRIPT) | GCTTCTGTCCCAAGAGGCACTAGCTGGGG |
| 341 | CODING | AACATTGGAGAAGTATCTCTTTGTAATGCTAAAAAGAAGTGAAAAT CAACAGACTTATCTAATGAATGCAGATGTGGCAGAAAGAATGAGT AGCACTACCGTTGACTCTGAAGAGAGA |
| 342 | CODING | ACTACTAGACTTGCTAAACTTGGACTGTTGTGAATTAGAACCTAAA ATTGAAGAGATTAATATTAGGCGCCTATATTTTGCTTCTAAATCAA GAAATAAAATTATTAGCAGTATGGTTTCTTTTACTGATGAACATGTT TGTATTGAACAAGGAACACATACTAATATCTATTGAGTGCCTACTA TGTGCTAATCTCCAACAAATTGATTTGGGGATGCTAAGAAGAATTA TGTGCCAGTGTTACCCTCAAGGAGCAATACTGTATATA |
| 343 | NON_CODING (ncTRANSCRIPT) | AATCTCATCTCTATGACATCCCTATCCTG |
| 344 | NON_CODING (ncTRANSCRIPT) | CTCAGTCTATGAAAGCCAGGTTAGCTTGCTTTCTTCCTCCCTAAATC CTCCATCCTCATGACCAACAAAGAAATAGTTGAATCATTTTCCAGG CACATCTTGGGGAGGATGTGGGGCCATTGGAGGCTGTCCTTCCTAG ATAAGTCTTTAGGAGTGAGAACAAGGAGTCTTACCCTCCTCTGTCC ACCCACCCCCATGAATGGGCCTGGCTCCAGCCAGGAGTTGTGGTTT TTCCTGAGCTCCTCACCTATCTCTTCTGGATTTCACATTGGCAAACG GGGTTGCAAAGTGCTCTTCGTGCTCTTTGGACAGTGCC |
| 345 | NON_CODING (ncTRANSCRIPT) | TGGTTGCATTGCACGTAGAAAGTGGAATAATGTAATGAGCTTTGAA ACCATAATAATGAATGTCTGAATAATGACATTATTCTTGCGTTTGT AATACTGTTAATTAAATCTATGTCGATCCTGTTGAATTCATAAAAT CATCTAAAAATTTTTCTAAATATACAGTGTTGTTTTCCCCATTGTAT |

TABLE 6-continued

| SEQ ID NO. | Type | Sequence |
|---|---|---|
| | | CTTGATCTCAAGCAACAAATGGTAAAAGTATAGCTATTAATGTCAT
TAAATGTGAATTGTTTCAACATTATGAAGGGTTCCTCTTGGTAAGT
GGCAGAAGGAGCCAGGCTTAGGTTTGAAGTGAGACTGACTTTATTC
CCTTCTT |
| 346 | NON_CODING (ncTRANSCRIPT) | CTCCTGAATGCTGGCCAGACAAATGGAAATCTGCCAGGGTTGGGTA
CCCCCATGACAGCAGCCAGCCTGCCCTCTTAGTCCCTGACAGCTGC
AGTGACAGCATCTGTGATTGCAAAGCGTGACAATTTATATCTCTCA
TTTCATCACACCATCTATCAGCAGACAGTCAGGCTTTAAAAATCAA
TCCCACACTGACTCAGTCCCCAGCAGAGATGGCCTCTGACAACAGT
ATCCACACTGCAGGCTGGACAAGGGCCCTATTAATTTTGAGACTCA
GCCAAATTTCCTTCTGACCCTAAGCTGGTGAATCCCTGCTCCTTTGC
TTTGGTTGGGGTTGGTGTGAGCTAAGGCTGTGATCCCATTTGCTCCT
ATGGCCTCCAGGTGGCCTGGGCCTCCATGAATGGGCCACATGGTCA
TACTGAATGCTTGATTACACTCAGACCTAGCAGTCGTCTGGGCGCA
GCTGGTTTATGGATCACTTT |
| 347 | NON_CODING (ncTRANSCRIPT) | ATGGCCTTTGAATCATACTTAAGTTT |
| 348 | CODING | ACCGAGGAGGAGATTCTCTTTAATTATCAAAGACACATCTTTTCAG
GGGGCCAACAAAGCATTTATTTCACCCGCCAAACTAAAGGAGAGTT
ATTCCAGTTTAGGAGGAAGATGCAAGCGGTTTGGGACCTTGAACA |
| 349 | NON_CODING (ncTRANSCRIPT) | TGGAGGCTAATCTTGTTTGTTATACTTTAGTCATTAATTCAAAGTAA
AGGAGTTGTTAATGAACTGGAAACTCCTTTTGAATTATGGTAGCAA
TCAGAATATTTTTATATTAGCCAGTTTTACCTTGAAGACCTATTTTT
AAAAACTACCTGTGTCTCTGGACTTAGTTGCAAATGCATATTAAAA
CAAAAATCCCCCAATTTCTGTGCTTTCTTATTTGAAAGGCCATTTCT
AGGGGGAAAACAGTTCCCAAACACATTATACATGTTGGAAAGTTT
ATCTCTAACCTTTTGAATTAAACAATTTCAGAATTGAAAACAGTAA
GGTGAATTTTAGGCCAATAACTCTTTTCTATAATCTTGACTCTTTTA
AGATTAGGCAGTTCAGATAGTCTTATACTA |
| 350 | NON_CODING (ncTRANSCRIPT) | ACCTAGTTGGCTTTCATCTAATTCATTGCCATTTTAAGTGTGTATTA
TTTTAGAGCAAACTTAGAAAAACAGCACATTTCTAGTAACTTACGA
CATTCGATGAATGATAAATGTTCAAGTTAGACTAAAGGAACTTTAT
TCCAACTTCTAGTAACTACTTTCTTCA |
| 351 | CODING | AGCATTATCTAAACTGCAGTCACTGTGAGGTAGACGAATGTCACAT
GGACCCTGAAAGCCACAA |
| 352 | NON_CODING (ncTRANSCRIPT) | TTCACAGGACTTCGCCACGCTGCTTTGGAATCTTTCACACCCCCTA
CCCCCAGATACCTTTGAAAAATTTGAGGTTCCTGTTCCTTGTTTCTC
AGTGTATTCATTTCTTCCCTGACTATGACATGTTAAAAAA |
| 353 | CODING | CTTCAACGATGAGAAGTTTGCAGAT |
| 354 | CODING | GGAAAGACGAGAACTATTTATATGACACCAACTATGGTAGCACAG
TAG |
| 355 | CODING | TGCCCCTAGATCTGACAGTGAAGAG |
| 356 | CODING | GCAGCAGTCCCAAATAGTCAAAATGCTACTATCTCTGTACCTCCAT
TGACTTCTGTTTCTGTAAAGCCTCAGCTTGGCTGTACTGAGGATTAT
TTGCTTTCCAAATTACCATCTGATGGCAAAGAAGTACCATTTGTGG
TGCCCAAGTTTAAGTTATCTTA |
| 357 | CODING | GTGGTGTATGCGGATATCCGAAAGAATTAA |
| 358 | CODING | GAAGTTCAGAAGCTACAGACTCTTGTTTCTG |
| 359 | CODING | GAAGCTTCTGCAGTTCAAGCGTTGGTTCTGGTCAATAGTAGAGAAG
ATGAGCATGACAGAACGACAAGATCTT |
| 360 | CODING | CTGTTGCTGAAACTTACTATCAGACAG |
| 361 | CODING | GCTCAGAAAAAGAAGTTCGAGCAGCAGCACTTGTATTACAGACAA
TCTGGGGATATAAGGAACTGCGGAAGCCA |
| 362 | CODING | CTTACCAGCGTTATAGGCCAGTATCAACTTCAAGTTCAACCACTCC
ATCCTCTTCACTTTCTACTATGAGCAGTTCACTGTATGCTTCAAGTC
AACTAAACAGGCCAAATAGTCTTGTAGGCATAACTTCTGCTTACTC
CA |
| 363 | CODING | TGTGCAAGTAGTACTCGATGGACTAAGTAAT |

TABLE 6-continued

| SEQ ID NO. | Type | Sequence |
|---|---|---|
| 364 | CODING | TTGCAAATTCCATATCTACAATGGTACACGTCCATGTGAATCAGTTTCC |
| 365 | CODING | CTGGCCAGTGATTCACGAAAACGCAAATTGCCATGTGATACT |
| 366 | CODING | TTGGATGACTGCAATGCCTTGGAAT |
| 367 | CODING | CTTCTTCCTGAATCACGATGGAAAAACCTTCTTAACCTTGATGTTATTAAG |
| 368 | CODING | TCCTCGTTTTATCCTGATGGTGGAG |
| 369 | CODING | TTTTTGACAACAGGTCCTATGATTCATTACACAG |
| 370 | CODING | GGACCACTGCATGGAATGTTAATCAATACTCCATATGTGACCAAAGACCTGCTGCAATCAAAGAGGTTCCAGGCACAATCCTTAGGGACAACATACATATATGATATCCCAGAGATGTTTCGGC |
| 371 | CODING | AACCTGTAAGTGTAATGGCTGGAAA |
| 372 | CODING | CGCCCTATTAGGAGAATTACACATATCTCAGGTACTTTAGAAGATGAAGATGAAGATAATGATGACATTGTCATGCTAGAGAAAAAAATACGAACATCTAGTATGCCAGAGCAGGCCCATAAAGTCTGTG |
| 373 | CODING | AAACCTAAGACTTGTGAGACTGATGC |
| 374 | CODING | CATGAACGGGGACCTGAAGTACTGA |
| 375 | CODING | AGTTTTTACAGATTACGAGCATGACAAA |
| 376 | CODING | TCCCTCTTATTCTGGAAGTGATATGCCAAGAAATG |
| 377 | CODING | AGACCTGGATTTTTTCCGGAAGATGTGGATTGACTGGAA |
| 378 | CODING | TAAAGATGATAATCAGGAAATAGCCAGCATGGAAAGACA |
| 379 | CODING | AGCAGTGATAATAGCGATACACATCAAAGTGGAGGTAGTGACATTGAAATGGATGAGCAACTTATTAATAGAACCAAACATGTGCAACAACGACTTTCAGACACAGAG |
| 380 | CODING | TTCAGAACAAGAGCTAGAGCGATTAAGAAGCGAAAATAAGGA |
| 381 | CODING | AAGAACCAGATGACTGCTTCACAGA |
| 382 | CODING | GTCGGCAGGTTCTAAAAGATCTAGTTA |
| 383 | NON_CODING (CDS_ANTISENSE) | ACCTTGCAACGGATGTCCTTGTTGATCAGCACGTTCTTGCCCTTGTAGTTGAAGATGACATGA |
| 384 | NON_CODING (CDS_ANTISENSE) | ATGATGATGCTGTTAACTACATTCAACAAAAATCCTTTAAAACAGCTGTTTTCAACCAACTTTCGCTGTGAATGTACTTTT |
| 385 | NON_CODING (CDS_ANTISENSE) | CTGCCAGCTGAATCAACAGGGTAAA |
| 386 | NON_CODING (CDS_ANTISENSE) | CCATCTTCAAGTTTGGACTCATAGACTTGGGTTAAAGATTTTACTTTTTGCTCCATTTCACTATTTTGTTTT |
| 387 | NON_CODING (CDS_ANTISENSE) | TGGGTCTTCTCTTCAAGCAACAGAC |
| 388 | NON_CODING (CDS_ANTISENSE) | GCATTTTGAGGACTTCGTTTGGATCCCAATTCAAACAAAATAACTGTGAAGAGATTTTTTCGAACAACAGAGGAGATTCAATTACACACTGGGTTACATGATCTGAAGGAACTGGCATTTTTTTAAATGTGTGATAACGGCACTGA |
| 389 | NON_CODING (CDS_ANTISENSE) | AGGGTGATTAGGAATTAACTGGACAAAGAAGAGGGAAAGTCTTTGCAAGTAGAGGAAAGAATCTGCTTGGAGCTCAGATAACTATTATTTGAAAACATAATGACATCTAGTTCAAACTTGTGACTGAGTTCCACAGTAGAATTCACAGAAAAAAAATTATTAAATATAATATTTCCATCAGTCTGTGTCTAAAAGATTAAAAAAGAGCAAATAACAATCTTAATAAACTGATGATAGATTATAGCCTCATCTCTTCCAACATCCGATTCTGTG |
| 390 | NON_CODING (INTERGENIC) | GAAATGTTCAAGATGGTCAGGAAAG |

TABLE 6-continued

| SEQ ID NO. | Type | Sequence |
|---|---|---|
| 391 | NON_CODING (INTERGENIC) | CCTGTTTCCTCTCGATATGCTACAG |
| 392 | NON_CODING (INTERGENIC) | CTGTTCATCCTGCTGTAGATCTGTT |
| 393 | NON_CODING (INTERGENIC) | AAATGTTGACAATTGGGACGATGTAAATGTAAAG |
| 394 | NON_CODING (INTERGENIC) | GCAAAGGTGTCCAAATTATGCAGAC |
| 395 | NON_CODING (INTERGENIC) | AGTTATAACATGAAGGGATTTTCATCTTTTGCTGTATGAAGGATAA TTGTTATATCACATTTGGGGGGTAATAACA |
| 396 | NON_CODING (INTERGENIC) | CAAAACGACTCACTGGGTTTTTCAT |
| 397 | NON_CODING (INTRONIC) | AGAGAAAGTGAAGATTCGATTTGAG |
| 398 | NON_CODING (INTRONIC) | TCAGAATTAAACCTGTGGCCCAGGT |
| 399 | NON_CODING (INTRONIC) | TGCCAAAGATTAAGGGGAGCCTTTG |
| 400 | NON_CODING (INTRONIC) | CGTCCGATTAGTGCCATGGCTGGCA |
| 401 | NON_CODING (INTRONIC) | CTCATGGGAAGGGAACTCCGTGTCA |
| 402 | NON_CODING (INTRONIC) | AGAGTTATGAAGGAACAGGTTGTCCTTGTCTGGAGTCAAGCTAAAC ACATGATTTGT |
| 403 | NON_CODING (INTRONIC) | GGATAGGAATAAAGCAAGACAGTTA |
| 404 | NON_CODING (INTRONIC) | TAAGATCTGTAACACTGAGGAAGTACCAATAAAGAGCTGCTAACA CT |
| 405 | NON_CODING (INTRONIC) | AGGACAAGAGCCCTAGAGTGGCCTG |
| 406 | NON_CODING (ncTRANSCRIPT) | GCAGATACACGTGGACAAAAGACTT |
| 407 | NON_CODING (ncTRANSCRIPT) | GTAACACAGCAGGAGCTCATGTTTT |
| 408 | NON_CODING (NON_UNIQUE) | ATGCCTACAATTCCTGCTACTTGAG |
| 409 | NON_CODING (NON_UNIQUE) | ATTGGCTTTTAGTTTATCAGTGAATAA |
| 410 | NON_CODING (UTR) | TCTCTGGGGAATTTCATTTGCATCTATGTTTTTAGCTATCTGTGAT AACTTGTTAAATATTAAAAAGATATTTTGCTTCTATTGGAACATTTG TATACTCGCAACTATATTTCTGTA |
| 411 | NON_CODING (UTR) | TCAGAAGTCGCTGTCCTTACTACTTTTGCGGAAGTATGGAAGTCAC AACTACACAGAGATTTCTCAGCCTACAAATTGTGTCTATACATTTCT AAG |
| 412 | NON_CODING (UTR) | CTTACATACCGTGAGAAGTTACGTAACATTTACTCCTTTGTAAATGT TTCCCTATCATCAGACAAA |
| 413 | NON_CODING (UTR) | CACTTCATATGGAGTTAAACTTGGTCAG |
| 414 | NON_CODING (UTR) | TGTACTTTTCAGAATATTATCGTGACACTTTCAACATGTAGGGATAT CAGCGTTTCTCT |
| 415 | NON_CODING (UTR) | CACTGTTGTAGTAAAGAGACATATTTCATGAATGGCATTGATGCTA ATAAATCCTTTGC |

TABLE 6-continued

| SEQ ID NO. | Type | Sequence |
|---|---|---|
| 416 | NON_CODING (UTR) | GGAGCACTACCATCTGTTTTCAACATGAAATGCCACACACATAGAA CTCCAACATCAATTTCATTGCACAGACTGACTGTAGTTAATTTTGTC ACAGAATCTATGGACTGAATCTAATGCTTCCAAAAA |
| 417 | NON_CODING (UTR) | CTGAAATGAGACTTTATTCTGAAAT |
| 418 | NON_CODING (UTR) | TTTTGTACAACAGTGGAATTTTCTGTCATGGATAATGTGCTTGAGTC CCTATAATCTATAGAC |
| 419 | NON_CODING (UTR) | TGTTTTTCCGCAATTGAAGGTTGTATGTAA |
| 420 | NON_CODING (UTR) | CCTTGCATATTACTTGAGCTTAAACTGACAACCTGGATGTAAATAG GAGCCTTTCTACTGG |
| 421 | NON_CODING (UTR) | TTCTCTTCTTTAGGCAATGATTAAGTT |
| 422 | NON_CODING (UTR) | CCACTGGCCTGTAATTGTTTGATATATTTGTTTAAACTCTTTGTATA ATGTCAGAGACTCATGTTTAATACATAGGTGATTTGTACCTCAGAG TATTTTTTAAAGGATTCTTTCCAAGCGAGATTTAATTATAAGGTAGT ACCTAATTTGTTCAATGTATAACATTCTCAGGATTGTAACACTTAA ATGATCAGACAGAATAATATTTTCTAGTTATTATGTGCAAGATGAG TTGCTATTTTTCTGATGCTCATTCTGATACAACTATTTTTCGTGTCAA ATATCTACTGTG |
| 423 | NON_CODING (UTR) | TACAAGCTTATTCACATTTTGCTTCCTAATCTTTTTGTTGTACAGGG ATTCAGGTTTCTTATTCTTACAACATGATTGTTTATATGTGAAGCAC ATCTTGCTGTTGCCTTATTTTTGATGCTTTTATTCATGACAAGAA |
| 424 | NON_CODING (UTR) | ACAGAATCAGGCATGCTGTTAATAAATA |
| 425 | NON_CODING (UTR) | TCTGATTTCATTGTTCGCTTCTGTAATTCTG |
| 426 | NON_CODING (UTR) | CAAGCTGATGATTGTTGCATTTTGGAGTTGCAACAACATTAAAACA |
| 427 | NON_CODING (UTR) | GGCCATGTGCTTTAACGTTACGGTAATACTTTACTTTAGGCATCCCT CCTGTTGCTAGCAGCCTTTTGACCTATCTGCAATGCAGTGTTCTCAG TAGGAAATGTTCATCTGTTACATGGAAAAAATGTTGATGGTGCATT GTAAAATTA |
| 428 | NON_CODING (UTR) | TGCTGGTTTAAGATGATTCAGATTATCCTTGT |
| 429 | NON_CODING (UTR) | TGAATGCGTGACAATAAGATATTCC |
| 430 | NON_CODING (UTR) | TGGCCCAGAAAGTGATTCATTTGTAA |
| 431 | NON_CODING (UTR) | GACAACCCGGGATCGTTTGCAAGTAACTGAATCCATTGCGACATTG TGAAGGCTTAAATGAGTTTAGATGGGAAATAGCGTTGTTATCGCCT TGGGTTTAAATTATTTGATGAGTTCCACTTGTATCATGGCCTACCCG AGGAGAAGAGGAGTTTGTTAACTGGGCCTATGTAGTAGCCTCATTT ACCATCGTTTGTATTACTGACCACATATGCTTGTCACTGGGAAAGA AGCCTGTTTCAGCTGCCTGAACGCAGTTTGGATGTCTTTGAGGACA GACATTGCCCGGAAACTCAGTCTATTTA |
| 432 | NON_CODING (UTR) | GTTAATATTGTCATCGATACAAATAAAGTGAAAT |
| 433 | NON_CODING (UTR) | CAATAACTGTGGTCTATACAGAGTCAATATATTTT |
| 434 | NON_CODING (UTR) | GTCGCCTGCGAGGCCGCTGGCCAGG |
| 435 | NON_CODING (UTR) | CAGGCCTTCTGCAAATCAGTGCTGG |
| 436 | NON_CODING (UTR_ANTISENSE) | TAAGGATGGAATTCAACTTTACCTA |

TABLE 6-continued

| SEQ ID NO. | Type | Sequence |
|---|---|---|
| 437 | NON_CODING (UTR_ANTISENSE) | TACACGTAAACCACAAAAGAGTAGCATTCCATTTTCTTGAAGTGCA CATGATATTATGAACAATACAAATGCATTATTTTTATCATTAATAGT TTAATCATTAATTATCTCATAAGTCAATGCAGAGAGTGAA |
| 438 | NON_CODING (UTR_ANTISENSE) | CTCACTTATTTAACTGGCAACTATCCATTTAGGTTAGGCAAAGGCA CGGTAACATGTTGCGCAGGATGTTTTACTGA |
| 439 | NON_CODING (UTR_ANTISENSE) | CAGGGGTATGGAACATGCTGTCATATTTCATTCATAACACACATGT ACTATAGCTCTAGGCAACAGATGGACAATCGCTTGTTTGAACTACA A |
| 440 | NON_CODING (UTR_ANTISENSE) | CCACATGGTCATCATTAGCCAGCTG |
| 441 | NON_CODING (UTR_ANTISENSE) | CTTTTGGATGTGATAAGCTTTGTAATTGTCTTTTAATGAGCTCTCAT CTTGGAGAGATACATTCT |
| 442 | CODING | GTGATCGCCTACTACGAGACAAAAA |
| 443 | CODING | ATTTATCTTCCACTGAATTGGCAGAAA |
| 444 | NON_CODING (INTRONIC) | GTCAGGTAAACATGTATGTTCAGTCCTTCACTA |
| 445 | NON_CODING (INTRONIC) | GGAACTATGAACTTGCCTATCTAAC |
| 446 | NON_CODING (INTRONIC_ ANTISENSE) | ACATGGAATGACTTAGTTACAGACCAGACATATTGTTACTGGGAAT G |
| 447 | NON_CODING (UTR) | AGAGGAATGTTTGCTACCTTTAGCGGTGAAAAAGAAAGAGAGTC AAGAATTTTGTTGGATTGTGTTTGTGTGTGCATATATTTGATATCAT CATTATATTTGTAATCTTTGGACTTGTAATCATAGCCTGTTTATTCT ACTGTGCCATTAAATATACTTTACCTTA |
| 448 | NON_CODING (UTR) | AAGTAATGAGCACTTTCTACTCAAGC |
| 449 | CODING | CATCCCTAGCACAGATATCTACAAAA |
| 450 | CODING | GTCCATCAGGATTCAAACTGTAATGGCATTTGG |
| 451 | CODING | AGTTTCTTGTCTTCTACAACAATGATCGGAGTAAGGCCTTTAAA |
| 452 | CODING | ACACAAACGTATATCGTATGTTCTCCAAAGAG |
| 453 | CODING | TTGACCTCAAATGCAGTGAGTTCTG |
| 454 | CODING | GGGCGTGATAGTGCACGCCTACAAA |
| 455 | CODING | GTGAGGGAATATGTCCAATTAATTAGTGTGTATGAAAAGAAACTGT TAAACCTAACTGTCCGAATTGACATCATGGAGAAGGATACCATTTC TTACACTG |
| 456 | CODING | TCTAGGACGAGCTATAGAAAAGCTATTGAGAGTATCTAGTTAATCA GTGCAGTAGTTGGAAACCTTGCTGGTGTATGTGATGTGCTTCTGTG CTTTTGAATGACTTTATCATCTAGTCTTTGTCTATTTTTCCTTTGATG TTCAAGTCCTAGTCTATAGGATTGGCAGTTTAA |
| 457 | CODING | TTGCTTTGATCGTTTAAAAGCATCATATGATACACTGTGTGTTT |
| 458 | NON_CODING (INTRONIC) | TATTCAATCTCTGGCACAATGCAGCCTCTGTAGAAAAGATATTAGG |
| 459 | NON_CODING (ncTRANSCRIPT) | ATGCAGCAATGCGTGCTCGACCATTCAAGGTTGAT |
| 460 | CODING | TTCAACTGCAGCTCGGGCGACTTCATCTTCTGCTGCGGGACTTGTG GCTTCCGGTTCTGCTGCACGTTTAAGAAGCGGCGACTGAACCAAAG CACCTGCACCAACTACGACACGCCGCTCTGGCTCAACACCGGCAAG CCCCCCGCCCGCAAGGACGACCCCTTGCACGACCCCACCAAGGAC AAGACCAACCTGATCGTCTACATCATCTGCGGGGTGGTGGCCGTCA TGGTGCTCGTGGGCATCTTCACCAAGCTGG |

TABLE 6-continued

| SEQ ID NO. | Type | Sequence |
|---|---|---|
| 461 | CODING | GGCCTACTGTGAAGCTCACGTGCGGGAAGATCCTCTCATCATTCCA GTGCCTGCATCAGAAAACCCCTTTCGCGAGAAGA |
| 462 | CODING | TCACTGAATTTTAACCGGACCTGGCAAGACTACAAGAGAGGTTTCG GCAGCCTGAATGACGAGGGGGAAGGAGAATTCTGGCTAGGCAATG ACTACCTCCACTTACTAACCCAAAGGGGCTCTGTTCTTAGGGTTGA ATTAGAGGACTGGGCTGGGAATGAAGCTTATGCAGAATATCACTTC CGGGTAGGCTCTGAGGCTGAAGGCTATGCCCTCCAAGTCTCCTCCT ATGAAGGCACTGCGGGTGATGCTCTGATTGAGGGTTCCGTAGAGGA AGGGGCAGAGTACACCTCTCACAACAACATGCAGTTCAGCACCTTT GACAGGGATGCAGACCAGTGGGAAGAGAACTGTGCAGAAGTCTAT GGGGGAGGCTGGTGGTATAATAACTGCCAAGCAGCCAATCTCAAT GGAATCTACTACCCTGGGGGCTCCTATGACCCAAGGAATAACAGTC CTTATGAGATTGAGAATGGAGTGGTCTGGGTTTCCTTTAGAGGGGC AGATTATTCCCTCAGGGCTGTTCGCATGAAAATTA |
| 463 | CODING | CCAGTTCCAGGCCTGGGGAGAATGTGACCTGAACACAGCCCTGAA GACCAGAACTGGAAGTCTGAAGCGAGCCCTGCACAATGCCGAATG CCAGAAGACTGTCACCATCTCCAAGCCCTGTGGCAAACTGACCAAG CCCAAACC |
| 464 | CODING | ATGAGTGCCAAATCTGCTATCAGCAAGGAAATTTTTGCACCTCTTG ATGAAAGGATGCTGGGAGCTGTCCAAGTCAAGAGGAGGACAAAGA AAAAGATTCCTTTCTTGGCAACTGGAGGTCAAGGCGAATATTTAAC TTATATCTGCC |
| 465 | CODING | GGTTCTGCTCCTCGACGGCCTGAACTGCAGGCAGTGTGGCGTGCAG CATGTGAAAAGGTGGTTCCTGCTGCTGGCGCTGCTCAACTCCGTCG TGAACCCCATCATCTACTCCTACAAGGACGAGGACATGTATGGCAC CATGAAGAAGATGATCTGCTGCTTCTCTCAGGAGAACCCAGAGAG GCGTCCCTCTCGCATCCCCTCCACAGTCCTCAGCAGGAGTGACACA GGCAGCCAGTACATAGAGGATA |
| 466 | CODING | TGGTCATCCGCGTGTTCATCGCCTCTTCCTCGGGCTTCGT |
| 467 | CODING | AGGAAGAACAGAGAGCCCGCAAAGACCT |
| 468 | CODING | TGCCACCCAGATGAACAACGCAGTGCCCACCTCTCCTCTGCTCCAG CAGATGGGCCATCCACATTCGTACCCGAACCTGGGCCAGATCTCCA ACCCCTATGAACAGCAGCCACCAGGAAAAGAGCTCAACAAGTACG CCTCCTTA |
| 469 | CODING | ACTGGGGTGACCTTAACCTGGTGCTGCCCTGTCTGGAGTACCACAA CAACACATGGACATGGCTAGACTTTGCCATGGCTGTCAAAAGGGAC AGCCGCAAAGCCCTGGTTG |
| 470 | NON_CODING (INTERGENIC) | TGGCACAGTCAGATGTCGAGAAACTTTGCTATGCCTCCGAAGTCAA TGCCC |
| 471 | NON_CODING (INTERGENIC) | CCTCACAATATGGAAAGACGGGACAACCTATGGAACTATCTGTGAC TTCCATGTACCAAGACAAGGACGCTATAGCTAGGGTAGTGAGACC |
| 472 | NON_CODING (INTRONIC) | CAGTGGATGAATGTCGGAACCTTATGAAATGTGACTCATCTGACCT TTCAGAGATTGGAACTGCCCCACAGTGCTGTTCTGCTAACTCTTCTT CTCTGCCCTCTAAAGTCCCTGCTTCCCTTTCTTTCCTTTTTAGTACCG GGGTGTACATAATCGATCCATCATAATCATCAGTTCATGACATGTT CTCATCATTGATCCATAGCACGGCCTTG |
| 473 | NON_CODING (INTRONIC) | CCTGCAAAGTAAGGTGTATGGGGAAGCAAGTAGATAGT |
| 474 | NON_CODING (INTRONIC) | GCTGATCTCACTGTGATCTTCCTGGTGTT |
| 475 | NON_CODING (INTRONIC) | GACTCGAGAAAAAACAGAGCTCAGACTTGAGACACGGGCTTCCCT CTATAGGGGTCAAAAACCAGGGCGGAGAGAGATAACCA |
| 476 | NON_CODING (INTRONIC) | TTGTACCTGCAGTTTTCGCAGAGTAGATCAAGGACTGCA |
| 477 | NON_CODING (ncTRANSCRIPT) | TTGTCTCTCAGTCGGCTAAGTGCTCTCCCACCAGGTCACCTAAAAC GACCAGCAGAGACACCCAAGAGGCTGAGCTGTGAGGATCACCTGA ACCTGAGCCTGGGAAGTGGAGGTTGCAGTGAGCTGTGATCACACC ACTGTGCTCCAGCCTGGGCAACGGAGTGAAACCCTGTCTCAAGAAA GGACCAGCAGTGACATTTGTTAAATATCGA GGGTGGTTGAACATCCACTATTTATAAGGAAATGTTATTTCCCACA |

TABLE 6-continued

| SEQ ID NO. | Type | Sequence |
|---|---|---|
| | | AATCTCATTCCTCAGAAATCAGTGAAAGACAGACCCTGTCTCGGAT TCTATAAAGCAGTGTGACTGATGTGGCCAAAC |
| 478 | NON_CODING (UTR) | CAGCGTCCTGGGAATGTCATTTCTGCTCCACTCCTTGGACTCGCTGA GCTGTCTCCGCCTCCACCTATCTTCCTACAGACCTCCCTTCTAGTTT TCTGTCAATTCTTTGAGCCAGCAAACTCCATCCAGTACATTCTTTCT TCTTTCATGAAAGAGCTTGAGTTGGATGTAAATATATATGACCTAA CAATTCCACCCCTAGGTGTATACCCTACAGAAATGTGTACATGTGT TCATCCAGAGACATGCTCTAAATCTTCACAAAAACACTCTCCATAA TAACCCCGAACAGGAAAGCACCCCAATGCCCATGTTGGCTGGATA AGCACATTAGGGTATATTCACACGATGGAATCCCAGACTGCAATGG GAATGAGCTGCAACTCCACCCCCAACTTGGAGTGTATTCACCAACC CTAGTGTTAACGAGATAAGGCAAAATGCACCATAGGATTCCATT TATATAAAGTTTAAAACCCAGCAAAATTCATCCATGCGGTTGCAAG TAGAGATCAGTCCTAAGAAGACAGTAACCAGAAGCGGGCATGAGG TGGTGCTTCTGGGGTGTTCTGTTTCTTGATCTGGTTGCCGGTTACCT GGGTGCTTTCCGTTTGTGAACATTCTTGGAGCTGTACACTTTTGATC TGGGCA |
| 479 | NON_CODING (UTR) | TCTGAATTCACCTCTCATCTGACGACTGACAGCTGCT |
| 480 | NON_CODING (UTR) | GCAAGCCGCAGAACGGAGCGATTTCCTCCGAGAAAGTTGAGGATG GAGCCTTTTTTCCGCACCGTCCCCGCGATGGCATGGGCCCCGAGA ATGCTGCCCCGAGGCTCCCAGTGTGGGGGAGCTCGGGGTCGCTGCG CCTCTAGCTTGAGCGCAGAAATCCGCGAATCACTCCGATCTTCGCG AACTCTGGCATCTTCTAGGAAAATCATTACTGCCAAAACTGAGGCG AGCTTTTC |
| 481 | CODING | ACCTGCACTGGCTCCTGCAAATGCAAAGAGT |
| 482 | CODING | CTGCTGCCCCATGAGCTGTGCCAAGTGTGCCCAGGGCTGCATCTGC AAAGGGGCATCAGAGAAGTGCAGCTGC |
| 483 | CODING | TGTGTCTGCAAAGGGACGTTGGAGAACT |
| 484 | CODING | CATGGGCTGAGCCAAGTGTGCCCACGGCTGCATCTGCAAAGGGAC GTCGGAGAAGTGCAGCTG |
| 485 | CODING | GAAAAGCGTGCAAGTATCAGTGATGCTGCCCTGTTAGAC |
| 486 | CODING | TGCAATTTCATCAGCACCAGAAAGTTTGGGAAGTTTTTCAGATGAG TAAAGGACCAG |
| 487 | CODING | CCAGTACAAACCTACCTACGTGGTGTACTACTCCCAGACTCCGTAC GCCTTCACGTCCTCCTCCATGCTGAGGCGCAATACACCGCTTCT |
| 488 | CODING | TGCTAGCAAACACCATCAGATTGTGAAAATGGACCT |
| 489 | CODING | GTATCTGGACTCTCTTAAGGCTATTGTTTTTA |
| 490 | CODING | ACCTTTGAAACTCACAACTCTACGACACCT |
| 491 | CODING | CCCTCCGATGCCTAATAAAGTTCTCTAGCCCACATCTTCTGGAAGC ATTGAAATCCTTAGCACCAGCGG |
| 492 | CODING | ACTGCTCACTTGCATACCCAACAAGAGAATGAA |
| 493 | CODING | GGAAGGACACCACTGGTACCAGCTGCGCCAGGCTCTGAACCAGCG GTTGCTGAAGCAGCGGAAGCAGCGCTCTATACGGATGCTTTCAAT GAGGTGATTGATGACTTTATGACTCGACTGGACCAGCTGCGGGCAG AGAGTGCTTCGGGGAACCAGGTGTCGGACATGGCTCAACT |
| 494 | CODING | TTGCTACATCCTGTTCGAGAAACGCATTGGCTGCCTGCAGCGATCC ATCCCCGAGGACACCGTGACCTTCGTCAGATCCATCGGGTTAATGT TCCAGAACTCACTCTATGCCACCTTCCTCCCCAAGTGGACTCGCCCC GTGCTGCCTTTCTGGAAGCGATACCTGGA |
| 495 | CODING | AGCTGATTGATGAGAAGCTCGAAGATATGGAGGCCCAACTGCAGG CAGCAGGGCCAGATGGCATCCAGGTGTCTGGCTAC |
| 496 | CODING | ACACGCTGACATGGGCCCTGTACCACCTCTCAAAGGACCCTGAGAT CCAGGAGGCCTTGCACGAGGAAGTGGTGGGTGTGGTGCCAGCCGG GCAAGTGCCCCAGCACAAGGACTTTGCCCACATGCCGTTGCTCAAA GCTGTGCTTAAGGAGACTCTGCG |

TABLE 6-continued

| SEQ ID NO. | Type | Sequence |
|---|---|---|
| 497 | CODING | ACAAACTCCCGGATCATAGAAAAGGAAATTGAAGTTGATGGCTTCCTCTTCC |
| 498 | CODING | GAGTGTGGCCCGCATTGTCCTGGTTCCCAATAAGAAA |
| 499 | CODING | GGTGCTGGGCCTACTAATGACTTCATTAACCGAGTCTTCCATACAGAATAGTGAGTGTCCACAACTTTGCGTATGTGAAATTCGTCCCTGGTTTACCCCACAGTCAACTTACAGAGAAGCCACCACTGTTGATTGCAATGACCTCCGCTTAACAAGGATTCCCAGTAACCTCTCTAGTGACACACAAGTGCTTCTCTTACAGAGCAATAACATCGCAAAGACTGTGGATGAGCTGCAGCAGCTTTTCAACTTGACTGAACTAGATTTCTCCCAAAACAACTTTACTAACATTAAGGAGGTCGGGCTGGCAAACCTAACCCAGCTCACAACGCTGCATTTGGAGGAAAATCAGATTACCGAGATGACTGATTACTGTCTACAAGACCTCAGCAACCTTCAAGAACTCTACATCAACCACAACCAAATTAGCACTATTTCTGCTCATGCTTTTGCAGGCTTAAAAAATCTATTAAGGCTCCACCTGAACTCCAACAAATTGAAAGTTATTGATAGTCGCTGGTTTGATTCTACACCCAACCTGGAAATTCTCATGATCGGAGAAAACCCTGTGATTGGAATTCTGGATATGAACTTCAAACCCCTCGCAAATTTGAGAAGCTTAGTTTTGGCAGGAATGTATCTCACTGATATTCCTGGAAATGCTTTGGTGGGTCTGGATAGCCTTGAGAGCCTGTCTTTTTATGATAACAAACTGGTTAAAGTCCCTCAACTTGCCCTGCAAAAAGTTCCAAATTTGAAATTCTTAGACCTCAACAAAAACCCCATTCACAAAATCCAAGAAGGGGACTTCAAAAATATGCTTCGGTTAAAAGAACTGGGAATCAACAATATGGGCGAGCTCGTTTCTGTCGACCGCTATGCCCTGGATAACTTGCCTGAACTCACAAAGCTGGAAGCCACCAATAACCCTAAACTCTCTTACATCCACCGCTTGGCTTTCCGAAGTGTCCCTGCTCTGGAAAGCTTGATGCTGAACAACAATGCCTTGAATGCCATTTACCAAAAGACAGTCGAATCCCTCCCCAATCGCGTGAGATCAGTATCCATAGCAATCCCCTCAGGTGTGACTGTGTGATCCACTGGATTAACTCCAACAAAACCAACATCCGCTTCATGGAGCCCCTGTCCATGTTCTGTGCCATGCCGCCCGAATATAAAGGGCACCAGGTGAAGGAAGTTTTAATCCAGGATTCGAGTGAACAGTGCCTCCCAATGATATCTCACGACAGCTTCCCAAATCGTTTAAACGTGGATATCGGCACGACGGTTTTCCTAGACTGTCGAGCCATGGCTGAGCCAGAACCTGAAATTTACTGGGTCACTCCCATTGGAAATAAGATAACTGTGGAAACCCTTTCAGATAAATACAAGCTAAGTAGCGAAGGTACCTTGGAAATATCTAACATACAAATTGAAGACTCAGGAAGATACACATGTGTTGCCCAGAATGTCCAAGGGGCAGACACTCGGGTGGCAACAATTAAGGTTAATGGGACCCTTCTGGATGGTACCCAGGTGCTAAAAATATACGTCAAGCAGACAGAATCCCATTCCATCTTAGTGTCCTGGAAAGTTAATTCCAATGTCATGACGTCAAACTTAAAATGGTCGTCTGCCACCATGAAGATTGATAACCCTCACATAACATATACTGCCAGGGTCCCAGTCGATGTCCATGAATA |
| 500 | CODING | AGGACCAACTTCTCAGCCGAATAGCTCCAAGCAAACTGTCCTGTCTTGGCAAGCTGCAATCGATGCTGCTAGACAGGCCAAGGCTGCC |
| 501 | CODING | TCTCCCAAAGAAAACGTCAGCAATACGCCAAGAGCAAA |
| 502 | CODING | AACAGCCGACCTGCCCGCGCCCTTTTCTGTTTATCACTCAATAACCCCATCCGAAGAGCCTGCATTAGTATAGTGGAA |
| 503 | CODING | GGCCTTAGCTATTTACATCCCATTC |
| 504 | CODING | GCGGGAACCACTCAAGCGGCAAATCTGGAGGCTTTGATGTCAAAGCCCTCCGTGCCTTTCGAGTGTTGCGACCACTTCGACTAGTGTCAGGAGTGC |
| 505 | CODING | TCAGGGAATGGACGCCAGTGTACTGCCAATGGCACGGAATGTAGGAGTGGCTGGGTTGGCCCGAACGGAGGCATCACCAACTTTGATAACTTTGCCTTTGCCATGCTTACTGTGTTTCAGTGCATCACC |
| 506 | CODING | TGATGCTATGGGATTTGAATTGCCCTGGGTGTATTTTGTCAGTCTCGTCATCTTTGGGTCATTTTTCGTACTAAATCTTGTACTTGGTGTATTGAGCGG |
| 507 | CODING | GTGTATTTTGTTAGTCTGATCATCCTTGGCTCATTTTTCGTCCTTAACCTG |
| 508 | CODING | ACAGTGGCCGACTTGCTTAAAGAGGATAAGAAGAAAAAGAAGTTTTGCTGCTTTCGGCAACGCAGGGCTAAAGATCA |
| 509 | CODING | TGGCGTCGCTGGAACCGATTCAATCGCAGAAGATGTAGGGCCGCCGTGAAGTCTGTCACGTTTTACTGGCTGGTTATCGTCCTGGTGTTTCTGA |

TABLE 6-continued

| SEQ ID NO. | Type | Sequence |
|---|---|---|
| 510 | CODING | TTGGCTCTGTTCACCTGCGAGATGCTGGTAAAAATGTACAGCTTGG GCCTCCAAGCATATTTCGTCTCTCTTTTCAACCGGTTTGATTGCTTC GTGGTGTGTGGTGGAATCACTGAGACGATCTTGGTGGAACTGGAAA TCATGTCTCCCCTGGGGATCTCTGTGTTTCGGTGTGTGCGCCTCTTA AGAATCT |
| 511 | CODING | GTGGCATCCTTATTAAACTCCATGAAGTCCATCGCTTCGCTGTTGCT TCTGCTTTTTCTCTTCATTATCATCTTTTCCTTGCTTGGGATGCAGCT GTTTGGCGGCAAGTTTAATTTTGATGAAACGCAAACCAAGCGGAGC ACCTTT |
| 512 | CODING | GCGAAGACTGGAATGCTGTGATGTACGATGGCATCATGGCTTACGG GGGCCCATCCTCTTCAGGAATGATC |
| 513 | CODING | ATATTCTACTGAATGTCTTCTTGGCCATCGCTGTA |
| 514 | CODING | GGCTGATGCTGAAAGTCTGAACACT |
| 515 | CODING | CAGAAGTCAACCAGATAGCCAACAGTGAC |
| 516 | CODING | CCCGTCCTCGAAGGATCTCGGAGTTGAACATGAAGGAAAAAATTG CCCCCATCCCTGAAGGGAGCGCTTTCTTCATTCTTAGCAA |
| 517 | CODING | ATCCGCGTAGGCTGCCACAAGCTCATCAACCACCACATCTTCACCA ACCTCATCCTTGTCTTCATCATGCTGAGCAGCGCTGCCCTGGCCGCA GAGGACCCCATCCGCAGCCACTCCTTCCGGAACACG |
| 518 | CODING | GGGTTACTTTGACTATGCCTTCACAGCCATCTTTACTGTTGAGATCC TGTTGAAG |
| 519 | CODING | TTGGAGCTTTCCTCCACAAAGGGGCCTTCTGCA |
| 520 | CODING | AGATTCTGAGGGTCTTAAGGGTCCTGCGTCCCCTCAGGGCCATCA |
| 521 | CODING | CACGTGGTCCAGTGCGTCTTCGTGGCCATCCGGACCATCGGCAACA TCATGATCGTCACCACCCTCCTG |
| 522 | CODING | GGGAAGTTCTATCGCTGTACGGATGAAGCCAAAA |
| 523 | CODING | TTGACAGTCCTGTGGTCCGTGAACGGATCTGGCAAAACAGTGATTT CAACTTCGACAACGTCCTCTCTGCTATGATGGCGCTCTTCACAGTCT C |
| 524 | CODING | TGGAGAGAACATCGGCCCAATCTACAACCACCGCGTGGAGATCTCC ATCTTCTTCATCATCTACATCATCATTGTAGCTTTCTTCATGATGAA CATCTTTGTGGGCTTTGTCATCGTTACATTTC |
| 525 | CODING | CAGTGTGTTGAATACGCCTTGAAAGCACGTCCCTTGCGGAGATACA TCCCCAAAAACCCCTACCAGTACAAGTTCTGGTACGTGGTGAACTC TTCGCC |
| 526 | CODING | CACTACGAGCAGTCCAAGATGTTCAATGATGCCATGGACATTCTGA ACATGGTCTTCACCGGGGTGTTCACCGTCGAGATGGTTTTGAAAGT C |
| 527 | CODING | GGAACACGTTTGACTCCCTCATCGTAATCGGCAGCATTATAGACGT GGCCCTCAG |
| 528 | CODING | CTATTTCACTGATGCATGGAACACTTTTGATGCCTTAATTGTTGTTG GTAGCGTCGTTGATATTGCTATAACTGAA |
| 529 | CODING | GTCCCTGTCCCAACTGCTACACCTGGG |
| 530 | CODING | AAGAGAGCAATAGAATCTCCATCACCTTTTTCCGTCTTTTCCGAGTG ATGCGATTGGTGAAGCTTCTCAGCAGGGGGGAAGGCATCCGGACA TTGCTGTGGA |
| 531 | CODING | GCGCTCCCGTATGTGGCCCTCCTCATAGCCATGCTGTTCT |
| 532 | CODING | GTTGCCATGAGAGATAACAACCAGATCAATAGGAACAATAACTTC CAGACGTTTCCCCAGGCGGTGCTGCT |
| 533 | CODING | TGAGTCAGATTACAACCCCGGGGAGGAGTATACATGTGGGAGCAA CTTTTGCCATTGTCTATTTCATCAGTTTTTACATGCTCTGTGCATT |

TABLE 6-continued

| SEQ ID NO. | Type | Sequence |
|---|---|---|
| 534 | CODING | ATCATCAATCTGTTTGTGGCTGTCATCATGGATAATTTCGACTATCTGACCCGGGACTGGTCTATTTTGGGGCCTCACCATTTAGATGAATTCA |
| 535 | CODING | AACACCTTGATGTGGTCACTCTGCTTCGACGCATCCAGCCTCCCCTGGGGTTTGGGAAGTTATGTCCACACAGGGTAGCGTGCA |
| 536 | CODING | CATGTTTAATGCAACCCTGTTTGCTTTGGTTCGAACGGCTCTTAAGATCAAGACCGAAG |
| 537 | CODING | ATTACTTGACCAAGTTGTCCCTCCAGCT |
| 538 | CODING | CGTGGGAAGTTCTATGCCACTTTCCTGATACAGGACTACTTTAGGAAATTCAAGAAACGGAAAGAACAAGGACTGGTGGGAAAGTACCCTGCGAAGAACACCACAATTGCCCTA |
| 539 | CODING | TGCTTGAACGGATGCTTTAGAATTTTCTGCCTGAGCTACGGCACCAAGCTGGTTAGTCGGAAGGCGTTTGTGGCTAAGGCCTTGAAA |
| 540 | CODING | GCGGGATTAAGGACACTGCATGACATTGGGCCAGAAATCCGGCGTGCTATATCGTGTGATTTGCAA |
| 541 | CODING | TGGTGCCCTGCTTGGAAACCATGTCAATCATGTTAATAGTGATAGGAGAGATTCCCTTCAGCAGACCAATACCACCCACCGTCCCCTGCATGTCCAAAGGCCTTCAATTCCACCTGCAAGTGATACTGAGAAACCGCTGTTTCCTCCAGCAGGAAATTCGGTGTGTCATAACCATCATAACCATAATTCCATAGGAAAGCAAGTTCCCACCTCAACAAATGCCAATCTCAATAATGCCAATATGTCCAAAGCTGCCCATG |
| 542 | CODING | GCTCCCAACTATTTGCCGGGAAGACCCAGAGATACATGGCTATTTCAGGGACCCCCACTGCTTGGGGGAGCAGGAGTATTTCAGTAGTGAGGAATGCTACGAGGATGACAGCTCGCCC |
| 543 | CODING | GGCTACTACAGCAGATACCCAGGCAGAAACATCGACTCTGAGAGGCCCCGAGGCTACCATCATCCCCAAGGATTCTTGGAGGACGATGACTCGCCCGTTTGCTATGATTCACGGAGATCTC |
| 544 | CODING | ATCCGAAGGCTTGGGACGCTATGCAAGGGACCCAAAATTTGTGTCAGCAACAAAACACGAAATCGCTGATGCCTGTGACCTCACCATCGACGAGATGGAGAGTGCAGCCAGCACCCTGCTTAATGGGAACGTGCGTCCCCGAGCCAACGGGATGTGGGCCCCCTCTCACACCGGCAGGACTATGAGCTACA |
| 545 | CODING | GATGTGGTCCATGTGATGCTCAATGGATCCCGCAGTAAAATCTTTGAC |
| 546 | CODING | TGGGAGTGTGGAAGTCCATAATTTGCAACCAGAGAAGGTTCAGACACTAGAGGCCTGGGTGATACATGGTGGAAG |
| 547 | CODING | CCTGAGGATTCATCTTGCACATCTGAGATC |
| 548 | CODING | GGTGCTGGACAAGTGTCAAGAGGTCATC |
| 549 | CODING | AGAAGGTTCTGGACAAGTGTCAAGAGGTCATC |
| 550 | CODING | TTAGTTGAAAAATGGAGAGATCAGCTTAGTAAAAGA |
| 551 | CODING | GTCACAACGGTGGTGGATGTAAAAGAGATCTTCAAGTCCTCATCACCCATCCCTCGAACTCAAGTCCCGCTCATTACAAATTCTTCTTGCCAGTGTCCACACATCCTGCCCCATCAAGATGTTCTCATCATGTGTTACGAGTGGCGCTCA |
| 552 | CODING | CGGTGCAAGTGTAAAAGGTGAAGCCAACTTTGGCAACGTATCTCAGCAAAAAC |
| 553 | CODING | CAGGAAAGGCCTCTTGATGTTGACTGTAAACGCCTAAGCCC |
| 554 | CODING | ATGTTAAGTGGATAGACATCACACCAG |
| 555 | CODING | GCGCATCCCTATGTGCCGGCACATGCCCTGGAACATCACGCGGATGCCCAACCACCTGCACCACAGCACGCAGGAGAACGCCATCCTGGCCATCGAGCAGTACGAGGAGCTGGTGGACGTGAACTGCAGCGCCGTGCTGCGCTTCTTCCTCTGTGCCATGTACGCGCCCATTTGCACCCTGGAGTTCCTGCACGACCCTATCAAG |
| 556 | CODING | ATGGTTTGGGCCACTTCCAATCGGATAG |

TABLE 6-continued

| SEQ ID NO. | Type | Sequence |
|---|---|---|
| 557 | CODING | GGATTGGAGAAGCACCATATAAAGTAGGGGTACCATGTTCATCTTG<br>TCCTCCAAGTTATGGGGGATCTTGTACTGACAATCTGTGTTTTCCAG<br>GAGTTACGTCAA |
| 558 | CODING | ACTTGGAGGTGGACCATTTCATGCACTGCAACATCTCCAGTCACAG<br>TGCGGATCTCCCCGTGAACGATGACTGGTCCCACCCGGGGATCCTC<br>TATGTCATCCCTGCAGTTTATGGGGTTATCATTCTGATAGGCCTCAT<br>TGGCAACATCACTTTGATCAAGATCTTCTGTACAGTCAAGTCCATG<br>CGAAACGTTCCAAACCTGTTCATTTCCAGTCTGGCTTTGGGAGACC<br>TGCTCCTCCTAATAACGTGTG |
| 559 | CODING | ATCCCGGAAGCGACTTGCCAAGACAGTGCTGGTGTTTGTGGGCCTG<br>TTCGCCTTCTGCTGGCTCCCCAATCATGTCATCTACCTGTACCGCTC<br>CTACCACTACTCTGAGGTGGACACCTCCATGCTCCACTTTGTCACCA<br>GCATCTGTGCCCGCCTCCTGGCCTTCACCAACTCCTGCGTGAACCCC<br>TTTGCCCTCTACCTGCTGAGCAAGAGTTTCAGGAAACAGTTCAACA<br>CTCAGCTGCTCTGTTGCCAGCCTGGCCTGATCATCCGGTCTCACAGC<br>ACTGGAAGGAGTACAACCTGCATGACCTCCCTCAAGAGTACCAACC<br>CCTCCGTGGCCACCTTTAGCCTCATCAATGG |
| 560 | NON_CODING<br>(INTERGENIC) | TAGTCTTGGCTCGACATGAGGATGGGGGTTTGGGACCAGTTCTGAG<br>TGAGAATCAGACTTGCCCCAAGTTGCCATTAGCTCCCCCTGCAGAA<br>TGTCTTCAGAATCGGGGCCCG |
| 561 | NON_CODING<br>(INTRONIC) | GAGCTTACCTTGAACCTTTGAATTGGGCCAAATTGCGATGACCACT<br>GCATCCTGGAAAATTTTATTTCACCAGCACTACAACTCCTCAACAG<br>CACCAACCAATAAACTATGGATTTTTGTACTAAGCCAGTTGCCTCTT<br>TCAAAACAACTTGTCAACTTGTCTAATCACCCTCAGCTTTTTTAAA<br>AACCCCTCCTCTACCCTCTCTCTTCAGAACACAAGTGGCTTCTAGCT<br>GAATCT |
| 562 | NON_CODING<br>(INTRONIC) | GATGCTTGACATCCCTAACTAGACAGATGAGGGTTGAAGTTAGTTT<br>TTGGTGGGGTTGGAGGTGAACATCAACTACCTTCCTAGTTCCAGGT<br>AATATAGAACATGGAGTGAAGTGTAGATAAATGGGTCTGGTGGGT<br>CCCGAGGTCATCTTATCACATAATGACTAATTTACATTATGGAACC<br>CAGTACAAAGTGTTCCAGTTAG |
| 563 | NON_CODING<br>(INTRONIC) | TAAAGCCACAAGTCACCCTTTGCTGAAGTCAGTATTAGTAGTTGGA<br>AGCAGTGTGTTATTCTTGACCCCATGAAGTGGCACTTATTAAGTAG<br>CTTGCTTTTCCATAATTATGGCCTAGCTTTTTAAAACCTACTATGAA<br>CACCACAAGCATAGAGTTTTCCAAAAG |
| 564 | NON_CODING<br>(INTRONIC) | TGGAGAACAACATTGGGGCCCTTGACTTTAGATTTCAGTGGGGACC<br>TACAAAAAGGAAAAATGGAAAGGGAATTCTGAAGTCTTAAGGTGG<br>GCTATCTGAAAGTTGGATCCCTGGGTGAAAAAGATTTTATAATATT<br>AGATGAGTTGAGAGAACCAATGTGAATTAAAGCTGACTGGCTTAA<br>AAAAAATAAACCCATCAAAATTAGTAAGGGAATAATGTTATTCATT<br>GCCTTTTTTCGTTGAGTTATGAAAGCTCTTCGAAGATGAAGGTTTT<br>ATGAAACTCAAGATCTCTCCAGAGGCCGGGCACAGTGGCTCACGCC<br>TGTAATTCCAGCACTTTGGGAGGCTGAGGTGAGCAGATTGCGAGTC<br>CAGAAGTGA |
| 565 | NON_CODING<br>(INTRONIC) | TGTGCAGCCGAAGAATGAGTGTAACATGATCCTTGCAACAGAAGA<br>AAAGGACACGGAGAGGTCATTTGGTAGGAGGCTCCACTGTGAGAT<br>GACCACCGATGATTACTTCTGCCGAAAACCTAGCAGTCACAGCA |
| 566 | NON_CODING<br>(INTRONIC) | TTTGGGATTGGTTTAGAGGCAGCTGAACGAAACTTATTTTTCATCTG<br>TAGTAAATACCTTTCATTTAATGTGAATGGTAAAATCAAAGGGCAG<br>ACGCTG |
| 567 | NON_CODING<br>(INTRONIC) | CTTGCCTGTGGCACCAGATGCCTTACAGTGGCCAGGAATGCTGCGG<br>GACAGTCTACTTTGATTGCTTTCTTTCCTCCATGGCTGAGATCTGAG<br>TGTAGTGTTAACTGGGCTTAAAAATCAAGTCCGTTGTATCTGCATG<br>GTCACGTAGTTCGGCATCTCATGGCTTTTGCACCTAGA |
| 568 | NON_CODING<br>(INTRONIC) | TGAATGACCATACAAGGACTCCATGGTATATTCTTGTAGATCATTA<br>GTTAATTATCAACAATTGGCTAATGATTAATGTTTGCCTGAGAGGC<br>TGACTTTTTGTCCATTAGTAATGACATCCCAGGAAACACCTGGCAG<br>AGTTCGTCTTTAATTTC |
| 569 | NON_CODING<br>(INTRONIC) | AGAGAGCCTCAAAATGACCAGAGTAGATGGACTCGTGTAGTAAAA<br>CTTTACCCAAAGTTGGTTTCCTAATGATATAATGTGAAACAGTCTAT<br>GTGCTATACAAATAATTATATCTCTTTTGTTAAGCCTTACGTCATTT<br>TGACAAAGGCTTTACTTGATTGAGTATTGACGGCTTTTCCA |

TABLE 6-continued

| SEQ ID NO. | Type | Sequence |
|---|---|---|
| 570 | NON_CODING (INTRONIC) | TTGGGGAAGAAGAATATCCAATCCG |
| 571 | NON_CODING (INTRONIC) | AGTGCAATGTGTCATGGGCTCTGAAGGTCTTACGTTGAGGAATGGC<br>AATATTATCAGAATTACGTGTCCAGCTTCCCAAGCTTACTACTTTGA |
| 572 | NON_CODING (INTRONIC) | CCCATTTTGAGGGACTGCCAAGCTGCTTGCCAAAGCAGCTGCGCCA<br>TTTTACATTACCACCAGCAACATGTGGAGGTTCCAATTTCTGTACGT<br>CTTTGCTAACACTTGTTATTGTCTATCTTTTTAATTATAGCCATCATA<br>GTGCATATGAAGTGGTATCTCATTGTAGTTTTGATTTGCATTTCTCT<br>GATGACTAATAATAGTGAGCATCTTTTCATGTGCTTATTAGCCGTTT<br>GTATCAAATCCTTTGCTCATTTTTAAATTGAATTTTTAAAATTATTG<br>GTTTGTGGCAGGGCATGGTGGCTCATGCCTGTAATCCCAGCACTTT<br>GGGAGGCCAAGGCGGGTCGGTCACCTGAGGCCAGGAGTTCGAGAC<br>CAGCCTGGCCAGCATGGTGAAACCCTGTCTCTACTAAAAATACAAA<br>AAATAGTCAGACATGGTCACAGGCA |
| 573 | NON_CODING (INTRONIC) | TCTGGACTTTCACCTTGGGACATTCTCAGTTTCCACCCCACTGTTTC<br>TGAGGGTCGAAAGGTTTGGGTGTATATGTAGGGAAAGATAATTGGT<br>AGGCTCTGAAGCACACAGTTCATTTGTTTTTCAATAAGGAAGAGTC<br>ATGTTAGAAATTTTGTCCTTTCTTCCAGAAGGTACACTATATAGCCT<br>GGAGCCACA |
| 574 | NON_CODING (INTRONIC) | TCCAAAGACAAGCTTAATGACTGCTGTGCCAACACACAAAACTACA<br>AGATACATTTAAGCA |
| 575 | NON_CODING (INTRONIC) | GTACCTCTCCAGATTAGACAAGATGATATTAAATATTTCCATCTTAC<br>AGATGAGCAAATTCAGACTTAGAGACGATAAGGTACTAGCCCCCT<br>GGAAAACAACTGCACTGAACCTAGGTCCTTTATTTCTGAACAAGAC<br>AGGCATCGTGTTGAACTTCATG |
| 576 | NON_CODING (INTRONIC) | TAGCCATTCTGCACTCTTCAGGAGAGAAGAACAACCTGGGGCCATG<br>TGTTCAATAAAGAGATGGGGCTGGCACATTGTTGAGGAGGAGAAG<br>GAGGATTTCAAATGGAGGGCTTTTTGAAGAAGGCATTGAACACCTC<br>CCCACCCACCCCTGCCCTGCACTTCTCCCTGTAGCTCAGAAACCTTT<br>TAATAGCCATGGGACCAACATCTAGCAGCTGGCTTGGTTTTGCTGG<br>TCCTTGCTTTAAAATGGGGATACATATCCCTGCTTTACAGACCTGCT<br>GTGG |
| 577 | NON_CODING (INTRONIC) | AGTTACGATTAATGTGAGCAGCTTCTCTCATTCCAGAAATGTGACC<br>TCTGGTTACAGCAAATGTGACAACATGAATTACCTTCAAT |
| 578 | NON_CODING (INTRONIC) | GAAGCAACCCATATATCCCTCAACGGGCGAATGGATAAACTCATTG<br>TGATGTATTTGTGTAATGGGATATTACAGAACAACAAAAGAAATG<br>AACTGCTGATAAAACAACGTGGATGAGTGTCAGAAACATTATG |
| 579 | NON_CODING (INTRONIC) | GTGGGTTTCAGAATCACTGGTGCTTTGAG |
| 580 | NON_CODING (INTRONIC) | AAGTACCCTGGGGAGAGAGTTTATGGAGTGTTCTTTGCTTGGATAA |
| 581 | NON_CODING (INTRONIC) | GGTGGGTCCAATATGTAGAAAGGCACACTTAGAACAGGACTATTTG<br>GATGTGTGGGAAGTGGGATCATTAAGTTCTGGTGAAAGAAACCT<br>ATGGTAGAGTTCTTTGATAAA |
| 582 | NON_CODING (INTRONIC) | GCAGGAGTTTTGTCCTCTACCAAGACCTTTCCTGAAAATCACTTATC<br>AAGACAGTTTCCTGTAAGAAAAAGCCATATCCCAGCTGATTTTCCT<br>TCCTGGGGCCAAAATCTGCTATTATTCGGCCTGAAAGCCTTGATGA<br>CTCTGTGTGTGTGTGTGTGTGTGTGTGTGTGTGTGTGTGTGTG<br>TGTGTGTGTGTGTGTATGGATGCTTGTGTGTGTATGGGGAAT<br>ATGTGATTAATGTGTGTTGGCTGCTGTTGTCTCTGATTTGGCTA |
| 583 | NON_CODING (INTRONIC) | TCCTGAGGACAGTTGCCAAGACCACACAAGCTTTGCTGGATGAGGG<br>CCGCCAAGAGGGGTTGCCAGACATTTTATGTGTCCTCTGAGATGCT<br>TTCTTTTCTGCTGAGGCTTCCCAAATCAAGCTGTTTCCTGGAACCTC<br>ACCAGGCTTCATGAAGGAGAACTATAGAACGATTATTGACCAGAA<br>ATTAATCAGCATTGTTGCTTGAGATTTAAACAATTTCCATAGCATGC<br>CCTTTTTTTGTCTGTTCTAAAGTGAGATACATTTATAATTGCTTTATT<br>TGTCTGGATCCAAATATAATGCAGATTAATTGTTATAAAACGATAG<br>CAAAATGAGCTGGATTGGGTGGCTTTTGGTAGTCCCCATTTGTAG<br>ATTTCAGCCGCTGAGCTTGTCCTTATT |
| 584 | NON_CODING (INTRONIC) | CTCCTAGTAAACCTCAGTGGCCTTAGGCTAGGGTTGGACATGTGAG<br>GGTGGTGTCTATTCCTGGAGAAATAACATCGCATTTGATTTTGCCA<br>CAGGAGCTTTCTATACAAGGTTAACAGCAATCCTGTTGTGAATTCC |

TABLE 6-continued

| SEQ ID NO. | Type | Sequence |
|---|---|---|
| | | TTGGCGCCTCATGTCTCCTAAACCCAGCTAAACTGACGGAGGCCAT G |
| 585 | NON_CODING (INTRONIC) | CTGAGATCCTGTAGAGTGCCCGGCTCTGGTCCAGAGGCGAGGGGTG CCAGGATGTCTCAGACACAGACAGCGGCCTTGTGCTTAGGCGTTCA TTATCTCATGGGGTAGCCCATTTTGAAGCAGTGCAGAAGGGCACAT ATTCAGTAGAGGTGCAGACCCAGAGGCTCTGTGAGCTGCACTAGA GAGATGAGGAGGCATCTCCCCCGGCGACTGACGATGGGCTGGCAT GCCTCCACCTCCGCCCCTCCGCCCCCTCGCCCTCCCAACCACCACCT TCCCTCTCTGCCTGCTACTCCCCTCTTACTTTCCCATTGATATTTTG TTGTTGTTTAAGCAAATTATTATTTTTTTAAATTTTAGCCTCAA GAGTCTTCATAATTTTTTAAGGGAACACTAGAGGTACTGC |
| 586 | NON_CODING (INTRONIC) | GGTGCAGGGTACTCTTTGGAAATTCTGGAGTGTAGCATTTTCTGGA TTTCCCAGCAGGTGGCCACACTTTACACACACATCAACGTTGTACT CAATGTCACCCAAGAGGTGGCTCTGGAGAATGTGGAAGCACTGTGT CAGCTGCAAAGTATTACGC |
| 587 | NON_CODING (INTRONIC) | TGTGCTGAGTTGACTTCTCTGTCCGCAGTTCCCCCTCCACCTGTGCT CTGGGTTGTTGATGTGCAGGTTAGAAGAGGGAGGTTGTTGAGGGTA TTAGTGTTGCAGGGGAGGCTGTT |
| 588 | NON_CODING (INTRONIC) | GCACCGTGTAGGCACTGCAGTGACAGTGTGGAATGAAATGGTTTCT TTCTTCGTGAAGCTTATATCTAATGATGGAGGCCAAAATGACAATT ACAAACTCGTATAAATGCTTTGAAAGAAAGGTTCATGTGCTGTGAG AGGGTTTAACAGGCACAACTGCTGTCAGTTTATTGGGTAGGAGCAT CCTGGAAGTGAAGAATGAGTAGTCCACATATCCAGGCAAGGTGGG ACAAGAAGCTAGGGCAAGGGTATTCTAGTCAAGGGAAAACCCACA GAAAGGAGGTACAGTAGGAAGGAGCAGAGGATGCTGGAGGAACT GAATGAAGCTAGGGTGACAGGAACTGGGAGAGCTGGAGATGAAGT CAGATGAAAGGAAAGAGACTGGCCGGCAGAATCCAGGTCACGTAG GACCTTTAGACTATGTC |
| 589 | NON_CODING (INTRONIC) | GAAAAGGTAGCAGGTGTTAATTATGGAATCTAGGTGAGGTAGGCA TATGGGTGTTC |
| 590 | NON_CODING (INTRONIC) | TGGTAGACTGAGAACTTAAGGATGCATATGATAATCTCCAGAGTAA TGACTTAAAAGGGGTACTAAAAAGCTAAAGAAGAGATAAAATGG AATATTAAATAGTACTAAATTATCCAAAATAAGTCAGAAAAGGAA GAAAAAGGAACAAAGAACATATAGTACCAACAACGAGATGGTAGA CAAACCCAGTAATATC |
| 591 | NON_CODING (INTRONIC) | CGTGGAACATTCACCGACATAGACCATATCTTGGCCATGAAAGTCT CATTACCTCTCGATTGAAATTTTACAAAGTATCTTTGTTCTAATGGC AGTAGATTTAAAACAGAAGCCAATAACAGGCTGTTTATAAACCTTC CCAAATGTTTGGAAATTAAATAACCTATAACTCAAAAAATAATAAA AATTAGAAAATACTTTGAAACTGATAAAATCCAACTGGGAAATTGT ATGATCCGTTGAATGCAGTGCTTGGAGGGACATTTATAGCTATATC |
| 592 | NON_CODING (INTRONIC) | ATGGCAGAGACTCAGGCTGTTTTGCCAAAACCCAGGTCGCTTTCCC CAGCTGTGCAGGCTCGTATTCTGCTGAAGCTGCTGTTGGTTATTCCT GGGACCCTGG |
| 593 | NON_CODING (INTRONIC) | CAGATGGGGTGTCACGGGGCCCTGACAAGGAAGGTCCACATGAGG GGAGATGATTACACTGGTGTGCTAGACCCAGGGGA |
| 594 | NON_CODING (INTRONIC) | TTCCTGCATGCCTATATGAAGTGGCGCCAAGGGGAAATAGAGACAT GGGAAGAAATACATGAGAAATGGACAGACAACATTGTCCGTTCCT GCCTGCAAGG |
| 595 | NON_CODING (INTRONIC) | CACGTCCCATATGGTGGATATAGGAACTGCATATGTGTGCAAGTGT AGTTTTGCATCTGCACGTGAATCTATGAATATCTAGATTTTCTAACC CACTTAAGGGCTGCATATG |
| 596 | NON_CODING (INTRONIC) | GGCCATGTTTGGAAAGCTACCTAGTGAAGAGTCCTTCCCCAGTCTG GTGTCCTCTAGGGGTGTCCAGCATAGCGTAGCCCACTTGCGTTCCA GCTCCACCAGTTCCCTTCATGTTGAAACCTCCTCCATCCCTTGTAGG GGAGATGGGGATGGAGTCTAATCGCTCTCTCTTCATCCGTGTACTG TTCCCTCGTCAACCCAGAAAGAACCCACTGTTCAGCCACAGCAGCC TGAGTGGGCTTTTCTAGTGACCCCACTCTGTATGGCCGCTCGAGAT CTAAAGGGCATTAGCTGGTATAGGCCACCTGTTAACTACTCGGGCC AGCTTTA |
| 597 | NON_CODING (INTRONIC) | GTGCTGTGTGGACGCAGTTTTCCGAGCTCTGTGTTGTTAGCATGTAA CTCT |

TABLE 6-continued

| SEQ ID NO. | Type | Sequence |
|---|---|---|
| 598 | NON_CODING (INTRONIC) | TGCATGTTCTACTTTCCATTGGGTTTGACCTCTCCATGATAACCC |
| 599 | NON_CODING (INTRONIC) | TAAGAGCCATGCCAAGGACTTCTCTCTTTGTCT |
| 600 | NON_CODING (INTRONIC) | GTAGACGTGTTGGTCACATGTGATGAG |
| 601 | NON_CODING (INTRONIC) | GGCAGACTGCGTGCTAATGGAAAGTGGAGCATGGCCGTCGCAGTGTGAGCGCAGAAGTGCGGACCTAGGC |
| 602 | NON_CODING (INTRONIC) | GAGTTCCTTTTGTATGCCAGTCCGCCATGACCTCCTGAGCGTCCGCCCTGCTCTCTGCAGAGACCCAGTCCAGAATACAGTGAGAAGTGGACAGGCCAGGAAGCTCAGATACACCCATTGAAACTAACACATACACCCGCATGCCAAAACCAATCCAGGCAACACCTCAGGTTCCATCTTAACGTGTCCACAGGAAACACCACCACACCCAAACCTCATCTAACATTGTCCGTCTTTAATTCGTGCTCAGAGCCAGTCTGGGGATGCCTCTTTGGAAGCAGTGTGGTCTAGTTTCAAGGACACTGGGAGTCAGGGAACCTGGGTTCTAGTCCCAGTTTCAGCATTCACTTGCTGCGTGACCTTGGGCAAGACACTTAACCTCTCTGTGCCTCAGTTTCCCCCATCTGTAAAATGGGGTTAATAATGTCGACCTACCTCACAGGGCTGTTGTGAGGAATAGCTAAGTGATTGTAAAGCACTTTGAACGTATAATTGCTTATTAAGACTACAACAATAATAATATCATATGCCTGTTTACTACCAGAACTTTAAGAAATTCTTGTTTTCCTTTGATCTCTTTTCTGTTCTGTACCATACTTACCCATTGAGAAGGAAAATTCCCCCCTTTTAAAGAAATCTAGGCAATGCACAAAGATGTCAACAGAGGTAACCCTGCAGGTTGCATTTTCACATCTTAAGAATAGCAGATTTTTGCCCAAGATGTTGGTCGATAAGGGTGTCTGATCTTGAATTCTCAGCTGATTCCAAGTGGTGGTTGGAGTCTGTACATCTGATGCTGAGCCCAAGACACCCAAAGTG |
| 603 | NON_CODING (INTRONIC) | TCATAGGCCCTTGAGACCGTGTGGATATAGTGAACCCAACTCTTGGTAGACTTG |
| 604 | NON_CODING (INTRONIC) | TTCTGGACTTAACACTCCTCAGCTGTAAAATGAGGTAGGAAATCTGATGTGATTTCTAGTTGGGGACATTCTAGAAGATTCCATATTGTATCTCAAATGACTGTTCAGAGACACAGTCTTTAGGTGCTCACTCTAGAGAGGACTGTGATAAGC |
| 605 | NON_CODING (INTRONIC) | ACAGAAGTGGTGTGCAGATCGTTTCAGATCAATTTATCATAAAATCTAAGTTGATAGGTGTTCTCTTAATGATGTTCTTATACTGCCTGTTCACCTTGACCCTTTAGCTTTGAGTAGATTAGAGAGTGTAGGGGAAAGATCTTTTTTCCCTTCAAATACTCAAAGGATCATGTGTTCTCTTGAGCAGTTCTGCAAATCCATATAGGA |
| 606 | NON_CODING (INTRONIC) | TTCATGAACTGTCGGCCTTCCTGTGTAAGTGGGTCAGGCACCATGTGACCTGCTCACTGCCAGTTTCTTCTTTGAATAGATGTTTATTTCATGGATCATTTTGAAGATTCTCCGTGGGTGTGCAACATGGTTTTTAGAATGTTGGGTAATTTCTCATGTGTTCTTTGAGATGGATGGCTTCTCAGTCGTCTTTGCAGTCAGCCACTGTAGACTTGAGTTTCTCTCTTGCTGTCTTCATTTTATTGCTCCATATCTGAGGAAAACCATGTGAAAAATCCCTAGACACATAGGAGCCCTGAGAAGTGGTGGCAGGGAATGCTTGGGGGACAAAACAGATTTTAGAGTTACGGGTATTTAATTAAAAAAAGAGAGACCCAGAATTGTTTTCACTTAAATGAGCAATTATATCTTTAACTTGGGGATGGAAATATGTTGTGAAATTTGTTTAGTCAGCTCCCTCTGAAATAAATAAAATTACAGTGATGATATCATTCTTGTTTAAATGTTTGAAAAGGTATCAAGACAAAGTGATTAAGGCCTAACTGTTTGCCAAATTTTCTTTAAAGCTCCATTTTGGGGTATTTCTATGCCAAAAAACATCTTAAACTGATGAACATATAGTTCTCCGCACTTGTATTGGCTGGTTTTTA |
| 607 | NON_CODING (INTRONIC) | TCCACTGGATATAGCCTCGACTGTACTCACCAGGTTCTCCACACCCTAAGCCACATGCCAGATTTGTTTAGCAGATTCAGTGGAGCAGGTTCATTCATGGGGCACCAAACCAAAGTCCTTTTAAAAACAGTTACCTATGATTTAAAAGTGTGAAGTGATTGTAGTATGATGGGAAACAGTGGGCCAACTATCATGAGAATTAGGAGATCTGGACAGCTACATGATCTCTTTGATCATATAGTTTTCTTACTTGCTCAGTGCAGCAGTAGTGCCAACCTGTCCTCAGACGGGGATGTAATA |
| 608 | NON_CODING (INTRONIC) | GGTTGTGGACCACTGAGCTAATGCAGTGCATCTCAGTGATTACTGTCCATCAGAAGCTTGTTAAAAAATATTCTTGAGCACCACCCCCAAAGGTTCTGGTTCAGTAGGTCAAGGGTGGGGCCCAAGAATTTGATTTCTATAATGCTTTTAAGTGAAGCCAATACAGACCACACTTAGAGTAACATGTTCTAATTTTTTTATGAACCAGGAATTAATAAACTGGGCAGATAGTAAAGCATTGCCCACAGAGGTTGAAAGAGACTTTCAGATTCATCG |

TABLE 6-continued

| SEQ ID NO. | Type | Sequence |
|---|---|---|
| | | AGTCTAATCTCATCAGATGGTTGAGCTTCTTCCACAAAATCCCCAC CAAGTGGGTCTCTTTGAATGCTCTACCAACAAGGATCC |
| 609 | NON_CODING (INTRONIC) | TCCAGGCCTTTTAATGAACAGTCTTCTGCTTTTTCTCTTAACAATAT AATTTCTCCTATGGAACAATTTGAAAGCCATGCATGCAAATTTAGA CTAAAAGCAATGGACACAAAAGAAACCTGTATACATTCTTCGGTAT TACGCACATGTGATGAGTGGTGCTTTTGGGCACTTGCCTGACAGTA GCTTGGACAGAAAAGACACTGGAGCCTCAGAGAATAACTATTGAA GCAATTCTGGAATTAAGAAATAAGGCCTGAAATGAGATGGTAAAA GATGTTAGAGGAAGAGAAGCAAGGTAAGACAAGGTGACACACAG AATCAGAAATGATGAACAGGAAGCAACTTTTAAAATAAATGTTTTC TGAGTAGCTACTAATATGCCAAGCCCTGTGCTGGGCATTGACATTG CAGCAGTGAACAAAACAGACACGATCCTGGCTCTCGTCAAGTTTAT ATTT |
| 610 | NON_CODING (INTRONIC) | GATGGAAAGTAAGGGCAACAAAATAAACTTGAGAGCCACAAACCT GTGGGTTACAGTTAAAATTATAAAACACTGTCAAAATTTAATTAAT TTTAGGAAGTTCACTTTGTCCTCACAACAGGTTTTTGAAGTATATTT TTCTAAGTATTTAATACGTACTCTTAACAGTCTGCAAATTTGCAAAA CCTGAAGTTAATGAGTGGTTAATTGACTTAAGATTTTTTCCAGAATC AAATTCCTTTCTCCATACATACATGCGTTG |
| 611 | NON_CODING (INTRONIC) | TGAGGGCCAAGACACAAGATGAAGCTTTGGCTTCTTAAAAAGATG GGACGAATGCATCTGTCAGTGGCTGGTTACAGCAATGGGTTAGAAT ATTTAATGAGGGAGGTCATCACTCCTGCTTCCCTT |
| 612 | NON_CODING (INTRONIC) | GGGTCACAAGCCAATAGACAAGCCAGTCCTTTTGAATCCTTTACTC ATGGCCTTGAGAGGAACCA |
| 613 | NON_CODING (INTRONIC) | GGGCTGGGATTATTGTCTTCATATACAAAGGATAGTCTTTTTTTTTT GTTTCTATTTTGCAAAGTACCCATTTTCAGCACAATACAAAAGGTA GATATAATGCTGTGTACTTTTTAAAATAATCTTTTGAATATTATACA TTCATACTGTCCAAAAATTAGAAAATATAAAAAGGAATACAGTGG AAGCCTCCATGACCCCACAGGTAACCACTAGCATTATTTTCTAGTA GTCTTTTATGTGTTTATTTTATGCAGTCTTTTATGTATTTTATGTAGT ATTTTATGCAGTCTTCCAATTTCCTTATGCATATACAAACATAAAAA TATATTCTGATAGTTTCTTCTTTTGTTACACGAAAATGGTATACTAT TCATAGGGTTGGGCACCTTGGTTTTGTTTTGTTTTTTTTTTCCATTT AAGAAAATATATTGGAAATATTTCTATATCTGTATGTAAAGAGTTT CCTCCTTTTCTTTCTTTTCCTTTTTTTAACAAATGTGTAATATTTAT ATTTTATGCCATAATTTATTTAACCAGCCCCTATTGATAGGAATATGG GTCATTTTTCAATCTTTCATTTTTACAAACAGCATGTATGAATAACT TGTGCATCTAAATAGTTTCACAAGAATACCTGTGGGATAATA |
| 614 | NON_CODING (INTRONIC) | TCTAATCCCGGCCTTGGCTTTCTGGTGACCAACCCCCATCCTGAAGC TGGCCAGGGACTGCCAGCCATCAATCAATCATTAGCATGCAAAAA GACATACTTTGGAGACTCCAAGGATTTTAGGAATTCTATGGCAGAA AATGGAGATGAACACCAAATAGAAGGCCGGGCACAGTGGCTCACG CTTGTAATCCCAACACTTTGGGAGACCAAGGTGGGTGATCACCTGA GGTCAGGAGTTTGAGACCAGCCTGGCCAACTTAGTGAAACCCTGTC TCTACTAGAAACACAAAAAATTAGCCAGGCGTGGTGGCAGGCGCC TGTAATCCCAGCTACTCAGGAGGCTGAGGCAAGAGAATCACTTGA ACCCAGGAGGCGGAGGTTGCAGTGAGCCGAGATGGCGCCACTGCA TTCCAGCCTGGGCAACAAGAACGAAATTCCGTCTCAAAAAAAAAA AAAAAAGACCAAATATATATTTCACAATATCATAGATAATGAATGG CATTTTTAAAAAAAAGTTTGTCTATTAACTGCTTACCGTGTTCTTGC CATGTAGGTTCTG |
| 615 | NON_CODING (INTRONIC) | ACAGGGGCGCATTTGCCTCACAAGGAACATTTGGCAATGTCGGGA GATATTCTGGGTTATACAAGTGGGAGATTAGGAATGCTACTGGCAT CTAGTGGGCAGAGGCCAGGATACTGTGAAACATCCTATAATGCAC AGGAGAGCTCCCTACAACAAACAATT |
| 616 | NON_CODING (INTRONIC) | TGCTTTGCGATGCATTTGAAATACCGTTTGTGGCCAGATAAATTAC GATTGCTTTTCAAGGTTACATGGTGTTTC |
| 617 | NON_CODING (INTRONIC) | GGTCCACAGAGAATAGTCCATGATCTGTACAAACATCCAGAGAGCT GCTTTCTCCCATGGCCTCCCACAGGTCTGACTGCCAGAGAGTAGAA GCAAGAGGGTGAAAATAGAGGAGTACCTGCTGTGCTGTCATTTCA GGTCTGCTCTGGAGAAGAACATGGGCTAAGAATTATCTTTTATGAT CTGAAAAAGCTGTCTGAAGTTCCTTCCAAGCTTATCAGCCTCCTAA CCTGAGCTTTAACAAAACCCGGTATGGTAGAGTCCTAGTGTGCCAA TCCAGCTTTC |
| 618 | NON_CODING (INTRONIC_ ANTISENSE) | TGGAGCTGCGTTGAATGCAAACTTGAGGTGTTTCCCTTGAGGAATT CTTGTCTTCAAACGTCTGCAGAGTAATGGACCATGTTACAACTTTCC TGTTC |

TABLE 6-continued

| SEQ ID NO. | Type | Sequence |
|---|---|---|
| 619 | NON_CODING (INTRONIC_ ANTISENSE) | GATGGCACTGATGCATTAGACCCTCAGCAGCCTGCAATTGCAAATC TGCGAGGTTTCATTCGGCCCATAAAGCAAACATTTGAACTTACACA GAATGAGCACTTAAATACGGGTGCAATAA |
| 620 | NON_CODING (INTRONIC_ ANTISENSE) | TGTAGCCCATTTGGTCACAGTAGCCTCACTTCTGCTACGCTTGCAAC AACAACTCTTTGGAAATCAACCGCTATTCTATATTTGTGTTCACGTT AGTG |
| 621 | NON_CODING (INTRONIC_ ANTISENSE) | GGGCCTAGGCTTTGTGCACACTGTTCGATGAAACCAAGGCTTACCA AGCTCTACTTTATTCCGTATCTGGATGGTCATTTCATTTCTCCTAGC CCACACCCAGACACACACTTCTCAAATACACACGACAATTTCACTA TCTCACAATCTCTTACTGTAACTTTGGCCTTCAGAAACACCCTTTGT TATATTGCAGGCGGCCAAGCATTAAGTCCAGCTGA |
| 622 | NON_CODING (ncTRANSCRIPT) | ACCTGTGCCAGCTCCTGCAAATGCAAAGAGTACAAATGCACCTCCT GC |
| 623 | NON_CODING (ncTRANSCRIPT) | CCATTGTATACCCTTCCTTGGTGAATGTTCTGATATTTGCTTCCCAT CCCAAGTTGTTTCAGCCCCTATTAG |
| 624 | NON_CODING (ncTRANSCRIPT) | CGGATCCGTGTTGCACCTTCTCCTGCTGCCACGTGTGAGGCAACTCT GCGTGTCTCCTAGCTGCTCCCTGACAGCTTCTCTGCATGTGTTTGGA CTCTGATGTCCTCTCAGTGTGTTGCTTTTGGATTGAACTGTGATTCT TTCTGCCTGTATCTGTCTGTGAGATTCCGTGTTTCCAATGC |
| 625 | NON_CODING (ncTRANSCRIPT) | GGAGATTTCAGATGGACCTAGAATGAGGAAGGCAGGCTACTCAAC AGTTGTGGATTTGGGAGTCTGGACACTCCTTGAGCTGTGCAGTTTT AATTCTTTCTTAAATAAAGATACAAAGGACAATTTAGGACATGGAA AACCCTAGCTA |
| 626 | NON_CODING (ncTRANSCRIPT) | TGACCTCTGGGGTAGGTTACTATCCTCTTTGTCCTGCCAGTACCCCT AGAAATTTGACTTAATTGCTGCATCTAGGGACTTAGGGATTTTTCCC AAATGCTGTGTAGAAAGTCACTGGAGTTAAATCTACTCCAACCATT TTTCTGCTGTTTCTTGAAAAGACAGGATGATTCATTTACATCTCTTT TCCTTCACAGAATCATGAGGGAAGTATTGTGATTACCAGTGTTAAG CATTTG |
| 627 | NON_CODING (UTR) | ACAGCTCCTCCTTCTTGATATTGCACATGCACTTCAGTTCATGGCTA GCTGTATAGCTTCCGTCTGTAAACTTGTATTTTCAAGAATCCTTGGT ATTGAATTTTTAGAAATGCTCACATAATTGTTGGGACTGATTCATTC CTCCACGATATGCCTCCTCTCTCTGATATCCTGCTAACTGTAGCCGT TGTGGCATTTGAGATGACAGGACATATATATATATGGCCCCACACT TGACCTTGAGTGCCTGAATGCTCTGAAATCAAGCATATGGCACAGC GCTCAAGACTTTTG |
| 628 | NON_CODING (UTR) | CCAGACTCGAGAGGTGGGAGGAACTCCTTGCACACACCCTGAGCTT TTGCCACTTCTATCATTTTTGAGCAACTCCCTCTCAGCTAAAAGGCC ACCCCTTTATCGCATTGCTGTCCTTGG |
| 629 | NON_CODING (UTR) | TGAAATAATTCATGCCACGGACCTGTGCACATGCCTGGAATTGAGA GACACAGTTAAAAGACTCCAAGTTGCTTTCTGCCTTTTGAAAACTC CTGAAAACCATCCCTTTGGACTCTGGAATTCTACACAGCTCAACCA AGACTTTGCTTGAATGTTTACATTTTCTGCTCGCTGTCCTACATATC ACAATA |
| 630 | NON_CODING (UTR) | CTGTGCTTTTACCAGTAGCATGACCCCTTCTGAAGCCATCCGTAGA AAGTACTTTGTCCTCCAAAAAGCTAACATACGGTTTTGAAGCAGCA TTGAAACTTTTGTAGCAATCTGGTCTATAGACTTTTAACTCAAGAA GCTAAGGCTAGACTTGTTACCTTCGTTGAA |
| 631 | NON_CODING (UTR) | AGAGGAGGGGACAAGCCAGTTCTCCTTTGCAGCAAAAAATTACAT GTATATATTATTAAGATAATATATACATTGGATTTTATTTTTTTAAA AAGTTTATTTTGCTCCATTTTTGAAAAAGAGAGAGCTTGGGTGGCG AGCGGTTTTTTTTTTAAATCAATTATCCTTATTTTCTGTTATTTGTCC CCGTCCCTCCCCACCCCCCTGCTGAAGCGAGAATAAGGGCAGGGAC CGCGGCTCCTACCTCTTGGTGATCCCCTTCCCCATTCCGCCCCCGCC TCAACGCCCAGCACAGTGCCCTGCACACAGTAGTCGCTCAATAAAT GTTCGTG |
| 632 | NON_CODING (UTR) | AGCCATCGGTCTAGCATATCAGTCACTGGGCCCAACATATCCATTT TTAAACCCTTTCCCCAAATACACTGCGTCCTGGTTCCTGTTTAGCT GTTCTGAAATACGGTGTGTAAGTAAGTCAGAACCCAGCTACCAGTG ATTATTGCGAGGGCAATGGGACCTCATAAATAAGGTTTTCTGTGAT GTGACGCCAGTTTACATAAGAGAATATCACTCCGATGGTCGGTTTC TGACTGTCACGCTAAGGGCAACTGTAAACTGGAATAATAATGCACT CGCAACCAGGTAAACTTAGATACACTAGTTTGTTTAAAATTATAGA |

TABLE 6-continued

| SEQ ID NO. | Type | Sequence |
|---|---|---|
| | | TTTACTGTACATGACTTGTAATATACTATAATTTGTATTTGTAAAGA<br>GATGGTCTATATTTTGTAATTACTGTATTGTATTTGAACTGCAGCAA<br>TATCCATGGGTCCTAATAATTGTAGTTCCCCACTAAAATCTAGAAA<br>TTATTAGTATTTTTACTCGGGCTATCCAGAAGTAGAAGAAATAGAG<br>CCAATTCTCATTTATTCAGCGAAAATCCTCTGGGGTTAAAATTTTAA<br>GTTTGAAAGAACTTGACACTACAGAAATTTTTCTAAAATATTTTGA<br>GTCACTATAAACCTATCATCTTTCCACAAGATATACCAGATGACTA<br>TTTGCAGTCTTTTCTTTGGGCAAGAGTTCCATGATTTTGATACTGTA<br>CCTTTGGATCCACCATGGGTTGCAACTGTCTTTGGTTTTGTTTGTTT<br>GACTTGAACCACCCTCTGGTAAGTAAGTAAGTGAATTACAGAGCAG<br>GTCCAGCTGGCTGCTCTGCCCCTTGGGTATCCATAGTTACGGTTTTC<br>TCTGTGGCCCACCCAGGGTGTTTTTTGCATCGCTGGTGCAGAAATG<br>CATAGGTGGATGAGATATAGCTGCTCTTGTCCTCTGGGGACTGGTG<br>GTGCTGCTTAAGAAATAAGGGGTGCTGGGGACAGAGGAGCAACGT<br>GGTGATCTATAGGATTGGAGTGTCGGGGTCTGTACAAATCGTATTG<br>TTGCCTTTTACAAAACTGCTGTACTGTATGTTCTCTTTGAGGGCTTT<br>TATATGCAATTGAATGAGGGCTGAAGTTTTCATTAGAATGCACTCA<br>CACTCTGACTGTACGTCCTGATGAAAACCCACTTTTGGATAATTAG<br>AACCGTCAAGGCTTCATTTTCTGTCAACAGAATTAGGCCGACTGTC<br>AGGTTACCTTGGCAGGGATTCCCTGCAATCAAAAAGATAGATGATA<br>GGTAGCAATTTTGGTCCAAAATTTTTAATAGTATACAGACAACCTG<br>TTAATTTTTTTTTTTTTTTTTTTGTAAATAACAAACACCACTTT<br>GTTATGAAGACCTTACAAACCTCTTCTTAAGACATTCTTACTCTGAT<br>CCAGGCAAAAACACTTCAAGGTTTGTAAATGACTCTTTCCTGACAT<br>AAATCCTTTTTTATTAAAATGCAAAATGTTCTTCAGAATAAAACTGT<br>GTAATAATTTTTATACTTGGGAGTGCTCCTTGCACAGAGCTGTCATT<br>TGCCAGTGAGAGCCTCCGACAGGGCAGGTACTGTGCCAGGGCAGC<br>TCTGAAATTATGGATATTCTTATCCTCCTGGTTCCTTCGGTGCCAAT<br>GGTAACCTAATACCAGCCGCAGGGAGCGCCATTTCTCCTAAAGGGC<br>TACACCACTGTCAACATTATCCTGGACTCTGTGTCTCTCTCTGTTGG<br>GTCTTGTGGCATCACATCAGGCCAAAATTGCCAGACCAGGACCCTA<br>AGTGTCTGATAGAGGCGATGATCTTTTCCAAAGTCAGTACTTACAA<br>ACTGGCATTCTTACAGGCTGCACCATTTCCTAGTATGTCTGCTTTAA<br>GCCTGGTTCAACCTCTCATCGAATA |
| 633 | NON_CODING (UTR) | CCAGTCGCTGTGGTTGTTTTAGCTCCTTGACTCCTTGTGGTTTATGT<br>CATCATACATGACTCAGCATACCTGCTGGTGCAGAGCTGAAGATTT<br>TGGAGGGTCCTCCACAATAAGGTCAATGCCAGAGACGGAAGCCTTT<br>TTCCCCAAAGTCTTAAAATAACTTATATCATCAGCATACCTTTATTG<br>TGATCTATCAATAGTCAAGAAAATTATTGTATAAGATTAGAATGA<br>AAATTGTATGTTAAGTTACTTCACTTTAATTCTCATGTGATCCTTTT<br>ATGTTATTTATATATTGGTAACATCCTTTCTATTGAAAAATCACCAC<br>ACCAAACCTCTCTTATTAGAACAGGCAAGTGAAGAAAAGTGAATG<br>CTCAAGTTTTTCAGAAAGCATTACATTTCCAAATGAATGACCTTGTT<br>GCATGATGTATTTTTGTACCCTTCCTACAGATAGTCAAACCATAAA<br>CTTCATGGTCATGGGTCATGTTGGTGAAAATTATTCTGTAGGATAT<br>AAGCTACCCACGTACTTGGTGCTTTACCCCAACCCTTCCAACAGTG<br>CTGTGAGGTTGGTATTATTTCATTTTTTAGATGAGAAAATGGGAGC<br>TCAGAGAGGTTATATATTTAAGTTGGTGCAAAAGTAATTGCAAGTT<br>TTGCCACCGAAAGGAATGGCAAAACCACAATTATTTTTGAACCAAC<br>CTAATAATTTACCGTAAGTCCTACATTTAGTATCAAGCTAGAGACT<br>GAATTTGAACTCAACTCTGTCCAACTCCAAAATTCATGTGCTTTTTC<br>CTTCTAGGCCTTTCATACCAAACTAATAGTAGTTTATATTCTCTTCC<br>AACAAATGCATATTGGATTAAATTGACTAGAATGGAATCTGGAATA<br>TAGTTCTTCTGGATGGCTCCAAAACACATGTTTT |
| 634 | NON_CODING (UTR) | TGTTGTTGCAATGTTAGTGATGTTTTAA |
| 635 | NONCODING (UTR) | AAATAATGCTTGTTACAATTCGACCTAATATGTGCATTGTAAAATA |
| 636 | NON_CODING (UTR) | GTTTGCCCTTTGGTACAGAAGGTGAGTTAAAGCTGGTGGAAAAGGC<br>TTATTGCATTGCATTCAGAGTAACCTGTGTGCATACTCTAGA |
| 637 | NON_CODING (UTR) | CAAAGTAAACTCGGTGGCCTCTTCT |
| 638 | NON_CODING (UTR) | CGAGGTGATGGGACTTCTTAACACACATTTCTATAATACCCATGAA<br>ATGATAATTTGTAAAATAACACTTAGTGATATCTGGAAATAATAAT<br>TCAATTAAGCAACCACGAATTTCACCCTGGAGATATTTTTCTTATT<br>TGAGTCCACCAAAGGATAATGCCAACTTATATAAGTTCTCAAATCA<br>TGCCTTCCGCTTAGTCTCATTTTATTCATTCAGTCGTCATGAGTTGA<br>GTGCTTACTACATGCAAGGCACTCTGCTAGTTATATTCTAATAATGC<br>AGAGATAATTAGACATGGTTCCCGCCCTCA |

TABLE 6-continued

| SEQ ID NO. | Type | Sequence |
|---|---|---|
| 639 | NON_CODING (UTR) | TTCCATACACGTTTGCAGTTTCTTGTACACATTTGGATACTTTGAAA GATGACAGATTGTTAAATCCATTCAATGGTAAAGAAACTCACCATC TGGAGATTGAGTCTACTTGTTAATGAATGACTAGCCCAATTATCCTT ATAAATTGAATATGGTGACCAAATGCTTTGATATCATACTACTCTG CCTTTGTGGGCACATATGTAGACACTACTAAAAATAAATATTTTTG GAGATTAAAATGGAGAATAGAAGTAATTACATTATTTAGGTCTTAA TCCAACTTTTTTCTAATATATCTAAACAATTGAAAGGGAAGCTTATT CATGGAATATTGGCTTGATTTATCTAGAAAGTTTTTCCTTCTTCAAT TTTACTATATTCATTCTACAGGAACAGCAATAAGTACTATTAAACA GAAGATGGCTACACTAAGTTCCAATTTTGTTGCTGAATTGCTTCTGT GAGTTCACTTTTCAGTTCTAAGGAAGAATAATATTTGCTACATATTT CACAGGGGTTCTTA |
| 640 | NON_CODING (UTR) | CCCACCTTTCCATGCTTAAGACAAAAATGTCTTAAATATAAAGCTG TGATTATATCAAAAATCCAGATAAATCATCAAATATATCAGATTAA GACCAGGGTTTACACACTTAGGCAATAGTC |
| 641 | NON_CODING (UTR) | GTTTTAATTCAACAGTCCAACATTATTTAGGTGTTACAGAGTGTAA ATATATTTCTTTGGGAGTTATTTTCTTTTTAAAATCTTTTTATAGCTT GGCAATGTCCAAAGTCAAATATCACCTAAACTGGTTAGATTACTTC TACAGCTAATAATATTGCAG |
| 642 | NON_CODING (UTR) | TGGCTACTTGACCTACAGCAAAAGCCATTTCTGTACCATAAAAATT TGTTGTGCAATATTAGAATTATCATATGTTTCCTACATCTGACAGCA CCTAAAATGTTTGATAATATTAACATGTATCTAAGAGGAAAAAAGA GTTAATATATTCTGGCACCCACTTTCCTAGTAATGTTTTCCATGATT TTCCAGTTCTGAGGCACTTATTAAAGTGCTTTTTTTTTTCTGAATTA ATTAGGTATTGGTAAAATATATTTTAAATTTAGTTAGCTTTATAAA CACAATTAGAATTACAATTAATTAACAGAGGTATAATTGTCTCACT TTCAGAAGTGATCATTTATTTTTATTTAGCACAGGTCATAAGAAAA ATATATAGAAAAATAATCAATTTCATATATAAAAGGATTATTTCTC CACCTTTAATTATTGGCCTATCATTTGTTAGTGTTATTTGGTCATATT ATTGAACTAATGTATTATTCCATTCAAAGTCTTTCTAGATTTAAAAA TGTATGCAAAAGCTTAGGATTATATCATGTGTAACTATTATATGATA ACATCCTAAACCTTCAGTTTAGATATATAATTGACTGGGTGTAATCT CTTTTGTAATCTGTTTTGACAGATTTCTTAAATTATGTTAGCATAAT CAAGGAAGATTTACCTTGAAGCACTTTCCAAATTGATACTTTCAAA CTTATTTTAAAGCAGTAGAACCTTTTCTATGAACTAAATCACATGC AAAACTCCAACCTGTAGTATACATAAAATGGACTTACTTATTCCTC TCACCTTCTCCAGTGCCTAGGAATATTCTTCTCTGAGCCCTAGGATT GATTCTATCACACAGAGCAACATTAATCTAAATGGTTTAGCTCCCT CTTTTTCTCTAAAAACAATCAGCTAATAAAAAAAAAATTTGAGGG CCTAAATTATTTCAATGGTTGTTTGAAATATTCAGTTCAGTTTGTAC CTGTTAGCAGTCTTTCAGTTTGGGGGAGAATTAAATACTGTGCTAA GCTGGTGCTTGGATACATATTACAGCATCTTGTGTTTATTTGACAA ACAGAATTTGGTGCCATAATATTTTGAGAATTAGAGAAGATTGTG ATGCATATATATAAACACTATTTTTAAAAAATATCTAAATATGTCTC ACATATTTATATAATCCTCAAATATACTGTACCATTTTAGATATTTT TTAAACAGATTAATTTGGAGAAGTTTTATTCATTACCTAATTCTGTG GCAAAAATGGTGCCTCTGATGTTGTGATATAGTATTGTCAGTGTGT ACATATATAAAACCTGTGTAAACCTCTGTCCTTATGA |
| 643 | NON_CODING (ncTRANSCRIPT) | TTCATCAACTCAGTCATCAAATTCC |
| 644 | NON_CODING (UTR) | TCTTCCCATGCACTATTCTGGAGGTTT |
| 645 | NON_CODING (UTR) | GCACACTCTGATCAACTCTTCTCTGCCGACAGTCATTTTGCTGAATT TCAGCCAAAATATTATGCATTTTGATGCTTTATTCAAGGCTATACC TCAAACTTTTTCTTCTCAGAATCCAGGATTTCACAGGATACTTGTAT ATATGGAAAACAAGCAAGTTTATATTTTTGGACAGGGAAATGTGTG TAAGAAAGTATATTAACAAATCAATGCCTCCGTCAAGCAAACAATC ATATGTATACTTTTTTTCTACGTTATCTCATCTCCTTGTTTTCAGTGT GCTTCAATAATGCAGGTTA |
| 646 | NON_CODING (UTR) | TTTCCAAAACTTGCACGTGTCCCTGAATTCCATCTGACTCTAATTTT ATGAGAATTGCAGAACTCTGATGGCAATAAATA |
| 647 | NON_CODING (UTR) | GCTTCAGGTGACCACAATAGCAACACCTCCCTATTCTGTTATTTCTT AGTGTAGGTAGACAATTCTTTCAGGAGCAGAGCAGCGTCCTATAAT CCTAGACCTTTTCATGACGTGTAAAAAATGATGTTTCATCCTCTGAT TGCCCCAATAAAAATCTTTGTTGTCCATCCCTATA |
| 648 | NON_CODING (UTR) | GTTTCGACAGCTGATTACACAGTTGCTGTCATAA |

TABLE 6-continued

| SEQ ID NO. | Type | Sequence |
|---|---|---|
| 649 | NON_CODING (UTR) | CTGGCAATATAGCAACTATGAAGAGAAAAGCTACTAATAAAATTA ACCCAACGCATAGAAGACTTT |
| 650 | NON_CODING (UTR) | TCTCTAGCTATAAGTCTTAATTATACAACAAAATACTATTTTTATAT TTATGTTTGGTAAATTCAATAACTTTCCTCATCATTTGGAAAGTCAA ATTGTTTATTGCTTCCCTACAGTTTTTTCTGAATC |
| 651 | NON_CODING (UTR) | CTGGGATTCTTACCCTACAAACCAG |
| 652 | NON_CODING (UTR) | TTCAAAGAAATACATCCTTGGTTTACACTCAAAAGTCAAATTAAAT TCTTTCCCAATGCCCCAACTAATTTTGAGATTCAGTC |
| 653 | NON_CODING (INTRONIC) | AGGGAAAAGTTAAGACGAATCACTG |
| 654 | NON_CODING (INTRONIC) | ATCTTCCAACAACGTTTGTCCTCAAAT |
| 655 | NON_CODING (UTR) | CCTATTACAGCTAATCTCGTTTTAAATCTGCTC |
| 656 | NON_CODING (INTRONIC) | TATGTAACAATCTTGCACAGTGCTGCTAATGTAAATTTCAGTTTTTC GCCTCTAGGACAAACA |
| 657 | NON_CODING (INTRONIC) | TTTGAAGTCAACTGTATCACGTCGCATAACCTAATCACAAAAGTAA TATCCACAAAATTAATAGTCCTACAGATGATGTAGGGTGTGTACAG CAGGAAGCAGGAAATCTTGGGGGTTGTCATAGAATTCTGCTAAATA TGCCTAGAGACACACATCCTTAACTGGACTTTAGGTTTATCATTTGT GTTCTCTGGCCTCAGTGTTTTCAATTTGTGGATCATGTACCAATAGC ATC |
| 658 | NON_CODING (INTRONIC) | GGCCTCATTAATATAGTGGCTGATGGTACCTACTAACCTTCAATGG GTCGCCTCCTACCTATTCTCATTTCATTAGCTTTTTGAAGGACAGGG TAGACTAGATCAAGAAAAGAGATAAAAAGAAATAGTACATATTCA CACTTATGTAATTACATCCCCTTCCATGGAAACTTGGGAATAAAGA GGGTATTTCAAGGTCATGTAGAAAAAGTAAAC |
| 659 | NON_CODING (INTRONIC) | GTTGTGGGATTAAGACATTAATTC |
| 660 | NON_CODING (UTR) | TCTCACTTTGCATTTAGTCAAAAGAAAAAATGCTTTATAGCAAAAT GAAAGAGAACATGAAATGCTTCTTTCTCAGTTTATTGGTTGAATGT GTATCTATTTGAGTCTGGAAATAACTAATGTGTTTGATAATTAGTTT AGTTTGTGGCTTCATGGAAACTCCCTGTAAACTAAAAGCTTCAGGG TTATGTCTATGTTCA |
| 661 | NON_CODING (INTRONIC) | AGCCCTCACTCTAAAGTCACTTGTCACACATTCTATCAAATAAGGG AGAAAAAAACAAACACTATATCCAATTATAGTTTTCCACCTGAAAC TACCAAAATAGAAAAAAAAATTTTCCTATTAAAATGGAAAAAGT CTAAGTGCTCAGGTAGAATCATTGAATTATCATTTTTGCTAGAGTTG ACCTTATGCATTTCAAGGCTGGCACCATCATGTACAGGAACAATAT GCTCATTGCTCCTCCCACCCATCCCCACCATGATGAAGAAAAGAGC TGATTAGTGAACAACTAATAAATATGTGCCATCTGGGTACTAGTAA CTTTA |
| 662 | NON_CODING (UTR) | CAGGTATAAGGTTAGATGCTACATCTAGGAGCATTCAAGATATACA TTAATTTAAACTTTTATTAGTCTAACTTTCTGTTAAGTCTCTTAGCTT TGAAACATAAAAGAGAAATCAAGCCCAAATTTTTAGAGGAAGGCT AAGGTATACTATTGGCAGTTGTAGTTTTAATTGTAATTGACTGATTA ACCAAGTAATTTATAAAATGTTACCTATACTGTCAGTG |
| 663 | NON_CODING (UTR) | CCGACTAACATGGTAATAGACCTGAATGCATAATGAGTTCTTACTT TGCTATCATCAAAAGACTTTTCATCACAGTTACATACTTTCTAATTT ATGGAAAAACAGCATTTGGAAAACAAATGTTTTGTTTTTATTTTTTT AAAGATTTAAAAAATAAATCAACTAGGGACTAGGAATCAACAACT GTGAGTGAGTTAAACTGTGTTGAAATACTAAAGGGTTGT |
| 664 | NON_CODING (INTERGENIC) | TTCTTGCCTAAACATTGGACTGTACTTTGCATTTTTTCTTTAAAAA TTTCTATTCTAACACAACTTGGTTGATTTTTCCTGGTCTACTTTATGG TTATTAGACATACTCATGGGTATTATTAGATTTCATAATGGTCAATG ATAATAGGAATTACATGGAGCCCAACAGAGAATATTTGCTCAATAC ATTTTTGTTAATATATTTAGGAACTTAATGGAGTCTCTCAGTG |

TABLE 6-continued

| SEQ ID NO. | Type | Sequence |
|---|---|---|
| 665 | NON_CODING (UTR) | CTAGAGTTCTCATTTATTCAGGATACCTATTCTTACTGTATTAAAAT TTGGATATGTGTTTCATTCTGTCTCAAAAATCACATTTTATTCTGAG AAGGTTGGTTAAAAGATGGCAGAA |
| 666 | NON_CODING (INTRONIC) | GTGCTAGTTGATATCATGATTGATTTGGTCTTCTTGG |
| 667 | NON_CODING (INTRONIC) | TTACGTTAGTACTGCAGAGGAAATAACTTGGAAGTTACAGGGAATA ACAATAGGTACTAGAAATTGAGTGCTATGGGTACGTATTAGATCGT TAGCTCATTTAGTATC |
| 668 | NON_CODING (INTRONIC) | CTATAGAAGGTTATTGTAGTTATCTTTAGTACTATGTTATTTTAGGA GGCCTGTGTTTAAATTTTACAATTCATTAACAGGACTGATGGCATTT TGTAGGAACTACTTAGGAACAAGTTTGCATTTC |
| 669 | NON_CODING (ncTRANSCRIPT) | GACACTTAGGTGATAACAATTCTGGTAT |
| 670 | NON_CODING (INTRONIC) | GGGCTCTCTAGAAAGGTAATTATTATCTGATATAATAGTTTAGTCT GTGATGCTTCTTTTAACATATTTGTAAGTTTTAACCAAATGGTTAAA GAAATTTGCTTTTTAACCCTTAAACCTCACATATCCACAAGTCTCTA AATTCCATAGGATGCTATGGATTTCTAGTTGCCTAGTTCATGTCTTT TACTTAGAAAACGTCAGAAAACCCAAACTTCTCGTGACTTCAAAAA GTGTAATTGTACCTGAAACTTCTTTTCCTTCAGATTTCTTATTTATGT TTTCTGATAGGTTTTTAAGATTAATCTTTTCAGAAGGATGCTCTAAA AATCTGGCCAATTTGATTATCCTCTTCCAACTTGGAAAAAATATGT ATTTAAAATGAGACTAGAATTTGAATGACCTTCTTTCATGGAACTC TGA |
| 671 | NON_CODING (UTR) | GTTGTTGCCTCTAACATGTATAAAGG |
| 672 | NON_CODING (CDS_ANTISENSE) | AAGTCATTATCTTGCTTTGGAATCATTATCTGGCATTATCAACTTGC ATTTGGTTCCACAACA |
| 673 | NON_CODING (INTRONIC) | GTGAGAAAAAACAAGTCATATAAAA |
| 674 | NON_CODING (INTRONIC) | AGGAATAATTGATCAAGATGACATAAAATTTACAAATTTATTTGTG CCTAATAATAGTCTCAAATTACATAAGGCAAAAACTGATAGAATGA AAGGAAGAAATAGGCAATTATAATTGGAAATTTTAATGTCTCTCAG AAGTTGATAGAGTAACCAACAAAAAATCAGCAGACAGAAAACCTG AACAACATTATCAGTCACTTTGA |
| 675 | NON_CODING (INTRONIC) | CTGGGCCCTTTACAGTTGATACCCAAAGCAG |
| 676 | NON_CODING (INTRONIC) | TCTGGGTACTAGGAGTAGACCATCCATTCTTGATTTGAACTGTTTCT GCAGGTACTCATTTGTTCAAACACTGCCTATTTCGTTTTGCAACAGA TCTATTTTAGAAAATCTTTATATTGAGCAAACAGCAGTCTCACTATA GCCTCTACTTGTTGGTCATAATCTGCCAGAGGAAGCTTACCTGATG ATGATGGTGCTGCTGCTGCTGATAATGATGGTGATGGTAATGACGA ACATGACACAAGATCACAGGCACTGTGCTAAGCATTAAACACATA CAATCTTATTTAATCCTCATAATGTTATGGCATAAATATTACCCCTC TTTTAAAGATGAACAAACAGATGATTAAAGGGGTAAAGTTGCTTTG ATCTTTAATATTAATTTGTGTCTTTCTCACTTCAAATTCAGCGATGA ACCCTATTCCTATG |
| 677 | NON_CODING (INTRONIC) | CCTTTGATCTTAAGATTGTTGGCAT |
| 678 | NON_CODING (INTERGENIC) | ACTGTGGCTTCAATAGCCTCATAGAAGTGTCCTTCCTTTTTAACAAA GGGAATCCAAGATGGCGGAAAGGTCCTAACATTGAGCATATAATC CATCTCTTTGCTAAACTAGATGTTTCCTTCCAGATTTCTATG |
| 679 | NON_CODING (INTRONIC) | ATGGAAGCAAAAGGGACAGACTTGAAGCTGTACTTCCAGACTCTC ATGGAAGCTCCAG |
| 680 | NON_CODING (INTRONIC) | GAGCAATGCTTAACCCATCGGAATGTATACCCTAAGCAAACTGTC AACCAGGCAAAGGGTGTTCTTTCTCTTCTGGCGCTCTGCTCTTCGTC CCTGTCCCCAGCAGCCCATCTGCTACTGGAACTTGTTCACAGAGTC CTTCTGCCAACTTATCATATTCTTGTTCCAGGAACTTTTCTGCTTTA AGTAAAGGATCTTCTCCCAACGAGTATGCTCCTGCATTTGCAGATA CAGCACAGCTCCATGCATTTGTAGCCCTGCCATATTAGTGTCCTAG C |

TABLE 6-continued

| SEQ ID NO. | Type | Sequence |
|---|---|---|
| 681 | NON_CODING (INTRONIC_ANTISENSE) | CCCTAGGTAGGAGATAACAAGTATGTACCATTACTGAATATTAAAT<br>CCTTCTTTACCATAGCTACAGTTAAGTAGGTGTATCTCAGAAACCT<br>AAGGTAGTTTTAAATGTAGTGAAATTGTCCACAGCAAGCTGGCCCA<br>AGTGCTCACATTTTATACCCGCTCTGTCTTAGTGCGTTGCAAGAGA<br>GGAGTATATACAGTAGTTCCCCCTTATCCACAGGGGTACATTCTAA<br>GACCCCCGGTGGGTGACTGAAACCACAGATAGTACCGAATCTTATA<br>CATACTATGTTTTTTTCTAAACATAAATACCTACAATAAAGTTTAA<br>TTTTTAAATTAGGCACCATAATTAATAATAAAACAGAACAGTTATA<br>ACAATATACTATAATAAAATTATGTGTATGTGATCTCTCTTTCTCTC<br>TCCCTCTCAAAATATTTTTAATATCTCTCCAGAATTCAGTGCAAATA<br>ATTCCATCATACTCACTTCAGAAAAGTGAAGATAGTCTTGTACATG<br>AGTAGATTCAAATTTTATTGTCGTGGTTTCCAAAGTTTTATTTTTCT<br>CACCCAATGGAACTTTTGATTCAAATAAAATATCCAAGGGATTTCAG<br>CTTATAAAACACACAAAATTGATAATGAGTTTTCCAAGGTACTGTG<br>TGTGTGAATGTGTATGTCTGTGTATGTGTGTGTCGTCTGTATGTTTT<br>TCCCACCTCTTGTAGAAGCTACGAAGCACCTTTCCATATTATTGAG<br>GTTTCCTGTACGTAGACTGA |
| 682 | NON_CODING (UTR) | ACCTGGACTGAAGTTCGCATTGAACTCTACAACATTCTGTGGGATA<br>TATTGTTCAAAAGATATTGTTGTTTTCCATGATTTAGCAAGCAACT<br>AATTTTCTCCCAAGCTGATTTTATTCAATATGGTTACGTTGGTTAAA<br>TA |
| 683 | NON_CODING (ncTRANSCRIPT) | CAGTATATGATATGGCAGAGTTGCACAGAAGAATCAGAACATTGTT<br>TTAGAGAAACGTTGGGCAATTAATTAAGCCAGCTGATTAAGTTTTA<br>A |
| 684 | NON_CODING (UTR) | TTCACCACTGTAGATCCCATGCATGGATCTATGTAGTATGCTCTGAC<br>TCTAATAGGACTGTATATACTGTTTTAAGAATGGGCTGAAATCAGA<br>ATGCCTGTTTGTGGTTTCATATGCAATAATATATTTTTTAAAAATG<br>TGGACTTCATAGGAAGGCGTGAGTACAATTAGTATAATGCATAACT<br>CATTGTTGTCCTAGATA |
| 685 | NON_CODING (UTR) | GCCAAAACCAATATGCTTATAAGAAATAATGAAAAGTTCATCCATT<br>TCTGATAAAGTTCTCTATGGCAAAGTCTTTCAAATACGAGATAACT<br>GCAAAATA |
| 686 | NON_CODING (UTR_ANTISENSE) | TTCCAAATACTCATGGTGCACAAGAAGGTTATGTATGCACAGTATT<br>TCTAATTTATTCAAATTCAATTTGAATTTGGTCTGAAGCTATCTTGT<br>ATGAAATGTTAGCTTTCCTGATATTTAATAATATTTATTATGTTTGC<br>ATATAAGCTCAAAAAATTAATGCAAAAGTATACTTTACTCATGGTT<br>ATCTTCAGGTAAATATTAGTGGTTATGTTTAAAAGCCTGATTTTATA<br>TAGATGAAGTTGAGAAAAAAAAAGAGTATGGAAAGGTAAATTAGG<br>TCTTAGTCTTGATTCTGTTACCAGCTGTTTGACCTTGAGTAACTCTT<br>CACCCTTCAATGGGCCCCAGTTTGCTCCTCTATGAATTTTAAGGGGT<br>TGGACTAGTTGACAGACCAGGCCCCTTCCAAGTCTAACATTTCAAA<br>ATCCTAACATTCCAGGTTCTATCATCTTGATA |
| 687 | NON_CODING (UTR) | TTGTATTTTGCATACTCAAGGTGAGAA |
| 688 | NON_CODING (UTR) | GATCTACCATACCCATTGACTAACT |
| 689 | NON_CODING (ncTRANSCRIPT) | GAGATACATCATCATATCACGGAAAG |
| 690 | NON_CODING (UTR) | ATCAGCTTTGAGTGAACTTTGACAGAAG |
| 691 | NON_CODING (UTR) | CCTGTACCCTTATGCAGAGCAAGCATTCCATCCTAAGTTATAAACT<br>ACAGTGATGTTTAATTTTGAAGCCAGGTCTACATTATTTAATTAATG<br>GCTTCAAAAGGTGGAGATGCACTTTATTTAATGTCTTTCCCTAGCTA<br>ATTCTTACTCTCACCTTAAATATGCTTTCTTGTTGCATATATGCACA<br>GATACACACACACACACACGAAAATAAATAAATGTTCATATTCT<br>TCTGTTCAACAGACATTTATTTTCTCCTCTCCCTTGAATAAGAAAT<br>AAGTTTTCCATTCCTATGAACTGTCTAATATCTTTCTATTACAGAAG<br>GGGAAACTGAGGCTGGGAAAGGCTAAATGACTTATC |
| 692 | NON_CODING (ncTRANSCRIPT) | GTCCTCAGTGTACCACTACTTAGAGATATGTATCATAAAAATAAAA<br>TCTGTAAACCATAGGTAATGATTATATAAAATACATAATATTTTTC<br>AATTTTGAAAACTCTAATTGTCCATTCTTGCTTGACTCTACTATTAA<br>GTTTGAAAATAGTTACCTTCAAAGGCCAAGAGAATTCTATTTGAAG<br>CATGCTCTGTAAGTTGCTTCCTAACATCCTTGGACTGAGAAATT |
| 693 | NON_CODING (ncTRANSCRIPT) | CTGGTTAATTAGCAATTTAAGACCAGAGCCAAATTATCCCAAGAGC<br>ATACATTCTTTTGGTTTTCCTAACTTTGTGAAAAAAATTGATGCAGC |

TABLE 6-continued

| SEQ ID NO. | Type | Sequence |
|---|---|---|
| | | TGTTTTTAACCCACGTTTTTATAGGACCTACTTCTTTGTAGATAACCA |
| 694 | NON_CODING (ncTRANSCRIPT) | TGATGCTGTCACTACCGTGGGAAATAAGATCTTT |
| 695 | NON_CODING (ncTRANSCRIPT) | CACCTGACATGAACCGTGAGGATGTTGACTACGCAATCCGGAAAGCTTTCCAAGTATGGAGTAATGTTACCCCCTTGAAATTCAGCAAGATTAACACAGGCATGG |
| 696 | NON_CODING (ncTRANSCRIPT) | AGATAAACAAACTTCCAGTGACAAA |
| 697 | NON_CODING (UTR_ANTISENSE) | TGCTTCAAGCCAATGCAAAAGTTCATACATTATATTCCCTATTTCATTGTGTTTAGAATATATTATATTGTTTAAATGCCACTACCACAGTGTAATTTTTTTTTTTTAATACTGAATCTCTGGAATAATGGTAAGGTCAAAATATATTGTATTGAGAGTTTAAAAATTAAGAGCAATTTTTAAAAATGTAACAAACATCTAAATATCTGACAATAAAATCTGAAATGCTGTAACTTCAACATTAACTGCACCATCCAAATTCTTGTGACTTACGCATTTTTGCCCAATTTAACCTTTCTGATGTTCCCCTGCCCCCAGACACCATAAATGCATTGTAA |
| 698 | NON_CODING (INTERGENIC) | TTCCAGGACTGTCATAATGATCTGTACTTCC |
| 699 | NON_CODING (INTERGENIC) | CTGCTGTGGTTTGTAAGAACTCATTGACTAACTCAAGGTCACAAAAATTTTCTCCTTTATTTTTTTCTAGACATTTTATAGCTTCAGGTTTTATACTGAGGTCTATGATTTATTTGGGATTAATTCGACAAATGTAAATTTGTCGAAAAGACTATTTTCTTTACTAAATTGCTTTTGCACCTTTATCACCAATCAGTTGTCTGTATATTCATGGGATTATTTCTAAACTC |
| 700 | NON_CODING (UTR) | ATTTACAGCTTGTAGCAATTATGTA |
| 701 | NON_CODING (UTR) | CTACCATAAAGTCCGTAAGTGAATACAACGAATGTAATTGACATAATAATTGAAAATCATTGACTATACCTAAAATAGTTC |
| 702 | NON_CODING (ncTRANSCRIPT) | GCTCTGGCTATATCAAATAAAAGTGTCAAGAGTGAGCATCCTTGCCTTGTGCTGAATCACAAAGGAATACCTTTCAGTTTTTCTCCATTGATTATGATAGCAGTGGGCTTTTCACAGTGGGCTTTACT |
| 703 | NON_CODING (INTRONIC) | TCTTAGCATCCAATCTTATGGACCATTTTCATACAAAGCC |
| 704 | NON_CODING (UTR) | CTCCAACAATAAAGCACAGAGTGGAT |
| 705 | NON_CODING (UTR) | TTAGATGTCATTGAATCCTTTTCAA |
| 706 | NON_CODING (UTR) | TTCTTAAAGTTTGGCAATAAATCCA |
| 707 | NON_CODING (UTR) | GTGGCCACATCATGCAAATATAGTCTCACCATTCCTAGG |
| 708 | NON_CODING (INTERGENIC) | TCTTGGCAGAACTGCTCTATTGCTCAAGGAAGACTTAGTTTCTGGAAATATTCCCCGGGTGAGTTAAGGGTTGTGTAAAAATGCAAGAATGGAATACGAAATGATTTTCATTTTGATGGTTACTTATGAAGTTTTTGTGTTCCGTAGAA |
| 709 | NON_CODING (UTR) | CATTCATCTTTGAATAACGTCTCCTTGTTT |
| 710 | NON_CODING (INTRONIC) | CAGAGCCAGATCTTTAGACGTGATGGATTCCCAAGTTTCGTTCTTAAAATAGACAAACTGAGGCCAAGAGTGCACCAGCCTGCCAAGCACAGACATGACACCTAAGGACTTTCCTCCCCTAAGTGTGTGGTTCTGGGGAGCCAGCCTTCCTTTGTCCTTCATAACCCCAGTCACTGCCTTTCAGCCTTCTGCCAGGTCTGGGGCTCAGATGGAGATAAGCTTTTCACAGAAGACCCTCACTCGAAAGATCCACCACTTATCTCCCATCTCCGACAGTGCATG |
| 711 | NON_CODING (CDS_ANTISENSE) | ATGTATTTTGTAGCAACTTCGATGGAGC |
| 712 | NON_CODING (CDS_ANTISENSE) | CTGACACGACACTTTTCTGTGGTTTC |

TABLE 6-continued

| SEQ ID NO. | Type | Sequence |
|---|---|---|
| 713 | NON_CODING (UTR) | GTACAATCACTACAACATGCTCTGCCACCCACTCCTTTTCCAGTGAC ACTACTTGAGCCACACACTTTC |
| 714 | NON_CODING (UTR) | CGTCTTTGGTCAGGAACTTTATAATGTGCTAT |
| 715 | NON_CODING (UTR) | AGCAGCCTTGACAAAACGTTCCTGGAACTCA |
| 716 | NON_CODING (UTR) | GCTATCCACAGCTTACAGCAATTTGATAAAATATACTTTTGTGAAC AAAAATTGAGACATTTACATTTTCTCCCTATGTGGTCGCTCCAGACT TGGGAAACTATTCATGAATATTTATATTGTATGGTAATATAGTTATT GCACAAGTTC |
| 717 | NON_CODING (UTR) | TTTGACTAGAATGTCGTATTTGAGGATATAAACCCATAGGTAATAA ACCCACAGGTACT |
| 718 | NON_CODING (INTRONIC) | TGCAAAATAACGACTTATCTGCTTTTC |
| 719 | NON_CODING (INTRONIC) | GCAATAGAAGACACGTCTAGCTTGAA |
| 720 | NON_CODING (INTRONIC) | GAACCATTGGAGATACTCATTACTCTTTGAAGGCTTACAGTGGAAT GAATTCAAATACGACTTATTTGAGGAATTGAAGTTGACTTTATGGA GCTGATAAGAATC |
| 721 | NON_CODING (UTR_ANTISENSE) | AGCGACCACATAGGGAGAAAATGTAAATGTCTCAATTTTTGTTCAC AAAAGTATATTTTATCAAATTGCTGTAAGCTGTGGATAGCTTAAAA GAAAAAAAGTTTCCTGAAATCTGGGAAACAAGACATTTAAAGAAT CAGCAAAATTTCAAATAAAAAATTATGAAAATATTATCCTCATTAG TTCATTTAGTCCCATGAAATTAATTATTTTCTCTGCTTGATCTTGGT GGACAGTTTCATGAAGCTGTCAGTTAGTTCATTAAAGTTTTGGAAA TTCTCAGACAGTGCAGTGGTATCAGAAACTTGTATTCAAGAGTACA GGTCAGA |
| 722 | NON_CODING (INTRONIC) | ATGCCTCATATTGTATCTAGATTGGTCTTAAACATGCTCTGCACTTC TCTGCCTTCATGGAAGACTTTTGCTGATATTTCCTTCACTTGATACA CTTTTGGCTTTTCCACCCTCTCCCTGCCCCCAATTTCTGCTTGCCAG AATAATATCTGTTCTTCTTTCATTCATTTATTTAACAACTATTGAGA CACTGTTGTAGGTGCTTGGATACACCTAGTGAACA |
| 723 | NON_CODING (INTRONIC) | AAAGAAGTGAAGCAAACGGATGGGA |
| 724 | NON_CODING (ncTRANSCRIPT) | TTCTGATGCTGTATTTAACCACTATA |
| 725 | NON_CODING (INTERGENIC) | CTGCCTCAGGGTAATCTGAATTTTCTATCTCAAGTTAGAGATTACTC TTCACCCCTTCCCAAGCAGATATTAAAGTCTCTTATTCTGTTTTTTTC CTTTAAAAAGTATCAGATCTGTCAAGAGTTGTTTCTTCAGAATCTTC TATTGCCAAAAACTGTTCTTATAATCTATTTTATCATTCACTCACTT TGTCACTGATTAACATATTAGCACCAAAGTTCAACCAATGCTTAC |
| 726 | NON_CODING (INTERGENIC) | TTTGCAAAAGCACGGATGTGGATGA |
| 727 | NON_CODING (INTRONIC) | ATGTCCATGTCCATCTTAATGTCTTT |
| 728 | NON_CODING (ncTRANSCRIPT) | AGGTACTGAATGACTAGGAAACAGGAA |
| 729 | NON_CODING (INTERGENIC) | GAGCACCTGATCTTCGGAGATGCCTG |
| 730 | NON_CODING (INTRONIC) | TCTGTGACAGTTGGTATTGTCAGTCTTTCACTAGAGATTTCAATGAG TTAAACATAAGCGACACTCAGTTCATTATTCTTAGTAATGAGGGAT GAAGACAGGACATAAGCAAAGTGAATAACAAAAATAGAAATTTTA TCCACAAAAAATCAATACCTCCTTTGCTCAGCTAATGTGCAATAGT GATAGTCTAGACAAATTAAAGAAATTCCATTTTATTTTAAACACTC TAGTTACTTTTGTGTAGTCTAACATATTGTACATATTAGGTACTCAC TAAATCTCCTTTGATTGGTTCCTTAGCCTTACTCTGAGATGTTTTAT TCAGTTAACAAATGCTTACATAATGCTTGCAGTGAGC |

TABLE 6-continued

| SEQ ID NO. | Type | Sequence |
|---|---|---|
| 731 | NON_CODING (INTRONIC) | GACAGATCTTCTTGTGTTTAGTGAA |
| 732 | NON_CODING (UTR) | TAGGATAATTGGTTCTAGAATTGAATTCAAAAGT |
| 733 | NON_CODING (INTERGENIC) | TTTTGGTAAGTGCTCAGGCAACCTG |
| 734 | NON_CODING (ncTRANSCRIPT) | ATTGCATGAACACATATTTGCTGCCAGAAATAATTATTACATTGCCTTCTTCATATTGAAAACTAACAGTTCTTAAAAGGGAAGCAGAGGTGTTAAAGAGCTTGGTTACAATTTATTGCTAAGAGTTTGGACTTTACATTAGGAAGATAGCCTCTGAAATACAACG |
| 735 | NON_CODING (UTR) | AATAATAATATTTAGGCATGAGCTCTT |
| 736 | NON_CODING (INTRONIC) | TGGTAATACGGGACTTTATTTGTGA |
| 737 | NON_CODING (ncTRANSCRIPT) | TAAGTAGGGAGTGGACTCCCTTCTC |
| 738 | NON_CODING (INTRONIC) | TGCCCTCTATAAACTTCGGACTGTGCACTCACATTAACAGTGTGTAAAAGGACTTGTTTCTTGTACACATTTGGCTAACATTAACTATACTAAATCTTTTCAAGCACCTGATGTAGTTTCTTTAATTATAGGTAGATTTGGACATTTTTTGGATACATTTCGTGGCTGTTTAACTTCTTTCCTTTAAATTGACTGAATGGCTTTGTCCATTTTTCTATTGAGTCATTTCATTTTTTTTCTGATTTGTTTGGATTTCTTTTTGTATAATTTATATTTTCCCTGGATAGTTGCAAGAAATTGTTAATAAATTGTTCTCCCTGGCTCCTTTCCTGTGGTATATCCCTGGTTCCCATGTCGTTATCTCTCCTTACTGTCCTCATTTCGAAGGCACACTTTC |
| 739 | NON_CODING (INTRONIC_ANTISENSE) | GCAACACCTCTTCCTCTTATTGAAA |
| 740 | NON_CODING (UTR) | GTAATTCGTATGCAAGAAGCTACAC |
| 741 | NON_CODING (INTRONIC) | ATTTAGGGATTAGTTACAGTTATGCTGTTTCGTAAAATTGGCATTTGATTCTATATTTTATGCATAGATTTTTTTTAAAAGCACTCTTCTGTAGAATTGCACTTAGACCA |
| 742 | NON_CODING (INTRONIC) | GCCTTCTTGATCTGGAAGTCAGAGG |
| 743 | NON_CODING (INTERGENIC) | TTTAGCATGAACTGGTGTTGAAATT |
| 744 | NON_CODING (UTR) | AGATGAGCTGCTCAGACTCTACAGCATGACGACTACAATTTCTTTTCATAAAACTTCTTCTCTTCTTGGAATTATTAATTCCTATCTGCTTCCTAGCTGATAAAGCTTAGAAAAGGCAGTTATTCCTTCTTTCCAACCAGCTTTGCTCGAGTTAGAA |
| 745 | NON_CODING (INTRONIC) | ACTTTACAGTCAGAATCAGACCACT |
| 746 | NON_CODING (CDS_ANTISENSE) | TGAGGACCTTGGTAATGTTTCTTCCTG |
| 747 | NON_CODING (ncTRANSCRIPT) | TTGCTTTGGTGGAATATGTATGCTA |
| 748 | NON_CODING (INTERGENIC) | TCACAACTCTATAAACCCAACCGAA |
| 749 | NON_CODING (CDS_ANTISENSE) | AGATGAAACAACTGAGGGCCAAAAA |
| 750 | NON_CODING (ncTRANSCRIPT) | GAGAATGAACTCCACCACTTACGAA |
| 751 | NON_CODING (INTRONIC_ANTISENSE) | ATGTCAGCTCCTTGTTTACCAATAA |

TABLE 6-continued

| SEQ ID NO. | Type | Sequence |
|---|---|---|
| 752 | NON_CODING (INTRONIC) | ACAACTATCTTAACTGCAAAACTTGTGTTCT |
| 753 | NON_CODING (INTRONIC) | ATGGGAGTAGGAAAGCTAATCAAAAA |
| 754 | NON_CODING (UTR) | TAAATCTATAATATGGCTGGAGGCA |
| 755 | NON_CODING (UTR) | GCTTCTCTCCAGACTTGGGCTTAAG |
| 756 | NON_CODING (ncTRANSCRIPT) | AAAAGAAGAGTAGTCCAAGGTGTGG |
| 757 | NON_CODING (UTR) | TTACTTAGTCTTCTATGTATAGCTATCAAGGA |
| 758 | NON_CODING (INTRONIC) | ATGCTGCAAAATGTACCAGTACCTG |
| 759 | NON_CODING (INTERGENIC) | ATGACTCTGACTAGCCAGCAGGAAG |
| 760 | NON_CODING (INTRONIC) | GCTGTCCTTTGTGTCAGCATCATGA |
| 761 | NON_CODING (INTRONIC) | AAGTGAAGTTTGAAGTCTGCTCTCTGCAAGAGGGTGGGAGTGGGT GGGAGAAGAGGCTTGTTTTAAAAGCCAAAAACAGAAAGTAAAAGA AATGGGAAAGTAAAACCAAAGCAGCAAGTGACTCTCTTCTGATGT GCACTTTTCATTTTCTCCCCCACATTTCAGTGTTAGAAAGAAAACG AGAGGAGCTAGGGAAAGAAGGAGTTGGGGACAGAAGACTAAGAT TTCAACGTGAAATTCCATTTACAAAGGCTTTACTGCAAACAATAGC TAATTTAGTCCTGTAAACATGCATTTATCATACATTTTAATTTTAAT ATTAAAAATACTGCATGTAAATGTTCTGAACTAAAGGTAGATAGCA ATATGTAGTTTGCCATAAAATGAATGCATGTCTTATTCTTTTCCATA GTTCTTCATTAATGAGACTTGTAGTCAAGAATAGATTGAAGATACC ATTCTCCTTGTGTAGTTCAAAAA |
| 762 | NON_CODING (INTERGENIC) | GCACAGCACAGCTTGGGTTATCTGG |
| 763 | NON_CODING (INTERGENIC) | ACCCTGCCCATTGGATGTTAGCTGA |
| 764 | NON_CODING (INTRONIC) | AAAATTTTATCATCTGGTCATGGTG |
| 765 | NON_CODING (INTRONIC) | ATTTGGGACAGCTTTACAATGTTAT |
| 766 | NON_CODING (INTRONIC) | TCAGGAACCTTTCAAAAATACATGC |
| 767 | NON_CODING (INTERGENIC) | CCCCTACCCTTTGTTCTCAGCAGCAAG |
| 768 | NON_CODING (UTR_ANTISENSE) | GACACTGTGAGCTTGATACTGCTGG |
| 769 | NON_CODING (INTRONIC) | GAAACCAAATGGTGTGCCACAAATTAGGGAACACAAGCAAAC |
| 770 | NON_CODING (INTERGENIC) | GAATGATCCATCTTCCTTAAGGCTGCTACACCATAACTAGGAGCTT TAAAAAAAGGGGGGGGCATTTACTCTCTGAGGCACTCAAAAAAG CACATGCTTTTAATTGAGGGATGGGGGTGACAATGGATCATTCTGT TGATTTTAACTATCTCATATTTGTTAACAGCATCATTTCCATGGATA GCTTTCTGAAAGACTGCCTATCCCACTTAGAGGTGAGGAGAAGTAAT AGGGGAGGAAACCCTGCCGAGCTGCAAAAAG |
| 771 | NON_CODING (INTRONIC) | GCCTAGGTGACCCAAAGTAATGGGA |
| 772 | NON_CODING (INTERGENIC) | CCTCCGCGCAATTCAGCTGCAGCTG |

TABLE 6-continued

| SEQ ID NO. | Type | Sequence |
|---|---|---|
| 773 | NON_CODING (CDS_ANTISENSE) | CCAGCTCCACTGAAACAGGGGAAAT |
| 774 | NON_CODING (INTRONIC) | GGTGCCCTAACCACTTCCTGAAATCTGGCCTGATTTTTAATAGCTTT TACCTAAGTTCCTCAGATTCTCTGATTCATAGTTTTCAAAATATCTT GTCTCCTATTTTTGTATATTGTTCTCGGCTTCTTCTGCATTTTAACTC AAGTATAGGCAATTCTCACTATATTTACTGGA |
| 775 | NON_CODING (INTRONIC) | TGAATGCCATAGTAGTGAATGAATACT |
| 776 | NON_CODING (INTRONIC) | CCTATATGGCATCGCAGTCTGCAAA |
| 777 | NON_CODING (ncTRANSCRIPT) | GTGGCTCTCAGACTTTACTAATCAT |
| 778 | NON_CODING (UTR) | ACTTGCTATACATAAGATGATTCAC |
| 779 | NON_CODING (INTRONIC) | GTATGCTTATCTGTTTATCTTAGCCAAA |
| 780 | NON_CODING (INTRONIC) | ATGCTGAAATACTTCTGCCTTTTAG |
| 781 | NON_CODING (CDS_ANTISENSE) | GTACTCATGACTCAACCACAGAAGA |
| 782 | NON_CODING (INTRONIC_ANTISENSE) | GCAGAAACGATGCAGTGGAGCATCAG |
| 783 | NON_CODING (INTRONIC) | ATGAATTCGGTTCCGTAAGTTTGAG |
| 784 | NON_CODING (INTRONIC) | CTGTAAGAGTCAGAGCTTTCTGGGA |
| 785 | NON_CODING (UTR) | CTTGATGTGACAGAGTAGTGTGTTTTCAT |
| 786 | NON_CODING (INTERGENIC) | CATAAAGAATGCACATGAACAGCAG |
| 787 | NON_CODING (INTERGENIC) | ATGCTGTACCCCTCGGAGACAAATTCCACCCTCGAGTGCG |
| 788 | NON_CODING (INTRONIC) | GCATGTTCAGAATCTTGGATCCCTAAGTTCAATATATTGGACATATT TAGGAACTCTGGAAATTATGTTGTTTTCACATATCTAGTAACTTACT AGATGAATCAGTAGATTTCATTAAAGTATATCTAATAACAGATAAT TATGATGTACTTCTGGGTTGACATGCATGTCTCTCATTATCAGCTAT CAGTATTAGTGTCATGCTTTGGAGACAGTTATCTTTTGAAGGTTTTG GGGTTCTTATGAACCTCATTTTTCCCAGGAAGTTTCTGTAATTCCTC CTATGCCTATTCTTGTCTTTTCTGTCTGCTTGCAGTGTAAGTTATTTA GATCAGAGGCAATTATTTTTCAGGAAGAAAGAAATCATCAAGTGA CACTCCTAAAGGCAGTA |
| 789 | NON_CODING (INTERGENIC) | TTTGAAACAGGTGACTCTAGCCATG |
| 790 | NON_CODING (INTRONIC) | GGATGTTCGGAGACCATTTTTCCAA |
| 791 | NON_CODING (INTRONIC) | TTCTGCTTCTGCTATAGGAGAGTGA |
| 792 | NON_CODING (INTERGENIC) | TGCATGTGCTTGTTGATACTCCGCA |
| 793 | NON_CODING (INTERGENIC) | ATAAAACTGTCAGGCCCAAATAAAT |
| 794 | NON_CODING (INTRONIC) | GACTTTGAGACAAGCTTAGGCATCA |

TABLE 6-continued

| SEQ ID NO. | Type | Sequence |
|---|---|---|
| 795 | NON_CODING (UTR) | CTCCTCTGGCCTCTAATAGTCAATGATTGTGTAGCCATGCCTATCAG TAAAAAGA |
| 796 | NON_CODING (CDS_ANTISENSE) | GAATCAAAACAGACGAGCAAAAGA |
| 797 | NON_CODING (ncTRANSCRIPT) | TTGAAGCCAGCCTGAACAATGGCAG |
| 798 | NON_CODING (INTRONIC) | ATCTCTGGGGTGTTACAGAGACAAA |
| 799 | NON_CODING (INTRONIC) | GATATTCAGAATTCAATTGCCAAGTGCCAAA |
| 800 | NON_CODING (INTRONIC) | ATTTGCATCTTTAAGTTCTACATTCACTTC |
| 801 | NON_CODING (UTR) | AGAACTTCAGCCAAAGCATCTGAGA |
| 802 | NON_CODING (INTRONIC) | CTCAGGATCCCAACCTTTATGTATCAGTTTGCCCTCTTGTTGAATAT ATTTACTGTCCAGTGCTACTCCCTCTATCTGTGTGAAAAAATTATTT CAAATTTCCACATCAGGAAAACATCCATGAATGCTTGCCAAGACAA CCGGGAAAAAAACAGTAAGGTCATATTCATGACTGTAAAACCCTG TTTC |
| 803 | NON_CODING (UTR) | TTCAAGTAGACCTAGAAGAGAGTTTTAAAAAACAAAACAATGTAA GTAAAGGATATTTCTGAATCTTAAAATTCATCCCATGTGTGATCAT AAACTCATAAAAATAATTTTAAGATGTCGGAAAAGGATACTTTGAT TAAATAAAAACACTCATGGATATGTAAAAACTGTCAAGATTAAAAT TTAATAGTTTCATTTATTTGTTATTTTATTTGTAAGAAATAGTGATG AACAAAGATCCTTTTTCATACTGATACCTGGTTGTATATTATTTGAT GCAACAGTTTTCTGAAATGATATTTCAAATTGCATCAAGAAATTAA AATCATCTATCTGAGTAGTCAAAATACAAG |
| 804 | NON_CODING (INTRONIC) | TTATGTCAAAACATTTCCAGAGACT |
| 805 | NON_CODING (INTRONIC) | GCAAAGCAGTTTAGCAATGACCAGATGTAATTCATTTTGGAGTTCT AAGTTTGAACTTAATCAATATGAACTTACAGCCATGGAAGAAGTGA TTATCATTTGTTATTTGCTGGCACAAGAA |
| 806 | NON_CODING (UTR) | GGGATAGTGAGGCATCGCAATGTAAGACTCGGGATTAGTACACAC TTGTTGATTAATGGAAA |
| 807 | NON_CODING (INTRONIC) | TGTCACCTCTTAGTACAAAGCCATGCCAGACACTGCACCTACTCTG CACTCTAATGAGAACAATCCGGAAAGGATGATTTTCAAGGGAGAG TGACCTCTTCCTGGAGATCTGAGGTTATGTTACAGTATTGTGGAGTT TTGTTGCTTAAAATTCTCCTCCTGTCCTCACAGGCAATTTTGCTAGA GTTGCAATCCTCACATTTG |
| 808 | NON_CODING (UTR) | GATCCAGCAATTACAACGGAGTCAAAAATTAAACCGGACCATCTCT CCAACT |
| 809 | NON_CODING (UTR) | TGCCAAGGAGGCGTATTCTTCAATATTTGGAATAGACGTGTTCTC |
| 810 | NON (INTRONIC_ ANTISENSE) | GTGCATACATTATGATACAGCCCTGATCTTTAAAAGGAGCAAAAAT CAGAGAATCGTATGTCTTAAAGAACTATTTCCTTACTTTTTTATGCT AGGTAATGCCCATGTGACAAACATGTAAATATTCATCAAAGACCAC ATGTATATATTTTAAAGGCATTTTTTCTTCTCCCCAACTGTATGTAT AGCTAGAATCTGCTTG |
| 811 | NON_CODING (INTRONIC) | ATTCTTTACTGAACTGTGATTTGACATT |
| 812 | NON_CODING (INTRONIC) | GTTAGTGATATTAACAGCGAAAAGAGATTTTTGT |
| 813 | NON_CODING (INTRONIC) | TTAAGTGAGGCATCTCAATTGCAAGATTTTCTCTGCATCGGTCAG |
| 814 | NON_CODING (INTRONIC) | CTTCATGCTTAATACAAACACTTCTAATGGCTCATTGATTATAATGT ATTATCACATTTTATTTTATCCTCAGACATGATTGACTTTCTAAAGG CTTGAATCAAA |

TABLE 6-continued

| SEQ ID NO. | Type | Sequence |
|---|---|---|
| 815 | NON_CODING (INTRONIC_ ANTISENSE) | ATGGCAGGATTCAACATCTATTTGCTTTATAAGATATTGATAAAAA TGTATCTCATTCATAATGGTGTAGCAACTACTTTTTAATGGGGTTTT ACTATGCTCTTTTGTTTCCATTGGCTTTATAAATTAGGATTTGACTTT GCTTTAATTACATGTTTTTAATTACCCAGTTATCTAGTTATCAAATG AAAATGTTATTACTAATATAATTGGAACTCATAAAATGCTTAGCTG |
| 816 | NON_CODING (INTRONIC) | TTTCCTTATTTCATGATTGTGGCCATT |
| 817 | NON_CODING (INTRONIC) | TTATGCAGATAAAACCTCCAGGTAGCAGGCTTCAGAGAGAATAGA TTATAAATGTTTCTTAGCAGACTTAAAAAGGTGCCAGAAGATCAGG GAAAAGACCTGGAAAGGGAAAGGGAATCTCTATAGAATGTCAATT ATCCTCACAAGAGATAGCTTTGTAGGGCCATTTCAAAATATATCAA AGGAATATATTTTAGGGTAAAATACTTCAGTTTCTTTCAGGGCCTTC TATGTGCCATATGATGCTGTACTAAAGTAAGGCTGGAATTT |
| 818 | NON_CODING (INTRONIC) | CTTCTGTTATCTCTTATTCCAGAGAAAAATCTGCTGTCACTAGATTA AATGCACTTTTTGAGTTGTCCTAATGACATCAGTTTGGTTTTCATTT TGAAAGAATTAGGGCATCTGACATTTCAGCCTTATCATAGTCCATT TTCAATT |
| 819 | NON_CODING (INTRONIC_ ANTISENSE) | TGAGGTGGCTTTGCCATTTTATACCCATAATTAAATAAAAGGGCAA AATCCCCCCTGATAAATACCATGTTTATCATGGCACATAAAACTTT ATGGCAGAAAGCCAAGGCCAATTGACATATATATTTAAAGGTACC ATGGAAAGTAAATGCTAACTCTGAATTTAAAACAGTGGGAAGATG ATTAGTAAGAGTTGGTTTCTTGAAAAGGAATTGTTCTGGTAATAGT CATCTTTAATGACTTCCACGGATTATTCAGTGTTTCTTTAGGGATAT GCATAGGACACTGGTGCTTCAGTAGAAACCCCAGTTTTGGTGTATT AAAGATACATCCATTCTTGACTGATCTTTAATCTAGAGTGTGGTTTT AGCCAAGTCTTTGAATCTCATTTAGTC |
| 820 | NON_CODING (UTR) | TTTAAGGTGAAATCTCTAATATTTATAAAAGTAGCAAAATAAATGC ATAATTAAAATATATTTGGACATAACAGACTTGGAAGCAGATGATA CAGACTTCTTTTTTTTCATAATCAGGTTAGTGTAAGAAATTGCCATTT GAAACAATCCATTTTGTAACTGAACCTTATGAAATATATGTATTTC ATGGTACGTATTCTC |
| 821 | NON_CODING (UTR) | TCACTGTGTAGAGAACATATATGCATAAACATAGGTCAATTATATG TCTCCATTAGAA |
| 822 | NON_CODING (INTRONIC) | GCAACTTTTCCGTCAATCAAAAATGATTCTG |
| 823 | NON_CODING (UTR) | GGTAAAGGATAGACTCACATTTACAAGTAGTGAAGGTCCAAGAGT TCTAAATACAGGAAATTTCTTAGGAACTCA |
| 824 | NON_CODING (INTRONIC) | CCTACCTCAGAGCTTCACATATATATATGAAAAAAAAAGTGCTTCA AATAACTAATAAGTTTAGGAAGTAGGCCTATCCTAAAGCACAAAA ATATTTTATTTATGAGTAAAAAATATTTTTATAAGTACATAATTATT TCAACAATATGTTACTTTTGTCATTTTTCCTACATATTCTTTTATATA TTTTGAACTGTAGACATGTAGCATATTCTAGCACATTGCAGTAATG ACAACT |
| 825 | NON_CODING (INTRONIC) | AAGGAAGATATTACTCTCATAATTCCATACTGGTGGAAACCTATCT GAGAATGTCTATTTCATTAATCCTCTTGAGTATGTTC |
| 826 | NON_CODING (UTR) | TATTCTTAGGGCTTTTGTGTATGTCTGACTTGTTTTAAATAACTTCC TCAGCAATGCAGACCTTAATTTTTATATTTTTTAAAGTAGCTAACA TAGCAGTAGGCACTTAAGCATTTAGTCAATGATATTGGTAGAAATA GTAAAATACATCCTTTAAATATATATCTAAGCATATATTTTAAAAG GAGCAAAAATAAAACCAAAGTGTTAGTAAATTTTGATTTATTAGAT ATTTTAGAAAAATAATAGAATTCTGAAGTTTTAAAAATGTCAGTAA TTAATTTATTTTCATTTTCAGAAATATATGCATGCAGTTATGTTTTA TTTGATTGTTGACTTAGGCTATGTCTGTATACAGTAACCA |
| 827 | NON_CODING (UTR) | GAATATCACTACCTCAGGTTACGGTACACAGGCTATAATTGATGAT GATG |
| 828 | NON_CODING (UTR) | TCCTGTCCCTTGACCTTAACTCTGATGGTTCTTCAC |
| 829 | NON_CODING (UTR_ANTISENSE) | TGGCGCCACTATACTGCTAAACCTATGCATGAAGGTAGTGACTAGG ATGGAAATCTGTCAGTGCTACAAAAATATGTATGAACAAAATAATT TTCACCCTTTGATAAAGCTACAAGATATAAAATTTAGAATACTTAT ATAATTTCATACTAGATATGTGAAAAATATGCCATGCTAGAACCAT CTTGTT |

TABLE 6-continued

| SEQ ID NO. | Type | Sequence |
|---|---|---|
| 830 | NON_CODING (ncTRANSCRIPT) | CATTGAGAGATACAAAGCGTTTTCTAGAGAGTGTTTCT |
| 831 | NON_CODING (ncTRANSCRIPT) | GTGACTATAGAGGCTAACAAGAATGGA |
| 832 | NON_CODING (UTR) | GAGGCAGCCCTTTCTTATGCAGAAAATACAATACGCACTGCATGAG<br>AAGCTTGAGAGTGGATTCTAATCCAGGTCTGTCGACCTTGGATATC<br>ATGCATGTGGGAAGGTGGGTGTGGTGAGAAAAGTTTTAAGGCAAG<br>AGTAGATGGCCATGTTCAACTTTACAAAATTTCTTGGAAAACTGGC<br>AGTATTTTGAACTGCATCTTCTTTGGTACCGGAACCTGCAGAAACA<br>GTGTGAGAAATTAAGTCCTGGTTCACTGCGCAGTAGCAAAGATGGT<br>C |
| 833 | NON_CODING (INTRONIC) | GCTCCCATTTTTTGCACTGGAATTACTTGCCAAATGGCCTTTTCACC<br>ATCTGAAATAGTTAATGTATTCACTTCTTAAATGAGCAAAAGTCTT<br>CAAACTATTAAGAAAGAGCCATAGACTGAGTGCAGGCACCAGTGT<br>GCTCTTATTACTGTGTCAATTAAATGAATGTATTTGAATGTTTGGAT<br>ACTTACCTCTGAATG |
| 834 | NON_CODING (INTRONIC) | CCTCTTACACATGACAAGTTTTGGCTTGTTGGTTTTTCAGAAGCGAA<br>GAAATATGGCATTGAAAATGATGCTGAGTGTGAAGAAATGTAGAG<br>GACTCATTTTTGATCCCCCAGGGAGACCTATTTTTACTATAAATTTA<br>CTCCAATAATGAGATGTGTAGGAGGATTTACCATTACATAGTTTTA<br>ATACATTTCAGCGTCATTGGAGACTAAACATTTTCTTTCAGAGTAA<br>CTGATAGTTTCTAGCTACCTAAATAAGGATCTTTTCTAAATCTGACA<br>AGAAATTTTGAAAGTTTTTTCACAATGGCATTCTAGAGTCATCTCTA<br>GAATGATGATATTAGATATTAATCATTATTTTATAAAGAAGACT<br>TAATGAATACATCTGATGAATGCATTGGTTATAAGGCTAATAGTTT<br>TACATATAAGCTAGAAACAAAATGAGTCTGTTTGTGAAATTATCTC<br>CTCTACTCTAGTGGAAGAATCTGTAGTGAGATTACTAATAAAGGAC<br>TAATGTTTTATCATTTGATTTGTTCAGATGGGTAATGCAAAAAAAA<br>CTTTAGCCTTCTGTGAAGTAACCTTAGGA |
| 835 | NON_CODING (UTR) | GTAAACAGATGTAATTAGAGACATTGGCTCTTTGTTTAGGCC |
| 836 | NON_CODING (UTR) | TGAGGGTATCAGAACCAATACTGGAC |
| 837 | NON_CODING (INTRONIC) | CCCTGTAAAACCCTTGGCTTCTATGAAGGCCATTGAATAACTGCGA<br>TATGCCTGTGAAAAATCACAAAAGGTGCAAAGTCCCCTCGCAATAA<br>AGATCAGTCACGATGAGATTTGCACCAATTGAACTTTTAAGATTGT<br>AAAATATTTTGTCTTGCAGAGCTGATGCATATCCATTAAAAAGTAT<br>ATCTTAGTGAGCCTTATCTTCAAGTTAGCAGCGAGAAGAGTAACAA<br>AAACGTGCCAATTTAAAATACTGAAATTCTGGGAAAATGTTTTACT<br>TATGAGTATTTCTTAGTATTGGGCTAGTGTGATAAAGATGGCAGCA<br>TGTTTTGATATCTACTCAGAAATTCATTTCACAAACGAAGATGTTTT<br>AGAGTTGGTGAACATACCTGGCCCATTACTGACAAAACCAATTACC<br>GTATTTATTGGTAATAGAGCTGTTTACAGGATGCTCACTGTAAAAA<br>GAAAGAGAAAGAAGAAAAAAAATCCTGCTTTTT<br>TTTTTTTTATCTCTCTCTTTTGAAACAAGAGAACAATCCCATTCAC<br>ACATAGTAGCTGCCTTCTTTG |
| 838 | NON_CODING (INTRONIC) | GATCCTGCTATGATTCTTCACTGGGGGGAAAGAAGATACATTTAGA<br>AAATTGGTTATCTCAGATTCTTAGTATGGTTTTAGTTAGTTAGTTTT<br>ACCACTTGGTAGAGTTAATGATTTGACAAATGACATTTGCTTCTTAT<br>TATCAGCCAGTTGGTTGCTAGCTTTAAAGA |
| 839 | NON_CODING (INTRONIC) | ACATATTTTCAAGTTGAATGTCTTCTGTTAATTTCTCTTTATTTTGTT<br>TGCCAGTGAATATAGAACCTCTTTT |
| 840 | NON_CODING (UTR) | CTTTTGAATTACAGAGATATAAATGAAGTATTATCTGTAAAAATTG<br>TTATAATTAGAGTTGTGATACAGAGTATATTTCCATTCAGACAATA<br>TATCATAAC |
| 841 | NON_CODING (INTRONIC) | TTTAGATGTTTAACTTGAACTGTTCTGAATT |
| 842 | NON_CODING (UTR) | TTCAATATTAGCAAGACAGCATGCCTTCAAATCAATCTGTAAAACT<br>AAGAAACTTAAATTTTAGTTCTTACTGCTTAATTCAAATAATAATTA<br>GTAAGCTAGCAAATAGTAATCTGTAAGCATAAGCTTATGCTTAAAT<br>TCAAGT |
| 843 | NON_CODING (ncTRANSCRIPT) | CATTGCTGTAATCTAGTGAGGCATCTTGGACTTCTG |
| 844 | NON_CODING (INTERGENIC) | TATATGCATCCTTTGACTTTGAATGGCTGCCATAATTGTTTACTGAG |

TABLE 6-continued

| SEQ ID NO. | Type | Sequence |
|---|---|---|
| 845 | NON_CODING (ncTRANSCRIPT) | TGTCAAACAATGTGTAACTCCAGTTATACAAACATTACTGTATCTC ATTGGGGATACGAAGCTCTACACACTTGAAGATGGTG |
| 846 | NON_CODING (ncTRANSCRIPT) | GTCCAGACTTGGAGTACAAGTAATAAGAAGAATAAAACTTAATCC CTTAAGTAGATTCACCATAAGTTAGCTCAGAGCAATTCCAGTGCAA GTATGGTCTGTGATCC |
| 847 | NON_CODING (UTR) | GCATTGGATTTACTAGACGAAAACCATACCTCTCTTCAATCAAAT GAAAACAAAGCAAATGAATACTGGACAGTCTTAACAATTTTATAA GTTATAAAATGACTTTAGAGCACCCTCCTTCATTACTTTTGCAAAAA CATACTGACTCAGGGCTCTTTTTTTCTTTTTGCATATGACAACTGTT ACTAGAAATACAGGCTACTGGTTTTGCATAGATCATTCATCTTAATT TTGGTACCAGTTAAAAATACAAATGTACTATATTGTAGTCATTTTA AGTACACAAAGGGCACAATCAAAATGAGATGCACTCATTTAAAT CTGCATTCAGTGAATGTATTGGGAGAAAAATAGGTCTTGCAGGTTT CCTTTTGAATTTTAAGTATCATAAATATTTTTAAAGTAAATAATACG GGGTGTCAGTAATATCTGCAGAATGAATGCAGTCTTTCATGCTAAT GAGTTAGTCTGGAAAAATAAAGTCTTATTTTCTATGTTTTATTCATA GAAATGGAGTATTAATTTTTAATATTTTCACCATATGTGATAACAA AGGATCTTTCATGAATGTCCAAGGGTAAGTCAGTATTAATTAATGC TGTATTACAAGGCAATGCTACCTTCTTTATTCCCCCTTTGAACTACC TTTGAAGTCACTATGAGCACATGGATAGAAATTTAACTTTTTTTGT AAAGCAAGCTTAAAATGTTTATGTATACATACCCAGCAACTTTTAT AAATGTGTTAAACAATTTTACTGATTTTTATAATAAATATTTTGGTA AGATTTTGAATAATATGAATTCAGGCAGATATACTAAACTGCTTTT ATTTACTTGTTTAGAAAATTGTATATATATGTTTGTGTATCCTAACA GCTGCTATGAA |
| 848 | NON_CODING (INTRONIC) | GCTTTGTAAATCAAACTGTGGACTAAATA |
| 849 | NON_CODING (INTRONIC) | GCTGCTCTTCATTTGATTTCGAGGCAAG |
| 850 | NON_CODING (INTRONIC) | TCTAGAAGGATTTATTGGCTTCATCAGACATAGGCTAGGATTCTCA CGGG |
| 851 | NON_CODING (INTRONIC) | AAGTGGCAGTACAACTGAGTATGGTG |
| 852 | NON_CODING (CDS_ANTISENSE) | CCATGGATTAGAAGCATTAGTTCTCAGTACTTGAAGACAAACTTCT AAAAAGAAAATATATGCTCTGAACATCTGAAATGGGCTAGACTTTC AAGTAAAATTGCTTCATTTCTCATTAACTGAAGAGCTATTGATCCA AGTCATACTTGCCATTTAATGTAAATTATTTTTAAACTTTGCTGTAC AAAACCATTAAGTG |
| 853 | NON_CODING (UTR) | GAAAAAGGGGTATCAGTCTAATCTCATGGAGAAAAACTACTTGCA AAAACTTCTTAAGAAGATGTCTTTTATTGTCTACAATGATTTCTAGT CTTTAAAAACTGTGTTTGAGATTTGTTTTTAGGTTGGTCGCTAATGA TGGCTGTATCTCCCTTCACTGTCTCTTCCTACATTACCACTACTACA TGCTGGCAAAGGTG |
| 854 | NON_CODING (INTRONIC) | GATTGAAAGCCAGCTATTTGGTAATGTTTG |
| 855 | NON_CODING (INTRONIC) | TTTTATGACCTAACAGCACAGATTGTGTT |
| 856 | NON_CODING (INTRONIC) | TCATCTTTGCCTAAACAGAGATTCT |
| 857 | NON_CODING (INTRONIC) | TCTGTAACAGTGATTCTCTTGGGTCATATAAAGGACTGAGTTATGG AGTTACCTACCCTCTTCGACTCATCTTTTAATTTGTCATAGAAAAAC AACTGTTGTACATTGTGTTAAAAGTTAAATTCTATGGCCAGAGTGT GATTTGGAAAAGAAAACTGAAGTAAGTTGGAAGCAGAGTGAAGAA AATAACTCTGCCATTTTCTTCCAACTCACCCTACAGCATCTCTGTTT TCCAGCCTCACTGGGTTAAGTCTTCAAATGTAGCCCTTTGCTTCTAA GACAATCCCATGTTACAAAGCATCAATAATCCTCCTCTGAACATTT TCCTCAAAAGTTCTAACTACAAAGCAGTTAGCCCTGATGTTCTGAT AAAAGTCTAA |
| 858 | NON_CODING (INTRONIC) | CCTTAAGCTGCTCGATTTCTTAAAG |
| 859 | NON_CODING (INTERGENIC) | TGGTTACCAAAGGCAACAGTTGTTATCCAGTGGG |

TABLE 6-continued

| SEQ ID NO. | Type | Sequence |
|---|---|---|
| 860 | NON_CODING (INTERGENIC) | TGGGTATCAGTGGATACACACGATGCAACAA |
| 861 | NON_CODING (INTERGENIC) | AGAGAGGCAACACTTATTATCCACAGGGTAACAGTGGTTACCAGC GATGCAATACTTATTATCCACCGGGTAACGGTGGTTACCAATGAGA CAT |
| 862 | NON_CODING (INTERGENIC) | GGCAACAACTATTATCCACCGTGTA |
| 863 | NON_CODING (INTERGENIC) | GTACCATTGATTACCCATGAGACAATGCTTATTTTCCCCCGGGGAA CAGTGGTTACCCTAGAGGCAATACTTATTATCCACAGGGTAACAGT GATAACCCTAGAGGCAATACTTATTATCCACTGGGTAACAGTGGTT ACCGACAAGGCAACACTTATTATCCAAAGGGCAACAGTGGTTACCC AGGAGGAAACAGGTATTATCCACCG |
| 864 | NON_CODING (INTERGENIC) | ACAGTCGTTATCTATGAGGCAGTACTTATTATCCACCTGGTTACAGT GGTTACCTGGGAGGCAATGCTTATTATCCACCGGGTAACAGTGGTT ACCCTCAAGGCAACAAGTATTATCCACCAGGTAACAGTGGTTACCC TAGAGGCAACACTAATTATCCATTGGGTAACAGTGGTTACTCGCAA GGCAACAATTATTATCCAGCAGGTAACAGTGGATACATGCGATGCA ACAATTATTATCCACCGGGTAACAGTGCTTACCCGTGAGGCAACAC TTATTATCCACGGGGTAACATTGATTACCCACAAGGCAATACTTAC TATCCTCTGGGTAACAGTGCTTTC |
| 865 | NON_CODING (INTERGENIC) | TAAACCAGGTATCAGTGGTTATGCATGAGGCGACACTTATTATTCA C |
| 866 | NON_CODING (INTERGENIC) | TAACATTTAGTATCCACTGGGTAAC |
| 867 | NON_CODING (INTERGENIC) | TTACCCATGAGGCAGCAAATATTATTC |
| 868 | NON_CODING (INTERGENIC) | TATCCACTGGGTCACAGTGCTTTTCCACGAGAGAATACTTATTATCC AATGGGTAACAGTGGTTACCCATAAGTCGATACATATTATCCACCA G |
| 869 | NON_CODING (INTERGENIC) | TGCGTAACAGTGGTTACCAACAAGACAACACTTATTATCCACTGGG TAACAATGGTTACCCACAAAACGTCACTTATTATCCACAGGGTAAC AGTGGTTACCCACGAGGCAACACTTATTATCCATGCATTAACAGTT GTTAC |
| 870 | NON_CODING (INTERGENIC) | AGGATCCACTGGGTACCAATGGTTGCCCACGAGGCAATACTTACTA TCCACTGGGTAACACTGGTTTCCCACGAGGCAACACTTTTTATCCA CCAGATAACAGTGGCTACGCACGAGATAACACTTATTTTCCACAGG GTAAGAATTGTTACCCACGACACAGCACTTATTATCAAGTGGGTAA TACTGGTTACGCAAGAGGCAACACTTATTATAAACCGGGGAACAGT GGTTACTCACAAGGCAATACTTATTATCCACAGGGTAACAGTTGTT ACCCACGAGGCAATACTTATTATCCACTGGGTAACAGTGATCACCC TAGAGGCAATACTTATTATCCACTGGGAAACAGTGGTTACCTACGA GGCAACACTTATTATCCACAGGATAACAGTGGTTACCCATGAGGCA ATACTTACTATCCACCAGGTAACAGTGGTTACCCATGAGGCAATAC TTATTATCCACTGGGTAACAGTGACTACCCATGAGGCAACACTTAT TATTGACCAGGTAACAGTGGTTACCCTAGAAGCAATACCTATTATC CAACAGATAACAGTGGTTACCCATGCGGTAATACTTATTATCCAGT GGGTAGCAGTGGTTACCCATAAGACAATCCTTATTATCCTCCGGGT AACAGTGGTGACCAATGAGGCAATACTTAGTATCCACCGGGTACCA ATGGTTACCCACGAGGCAATACTTACTATCCACCAGGTAACACTGG TTTCCCACGAGGCGACACTTAATATCCACCGGGTCACAGTGGTTAC CCATGAGGCAACACTTATTATCCACAGGGTAAGAGTTGTTACCCAC GAGGCAACACTTATTATCCAGCGGGTAACACTGGTTACCCACGAGG CAACACTTATTACAAACTGGATAACAGTGGTTTCCCACGAGGCAAT ACTTATTATGCAGCAGATTACAGTGGTTACCCATGAGGCAATACTT ATTATCCGCCAGGTAAGAGTGGTTACCCATGAGGCAATACTTATTA TCAACTGGGTAACACTGGTTTCCCATGAGGCAACACTTATTATCCA TCGGGTAACCGTGCTTACCCACAAGGCAACACTTATTATCCACATG GTAACAGTGGTTACCAAGGAGGCAATACTTATTACGCATTGGGTAA CAGTGGTTACCCACGAGGCAGTACTTTTTATCCACCGGGTAACAGT GGTTACCCTAGAGGCAACACTTATTATCCATTGGGTAACAGTGGTT ACCCTAAAGGCAACACTTATTATGCACCGGGTAACACCGGTTACCC GTGAGGCAACTATTATTTTCCACTGGGTAACAGTGGTTAGCACGA GGCAACACGTATTATCCACCGGTTAACAGTGGTTACCCACGAGGCA ACATTTGATATCCAGCAGATA |
| 871 | NON_CODING (INTERGENIC) | ATCAGGCAAAAGTTAGTATCCAGCGG |

TABLE 6-continued

| SEQ ID NO. | Type | Sequence |
|---|---|---|
| 872 | NON_CODING (INTERGENIC) | TTTCCTACGAGGCAATACATATTACCCAATGGGTAACAGTGGTAAC<br>CCACGAGGCAATACGTATTATCCACAGGGTAACAGTGGTTACCTAT<br>GAGGCAATACTTATTATCAACTGGTTAACAGTGGTATCCCATGAAG<br>C |
| 873 | NON_CODING (INTERGENIC) | CCACGAGGCAATTCTTGTTATCCATAGG |
| 874 | NON_CODING (INTERGENIC) | GGCCATACATATTATCCACCGGGTGACAGTGGTTACCCAAGAGGCA<br>ATACTTATTATCCATGTGGTAGAAGTGGTTGCCCATGAGGCAATAC<br>TTATTATCCACTGGGTAACAGTGGTTACCCAAGAGGCAATACTTAT<br>TATACACCCAGTAACAGTGGTTACCCACAGTGCAACACTTATTATC<br>CACTGGGTAACTGTGGTTACGCATGAGGCAACTCGTATTACCCACT<br>GGGAAACAGTGGTAACCCACGAGGCAATACGTATTATCCAACAGG<br>TAACAGTGGTTACCCACAAGGCCACACGTATTATCCACTGGGTAAC<br>AGTGGTTACCCACAAGGCAATACTTATTATCCAGTCATTAGAAGTG<br>GTTACCCA |
| 875 | NON_CODING (INTRONIC) | ATCAAGTTCACTAAAGCAGGAATGA |
| 876 | NON_CODING (INTRONIC) | TTCTGGAGGAAACTTGTAATATTGGAGA |
| 877 | NON_CODING (INTERGENIC) | TTTAAGCAACAGTTTGACTGCATACAAAATTCCTGGGTCACATC |
| 878 | NON_CODING (INTERGENIC) | TTCTCTACTGCAATGCTGAGGTCTCAGTAAATCGATTTTTGTCTGTG<br>CA |
| 879 | NON_CODING (ncTRANSCRIPT) | GAGTGCTCACTCCATAAGACCCTTACATT |
| 880 | NON_CODING (ncTRANSCRIPT) | TGTGTAACTGCACACGGCCTATCTCATCTGAATAAGGCCTTACTCTC<br>AGACCCTTTTGCAGTACAGCAGGGGTGCTGATAACCAAGGCCCAT<br>TTTCCTGGCCTGTTATGTGTGTGATTATATTTGTCCAGGTTTCTGTGT<br>ACTAGACAAGGAAGCCTCCTCTGCCCCATCCCATCTACGCATAATC<br>TTTCTTT |
| 881 | NON_CODING (ncTRANSCRIPT) | GTGCCAGCTCCATAAGAACCTTACATT |
| 882 | NON_CODING (ncTRANSCRIPT) | CAACCATGCACCTTGGACATAAATGTGTGTAACTGCACATGGCCCA<br>TCCCATCTGAATAAGGTCCTACTCTCAGACCCCTTTTGCAGTACAGT<br>AGGTGTGCTGATAACCAAGGCCCCTCTTCCTGGCCTGTTAACGTAT<br>GTGATTATATTTGTCTGGGTTCCAGTGTATAAGACATG |
| 883 | NON_CODING (ncTRANSCRIPT) | TGAGCATAGGCACTCACCTTGGACATGAATGTGCATAACTGCACAT<br>GGCCCATCCCATCTGAATAAGGTCCTACTCTCAGACCCTTTTTGCAG<br>TACAGCAGGGGTGCTGATCACCAAGGCCCCTTTTCCTGGCCTGTTA<br>TGTGTGTGATTATATTTGTTCCAGTTCCTGTGTAATAGACATGG |
| 884 | NON_CODING (ncTRANSCRIPT) | TCCACTCCATATACCCTTACATTTGGACAAT |
| 885 | NON_CODING (ncTRANSCRIPT) | CCCTCTCCATAAGACGCTTACGTTTGGA |
| 886 | NON_CODING (ncTRANSCRIPT) | GCACCTTAGACATGGATTTGCATAACTACACACAGCTCAACCTATC<br>TGAATAAAATCCTACTCTCAGACCCCTTTTGCAGTACAGCAGGGGT<br>GCTGATCACCAAGGCCCTTTTTCCTGGCCTGGTATGCGTGTGATTAT<br>GTTTGTCCCGGTTCCTGTGTATTAGACATG |
| 887 | NON_CODING (ncTRANSCRIPT) | GGAGTGCCCACTCCATAAGACTCTCACATTTG |
| 888 | NON_CODING (ncTRANSCRIPT) | TTATTTGGAGAGTCTAGGTGCACAAT |
| 889 | NON_CODING (ncTRANSCRIPT) | TTTCGTTGTATCCTGCCTGCCTAGCATCCAGTTCCTCCCCAGCCCTG<br>CTCCCAGCAAACCCTAGTCTAGCCCCAGCCCTACTCCCACCCCGC<br>CCCAGCCCTGCCCCAGCCCCAGTCCCTAACCCCCCAGCCCTAGCC<br>CCAGTCCCAGTCCTAGTTCCTCAGTCCCGCCCAGCTTCTCTCGAAAG<br>TCACTCTAATTTTCATTGATTCAGTGCTCAAAATAAGTTGTCCATTG<br>CTTATCCTATTATACTGGGATATTCCGTTTACCCTTGGCATTGCTGA<br>TCTTCAGTACTGACTCCTTGACCATTTTCAGTTAATGCATACAATCC |

TABLE 6-continued

| SEQ ID NO. | Type | Sequence |
|---|---|---|
| | | CATTTGTCTGTGATCTCAGGACAAAGAATTTCCTTACTCGGTACGTT GAAGTTAGGGAATGTCAATTGAGAGCTTTCTATCAGAGCATTATTG CCCACAATTTGAGTTACTTATCATTTTCTCGATCCCCTGCCCTTAAA GGAGAAACCATTTCTCTGTCATTGCTTCTGTAGTCACAGTCCCAATT TTGAGTAGTGATCTTTTCTTGTGTACTGTGTTGGCCACCTAAAACTC TTTGCATTGAGTAAAATTCTAATTGCCAATAATCCTACCCATTGGAT TAGACAGCACTCTGAACCCCATTTGCATTCAGCAGGGGGTCGCAGA CAACCCGTCTTTTGTTGGACAGTTAAAATGCTCAGTCCCAATTGTCA TAGCTTTGCCTATTAAACAAAGGCACCCTACTGCGCTTTTTGCTGTG CTTCTGGAGAATCCTGCTGTTCTTGGACAATTAAAGAACAAAGTAG TAATTGCTAATTGTCTCACCCATTAATCATGAAGACTACCAGTCGC CCTTGCATTTGCCTTGAGGCAGCGCTGACTACCTGAGATTTAAGAG TTTCTTAAATTATTGAGTAAAATCCCAATTATCCATAGTTCTGTTAG TTACACTATGGCCTTTGCAAACATCTTTGCATAACAGCAGTGGGAC TGACTCATTCTTAGAGCCCCTTCCCTTGGAATATTAATGGATACAAT AGTAATTATTCATGGTTCTGCGTAACAGAGAAGACCCACTTATGTG TATGCCTTTATCATTGCTCCTAGATAGTGTGACTACCTACCACCTT GCATTAATATGTAAAACACTAATTGCCCATAGTCCCACTCATTAGT CTAGGATGTCCTCTTTGCCATTGCTGCTGAGTTCTGACTACCCAAGT TTCCTTCTCTTAAACAGTTGATATGCATAATTGCATATATTCATGGT TCTGTGCAATAAAAATGGATTCTCACCCCATCCCACCTTCTGTGGG ATGTTGCTAACGAGTGCAGATTATTCAATAACAGCTCTTGAACAGT TAATTTGCACAGTTGCAATTGTCCAGAGTCCTGTCCATTAGAAAGG GACTCTGTATCCTATTTGCACGCTACAATGTGGGCTGATCACCCAA GGACTCTTCTTGTGCATTGATGTTCATAATTGTATTTGTCCACGATC TTGTGCACTAACCCTTCCACTCCCTTTGTATTCCAGCAGGGGACCCT TACTACTCAAGACCTCTGTACTAGGACAGTTTATGTGCACAATCCT AATTGATTAGAACTGAGTCTTTTATATCAAGGTCCCTGCATCATCTT TGCTTTACATCAAGAGGGTGCTGGTTACCTAATGCCCCTCCTCCAG AAATTATTGATGTGCAAAATGCAATTTCCCTATCTGCTGTTAGTCTG GGGTCTCATCCCCTCATATTCCTTTTGTCTTACAGCAGGGGTACTT GGGACTGTTAATGCGCATAATTGCAATTATGGTCTTTTCCATTAAAT TAAGATCCCAACTGCTCACACCCTCTTAGCATTACAGTAGAGGGTG CTAATCACAAGGACATTTCTTTTGTACTGTTAATGTGCTACTTGCAT TTGTCCCTCTTCCTGTGCACTAAAGACCCCACTCACTTCCCTAGTGT TCAGCAGTGGATGACCTCTAGTCAAGACCTTTGCACTAGGATAGTT AATGTGAACCATGGCAACTGATCACAACAATGTCTTTCAGATCAGA TCCATTTTATCCTCCTTGTTTTACAGCAAGGGATATTAATTACCTAT GTTACCTTTCCCTGGGACTATGAATGTGCA |
| 890 | NON_CODING (ncTRANSCRIPT) | GCCGTGGATACCTGCCTTTTAATTCTTTTTTATTCGCCCATCGGGGC CGCGGATACCTGCTTTTTATTTTTTTTCCTTAGCCCATCGGGGTAT CGGATACCTGCTGATTCCCTTCCCCTCTGAACCCCCAACACTCTGGC CCATCGGGGTGACGGATATCTGCTTTTTAAAAATTTTCTTTTTTTGG CCCATCGGGGCTTCGGATACCTGCTTTTTTTTTTTATTTTTCCTTG CCCATCGGGGCCTCGGATACCTGCTTTAATTTTTGTTTTTCTGGCCC ATCGGGGCCGCGGATACCTGCTTTGATTTTTTTTTTTCATCGCCCAT CGGTGCTTTTTATGGATGAAAAAATGTTGGTTTTGTGGGTTGTTGCA CTCTCTGGAATATCTACACTTTTTTTTGCTGCTGATCATTTGGTGGT GTGTGAGTGTACCTACCGCTTTGGCAGAGAATGACTCTGCAGTTAA GCTAAGGGCGTGTTCAGATTGTGGAGGAAAAGTGGCCGCCATTTTA GACTTGCCGCATAACTCGGCTTAGGGCTAGTC |
| 891 | NON_CODING (ncTRANSCRIPT) | ATGGTGATTACTTTCTGTGGGGCTCGGAACTACATGCCCTAGGATA TAAAAATGATGTTATCATTATAGAGTGCTCACAGAAGGAAATGAA GTAATATAGGTGTGAGATCCAGACCAAAAGTCATTTAACAAGTTTA TTCAGTGATGAAAACATGGGACAAATGGACTAATATAAGCGCAGTG TACTAAGCTGAGTAGAGAGATAAAGTCCTGTCCAGAAGATACATG CTTCCTGGCCTGATTGAGGAGATGGAAAATTTTTGCAAAAAACAAG GTGTTGTGGTCTTCCATCCAGTTTCTTAGTGCTGATGATAAAAGTG AATTAGACCCACCTTGACCTGGCCTACAGAAGTAAAGGAGTAAAA ATAAATGCCTCAGGCGTGCTTTTTGATTCATTTGATAAACAAAGCA TCTTTTATGTGGAATATACCATTCTGGGTCCTGAGGATAAGAGAGA TGAGGGCATTAGATCACTGACAGCTGAAGATAGAAGAACATCTTTG GTTTGATTGTTAAATAATATTTCAATGCCTATTCTCTGCAAGGTAC TATGTTTCGTAATTAAATAGGTCTGGCCCAGAAGACCCACTCAAT TGCCTTTGAGATTAAAAAAAAAAAAAAAAGAAAGAAAAATGCAA GTTTCTTTCAAAATAAAGAGACATTTTTCCTAGTTTCAGGAATCCCC CAAATCACTTCCTCATTGGCTTAGTTTAAAGCCAGGAGACTGATAA AAGGGCTCAGGGTTTGTTCTTTAATTCATTAACTAAACATTCTGCTT TTATTACAGTTAAATGGTTCAAGATGTAACAACTAGTTTTAAAGGT ATTTGCTCATTGGTCTGGCTTAGAGACAGGAAGACATATGAGCAAT AAAAAAAAGATTCTTTTGCATTTACCAATTTAGTAAAAATTTATTA AAACTGAATAAAGTGCTGTTCTTAAGTGCTTGAAAGACGTAAACCA AAGTGCACTTTATCTCATTTATCTTATGGTGGAAACACAGGAACAA ATTCTCTAAGAGACTGTGTTCTTTAGTTGAGAAGAAACTTCATTGA GTAGCTGTGATATGTTCGATACTAAGGAAAAACTAAACAGATCACC |

TABLE 6-continued

| SEQ ID NO. | Type | Sequence |
|---|---|---|
| | | TTTGACATGCGTTGTAGAGTGGGAATAAGAGAGGGCTTTTTATTTT<br>TTCGTTCATACGAGTATTGATGAAGATGATACTAAATGCTAAATGA<br>AATATATCTGCTCCAAAAGGCATTTATTCTGACTTGGAGATGCAAC<br>AAAAACACAAAAATGGAATGAAGTGATACTCTTCATCAAACAGAA<br>GTGACTGTTATCTCAACCATTTTGTTAAATCCTAAACAGAAAACAA<br>AAAAAATCATGACGAAAAGACACTTGCTTATTAATTGGCTTGGAAA<br>GTAGAATATAGGAGAAAGGTTACTGTTTATTTTTTTTCATGTATTCA<br>TTCATTCTACAAATATATTCGGGTGCCAATAGGTACTTGGTATAAG<br>GTTTTTGGCCCCAGAGACATGGGAAAAAAATGCATGCCTTCCCAGA<br>GAATGCCTAATACTTTCCTTTTGGCTTGTTTTCTTGTTAGGGGCATG<br>GCTTAGTCCCTAAATAACATTGTGTGGTTTAATTCCTACTCCGTATC<br>TCTTCTACCACTCTGGCCACTACGATAAGCAGGTA |
| 892 | NON_CODING<br>(ncTRANSCRIPT) | TGTGAACTCACTGTTAAAGGCACTGAAAATTTATCATATTTCATTTA<br>GCCACAGCCAAAAATAAGGCAATACCTATGTTAGCATTTTGTGAAC<br>TCTAAGGCACCA |
| 893 | NON_CODING<br>(ncTRANSCRIPT) | GGACTAAGCTTGTTGTGGTCACCTATAATGTGCCAGATACCATGCT<br>GGGTGCTAGAGCTACCAAAGGGGGAAAAGTATTCTCATAGAACAA<br>AAAATTTCAGAAAGGTGCATATTAAAGTGCTTTGTAAACTAAAGCA<br>TGATACAAATGTCAATGGGCTACATATTTATGAATGAATGAATGGA<br>TGAATGAATATTAAGTGCCTCTTACATACCAGCTATTTTGGGTACTG<br>TAAAATACAAGATTAATTCTCCTATGTAATAAGAGGAAAGTTTATC<br>CTCTATACTATTCAGATGTAAGGAATGATATATTGCTTAATTTTAAA<br>CAATCAAGACTTTACTGGTGAGGTTAAGTTAAATTATTACTGATAC<br>ATTTTTCCAGGTAACCAGGAAAGAGCTAGTATGAGGAAATGAAGT<br>AATAGATGTGAGATCCAGACCGAAAGTCACTTAATTCAGCTTGCGA<br>ATGTGCTTTCTA |
| 894 | NON_CODING<br>(ncTRANSCRIPT) | GGGGACAGCCTGAACTCCCTGCTCATAGTAGTGGCCAAATAATTTG<br>GTGGACTGTGCCAACGCTACTCCTGGGTTTAATACCCATCTCTAGG<br>CTTAAAGATGAGAGAACCTGGGACTGTTGAGCATGTTTAATACTTT<br>CCTTGATTTTTTCTTCCTGTTTATGTGGGAAGTTGATTTAAATGAC<br>TGATAATGTGTATGAAAGCACTGTAAAACATAAGAGAAAAACCAA<br>TTAGTGTATTGGCAATCATGCAGTTAACATTTGAAAGTGCAGTGTA<br>AATTGTGAAGCATTATGTAAATCAGGGGTCCACAGTTTTTCTGTAA<br>GGGGTCAAATCATAAATACTTTAGACTGTGGGCCATATGGTTTCTG<br>TTACATATTTGTTTTTAAACAACGTTTTTATAAGGTCAAAATCATT<br>CTTAGTTTTTGAGCCAATTGGATTTGGCCTGCTGTTCATAGCTTA |
| 895 | NON_CODING<br>(ncTRANSCRIPT) | TCTCAAGACTAACGGCCGGAATCTGGAGGCCCATGACCCAGAACC<br>CAGGAAGGATAGAAGCTTGAAGACCTGGGGAAATCCCAAGATGAG<br>AACCCTAAACCCTACCTCTTTTCTATTGTTTACACTTCTTACTCTTAG<br>ATATTTCCAGTTCTCCTGTTTATCTTTAAGCCTGATTCTTTTGAGATG<br>TACTTTTTGATGTTGCCGGTTACCTTTAGATTGACAGTATTATGCCT<br>GGGCCAGTCTTGAGCCAGCTTTAAATCACAGCTTTTACCTATTTGTT<br>AGGCTATAGTGTTTTGTAAACTTCTGTTTCTATTCACATCTTCTCCA<br>CTTGAGAGAGACACCAAAATCCAGTCAGTATCTAATCTGGCTTTTG<br>TTAACTTCCCTCAGGAGCAGACATTCATATA |
| 896 | NON_CODING<br>(ncTRANSCRIPT) | TGTCTCCTTTTTGGGTCACATGCTGTGTGCTTTTTGTCCTTTTCTTGT<br>TCTGTCTACCTCTCCTTTCTCTGCCTACCTCTCTTTTCTCTTTGTGAA<br>CTGTGATTATTGTTACCCCTTCCCCTTCTCGTTCGTTTTAAATTTCA<br>CCTTTTTTCTGAGTCTGGCCTCCTTTCTGCTGTTTCTACTTTTTATCT<br>CACACATTTCTCATTTCTGCATTTCCTTTCTGCCTCTCTTGGGCTATTCT<br>CTCTCTCCTCCCCTGCGTGCCTCAGCATCTCTTGCTGTTTGTGATTTT<br>CTATTTCAGTATTAATCTCTGTTGGCTTGTATTTGTTCTCTGCTTCTT<br>CCCTTTCTACTCACCTTTGAGTATTTCAGCCTCTTCATGAATCTATCT<br>CCCTCTCTTTTGATTTCATGTAATCTCTCCTTAAATATTTCTTTGCATA<br>TGTGGGCAAGTGTACGTGTGTGTGTGTCATGTGTGGCAGAGGGGCT<br>TCCTAACCCCTGCCTGATAGGTGCAGAACGTCGGCTATCAGAGCAA<br>GCATTGTGGAGCGGTTCCTTATGCCAGGCTGCCATGTGAGATGATC<br>CAAGACCAAAACAAGGCCCTAGACTGCAGTAAAACCCAGAACTCA<br>AGTAGGGCAGAAGGTGGAAGGCTCATATGGATAGAAGGCCCAAAG<br>TATAAGACAGATGGTTTGAGACTTGAGACCCGAGGACTAAGATGG<br>AAAGCCCA |
| 897 | NON_CODING<br>(ncTRANSCRIPT) | TCATTGTTCCTATCTGCCAAATCATTATACTTCCTACAAGCAGTGCA<br>GAGAGCTGAGTCTTCAGCAGGTCCAAGAAATTTGAACACACTGAA<br>GGAAGTCAGCCTTCCCACCTGAAGATCAACATGCCTGGCACTCTAG<br>CACTTGAGGATA |
| 898 | NON_CODING<br>(ncTRANSCRIPT) | CCTCAGAAGAATAGGCTTGTTGTTTTACAGTGTTAGTGATCCATTCC<br>CTTTGACGATCCCTAGGTGGAGATGGGGCATGAGGATCCTCCAGGG<br>GAAAAGCTCACTACCACTGGGCAACAACCCTAGGTCAGGAGGTTCT<br>GTCAAGATACTTTCCTGGTCCCAGATAGG |

TABLE 6-continued

| SEQ ID NO. | Type | Sequence |
|---|---|---|
| 899 | NON_CODING (ncTRANSCRIPT) | CCCATTGAAGATACCACGCTGCATGTGTCCTTAGTAGTCATGTCTCCTTA |
| 900 | NON_CODING (ncTRANSCRIPT) | AAGAATATTGTTTCTCGGAGAAGGATGTCAAAAGATCGGCCCAGCTCAGGGAGCAGTTTGCCCTACTAGCTCCTCGGACAGCTGTAAAGAAGAGTCTCTGGCTCTTTAGAATACT |
| 901 | NON_CODING (ncTRANSCRIPT) | GGGTGCCCACTCCTTATGATCTTTACATTTGAACAGTTAATGTGAATAATTGCAGTTGTCCACAACCCTATCACTTCTAGGACCATTATACCTCTTTTGCATTACTGTGGGGTATACTGTTTCCCTCCAAGGCCCCTTCTGGTGGACTATCAACATATAATTGAAATTTTCTTTTGTCTTTGTCAGTAGATTAAGGTCATACCCCATCACCTTTCCTTTGTAGTACAACAGGGTGTCCTGATCAACCAAAGTCCTGTTGTTTTGGACTGTTAATATGTGCAATTACATTTGCTCCTGATCTGTGCACTAGATAAGGATCCTACCTACTTTCTTAGTGTTTTTAGCAGGTAGTGCCCACTACTCAAGACTGTCACTTGGAATGTTCATGTGCACAAACTCAATTCTCTAAGCATGTTCCTGTACCACCTTTGCTTTAGAGCAGGGGGATGATATTCACTAAGTGCCCCTTCTTTTGGACTTAATATGCATTAATGCAATTGTCCACCTCTTCTTTTAGACTAAGAGTTGATCTCCACATATTCCCCTTGCATCAGGGGCATGTTAATTATGAATGAACCCTTTTCTTTTAATATTAATGTCATAATTGTATTTGTGGACCTGTGTAGGAGAAAAAGACCCTATGTTCCTCCCATTACCCTTTGGATTGCTGCTGAGAAGTGTTAACTACTCATAATCTCAGCTCTTGGACAATTAATAGCATTAATAACAATTATCAAGGGCACTGATCATTAGATAAGACTCCTGCTTCCTCGTTGCTTACATCGGGGGTACTGACCCACTAAGGCCCCTTGTACTGTTAATGTGAATATTTGCAATTATATATGTCTCCTTCTGGTAGAGTGGGATATTATGCCCTAGTATCCCCTTTGCATTACTGCAGGGGCTGCTGACTACTCAAAACTTCTCCTGGGACTGTTAATAGGCACAATGGCAGTTATCAATGGTTTTCTCCCTCCCTGACCTTGTTAAGCAAGCGCCCCACCCCACCCTTAGTTTCCCATGGCATAATAAAGTATAAGCATTGGAGTATTCCATGCACTTGTCTATCAAACAGTGGTCCATACTCCCAACCCTTTTGCATTGCGCCAGTGTGTAAAATCACAGGTAGCCATGGTGTCATGCTTTATATACGAAGTCTTCCCTCTCTCTGCCCCTTGTGTGCCCTTGGCCCCTTTTTACAGACTATTGCTCACAATCTCAGGTGTCCATATTTGCAGCTATTAGGTAAGATTGTGCTGTCTCCCTCTTCCCTTCCCTCTGCCCTGCCCCTTTTGCCTCTTTGCTGGGTAATGTTGACCAGACAAGGCCCTTTCTCTTGGACTTAAACAATTCTCAGTTGCACTTTCCTTGGTCCCACCCATTATACATGAACCCCTCTACTTCCTTTCGCATTGCTTCTGAGTATGCTGACTACCCAAAGCCCCTTCTGTGTTATTAATAAACACAGTACTGATTGTCCCATTTTTCAGCCCATCAGTCCAAGATCTCCCTACCACTTTGGTGTGTTGGTGCAGTGTTGACTATGAAAAGCAGGCCTGAACTAGGTGGATAAGCCTTCACTCATTTTCTTTCATTTATTAATGATCCTAGTTTCAATTATTGTCAGATTCTGGGGACAAGAACCATTCTTGCCCACCTGTGTTACTGCTTTACTG |
| 902 | NON_CODING (UTR) | TTTGCAGCAAAGTCACCCTTACAAAGAAGCTAATATGGAAACCACATGTAACTTAGCCAGACTATATTGTGTAGCTTCAAGAACTTGCAGTACATTACCAGCTGTGATTCTCCTGATAATTCAAGGGAGCTCAAAGTCACAAGAAGAAAAATGAAAGGAAAAAACAGCAGCCCTATTCAGAAATTGGTTTGAAGATGTAATTGCTCTAGTTTGGATTA |
| 903 | NON_CODING (UTR) | ATGGTGGCTGTAAAACTAGGATCCCTGACGATTG |

TABLE 7

| Gene | Transcripts | Comparison |
|---|---|---|
| ACPP | ACPP-001(protein_coding) | PvsM |
| | ACPP-005(retained_intron) | PvsM NvsM |
| ANK3 | ANK3-021(retained_intron) | NvsP |
| AR | AR-001(protein_coding) | NvsM |
| | AR-005(nonsense_mediated_decay) | PvsM NvsM |
| | AR-203 (protein_coding) | NvsM |
| CD44 | CD44-014(retained_intron) | NvsM |
| CHRAC1 | CHRAC1-005(retained_intron) | NvsM |
| COL1A2 | COL1A2-002(retained_intron) | NvsM |
| | COL1A2-005(retained_intron) | NvsM |
| | COL1A2-006(retained_intron) | NvsM |
| | COL1A2-012(retained_intron) | NvsM |
| DLGAP1 | DLGAP1-008(processed_transcript) | PvsM |
| | DLGAP1-010(processed_transcript) | PvsM |
| | DLGAP1-201(protein_coding) | PvsM NvsM |
| ETV6 | ETV6-002(processed_transcript) | NvsM |
| | ETV6-003(processed_transcript) | PvsM NvsM |
| | ETV6-004(protein_coding) | NvsM |
| FBLN1 | FBLN1-001(protein_coding) | PvsM NvsM |
| | FBLN1-016(processed_transcript) | NvsM |
| FGFR1 | FGFR1-005(protein_coding) | NvsM |
| FGFR2 | FGFR2-008(processed_transcript) | ALL |
| | FGFR2-016(protein_coding) | ALL |
| | FGFR2-201(protein_coding) | PvsM NvsM |
| ILK | ILK-011(processed_transcript) | NvsM |
| | ILK-012(processed_transcript) | NvsM |
| KHDRBS3 | KHDRBS3-003(retained_intron) | PvsM |
| MYLK | MYLK-001(protein_coding) | NvsM |
| | MYLK-014(retained_intron) | NvsM |
| PASK | PASK-015(retained_intron) | PvsM |
| PDLIM5 | PDLIM5-010(protein_coding) | PvsM |
| | PDLIM5-017(processed_transcript) | PvsM NvsM |

TABLE 7-continued

| Gene | Transcripts | Comparison |
|---|---|---|
| POLR1C | POLR1C-002(retained_intron) | NvsM |
| ST6GAL1 | ST6GAL1-021(retained_intron) | PvsM |
| THBS1 | THBS1-001(protein_coding) | PvsM |
|  | THBS1-004(processed_transcript) | PvsM |
|  | THBS1-008(retained_intron) | PvsM |

TABLE 8

|  |  | Mean Fold Difference | | |
|---|---|---|---|---|
|  | Transcript | P vs N | M vs P | M vs N |
| TOP | ACOT11-001 | 0.79 | 0.77 | 0.61 |
|  | AOX1-001 | 0.79 | 0.56 | 0.44 |
|  | C19orf46-002 | 1.24* | 1.23* | 1.53* |
|  | C8orf84-001 | 0.76 | 0.75 | 0.57 |
|  | COCH-202 | 0.76 | 0.83 | 0.63 |
|  | CTA-55110.1-001 | 0.83 | 0.68 | 0.56 |
|  | DMD-024 | 0.74 | 0.82 | 0.60 |
|  | FGF10-002 | 0.83 | 0.64 | 0.53 |
|  | FGFR2-008 | 0.76 | 0.79 | 0.60 |
|  | FGFR2-016 | 0.74 | 0.67 | 0.49 |
|  | GABRE-006 | 0.79 | 0.83 | 0.66 |
|  | GNAL-001 | 0.82 | 0.69 | 0.57 |
|  | GNAO1-002 | 0.78 | 0.75 | 0.58 |
|  | HEATR8-006 | 0.80 | 0.80 | 0.64 |
|  | ISL1-002 | 0.80 | 0.81 | 0.65 |
|  | NR2F2-202 | 0.82 | 0.82 | 0.68 |
|  | PCP4-004 | 0.81 | 0.72 | 0.58 |
|  | PDE5A-005 | 0.74 | 0.79 | 0.59 |
|  | PDZRN4-202 | 0.80 | 0.71 | 0.57 |
|  | RSRC2-017 | 1.27* | 1.28* | 1.63* |
|  | TGM4-001 | 0.68 | 0.62 | 0.42 |
|  | TSPAN2-001 | 0.80 | 0.77 | 0.61 |
| Bottom | ABCC4-004 | 1.35* | 0.81 | N.A. |
|  | ALK-001 | 1.24* | 0.83 | N.A. |
|  | ATP1A1-002 | 1.23* | 0.71 | N.A. |
|  | NAMPT-006 | 1.34* | 0.73 | N.A. |
|  | NAMPT-007 | 1.75* | 0.57 | N.A. |
|  | RP11-627G23.1-004 | 1.38* | 0.78 | N.A. |

TABLE 9

|  | TS-PSRs | | | Genes | | |
|---|---|---|---|---|---|---|
| Classifier | OR | OR CI (95%) | P-value | OR | OR CI (95%) | P-value |
| KNN-positive | 13 | [2.5-99] | <0.005 | 3.8 | [1.0-14.3] | 0.05 |
| Nomogram* | 6.6 | [2.3-20] | <0.001 | 7.9 | [2.9-22.6] | <0.0001 |

TABLE 10

| Variable | Categories | N (%) |
|---|---|---|
| Age | <70 yrs | 132 (53) |
|  | ≥70 yrs | 119 (47) |

TABLE 10-continued

| Variable | Categories | N (%) |
|---|---|---|
| Gender | Male | 205 (82) |
|  | Female | 46 (18) |
| Ethnicity | Caucasian | 222 (88) |
|  | Other | 29 (12) |
| Pathologic Stage | T2N0 | 62 (25) |
|  | T3N0 | 75 (30) |
|  | T4N0 | 25 (10) |
|  | Any T N1-3 | 89 (35) |
| Intravesical therapy | No | 196 (78) |
|  | Yes | 55 (22) |
| Adjuvant chemotherapy | No | 150 (60) |
|  | Yes | 101 (40) |
| Age of FFPE blocks | <15 yrs | 160 (64) |
|  | ≥15 yrs | 91 (36) |

TABLE 11

|  | Hazard ratio | 95% CI | p-value |
|---|---|---|---|
| Gender | 0.92 | 0.49-1.71 | 0.78 |
| Age (<70 vs ≥70) | 1.42 | 0.87-2.30 | 0.16 |
| Ethnicity | 0.89 | 0.42-1.88 | 0.75 |
| T stage | 2.46 | 1.05-5.72 | 0.04 |
| Lymph nodes | 3.37 | 2.07-5.49 | <0.001 |
| Lymphovascular invasion (LVI) | 1.05 | 0.97-1.14 | 0.25 |
| Adjuvant Chemotherapy | 0.88 | 0.72-1.06 | 0.18 |

TABLE 12

| Variable | Parameter | Training AUC | Testing AUC |
|---|---|---|---|
| Gender | M/F | 0.48 | 0.56 |
| Age | <70/≥70 | 0.51 | 0.48 |
| Race | Caucasian/Other | 0.49 | 0.54 |
| Tumor Stage | 1, 2, 3, 4 | 0.62 | 0.66 |
| Node Status | Yes/No | 0.66 | 0.65 |
| LVI | Yes/No | 0.64 | 0.63 |
| Clinical Classifier 1 | Logistic Model | 0.73 | 0.71 |
| Clinical Classifier 2 | Cox model | 0.72 | 0.72 |

TABLE 13

| Genomic & Clinicopathologic Factors | Hazard Ratio (95% CI) | P value |
|---|---|---|
| GC* | 2.20 (1.22-3.92) | 0.00841 |
| Age | 1.55 (0.34-7.10) | 0.58 |
| Ethnicity | 0.22 (0.01-3.46) | 0.28 |
| Gender | 0.69 (0.11-4.40) | 0.70 |
| Pathological stage | 1.02 (0.32-3.26) | 0.97 |
| Lymph node involvement | 3.51 (0.76-16.25) | 0.11 |
| Lymphovascular invasion | 2.90 (0.52-16.07) | 0.22 |
| Block age | 0.99 (0.80-1.22) | 0.93 |
| Intravesical treatment | 3.64 (0.64-20.64) | 0.14 |
| Adjuvant chemotherapy | 4.31 (0.91-20.43) | 0.07 |

*per 0.1 unit increment

TABLE 14

| celfile | Batch | PatientId | AdjCTx | Age | Blockage | Gender | IV_Rx | LNI | LVI | OS_Event | OS_Event_Time |
|---|---|---|---|---|---|---|---|---|---|---|---|
| AA682-HuEx-1_0-st-v2-01-1_118.CEL | 3 | 1646 | 0 | 69 | 18 | male | 0 | 1 | 1 | 1 | 10 |
| AA629-HuEx-1_0-st-v2-01-1_132.CEL | 2 | 1650 | 0 | 59 | 12 | male | 1 | 0 | 0 | 0 | 113 |

TABLE 14-continued

| | | | | | | | | | | |
|---|---|---|---|---|---|---|---|---|---|---|
| AA684-HuEx-1_0-st-v2-01-1_142.CEL | 3 | 1652 | 0 | 69 | 19 | female | 0 | 0 | 1 | 1 | 19 |
| AA736-HuEx-1_0-st-v2-02-2_145.CEL | 6 | 1655 | 1 | 40 | 17 | male | 0 | 0 | 1 | 0 | 179 |
| AA685-HuEx-1_0-st-v2-01-1_157.CEL | 3 | 1657 | 1 | 57 | 15 | female | 0 | 1 | 1 | 1 | 10 |
| AA739-HuEx-1_0-st-v2-02-2_166.CEL | 6 | 1662 | 0 | 78 | 8 | male | 0 | 1 | 0 | 1 | 2 |
| AA579-HuEx-1_0-st-v2-01-1_220.CEL | 1 | 1678 | 0 | 72 | 10 | male | 0 | 0 | 1 | 1 | 5 |
| AA636-HuEx-1_0-st-v2-01-1_226.CEL | 6 | 1680 | 0 | 76 | 10 | female | 0 | 1 | 1 | 1 | 12 |
| AA856-HuEx-1_0-st-v2-01-1_274.CEL | 5 | 1691 | 1 | 68 | 10 | male | 0 | 1 | NA | 0 | 90 |
| AA746-HuEx-1_0-st-v2-01-1_292.CEL | 4 | 1697 | 1 | 49 | 16 | female | 0 | 0 | 1 | 1 | 21 |
| AA694-HuEx-1_0-st-v2-01-1_293.CEL | 3 | 1698 | 1 | 69 | 13 | male | 0 | 0 | 1 | 1 | 77 |
| AA585-HuEx-1_0-st-v2-01-1_294.CEL | 1 | 1699 | 0 | 89 | 9 | male | 0 | 0 | NA | 1 | 3 |
| AA696-HuEx-1_0-st-v2-01-1_299.CEL | 3 | 1702 | 1 | 77 | 9 | male | 0 | 1 | 1 | 1 | 9 |
| AA697-HuEx-1_0-st-v2-01-1_311.CEL | 3 | 1705 | 1 | 67 | 15 | male | 0 | 0 | 1 | 1 | 18 |
| AA750-HuEx-1_0-st-v2-01-1_343.CEL | 4 | 1712 | 1 | 68 | 10 | male | 0 | 1 | 1 | 0 | 83 |
| AA643-HuEx-1_0-st-v2-01-1_369.CEL | 6 | 1716 | 0 | 70 | 19 | male | 0 | 0 | 0 | 1 | 24 |
| AA699-HuEx-1_0-st-v2-01-1_373.CEL | 6 | 1717 | 1 | 50 | 10 | male | 1 | 1 | 1 | 0 | 90 |
| AA753-HuEx-1_0-st-v2-01-1_376.CEL | 4 | 1719 | 0 | 66 | 10 | male | 0 | 0 | 1 | 0 | 83 |
| AA755-HuEx-1_0-st-v2-01-1_390.CEL | 4 | 1723 | 0 | 72 | 10 | male | 0 | 0 | NA | 1 | 14 |
| AA798-HuEx-1_0-st-v2-01-1_414.CEL | 5 | 1731 | 0 | 70 | 12 | male | 1 | 0 | NA | 1 | 20 |
| AA702-HuEx-1_0-st-v2-01-1_420.CEL | 6 | 1733 | 0 | 65 | 19 | male | 0 | 0 | 1 | 1 | 42 |
| AA704-HuEx-1_0-st-v2-01-1_444.CEL | 6 | 1740 | 1 | 74 | 19 | male | 0 | 0 | 0 | 1 | 11 |
| AA802-HuEx-1_0-st-v2-01-1_469.CEL | 5 | 1747 | 0 | 72 | 14 | male | 1 | 0 | 0 | 0 | 130 |
| AA762-HuEx-1_0-st-v2-01-1_481.CEL | 4 | 1752 | 1 | 64 | 17 | male | 0 | 1 | 1 | 1 | 38 |
| AA763-HuEx-1_0-st-v2-01-1_485.CEL | 4 | 1753 | 1 | 48 | 8 | male | 1 | 0 | 0 | 0 | 69 |
| AA594-HuEx-1_0-st-v2-01-1_493.CEL | 1 | 1754 | 1 | 61 | 15 | male | 0 | 1 | 1 | 0 | 155 |
| AA705-HuEx-1_0-st-v2-01-1_506.CEL | 6 | 1756 | 1 | 66 | 9 | male | 0 | 0 | 0 | 0 | 73 |
| AA597-HuEx-1_0-st-v2-01-1_529_2.CEL | 6 | 1763 | 1 | 68 | 19 | male | 0 | 1 | 1 | 1 | 11 |

TABLE 14-continued

| | | | | | | | | | | |
|---|---|---|---|---|---|---|---|---|---|---|
| AA805-HuEx-1_0-st-v2-01-1_560.CEL | 5 | 1768 | 1 | 58 | 13 | male | 0 | 1 | 1 | 1 | 18 |
| AA766-HuEx-1_0-st-v2-01-1_562.CEL | 4 | 1769 | 1 | 42 | 20 | male | 0 | 1 | 0 | 0 | 203 |
| AA767-HuEx-1_0-st-v2-01-1_569.CEL | 4 | 1771 | 1 | 54 | 9 | female | 0 | 1 | 1 | 1 | 11 |
| AA806-HuEx-1_0-st-v2-01-1_594.CEL | 5 | 1775 | 0 | 64 | 14 | male | 0 | 1 | 1 | 1 | 8 |
| AA602-HuEx-1_0-st-v2-01-1_623.CEL | 6 | 1785 | 0 | 71 | 17 | male | 0 | 0 | 0 | 0 | 169 |
| AA771-HuEx-1_0-st-v2-01-1_651.CEL | 4 | 1798 | 0 | 74 | 17 | male | 0 | 0 | 0 | 1 | 124 |
| AA772-HuEx-1_0-st-v2-01-1_652.CEL | 4 | 1799 | 0 | 48 | 9 | male | 0 | 0 | 0 | 0 | 76 |
| AA808-HuEx-1_0-st-v2-01-1_656.CEL | 5 | 1801 | 0 | 52 | 13 | male | 0 | 0 | 1 | 1 | 6 |
| AA849-HuEx-1_0-st-v2-01-1_664.CEL | 6 | 1802 | 0 | 85 | 15 | male | 0 | 0 | 0 | 1 | 15 |
| AA774-HuEx-1_0-st-v2-01-1_666.CEL | 4 | 1804 | 0 | 81 | 8 | male | 0 | 0 | 1 | 0 | 78 |
| AA662-HuEx-1_0-st-v2-01-1_703.CEL | 6 | 1814 | 0 | 55 | 14 | male | 1 | 0 | 0 | 0 | 143 |
| AA607-HuEx-1_0-st-v2-01-1_709.CEL | 1 | 1817 | 0 | 66 | 18 | male | 0 | 0 | 0 | 1 | 6 |
| AA719-HuEx-1_0-st-v2-01-1_726.CEL | 3 | 1822 | 0 | 72 | 8 | female | 0 | 0 | 0 | 0 | 69 |
| AA721-HuEx-1_0-st-v2-01-1_756.CEL | 3 | 1832 | 0 | 71 | 18 | female | 0 | 0 | 1 | 1 | 20 |
| AA666-HuEx-1_0-st-v2-01-1_763.CEL | 6 | 1834 | 1 | 63 | 11 | male | 0 | 0 | NA | 1 | 41 |
| AA722-HuEx-1_0-st-v2-01-1_777.CEL | 3 | 1837 | 0 | 49 | 16 | male | 0 | 0 | 0 | 0 | 159 |
| AA780-HuEx-1_0-st-v2-01-1_779.CEL | 4 | 1838 | 1 | 60 | 9 | male | 0 | 0 | 0 | 0 | 76 |
| AA781-HuEx-1_0-st-v2-02-2_800.CEL | 6 | 1842 | 0 | 47 | 14 | male | 0 | 0 | 0 | 1 | 18 |
| AA667-HuEx-1_0-st-v2-01-1_826.CEL | 6 | 1848 | 0 | 78 | 12 | male | 0 | 0 | NA | 0 | 112 |
| AA619-HuEx-1_0-st-v2-01-1_881.CEL | 1 | 1868 | 0 | 67 | 9 | male | 0 | 0 | 0 | 1 | 60 |
| AA625-HuEx-1_0-st-v2-01-1_956.CEL | 1 | 1887 | 0 | 79 | 13 | female | 0 | 1 | 1 | 0 | 120 |
| AA732-HuEx-1_0-st-v2-01-1_957.CEL | 6 | 1888 | 0 | 86 | 12 | male | 0 | 0 | 1 | 1 | 15 |
| AA680-HuEx-1_0-st-v2-01-1_958.CEL | 6 | 1889 | 1 | 56 | 17 | male | 0 | 1 | 1 | 1 | 172 |
| AA733-HuEx-1_0-st-v2-01-1_959.CEL | 6 | 1890 | 1 | 63 | 16 | male | 0 | 1 | 1 | 1 | 8 |
| AA574-HuEx-1_0-st-v2-01-1_120.CEL | 1 | 1647 | 0 | 67 | 17 | male | 0 | 0 | 0 | 1 | 66 |
| AA628-HuEx-1_0-st-v2-01-1_130.CEL | 2 | 1649 | 0 | 65 | 18 | male | 0 | 0 | 1 | 1 | 27 |

TABLE 14-continued

| | | | | | | | | | | |
|---|---|---|---|---|---|---|---|---|---|---|
| AA683-HuEx-1_0-st-v2-01-1_135.CEL | 3 | 1651 | 0 | 70 | 9 | female | 0 | 0 | 0 | 1 | 11 |
| AA575-HuEx-1_0-st-v2-01-1_143.CEL | 1 | 1653 | 0 | 48 | 9 | female | 0 | 0 | NA | 1 | 3 |
| AA630-HuEx-1_0-st-v2-01-1_144.CEL | 2 | 1654 | 0 | 86 | 13 | female | 0 | 0 | 1 | 1 | 73 |
| AA846-HuEx-1_0-st-v2-01-1_159.CEL | 2 | 1658 | 0 | 67 | 16 | male | 0 | 1 | 1 | 1 | 68 |
| AA576-HuEx-1_0-st-v2-01-1_162.CEL | 1 | 1659 | 0 | 68 | 20 | male | 0 | 0 | 0 | 1 | 71 |
| AA686-HuEx-1_0-st-v2-01-1_165.CEL | 3 | 1661 | 1 | 64 | 17 | male | 0 | 0 | 0 | 0 | 149 |
| AA687-HuEx-1_0-st-v2-01-1_167.CEL | 3 | 1663 | 0 | 64 | 14 | male | 0 | 0 | 0 | 0 | 133 |
| AA631-HuEx-1_0-st-v2-01-1_173.CEL | 2 | 1665 | 1 | 52 | 18 | male | 0 | 1 | 0 | 1 | 15 |
| AA577-HuEx-1_0-st-v2-01-1_184.CEL | 1 | 1667 | 1 | 71 | 10 | male | 0 | 1 | 0 | 1 | 15 |
| AA578-HuEx-1_0-st-v2-01-1_186.CEL | 1 | 1668 | 0 | 54 | 9 | male | 0 | 1 | 1 | 1 | 13 |
| AA632-HuEx-1_0-st-v2-01-1_195.CEL | 2 | 1669 | 1 | 50 | 12 | male | 0 | 0 | 1 | 1 | 30 |
| AA848-HuEx-1_0-st-v2-01-1_198.CEL | 3 | 1670 | 1 | 62 | 12 | male | 1 | 0 | 1 | 0 | 107 |
| AA689-HuEx-1_0-st-v2-01-1_199.CEL | 3 | 1671 | 0 | 74 | 13 | male | 0 | 0 | 1 | 1 | 6 |
| AA633-HuEx-1_0-st-v2-01-1_203.CEL | 2 | 1672 | 0 | 83 | 15 | male | 1 | 0 | 0 | 1 | 31 |
| AA690-HuEx-1_0-st-v2-01-1_211.CEL | 3 | 1673 | 0 | 68 | 14 | male | 0 | 0 | 0 | 0 | 108 |
| AA634-HuEx-1_0-st-v2-01-1_213.CEL | 2 | 1674 | 0 | 93 | 16 | male | 0 | 0 | 1 | 1 | 13 |
| AA691-HuEx-1_0-st-v2-01-1_214.CEL | 3 | 1675 | 0 | 74 | 10 | male | 0 | 0 | 0 | 1 | 25 |
| AA635-HuEx-1_0-st-v2-01-1_218.CEL | 2 | 1676 | 0 | 74 | 19 | male | 1 | 1 | 1 | 1 | 78 |
| AA692-HuEx-1_0-st-v2-01-1_224.CEL | 3 | 1679 | 0 | 83 | 10 | male | 0 | 1 | 1 | 1 | 5 |
| AA580-HuEx-1_0-st-v2-01-1_227.CEL | 1 | 1681 | 0 | 58 | 17 | male | 0 | 0 | 0 | 1 | 45 |
| AA637-HuEx-1_0-st-v2-01-1_228.CEL | 2 | 1682 | 0 | 81 | 15 | male | 0 | 0 | 1 | 1 | 7 |
| AA693-HuEx-1_0-st-v2-01-1_230.CEL | 3 | 1683 | 0 | 71 | 10 | male | 1 | 0 | 1 | 1 | 25 |
| AA581-HuEx-1_0-st-v2-01-1_235.CEL | 1 | 1684 | 0 | 78 | 10 | male | 0 | 0 | 0 | 0 | 90 |
| AA638-HuEx-1_0-st-v2-01-1_258.CEL | 2 | 1688 | 1 | 64 | 15 | female | 0 | 1 | 1 | 1 | 55 |
| AA639-HuEx-1_0-st-v2-01-1_267.CEL | 2 | 1689 | 1 | 70 | 9 | male | 0 | 1 | 1 | 1 | 10 |
| AA582-HuEx-1_0-st-v2-01-1_272.CEL | 1 | 1690 | 1 | 57 | 16 | male | 1 | 1 | 0 | 1 | 19 |

TABLE 14-continued

| | | | | | | | | | | |
|---|---|---|---|---|---|---|---|---|---|---|
| AA640-HuEx-1_0-st-v2-01-1_281.CEL | 2 | 1694 | 1 | 72 | 10 | female | 0 | 1 | 1 | 1 | 18 |
| AA583-HuEx-1_0-st-v2-01-1_284.CEL | 1 | 1695 | 1 | 71 | 19 | male | 1 | 1 | 1 | 1 | 24 |
| AA584-HuEx-1_0-st-v2-01-1_286.CEL | 1 | 1696 | 0 | 61 | 18 | male | 0 | 1 | 0 | 1 | 12 |
| AA695-HuEx-1_0-st-v2-01-1_295.CEL | 3 | 1700 | 1 | 73 | 9 | male | 0 | 1 | NA | 0 | 72 |
| AA586-HuEx-1_0-st-v2-01-1_296.CEL | 1 | 1701 | 1 | 71 | 9 | male | 0 | 0 | NA | 1 | 32 |
| AA587-HuEx-1_0-st-v2-01-1_309.CEL | 1 | 1704 | 0 | 73 | 19 | male | 0 | 0 | 0 | 1 | 175 |
| AA641-HuEx-1_0-st-v2-01-1_314.CEL | 2 | 1706 | 1 | 66 | 12 | male | 0 | 1 | 1 | 1 | 56 |
| AA847-HuEx-1_0-st-v2-01-1_338.CEL | 2 | 1709 | 0 | 68 | 11 | male | 0 | 0 | 0 | 1 | 29 |
| AA698-HuEx-1_0-st-v2-01-1_342.CEL | 3 | 1711 | 0 | 76 | 13 | male | 0 | 0 | 1 | 0 | 94 |
| AA642-HuEx-1_0-st-v2-01-1_368.CEL | 2 | 1715 | 0 | 44 | 11 | female | 0 | 0 | 1 | 1 | 21 |
| AA588-HuEx-1_0-st-v2-01-1_375.CEL | 2 | 1718 | 1 | 72 | 12 | male | 0 | 1 | 0 | 0 | 112 |
| AA644-HuEx-1_0-st-v2-01-1_382.CEL | 2 | 1721 | 0 | 73 | 11 | male | 0 | 0 | 0 | 1 | 47 |
| AA700-HuEx-1_0-st-v2-01-1_393.CEL | 3 | 1724 | 1 | 78 | 10 | male | 1 | 1 | 1 | 1 | 36 |
| AA589-HuEx-1_0-st-v2-01-1_396.CEL | 1 | 1725 | 1 | 51 | 13 | male | 1 | 0 | 0 | 0 | 126 |
| AA701-HuEx-1_0-st-v2-01-1_402.CEL | 3 | 1727 | 1 | 67 | 16 | male | 0 | 0 | 0 | 0 | 151 |
| AA590-HuEx-1_0-st-v2-01-1_430.CEL | 1 | 1736 | 0 | 78 | 13 | male | 0 | 0 | 1 | 1 | 7 |
| AA591-HuEx-1_0-st-v2-01-1_436.CEL | 1 | 1737 | 0 | 66 | 12 | male | 1 | 0 | 0 | 0 | 111 |
| AA645-HuEx-1_0-st-v2-01-1_437.CEL | 2 | 1738 | 1 | 55 | 12 | female | 0 | 1 | 0 | 0 | 105 |
| AA703-HuEx-1_0-st-v2-01-1_441.CEL | 3 | 1739 | 1 | 67 | 10 | male | 0 | 1 | NA | 1 | 50 |
| AA646-HuEx-1_0-st-v2-01-1_454.CEL | 2 | 1742 | 1 | 70 | 14 | male | 1 | 0 | 0 | 0 | 153 |
| AA592-HuEx-1_0-st-v2-01-1_455.CEL | 1 | 1743 | 1 | 68 | 17 | male | 0 | 0 | NA | 0 | 170 |
| AA593-HuEx-1_0-st-v2-01-1_475.CEL | 1 | 1748 | 0 | 75 | 14 | female | 0 | 0 | 0 | 0 | 112 |
| AA647-HuEx-1_0-st-v2-01-1_476.CEL | 2 | 1749 | 1 | 74 | 13 | male | 0 | 0 | 0 | 0 | 119 |
| AA648-HuEx-1_0-st-v2-01-1_477.CEL | 2 | 1750 | 0 | 60 | 14 | male | 0 | 0 | 0 | 0 | 132 |
| AA649-HuEx-1_0-st-v2-01-1_479.CEL | 2 | 1751 | 0 | 70 | 9 | female | 0 | 1 | 1 | 1 | 13 |
| AA650-HuEx-1_0-st-v2-01-1_504.CEL | 2 | 1755 | 0 | 81 | 14 | male | 1 | 0 | 0 | 1 | 60 |

TABLE 14-continued

| | | | | | | | | | | |
|---|---|---|---|---|---|---|---|---|---|---|
| AA651-HuEx-1_0-st-v2-01-1_510.CEL | 2 | 1758 | 0 | 82 | 10 | female | 0 | 0 | NA | 1 | 17 |
| AA595-HuEx-1_0-st-v2-01-1_512.CEL | 1 | 1759 | 1 | 67 | 10 | female | 0 | 0 | NA | 0 | 97 |
| AA706-HuEx-1_0-st-v2-01-1_517.CEL | 3 | 1760 | 0 | 91 | 9 | female | 0 | 0 | 1 | 1 | 4 |
| AA596-HuEx-1_0-st-v2-01-1_528.CEL | 1 | 1762 | 1 | 47 | 9 | male | 0 | 1 | 1 | 0 | 76 |
| AA845-HuEx-1_0-st-v2-01-1_547.CEL | 2 | 1764 | 0 | 55 | 9 | female | 0 | 0 | NA | 0 | 69 |
| AA598-HuEx-1_0-st-v2-01-1_552.CEL | 1 | 1765 | 0 | 77 | 13 | male | 1 | 1 | NA | 1 | 4 |
| AA707-HuEx-1_0-st-v2-01-1_567.CEL | 3 | 1770 | 1 | 73 | 16 | male | 0 | 1 | 1 | 0 | 115 |
| AA599-HuEx-1_0-st-v2-01-1_579.CEL | 1 | 1772 | 0 | 67 | 10 | male | 0 | 1 | 0 | 1 | 19 |
| AA600-HuEx-1_0-st-v2-01-1_586.CEL | 1 | 1773 | 1 | 51 | 8 | male | 0 | 0 | 1 | 0 | 66 |
| AA653-HuEx-1_0-st-v2-01-1_591.CEL | 2 | 1774 | 0 | 76 | 8 | male | 1 | 0 | 0 | 1 | 36 |
| AA654-HuEx-1_0-st-v2-01-1_596.CEL | 2 | 1776 | 0 | 57 | 13 | female | 0 | 1 | 1 | 1 | 41 |
| AA655-HuEx-1_0-st-v2-01-1_597.CEL | 2 | 1777 | 0 | 75 | 19 | male | 0 | 0 | 0 | 1 | 128 |
| AA656-HuEx-1_0-st-v2-01-1_600.CEL | 2 | 1778 | 0 | 63 | 19 | male | 0 | 0 | 0 | 1 | 102 |
| AA657-HuEx-1_0-st-v2-01-1_608.CEL | 2 | 1779 | 0 | 78 | 12 | male | 1 | 0 | 0 | 0 | 99 |
| AA601-HuEx-1_0-st-v2-01-1_612.CEL | 1 | 1780 | 0 | 77 | 17 | male | 0 | 1 | 1 | 1 | 13 |
| AA708-HuEx-1_0-st-v2-01-1_616.CEL | 3 | 1781 | 0 | 77 | 17 | male | 0 | 1 | 1 | 1 | 2 |
| AA709-HuEx-1_0-st-v2-01-1_619.CEL | 3 | 1783 | 0 | 86 | 14 | male | 1 | 0 | 0 | 1 | 8 |
| AA603-HuEx-1_0-st-v2-01-1_626.CEL | 1 | 1786 | 0 | 66 | 14 | male | 1 | 0 | 0 | 0 | 127 |
| AA658-HuEx-1_0-st-v2-01-1_627.CEL | 2 | 1787 | 1 | 64 | 11 | male | 0 | 0 | 0 | 0 | 91 |
| AA659-HuEx-1_0-st-v2-01-1_630_2.CEL | 2 | 1788 | 0 | 74 | 15 | male | 0 | 0 | 1 | 1 | 11 |
| AA604-HuEx-1_0-st-v2-01-1_640.CEL | 1 | 1789 | 0 | 72 | 11 | male | 1 | 0 | 1 | 1 | 17 |
| AA710-HuEx-1_0-st-v2-01-1_643.CEL | 3 | 1791 | 0 | 65 | 12 | male | 1 | 0 | 1 | 0 | 107 |
| AA660-HuEx-1_0-st-v2-01-1_644.CEL | 2 | 1792 | 0 | 85 | 9 | male | 0 | 0 | NA | 1 | 14 |
| AA711-HuEx-1_0-st-v2-01-1_645.CEL | 3 | 1793 | 1 | 78 | 10 | male | 1 | 1 | 1 | 1 | 5 |
| AA712-HuEx-1_0-st-v2-01-1_646.CEL | 3 | 1794 | 1 | 65 | 12 | female | 0 | 0 | 0 | 0 | 108 |
| AA713-HuEx-1_0-st-v2-01-1_647.CELe | 3 | 1795 | 1 | 61 | 11 | female | 1 | 1 | 0 | 1 | 24 |

TABLE 14-continued

| | | | | | | | | | | |
|---|---|---|---|---|---|---|---|---|---|---|
| AA605-HuEx-1_0-st-v2-01-1_648.CEL | 1 | 1796 | 0 | 77 | 17 | male | 0 | 0 | 0 | 1 | 69 |
| AA714-HuEx-1_0-st-v2-01-1_655.CEL | 3 | 1800 | 0 | 81 | 11 | male | 1 | 1 | 1 | 1 | 15 |
| AA716-HuEx-1_0-st-v2-01-1_668.CEL | 3 | 1805 | 0 | 67 | 18 | male | 0 | 0 | 0 | 0 | 168 |
| AA661-HuEx-1_0-st-v2-01-1_673.CEL | 2 | 1806 | 0 | 64 | 17 | male | 0 | 0 | 1 | 0 | 172 |
| AA606-HuEx-1_0-st-v2-01-1_686.CEL | 1 | 1809 | 0 | 68 | 12 | male | 1 | 0 | NA | 0 | 118 |
| AA717-HuEx-1_0-st-v2-01-1_691.CEL | 3 | 1811 | 1 | 63 | 9 | female | 0 | 1 | 1 | 1 | 10 |
| AA718-HuEx-1_0-st-v2-01-1_693.CEL | 3 | 1812 | 1 | 58 | 14 | male | 0 | 1 | 1 | 0 | 135 |
| AA663-HuEx-1_0-st-v2-01-1_708.CEL | 2 | 1816 | 0 | 74 | 13 | male | 0 | 0 | 0 | 1 | 7 |
| AA608-HuEx-1_0-st-v2-01-1_717.CEL | 1 | 1820 | 0 | 66 | 11 | male | 0 | 0 | 0 | 0 | 104 |
| AA609-HuEx-1_0-st-v2-01-1_722.CEL | 1 | 1821 | 0 | 67 | 15 | female | 0 | 0 | 0 | 1 | 37 |
| AA610-HuEx-1_0-st-v2-01-1_734.CEL | 1 | 1824 | 0 | 83 | 13 | female | 0 | 0 | 1 | 1 | 31 |
| AA664-HuEx-1_0-st-v2-01-1_738.CEL | 2 | 1825 | 1 | 61 | 8 | male | 0 | 1 | NA | 0 | 76 |
| AA611-HuEx-1_0-st-v2-01-1_740.CEL | 1 | 1826 | 1 | 69 | 11 | male | 1 | 1 | 1 | 1 | 13 |
| AA665-HuEx-1_0-st-v2-01-1_744.CEL | 2 | 1827 | 0 | 53 | 9 | male | 0 | 0 | 0 | 0 | 50 |
| AA612-HuEx-1_0-st-v2-01-1_750.CEL | 1 | 1829 | 1 | 70 | 8 | male | 0 | 1 | 1 | 1 | 47 |
| AA720-HuEx-1_0-st-v2-01-1_752.CEL | 3 | 1830 | 0 | 63 | 9 | male | 1 | 0 | NA | 0 | 87 |
| AA613-HuEx-1_0-st-v2-01-1_753.CEL | 1 | 1831 | 0 | 81 | 11 | female | 0 | 0 | 0 | 1 | 10 |
| AA614-HuEx-1_0-st-v2-01-1_767.CEL | 1 | 1835 | 0 | 49 | 16 | male | 0 | 0 | 0 | 0 | 129 |
| AA615-HuEx-1_0-st-v2-01-1_781.CEL | 1 | 1839 | NA | 65 | 12 | male | 0 | 1 | 1 | 1 | 16 |
| AA723-HuEx-1_0-st-v2-01-1_816.CEL | 3 | 1845 | 1 | 52 | 14 | female | 0 | 1 | 1 | 1 | 25 |
| AA724-HuEx-1_0-st-v2-01-1_822.CEL | 3 | 1847 | 0 | 78 | 18 | male | 1 | 0 | NA | 1 | 97 |
| AA668-HuEx-1_0-st-v2-01-1_827.CEL | 2 | 1849 | 1 | 77 | 9 | male | 1 | 1 | 1 | 1 | 10 |
| AA669-HuEx-1_0-st-v2-01-1_828.CEL | 2 | 1850 | 0 | 63 | 17 | male | 1 | 0 | 0 | 0 | 160 |
| AA670-HuEx-1_0-st-v2-01-1_832.CEL | 2 | 1851 | 1 | 50 | 9 | male | 0 | 1 | 1 | 1 | 25 |
| AA616-HuEx-1_0-st-v2-01-1_842.CEL | 1 | 1853 | 0 | 75 | 10 | male | 1 | 0 | NA | 0 | 90 |
| AA671-HuEx-1_0-st-v2-01-1_844.CEL | 2 | 1854 | 1 | 59 | 9 | male | 0 | 1 | 1 | 1 | 15 |

TABLE 14-continued

| | | | | | | | | | | | |
|---|---|---|---|---|---|---|---|---|---|---|---|
| AA725-HuEx-1_0-st-v2-01-1_846.CEL | 3 | 1855 | 0 | 75 | 13 | male | 0 | 0 | 1 | 0 | 110 |
| AA672-HuEx-1_0-st-v2-01-1_850.CEL | 2 | 1857 | 0 | 65 | 12 | male | 0 | 0 | NA | 1 | 19 |
| AA617-HuEx-1_0-st-v2-01-1_852.CEL | 1 | 1858 | 0 | 54 | 12 | male | 0 | 0 | 0 | 0 | 114 |
| AA673-HuEx-1_0-st-v2-01-1_857.CEL | 2 | 1860 | 0 | 68 | 10 | female | 0 | 0 | 1 | 1 | 3 |
| AA618-HuEx-1_0-st-v2-01-1_869.CEL | 1 | 1863 | 1 | 72 | 9 | male | 1 | 1 | 1 | 1 | 10 |
| AA726-HuEx-1_0-st-v2-01-1_872.CEL | 3 | 1864 | 1 | 61 | 9 | male | 1 | 0 | 0 | 0 | 92 |
| AA674-HuEx-1_0-st-v2-01-1_877.CEL | 2 | 1866 | 0 | 58 | 18 | male | 0 | 0 | 0 | 0 | 175 |
| AA675-HuEx-1_0-st-v2-01-1_878.CEL | 2 | 1867 | 1 | 66 | 18 | male | 1 | 0 | 0 | 0 | 174 |
| AA727-HuEx-1_0-st-v2-01-1_892.CEL | 3 | 1870 | 0 | 73 | 8 | male | 0 | 0 | 0 | 1 | 45 |
| AA620-HuEx-1_0-st-v2-01-1_894.CEL | 1 | 1871 | 0 | 76 | 15 | male | 0 | 0 | 1 | 1 | 22 |
| AA728-HuEx-1_0-st-v2-01-1_895.CEL | 3 | 1872 | 1 | 79 | 16 | male | 0 | 1 | 1 | 1 | 36 |
| AA621-HuEx-1_0-st-v2-01-1_902.CEL | 1 | 1873 | 1 | 66 | 9 | female | 0 | 1 | 1 | 1 | 11 |
| AA676-HuEx-1_0-st-v2-01-1_906.CEL | 2 | 1874 | 0 | 82 | 7 | male | 1 | 0 | 1 | 0 | 47 |
| AA622-HuEx-1_0-st-v2-01-1_907.CEL | 1 | 1875 | 1 | 52 | 16 | male | 0 | 0 | 0 | 0 | 130 |
| AA677-HuEx-1_0-st-v2-01-1_911.CEL | 2 | 1877 | 0 | 81 | 17 | male | 0 | 1 | 1 | 1 | 5 |
| AA678-HuEx-1_0-st-v2-01-1_914.CEL | 2 | 1878 | 1 | 66 | 20 | male | 0 | 1 | 1 | 1 | 32 |
| AA729-HuEx-1_0-st-v2-01-1_916.CEL | 3 | 1879 | 0 | 73 | 11 | female | 0 | 0 | 0 | 1 | 8 |
| AA623-HuEx-1_0-st-v2-01-1_924.CEL | 1 | 1881 | 0 | 85 | 17 | male | 0 | 0 | 1 | 1 | 5 |
| AA730-HuEx-1_0-st-v2-01-1_926.CEL | 3 | 1883 | 0 | 80 | 16 | female | 0 | 0 | 0 | 1 | 61 |
| AA731-HuEx-1_0-st-v2-01-1_928.CEL | 3 | 1884 | 1 | 70 | 18 | male | 0 | 1 | 1 | 1 | 11 |
| AA679-HuEx-1_0-st-v2-01-1_932.CEL | 2 | 1885 | 1 | 68 | 20 | male | 0 | 1 | 0 | 1 | 46 |
| AA624-HuEx-1_0-st-v2-01-1_951.CEL | 1 | 1886 | 0 | 76 | 9 | male | 0 | 0 | 0 | 0 | 76 |
| AA681-HuEx-1_0-st-v2-01-1_961.CEL | 2 | 1891 | 1 | 68 | 12 | female | 1 | 1 | 1 | 1 | 23 |
| AA626-HuEx-1_0-st-v2-01-1_963.CEL | 1 | 1892 | 0 | 69 | 9 | male | 0 | 1 | 0 | 1 | 3 |
| AA734-HuEx-1_0-st-v2-01-1_968.CEL | 3 | 1893 | 0 | 31 | 20 | female | 0 | 0 | 0 | 1 | 15 |
| AA841-HuEx-1_0-st-v2-01-1_983.CEL | 1 | 1894 | 0 | 66 | 8 | male | 0 | 0 | 0 | 0 | 71 |

TABLE 14-continued

| | | | | | | | | | | |
|---|---|---|---|---|---|---|---|---|---|---|
| AA735-HuEx-1_0-st-v2-01-1_887-A.CEL | 3 | 1896 | 0 | 70 | 10 | male | 0 | 0 | NA | 0 | 102 |
| AA790-HuEx-1_0-st-v2-01-1_122.CEL | 5 | 1648 | 0 | 67 | 18 | female | 0 | 0 | 1 | 1 | 15 |
| AA737-HuEx-1_0-st-v2-01-1_155.CEL | 4 | 1656 | 0 | 66 | 19 | female | 1 | 0 | 1 | 1 | 32 |
| AA738-HuEx-1_0-st-v2-01-1_163.CEL | 4 | 1660 | 1 | 66 | 17 | male | 0 | 0 | 0 | 0 | 168 |
| AA740-HuEx-1_0-st-v2-01-1_168.CEL | 4 | 1664 | 1 | 68 | 9 | male | 0 | 1 | 1 | 1 | 6 |
| AA741-HuEx-1_0-st-v2-01-1_182.CEL | 4 | 1666 | 0 | 78 | 11 | male | 0 | 0 | 0 | 1 | 102 |
| AA742-HuEx-1_0-st-v2-01-1_219.CEL | 4 | 1677 | 0 | 68 | 9 | female | 0 | 1 | 1 | 1 | 19 |
| AA743-HuEx-1_0-st-v2-01-1_238.CEL | 4 | 1685 | 0 | 61 | 17 | male | 0 | 0 | 1 | 0 | 175 |
| AA744-HuEx-1_0-st-v2-01-1_240.CEL | 4 | 1686 | 1 | 55 | 12 | male | 0 | 1 | 1 | 1 | 14 |
| AA745-HuEx-1_0-st-v2-01-1_252.CEL | 4 | 1687 | 0 | 74 | 11 | male | 0 | 1 | 1 | 1 | 81 |
| AA792-HuEx-1_0-st-v2-01-1_276.CEL | 5 | 1692 | 1 | 71 | 10 | male | 0 | 0 | 0 | 1 | 24 |
| AA857-HuEx-1_0-st-v2-01-1_280.CEL | 5 | 1693 | 1 | 80 | 11 | male | 0 | 1 | 0 | 1 | 25 |
| AA747-HuEx-1_0-st-v2-01-1_306.CEL | 4 | 1703 | 1 | 71 | 19 | male | 1 | 0 | 0 | 1 | 57 |
| AA748-HuEx-1_0-st-v2-01-1_318.CEL | 4 | 1707 | 1 | 68 | 10 | male | 0 | 0 | 0 | 0 | 94 |
| AA794-HuEx-1_0-st-v2-01-1_337.CEL | 5 | 1708 | 0 | 65 | 14 | male | 0 | 0 | 0 | 0 | 131 |
| AA749-HuEx-1_0-st-v2-01-1_341.CEL | 4 | 1710 | 1 | 68 | 12 | female | 0 | 0 | 1 | 1 | 10 |
| AA751-HuEx-1_0-st-v2-01-1_352.CEL | 4 | 1713 | 1 | 80 | 16 | male | 1 | 0 | 0 | 1 | 11 |
| AA752-HuEx-1_0-st-v2-01-1_354.CEL | 4 | 1714 | 1 | 74 | 12 | male | 0 | 0 | 0 | 1 | 18 |
| AA795-HuEx-1_0-st-v2-01-1_377.CEL | 5 | 1720 | 0 | 71 | 11 | male | 0 | 1 | 1 | 1 | 28 |
| AA754-HuEx-1_0-st-v2-01-1_387.CEL | 4 | 1722 | 1 | 63 | 10 | male | 0 | 0 | 1 | 1 | 101 |
| AA756-HuEx-1_0-st-v2-01-1_397.CEL | 4 | 1726 | 0 | 53 | 9 | male | 0 | 0 | 1 | 1 | 13 |
| AA757-HuEx-1_0-st-v2-01-1_403.CEL | 4 | 1728 | 0 | 81 | 8 | male | 0 | 0 | 1 | 1 | 36 |
| AA796-HuEx-1_0-st-v2-01-1_411.CEL | 5 | 1729 | 1 | 55 | 12 | male | 0 | 0 | 0 | 0 | 107 |
| AA797-HuEx-1_0-st-v2-01-1_412.CEL | 5 | 1730 | 0 | 75 | 10 | female | 0 | 0 | 0 | 0 | 94 |
| AA758-HuEx-1_0-st-v2-01-1_419.CEL | 4 | 1732 | 0 | 60 | 12 | male | 0 | 0 | 0 | 0 | 112 |
| AA799-HuEx-1_0-st-v2-01-1_423.CEL | 5 | 1734 | 0 | 67 | 11 | male | 0 | 1 | 1 | 1 | 5 |

TABLE 14-continued

| celfile | | | | | | | | | | |
|---|---|---|---|---|---|---|---|---|---|---|
| AA800-HuEx-1_0-st-v2-01-1_431.CEL | 5 | 1736 | 1 | 69 | 17 | female | 0 | 0 | 1 | 0 | 157 |
| AA759-HuEx-1_0-st-v2-01-1_445.CEL | 4 | 1741 | 1 | 70 | 12 | male | 0 | 0 | 0 | 0 | 100 |
| AA801-HuEx-1_0-st-v2-01-1_458.CEL | 5 | 1744 | 0 | 79 | 9 | male | 1 | 1 | NA | 1 | 43 |
| AA760-HuEx-1_0-st-v2-01-1_459.CEL | 4 | 1745 | 1 | 60 | 18 | male | 0 | 0 | 1 | 1 | 26 |
| AA761-HuEx-1_0-st-v2-01-1_467.CEL | 4 | 1746 | 0 | 68 | 13 | male | 1 | 1 | NA | 0 | 111 |
| AA764-HuEx-1_0-st-v2-01-1_508.CEL | 4 | 1757 | 0 | 76 | 13 | male | 1 | 0 | 1 | 1 | 40 |
| AA803-HuEx-1_0-st-v2-01-1_522.CEL | 5 | 1761 | NA | 81 | 9 | male | 0 | 0 | 1 | 1 | 9 |
| AA765-HuEx-1_0-st-v2-01-1_557.CEL | 4 | 1766 | 1 | 58 | 15 | male | 0 | 1 | 1 | 1 | 20 |
| AA804-HuEx-1_0-st-v2-01-1_558.CEL | 5 | 1767 | 1 | 74 | 15 | male | 1 | 1 | 1 | 1 | 34 |
| AA768-HuEx-1_0-st-v2-01-1_618.CEL | 4 | 1782 | 0 | 71 | 20 | male | 0 | 0 | 0 | 1 | 10 |
| AA769-HuEx-1_0-st-v2-01-1_622.CEL | 4 | 1784 | 1 | 67 | 19 | male | 0 | 1 | 0 | 1 | 27 |
| AA807-HuEx-1_0-st-v2-01-1_641.CEL | 5 | 1790 | 0 | 67 | 14 | male | 1 | 0 | 1 | 1 | 21 |
| AA770-HuEx-1_0-st-v2-01-1_649.CEL | 4 | 1797 | 1 | 70 | 18 | male | 0 | 1 | 1 | 1 | 60 |
| AA773-HuEx-1_0-st-v2-01-1_665.CEL | 4 | 1803 | 1 | 70 | 9 | male | 0 | 1 | 1 | 1 | 16 |
| AA775-HuEx-1_0-st-v2-01-1_676.CEL | 4 | 1807 | 1 | 74 | 9 | female | 0 | 1 | 1 | 1 | 27 |
| AA809-HuEx-1_0-st-v2-01-1_685.CEL | 5 | 1808 | 0 | 73 | 14 | female | 0 | 0 | 0 | 1 | 100 |
| AA810-HuEx-1_0-st-v2-01-1_690.CEL | 5 | 1810 | 0 | 76 | 9 | male | 0 | 0 | 1 | 1 | 4 |
| AA852-HuEx-1_0-st-v2-01-1_695.CEL | 4 | 1813 | 0 | 72 | 12 | female | 0 | 0 | NA | 0 | 119 |
| AA811-HuEx-1_0-st-v2-01-1_707.CEL | 5 | 1815 | 0 | 46 | 16 | male | 1 | 0 | 1 | 1 | 39 |
| AA777-HuEx-1_0-st-v2-01-1_713.CEL | 4 | 1818 | 0 | 62 | 11 | male | 0 | 0 | 0 | 1 | 37 |
| AA778-HuEx-1_0-st-v2-01-1_716.CEL | 4 | 1819 | 0 | 59 | 9 | male | 1 | 1 | 1 | 1 | 51 |

| celfile | P-Stage | Race | Rec_Event | Rec_Event_Time | qc.10.20.pass | qc.15.20.pass | qc.20.25.pass |
|---|---|---|---|---|---|---|---|
| AA682-HuEx-1_0-st-v2-01-1_118.CEL | 11 | non-white | 1 | 9 | 0 | 0 | 0 |
| AA629-HuEx-1_0-st-v2-01-1_132.CEL | 12 | non-white | 0 | 113 | 0 | 0 | 0 |
| AA684-HuEx-1_0-st-v2-01-1_142.CEL | 13 | white | 0 | 19 | 1 | 0 | 0 |
| AA736-HuEx-1_0-st-v2-02-2_145.CEL | 12 | white | 0 | 179 | 0 | 0 | 0 |

TABLE 14-continued

| | | | | | | | |
|---|---|---|---|---|---|---|---|
| AA685-HuEx-1_0-st-v2-01-1_157.CEL | 14 | white | 1 | 9 | 0 | 0 | 0 |
| AA739-HuEx-1_0-st-v2-02-2_166.CEL | 11 | white | 0 | 2 | 1 | 0 | 0 |
| AA579-HuEx-1_0-st-v2-01-1_220.CEL | 13 | white | 1 | 3 | 0 | 0 | 0 |
| AA636-HuEx-1_0-st-v2-01-1_226.CEL | 12 | white | 0 | 12 | 0 | 0 | 0 |
| AA856-HuEx-1_0-st-v2-01-1_274.CEL | 11 | white | 0 | 90 | 0 | 0 | 0 |
| AA746-HuEx-1_0-st-v2-01-1_292.CEL | 14 | white | 1 | 3 | 0 | 0 | 0 |
| AA694-HuEx-1_0-st-v2-01-1_293.CEL | 13 | white | 1 | 63 | 0 | 0 | 0 |
| AA585-HuEx-1_0-st-v2-01-1_294.CEL | 13 | white | 0 | 3 | 0 | 0 | 0 |
| AA696-HuEx-1_0-st-v2-01-1_299.CEL | 13 | white | 1 | 7 | 0 | 0 | 0 |
| AA697-HuEx-1_0-st-v2-01-1_311.CEL | 12 | white | 1 | 12 | 1 | 0 | 0 |
| AA750-HuEx-1_0-st-v2-01-1_343.CEL | 12 | white | 0 | 83 | 1 | 0 | 0 |
| AA643-HuEx-1_0-st-v2-01-1_369.CEL | 13 | white | 1 | 14 | 1 | 1 | 0 |
| AA699-HuEx-1_0-st-v2-01-1_373.CEL | 12 | white | 0 | 90 | 0 | 0 | 0 |
| AA753-HuEx-1_0-st-v2-01-1_376.CEL | 12 | white | 0 | 83 | 0 | 0 | 0 |
| AA755-HuEx-1_0-st-v2-01-1_390.CEL | 12 | white | 0 | 14 | 0 | 0 | 0 |
| AA798-HuEx-1_0-st-v2-01-1_414.CEL | 12 | white | 1 | 6 | 0 | 0 | 0 |
| AA702-HuEx-1_0-st-v2-01-1_420.CEL | 12 | white | 0 | 42 | 1 | 1 | 1 |
| AA704-HuEx-1_0-st-v2-01-1_444.CEL | 13 | white | 1 | 8 | 0 | 0 | 0 |
| AA802-HuEx-1_0-st-v2-01-1_469.CEL | 12 | white | 0 | 130 | 0 | 0 | 0 |
| AA762-HuEx-1_0-st-v2-01-1_481.CEL | 12 | white | 1 | 8 | 1 | 0 | 0 |
| AA763-HuEx-1_0-st-v2-01-1_485.CEL | 12 | white | 0 | 69 | 0 | 0 | 0 |
| AA594-HuEx-1_0-st-v2-01-1_493.CEL | 12 | white | 0 | 155 | 0 | 0 | 0 |
| AA705-HuEx-1_0-st-v2-01-1_506.CEL | 12 | non-white | 0 | 73 | 1 | 1 | 1 |
| AA597-HuEx-1_0-st-v2-01-1_529_2.CEL | 13 | white | 1 | 8 | 1 | 1 | 1 |
| AA805-HuEx-1_0-st-v2-01-1_560.CEL | 12 | white | 1 | 13 | 0 | 0 | 0 |
| AA766-HuEx-1_0-st-v2-01-1_562.CEL | 11 | white | 0 | 203 | 1 | 0 | 0 |

TABLE 14-continued

| | | | | | | | |
|---|---|---|---|---|---|---|---|
| AA767-HuEx-1_0-st-v2-01-1_569.CEL | 13 | white | 1 | 9 | 0 | 0 | 0 |
| AA806-HuEx-1_0-st-v2-01-1_594.CEL | 14 | white | 0 | 8 | 0 | 0 | 0 |
| AA602-HuEx-1_0-st-v2-01-1_623.CEL | 12 | white | 0 | 169 | 0 | 0 | 0 |
| AA771-HuEx-1_0-st-v2-01-1_651.CEL | 13 | white | 0 | 124 | 1 | 0 | 0 |
| AA772-HuEx-1_0-st-v2-01-1_652.CEL | 12 | white | 0 | 76 | 1 | 0 | 0 |
| AA808-HuEx-1_0-st-v2-01-1_656.CEL | 13 | non-white | 0 | 6 | 0 | 0 | 0 |
| AA849-HuEx-1_0-st-v2-01-1_664.CEL | 13 | white | 1 | 12 | 1 | 1 | 1 |
| AA774-HuEx-1_0-st-v2-01-1_666.CEL | 13 | white | 0 | 78 | 0 | 0 | 0 |
| AA662-HuEx-1_0-st-v2-01-1_703.CEL | 12 | white | 0 | 143 | 1 | 0 | 0 |
| AA607-HuEx-1_0-st-v2-01-1_709.CEL | 14 | white | 0 | 6 | 0 | 0 | 0 |
| AA719-HuEx-1_0-st-v2-01-1_726.CEL | 13 | non-white | 0 | 69 | 1 | 0 | 0 |
| AA721-HuEx-1_0-st-v2-01-1_756.CEL | 13 | non-white | 0 | 20 | 0 | 0 | 0 |
| AA666-HuEx-1_0-st-v2-01-1_763.CEL | 13 | white | 1 | 20 | 1 | 1 | 0 |
| AA722-HuEx-1_0-st-v2-01-1_777.CEL | 12 | white | 0 | 159 | 0 | 0 | 0 |
| AA780-HuEx-1_0-st-v2-01-1_779.CEL | 13 | white | 0 | 76 | 0 | 0 | 0 |
| AA781-HuEx-1_0-st-v2-02-2_800.CEL | 12 | white | 0 | 18 | 1 | 1 | 0 |
| AA667-HuEx-1_0-st-v2-01-1_826.CEL | 12 | white | 0 | 112 | 1 | 1 | 1 |
| AA619-HuEx-1_0-st-v2-01-1_881.CEL | 12 | white | 0 | 60 | 0 | 0 | 0 |
| AA625-HuEx-1_0-st-v2-01-1_956.CEL | 13 | white | 0 | 120 | 0 | 0 | 0 |
| AA732-HuEx-1_0-st-v2-01-1_957.CEL | 14 | white | 1 | 13 | 1 | 1 | 1 |
| AA680-HuEx-1_0-st-v2-01-1_958.CEL | 12 | white | 0 | 172 | 0 | 0 | 0 |
| AA733-HuEx-1_0-st-v2-01-1_959.CEL | 13 | white | 1 | 7 | 1 | 1 | 0 |
| AA574-HuEx-1_0-st-v2-01-1_120.CEL | 14 | white | 1 | 56 | 1 | 1 | 0 |
| AA628-HuEx-1_0-st-v2-01-1_130.CEL | 13 | white | 0 | 27 | 1 | 1 | 0 |
| AA683-HuEx-1_0-st-v2-01-1_135.CEL | 14 | white | 0 | 11 | 1 | 1 | 1 |
| AA575-HuEx-1_0-st-v2-01-1_143.CEL | 13 | white | 0 | 3 | 1 | 1 | 1 |

TABLE 14-continued

| | | | | | | | |
|---|---|---|---|---|---|---|---|
| AA630-HuEx-1_0-st-v2-01-1_144.CEL | 13 | non-white | 0 | 73 | 1 | 1 | 0 |
| AA846-HuEx-1_0-st-v2-01-1_159.CEL | 13 | non-white | 0 | 68 | 1 | 1 | 1 |
| AA576-HuEx-1_0-st-v2-01-1_162.CEL | 14 | white | 0 | 71 | 1 | 1 | 1 |
| AA686-HuEx-1_0-st-v2-01-1_165.CEL | 12 | white | 0 | 149 | 1 | 1 | 1 |
| AA687-HuEx-1_0-st-v2-01-1_167.CEL | 12 | non-white | 0 | 133 | 1 | 1 | 1 |
| AA631-HuEx-1_0-st-v2-01-1_173.CEL | 11 | white | 1 | 14 | 1 | 1 | 0 |
| AA577-HuEx-1_0-st-v2-01-1_184.CEL | 13 | white | 1 | 14 | 1 | 1 | 1 |
| AA578-HuEx-1_0-st-v2-01-1_186.CEL | 13 | white | 1 | 4 | 1 | 1 | 1 |
| AA632-HuEx-1_0-st-v2-01-1_195.CEL | 14 | white | 1 | 24 | 1 | 1 | 1 |
| AA848-HuEx-1_0-st-v2-01-1_198.CEL | 14 | white | 0 | 107 | 1 | 1 | 1 |
| AA689-HuEx-1_0-st-v2-01-1_199.CEL | 13 | white | 1 | 4 | 1 | 1 | 1 |
| AA633-HuEx-1_0-st-v2-01-1_203.CEL | 13 | white | 0 | 31 | 1 | 1 | 1 |
| AA690-HuEx-1_0-st-v2-01-1_211.CEL | 13 | white | 0 | 108 | 1 | 1 | 0 |
| AA634-HuEx-1_0-st-v2-01-1_213.CEL | 14 | white | 1 | 7 | 1 | 1 | 1 |
| AA691-HuEx-1_0-st-v2-01-1_214.CEL | 12 | white | 0 | 25 | 1 | 1 | 1 |
| AA635-HuEx-1_0-st-v2-01-1_218.CEL | 13 | white | 0 | 78 | 1 | 1 | 1 |
| AA692-HuEx-1_0-st-v2-01-1_224.CEL | 13 | white | 0 | 5 | 1 | 1 | 1 |
| AA580-HuEx-1_0-st-v2-01-1_227.CEL | 13 | white | 0 | 45 | 1 | 1 | 0 |
| AA637-HuEx-1_0-st-v2-01-1_228.CEL | 13 | white | 1 | 7 | 1 | 1 | 1 |
| AA693-HuEx-1_0-st-v2-01-1_230.CEL | 12 | white | 1 | 18 | 1 | 1 | 1 |
| AA581-HuEx-1_0-st-v2-01-1_235.CEL | 14 | white | 0 | 90 | 1 | 1 | 1 |
| AA638-HuEx-1_0-st-v2-01-1_258.CEL | 13 | white | 1 | 37 | 1 | 1 | 1 |
| AA639-HuEx-1_0-st-v2-01-1_267.CEL | 13 | white | 0 | 10 | 1 | 1 | 1 |
| AA582-HuEx-1_0-st-v2-01-1_272.CEL | 12 | white | 1 | 8 | 1 | 1 | 1 |
| AA640-HuEx-1_0-st-v2-01-1_281.CEL | 13 | white | 1 | 12 | 1 | 1 | 1 |
| AA583-HuEx-1_0-st-v2-01-1_284.CEL | 13 | white | 1 | 23 | 1 | 1 | 0 |

TABLE 14-continued

| | | | | | | | |
|---|---|---|---|---|---|---|---|
| AA584-HuEx-1_0-st-v2-01-1_286.CEL | 14 | white | 1 | 7 | 1 | 1 | 0 |
| AA695-HuEx-1_0-st-v2-01-1_295.CEL | 13 | white | 0 | 72 | 1 | 1 | 0 |
| AA586-HuEx-1_0-st-v2-01-1_296.CEL | 13 | white | 1 | 20 | 1 | 1 | 1 |
| AA587-HuEx-1_0-st-v2-01-1_309.CEL | 12 | white | 0 | 175 | 1 | 1 | 0 |
| AA641-HuEx-1_0-st-v2-01-1_314.CEL | 12 | white | 1 | 50 | 1 | 1 | 1 |
| AA847-HuEx-1_0-st-v2-01-1_338.CEL | 12 | white | 1 | 24 | 1 | 1 | 1 |
| AA698-HuEx-1_0-st-v2-01-1_342.CEL | 13 | white | 0 | 94 | 1 | 1 | 1 |
| AA642-HuEx-1_0-st-v2-01-1_368.CEL | 12 | white | 1 | 12 | 1 | 1 | 1 |
| AA588-HuEx-1_0-st-v2-01-1_375.CEL | 11 | white | 0 | 112 | 1 | 1 | 1 |
| AA644-HuEx-1_0-st-v2-01-1_382.CEL | 13 | white | 1 | 35 | 1 | 1 | 1 |
| AA700-HuEx-1_0-st-v2-01-1_393.CEL | 13 | white | 1 | 18 | 1 | 1 | 1 |
| AA589-HuEx-1_0-st-v2-01-1_396.CEL | 14 | white | 1 | 70 | 1 | 1 | 1 |
| AA701-HuEx-1_0-st-v2-01-1_402.CEL | 14 | white | 0 | 151 | 1 | 1 | 1 |
| AA590-HuEx-1_0-st-v2-01-1_430.CEL | 13 | white | 1 | 3 | 1 | 1 | 1 |
| AA591-HuEx-1_0-st-v2-01-1_436.CEL | 12 | white | 0 | 111 | 1 | 1 | 1 |
| AA645-HuEx-1_0-st-v2-01-1_437.CEL | 13 | white | 0 | 105 | 1 | 1 | 1 |
| AA703-HuEx-1_0-st-v2-01-1_441.CEL | 14 | white | 1 | 40 | 1 | 1 | 1 |
| AA646-HuEx-1_0-st-v2-01-1_454.CEL | 14 | white | 0 | 153 | 1 | 1 | 1 |
| AA592-HuEx-1_0-st-v2-01-1_455.CEL | 12 | white | 0 | 170 | 1 | 1 | 1 |
| AA593-HuEx-1_0-st-v2-01-1_475.CEL | 12 | non-white | 0 | 112 | 1 | 1 | 1 |
| AA647-HuEx-1_0-st-v2-01-1_476.CEL | 13 | white | 0 | 119 | 1 | 1 | 1 |
| AA648-HuEx-1_0-st-v2-01-1_477.CEL | 13 | white | 0 | 132 | 1 | 1 | 1 |
| AA649-HuEx-1_0-st-v2-01-1_479.CEL | 13 | white | 1 | 4 | 1 | 1 | 1 |
| AA650-HuEx-1_0-st-v2-01-1_504.CEL | 12 | white | 1 | 48 | 1 | 1 | 1 |
| AA651-HuEx-1_0-st-v2-01-1_510.CEL | 13 | white | 0 | 17 | 1 | 1 | 1 |
| AA595-HuEx-1_0-st-v2-01-1_512.CEL | 13 | non-white | 0 | 97 | 1 | 1 | 1 |

TABLE 14-continued

| | | | | | | | |
|---|---|---|---|---|---|---|---|
| AA706-HuEx-1_0-st-v2-01-1_517.CEL | 13 | white | 1 | 4 | 1 | 1 | 1 |
| AA596-HuEx-1_0-st-v2-01-1_528.CEL | 12 | white | 1 | 4 | 1 | 1 | 0 |
| AA845-HuEx-1_0-st-v2-01-1_547.CEL | 12 | non-white | 0 | 69 | 1 | 1 | 1 |
| AA598-HuEx-1_0-st-v2-01-1_552.CEL | 14 | white | 1 | 3 | 1 | 1 | 1 |
| AA707-HuEx-1_0-st-v2-01-1_567.CEL | 13 | white | 0 | 115 | 1 | 1 | 1 |
| AA599-HuEx-1_0-st-v2-01-1_579.CEL | 11 | white | 0 | 19 | 1 | 1 | 1 |
| AA600-HuEx-1_0-st-v2-01-1_586.CEL | 13 | white | 0 | 66 | 1 | 1 | 1 |
| AA653-HuEx-1_0-st-v2-01-1_591.CEL | 12 | white | 0 | 36 | 1 | 1 | 1 |
| AA654-HuEx-1_0-st-v2-01-1_596.CEL | 14 | white | 1 | 23 | 1 | 1 | 1 |
| AA655-HuEx-1_0-st-v2-01-1_597.CEL | 12 | white | 0 | 128 | 1 | 1 | 1 |
| AA656-HuEx-1_0-st-v2-01-1_600.CEL | 13 | white | 1 | 18 | 1 | 1 | 1 |
| AA657-HuEx-1_0-st-v2-01-1_608.CEL | 14 | white | 1 | 65 | 1 | 1 | 1 |
| AA601-HuEx-1_0-st-v2-01-1_612.CEL | 13 | white | 0 | 13 | 1 | 1 | 1 |
| AA708-HuEx-1_0-st-v2-01-1_616.CEL | 14 | white | 0 | 2 | 1 | 1 | 1 |
| AA709-HuEx-1_0-st-v2-01-1_619.CEL | 13 | white | 0 | 8 | 1 | 1 | 1 |
| AA603-HuEx-1_0-st-v2-01-1_626.CEL | 14 | white | 0 | 127 | 1 | 1 | 0 |
| AA658-HuEx-1_0-st-v2-01-1_627.CEL | 13 | white | 0 | 91 | 1 | 1 | 1 |
| AA659-HuEx-1_0-st-v2-01-1_630_2.CEL | 12 | white | 0 | 11 | 1 | 1 | 1 |
| AA604-HuEx-1_0-st-v2-01-1_640.CEL | 12 | non-white | 1 | 15 | 1 | 1 | 1 |
| AA710-HuEx-1_0-st-v2-01-1_643.CEL | 12 | white | 0 | 107 | 1 | 1 | 1 |
| AA660-HuEx-1_0-st-v2-01-1_644.CEL | 13 | white | 1 | 8 | 1 | 1 | 1 |
| AA711-HuEx-1_0-st-v2-01-1_645.CEL | 14 | white | 1 | 4 | 1 | 1 | 1 |
| AA712-HuEx-1_0-st-v2-01-1_646.CEL | 13 | white | 0 | 108 | 1 | 1 | 1 |
| AA713-HuEx-1_0-st-v2-01-1_647.CEL | 12 | non-white | 1 | 16 | 1 | 1 | 1 |
| AA605-HuEx-1_0-st-v2-01-1_648.CEL | 14 | white | 0 | 69 | 1 | 1 | 1 |
| AA714-HuEx-1_0-st-v2-01-1_655.CEL | 11 | white | 1 | 15 | 1 | 1 | 1 |

TABLE 14-continued

| | | | | | | | |
|---|---|---|---|---|---|---|---|
| AA716-HuEx-1_0-st-v2-01-1_668.CEL | 13 | white | 0 | 168 | 1 | 1 | 0 |
| AA661-HuEx-1_0-st-v2-01-1_673.CEL | 13 | white | 0 | 172 | 1 | 1 | 1 |
| AA606-HuEx-1_0-st-v2-01-1_686.CEL | 13 | white | 0 | 118 | 1 | 1 | 1 |
| AA717-HuEx-1_0-st-v2-01-1_691.CEL | 13 | non-white | 1 | 8 | 1 | 1 | 1 |
| AA718-HuEx-1_0-st-v2-01-1_693.CEL | 12 | white | 0 | 135 | 1 | 1 | 1 |
| AA663-HuEx-1_0-st-v2-01-1_708.CEL | 12 | white | 0 | 7 | 1 | 1 | 1 |
| AA608-HuEx-1_0-st-v2-01-1_717.CEL | 12 | white | 1 | 76 | 1 | 1 | 1 |
| AA609-HuEx-1_0-st-v2-01-1_722.CEL | 13 | white | 1 | 34 | 1 | 1 | 1 |
| AA610-HuEx-1_0-st-v2-01-1_734.CEL | 13 | white | 0 | 31 | 1 | 1 | 1 |
| AA664-HuEx-1_0-st-v2-01-1_738.CEL | 14 | white | 1 | 63 | 1 | 1 | 1 |
| AA611-HuEx-1_0-st-v2-01-1_740.CEL | 14 | white | 1 | 12 | 1 | 1 | 1 |
| AA665-HuEx-1_0-st-v2-01-1_744.CEL | 13 | non-white | 0 | 50 | 1 | 1 | 1 |
| AA612-HuEx-1_0-st-v2-01-1_750.CEL | 13 | white | 1 | 12 | 1 | 1 | 1 |
| AA720-HuEx-1_0-st-v2-01-1_752.CEL | 12 | white | 1 | 4 | 1 | 1 | 1 |
| AA613-HuEx-1_0-st-v2-01-1_753.CEL | 12 | white | 0 | 10 | 1 | 1 | 1 |
| AA614-HuEx-1_0-st-v2-01-1_767.CEL | 12 | white | 0 | 129 | 1 | 1 | 1 |
| AA615-HuEx-1_0-st-v2-01-1_781.CEL | 12 | white | 1 | 11 | 1 | 1 | 1 |
| AA723-HuEx-1_0-st-v2-01-1_816.CEL | 12 | white | 1 | 7 | 1 | 1 | 1 |
| AA724-HuEx-1_0-st-v2-01-1_822.CEL | 14 | white | 1 | 44 | 1 | 1 | 1 |
| AA668-HuEx-1_0-st-v2-01-1_827.CEL | 14 | non-white | 1 | 8 | 1 | 1 | 1 |
| AA669-HuEx-1_0-st-v2-01-1_828.CEL | 12 | white | 0 | 160 | 1 | 1 | 1 |
| AA670-HuEx-1_0-st-v2-01-1_832.CEL | 12 | white | 1 | 14 | 1 | 1 | 1 |
| AA616-HuEx-1_0-st-v2-01-1_842.CEL | 12 | white | 0 | 90 | 1 | 1 | 1 |
| AA671-HuEx-1_0-st-v2-01-1_844.CEL | 13 | non-white | 1 | 11 | 1 | 1 | 1 |
| AA725-HuEx-1_0-st-v2-01-1_846.CEL | 12 | white | 0 | 110 | 1 | 1 | 1 |
| AA672-HuEx-1_0-st-v2-01-1_850.CEL | 14 | white | 0 | 19 | 1 | 1 | 1 |

TABLE 14-continued

| | | | | | | | |
|---|---|---|---|---|---|---|---|
| AA617-HuEx-1_0-st-v2-01-1_852.CEL | 12 | white | 0 | 114 | 1 | 1 | 0 |
| AA673-HuEx-1_0-st-v2-01-1_857.CEL | 13 | white | 0 | 3 | 1 | 1 | 1 |
| AA618-HuEx-1_0-st-v2-01-1_869.CEL | 14 | white | 1 | 3 | 1 | 1 | 1 |
| AA726-HuEx-1_0-st-v2-01-1_872.CEL | 13 | white | 0 | 92 | 1 | 1 | 1 |
| AA674-HuEx-1_0-st-v2-01-1_877.CEL | 12 | white | 0 | 175 | 1 | 1 | 1 |
| AA675-HuEx-1_0-st-v2-01-1_878.CEL | 14 | white | 0 | 174 | 1 | 1 | 1 |
| AA727-HuEx-1_0-st-v2-01-1_892.CEL | 13 | white | 1 | 16 | 1 | 1 | 1 |
| AA620-HuEx-1_0-st-v2-01-1_894.CEL | 14 | white | 1 | 11 | 1 | 1 | 1 |
| AA728-HuEx-1_0-st-v2-01-1_895.CEL | 12 | white | 1 | 33 | 1 | 1 | 0 |
| AA621-HuEx-1_0-st-v2-01-1_902.CEL | 13 | non-white | 1 | 9 | 1 | 1 | 1 |
| AA676-HuEx-1_0-st-v2-01-1_906.CEL | 12 | white | 0 | 47 | 1 | 1 | 1 |
| AA622-HuEx-1_0-st-v2-01-1_907.CEL | 13 | white | 0 | 130 | 1 | 1 | 0 |
| AA677-HuEx-1_0-st-v2-01-1_911.CEL | 14 | white | 1 | 5 | 1 | 1 | 1 |
| AA678-HuEx-1_0-st-v2-01-1_914.CEL | 13 | white | 1 | 12 | 1 | 1 | 1 |
| AA729-HuEx-1_0-st-v2-01-1_916.CEL | 13 | non-white | 0 | 8 | 1 | 1 | 1 |
| AA623-HuEx-1_0-st-v2-01-1_924.CEL | 13 | white | 1 | 5 | 1 | 1 | 1 |
| AA730-HuEx-1_0-st-v2-01-1_926.CEL | 12 | white | 0 | 61 | 1 | 1 | 0 |
| AA731-HuEx-1_0-st-v2-01-1_928.CEL | 14 | white | 1 | 10 | 1 | 1 | 1 |
| AA679-HuEx-1_0-st-v2-01-1_932.CEL | 14 | non-white | 1 | 32 | 1 | 1 | 1 |
| AA624-HuEx-1_0-st-v2-01-1_951.CEL | 13 | white | 0 | 76 | 1 | 1 | 1 |
| AA681-HuEx-1_0-st-v2-01-1_961.CEL | 11 | white | 0 | 23 | 1 | 1 | 1 |
| AA626-HuEx-1_0-st-v2-01-1_963.CEL | 14 | white | 0 | 3 | 1 | 1 | 1 |
| AA734-HuEx-1_0-st-v2-01-1_968.CEL | 13 | white | 1 | 3 | 1 | 1 | 1 |
| AA841-HuEx-1_0-st-v2-01-1_983.CEL | 12 | non-white | 0 | 71 | 1 | 1 | 1 |
| AA735-HuEx-1_0-st-v2-01-1_887-A.CEL | 12 | white | 0 | 102 | 1 | 1 | 1 |
| AA790-HuEx-1_0-st-v2-01-1_122.CEL | 13 | white | 0 | 15 | 1 | 1 | 0 |

TABLE 14-continued

| | | | | | | | |
|---|---|---|---|---|---|---|---|
| AA737-HuEx-1_0-st-v2-01-1_155.CEL | 13 | white | 1 | 9 | 1 | 1 | 0 |
| AA738-HuEx-1_0-st-v2-01-1_163.CEL | 12 | white | 0 | 168 | 1 | 1 | 1 |
| AA740-HuEx-1_0-st-v2-01-1_168.CEL | 13 | white | 0 | 6 | 1 | 1 | 0 |
| AA741-HuEx-1_0-st-v2-01-1_182.CEL | 13 | white | 0 | 102 | 1 | 1 | 1 |
| AA742-HuEx-1_0-st-v2-01-1_219.CEL | 13 | white | 1 | 6 | 1 | 1 | 0 |
| AA743-HuEx-1_0-st-v2-01-1_238.CEL | 13 | white | 0 | 175 | 1 | 1 | 1 |
| AA744-HuEx-1_0-st-v2-01-1_240.CEL | 14 | non-white | 1 | 12 | 1 | 1 | 0 |
| AA745-HuEx-1_0-st-v2-01-1_252.CEL | 13 | white | 0 | 81 | 1 | 1 | 1 |
| AA792-HuEx-1_0-st-v2-01-1_276.CEL | 13 | non-white | 1 | 15 | 1 | 1 | 0 |
| AA857-HuEx-1_0-st-v2-01-1_280.CEL | 13 | white | 1 | 25 | 1 | 1 | 1 |
| AA747-HuEx-1_0-st-v2-01-1_306.CEL | 13 | white | 1 | 57 | 1 | 1 | 1 |
| AA748-HuEx-1_0-st-v2-01-1_318.CEL | 13 | white | 0 | 94 | 1 | 1 | 1 |
| AA794-HuEx-1_0-st-v2-01-1_337.CEL | 12 | white | 0 | 131 | 1 | 1 | 0 |
| AA749-HuEx-1_0-st-v2-01-1_341.CEL | 13 | white | 1 | 6 | 1 | 1 | 1 |
| AA751-HuEx-1_0-st-v2-01-1_352.CEL | 13 | white | 1 | 7 | 1 | 1 | 0 |
| AA752-HuEx-1_0-st-v2-01-1_354.CEL | 13 | white | 1 | 12 | 1 | 1 | 1 |
| AA795-HuEx-1_0-st-v2-01-1_377.CEL | 14 | white | 1 | 20 | 1 | 1 | 1 |
| AA754-HuEx-1_0-st-v2-01-1_387.CEL | 12 | non-white | 1 | 90 | 1 | 1 | 0 |
| AA756-HuEx-1_0-st-v2-01-1_397.CEL | 13 | white | 0 | 13 | 1 | 1 | 1 |
| AA757-HuEx-1_0-st-v2-01-1_403.CEL | 13 | white | 0 | 36 | 1 | 1 | 0 |
| AA796-HuEx-1_0-st-v2-01-1_411.CEL | 13 | white | 0 | 107 | 1 | 1 | 1 |
| AA797-HuEx-1_0-st-v2-01-1_412.CEL | 13 | white | 0 | 94 | 1 | 1 | 1 |
| AA758-HuEx-1_0-st-v2-01-1_419.CEL | 12 | white | 0 | 112 | 1 | 1 | 1 |
| AA799-HuEx-1_0-st-v2-01-1_423.CEL | 14 | white | 1 | 5 | 1 | 1 | 1 |
| AA800-HuEx-1_0-st-v2-01-1_431.CEL | 13 | white | 0 | 157 | 1 | 1 | 1 |
| AA759-HuEx-1_0-st-v2-01-1_445.CEL | 14 | non-white | 0 | 100 | 1 | 1 | 1 |

TABLE 14-continued

| celfile | | | | | | | |
|---|---|---|---|---|---|---|---|
| AA801-HuEx-1_0-st-v2-01-1_458.CEL | 14 | non-white | 1 | 12 | 1 | 1 | 1 |
| AA760-HuEx-1_0-st-v2-01-1_459.CEL | 13 | white | 0 | 26 | 1 | 1 | 1 |
| AA761-HuEx-1_0-st-v2-01-1_467.CEL | 12 | white | 0 | 111 | 1 | 1 | 1 |
| AA764-HuEx-1_0-st-v2-01-1_508.CEL | 13 | white | 1 | 26 | 1 | 1 | 0 |
| AA803-HuEx-1_0-st-v2-01-1_522.CEL | 14 | white | 0 | 9 | 1 | 1 | 1 |
| AA765-HuEx-1_0-st-v2-01-1_557.CEL | 14 | white | 1 | 16 | 1 | 1 | 0 |
| AA804-HuEx-1_0-st-v2-01-1_558.CEL | 14 | white | 1 | 28 | 1 | 1 | 1 |
| AA768-HuEx-1_0-st-v2-01-1_618.CEL | 12 | white | 1 | 4 | 1 | 1 | 0 |
| AA769-HuEx-1_0-st-v2-01-1_622.CEL | 11 | white | 1 | 23 | 1 | 1 | 1 |
| AA807-HuEx-1_0-st-v2-01-1_641.CEL | 13 | white | 1 | 11 | 1 | 1 | 1 |
| AA770-HuEx-1_0-st-v2-01-1_649.CEL | 13 | white | 0 | 60 | 1 | 1 | 1 |
| AA773-HuEx-1_0-st-v2-01-1_665.CEL | 13 | white | 1 | 7 | 1 | 1 | 1 |
| AA775-HuEx-1_0-st-v2-01-1_676.CEL | 13 | white | 1 | 15 | 1 | 1 | 1 |
| AA809-HuEx-1_0-st-v2-01-1_685.CEL | 13 | white | 0 | 100 | 1 | 1 | 0 |
| AA810-HuEx-1_0-st-v2-01-1_690.CEL | 14 | white | 1 | 4 | 1 | 1 | 1 |
| AA852-HuEx-1_0-st-v2-01-1_695.CEL | 12 | non-white | 0 | 119 | 1 | 1 | 0 |
| AA811-HuEx-1_0-st-v2-01-1_707.CEL | 12 | white | 0 | 39 | 1 | 1 | 1 |
| AA777-HuEx-1_0-st-v2-01-1_713.CEL | 12 | non-white | 1 | 14 | 1 | 1 | 0 |
| AA778-HuEx-1_0-st-v2-01-1_716.CEL | T4 | white | 1 | 8 | 1 | 1 | 0 |

| celfile | qc.20.30.pass | qc.30.40.pass | Percent Present Set | GC | GCC |
|---|---|---|---|---|---|
| AA682-HuEx-1_0-st-v2-01-1_118.CEL | 0 | 0 | 9.65862 | NA | NA |
| AA629-HuEx-1_0-st-v2-01-1_132.CEL | 0 | 0 | 16.4473 | NA | NA |
| AA684-HuEx-1_0-st-v2-01-1_142.CEL | 0 | 0 | 10.8961 | NA | NA |
| AA736-HuEx-1_0-st-v2-02-2_145.CEL | 0 | 0 | 7.92935 | NA | NA |
| AA685-HuEx-1_0-st-v2-01-1_157.CEL | 0 | 0 | 8.87618 | NA | NA |
| AA739-HuEx-1_0-st-v2-02-2_166.CEL | 0 | 0 | 12.3508 | NA | NA |

TABLE 14-continued

| | | | | | | |
|---|---|---|---|---|---|---|
| AA579-HuEx-1_0-st-v2-01-1_220.CEL | 0 | 0 | 42.4653 | NA | NA | NA |
| AA636-HuEx-1_0-st-v2-01-1_226.CEL | 0 | 0 | 9.35561 | NA | NA | NA |
| AA856-HuEx-1_0-st-v2-01-1_274.CEL | 0 | 0 | 27.2338 | NA | NA | NA |
| AA746-HuEx-1_0-st-v2-01-1_292.CEL | 0 | 0 | 9.0163 | NA | NA | NA |
| AA694-HuEx-1_0-st-v2-01-1_293.CEL | 0 | 0 | 13.7011 | NA | NA | NA |
| AA585-HuEx-1_0-st-v2-01-1_294.CEL | 0 | 0 | 50.6811 | NA | NA | NA |
| AA696-HuEx-1_0-st-v2-01-1_299.CEL | 0 | 0 | 39.3282 | NA | NA | NA |
| AA697-HuEx-1_0-st-v2-01-1_311.CEL | 0 | 0 | 13.9019 | NA | NA | NA |
| AA750-HuEx-1_0-st-v2-01-1_343.CEL | 0 | 0 | 14.9777 | NA | NA | NA |
| AA643-HuEx-1_0-st-v2-01-1_369.CEL | 0 | 0 | 16.8539 | NA | NA | NA |
| AA699-HuEx-1_0-st-v2-01-1_373.CEL | 0 | 0 | 10.7207 | NA | NA | NA |
| AA753-HuEx-1_0-st-v2-01-1_376.CEL | 0 | 0 | 6.79608 | NA | NA | NA |
| AA755-HuEx-1_0-st-v2-01-1_390.CEL | 0 | 0 | 16.6886 | NA | NA | NA |
| AA798-HuEx-1_0-st-v2-01-1_414.CEL | 0 | 0 | 12.711 | NA | NA | NA |
| AA702-HuEx-1_0-st-v2-01-1_420.CEL | 1 | 0 | 27.9437 | NA | NA | NA |
| AA704-HuEx-1_0-st-v2-01-1_444.CEL | 0 | 0 | 6.87799 | NA | NA | NA |
| AA802-HuEx-1_0-st-v2-01-1_469.CEL | 0 | 0 | 18.9741 | NA | NA | NA |
| AA762-HuEx-1_0-st-v2-01-1_481.CEL | 0 | 0 | 13.4185 | NA | NA | NA |
| AA763-HuEx-1_0-st-v2-01-1_485.CEL | 0 | 0 | 36.6512 | NA | NA | NA |
| AA594-HuEx-1_0-st-v2-01-1_493.CEL | 0 | 0 | 11.2307 | NA | NA | NA |
| AA705-HuEx-1_0-st-v2-01-1_506.CEL | 1 | 0 | 29.4208 | NA | NA | NA |
| AA597-HuEx-1_0-st-v2-01-1_529_2.CEL | 1 | 0 | 20.2292 | NA | NA | NA |
| AA805-HuEx-1_0-st-v2-01-1_560.CEL | 0 | 0 | 19.9348 | NA | NA | NA |
| AA766-HuEx-1_0-st-v2-01-1_562.CEL | 0 | 0 | 10.8515 | NA | NA | NA |
| AA767-HuEx-1_0-st-v2-01-1_569.CEL | 0 | 0 | 44.9042 | NA | NA | NA |
| AA806-HuEx-1_0-st-v2-01-1_594.CEL | 0 | 0 | 35.3453 | NA | NA | NA |

TABLE 14-continued

| | | | | | |
|---|---|---|---|---|---|
| AA602-HuEx-1_0-st-v2-01-1_623.CEL | 0 | 0 | 5.91103 | NA | NA | NA |
| AA771-HuEx-1_0-st-v2-01-1_651.CEL | 0 | 0 | 14.8189 | NA | NA | NA |
| AA772-HuEx-1_0-st-v2-01-1_652.CEL | 0 | 0 | 14.828 | NA | NA | NA |
| AA808-HuEx-1_0-st-v2-01-1_656.CEL | 0 | 0 | 16.3954 | NA | NA | NA |
| AA849-HuEx-1_0-st-v2-01-1_664.CEL | 1 | 0 | 20.492 | NA | NA | NA |
| AA774-HuEx-1_0-st-v2-01-1_666.CEL | 0 | 0 | 42.3303 | NA | NA | NA |
| AA662-HuEx-1_0-st-v2-01-1_703.CEL | 0 | 0 | 10.1421 | NA | NA | NA |
| AA607-HuEx-1_0-st-v2-01-1_709.CEL | 0 | 0 | 19.8998 | NA | NA | NA |
| AA719-HuEx-1_0-st-v2-01-1_726.CEL | 0 | 0 | 14.0108 | NA | NA | NA |
| AA721-HuEx-1_0-st-v2-01-1_756.CEL | 0 | 0 | 19.172 | NA | NA | NA |
| AA666-HuEx-1_0-st-v2-01-1_763.CEL | 0 | 0 | 16.328 | NA | NA | NA |
| AA722-HuEx-1_0-st-v2-01-1_777.CEL | 0 | 0 | 7.71556 | NA | NA | NA |
| AA780-HuEx-1_0-st-v2-01-1_779.CEL | 0 | 0 | 34.3543 | NA | NA | NA |
| AA781-HuEx-1_0-st-v2-02-2_800.CEL | 0 | 0 | 15.2955 | NA | NA | NA |
| AA667-HuEx-1_0-st-v2-01-1_826.CEL | 1 | 0 | 23.8016 | NA | NA | NA |
| AA619-HuEx-1_0-st-v2-01-1_881.CEL | 0 | 0 | 38.3754 | NA | NA | NA |
| AA625-HuEx-1_0-st-v2-01-1_956.CEL | 0 | 0 | 15.5688 | NA | NA | NA |
| AA732-HuEx-1_0-st-v2-01-1_957.CEL | 1 | 0 | 25.7658 | NA | NA | NA |
| AA680-HuEx-1_0-st-v2-01-1_958.CEL | 0 | 0 | 5.83528 | NA | NA | NA |
| AA733-HuEx-1_0-st-v2-01-1_959.CEL | 0 | 0 | 19.708 | NA | NA | NA |
| AA574-HuEx-1_0-st-v2-01-1_120.CEL | 0 | 0 | 18.3853 | trn | 0.714286 | 0.498007 |
| AA628-HuEx-1_0-st-v2-01-1_130.CEL | 0 | 0 | 17.1642 | trn | 0.571429 | 0.566006 |
| AA683-HuEx-1_0-st-v2-01-1_135.CEL | 0 | 0 | 28.4031 | trn | 0.333333 | 0.12917 |
| AA575-HuEx-1_0-st-v2-01-1_143.CEL | 1 | 1 | 33.2624 | trn | 0.428571 | NA |
| AA630-HuEx-1_0-st-v2-01-1_144.CEL | 0 | 0 | 19.9707 | trn | 0.619048 | 0.470843 |
| AA846-HuEx-1_0-st-v2-01-1_159.CEL | 1 | 1 | 32.0879 | trn | 0.761905 | 0.90905 |

TABLE 14-continued

| | | | | | |
|---|---|---|---|---|---|
| AA576-HuEx-1_0-st-v2-01-1_162.CEL | 1 | 0 | 23.9048 trn | 0.285714 | 0.111354 |
| AA686-HuEx-1_0-st-v2-01-1_165.CEL | 1 | 0 | 26.9212 trn | 0.285714 | 0.123361 |
| AA687-HuEx-1_0-st-v2-01-1_167.CEL | 1 | 1 | 82.5709 trn | 0.238095 | 0.100865 |
| AA631-HuEx-1_0-st-v2-01-1_173.CEL | 0 | 0 | 19.8189 trn | 0.285714 | 0.395288 |
| AA577-HuEx-1_0-st-v2-01-1_184.CEL | 1 | 0 | 25.9857 trn | 0.571429 | 0.594805 |
| AA578-HuEx-1_0-st-v2-01-1_186.CEL | 1 | 1 | 40.6266 trn | 0.666667 | 0.902539 |
| AA632-HuEx-1_0-st-v2-01-1_195.CEL | 1 | 1 | 86.5852 trn | 0.428571 | 0.505144 |
| AA848-HuEx-1_0-st-v2-01-1_198.CEL | 1 | 1 | 80.4682 trn | 0.190476 | 0.303659 |
| AA689-HuEx-1_0-st-v2-01-1_199.CEL | 1 | 0 | 25.311 trn | 0.285714 | 0.204983 |
| AA633-HuEx-1_0-st-v2-01-1_203.CEL | 1 | 0 | 26.1989 trn | 0.285714 | 0.132257 |
| AA690-HuEx-1_0-st-v2-01-1_211.CEL | 0 | 0 | 15.5687 trn | 0.619048 | 0.379821 |
| AA634-HuEx-1_0-st-v2-01-1_213.CEL | 1 | 0 | 21.8405 trn | 0.714286 | 0.533344 |
| AA691-HuEx-1_0-st-v2-01-1_214.CEL | 1 | 1 | 81.409 trn | 0.190476 | 0.062719 |
| AA635-HuEx-1_0-st-v2-01-1_218.CEL | 1 | 1 | 43.8173 trn | 0.47619 | 0.797366 |
| AA692-HuEx-1_0-st-v2-01-1_224.CEL | 1 | 0 | 20.0017 trn | 0.47619 | 0.617298 |
| AA580-HuEx-1_0-st-v2-01-1_227.CEL | 0 | 0 | 19.7804 trn | 0.285714 | 0.143443 |
| AA637-HuEx-1_0-st-v2-01-1_228.CEL | 1 | 1 | 81.9929 trn | 0.380952 | 0.248786 |
| AA693-HuEx-1_0-st-v2-01-1_230.CEL | 1 | 0 | 26.0979 trn | 0.380952 | 0.454064 |
| AA581-HuEx-1_0-st-v2-01-1_235.CEL | 1 | 1 | 41.302 trn | 0.238095 | 0.069548 |
| AA638-HuEx-1_0-st-v2-01-1_258.CEL | 1 | 0 | 29.038 trn | 0.666667 | 0.873885 |
| AA639-HuEx-1_0-st-v2-01-1_267.CEL | 1 | 1 | 85.1116 trn | 0.52381 | 0.746824 |
| AA582-HuEx-1_0-st-v2-01-1_272.CEL | 1 | 0 | 24.8041 trn | 0.428571 | 0.677148 |
| AA640-HuEx-1_0-st-v2-01-1_281.CEL | 1 | 0 | 26.1611 trn | 0.619048 | 0.814131 |
| AA583-HuEx-1_0-st-v2-01-1_284.CEL | 0 | 0 | 17.5976 trn | 0.333333 | 0.685014 |
| AA584-HuEx-1_0-st-v2-01-1_286.CEL | 0 | 0 | 19.1203 trn | 0.428571 | 0.498466 |
| AA695-HuEx-1_0-st-v2-01-1_295.CEL | 0 | 0 | 18.3506 trn | 0.619048 | NA |

TABLE 14-continued

| | | | | | |
|---|---|---|---|---|---|
| AA586-HuEx-1_0-st-v2-01-1_296.CEL | 1 | 1 | 34.6682 trn | 0.571429 | NA |
| AA587-HuEx-1_0-st-v2-01-1_309.CEL | 0 | 0 | 19.3913 trn | 0.285714 | 0.097794 |
| AA641-HuEx-1_0-st-v2-01-1_314.CEL | 1 | 1 | 41.2583 trn | 0.428571 | 0.67796 |
| AA847-HuEx-1_0-st-v2-01-1_338.CEL | 1 | 1 | 41.036 trn | 0619048 | 0.379821 |
| AA698-HuEx-1_0-st-v2-01-1_342.CEL | 1 | 0 | 27.0603 trn | 0.666667 | 0.598666 |
| AA642-HuEx-1_0-st-v2-01-1_368.CEL | 1 | 1 | 38.6051 trn | 0.666667 | 0.790496 |
| AA588-HuEx-1_0-st-v2-01-1_375.CEL | 1 | 1 | 30.4825 trn | 0.428571 | 0.419424 |
| AA644-HuEx-1_0-st-v2-01-1_382.CEL | 1 | 1 | 36.1872 trn | 0.619048 | 0346308 |
| AA700-HuEx-1_0-st-v2-01-1_393.CEL | 1 | 1 | 35.3889 trn | 0.47619 | 0.777976 |
| AA589-HuEx-1_0-st-v2-01-1_396.CEL | 1 | 1 | 30.6512 trn | 0.380952 | 0.377586 |
| AA701-HuEx-1_0-st-v2-01-1_402.CEL | 1 | 0 | 26.802 trn | 0.333333 | 0.139276 |
| AA590-HuEx-1_0-st-v2-01-1_430.CEL | 1 | 0 | 21.0747 trn | 0.714286 | 0.638435 |
| AA591-HuEx-1_0-st-v2-01-1_436.CEL | 1 | 1 | 33.7772 trn | 0.333333 | 0.238398 |
| AA645-HuEx-1_0-st-v2-01-1_437.CEL | 1 | 1 | 39.2918 trn | 0.571429 | 0.70012 |
| AA703-HuEx-1_0-st-v2-01-1_441.CEL | 1 | 0 | 20.3831 trn | 0.809524 | NA |
| AA646-HuEx-1_0-st-v2-01-1_454.CEL | 1 | 1 | 36.2867 trn | 0.285714 | 0.181807 |
| AA592-HuEx-1_0-st-v2-01-1_455.CEL | 1 | 0 | 27.4093 trn | 0.333333 | NA |
| AA593-HuEx-1_0-st-v2-01-1_475.CEL | 1 | 1 | 31.6379 trn | 0.285714 | 0.092794 |
| AA647-HuEx-1_0-st-v2-01-1_476.CEL | 1 | 1 | 43.307 trn | 0.47619 | 0.206802 |
| AA648-HuEx-1_0-st-v2-01-1_477.CEL | 1 | 1 | 30.9764 trn | 0.428571 | 0.237764 |
| AA649-HuEx-1_0-st-v2-01-1_479.CEL | 1 | 1 | 42.7328 trn | 0.428571 | 0.652129 |
| AA650-HuEx-1_0-st-v2-01-1_504.CEL | 1 | 0 | 27.342 trn | 0.285714 | 0.139056 |
| AA651-HuEx-1_0-st-v2-01-1_510.CEL | 1 | 1 | 36.3301 trn | 0.571429 | NA |
| AA595-HuEx-1_0-st-v2-01-1_512.CEL | 0 | 0 | 26.5464 trn | 0.52381 | NA |
| AA706-HuEx-1_0-st-v2-01-1_517.CEL | 1 | 1 | 36.0797 trn | 0.714286 | 0.547747 |
| AA596-HuEx-1_0-st-v2-01-1_528.CEL | 0 | 0 | 15.7068 trn | 0.47619 | 0.820845 |

TABLE 14-continued

| | | | | | |
|---|---|---|---|---|---|
| AA845-HuEx-1_0-st-v2-01-1_547.CEL | 0 | 0 | 25.0048 trn | 0.47619 | NA |
| AA598-HuEx-1_0-st-v2-01-1_552.CEL | 1 | 1 | 36.0621 trn | 0.47619 | NA |
| AA707-HuEx-1_0-st-v2-01-1_567.CEL | 1 | 0 | 25.8532 trn | 0.380952 | 0.578042 |
| AA599-HuEx-1_0-st-v2-01-1_579.CEL | 1 | 1 | 38.0983 trn | 0.619048 | 0.674044 |
| AA600-HuEx-1_0-st-v2-01-1_586.CEL | 1 | 0 | 24.5212 trn | 0.333333 | 0.386568 |
| AA653-HuEx-1_0-st-v2-01-1_591.CEL | 1 | 0 | 37.2906 trn | 0.285714 | 0.157341 |
| AA654-HuEx-1_0-st-v2-01-1_596.CEL | 1 | 1 | 41.2555 trn | 0.666667 | 0.894613 |
| AA655-HuEx-1_0-st-v2-01-1_597.CEL | 1 | 1 | 33.7621 trn | 0.285714 | 0.092794 |
| AA656-HuEx-1_0-st-v2-01-1_600.CEL | 1 | 0 | 23.2758 trn | 0.761905 | 0.582902 |
| AA657-HuEx-1_0-st-v2-01-1_608.CEL | 1 | 0 | 27.325 trn | 0.619048 | 0.4627 |
| AA601-HuEx-1_0-st-v2-01-1_612.CEL | 1 | 0 | 21.2178 trn | 0.428571 | 0.604777 |
| AA708-HuEx-1_0-st-v2-01-1_616.CEL | 1 | 0 | 23.2791 trn | 0.666667 | 0.826174 |
| AA709-HuEx-1_0-st-v2-01-1_619.CEL | 1 | 0 | 28.8194 trn | 0.52381 | 0.302628 |
| AA603-HuEx-1_0-st-v2-01-1_626.CEL | 0 | 0 | 16.4245 trn | 0.571429 | 0.492965 |
| AA658-HuEx-1_0-st-v2-01-1_627.CEL | 1 | 1 | 39.2526 trn | 0.52381 | 0.304144 |
| AA659-HuEx-1_0-st-v2-01-1_630_2.CEL | 1 | 0 | 21.7147 trn | 0.47619 | 0.389655 |
| AA604-HuEx-1_0-st-v2-01-1_640.CEL | 1 | 0 | 25.4692 trn | 0.666667 | 0.758916 |
| AA710-HuEx-1_0-st-v2-01-1_643.CEL | 1 | 0 | 26.8504 trn | 0.142857 | 0.24166 |
| AA660-HuEx-1_0-st-v2-01-1_644.CEL | 1 | 1 | 33.4575 trn | 0.714286 | NA |
| AA711-HuEx-1_0-st-v2-01-1_645.CEL | 1 | 1 | 34.7123 trn | 0.761905 | 0.931752 |
| AA712-HuEx-1_0-st-v2-01-1_646.CEL | 1 | 1 | 81.0272 trn | 0.238095 | 0.098265 |
| AA713-HuEx-1_0-st-v2-01-1_647.CEL | 1 | 0 | 22.7 trn | 0.285714 | 0.486177 |
| AA605-HuEx-1_0-st-v2-01-1_648.CEL | 1 | 0 | 23.5929 trn | 0.095238 | 0.037519 |
| AA714-HuEx-1_0-st-v2-01-1_655.CEL | 1 | 1 | 87.2293 trn | 0.571429 | 0.834829 |
| AA716-HuEx-1_0-st-v2-01-1_668.CEL | 0 | 0 | 17.8395 trn | 0.142857 | 0.061342 |
| AA661-HuEx-1_0-st-v2-01-1_673.CEL | 1 | 1 | 88.4027 trn | 0.47619 | 0.460393 |

TABLE 14-continued

| | | | | | |
|---|---|---|---|---|---|
| AA606-HuEx-1_0-st-v2-01-1_686.CEL | 1 | 0 | 24.6641 trn | 0.47619 | NA |
| AA717-HuEx-1_0-st-v2-01-1_691.CEL | 1 | 1 | 87.6296 trn | 0.619048 | 0.850444 |
| AA718-HuEx-1_0-st-v2-01-1_693.CEL | 1 | 0 | 22.3175 trn | 0.333333 | 0.627867 |
| AA663-HuEx-1_0-st-v2-01-1_708.CEL | 1 | 1 | 85.2171 trn | 0.333333 | 0.116673 |
| AA608-HuEx-1_0-st-v2-01-1_717.CEL | 1 | 1 | 82.3636 trn | 0.619048 | 0.393576 |
| AA609-HuEx-1_0-st-v2-01-1_722.CEL | 1 | 1 | 80.2338 trn | 0.809524 | 0.609537 |
| AA610-HuEx-1_0-st-v2-01-1_734.CEL | 1 | 0 | 20.643 trn | 0.666667 | 0.549068 |
| AA664-HuEx-1_0-st-v2-01-1_738.CEL | 1 | 1 | 51.905 trn | 0.333333 | NA |
| AA611-HuEx-1_0-st-v2-01-1_740.CEL | 1 | 0 | 88.6613 trn | 0.619048 | 0.899792 |
| AA665-HuEx-1_0-st-v2-01-1_744.CEL | 1 | 1 | 40.653 trn | 0.47619 | 0.324031 |
| AA612-HuEx-1_0-st-v2-01-1_750.CEL | 1 | 0 | 22.8988 trn | 0.714286 | 0.879576 |
| AA720-HuEx-1_0-st-v2-01-1_752.CEL | 1 | 1 | 87.5981 trn | 0.47619 | NA |
| AA613-HuEx-1_0-st-v2-01-1_753.CEL | 1 | 0 | 20.9361 trn | 0.095238 | 0.038548 |
| AA614-HuEx-1_0-st-v2-01-1_767.CEL | 1 | 0 | 25.7961 trn | 0.666667 | 0.571351 |
| AA615-HuEx-1_0-st-v2-01-1_781.CEL | 1 | 1 | 90.9451 trn | 0.571429 | 0.810524 |
| AA723-HuEx-1_0-st-v2-01-1_816.CEL | 1 | 1 | 84.859 trn | 0.619048 | 0.886662 |
| AA724-HuEx-1_0-st-v2-01-1_822.CEL | 1 | 0 | 27.8093 trn | 0.714286 | NA |
| AA668-HuEx-1_0-st-v2-01-1_827.CEL | 1 | 0 | 24.3978 trn | 0.380952 | 0.696265 |
| AA669-HuEx-1_0-st-v2-01-1_828.CEL | 1 | 1 | 33.7277 trn | 0.285714 | 0.213972 |
| AA670-HuEx-1_0-st-v2-01-1_832.CEL | 1 | 0 | 29.3556 trn | 0.333333 | 0.680285 |
| AA616-HuEx-1_0-st-v2-01-1_842.CEL | 1 | 0 | 22.0787 trn | 0.590909 | NA |
| AA671-HuEx-1_0-st-v2-01-1_844.CEL | 1 | 1 | 49.7328 trn | 0.333333 | 0.621067 |
| AA725-HuEx-1_0-st-v2-01-1_846.CEL | 1 | 0 | 26.3833 trn | 0.238095 | 0.166436 |
| AA672-HuEx-1_0-st-v2-01-1_850.CEL | 1 | 1 | 42.364 trn | 0.714286 | NA |
| AA617-HuEx-1_0-st-v2-01-1_852.CEL | 0 | 0 | 19.5706 trn | 0.333333 | 0.190879 |
| AA673-HuEx-1_0-st-v2-01-1_857.CEL | 1 | 1 | 81.4528 trn | 0.333333 | 0.277928 |

TABLE 14-continued

| | | | | | |
|---|---|---|---|---|---|
| AA618-HuEx-1_0-st-v2-01-1_869.CEL | 1 | 1 | 44.3887 trn | 0.619048 | 0.89167 |
| AA726-HuEx-1_0-st-v2-01-1_872.CEL | 1 | 1 | 87.5466 trn | 0.619048 | 0.585047 |
| AA674-HuEx-1_0-st-v2-01-1_877.CEL | 1 | 0 | 29.6863 trn | 0.619048 | 0.45009 |
| AA675-HuEx-1_0-st-v2-01-1_878.CEL | 1 | 1 | 85.1356 trn | 0.285714 | 0.199704 |
| AA727-HuEx-1_0-st-v2-01-1_892.CEL | 1 | 1 | 87.4076 trn | 0.380952 | 0.145711 |
| AA620-HuEx-1_0-st-v2-01-1_894.CEL | 1 | 0 | 20.6594 trn | 0.714286 | 0.651713 |
| AA728-HuEx-1_0-st-v2-01-1_895.CEL | 0 | 0 | 16.4462 trn | 0.428571 | 0.590833 |
| AA621-HuEx-1_0-st-v2-01-1_902.CEL | 1 | 1 | 81.6921 trn | 0.761905 | 0.911419 |
| AA676-HuEx-1_0-st-v2-01-1_906.CEL | 1 | 1 | 87.3924 trn | 0.380952 | 0.376774 |
| AA622-HuEx-1_0-st-v2-01-1_907.CEL | 0 | 0 | 16.2054 trn | 0.238095 | 0.137093 |
| AA677-HuEx-1_0-st-v2-01-1_911.CEL | 1 | 0 | 29.8555 trn | 0.363636 | 0.500079 |
| AA678-HuEx-1_0-st-v2-01-1_914.CEL | 1 | 0 | 23.862 trn | 0.380952 | 0.62662 |
| AA729-HuEx-1_0-st-v2-01-1_916.CEL | 1 | 1 | 36.9093 trn | 0.380952 | 0.145711 |
| AA623-HuEx-1_0-st-v2-01-1_924.CEL | 1 | 0 | 27.7507 trn | 0.285714 | 0.157834 |
| AA730-HuEx-1_0-st-v2-01-1_926.CEL | 0 | 0 | 19.4855 trn | 0.285714 | 0.081287 |
| AA731-HuEx-1_0-st-v2-01-1_928.CEL | 1 | 0 | 25.638 trn | 0.380952 | 0.599106 |
| AA679-HuEx-1_0-st-v2-01-1_932.CEL | 1 | 0 | 22.014 trn | 0.52381 | 0.560748 |
| AA624-HuEx-1_0-st-v2-01-1_951.CEL | 1 | 1 | 87.6194 trn | 0.380952 | 0.135211 |
| AA681-HuEx-1_0-st-v2-01-1_961.CEL | 1 | 1 | 38.9953 trn | 0.333333 | 0.703477 |
| AA626-HuEx-1_0-st-v2-01-1_963.CEL | 1 | 1 | 38.754 trn | 0.272727 | 0.272899 |
| AA734-HuEx-1_0-st-v2-01-1_968.CEL | 1 | 1 | 33.0472 trn | 0.333333 | 0.314901 |
| AA841-HuEx-1_0-st-v2-01-1_983.CEL | 1 | 1 | 43.1947 trn | 0.52381 | 0.29201 |
| AA735-HuEx-1_0-st-v2-01-1_887-A.CEL | 1 | 1 | 38.5059 trn | 0.190476 | NA |
| AA790-HuEx-1_0-st-v2-01-1_122.CEL | 0 | 0 | 16.4732 tst | 0.619048 | 0.606886 |
| AA737-HuEx-1_0-st-v2-01-1_155.CEL | 0 | 0 | 19.4884 tst | 0.666667 | 0.789306 |
| AA738-HuEx-1_0-st-v2-01-1_163.CEL | 1 | 0 | 24.3258 tst | 0.333333 | 0.142789 |

TABLE 14-continued

| | | | | | |
|---|---|---|---|---|---|
| AA740-HuEx-1_0-st-v2-01-1_168.CEL | 0 | 0 | 18.8438 tst | 0.47619 | 0.71363 |
| AA741-HuEx-1_0-st-v2-01-1_182.CEL | 1 | 1 | 90.9373 tst | 0.333333 | 0.10524 |
| AA742-HuEx-1_0-st-v2-01-1_219.CEL | 0 | 0 | 16.0158 tst | 0.47619 | 0.71363 |
| AA743-HuEx-1_0-st-v2-01-1_238.CEL | 1 | 0 | 27.8375 tst | 0.285714 | 0.273203 |
| AA744-HuEx-1_0-st-v2-01-1_240.CEL | 0 | 0 | 16.0941 tst | 0.714286 | 0.918596 |
| AA745-HuEx-1_0-st-v2-01-1_252.CEL | 1 | 0 | 25.5354 tst | 0.428571 | 0.625371 |
| AA792-HuEx-1_0-st-v2-01-1_276.CEL | 0 | 0 | 20.2035 tst | 0.47619 | 0.221437 |
| AA857-HuEx-1_0-st-v2-01-1_280.CEL | 1 | 1 | 38.0538 tst | 0.47619 | 0.418125 |
| AA747-HuEx-1_0-st-v2-01-1_306.CEL | 1 | 0 | 27.0322 tst | 0.333333 | 0.213076 |
| AA748-HuEx-1_0-st-v2-01-1_318.CEL | 1 | 0 | 20.3642 tst | 0.333333 | 0.135836 |
| AA794-HuEx-1_0-st-v2-01-1_337.CEL | 0 | 0 | 16.2502 tst | 0.238095 | 0.098265 |
| AA749-HuEx-1_0-st-v2-01-1_341.CEL | 1 | 1 | 42.8271 tst | 0.380952 | 0.325613 |
| AA751-HuEx-1_0-st-v2-01-1_352.CEL | 0 | 0 | 18.6045 tst | 0.619048 | 0.448316 |
| AA752-HuEx-1_0-st-v2-01-1_354.CEL | 1 | 1 | 31.3183 tst | 0.52381 | 0.246448 |
| AA795-HuEx-1_0-st-v2-01-1_377.CEL | 0 | 0 | 28.1588 tst | 0.666667 | 0.849764 |
| AA754-HuEx-1_0-st-v2-01-1_387.CEL | 0 | 0 | 16.18 tst | 0.333333 | 0.307941 |
| AA756-HuEx-1_0-st-v2-01-1_397.CEL | 1 | 1 | 38.3485 tst | 0.285714 | 0.3216 |
| AA757-HuEx-1_0-st-v2-01-1_403.CEL | 0 | 0 | 17.2699 tst | 0.333333 | 0.208867 |
| AA796-HuEx-1_0-st-v2-01-1_411.CEL | 1 | 0 | 27.0163 tst | 0.238095 | 0.127122 |
| AA797-HuEx-1_0-st-v2-01-1_412.CEL | 1 | 1 | 31.3986 tst | 0.47619 | 0.202085 |
| AA758-HuEx-1_0-st-v2-01-1_419.CEL | 1 | 1 | 40.5702 tst | 0.333333 | 0.165438 |
| AA799-HuEx-1_0-st-v2-01-1_423.CEL | 1 | 1 | 33.0817 tst | 0.428571 | 0.671596 |
| AA800-HuEx-1_0-st-v2-01-1_431.CEL | 1 | 1 | 36.4681 tst | 0.238095 | 0.191995 |
| AA759-HuEx-1_0-st-v2-01-1_445.CEL | 1 | 0 | 27.702 tst | 0.52381 | 0.268618 |
| AA801-HuEx-1_0-st-v2-01-1_458.CEL | 1 | 1 | 83.1966 tst | 0.52381 | NA |
| AA760-HuEx-1_0-st-v2-01-1_459.CEL | 1 | 0 | 26.771 tst | 0.428571 | 0.433048 |

TABLE 14-continued

| | | | | | |
|---|---|---|---|---|---|
| AA761-HuEx-1_0-st-v2-01-1_467.CEL | 1 | 0 | 21.3604 tst | 0.47619 | NA |
| AA764-HuEx-1_0-st-v2-01-1_508.CEL | 0 | 0 | 19.7612 tst | 0.190476 | 0.225144 |
| AA803-HuEx-1_0-st-v2-01-1_522.CEL | 1 | 1 | 87.0205 tst | 0.428571 | 0.293503 |
| AA765-HuEx-1_0-st-v2-01-1_557.CEL | 0 | 0 | 17.5484 tst | 0.571429 | 0.839756 |
| AA804-HuEx-1_0-st-v2-01-1_558.CEL | 1 | 0 | 26.8291 tst | 0.761905 | 0.938769 |
| AA768-HuEx-1_0-st-v2-01-1_618.CEL | 0 | 0 | 17.0565 tst | 0.52381 | 0.262959 |
| AA769-HuEx-1_0-st-v2-01-1_622.CEL | 1 | 0 | 21.1354 tst | 0.285714 | 0.29731 |
| AA807-HuEx-1_0-st-v2-01-1_641.CEL | 1 | 0 | 29.0506 tst | 0.809524 | 0.877799 |
| AA770-HuEx-1_0-st-v2-01-1_649.CEL | 1 | 0 | 29.6962 tst | 0.190476 | 0.376383 |
| AA773-HuEx-1_0-st-v2-01-1_665.CEL | 1 | 0 | 21.4004 tst | 0.380952 | 0.599106 |
| AA775-HuEx-1_0-st-v2-01-1_676.CEL | 1 | 0 | 26.7034 tst | 0.47619 | 0.676794 |
| AA809-HuEx-1_0-st-v2-01-1_685.CEL | 0 | 0 | 17.675 tst | 0.52381 | 0.251874 |
| AA810-HuEx-1_0-st-v2-01-1_690.CEL | 1 | 1 | 87.4839 tst | 0.47619 | 0.375953 |
| AA852-HuEx-1_0-st-v2-01-1_695.CEL | 0 | 0 | 18.8276 tst | 0.333333 | NA |
| AA811-HuEx-1_0-st-v2-01-1_707.CEL | 1 | 0 | 22.2554 tst | 0.47619 | 0.729893 |
| AA777-HuEx-1_0-st-v2-01-1_713.CEL | 0 | 0 | 16.3117 tst | 0.666667 | 0.477605 |
| AA778-HuEx-1_0-st-v2-01-1_716.CEL | 0 | 0 | 15.5155 tst | 0.52381 | 0.884073 |

TABLE 15

| Probe set ID | Category | Gene Symbol |
|---|---|---|
| 3337703 | CODING | PPP6R3 |
| 3326487 | CODING | EHF |
| 3160006 | CODING | SMARCA2 |
| 3576730 | CODING | TC2N |
| 2365991 | CODING | MPZL1 |
| 3536951 | CODING | KTN1 |
| 3147328 | CODING | UBR5 |
| 2852379 | CODING | ZFR |
| 3331573 | CODING | CTNND1 |
| 3463598 | CODING | PPP1R12A |
| 2703240 | CODING | KPNA4 |
| 3974728 | CODING | USP9X |
| 3887661 | CODING | NCOA3 |
| 2758874 | CODING | CYTL1 |
| 2823854 | CODING | WDR36 |
| 2975719 | CODING | BCLAF1 |
| 2458376 | CODING | PARP1; ENAH |
| 3754530 | CODING | ACACA |
| 3757658 | CODING | KAT2A |
| 3659319 | CODING | LONP2 |
| 3463528 | CODING | PAWR |
| 2799051 | CODING | SLC6A19 |
| 2554001 | CODING | PNPT1 |
| 3012438 | CODING | AKAP9 |
| 4024378 | CODING | CDR1 |
| 3165799 | CODING | IFT74 |
| 2555411 | CODING | USP34 |
| 3536996 | CODING | KTN1 |
| 2669750 | CODING | SCN10A |
| 3148620 | CODING | EIF3E |
| 3851902 | NON_CODING (CDS_ANTISENSE) | CALR |
| 2651515 | NON_CODING (CDS_ANTISENSE) | MECOM |
| 3111306 | NON_CODING (CDS_ANTISENSE) | RSPO2 |
| 2669316 | NON_CODING (CDS_ANTISENSE) | GOLGA4 |
| 3560055 | NON_CODING (CDS_ANTISENSE) | AKAP6 |
| 3484750 | NON_CODING (CDS_ANTISENSE) | N4BP2L2 |
| 2651521 | NON_CODING (CDS_ANTISENSE) | MECOM |
| 3002694 | NON_CODING (INTRONIC) | EGFR |
| 3384586 | NON_CODING (INTRONIC) | DLG2 |
| 3986003 | NON_CODING (INTRONIC) | IL1RAPL2 |
| 3476549 | NON_CODING (INTRONIC) | NCOR2 |
| 3875037 | NON_CODING (INTRONIC) | RP5-828H9.1 |

TABLE 15-continued

| Probe set ID | Category | Gene Symbol |
|---|---|---|
| 3524631 | NON_CODING (INTRONIC) | ARGLU1 |
| 3384580 | NON_CODING (INTRONIC) | DLG2 |
| 3932938 | NON_CODING (INTRONIC) | TMPRSS3; AL773572.7 |
| 3581867 | NON_CODING (INTRONIC) | IGHG3 |
| 3253347 | NON_CODING (ncTRANSCRIPT) | RP11-428P16.2 |
| 2956494 | NON_CODING (ncTRANSCRIPT) | CYP2AC1P |
| 2705151 | NON_CODING (UTR) | RPL22L1 |
| 3666869 | NON_CODING (UTR) | NFAT5 |
| 2318755 | NON_CODING (UTR) | PARK7 |
| 3969511 | NON_CODING (UTR) | OFD1 |
| 3719123 | NON_CODING (UTR) | ZNHIT3 |
| 3421223 | NON_CODING (UTR) | NUP107 |
| 3739125 | NON_CODING (UTR) | FN3KRP |
| 2553585 | NON_CODING (UTR) | RTN4 |
| 2405285 | NON_CODING (UTR) | TMEM54 |
| 2473624 | NON_CODING (UTR) | RAB10 |
| 3593171 | NON_CODING (UTR) | DUT |
| 2663553 | NON_CODING (UTR) | NUP210 |
| 2874688 | NON_CODING (UTR) | HINT1 |
| 3628924 | NON_CODING (UTR) | FAM96A |
| 3066770 | NON_CODING (UTR) | SYPL1 |
| 3936897 | NON_CODING (UTR) | MRPL40 |
| 3505453 | NON_CODING (UTR) | MIPEP |
| 3368555 | NON_CODING (UTR) | CSTF3 |
| 3985635 | NON_CODING (UTR) | TCEAL4 |
| 3816402 | NON_CODING (UTR) | OAZ1 |
| 2361095 | NON_CODING (UTR) | MSTO1; RP11-243J18.3; DAP3 |
| 2451873 | NON_CODING (UTR) | ETNK2 |
| 2414960 | NON_CODING (UTR) | TACSTD2 |
| 3005357 | NON_CODING (UTR) | CRCP |
| 3776446 | NON_CODING (UTR) | MYL12A |
| 3260965 | NON_CODING (UTR) | LZTS2 |
| 3619236 | NON_CODING (UTR) | BMF |
| 3454547 | NON_CODING (UTR_ANTISENSE) | METTL7A |
| 2735017 | NON_CODING (UTR_ANTISENSE) | SPARCL1 |
| 3061144 | NON_CODING (UTR_ANTISENSE) | ANKIB1 |
| 2710217 | NON_CODING (UTR_ANTISENSE) | LPP |
| 3005652 | NON_CODING (UTR_ANTISENSE) | GS1-124K5.12 |
| 3854371 | NON_CODING (UTR_ANTISENSE) | MRPL34 |
| 3337703 | CODING | PPP6R3 |

TABLE 16

| Machine Learning Algorithm | Feature Selection Method | # Features Selected | Standardization Method | AUC Training | AUC Testing |
|---|---|---|---|---|---|
| Naïve Bayes (NB) | Ranking based on Median Fold Difference | Top 20 | Percentile Rank | 0.81 | 0.73 |
| K-Nearest Neighbours (KNN) | Ranking based on Median Fold Difference and Random Forest-based Gini Importance | Top 12 | Z-score | 0.72 | 0.73 |
| Generalized Linear Model (GLM) | Ranking by Area Under the ROC curve (AUC) | 2 based on random selection within the top 100 | none | 0.77 | 0.74 |
| N.A. | Ranking by Area Under the ROC curve (AUC) | 1 based on random selection within the top 100 | none | 0.69 | 0.71 |

TABLE 17

| SEQ ID NO.: | Probe set ID | Gene | Classifier(s) | Chromosome | Start | End | Strand |
|---|---|---|---|---|---|---|---|
| 353 | 3337703 | PPP6R3 | NB20 | chr11 | 68355451 | 68355475 | 1 |
| 354 | 3326487 | EHF | KNN12, NB20 | chr11 | 34673110 | 34673157 | 1 |
| 355 | 3160006 | SMARCA2 | KNN12, NB20 | chr9 | 2073575 | 2073599 | 1 |
| 356 | 3576730 | TC2N | NB20 | chr14 | 92278706 | 92278866 | −1 |
| 357 | 2365991 | MPZL1 | NB20 | chr1 | 167757129 | 167757158 | 1 |
| 358 | 3536951 | KTN1 | NB20 | chr14 | 56108443 | 56108473 | 1 |
| 359 | 3147328 | UBR5 | NB20 | chr8 | 103269860 | 103269932 | −1 |
| 360 | 2852379 | ZFR | NB20 | chr5 | 32417753 | 32417779 | −1 |
| 361 | 3331573 | CTNND1 | KNN12, NB20 | chr11 | 57577586 | 57577659 | 1 |
| 366 | 2758874 | CYTL1 | KNN12 | chr4 | 5016922 | 5016946 | −1 |
| 369 | 2458376 | ENAH | KNN12 | chr1 | 225692693 | 225692726 | −1 |
| 383 | 3851902 | CALR | NB20 | chr19 | 13050901 | 13050963 | 1 |
| 384 | 2651515 | MECOM | NB20 | chr3 | 169003654 | 169003734 | 1 |
| 385 | 3111306 | RSPO2 | NB20 | chr8 | 109084359 | 109084383 | 1 |
| 387 | 3560055 | AKAP6 | KNN12 | chr14 | 32985209 | 32985233 | −1 |
| 390 | 2886458 | chr5-: 168794202-168794226 | KNN12, NB20 | chr5 | 168794202 | 168794226 | −1 |
| 391 | 2537212 | chr2-: 343842-343866 | NB20 | chr2 | 343842 | 343866 | −1 |
| 397 | 3002694 | EGFR | NB20 | chr7 | 55163823 | 55163847 | 1 |
| 398 | 3384586 | DLG2 | KNN12, NB20 | chr11 | 83467292 | 83467316 | −1 |
| 399 | 3986003 | IL1RAPL2 | KNN12, NB20 | chrX | 104682956 | 104682980 | 1 |
| 410 | 3666869 | NFAT5 | NB20 | chr16 | 69738402 | 69738519 | 1 |
| 411 | 2318755 | PARK7 | NB20 | chr1 | 8045210 | 8045305 | 1 |
| 421 | 2874688 | HINT1 | KNN12 | chr5 | 130495094 | 130495120 | −1 |
| 422 | 3628924 | FAM96A | KNN12 | chr15 | 64364822 | 64365114 | −1 |
| 434 | 3260965 | LZTS2 | KNN12 | chr10 | 102762254 | 102762278 | 1 |
| 436 | 3454547 | METTL7A | NB20 | chr12 | 51324677 | 51324701 | −1 |
| 458 | 2704702 | MECOM | SINGLE_PSR, GLM2 | chr3 | 169245434 | 169245479 | −1 |
| 459 | 3286471 | HNRNPA3P1 | GLM2 | chr10 | 44285533 | 44285567 | −1 |

TABLE 18

| Machine Learning Algorithm | Feature Selection Method | # Features Selected | Standardization Method | AUC Training | AUC Testing |
|---|---|---|---|---|---|
| Support Vector Machine (SVM) | Ranking by Area Under the ROC curve (AUC) | Top 20 | None | 0.95 | 0.75 |
| Support Vector Machine (SVM) | Ranking by Area Under the ROC curve (AUC) | Top 11 | None | 0.96 | 0.8 |
| Support Vector Machine (SVM) | Ranking by Area Under the ROC curve (AUC) | Top 5 | None | 0.98 | 0.78 |
| Generalized Linear Model (GLM) | Ranking by Area Under the ROC curve (AUC) | 2 based on random selection within the top 100 | None | 0.86 | 0.79 |

TABLE 19

| SEQ ID NO.: | Probe set ID | Gene | Classifier(s) | Chromosome | Start | End | Strand |
|---|---|---|---|---|---|---|---|
| 460 | 3648760 | SHISA9 | SVM11, SVM20 | chr16 | 12996183 | 12996441 | 1 |
| 461 | 2461946 | GNG4 | SVM11, SVM5, SVM20 | chr1 | 235715432 | 235715511 | −1 |
| 462 | 2790629 | FGA | SVM11, SVM5, SVM20 | chr4 | 155505296 | 155505833 | −1 |
| 463 | 3074872 | PTN | SVM11, SVM5, SVM20 | chr7 | 136935982 | 136936125 | −1 |

TABLE 19-continued

| SEQ ID NO.: | Probe set ID | Gene | Classifier(s) | Chromosome | Start | End | Strand |
|---|---|---|---|---|---|---|---|
| 464 | 3558478 | STXBP6 | SVM11, SVM5, SVM20 | chr14 | 25443877 | 25444024 | −1 |
| 465 | 2420621 | LPAR3 | SVM20 | chr1 | 85279570 | 85279820 | −1 |
| 466 | 2914697 | SH3BGRL2 | SVM20 | chr6 | 80341180 | 80341219 | 1 |
| 467 | 3501746 | ARHGEF7 | SVM20 | chr13 | 111955366 | 111955393 | 1 |
| 468 | 3648824 | SHISA9 | SVM20 | chr16 | 13297252 | 13297396 | 1 |
| 469 | 3750877 | KIAA0100 | SVM20 | chr17 | 26942687 | 26942797 | −1 |
| 470 | 3276127 | chr10-: 7129102-7129152 | GLM2 | chr10 | 7129102 | 7129152 | −1 |
| 471 | 3648839 | chr16+: 13333744-13333834 | SVM11, SVM20 | chr16 | 13333744 | 13333834 | 1 |
| 472 | 3558521 | STXBP6 | SVM11, GLM2, SVM20 | chr14 | 25349924 | 25350138 | −1 |
| 473 | 3558522 | STXBP6 | SVM11, SVM5, SVM20 | chr14 | 25350244 | 25350281 | −1 |
| 474 | 2461975 | GNG4 | SVM20 | chr1 | 235807028 | 235807056 | −1 |
| 475 | 3648778 | SHISA9 | SVM20 | chr16 | 13053399 | 13053481 | 1 |
| 476 | 3648792 | SHISA9 | SVM20 | chr16 | 13156216 | 13156254 | 1 |
| 477 | 3091419 | EPHX2 | SVM11, SVM20 | chr8 | 27369439 | 27369789 | 1 |
| 478 | 2461940 | GNG4 | SVM11, SVM20 | chr1 | 235711039 | 235711691 | −1 |
| 479 | 2461962 | GNG4 | SVM11, SVM20 | chr1 | 235758756 | 235758792 | −1 |
| 480 | 3558502 | STXBP6 | SVM20 | chr14 | 25518570 | 25518806 | −1 |

TABLE 20

| # ICE Blocks per comparison, per correlation threshold | | Comparison | | | | |
|---|---|---|---|---|---|---|
| | | Normal vs. Primary | Primary vs. Metastasis | Normal vs. Metastasis | GS6 vs GS7+ | BCR vs non-BCR |
| Correlation Threshold | 0.9 | 7675 (3580) | 8853 (3503) | 12978 (5785) | 7864 (545) | 7873 (506) |
| | 0.8 | 17288 (7019) | 17773 (5622) | 24433 (8445) | 17415 (875) | 17378 (1090) |
| | 0.7 | 27434 (8625) | 29120 (6729) | 44999 (10642) | 28103 (1225) | 28068 (1423) |
| | 0.6 | 46626 (11180) | 50840 (8152) | 71519 (14561) | 49170 (1612) | 48994 (2177) |

TABLE 21A

| # ICE Blocks per comparison, per correlation threshold | | Normal versus Primary | | | | | |
|---|---|---|---|---|---|---|---|
| | | CDS Only | Intronic Only | Intergenic Only | Antisense Only | Multigene | All Other Combinations |
| Correlation Threshold | 0.9 | 2310 | 245 | 34 | 26 | 33 | 932 |
| | 0.8 | 3196 | 586 | 118 | 96 | 189 | 2834 |
| | 0.7 | 2677 | 799 | 249 | 242 | 430 | 4228 |
| | 0.6 | 2248 | 1026 | 649 | 532 | 992 | 5733 |

TABLE 21B

| # ICE Blocks per comparison, per correlation threshold | | CDS Only | Intronic Only | Intergenic Only | Antisense Only | Multigene | All Other Combinations |
|---|---|---|---|---|---|---|---|
| | | \multicolumn{6}{c}{Primary versus Metastasis} | | | | | |
| Correlation Threshold | 0.9 | 2058 | 253 | 32 | 28 | 43 | 1089 |
| | 0.8 | 2055 | 567 | 76 | 82 | 163 | 2679 |
| | 0.7 | 1728 | 677 | 144 | 185 | 408 | 3587 |
| | 0.6 | 1489 | 718 | 324 | 378 | 808 | 4435 |

TABLE 21C

| # ICE Blocks per comparison, per correlation threshold | | CDS Only | Intronic Only | Intergenic Only | Antisense Only | Multigene | All Other Combinations |
|---|---|---|---|---|---|---|---|
| | | \multicolumn{6}{c}{Primary versus Metastasis} | | | | | |
| Correlation Threshold | 0.9 | 2058 | 253 | 32 | 28 | 43 | 1089 |
| | 0.8 | 2055 | 567 | 76 | 82 | 163 | 2679 |
| | 0.7 | 1728 | 677 | 144 | 185 | 408 | 3587 |
| | 0.6 | 1489 | 718 | 324 | 378 | 808 | 4435 |

TABLE 21D

| # ICE Blocks per comparison, per correlation threshold | | CDS Only | Intronic Only | Intergenic Only | Antisense Only | Multigene | All Other Combinations |
|---|---|---|---|---|---|---|---|
| | | \multicolumn{6}{c}{Normal versus Metastasis} | | | | | |
| Correlation Threshold | 0.9 | 3064 | 386 | 61 | 46 | 82 | 2146 |
| | 0.8 | 2561 | 771 | 181 | 186 | 388 | 4358 |
| | 0.7 | 2103 | 1018 | 486 | 495 | 956 | 5584 |
| | 0.6 | 1685 | 1464 | 1125 | 1204 | 1987 | 7096 |

TABLE 21E

| # ICE Blocks per comparison, per correlation threshold | | CDS Only | Intronic Only | Intergenic Only | Antisense Only | Multigene | All Other Combinations |
|---|---|---|---|---|---|---|---|
| | | \multicolumn{6}{c}{GS6 versus GS7+} | | | | | |
| Correlation Threshold | 0.9 | 285 | 45 | 10 | 3 | 14 | 188 |
| | 0.8 | 287 | 77 | 28 | 16 | 55 | 412 |
| | 0.7 | 298 | 126 | 39 | 41 | 105 | 616 |
| | 0.6 | 267 | 147 | 77 | 89 | 174 | 858 |

TABLE 21F

| # ICE Blocks per comparison, per correlation threshold | | CDS Only | Intronic Only | Intergenic Only | Antisense Only | Multigene | All Other Combinations |
|---|---|---|---|---|---|---|---|
| | | \multicolumn{6}{c}{BCR versus Non-BCR} | | | | | |
| Correlation Threshold | 0.9 | 213 | 112 | 11 | 5 | 11 | 154 |
| | 0.8 | 305 | 277 | 18 | 16 | 47 | 427 |
| | 0.7 | 241 | 320 | 55 | 54 | 129 | 624 |
| | 0.6 | 225 | 367 | 199 | 151 | 273 | 962 |

TABLE 22

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| Block_2190 | 0.000002 | chr14: 25325143 . . . 25326345; − | 1 | STXBP6; | CODING (100%); | 2 | 3558448; 3558449 |
| Block_4398 | 0.000005 | chr20: 52612441 . . . 52674693; − | 1 | BCAS1; | CODING (100%); | 3 | 3910385; 3910393; 3910394 |
| Block_5988 | 0.000015 | chr5: 120022459 . . . 120022612; + | 1 | PRR16; | UTR (100%); | 2 | 2825939; 2825940 |
| Block_6655 | 0.000033 | chr7: 136935982 . . . 136938338; − | 1 | PTN; | CODING (100%); | 2 | 3074872; 3074873 |
| Block_5987 | 0.000044 | chr5: 120021701 . . . 120022162; + | 1 | PRR16; | CODING (100%); | 2 | 2825937; 2825938 |
| Block_331 | 0.000049 | chr1: 169483568 . . . 169551730; − | 1 | F5; | CODING (100%); | 25 | 2443374; 2443375; 2443378; 2443381; 2443382; 2443383; 2443384; 2443385; 2443388; 2443389; 2443391; 2443392; 2443393; 2443395; 2443396; 2443397; 2443398; 2443399; 2443400; 2443403; 2443404; 2443405; 2443406; 2443407; 2443412 |
| Block_7716 | 0.000074 | chrX: 16142105 . . . 16175029; + | 2 | GRPR; RP11-431J24.2; | CODING (50%); INTRONIC_AS (50%); | 4 | 3970026; 3970034; 3970036; 3970039 |
| Block_6372 | 0.000087 | chr6: 38800098 . . . 38831738; + | 1 | DNAH8; | CODING (100%); | 13 | 2905993; 2905995; 2905996; 2905997; 2905999; 2906000; 2906001; 2906002; 2906003; 2906004; 2906005; 2906010; 2906012 |
| Block_4271 | 0.000112 | chr2: 219676945 . . . 219679977; + | 1 | CYP27A1; | CODING (85.71%); UTR (14.28%); | 7 | 2528108; 2528110; 2528111; 2528112; 2528113; 2528115; 2528118 |
| Block_4397 | 0.000132 | chr20: 52574002 . . . 52601991; − | 1 | BCAS1; | CODING (100%); | 3 | 3910367; 3910373; 3910378 |
| Block_5000 | 0.000132 | chr3: 3886073 . . . 3890904; + | 2 | LRRN1; SUMF1; | INTRONIC_AS (40%); CODING (20%); UTR (40%); | 5 | 2608321; 2608324; 2608326; 2608331; 2608332 |
| Block_1039 | 0.00014 | chr10: 43609044 . . . 43610087; + | 1 | RET; | CODING (100%); | 2 | 3243869; 3243870 |
| Block_3838 | 0.000197 | chr2: 100484261 . . . 100509150; − | 1 | AFF3; | INTRONIC (100%); | 2 | 2567082; 2567086 |
| Block_7796 | 0.000205 | chrX: 105153170 . . . 105156727; + | 1 | NRK; | CODING (100%); | 2 | 3986120; 3986121 |
| Block_5986 | 0.000209 | chr5: 119801697 . . . 119998479; + | 1 | PRR16; | UTR (16.66%); INTRONIC (83.33%); | 6 | 2825917; 2825921; 2825922; 2825923; 2825928; 2825932 |
| Block_1733 | 0.000213 | chr12: 103234188 . . . 103249107; − | 1 | PAH; | CODING (100%); | 3 | 3468486; 3468494; 3468504 |
| Block_3839 | 0.000218 | chr2: 100667261 . . . 100690911; − | 1 | AFF3; | INTRONIC (100%); | 2 | 2567016; 2567024 |
| Block_6879 | 0.000218 | chr8: 22570904 . . . 22582442; − | 1 | PEBP4; | CODING (100%); | 2 | 3127612; 3127614 |
| Block_413 | 0.00025 | chr1: 235712540 . . . 235715511; − | 1 | GNG4; | CODING (25%); UTR (75%); | 4 | 2461942; 2461944; 2461945; 2461946 |
| Block_4396 | 0.00027 | chr20: 52571654 . . . 52574704; − | 1 | BCAS1; | INTRONIC (100%); | 2 | 3910366; 3910368 |
| Block_7431 | 0.000292 | chr9: 96069125 . . . 96069401; + | 1 | WNK2; | ncTRANSCRIPT (100%); | 2 | 3179784; 3179785 |
| Block_1146 | 0.000309 | chr10: 123779283 . . . 123781483; + | 1 | TACC2; | ncTRANSCRIPT (50%); UTR (50%); | 2 | 3268069; 3268071 |
| Block_7640 | 0.000315 | chrX: 106959080 . . . 106959334; − | 1 | TSC22D3; | CODING (50%); UTR (50%); | 2 | 4017408; 4017410 |
| Block_6371 | 0.000328 | chr6: 38783258 . . . 38783411; + | 1 | DNAH8; | CODING (100%); | 2 | 2905985; 2905986 |
| Block_1735 | 0.000361 | chr12: 103306570 . . . 103306674; − | 1 | PAH; | CODING (100%); | 2 | 3468531; 4053738 |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| Block_4308 | 0.000428 | chr2: 242135147 . . . 242164581; + | 1 | ANO7; | CODING (91.66%); UTR (8.33%); | 24 | 2536222; 2536226; 2536228; 2536229; 2536231; 2536232; 2536233; 2536234; 2536235; 2536236; 2536237; 2536238; 2536240; 2536241; 2536243; 2536245; 2536248; 2536249; 2536252; 2536253; 2536256; 2536260; 2536261; 2536262 |
| Block_3836 | 0.000436 | chr2: 100377851 . . . 100400837; − | 1 | AFF3; | INTRONIC (100%); | 2 | 2566945; 2566952 |
| Block_6570 | 0.000497 | chr7: 37946647 . . . 37956059; − | 1 | SFRP4; | CODING (66.66%); UTR (33.33%); | 9 | 3046448; 3046449; 3046450; 3046457; 3046459; 3046460; 3046461; 3046462; 3046465 |
| Block_1532 | 0.000507 | chr11: 114311909 . . . 114320545; + | 1 | REXO2; | CODING (33.33%); INTRONIC (66.66%); | 6 | 3349958; 3349959; 3349966; 3349970; 3349975; 3349979 |
| Block_2087 | 0.000507 | chr13: 24464154 . . . 24465613; + | 1 | RP11-45B20.3; | ncTRANSCRIPT (100%); | 2 | 3481518; 3481519 |
| Block_2922 | 0.000536 | chr16: 81047741 . . . 81065037; + | 1 | CENPN; | CODING (80%); UTR (10%); INTRONIC (10%); | 10 | 3670638; 3670639; 3670641; 3670644; 3670645; 3670650; 3670659; 3670660; 3670661; 3670666 |
| Block_3281 | 0.000588 | chr17: 65027167 . . . 65028692; + | 2 | CACNG4; AC005544.1; | CODING (50%); UTR (50%); | 2 | 3732138; 3732139 |
| Block_5080 | 0.000657 | chr3: 53528861 . . . 53847736; + | 1 | CACNA1D; | ncTRANSCRIPT (1.09%); CODING (49.45%); UTR (2.19%); INTRONIC (47.25%); | 91 | 2624389; 2624393; 2624394; 2624395; 2624397; 2624398; 2624399; 2624400; 2624401; 2624402; 2624403; 2624404; 2624405; 2624406; 2624407; 2624408; 2624529; 2624531; 2624533; 2624537; 2624411; 2624412; 2624413; 2624415; 2624416; 2624417; 2624421; 2624422; 2624424; 2624426; 2624427; 2624428; 2624429; 2624430; 2624432; 2624434; 2624435; 2624438; 2624439; 2624440; 2624441; 2624442; 2624443; 2624444; 2624446; 2624453; 2624458; 2624459; 2624460; 2624461; 2624462; 2624465; 2624466; 2624467; 2624470; 2624472; 2624473; 2624475; 2624477; 2624479; 2624480; 2624481; 2624482; 2624484; 2624485; 2624487; 2624488; 2624490; 2624491; 2624492; 2624493; 2624494; 2624495; 2624496; 2624499; 2624500; 2624501; 2624502; 2624503; 2624504; 2624505; 2624507; 2624508; 2624511; 2624512; 2624515; |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| | | | | | | | 2624516; 2624518; 2624519; 2624526; 2624527 |
| Block_6033 | 0.000669 | chr5: 149357733 ... 149361471; + | 1 | SLC26A2; | CODING (50%); UTR (50%); | 2 | 2835310; 2835314 |
| Block_1566 | 0.000733 | chr11: 129722378 ... 129729817; + | 1 | TMEM45B; | CODING (85.71%); UTR (14.28%); | 7 | 3356054; 3356055; 3356056; 3356058; 3356061; 3356063; 3356066 |
| Block_1222 | 0.000746 | chr11: 30601825 ... 30602041; − | 1 | MPPED2; | CODING (50%); UTR (50%); | 2 | 3367741; 3367743 |
| Block_2090 | 0.00076 | chr13: 26145795 ... 26156094; + | 1 | ATP8A2; | CODING (100%); | 3 | 3482326; 3482335; 3482336 |
| Block_4334 | 0.000774 | chr20: 10619700 ... 10620579; − | 1 | JAG1; | CODING (33.33%); UTR (66.66%); | 3 | 3897508; 3897509; 3897512 |
| Block_2162 | 0.000788 | chr13: 111932910 ... 111938586; + | 1 | ARHGEF7; | CODING (100%); | 2 | 3501728; 3501736 |
| Block_2628 | 0.000788 | chr15: 74005696 ... 74005846; + | 1 | CD276; | UTR (100%); | 2 | 3601259; 3601260 |
| Block_5303 | 0.000803 | chr4: 80898781 ... 80905088; − | 1 | ANTXR2; | CODING (100%); | 3 | 2775016; 2775017; 2775018; |
| Block_213 | 0.000832 | chr1: 85277703 ... 85279820; − | 1 | LPAR3; | CODING (33.33%); UTR (66.66%); | 3 | 2420617; 2420619; 2420621 |
| Block_773 | 0.000863 | chr1: 220870275 ... 220872267; + | 1 | C1orf115; | UTR (100%); | 2 | 2381258; 2381260 |
| Block_3219 | 0.000927 | chr17: 40932892 ... 40945698; + | 1 | WNK4; | CODING (100%); | 8 | 3722087; 3722090; 3722094; 3722095; 3722100; 3722101; 3722105; 3722106 |
| Block_7722 | 0.001069 | chrX: 18643259 ... 18646559; + | 1 | CDKL5; | CODING (100%); | 2 | 3970693; 3970698 |
| Block_5415 | 0.001107 | chr4: 170016681 ... 170017797; − | 1 | SH3RF1; | CODING (66.66%); UTR (33.33%); | 3 | 2793150; 2793151; 2793152 |
| Block_6420 | 0.001127 | chr6: 80383340 ... 80406282; + | 1 | SH3BGRL2; | CODING (100%); | 2 | 2914706; 2914708 |
| Block_6142 | 0.001147 | chr6: 38890758 ... 38901026; − | 1 | RP1-207H1.3; | ncTRANSCRIPT (85.71%); INTRONIC (14.28%); | 7 | 2952718; 2952719; 2952720; 2952721; 2952723; 2952724; 2952725 |
| Block_3837 | 0.001188 | chr2: 100426047 ... 100692345; − | 1 | AFF3; | CODING (6.55%); ncTRANSCRIPT (3.27%); INTRONIC (90.16%); | 61 | 2566957; 2566960; 2566961; 2566965; 2566966; 2566971; 2567075; 2567076; 2567084; 2567063; 2566976; 2567087; 2567088; 2566977; 2567064; 2567097; 2567067; 2567069; 2567101; 2567103; 2567071; 2566979; 2566982; 2566983; 2566984; 2566985; 2567105; 2567111; 2567113; 2567115; 2567106; 2566987; 2566988; 2566991; 2566993; 2566994; 2566996; 2566997; 2567121; 2566998; 2567125; 2567000; 2567001; 2567002; 2567003; 2567005; 2567007; 2567008; 2567010; 2567011; 2567012; 2567013; 2567014; 2567015; 2567017; 2567018; 2567019; 2567020; 2567022; 2567023; 2567127 |
| Block_1378 | 0.001391 | chr 11: 134022950 ... 134052868; − | 1 | NCAPD3; | ncTRANSCRIPT (45.45%); INTRONIC | 11 | 3399552; 3399554; 3399556; 3399558; 3399559; 3399560; |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| | | | | | (54.54%); | | 3399561; 3399568; 3399575; 3399578; 3399582 |
| Block_3834 | 0.001415 | chr2: 100199328 . . . 100318709; − | 1 | AFF3; | CODING (22.72%); UTR (4.54%); INTRONIC (72.72%); | 22 | 2566873; 2566875; 2566880; 2566885; 2566886; 2566888; 2566893; 2566898; 2566900; 2566902; 2566905; 2566906; 2566908; 2566910; 2566911; 2566912; 2566915; 2566919; 2566920; 2566922; 2566924; 2566929 |
| Block_4395 | 0.001569 | chr20: 52560335 . . . 52561534; − | 1 | BCAS1; | CODING (50%); UTR (50%); | 2 | 3910362; 3910363 |
| Block_6520 | 0.001624 | chr6: 160770298 . . . 160864773; + | 2 | AL591069.1; SLC22A3; | ncTRANSCRIPT (3.44%); CODING (27.58%); INTRONIC (68.96%); | 29 | 2934526; 2934527; 2934531; 2934533; 2934535; 2934580; 2934582; 2934585; 2934586; 2934536; 2934537; 2934538; 2934539; 2934541; 2934543; 2934545; 2934547; 2934548; 2934549; 2934550; 2934551; 2934554; 2934556; 2934557; 2934558; 2934559; 2934560; 2934561; 2934562 |
| Block_3917 | 0.001652 | chr2: 178762785 . . . 178769891; − | 1 | PDE11A; | CODING (100%); | 2 | 2589116; 2589118 |
| Block_3752 | 0.001681 | chr2: 42662806 . . . 42670619; − | 1 | KCNG3; | INTERGENIC (50%); UTR (50%); | 2 | 2550177; 2550178 |
| Block_7162 | 0.001739 | chr9: 3262938 . . . 3271101; − | 1 | RFX3; | CODING (100%); | 2 | 3196865; 3196873 |
| Block_5975 | 0.001769 | chr5: 113698875 . . . 113699698; + | 1 | KCNN2; | CODING (100%); | 2 | 2824632; 2824635 |
| Block_6604 | 0.001769 | chr7: 87907478 . . . 87920296; − | 1 | STEAP4; | CODING (75%); UTR (25%); | 12 | 3060339; 3060340; 3060341; 3060342; 3060343; 3060344; 3060347; 3060348; 3060350; 3060351; 3060352; 3060353 |
| Block_4200 | 0.0018 | chr2: 181852076 . . . 181894023; + | 1 | UBE2E3; | CODING (20%); INTRONIC (80%); | 5 | 2518175; 2518178; 2518179; 2518180; 2518184 |
| Block_4201 | 0.0018 | chr2: 181920432 . . . 181924616; + | 1 | UBE2E3; | INTRONIC (100%); | 3 | 2518192; 2518193; 2518197 |
| Block_3913 | 0.001926 | chr2: 178528594 . . . 178540212; − | 1 | PDE11A; | CODING (100%); | 2 | 2589038; 2589043 |
| Block_5936 | 0.001926 | chr5: 79361251 . . . 79378964; + | 1 | THBS4; | CODING (100%); | 10 | 2817602; 2817603; 2817605; 2817606; 2817609; 2817611; 2817614; 2817615; 2817620; 2817621 |
| Block_3916 | 0.001959 | chr2: 178681582 . . . 178705094; − | 1 | PDE11A; | CODING (100%); | 3 | 2589101; 2589102; 2589105 |
| Block_4125 | 0.001959 | chr2: 101541626 . . . 101564800; + | 1 | NPAS2; | CODING (100%); | 4 | 2496436; 2496440; 2496446; 2496448 |
| Block_2925 | 0.001992 | chr16: 84479997 . . . 84485677; + | 1 | ATP2C2; | CODING (100%); | 2 | 3671768; 3671774 |
| Block_874 | 0.002026 | chr10: 33545282 . . . 33559775; − | 1 | NRP1; | CODING (100%); | 3 | 3284370; 3284373; 3284377 |
| Block_4971 | 0.002061 | chr3: 184910469 . . . 184922544; − | 1 | EHHADH; | CODING (100%); | 3 | 2708726; 2708727; 2708733 |
| Block_2216 | 0.002131 | chr14: 51379747 . . . 51387339; − | 1 | PYGL; | CODING (100%); | 2 | 3564224; 3564231 |
| Block_6886 | 0.002131 | chr8: 27317314 . . . 27336535; − | 1 | CHRNA2; | CODING (60%); UTR (40%); | 10 | 3129025; 3129030; 3129034; 3129038; 3129039; 3129040; |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| | | | | | | | 3129044; 3129045; 3129046; 3129047 |
| Block_1533 | 0.002167 | chr11: 114311389 . . . 114314645; + | 1 | REXO2; | CODING (100%); | 2 | 3349956; 3349963 |
| Block_4336 | 0.002167 | chr20: 10632779 . . . 10644662; − | 1 | JAG1; | CODING (100%); | 4 | 3897552; 3897558; 3897559; 3897568 |
| Block_4349 | 0.002167 | chr20: 20596706 . . . 20621488; − | 1 | RALGAPA2; | CODING (100%); | 5 | 3900218; 3900220; 3900228; 3900233; 3900235 |
| Block_1576 | 0.002204 | chr11: 134147231 . . . 134188819; + | 1 | GLB1L3; | CODING (100%); | 13 | 3357348; 3357349; 3357360; 3357363; 3357369; 3357370; 3357371; 3357375; 3357382; 3357383; 3357384; 3357386; 3357387 |
| Block_3611 | 0.002204 | chr19: 32080316 . . . 32084433; + | 0 | | INTERGENIC (100%); | 2 | 3828710; 3828717 |
| Block_1649 | 0.002241 | chr12: 44913789 . . . 44915959; − | 1 | NELL2; | CODING (100%); | 2 | 3451835; 3451838 |
| Block_5976 | 0.002317 | chr5: 113740155 . . . 113740553; + | 1 | KCNN2; | CODING (100%); | 2 | 2824643; 2824644 |
| Block_1964 | 0.002476 | chr12: 121134218 . . . 121137627; + | 1 | MLEC; | CODING (50%); UTR (50%); | 2 | 3434542; 3434546 |
| Block_2762 | 0.002476 | chr16: 56701878 . . . 56701935; − | 1 | MT1G; | CODING (50%); UTR (50%); | 2 | 3693007; 3693008 |
| Block_4864 | 0.002476 | chr3: 116058173 . . . 116094106; − | 1 | LSAMP; | INTRONIC (100%); | 3 | 2690112; 2690113; 2690118 |
| Block_829 | 0.002559 | chr1: 247712494 . . . 247739511; + | 1 | C1orf150; | CODING (66.66%); UTR (33.33%); | 3 | 2390125; 2390128; 2390134 |
| Block_2311 | 0.002602 | chr14: 38054451 . . . 38055847; + | 0 | | INTERGENIC (100%); | 4 | 3533031; 3533035; 3533037; 3533039 |
| Block_2822 | 0.002602 | chr16: 8875186 . . . 8878061; + | 1 | ABAT; | CODING (20%); UTR (80%); | 5 | 3647480; 3647481; 3647483; 3647484; 3647485 |
| Block_5310 | 0.002602 | chr4: 82026968 . . . 82031699; − | 1 | PRKG2; | CODING (100%); | 2 | 2775219; 2775221 |
| Block_7638 | 0.002602 | chrX: 106957270 . . . 106960029; − | 1 | TSC22D3; | CODING (50%); UTR (50%); | 6 | 4017398; 4017399; 4017400; 4017403; 4017409; 4017414 |
| Block_1652 | 0.002645 | chr12: 45168545 . . . 45173801; − | 1 | NELL2; | CODING (100%); | 4 | 3451885; 3451888; 3451889; 3451891 |
| Block_1917 | 0.002645 | chr12: 81528607 . . . 81545849; + | 1 | ACSS3; | CODING (100%); | 4 | 3424233; 3424234; 3424243; 3424244 |
| Block_1933 | 0.002779 | chr12: 102113921 . . . 102117625; + | 1 | CHPT1; | CODING (100%); | 2 | 3428698; 3428702 |
| Block_3096 | 0.002872 | chr17: 74622431 . . . 74625201; − | 1 | ST6GALNAC1; | CODING (100%); | 6 | 3771721; 3771722; 3771723; 3771725; 3771726; 3771727 |
| Block_3273 | 0.002872 | chr17: 59093209 . . . 59112144; + | 1 | BCAS3; | CODING (100%); | 2 | 3729624; 3729628 |
| Block_3832 | 0.002872 | chr2: 100165334 . . . 100170892; − | 1 | AFF3; | CODING (50%); UTR (50%); | 4 | 2566847; 2566849; 2566850; 2566851 |
| Block_6032 | 0.002872 | chr5: 149357507 . . . 149366444; + | 1 | SLC26A2; | CODING (57.14%); UTR (42.85%); | 7 | 2835309; 2835311; 2835312; 2835313; 2835315; 2835316; 2835317 |
| Block_214 | 0.003016 | chr1: 85331090 . . . 85331666; − | 1 | LPAR3; | CODING (100%); | 2 | 2420633; 2420635 |
| Block_4670 | 0.003016 | chr22: 32480910 . . . 32482314; + | 1 | SLC5A1; | CODING (100%); | 2 | 3943253; 3943255 |
| Block_5621 | 0.003016 | chr4: 159812601 . . . 159828286; + | 1 | FNIP2; | CODING (50%); UTR (50%); | 6 | 2749669; 2749671; 2749675; 2749676; 2749677; 2749678 |
| Block_7835 | 0.003016 | chrX: 152770164 . . . 152773851; + | 1 | BGN; | CODING (100%); | 6 | 3995642; 3995651; 3995654; 3995657; 3995659; 3995661 |
| Block_4022 | 0.003115 | chr2: 1718308 . . . 11721346; + | 1 | GREB1; | UTR (50%); INTRONIC (50%); | 2 | 2469846; 2469850 |
| Block_6521 | 0.003218 | chr6: 160866011 . . . 160868068; + | 1 | SLC22A3; | INTRONIC (100%); | 3 | 2934564; 2934565; 2934567 |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| Block_4344 | 0.003271 | chr20: 20475772 . . . 20507004; − | 1 | RALGAPA2; | CODING (100%); | 7 | 3900137; 3900143; 3900149; 3900150; 3900152; 3900154; 3900156 |
| Block_3505 | 0.003324 | chr19: 15297695 . . . 15302661; − | 1 | NOTCH3; | CODING (100%); | 5 | 3853157; 3853158; 3853159; 3853161; 3853166 |
| Block_4335 | 0.003324 | chr20: 10621471 . . . 10630262; − | 1 | JAG1; | CODING (100%); | 16 | 3897514; 3897515; 3897516; 3897517; 3897518; 3897519; 3897520; 3897527; 3897529; 3897531; 3897533; 3897535; 3897536; 3897537; 3897539; 3897540 |
| Block_3168 | 0.003433 | chr17: 7945688 . . . 7951882; + | 1 | ALOX15B; | CODING (100%); | 11 | 3709424; 3709426; 3709428; 3709429; 3709430; 3709432; 3709433; 3709435; 3709437; 3709438; 3709440 |
| Block_456 | 0.003433 | chr1: 19981582 . . . 19984800; + | 1 | NBL1; | CODING (66.66%); UTR (33.33%); | 3 | 2323777; 2323778; 2323782 |
| Block_1377 | 0.003489 | chr11: 134022430 . . . 134095174; − | 1 | NCAPD3; | CODING (90.47%); UTR (7.14%); INTRONIC (2.38%); | 42 | 3399550; 3399551; 3399553; 3399555; 3399562; 3399563; 3399565; 3399566; 3399567; 3399569; 3399570; 3399571; 3399572; 3399573; 3399574; 3399576; 3399577; 3399579; 3399580; 3399581; 3399583; 3399584; 3399585; 3399587; 3399588; 3399589; 3399590; 3399591; 3399592; 3399593; 3399594; 3399595; 3399597; 3399598; 3399600; 3399601; 3399602; 3399603; 3399605; 3399606; 3399607; 3399613 |
| Block_1505 | 0.003545 | chr11: 92085296 . . . 92088273; + | 1 | FAT3; | CODING (100%); | 3 | 3344438; 3344439; 3344440 |
| Block_4671 | 0.003545 | chr22: 32498039 . . . 32507284; + | 1 | SLC5A1; | CODING (60%); UTR (40%); | 5 | 3943258; 3943259; 3943261; 3943263; 3943265 |
| Block_743 | 0.003603 | chr1: 203275102 . . . 203275613; + | 1 | BTG2; | INTRONIC (100%); | 3 | 2375667; 2375668; 2375670 |
| Block_4306 | 0.003661 | chr2: 241404507 . . . 241405065; + | 1 | GPC1; | CODING (100%); | 2 | 2535800; 2535802 |
| Block_6592 | 0.003661 | chr7: 80546027 . . . 80548317; − | 1 | SEMA3C; | CODING (50%); UTR (50%); | 2 | 3058814; 3058816 |
| Block_4345 | 0.003841 | chr20: 20486102 . . . 20517400; − | 1 | RALGAPA2; | CODING (100%); | 5 | 3900146; 3900151; 3900155; 3900164; 3900167 |
| Block_1651 | 0.003902 | chr12: 45059307 . . . 45097550; − | 1 | NELL2; | CODING (100%); | 2 | 3451868; 3451874 |
| Block_7859 | 0.003902 | chrY: 14799855 . . . 14802344; + | 1 | TTTY15; | ncTRANSCRIPT (100%); | 2 | 4030072; 4030074 |
| Block_2091 | 0.003965 | chr13: 26411312 . . . 26434996; + | 1 | ATP8A2; | CODING (100%); | 2 | 3482379; 3482386 |
| Block_4935 | 0.003965 | chr3: 142567065 . . . 142567284; − | 1 | PCOLCE2; | CODING (100%); | 2 | 2699027; 2699028 |
| Block_1366 | 0.004093 | chr11: 124617431 . . . 124619754; − | 1 | VSIG2; | CODING (100%); | 2 | 3396086; 3396095 |
| Block_1999 | 0.004093 | chr13: 38158866 . . . 38162106; − | 1 | POSTN; | CODING (100%); | 2 | 3510099; 3510102 |
| Block_2897 | 0.004158 | chr16: 67202953 . . . 67203210; + | 1 | HSF4; | CODING (100%); | 2 | 3665255; 3665257; |
| Block_3442 | 0.004292 | chr18: 56585564 . . . 56587447; + | 1 | ZNF532; | CODING (100%); | 3 | 3790379; 3790380; 3790381 |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| Block_5409 | 0.004429 | chr4: 159046177 . . . 159048546; − | 1 | FAM198B; | UTR (100%); | 4 | 2791422; 2791423; 2791424; 2791425 |
| Block_6505 | 0.004429 | chr7: 87910829 . . . 87912896; − | 1 | STEAP4; | UTR (50%); INTRONIC (50%); | 2 | 3060345; 3060349 |
| Block_7860 | 0.004429 | chrY: 14838600 . . . 14968421; + | 1 | USP9Y; | CODING (100%); | 18 | 4030087; 4030096; 4030104; 4030112; 4030113; 4030115; 4030116; 4030119; 4030120; 4030125; 4030126; 4030127; 4030128; 4030134; 4030144; 4030146; 4030149; 4030153 |
| Block_873 | 0.004429 | chr10: 33491851 . . . 33515213; − | 1 | NRP1; | CODING (100%); | 4 | 3284334; 3284341; 3284346; 3284351 |
| Block_1221 | 0.004499 | chr11: 30443973 . . . 30517053; − | 1 | MPPED2; | CODING (16.66%); ncTRANSCRIPT (8.33%); INTRONIC (75%) | 12 | 3367684; 3367688; 3367691; 3367693; 3367696; 3367697; 3367702; 3367706; 3367707; 3367710; 3367712; 3367714 |
| Block_3512 | 0.004499 | chr19: 18893864 . . . 18897074; − | 1 | COMP; | CODING (100%); | 2 | 3855221; 3855230 |
| Block_3914 | 0.00457 | chr2: 178565861 . . . 178592888; − | 1 | PDE11A; | CODING (100%); | 4 | 2589055; 2589058; 2589064; 2589065 |
| Block_5309 | 0.00457 | chr4: 80992745 . . . 80993659; − | 1 | ANTXR2; | CODING (100%); | 2 | 2775042; 2775043 |
| Block_3446 | 0.004716 | chr18: 56819806 . . . 56824879; + | 1 | SEC11C; | CODING (100%); | 2 | 3790485; 3790494 |
| Block_453 | 0.004716 | chr1: 16332765 . . . 16333026; + | 1 | C1orf64; | CODING (50%); UTR (50%); | 2 | 2322216; 2322218 |
| Block_169 | 0.00479 | chr1: 53373542 . . . 53377448; − | 1 | ECHDC2; | CODING (100%); | 2 | 2413055; 2413058 |
| Block_3443 | 0.00479 | chr18: 56623078 . . . 56648694; + | 1 | ZNF532; | INTRONIC (100%); | 6 | 3790396; 3790398; 3790399; 3790401; 3790403; 3790404 |
| Block_5081 | 0.00479 | chr3: 53736689 . . . 53753808; + | 1 | CACNA1D; | CODING (100%); | 3 | 2624448; 2624454; 2624457 |
| Block_4829 | 0.004865 | chr3: 86988621 . . . 87039865; − | 1 | VGLL3; | CODING (58.82%); UTR (41.17%); | 17 | 2684857; 2684831; 2684832; 2684833; 2684835; 2684859; 2684861; 2684863; 2684865; 2684867; 2684869; 2684871; 2684873; 2684877; 2684879; 2684881; 2684883 |
| Block_886 | 0.004942 | chr10: 61551607 . . . 61572483; − | 1 | CCDC6; | CODING (71.42%); UTR (28.57%); | 7 | 3290791; 3290792; 3290796; 3290799; 3290802; 3290803; 3290807 |
| Block_1330 | 0.005019 | chr11: 106555201 . . . 106558073; − | 1 | GUCY1A2; | UTR (100%); | 2 | 3389670; 3389672 |
| Block_3835 | 0.005019 | chr2: 100372047 . . . 100415240; − | 1 | AFF3; | INTRONIC (100%); | 5 | 2566941; 2566942; 2566948; 2566949; 2566955 |
| Block_481 | 0.005019 | chr1: 27676149 . . . 27677810; + | 1 | SYTL1; | CODING (100%); | 3 | 2327014; 2327022; 2327025 |
| Block_3688 | 0.005098 | chr19: 55315113 . . . 55315146; + | 1 | KIR2DL4; | CODING (100%); | 2 | 3841790; 4052980 |
| Block_4342 | 0.005098 | chr20: 20370667 . . . 20373784; − | 1 | RALGAPA2; | CODING (33.33%); UTR (66.66%); | 3 | 3900089; 3900090; 3900092 |
| Block_6457 | 0.005098 | chr6: 138657744 . . . 138658255; + | 1 | KIAA1244; | UTR (100%); | 3 | 2927694; 2927695; 2927696 |
| Block_5167 | 0.005178 | chr3: 156170688 . . . 156192603; + | 1 | KCNAB1; | CODING (100%); | 3 | 2649038; 2649044; 2649051 |
| Block_5620 | 0.005178 | chr4: 159772477 . . . 159790535; + | 1 | FNIP2; | CODING (100%); | 9 | 2749639; 2749640; 2749644; 2749646; 2749647; 2749648; 2749650; 2749651; 2749652 |
| Block_1250 | 0.005258 | chr11: 61290559 . . . 61291972; − | 1 | SYT7; | CODING (100%); | 3 | 3375403; 3375404; 3375405; |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| Block_2089 | 0.005258 | chr13: 26104137 . . . 26163815; + | 1 | ATP8A2; | CODING (100%); | 12 | 3482305; 3482309; 3482310; 3482313; 3482314; 3482316; 3482319; 3482321; 3482322; 3482330; 3482333; 3482337 |
| Block_3915 | 0.005258 | chr2: 178621229 . . . 178630397; − | 1 | PDE11A; | INTRONIC (100%); | 3 | 2589079; 2589083; 2589089 |
| Block_5060 | 0.00534 | chr3: 48289117 . . . 48312089; + | 1 | ZNF589; | CODING (55.55%); UTR (44.44%); | 9 | 2621590; 2621598; 2621602; 2621603; 2621604; 2621606; 2621607; 2621608; 2621609 |
| Block_5619 | 0.00534 | chr4: 159750328 . . . 159754780; + | 1 | FNIP2; | CODING (100%); | 4 | 2749625; 2749626; 2749627; 2749629 |
| Block_2896 | 0.005508 | chr16: 67199438 . . . 67201057; + | 1 | HSF4; | ncTRANSCRIPT (20%); CODING (80%); | 5 | 3665235; 3665240; 3665244; 3665245; 3665246 |
| Block_3964 | 0.005508 | chr2: 204309603 . . . 204313496; − | 1 | RAPH1; | CODING (100%); | 3 | 2595578; 2595581; 2595583 |
| Block_4025 | 0.00568 | chr2: 13872471 . . . 13926374; + | 2 | NCRNA00276; AC016730.1; | INTRONIC (50%); INTRONIC_AS (50%); | 2 | 2470336; 2470352 |
| Block_4861 | 0.00568 | chr3: 115524258 . . . 115529246; − | 1 | LSAMP; | CODING (20%); INTERGENIC (60%); UTR (20%); | 5 | 2690021; 2690022; 2690023; 2690025; 2690027 |
| Block_1220 | 0.005947 | chr11: 30431953 . . . 30439165; − | 1 | MPPED2; | CODING (75%); UTR (25%); | 4 | 3367675; 3367676; 3367679; 3367680 |
| Block_736 | 0.005947 | chr1: 201285703 . . . 201293641; + | 1 | PKP1; | CODING (100%); | 4 | 2374622; 2374628; 2374629; 2374631 |
| Block_7442 | 0.005947 | chr9: 101589035 . . . 101611356; + | 1 | GALNT12; | CODING (100%); | 5 | 3181611; 3181614; 3181620; 3181622; 3181628; |
| Block_7533 | 0.005947 | chrX: 1505524 . . . 1506210; − | 1 | SLC25A6; | CODING (100%); | 3 | 3997378; 4033179; 4033181 |
| Block_1251 | 0.006039 | chr11: 61295389 . . . 61300540; − | 1 | SYT7; | CODING (100%); | 2 | 3375406; 3375409 |
| Block_3169 | 0.006039 | chr17: 7960222 . . . 7966722; + | 0 | | INTERGENIC (100%); | 6 | 3709445; 3709446; 3709448; 3709451; 3709453; 3709455 |
| Block_3903 | 0.006039 | chr2: 169094505 . . . 169097430; − | 1 | STK39; | INTRONIC (100%); | 2 | 2585794; 2585796 |
| Block_1997 | 0.006132 | chr13: 38154719 . . . 38164537; − | 1 | POSTN; | CODING (100%); | 3 | 3510096; 3510097; 3510103 |
| Block_4863 | 0.006226 | chr3: 115984267 . . . 116001005; − | 1 | LSAMP; | INTRONIC (100%); | 3 | 2690278; 2690273; 2690288 |
| Block_7046 | 0.006226 | chr8: 27358443 . . . 27380016; + | 1 | EPHX2; | CODING (100%); | 6 | 3091408; 3091410; 3091412; 3091414; 3091418; 3091427 |
| Block_3912 | 0.006321 | chr2: 178493807 . . . 178494276; − | 1 | PDE11A; | CODING (50%); UTR (50%); | 2 | 2589025; 2589028 |
| Block_4194 | 0.006321 | chr2: 173885368 . . . 173891966; + | 1 | RAPGEF4; | CODING (100%); | 2 | 2515897; 2515902 |
| Block_4979 | 0.006418 | chr3: 189674965 . . . 189681873; − | 1 | LEPREL1; | CODING (75%); UTR (25%); | 4 | 2710476; 2710477; 2710483; 2710484 |
| Block_5977 | 0.006615 | chr5: 113798749 . . . 113808838; + | 1 | KCNN2; | CODING (100%); | 3 | 2824655; 2824656; 2824657 |
| Block_1534 | 0.006818 | chr11: 114315278 . . . 114320629; + | 1 | REXO2; | CODING (100%); | 3 | 3349968; 3349972; 3349980 |
| Block_4346 | 0.006818 | chr20: 20552104 . . . 20563856; − | 1 | RALGAPA2; | CODING (100%); | 3 | 3900185; 3900187; 3900191 |
| Block_1731 | 0.006922 | chr12: 102173985 . . . 102190536; − | 1 | GNPTAB; | CODING (100%); | 3 | 3468148; 3468152; 3468159; |
| Block_4980 | 0.006922 | chr3: 189689680 . . . 189713231; − | 1 | LEPREL1; | CODING (100%); | 12 | 2710494; 2710495; 2710496; 2710498; 2710502; 2710503; 2710504; 2710505; 2710506; 2710509; 2710510; 2710511 |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| Block_5661 | 0.007241 | chr5: 29476852 . . . 29477004; − | 0 | | INTERGENIC (100%); | 2 | 2851724; 2851725 |
| Block_7425 | 0.007241 | chr9: 90301466 . . . 90312118; + | 1 | DAPK1; | CODING (100%); | 2 | 3177954; 3177956 |
| Block_5416 | 0.00735 | chr4: 170037444 . . . 170043285; − | 1 | SH3RF1; | CODING (100%); | 3 | 2793155; 2793156; 2793159 |
| Block_5567 | 0.007461 | chr4: 108866136 . . . 108873298; + | 1 | CYP2U1; | CODING (66.66%); UTR (33.33%); | 6 | 2738706; 2738707; 2738708; 2738712; 2738714; 2738715 |
| Block_6698 | 0.007461 | chr7: 12620691 . . . 12691507; + | 1 | SCIN; | CODING (100%); | 9 | 2990415; 2990418; 2990420; 2990421; 2990424; 2990425; 2990427; 2990430; 2990431 |
| Block_4865 | 0.007573 | chr3: 116123466 . . . 116161481; − | 1 | LSAMP; | INTRONIC (100%); | 5 | 2690300; 2690302; 2690304; 2690131; 2690132 |
| Block_6522 | 0.007573 | chr6: 160868751 . . . 160872088; + | 1 | SLC22A3; | CODING (100%); | 2 | 2934572; 2934575 |
| Block_2419 | 0.007687 | chr15: 23006467 . . . 23014513; − | 1 | NIPA2; | CODING (100%); | 2 | 3613310; 3613312 |
| Block_6164 | 0.007687 | chr6: 55739210 . . . 55740206; − | 1 | BMP5; | CODING (75%); UTR (25%); | 4 | 2958199; 2958200; 2958201; 2958202 |
| Block_2128 | 0.007919 | chr13: 76379046 . . . 76382387; + | 1 | LMO7; | INTRONIC (100%); | 3 | 3494196; 3494197; 3494206 |
| Block_3455 | 0.007919 | chr19: 282756 . . . 287715; − | 1 | PPAP2C; | CODING (100%); | 2 | 3844475; 3844477 |
| Block_4347 | 0.007919 | chr20: 20582326 . . . 20586044; − | 1 | RALGAPA2; | CODING (100%); | 2 | 3900205; 3900207 |
| Block_5364 | 0.008158 | chr4: 120442102 . . . 120528393; − | 1 | PDE5A; | CODING (100%); | 11 | 2783626; 2783629; 2783637; 2783638; 2783644; 2783650; 2783652; 2783654; 2783659; 2783662; 2783663 |
| Block_7048 | 0.008279 | chr8: 27398133 . . . 27402173; + | 1 | EPHX2; | CODING (50%); UTR (50%); | 2 | 3091435; 3091442 |
| Block_1772 | 0.008528 | chr12: 118470966 . . . 118480761; − | 1 | WSB2; | CODING (80%); UTR (20%); | 5 | 3473729; 3473732; 3473735; 3473736; 3473739 |
| Block_3445 | 0.008528 | chr18: 56820014 . . . 56824583; + | 1 | SEC11C; | UTR (20%); INTRONIC (80%); | 5 | 3790486; 3790487; 3790489; 3790492; 3790493 |
| Block_1105 | 0.008654 | chr10: 102732697 . . . 102737466; + | 1 | SEMA4G; | CODING (100%); | 2 | 3260899; 3260903 |
| Block_1978 | 0.008654 | chr13: 24254773 . . . 24280276; − | 0 | | INTERGENIC (100%); | 8 | 3505432; 3505434; 3505436; 3505438; 3505440; 3505442; 3505444; 3505446 |
| Block_5305 | 0.008782 | chr4: 80929675 . . . 80954689; − | 1 | ANTXR2; | CODING (100%); | 3 | 2775023; 2775024; 2775031 |
| Block_1998 | 0.008912 | chr13: 38158126 . . . 38166301; − | 1 | POSTN; | CODING (100%); | 4 | 3510098; 3510100; 3510101; 3510105 |
| Block_4944 | 0.008912 | chr3: 148895685 . . . 148939500; − | 1 | CP; | CODING (100%); | 9 | 2700263; 2700272; 2700276; 2700284; 2700287; 2700288; 2700289; 2700292; 2700300; |
| Block_3901 | 0.009044 | chr2: 168920012 . . . 168921891; − | 1 | STK39; | CODING (100%); | 2 | 2585735; 2585736; |
| Block_4348 | 0.009044 | chr20: 20591959 . . . 20601268; − | 1 | RALGAPA2; | CODING (100%); | 3 | 3900211; 3900212; 3900221 |
| Block_6149 | 0.009044 | chr6: 46821609 . . . 46836749; − | 1 | GPR116; | CODING (85.71%); UTR (14.28%); | 7 | 2955866; 2955877; 2955879; 2955881; 2955884; 2955885; 2955887 |
| Block_1274 | 0.009177 | chr11: 65197863 . . . 65204294; − | 1 | NEAT1; | ncTRANSCRIPT_AS (100%); | 3 | 3377621; 3377623; 3377630 |
| Block_1797 | 0.009177 | chr12: 125398337 . . . 125399059; − | 1 | UBC; | UTR (100%); | 5 | 3476772; 3476773; 3476774; 3476775; 3476776 |
| Block_461 | 0.009177 | chr1: 24766662 . . . 24799256; + | 1 | NIPAL3; | CODING (83.33%); UTR (16.66%); | 12 | 2325438; 2325443; 2325444; 2325445; 2325448; 2325449; |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| | | | | | | | 2325452; 2325453; 2325457; 2325462; 2325463; 2325464 |
| Block_5410 | 0.009177 | chr4: 159052021 . . . 159091694; − | 1 | FAM198B; | CODING (100%); | 3 | 2791428; 2791433; 2791438 |
| Block_6449 | 0.009177 | chr6: 132190499 . . . 132196962; + | 1 | ENPP1; | CODING (100%); | 2 | 2925975; 2925979 |
| Block_2924 | 0.009312 | chr16: 84449114 . . . 84482221; + | 1 | ATP2C2; | CODING (100%); | 4 | 3671751; 3671757; 3671766; 3671769 |
| Block_6700 | 0.009312 | chr7: 16815929 . . . 16823939; + | 1 | TSPAN13; | CODING (80%); UTR (20%); | 5 | 2991161; 2991163; 2991164; 2991165; 2991172 |
| Block_7016 | 0.009312 | chr8: 424465 . . . 424757; + | 0 | | INTERGENIC (100%); | 2 | 3082591; 3082592; |
| Block_6140 | 0.009449 | chr6: 38643851 . . . 38649827; − | 1 | GLO1; | CODING (66.66%); UTR (33.33%); | 3 | 2952681; 2952683; 2952684 |
| Block_2442 | 0.009588 | chr15: 42445498 . . . 42446391; − | 1 | PLA2G4F; | CODING (100%); | 2 | 3620449; 3620451 |
| Block_2631 | 0.009588 | chr15: 75108788 . . . 75123934; + | 2 | CPLX3; LMAN1L; | CODING (55%); UTR (25%); INTRONIC (20%); | 20 | 3601898; 3601899; 3601900; 3601902; 3601904; 3601906; 3601909; 3601911; 3601912; 3601919; 3601921; 3601914; 3601923; 3601926; 3601933; 3601934; 3601936; 3601937; 3601939; 3601940 |
| Block_124 | 0.009728 | chr1: 25573295 . . . 25573974; − | 1 | C1orf63; | CODING (33.33%); UTR (66.66%); | 3 | 2402129; 2402130; 2402134 |
| Block_1788 | 0.009728 | chr12: 123212329 . . . 123213804; − | 1 | GPR81; | UTR (100%); | 2 | 3475776; 3475778 |
| Block_2163 | 0.009871 | chr13: 111940732 . . . 111953191; + | 1 | ARHGEF7; | CODING (100%); | 2 | 3501737; 3501744 |
| Block_4943 | 0.009871 | chr3: 148896342 . . . 148897449; − | 1 | CP; | CODING (100%); | 2 | 2700265; 2700267 |
| Block_7740 | 0.009871 | chrX: 43571128 . . . 43605327; + | 1 | MAOA; | CODING (92.85%); UTR (7.14%); | 14 | 4055670; 4055678; 4055680; 3975248; 4055682; 3975250; 3975251; 4055686; 3975252; 3975253; 3975256; 3975258; 3975259; 3975260 |
| Block_5168 | 0.010015 | chr3: 156249230 . . . 156254535; + | 1 | KCNAB1; | CODING (100%); | 2 | 2649070; 2649077 |
| Block_5185 | 0.010015 | chr3: 175165052 . . . 175293963; + | 1 | NAALADL2; | CODING (100%); | 4 | 2653186; 2653187; 2653188; 2653192 |
| Block_462 | 0.010161 | chr1: 24840908 . . . 24867125; + | 1 | RCAN3; | INTERGENIC (14.28%); CODING (57.14%); UTR (28.57%); | 7 | 2325485; 2325490; 2325491; 2325494; 2325497; 2325498; 2325499 |
| Block_3672 | 0.01061 | chr19: 52462246 . . . 52469039; + | 1 | AC011460.1; | INTRONIC (100%); | 4 | 3839986; 3839988; 3839990; 3839992 |
| Block_4273 | 0.01061 | chr2: 220283450 . . . 220283756; + | 1 | DES; | CODING (100%); | 2 | 2528481; 2528482 |
| Block_3289 | 0.010764 | chr17: 66038430 . . . 66039426; + | 1 | KPNA2; | CODING (100%); | 5 | 3732630; 4041134; 3732632; 3732633; 4041130 |
| Block_5774 | 0.010764 | chr5: 132163477 . . . 132164924; − | 1 | SHROOM1; | INTRONIC (100%); | 2 | 2875520; 2875521 |
| Block_2489 | 0.01092 | chr15: 59428644 . . . 59450551; − | 1 | MYO1E; | CODING (50%); UTR (50%); | 2 | 3626828; 3626837 |
| Block_6910 | 0.01092 | chr8: 42033008 . . . 42050729; − | 1 | PLAT; | CODING (84.61%); UTR (15.38%); | 13 | 3133235; 3133236; 3133241; 3133242; 3133244; 3133248; 3133252; 3133254; 3133257; 3133259; 3133260; 3133263; 3133264 |
| Block_5841 | 0.011077 | chr5: 176981427 . . . 176981459; − | 1 | FAM193B; | CODING (100%); | 2 | 2888991; 2889081 |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| Block_6141 | 0.011077 | chr6: 38644052 ... 38650635; − | 1 | GLO1; | CODING (66.66%); UTR (33.33%); | 3 | 2952682; 2952685; 2952686 |
| Block_326 | 0.011237 | chr1: 163112906 ... 163122506; − | 1 | RGS5; | CODING (42.85%); UTR (57.14%); | 7 | 2441391; 2441393; 2441394; 2441395; 2441396; 2441398; 2441399 |
| Block_1996 | 0.011399 | chr13: 38137470 ... 38138697; − | 1 | POSTN; | CODING (100%); | 2 | 3510070; 3510072 |
| Block_2083 | 0.011399 | chr13: 24157611 ... 24190183; + | 1 | TNFRSF19; | CODING (60%); ncTRANSCRIPT (20%); INTRONIC (20%); | 5 | 3481424; 3481425; 3481429; 3481433; 3481434 |
| Block_2847 | 0.011399 | chr16: 28506463 ... 28506488; + | 1 | APOBR; | CODING (100%); | 2 | 3686631; 3686648 |
| Block_5302 | 0.011399 | chr4: 80887049 ... 80896290; − | 1 | ANTXR2; | INTRONIC (100%); | 2 | 2775010; 2775011 |
| Block_607 | 0.011563 | chr1: 110211967 ... 110214138; + | 1 | GSTM2; | CODING (100%); | 4 | 2350963; 2350964; 2350971; 2350973 |
| Block_6224 | 0.011563 | chr6: 110932448 ... 110991713; − | 1 | CDK19; | CODING (80%); UTR (20%); | 10 | 2969474; 2969475; 2969476; 2969479; 2969485; 2969488; 2969489; 2969493; 2969496; 2969499 |
| Block_3268 | 0.011729 | chr17: 57724893 ... 57733355; + | 1 | CLTC; | CODING (100%); | 2 | 3729179; 3729186 |
| Block_4504 | 0.011729 | chr21: 29897038 ... 29922984; − | 1 | AF131217.1; | INTRONIC (100%); | 2 | 3927867; 3927875 |
| Block_1960 | 0.011897 | chr12: 119631512 ... 119632155; + | 1 | HSPB8; | CODING (50%); UTR (50%); | 2 | 3434022; 3434023 |
| Block_228 | 0.011897 | chr1: 94995124 ... 95006762; − | 1 | F3; | ncTRANSCRIPT (12.5%); CODING (62.5%); UTR (12.5%); INTRONIC (12.5%); | 8 | 2423915; 2423916; 2423918; 2423920; 2423923; 2423928; 2423929; 2423930 |
| Block_7829 | 0.011897 | chrX: 135288595 ... 135292180; + | 1 | FHL1; | CODING (100%); | 6 | 3992433; 3992434; 3992435; 3992439; 3992440; 3992448 |
| Block_4343 | 0.012239 | chr20: 20469819 ... 20475748; − | 1 | RALGAPA2; | INTRONIC (100%); | 4 | 3900130; 3900133; 3900135; 3900136 |
| Block_7167 | 0.012239 | chr9: 5335054 ... 5339746; − | 1 | RLN1; | CODING (75%); UTR (25%); | 4 | 3197515; 3197516; 3197518; 3197520 |
| Block_2732 | 0.012414 | chr16: 28123180 ... 28123325; − | 1 | XPO6; | CODING (100%); | 2 | 3686351; 3686352 |
| Block_4075 | 0.012414 | chr2: 47604162 ... 47606139; + | 1 | EPCAM; | CODING (100%); | 2 | 2480978; 2480980 |
| Block_7007 | 0.012414 | chr8: 144695086 ... 144697077; − | 1 | TSTA3; | CODING (100%); | 6 | 3157663; 3157665; 3157670; 3157671; 3157674; 3157675 |
| Block_969 | 0.012414 | chr10: 100219332 ... 100249939; − | 1 | HPSE2; | CODING (100%); | 2 | 3302888; 3302896 |
| Block_3397 | 0.01259 | chr18: 13574674 ... 13585570; + | 1 | C18orf1; | INTRONIC (100%); | 2 | 3780272; 3780043 |
| Block_1932 | 0.012769 | chr2: 102011150 ... 102079590; + | 1 | MYBPC1; | CODING (69.44%); UTR (2.77%); INTRONIC (27.77%); | 36 | 3428611; 3428612; 3428613; 3428617; 3428619; 3428620; 3428623; 3428624; 3428625; 3428626; 3428627; 3428628; 3428629; 3428630; 3428631; 3428634; 3428635; 3428636; 3428637; 3428638; 3428639; 3428640; 3428641; 3428642; 3428643; 3428644; 3428646; 3428647; 3428648; 3428650; 3428651; 3428654; |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| Block_6157 | 0.012769 | chr6: 49695711 ... 49704193; − | 1 | CRISP3; | CODING (87.5%); UTR (12.5%); | 8 | 3428655; 3428659; 3428665; 3428666; 2956567; 2956568; 2956569; 2956571; 2956572; 2956573; 2956574; 2956575 |
| Block_5365 | 0.01295 | chr4: 121954556 ... 121966964; − | 1 | C4orf31; | CODING (33.33%); INTERGENIC (33.33%); UTR (33.33%); | 3 | 2783896; 2783898; 2783906 |
| Block_1650 | 0.013134 | chr12: 44902385 ... 44926477; − | 1 | NELL2; | CODING (66.66%); UTR (33.33%); | 3 | 3451832; 3451841; 3451843 |
| Block_3093 | 0.013134 | chr17: 74139170 ... 74158083; − | 1 | RNF157; | CODING (62.5%); UTR (37.5%); | 8 | 3771400; 3771403; 3771404; 3771411; 3771416; 3771419; 3771421; 3771424 |
| Block_5093 | 0.013134 | chr3: 68057255 ... 68057279; + | 1 | FAM19A1; | INTRONIC (100%); | 2 | 2628487; 4047275 |
| Block_7271 | 0.013134 | chr9: 114190325 ... 114199375; − | 1 | KIAA0368; | CODING (100%); | 3 | 3220621; 3220627; 3220629 |
| Block_243 | 0.013319 | chr1: 110282086 ... 110282515; − | 1 | GSTM3; | CODING (100%); | 2 | 2427224; 2427226 |
| Block_5281 | 0.013507 | chr4: 66465162 ... 66468022; − | 1 | EPHA5; | CODING (66.66%); INTRONIC (33.33%); | 3 | 2771409; 2771411; 2771412 |
| Block_931 | 0.013507 | chr10: 81319697 ... 81319724; − | 1 | SFTPA2; | ncTRANSCRIPT (100%); | 2 | 3297075; 3297138 |
| Block_4894 | 0.013698 | chr3: 123452947 ... 123456357; − | 1 | MYLK; | CODING (100%); | 2 | 2692532; 2692536 |
| Block_1775 | 0.013891 | chr12: 118636857 ... 118639157; − | 1 | TAOK3; | CODING (100%); | 2 | 3473836; 3473838 |
| Block_2881 | 0.013891 | chr16: 56692595 ... 56693058; + | 1 | MT1F; | CODING (100%); | 2 | 3662206; 3662208 |
| Block_5117 | 0.013891 | chr3: 121603566 ... 121604258; + | 1 | EAF2; | INTRONIC (100%); | 2 | 2638711; 2638712; |
| Block_5827 | 0.013891 | chr5: 176919406 ... 176919436; − | 1 | PDLIM7; | CODING (100%); | 2 | 2888869; 2889110 |
| Block_7423 | 0.013891 | chr9: 90254565 ... 90261474; + | 1 | DAPK1; | CODING (100%); | 7 | 3177926; 3177928; 3177929; 3177930; 3177932; 3177933; 3177934 |
| Block_2772 | 0.014086 | chr16: 66651699 ... 66655784; − | 1 | CMTM4; | UTR (100%); | 4 | 3695162; 3695163; 3695166; 3695167 |
| Block_3936 | 0.014086 | chr2: 180306906 ... 180409688; − | 1 | ZNF385B; | ncTRANSCRIPT (7.69%); CODING (53.84%); UTR (23.07%); INTRONIC (15.38%); | 13 | 2590020; 2590021; 2590022; 2590027; 2590028; 2590029; 2590033; 2590034; 2590038; 2590039; 2590129; 2590044; 2590045 |
| Block_6264 | 0.014086 | chr6: 136888801 ... 136926464; − | 1 | MAP3K5; | CODING (100%); | 6 | 2975883; 2975891; 2975893; 2975896; 2975900; 2975901 |
| Block_4719 | 0.014283 | chr22: 48088744 ... 48107002; + | 1 | RP11-191L9.4; | INTRONIC (100%); | 2 | 3949444; 3949447 |
| Block_6353 | 0.014283 | chr6: 31785240 ... 31797461; + | 2 | HSPA1B; HSPA1A; | CODING (100%); | 2 | 2902713; 2902730 |
| Block_6562 | 0.014283 | chr7: 27234981 ... 27237774; − | 1 | HOXA13; | UTR (100%); | 2 | 3042998; 3043001 |
| Block_6873 | 0.014283 | chr8: 19315164 ... 19315317; − | 1 | CSGALNACT1; | CODING (50%); UTR (50%); | 2 | 3126531; 3126532 |
| Block_7134 | 0.014283 | chr8: 104709474 ... 104778764; + | 1 | RIMS2; | CODING (100%); | 3 | 3110435; 3110437; 3110438 |
| Block_7639 | 0.014283 | chrX: 106957605 ... 106957732; − | 1 | TSC22D3; | UTR (100%); | 2 | 4017401; 4017402 |
| Block_3675 | 0.014483 | chr19: 53945049 ... 53945553; + | 1 | CTD-2224J9.2; | ncTRANSCRIPT (100%); | 2 | 3840864; 3840869 |
| Block_6206 | 0.014483 | chr6: 94066465 ... 94068123; − | 1 | EPHA7; | CODING (100%); | 2 | 2965235; 2965237 |
| Block_2713 | 0.014686 | chr16: 15797034 ... 15950855; − | 1 | MYH11; | CODING (97.67%); UTR (2.32%); | 43 | 3682029; 3682030; 3682034; 3682035; 3682037; 3682041; 3682042; 3682043; 3682044; 3682045; |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| | | | | | | | 3682046; 3682047; 3682049; 3682050; 3682052; 3682054; 3682057; 3682062; 3682066; 3682067; 3682068; 3682071; 3682072; 3682076; 3682078; 3682079; 3682080; 3682082; 3682083; 3682084; 3682086; 3682091; 3682092; 3682094; 3682099; 3682103; 3682107; 3682109; 3682113; 3682118; 3682122; 3682129; 368213 |
| Block_3833 | 0.014686 | chr2: 100175340 . . . 100185376; − | 1 | AFF3; | CODING (100%); | 3 | 2566859; 2566862; 2566863 |
| Block_5016 | 0.014686 | chr3: 19295194 . . . 19322810; + | 1 | KCNH8; | CODING (100%); | 2 | 2613308; 2613316 |
| Block_6327 | 0.014686 | chr6: 16279026 . . . 16290811; + | 1 | GMPR; | CODING (100%); | 3 | 2896566; 2896570; 2896575 |
| Block_2885 | 0.014891 | chr16: 56972888 . . . 56975332; + | 1 | HERPUD1; | INTRONIC (100%); | 2 | 3662400; 3662405 |
| Block_2888 | 0.014891 | chr16: 57159781 . . . 57168720; + | 1 | CPNE2; | CODING (100%); | 2 | 3662570; 3662575 |
| Block_1339 | 0.015098 | chr11: 111779401 . . . 111782388; − | 1 | CRYAB; | CODING (75%); UTR (25%); | 4 | 3391171; 3391173; 3391176; 3391181 |
| Block_6265 | 0.015308 | chr6: 136934261 . . . 136944102; − | 1 | MAP3K5; | CODING (100%); | 2 | 2975904; 297590 |
| Block_4088 | 0.015521 | chr2: 61333740 . . . 61335484; + | 1 | KIAA1841; | CODING (100%); | 2 | 2484488; 2484489 |
| Block_6205 | 0.015736 | chr6: 93953170 . . . 93982106; − | 1 | EPHA7; | CODING (100%); | 9 | 2965209; 2965210; 2965211; 2965214; 2965218; 2965219; 2965222; 2965223; 2965224 |
| Block_6418 | 0.015736 | chr6: 76591424 . . . 76617955; + | 1 | MYO6; | CODING (14.28%); INTRONIC (85.71%); | 14 | 2914115; 2914118; 2914123; 2914124; 2914125; 2914126; 2914128; 2914130; 2914131; 2914134; 2914135; 2914136; 2914137; 2914139 |
| Block_709 | 0.015736 | chr1: 183079624 . . . 183111896; + | 1 | LAMC1; | CODING (100%); | 15 | 2371095; 2371102; 2371106; 2371107; 2371111; 2371115; 2371118; 2371120; 2371121; 2371122; 2371123; 2371124; 2371128; 2371132; 2371136 |
| Block_5054 | 0.015953 | chr3: 44926817 . . . 44955803; + | 1 | TGM4; | ncTRANSCRIPT (4.16%); CODING (79.16%); UTR (8.33%); INTRONIC (8.33%); | 24 | 2620356; 2620357; 2620358; 2620359; 2620360; 2620361; 2620362; 2620364; 2620366; 2620367; 2620368; 2620371; 2620373; 2620374; 2620375; 2620376; 2620381; 2620382; 2620384; 2620386; 2620387; 2620388; 2620389; 2620390 |
| Block_2887 | 0.016174 | chr16: 57155009 . . . 57155672; + | 1 | CPNE2; | CODING (100%); | 2 | 3662564; 3662565 |
| Block_4137 | 0.016174 | chr2: 111556187 . . . 111562970; + | 1 | ACOXL; | CODING (100%); | 3 | 2500189; 2500190; 2500193 |
| Block_1980 | 0.016397 | chr13: 24334264 . . . 24334353; − | 1 | MIPEP; | CODING (100%); | 2 | 3505466; 3505467 |
| Block_6665 | 0.016851 | chr7: 148701024 . . . 148716114; − | 1 | PDIA4; | CODING (100%); | 8 | 3078437; 3078440; 3078441; 3078445; 3078446; 3078447; 3078449; 3078453 |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| Block_1982 | 0.017083 | chr13: 24384023 . . . 24460604; − | 1 | MIPEP; | CODING (100%); | 13 | 3505485; 3505494; 3505495; 3505497; 3505499; 3505500; 3505504; 3505505; 3505506; 3505507; 3505508; 3505512; 3505517 |
| Block_2679 | 0.017083 | chr15: 101422111 . . . 101422244; + | 1 | ALDH1A3; | INTRONIC (100%); | 2 | 3611631; 3611632 |
| Block_3008 | 0.017317 | chr17: 38545810 . . . 38546338; − | 1 | TOP2A; | CODING (100%); | 2 | 3756196; 3756197 |
| Block_5308 | 0.017317 | chr4: 80957129 . . . 80976604; − | 1 | ANTXR2; | CODING (100%); | 3 | 2775032; 2775037; 2775038 |
| Block_6709 | 0.017317 | chr7: 27224759 . . . 27225870; + | 1 | HOXA11-AS1; | ncTRANSCRIPT (100%); | 5 | 2994152; 2994154; 2994156; 2994159; 2994160 |
| Block_2215 | 0.017553 | chr14: 51378696 . . . 51382203; − | 1 | PYGL; | CODING (100%); | 3 | 3564220; 3564225; 3564227 |
| Block_6943 | 0.017553 | chr8: 73978218 . . . 73982163; − | 1 | C8orf84; | CODING (50%); UTR (50%); | 4 | 3140490; 3140491; 3140492; 3140493 |
| Block_2491 | 0.017793 | chr15: 59480325 . . . 59497655; − | 1 | MYO1E; | CODING (100%); | 4 | 3626865; 3626867; 3626869; 3626871 |
| Block_6591 | 0.017793 | chr7: 80372319 . . . 80456803; − | 1 | SEMA3C; | CODING (87.5%); UTR (12.5%); | 16 | 3058760; 3058761; 3058762; 3058766; 3058768; 3058773; 3058778; 3058780; 3058784; 3058786; 3058787; 3058788; 3058789; 3058790; 3058794; 3058796 |
| Block_7430 | 0.017793 | chr9: 96026229 . . . 96031027; + | 1 | WNK2; | CODING (100%); | 2 | 3179747; 3179752 |
| Block_1045 | 0.018281 | chr10: 51555733 . . . 51556843; + | 1 | MSMB; | CODING (100%); | 2 | 3246411; 3246412 |
| Block_2756 | 0.018281 | chr16: 54953317 . . . 54954239; − | 1 | CRNDE; | ncTRANSCRIPT (50%); INTRONIC (50%); | 2 | 3692520; 3692521 |
| Block_363 | 0.018281 | chr1: 203310039 . . . 203317324; − | 1 | FMOD; | CODING (40%); UTR (60%); | 10 | 2451698; 2451699; 2451700; 2451701; 2451702; 2451703; 2451704; 2451710; 2451711; 2451712 |
| Block_370 | 0.018281 | chr1: 205627208 . . . 205634013; − | 1 | SLC45A3; | CODING (75%); UTR (25%); | 8 | 2452616; 2452617; 2452618; 2452619; 2452621; 2452622; 2452623; 2452624 |
| Block_6688 | 0.018281 | chr7: 2565880 . . . 2566535; + | 1 | LFNG; | CODING (100%); | 2 | 2987566; 2987568 |
| Block_7188 | 0.018281 | chr9: 35682105 . . . 35689177; − | 1 | TPM2; | CODING (100%); | 6 | 3204723; 3204730; 3204734; 3204737; 3204739; 3204740 |
| Block_1179 | 0.018529 | chr11: 2016621 . . . 2017401; − | 1 | H19; | ncTRANSCRIPT (100%); | 4 | 3359080; 3359084; 3359085; 3359087 |
| Block_7359 | 0.018529 | chr9: 140375422 . . . 140389574; − | 1 | PNPLA7; | CODING (100%); | 3 | 3231051; 3231059; 3231063 |
| Block_1193 | 0.018781 | chr11: 6653316 . . . 6661474; − | 1 | DCHS1; | CODING (100%); | 2 | 3361093; 3361099 |
| Block_1474 | 0.018781 | chr11: 65194527 . . . 65211475; + | 1 | NEAT1; | ncTRANSCRIPT (100%); | 8 | 3335225; 3335227; 3335229; 3335231; 3335233; 3335235; 3335239; 3335240 |
| Block_2362 | 0.018781 | chr14: 68113486 . . . 68115462; + | 1 | ARG2; | INTRONIC (100%); | 2 | 3541413; 3541416 |
| Block_2983 | 0.019035 | chr17: 26958501 . . . 26966660; − | 1 | KIAA0100; | CODING (100%); | 5 | 3750898; 3750901; 3750909; 3750911; 3750917 |
| Block_6098 | 0.019035 | chr6: 24666778 . . . 24666965; − | 1 | TDP2; | CODING (100%); | 2 | 2945667; 2945670 |
| Block_6856 | 0.019035 | chr7: 155100327 . . . 155101637; + | 1 | INSIG1; | UTR (100%); | 2 | 3033258; 3033259 |
| Block_1040 | 0.019292 | chr10: 43615579 . . . 43622087; + | 1 | RET; | CODING (100%); | 3 | 3243877; 3243878; 3243881 |
| Block_1047 | 0.019292 | chr10: 51562272 . . . 51562497; + | 1 | MSMB; | CODING (50%); UTR (50%); | 2 | 3246417; 3246418 |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| Block_4023 | 0.019292 | chr2: 11724711 ... 11731961; + | 1 | GREB1; | UTR (50%); INTRONIC (50%); | 2 | 2469853; 2469863 |
| Block_1044 | 0.019553 | chr10: 51532298 ... 51535286; + | 2 | TIMM23B; RP11-481A12.2; | ncTRANSCRIPT (50%); INTRONIC (50%); | 4 | 3246373; 3246408; 3246374; 3246376 |
| Block_2252 | 0.019553 | chr14: 76446944 ... 76447361; − | 1 | TGFB3; | CODING (50%); UTR (50%); | 2 | 3572536; 3572538 |
| Block_2547 | 0.019553 | chr15: 90328249 ... 90349999; − | 1 | ANPEP; | CODING (92%); UTR (8%); | 25 | 3638608; 3638609; 3638610; 3638611; 3638612; 3638614; 3638615; 3638616; 3638622; 3638623; 3638624; 3638625; 3638631; 3638633; 3638635; 3638637; 3638639; 3638640; 3638641; 3638643; 3638644; 3638645; 3638646; 3638648; 3638649 |
| Block_4065 | 0.019553 | chr2: 39944177 ... 39944970; + | 1 | TMEM178; | CODING (33.33%); UTR (66.66%); | 3 | 2478298; 2478299; 2478300 |
| Block_4351 | 0.019553 | chr20: 20634174 ... 20661443; − | 1 | RALGAPA2; | CODING (100%); | 2 | 3900240; 3900249 |
| Block_5767 | 0.019553 | chr5: 121405764 ... 121406282; − | 1 | LOX; | CODING (100%); | 3 | 2872855; 2872856; 2872857 |
| Block_1076 | 0.019816 | chr10: 77453352 ... 77454380; + | 1 | C10orf11; | INTRONIC (100%); | 2 | 3252742; 3252954 |
| Block_3269 | 0.020083 | chr17: 57741220 ... 57763148; + | 1 | CLTC; | CODING (100%); | 16 | 3729191; 3729193; 3729194; 3729195; 3729196; 3729199; 3729201; 3729202; 3729206; 3729207; 3729208; 3729209; 3729210; 3729213; 3729216; 3729218 |
| Block_3886 | 0.020083 | chr2: 162883071 ... 162891670; − | 1 | DPP4; | UTR (33.33%); INTRONIC (66.66%); | 3 | 2584060; 2584063; 2584065 |
| Block_5453 | 0.020083 | chr4: 15839733 ... 15852471; + | 1 | CD38; | INTERGENIC (20%); CODING (60%); UTR (20%); | 5 | 2719689; 2719692; 2719694; 2719695; 2719696 |
| Block_1965 | 0.020352 | chr12: 121138015 ... 121138614; + | 1 | MLEC; | UTR (100%); | 2 | 3434547; 3434548 |
| Block_3245 | 0.020352 | chr17: 45753775 ... 45754478; + | 1 | KPNB1; | CODING (100%); | 2 | 3724808; 3724810 |
| Block_6543 | 0.020352 | chr7: 6502772 ... 6505843; − | 1 | KDELR2; | CODING (100%); | 2 | 3037394; 3037396 |
| Block_7361 | 0.020625 | chr9: 140437902 ... 140444736; + | 1 | PNPLA7; | CODING (75%); UTR (25%); | 4 | 3231109; 3231112; 3231115; 3231117 |
| Block_7520 | 0.020625 | chrX: 229408 ... 229432; − | 1 | GTPBP6; | ncTRANSCRIPT (100%); | 2 | 3997098; 4032902 |
| Block_1934 | 0.020901 | chr12: 104335273 ... 104336343; + | 1 | HSP90B1; | CODING (100%); | 4 | 3429327; 3429329; 3429330; 3429331 |
| Block_6150 | 0.020901 | chr6: 46846004 ... 46851982; − | 1 | GPR116; | CODING (100%); | 5 | 2955898; 2955900; 2955904; 2955908; 2955911 |
| Block_6388 | 0.020901 | chr6: 44752539 ... 44800262; + | 1 | SUPT3H; | INTRONIC_AS (33.33%); INTERGENIC (33.33%); CODING_AS (33.33%); | 3 | 2908668; 2908682; 2908684 |
| Block_1716 | 0.02118 | chr12: 81655761 ... 81661862; − | 1 | PPFIA2; | CODING (100%); | 2 | 3463825; 3463833 |
| Block_1734 | 0.02118 | chr12: 103238114 ... 103246723; − | 1 | PAH; | CODING (100%); | 3 | 3468493; 3468497; 3468501 |
| Block_330 | 0.02118 | chr1: 169434441 ... 169446972; − | 1 | SLC19A2; | CODING (85.71%); UTR | 7 | 2443338; 2443339; 2443342; 2443344; |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| | | | | | (14.28%); | | 2443345; 2443351; 2443352 |
| Block_1239 | 0.021462 | chr11: 49175403 . . . 49229959; − | 1 | FOLH1; | CODING (100%); | 3 | 3372906; 3372936; 3372937 |
| Block_2310 | 0.021462 | chr14: 38033662 . . . 38058763; + | 0 | | INTERGENIC (100%); | 4 | 3533021; 3533028; 3533041; 3533045 |
| Block_3594 | 0.021748 | chr19: 15729440 . . . 15730475; + | 1 | CYP4F8; | CODING (50%); INTRONIC (50%); | 2 | 3823269; 3823272 |
| Block_6355 | 0.021748 | chr6: 31901946 . . . 31903811; + | 1 | C2; | CODING (100%); | 2 | 2902816; 2902819 |
| Block_6731 | 0.021748 | chr7: 56130382 . . . 56131617; + | 1 | CCT6A; | CODING (33.33%); UTR (66.66%); | 3 | 3003220; 3003225; 3003226 |
| Block_2492 | 0.022037 | chr15: 59506427 . . . 59506888; − | 1 | MYO1E; | CODING (100%); | 2 | 3626878; 3626879 |
| Block_4981 | 0.022037 | chr3: 189787406 . . . 189823386; − | 1 | LEPREL1; | INTRONIC (100%); | 2 | 2710531; 2710536 |
| Block_6399 | 0.022037 | chr6: 57311563 . . . 57324709; + | 1 | PRIM2; | INTRONIC (100%); | 2 | 2911450; 2911483 |
| Block_7292 | 0.022037 | chr9: 128000931 . . . 128003092; − | 1 | HSPA5; | CODING (100%); | 4 | 3225407; 3225408; 3225411; 3225416 |
| Block_3621 | 0.022329 | chr19: 35611982 . . . 35613858; + | 1 | FXYD3; | CODING (100%); | 3 | 3830179; 3830181; 3830183 |
| Block_7270 | 0.022329 | chr9: 114176751 . . . 114182394; − | 1 | KIAA0368; | CODING (100%); | 4 | 3220599; 3220601; 3220603; 3220609 |
| Block_4024 | 0.022625 | chr2: 13749190 . . . 13929969; + | 3 | NCRNA00276; AC016730.1; AC092635.1; | INTERGENIC (53.33%); ncTRANSCRIPT (20%); INTRONIC (6.66%); INTRONIC_AS (20%); | 15 | 2470320; 2470321; 2470322; 2470323; 2470324; 2470325; 2470328; 2470330; 2470331; 2470333; 2470334; 2470335; 2470344; 2470346; 2470354 |
| Block_5388 | 0.022625 | chr4: 143326360 . . . 143383879; − | 1 | INPP4B; | CODING (66.66%); UTR (33.33%); | 6 | 2787554; 2787555; 2787562; 2787563; 2787564; 2787567 |
| Block_6426 | 0.022625 | chr6: 88210238 . . . 88218297; + | 1 | SLC35A1; | CODING (100%); | 5 | 2916360; 2916361; 2916363; 2916365; 2916372 |
| Block_2538 | 0.022924 | chr15: 76254177 . . . 76301622; − | 1 | NRG4; | CODING (66.66%); UTR (33.33%); | 3 | 3633708; 3633710; 3633715 |
| Block_7429 | 0.022924 | chr9: 95993221 . . . 96000589; + | 1 | WNK2; | CODING (100%); | 3 | 3179723; 3179725; 3179726 |
| Block_1325 | 0.023226 | chr11: 102269452 . . . 102272423; − | 1 | TMEM123; | CODING (50%); UTR (50%); | 2 | 3388634; 3388639 |
| Block_2166 | 0.023226 | chr13: 113751561 . . . 113752679; + | 2 | MCF2L; AL137002.1; | CODING (50%); UTR (50%); | 2 | 3502390; 3502391 |
| Block_2361 | 0.023226 | chr14: 68086731 . . . 68118330; + | 1 | ARG2; | CODING (87.5%); UTR (12.5%); | 8 | 3541396; 3541398; 3541407; 3541412; 3541414; 3541415; 3541420; 3541421 |
| Block_2982 | 0.023226 | chr17: 26948047 . . . 26962543; − | 1 | KIAA0100; | CODING (100%); | 6 | 3750892; 3750900; 3750904; 3750905; 3750907; 3750910 |
| Block_4388 | 0.023226 | chr20: 48122492 . . . 48160955; − | 1 | PTGIS; | CODING (60%); INTERGENIC (20%); UTR (20%); | 5 | 3908938; 3908939; 3908943; 3908951; 3908952 |
| Block_4862 | 0.023226 | chr3: 115561318 . . . 115571410; − | 1 | LSAMP; | CODING (100%); | 2 | 2690039; 2690041 |
| Block_4905 | 0.023226 | chr3: 129123093 . . . 129137223; − | 1 | C3orf25; | CODING (100%); | 2 | 2694763; 2694771 |
| Block_1408 | 0.023532 | chr11: 17304338 . . . 17352512; + | 1 | NUCB2; | CODING (91.66%); UTR (8.33%); | 12 | 3322265; 3322271; 3322272; 3322276; 3322277; 3322278; 3322279; 3322280; 3322281; 3322283; 3322287; 3322289 |
| Block_2086 | 0.023532 | chr13: 24289383 . . . 24309286; + | 1 | MIPEP; | INTERGENIC (72.72%); | 11 | 3481477; 3481478; 3481487; 3481489; |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| | | | | | ncTRANSCRIPT_AS (18.18%); INTRONIC_AS (9.09%); | | 3481491; 3481493; 3481479; 3481475; 3481480; 3481481; 3481495 |
| Block_2821 | 0.023532 | chr16: 8839879 . . . 8862784; + | 1 | ABAT; | CODING (100%); | 6 | 3647456; 3647459; 3647462; 3647467; 3647468; 3647472 |
| Block_5471 | 0.023532 | chr4: 41395354 . . . 41395449; + | 1 | LIMCH1; | INTRONIC (100%); | 2 | 2725082; 2725083 |
| Block_745 | 0.023532 | chr1: 203311379 . . . 203316520; + | 1 | FMOD; | ncTRANSCRIPT_AS (50%); INTRONIC_AS (50%); | 2 | 2375681; 2375682 |
| Block_2886 | 0.023842 | chr16: 56975974 . . . 56977926; + | 1 | HERPUD1; | INTERGENIC (50%); INTRONIC (50%); | 2 | 3662406; 3662413 |
| Block_4945 | 0.023842 | chr3: 149086852 . . . 149095329; − | 1 | TM4SF1; | CODING (80%); UTR (20%); | 5 | 2700368; 2700372; 2700374; 2700376; 2700379 |
| Block_6419 | 0.023842 | chr6: 76604531 . . . 76626280; + | 1 | MYO6; | CODING (62.5%); UTR (37.5%); | 8 | 2914127; 2914129; 2914138; 2914140; 2914146; 2914147; 2914148; 2914149 |
| Block_6154 | 0.024155 | chr6: 47251674 . . . 47252155; − | 1 | TNFRSF21; | CODING (100%); | 2 | 2956076; 2956077 |
| Block_1388 | 0.024471 | chr11: 4730763 . . . 4740320; + | 2 | AC103710.1; MMP26; | CODING (25%); INTRONIC (75%); | 4 | 3318188; 3318189; 3318226; 3318229 |
| Block_2898 | 0.024471 | chr16: 67203603 . . . 67203747; + | 1 | HSF4; | CODING (100%); | 2 | 3665259; 3665260 |
| Block_4522 | 0.024791 | chr21: 39858595 . . . 39862882; − | 1 | ERG; | INTRONIC (100%); | 2 | 3931864; 3931914 |
| Block_5306 | 0.024791 | chr4: 80918912 . . . 80949988; − | 1 | ANTXR2; | INTRONIC (100%); | 3 | 2775059; 2775027; 2775028 |
| Block_2184 | 0.025443 | chr14: 23816393 . . . 23816935; − | 1 | SLC22A17; | CODING (100%); | 2 | 3557354; 3557358 |
| Block_2254 | 0.025443 | chr14: 80666635 . . . 80668673; − | 1 | DIO2; | UTR (100%); | 2 | 3573882; 3573883 |
| Block_2435 | 0.025443 | chr15: 37217501 . . . 37225462; − | 1 | MEIS2; | INTRONIC (100%); | 2 | 3618372; 3618379 |
| Block_2648 | 0.025774 | chr15: 86212981 . . . 86228071; + | 1 | AKAP13; | CODING (100%); | 3 | 3606399; 3606405; 3606409 |
| Block_3540 | 0.025774 | chr19: 51410040 . . . 51412584; − | 1 | KLK4; | CODING (85.71%); UTR (14.28%); | 7 | 3868736; 3868737; 3868738; 3868740; 3868741; 3868743; 3868745 |
| Block_3894 | 0.025774 | chr2: 166737190 . . . 166758405; − | 1 | TTC21B; | CODING (100%); | 4 | 2585261; 2585265; 2585273; 2585274 |
| Block_4572 | 0.025774 | chr21: 42648718 . . . 42652968; + | 0 | | INTERGENIC (100%); | 2 | 3921988; 3921989 |
| Block_1981 | 0.026108 | chr13: 24348459 . . . 24352051; − | 1 | MIPEP; | INTRONIC (100%); | 3 | 3505475; 3505477; 3505478 |
| Block_2146 | 0.026108 | chr13: 99099031 . . . 99100596; + | 1 | FARP1; | CODING (50%); UTR (50%); | 2 | 3498038; 3498041 |
| Block_5418 | 0.026108 | chr4: 170137651 . . . 170167646; − | 1 | SH3RF1; | INTRONIC (100%); | 2 | 2793179; 2793181 |
| Block_1963 | 0.026447 | chr12: 121132919 . . . 121134161; + | 1 | MLEC; | CODING (100%); | 2 | 3434539; 3434541 |
| Block_6398 | 0.026447 | chr6: 57270903 . . . 57311752; + | 1 | PRIM2; | ncTRANSCRIPT (14.28%); INTRONIC (85.71%); | 7 | 2911447; 2911470; 2911448; 2911473; 2911475; 2911451; 2911452 |
| Block_1159 | 0.026789 | chr10: 125726574 . . . 125726620; + | 0 | | INTERGENIC (100%); | 2 | 3311091; 4038113 |
| Block_182 | 0.026789 | chr1: 59246516 . . . 59249254; − | 1 | JUN; | CODING (33.33%); UTR (66.66%); | 9 | 2415086; 2415088; 2415090; 2415091; 2415093; 2415094; 2415096; 2415098; 2415099 |
| Block_2594 | 0.026789 | chr15: 57745886 . . . 57754067; + | 1 | CGNL1; | CODING (100%); | 2 | 3595336; 3595342 |
| Block_2880 | 0.026789 | chr16: 56667710 . . . 56678081; + | 4 | MT1JP; MT1DP; | ncTRANSCRIPT (20%); | 5 | 3662156; 3662163; 3662122; 3662124; |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| | | | | MT1M; MT1A; TRPM4; | CODING (80%); | | 3662175 |
| Block_3661 | 0.026789 | chr19: 49699887 . . . 49703683; + | 1 | | CODING (100%); | 2 | 3838347; 3838348 |
| Block_5184 | 0.026789 | chr3: 174951778 . . . 174974294; + | 1 | NAALADL2; | CODING (100%); | 3 | 2653162; 2653163; 2653164 |
| Block_241 | 0.027135 | chr1: 110276731 . . . 110279596; − | 1 | GSTM3; | UTR (100%); | 2 | 2427209; 2427213 |
| Block_2441 | 0.027135 | chr15: 42437997 . . . 42439930; − | 1 | PLA2G4F; | CODING (100%); | 3 | 3620436; 3620439; 3620441 |
| Block_3238 | 0.027135 | chr17: 44828869 . . . 44832729; + | 1 | NSF; | CODING (100%); | 2 | 3724262; 3724264 |
| Block_6472 | 0.027135 | chr6: 144904413 . . . 144904734; + | 1 | UTRN; | CODING (50%); UTR (50%); | 2 | 2929285; 2929286 |
| Block_6883 | 0.027135 | chr8: 26611808 . . . 26614843; − | 1 | ADRA1A; | CODING (50%); INTRONIC (50%); | 2 | 3128825; 3128829 |
| Block_7532 | 0.027135 | chrX: 1505179 . . . 1505423; − | 1 | SLC25A6; | UTR (100%); | 2 | 3997377; 4033178 |
| Block_1298 | 0.027485 | chr11: 72468829 . . . 72470411; − | 1 | STARD10; | CODING (100%); | 2 | 3381326; 3381331 |
| Block_3532 | 0.027839 | chr19: 46280628 . . . 46281019; − | 1 | DMPK; | CODING (100%); | 2 | 3865653; 3865654 |
| Block_6942 | 0.027839 | chr8: 72211297 . . . 72246402; − | 1 | EYA1; | CODING (100%); | 6 | 3140094; 3140095; 3140101; 3140103; 3140106; 3140109 |
| Block_7269 | 0.027839 | chr9: 114151836 . . . 114170935; − | 1 | KIAA0368; | CODING (100%); | 4 | 3220569; 3220571; 3220577; 3220589 |
| Block_751 | 0.027839 | chr1: 207497909 . . . 207504583; + | 1 | CD55; | CODING (100%); | 3 | 2377239; 2377242; 2377245 |
| Block_1050 | 0.028197 | chr10: 60559972 . . . 60573731; + | 1 | BICC1; | CODING (100%); | 2 | 3247880; 3247887 |
| Block_7720 | 0.028197 | chrX: 18597972 . . . 18606218; + | 1 | CDKL5; | CODING (100%); | 2 | 3970672; 3970676 |
| Block_7402 | 0.028925 | chr9: 71080046 . . . 71114251; + | 1 | PGM5; | CODING (100%); | 4 | 3173537; 3173540; 3173541; 3173543 |
| Block_1619 | 0.029294 | chr12: 16703175 . . . 16713472; − | 1 | LMO3; | CODING (66.66%); UTR (33.33%); | 3 | 3446141; 3446142; 3446145 |
| Block_4177 | 0.029294 | chr2: 160082200 . . . 160087326; + | 1 | TANC1; | CODING (100%); | 2 | 2512182; 2512191 |
| Block_4425 | 0.029294 | chr20: 21312923 . . . 21329067; + | 1 | XRN2; | CODING (100%); | 4 | 3879487; 3879492; 3879498; 3879506 |
| Block_7830 | 0.029294 | chrX: 135289915 . . . 135291372; + | 1 | FHL1; | INTRONIC (100%); | 2 | 3992437; 3992441 |
| Block_1575 | 0.029668 | chr11: 134130954 . . . 134131239; + | 1 | ACAD8; | CODING (100%); | 2 | 3357326; 3357327 |
| Block_2381 | 0.030046 | chr14: 88553185 . . . 88560834; + | 0 | | INTERGENIC (100%); | 2 | 3547415; 3547424 |
| Block_5332 | 0.030046 | chr4: 89199385 . . . 89199620; − | 1 | PPM1K; | CODING (100%); | 2 | 2777363; 2777364; |
| Block_6163 | 0.030046 | chr6: 55618961 . . . 55620476; − | 1 | BMP5; | CODING (50%); UTR (50%); | 2 | 2958174; 2958176 |
| Block_6705 | 0.030046 | chr7: 23286477 . . . 23314622; + | 1 | GPNMB; | CODING (90%); UTR (10%); | 10 | 2992816; 2992825; 2992827; 2992831; 2992832; 2992840; 2992842; 2992845; 2992847; 2992848 |
| Block_6774 | 0.030046 | chr7: 99159637 . . . 99167388; + | 1 | ZNF655; | CODING (20%); ncTRANSCRIPT (20%); UTR (20%); INTRONIC (40%); | 5 | 3014911; 3014912; 3014913; 3014917; 3014954 |
| Block_7531 | 0.030046 | chrX: 1505060 . . . 1505127; − | 1 | SLC25A6; | UTR (100%); | 2 | 3997376; 4033177 |
| Block_1730 | 0.030428 | chr12: 102153818 . . . 102164296; − | 1 | GNPTAB; | CODING (100%); | 9 | 3468120; 3468121; 3468122; 3468123; 3468126; 3468131; 3468134; 3468135; 3468136 |
| Block_4021 | 0.030428 | chr2: 11680067 . . . 11782662; + | 1 | GREB1; | CODING (87.87%); UTR (12.12%); | 33 | 2469828; 2469836; 2469837; 2469841; 2469849; 2469857; 2469861; 2469865; |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| | | | | | | | 2469866; 2469867; 2469868; 2469869; 2469870; 2469874; 2469876; 2469877; 2469880; 2469881; 2469882; 2469884; 2469887; 2469889; 2469891; 2469892; 2469893; 2469894; 2469896; 2469897; 2469898; 2469899; 2469900; 2469901; 2469902 |
| Block_4231 | 0.030428 | chr2: 198948634 ... 198950883; + | 1 | PLCL1; | CODING (100%); | 2 | 2521607; 2521608 |
| Block_265 | 0.030814 | chr1: 144892521 ... 144892549; − | 1 | PDE4DIP; | CODING (100%); | 2 | 2431960; 4042079 |
| Block_6777 | 0.030814 | chr7: 99169519 ... 99170579; + | 1 | ZNF655; | CODING (50%); INTRONIC (50%); | 2 | 3014924; 3014928 |
| Block_2757 | 0.031205 | chr16: 55844435 ... 55855323; − | 1 | CES1; | CODING (100%); | 6 | 3692709; 3661846; 3692711; 3661834; 3661831; 3692722 |
| Block_4573 | 0.031205 | chr21: 42694866 ... 42729633; + | 1 | FAM3B; | CODING (87.5%); UTR (12.5%); | 8 | 3922003; 3922012; 3922017; 3922023; 3922027; 3922028; 3922031; 3922032 |
| Block_6941 | 0.031205 | chr8: 72156865 ... 72182058; − | 1 | EYA1; | CODING (100%); | 2 | 3140079; 3140083 |
| Block_3246 | 0.0316 | chr17: 45755412 ... 45755765; + | 1 | KPNB1; | CODING (100%); | 2 | 3724811; 3724812 |
| Block_5372 | 0.0316 | chr4: 138451013 ... 138453177; − | 1 | PCDH18; | CODING (100%); | 4 | 4047508; 2786238; 2786239; 4047511 |
| Block_710 | 0.0316 | chr1: 183077411 ... 183087270; + | 1 | LAMC1; | CODING (100%); | 3 | 2371094; 2371103; 2371108 |
| Block_1362 | 0.031998 | chr11: 122929505 ... 122930647; − | 1 | HSPA8; | CODING (100%); | 4 | 3395428; 3395433; 3395438; 3395439 |
| Block_139 | 0.031998 | chr1: 38041207 ... 38042091; − | 1 | GNL2; | CODING (100%); | 2 | 2407202; 2407204 |
| Block_242 | 0.031998 | chr1: 110280148 ... 110280790; − | 1 | GSTM3; | CODING (100%); | 2 | 2427219; 2427222 |
| Block_2615 | 0.031998 | chr15: 69855990 ... 69863685; + | 1 | AC100826.1; | ncTRANSCRIPT (80%); INTRONIC (20%); | 5 | 3599886; 3599887; 3599888; 3599890; 3599891 |
| Block_6882 | 0.031998 | chr8: 23540117 ... 23540330; − | 1 | NKX3-1; | CODING (100%); | 3 | 3127991; 3127992; 3127994 |
| Block_1049 | 0.032402 | chr10: 60553245 ... 60556259; + | 1 | BICC1; | CODING (100%); | 2 | 3247875; 3247877 |
| Block_2731 | 0.032402 | chr16: 28109882 ... 28137158; − | 1 | XPO6; | CODING (100%); | 8 | 3686341; 3686343; 3686347; 3686348; 3686349; 3686353; 3686356; 3686361 |
| Block_7314 | 0.032402 | chr9: 136230241 ... 136230349; − | 1 | SURF4; | CODING (100%); | 2 | 3228678; 4051970 |
| Block_3435 | 0.032809 | chr18: 56054957 ... 56057598; + | 1 | NEDD4L; | INTRONIC (100%); | 7 | 3790090; 3790091; 3790092; 3790094; 3790095; 3790097; 3790098 |
| Block_4064 | 0.032809 | chr2: 39931241 ... 39931334; + | 1 | TMEM178; | CODING (100%); | 2 | 2478287; 2478288 |
| Block_4333 | 0.032809 | chr20: 6090960 ... 6096685; − | 1 | FERMT1; | CODING (100%); | 2 | 3896652; 3896654 |
| Block_1256 | 0.033221 | chr11: 62303454 ... 62304039; − | 1 | AHNAK; | CODING (50%); UTR (50%); | 2 | 3375784; 3375785 |
| Block_5294 | 0.033221 | chr4: 76846890 ... 76861308; − | 1 | NAAA; | CODING (100%); | 2 | 2773891; 2773897 |
| Block_6360 | 0.033638 | chr6: 32868955 ... 32870947; + | 1 | AL669918.1; | ncTRANSCRIPT (100%); | 2 | 2903325; 2903327 |
| Block_6542 | 0.033638 | chr7: 6210524 ... 6210945; − | 1 | CYTH3; | CODING (100%); | 2 | 3037270; 3037272 |
| Block_1389 | 0.034059 | chr11: 4788501 ... 5009539; + | 6 | OR51F2; OR51A8P; OR51H2P; | CODING (46.15%); ncTRANSCRIPT | 13 | 3318193; 3318195; 3318240; 3318241; 3318242; 3318200; |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| | | | | OR51T1; MMP26; OR51N1P; | (38.46%); UTR (7.69%); INTRONIC (7.69%); | | 3318205; 3318206; 3318210; 3318211; 3318246; 3318247; 3318215 |
| Block_876 | 0.034059 | chr10: 43881590 . . . 43882061; − | 1 | HNRNPF; | UTR (100%); | 2 | 3286289; 3286290 |
| Block_2883 | 0.034484 | chr16: 56968915 . . . 56970561; + | 1 | HERPUD1; | INTRONIC (100%); | 3 | 3662392; 3662394; 3662396 |
| Block_2971 | 0.034484 | chr17: 17398026 . . . 17399476; − | 1 | RASD1; | CODING (80%); UTR (20%); | 5 | 3747795; 3747796; 3747797; 3747799; 3747801 |
| Block_5102 | 0.034484 | chr3: 105243191 . . . 105266352; + | 1 | ALCAM; | CODING (100%); | 5 | 2634545; 2634550; 2634552; 2634561; 2634562 |
| Block_5301 | 0.034484 | chr4: 80825530 . . . 80828621; − | 1 | ANTXR2; | CODING (16.66%); UTR (83.33%); | 6 | 2774995; 2774996; 2774997; 2774999; 2775000; 2775001 |
| Block_5537 | 0.034484 | chr4: 89588558 . . . 89602441; + | 1 | HERC3; | CODING (100%); | 3 | 2735499; 2735503; 2735510 |
| Block_3902 | 0.035348 | chr2: 168986056 . . . 168997267; − | 1 | STK39; | CODING (100%); | 2 | 2585761; 2585766 |
| Block_1515 | 0.035787 | chr11: 108010817 . . . 108017045; + | 1 | ACAT1; | CODING (100%); | 2 | 3347636; 3347644 |
| Block_158 | 0.035787 | chr1: 51768040 . . . 51768245; − | 1 | TTC39A; | CODING (100%); | 2 | 2412328; 2412330 |
| Block_168 | 0.035787 | chr1: 53363109 . . . 53370744; − | 1 | ECHDC2; | CODING (100%); | 3 | 2413037; 2413040; 2413044 |
| Block_3529 | 0.035787 | chr19: 45016075 . . . 45029277; − | 1 | CEACAM20; | ncTRANSCRIPT (100%); | 8 | 3864953; 3864956; 3864957; 3864959; 3864961; 3864962; 3864964; 3864967 |
| Block_6470 | 0.035787 | chr6: 144835069 . . . 144872213; + | 1 | UTRN; | CODING (100%); | 5 | 2929254; 2929260; 2929262; 2929268; 2929274 |
| Block_7040 | 0.035787 | chr8: 26265556 . . . 26265860; + | 1 | BNIP3L; | CODING (100%); | 2 | 3091030; 3091031 |
| Block_2735 | 0.036231 | chr16: 28493570 . . . 28493624; − | 1 | CLN3; | INTRONIC (100%); | 2 | 3654751; 3654816 |
| Block_6533 | 0.036231 | chr6: 168351907 . . . 168352865; + | 1 | MLLT4; | CODING (100%); | 2 | 2936935; 2936937 |
| Block_881 | 0.036231 | chr10: 46969414 . . . 46969439; − | 1 | SYT15; | CODING (100%); | 2 | 3287392; 4038216 |
| Block_5436 | 0.036679 | chr4: 187516851 . . . 187557363; − | 1 | FAT1; | CODING (100%); | 17 | 2797405; 2797407; 2797408; 2797410; 2797411; 2797414; 2797415; 2797418; 2797423; 2797426; 2797427; 2797430; 2797433; 2797435; 2797437; 2797438; 2797446 |
| Block_5623 | 0.036679 | chr4: 165691596 . . . 165722585; + | 1 | RP11-294O2.2; | ncTRANSCRIPT (100%); | 2 | 2750414; 2750417 |
| Block_3420 | 0.037132 | chr18: 48581190 . . . 48586286; + | 1 | SMAD4; | CODING (100%); | 2 | 3788324; 3788330 |
| Block_3937 | 0.037132 | chr2: 181436457 . . . 181469005; − | 1 | AC009478.1; | ncTRANSCRIPT (50%); INTRONIC (50%); | 2 | 2590308; 2590313 |
| Block_5634 | 0.037132 | chr4: 174109607 . . . 174135233; + | 1 | GALNT7; | INTRONIC (100%); | 2 | 2751944; 2751947 |
| Block_5681 | 0.03759 | chr5: 40760621 . . . 40767760; − | 1 | AC008810.1; | CODING (50%); UTR (50%); | 4 | 2854740; 2854741; 2854743; 2854749 |
| Block_6148 | 0.03759 | chr6: 46669622 . . . 46690628; − | 2 | TDRD6; PLA2G7; | CODING (76.92%); UTR_AS (15.38%); CODING_AS (7.69%); | 13 | 2955823; 2955825; 2955826; 2955830; 2955835; 2955836; 2955837; 2955838; 2955839; 2955840; 2955841; 2955842; 2955844 |
| Block_6211 | 0.03759 | chr6: 99853979 . . . 99857124; − | 1 | SFRS18; | CODING (100%); | 2 | 2966275; 2966279 |
| Block_1312 | 0.038053 | chr11: 85445044 . . . 85469138; − | 1 | SYTL2; | CODING (83.33%); UTR (16.66%); | 6 | 3385111; 3385113; 3385114; 3385117; 3385121; 3385123 |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| Block_2926 | 0.038053 | chr16: 84495374 ... 84497337; + | 1 | ATP2C2; | CODING (100%); | 2 | 3671793; 3671798 |
| Block_4520 | 0.038053 | chr21: 39752360 ... 39852761; − | 1 | ERG; | ncTRANSCRIPT (4.61%); CODING (20%); UTR (13.84%); INTRONIC (61.53%); | 65 | 3931784; 3931785; 3931786; 3931787; 3931788; 3931789; 3931790; 3931791; 3931792; 3931793; 3931794; 3931796; 3931798; 3931799; 3931800; 3931801; 3931802; 3931803; 3931804; 3931806; 3931807; 3931808; 3931809; 3931810; 3931811; 3931813; 3931814; 3931815; 3931816; 3931817; 3931818; 3931819; 3931820; 3931821; 3931822; 3931824; 3931827; 3931828; 3931829; 3931830; 3931831; 3931832; 3931833; 3931835; 3931836; 3931837; 3931838; 3931840; 3931841; 3931843; 3931844; 3931845; 3931846; 3931848; 3931849; 3931851; 3931852; 3931853; 3931854; 3931856; 3931857; 3931858; 3931859; 3931861; 3931862 |
| Block_6855 | 0.038053 | chr7: 155093280 ... 155100014; + | 1 | INSIG1; | CODING (100%); | 4 | 3033244; 3033247; 3033249; 3033256 |
| Block_7161 | 0.038053 | chr9: 3223306 ... 3228889; − | 1 | RFX3; | CODING (50%); UTR (50%); | 2 | 3196843; 3196849 |
| Block_2625 | 0.03852 | chr15: 73028188 ... 73029911; + | 1 | BBS4; | CODING (100%); | 3 | 3600996; 3600997; 3600999 |
| Block_7163 | 0.03852 | chr9: 3277354 ... 3301613; − | 1 | RFX3; | CODING (100%); | 4 | 3196877; 3196878; 3196879; 3196881 |
| Block_34 | 0.038993 | chr1: 2336552 ... 2337237; − | 1 | PEX10; | CODING (50%); UTR (50%); | 2 | 2392426; 2392427 |
| Block_4718 | 0.038993 | chr22: 48031017 ... 48082931; + | 1 | RP11-191L9.4; | ncTRANSCRIPT (100%); | 3 | 3949433; 3949438; 3949440 |
| Block_6477 | 0.038993 | chr6: 145142024 ... 145157563; + | 1 | UTRN; | CODING (100%); | 3 | 2929340; 2929344; 2929351 |
| Block_3502 | 0.03947 | chr19: 13050901 ... 13051160; − | 1 | CALR; | CODING_AS (100%); | 2 | 3851902; 3851903 |
| Block_5414 | 0.03947 | chr4: 169919358 ... 169928001; − | 1 | CBR4; | CODING (33.33%); INTRONIC (66.66%); | 3 | 2793091; 2793093; 2793098 |
| Block_7223 | 0.03947 | chr9: 93983092 ... 93983273; − | 1 | AUH; | CODING (100%); | 2 | 3214385; 3214386 |
| Block_2127 | 0.039952 | chr13: 76374862 ... 76378658; + | 1 | LMO7; | CODING (100%); | 2 | 3494192; 3494194 |
| Block_3580 | 0.039952 | chr19: 11210844 ... 11213743; + | 1 | LDLR; | INTRONIC (100%); | 2 | 3821020; 3821024 |
| Block_4531 | 0.039952 | chr21: 42839814 ... 42841274; − | 1 | TMPRSS2; | ncTRANSCRIPT (66.66%); INTRONIC (33.33%); | 3 | 3933046; 3933048; 3933049 |
| Block_5329 | 0.039952 | chr4: 88261689 ... 88293951; − | 1 | HSD17B11; | CODING (100%); | 2 | 2777078; 2777086 |
| Block_5367 | 0.039952 | chr4: 122590800 ... 122592788; − | 1 | ANXA5; | CODING (100%); | 2 | 2784046; 2784049 |
| Block_1456 | 0.040439 | chr11: 58385590 ... 58387157; + | 1 | ZFP91; | UTR (100%); | 2 | 3331770; 3331771 |
| Block_376 | 0.040439 | chr1: 216824320 ... 216850671; − | 1 | ESRRG; | CODING (100%); | 2 | 2455970; 2455975 |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| Block_7353 | 0.040439 | chr9: 140356003 . . . 140357262; − | 1 | PNPLA7; | CODING (100%); | 6 | 3231020; 4051802; 3231024; 4051804; 3231029; 4051807 |
| Block_1476 | 0.040932 | chr11: 65273777 . . . 65273907; + | 1 | MALAT1; | ncTRANSCRIPT (100%); | 2 | 3335195; 3335196 |
| Block_5017 | 0.040932 | chr3: 19389238 . . . 19498406; + | 1 | KCNH8; | CODING (100%); | 6 | 2613328; 2613336; 2613337; 2613340; 2613342; 2613344 |
| Block_6874 | 0.040932 | chr8: 19325762 . . . 19339547; − | 1 | CSGALNACT1; | INTRONIC (100%); | 4 | 3126537; 3126539; 3126540; 3126543 |
| Block_258 | 0.041429 | chr1: 120295908 . . . 120307209; − | 1 | HMGCS2; | CODING (100%); | 9 | 2431038; 2431042; 2431044; 2431047; 2431050; 2431051; 2431056; 2431057; 2431058 |
| Block_3899 | 0.041429 | chr2: 168825060 . . . 168864496; − | 1 | STK39; | INTRONIC (100%); | 2 | 2585709; 2585717 |
| Block_4051 | 0.041429 | chr2: 30748528 . . . 30785140; + | 1 | LCLAT1; | CODING (100%); | 2 | 2475742; 2475748 |
| Block_5419 | 0.041429 | chr4: 170190133 . . . 170190434; − | 1 | SH3RF1; | CODING (50%); UTR (50%); | 2 | 2793189; 2793190 |
| Block_6180 | 0.041429 | chr6: 75822940 . . . 75902036; − | 1 | COL12A1; | CODING (100%); | 40 | 2961207; 2961209; 2961210; 2961211; 2961218; 2961222; 2961224; 2961225; 2961227; 2961229; 2961230; 2961231; 2961232; 2961233; 2961234; 2961237; 2961239; 2961240; 2961242; 2961244; 2961247; 2961248; 2961251; 2961252; 2961253; 2961254; 2961256; 2961257; 2961258; 2961259; 2961260; 2961261; 2961263; 2961264; 2961266; 2961267; 2961268; 2961270; 2961271; 2961273 |
| Block_7008 | 0.041429 | chr8: 144698291 . . . 144698872; − | 1 | TSTA3; | CODING (100%); | 2 | 3157677; 3157679 |
| Block_5786 | 0.041931 | chr5: 140907177 . . . 140908450; − | 1 | DIAPH1; | CODING (100%); | 3 | 2878674; 2878677; 2878678 |
| Block_7480 | 0.041931 | chr9: 133339512 . . . 133342185; + | 1 | ASS1; | CODING (100%); | 2 | 3191541; 3191544 |
| Block_1345 | 0.042439 | chr11: 117708078 . . . 117708992; − | 1 | FXYD6; | CODING (50%); UTR (50%); | 2 | 3393486; 3393487 |
| Block_4268 | 0.042439 | chr2: 219204527 . . . 219208304; + | 1 | PNKD; | CODING (100%); | 2 | 2527695; 2527701 |
| Block_6945 | 0.042439 | chr8: 74705646 . . . 74722855; − | 1 | UBE2W; | CODING (33.33%); UTR (66.66%); | 3 | 3140775; 3140777; 3140784 |
| Block_7232 | 0.042439 | chr9: 95043034 . . . 95050521; − | 1 | IARS; | CODING (100%); | 4 | 3214728; 3214733; 3214735; 3214738 |
| Block_7440 | 0.042439 | chr9: 100823070 . . . 100840627; + | 1 | NANS; | CODING (100%); | 3 | 3181467; 3181476; 3181477 |
| Block_2098 | 0.042952 | chr13: 32749690 . . . 32759246; + | 1 | FRY; | CODING (100%); | 2 | 3484547; 3484554 |
| Block_3188 | 0.042952 | chr17: 28770823 . . . 28794571; + | 1 | CPD; | CODING (61.53%); UTR (38.46%); | 13 | 3716448; 3716452; 3716456; 3716462; 3716464; 3716465; 3716467; 3716468; 3716469; 3716470; 3716471; 3716472; 3716473 |
| Block_3884 | 0.042952 | chr2: 162849805 . . . 162851512; − | 1 | DPP4; | CODING (100%); | 2 | 2584026; 2584027 |
| Block_4710 | 0.042952 | chr22: 45914565 . . . 45921519; + | 1 | FBLN1; | CODING (100%); | 2 | 3948657; 3948663 |
| Block_5278 | 0.042952 | chr4: 52890189 . . . 52896012; − | 1 | SGCB; | CODING (100%); | 2 | 2768987; 2768991 |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| Block_5417 | 0.042952 | chr4: 170057497 . . . 170077777; − | 1 | SH3RF1; | CODING (100%); | 3 | 2793167; 2793171; 2793172 |
| Block_5452 | 0.042952 | chr4: 15780104 . . . 15826604; + | 1 | CD38; | CODING (100%); | 4 | 2719662; 2719664; 2719672; 2719679 |
| Block_6207 | 0.042952 | chr6: 94120488 . . . 94124485; − | 1 | EPHA7; | CODING (100%); | 2 | 2965246; 2965247 |
| Block_1773 | 0.043469 | chr12: 118588359 . . . 118588947; − | 1 | TAOK3; | CODING (66.66%); UTR (33.33%); | 3 | 3473806; 3473807; 3473808 |
| Block_298 | 0.043469 | chr1: 154557366 . . . 154558321; − | 1 | ADAR; | CODING (100%); | 2 | 2436758; 2436762 |
| Block_4455 | 0.043469 | chr20: 37174997 . . . 37199484; + | 1 | RALGAPB; | CODING (100%); | 5 | 3884695; 3884701; 3884707; 3884708; 3884716 |
| Block_5162 | 0.043469 | chr3: 153973294 . . . 153975253; + | 1 | ARHGEF26; | CODING (50%); UTR (50%); | 2 | 2648576; 2648579 |
| Block_5625 | 0.043469 | chr4: 166301254 . . . 166375499; + | 1 | CPE; | CODING (6.25%); UTR (12.5%); INTRONIC (81.25%); | 16 | 2750634; 2750635; 2750636; 2750638; 2750639; 2750640; 2750642; 2750643; 2750680; 2750646; 2750647; 2750649; 2750650; 2750653; 2750655; 2750659 |
| Block_6152 | 0.043469 | chr6: 47199596 . . . 47199895; − | 1 | TNFRSF21; | UTR (100%); | 2 | 2956054; 2956055 |
| Block_7360 | 0.043469 | chr9: 140403604 . . . 140404196; − | 1 | PNPLA7; | CODING (50%); INTRONIC (50%); | 2 | 3231080; 3231081 |
| Block_3670 | 0.043993 | chr19: 51380028 . . . 51380127; + | 1 | KLK2; | INTRONIC (100%); | 2 | 3839576; 3839577 |
| Block_4440 | 0.043993 | chr20: 32232190 . . . 32236720; + | 1 | CBFA2T2; | CODING (33.33%); UTR (66.66%); | 3 | 3882597; 3882598; 3882603 |
| Block_6431 | 0.043993 | chr6: 106967344 . . . 106975345; + | 1 | AIM1; | CODING (100%); | 5 | 2919813; 2919814; 2919815; 2919816; 2919820 |
| Block_7138 | 0.043993 | chr8: 120255695 . . . 120257606; + | 1 | MAL2; | ncTRANSCRIPT (100%) | 3 | 3113192; 3113193; 3113194 |
| Block_7231 | 0.043993 | chr9: 95013006 . . . 95033327; − | 1 | IARS; | CODING (100%); | 7 | 3214701; 3214708; 3214713; 3214714; 3214716; 3214719; 3214721 |
| Block_7316 | 0.043993 | chr9: 136231716 . . . 136231744; − | 1 | SURF4; | CODING (100%); | 2 | 3228682; 4051974 |
| Block_374 | 0.044521 | chr1: 207102212 . . . 207112808; − | 1 | PIGR; | CODING (90.90%); UTR (9.09%); | 11 | 2453007; 2453010; 2453011; 2453012; 2453013; 2453015; 2453016; 2453018; 2453019; 2453020; 2453021 |
| Block_4771 | 0.044521 | chr3: 49062361 . . . 49062661; − | 1 | IMPDH2; | CODING (100%); | 2 | 2673881; 2673882 |
| Block_6871 | 0.044521 | chr8: 19261989 . . . 19277968; − | 1 | CSGALNACT1; | CODING (80%); UTR (20%); | 5 | 3126508; 3126509; 3126514; 3126520; 3126522 |
| Block_3592 | 0.045055 | chr19: 13264023 . . . 13264647; + | 1 | IER2; | CODING (100%); | 2 | 3822220; 3822222 |
| Block_5515 | 0.045055 | chr4: 79475596 . . . 79503433; + | 1 | ANXA3; | CODING (50%); UTR (50%); | 2 | 2732851; 2732860 |
| Block_6620 | 0.045055 | chr7: 99267347 . . . 99272139; − | 1 | CYP3A5; | ncTRANSCRIPT (66.66%); INTRONIC (33.33%); | 3 | 3063437; 3063444; 3063447 |
| Block_1688 | 0.045594 | chr12: 57648708 . . . 57650291; − | 1 | R3HDM2; | CODING (100%); | 2 | 3458457; 3458461 |
| Block_2958 | 0.045594 | chr17: 4175402 . . . 4186127; − | 1 | UBE2G1; | UTR (100%); | 2 | 3742072; 3742078 |
| Block_698 | 0.045594 | chr1: 178408557 . . . 178421750; + | 1 | RASAL2; | CODING (100%); | 4 | 2369197; 2369198; 2369199; 2369205 |
| Block_7807 | 0.045594 | chrX: 107923910 . . . 107923944; + | 1 | COL4A5; | CODING (100%); | 2 | 3986840; 4055605 |
| Block_2251 | 0.046139 | chr14: 76424744 . . . 76448197; − | 1 | TGFB3; | INTERGENIC (9.09%); CODING | 11 | 3572518; 3572524; 3572528; 3572529; 3572533; 3572534; |

TABLE 22-continued

| ICE Block ID | Wilcoxon P-value | Chromosomal Coordinates | # of Genes | Overlapping Genes | Category (Composition %) | PSRs | Probe Set ID(s) |
|---|---|---|---|---|---|---|---|
| | | | | | (45.45%); UTR (45.45%); | | 3572539; 3572540; 3572541; 3572542; 3572543 |
| Block_3274 | 0.046139 | chr17: 59479110 . . . 59480539; + | 1 | TBX2; | CODING (100%); | 2 | 3729850; 3729852 |
| Block_412 | 0.046139 | chr1: 235643382 . . . 235658086; − | 1 | B3GALNT2; | CODING (100%); | 3 | 2461913; 2461914; 2461921 |
| Block_2884 | 0.046689 | chr16: 56969154 . . . 56977753; + | 1 | HERPUD1; | CODING (80%); UTR (20%); | 10 | 3662393; 3662395; 3662397; 3662401; 3662402; 3662403; 3662407; 3662408; 3662411; 3662412 |
| Block_3707 | 0.046689 | chr2: 10580851 . . . 10585351; − | 1 | ODC1; | CODING (91.66%); UTR (8.33%); | 12 | 2540164; 2540166; 2540167; 2540169; 2540171; 2540172; 2540173; 2540174; 2540175; 2540176; 2540178; 2540180 |
| Block_6266 | 0.046689 | chr6: 136990497 . . . 137041697; − | 1 | MAP3K5; | CODING (100%); | 6 | 2975930; 2975936; 2975938; 2975939; 2975940; 2975946 |
| Block_947 | 0.046689 | chr10: 95185842 . . . 95191270; − | 1 | MYOF; | CODING (100%); | 2 | 3300707; 3300708 |
| Block_2092 | 0.047245 | chr13: 26434339 . . . 26436545; + | 1 | ATP8A2; | CODING (100%); | 2 | 3482385; 3482388 |
| Block_6585 | 0.047245 | chr7: 51095830 . . . 51098577; − | 1 | COBL; | CODING (100%); | 3 | 3050639; 3050644; 3050648 |
| Block_7357 | 0.047245 | chr9: 140358830 . . . 140358908; − | 1 | PNPLA7; | CODING (100%); | 2 | 3231037; 4051814 |
| Block_1824 | 0.047806 | chr12: 12037385 . . . 12047640; + | 1 | ETV6; | CODING (100%); | 3 | 3405156; 3405162; 3405164 |
| Block_439 | 0.047806 | chr1: 11888539 . . . 11889339; + | 1 | CLCN6; | CODING (100%); | 3 | 2320500; 2320501; 2320502 |
| Block_6029 | 0.047806 | chr5: 148804031 . . . 148811072; + | 1 | RP11-394O4.2; | INTERGENIC (50%); ncTRANSCRIPT (50%); | 8 | 2835105; 2835106; 2835107; 2835108; 2835111; 2835120; 2835124; 2835127 |
| Block_6466 | 0.047806 | chr6: 144724259 . . . 144768883; + | 1 | UTRN; | CODING (100%); | 8 | 2929201; 2929208; 2929210; 2929214; 2929215; 2929216; 2929223; 2929227 |
| Block_1059 | 0.048945 | chr10: 70728765 . . . 70741336; + | 1 | DDX21; | CODING (100%); | 5 | 3250074; 3250076; 3250079; 3250084; 3250086 |
| Block_7268 | 0.048945 | chr9: 114128562 . . . 114137482; − | 1 | KIAA0368; | CODING (100%); | 4 | 3220517; 3220518; 3220524; 3220527 |
| Block_7643 | 0.048945 | chrX: 114345684 . . . 114357459; − | 1 | LRCH2; | CODING (50%); UTR (50%); | 2 | 4018756; 4018762 |
| Block_2984 | 0.049523 | chr17: 26966940 . . . 26969094; − | 1 | KIAA0100; | CODING (100%); | 3 | 3750919; 3750921; 3750923 |

TABLE 23

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| Block_6592 | 0.000072 | chr7: 37946647 . . . 37956059; − | 1 | SFRP4; | CODING (66.66%); UTR (33.33%); | 9 | 3046448; 3046449; 3046450; 3046457; 3046459; 3046460; 3046461; 3046462; 3046465; |
| Block_4226 | 0.000089 | chr2: 189863400 . . . 189867071; + | 1 | COL3A1; | CODING (100%); | 2 | 2519614; 2519620; |
| Block_4627 | 0.000116 | chr22: 29191774 . . . 29195014; − | 1 | XBP1; | ncTRANSCRIPT (33.33%); INTRONIC (66.66%); | 3 | 3956596; 3956601; 3956603; |
| Block_6930 | 0.000183 | chr8: 48649878 . . . 48650049; − | 1 | CEBPD; | CODING (100%); | 2 | 3134023; 3134024; |
| Block_7113 | 0.00028 | chr8: 75737169 . . . 75767196; + | 1 | PI15; | CODING (43.75%); UTR | 16 | 3103704; 3103705; 3103706; 3103707; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| | | | | | (43.75%); INTRONIC (12.5%); | | 3103708; 3103710; 3103712; 3103713; 3103714; 3103715; 3103717; 3103718; 3103720; 3103721; 3103725; 3103726; |
| Block_5470 | 0.000286 | chr4: 15839733 . . . 15852471; + | 1 | CD38; | INTERGENIC (20%); CODING (60%); UTR (20%); | 5 | 2719689; 2719692; 2719694; 2719695; 2719696; |
| Block_5155 | 0.000299 | chr3: 132043108 . . . 132068493; + | 1 | ACPP; | ncTRANSCRIPT (15.38%); INTRONIC (84.61%); | 13 | 2642733; 2642735; 2642738; 2642739; 2642740; 2642741; 2642744; 2642745; 2642746; 2642747; 2642748; 2642750; 2642753; |
| Block_3531 | 0.000313 | chr19: 39897525 . . . 39899806; − | 1 | ZFP36; | UTR_AS (25%); CODING_AS (75%); | 4 | 3862010; 3862011; 3862006; 3862007; |
| Block_1992 | 0.00032 | chr13: 38158126 . . . 38166301; − | 1 | POSTN; | CODING (100%); | 4 | 3510098; 3510100; 3510101; 3510105; |
| Block_4227 | 0.000372 | chr2: 189867682 . . . 189873745; + | 1 | COL3A1; | CODING (100%); | 7 | 2519621; 2519623; 2519628; 2519629; 2519634; 2519637; 2519644; |
| Block_5813 | 0.000424 | chr5: 148880617 . . . 148880811; − | 1 | CTB-89H12.4; | ncTRANSCRIPT (100%); | 2 | 2880917; 2880918; |
| Block_6391 | 0.000433 | chr6: 38840803 . . . 38841129; + | 1 | DNAH8; | CODING (100%); | 2 | 2906020; 2906021; |
| Block_5469 | 0.000452 | chr4: 15780104 . . . 15826604; + | 1 | CD38; | CODING (100%); | 4 | 2719662; 2719664; 2719672; 2719679; |
| Block_1127 | 0.000595 | chr10: 114710550 . . . 114711012; + | 1 | TCF7L2; | CODING (100%); | 2 | 3264623; 3264624; |
| Block_6388 | 0.000634 | chr6: 38783258 . . . 38783411; + | 1 | DNAH8; | CODING (100%); | 2 | 2905985; 2905986; |
| Block_3521 | 0.000718 | chr19: 18893864 . . . 18897074; − | 1 | COMP; | CODING (100%); | 2 | 3855221; 3855230; |
| Block_2375 | 0.000812 | chr14: 88553185 . . . 88560834; + | 0 | | INTERGENIC (100%); | 2 | 3547415; 3547424; |
| Block_6389 | 0.000829 | chr6: 38800098 . . . 38831738; + | 1 | DNAH8; | CODING (100%); | 14 | 2905993; 2905995; 2905996; 2905997; 2905999; 2906000; 2906001; 2906002; 2906003; 2906004; 2906005; 2906006; 2906010; 2906012; |
| Block_2896 | 0.000846 | chr16: 67202953 . . . 67203210; + | 1 | HSF4; | CODING (100%); | 2 | 3665255; 3665257; |
| Block_1579 | 0.000882 | chr12: 3718615 . . . 3753793; − | 1 | EFCAB4B; | CODING (60%); INTRONIC (40%); | 10 | 3440929; 3440999; 3441000; 3440930; 3440936; 3440938; 3440941; 3440942; 3440951; 3440952; |
| Block_3687 | 0.000918 | chr19: 53945049 . . . 53945553; + | 1 | CTD-2224J9.2; | ncTRANSCRIPT (100%); | 2 | 3840864; 3840869; |
| Block_3688 | 0.000957 | chr19: 53957950 . . . 53961428; + | 1 | ZNF761; | ncTRANSCRIPT (100%); | 6 | 3840917; 3840921; 3840923; 3840935; 3840937; 3840939; |
| Block_939 | 0.000996 | chr10: 88820216 . . . 88820346; − | 1 | GLUD1; | ncTRANSCRIPT (100%); | 2 | 3298991; 4038370; |
| Block_4225 | 0.001058 | chr2: 189839219 . . . 189861926; + | 1 | COL3A1; | CODING (100%); | 15 | 2519583; 2519585; 2519586; 2519588; 2519589; 2519590; 2519595; 2519596; 2519598; 2519599; 2519601; 2519602; 2519604; 2519605; 2519610; |
| Block_3653 | 0.001147 | chr19: 41223728 . . . 41231316; + | 1 | ITPKC; | CODING (80%); INTRONIC (20%); | 5 | 3833738; 3833739; 3833740; 3833741; 3833743; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| Block_7267 | 0.001147 | chr9: 99370376 . . . 99375212; − | 1 | CDC14B; | INTRONIC (100%); | 2 | 3216428; 3216429; |
| Block_1991 | 0.00117 | chr13: 38154719 . . . 38164537; − | 1 | POSTN; | CODING (100%); | 3 | 3510096; 3510097; 3510103; |
| Block_3042 | 0.001292 | chr17: 48262881 . . . 48277296; − | 1 | COL1A1; | CODING (100%); | 39 | 3762204; 3762206; 3762207; 3762208; 3762210; 3762211; 3762212; 3762215; 3762216; 3762217; 3762218; 3762220; 3762221; 3762222; 3762223; 3762225; 3762226; 3762227; 3762228; 3762229; 3762234; 3762235; 3762236; 3762238; 3762241; 3762242; 3762243; 3762244; 3762245; 3762246; 3762249; 3762252; 3762253; 3762254; 3762256; 3762257; 3762263; 3762264; 3762268; |
| Block_6371 | 0.001345 | chr6: 31785240 . . . 31797461; + | 2 | HSPA1B; HSPA1A; | CODING (100%); | 2 | 2902713; 2902730; |
| Block_5279 | 0.001372 | chr4: 40592576 . . . 40629213; − | 1 | RBM47; | INTRONIC (100%); | 4 | 2766856; 2766859; 2766860; 2766861; |
| Block_3023 | 0.001455 | chr17: 40538906 . . . 40539322; − | 1 | STAT3; | INTRONIC (100%); | 2 | 3757901; 3757902; |
| Block_4139 | 0.001455 | chr2: 101541626 . . . 101564800; + | 1 | NPAS2; | CODING (100%); | 4 | 2496436; 2496440; 2496446; 2496448; |
| Block_2374 | 0.001605 | chr14: 88550504 . . . 88559014; + | 0 |  | INTERGENIC (100%); | 5 | 3547412; 3547413; 3547419; 3547420; 3547422; |
| Block_3981 | 0.001605 | chr2: 208628777 . . . 208631527; − | 1 | FZD5; | UTR (100%); | 4 | 2596768; 2596769; 2596771; 2596775; |
| Block_7365 | 0.001636 | chr9: 140354426 . . . 140354842; − | 1 | PNPLA7; | UTR (100%); | 2 | 3231011; 4051791; |
| Block_6370 | 0.001701 | chr6: 31795534 . . . 31795716; + | 1 | HSPA1B; | CODING (100%); | 2 | 2902726; 2902727; |
| Block_6484 | 0.001701 | chr6: 144635551 . . . 144635647; + | 1 | UTRN; | INTRONIC (100%); | 2 | 2929396; 2929397; |
| Block_6152 | 0.001947 | chr6: 35545311 . . . 35555083; − | 1 | FKBP5; | INTRONIC (100%); | 2 | 2951580; 2951584; |
| Block_1926 | 0.001985 | chr12: 102011150 . . . 102079590; + | 1 | MYBPC1; | CODING (69.44%); UTR (2.77%); INTRONIC (27.77%); | 36 | 3428611; 3428612; 3428613; 3428617; 3428619; 3428620; 3428623; 3428624; 3428625; 3428626; 3428627; 3428628; 3428629; 3428630; 3428631; 3428634; 3428635; 3428636; 3428637; 3428638; 3428639; 3428640; 3428641; 3428642; 3428643; 3428644; 3428646; 3428647; 3428648; 3428650; 3428651; 3428654; 3428655; 3428659; 3428665; 3428666; |
| Block_4322 | 0.002062 | chr2: 242135147 . . . 242164581; + | 1 | ANO7; | CODING (91.66%); UTR (8.33%); | 24 | 2536222; 2536226; 2536228; 2536229; 2536231; 2536232; 2536233; 2536234; 2536235; 2536236; 2536237; 2536238; 2536240; 2536241; 2536243; 2536245; 2536248; 2536249; 2536252; 2536253; 2536256; 2536260; 2536261; 2536262; |
| Block_3449 | 0.002102 | chr18: 56647020 . . . 56648694; + | 1 | ZNF532; | INTRONIC (100%); | 3 | 3790402; 3790403; 3790404; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| Block_1427 | 0.002268 | chr11: 35166517 . . . 35193320; + | 1 | CD44; | INTRONIC (100%); | 2 | 3326642; 3326650; |
| Block_3648 | 0.002312 | chr19: 39897722 . . . 39899906; + | 1 | ZFP36; | CODING (25%); UTR (12.5%); INTRONIC (62.5%); | 8 | 3832980; 3832981; 3832982; 3832984; 3832985; 3832986; 3832987; 3832988; |
| Block_2832 | 0.002493 | chr16: 19433756 . . . 19439293; + | 1 | TMC5; | INTRONIC (100%); | 2 | 3650948; 3650949; |
| Block_5745 | 0.002493 | chr5: 86688587 . . . 86688721; − | 1 | CCNH; | ncTRANSCRIPT (100%); | 2 | 2865880; 2865881; |
| Block_2304 | 0.002588 | chr14: 38054451 . . . 38055847; + | 0 | | INTERGENIC (100%); | 4 | 3533031; 3533035; 3533037; 3533039; |
| Block_1993 | 0.002637 | chr13: 38158866 . . . 38162106; − | 1 | POSTN; | CODING (100%); | 2 | 3510099; 3510102; |
| Block_6649 | 0.002687 | chr7: 105893270 . . . 105922863; − | 1 | NAMPT; | ncTRANSCRIPT (20%); INTRONIC (80%); | 20 | 3066831; 3066833; 3066836; 3066837; 3066838; 3066839; 3066840; 3066841; 3066843; 3066844; 3066846; 3066847; 3066848; 3066849; 3066850; 3066853; 3066854; 3066859; 3066861; 3066862; |
| Block_2897 | 0.002738 | chr16: 67203603 . . . 67203747; + | 1 | HSF4; | CODING (100%); | 2 | 3665259; 3665260; |
| Block_5232 | 0.002789 | chr3: 186759705 . . . 186769256; + | 1 | ST6GAL1; | ncTRANSCRIPT (66.66%); UTR (33.33%); | 3 | 2656853; 2656859; 2656860; |
| Block_1128 | 0.002895 | chr10: 114723487 . . . 114732026; + | 1 | TCF7L2; | INTRONIC (100%); | 2 | 3264632; 3264636; |
| Block_2631 | 0.002895 | chr15: 78557858 . . . 78567151; + | 1 | DNAJA4; | ncTRANSCRIPT (66.66%); CODING (33.33%); | 3 | 3603257; 3603266; 3603267; |
| Block_3099 | 0.002949 | chr17: 76354002 . . . 76355176; − | 1 | SOCS3; | CODING (25%); UTR (75%); | 4 | 3772289; 3772290; 3772292; 3772293; |
| Block_3597 | 0.003118 | chr19: 12902599 . . . 12904034; + | 1 | JUNB; | CODING (66.66%) UTR (33.33%); | 3 | 3821896; 3821898; 3821899; |
| Block_3448 | 0.003176 | chr18: 56623078 . . . 56646570; + | 1 | ZNF532; | INTRONIC (100%); | 4 | 3790396; 3790398; 3790399; 3790401; |
| Block_1429 | 0.003234 | chr11: 35211649 . . . 35229188; + | 1 | CD44; | ncTRANSCRIPT (40%); INTRONIC (60%); | 15 | 3326671; 3326672; 3326674; 3326676; 3326677; 3326679; 3326680; 3326681; 3326684; 3326692; 3326695; 3326701; 3326703; 3326704; 3326708; |
| Block_2471 | 0.003234 | chr15: 55543544 . . . 55562575; − | 1 | RAB27A; | UTR (50%); INTRONIC (50%); | 2 | 3625289; 3625295; |
| Block_2895 | 0.003294 | chr16: 67199438 . . . 67201057; + | 1 | HSF4; | ncTRANSCRIPT (20%); CODING (80%); | 5 | 3665235; 3665240; 3665244; 3665245; 3665246; |
| Block_1542 | 0.003355 | chr11: 118379852 . . . 118380821; + | 1 | MLL; | CODING (100%); | 2 | 3351445; 3351446; |
| Block_1185 | 0.003481 | chr11: 3800418 . . . 3803305; − | 1 | NUP98; | CODING (100%); | 2 | 3359982; 3359983; |
| Block_3591 | 0.003481 | chr19: 11210844 . . . 11213743; + | 1 | LDLR; | INTRONIC (100%); | 2 | 3821020; 3821024; |
| Block_4284 | 0.003676 | chr2: 219676945 . . . 219679977; + | 1 | CYP27A1; | CODING (85.71%); UTR (14.28%); | 7 | 2528108; 2528110; 2528111; 2528112; 2528113; 2528115; 2528118; |
| Block_834 | 0.003676 | chr1: 247712494 . . . 247739511; + | 1 | C1orf150; | CODING (66.66%); UTR (33.33%); | 3 | 2390125; 2390128; 2390134; |
| Block_1825 | 0.003743 | chr12: 13350040 . . . 13366545; + | 2 | EMP1; AC079628.1; | UTR (50%); INTRONIC (50%); | 6 | 3405757; 3405758; 3405760; 3405766; 3405770; 3405772; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| Block_3512 | 0.003812 | chr19: 15297695 . . . 15302661; − | 1 | NOTCH3; | CODING (100%); | 5 | 3853157; 3853158; 3853159; 3853161; 3853166; |
| Block_4229 | 0.003812 | chr2: 189875001 . . . 189877194; + | 1 | COL3A1; | CODING (60%); UTR (40%); | 5 | 2519649; 2519652; 2519656; 2519657; 2519658; |
| Block_5137 | 0.003812 | chr3: 121603566 . . . 121604258; + | 1 | EAF2; | INTRONIC (100%) | 2 | 2638711; 2638712; |
| Block_5780 | 0.003952 | chr5: 115146858 . . . 115148955; − | 1 | CDO1; | CODING (100%); | 2 | 2871912; 2871914; |
| Block_5954 | 0.003952 | chr5: 82785957 . . . 82786199; + | 1 | VCAN; | CODING (100%); | 2 | 2818532; 2818533; |
| Block_1472 | 0.004024 | chr11: 65273777 . . . 65273907; + | 1 | MALAT1; | ncTRANSCRIPT (100%); | 2 | 3335195; 3335196; |
| Block_5764 | 0.004024 | chr5: 95243613 . . . 95288598; − | 1 | ELL2; | ncTRANSCRIPT (8.33%); INTRONIC (91.66%); | 12 | 2867907; 2867915; 2867916; 2867924; 2867925; 2867926; 2867930; 2867931; 2867932; 2867934; 2867940; 2867941; |
| Block_7742 | 0.004097 | chrX: 23802057 . . . 23803407; + | 1 | SAT1; | ncTRANSCRIPT (40%) CODING (20%); UTR (40%); | 5 | 3971816; 3971817; 3971818; 3971820; 3971821; |
| Block_5765 | 0.004247 | chr5: 95257267 . . . 95259483; − | 1 | ELL2; | INTRONIC (100%); | 4 | 2867919; 2867921; 2867922; 2867923; |
| Block_6642 | 0.004247 | chr7: 99267347 . . . 99272139; − | 1 | CYP3A5; | ncTRANSCRIPT (66.66%); INTRONIC (33.33%); | 3 | 3063437; 3063444; 3063447; |
| Block_4409 | 0.004324 | chr20: 52560335 . . . 52561534; − | 1 | BCAS1; | CODING (50%); UTR (50%); | 2 | 3910362; 3910363; |
| Block_7846 | 0.004324 | chrX: 152770164 . . . 152773851; + | 1 | BGN; | CODING (100%); | 6 | 3995642; 3995651; 3995654; 3995657; 3995659; 3995661; |
| Block_5950 | 0.004402 | chr5: 79361251 . . . 79378964; + | 1 | THBS4; | CODING (100%); | 10 | 2817602; 2817603; 2817605; 2817606; 2817609; 2817611; 2817614; 2817615; 2817620; 2817621; |
| Block_3980 | 0.004482 | chr2: 208627560 . . . 208629500; − | 1 | FZD5; | UTR (100%); | 3 | 2596764; 2596765; 2596772; |
| Block_7065 | 0.004482 | chr8: 27398133 . . . 27402173; + | 1 | EPHX2; | CODING (50%); UTR (50%); | 2 | 3091435; 3091442; |
| Block_2156 | 0.004562 | chr13: 111940732 . . . 111953191; + | 1 | ARHGEF7; | CODING (100%); | 2 | 3501737; 3501744; |
| Block_2613 | 0.004644 | chr15: 71803346 . . . 71808234; + | 1 | THSD4; | INTRONIC (100%); | 2 | 3600358; 3600361; |
| Block_4875 | 0.004644 | chr3: 114412375 . . . 114429160; − | 1 | ZBTB20; | UTR (100%); | 2 | 2689628; 2689631; |
| Block_1342 | 0.004727 | chr11: 116914101 . . . 116935147; − | 1 | SIK3; | INTRONIC (100%); | 4 | 3393111; 3393112; 3393115; 3393116; |
| Block_2614 | 0.004727 | chr15: 71839666 . . . 71889637; + | 1 | THSD4; | CODING (12.5%); UTR (12.5%); INTRONIC (75%); | 8 | 3600365; 3600366; 3600482; 3600486; 3600368; 3600478; 3600371; 3600372; |
| Block_2658 | 0.004727 | chr15: 93482832 . . . 93486203; + | 1 | CHD2; | CODING (100%); | 2 | 3609197; 3609200; |
| Block_3283 | 0.004727 | chr17: 65027167 . . . 65028692; + | 2 | CACNG4; AC005544.1; | CODING (50%); UTR (50%); | 2 | 3732138; 3732139; |
| Block_2002 | 0.004812 | chr13: 45113061 . . . 45146842; − | 1 | TSC22D1; | INTRONIC (100%); | 7 | 3512332; 3512337; 3512338; 3512339; 3512341; 3512342; 3512344; |
| Block_2833 | 0.004812 | chr16: 19441750 . . . 19460940; + | 1 | TMC5; | CODING (60%); UTR (40%); | 5 | 3650950; 3650954; 3650955; 3650957; 3650958; |
| Block_847 | 0.004812 | chr10: 7392799 . . . 7409508; − | 1 | SFMBT2; | INTRONIC (100%); | 3 | 3276296; 3276241; 3276242; |
| Block_1469 | 0.004898 | chr11: 65191129 . . . 65191996; + | 1 | NEAT1; | ncTRANSCRIPT (100%); | 2 | 3335211; 3335215; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| Block_853 | 0.004986 | chr10: 18874889 ... 18903446; − | 1 | NSUN6; | CODING (100%); | 2 | 3280258; 3280265; |
| Block_3682 | 0.005074 | chr19: 51380028 ... 51380127; + | 1 | KLK2; | INTRONIC (100%); | 2 | 3839576; 3839577; |
| Block_3573 | 0.005165 | chr19: 2476367 ... 2477960; + | 1 | GADD45B; | CODING (75%); UTR (25%); | 4 | 3816512; 3816515; 3816519; 3816524; |
| Block_4876 | 0.005165 | chr3: 114435628 ... 114450706; − | 1 | ZBTB20; | INTRONIC (100%); | 2 | 2689633; 2689638; |
| Block_6288 | 0.005165 | chr6: 143251252 ... 143252058; − | 1 | HIVEP2; | INTRONIC (100%); | 2 | 2977329; 2977355; |
| Block_6338 | 0.005165 | chr6: 10556781 ... 10566189; + | 1 | GCNT2; | CODING (50%); INTRONIC (50%); | 2 | 2894601; 2894610; |
| Block_7142 | 0.005256 | chr8: 102506747 ... 102518399; + | 1 | GRHL2; | INTRONIC (100%); | 2 | 3109702; 3109705; |
| Block_1361 | 0.005349 | chr11: 122932160 ... 122932410; − | 1 | HSPA8; | UTR (100%); | 2 | 3395451; 3395452; |
| Block_2612 | 0.00554 | chr15: 71716691 ... 71716939; + | 1 | THSD4; | INTRONIC (100%); | 2 | 3600342; 3600343; |
| Block_6390 | 0.00554 | chr6: 38828265 ... 38834650; + | 1 | DNAH8; | CODING (100%); | 2 | 2906008; 2906016; |
| Block_748 | 0.00554 | chr1: 203275102 ... 203275613; + | 1 | BTG2; | INTRONIC (100%); | 3 | 2375667; 2375668; 2375670; |
| Block_1894 | 0.005638 | chr12: 69019900 ... 69035432; + | 1 | RAP1B; | INTRONIC (100%); | 2 | 3421126; 3421130; |
| Block_3970 | 0.005638 | chr2: 201719352 ... 201719803; − | 1 | CLK1; | CODING (100%); | 2 | 2594506; 2594508; |
| Block_6229 | 0.005737 | chr6: 99860469 ... 99860591; − | 1 | SFRS18; | CODING (100%); | 2 | 2966287; 2966288; |
| Block_2303 | 0.005838 | chr14: 38033662 ... 38058763; + | 0 | | INTERGENIC (100%); | 4 | 3533021; 3533028; 3533041; 3533045; |
| Block_7715 | 0.005838 | chrX: 2619960 ... 2620197; + | 1 | CD99; | INTRONIC (100%); | 2 | 3966874; 4028497; |
| Block_3508 | 0.006044 | chr19: 12902622 ... 12904019; − | 1 | JUNB; | CODING_AS (100%); | 2 | 3851771; 3851773; |
| Block_6785 | 0.006044 | chr7: 94028361 ... 94059882; + | 1 | COL1A2; | CODING (97.56%); UTR (2.43%); | 41 | 3013083; 3013086; 3013095; 3013096; 3013098; 3013102; 3013103; 3013105; 3013106; 3013107; 3013109; 3013110; 3013111; 3013113; 3013114; 3013115; 3013116; 3013118; 3013119; 3013120; 3013124; 3013125; 3013127; 3013128; 3013129; 3013130; 3013135; 3013137; 3013139; 3013141; 3013142; 3013143; 3013146; 3013148; 3013151; 3013155; 3013156; 3013157; 3013158; 3013160; 3013161; |
| Block_1771 | 0.00615 | chr12: 118636857 ... 118639157; − | 1 | TAOK3; | CODING (100%); | 2 | 3473836; 3473838; |
| Block_4997 | 0.00615 | chr3: 187460081 ... 187461297; − | 1 | BCL6; | INTRONIC (100%); | 3 | 2709837; 2709817; 2709839; |
| Block_2787 | 0.006477 | chr16: 72984427 ... 72992414; − | 1 | ZFHX3; | CODING (100%); | 2 | 3698340; 3698347; |
| Block_4873 | 0.006477 | chr3: 114353933 ... 114405567; − | 1 | ZBTB20; | INTRONIC (100%); | 6 | 2689789; 2689794; 2689798; 2689807; 2689809; 2689776; |
| Block_1826 | 0.006589 | chr12: 13364471 ... 13366481; + | 1 | EMP1; | CODING (100%); | 2 | 3405769; 3405771; |
| Block_6318 | 0.006589 | chr6: 160103692 ... 160113602; − | 1 | SOD2; | CODING (20%); UTR (40%); INTRONIC (40%); | 5 | 2982328; 2982330; 2982332; 2982333; 2982335; |
| Block_4898 | 0.006703 | chr3: 120389279 ... 120401114; − | 1 | HGD; | CODING (66.66%); UTR (33.33%); | 6 | 2691446; 4047079; 2691452; 4047076; 2691462; 4047071; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| Block_5788 | 0.006819 | chr5: 131820117 ... 131822522; − | 1 | IRF1; | CODING (100%); | 2 | 2875353; 2875362; |
| Block_5824 | 0.006819 | chr5: 151041302 ... 151054230; − | 1 | SPARC; | CODING (53.84%); UTR (46.15%); | 13 | 2882119; 2882120; 2882121; 2882122; 2882123; 2882125; 2882128; 2882131; 2882133; 2882137; 2882139; 2882142; 2882143; |
| Block_1145 | 0.006937 | chr10: 123779283 ... 123781483; + | 1 | TACC2; | ncTRANSCRIPT (50%); UTR (50%); | 2 | 3268069; 3268071; |
| Block_3689 | 0.007178 | chr19: 53959452 ... 53959887; + | 1 | ZNF761; | ncTRANSCRIPT (100%); | 2 | 3840925; 3840931; |
| Block_4535 | 0.007301 | chr21: 36252858 ... 36260789; − | 1 | RUNX1; | CODING (33.33%); UTR (66.66%); | 3 | 3930427; 3930435; 3930438; |
| Block_5434 | 0.007682 | chr4: 170137651 ... 170167646; − | 1 | SH3RF1; | INTRONIC (100%); | 2 | 2793179; 2793181; |
| Block_4228 | 0.007946 | chr2: 189873814 ... 189875606; + | 1 | COL3A1; | CODING (100%); | 3 | 2519645; 2519648; 2519653; |
| Block_4973 | 0.007946 | chr3: 156865888 ... 156874463; − | 1 | CCNL1; | ncTRANSCRIPT (35.71%); CODING (28.57%); UTR (21.42%); INTRONIC (14.28%); | 14 | 2702330; 2702333; 2702335; 2702342; 2702344; 2702345; 2702346; 2702348; 2702352; 2702355; 2702356; 2702357; 2702358; 2702359; |
| Block_5911 | 0.007946 | chr5: 60648670 ... 60667704; + | 1 | ZSWIM6; | INTRONIC (100%); | 4 | 2811300; 2811301; 2811302; 2811303; |
| Block_2183 | 0.008081 | chr14: 25325143 ... 25326345; − | 1 | STXBP6; | CODING (100%); | 2 | 3558448; 3558449; |
| Block_3447 | 0.008218 | chr18: 56585564 ... 56587447; + | 1 | ZNF532; | CODING (100%); | 3 | 3790379; 3790380; 3790381; |
| Block_5955 | 0.008218 | chr5: 82832827 ... 82876595; + | 1 | VCAN; | CODING (88.88%); UTR (11.11%); | 9 | 2818559; 2818561; 2818568; 2818571; 2818572; 2818573; 2818577; 2818578; 2818582; |
| Block_4412 | 0.008499 | chr20: 52612441 ... 52674693; − | 1 | BCAS1; | CODING (100%); | 3 | 3910385; 3910393; 3910394; |
| Block_4770 | 0.008499 | chr3: 39183443 ... 39186746; − | 1 | CSRNP1; | CODING (75%); UTR (25%); | 4 | 2669932; 2669935; 2669936; 2669937; |
| Block_3590 | 0.008642 | chr19: 11210938 ... 11241992; + | 1 | LDLR; | CODING (100%); | 17 | 3821022; 3821023; 3821026; 3821029; 3821031; 3821034; 3821035; 3821036; 3821037; 3821041; 3821042; 3821044; 3821045; 3821046; 3821048; 3821052; 3821054; |
| Block_6089 | 0.008642 | chr6: 2116070 ... 2117790; − | 1 | GMDS; | CODING (100%); | 2 | 2938767; 2938771; |
| Block_7272 | 0.008936 | chr9: 110248037 ... 110250537; − | 1 | KLF4; | CODING (100%); | 4 | 3219229; 3219230; 3219233; 3219235; |
| Block_1183 | 0.009085 | chr 11: 3792978 ... 3793149; − | 1 | NUP98; | CODING (100%); | 2 | 3359975; 3359977; |
| Block_1990 | 0.009085 | chr13: 38137470 ... 38138697; − | 1 | POSTN; | CODING (100%); | 2 | 3510070; 3510072; |
| Block_4411 | 0.009085 | chr20: 52574002 ... 52601991; − | 1 | BCAS1; | CODING (100%); | 3 | 3910367; 3910373; 3910378; |
| Block_6454 | 0.009085 | chr6: 108942915 ... 108943132; + | 1 | FOXO3; | INTRONIC (100%); | 2 | 2920517; 2920518; |
| Block_6540 | 0.009085 | chr6: 160770298 ... 160864773; + | 2 | AL591069.1; SLC22A3; | ncTRANSCRIPT (3.44%); CODING (27.58%); INTRONIC (68.96%); | 29 | 2934526; 2934527; 2934531; 2934533; 2934535; 2934580; 2934582; 2934585; 2934586; 2934536; 2934537; 2934538; 2934539; 2934541; 2934543; 2934545; 2934547; 2934548; 2934549; 2934550; 2934551; 2934554; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| | | | | | | | 2934556; 2934557; 2934558; 2934559; 2934560; 2934561; 2934562; |
| Block_7064 | 0.009085 | chr8: 27382879 . . . 27399020; + | 1 | EPHX2; | CODING (100%); | 3 | 3091429; 3091433; 3091436; |
| Block_5912 | 0.009238 | chr5: 60699060 . . . 60705963; + | 1 | ZSWIM6; | INTRONIC (100%); | 2 | 2811311; 2811314; |
| Block_6369 | 0.009238 | chr6: 31785537 . . . 31785681; + | 1 | HSPA1A; | UTR (100%); | 2 | 2902715; 2902716; |
| Block_2101 | 0.009392 | chr13: 41890982 . . . 41891060; + | 1 | NAA16; | CODING (100%); | 2 | 3486890; 3486891; |
| Block_6340 | 0.009392 | chr6: 10697570 . . . 10707720; + | 1 | PAK1IP1; | CODING (100%); | 6 | 2894670; 2894671; 2894673; 2894676; 2894677; 2894681; |
| Block_6407 | 0.009392 | chr6: 44752539 . . . 44800262; + | 1 | SUPT3H; | INTRONIC_AS (33.33%); INTERGENIC (33.33%); CODING_AS (33.33%); | 3 | 2908668; 2908682; 2908684; |
| Block_7862 | 0.009392 | chrY: 21186129 . . . 21189006; − | 1 | NCRNA00185; | INTRONIC (100%); | 2 | 4035800; 4035801; |
| Block_1729 | 0.009708 | chr12: 103234188 . . . 103249107; − | 1 | PAH; | CODING (100%); | 3 | 3468486; 3468494; 3468504; |
| Block_4002 | 0.009708 | chr2: 227657803 . . . 227659434; − | 1 | IRS1; | INTRONIC (100%); | 2 | 2602032; 2602033; |
| Block_6542 | 0.009708 | chr6: 160868751 . . . 160872088; + | 1 | SLC22A3; | CODING (100%); | 2 | 2934572; 2934575; |
| Block_1913 | 0.009869 | chr12: 93774378 . . . 93775567; + | 1 | NUDT4; | INTRONIC (100%); | 3 | 3426176; 3426178; 3426180; |
| Block_4996 | 0.010033 | chr3: 187457927 . . . 187458752; − | 1 | BCL6; | INTRONIC (100%); | 2 | 2709814; 2709815; |
| Block_6541 | 0.010033 | chr6: 160866011 . . . 160868068; + | 1 | SLC22A3; | INTRONIC (100%); | 3 | 2934564; 2934565; 2934567; |
| Block_7019 | 0.010033 | chr8: 135820790 . . . 135827602; − | 0 | | INTERGENIC (100%); | 2 | 3154820; 3154823; |
| Block_5230 | 0.010199 | chr3: 186696431 . . . 186720502; + | 1 | ST6GAL1; | UTR (33.33%); INTRONIC (66.66%); | 3 | 2656910; 2656906; 2656846; |
| Block_4974 | 0.010368 | chr3: 156866425 . . . 156867848; − | 1 | CCNL1; | ncTRANSCRIPT (100%); | 2 | 2702334; 2702341; |
| Block_5229 | 0.010368 | chr3: 186656184 . . . 186662034; + | 1 | ST6GAL1; | INTRONIC (100%); | 2 | 2656876; 2656884; |
| Block_2155 | 0.010539 | chr13: 111932910 . . . 111938586; + | 1 | ARHGEF7; | CODING (100%); | 2 | 3501728; 3501736; |
| Block_5727 | 0.010539 | chr5: 68588077 . . . 68595899; − | 1 | CCDC125; | CODING (100%); | 2 | 2860627; 2860632; |
| Block_4872 | 0.010713 | chr3: 114311442 . . . 114318066; − | 1 | ZBTB20; | INTRONIC (100%); | 3 | 2689598; 2689599; 2689601; |
| Block_6449 | 0.010713 | chr6: 106967344 . . . 106975345; + | 1 | AIM1; | CODING (100%); | 5 | 2919813; 2919814; 2919815; 2919816; 2919820; |
| Block_1048 | 0.010889 | chr10: 51550046 . . . 51562146; + | 1 | MSMB; | ncTRANSCRIPT (22.22%); INTRONIC (77.77%); | 9 | 3246410; 3246413; 3246427; 3246428; 3246429; 3246430; 3246431; 3246414; 3246415; |
| Block_2517 | 0.010889 | chr15: 66072454 . . . 66076243; − | 1 | DENND4A; | INTRONIC (100%); | 2 | 3629917; 3629918; |
| Block_6088 | 0.010889 | chr6: 1930342 . . . 1961193; − | 1 | GMDS; | CODING (100%); | 3 | 2938731; 2938739; 2938741; |
| Block_7063 | 0.010889 | chr8: 27358443 . . . 27380016; + | 1 | EPHX2; | CODING (100%); | 6 | 3091408; 3091410; 3091412; 3091414; 3091418; 3091427; |
| Block_6674 | 0.011068 | chr7: 130764976 . . . 130789833; − | 1 | AC058791.2; | ncTRANSCRIPT (16.66%); INTRONIC (83.33%); | 6 | 3072944; 3072948; 3072856; 3072860; 3072861; 3072863; |
| Block_7280 | 0.011068 | chr9: 112963294 . . . 112963740; − | 1 | C9orf152; | CODING (100%); | 3 | 3220143; 3220147; 3220149; |
| Block_1093 | 0.011249 | chr10: 93702200 . . . 93713592; + | 1 | BTAF1; | CODING (100%); | 2 | 3257953; 3257956; |
| Block_1783 | 0.011249 | chr12: 123212329 . . . 123213804; − | 1 | GPR81; | UTR (100%); | 2 | 3475776; 3475778; |
| Block_1262 | 0.011433 | chr11: 62559948 . . . 62563808; − | 1 | NXF1; | CODING (100%); | 5 | 3376159; 3376162; 3376163; 3376165; 3376169; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| Block_2366 | 0.011433 | chr14: 73572725 . . . 73572938; + | 1 | RBM25; | CODING (100%); | 2 | 3543443; 3543444; |
| Block_4428 | 0.01162 | chr20: 6004032 . . . 6005887; + | 1 | CRLS1; | ncTRANSCRIPT (50%); INTRONIC (50%); | 2 | 3875259; 3875261; |
| Block_4828 | 0.01162 | chr3: 71080277 . . . 71088814; − | 1 | FOXP1; | INTRONIC (100%); | 4 | 2681951; 2681956; 2681814; 2681815; |
| Block_7607 | 0.01181 | chrX: 67413739 . . . 67518927; − | 1 | OPHN1; | CODING (100%); | 6 | 4011226; 4011231; 4011234; 4011241; 4011242; 4011244; |
| Block_2003 | 0.012595 | chr13: 45147330 . . . 45150071; − | 1 | TSC22D1; | CODING (100%); | 8 | 3512345; 3512347; 3512348; 3512350; 3512351; 3512352; 3512354; 3512355; |
| Block_4410 | 0.012595 | chr20: 52571654 . . . 52574704; − | 1 | BCAS1; | INTRONIC (100%); | 2 | 3910366; 3910368; |
| Block_6796 | 0.012595 | chr7: 99169875 . . . 99170304; + | 1 | ZNF655; | CODING (100%); | 2 | 3014925; 3014926; |
| Block_1572 | 0.012798 | chr11: 134147231 . . . 134188819; + | 1 | GLB1L3; | CODING (100%); | 13 | 3357348; 3357349; 3357360; 3357363; 3357369; 3357370; 3357371; 3357375; 3357382; 3357383; 3357384; 3357386; 3357387; |
| Block_4895 | 0.013005 | chr3: 120363705 . . . 120364125; − | 1 | HGD; | INTRONIC (100%); | 2 | 2691410; 4047097; |
| Block_6178 | 0.013005 | chr6: 53200331 . . . 53207275; − | 2 | ELOVL5; RP3-483K16.2; | ncTRANSCRIPT (50%); INTRONIC (50%); | 4 | 2957648; 2957651; 2957653; 2957655; |
| Block_6315 | 0.013005 | chr6: 159216475 . . . 159227934; − | 1 | EZR; | INTRONIC (100%); | 2 | 2981955; 2981961; |
| Block_4534 | 0.013214 | chr21: 36238786 . . . 36251434; − | 1 | RUNX1; | INTRONIC (100%); | 5 | 3930422; 3930512; 3930426; 3930520; 3930522; |
| Block_7689 | 0.013214 | chrX: 138182745 . . . 138221675; − | 1 | FGF13; | INTRONIC (100%); | 2 | 4024065; 4023962; |
| Block_1415 | 0.013426 | chr11: 32953313 . . . 32976949; + | 1 | QSER1; | CODING (100%); | 4 | 3325783; 3325784; 3325787; 3325791; |
| Block_6641 | 0.013426 | chr7: 99250225 . . . 99260505; − | 1 | CYP3A5; | CODING (100%); | 2 | 3063412; 3063422; |
| Block_1720 | 0.013641 | chr12: 93959391 . . . 93960697; − | 1 | AC025260.2; | ncTRANSCRIPT (50%); INTRONIC (50%); | 2 | 3465863; 3465865; |
| Block_1827 | 0.01386 | chr12: 13366615 . . . 13369004; + | 1 | EMP1; | CODING (66.66%); UTR (33.33%); | 3 | 3405774; 3405777; 3405778; |
| Block_7001 | 0.01386 | chr8: 116555732 . . . 116584992; − | 1 | TRPS1; | INTRONIC (100%); | 3 | 3149560; 3149563; 3149566; |
| Block_4874 | 0.014081 | chr3: 114406132 . . . 114412366; − | 1 | ZBTB20; | ncTRANSCRIPT (20%); INTRONIC (80%); | 5 | 2689618; 2689620; 2689621; 2689622; 2689627; |
| Block_6329 | 0.014081 | chr6: 170594681 . . . 170595380; − | 1 | DLL1; | CODING (100%); | 2 | 2986376; 2986377; |
| Block_3850 | 0.014305 | chr2: 100484261 . . . 100509150; − | 1 | AFF3; | INTRONIC (100%); | 2 | 2567082; 2567086; |
| Block_1603 | 0.014533 | chr12: 10856860 . . . 10871920; − | 1 | CSDA; | ncTRANSCRIPT (50%); INTRONIC (50%); | 12 | 3444265; 3444266; 3444274; 3444275; 3444280; 3444281; 3444283; 3444286; 3444287; 3444288; 3444289; 3444291; |
| Block_3511 | 0.014533 | chr19: 14626171 . . . 14627750; − | 1 | DNAJB1; | CODING (33.33%); UTR (66.66%); | 3 | 3852788; 3852789; 3852793; |
| Block_4890 | 0.014533 | chr3: 120347285 . . . 120347311; − | 1 | HGD; | CODING (100%); | 2 | 2691370; 4047116; |
| Block_2332 | 0.014998 | chr14: 60398687 . . . 60411444; + | 1 | LRRC9; | ncTRANSCRIPT (100%); | 2 | 3538417; 3538420; |
| Block_5744 | 0.014998 | chr5: 86682116 . . . 86683398; − | 1 | RASA1; | INTRONIC_AS (100%); | 2 | 2865872; 2865875; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| Block_601 | 0.014998 | chr1: 104076371 ... 104078044; + | 1 | RNPC3; | CODING (100%); | 3 | 2349363; 2349364; 2349365; |
| Block_7215 | 0.014998 | chr9: 73021937 ... 73022490; − | 1 | KLF9; | INTRONIC (100%); | 2 | 3209008; 3209009; |
| Block_7366 | 0.014998 | chr9: 140354863 ... 140355186; − | 1 | PNPLA7; | CODING (100%); | 4 | 3231012; 4051792; 3231015; 4051795; |
| Block_7376 | 0.014998 | chr9: 140437902 ... 140444736; − | 1 | PNPLA7; | CODING (75%); UTR (25%); | 4 | 3231109; 3231112; 3231115; 3231117; |
| Block_7441 | 0.015235 | chr9: 92219943 ... 92220976; + | 1 | GADD45G; | CODING (80%); UTR (20%); | 5 | 3178680; 3178681; 3178683; 3178685; 3178687; |
| Block_5812 | 0.015476 | chr5: 148876962 ... 148929959; − | 2 | CTB-89H12.4; CSNK1A1; | CODING (9.52%); ncTRANSCRIPT (14.28%); UTR (9.52%); INTRONIC (66.66%); | 21 | 2880949; 2880951; 2880958; 2880960; 2880964; 2880968; 2880973; 2880983; 2880985; 2880889; 2880890; 2880987; 2880892; 2880893; 2880896; 2880901; 2880989; 2880991; 2880993; 2880995; 2880997; |
| Block_6536 | 0.015476 | chr6: 160174501 ... 160176484; + | 1 | WTAP; | CODING (100%); | 2 | 2934120; 2934122; |
| Block_4877 | 0.015719 | chr3: 114455332 ... 114550610; − | 1 | ZBTB20; | UTR (9.09%); INTRONIC (90.90%); | 11 | 2689639; 2689640; 2689641; 2689647; 2689655; 2689824; 2689825; 2689826; 2689829; 2689658; 2689838; |
| Block_4892 | 0.015719 | chr3: 120352074 ... 120352166; − | 1 | HGD; | CODING (100%); | 2 | 2691378; 4047112; |
| Block_5014 | 0.015719 | chr3: 196118688 ... 196120490; − | 1 | UBXN7; | CODING (100%); | 2 | 2712875; 2712876; |
| Block_7724 | 0.015719 | chrX: 2653716 ... 2653766; + | 1 | CD99; | INTRONIC (100%); | 2 | 3966880; 4028503; |
| Block_4041 | 0.015967 | chr2: 14775429 ... 14775897; + | 1 | FAM84A; | UTR (100%); | 2 | 2470490; 2470491; |
| Block_4759 | 0.016217 | chr3: 27490249 ... 27493978; − | 1 | SLC4A7; | CODING (100%); | 2 | 2666957; 2666959; |
| Block_5187 | 0.016217 | chr3: 156395446 ... 156424304; + | 1 | TIPARP; | CODING (75%); UTR (25%); | 12 | 2649140; 2649141; 2649142; 2649149; 2649150; 2649151; 2649152; 2649154; 2649155; 2649156; 2649158; 2649160; |
| Block_5728 | 0.016217 | chr5: 68581172 ... 68599751; − | 1 | CCDC125; | CODING (100%); | 2 | 2860623; 2860634; |
| Block_2879 | 0.016472 | chr16: 56667710 ... 56678081; + | 4 | MT1JP; MT1DP; MT1M; MT1A; | ncTRANSCRIPT (20%); CODING (80%); | 5 | 3662156; 3662163; 3662122; 3662124; 3662175; |
| Block_3849 | 0.016472 | chr2: 100426047 ... 100692345; − | 1 | AFF3; | CODING (6.55%); ncTRANSCRIPT (3.27%); INTRONIC (90.16%); | 61 | 2566957; 2566960; 2566961; 2566965; 2566966; 2566971; 2567075; 2567076; 2567084; 2567063; 2566976; 2567087; 2567088; 2566977; 2567064; 2567097; 2567067; 2567069; 2567101; 2567103; 2567071; 2566979; 2566982; 2566983; 2566984; 2566985; 2567105; 2567111; 2567113; 2567115; 2567106; 2566987; 2566988; 2566991; 2566993; 2566994; 2566996; 2566997; 2567121; 2566998; 2567125; 2567000; 2567001; 2567002; 2567003; 2567005; 2567007; 2567008; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| | | | | | | | 2567010; 2567011; 2567012; 2567013; 2567014; 2567015; 2567017; 2567018; 2567019; 2567020; 2567022; 2567023; 2567127; |
| Block_4871 | 0.016472 | chr3: 114304388 . . . 114307096; − | 1 | ZBTB20; | INTRONIC (100%); | 2 | 2689592; 2689595; |
| Block_7460 | 0.016472 | chr9: 102594989 . . . 102628250; + | 1 | NR4A3; | CODING (80%); UTR (20%); | 5 | 3182004; 3182005; 3182010; 3182012; 3182015; |
| Block_7690 | 0.016472 | chrX: 138283258 . . . 138284475; − | 1 | FGF13; | INTRONIC (100%); | 2 | 4023972; 4023973; |
| Block_5769 | 0.016729 | chr5: 98208150 . . . 98209408; − | 1 | CHD1; | CODING (100%); | 2 | 2868550; 2868554; |
| Block_6035 | 0.01699 | chr5: 142273810 . . . 142281592; + | 1 | ARHGAP26; | CODING (100%); | 2 | 2833347; 2833348; |
| Block_2057 | 0.017255 | chr13: 107220269 . . . 107220463; − | 1 | ARGLU1; | UTR (100%); | 2 | 3524638; 3524639; |
| Block_4034 | 0.017255 | chr2: 10133339 . . . 10136095; + | 1 | GRHL1; | CODING (100%); | 2 | 2469190; 2469193; |
| Block_5298 | 0.017255 | chr4: 66465162 . . . 66468022; − | 1 | EPHA5; | CODING (66.66%); INTRONIC (33.33%); | 3 | 2771409; 2771411; 2771412; |
| Block_6483 | 0.017255 | chr6: 144615778 . . . 144641963; + | 1 | UTRN; | INTRONIC (100%); | 4 | 2929179; 2929184; 2929185; 2929186; |
| Block_2666 | 0.017523 | chr15: 99256649 . . . 99277206; + | 1 | IGF1R; | INTRONIC (100%); | 2 | 3610818; 3610825; |
| Block_2758 | 0.017523 | chr16: 56701878 . . . 56701935; − | 1 | MT1G; | CODING (50%); UTR (50%); | 2 | 3693007; 3693008; |
| Block_4893 | 0.017523 | chr3: 120357311 . . . 120357397; − | 1 | HGD; | CODING (100%); | 2 | 2691386; 4047108; |
| Block_6349 | 0.017523 | chr6: 18392721 . . . 18401507; + | 1 | RNF144B; | INTRONIC (100%); | 2 | 2897184; 2897227; |
| Block_7144 | 0.017523 | chr8: 102593447 . . . 102596253; + | 1 | GRHL2; | INTRONIC (100%); | 2 | 3109729; 3109731; |
| Block_1049 | 0.017795 | chr10: 51562272 . . . 51562497; + | 1 | MSMB; | CODING (50%); UTR (50%); | 2 | 3246417; 3246418; |
| Block_2195 | 0.017795 | chr14: 38041009 . . . 38048612; − | 0 | | INTERGENIC (100%); | 2 | 3561714; 3561715; |
| Block_2885 | 0.017795 | chr16: 56975974 . . . 56977926; + | 1 | HERPUD1; | INTERGENIC (50%); INTRONIC (50%); | 2 | 3662406; 3662413; |
| Block_3767 | 0.017795 | chr2: 43793837 . . . 43793938; − | 1 | THADA; | CODING (100%); | 2 | 2550679; 2550680; |
| Block_3865 | 0.017795 | chr2: 121999944 . . . 122005845; − | 1 | TFCP2L1; | CODING (100%); | 3 | 2573617; 2573621; 2573622; |
| Block_5763 | 0.017795 | chr5: 95242076 . . . 95243501; − | 1 | ELL2; | INTRONIC (100%); | 2 | 2867901; 2867906; |
| Block_6151 | 0.017795 | chr6: 35542614 . . . 35588051; − | 1 | FKBP5; | CODING (80%); UTR (20%); | 10 | 2951575; 2951576; 2951579; 2951581; 2951583; 2951587; 2951589; 2951593; 2951595; 2951596; |
| Block_1340 | 0.018071 | chr11: 115219890 . . . 115222358; − | 1 | CADM1; | INTRONIC (100%); | 2 | 3392454; 3392441; |
| Block_3892 | 0.018071 | chr2: 160303401 . . . 160304888; − | 1 | BAZ2B; | CODING (100%); | 2 | 2583084; 2583085; |
| Block_4924 | 0.018071 | chr3: 129123093 . . . 129137223; − | 1 | C3orf25; | CODING (100%); | 2 | 2694763; 2694771; |
| Block_626 | 0.018071 | chr1: 116933667 . . . 116939211; + | 1 | ATP1A1; | INTRONIC (100%); | 4 | 2353509; 2353512; 2353513; 2353517; |
| Block_3422 | 0.018351 | chr18: 39623725 . . . 39629533; + | 1 | PIK3C3; | CODING (100%); | 2 | 3786127; 3786129; |
| Block_3756 | 0.018351 | chr2: 38975252 . . . 38976820; − | 1 | SRSF7; | CODING (80%); UTR (20%); | 5 | 2548982; 2548985; 2548989; 2548990; 2548993; |
| Block_4870 | 0.018351 | chr3: 114214433 . . . 114219034; − | 1 | ZBTB20; | INTRONIC (100%); | 5 | 2689743; 2689744; 2689754; 2689756; 2689758; |
| Block_5617 | 0.018634 | chr4: 148786000 . . . 148787937; + | 1 | ARHGAP10; | CODING (100%); | 2 | 2746731; 2746736; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| Block_5746 | 0.018634 | chr5: 86686709 . . . 86690299; − | 2 | CCNH; RASA1; | CODING (50%); UTR_AS (50%); | 2 | 2865878; 2865887; |
| Block_7422 | 0.018634 | chr9: 75773460 . . . 75785150; + | 1 | ANXA1; | CODING (90.90%); UTR (9.09%); | 11 | 3174830; 3174831; 3174835; 3174838; 3174840; 3174845; 3174847; 3174850; 3174853; 3174856; 3174857; |
| Block_3565 | 0.019212 | chr19: 863256 . . . 863423; + | 1 | CFD; | UTR (100%); | 2 | 3815252; 3815253; |
| Block_4878 | 0.019507 | chr3: 114465255 . . . 114510905; − | 1 | ZBTB20; | ncTRANSCRIPT (14.28%); INTRONIC (85.71%); | 7 | 2689643; 2689645; 2689646; 2689649; 2689651; 2689654; 2689656; |
| Block_5523 | 0.019507 | chr4: 77512391 . . . 77515089; + | 1 | SHROOM3; | INTRONIC (100%); | 2 | 2732215; 2732103; |
| Block_7219 | 0.019507 | chr9: 74360664 . . . 74362413; − | 1 | TMEM2; | INTRONIC (100%); | 2 | 3209449; 3209451; |
| Block_745 | 0.019507 | chr1: 201980268 . . . 201985198; + | 1 | ELF3; | CODING (77.77%); UTR (22.22%); | 9 | 2375017; 2375020; 2375022; 2375027; 2375028; 2375031; 2375033; 2375034; 2375035; |
| Block_4894 | 0.019805 | chr3: 120357401 . . . 120369669; − | 1 | HGD; | ncTRANSCRIPT (9.09%); CODING (63.63%); INTRONIC (27.27%); | 22 | 2691388; 4047107; 2691394; 4047105; 2691396; 4047104; 2691400; 4047102; 2691404; 4047100; 2691406; 4047099; 2691408; 4047098; 2691414; 4047095; 2691416; 4047094; 2691418; 4047093; 2691420; 4047092; |
| Block_7368 | 0.019805 | chr9: 140356003 . . . 140357262; − | 1 | PNPLA7; | CODING (100%); | 6 | 3231020; 4051802; 3231024; 4051804; 3231029; 4051807; |
| Block_1146 | 0.020108 | chr10: 123988023 . . . 123990167; + | 1 | TACC2; | CODING (33.33%); INTRONIC (66.66%); | 3 | 3268174; 3268175; 3268178; |
| Block_1818 | 0.020108 | chr12: 11836357 . . . 11863628; + | 1 | ETV6; | INTRONIC (100%); | 4 | 3405070; 3405071; 3405073; 3405079; |
| Block_2437 | 0.020415 | chr15: 42445498 . . . 42446391; − | 1 | PLA2G4F; | CODING (100%); | 2 | 3620449; 3620451; |
| Block_334 | 0.020415 | chr1: 169693470 . . . 169702101; − | 1 | SELE; | CODING (81.81%); UTR (18.18%); | 11 | 2443481; 2443482; 2443486; 2443489; 2443490; 2443492; 2443494; 2443495; 2443496; 2443499; 2443501; |
| Block_7796 | 0.020415 | chrX: 70775823 . . . 70776629; + | 1 | OGT; | CODING (100%); | 2 | 3981142; 3981144; |
| Block_1893 | 0.020726 | chr12: 69006519 . . . 69013759; + | 1 | RAP1B; | INTRONIC (100%); | 3 | 3421121; 3421122; 3421123; |
| Block_5714 | 0.020726 | chr5: 58481017 . . . 58511763; − | 1 | PDE4D; | CODING (100%); | 4 | 2858211; 2858215; 2858221; 2858222; |
| Block_5866 | 0.020726 | chr5: 180278404 . . . 180278437; − | 1 | ZFP62; | CODING (100%); | 2 | 2890930; 4047645; |
| Block_4533 | 0.02104 | chr21: 36193606 . . . 36197820; − | 1 | RUNX1; | UTR (50%); INTRONIC (50%); | 2 | 3930392; 3930397; |
| Block_6626 | 0.02104 | chr7: 87910829 . . . 87912896; − | 1 | STEAP4; | UTR (50%); INTRONIC (50%); | 2 | 3060345; 3060349; |
| Block_3539 | 0.02136 | chr19: 45016075 . . . 45029277; − | 1 | CEACAM20; | ncTRANSCRIPT (100%); | 8 | 3864953; 3864956; 3864957; 3864959; 3864961; 3864962; 3864964; 3864967; |
| Block_3551 | 0.02136 | chr19: 51410040 . . . 51412584; − | 1 | KLK4; | CODING (85.71%); UTR (14.28%); | 7 | 3868736; 3868737; 3868738; 3868740; 3868741; 3868743; 3868745; |
| Block_3894 | 0.02136 | chr2: 160885361 . . . 160898634; − | 1 | PLA2R1; | CODING (100%); | 3 | 2583439; 2583441; 2583443; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| Block_2870 | 0.021683 | chr16: 53260310 . . . 53269212; + | 1 | CHD9; | CODING (100%); | 2 | 3660920; 3660927; |
| Block_6631 | 0.021683 | chr7: 95213206 . . . 95224446; − | 1 | PDK4; | CODING (91.66%); UTR (8.33%); | 12 | 3062083; 3062084; 3062087; 3062089; 3062091; 3062096; 3062099; 3062100; 3062102; 3062103; 3062105; 3062108; |
| Block_5961 | 0.02201 | chr5: 95087958 . . . 95103870; + | 1 | RHOBTB3; | CODING (100%); | 3 | 2820942; 2820947; 2820954; |
| Block_6316 | 0.02201 | chr6: 159222851 . . . 159229779; − | 1 | EZR; | INTRONIC (100%); | 2 | 2981957; 2981963; |
| Block_6886 | 0.02201 | chr8: 17573279 . . . 17612789; − | 1 | MTUS1; | CODING (100%); | 4 | 3125964; 3125967; 3125973; 3125975; |
| Block_1915 | 0.022342 | chr12: 93968968 . . . 93969774; + | 1 | SOCS2; | UTR (100%); | 4 | 3426279; 3426280; 3426281; 3426282; |
| Block_1263 | 0.022679 | chr11: 62568586 . . . 62571024; − | 1 | NXF1; | CODING (100%); | 3 | 3376178; 3376180; 3376187; |
| Block_7564 | 0.022679 | chrX: 11369976 . . . 11398542; − | 1 | ARHGAP6; | INTRONIC (100%); | 2 | 3999693; 3999639; |
| Block_7605 | 0.022679 | chrX: 67272384 . . . 67284017; − | 1 | OPHN1; | CODING (100%); | 2 | 4011206; 4011209; |
| Block_4815 | 0.023019 | chr3: 64630315 . . . 64636668; − | 1 | ADAMTS9; | UTR (50%); INTRONIC (50%); | 2 | 2680133; 2680139; |
| Block_5174 | 0.023019 | chr3: 150128646 . . . 150129079; + | 1 | TSC22D2; | CODING (100%); | 2 | 2647664; 2647665; |
| Block_3214 | 0.023364 | chr17: 39969468 . . . 39976700; + | 1 | FKBP10; | CODING (100%); | 5 | 3721456; 3721461; 3721462; 3721465; 3721472; |
| Block_3456 | 0.023714 | chr18: 59958780 . . . 59972846; + | 1 | KIAA1468; | CODING (75%); UTR (25%); | 4 | 3791229; 3791231; 3791236; 3791237; |
| Block_4141 | 0.024068 | chr2: 102781282 . . . 102792104; + | 1 | IL1R1; | CODING (100%); | 7 | 2497000; 2497001; 2497002; 2497004; 2497007; 2497010; 2497012; |
| Block_6797 | 0.024068 | chr7: 99169519 . . . 99170579; + | 1 | ZNF655; | CODING (50%) INTRONIC (50%); | 2 | 3014924; 3014928; |
| Block_7300 | 0.024068 | chr9: 124124355 . . . 124128420; − | 1 | STOM; | UTR (50%); INTRONIC (50%); | 2 | 3223950; 3223954; |
| Block_1042 | 0.024426 | chr10: 43615579 . . . 43622087; + | 1 | RET; | CODING (100%); | 3 | 3243877; 3243878; 3243881; |
| Block_3534 | 0.024426 | chr19: 40540451 . . . 40540826; − | 1 | ZNF780B; | CODING (100%); | 2 | 3862345; 3862347; |
| Block_3668 | 0.024426 | chr19: 49377023 . . . 49378997; + | 1 | PPP1R15A; | CODING (100%); | 4 | 3838008; 3838010; 3838011; 3838013; |
| Block_4625 | 0.024426 | chr22: 29190562 . . . 29191698; − | 1 | XBP1; | CODING (66.66%); UTR (33.33%); | 3 | 3956591; 3956593; 3956594; |
| Block_6815 | 0.024426 | chr7: 104749510 . . . 104750810; + | 1 | MLL5; | CODING (100%); | 2 | 3017637; 3017638; |
| Block_37 | 0.024789 | chr1: 8072266 . . . 8082267; − | 1 | ERRFI1; | ncTRANSCRIPT (10%); CODING (30%); UTR (30%); INTRONIC (30%); | 10 | 2395182; 2395184; 2395187; 2395188; 2395189; 2395190; 2395191; 2395192; 2395193; 2395195; |
| Block_5138 | 0.024789 | chr3: 121615255 . . . 121660380; + | 1 | SLC15A2; | CODING (90.47%); UTR (9.52%); | 21 | 2638732; 2638733; 2638734; 2638735; 2638737; 2638738; 2638742; 2638743; 2638744; 2638745; 2638746; 2638749; 2638750; 2638751; 2638754; 2638756; 2638757; 2638758; 2638760; 2638761; 2638762; |
| Block_6328 | 0.024789 | chr6: 169616207 . . . 169620400; − | 1 | THBS2; | CODING (16.66%); UTR (83.33%); | 6 | 2985811; 2985812; 2985813; 2985814; 2985815; 2985816; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| Block_6611 | 0.024789 | chr7: 75721390 . . . 75729255; − | 1 | AC005077.12; | ncTRANSCRIPT (100%); | 2 | 3057596; 3057600; |
| Block_940 | 0.024789 | chr10: 88848954 . . . 88853651; − | 1 | GLUD1; | UTR (60%); INTRONIC (40%); | 5 | 3299016; 4038350; 3299019; 3299020; 3299022; |
| Block_2230 | 0.025157 | chr14: 69421708 . . . 69430379; − | 1 | ACTN1; | INTRONIC (100%); | 2 | 3569890; 3569894; |
| Block_2275 | 0.025157 | chr14: 102548195 . . . 102552551; − | 1 | HSP90AA1; | INTRONIC (100%); | 6 | 3580183; 3580189; 3580195; 3580199; 3580201; 3580206; |
| Block_2928 | 0.025157 | chr16: 84910468 . . . 84914235; + | 1 | CRISPLD2; | INTRONIC (100%); | 2 | 3671967; 3671971; |
| Block_7374 | 0.025157 | chr9: 140375422 . . . 140389574; − | 1 | PNPLA7; | CODING (100%); | 3 | 3231051; 3231059; 3231063; |
| Block_949 | 0.025157 | chr10: 95066684 . . . 95066750; − | 1 | MYOF; | CODING (50%); UTR (50%); | 2 | 3300605; 3300606; |
| Block_2931 | 0.02553 | chr16: 89758258 . . . 89759855; + | 1 | CDK10; | CODING (100%); | 3 | 3674319; 3674324; 3674326; |
| Block_4003 | 0.02553 | chr2: 227661614 . . . 227662290; − | 1 | IRS1; | CODING (100%); | 2 | 2602044; 2602045; |
| Block_4979 | 0.02553 | chr3: 160803580 . . . 160804455; − | 1 | B3GALNT1; | CODING (100%); | 2 | 2703388; 2703390; |
| Block_2786 | 0.025907 | chr16: 72827353 . . . 72832458; − | 1 | ZFHX3; | CODING (100%); | 2 | 3698277; 3698282; |
| Block_3856 | 0.025907 | chr2: 106005706 . . . 106013825; − | 1 | FHL2; | INTRONIC (100%); | 2 | 2568719; 2568727; |
| Block_5618 | 0.025907 | chr4: 148800406 . . . 148834290; + | 1 | ARHGAP10; | CODING (100%); | 2 | 2746744; 2746753; |
| Block_6861 | 0.025907 | chr7: 139083359 . . . 139090458; + | 1 | LUC7L2; | CODING (100%); | 3 | 3027013; 3027014; 3027015; |
| Block_2302 | 0.026289 | chr14: 38038123 . . . 38038868; + | 0 | | INTERGENIC (100%); | 2 | 3533022; 3533023; |
| Block_5707 | 0.026289 | chr5: 54786572 . . . 54830000; − | 1 | PPAP2A; | INTRONIC (100%); | 8 | 2857242; 2857264; 2857273; 2857275; 2857280; 2857282; 2857246; 2857254; |
| Block_3672 | 0.026677 | chr19: 49606718 . . . 49606842; + | 1 | SNRNP70; | UTR (100%); | 2 | 3838212; 3838213; |
| Block_4626 | 0.026677 | chr22: 29192148 . . . 29195118; − | 1 | XBP1; | CODING (100%); | 3 | 3956598; 3956600; 3956604; |
| Block_4994 | 0.026677 | chr3: 185643370 . . . 185644451; − | 1 | TRA2B; | CODING (100%); | 2 | 2709093; 2709095; |
| Block_7143 | 0.026677 | chr8: 102555510 . . . 102565001; + | 1 | GRHL2; | CODING (100%); | 2 | 3109712; 3109716; |
| Block_3735 | 0.027069 | chr2: 24535214 . . . 24536392; − | 1 | ITSN2; | CODING (100%); | 2 | 2544325; 2544328; |
| Block_3847 | 0.027069 | chr2: 100372047 . . . 100415240; − | 1 | AFF3; | INTRONIC (100%); | 5 | 2566941; 2566942; 2566948; 2566949; 2566955; |
| Block_4519 | 0.027069 | chr21: 29811695 . . . 29818793; − | 1 | AF131217.1; | ncTRANSCRIPT (50%); INTERGENIC (50%); | 4 | 3927812; 3927814; 3927818; 3927819; |
| Block_5170 | 0.027069 | chr3: 141596514 . . . 141622381; + | 1 | ATP1B3; | INTRONIC (100%); | 6 | 2645770; 2645771; 2645775; 2645776; 2645777; 2645780; |
| Block_1940 | 0.027465 | chr12: 110720638 . . . 110723521; + | 1 | ATP2A2; | INTRONIC (100%); | 2 | 3431489; 3431491; |
| Block_5676 | 0.027465 | chr5: 29476852 . . . 29477004; − | 0 | | INTERGENIC (100%); | 2 | 2851724; 2851725; |
| Block_6897 | 0.027465 | chr8: 22570904 . . . 22582442; − | 1 | PEBP4; | CODING (100%); | 2 | 3127612; 3127614; |
| Block_1730 | 0.027867 | chr12: 103238114 . . . 103246723; − | 1 | PAH; | CODING (100%); | 3 | 3468493; 3468497; 3468501; |
| Block_1770 | 0.027867 | chr12: 118597975 . . . 118610428; − | 1 | TAOK3; | CODING (100%); | 2 | 3473817; 3473823; |
| Block_5708 | 0.027867 | chr5: 55243448 . . . 55246076; − | 1 | IL6ST; | CODING (25%); ncTRANSCRIPT (25%); INTRONIC (50%); | 4 | 2857431; 2857432; 2857433; 2857435; |
| Block_7242 | 0.027867 | chr9: 94180062 . . . 94184577; − | 1 | NFIL3; | INTRONIC (100%); | 2 | 3214459; 3214464; |
| Block_1097 | 0.028274 | chr10: 93753461 . . . 93756275; + | 1 | BTAF1; | CODING (100%); | 3 | 3257988; 3257990; 3257991; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| Block_1270 | 0.028274 | chr11: 64536711 . . . 64540977; − | 1 | SF1; | CODING (100%); | 3 | 3377068; 3377069; 3377075; |
| Block_1523 | 0.028274 | chr11: 114028398 . . . 114028592; + | 1 | ZBTB16; | INTRONIC (100%); | 2 | 3349769; 3349770; |
| Block_2882 | 0.028274 | chr16: 56968915 . . . 56970561; + | 1 | HERPUD1; | INTRONIC (100%); | 3 | 3662392; 3662394; 3662396; |
| Block_2912 | 0.028274 | chr16: 69727019 . . . 69727890; + | 1 | NFAT5; | CODING (100%); | 3 | 3666854; 3666855; 3666860; |
| Block_5233 | 0.028274 | chr3: 186790651 . . . 186795948; + | 1 | ST6GAL1; | CODING (80%); UTR (20%); | 5 | 2656865; 2656867; 2656868; 2656869; 2656870; |
| Block_5487 | 0.028274 | chr4: 40104120 . . . 40104817; + | 1 | N4BP2; | CODING (100%); | 2 | 2724618; 2724619; |
| Block_7363 | 0.028274 | chr9: 140350912 . . . 140350938; − | 1 | NELF; | CODING (100%); | 2 | 3231002; 4051780; |
| Block_7688 | 0.028274 | chrX: 138158562 . . . 138160882; − | 1 | FGF13; | INTRONIC (100%); | 2 | 4024012; 4023960; |
| Block_7633 | 0.028686 | chrX: 76938144 . . . 76938170; − | 1 | ATRX; | CODING (100%); | 2 | 4013275; 4055301; |
| Block_1337 | 0.029104 | chr11: 111779401 . . . 111782388; − | 1 | CRYAB; | CODING (75%); UTR (25%); | 4 | 3391171; 3391173; 3391176; 3391181; |
| Block_3757 | 0.029104 | chr2: 38976048 . . . 38976240; − | 1 | SRSF7; | UTR (100%); | 2 | 2548987; 2548988; |
| Block_5217 | 0.029104 | chr3: 182987375 . . . 182988389; + | 1 | B3GNT5; | CODING (75%); UTR (25%); | 4 | 2654979; 2654980; 2654981; 2654983; |
| Block_7420 | 0.029104 | chr9: 72912918 . . . 72915067; + | 1 | SMC5; | CODING (100%); | 2 | 3174237; 3174238; |
| Block_7630 | 0.029104 | chrX: 76912053 . . . 76912120; − | 1 | ATRX; | CODING (100%); | 2 | 4013266; 4055308; |
| Block_2316 | 0.029526 | chr14: 52794058 . . . 52794156; + | 1 | PTGER2; | CODING (100%); | 2 | 3535798; 3535799; |
| Block_2728 | 0.029526 | chr16: 28123180 . . . 28123325; − | 1 | XPO6; | CODING (100%); | 2 | 3686351; 3686352; |
| Block_2900 | 0.029526 | chr16: 68155896 . . . 68160503; + | 1 | NFATC3; | CODING (100%); | 5 | 3666049; 3666050; 3666052; 3666053; 3666055; |
| Block_5704 | 0.029526 | chr5: 54721975 . . . 54822340; − | 1 | PPAP2A; | CODING (4%); INTRONIC (96%); | 25 | 2857212; 2857213; 2857218; 2857219; 2857221; 2857222; 2857224; 2857226; 2857227; 2857231; 2857232; 2857238; 2857240; 2857241; 2857243; 2857244; 2857269; 2857271; 2857277; 2857284; 2857267; 2857247; 2857248; 2857249; 2857250; |
| Block_5989 | 0.029526 | chr5: 113698875 . . . 113699698; + | 1 | KCNN2; | CODING (100%); | 2 | 2824632; 2824635; |
| Block_6904 | 0.029526 | chr8: 27317314 . . . 27336535; − | 1 | CHRNA2; | CODING (60%); UTR (40%); | 10 | 3129025; 3129030; 3129034; 3129038; 3129039; 3129040; 3129044; 3129045; 3129046; 3129047; |
| Block_2245 | 0.029954 | chr14: 76424744 . . . 76448197; − | 1 | TGFB3; | INTERGENIC (9.09%); CODING (45.45%); UTR (45.45%); | 11 | 3572518; 3572524; 3572528; 3572529; 3572533; 3572534; 3572539; 3572540; 3572541; 3572542; 3572543; |
| Block_6439 | 0.029954 | chr6: 80383340 . . . 80406282; + | 1 | SH3BGRL2; | CODING (100%); | 2 | 2914706; 2914708; |
| Block_6719 | 0.029954 | chr7: 12620691 . . . 12691507; + | 1 | SCIN; | CODING (100%); | 9 | 2990415; 2990418; 2990420; 2990421; 2990424; 2990425; 2990427; 2990430; 2990431; |
| Block_1375 | 0.030387 | chr11: 134022430 . . . 134095174; − | 1 | NCAPD3; | CODING (90.47%); UTR (7.14%); INTRONIC (2.38%); | 42 | 3399550; 3399551; 3399553; 3399555; 3399562; 3399563; 3399565; 3399566; 3399567; 3399569; 3399570; 3399571; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| | | | | | | | 3399572; 3399573; 3399574; 3399576; 3399577; 3399579; 3399580; 3399581; 3399583; 3399584; 3399585; 3399587; 3399588; 3399589; 3399590; 3399591; 3399592; 3399593; 3399594; 3399595; 3399597; 3399598; 3399600; 3399601; 3399602; 3399603; 3399605; 3399606; 3399607; 3399613; |
| Block_2444 | 0.030387 | chr15: 42730835 ... 42737120; − | 1 | ZFP106; | CODING (100%); | 3 | 3620619; 3620620; 3620629; |
| Block_3525 | 0.030387 | chr19: 23543094 ... 23545314; − | 1 | ZNF91; | CODING (100%); | 2 | 3857111; 3857120; |
| Block_3864 | 0.030387 | chr2: 121989436 ... 121995260; − | 1 | TFCP2L1; | CODING (100%); | 3 | 2573607; 2573609; 2573613; |
| Block_5724 | 0.030387 | chr5: 59683251 ... 59770534; − | 1 | PDE4D; | INTRONIC (100%); | 9 | 2858550; 2858561; 2858551; 2858552; 2858565; 2858431; 2858567; 2858575; 2858577; |
| Block_2138 | 0.030825 | chr13: 99098380 ... 99099024; + | 1 | FARP1; | CODING (100%); | 2 | 3498035; 3498037; |
| Block_2878 | 0.030825 | chr16: 56642626 ... 56643147; + | 1 | MT2A; | INTRONIC (100%); | 3 | 3662111; 3662112; 3662115; |
| Block_6479 | 0.030825 | chr6: 144070122 ... 144075017; + | 1 | PHACTR2; | CODING (100%); | 2 | 2928962; 2928964; |
| Block_1627 | 0.031269 | chr12: 26755308 ... 26755636; − | 1 | ITPR2; | CODING (100%); | 2 | 3448289; 3448290; |
| Block_3754 | 0.031269 | chr2: 38973291 ... 38973876; − | 1 | SRSF7; | CODING (100%); | 2 | 2548976; 2548978; |
| Block_5751 | 0.031269 | chr5: 90667505 ... 90675837; − | 1 | ARRDC3; | ncTRANSCRIPT (33.33%); INTRONIC (66.66%); | 6 | 2866739; 2866710; 2866715; 2866719; 2866723; 2866741; |
| Block_612 | 0.031269 | chr1: 110211967 ... 110214138; + | 1 | GSTM2; | CODING (100%); | 4 | 2350963; 2350964; 2350971; 2350973; |
| Block_6189 | 0.031269 | chr6: 56479851 ... 56507576; − | 1 | DST; | CODING (96.29%); UTR (3.70%); | 27 | 2958476; 2958479; 2958484; 2958485; 2958486; 2958487; 2958488; 2958489; 2958490; 2958491; 2958493; 2958494; 2958496; 2958497; 2958498; 2958500; 2958501; 2958502; 2958505; 2958506; 2958507; 2958508; 2958509; 2958510; 2958511; 2958512; 2958513; |
| Block_906 | 0.031269 | chr10: 64988219 ... 65015457; − | 1 | JMJD1C; | INTRONIC (100%); | 4 | 3291839; 3291736; 3291737; 3291741; |
| Block_1499 | 0.031719 | chr11: 82878465 ... 82878887; + | 1 | PCF11; | CODING (100%); | 2 | 3342544; 3342545; |
| Block_2187 | 0.031719 | chr14: 30374876 ... 30385713; − | 1 | PRKD1; | INTRONIC (100%); | 2 | 3559283; 3559284; |
| Block_3198 | 0.031719 | chr17: 32583269 ... 32584108; + | 1 | CCL2; | CODING (66.66%); UTR (33.33%); | 3 | 3718173; 3718175; 3718176; |
| Block_4897 | 0.031719 | chr3: 120370215 ... 120370855; − | 1 | HGD; | INTRONIC (100%); | 2 | 2691428; 4047088; |
| Block_6093 | 0.031719 | chr6: 3270435 ... 3287296; − | 1 | SLC22A23; | CODING (50%); UTR (50%); | 4 | 2939302; 2939303; 2939307; 2939313; |
| Block_6632 | 0.031719 | chr7: 95215175 ... 95216702; − | 1 | PDK4; | INTRONIC (100%); | 2 | 3062085; 3062088; |
| Block_2121 | 0.032173 | chr13: 76379046 ... 76379380; + | 1 | LMO7; | INTRONIC (100%); | 2 | 3494196; 3494197; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| Block_460 | 0.032173 | chr1: 19981582 . . . 19984800; + | 1 | NBL1; | CODING (66.66%); UTR (33.33%); | 3 | 2323777; 2323778; 2323782; |
| Block_5035 | 0.032173 | chr3: 19190143 . . . 19190250; + | 1 | KCNH8; | CODING (50%); UTR (50%); | 2 | 2613294; 2613295; |
| Block_5642 | 0.032173 | chr4: 166301254 . . . 166375499; + | 1 | CPE; | CODING (6.25%); UTR (12.5%); INTRONIC (81.25%); | 16 | 2750634; 2750635; 2750636; 2750638; 2750639; 2750640; 2750642; 2750643; 2750680; 2750646; 2750647; 2750649; 2750650; 2750653; 2750655; 2750659; |
| Block_5909 | 0.032173 | chr5: 56526692 . . . 56531821; + | 1 | GPBP1; | CODING (100%); | 2 | 2810484; 2810487; |
| Block_7744 | 0.032173 | chrX: 23803557 . . . 23803771; + | 1 | SAT1; | ncTRANSCRIPT (50%); INTRONIC (50%); | 2 | 3971823; 3971825; |
| Block_4816 | 0.032634 | chr3: 64666890 . . . 64672644; − | 1 | ADAMTS9; | CODING (100%); | 4 | 2680160; 2680168; 2680170; 2680172; |
| Block_5167 | 0.032634 | chr3: 140251178 . . . 140275496; + | 1 | CLSTN2; | CODING (100%); | 2 | 2645167; 2645174; |
| Block_5713 | 0.032634 | chr5: 58442688 . . . 58450083; − | 1 | PDE4D; | INTRONIC (100%); | 3 | 2858190; 2858192; 2858194; |
| Block_5967 | 0.032634 | chr5: 96215443 . . . 96222457; + | 1 | ERAP2; | CODING (100%); | 2 | 2821370; 2821373; |
| Block_2001 | 0.0331 | chr13: 45048688 . . . 45053829; − | 1 | TSC22D1; | INTRONIC (100%); | 2 | 3512320; 3512324; |
| Block_2049 | 0.0331 | chr13: 95873854 . . . 95889452; − | 1 | ABCC4; | INTRONIC (100%); | 5 | 3521282; 3521283; 3521284; 3521286; 3521293; |
| Block_6693 | 0.0331 | chr7: 151864248 . . . 151873818; − | 1 | MLL3; | CODING (100%); | 4 | 3080082; 3080086; 3080088; 3080089; |
| Block_7514 | 0.0331 | chr9: 136333151 . . . 136333198; + | 1 | C9orf7; | INTRONIC (100%); | 2 | 3193029; 4050936; |
| Block_127 | 0.033572 | chr1: 25573295 . . . 25573974; − | 1 | C1orf63; | CODING (33.33%); UTR (66.66%); | 3 | 2402129; 2402130; 2402134; |
| Block_4749 | 0.033572 | chr3: 18427936 . . . 18438764; − | 1 | SATB1; | CODING (100%); | 3 | 2665227; 2665231; 2665233; |
| Block_5231 | 0.033572 | chr3: 186760464 . . . 186769107; + | 1 | ST6GAL1; | CODING (66.66%); UTR (33.33%); | 3 | 2656855; 2656857; 2656858; |
| Block_6269 | 0.033572 | chr6: 132617405 . . . 132618041; − | 1 | MOXD1; | UTR (100%); | 2 | 2974428; 2974429; |
| Block_852 | 0.033572 | chr10: 18837090 . . . 18840876; − | 1 | NSUN6; | CODING (100%); | 2 | 3280249; 3280253; |
| Block_2202 | 0.034049 | chr14: 50296082 . . . 50298964; − | 1 | NEMF; | CODING (100%); | 3 | 3563511; 3563512; 3563514; |
| Block_3855 | 0.034049 | chr2: 106002513 . . . 106013154; − | 1 | FHL2; | CODING (50%); INTRONIC (50%); | 2 | 2568717; 2568725; |
| Block_4103 | 0.034049 | chr2: 61333740 . . . 61335484; + | 1 | KIAA1841; | CODING (100%); | 2 | 2484488; 2484489; |
| Block_4837 | 0.034049 | chr3: 71622652 . . . 71629752; − | 2 | RP11-154H23.1; FOXP1; | ncTRANSCRIPT (50%); INTRONIC (50%); | 2 | 2682247; 2682249; |
| Block_6424 | 0.034049 | chr6: 71125002 . . . 71264155; + | 2 | RNU7-48P; FAM135A; | ncTRANSCRIPT (6.66%); CODING (63.33%); UTR (3.33%); INTRONIC (26.66%); | 30 | 2912782; 2912787; 2912788; 2912795; 2912802; 2912803; 2912806; 2912808; 2912809; 2912813; 2912814; 2912815; 2912816; 2912817; 2912818; 2912819; 2912820; 2912822; 2912824; 2912828; 2912829; 2912831; 2912832; 2912833; 2912838; 2912839; 2912841; 2912842; 2912847; 2912849; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| Block_6453 | 0.034049 | chr6: 108938446 . . . 108942121; + | 1 | FOXO3; | INTRONIC (100%); | 2 | 2920510; 2920512; |
| Block_1077 | 0.034532 | chr10: 77453352 . . . 77454380; + | 1 | C10orf11; | INTRONIC (100%); | 2 | 3252742; 3252954; |
| Block_1250 | 0.034532 | chr11: 61295389 . . . 61300540; − | 1 | SYT7; | CODING (100%); | 2 | 3375406; 3375409; |
| Block_6190 | 0.034532 | chr6: 56503045 . . . 56504056; − | 1 | DST; | ncTRANSCRIPT (50%); INTRONIC (50%); | 2 | 2958503; 2958504; |
| Block_6677 | 0.034532 | chr7: 136935982 . . . 136938338; − | 1 | PTN; | CODING (100%); | 2 | 3074872; 3074873; |
| Block_911 | 0.034532 | chr10: 70276866 . . . 70276996; − | 1 | SLC25A16; | UTR (100%); | 2 | 3292763; 3292764; |
| Block_993 | 0.034532 | chr10: 118687375 . . . 118704523; − | 1 | KIAA1598; | CODING (100%); | 2 | 3308529; 3308533; |
| Block_3168 | 0.035021 | chr17: 7945688 . . . 7951882; + | 1 | ALOX15B; | CODING (100%); | 11 | 3709424; 3709426; 3709428; 3709429; 3709430; 3709432; 3709433; 3709435; 3709437; 3709438; 3709440; |
| Block_3739 | 0.035021 | chr2: 31749837 . . . 31754527; − | 1 | SRD5A2; | ncTRANSCRIPT (100%); | 3 | 2547235; 2547237; 2547238; |
| Block_3049 | 0.035516 | chr17: 56492694 . . . 56494638; − | 1 | RNF43; | INTERGENIC (25%); CODING (25%); UTR (50%); | 4 | 3764435; 3764437; 3764438; 3764441; |
| Block_5576 | 0.035516 | chr4: 106474899 . . . 106477521; + | 1 | ARHGEF38; | INTRONIC (100%); | 4 | 2738247; 2738268; 2738270; 2738248; |
| Block_5770 | 0.035516 | chr5: 98224781 . . . 98231958; − | 1 | CHD1; | CODING (100%); | 4 | 2868574; 2868577; 2868578; 2868580; |
| Block_7247 | 0.035516 | chr9: 95146567 . . . 95155495; − | 1 | OGN; | CODING (50%); UTR (50%); | 6 | 3214802; 3214803; 3214804; 3214806; 3214807; 3214810; |
| Block_7810 | 0.035516 | chrX: 105153170 . . . 105156727; + | 1 | NRK; | CODING (100%); | 2 | 3986120; 3986121; |
| Block_1289 | 0.036017 | chr11: 70824339 . . . 70830068; − | 1 | SHANK2; | CODING (100%); | 2 | 3380586; 3380591; |
| Block_2429 | 0.036017 | chr15: 37195097 . . . 37210290; − | 1 | MEIS2; | INTRONIC (100%); | 3 | 3618360; 3618366; 3618367; |
| Block_2493 | 0.036017 | chr15: 60677881 . . . 60688620; − | 1 | ANXA2; | INTRONIC (100%); | 9 | 3627332; 3627334; 3627336; 3627341; 3627343; 3627345; 3627346; 3627348; 3627349; |
| Block_3679 | 0.036017 | chr19: 51359727 . . . 51362135; + | 1 | KLK3; | UTR (50%); INTRONIC (50%); | 2 | 3839545; 3839552; |
| Block_6037 | 0.036017 | chr5: 145843146 . . . 145843355; + | 1 | TCERG1; | CODING (100%); | 2 | 2834115; 2834117; |
| Block_7373 | 0.036017 | chr9: 140361786 . . . 140361907; − | 1 | PNPLA7; | CODING (100%); | 2 | 3231040; 4051817; |
| Block_2894 | 0.036524 | chr16: 67159862 . . . 67178779; + | 1 | C16orf70; | CODING (100%); | 6 | 3665168; 3665171; 3665173; 3665177; 3665179; 3665183; |
| Block_3987 | 0.036524 | chr2: 216226027 . . . 216299511; − | 1 | FN1; | CODING (94.73%); UTR (5.26%); | 57 | 2598267; 2598268; 2598269; 2598270; 2598271; 2598273; 2598276; 2598277; 2598280; 2598281; 2598284; 2598286; 2598288; 2598289; 2598290; 2598294; 2598296; 2598299; 2598301; 2598302; 2598304; 2598306; 2598307; 2598308; 2598310; 2598313; 2598314; 2598318; 2598321; 2598324; 2598325; 2598328; 2598329; 2598330; 2598331; 2598334; 2598335; 2598338; 2598339; 2598340; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| | | | | | | | 2598342; 2598344; 2598346; 2598352; 2598353; 2598354; 2598356; 2598357; 2598358; 2598360; 2598362; 2598363; 2598367; 2598371; 2598372; 2598373; 2598374; |
| Block_416 | 0.036524 | chr1: 235712540 . . . 235715511; − | 1 | GNG4; | CODING (25%); UTR (75%); | 4 | 2461942; 2461944; 2461945; 2461946; |
| Block_7241 | 0.036524 | chr9: 94171357 . . . 94172980; − | 1 | NFIL3; | CODING (33.33%); UTR (66.66%); | 3 | 3214452; 3214453; 3214454; |
| Block_1192 | 0.037037 | chr11: 8132291 . . . 8148335; − | 1 | RIC3; | CODING (100%); | 2 | 3361638; 3361639; |
| Block_1431 | 0.037037 | chr11: 35226060 . . . 35227773; + | 1 | CD44; | CODING (100%); | 2 | 3326700; 3326705; |
| Block_1945 | 0.037037 | chr12: 111558155 . . . 111620438; + | 1 | CUX2; | INTRONIC (100%); | 3 | 3431789; 3431792; 3431795; |
| Block_2436 | 0.037037 | chr15: 42437997 . . . 42439930; − | 1 | PLA2G4F; | CODING (100%); | 3 | 3620436; 3620439; 3620441; |
| Block_6629 | 0.037037 | chr7: 92354966 . . . 92355105; − | 1 | CDK6; | CODING (100%); | 2 | 3061361; 3061362; |
| Block_7095 | 0.037037 | chr8: 42798476 . . . 42805590; + | 1 | HOOK3; | CODING (100%); | 2 | 3096385; 3096387; |
| Block_3287 | 0.037557 | chr17: 65941696 . . . 65941965; + | 1 | BPTF; | CODING (100%); | 2 | 3732514; 3732516; |
| Block_5073 | 0.037557 | chr3: 42678445 . . . 42687432; + | 1 | NKTR; | CODING (100%); | 3 | 2619384; 2619390; 2619399; |
| Block_4586 | 0.038082 | chr21: 42541819 . . . 42601866; + | 1 | BACE2; | INTRONIC (100%); | 8 | 3921943; 3921944; 3921945; 3921949; 3921950; 3921951; 3921991; 3921961; |
| Block_7687 | 0.038082 | chrX: 138063436 . . . 138104840; − | 1 | FGF13; | INTRONIC (100%); | 4 | 4024021; 4024027; 4024008; 4024011; |
| Block_7797 | 0.038082 | chrX: 70782986 . . . 70784559; + | 1 | OGT; | CODING (100%); | 3 | 3981153; 3981154; 3981155; |
| Block_7864 | 0.038082 | chrY: 21903642 . . . 21905110; − | 1 | KDM5D; | CODING (100%); | 2 | 4036111; 4036113; |
| Block_328 | 0.038614 | chr1: 163112906 . . . 163122506; − | 1 | RGS5; | CODING (42.85%); UTR (57.14%); | 7 | 2441391; 2441393; 2441394; 2441395; 2441396; 2441398; 2441399; |
| Block_5056 | 0.038614 | chr3: 37356931 . . . 37360665; + | 1 | GOLGA4; | CODING (100%); | 2 | 2617089; 2617093; |
| Block_7459 | 0.038614 | chr9: 102590326 . . . 102590574; + | 1 | NR4A3; | CODING (100%); | 2 | 3181993; 3181994; |
| Block_1339 | 0.039152 | chr11: 115211747 . . . 115213046; − | 1 | CADM1; | INTRONIC (100%); | 2 | 3392448; 3392450; |
| Block_1817 | 0.039152 | chr12: 11805464 . . . 11817168; + | 1 | ETV6; | INTRONIC (100%); | 3 | 3405046; 3405051; 3405055; |
| Block_6459 | 0.039152 | chr6: 116431503 . . . 116431626; + | 1 | NT5DC1; | INTRONIC (100%); | 2 | 2922530; 2922531; |
| Block_7222 | 0.039152 | chr9: 74978264 . . . 74978497; − | 1 | ZFAND5; | UTR (50%); INTRONIC (50%); | 2 | 3209642; 3209643; |
| Block_3275 | 0.039696 | chr17: 59093209 . . . 59112144; + | 1 | BCAS3; | CODING (100%); | 2 | 3729624; 3729628; |
| Block_6094 | 0.039696 | chr6: 3304594 . . . 3307353; − | 1 | SLC22A23; | INTRONIC (100%); | 2 | 2939326; 2939328; |
| Block_7372 | 0.039696 | chr9: 140358830 . . . 140358908; − | 1 | PNPLA7; | CODING (100%); | 2 | 3231037; 4051814; |
| Block_7611 | 0.039696 | chrX: 73434306 . . . 73442101; − | 0 | | INTERGENIC (100%); | 2 | 4012764; 4012770; |
| Block_260 | 0.040246 | chr1: 120295908 . . . 120307209; − | 1 | HMGCS2; | CODING (100%); | 9 | 2431038; 2431042; 2431044; 2431047; 2431050; 2431051; 2431056; 2431057; 2431058; |
| Block_7111 | 0.040246 | chr8: 70570914 . . . 70572224; + | 1 | SULF1; | UTR (100%); | 2 | 3102461; 3102463; |
| Block_1095 | 0.040803 | chr10: 93722326 . . . 93723946; + | 1 | BTAF1; | CODING (100%); | 2 | 3257967; 3257969; |
| Block_6228 | 0.040803 | chr6: 99853979 . . . 99857124; − | 1 | SFRS18; | CODING (100%); | 2 | 2966275; 2966279; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| Block_1954 | 0.041367 | chr12: 119631512 . . . 119632155; + | 1 | HSPB8; | CODING (50%); UTR (50%); | 2 | 3434022; 3434023; |
| Block_2868 | 0.041367 | chr16: 48395568 . . . 48396210; + | 1 | SIAH1; | CODING_AS (100%); | 3 | 3659376; 3659377; 3659378; |
| Block_5186 | 0.041367 | chr3: 156249230 . . . 156254535; + | 1 | KCNAB1; | CODING (100%); | 2 | 2649070; 2649077; |
| Block_5326 | 0.041367 | chr4: 80992745 . . . 80993659; − | 1 | ANTXR2; | CODING (100%); | 2 | 2775042; 2775043; |
| Block_749 | 0.041367 | chr1: 203276405 . . . 203277831; + | 1 | BTG2; | CODING (33.33%); UTR (66.66%); | 3 | 2375671; 2375672; 2375673; |
| Block_186 | 0.041937 | chr1: 59247791 . . . 59248778; − | 1 | JUN; | CODING (50%); UTR (50%); | 2 | 2415092; 2415095; |
| Block_161 | 0.042514 | chr1: 51768040 . . . 51768245; − | 1 | TTC39A; | CODING (100%); | 2 | 2412328; 2412330; |
| Block_2076 | 0.042514 | chr13: 24157611 . . . 24190183; + | 1 | TNFRSF19; | CODING (60%); ncTRANSCRIPT (20%); INTRONIC (20%); | 5 | 3481424; 3481425; 3481429; 3481433; 3481434; |
| Block_3220 | 0.042514 | chr17: 40932892 . . . 40945698; + | 1 | WNK4; | CODING (100%); | 8 | 3722087; 3722090; 3722094; 3722095; 3722100; 3722101; 3722105; 3722106; |
| Block_3425 | 0.042514 | chr18: 48581190 . . . 48586286; + | 1 | SMAD4; | CODING (100%); | 2 | 3788324; 3788330; |
| Block_3684 | 0.042514 | chr19: 52462246 . . . 52469039; + | 1 | AC011460.1; | INTRONIC (100%); | 4 | 3839986; 3839988; 3839990; 3839992; |
| Block_4891 | 0.042514 | chr3: 120351994 . . . 120352038; − | 1 | HGD; | CODING (100%); | 2 | 2691376; 4047113; |
| Block_5619 | 0.042514 | chr4: 148860985 . . . 148876520; + | 1 | ARHGAP10; | CODING (100%); | 3 | 2746763; 2746767; 2746769; |
| Block_5894 | 0.042514 | chr5: 38886367 . . . 38906492; + | 1 | OSMR; | UTR (33.33%); INTRONIC (66.66%); | 3 | 2807398; 2807399; 2807405; |
| Block_3009 | 0.043098 | chr17: 39079241 . . . 39084827; − | 1 | KRT23; | CODING (100%); | 4 | 3756593; 3756596; 3756602; 3756603; |
| Block_5560 | 0.043098 | chr4: 95507630 . . . 95508222; + | 1 | PDLIM5; | CODING (33.33%); INTRONIC (66.66%); | 3 | 2736395; 2736396; 2736397; |
| Block_5893 | 0.043098 | chr5: 38883930 . . . 38886253; + | 1 | OSMR; | CODING (100%); | 2 | 2807390; 2807396; |
| Block_2154 | 0.043688 | chr13: 111896260 . . . 111920011; + | 1 | ARHGEF7; | CODING (100%); | 2 | 3501707; 3501714; |
| Block_2385 | 0.043688 | chr14: 95081422 . . . 95084915; + | 1 | SERPINA3; | ncTRANSCRIPT (100%); | 3 | 3549773; 3549776; 3549777; |
| Block_3557 | 0.043688 | chr19: 52568528 . . . 52579356; − | 1 | ZNF841; | CODING (100%); | 4 | 3869431; 3869432; 3869434; 3869435; |
| Block_3704 | 0.043688 | chr19: 57802283 . . . 57804159; + | 1 | ZNF460; | CODING (66.66%); UTR (33.33%); | 3 | 3843164; 3843166; 3843168; |
| Block_4020 | 0.043688 | chr2: 239176702 . . . 239180131; − | 1 | PER2; | CODING (100%); | 2 | 2605780; 2605784; |
| Block_6547 | 0.043688 | chr6: 168272897 . . . 168281196; + | 1 | MLLT4; | CODING (100%); | 6 | 2936868; 4048405; 2936869; 4048403; 4048399; 2936875; |
| Block_665 | 0.043688 | chr1: 156100418 . . . 156106788; + | 1 | LMNA; | CODING (100%); | 7 | 2361313; 2361314; 2361316; 2361317; 2361320; 2361322; 2361325; |
| Block_1064 | 0.044285 | chr10: 71119734 . . . 71128378; + | 1 | HK1; | CODING (100%); | 2 | 3250324; 3250327; |
| Block_4291 | 0.044285 | chr2: 223758226 . . . 223772451; + | 1 | ACSL3; | INTRONIC (100%); | 2 | 2529553; 2529557; |
| Block_5884 | 0.044285 | chr5: 14602311 . . . 14607558; + | 1 | FAM105A; | CODING (100%); | 2 | 2802711; 2802714; |
| Block_1047 | 0.044889 | chr10: 51555733 . . . 51556843; + | 1 | MSMB; | CODING (100%); | 2 | 3246411; 3246412; |
| Block_2056 | 0.044889 | chr13: 107211047 . . . 107211667; − | 1 | ARGLU1; | CODING (50%); INTRONIC (50%); | 2 | 3524631; 3524633; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| Block_6885 | 0.044889 | chr8: 17503466 ... 17507465; − | 1 | MTUS1; | CODING (100%); | 3 | 3125921; 3125923; 3125925; |
| Block_7779 | 0.044889 | chrX: 53114856 ... 53115271; + | 1 | TSPYL2; | CODING (100%); | 2 | 3978189; 3978190; |
| Block_1046 | 0.0455 | chr10: 51532298 ... 51535286; + | 2 | TIMM23B; RP11-481A12.2; | ncTRANSCRIPT (50%); INTRONIC (50%); | 4 | 3246373; 3246408; 3246374; 3246376; |
| Block_3683 | 0.0455 | chr19: 51380495 ... 51381606; + | 1 | KLK2; | INTRONIC (100%); | 2 | 3839580; 3839583; |
| Block_377 | 0.0455 | chr1: 207102212 ... 207112808; − | 1 | PIGR; | CODING (90.90%); UTR (9.09%); | 11 | 2453007; 2453010; 2453011; 2453012; 2453013; 2453015; 2453016; 2453018; 2453019; 2453020; 2453021; |
| Block_4748 | 0.0455 | chr3: 17413596 ... 17425454; − | 1 | TBC1D5; | CODING (100%); | 5 | 2664953; 2664954; 2664955; 2664956; 2664957; |
| Block_6405 | 0.0455 | chr6: 44216514 ... 44217722; + | 1 | HSP90AB1; | INTRONIC (100%); | 2 | 2908484; 2908490; |
| Block_181 | 0.046118 | chr1: 57025279 ... 57038895; − | 1 | PPAP2B; | INTRONIC (100%); | 2 | 2414403; 2414411; |
| Block_2341 | 0.046118 | chr14: 64444642 ... 64447421; + | 1 | SYNE2; | CODING (100%); | 2 | 3539761; 3539763; |
| Block_2611 | 0.046118 | chr15: 71574554 ... 71586847; + | 1 | THSD4; | INTRONIC (100%); | 2 | 3600324; 3600327; |
| Block_3692 | 0.046118 | chr19: 54080729 ... 54081190; + | 1 | ZNF331; | CODING (100%); | 2 | 3840996; 3840998; |
| Block_7486 | 0.046118 | chr9: 130914205 ... 130914547; + | 1 | LCN2; | CODING (100%); | 2 | 3190204; 3190205; |
| Block_1338 | 0.046743 | chr11: 115099833 ... 115111135; − | 1 | CADM1; | CODING (100%); | 3 | 3392393; 3392394; 3392398; |
| Block_2668 | 0.046743 | chr15: 99372148 ... 99385603; + | 1 | IGF1R; | INTRONIC (100%); | 3 | 3610947; 3610951; 3610955; |
| Block_2766 | 0.046743 | chr16: 65005837 ... 65022233; − | 1 | CDH11; | CODING (100%); | 3 | 3694677; 3694684; 3694691; |
| Block_4086 | 0.046743 | chr2: 46529640 ... 46533141; + | 1 | EPAS1; | INTRONIC (100%); | 2 | 2480399; 2480401; |
| Block_4584 | 0.046743 | chr21: 40179160 ... 40196766; + | 1 | ETS2; | CODING (40.90%); UTR (18.18%); INTRONIC (40.90%); | 22 | 3921087; 3921088; 3921089; 3921091; 3921092; 3921094; 3921096; 3921097; 3921098; 3921099; 3921100; 3921101; 3921102; 3921104; 3921105; 3921107; 3921109; 3921112; 3921115; 3921116; 3921118; 3921119; |
| Block_5358 | 0.046743 | chr4: 102196342 ... 102200906; − | 1 | PPP3CA; | INTRONIC (100%); | 2 | 2779709; 2779739; |
| Block_5575 | 0.046743 | chr4: 106155858 ... 106158231; + | 1 | TET2; | CODING (100%); | 2 | 2738167; 2738170; |
| Block_5710 | 0.046743 | chr5: 56219003 ... 56219619; − | 1 | MIER3; | CODING (100%); | 2 | 2857736; 2857737; |
| Block_1923 | 0.047375 | chr12: 97945516 ... 97949840; + | 1 | RMST; | INTRONIC (100%); | 2 | 3427537; 3427541; |
| Block_2122 | 0.047375 | chr13: 76395328 ... 76397948; + | 1 | LMO7; | CODING (100%); | 2 | 3494214; 3494216; |
| Block_2950 | 0.047375 | chr17: 3743397 ... 3746434; − | 1 | C17orf85; | CODING (100%); | 2 | 3741707; 3741708; |
| Block_2090 | 0.048014 | chr13: 31231614 ... 31232191; + | 1 | USPL1; | CODING (100%); | 2 | 3484044; 3484045; |
| Block_2246 | 0.048014 | chr14: 76446944 ... 76447361; − | 1 | TGFB3; | CODING (50%); UTR (50%); | 2 | 3572536; 3572538; |
| Block_6421 | 0.048014 | chr6: 64286908 ... 64288684; + | 1 | PTP4A1; | INTRONIC (100%); | 3 | 2911920; 2911921; 2911925; |
| Block_6888 | 0.048014 | chr8: 18725208 ... 18729431; − | 1 | PSD3; | CODING (100%); | 2 | 3126326; 3126328; |
| Block_1477 | 0.048661 | chr11: 66391897 ... 66392352; + | 1 | RBM14; | CODING (100%); | 2 | 3336384; 3336386; |
| Block_1662 | 0.048661 | chr12: 52485769 ... 52486601; − | 0 | | INTERGENIC (100%); | 2 | 3455115; 3455117; |

TABLE 23-continued

| ICE Block ID | Wilcoxon P-value | Chromosomal Coordinates | # of Genes | Overlapping Genes | Category (Composition %) | # of PSRs | Probe set ID(s) |
|---|---|---|---|---|---|---|---|
| Block_171 | 0.048661 | chr1: 53363109 . . . 53370744; − | 1 | ECHDC2; | CODING (100%); | 3 | 2413037; 2413040; 2413044; |
| Block_6153 | 0.048661 | chr6: 35623219 . . . 35655662; − | 1 | FKBP5; | INTRONIC (100%); | 7 | 2951608; 2951610; 2951614; 2951615; 2951616; 2951619; 2951627; |
| Block_7713 | 0.048661 | chrX: 2541426 . . . 2541450; + | 1 | CD99P1; | ncTRANSCRIPT (100%); | 2 | 3966810; 4028424; |
| Block_875 | 0.048661 | chr10: 33195427 . . . 33195769; − | 1 | ITGB1; | CODING (50%); INTRONIC (50%); | 2 | 3284196; 3284197; |
| Block_934 | 0.048661 | chr10: 79593681 . . . 79603456; − | 1 | DLG5; | CODING (100%); | 3 | 3296448; 3296449; 3296455; |
| Block_1166 | 0.049314 | chr10: 128816976 . . . 128817096; + | 1 | DOCK1; | CODING (100%); | 2 | 3269979; 3269980; |
| Block_1946 | 0.049314 | chr12: 111655706 . . . 111701632; + | 1 | CUX2; | CODING (100%); | 2 | 3431801; 3431809; |
| Block_2243 | 0.049314 | chr14: 75745675 . . . 75748413; − | 1 | FOS; | CODING_AS (100%); | 2 | 3572391; 3572392; |
| Block_4019 | 0.049314 | chr2: 239162223 . . . 239164537; − | 1 | PER2; | CODING (100%); | 2 | 2605759; 2605760; |
| Block_4293 | 0.049314 | chr2: 223781554 . . . 223782703; + | 1 | ACSL3; | ncTRANSCRIPT (50%); INTRONIC (50%); | 2 | 2529572; 2529573; |
| Block_6218 | 0.049314 | chr6: 90385836 . . . 90387413; − | 1 | MDN1; | CODING (100%); | 2 | 2964413; 2964414; |
| Block_3693 | 0.049976 | chr19: 54080311 . . . 54081259; + | 1 | ZNF331; | CODING (50%); UTR (50%); | 2 | 3840995; 3840999; |
| Block_819 | 0.049976 | chr1: 229242103 . . . 229242133; + | 0 | | INTERGENIC (100%); | 2 | 2384497; 4042435; |

TABLE 24

| SEQ ID NO.: | Block ID | Comparison | Probe Set ID |
|---|---|---|---|
| 293 | Block_7113 | BCR | 3103710 |
| 297 | Block_7113 | BCR | 3103707 |
| 300 | Block_7113 | BCR | 3103712 |
| 303 | Block_7113 | BCR | 3103708 |
| 309 | Block_7113 | BCR | 3103706 |
| 311 | Block_7113 | BCR | 3103713 |
| 312 | Block_7113 | BCR | 3103715 |
| 316 | Block_7113 | BCR | 3103704 |
| 481 | Block_2879 | BCR | 3662122 |
| 482 | Block_2879 | BCR | 3662124 |
| 483 | Block_2879 | BCR | 3662156 |
| 484 | Block_2879 | BCR | 3662163 |
| 485 | Block_2922 | GS | 3670638 |
| 486 | Block_2922 | GS | 3670639 |
| 487 | Block_2922 | GS | 3670641 |
| 488 | Block_2922 | GS | 3670644 |
| 489 | Block_2922 | GS | 3670645 |
| 490 | Block_2922 | GS | 3670650 |
| 491 | Block_2922 | GS | 3670659 |
| 492 | Block_2922 | GS | 3670660 |
| 493 | Block_4271 | GS | 2528108 |
| 494 | Block_4271 | GS | 2528110 |
| 495 | Block_4271 | GS | 2528111 |
| 496 | Block_4271 | GS | 2528112 |
| 497 | Block_4271 | GS | 2528113 |
| 498 | Block_4271 | GS | 2528115 |
| 499 | Block_5000 | GS | 2608324 |
| 500 | Block_5080 | GS | 2624393 |
| 501 | Block_5080 | GS | 2624394 |
| 502 | Block_5080 | GS | 2624395 |
| 503 | Block_5080 | GS | 2624399 |
| 504 | Block_5080 | GS | 2624416 |
| 505 | Block_5080 | GS | 2624421 |
| 506 | Block_5080 | GS | 2624427 |
| 507 | Block_5080 | GS | 2624429 |
| 508 | Block_5080 | GS | 2624453 |
| 509 | Block_5080 | GS | 2624459 |
| 510 | Block_5080 | GS | 2624460 |
| 511 | Block_5080 | GS | 2624461 |
| 512 | Block_5080 | GS | 2624462 |
| 513 | Block_5080 | GS | 2624465 |
| 514 | Block_5080 | GS | 2624466 |
| 515 | Block_5080 | GS | 2624467 |
| 516 | Block_5080 | GS | 2624470 |
| 517 | Block_5080 | GS | 2624472 |
| 518 | Block_5080 | GS | 2624473 |
| 519 | Block_5080 | GS | 2624475 |
| 520 | Block_5080 | GS | 2624477 |
| 521 | Block_5080 | GS | 2624479 |
| 522 | Block_5080 | GS | 2624480 |
| 523 | Block_5080 | GS | 2624481 |
| 524 | Block_5080 | GS | 2624482 |
| 525 | Block_5080 | GS | 2624484 |
| 526 | Block_5080 | GS | 2624485 |
| 527 | Block_5080 | GS | 2624487 |
| 528 | Block_5080 | GS | 2624488 |
| 529 | Block_5080 | GS | 2624491 |
| 530 | Block_5080 | GS | 2624494 |
| 531 | Block_5080 | GS | 2624499 |
| 532 | Block_5080 | GS | 2624500 |
| 533 | Block_5080 | GS | 2624501 |
| 534 | Block_5080 | GS | 2624502 |
| 535 | Block_5080 | GS | 2624503 |
| 536 | Block_5080 | GS | 2624504 |
| 537 | Block_5080 | GS | 2624505 |
| 538 | Block_5080 | GS | 2624507 |
| 539 | Block_5080 | GS | 2624511 |
| 540 | Block_5080 | GS | 2624515 |
| 541 | Block_5080 | GS | 2624516 |
| 542 | Block_5080 | GS | 2624518 |

TABLE 24-continued

| SEQ ID NO.: | Block ID | Comparison | Probe Set ID |
|---|---|---|---|
| 543 | Block_5080 | GS | 2624519 |
| 544 | Block_5080 | GS | 2624526 |
| 545 | Block_5470 | BCR | 2719689 |
| 546 | Block_5470 | BCR | 2719692 |
| 547 | Block_5470 | BCR | 2719694 |
| 548 | Block_6371 | BCR | 2902713 |
| 549 | Block_6371 | BCR | 2902730 |
| 550 | Block_6592 | BCR | 3046457 |
| 551 | Block_6592 | BCR | 3046459 |
| 552 | Block_6592 | BCR | 3046460 |
| 553 | Block_6592 | BCR | 3046461 |
| 554 | Block_6592 | BCR | 3046462 |
| 555 | Block_6592 | BCR | 3046465 |
| 556 | Block_7113 | BCR | 3103714 |
| 557 | Block_7113 | BCR | 3103717 |
| 558 | Block_7716 | GS | 3970026 |
| 559 | Block_7716 | GS | 3970034 |
| 560 | Block_5470 | BCR | 2719696 |
| 561 | Block_2922 | GS | 3670666 |
| 562 | Block_4627 | BCR | 3956596 |
| 563 | Block_4627 | BCR | 3956601 |
| 564 | Block_5080 | GS | 2624397 |
| 565 | Block_5080 | GS | 2624398 |
| 566 | Block_5080 | GS | 2624400 |
| 567 | Block_5080 | GS | 2624401 |
| 568 | Block_5080 | GS | 2624402 |
| 569 | Block_5080 | GS | 2624403 |
| 570 | Block_5080 | GS | 2624404 |
| 571 | Block_5080 | GS | 2624405 |
| 572 | Block_5080 | GS | 2624406 |
| 573 | Block_5080 | GS | 2624407 |
| 574 | Block_5080 | GS | 2624408 |
| 575 | Block_5080 | GS | 2624411 |
| 576 | Block_5080 | GS | 2624412 |
| 577 | Block_5080 | GS | 2624413 |
| 578 | Block_5080 | GS | 2624415 |
| 579 | Block_5080 | GS | 2624417 |
| 580 | Block_5080 | GS | 2624422 |
| 581 | Block_5080 | GS | 2624424 |
| 582 | Block_5080 | GS | 2624426 |
| 583 | Block_5080 | GS | 2624428 |
| 584 | Block_5080 | GS | 2624432 |
| 585 | Block_5080 | GS | 2624434 |
| 586 | Block_5080 | GS | 2624435 |
| 587 | Block_5080 | GS | 2624438 |
| 588 | Block_5080 | GS | 2624439 |
| 589 | Block_5080 | GS | 2624440 |
| 590 | Block_5080 | GS | 2624441 |
| 591 | Block_5080 | GS | 2624442 |
| 592 | Block_5080 | GS | 2624443 |
| 593 | Block_5080 | GS | 2624444 |
| 594 | Block_5080 | GS | 2624446 |
| 595 | Block_5080 | GS | 2624458 |
| 596 | Block_5080 | GS | 2624490 |
| 597 | Block_5080 | GS | 2624492 |
| 598 | Block_5080 | GS | 2624493 |
| 599 | Block_5080 | GS | 2624495 |
| 600 | Block_5080 | GS | 2624496 |
| 601 | Block_5080 | GS | 2624508 |
| 602 | Block_5080 | GS | 2624512 |
| 603 | Block_5080 | GS | 2624529 |
| 604 | Block_5080 | GS | 2624531 |
| 605 | Block_5080 | GS | 2624533 |
| 606 | Block_5080 | GS | 2624537 |
| 607 | Block_5155 | BCR | 2642733 |
| 608 | Block_5155 | BCR | 2642735 |
| 609 | Block_5155 | BCR | 2642740 |
| 610 | Block_5155 | BCR | 2642741 |
| 611 | Block_5155 | BCR | 2642744 |
| 612 | Block_5155 | BCR | 2642745 |
| 613 | Block_5155 | BCR | 2642746 |
| 614 | Block_5155 | BCR | 2642747 |
| 615 | Block_5155 | BCR | 2642748 |
| 616 | Block_5155 | BCR | 2642750 |
| 617 | Block_5155 | BCR | 2642753 |
| 618 | Block_5000 | GS | 2608331 |
| 619 | Block_5000 | GS | 2608332 |
| 620 | Block_7716 | GS | 3970036 |
| 621 | Block_7716 | GS | 3970039 |
| 622 | Block_2879 | BCR | 3662175 |
| 623 | Block_4627 | BCR | 3956603 |
| 624 | Block_5080 | GS | 2624430 |
| 625 | Block_5155 | BCR | 2642738 |
| 626 | Block_5155 | BCR | 2642739 |
| 627 | Block_2922 | GS | 3670661 |
| 628 | Block_4271 | GS | 2528118 |
| 629 | Block_5000 | GS | 2608321 |
| 630 | Block_5000 | GS | 2608326 |
| 631 | Block_5080 | GS | 2624389 |
| 632 | Block_5080 | GS | 2624527 |
| 633 | Block_5470 | BCR | 2719695 |
| 634 | Block_6592 | BCR | 3046448 |
| 635 | Block_6592 | BCR | 3046449 |
| 636 | Block_6592 | BCR | 3046450 |
| 637 | Block_7113 | BCR | 3103705 |
| 638 | Block_7113 | BCR | 3103718 |
| 639 | Block_7113 | BCR | 3103720 |
| 640 | Block_7113 | BCR | 3103721 |
| 641 | Block_7113 | BCR | 3103725 |
| 642 | Block_7113 | BCR | 3103726 |

TABLE 25

|  | Train | Test |
|---|---|---|
| Low Risk | 13 | 12 |
| Upgraded | 16 | 15 |

TABLE 26

| SEQ ID NO: | Probe Set ID | GENE SYMBOL | DESCRIPTION |
|---|---|---|---|
| 442 | 2343088 | AK5 | adenylate kinase 5 |
| 443 | 2476697 | RASGRP3 | RAS guanyl releasing protein 3 (calcium and DAG-regulated) |
| 444 | 2518183 | UBE2E3 | ubiquitin-conjugating enzyme E2E 3 (UBC4/5 homolog, yeast) |
| 445 | 2523351 | BMPR2 | bone morphogenetic protein receptor, type II (serine/threonine kinase) |
| 446 | 2609586 | RP11-58B17.1-015 | |
| 447 | 2791421 | FAM198B | family with sequence similarity 198, member B |
| 448 | 2825939 | PRR16 | proline rich 16 |
| 449 | 3018630 | SLC26A4 | solute carrier family 26, member 4 |
| 450 | 3046126 | AOAH | acyloxyacyl hydrolase (neutrophil) |
| 451 | 3245912 | WDFY4 | WDFY family member 4 |
| 452 | 3331849 | GLYATL1 | glycine-N-acyltransferase-like 1 |
| 453 | 3332352 | MS4A6E MS4A7 MS4A14 | membrane-spanning 4-domains, subfamily A, member 6E; 7; 14 |
| 454 | 3374811 | AP000640.10 | NA |
| 455 | 3490910 | OLFM4 | olfactomedin 4 |
| 456 | 3490922 | OLFM4 | olfactomedin 4 |
| 457 | 4030108 | USP9Y | ubiquitin specific peptidase 9, Y-linked |

TABLE 27

| SEQ ID NO.: | Probe Set ID | Overlapping Gene |
|---|---|---|
| 436 | 3454547 | METTL7A |
| 643 | 2351754 | RP11-165H20.1 |
| 644 | 2352207 | WNT2B |
| 645 | 2425758 | COL11A1 |
| 646 | 2425760 | COL11A1 |
| 647 | 2439143 | CD5L |
| 648 | 2443478 | SELE |
| 649 | 2445999 | ANGPTL1 |
| 650 | 2497104 | IL1RL1; IL18R1 |
| 651 | 2537182 | FAM150B |
| 652 | 2557961 | GKN2 |
| 653 | 2563801 | AC096579.13; AC096579.7 |
| 654 | 2590074 | ZNF385B |
| 655 | 2597353 | ACADL |
| 656 | 2630510 | ROBO2 |
| 657 | 2665784 | ZNF385D |
| 658 | 2690307 | LSAMP |
| 659 | 2690547 | LSAMP; RP11-384F7.2 |
| 660 | 2735071 | SPP1 |
| 661 | 2745931 | HHIP |
| 662 | 2745967 | HHIP |
| 663 | 2763608 | PPARGC1A |
| 664 | 2773359 | |
| 665 | 2773360 | PPBP |
| 666 | 2877981 | DNAJC18 |
| 667 | 2899180 | HIST1H2BD |
| 668 | 2931616 | AKAP12 |
| 669 | 2992595 | IL6 |
| 670 | 3010526 | CD36 |
| 671 | 3039672 | SOSTDC1 |
| 672 | 3066159 | LHFPL3 |
| 673 | 3090264 | ADAM28 |
| 674 | 3094812 | TACC1 |
| 675 | 3094826 | TACC1 |
| 676 | 3111647 | PKHD1L1 |
| 677 | 3125131 | DLC1 |
| 678 | 3127576 | |
| 679 | 3128830 | ADRA1A |
| 680 | 3128833 | ADRA1A |
| 681 | 3142382 | RP11-157I4.4 |
| 682 | 3142383 | FABP4 |
| 683 | 3148249 | RP11-152P17.2 |
| 684 | 3165878 | TEK |
| 685 | 3214804 | OGN |
| 686 | 3217691 | NR4A3 |
| 687 | 3219225 | KLF4 |
| 688 | 3248306 | CDK1 |
| 689 | 3256240 | AGAP11 |
| 690 | 3290059 | PCDH15 |
| 691 | 3324452 | FIBIN |
| 692 | 3388860 | MMP12 |
| 693 | 3388865 | MMP12 |
| 694 | 3388870 | MMP12 |
| 695 | 3388876 | MMP12 |
| 696 | 3388879 | MMP12 |
| 697 | 3420066 | WIF1 |
| 698 | 3424154 | |
| 699 | 3443978 | |
| 700 | 3452294 | SLC38A1 |
| 701 | 3461802 | PTPRB |
| 702 | 3489790 | DLEU1 |
| 703 | 3517284 | DACH1 |
| 704 | 3587566 | GREM1 |
| 705 | 3589514 | THBS1 |
| 706 | 3598183 | AC069368.3; PLEKHO2 |
| 707 | 3620424 | PLA2G4F |
| 708 | 3624798 | |
| 709 | 3629110 | CSNK1G1; KIAA0101 |
| 710 | 3662123 | MT1A |
| 711 | 3716397 | BLMH |
| 712 | 3720984 | TOP2A |
| 713 | 3751793 | SLC6A4 |
| 714 | 3763391 | TMEM100 |
| 715 | 3834346 | CEACAM5 |
| 716 | 3834373 | CEACAM5 |
| 717 | 3834374 | CEACAM5 |
| 718 | 3847635 | RFX2 |
| 719 | 3847641 | RFX2 |
| 720 | 3863109 | ATP5SL |
| 721 | 3863235 | CEACAM5 |

TABLE 28

| SEQ ID NO.: | Probe Set ID | Overlapping Gene |
|---|---|---|
| 722 | 2325656 | CLIC4 |
| 723 | 2340120 | CACHD1 |
| 724 | 2343484 | IFI44L |
| 725 | 2370193 | |
| 726 | 2372698 | |
| 727 | 2425831 | COL11A1 |
| 728 | 2432674 | POLR3C |
| 729 | 2451729 | |
| 730 | 2464140 | AKT3; RP11-370K11.1 |
| 731 | 2475754 | LCLAT1 |
| 732 | 2477458 | QPCT |
| 733 | 2513024 | |
| 734 | 2525590 | MAP2 |

TABLE 28-continued

| SEQ ID NO.: | Probe Set ID | Overlapping Gene |
|---|---|---|
| 735 | 2525606 | MAP2 |
| 736 | 2555049 | BCL11A |
| 737 | 2560264 | AUP1 |
| 738 | 2570667 | BUB1 |
| 739 | 2580618 | LYPD6 |
| 740 | 2585026 | SCN3A |
| 741 | 2585470 | SCN9A |
| 742 | 2619699 | SNRK |
| 743 | 2643586 | |
| 744 | 2647355 | TM4SF4 |
| 745 | 2653664 | KCNMB2 |
| 746 | 2654937 | MCCC1 |
| 747 | 2658328 | RP11-175P19.3 |
| 748 | 2658606 | |
| 749 | 2685706 | EPHA6 |
| 750 | 2700315 | CPHL1P |
| 751 | 2701244 | MBNL1 |
| 752 | 2709053 | IGF2BP2 |
| 753 | 2722908 | PCDH7 |
| 754 | 2726525 | OCIAD1 |
| 755 | 2730161 | CSN1S1 |
| 756 | 2779454 | DNAJB14 |
| 757 | 2794412 | HPGD |
| 758 | 2800740 | ADCY2 |
| 759 | 2853946 | |
| 760 | 2884854 | GABRB2 |
| 761 | 2909786 | C6orf141 |
| 762 | 2915096 | |
| 763 | 2917256 | |
| 764 | 2921416 | SLC16A10 |
| 765 | 2925362 | LAMA2 |
| 766 | 2933343 | SNX9 |
| 767 | 2934286 | |
| 768 | 2953202 | RP1-278E11.5 |
| 769 | 2959207 | LGSN |
| 770 | 2959221 | |
| 771 | 2977998 | EPM2A |
| 772 | 2982935 | |
| 773 | 2983725 | PACRG |
| 774 | 2991528 | HDAC9 |
| 775 | 2993670 | CBX3 |
| 776 | 2996608 | BMPER |
| 777 | 3004356 | ZNF679; RP11-3N2.13; RP11-3N2.1 |
| 778 | 3004687 | ZNF138 |
| 779 | 3013087 | COL1A2 |
| 780 | 3070073 | FAM3C |
| 781 | 3083209 | CSMD1 |
| 782 | 3098089 | ST18 |
| 783 | 3100188 | RAB2A |
| 784 | 3100290 | CHD7 |
| 785 | 3105938 | CPNE3 |
| 786 | 3106163 | |
| 787 | 3118048 | |
| 788 | 3124338 | XKR6 |
| 789 | 3128057 | |
| 790 | 3147448 | UBR5 |
| 791 | 3153550 | ASAP1 |
| 792 | 3154681 | |
| 793 | 3194227 | |
| 794 | 3241027 | MAP3K8 |
| 795 | 3246418 | TIMM23B; MSMB |
| 796 | 3280411 | C10orf112 |
| 797 | 3287743 | RP11-463P17.1 |
| 798 | 3305180 | COL17A1 |
| 799 | 3308634 | PDZD8 |
| 800 | 3342551 | PCF11 |
| 801 | 3393506 | RP11-728F11.6; FXYD6 |

TABLE 29

| SEQ ID NO.: | Probe Set ID | Overlapping Gene |
|---|---|---|
| 653 | 2563801 | AC096579.13; AC096579.7 |
| 663 | 2763608 | PPARGC1A |
| 685 | 3214804 | OGN |
| 802 | 2345084 | CLCA4 |
| 803 | 2345093 | CLCA4 |
| 804 | 2353490 | ATP1A1 |
| 805 | 2374204 | NR5A2 |
| 806 | 2451596 | CHI3L1 |
| 807 | 2456712 | SLC30A10 |
| 808 | 2490340 | REG1A |
| 809 | 2513937 | B3GALT1 |
| 810 | 2513980 | AC016723.4 |
| 811 | 2533060 | UGT1A8; UGT1A10; UGT1A9 |
| 812 | 2563797 | AC096579.13; AC096579.7 |
| 813 | 2563798 | AC096579.13; AC096579.7 |
| 814 | 2594140 | SATB2 |
| 815 | 2633196 | CPOX |
| 816 | 2635219 | HHLA2 |
| 817 | 2730869 | SLC4A4 |
| 818 | 2767399 | ATP8A1 |
| 819 | 2772567 | ENAM |
| 820 | 2772569 | IGJ |
| 821 | 2772570 | IGJ |
| 822 | 2775911 | PLAC8 |
| 823 | 2779235 | ADH1B |
| 824 | 2782578 | CAMK2D |
| 825 | 2872078 | SEMA6A |
| 826 | 2923919 | PKIB |
| 827 | 2974957 | SLC2A12 |
| 828 | 2985814 | THBS2 |
| 829 | 3018675 | SLC26A3 |
| 830 | 3023440 | AHCYL2 |
| 831 | 3039871 | AGR3; RAD17P1 |
| 832 | 3047577 | AC005027.3; INHBA |
| 833 | 3062085 | PDK4 |
| 834 | 3062104 | PDK4 |
| 835 | 3090313 | ADAMDEC1 |
| 836 | 3103850 | HNF4G |
| 837 | 3105612 | CA2 |
| 838 | 3105614 | CA2 |
| 839 | 3105622 | CA2 |
| 840 | 3105629 | CA2 |
| 841 | 3141870 | TPD52 |
| 842 | 3142977 | CA1 |
| 843 | 3142991 | CA1 |
| 844 | 3163930 | |
| 845 | 3165029 | CDKN2B-AS1 |
| 846 | 3165030 | CDKN2B-AS1 |
| 847 | 3174167 | MAMDC2 |
| 848 | 3174519 | GDA |
| 849 | 3175362 | PCSK5 |
| 850 | 3175465 | PCSK5 |
| 851 | 3246960 | PRKG1 |
| 852 | 3258838 | NOC3L |
| 853 | 3332433 | MS4A12 |
| 854 | 3348424 | C11orf93 |
| 855 | 3364272 | RP11-396O20.2 |
| 856 | 3385068 | SYTL2 |
| 857 | 3392098 | FAM55D |
| 858 | 3392111 | FAM55D |
| 859 | 3392128 | |
| 860 | 3392143 | |
| 861 | 3392145 | |
| 862 | 3392151 | |
| 863 | 3392154 | |
| 864 | 3392167 | |
| 865 | 3392170 | |
| 866 | 3392175 | |
| 867 | 3392180 | |
| 868 | 3392181 | |
| 869 | 3392189 | |
| 870 | 3392191 | |
| 871 | 3392197 | |
| 872 | 3392211 | |
| 873 | 3392215 | |
| 874 | 3392223 | |
| 875 | 3407503 | PDE3A |
| 876 | 3407520 | PDE3A |
| 877 | 3449955 | |
| 878 | 3449956 | |

TABLE 30

| SEQ ID NO.: | Probe Set ID | Overlapping Gene |
|---|---|---|
| 879 | 4012531 | XIST |
| 880 | 4012532 | XIST |
| 881 | 4012534 | XIST |
| 882 | 4012535 | XIST |
| 883 | 4012537 | XIST |
| 884 | 4012538 | XIST |
| 885 | 4012540 | XIST |
| 886 | 4012541 | XIST |
| 887 | 4012542 | XIST |
| 888 | 4012545 | XIST |
| 889 | 4012546 | XIST |
| 890 | 4012550 | XIST |
| 891 | 4012570 | XIST |

TABLE 30-continued

| SEQ ID NO.: | Probe Set ID | Overlapping Gene |
|---|---|---|
| 892 | 4012571 | XIST |
| 893 | 4012573 | XIST |
| 894 | 4012575 | XIST |
| 895 | 4012577 | XIST |
| 896 | 4012579 | XIST |
| 897 | 4012585 | XIST |
| 898 | 4012589 | XIST |
| 899 | 4012595 | XIST |
| 900 | 4012597 | XIST |
| 901 | 4012599 | XIST |
| 902 | 4030193 | DDX3Y |
| 903 | 4036117 | KDM5D |

What is claimed is:

1. A method of treating prostate cancer in a subject, comprising:
   (a) obtaining or having obtained an expression level in a sample from a subject for a plurality of targets, wherein the plurality of targets comprises at least two targets selected from the group consisting of SEQ ID NOs: 103, 218, 275, 301, 321, 607, 707, 795, 828 and 832;
   (b) determining that the subject is at risk of developing metastatic prostate cancer based on said expression level, or determining that the subject is not at risk of developing metastatic prostate cancer based on said expression level; and
   (c) administering a prostate cancer treatment to the subject if the subject is determined to be at risk of developing metastatic prostate cancer based on said expression level, or monitoring without administering the prostate cancer treatment to the subject if the subject is determined to not be at risk of developing metastatic prostate cancer based on said expression level.

2. The method of claim 1, wherein the treatment is selected from the group consisting of surgery, a chemotherapeutic agent, radiation therapy, a biological therapeutic, cancer vaccine, gene therapy or a combination thereof.

3. The method of claim 2, wherein the treatment is prostatectomy, a chemotherapeutic agent, anti-androgen therapy or a combination thereof.

4. The method of claim 1, wherein the sample is selected from the group consisting of tissue, blood, plasma, serum, urine, a urine supernatant, a urine cell pellet, semen, prostatic secretions and prostate cells.

5. The method of claim 1, wherein said obtaining comprises a method selected from the group consisting of a sequencing technique, a nucleic acid hybridization technique, and nucleic acid amplification technique, and an immunoassay.

6. The method of claim 5, wherein the nucleic acid amplification technique is polymerase chain reaction, reverse transcription polymerase chain reaction, transcription-mediated amplification, ligase chain reaction, strand displacement amplification or nucleic acid sequence-based amplification.

7. The method of claim 1, wherein administering a prostate cancer treatment comprises administering cisplatin, carboplatin, oxaliplatin, mechlorethamine, cyclophosphamide, chlorambucil, ifosfamide, vincristine, vinblastine, vinorelbine, vindesine, paclitaxel, docetaxel, podophyllotoxin, irinotecan, topotecan, amsacrine, etoposide, etoposide phosphate, teniposide, actinomycin, anthracyclines, doxorubicin, daunorubicin, valrubicin, idarubicin, epirubicin, bleomycin, plicamycin, mitomycin, tositumomab, samarium-153-lexidronam, strontium-89 chloride, interferon alpha, interferon beta, interferon gamma, interleukin-2, interleukin 7, interleukin 12, G-CSF, GM-CSF, rituximab, trastuzumab, bacillus Calmette-Guerin (BCG), levamisole, porfimer sodium, mitoxantrone, prednisone, samarium, strontium, finasteride, or dutasteride.

* * * * *